US010479780B2

(12) United States Patent
Ebiike et al.

(10) Patent No.: US 10,479,780 B2
(45) Date of Patent: Nov. 19, 2019

(54) AMINOPYRAZOLE DERIVATIVES

(71) Applicants: Chugai Seiyaku Kabushiki Kaisha, Tokyo (JP); F. Hoffmann-La Roche AG, Basel (CH)

(72) Inventors: Hirosato Ebiike, Kanagawa (JP); Toshihiro Aoki, Kanagawa (JP); Takashi Chiba, Kanagawa (JP); Masami Kochi, Kanagawa (JP); Kimitaka Nakama, Kanagawa (JP); Satoshi Niizuma, Shizuoka (JP); Hiroki Nishii, Kanagawa (JP); Jun Ohwada, Tokyo (JP); Hiroyuki Shimamura, Kanagawa (JP); Aiko Suge, Shizuoka (JP); Yoshito Nakanishi, Kanagawa (JP); Natsuki Kobayashi, Kanagawa (JP)

(73) Assignees: Chugai Seiyaku Kabushiki Kaisha, Tokyo (JP); F. Hoffmann-La Roche AG, Basel (CH)

( * ) Notice: Subject to any disclaimer, the term of this patent is extended or adjusted under 35 U.S.C. 154(b) by 0 days.

(21) Appl. No.: 15/736,821

(22) PCT Filed: Jun. 17, 2016

(86) PCT No.: PCT/JP2016/068039
§ 371 (c)(1),
(2) Date: Dec. 15, 2017

(87) PCT Pub. No.: WO2016/204261
PCT Pub. Date: Dec. 22, 2016

(65) Prior Publication Data
US 2018/0362509 A1 Dec. 20, 2018

(30) Foreign Application Priority Data
Jun. 17, 2015 (JP) .................. 2015-122104

(51) Int. Cl.
*C07D 403/06* (2006.01)
*C07D 401/14* (2006.01)

(52) U.S. Cl.
CPC ......... *C07D 403/06* (2013.01); *C07D 401/14* (2013.01)

(58) Field of Classification Search
None
See application file for complete search history.

(56) References Cited

U.S. PATENT DOCUMENTS

| 6,316,466 | B1 | 11/2001 | Goldstein et al. |
| 6,444,696 | B1 | 9/2002 | Goldstein et al. |
| 7,863,314 | B2 | 1/2011 | Fryszman et al. |
| 8,829,199 | B2 | 9/2014 | Taka et al. |
| 9,102,692 | B2 | 8/2015 | Taka et al. |
| 9,126,969 | B2 | 9/2015 | Cherrier et al. |
| 10,391,081 | B2 | 8/2019 | Nakanishi et al. |
| 2015/0238607 | A1 | 8/2015 | Nihira et al. |
| 2015/0307945 | A1 | 10/2015 | Nakanishi et al. |
| 2016/0317499 | A1 | 11/2016 | Nakanishi et al. |

FOREIGN PATENT DOCUMENTS

| CN | 102099335 | 6/2011 |
| EP | 1 218 346 | 7/2002 |
| EP | 1 641 764 | 4/2006 |
| EP | 2 471 786 | 7/2012 |
| EP | 2 657 233 | 10/2013 |
| EP | 2 902 029 | 8/2015 |
| ES | 2393950 | 1/2013 |
| FR | 2831537 | 5/2003 |
| JP | 2002-513784 | 5/2002 |
| JP | 2003-509495 | 3/2003 |
| JP | 2007-521278 | 8/2007 |
| JP | 2011-528686 | 11/2011 |
| JP | 2012-180344 | 9/2012 |
| JP | 2013-144679 | 7/2013 |
| WO | WO 94/13643 | 6/1994 |
| WO | WO 99/57101 | 11/1999 |
| WO | WO 01/12600 | 2/2001 |
| WO | WO 01/21591 | 3/2001 |
| WO | WO 03/035065 | 5/2003 |
| WO | WO 2004/096792 | 11/2004 |
| WO | WO 2005/009973 | 2/2005 |
| WO | WO 2006/134318 | 12/2006 |
| WO | WO 2007/077435 | 7/2007 |
| WO | WO 2010/010017 | 1/2010 |
| WO | WO 2011/016528 | 2/2011 |

(Continued)

OTHER PUBLICATIONS

Getlik et al., "Hybrid Compound Design to Overcome the Gatekeeper T338M Mutation in cSrc," J Med Chem, Jul. 9, 2009, 52(13):3915-26. doi: 10.1021/jm9002928.
Goyal et al., "Polyclonal Secondary FGFR2 Mutations Drive Acquired Resistance to FGFR Inhibition in Patients with FGFR2 Fusion—Positive Cholangiocarcinoma," Cancer Discov, Mar. 2017, 7(3):252-263. doi: 10.1158/2159-8290.CD-16-1000. Epub Dec. 29, 2016.
U.S. Appl. No. 15/108,014, Nakanishi et al., filed Jun. 24, 2016.
Luqmani, et al., "Expression of basic fibroblast growth factor, FGFR1 and FGFR2 in normal and malignant human breast, and comparison with other normal tissues," Br J Cancer. Aug. 1992;66(2):273-80.
International Preliminary Report on Patentability for App. Ser. No. PCT/JP2016/068039, dated Dec. 28, 2016, 8 pages.
Benati et al., "Src Family Kinases as Potential Therapeutic Targets for Malignancies and Immunological Disorders," Curr. Med. Chem., 2008:15(12):1154-65.

(Continued)

*Primary Examiner* — Kamal A Saeed
(74) *Attorney, Agent, or Firm* — Fish & Richardson P.C.

(57) ABSTRACT

An objective of the present invention is to provide low-molecular-weight compounds that can inhibit Src family kinases. The present invention relates to compounds represented by general formula (I) or pharmacologically acceptable salts thereof. In the formula, $Ar^1$ is optionally substituted $C_{6-10}$ arylene or 5- to 10-membered heteroarylene, and $Ar^2$ is optionally substituted $C_{6-10}$ aryl or 5- to 10-membered heteroaryl. $R^1$ and $R^2$ are defined as described in the specification.

20 Claims, No Drawings

(56) References Cited

FOREIGN PATENT DOCUMENTS

| WO | WO 2012/067831 | 5/2012 |
|---|---|---|
| WO | WO 2014/050781 | 4/2014 |
| WO | WO 2014/051022 | 4/2014 |
| WO | WO 2015/016295 | 2/2015 |
| WO | WO 2015/086635 | 6/2015 |
| WO | WO 2015/086636 | 6/2015 |
| WO | WO 2015/086642 | 6/2015 |
| WO | WO 2015/099127 | 7/2015 |
| WO | WO 2016/204261 | 12/2016 |
| WO | WO 2017/017516 | 2/2017 |
| WO | WO 2017/028816 | 2/2017 |

OTHER PUBLICATIONS

Ebiike et al., "Discovery of [5-Amino-1-(2-methyl-3H-benzimidazol-5-yl)pyrazol-4-yl]-(1H-indol-2-yl)methanone (CHS 183284/Debio 1347), An Orally Available and Selective Fibroblast Growth Factor Receptor (FGFR) Inhibitor," J. Med. Chem., Dec. 8, 2016:59(23):10586-10600. Epub Nov. 29, 2016.

Nakanishi et al., "The fibroblast growth factor receptor genetic status as a potential predictor of the sensitivity to CH5183284/Debio 1347, a novel selective FGFR inhibitor," Mol Cancer Ther., Nov. 2014;13(11):2547-58. doi: 10.1158/1535-7163.MCT-14-0248. Epub Aug. 28, 2014.

Puls et al., "Current Status of Src Inhibitors in Solid Tumor Malignancies," Oncologist, 2011:16(5):566-78. doi:10.1634/theoncologist. Apr. 8, 2010. Epub Apr. 26, 2011.

Yeatman et al., "A Renaissance for SRC," Nat. Rev. Cancer, Jun. 2004:4(6):470-80.

International Search Report for App. Ser. No. PCT/JP2016/068039, dated Sep. 13, 2016, 3 pages.

Kas et al., "Transcriptomics and Transposon Mutagenesis Identify Multiple Mechanisms of Resistance to the FGFR Inhibitor AZD4547," Cancer Res, Oct. 1, 2018, 78(19):5668-5679. doi: 10.1158/0008-5472.CAN-18-0757. Epub Aug. 16, 2018.

U.S. Appl. No. 16/516,566, Nakanishi et al., filed Jul. 19, 2019.

Akiyama et al., "CH5183284/Debio 1347: A Novel Orally Available Selective FGFR1/2/3 Inhibitor," The Japanese Association for Molecular Target Therapy of Cancer, Gakujutsu Shukai Program/Shorokushu, May 2014, vol. 18, p. 85 (with English translation).

Byron et al., "Inhibition of Activated , Fibroblast Growth Factor Receptor 2 in Endometrial Cancer Cells Induces Cell Death Despite PTEN Abrogation," Cancer Res, Sep. 1, 2008, 68(17):6902-7.

Byron et al., "The N550K/H Mutations in FGFR2 Confer Differential Resistance to PD173074, Dovitinib, and Ponatinib ATP-Competitive Inhibitors," Neoplasia, Aug. 2013, 15(8):975-88.

Cappellen et al., "Frequent activating mutations of FGFR3 in human bladder and cervix carcinomas," Nat Genet, Sep. 1999, 23(1):18-20.

Cheng et al., "Novel Agents for the Treatment of Pancreatic Adenocarcinoma," JOP J Pancreas (Online), Jul. 8, 2011, 12(4):334-338.

Ebiike et al., "Design and preclinical profile of CH5183284/Debio 1347, a novel orally available and selective FGFR inhibitor acting on a gatekeeper mutant of FGFR2," American Association for Cancer Research Annual Meeting 2014, Apr. 7, 2014, Abstract No. 2533.

Elsheikh et al., "FGFR1 amplification in breast carcinomas: a chromogenic in situ hybridisation analysis," Breast Cancer Res, Mar. 2007, 9(2):R23.

Eswarakumar et al., "Cellular signaling by fibroblast growth factor receptors," Cytokine Growth Factor Rev, Apr. 2005, 16(2):139-49. Epub Feb. 1, 2005.

Fonseca et al., "Clinical and biologic implications of recurrent genomic aberrations in myeloma," Blood, Jun. 1, 2003, 101(11):4569-75.

Gavine et al., "AZD4547: An Orally Bioavailable, Potent, and Selective Inhibitor of the Fibroblast Growth Factor Receptor Tyrosine Kinase Family," Cancer Res, Apr. 2012, 72(8):2045-56. doi: 10.1158/0008-5472.CAN-11-3034. Epub Feb. 27, 2012.

Golub et al., "Molecular Classification of Cancer: Class Discovery and Class Prediction by Gene Expression Monitoring," Science, Oct. 15, 1999, 286(5439):531-537.

Guagnano et al., "Discovery of 3-(2,6-Dichloro-3,5-dimethoxyphenyl)-1-{6-[4-(4-ethyl-piperazin-1-yl)-phenylamino]-pyrimidin-4-yl}-1-methyl-urea (NVP-BGJ398), a Potent and Selective Inhibitor of the Fibroblast Growth Factor Receptor Family of Receptor Tyrosine Kinase," J Med Chem, Oct. 2011, 54(20):7066-83. doi: 10.1021/jm2006222. Epub Sep. 21, 2011.

Heiskanen et al., "CGH, cDNA and tissue microarray analyses implicate FGFR2 amplification in a small subset of breast tumors," Anal. Cell Pathol, Mar. 2001, 22(4):229-34.

Macdonald et al., "The 8p11 Myeloproliferative Syndrome: A Distinct Clinical Entity Caused by Constitutive Activation of FGFR1," Acta Haematol, Mar. 2002, 107(2):101-7.

Peng et al., "Alterations of chromosomal copy number during progression of diffuse-type gastric carcinomas: metaphase- and array-based comparative genomic hybridization analyses of multiple samples from individual," J Pathol, Jun. 2003, 201(3):439-50.

Rand et al., "Sequence survey of receptor tyrosine kinases reveals mutations in glioblastomas," Proc Natl Acad Sci USA, Oct. 4, 2005, 102(40):14344-9. Epub Sep. 26, 2005.

Sakamoto, "ALK Inhibitor," Nihon Yakurigaku Zasshi, 2013, 142(1):48-50 (with English translation).

Tan et al., "Development of covalent inhibitors that can overcome resistance to first-generation FGFR kinase inhibitors," Proc Natl Acad Sci USA, Nov. 11, 2014 111(45):E4869-77. doi:10.1073/pnas. 1403438111. Epub Oct. 27, 2014.

Wang et al., "Antisense targeting of basic fibroblast growth factor and fibroblast growth factor receptor-1 in human melanomas blocks intratumoral angiogenesis and tumor growth," Nat Med, Aug. 1997, 3(8):887-93.

Zhao et al., "Homozygous Deletions and Chromosome Amplifications in Human Lung Carcinomas Revealed by Single Nucleotide Polymorphism Array Analysis," Cancer Res, Jul. 1, 2005, 65(13):5561-70.

AMINOPYRAZOLE DERIVATIVES

CROSS-REFERENCE TO RELATED APPLICATIONS

This application is the National Stage of International Application Serial No. PCT/JP2016/068039, filed on Jun. 17, 2016, which claims the benefit of Japanese Application Serial No. 2015-122104, filed on Jun. 17, 2015.

TECHNICAL FIELD

The present invention relates to aminopyrazole derivatives and uses thereof.

BACKGROUND ART

Cancer is one of the major causes of death worldwide, and 7.9 million people died from cancer, accounting for 13% of the total deaths in 2007. With the increase in the aging population worldwide, the number of cancer patients is expected to increase. As reported by the World Health Organization, it is estimated that 13 million people will die from cancer in 2030. In recent years, many molecular targeted drugs against specific molecules as therapeutic targets have been developed, some of which have been confirmed to be clinically effective in prolonging the survival time of patients. Examples of such drugs include tyrosine kinase inhibitors such as imatinib, erlotinib, and trastuzumab. Many of such molecular targeted drugs will be effective against cancers that are aberrantly activated by amplification, mutation, and translocation of target genes, overexpression of target proteins, and the like. Conversely, these molecularly targeted drugs presumably cannot treat patients with cancers caused by genes that are not targeted by the drugs, and it is desirable to develop novel pharmaceutical agents for patients for whom existing pharmaceutical agents are not effective.

The Src kinase family is a family of non-receptor tyrosine kinases, and is composed of Src, Fyn, Yes1, Lck, Lyn, Hck, Fgr, and Blk. The Src kinase family interacts with, for example, receptors such as receptor tyrosine kinases and membrane proteins such as integrins, and carries out various signal transductions such as cell proliferation, cell adhesion, and angiogenesis (Non-patent Document 1). The Src kinase family is known to be overexpressed in various types of cancers, and it is known to be associated with cancer malignancy and survival (Non-patent Document 2). For these reasons, it is considered that inhibition of the Src family kinases in cancer tissues can be a promising therapy for various types of cancers, and Src family kinase inhibitors such as dasatinib and bosutinib have been developed. However, existing Src family kinase inhibitors do not show a sufficient effect clinically as Src family kinase inhibitors due to their poor kinase selectivity (Non-patent Document 3). Accordingly, more selective and potent Src family kinase inhibitors are desired.

CITATION LIST

Non-Patent Documents

[Non-patent Document 1] Nat. Rev. Cancer, June; 4(6), 470, 2004
[Non-patent Document 2] Curr. Med. Chem., 15(12), 1154, 2008
[Non-patent Document 3] Oncologist, 16(5), 566, 2011

SUMMARY OF THE INVENTION

Problems to be Solved by the Invention

An objective of the present invention is to provide low-molecular-weight compounds that can inhibit Src family kinases.

Means for Solving the Problems

Specifically, the present invention includes:
[1] a compound represented by general formula (I) below:

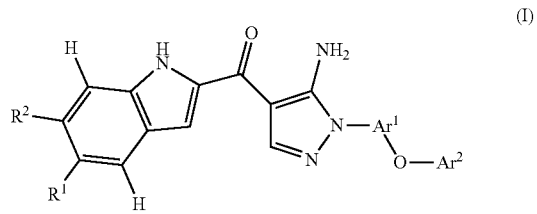

(I)

[wherein $Ar^1$ is $C_{6-10}$ arylene or 5- to 10-membered heteroarylene optionally substituted with a group selected from Group R;

$Ar^2$ is $C_{6-10}$ aryl or 5- to 10-membered heteroaryl optionally substituted with a group selected from Group R;

$R^1$ and $R^2$ are each independently a halogen atom, $C_{1-6}$ alkyl, $C_{3-6}$ cycloalkyl, $C_{1-6}$ haloalkyl, $C_{2-6}$ alkenyl, $C_{2-6}$ alkynyl, cyano, nitro, $NR^5R^6$, $OR^7$, $SR^8$, $SOR^8$, $SO_2R^8$, $CONR^9R^{10}$, 4- to 6-membered heterocyclyl optionally substituted with a group selected from Group Q, 5- to 10-membered heteroaryl optionally substituted with a group selected from Group Q, or $C_{6-10}$ aryl optionally substituted with a group selected from Group P, where the 4- to 6-membered heterocyclyl optionally substituted with a group selected from Group Q may be further linked to 4- to 6-membered heterocyclyl optionally substituted with a group selected from 4- to 6-membered heterocyclyl or $C_{6-10}$ aryl-$C_{1-6}$ alkyl, or to $C_{3-6}$ cycloalkyl through a spiro linkage;

$R^5$ and $R^6$ are each independently a hydrogen atom, $C_{1-6}$ alkyl optionally substituted with 4- to 6-membered heterocyclyl, amino-$C_{1-6}$ alkyl, $C_{1-6}$ alkylcarbonyl optionally substituted with a halogen atom, —$SO_2R^{30}$, —$C(O)OR^{31}$, —$C(O)NR^{32}R^{33}$, 4- to 6-membered heterocyclylcarbonyl, or 4- to 6-membered heterocyclyl optionally substituted with a group selected from Group Q; or alternatively, $R^5$ and $R^6$ form 4- to 6-membered heterocyclyl optionally substituted with a group selected from Group Q together with the nitrogen atom to which they are bonded;

$R^7$ is a hydrogen atom; $C_{1-6}$ alkyl which may have, as a substituent, a group selected from amino, a halogen atom, and hydroxy; 4- to 6-membered heterocyclyl optionally substituted with a group selected from Group Q; or $C_{1-6}$ alkyl having, as a substituent, 4- to 10-membered heterocyclyl optionally substituted with a group selected from Group Q;

$R^8$ is $C_{1-6}$ alkyl, halo-$C_{1-6}$ alkyl, or 4- to 6-membered heterocyclyl optionally substituted with a group selected from Group Q;

$R^9$ and $R^{10}$ are each independently a hydrogen atom or $C_{1-6}$ alkyl; or alternatively, $R^9$ and $R^{10}$ form 4- to 6-membered heterocyclyl optionally substituted with a group selected from Group Q together with the nitrogen atom to which they are bonded;

$R^{30}$ is optionally substituted $C_{1-6}$ alkyl, $C_{3-6}$ cycloalkyl which may have dihydroxy-$C_{1-6}$ alkyl as a substituent, $C_{6-10}$ aryl optionally substituted with a group selected from Group P, 5- to 10-membered heterocyclyl optionally substituted with a group selected from Group Q, 5- to 10-membered heteroaryl optionally substituted with a group selected from Group Q, or —$NR^{34}R^{35}$, where the substituent in the optionally substituted $C_{1-6}$ alkyl is selected from the group consisting of a halogen atom, 4- to 6-membered heterocyclyl optionally substituted with a group selected from Group Q, —$C(O)NR^{36}R^{37}$, and $C_{6-10}$ aryl;

$R^{31}$ represents $C_{1-6}$ alkyl which may have fluorene as a substituent;

$R^{32}$ and $R^{33}$ are each independently a hydrogen atom, or $C_{1-6}$ alkyl optionally substituted with a group selected from the group consisting of $C_{1-6}$ alkoxycarbonyl and 5- to 10-membered heteroaryl; or alternatively, $R^{32}$ and $R^{33}$ form 4- to 6-membered heterocyclyl together with the nitrogen atom to which they are bonded;

$R^{34}$ and $R^{35}$ are each independently a hydrogen atom, $C_{1-6}$ alkyl optionally substituted with a group selected from hydroxy and $C_{1-6}$ alkoxy, 4- to 6-membered heterocyclyl optionally substituted with a group selected from Group Q, $C_{3-6}$ cycloalkyl, or $C_{1-6}$ alkoxy; or alternatively, $R^{34}$ and $R^{35}$ form 4- to 6-membered heterocyclyl optionally substituted with a group selected from Group Q together with the nitrogen atom to which they are bonded; and $R^{36}$ and $R^{37}$ are each independently a hydrogen atom, $C_{1-6}$ alkyl, or 4- to 6-membered heterocyclyl optionally substituted with a group selected from Group Q; or alternatively, $R^{36}$ and $R^{37}$ form 4- to 6-membered heterocyclyl optionally substituted with a substituent selected from Group Q together with the nitrogen atom to which they are bonded;
<Group P> a halogen atom, cyano, hydroxy, —$NR^{50}R^{51}$, $C_{1-6}$ alkyl, $C_{1-6}$ alkoxy, $C_{1-6}$ alkoxycarbonyl, 5- to 10-membered heteroaryl, and $C_{1-6}$ haloalkyl;

where $R^{50}$ and $R^{51}$ are each independently a hydrogen atom or $C_{1-6}$ alkyl;
<Group Q> cyano, a halogen atom, $C_{1-6}$ alkyl which may have a substituent, $C_{1-6}$ alkoxy, $C_{3-6}$ cycloalkyl, 4- to 6-membered heterocyclyl which may have oxo as a substituent, $C_{1-6}$ alkylcarbonyl, $C_{1-6}$ alkylsulfonyl, $C_{3-6}$ cycloalkylsulfonyl, $C_{1-6}$ alkyloxycarbonyl, amino-$C_{1-6}$ alkylcarbonyl, oxo, thioxo, hydroxy, and —$NR^{52}R^{53}$;

where the substituent in the above-mentioned $C_{1-6}$ alkyl which may have a substituent is selected from a halogen atom, hydroxy, 5- to 10-membered heteroaryl, and $C_{6-10}$ aryl, where the $C_{6-10}$ aryl may have hydroxy as a substituent;

$R^{52}$ and $R^{53}$ each represents a hydrogen atom, $C_{1-6}$ alkyl, $C_{1-6}$ alkylsulfonyl which may have a halogen atom as a substituent, $C_{6-10}$ arylsulfonyl, $C_{6-10}$ aryl-$C_{1-6}$ alkylsulfonyl, or —$C(O)OR^{54}$, and $R^{54}$ represents $C_{1-6}$ alkyl which may have a group selected from phenyl, fluorene, and 5- to 10-membered heteroaryl as a substituent;
<Group R> a halogen atom, $C_{1-6}$ alkyl, $C_{1-6}$ alkoxy, $C_{1-6}$ haloalkyl, $C_{2-6}$ alkenyl, $C_{2-6}$ alkynyl, $C_{3-6}$ cycloalkyl, nitro, —$NR^{60}R^{61}$ {where $R^{60}$ and $R^{61}$ are identical or different, and are each a hydrogen atom, optionally substituted $C_{1-6}$ alkyl (in which the substituent is hydroxy, $C_{1-6}$ alkoxycarbonyl, carboxyl, or carboxamide), or amino-$C_{1-6}$ alkyl; or alternatively, $R^{60}$ and $R^{61}$ form a 4- to 6-membered heterocycle together with the nitrogen atom to which they are bonded}], or a pharmaceutically acceptable salt thereof;

[2] the compound or a pharmaceutically acceptable salt thereof according to [1], wherein Group R in $Ar^1$ is selected from the group consisting of a halogen atom, $C_{1-6}$ alkyl, and $C_{1-6}$ alkoxy;

[3] the compound or a pharmaceutically acceptable salt thereof according to [1] or [2], wherein Group R in $Ar^2$ is selected from the group consisting of a halogen atom, $C_{1-6}$ alkyl, and $C_{1-6}$ alkoxy;

[4] the compound or a pharmaceutically acceptable salt thereof according to any one of [1] to [3], wherein $Ar^1$ is phenylene or pyridylene optionally substituted with a group selected from Group R;

[5] the compound or a pharmaceutically acceptable salt thereof according to any one of [1] to [4], wherein $Ar^2$ is phenyl or pyridyl optionally substituted with a group selected from Group R;

[6] the compound or a pharmaceutically acceptable salt thereof according to any one of [1] to [5], wherein $R^1$ is a halogen atom, $C_{1-6}$ alkyl, $C_{3-6}$ cycloalkyl, $NR^5R^6$, $OR^7$, $SR^8$, or 4- to 6-membered heterocyclyl optionally substituted with $C_{1-6}$ alkyl;

$R^5$ and $R^6$ are each independently a hydrogen atom, $C_{1-6}$ alkyl optionally substituted with 4- to 6-membered heterocyclyl, or —$SO_2R^{30}$;

$R^7$ is a hydrogen atom, $C_{1-6}$ alkyl which may have a halogen atom or hydroxy as a substituent, 4- to 6-membered heterocyclyl optionally substituted with a group selected from Group Q, or $C_{1-6}$ alkyl having 4- to 10-membered heterocyclyl optionally substituted with a group selected from Group Q as a substituent;
<Group Q>

$C_{1-6}$ alkyl which may have hydroxy as a substituent, $C_{3-6}$ cycloalkyl, 4- to 6-membered heterocyclyl which may have oxo as a substituent, and $C_{1-6}$ alkylsulfonyl;

$R^8$ is halo-$C_{1-6}$ alkyl; and $R^{30}$ is $C_{1-6}$ alkyl;

[7] the compound or a pharmaceutically acceptable salt thereof according to any one of [1] to [6], wherein $R^2$ is a halogen atom, $C_{1-6}$ alkyl, $NR^5R^6$, $OR^7$, 4- to 6-membered heterocyclyl optionally substituted with a group selected from Group Q, 5- to 10-membered heteroaryl optionally substituted with a group selected from Group Q, or $C_{6-10}$ aryl optionally substituted with a group selected from Group P, where the 4- to 6-membered heterocyclyl optionally substituted with a group selected from Group Q may be further linked to 4- to 6-membered heterocyclyl optionally substituted with a group selected from 4- to 6-membered heterocyclyl and $C_{6-10}$ aryl-$C_{1-6}$ alkyl, or to $C_{3-6}$ cycloalkyl through a spiro linkage;

$R^5$ and $R^6$ are each independently a hydrogen atom, $C_{1-6}$ alkyl optionally substituted with 4- to 6-membered heterocyclyl, $C_{1-6}$ alkylcarbonyl optionally substituted with a halogen atom, —$SO_2R^{30}$, —$C(O)OR^{31}$, —$C(O)NR^{32}R^{33}$, or 4- to 6-membered heterocyclyl optionally substituted with a group selected from Group Q;

$R^7$ is a hydrogen atom, $C_{1-6}$ alkyl, or $C_{1-6}$ alkyl having 4- to 6-membered heterocyclyl as a substituent;

$R^{30}$ is optionally substituted $C_{1-6}$ alkyl, $C_{3-6}$ cycloalkyl which may have dihydroxy-$C_{1-6}$ alkyl as a substituent, $C_{6-10}$ aryl optionally substituted with a group selected from Group P, 5- to 10-membered heterocyclyl optionally substituted with a group selected from Group Q, 5- to 10-membered heteroaryl optionally substituted with a group selected from Group Q, or —$NR^{34}R^{35}$, where the substituent in the optionally substituted $C_{1-6}$ alkyl is selected from the group consisting of a halogen atom, 4- to 6-membered heterocyclyl optionally substituted with a group selected from Group Q, —$C(O)NR^{36}R^{37}$, and $C_{6-10}$ aryl;

$R^{31}$ represents $C_{1-6}$ alkyl which may have fluorene as a substituent;

$R^{32}$ and $R^{33}$ are each independently a hydrogen atom, or $C_{1-6}$ alkyl optionally substituted with a group selected from the group consisting of $C_{1-6}$ alkoxycarbonyl and 5- to 10-membered heteroaryl; or alternatively, $R^{32}$ and $R^{33}$ form 4- to 6-membered heterocyclyl together with the nitrogen atom to which they are bonded;

$R^{34}$ and $R^{35}$ are each independently a hydrogen atom, $C_{1-6}$ alkyl optionally substituted with a group selected from hydroxy and $C_{1-6}$ alkoxy, 4- to 6-membered heterocyclyl optionally substituted with a group selected from Group Q, $C_{3-6}$ cycloalkyl, or $C_{1-6}$ alkoxy; and $R^{36}$ and $R^{37}$ are each independently a hydrogen atom or $C_{1-6}$ alkyl; or alternatively, $R^{36}$ and $R^{37}$ form 4- to 6-membered heterocyclyl optionally substituted with a substituent selected from Group Q together with the nitrogen atom to which they are bonded;

<Group P>
a halogen atom, cyano, $C_{1-6}$ alkyl, $C_{1-6}$ alkoxy, and $C_{1-6}$ haloalkyl;

<Group Q>
cyano, a halogen atom, $C_{1-6}$ alkyl which may have a substituent, $C_{1-6}$ alkoxy, 4- to 6-membered heterocyclyl, $C_{1-6}$ alkylcarbonyl, $C_{1-6}$ alkylsulfonyl, $C_{3-6}$ cycloalkylsulfonyl, $C_{1-6}$ alkyloxycarbonyl, amino-$C_{1-6}$ alkylcarbonyl, oxo, thioxo, hydroxy, and —$NR^{52}R^{53}$.

where the substituent in the above-mentioned $C_{1-6}$ alkyl which may have a substituent is selected from a halogen atom, hydroxy, 5- to 10-membered heteroaryl, and $C_{6-10}$ aryl, where the $C_{6-10}$ aryl may have hydroxy as a substituent;

$R^{52}$ and $R^{53}$ each represents a hydrogen atom, $C_{1-6}$ alkyl, $C_{1-6}$ alkylsulfonyl which may have a halogen atom as a substituent, $C_{6-10}$ arylsulfonyl, $C_{6-10}$ aryl-$C_{1-6}$ alkylsulfonyl, or —$C(O)OR^{54}$, and $R^{54}$ represents $C_{1-6}$ alkyl which may have a group selected from phenyl, fluorene, and 5- to 10-membered heteroaryl as a substituent;

[8] tert-butyl 3-[2-[5-amino-1-[4-(2-fluorophenoxy)-3-methylphenyl]pyrazole-4-carbonyl]-5-methyl-1H-indol-6-yl]-2,4-dioxo-1,3,8-triazaspiro[4.5]decane-8-carboxylate or a pharmaceutically acceptable salt thereof;

[9] a pharmacological composition comprising the compound or a pharmaceutically acceptable salt thereof according to any one of [1] to [8], and a carrier;

[10] a Src family kinase inhibitor comprising the compound or a pharmaceutically acceptable salt thereof according to any one of [1] to [8] as an active ingredient;

[11] a therapeutic or prophylactic agent for cancer comprising the compound or a pharmaceutically acceptable salt thereof according to any one of [1] to [8] as an active ingredient;

[12] the prophylactic or therapeutic agent for cancer according to [11], wherein the cancer is selected from the group consisting of esophageal cancer, lung cancer, and bile duct cancer;

[13] a method for treating or preventing cancer, comprising administering a pharmaceutically effective amount of a composition comprising the compound or a pharmaceutically acceptable salt thereof according to any one of [1] to [8] to a patient in need of cancer treatment or prevention;

[14] use of the compound or a pharmaceutically acceptable salt thereof according to any one of [1] to [8] for the manufacture of a therapeutic or prophylactic agent for cancer; and

[15] the compound or a pharmaceutically acceptable salt thereof according to any one of [1] to [8] for use in the treatment or prevention of cancer.

Effects of the Invention

The compounds or pharmaceutically acceptable salts thereof of the present invention have a Src family kinase inhibitory effect in cancer tissues. In addition, the compounds of the present invention have a Src family kinase inhibitory effect more selective and potent than those of existing Src family kinase inhibitors and can prevent and/or treat cancer.

MODE FOR CARRYING OUT THE INVENTION

The present invention relates to aminopyrazole derivatives and uses thereof. The present inventors have synthesized the compounds represented by the formula (I) or pharmaceutically acceptable salts thereof or their isomers for the first time and have found that the compounds or pharmaceutically acceptable salts thereof or their isomers have a Src family kinase inhibitory effect.

(General Formula I)

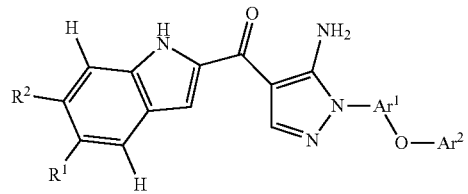

The "alkyl" herein refers to a monovalent group derived by removing any one hydrogen atom from an aliphatic hydrocarbon, and has a subset of hydrocarbyl or hydrocarbon group structures not containing a heteroatom or an unsaturated carbon-carbon bond but containing hydrogen and carbon atoms in its backbone. The alkyl includes linear and branched structures. Preferred examples of the alkyl include alkyl having 1 to 6 carbon atoms ($C_{1-6}$; hereinafter, "$C_{p-q}$" means that the number of carbon atoms is p to q), $C_{1-5}$ alkyl, $C_{1-4}$ alkyl, and $C_{1-3}$ alkyl.

Specific examples of the alkyl include methyl, ethyl, n-propyl, isopropyl, n-butyl, isobutyl, s-butyl, t-butyl, pentyl, isopentyl, 2,3-dimethylpropyl, 3,3-dimethylbutyl, and hexyl.

The "alkenyl" herein refers to a monovalent hydrocarbon group having at least one double bond (two adjacent SP2 carbon atoms) and includes linear and branched ones. Depending on the configuration of the double bond and the substituent (if present), the geometric form of the double bond can be an entgegen (E) or zuzammen (Z) configuration or a cis or trans configuration. Examples of the alkenyl preferably include $C_{2-6}$ alkenyl, more preferably $C_{2-5}$ alkenyl, and still more preferably $C_{2-4}$ alkenyl.

Specific examples of the alkenyl include vinyl, allyl, 1-propenyl, 2-propenyl, 1-butenyl, 2-butenyl (including cis and trans), 3-butenyl, pentenyl, and hexenyl.

The "alkynyl" herein refers to a monovalent hydrocarbon group having at least one triple bond (two adjacent SP carbon atoms) and includes linear and branched ones. Examples preferably include $C_{2-6}$ alkynyl, more preferably $C_{2-5}$ alkynyl, and still more preferably $C_{2-4}$ alkynyl.

Specific examples of the alkynyl include ethynyl, 1-propynyl, propargyl, 3-butynyl, pentynyl, and hexynyl.

The alkenyl or alkynyl can have one, two or more double bonds or triple bonds, respectively.

The "cycloalkyl" herein refers to a saturated or partially saturated cyclic monovalent aliphatic hydrocarbon group and includes single rings, bicyclo rings, and spiro rings. Preferred examples of the cycloalkyl include $C_{3-6}$ cycloalkyl. Specific examples of the cycloalkyl include cyclopropyl, cyclobutyl, cyclopentyl, and cyclohexyl.

The "halogen atom" herein refers to a fluorine atom, a chlorine atom, a bromine atom, or an iodine atom.

The "haloalkyl" herein refers to one in which any one or more hydrogen atom(s) of the above-mentioned alkyl is replaced by a halogen atom(s) and includes linear or branched structures. Examples include halo-$C_{1-6}$ alkyl.

The "hydroxyalkyl" herein refers to one in which any one or more hydrogen atom(s) of the above-mentioned alkyl is replaced by a hydroxyl group(s) and includes linear or branched structures. Examples include monohydroxy-$C_{1-6}$ alkyl and dihydroxy-$C_{1-6}$ alkyl.

The "aminoalkyl" herein refers to one in which any one or more hydrogen atom(s) of the above-mentioned alkyl is replaced by amino and includes linear or branched structures. Examples include $C_{1-6}$ aminoalkyl.

The "alkoxy" herein refers to an oxy group to which the above-defined "alkyl" is bonded and preferably includes $C_{1-6}$ alkoxy, $C_{1-4}$ alkoxy, and $C_{1-3}$ alkoxy. Specific examples of the alkoxy include methoxy, ethoxy, 1-propoxy, 2-propoxy, n-butoxy, i-butoxy, sec-butoxy, and tert-butoxy.

The "alkoxyalkyl" herein refers to one in which any one or more hydrogen atom(s) of the above-mentioned alkyl is replaced by alkoxy and includes linear or branched structures. Examples include $C_{1-6}$ alkoxy-$C_{1-6}$ alkyl.

The "haloalkoxy" herein refers to one in which any one or more hydrogen atom(s) of an alkyl of the above-defined "alkoxy" is replaced by a halogen atom(s), and includes linear or branched structures. Examples include halo-$C_{1-6}$ alkoxy.

The "acyl" herein refers to carbonyl to which the above-mentioned alkyl is bonded (i.e., alkyl-CO—) and includes linear or branched structures. Examples include $C_{1-6}$ acyl.

The "alkylcarbonyl" herein refers to carbonyl to which the above-mentioned alkyl is bonded (i.e., alkyl-CO—) and includes linear or branched structures. Examples include $C_{1-6}$ alkylcarbonyl.

The "aryl" herein refers to a monovalent aromatic hydrocarbon ring. The aryl may be monocyclic or a condensed-ring. The number of carbon atoms constituting the ring is preferably 6 to 10 ($C_{6-10}$ aryl).

Specific examples of the aryl include phenyl and naphthalene.

The "arylene" herein is a divalent group derived by removing any one hydrogen atom from the above-mentioned aryl. The arylene ring may be monocyclic or condensed-ring. The number of atoms constituting the ring is preferably 6 to 10 ($C_{6-10}$ arylene).

Specific examples of the arylene include phenylene and divalent naphthalene.

The "arylalkyl" herein refers to a group in which any hydrogen atom in the above-defined "alkyl" is replaced by the above-defined "aryl." Preferred examples of the arylalkyl include $C_{6-10}$ aryl-$C_{1-4}$ alkyl and $C_{6-10}$ aryl-$C_{1-3}$ alkyl. Specific examples include benzyl, phenethyl, and naphthylmethyl.

The "heterocyclyl" herein refers to a non-aromatic monovalent heterocycle containing preferably 1 to 5 heteroatoms in the ring-forming atoms. The heterocycle may have a double bond and/or a triple bond in the ring, carbon atom(s) in the ring may be oxidized to form carbonyl, and the heterocycle may be monocyclic or condensed-ring. The number of atoms constituting the ring is preferably 4 to 10 (4- to 10-membered heterocyclyl), and more preferably 4 to 6 (4- to 6-membered heterocyclyl).

Specific examples of the heterocyclyl include azetidinyl, oxetanyl, dihydrofuryl, tetrahydrofuryl, dihydropyranyl, tetrahydropyranyl, tetrahydropyridyl, tetrahydropyrimidyl, morpholinyl, thiomorpholinyl, pyrrolidinyl, piperidinyl, piperazinyl, pyrazolidinyl, imidazolinyl, imidazolidinyl, oxazolidinyl, isoxazolidinyl, thiazolidinyl, isothiazolidinyl, 1,2-thiazinane, thiadiazolidinyl, azetidinyl, oxazolidone, benzodioxanyl, benzoxazolyl, dioxolanyl, dioxanyl, tetrahydropyrrolo[1,2-c]imidazole, thietanyl, 3,6-diazabicyclo[3.1.1]heptanyl, 2,5-diazabicyclo[2.2.1]heptanyl, 3-oxa-8-azabicyclo[3.2.1]octanyl, and sultam.

The "heteroaryl" herein refers to an aromatic monovalent heterocycle containing preferably 1 to 5 heteroatoms in the ring-forming atoms. The heteroaryl may be partially saturated, and may be monocyclic or a condensed-ring (for example, bicyclic heteroaryl in which an aryl ring is condensed with a heteroaryl ring). The number of atoms constituting the ring is preferably 5 to 10 (5- to 10-membered heteroaryl).

Specific examples of the heteroaryl include furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyrimidyl, pyridazinyl, pyrazinyl, triazinyl, benzofuranyl, benzothienyl, benzothiadiazolyl, benzothiazolyl, benzoxazolyl, benzoxadiazolyl, benzimidazolyl, indolyl, isoindolyl, azaindolyl, indazolyl, quinolyl, isoquinolyl, cinnolinyl, quinazolinyl, quinoxalinyl, benzodioxolyl, indolizinyl, imidazopyridyl, and fluorenyl.

The "heteroarylene" herein refers to a divalent group derived by removing any one hydrogen atom from the heteroaryl. The heteroarylene may be partially saturated, and may be monocyclic or a condensed-ring (for example, bicyclic heteroarylene in which an aryl ring is condensed with a heteroaryl ring). The number of atoms constituting the ring is preferably 5 to 10 (5- to 10-membered heteroarylene).

Examples include pyridylene.

The "heteroatom" herein refers to a nitrogen atom (N), an oxygen atom (O), or a sulfur atom (S).

The "amino" herein refers to a group represented by $NH_2$.

The "carboxyl" herein refers to a group represented by COOH.

The "carboxylic amide" herein refers to a group represented by $CONH_2$.

The "monoalkylamino" herein refers to amino to which one "alkyl" defined above is bonded. Preferred examples of the monoalkylamino include mono-$C_{1-6}$ alkylamino.

The "dialkylamino" herein refers to amino to which two "alkyl" defined above are bonded, where the alkyls may be identical or different. Preferred examples of the dialkylamino include di-$C_{1-6}$ alkylamino.

The "alkylsulfonyl" herein refers to sulfonyl to which the "alkyl" defined above is bonded (i.e., alkyl-SO$_2$—). Preferred examples of the alkylsulfonyl include C$_{1-6}$ alkylsulfonyl and C$_{1-3}$ alkylsulfonyl, and methylsulfonyl, ethylsulfonyl, n-propylsulfonyl, i-propylsulfonyl and such are specifically included.

The "sulfamide" herein refers to a group in which an alkyl of the above-described alkylsulfonyl is replaced by amino and includes linear or branched structures.

The "cycloalkylsulfonyl" herein refers to sulfonyl to which the "cycloalkyl" defined above is bonded (i.e., cycloalkyl-SO$_2$—). Preferred examples of the cycloalkylsulfonyl include C$_{3-6}$ cycloalkylsulfonyl and C$_{3-5}$ cycloalkylsulfonyl, and cyclopropylsulfonyl, cyclobutylsulfonyl, cyclopentylsulfonyl, cyclohexylsulfonyl and such are specifically included.

The "heteroarylsulfonyl" herein refers to sulfonyl to which the "heteroaryl" defined above is bonded (i.e., heteroaryl-SO$_2$—).

The "arylsulfonyl" herein refers to sulfonyl to which the "aryl" defined above is bonded (i.e., aryl-SO$_2$—). Preferred examples of the arylsulfonyl include C$_{6-10}$ arylsulfonyl and C$_6$ arylsulfonyl, and phenylsulfonyl and such are specifically included.

The "arylalkylsulfonyl" herein refers to sulfonyl to which the "arylalkyl" defined above is bonded (i.e., arylalkyl-SO$_2$—). Preferred examples of the arylalkylsulfonyl include C$_{6-10}$ aryl-C$_{1-6}$ alkylsulfonyl.

The "heterocyclylcarbonyl" herein refers to carbonyl to which the heterocyclyl is bonded (i.e., heterocyclyl-CO—). Examples include 4- to 10-membered heterocyclylcarbonyl and 4- to 6-membered heterocyclylcarbonyl.

The "alkyloxycarbonyl" herein refers to carbonyl to which the "alkoxy" defined above is bonded (i.e., alkoxy-C(O)—). Examples of the carbonyl to which C$_{1-6}$ alkoxy is bonded include C$_{1-6}$ alkyloxycarbonyl.

The "aminoalkylcarbonyl" herein refers to carbonyl to which the "aminoalkyl" defined above is bonded (i.e., aminoalkyl-C(O)—). Examples of the carbonyl to which C$_{1-6}$ aminoalkyl is bonded include amino-C$_{1-6}$ alkylcarbonyl.

The "oxo" herein refers to a group represented by "=O", and the "thioxo" refers to a group represented by "=S".

The compounds according to the present invention, whether free forms or pharmaceutically acceptable salts, are included in the present invention. Examples of such "salts" include inorganic acid salts, organic acid salts, inorganic base salts, organic base salts, and acidic or basic amino acid salts.

Preferred examples of the inorganic acid salts include hydrochlorides, hydrobromides, hydroiodides, phosphates, and sulfates. Preferred examples of the organic acid salts include acetates, succinates, fumarates, malates, benzoates, and 4-toluenesulfonates.

Preferred examples of the inorganic base salts include alkali metal salts such as sodium salts and potassium salts, alkaline earth metal salts such as calcium salts and magnesium salts, aluminum salts, and ammonium salts. Preferred examples of the organic base salts include diethylamine salts, diethanolamine salts, meglumine salts, and N,N-dibenzylethylenediamine salts.

Preferred examples of the acidic amino acid salts include aspartates and glutamates. Preferred examples of the basic amino acid salts include arginine salts, lysine salts, and ornithine salts.

The compounds according to the present invention or pharmaceutically acceptable salts thereof include, depending on the type of substituent(s), possible stereoisomers, tautomers, or atropisomers (isomers that can be separated due to restricted rotation).

The compounds of the present invention or pharmaceutically acceptable salts thereof may form hydrates by absorbing moisture or adsorbing water when left in the atmosphere. Such hydrates are also included in the salts of the present invention.

The compounds according to the present invention or pharmaceutically acceptable salts thereof include crystalline polymorphs and solvates. Crystalline polymorphs refer to different crystalline forms. Solvates refer to hydrates of compounds formed when, for example, they are left in the atmosphere to absorb moisture, or crystals of compounds formed while they incorporate solvents or the like used in synthesizing them. Solvents incorporated into a crystal are one to multiple solvents per one compound molecule, or multiple compound molecules per one solvent molecule are incorporated. Solvates which simultaneously incorporate multiple types of solvents are also included.

The compounds according to the present invention or pharmaceutically acceptable salts thereof include their prodrugs. Prodrugs are derivatives of the compounds of the present invention which have chemically or metabolically decomposable groups and are converted back to the original compounds after administration in vivo to exhibit their original efficacy, and include complexes not formed with covalent bonds, and salts.

The compounds according to the present invention or pharmaceutically acceptable salts thereof include those in which one or more atoms in the molecule are preferentially replaced by isotopes whose abundance ratio in nature is small. In the present invention, isotopes refer to atoms identical in atomic number (proton number) but different in mass number (sum of the number of protons and the number of neutrons). Examples of the atoms contained in the compounds of the present invention to be replaced by isotopes include a hydrogen atom, a carbon atom, a nitrogen atom, an oxygen atom, a phosphorus atom, a sulfur atom, a fluorine atom, and a chlorine atom. Such isotopes include $^2$H, $^3$H, $^{13}$C, $^{14}$C, $^{15}$N, $^{17}$O, $^{18}$O, $^{31}$P, $^{32}$P, $^{35}$S, $^{18}$F, and $^{36}$Cl. In particular, radioisotopes that decay by emitting radiation, such as $^3$H and $^{14}$C, are useful in tissue distribution tests or the like for the compounds of the present invention. Stable isotopes not generating radiation do not change their abundance ratio because they do not decay, and such isotopes are also safe and easy to handle because they do not emit radiation. The substituents in which compounds of the present invention are substituted with isotope atoms can be synthesized according to conventional methods by replacing a reagent used for synthesis with a reagent containing a corresponding isotope atom.

The compounds represented by the formula (I) according to the present invention are preferably as follows.

(1) R$^1$ and R$^2$ are preferably as follows.

Specifically, R$^1$ and R$^2$ are preferably each independently a halogen atom, C$_{1-6}$ alkyl, C$_{3-6}$ cycloalkyl, NR$^5$R$^6$, OR$^7$, SR$^8$, 4- to 6-membered heterocyclyl optionally substituted with a group selected from Group Q, 5- to 10-membered heteroaryl optionally substituted with a group selected from Group Q, or C$_{6-10}$ aryl optionally substituted with a group selected from Group P, where the 4- to 6-membered heterocyclyl optionally substituted with a group selected from Group Q may further be linked to 4- to 6-membered heterocyclyl optionally substituted with a group selected from 4- to 6-membered heterocyclyl or $C_{6-10}$ aryl-$C_{1-6}$ alkyl, or to $C_{3-6}$ cycloalkyl through a spiro linkage.

Preferably, $R^5$ and $R^6$ are each independently a hydrogen atom, $C_{1-6}$ alkyl optionally substituted with 4- to 6-membered heterocyclyl, $C_{1-6}$ alkylcarbonyl optionally substituted with a halogen atom, $-SO_2R^{30}$, $-C(O)OR^{31}$, $-C(O)NR^{32}R^{33}$, or 4- to 6-membered heterocyclyl optionally substituted with a group selected from Group Q, or alternatively, $R^5$ and $R^6$ form 4- to 6-membered heterocyclyl optionally substituted with a group selected from Group Q together with the nitrogen atom to which they are bonded.

$R^7$ is preferably a hydrogen atom, $C_{1-6}$ alkyl which may have a halogen atom or hydroxy as a substituent, 4- to 6-membered heterocyclyl optionally substituted with a group selected from Group Q, or $C_{1-6}$ alkyl having 4- to 10-membered heterocyclyl optionally substituted with a group selected from Group Q as a substituent.

$R^8$ is preferably $C_{1-6}$ alkyl or halo-$C_{1-6}$ alkyl.

Preferably, $R^{30}$ is optionally substituted $C_{1-6}$ alkyl, $C_{3-6}$ cycloalkyl which may have dihydroxy-$C_{1-6}$ alkyl as a substituent, $C_{6-10}$ aryl optionally substituted with a group selected from Group P, 5- to 10-membered heterocyclyl optionally substituted with a group selected from Group Q, 5- to 10-membered heteroaryl optionally substituted with a group selected from Group Q, or $-NR^{34}R^{35}$, where the substituent in the optionally substituted $C_{1-6}$ alkyl is preferably selected from the group consisting of a halogen atom, 4- to 6-membered heterocyclyl optionally substituted with a group selected from Group Q, $-C(O)NR^{36}R^{37}$, and $C_{6-10}$ aryl.

$R^{31}$ preferably represents $C_{1-6}$ alkyl which may have fluorene as a substituent.

Preferably, $R^{32}$ and $R^{33}$ are each independently a hydrogen atom, or $C_{1-6}$ alkyl optionally substituted with a group selected from the group consisting of $C_{1-6}$ alkoxycarbonyl and 5- to 10-membered heteroaryl, or alternatively, $R^{32}$ and $R^{33}$ form 4- to 6-membered heterocyclyl together with the nitrogen atom to which they are bonded.

Preferably, $R^{34}$ and $R^{35}$ are each independently a hydrogen atom, $C_{1-6}$ alkyl optionally substituted with a group selected from hydroxy and $C_{1-6}$ alkoxy, 4- to 6-membered heterocyclyl optionally substituted with a group selected from Group Q, $C_{3-6}$ cycloalkyl, or $C_{1-6}$ alkoxy, or $R^{34}$ and $R^{35}$ together with the nitrogen atom to which they are bonded form 4- to 6-membered heterocyclyl optionally substituted with a group selected from Group Q.

Preferably, $R^{36}$ and $R^{37}$ are each independently a hydrogen atom, $C_{1-6}$ alkyl, or 4- to 6-membered heterocyclyl optionally substituted with a group selected from Group Q, or $R^{36}$ and $R^{37}$ together with the nitrogen atom to which they are bonded form 4- to 6-membered heterocyclyl optionally substituted with a substituent selected from Group Q.

<Group P> is preferably as follows:

a halogen atom, cyano, hydroxy, $-NR^{50}R^{51}$, $C_{1-6}$ alkyl, $C_{1-6}$ alkoxy, $C_{1-6}$ alkoxycarbonyl, 5- to 10-membered heteroaryl, and $C_{1-6}$ haloalkyl;

where $R^{50}$ and $R^{51}$ are each independently a hydrogen atom or $C_{1-6}$ alkyl.

<Group Q> is preferably as follows:

cyano, a halogen atom, $C_{1-6}$ alkyl which may have a substituent, $C_{1-6}$ alkoxy, $C_{3-6}$ cycloalkyl, 4- to 6-membered heterocyclyl which may have oxo as a substituent, $C_{1-6}$ alkylcarbonyl, $C_{1-6}$ alkylsulfonyl, $C_{3-6}$ cycloalkylsulfonyl, $C_{1-6}$ alkyloxycarbonyl, amino-$C_{1-6}$ alkylcarbonyl, oxo, thioxo, hydroxy, and $-NR^{52}R^{53}$;

where the substituent in the $C_{1-6}$ alkyl which may have a substituent is selected from a halogen atom, hydroxy, 5- to 10-membered heteroaryl, and $C_{6-10}$ aryl, where the $C_{6-10}$ aryl may have hydroxy as a substituent;

$R^{52}$ and $R^{53}$ each represent a hydrogen atom, $C_{1-6}$ alkyl, $C_{1-6}$ alkylsulfonyl which may have a halogen atom as a substituent, $C_{6-10}$ arylsulfonyl, $C_{6-10}$ alkylsulfonyl, or $-C(O)OR^{54}$, and $R^{54}$ represents $C_{1-6}$ alkyl which may have, as a substituent, a group selected from phenyl, fluorene, and 5- to 10-membered heteroaryl.

(2) More preferably, $R^1$ is as follows.

$R^1$ is preferably a halogen atom, $C_{1-6}$ alkyl, $C_{3-6}$ cycloalkyl, $NR^5R^6$, $OR^7$, $SR^8$, or 4- to 6-membered heterocyclyl optionally substituted with $C_{1-6}$ alkyl.

Preferably, $R^5$ and $R^6$ are each independently a hydrogen atom, $C_{1-6}$ alkyl optionally substituted with 4- to 6-membered heterocyclyl, or $-SO_2R^{30}$.

$R^7$ is preferably a hydrogen atom, $C_{1-6}$ alkyl which may have a halogen atom or hydroxy as a substituent, 4- to 6-membered heterocyclyl optionally substituted with a group selected from Group Q, or $C_{1-6}$ alkyl having, as a substituent, 4- to 10-membered heterocyclyl optionally substituted with a group selected from Group Q.

<Group Q> is preferably as follows:

$C_{1-6}$ alkyl which may have hydroxy as a substituent, $C_{3-6}$ cycloalkyl, 4- to 6-membered heterocyclyl which may have oxo as a substituent, and $C_{1-6}$ alkylsulfonyl.

$R^8$ is preferably halo-$C_{1-6}$ alkyl.

$R^{30}$ is preferably $C_{1-6}$ alkyl.

(3) More preferably, $R^2$ is as follows.

$R^2$ is preferably a halogen atom, $C_{1-6}$ alkyl, $NR^5R^6$, $OR^7$, 4- to 6-membered heterocyclyl optionally substituted with a group selected from Group Q, 5- to 10-membered heteroaryl optionally substituted with a group selected from Group Q, or $C_{6-10}$ aryl optionally substituted with a group selected from Group P, where the 4- to 6-membered heterocyclyl optionally substituted with a group selected from Group Q may further be linked to 4- to 6-membered heterocyclyl optionally substituted with a group selected from 4- to 6-membered heterocyclyl or $C_{6-10}$ aryl-$C_{1-6}$ alkyl, or to $C_{3-6}$ cycloalkyl through a spiro linkage.

Preferably, $R^5$ and $R^6$ are each independently a hydrogen atom, $C_{1-6}$ alkyl optionally substituted with 4- to 6-membered heterocyclyl, $C_{1-6}$ alkylcarbonyl optionally substituted with a halogen atom, $-SO_2R^{30}$, $-C(O)OR^{31}$, $-C(O)NR^{32}R^{33}$, or 4- to 6-membered heterocyclyl optionally substituted with a group selected from Group Q.

$R^7$ is preferably a hydrogen atom, $C_{1-6}$ alkyl, or $C_{1-6}$ alkyl having 4- to 6-membered heterocyclyl as a substituent.

Preferably, $R^{30}$ is optionally substituted $C_{1-6}$ alkyl, $C_{3-6}$ cycloalkyl which may have dihydroxy-$C_{1-6}$ alkyl as a substituent, $C_{6-10}$ aryl optionally substituted with a group selected from Group P, 5- to 10-membered heterocyclyl optionally substituted with a group selected from Group Q, 5- to 10-membered heteroaryl optionally substituted with a group selected from Group Q, or $-NR^{34}R^{35}$, where the substituent in the optionally substituted $C_{1-6}$ alkyl is selected from the group consisting of a halogen atom, 4- to 6-membered heterocyclyl optionally substituted with a group selected from Group Q, $-C(O)NR^{36}R^{37}$, and $C_{6-10}$ aryl.

$R^{31}$ preferably represents $C_{1-6}$ alkyl which may have fluorene as a substituent.

Preferably, $R^{32}$ and $R^{33}$ are each independently a hydrogen atom, or $C_{1-6}$ alkyl optionally substituted with a group selected from the group consisting of $C_{1-6}$ alkoxycarbonyl and 5- to 10-membered heteroaryl, or $R^{32}$ and $R^{33}$ together with the nitrogen atom to which they are bonded form 4- to 6-membered heterocyclyl.

Preferably, $R^{34}$ and $R^{35}$ are each independently a hydrogen atom, $C_{1-6}$ alkyl optionally substituted with a group selected from hydroxy and $C_{1-6}$ alkoxy, 4- to 6-membered heterocyclyl optionally substituted with a group selected from Group Q, $C_{3-6}$ cycloalkyl, or $C_{1-6}$ alkoxy.

Preferably, $R^{36}$ and $R^{37}$ are each independently a hydrogen atom or $C_{1-6}$ alkyl, or $R^{36}$ and $R^{37}$ together with the nitrogen atom to which they are bonded form 4- to 6-membered heterocyclyl optionally substituted with a substituent selected from Group Q.

<Group P>
a halogen atom, cyano, $C_{1-6}$ alkyl, $C_{1-6}$ alkoxy, and $C_{1-6}$ haloalkyl;

<Group Q>
cyano, a halogen atom, $C_{1-6}$ alkyl which may have a substituent, $C_{1-6}$ alkoxy, 4- to 6-membered heterocyclyl, $C_{1-6}$ alkylcarbonyl, $C_{1-6}$ alkylsulfonyl, $C_{3-6}$ cycloalkylsulfonyl, $C_{1-6}$ alkyloxycarbonyl, amino-$C_{1-6}$ alkylcarbonyl, oxo, thioxo, hydroxy, and —$NR^{52}R^{53}$;

where the substituent in the $C_{1-6}$ alkyl which may have a substituent is selected from a halogen atom, hydroxy, 5- to 10-membered heteroaryl, and $C_{6-10}$ aryl, where the $C_{6-10}$ aryl may have hydroxy as a substituent;

$R^{52}$ and $R^{53}$ each represent a hydrogen atom, $C_{1-6}$ alkyl, $C_{1-6}$ alkylsulfonyl which may have a halogen atom as a substituent, $C_{6-10}$ arylsulfonyl, $C_{6-10}$ aryl-$C_{1-6}$ alkylsulfonyl, or —$C(O)OR^{54}$, and $R^{54}$ represents $C_{1-6}$ alkyl which may have, as a substituent, a group selected from phenyl, fluorene, and 5- to 10-membered heteroaryl.

(4) Still more preferably, $R^2$ is as follows.

$R^2$ is preferably a halogen atom, $C_{1-6}$ alkyl, $NR^5R^6$, $OR^7$, 4- to 6-membered heterocyclyl optionally substituted with a group selected from Group Q1, 5- to 10-membered heteroaryl optionally substituted with $C_{1-6}$ alkyl, or $C_{6-10}$ aryl optionally substituted with a group selected from Group P1, where the 4- to 6-membered heterocyclyl optionally substituted with a group selected from Group Q1 may further be linked to 4- to 6-membered heterocyclyl optionally substituted with a group selected from 4- to 6-membered heterocyclyl or $C_{6-10}$ aryl-$C_{1-6}$ alkyl, or to $C_{3-6}$ cycloalkyl through a spiro linkage.

<Group P1>
a halogen atom and $C_{1-6}$ haloalkyl;

<Group Q1>
$C_{1-6}$ alkyl which may have a substituent, 4- to 6-membered heterocyclyl, $C_{1-6}$ alkylcarbonyl, $C_{1-6}$ alkylsulfonyl, $C_{3-6}$ cycloalkylsulfonyl, $C_{1-6}$ alkyloxycarbonyl, amino-$C_{1-6}$ alkylcarbonyl, oxo, thioxo, hydroxy, and —$NR^{52}R^{53}$;

where the substituent in the $C_{1-6}$ alkyl which may have a substituent is selected from a halogen atom, hydroxy, 5- to 10-membered heteroaryl, and $C_{6-10}$ aryl, where the $C_{6-10}$ aryl may have hydroxy as a substituent;

$R^{52}$ and $R^{53}$ each represent a hydrogen atom, $C_{1-6}$ alkyl, $C_{1-6}$ alkylsulfonyl which may have a halogen atom as a substituent, $C_{6-10}$ arylsulfonyl, $C_{6-10}$ aryl-$C_{1-6}$ alkylsulfonyl, or —$C(O)OR^{54}$, and $R^{54}$ represents $C_{1-6}$ alkyl which may have a group selected from phenyl, fluorene, and 5- to 10-membered heteroaryl as a substituent.

Preferably, $R^5$ and $R^6$ are each independently a hydrogen atom, $C_{1-6}$ alkyl optionally substituted with 4- to 6-membered heterocyclyl, $C_{1-6}$ alkylcarbonyl optionally substituted with a halogen atom, —$SO_2R^{30}$, —$C(O)OR^{31}$, —$C(O)NR^{32}R^{33}$, or 4- to 6-membered heterocyclyl optionally substituted with a group selected from Group Q2.

<Group Q2>
$C_{1-6}$ alkyl, 4- to 6-membered heterocyclyl, and $C_{1-6}$ alkylsulfonyl.

$R^7$ is preferably a hydrogen atom, $C_{1-6}$ alkyl, or $C_{1-6}$ alkyl having 4- to 6-membered heterocyclyl as a substituent.

Preferably, $R^{30}$ is optionally substituted $C_{1-6}$ alkyl, $C_{3-6}$ cycloalkyl which may have dihydroxy-$C_{1-6}$ alkyl as a substituent, $C_{6-10}$ aryl optionally substituted with a group selected from Group P3, 5- to 10-membered heterocyclyl optionally substituted with a group selected from Group Q3, 5- to 10-membered heteroaryl optionally substituted with a group selected from Group Q3, or —$NR^{34}R^{35}$, where the substituent in the optionally substituted $C_{1-6}$ alkyl is selected from the group consisting of a halogen atom, 4- to 6-membered heterocyclyl, —$C(O)NR^{36}R^{37}$, and $C_{6-10}$ aryl.

<Group P3>
a halogen atom, cyano, $C_{1-6}$ alkyl, $C_{1-6}$ alkoxy, and $C_{1-6}$ haloalkyl;

<Group Q3>
cyano, a halogen atom, $C_{1-6}$ alkyl which may have a substituent, $C_{1-6}$ alkoxy, and —$NR^{52}R^{53}$;

where the substituent in the $C_{1-6}$ alkyl which may have a substituent is a halogen atom; and $R^{52}$ and $R^{53}$ are each a hydrogen atom or $C_{1-6}$ alkyl.

$R^{31}$ is preferably $C_{1-6}$ alkyl which may have fluorene as a substituent.

Preferably, $R^{32}$ and $R^{33}$ are each independently a hydrogen atom, or $C_{1-6}$ alkyl optionally substituted with a group selected from the group consisting of $C_{1-6}$ alkoxycarbonyl and 5- to 10-membered heteroaryl, or alternatively, $R^{32}$ and $R^{33}$ form 4- to 6-membered heterocyclyl together with the nitrogen atom to which they are bonded.

Preferably, $R^{34}$ and $R^{35}$ are each independently a hydrogen atom, $C_{1-6}$ alkyl optionally substituted with a group selected from hydroxy and $C_{1-6}$ alkoxy, 4- to 6-membered heterocyclyl optionally substituted with a group selected from Group Q4, $C_{3-6}$ cycloalkyl, or $C_{1-6}$ alkoxy.

<Group Q4>
$C_{1-6}$ alkyl.

Preferably, $R^{36}$ and $R^{37}$ are each independently a hydrogen atom or $C_{1-6}$ alkyl, or alternatively, $R^{36}$ and $R^{37}$ form 4- to 6-membered heterocyclyl optionally substituted with a substituent selected from Group Q5 together with the nitrogen atom to which they are bonded.

<Group Q5>
$C_{1-6}$ alkyl.

(5) In the formula —$Ar^1$—O—$Ar^2$ mentioned above, $Ar^1$ is $C_{6-10}$ arylene or 5- to 10-membered heteroarylene, and $Ar^2$ represents $C_{6-10}$ aryl or 5- to 10-membered heteroaryl, where the $Ar^1$ and $Ar^2$ may each independently have one or more substituents selected from Group R.

$Ar^1$ preferably includes 6-membered heteroaryl or 6-membered aryl, and more preferably pyridylene or phenylene.

In the formula (I), when $Ar^1$ is 6-membered heteroaryl or 6-membered aryl, the aminopyrazole ring and $Ar^2$—O— (i.e., the group excluding the substituent selected from Group R) which are bonded to $Ar^1$ to form the backbone may be bonded to $Ar^1$ at the ortho, meta, or para position. In particular, the aminopyrazole ring and $Ar^2$—O— are preferably bonded to $Ar^1$ at the para position.

Ar² preferably includes 6-membered heteroaryl or 6-membered aryl. 6-membered heteroaryl preferably includes pyridyl. 6-membered aryl preferably includes phenyl.

Group R preferably includes a halogen atom, $C_{1-6}$ alkyl, and $C_{1-6}$ alkoxy, and more preferably a halogen atom and $C_{1-6}$ alkyl.

Such specific compounds of the present invention include, for example, the following compounds; however, the scope of the present invention is not to be construed as being limited to these compounds. The numbers within parentheses represent Example Nos.

(4-1-001) N-[2-[5-amino-1-[6-(2,6-difluorophenoxy)-4-methylpyridin-3-yl]pyrazole-4-carbonyl]-5-methyl-1H-indol-6-yl]methanesulfonamide, (4-1-002) N-[2-[5-amino-1-[4-(2-fluorophenoxy)-2-methylphenyl]pyrazole-4-carbonyl]-5-fluoro-1H-indol-6-yl]methanesulfonamide, (4-1-003) N-[2-[5-amino-1-(2-chloro-4-pyridin-2-yloxyphenyl)pyrazole-4-carbonyl]-5-fluoro-1H-indol-6-yl]methanesulfonamide, (4-1-004) N-[2-[5-amino-1-[4-(2-fluorophenoxy)-2-methylphenyl]pyrazole-4-carbonyl]-5-methoxy-1H-indol-6-yl]methanesulfonamide, (4-1-005) N-[2-[5-amino-1-[4-(2,3-difluorophenoxy)-2-methylphenyl]pyrazole-4-carbonyl]-5-methoxy-1H-indol-6-yl]methanesulfonamide, (4-1-006) N-[2-[5-amino-1-[2-fluoro-4-(2-fluorophenoxy)-6-methylphenyl]pyrazole-4-carbonyl]-5-methoxy-1H-indol-6-yl]methanesulfonamide, (4-1-007) N-[2-[5-amino-1-(2-fluoro-6-methyl-4-phenoxyphenyl)pyrazole-4-carbonyl]-5-methoxy-1H-indol-6-yl]methanesulfonamide, (4-1-008) N-[2-[5-amino-1-[6-(2-fluorophenoxy)-4-methylpyridin-3-yl]pyrazole-4-carbonyl]-5-methoxy-1H-indol-6-yl]methanesulfonamide, (4-1-009) N-[2-[5-amino-1-[6-(2,6-difluorophenoxy)-4-methylpyridin-3-yl]pyrazole-4-carbonyl]-5-methoxy-1H-indol-6-yl]methanesulfonamide, (4-1-010) N-[2-[5-amino-1-[6-(2-chlorophenoxy)-4-methylpyridin-3-yl]pyrazole-4-carbonyl]-5-methoxy-1H-indol-6-yl]methanesulfonamide, (4-1-011) N-[2-[5-amino-1-[6-(3-chlorophenoxy)-4-methylpyridin-3-yl]pyrazole-4-carbonyl]-5-methoxy-1H-indol-6-yl]methanesulfonamide, (4-1-012) tert-butyl 4-[2-[5-amino-1-[6-(2,6-difluorophenoxy)-4-methylpyridin-3-yl]pyrazole-4-carbonyl]-5-(difluoromethoxy)-1H-indol-6-yl]piperidine-1-carboxylate, (4-1-013) N-[2-[5-amino-1-[4-(2-fluorophenoxy)-2-methylphenyl]pyrazole-4-carbonyl]-6-methoxy-1H-indol-5-yl]methanesulfonamide, (4-1-014) N-[2-[5-amino-1-[6-(2-fluorophenoxy)-4-methylpyridin-3-yl]pyrazole-4-carbonyl]-6-methoxy-1H-indol-5-yl]methanesulfonamide, (4-1-015) [5-amino-1-[4-(2-fluorophenoxy)-2-methylphenyl]pyrazol-4-yl]-[5-(2,2-difluoroethoxy)-6-morpholin-4-yl-1H-indol-2-yl]methanone, (4-1-016) [5-amino-1-[6-(2,6-difluorophenoxy)-4-methylpyridin-3-yl]pyrazol-4-yl]-[5-(2,2-difluoroethoxy)-6-morpholin-4-yl-1H-indol-2-yl]methanone, (4-1-017) N-[2-[5-amino-1-[6-(2,6-difluorophenoxy)-4-methylpyridin-3-yl]pyrazole-4-carbonyl]-5-methyl-1H-indol-6-yl]cyclopropanesulfonamide, (4-2-001) [5-amino-1-[4-(2-fluorophenoxy)-2-methylphenyl]pyrazol-4-yl]-[6-fluoro-5-(1-propan-2-ylpiperidin-4-yl)-1H-indol-2-yl]methanone, (4-2-002) [5-amino-1-[4-(2,3-difluorophenoxy)-2-methylphenyl]pyrazol-4-yl]-[6-fluoro-5-(1-propan-2-ylpiperidin-4-yl)-1H-indol-2-yl]methanone, (4-2-003) [5-amino-1-[4-(3-chlorophenoxy)-2-methylphenyl]pyrazol-4-yl]-[6-fluoro-5-(1-propan-2-ylpiperidin-4-yl)-1H-indol-2-yl]methanone, (4-2-004) [5-amino-1-[4-(2,3-difluorophenoxy)phenyl]pyrazol-4-yl]-[6-fluoro-5-(1-propan-2-ylpiperidin-4-yl)-1H-indol-2-yl]methanone, (4-2-005) [5-amino-1-[4-(3-chlorophenoxy)phenyl]pyrazol-4-yl]-[6-fluoro-5-(1-propan-2-ylpiperidin-4-yl)-1H-indol-2-yl]methanone, (4-2-006) [5-amino-1-[4-(3-fluorophenoxy)phenyl]pyrazol-4-yl]-[6-fluoro-5-(1-propan-2-ylpiperidin-4-yl)-1H-indol-2-yl]methanone, (4-2-007) [5-amino-1-[4-(2,3-difluorophenoxy)-2-fluorophenyl]pyrazol-4-yl]-[6-fluoro-5-(1-propan-2-ylpiperidin-4-yl)-1H-indol-2-yl]methanone, (4-2-008) [5-amino-1-[4-(2-chlorophenoxy)-2-fluorophenyl]pyrazol-4-yl]-[6-fluoro-5-(1-propan-2-ylpiperidin-4-yl)-1H-indol-2-yl]methanone, (4-2-009) [5-amino-1-[2-fluoro-4-(2-fluorophenoxy)phenyl]pyrazol-4-yl]-[6-fluoro-5-(1-propan-2-ylpiperidin-4-yl)-1H-indol-2-yl]methanone, (4-2-010) [5-amino-1-[4-(2-fluorophenoxy)-2-methylphenyl]pyrazol-4-yl]-[5-fluoro-6-(1-propan-2-ylpiperidin-4-yl)-1H-indol-2-yl]methanone, (4-2-011) [5-amino-1-[4-(2,3-difluorophenoxy)-2-methylphenyl]pyrazol-4-yl][5-fluoro-6-(1-propan-2-ylpiperidin-4-yl)-1H-indol-2-yl]methanone, (4-2-012) [5-amino-1-[4-(2-chlorophenoxy)-2-methylphenyl]pyrazol-4-yl]-[5-fluoro-6-(1-propan-2-ylpiperidin-4-yl)-1H-indol-2-yl]methanone, (4-2-013) [5-amino-1-[4-(3-chlorophenoxy)-2-methylphenyl]pyrazol-4-yl]-[5-fluoro-6-(1-propan-2-ylpiperidin-4-yl)-1H-indol-2-yl]methanone, (4-2-014) [5-amino-1-[4-(2-fluorophenoxy)-3-methylphenyl]pyrazol-4-yl]-[5-fluoro-6-(1-propan-2-ylpiperidin-4-yl)-1H-indol-2-yl]methanone, (4-2-015) N-[2-[5-amino-1-[4-(2-fluorophenoxy)-2-methylphenyl]pyrazole-4-carbonyl]-5-fluoro-1H-indol-6-yl]-3-fluoropropane-1-sulfonamide, (4-2-016) N-[2-[5-amino-1-[4-(2,3-difluorophenoxy)-2-methylphenyl]pyrazole-4-carbonyl]-5-fluoro-1H-indol-6-yl]-3-fluoropropane-1-sulfonamide, (4-2-017) N-[2-[5-amino-1-(2-methyl-4-pyridin-2-yloxyphenyl)pyrazole-4-carbonyl]-5-fluoro-1H-indol-6-yl]-3-fluoropropane-1-sulfonamide, (4-2-018) N-[2-[5-amino-1-(2-chloro-4-pyridin-2-yloxyphenyl)pyrazole-4-carbonyl]-5-fluoro-1H-indol-6-yl]-3-fluoropropane-1-sulfonamide, (4-2-019) N-[2-[5-amino-1-[2-fluoro-4-(2-fluorophenoxy)-6-methylphenyl]pyrazole-4-carbonyl]-5-fluoro-1H-indol-6-yl]-3-fluoropropane-1-sulfonamide, (4-2-020) N-[2-[5-amino-1-[6-(2-fluorophenoxy)-4-methylpyridin-3-yl]pyrazole-4-carbonyl]-5-fluoro-1H-indol-6-yl]-3-fluoropropane-1-sulfonamide, (4-2-021) N-[2-[5-amino-1-[6-(2,6-difluorophenoxy)-4-methylpyridin-3-yl]pyrazole-4-carbonyl]-5-fluoro-1H-indol-6-yl]-3-fluoropropane-1-sulfonamide, (4-2-022) N-[2-[5-amino-1-[6-(2,3-difluorophenoxy)-4-methylpyridin-3-yl]pyrazole-4-carbonyl]-5-fluoro-1H-indol-6-yl]-3-fluoropropane-1-sulfonamide, (4-2-023) N-[2-[5-amino-1-[6-(2-chlorophenoxy)-4-methylpyridin-3-yl]pyrazole-4-carbonyl]-5-fluoro-1H-indol-6-yl]-3-fluoropropane-1-sulfonamide, (4-2-024) N-[2-[5-amino-1-[6-(2-chloro-6-fluorophenoxy)-4-methylpyridin-3-yl]pyrazole-4-carbonyl]-5-fluoro-1H-indol-6-yl]-3-fluoropropane-1-sulfonamide, (4-2-025) N-[2-[5-amino-1-[4-methyl-6-(2-methylphenoxy)pyridin-3-yl]pyrazole-4-carbonyl]-5-fluoro-1H-indol-6-yl]-3-fluoropropane-1-sulfonamide, (4-2-026) N-[2-[5-amino-1-[6-(3-chlorophenoxy)-4-methylpyridin-3-yl]pyrazole-4-carbonyl]-5-fluoro-1H-indol-6-yl]-3-fluoropropane-1-sulfonamide, (4-2-027) N-[2-[5-amino-1-[6-(4-fluorophenoxy)-4-methylpyridin-3-yl]pyrazole-4-carbonyl]-5-fluoro-1H-indol-6-yl]-3-fluoropropane-1-sulfonamide, (4-2-028) N-[2-[5-amino-1-[6-(3,5-difluorophenoxy)-4-methylpyridin-3-yl]pyrazole-4-carbonyl]-5-fluoro-1H-indol-6-yl]-3-fluoropropane-1-sulfonamide, (4-2-029) N-[2-[5-amino-1-[4-(2,3-difluorophenoxy)-2-methylphenyl]pyrazole-4-carbonyl]-5-fluoro-1H-indol-6-yl]methanesulfonamide, (4-2-030) N-[2-[5-amino-1-[6-(2,5-difluorophenoxy)-4-methylpyridin-3-yl]pyrazole-4-carbonyl]-5-fluoro-1H-indol-6-yl]methanesulfonamide, (4-2-031) N-[2-[5-amino-1-[6-(2,6-difluorophenoxy)-4-methylpyridin-3-yl]pyrazole-4-carbonyl]-5-fluoro-1H-indol-6-yl]methanesulfonamide, (4-2-032) N-[2-[5-amino-1-[6-(2,3-difluorophenoxy)-4-methylpyridin-3-yl]pyrazole-4-carbonyl]-5-fluoro-1H-indol-6-yl]methanesulfonamide, (4-2-033) N-[2-[5-amino-1-[6-(2-chlorophenoxy)-4-methylpyridin-3-yl]pyrazole-4-carbonyl]-5-fluoro-1H-indol-6-yl]methanesulfonamide, (4-2-034) N-[2-[5-amino-1-[6-(2-chloro-5-fluorophenoxy)-4-methylpyridin-3-yl]pyrazole-4-carbonyl]-5-fluoro-1H-indol-6-yl]methanesulfonamide, (4-2-035) N-[2-[5-amino-1-[6-(2-chloro-6-fluorophenoxy)-4-methylpyridin-3-yl]pyrazole-4-carbonyl]-5-fluoro-1H-indol-6-yl]methanesulfonamide, (4-2-036) N-[2-[5-amino-1-[4-methyl-6-(2-methylphenoxy)pyridin-3-yl]pyrazole-4-carbonyl]-5-fluoro-1H-indol-6-yl]methanesulfonamide, (4-2-037) N-[2-[5-amino-1-[6-(3-chlorophenoxy)-4-methylpyridin-3-yl]pyrazole-4-carbonyl]-5-fluoro-1H-indol-6-yl]methanesulfonamide, (4-2-038) N-[2-[5-amino-1-[6-(3-fluorophenoxy)-4-methylpyridin-3-yl]pyrazole-4-carbonyl]-5-fluoro-1H-indol-6-yl]methanesulfonamide, (4-2-039) N-[2-[5-amino-1-[6-(4-fluorophenoxy)-4-methylpyridin-3-yl]pyrazole-4-carbonyl]-5-fluoro-1H-indol-6-yl]methanesulfonamide, (4-2-040) N-[2-[5-amino-1-[4-(2-fluorophenoxy)-2-methylphenyl]pyrazole-4-carbonyl]-5-fluoro-1H-indol-6-yl]cyclopropanesulfonamide, (4-2-041) N-[2-[5-amino-1-[4-(2,3-difluorophenoxy)-2-methylphenyl]pyrazole-4-carbonyl]-5-fluoro-1H-indol-6-yl]cyclopropanesulfonamide, (4-2-042) N-[2-[5-amino-1-[4-(2-fluorophenoxy)-2,6-dimethylphenyl]pyrazole-4-carbonyl]-5-fluoro-1H-indol-6-yl]cyclopropanesulfonamide, (4-2-043) N-[2-[5-amino-1-[6-(2-fluorophenoxy)-4-methylpyridin-3-yl]pyrazole-4-carbonyl]-5-fluoro-1H-indol-6-yl]cyclopropanesulfonamide, (4-2-044) N-[2-[5-amino-1-[6-(2,6-difluorophenoxy)-4-methylpyridin-3-yl]pyrazole-4-carbonyl]-5-fluoro-1H-indol-6-yl]cyclopropanesulfonamide, (4-2-045) N-[2-[5-amino-1-[6-(2,3-difluorophenoxy)-4-methylpyridin-3-yl]pyrazole-4-carbonyl]-5-fluoro-1H-indol-6-yl]cyclopropanesulfonamide, (4-2-046) N-[2-[5-amino-1-[6-(2-chloro-6-fluorophenoxy)-4-methylpyridin-3-yl]pyrazole-4-carbonyl]-5-fluoro-1H-indol-6-yl]cyclopropanesulfonamide, (4-2-047) N-[2-[5-amino-1-[4-methyl-6-(2-methylphenoxy)pyridin-3-yl]pyrazole-4-carbonyl]-5-fluoro-1H-indol-6-yl]cyclopropanesulfonamide, (4-2-048) N-[2-[5-amino-1-[6-(3-fluorophenoxy)-4-methylpyridin-3-yl]pyrazole-4-carbonyl]-5-fluoro-1H-indol-6-yl]cyclopropanesulfonamide, (4-2-049) N-[2-[5-amino-1-[4-(2-fluorophenoxy)-2-methylphenyl]pyrazole-4-carbonyl]-6-methyl-1H-indol-5-yl]methanesulfonamide, (4-2-050) N-[2-[5-amino-1-[4-(2,3-difluorophenoxy)-2-methylphenyl]pyrazole-4-carbonyl]-6-methyl-1H-indol-5-yl]methanesulfonamide, (4-2-051) N-[2-[5-amino-1-[2-fluoro-4-(2-fluorophenoxy)-6-methylphenyl]pyrazole-4-carbonyl]-6-methyl-1H-indol-5-yl]methanesulfonamide, (4-2-052) N-[2-[5-amino-1-[6-(2-fluorophenoxy)-4-methylpyridin-3-yl]pyrazole-4-carbonyl]-6-methyl-1H-indol-5-yl]methanesulfonamide, (4-2-053) N-[2-[5-amino-1-[4-(2-fluorophenoxy)-2-methylphenyl]pyrazole-4-carbonyl]-5-methyl-1H-indol-6-yl]methanesulfonamide, (4-2-054) N-[2-[5-amino-1-[4-(2,3-difluorophenoxy)-2-methylphenyl]pyrazole-4-carbonyl]-5-methyl-1H-indol-6-yl]methanesulfonamide, (4-2-055) N-[2-[5-amino-1-[2-fluoro-4-(2-fluorophenoxy)-6-methylphenyl]pyrazole-4-carbonyl]-5-methyl-1H-indol-6-yl]methanesulfonamide, (4-2-056) N-[2-[5-amino-1-[4-(2,3-difluorophenoxy)-2-fluoro-6-methylphenyl]pyrazole-4-carbonyl]-5-methyl-1H-indol-6-yl]methanesulfonamide, (4-2-057) N-[2-[5-amino-1-[4-(2,5-difluorophenoxy)-2-fluoro-6-methylphenyl]pyrazole-4-carbonyl]-5-methyl-1H-indol-6-yl]methanesulfonamide, (4-2-058) N-[2-[5-amino-1-[4-(2-chlorophenoxy)-2-fluoro-6-methylphenyl]pyrazole-4-carbonyl]-5-methyl-1H-indol-6-yl]methanesulfonamide, (4-2-059) N-[2-[5-amino-1-[4-(3-chlorophenoxy)-2-fluoro-6-methylphenyl]pyrazole-4-carbonyl]-5-methyl-1H-indol-6-yl]methanesulfonamide, (4-2-060) N-[2-[5-amino-1-(2-fluoro-6-methyl-4-phenoxyphenyl)pyrazole-4-carbonyl]-5-methyl-1H-indol-6-yl]methanesulfonamide, (4-2-061) N-[2-[5-amino-1-[6-(2-fluorophenoxy)-4-methylpyridin-3-yl]pyrazole-4-carbonyl]-5-methyl-1H-indol-6-yl]methanesulfonamide, (4-2-062) N-[2-[5-amino-1-[6-(2,3-difluorophenoxy)-4-methylpyridin-3-yl]pyrazole-4-carbonyl]-5-methyl-1H-indol-6-yl]methanesulfonamide, (4-2-063) N-[2-[5-amino-1-[6-(2-chlorophenoxy)-4-methylpyridin-3-yl]pyrazole-4-carbonyl]-5-methyl-1H-indol-6-yl]methanesulfonamide, (4-2-064) N-[2-[5-amino-1-[6-(2-chloro-6-fluorophenoxy)-4-methylpyridin-3-yl]pyrazole-4-carbonyl]-5-methyl-1H-indol-6-yl]methanesulfonamide, (4-2-065) N-[2-[5-amino-1-[4-methyl-6-(2-methylphenoxy)pyridin-3-yl]pyrazole-4-carbonyl]-5-methyl-1H-indol-6-yl]methanesulfonamide, (4-2-066) N-[2-[5-amino-1-[6-(3-chlorophenoxy)-4-methylpyridin-3-yl]pyrazole-4-carbonyl]-5-methyl-1H-indol-6-yl]methanesulfonamide, (4-2-067) N-[2-[5-amino-1-[6-(4-fluorophenoxy)-4-methylpyridin-3-yl]pyrazole-4-carbonyl]-5-methyl-1H-indol-6-yl]methanesulfonamide, (4-2-068) N-[2-[5-amino-1-[4-(2-fluorophenoxy)-2-methylphenyl]pyrazole-4-carbonyl]-5-methyl-1H-indol-6-yl]-3-fluoropropane-1-sulfonamide,
(4-2-069) N-[2-[5-amino-1-[4-(2,3-difluorophenoxy)-2-methylphenyl]pyrazole-4-carbonyl]-5-methyl-1H-indol-6-yl]-3-fluoropropane-1-sulfonamide,
(4-2-070) N-[2-[5-amino-1-[2-fluoro-4-(2-fluorophenoxy)-6-methylphenyl]pyrazole-4-carbonyl]-5-methyl-1H-indol-6-yl]-3-fluoropropane-1-sulfonamide,
(4-2-071) N-[2-[5-amino-1-[4-(2,3-difluorophenoxy)-2-fluoro-6-methylphenyl]pyrazole-4-carbonyl]-5-methyl-1H-indol-6-yl]-3-fluoropropane-1-sulfonamide,
(4-2-072) N-[2-[5-amino-1-[6-(2-fluorophenoxy)-4-methylpyridin-3-yl]pyrazole-4-carbonyl]-5-methyl-1H-indol-6-yl]-3-fluoropropane-1-sulfonamide,
(4-2-073) N-[2-[5-amino-1-[6-(2,6-difluorophenoxy)-4-methylpyridin-3-yl]pyrazole-4-carbonyl]-5-methyl-1H-indol-6-yl]-3-fluoropropane-1-sulfonamide,
(4-2-074) N-[2-[5-amino-1-[6-(2-chlorophenoxy)-4-methylpyridin-3-yl]pyrazole-4-carbonyl]-5-methyl-1H-indol-6-yl]-3-fluoropropane-1-sulfonamide,
(4-2-075) N-[2-[5-amino-1-[6-(3-chlorophenoxy)-4-methylpyridin-3-yl]pyrazole-4-carbonyl]-5-methyl-1H-indol-6-yl]-3-fluoropropane-1-sulfonamide,
(4-2-076) N-[2-[5-amino-1-[6-(4-fluorophenoxy)-4-methylpyridin-3-yl]pyrazole-4-carbonyl]-5-methyl-1H-indol-6-yl]-3-fluoropropane-1-sulfonamide,
(4-2-077) N-[2-[5-amino-1-[4-(2-fluorophenoxy)-2-methylphenyl]pyrazole-4-carbonyl]-5-chloro-1H-indol-6-yl]methanesulfonamide,
(4-2-078) N-[2-[5-amino-1-[4-(2,3-difluorophenoxy)-2-methylphenyl]pyrazole-4-carbonyl]-5-chloro-1H-indol-6-yl]methanesulfonamide,
(4-2-079) N-[2-[5-amino-1-[2-fluoro-4-(2-fluorophenoxy)-6-methylphenyl]pyrazole-4-carbonyl]-5-chloro-1H-indol-6-yl]methanesulfonamide,
(4-2-080) N-[2-[5-amino-1-[4-(2,3-difluorophenoxy)-2-fluoro-6-methylphenyl]pyrazole-4-carbonyl]-5-chloro-1H-indol-6-yl]methanesulfonamide,
(4-2-081) N-[2-[5-amino-1-[4-(2,5-difluorophenoxy)-2-fluoro-6-methylphenyl]pyrazole-4-carbonyl]-5-chloro-1H-indol-6-yl]methanesulfonamide,
(4-2-082) N-[2-[5-amino-1-[4-(2-chlorophenoxy)-2-fluoro-6-methylphenyl]pyrazole-4-carbonyl]-5-chloro-1H-indol-6-yl]methanesulfonamide,
(4-2-083) N-[2-[5-amino-1-[4-(3-chlorophenoxy)-2-fluoro-6-methylphenyl]pyrazole-4-carbonyl]-5-chloro-1H-indol-6-yl]methanesulfonamide,
(4-2-084) N-[2-[5-amino-1-(2-fluoro-6-methyl-4-phenoxyphenyl)pyrazole-4-carbonyl]-5-chloro-1H-indol-6-yl]methanesulfonamide,
(4-2-085) N-[2-[5-amino-1-[6-(2-fluorophenoxy)-4-methylpyridin-3-yl]pyrazole-4-carbonyl]-5-chloro-1H-indol-6-yl]methanesulfonamide,
(4-2-086) N-[2-[5-amino-1-[6-(2,6-difluorophenoxy)-4-methylpyridin-3-yl]pyrazole-4-carbonyl]-5-chloro-1H-indol-6-yl]methanesulfonamide,
(4-2-087) N-[2-[5-amino-1-[6-(2,3-difluorophenoxy)-4-methylpyridin-3-yl]pyrazole-4-carbonyl]-5-chloro-1H-indol-6-yl]methanesulfonamide,
(4-2-088) N-[2-[5-amino-1-[6-(2-chlorophenoxy)-4-methylpyridin-3-yl]pyrazole-4-carbonyl]-5-chloro-1H-indol-6-yl]methanesulfonamide,
(4-2-089) N-[2-[5-amino-1-[6-(2-chloro-6-fluorophenoxy)-4-methylpyridin-3-yl]pyrazole-4-carbonyl]-5-chloro-1H-indol-6-yl]methanesulfonamide,
(4-2-090) N-[2-[5-amino-1-[4-methyl-6-(2-methylphenoxy)pyridin-3-yl]pyrazole-4-carbonyl]-5-chloro-1H-indol-6-yl]methanesulfonamide,
(4-2-091) N-[2-[5-amino-1-[6-(3-chlorophenoxy)-4-methylpyridin-3-yl]pyrazole-4-carbonyl]-5-chloro-1H-indol-6-yl]methanesulfonamide,
(4-2-092) N-[2-[5-amino-1-[6-(4-fluorophenoxy)-4-methylpyridin-3-yl]pyrazole-4-carbonyl]-5-chloro-1H-indol-6-yl]methanesulfonamide,
(4-2-093) N-[2-[5-amino-1-[2-fluoro-4-(2-fluorophenoxy)-6-methylphenyl]pyrazole-4-carbonyl]-6-chloro-1H-indol-5-yl]methanesulfonamide,
(4-2-094) N-[2-[5-amino-1-[4-(2,3-difluorophenoxy)-2-fluoro-6-methylphenyl]pyrazole-4-carbonyl]-6-chloro-1H-indol-5-yl]methanesulfonamide,
(4-2-095) N-[2-[5-amino-1-(2-fluoro-6-methyl-4-phenoxyphenyl)pyrazole-4-carbonyl]-6-chloro-1H-indol-5-yl]methanesulfonamide,
(4-2-096) N-[2-[5-amino-1-[6-(2-fluorophenoxy)-4-methylpyridin-3-yl]pyrazole-4-carbonyl]-6-chloro-1H-indol-5-yl]methanesulfonamide,
(4-2-097) N-[2-[5-amino-1-[4-(2-fluorophenoxy)-2-methylphenyl]pyrazole-4-carbonyl]-6-fluoro-1H-indol-5-yl]methanesulfonamide,
(4-2-098) N-[2-[5-amino-1-[4-(2,3-difluorophenoxy)-2-methylphenyl]pyrazole-4-carbonyl]-6-fluoro-1H-indol-5-yl]methanesulfonamide,
(4-2-099) N-[2-[5-amino-1-[2-fluoro-4-(2-fluorophenoxy)-6-methylphenyl]pyrazole-4-carbonyl]-6-fluoro-1H-indol-5-yl]methanesulfonamide,
(4-2-100) N-[2-[5-amino-1-[4-(2,3-difluorophenoxy)-2-fluoro-6-methylphenyl]pyrazole-4-carbonyl]-6-fluoro-1H-indol-5-yl]methanesulfonamide,
(4-2-101) N-[2-[5-amino-1-[4-(2,5-difluorophenoxy)-2-fluoro-6-methylphenyl]pyrazole-4-carbonyl]-6-fluoro-1H-indol-5-yl]methanesulfonamide,
(4-2-102) N-[2-[5-amino-1-[4-(2-chlorophenoxy)-2-fluoro-6-methylphenyl]pyrazole-4-carbonyl]-6-fluoro-1H-indol-5-yl]methanesulfonamide,
(4-2-103) N-[2-[5-amino-1-(2-fluoro-6-methyl-4-phenoxyphenyl)pyrazole-4-carbonyl]-6-fluoro-1H-indol-5-yl]methanesulfonamide,
(4-2-104) N-[2-[5-amino-1-[6-(2-fluorophenoxy)-4-methylpyridin-3-yl]pyrazole-4-carbonyl]-6-fluoro-1H-indol-5-yl]methanesulfonamide,
(4-2-105) N-[2-[5-amino-1-[4-(2-fluorophenoxy)-2-methylphenyl]pyrazole-4-carbonyl]-5-methyl-1H-indol-6-yl]morpholine-4-sulfonamide,
(4-2-106) N-[2-[5-amino-1-[4-(2,3-difluorophenoxy)-2-methylphenyl]pyrazole-4-carbonyl]-5-methyl-1H-indol-6-yl]morpholine-4-sulfonamide,
(4-2-107) N-[2-[5-amino-1-[2-fluoro-4-(2-fluorophenoxy)-6-methylphenyl]pyrazole-4-carbonyl]-5-methyl-1H-indol-6-yl]morpholine-4-sulfonamide,
(4-2-108) N-[2-[5-amino-1-[6-(2-fluorophenoxy)-4-methylpyridin-3-yl]pyrazole-4-carbonyl]-5-methyl-1H-indol-6-yl]morpholine-4-sulfonamide,
(4-2-109) N-[2-[5-amino-1-[6-(2,6-difluorophenoxy)-4-methylpyridin-3-yl]pyrazole-4-carbonyl]-5-methyl-1H-indol-6-yl]morpholine-4-sulfonamide,
(4-2-110) N-[2-[5-amino-1-[6-(2-chlorophenoxy)-4-methylpyridin-3-yl]pyrazole-4-carbonyl]-5-methyl-1H-indol-6-yl]morpholine-4-sulfonamide,
(4-2-111) N-[2-[5-amino-1-[6-(3-chlorophenoxy)-4-methylpyridin-3-yl]pyrazole-4-carbonyl]-5-methyl-1H-indol-6-yl]morpholine-4-sulfonamide, (4-2-112) [5-amino-1-[4-(2-fluorophenoxy)-2-methylphenyl]pyrazol-4-yl]-[6-(1,1-dioxo-1,2-thiazolidin-2-yl)-5-methyl-1H-indol-2-yl]methanone,
(4-2-113) [5-amino-1-[4-(2,3-difluorophenoxy)-2-methylphenyl]pyrazol-4-yl]-[6-(1,1-dioxo-1,2-thiazolidin-2-yl)-5-methyl-1H-indol-2-yl]methanone,
(4-2-114) [5-amino-1-[2-fluoro-4-(2-fluorophenoxy)-6-methylphenyl]pyrazol-4-yl]-[6-(1,1-dioxo-1,2-thiazolidin-2-yl)-5-methyl-1H-indol-2-yl]methanone,
(4-2-115) [5-amino-1-[4-(2,3-difluorophenoxy)-2-fluoro-6-methylphenyl]pyrazol-4-yl]-[6-(1,1-dioxo-1,2-thiazolidin-2-yl)-5-methyl-1H-indol-2-yl]methanone,
(4-2-116) [5-amino-1-[6-(2,6-difluorophenoxy)-4-methylpyridin-3-yl]pyrazol-4-yl]-[6-(1,1-dioxo-1,2-thiazolidin-2-yl)-5-methyl-1H-indol-2-yl]methanone,
(4-2-117) [5-amino-1-[6-(2-chlorophenoxy)-4-methylpyridin-3-yl]pyrazol-4-yl]-[6-(1,1-dioxo-1,2-thiazolidin-2-yl)-5-methyl-1H-indol-2-yl]methanone,
(4-2-118) [5-amino-1-[6-(3-chlorophenoxy)-4-methylpyridin-3-yl]pyrazol-4-yl]-[6-(1,1-dioxo-1,2-thiazolidin-2-yl)-5-methyl-1H-indol-2-yl]methanone,
(4-2-119) [5-amino-1-[6-(4-fluorophenoxy)-4-methylpyridin-3-yl]pyrazol-4-yl]-[6-(1,1-dioxo-1,2-thiazolidin-2-yl)-5-methyl-1H-indol-2-yl]methanone,
(4-2-120) [5-amino-1-[2-fluoro-4-(2-fluorophenoxy)-6-methylphenyl]pyrazol-4-yl]-[6-(1,1-dioxo-1,2-thiazolidin-2-yl)-5-methoxy-1H-indol-2-yl]methanone,
(4-2-121) [5-amino-1-[6-(2,6-difluorophenoxy)-4-methylpyridin-3-yl]pyrazol-4-yl]-[6-(1,1-dioxo-1,2-thiazolidin-2-yl)-5-methoxy-1H-indol-2-yl]methanone,
(4-2-122) [5-amino-1-[4-(2-fluorophenoxy)-2-methylphenyl]pyrazol-4-yl]-(5-methyl-6-morpholin-4-yl-1H-indol-2-yl)methanone,
(4-2-123) [5-amino-1-[6-(2-fluorophenoxy)-4-methylpyridin-3-yl]pyrazol-4-yl]-(5-methyl-6-morpholin-4-yl-1H-indol-2-yl)methanone,
(4-2-124) [5-amino-1-[6-(2,6-difluorophenoxy)-4-methylpyridin-3-yl]pyrazol-4-yl]-(5-methyl-6-morpholin-4-yl-1H-indol-2-yl)methanone,
(4-2-125) [5-amino-1-[6-(2,6-difluorophenoxy)-4-methylpyridin-3-yl]pyrazol-4-yl]-[5-methyl-6-(4-morpholin-4-ylpiperidin-1-yl)-1H-indol-2-yl]methanone,
(4-2-126) N-[2-[5-amino-1-[6-(2,6-difluorophenoxy)-4-methylpyridin-3-yl]pyrazole-4-carbonyl]-5-fluoro-1H-indol-6-yl]-N-ethylmethanesulfonamide,
(4-2-127) N-[2-[5-amino-1-[6-(2,6-difluorophenoxy)-4-methylpyridin-3-yl]pyrazole-4-carbonyl]-5-fluoro-1H-indol-6-yl]-N-(oxan-4-yl)methanesulfonamide,
(4-2-128) N-[2-[5-amino-1-[6-(2,6-difluorophenoxy)-4-methylpyridin-3-yl]pyrazole-4-carbonyl]-5-fluoro-1H-indol-6-yl]-N-(2-morpholin-4-ylethyl)methanesulfonamide,
(4-2-129) N-[2-[5-amino-1-[6-(2-fluorophenoxy)-4-methylpyridin-3-yl]pyrazole-4-carbonyl]-6-(2-morpholin-4-ylethoxy)-1H-indol-5-yl]methanesulfonamide,
(4-2-130) N-[2-[5-amino-1-[6-(2-fluorophenoxy)-4-methylpyridin-3-yl]pyrazole-4-carbonyl]-6-hydroxy-1H-indol-5-yl]-N-(2-morpholin-4-ylethyl)methanesulfonamide,
(4-3-001) [5-amino-1-[4-(2,3-difluorophenoxy)-2-fluoro-6-methylphenyl]pyrazol-4-yl]-(6-amino-5-fluoro-1H-indol-2-yl)methanone,
(4-4-001) [5-amino-1-[6-(2,6-difluorophenoxy)-4-methylpyridin-3-yl]pyrazol-4-yl]-[5-(difluoromethoxy)-6-piperidin-4-yl-1H-indol-2-yl]methanone,
(4-5-001) N-[2-[5-amino-1-[6-(2-fluorophenoxy)-4-methylpyridin-3-yl]pyrazole-4-carbonyl]-5-fluoro-1H-indol-6-yl]morpholine-4-sulfonamide,
(4-5-002) N-[2-[5-amino-1-[4-(2-fluorophenoxy)-2-methylphenyl]pyrazole-4-carbonyl]-5-fluoro-1H-indol-6-yl]morpholine-4-sulfonamide,
(4-5-003) [5-amino-1-[4-(2-fluorophenoxy)-2-methylphenyl]pyrazol-4-yl]-[5-fluoro-6-(oxan-4-ylsulfamoylamino)-1H-indol-2-yl]methanone,
(4-5-004) [5-amino-1-[4-(2-fluorophenoxy)-2-methylphenyl]pyrazol-4-yl]-[5-fluoro-6-(propan-2-ylsulfamoylamino)-1H-indol-2-yl]methanone,
(4-5-005) [5-amino-1-[4-(2-fluorophenoxy)-2-methylphenyl]pyrazol-4-yl]-[5-fluoro-6-(oxetan-3-ylsulfamoylamino)-1H-indol-2-yl]methanone,
(4-5-006) [5-amino-1-[4-(2-fluorophenoxy)-2-methylphenyl]pyrazol-4-yl]-[6-(cyclobutylsulfamoylamino)-5-fluoro-1H-indol-2-yl]methanone,
(4-5-007) [5-amino-1-[4-(2-fluorophenoxy)-2-methylphenyl]pyrazol-4-yl]-[5-fluoro-6-(2-methoxyethylsulfamoylamino)-1H-indol-2-yl]methanone,
(4-5-008) [5-amino-1-[4-(2-fluorophenoxy)-2-methylphenyl]pyrazol-4-yl]-[5-fluoro-6-[(3-methyloxetan-3-yl)sulfamoylamino]-1H-indol-2-yl]methanone,
(4-5-009) [5-amino-1-[4-(2-fluorophenoxy)-2-methylphenyl]pyrazol-4-yl]-[5-fluoro-6-(methoxysulfamoylamino)-1H-indol-2-yl]methanone,
(4-5-010) [5-amino-1-[4-(2-fluorophenoxy)-2-methylphenyl]pyrazol-4-yl]-[6-(cyclopropylsulfamoylamino)-5-fluoro-1H-indol-2-yl]methanone,
(4-5-011) N-[2-[5-amino-1-[4-(2,3-difluorophenoxy)-2-fluoro-6-methylphenyl]pyrazole-4-carbonyl]-5-fluoro-1H-indol-6-yl]morpholine-4-sulfonamide,
(4-5-012) [5-amino-1-[6-(2-fluorophenoxy)-4-methylpyridin-3-yl]pyrazol-4-yl]-[5-fluoro-6-(oxan-4-ylsulfamoylamino)-1H-indol-2-yl]methanone,
(4-6-001) [5-amino-1-[6-(2-fluorophenoxy)-4-methylpyridin-3-yl]pyrazol-4-yl]-[5-fluoro-6-(2-hydroxyethylsulfamoylamino)-1H-indol-2-yl]methanone,
(4-6-002) [5-amino-1-[4-(2-fluorophenoxy)-2-methylphenyl]pyrazol-4-yl]-[5-fluoro-6-(2-hydroxyethylsulfamoylamino)-1H-indol-2-yl]methanone,
(4-6-003) [5-amino-1-[4-(2-fluorophenoxy)-2-methylphenyl]pyrazol-4-yl]-[5-fluoro-6-[(1-hydroxy-2-methylpropan-2-yl)sulfamoylamino]-1H-indol-2-yl]methanone,
(4-6-004) [5-amino-1-[4-(2-fluorophenoxy)-2-methylphenyl]pyrazol-4-yl]-[5-fluoro-6-[(2-hydroxy-2-methylpropyl)sulfamoylamino]-1H-indol-2-yl]methanone,
(4-7-001) N-[2-[5-amino-1-[6-(2-fluorophenoxy)-4-methylpyridin-3-yl]pyrazole-4-carbonyl]-5-fluoro-1H-indol-6-yl]methanesulfonamide,
(4-7-002) N-[2-[5-amino-1-[4-(2-fluorophenoxy)-2-methylphenyl]pyrazole-4-carbonyl]-5-fluoro-1H-indol-6-yl]-1-(1,4-dioxan-2-yl)methanesulfonamide,
(4-7-003) N-[2-[5-amino-1-[2-fluoro-4-(2-fluorophenoxy)-6-methylphenyl]pyrazole-4-carbonyl]-5-fluoro-1H-indol-6-yl]methanesulfonamide,
(4-7-004) N-[2-[5-amino-1-[2-fluoro-4-(2-fluorophenoxy)-6-methylphenyl]pyrazole-4-carbonyl]-5-fluoro-1H-indol-6-yl]cyclopropanesulfonamide,
(4-7-005) N-[2-[5-amino-1-[4-(2,3-difluorophenoxy)-2-fluoro-6-methylphenyl]pyrazole-4-carbonyl]-5-fluoro-1H-indol-6-yl]methanesulfonamide,
(4-7-006) N-[2-[5-amino-1-[4-(2,3-difluorophenoxy)-2-fluoro-6-methylphenyl]pyrazole-4-carbonyl]-5-fluoro-1H-indol-6-yl]cyclopropanesulfonamide,
(4-7-007) N-[2-[5-amino-1-[4-(2,5-difluorophenoxy)-2-fluoro-6-methylphenyl]pyrazole-4-carbonyl]-5-fluoro-1H-indol-6-yl]methanesulfonamide, (4-7-008) N-[2-[5-amino-1-[4-(2,5-difluorophenoxy)-2-fluoro-6-methylphenyl]pyrazole-4-carbonyl]-5-fluoro-1H-indol-6-yl]cyclopropanesulfonamide, (4-7-009) N-[2-[5-amino-1-[4-(2-chlorophenoxy)-2-fluoro-6-methylphenyl]pyrazole-4-carbonyl]-5-fluoro-1H-indol-6-yl]methanesulfonamide, (4-7-010) N-[2-[5-amino-1-[4-(2-chlorophenoxy)-2-fluoro-6-methylphenyl]pyrazole-4-carbonyl]-5-fluoro-1H-indol-6-yl]cyclopropanesulfonamide, (4-7-011) N-[2-[5-amino-1-[4-(3-chlorophenoxy)-2-fluoro-6-methylphenyl]pyrazole-4-carbonyl]-5-fluoro-1H-indol-6-yl]methanesulfonamide, (4-7-012) N-[2-[5-amino-1-[4-(3-chlorophenoxy)-2-fluoro-6-methylphenyl]pyrazole-4-carbonyl]-5-fluoro-1H-indol-6-yl]cyclopropanesulfonamide, (4-7-013) N-[2-[5-amino-1-(2-fluoro-6-methyl-4-phenoxyphenyl)pyrazole-4-carbonyl]-5-fluoro-1H-indol-6-yl]methanesulfonamide, (4-7-014) N-[2-[5-amino-1-(2-fluoro-6-methyl-4-phenoxyphenyl)pyrazole-4-carbonyl]-5-fluoro-1H-indol-6-yl]cyclopropanesulfonamide, (4-7-015) N-[2-[5-amino-1-[6-(2-chlorophenoxy)-4-methylpyridin-3-yl]pyrazole-4-carbonyl]-5-fluoro-1H-indol-6-yl]cyclopropanesulfonamide, (4-7-016) N-[2-[5-amino-1-[6-(3-chlorophenoxy)-4-methylpyridin-3-yl]pyrazole-4-carbonyl]-5-fluoro-1H-indol-6-yl]cyclopropanesulfonamide, (4-8-001) N-[2-[5-amino-1-[4-(2-fluorophenoxy)-2-methylphenyl]pyrazole-4-carbonyl]-5-fluoro-1H-indol-6-yl]-1-(2,3-dihydroxypropyl)cyclopropane-1-sulfonamide, (4-9-001) [5-amino-1-[6-(2-fluorophenoxy)-4-methylpyridin-3-yl]pyrazol-4-yl]-[6-(1,1-dioxo-1,2-thiazolidin-2-yl)-5-fluoro-1H-indol-2-yl]methanone hydrochloride, (4-9-002) [5-amino-1-[6-(2,6-difluorophenoxy)-4-methylpyridin-3-yl]pyrazol-4-yl]-[6-(1,1-dioxo-1,2-thiazolidin-2-yl)-5-fluoro-1H-indol-2-yl]methanone, (4-10-001) 2-[[2-[5-amino-1-[6-(2-fluorophenoxy)-4-methylpyridin-3-yl]pyrazole-4-carbonyl]-5-fluoro-1H-indol-6-yl]sulfamoyl]-N,N-diethylacetamide, (4-10-002) 2-[[2-[5-amino-1-[4-(2-fluorophenoxy)-2-methylphenyl]pyrazole-4-carbonyl]-5-fluoro-1H-indol-6-yl]sulfamoyl]-N-propan-2-ylacetamide, (4-10-003) N-[2-[5-amino-1-[4-(2-fluorophenoxy)-2-methylphenyl]pyrazole-4-carbonyl]-5-fluoro-1H-indol-6-yl]-2-oxo-2-(4-propan-2-ylpiperazin-1-yl)ethanesulfonamide 2,2,2-trifluoroacetate (4-10-004) N-[2-[5-amino-1-[4-(2-fluorophenoxy)-2-methylphenyl]pyrazole-4-carbonyl]-5-fluoro-1H-indol-6-yl]-2-morpholin-4-yl-2-oxoethanesulfonamide, (4-10-005) N-[2-[5-amino-1-[6-(2-fluorophenoxy)-4-methylpyridin-3-yl]pyrazole-4-carbonyl]-5-fluoro-1H-indol-6-yl]-2-oxo-2-pyrrolidin-1-ylethanesulfonamide, (4-10-006) N-[2-[5-amino-1-[6-(2-fluorophenoxy)-4-methylpyridin-3-yl]pyrazole-4-carbonyl]-5-fluoro-1H-indol-6-yl]-2-morpholin-4-yl-2-oxoethanesulfonamide, (4-10-007) N-[2-[5-amino-1-[4-(2-fluorophenoxy)-2-methylphenyl]pyrazole-4-carbonyl]-5-methyl-1H-indol-6-yl]-2-morpholin-4-yl-2-oxoethanesulfonamide, (4-10-008) 2-[[2-[5-amino-1-[4-(2-fluorophenoxy)-2-methylphenyl]pyrazole-4-carbonyl]-5-methyl-1H-indol-6-yl]sulfamoyl]-N-propan-2-ylacetamide, (4-10-009) N-[2-[5-amino-1-[2-fluoro-4-(2-fluorophenoxy)-6-methylphenyl]pyrazole-4-carbonyl]-5-methyl-1H-indol-6-yl]-2-morpholin-4-yl-2-oxoethanesulfonamide, (4-10-010) N-[2-[5-amino-1-[6-(2,6-difluorophenoxy)-4-methylpyridin-3-yl]pyrazole-4-carbonyl]-5-methyl-1H-indol-6-yl]-2-morpholin-4-yl-2-oxoethanesulfonamide, (4-10-011) 2-[[2-[5-amino-1-[4-(2-fluorophenoxy)-2-methylphenyl]pyrazole-4-carbonyl]-5-methoxy-1H-indol-6-yl]sulfamoyl]-N-propan-2-ylacetamide, (4-10-012) N-[2-[5-amino-1-[4-(2-fluorophenoxy)-2-methylphenyl]pyrazole-4-carbonyl]-5-methoxy-1H-indol-6-yl]-2-morpholin-4-yl-2-oxoethanesulfonamide, (4-10-013) N-[2-[5-amino-1-[2-fluoro-4-(2-fluorophenoxy)-6-methylphenyl]pyrazole-4-carbonyl]-5-methoxy-1H-indol-6-yl]-2-morpholin-4-yl-2-oxoethanesulfonamide, (4-10-014) N-[2-[5-amino-1-[6-(2-fluorophenoxy)-4-methylpyridin-3-yl]pyrazole-4-carbonyl]-5-methoxy-1H-indol-6-yl]-2-oxo-2-pyrrolidin-1-ylethanesulfonamide, (4-10-015) 2-[[2-[5-amino-1-[6-(2-fluorophenoxy)-4-methylpyridin-3-yl]pyrazole-4-carbonyl]-5-methoxy-1H-indol-6-yl]sulfamoyl]-N-propan-2-ylacetamide, (4-10-016) N-[2-[5-amino-1-[6-(2-fluorophenoxy)-4-methylpyridin-3-yl]pyrazole-4-carbonyl]-5-methoxy-1H-indol-6-yl]-2-morpholin-4-yl-2-oxoethanesulfonamide, (4-10-017) N-[2-[5-amino-1-[6-(2,6-difluorophenoxy)-4-methylpyridin-3-yl]pyrazole-4-carbonyl]-5-methoxy-1H-indol-6-yl]-2-oxo-2-pyrrolidin-1-ylethanesulfonamide, (4-11-001) N-[2-[5-amino-1-[6-(2-fluorophenoxy)-4-methylpyridin-3-yl]pyrazole-4-carbonyl]-5-methoxy-1H-indol-6-yl]acetamide, (4-12-001) N-[2-[5-amino-1-[6-(2-fluorophenoxy)-4-methylpyridin-3-yl]pyrazole-4-carbonyl]-5-methoxy-1H-indol-6-yl]morpholine-4-sulfonamide, (4-12-002) N-[2-[5-amino-1-[6-(2-fluorophenoxy)-4-methylpyridin-3-yl]pyrazole-4-carbonyl]-5-methoxy-1H-indol-6-yl]morpholine-4-carboxamide, (4-12-003) N-[2-[5-amino-1-[4-(2-fluorophenoxy)-2-methylphenyl]pyrazole-4-carbonyl]-5-methoxy-1H-indol-6-yl]morpholine-4-sulfonamide, (4-13-001) N-[2-[5-amino-1-[6-(2-fluorophenoxy)-4-methylpyridin-3-yl]pyrazole-4-carbonyl]-5-methoxy-1H-indol-6-yl]-3-fluoropropane-1-sulfonamide, (4-13-002) N-[2-[5-amino-1-[4-(2-fluorophenoxy)-2-methylphenyl]pyrazole-4-carbonyl]-5-methoxy-1H-indol-6-yl]-3-fluoropropane-1-sulfonamide, (4-14-001) [5-amino-1-[6-(2-fluorophenoxy)-4-methylpyridin-3-yl]pyrazol-4-yl]-[6-(1,1-dioxo-1,2-thiazolidin-2-yl)-5-methoxy-1H-indol-2-yl]methanone, (4-14-002) [5-amino-1-[4-(2-fluorophenoxy)-2-methylphenyl]pyrazol-4-yl]-[6-(1,1-dioxo-1,2-thiazolidin-2-yl)-5-methoxy-1H-indol-2-yl]methanone, (4-15-001) N-[2-[5-amino-1-[6-(2-fluorophenoxy)-4-methylpyridin-3-yl]pyrazole-4-carbonyl]-5-methyl-1H-indol-6-yl]-2-morpholin-4-yl-2-oxoethanesulfonamide, (4-16-001) [5-amino-1-[6-(2-fluorophenoxy)-4-methylpyridin-3-yl]pyrazol-4-yl]-[6-(1,1-dioxo-1,2-thiazolidin-2-yl)-5-methyl-1H-indol-2-yl]methanone hydrochloride, (4-17-001) 1-[4-[2-[5-amino-1-[6-(2,6-difluorophenoxy)-4-methylpyridin-3-yl]pyrazole-4-carbonyl]-5-(2,2-difluoroethoxy)-1H-indol-6-yl]piperidin-1-yl]ethanone, (4-17-002) 1-[4-[2-[5-amino-1-[4-(2-fluorophenoxy)-2-methylphenyl]pyrazole-4-carbonyl]-5-(difluoromethoxy)-1H-indol-6-yl]piperidin-1-yl]ethanone, (4-17-003) [5-amino-1-[4-(2-fluorophenoxy)-2-methylphenyl]pyrazol-4-yl]-[5-(difluoromethoxy)-6-(1-methylsulfonylpiperidin-4-yl)-1H-indol-2-yl]methanone, (4-17-004) [5-amino-1-[4-(2-fluorophenoxy)-2-methylphenyl]pyrazol-4-yl]-[6-(1-cyclopropylsulfonylpiperidin-4-yl)-5-(difluoromethoxy)-1H-indol-2-yl]methanone, (4-17-005) 1-[4-[2-[5-amino-1-[2-fluoro-4-(2-fluorophenoxy)-6-methylphenyl]pyrazole-4-carbonyl]-5-(difluoromethoxy)-1H-indol-6-yl]piperidin-1-yl]ethanone,
(4-17-006) [5-amino-1-[2-fluoro-4-(2-fluorophenoxy)-6-methylphenyl]pyrazol-4-yl]-[5-(difluoromethoxy)-6-(1-methylsulfonylpiperidin-4-yl)-1H-indol-2-yl]methanone,
(4-17-007) [5-amino-1-[2-fluoro-4-(2-fluorophenoxy)-6-methylphenyl]pyrazol-4-yl]-[6-(1-cyclopropylsulfonylpiperidin-4-yl)-5-(difluoromethoxy)-1H-indol-2-yl]methanone,
(4-17-008) 1-[4-[2-[5-amino-1-[6-(2-fluorophenoxy)-4-methylpyridin-3-yl]pyrazole-4-carbonyl]-5-(difluoromethoxy)-1H-indol-6-yl]piperidin-1-yl]ethanone,
(4-17-009) [5-amino-1-[6-(2-fluorophenoxy)-4-methylpyridin-3-yl]pyrazol-4-yl]-[5-(difluoromethoxy)-6-(1-methylsulfonylpiperidin-4-yl)-1H-indol-2-yl]methanone,
(4-17-010) [5-amino-1-[6-(2-fluorophenoxy)-4-methylpyridin-3-yl]pyrazol-4-yl]-[6-(1-cyclopropylsulfonylpiperidin-4-yl)-5-(difluoromethoxy)-1H-indol-2-yl]methanone,
(4-17-011) 1-[4-[2-[5-amino-1-[6-(2,6-difluorophenoxy)-4-methylpyridin-3-yl]pyrazole-4-carbonyl]-5-(difluoromethoxy)-1H-indol-6-yl]piperidin-1-yl]ethanone,
(4-17-012) [5-amino-1-[6-(2,6-difluorophenoxy)-4-methylpyridin-3-yl]pyrazol-4-yl]-[5-(difluoromethoxy)-6-(1-methylsulfonylpiperidin-4-yl)-1H-indol-2-yl]methanone,
(4-17-013) [5-amino-1-[6-(2,6-difluorophenoxy)-4-methylpyridin-3-yl]pyrazol-4-yl]-[6-(1-cyclopropylsulfonylpiperidin-4-yl)-5-(difluoromethoxy)-1H-indol-2-yl]methanone,
(4-17-014) 1-[4-[2-[5-amino-1-[4-(2-fluorophenoxy)-2-methylphenyl]pyrazole-4-carbonyl]-5-(2,2-difluoroethoxy)-1H-indol-6-yl]piperidin-1-yl]ethanone,
(4-17-015) [5-amino-1-[4-(2-fluorophenoxy)-2-methylphenyl]pyrazol-4-yl]-[5-(2,2-difluoroethoxy)-6-(1-methylsulfonylpiperidin-4-yl)-1H-indol-2-yl]methanone,
(4-17-016) [5-amino-1-[4-(2-fluorophenoxy)-2-methylphenyl]pyrazol-4-yl]-[6-(1-cyclopropylsulfonylpiperidin-4-yl)-5-(2,2-difluoroethoxy)-1H-indol-2-yl]methanone,
(4-17-017) 1-[4-[2-[5-amino-1-[2-fluoro-4-(2-fluorophenoxy)-6-methylphenyl]pyrazole-4-carbonyl]-5-(2,2-difluoroethoxy)-1H-indol-6-yl]piperidin-1-yl]ethanone,
(4-17-018) [5-amino-1-[2-fluoro-4-(2-fluorophenoxy)-6-methylphenyl]pyrazol-4-yl]-[5-(2,2-difluoroethoxy)-6-(1-methylsulfonylpiperidin-4-yl)-1H-indol-2-yl]methanone,
(4-17-019) [5-amino-1-[2-fluoro-4-(2-fluorophenoxy)-6-methylphenyl]pyrazol-4-yl]-[6-(1-cyclopropylsulfonylpiperidin-4-yl)-5-(2,2-difluoroethoxy)-1H-indol-2-yl]methanone,
(4-17-020) 1-[4-[2-[5-amino-1-[6-(2-fluorophenoxy)-4-methylpyridin-3-yl]pyrazole-4-carbonyl]-5-(2,2-difluoroethoxy)-1H-indol-6-yl]piperidin-1-yl]ethanone,
(4-17-021) [5-amino-1-[6-(2-fluorophenoxy)-4-methylpyridin-3-yl]pyrazol-4-yl]-[5-(2,2-difluoroethoxy)-6-(1-methylsulfonylpiperidin-4-yl)-1H-indol-2-yl]methanone,
(4-17-022) [5-amino-1-[6-(2-fluorophenoxy)-4-methylpyridin-3-yl]pyrazol-4-yl]-[6-(1-cyclopropylsulfonylpiperidin-4-yl)-5-(2,2-difluoroethoxy)-1H-indol-2-yl]methanone,
(4-17-023) [5-amino-1-[6-(2,6-difluorophenoxy)-4-methylpyridin-3-yl]pyrazol-4-yl]-[5-(2,2-difluoroethoxy)-6-(1-methylsulfonylpiperidin-4-yl)-1H-indol-2-yl]methanone,
(4-17-024) [5-amino-1-[6-(2,6-difluorophenoxy)-4-methylpyridin-3-yl]pyrazol-4-yl]-[6-(1-cyclopropylsulfonylpiperidin-4-yl)-5-(2,2-difluoroethoxy)-1H-indol-2-yl]methanone,
(4-18-001) 2-amino-1-[4-[2-[5-amino-1-[6-(2,6-difluorophenoxy)-4-methylpyridin-3-yl]pyrazole-4-carbonyl]-5-(2,2-difluoroethoxy)-1H-indol-6-yl]piperidin-1-yl]ethanone,
(4-18-002) 2-amino-1-[4-[2-[5-amino-1-[4-(2-fluorophenoxy)-2-methylphenyl]pyrazole-4-carbonyl]-5-(difluoromethoxy)-1H-indol-6-yl]piperidin-1-yl]ethanone,
(4-18-003) 2-amino-1-[4-[2-[5-amino-1-[6-(2,6-difluorophenoxy)-4-methylpyridin-3-yl]pyrazole-4-carbonyl]-5-(difluoromethoxy)-1H-indol-6-yl]piperidin-1-yl]ethanone,
(4-18-004) 2-amino-1-[4-[2-[5-amino-1-[4-(2-fluorophenoxy)-2-methylphenyl]pyrazole-4-carbonyl]-5-(2,2-difluoroethoxy)-1H-indol-6-yl]piperidin-1-yl]ethanone,
(4-19-001) N-[2-[5-amino-1-[6-(2,6-difluorophenoxy)-4-methylpyridin-3-yl]pyrazole-4-carbonyl]-5-methoxy-1H-indol-6-yl]-3-fluoropropane-1-sulfonamide,
(4-20-001) 2-[5-amino-1-[4-(2-fluorophenoxy)-2-methylphenyl]pyrazole-4-carbonyl]-5-fluoro-6-(sulfamoylamino)-1H-indole,
(4-20-002) 2-[5-amino-1-[4-(2,3-difluorophenoxy)-2-methylphenyl]pyrazole-4-carbonyl]-5-fluoro-6-(sulfamoylamino)-1H-indole,
(4-20-003) 2-[5-amino-1-[4-(2-fluorophenoxy)-3-methylphenyl]pyrazole-4-carbonyl]-5-fluoro-6-(sulfamoylamino)-1H-indole,
(4-21-001) 1-[2-[5-amino-1-[6-(2,6-difluorophenoxy)-4-methylpyridin-3-yl]pyrazole-4-carbonyl]-5-(2,2-difluoroethoxy)-1H-indol-6-yl]pyrrolidin-2-one,
(4-21-002) 1-[2-[5-amino-1-[4-(2-fluorophenoxy)-2-methylphenyl]pyrazole-4-carbonyl]-5-(2,2-difluoroethoxy)-1H-indol-6-yl]pyrrolidin-2-one,
(4-21-003) 3-[2-[5-amino-1-[4-(2-fluorophenoxy)-2-methylphenyl]pyrazole-4-carbonyl]-5-(2,2-difluoroethoxy)-1H-indol-6-yl]-1,3-oxazolidin-2-one,
(4-21-004) 1-[2-[5-amino-1-[2-fluoro-4-(2-fluorophenoxy)-6-methylphenyl]pyrazole-4-carbonyl]-5-(2,2-difluoroethoxy)-1H-indol-6-yl]pyrrolidin-2-one,
(4-21-005) 3-[2-[5-amino-1-[6-(2,6-difluorophenoxy)-4-methylpyridin-3-yl]pyrazole-4-carbonyl]-5-(2,2-difluoroethoxy)-1H-indol-6-yl]-1,3-oxazolidin-2-one,
(4-21-006) 1-[2-[5-amino-1-[4-(2-fluorophenoxy)-2-methylphenyl]pyrazole-4-carbonyl]-5-(difluoromethoxy)-1H-indol-6-yl]pyrrolidin-2-one,
(4-21-007) 3-[2-[5-amino-1-[4-(2-fluorophenoxy)-2-methylphenyl]pyrazole-4-carbonyl]-5-(difluoromethoxy)-1H-indol-6-yl]-1,3-oxazolidin-2-one,
(4-21-008) 1-[2-[5-amino-1-[6-(2,6-difluorophenoxy)-4-methylpyridin-3-yl]pyrazole-4-carbonyl]-5-(difluoromethoxy)-1H-indol-6-yl]pyrrolidin-2-one,
(4-21-009) 3-[2-[5-amino-1-[6-(2,6-difluorophenoxy)-4-methylpyridin-3-yl]pyrazole-4-carbonyl]-5-(difluoromethoxy)-1H-indol-6-yl]-1,3-oxazolidin-2-one,
(4-22-001) N-[2-[5-amino-1-[4-(2-fluorophenoxy)-2-methylphenyl]pyrazole-4-carbonyl]-5-(difluoromethoxy)-1H-indol-6-yl]morpholine-4-sulfonamide,
(4-22-002) N-[2-[5-amino-1-[6-(2-fluorophenoxy)-4-methylpyridin-3-yl]pyrazole-4-carbonyl]-5-(difluoromethoxy)-1H-indol-6-yl]morpholine-4-sulfonamide,
(4-22-003) N-[2-[5-amino-1-[6-(2,6-difluorophenoxy)-4-methylpyridin-3-yl]pyrazole-4-carbonyl]-5-(difluoromethoxy)-1H-indol-6-yl]morpholine-4-sulfonamide,
(4-22-004) N-[2-[5-amino-1-[6-(2-fluorophenoxy)-4-methylpyridin-3-yl]pyrazole-4-carbonyl]-5-morpholin-4-yl-1H-indol-6-yl]morpholine-4-sulfonamide, (4-22-005) N-[2-[5-amino-1-[4-(2-fluorophenoxy)-2-methylphenyl]pyrazole-4-carbonyl]-5-(2,2-difluoroethoxy)-1H-indol-6-yl]morpholine-4-sulfonamide, (4-22-006) N-[2-[5-amino-1-[6-(2-fluorophenoxy)-4-methylpyridin-3-yl]pyrazole-4-carbonyl]-5-(2,2-difluoroethoxy)-1H-indol-6-yl]morpholine-4-sulfonamide, (4-23-001) [5-amino-1-[6-(2,6-difluorophenoxy)-4-methylpyridin-3-yl]pyrazol-4-yl]-[5-(2,2-difluoroethoxy)-6-(4-methylsulfonylpiperazin-1-yl)-1H-indol-2-yl]methanone, (4-23-002) [5-amino-1-[4-(2-fluorophenoxy)-2-methylphenyl]pyrazol-4-yl]-[5-(difluoromethoxy)-6-(4-methylsulfonylpiperazin-1-yl)-1H-indol-2-yl]methanone, (4-23-003) [5-amino-1-[2-fluoro-4-(2-fluorophenoxy)-6-methylphenyl]pyrazol-4-yl]-[5-(difluoromethoxy)-6-(4-methylsulfonylpiperazin-1-yl)-1H-indol-2-yl]methanone, (4-23-004) [5-amino-1-[6-(2-fluorophenoxy)-4-methylpyridin-3-yl]pyrazol-4-yl]-[5-(difluoromethoxy)-6-(4-methylsulfonylpiperazin-1-yl)-1H-indol-2-yl]methanone, (4-23-005) [5-amino-1-[4-(2-fluorophenoxy)-2-methylphenyl]pyrazol-4-yl]-[5-(2,2-difluoroethoxy)-6-(4-methylsulfonylpiperazin-1-yl)-1H-indol-2-yl]methanone, (4-23-006) [5-amino-1-[2-fluoro-4-(2-fluorophenoxy)-6-methylphenyl]pyrazol-4-yl]-[5-(2,2-difluoroethoxy)-6-(4-methylsulfonylpiperazin-1-yl)-1H-indol-2-yl]methanone, (4-23-007) [5-amino-1-[6-(2-fluorophenoxy)-4-methylpyridin-3-yl]pyrazol-4-yl]-[5-(2,2-difluoroethoxy)-6-(4-methylsulfonylpiperazin-1-yl)-1H-indol-2-yl]methanone, (4-23-008) [5-amino-1-[6-(2,6-difluorophenoxy)-4-methylpyridin-3-yl]pyrazol-4-yl]-[5-(2,2-difluoroethoxy)-6-(oxetan-3-ylamino)-1H-indol-2-yl]methanone, (4-23-009) [5-amino-1-[4-(2-fluorophenoxy)-2-methylphenyl]pyrazol-4-yl]-[5-(difluoromethoxy)-6-(oxetan-3-ylamino)-1H-indol-2-yl]methanone, (4-23-010) [5-amino-1-[4-(2-fluorophenoxy)-2-methylphenyl]pyrazol-4-yl]-[5-(difluoromethoxy)-6-[(1-methylsulfonylpiperidin-4-yl)amino]-1H-indol-2-yl]methanone, (4-23-011) [5-amino-1-[2-fluoro-4-(2-fluorophenoxy)-6-methylphenyl]pyrazol-4-yl]-[5-(difluoromethoxy)-6-(oxetan-3-ylamino)-1H-indol-2-yl]methanone, (4-23-012) [5-amino-1-[2-fluoro-4-(2-fluorophenoxy)-6-methylphenyl]pyrazol-4-yl]-[5-(difluoromethoxy)-6-[(1-methylsulfonylpiperidin-4-yl)amino]-1H-indol-2-yl]methanone, (4-23-013) [5-amino-1-[6-(2-fluorophenoxy)-4-methylpyridin-3-yl]pyrazol-4-yl]-[5-(difluoromethoxy)-6-(oxetan-3-ylamino)-1H-indol-2-yl]methanone, (4-23-014) [5-amino-1-[6-(2,6-difluorophenoxy)-4-methylpyridin-3-yl]pyrazol-4-yl]-[5-(difluoromethoxy)-6-(oxetan-3-ylamino)-1H-indol-2-yl]methanone, (4-23-015) [5-amino-1-[6-(2,6-difluorophenoxy)-4-methylpyridin-3-yl]pyrazol-4-yl]-[5-(difluoromethoxy)-6-[(1-methylsulfonylpiperidin-4-yl)amino]-1H-indol-2-yl]methanone, (4-23-016) [5-amino-1-[4-(2-fluorophenoxy)-2-methylphenyl]pyrazol-4-yl]-[5-(2,2-difluoroethoxy)-6-(oxetan-3-ylamino)-1H-indol-2-yl]methanone, (4-23-017) [5-amino-1-[4-(2-fluorophenoxy)-2-methylphenyl]pyrazol-4-yl]-[5-(2,2-difluoroethoxy)-6-[(1-methylsulfonylpiperidin-4-yl)amino]-1H-indol-2-yl]methanone, (4-23-018) [5-amino-1-[4-(2-fluorophenoxy)-2-methylphenyl]pyrazol-4-yl]-[5-(2,2-difluoroethoxy)-6-[(1-methylsulfonylazetidin-3-yl)amino]-1H-indol-2-yl]methanone, (4-23-019) [5-amino-1-[2-fluoro-4-(2-fluorophenoxy)-6-methylphenyl]pyrazol-4-yl]-[5-(2,2-difluoroethoxy)-6-(oxetan-3-ylamino)-1H-indol-2-yl]methanone, (4-23-020) [5-amino-1-[6-(2-fluorophenoxy)-4-methylpyridin-3-yl]pyrazol-4-yl]-[5-(2,2-difluoroethoxy)-6-(oxetan-3-ylamino)-1H-indol-2-yl]methanone, (4-23-021) [5-amino-1-[6-(2,6-difluorophenoxy)-4-methylpyridin-3-yl]pyrazol-4-yl]-[5-(2,2-difluoroethoxy)-6-[(1-methylsulfonylpiperidin-4-yl)amino]-1H-indol-2-yl]methanone, (4-23-022) [5-amino-1-[6-(2,6-difluorophenoxy)-4-methylpyridin-3-yl]pyrazol-4-yl]-[5-(2,2-difluoroethoxy)-6-[(1-methylsulfonylazetidin-3-yl)amino]-1H-indol-2-yl]methanone, (4-23-023) [5-amino-1-[4-(2-fluorophenoxy)-2-methylphenyl]pyrazol-4-yl]-[5-(difluoromethoxy)-6-[(1-methylsulfonylazetidin-3-yl)amino]-1H-indol-2-yl]methanone, (4-23-024) [5-amino-1-[2-fluoro-4-(2-fluorophenoxy)-6-methylphenyl]pyrazol-4-yl]-[5-(difluoromethoxy)-6-[(1-methylsulfonylazetidin-3-yl)amino]-1H-indol-2-yl]methanone, (4-23-025) [5-amino-1-[6-(2-fluorophenoxy)-4-methylpyridin-3-yl]pyrazol-4-yl]-[5-(difluoromethoxy)-6-[(1-methylsulfonylazetidin-3-yl)amino]-1H-indol-2-yl]methanone, (4-23-026) [5-amino-1-[6-(2-fluorophenoxy)-4-methylpyridin-3-yl]pyrazol-4-yl]-[5-(difluoromethoxy)-6-[(1-methylsulfonylpiperidin-4-yl)amino]-1H-indol-2-yl]methanone, (4-23-027) [5-amino-1-[2-fluoro-4-(2-fluorophenoxy)-6-methylphenyl]pyrazol-4-yl]-[5-(2,2-difluoroethoxy)-6-[(1-methylsulfonylazetidin-3-yl)amino]-1H-indol-2-yl]methanone, (4-23-028) [5-amino-1-[2-fluoro-4-(2-fluorophenoxy)-6-methylphenyl]pyrazol-4-yl]-[5-(2,2-difluoroethoxy)-6-[(1-methylsulfonylpiperidin-4-yl)amino]-1H-indol-2-yl]methanone, (4-23-029) 1-[2-[5-amino-1-[6-(2,6-difluorophenoxy)-4-methylpyridin-3-yl]pyrazole-4-carbonyl]-5-(2,2-difluoroethoxy)-1H-indol-6-yl]-6-methylpyrimidine-2,4-dione, (4-23-030) 1-[2-[5-amino-1-[4-(2-fluorophenoxy)-2-methylphenyl]pyrazole-4-carbonyl]-5-(2,2-difluoroethoxy)-1H-indol-6-yl]-6-methylpyrimidine-2,4-dione, (4-23-031) 1-[2-[5-amino-1-[4-(2-fluorophenoxy)-2-methylphenyl]pyrazole-4-carbonyl]-5-(difluoromethoxy)-1H-indol-6-yl]-6-methylpyrimidine-2,4-dione, (4-23-032) 3-[2-[5-amino-1-[6-(2,6-difluorophenoxy)-4-methylpyridin-3-yl]pyrazole-4-carbonyl]-5-(2,2-difluoroethoxy)-1H-indol-6-yl]-5,5-dimethylimidazolidine-2,4-dione, (4-23-033) 3-[2-[5-amino-1-[4-(2-fluorophenoxy)-2-methylphenyl]pyrazole-4-carbonyl]-5-(2,2-difluoroethoxy)-1H-indol-6-yl]-5,5-dimethylimidazolidine-2,4-dione, (4-23-034) 3-[2-[5-amino-1-[6-(2,6-difluorophenoxy)-4-methylpyridin-3-yl]pyrazole-4-carbonyl]-5-(difluoromethoxy)-1H-indol-6-yl]-5,5-dimethylimidazolidine-2,4-dione, (4-23-035) 3-[2-[5-amino-1-[4-(2-fluorophenoxy)-2-methylphenyl]pyrazole-4-carbonyl]-5-(difluoromethoxy)-1H-indol-6-yl]-5,5-dimethylimidazolidine-2,4-dione, (4-23-036) 3-[2-[5-amino-1-[6-(2,6-difluorophenoxy)-4-methylpyridin-3-yl]pyrazole-4-carbonyl]-5-(2,2-difluoroethoxy)-1H-indol-6-yl]-5,5-dimethyl-2-sulfanylideneimidazolidin-4-one, (4-23-037) 3-[2-[5-amino-1-[4-(2-fluorophenoxy)-2-methylphenyl]pyrazole-4-carbonyl]-5-(2,2-difluoroethoxy)-1H-indol-6-yl]-5,5-dimethyl-2-sulfanylideneimidazolidin-4-one, (4-23-038) 3-[2-[5-amino-1-[6-(2,6-difluorophenoxy)-4-methylpyridin-3-yl]pyrazole-4-carbonyl]-5-(difluoromethoxy)-1H-indol-6-yl]-5,5-dimethyl-2-sulfanylideneimidazolidin-4-one, (4-23-039) 3-[2-[5-amino-1-[4-(2-fluorophenoxy)-2-methylphenyl]pyrazole-4-carbonyl]-5-(difluoromethoxy)-1H-indol-6-yl]-5,5-dimethyl-2-sulfanylideneimidazolidin-4-one, (4-24-001) N-[2-[5-amino-1-[4-(2-fluorophenoxy)-2-methylphenyl]pyrazole-4-carbonyl]-5-(difluoromethoxy)-1H-indol-6-yl]cyclopropanesulfonamide, (4-24-002) N-[2-[5-amino-1-[4-(2-fluorophenoxy)-2-methylphenyl]pyrazole-4-carbonyl]-5-(difluoromethoxy)-1H-indol-6-yl]methanesulfonamide, (4-24-003) N-[2-[5-amino-1-[4-(2-fluorophenoxy)-2-methylphenyl]pyrazole-4-carbonyl]-5-(difluoromethoxy)-1H-indol-6-yl]-3-fluoropropane-1-sulfonamide, (4-24-004) N-[2-[5-amino-1-[4-(2-fluorophenoxy)-2-methylphenyl]pyrazole-4-carbonyl]-5-(difluoromethoxy)-1H-indol-6-yl]-3,3-difluoropropane-1-sulfonamide, (4-24-005) N-[2-[5-amino-1-[2-fluoro-4-(2-fluorophenoxy)-6-methylphenyl]pyrazole-4-carbonyl]-5-(difluoromethoxy)-1H-indol-6-yl]cyclopropanesulfonamide, (4-24-006) N-[2-[5-amino-1-[2-fluoro-4-(2-fluorophenoxy)-6-methylphenyl]pyrazole-4-carbonyl]-5-(difluoromethoxy)-1H-indol-6-yl]-3-fluoropropane-1-sulfonamide, (4-24-007) N-[2-[5-amino-1-[6-(2-fluorophenoxy)-4-methylpyridin-3-yl]pyrazole-4-carbonyl]-5-(difluoromethoxy)-1H-indol-6-yl]cyclopropanesulfonamide, (4-24-008) N-[2-[5-amino-1-[6-(2-fluorophenoxy)-4-methylpyridin-3-yl]pyrazole-4-carbonyl]-5-(difluoromethoxy)-1H-indol-6-yl]methanesulfonamide, (4-24-009) N-[2-[5-amino-1-[6-(2-fluorophenoxy)-4-methylpyridin-3-yl]pyrazole-4-carbonyl]-5-(difluoromethoxy)-1H-indol-6-yl]-3-fluoropropane-1-sulfonamide, (4-24-010) N-[2-[5-amino-1-[6-(2,6-difluorophenoxy)-4-methylpyridin-3-yl]pyrazole-4-carbonyl]-5-(difluoromethoxy)-1H-indol-6-yl]cyclopropanesulfonamide, (4-24-011) N-[2-[5-amino-1-[6-(2,6-difluorophenoxy)-4-methylpyridin-3-yl]pyrazole-4-carbonyl]-5-(difluoromethoxy)-1H-indol-6-yl]methanesulfonamide, (4-24-012) N-[2-[5-amino-1-[6-(2,6-difluorophenoxy)-4-methylpyridin-3-yl]pyrazole-4-carbonyl]-5-(difluoromethoxy)-1H-indol-6-yl]-3-fluoropropane-1-sulfonamide, (4-24-013) N-[2-[5-amino-1-[4-(2-fluorophenoxy)-2-methylphenyl]pyrazole-4-carbonyl]-5-morpholin-4-yl-1H-indol-6-yl]methanesulfonamide, (4-24-014) N-[2-[5-amino-1-[6-(2-fluorophenoxy)-4-methylpyridin-3-yl]pyrazole-4-carbonyl]-5-morpholin-4-yl-1H-indol-6-yl]cyclopropanesulfonamide, (4-24-015) N-[2-[5-amino-1-[6-(2-fluorophenoxy)-4-methylpyridin-3-yl]pyrazole-4-carbonyl]-5-morpholin-4-yl-1H-indol-6-yl]methanesulfonamide, (4-24-016) N-[2-[5-amino-1-[6-(2-fluorophenoxy)-4-methylpyridin-3-yl]pyrazole-4-carbonyl]-5-morpholin-4-yl-1H-indol-6-yl]-3-fluoropropane-1-sulfonamide, (4-24-017) N-[2-[5-amino-1-[6-(2,6-difluorophenoxy)-4-methylpyridin-3-yl]pyrazole-4-carbonyl]-5-morpholin-4-yl-1H-indol-6-yl]cyclopropanesulfonamide, (4-24-018) N-[2-[5-amino-1-[6-(2,6-difluorophenoxy)-4-methylpyridin-3-yl]pyrazole-4-carbonyl]-5-morpholin-4-yl-1H-indol-6-yl]methanesulfonamide, (4-24-019) N-[2-[5-amino-1-[6-(2,6-difluorophenoxy)-4-methylpyridin-3-yl]pyrazole-4-carbonyl]-5-morpholin-4-yl-1H-indol-6-yl]-3-fluoropropane-1-sulfonamide, (4-24-020) N-[2-[5-amino-1-[4-(2-fluorophenoxy)-2-methylphenyl]pyrazole-4-carbonyl]-5-(2,2-difluoroethoxy)-1H-indol-6-yl]cyclopropanesulfonamide, (4-24-021) N-[2-[5-amino-1-[4-(2-fluorophenoxy)-2-methylphenyl]pyrazole-4-carbonyl]-5-(2,2-difluoroethoxy)-1H-indol-6-yl]methanesulfonamide, (4-24-022) N-[2-[5-amino-1-[4-(2-fluorophenoxy)-2-methylphenyl]pyrazole-4-carbonyl]-5-(2,2-difluoroethoxy)-1H-indol-6-yl]-3-fluoropropane-1-sulfonamide, (4-24-023) N-[2-[5-amino-1-[4-(2-fluorophenoxy)-2-methylphenyl]pyrazole-4-carbonyl]-5-(2,2-difluoroethoxy)-1H-indol-6-yl]-3,3-difluoropropane-1-sulfonamide, (4-24-024) N-[2-[5-amino-1-[2-fluoro-4-(2-fluorophenoxy)-6-methylphenyl]pyrazole-4-carbonyl]-5-(2,2-difluoroethoxy)-1H-indol-6-yl]cyclopropanesulfonamide, (4-24-025) N-[2-[5-amino-1-[2-fluoro-4-(2-fluorophenoxy)-6-methylphenyl]pyrazole-4-carbonyl]-5-(2,2-difluoroethoxy)-1H-indol-6-yl]methanesulfonamide, (4-24-026) N-[2-[5-amino-1-[2-fluoro-4-(2-fluorophenoxy)-6-methylphenyl]pyrazole-4-carbonyl]-5-(2,2-difluoroethoxy)-1H-indol-6-yl]-3-fluoropropane-1-sulfonamide, (4-24-027) N-[2-[5-amino-1-[6-(2-fluorophenoxy)-4-methylpyridin-3-yl]pyrazole-4-carbonyl]-5-(2,2-difluoroethoxy)-1H-indol-6-yl]cyclopropanesulfonamide, (4-24-028) N-[2-[5-amino-1-[6-(2-fluorophenoxy)-4-methylpyridin-3-yl]pyrazole-4-carbonyl]-5-(2,2-difluoroethoxy)-1H-indol-6-yl]methanesulfonamide, (4-24-029) N-[2-[5-amino-1-[6-(2-fluorophenoxy)-4-methylpyridin-3-yl]pyrazole-4-carbonyl]-5-(2,2-difluoroethoxy)-1H-indol-6-yl]-3-fluoropropane-1-sulfonamide, (4-24-030) N-[2-[5-amino-1-[6-(2,6-difluorophenoxy)-4-methylpyridin-3-yl]pyrazole-4-carbonyl]-5-(2,2-difluoroethoxy)-1H-indol-6-yl]cyclopropanesulfonamide, (4-24-031) N-[2-[5-amino-1-[6-(2,6-difluorophenoxy)-4-methylpyridin-3-yl]pyrazole-4-carbonyl]-5-(2,2-difluoroethoxy)-1H-indol-6-yl]methanesulfonamide, (4-24-032) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-3-fluoropropane-1-sulfonamide, (4-24-033) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-3,3-difluoropropane-1-sulfonamide, (4-24-034) N-[2-[5-amino-1-[4-(2-fluorophenoxy)-2-methylphenyl]pyrazole-4-carbonyl]-5-(2-morpholin-4-ylethoxy)-1H-indol-6-yl]methanesulfonamide, (4-24-035) N-[2-[5-amino-1-[6-(2,6-difluorophenoxy)-4-methylpyridin-3-yl]pyrazole-4-carbonyl]-5-methoxy-1H-indol-6-yl]cyclopropanesulfonamide, (4-24-036) N-[2-[5-amino-1-[4-(2-fluorophenoxy)-2-methylphenyl]pyrazole-4-carbonyl]-5-(oxan-4-yloxy)-1H-indol-6-yl]methanesulfonamide, (4-24-037) N-[2-[5-amino-1-[4-(2-fluorophenoxy)-2-methylphenyl]pyrazole-4-carbonyl]-5-[2-[(1S,5R)-6-methylsulfonyl-3,6-diazabicyclo[3.1.1]heptan-3-yl]ethoxy]-1H-indol-6-yl]methanesulfonamide, (4-24-038) N-[2-[5-amino-1-[4-(2-fluorophenoxy)-2-methylphenyl]pyrazole-4-carbonyl]-5-[2-[(1S,4S)-2-methylsulfonyl-2,5-diazabicyclo[2.2.1]heptan-5-yl]ethoxy]-1H-indol-6-yl]methanesulfonamide, (4-24-039) N-[2-[5-amino-1-[4-(2-fluorophenoxy)-2-methylphenyl]pyrazole-4-carbonyl]-5-[2-[(1S,5R)-3-oxa-8-azabicyclo[3.2.1]octan-8-yl]ethoxy]-1H-indol-6-yl]methanesulfonamide, (4-25-001) [5-amino-1-[6-(2-fluorophenoxy)-4-methylpyridin-3-yl]pyrazol-4-yl]-[5-(2,2-difluoroethoxy)-6-(1,1-dioxo-1,2-thiazolidin-2-yl)-1H-indol-2-yl]methanone, (4-25-002) [5-amino-1-[4-(2-fluorophenoxy)-2-methylphenyl]pyrazol-4-yl]-[5-(difluoromethoxy)-6-(1,1-dioxo-1,2-thiazolidin-2-yl)-1H-indol-2-yl]methanone, (4-25-003) [5-amino-1-[2-fluoro-4-(2-fluorophenoxy)-6-methylphenyl]pyrazol-4-yl]-[5-(difluoromethoxy)-6-(1,1-dioxo-1,2-thiazolidin-2-yl)-1H-indol-2-yl]methanone, (4-25-004) [5-amino-1-[6-(2-fluorophenoxy)-4-methylpyridin-3-yl]pyrazol-4-yl]-[5-(difluoromethoxy)-6-(1,1-dioxo-1,2-thiazolidin-2-yl)-1H-indol-2-yl]methanone, (4-25-005) [5-amino-1-[6-(2,6-difluorophenoxy)-4-methylpyridin-3-yl]pyrazol-4-yl]-[5-(difluoromethoxy)-6-(1,1-dioxo-1,2-thiazolidin-2-yl)-1H-indol-2-yl]methanone, (4-25-006) [5-amino-1-[4-(2-fluorophenoxy)-2-methylphenyl]pyrazol-4-yl]-[6-(1,1-dioxo-1,2-thiazolidin-2-yl)-5-morpholin-4-yl-1H-indol-2-yl]methanone, (4-25-007) [5-amino-1-[6-(2-fluorophenoxy)-4-methylpyridin-3-yl]pyrazol-4-yl]-[6-(1,1-dioxo-1,2-thiazolidin-2-yl)-5-morpholin-4-yl-1H-indol-2-yl]methanone, (4-25-008) [5-amino-1-[6-(2,6-difluorophenoxy)-4-methylpyridin-3-yl]pyrazol-4-yl]-[6-(1,1-dioxo-1,2-thiazolidin-2-yl)-5-morpholin-4-yl-1H-indol-2-yl]methanone, (4-25-009) [5-amino-1-[4-(2-fluorophenoxy)-2-methylphenyl]pyrazol-4-yl]-[5-(2,2-difluoroethoxy)-6-(1,1-dioxo-1,2-thiazolidin-2-yl)-1H-indol-2-yl]methanone, (4-25-010) [5-amino-1-[2-fluoro-4-(2-fluorophenoxy)-6-methylphenyl]pyrazol-4-yl]-[5-(2,2-difluoroethoxy)-6-(1,1-dioxo-1,2-thiazolidin-2-yl)-1H-indol-2-yl]methanone, (4-25-011) [5-amino-1-[6-(2,6-difluorophenoxy)-4-methylpyridin-3-yl]pyrazol-4-yl]-[5-(2,2-difluoroethoxy)-6-(1,1-dioxo-1,2-thiazolidin-2-yl)-1H-indol-2-yl]methanone, (4-25-012) [5-amino-1-[4-(2-fluorophenoxy)-2-methylphenyl]pyrazol-4-yl]-[6-(1,1-dioxo-1,2-thiazolidin-2-yl)-5-(2-morpholin-4-ylethoxy)-1H-indol-2-yl]methanone, (4-25-013) 1-[2-[5-amino-1-[6-(2-fluorophenoxy)-4-methylpyridin-3-yl]pyrazole-4-carbonyl]-5-(2,2-difluoroethoxy)-1H-indol-6-yl]pyrrolidin-2-one (4-25-014) 1-[2-[5-amino-1-[6-(2-fluorophenoxy)-4-methylpyridin-3-yl]pyrazole-4-carbonyl]-5-(difluoromethoxy)-1H-indol-6-yl]pyrrolidin-2-one (4-25-015) 1-[2-[5-amino-1-[2-fluoro-4-(2-fluorophenoxy)-6-methylphenyl]pyrazole-4-carbonyl]-5-(difluoromethoxy)-1H-indol-6-yl]pyrrolidin-2-one (4-25-016) 3-[2-[5-amino-1-[6-(2-fluorophenoxy)-4-methylpyridin-3-yl]pyrazole-4-carbonyl]-5-(2,2-difluoroethoxy)-1H-indol-6-yl]-1,3-oxazolidin-2-one (4-25-017) 3-[2-[5-amino-1-[2-fluoro-4-(2-fluorophenoxy)-6-methylphenyl]pyrazole-4-carbonyl]-5-(2,2-difluoroethoxy)-1H-indol-6-yl]-1,3-oxazolidin-2-one (4-25-018) 3-[2-[5-amino-1-[6-(2-fluorophenoxy)-4-methylpyridin-3-yl]pyrazole-4-carbonyl]-5-(difluoromethoxy)-1H-indol-6-yl]-1,3-oxazolidin-2-one (4-25-019) 3-[2-[5-amino-1-[2-fluoro-4-(2-fluorophenoxy)-6-methylphenyl]pyrazole-4-carbonyl]-5-(difluoromethoxy)-1H-indol-6-yl]-1,3-oxazolidin-2-one (4-25-020) [5-amino-1-[6-(2-fluorophenoxy)-4-methylpyridin-3-yl]pyrazol-4-yl]-[5-(2,2-difluoroethoxy)-6-morpholin-4-yl-1H-indol-2-yl]methanone, (4-25-021) [5-amino-1-[2-fluoro-4-(2-fluorophenoxy)-6-methylphenyl]pyrazol-4-yl]-[5-(2,2-difluoroethoxy)-6-morpholin-4-yl-1H-indol-2-yl]methanone, (4-25-022) [5-amino-1-[6-(2-fluorophenoxy)-4-methylpyridin-3-yl]pyrazol-4-yl]-[5-(difluoromethoxy)-6-morpholin-4-yl-1H-indol-2-yl]methanone, (4-25-023) [5-amino-1-[6-(2,6-difluorophenoxy)-4-methylpyridin-3-yl]pyrazol-4-yl]-[5-(difluoromethoxy)-6-morpholin-4-yl-1H-indol-2-yl]methanone, (4-25-024) [5-amino-1-[4-(2-fluorophenoxy)-2-methylphenyl]pyrazol-4-yl]-[5-(difluoromethoxy)-6-morpholin-4-yl-1H-indol-2-yl]methanone, (4-25-025) [5-amino-1-[2-fluoro-4-(2-fluorophenoxy)-6-methylphenyl]pyrazol-4-yl]-[5-(difluoromethoxy)-6-morpholin-4-yl-1H-indol-2-yl]methanone, (4-25-026) [5-amino-1-[6-(2-fluorophenoxy)-4-methylpyridin-3-yl]pyrazol-4-yl]-[5-(2,2-difluoroethoxy)-6-(4-morpholin-4-ylpiperidin-1-yl)-1H-indol-2-yl]methanone, (4-25-027) [5-amino-1-[6-(2,6-difluorophenoxy)-4-methylpyridin-3-yl]pyrazol-4-yl]-[5-(2,2-difluoroethoxy)-6-(4-morpholin-4-ylpiperidin-1-yl)-1H-indol-2-yl]methanone, (4-25-028) [5-amino-1-[4-(2-fluorophenoxy)-2-methylphenyl]pyrazol-4-yl]-[5-(2,2-difluoroethoxy)-6-(4-morpholin-4-ylpiperidin-1-yl)-1H-indol-2-yl]methanone, (4-25-029) [5-amino-1-[2-fluoro-4-(2-fluorophenoxy)-6-methylphenyl]pyrazol-4-yl]-[5-(2,2-difluoroethoxy)-6-(4-morpholin-4-ylpiperidin-1-yl)-1H-indol-2-yl]methanone, (4-25-030) [5-amino-1-[6-(2-fluorophenoxy)-4-methylpyridin-3-yl]pyrazol-4-yl]-[5-(difluoromethoxy)-6-(4-morpholin-4-ylpiperidin-1-yl)-1H-indol-2-yl]methanone, (4-25-031) [5-amino-1-[6-(2,6-difluorophenoxy)-4-methylpyridin-3-yl]pyrazol-4-yl]-[5-(difluoromethoxy)-6-(4-morpholin-4-ylpiperidin-1-yl)-1H-indol-2-yl]methanone, (4-25-032) [5-amino-1-[4-(2-fluorophenoxy)-2-methylphenyl]pyrazol-4-yl]-[5-(difluoromethoxy)-6-(4-morpholin-4-ylpiperidin-1-yl)-1H-indol-2-yl]methanone, (4-26-001) N-[2[5-amino-1-[4-(2-fluorophenoxy)-2-methylphenyl]pyrazole-4-carbonyl]-5-fluoro-1H-indol-6-yl]-2-oxo-2-pyrrolidin-1-ylethanesulfonamide.

Such compounds of the present invention or pharmaceutically acceptable salts thereof are useful as compounds having an Src family kinase inhibitory effect and are useful for preventing and/or treating cancer.

Examples of the cancer include blood cancer and solid cancer, and preferably include esophageal cancer, lung cancer, and bile duct cancer.

The compounds according to the present invention or pharmaceutically acceptable salts thereof or their isomers can be formulated by conventional methods into tablets, powders, fine granules, granules, coated tablets, capsules, syrups, troches, inhalations, suppositories, injections, ointments, ophthalmic ointments, ophthalmic preparations, nasal preparations, ear preparations, cataplasms, lotions, and the like. Commonly used excipients, binders, lubricants, colorants, correctives, and as necessary, stabilizers, emulsifiers, absorption promoters, surfactants, pH adjusters, preservatives, antioxidants, and the like can be used for formulation, and they are blended with ingredients commonly used as raw materials of pharmaceutical preparations and formulated by conventional methods.

For example, oral preparations are manufactured by adding excipients and as necessary, binders, disintegrants, lubricants, colorants, correctives, and the like to the compounds according to the present invention or pharmaceutically acceptable salts thereof or their isomers, and then formulating them into powders, fine granules, granules, tablets, coated tablets, capsules, and the like by conventional methods.

Examples of these ingredients include animal and vegetable oils such as soybean oil, beef tallow, and synthetic glyceride; hydrocarbons such as liquid paraffin, squalane, and solid paraffin; ester oils such as octyldodecyl myristate and isopropyl myristate; higher alcohols such as cetostearyl alcohol and behenyl alcohol; silicone resin; silicone oil; surfactants such as polyoxyethylene fatty acid ester, sorbitan fatty acid ester, glycerol fatty acid ester, polyoxyethylene sorbitan fatty acid ester, polyoxyethylene hydrogenated castor oil, and a polyoxyethylene-polyoxypropylene block copolymer; water-soluble polymers such as hydroxyethylcellulose, polyacrylic acid, a carboxyvinyl polymer, polyethylene glycol, polyvinylpyrrolidone, and methylcellulose; lower alcohols such as ethanol and isopropanol; polyhydric alcohols such as glycerol, propylene glycol, dipropylene glycol, and sorbitol; sugars such as glucose and sucrose; inorganic powders such as silicic anhydride, magnesium aluminum silicate, and aluminum silicate; and purified water.

Examples of excipients include lactose, corn starch, white soft sugar, glucose, mannitol, sorbitol, microcrystalline cellulose, and silicon dioxide.

Examples of binders include polyvinyl alcohol, polyvinyl ether, methylcellulose, ethylcellulose, acacia, tragacanth, gelatin, shellac, hydroxypropylmethylcellulose, hydroxypropylcellulose, polyvinylpyrrolidone, a polypropylene glycol-polyoxyethylene block polymer, and meglumine.

Examples of disintegrants include starch, agar, gelatin powder, microcrystalline cellulose, calcium carbonate, sodium bicarbonate, calcium citrate, dextrin, pectin, and carboxymethylcellulose calcium.

Examples of lubricants include magnesium stearate, talc, polyethylene glycol, silica, and hydrogenated vegetable oil.

Colorants used are those approved as additives to pharmaceuticals. Correctives used are cocoa powder, peppermint camphor, empasm, mentha oil, borneol, powdered cinnamon bark, and the like.

It is obviously possible to sugar-coat or otherwise coat these tablets and granules appropriately as necessary. Liquid preparations such as syrups and injectable preparations are manufactured by adding pH adjusters, solubilizers, tonicity adjusting agents, and the like, and as necessary, solubilizing agents, stabilizers, and the like to the compounds according to the present invention or pharmaceutically acceptable salts thereof, and formulating them by conventional methods.

The method of manufacturing external preparations is not limited, and they can be manufactured by conventional methods. Specifically, various raw materials commonly used for pharmaceuticals, quasi drugs, cosmetics, and the like can be used as base ingredients for formulation. Specific examples of the base ingredients used include raw materials such as animal and vegetable oils, mineral oils, ester oils, waxes, higher alcohols, fatty acids, silicone oil, surfactants, phospholipids, alcohols, polyhydric alcohols, water-soluble polymers, clay minerals, and purified water. Further, pH adjusters, antioxidants, chelating agents, preservatives and fungicides, colorants, flavors, and the like may be added as necessary. However, the base ingredients for external preparations according to the present invention are not limited to these materials.

Ingredients such as ingredients having a differentiation-inducing effect, blood flow promoters, bactericides, anti-inflammatory agents, cell activators, vitamins, amino acids, humectants, and keratolytic agents may also be blended as necessary. The aforementioned base ingredients are added in an amount corresponding to the concentration usually chosen for the manufacture of external preparations.

The mode of administration of the compounds according to the present invention or pharmaceutically acceptable salts thereof or their isomers is not particularly limited, and they may be orally or parenterally administered by methods commonly used. For example, they can be formulated into preparations such as tablets, powders, granules, capsules, syrups, troches, inhalations, suppositories, injections, ointments, ophthalmic ointments, ophthalmic preparations, nasal preparations, ear preparations, cataplasms, and lotions, and administered.

The dosage of the medicament according to the present invention can be appropriately selected depending on the severity of the symptom, the age, the sex, the body weight, the mode of administration, the type of the salt, the specific type of the disease, and the like.

Although the dosage significantly varies according to the type of the disease, the severity of the symptom, the age, and the sex difference of the patient, and the difference in sensitivity to drugs between the patients, and the like, the dosage is usually about 0.03 to 1000 mg, preferably 0.1 to 500 mg, and more preferably 0.1 to 100 mg per day for adults, and is administered in one to several doses per day. For injections, the dosage is usually about 1 µg/kg to 3000 µg/kg, preferably about 3 µg/kg to 1000 µg/kg.

In the manufacture of the compounds according to the present invention, raw material compounds and various reagents may form salts, hydrates, or solvates. They would vary according to the starting material, the solvent used, and the like, and are not particularly limited as long as they do not inhibit the reaction.

It is needless to say that the solvent used also varies according to the starting material, the reagent, and the like, and is not particularly limited as long as it does not inhibit the reaction and dissolves the starting material to a certain extent.

Various isomers (e.g., geometric isomers, optical isomers based on asymmetric carbons, rotamers, stereoisomers, tautomers, and atropisomers) can be purified and isolated using common separation means, e.g., recrystallization, diastereomeric salt formation, enzymatic resolution, and various chromatography methods (e.g., thin-layer chromatography, column chromatography, high performance liquid chromatography, and gas chromatography).

When the compounds according to the present invention are obtained as free forms, they can be converted to salts that may be formed by the compounds or to solvates of the compounds according to conventional methods. When the compounds according to the present invention are obtained as salts or solvates of the compounds, they can be converted to free forms of the compounds according to conventional methods.

The compounds according to the present invention can be isolated and purified by applying common chemical operations such as extraction, concentration, evaporation, crystallization, filtration, recrystallization, and various chromatography methods.

All prior art documents cited herein are hereby incorporated by reference.

The methods for preparing the compounds that are active ingredients of the medicaments of the present invention will be described in more detail with reference to Examples, but the present invention is not to be construed as being limited thereto. The order of reaction steps such as substituent introduction can also be changed as necessary.

Raw material compounds used in the preparation of the compounds of general formula [I] may be those commercially available, or may be those prepared by conventional methods as necessary. Reagents used in the preparation may be those commercially available, or may be those prepared before use by conventional methods as necessary. Solvents used in the preparation, in particular, those used when handling compounds unstable to moisture, oxygen, or the like, may be commercially available dehydrated or degassed solvents, or may be solvents dehydrated or degassed by conventional methods as necessary.

When the compounds are prepared by handling compounds unstable to moisture, oxygen, or the like, the preparation is performed in a reaction system in which the internal atmosphere is replaced by an inert atmosphere, specifically, well-dried nitrogen or argon. The preparation is performed by varying the temperature of the reaction system according to the properties and reactivity of compounds. The optimum reaction temperature is from −100° C. (cooled with liquid nitrogen) to a temperature near the boiling point of the solvent. A reaction temperature which is the boiling point of the solvent or higher, for example, about 250° C. to 300° C. may be used in a reaction performed in a closed system such as a reaction using microwaves.

Protecting groups (PG) represent, for example, methyl, ethyl, tert-butyl, benzyl, substituted benzyl, acetyl, tert-butoxycarbonyl, benzyloxycarbonyl, methanesulfonyl, trifluoromethanesulfonyl, trimethylsilyl, triethylsilyl, triisopropylsilyl, tert-butyldimethylsilyl, and tetrahydropyranyl. In the preparation methods shown below, the preparation can be carried out using means such as protection and deprotection of functional groups, when the defined groups are subjected to an undesirable chemical conversion under the conditions of the methods performed.

Examples of selection and detachment of the protecting group may include the methods described in Greene and Wuts, "Protective Groups in Organic Sythesis" (Fourth edition, Wiley, 2006), which may be appropriately used depending on the reaction conditions.

Substituent introduction and functional group conversion reactions can be carried out by, for example, the methods described in Smith and March, "March's Advanced Organic Chemistry", Seventh edition, Wiley, 2013 or Richard C. Larock, "Comprehensive Organic Transformations", Second edition, Wiley, 2010.

[General Synthesis Methods]

In the following general synthesis methods for the compounds of the present application, $Ar^1$, $Ar^2$, $R^1$, $R^2$, and the like are defined according to the specific definitions described below, otherwise, the definitions for the above general formula may be applied.

A ketonitrile compound of formula 2 can be obtained by the reaction of an ester compound of formula 1 with an acetonitrile anion produced by subjecting acetonitrile with a base. The compound of formula 1 is commercially available or can be prepared by a method known in the art. For example, indole-2-carboxylic acid ethyl ester is commercially available.

The compound of formula 1 can be prepared by heating a corresponding carboxylic acid with an alcohol in the presence of an acid (such as sulfuric acid). It can also be prepared by reacting a corresponding carboxylic acid with a chlorinating agent such as thionyl chloride or oxalyl chloride in a solvent (such as dichloromethane or dimethylformamide) and then subjecting the prepared acid chloride with an alcohol (alkyl-OH) and a base (such as TEA or DIPEA). The alcohol is a lower alcohol having 1 to 6 carbon atoms which may be linear or branched, and is preferably methanol, ethanol, 2-propanol, or 1-propanol.

The compound of formula 2 can be prepared by a method known in the art. It can be prepared by treating acetonitrile with a base (such as LHMDS, LDA, or NaHMDS) in a solvent (such as tetrahydrofuran) and reacting the produced acetonitrile anion with the compound of formula 1 obtained above. Depending on the functional group on the indole, a protecting group (PG) can be used as necessary to prepare the target compound efficiently. Examples of selection and detachment of the protecting group may include the methods described in Greene and Wuts, "Protective Groups in Organic Synthesis" (Fourth edition, Wiley, 2006), which may be appropriately used depending on the reaction conditions. Arylsulfonyl groups (such as benzenesulfonyl and toluenesulfonyl groups), silyl groups (such as trimethylsilyl and trimethylsilylethoxymethyl groups), carbamoyl groups (such as Boc and Cbz groups), and the like can be used for protecting NH or OH groups.

A compound of formula 3 can be prepared by a method known in the art. An enamine compound (formula 3) can be prepared by reacting the ketonitrile compound obtained above (formula 2) with N,N-dimethylformamide dimethylacetal in a solvent (such as tetrahydrofuran, toluene, or dimethylformamide, or a mixed solvent thereof). A compound of formula 4 can be prepared by a method known in the art. An enol ether compound (formula 4) can be prepared by reacting the ketonitrile compound of formula 2 obtained above with triethyl orthoformate in a solvent (such as acetic anhydride or acetonitrile) with heating.

The compound of general formula [I] can be prepared by a method known in the art. It can be prepared by reacting the enamine compound of formula 3 or the enol ether compound of formula 4 with an arylhydrazine compound of formula 5 in a solvent (such as dimethylformamide, dimethylacetamide, 1-methyl-2-pyrrolidinone, or ethanol) in the presence of a base (such as TEA or 4-methylmorpholine), or in a solvent (such as dimethylformamide, dimethylacetamide, 1-methyl-2-pyrrolidinone, or ethanol) in the absence of a base.

The arylhydrazine compound of formula 5 used can be, for example, a free form (where $R^{15}$=H), an acid salt, or a compound protected with a Boc group (where $R^{15}$=Boc). For example, the free form can be produced from an acid salt using a base (such as TEA or 4-methylmorpholine) and used for preparing the compound of general formula [I]. The protected arylhydrazine compound of formula 5 can also be used for preparing the compound of general formula [I] by reacting with the compound of formula 3 or 4 while producing a deprotected compound using an acid such as hydrochloric acid or methanesulfonic acid. Alternatively, after the acid salt of formula 5 is converted to a free form, or after the compound of formula 5 protected with a Boc group is deprotected with an acid and converted to an acid salt, it can be used for preparing the compound of general formula [I] following isolation or without isolation.

In the preparation of a compound having an NH or OH group as a functional group on the indole, a protecting group (PG) can be used as necessary to prepare the target compound efficiently. Arylsulfonyl groups (such as benzenesulfonyl and toluenesulfonyl groups), silyl groups (such as trimethylsilyl and trimethylsilylethoxymethyl groups), carbamoyl groups (such as Boc and Cbz groups), and the like can be used for protecting NH or OH groups. The compound of general formula [I] can be prepared by derivatizing a ketonitrile compound (formula 2) obtained by using a compound of formula 1 in which an NH or OH group or the like is protected to an enamine compound (formula 3) or an enol ether compound (formula 4), then reacting it with a compound of formula 5 to form an aminopyrazole ring to obtain a protected compound of general formula [1], and subsequently deprotecting the resulting protected compound.

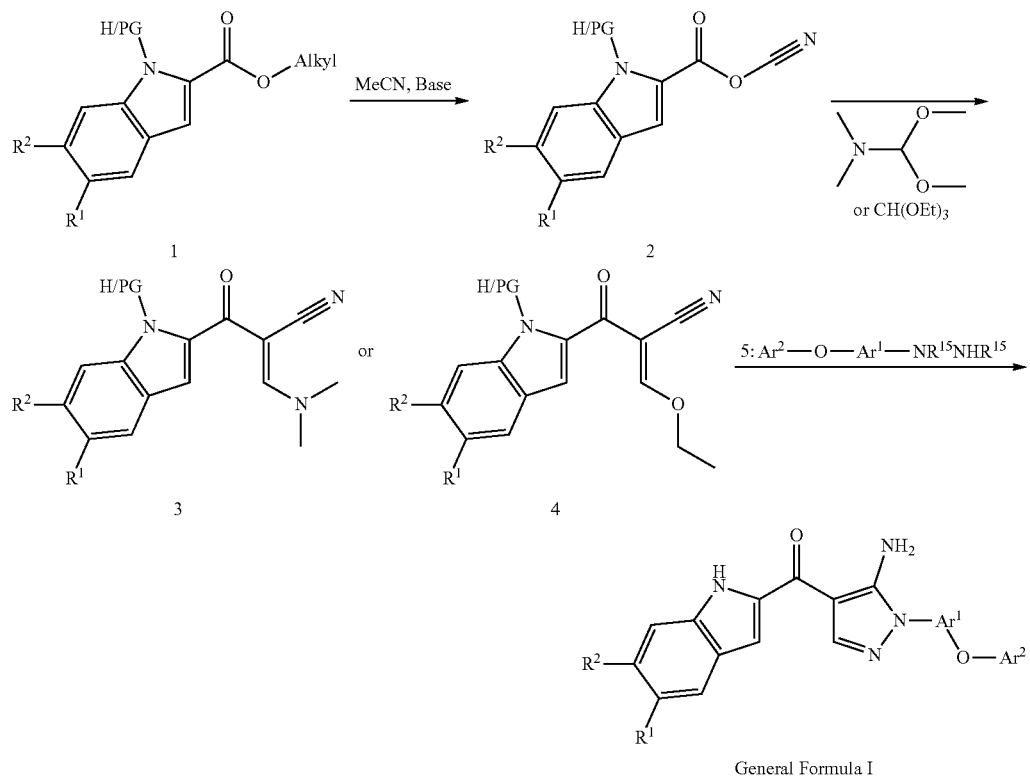

General Formula I (Preparation Method A-2)

A compound of formula 1 can be prepared by introducing an alkoxycarbonyl group into a compound of formula 7 in which a protecting group is introduced into a commercially available indole by a method known in the art. The compound of formula 1 into which an alkoxycarbonyl group (—$CO_2$ alkyl) is introduced can be prepared by subjecting the compound of formula 7 with a base (such as LDA or butyllithium) and then a carbonyl source (such as methyl chloroformate or ethyl chloroformate) in a solvent (such as tetrahydrofuran).

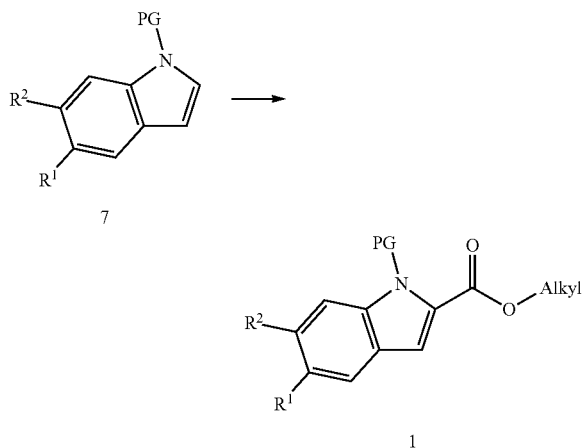

(Preparation Method A-3)

An ester compound (formula 1) can be prepared by the method of Fischer et al. (Chem. Ber., 19, 1563, 1886) using commercially available compounds of formulas 10 (where $R^{15}$=H) and 12. The compound of formula 1 can be prepared by subjecting the compound of formula 12 with the compound of formula 10 (where $R^{15}$=H) in a solvent (such as methanol or ethanol) to provide a compound of formula 11, and then subjecting the compound of formula 11 with an acid (such as hydrochloric acid, sulfuric acid, methanesulfonic acid, trifluoroacetic acid, or polyphosphoric acid) in a solvent (such as methanol, ethanol, or toluene) or without a solvent.

The compound of formula 10 (where $R^{15}$=H) can be prepared by subjecting a commercially available compound of formula 9 with a diazotization reagent (such as sodium nitrite or tert-butyl nitrite) in a solvent (such as methanol, ethanol, acetonitrile, or water) or without a solvent in the presence of an acid (such as hydrochloric acid, sulfuric acid, methanesulfonic acid, or trifluoroacetic acid) by a method known in the art, and treating the produced diazonium salt with a reducing agent (such as tin chloride). The compound of formula 10 (where $R^{15}$=H) can be prepared both as a free form and as a salt of an appropriate acid (such as hydrochloric acid, sulfuric acid, methanesulfonic acid, or trifluoroacetic acid).

The compound of formula 9 as a raw material for the compound of formula 10 can be prepared from a commercially available compound of formula 8a by a method known in the art. The compound of formula 9 can be prepared by subjecting the compound of formula 8a to nitro group reduction reaction (a method using a reducing agent such as sodium hydrosulfite, zinc, or tin chloride, or a reduction reaction performed using a palladium catalyst or the like in a hydrogen atmosphere) in a solvent (such as methanol, ethanol, acetonitrile, or tetrahydrofuran). The compound of formula 9 can be prepared both as a free form and as a salt of an appropriate acid (such as hydrochloric acid, sulfuric acid, methanesulfonic acid, or trifluoroacetic acid).

The compound of formula 9 or 10 (where $R^{15}$=H) can be prepared from a commercially available compound of formula 8b by a method known in the art, for example, the method of Buchwald et al. (Organic synthesis, 78, 23; Coll. Vol. 10: 423).

The compound of formula 9 can be prepared using an appropriate reagent as a nitrogen source, for example, tert-butyl carbamate or acetamide, in a solvent (such as N,N-dimethylformamide, N,N-dimethylacetamide, tetrahydrofuran, or 1,4-dioxane) in the presence of a catalyst (such as palladium acetate or copper iodide), a ligand (such as N,N-dimethylglycine, 1-methylimidazole, pyridine-2-carboxylic acid, or ethyl 2-oxocyclohexane-1-carboxylate), and a base (such as potassium carbonate, cesium carbonate, or potassium phosphate).

The compound of formula 10 (where each $R^{15}$ is independently H or Boc) can be prepared by subjecting the compound of formula 8b with an appropriate reagent as a hydrazine source, for example, tert-butyl carbazate or di-tert-butyl hydrazodicarboxylate. The compound of formula 10 (where $R^{15}$=H) can be prepared by the method described above using the compound of formula 9 obtained here.

The compound of formula 10 (where $R^{15}$=Boc) can also be prepared by treating the compound of formula 8b with a base (such as isopropylmagnesium chloride or butyllithium) in a solvent (such as tetrahydrofuran or 1,4-dioxane), and then treating with a reagent as a hydrazine source (such as di-tert-butyl azodicarboxylate).

The compound of formula 10 where one or two $R^{15}$(s) are a Boc group(s) can be prepared into an acid salt of formula 10 after removing the Boc group(s) with an appropriate acid (such as hydrochloric acid, sulfuric acid, methanesulfonic acid, or trifluoroacetic acid). The compound of formula 10 can also be used for preparing the compound of formula 11 without removing the Boc group(s) in this step and removing the Boc group(s) in the reaction solution in the next step.

of formula 11 can obviously be used for preparing the compound of formula 1 by a method such as that of Fischer et al. (Chem. Ber., 19, 1563, 1886).

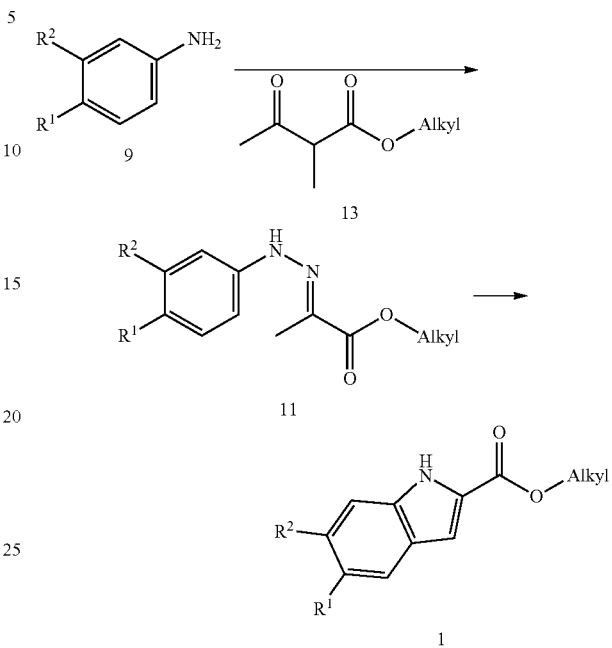

(Preparation Method A-4)

An ester compound of formula 1 can be prepared from a compound of formula 9 by a method known in the art. A compound of formula 14 can be prepared by subjecting the compound of formula 9 with an iodinating agent (such as iodine or N-iodosuccinimide) and, as necessary, a base (such as sodium bicarbonate or pyridine) in a solvent (such as N,N-dimethylformamide, N,N-dimethylacetamide, metha-

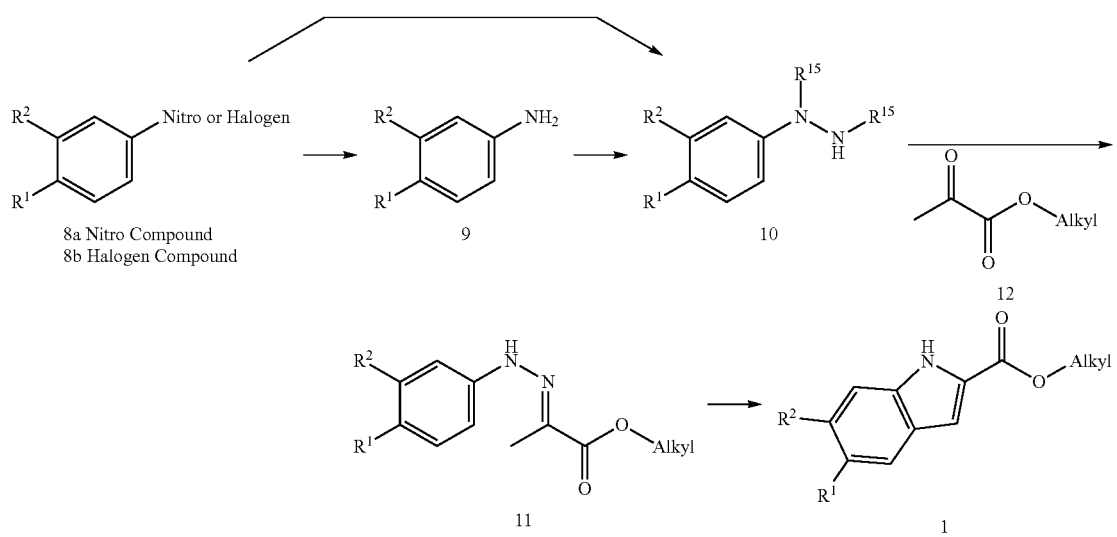

The compound of formula 11 can be prepared by subjecting a diazonium salt prepared from the compound of formula 9 with a compound of formula 13 by the method of Japp et al. (Chem. Ber., 20, 2942, 1887). Like the compound of formula 11 previously described, the obtained compound nol, ethanol, or acetic acid). A compound of formula 15 can be prepared from the compound of formula 14 by a method known in the art. A compound of formula 16 can be prepared from the compound of formula 15 and a compound of formula 17 (such as methyl propiolate) by a method such as that of Peres et al. (J. Med. Chem., 52, 5826, 2009) or Paley et al. (J. Org. Chem., 74, 1611, 2009). The compound of formula 1 can be prepared from the compound of formula 16 by a method such as that of Hiroya et al. (Org. Lett., 6, 2953, 2004. Tetrahedron, 61, 12330, 2005. J. Org. Chem., 69, 1126, 2004).

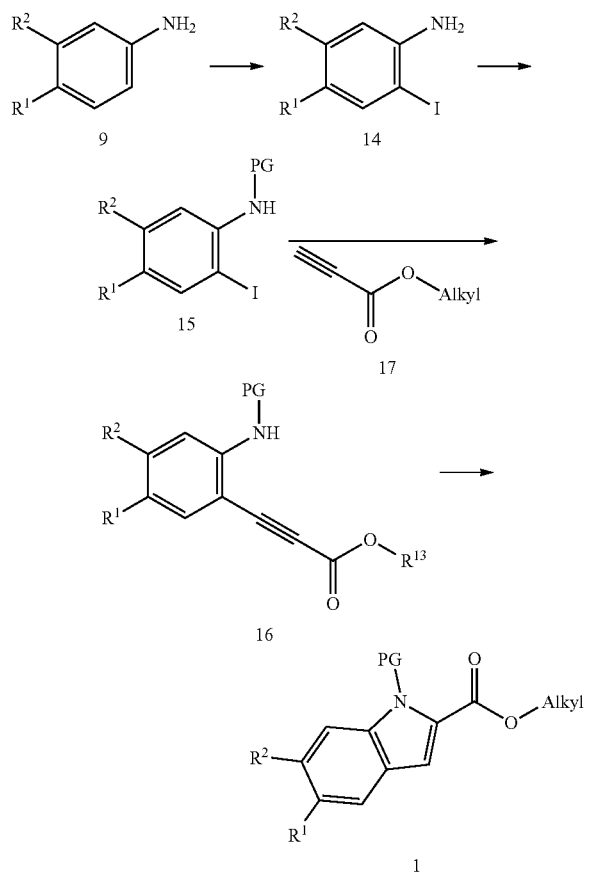

(Preparation Method A-5)

An ester compound of formula 1 can be prepared from a compound of formula 9. The compound of formula 9 can be converted to a compound of formula 18 by treating with a halogenating agent (such as iodine, N-iodosuccinimide, bromine, or N-bromosuccinimide) and, as necessary, a base (such as sodium bicarbonate or pyridine) in a solvent (such as N,N-dimethylformamide, N,N-dimethylacetamide, methanol, ethanol, or acetic acid). The ester compound of formula 1 can be prepared from the compound of formula 18 and pyruvic acid through a compound of formula 6 by a method such as that of Mayes et al. (Org. Process. Res. Dev., 14(5), 1248, 2010). The halogen group in formula 18 is chlorine, bromine, or iodine, and preferably bromine or iodine.

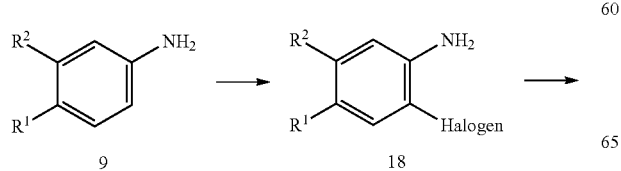

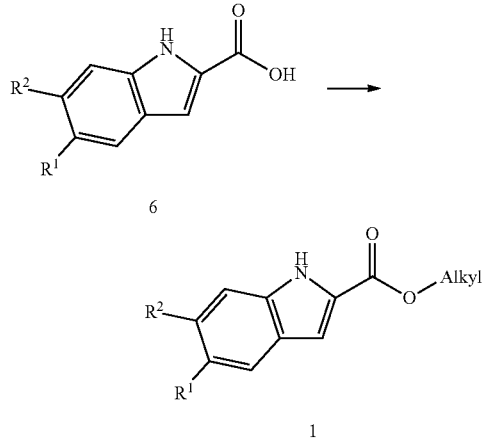

(Preparation Method A-6)

An ester compound of formula 1 can be prepared from a compound of formula 19 by a method such as that of Gore et al. (J. Med. Chem., 56, 3725, 2013) or Nicolaou et al. (Tetrahedron, 63, 6088, 2007). The compound of formula 19 can be converted to a compound of formula 20 by treating with a compound of formula 21 in a solvent (such as methanol, ethanol, or dimethylformamide) in the presence of a base (such as sodium methoxide, sodium ethoxide, or sodium hydride). The ester compound of formula 1 can be prepared by subjecting the compound of formula 20 to nitro group reduction reaction (a method using a reducing agent such as sodium hydrosulfite, zinc, or tin chloride, or a reduction reaction performed using a palladium catalyst or the like in a hydrogen atmosphere) in a solvent (such as methanol, ethanol, acetic acid, tetrahydrofuran, ethylene glycol dimethyl ether, or water, or a mixed solvent thereof).

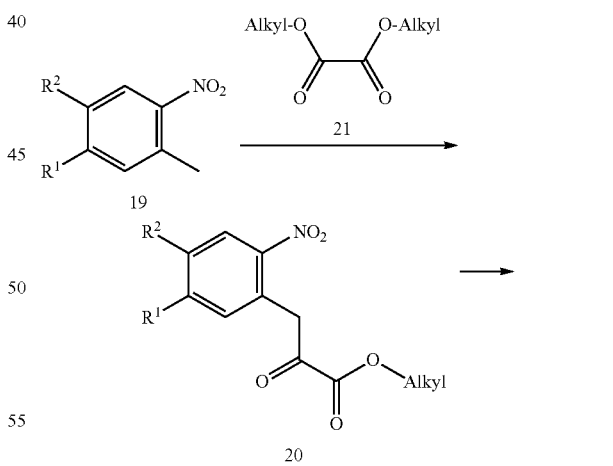

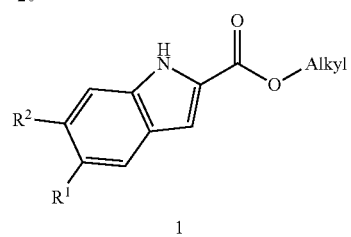

(Preparation Method A-7)

An ester compound of formula 1 can be prepared from a compound of formula 22 by a method such as that of Knittel et al. (Synthesis, 186, 1985). It can be prepared by subjecting the compound of formula 22 with a 2-azidoacetate ester derivative in a solvent (such as methanol or ethanol) in the presence of a base (such as sodium methoxide), and then heating it in a solvent (such as tetrahydrofuran, toluene, or xylene).

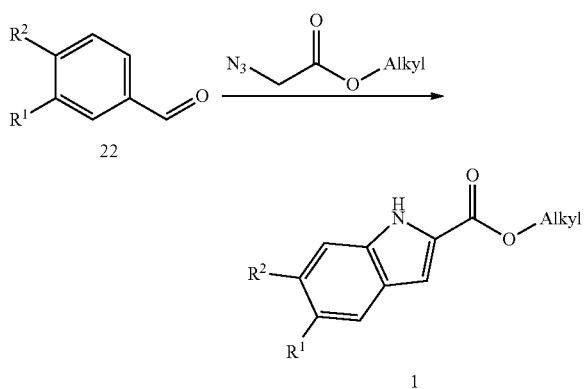

(Preparation Method A-8)

The functional groups of $R^1$ and $R^2$ in an ester compound of formula 1 can be converted each independently or at the same time by a method known in the art. The functional group conversion described below may be performed before forming an indole ring, after forming an indole ring, or after converting to the compound of general formula I.

Depending on the functional group of $R^1$ or $R^2$, a protecting group can be used as necessary to prepare the target compound efficiently. Arylsulfonyl groups (such as benzenesulfonyl and toluenesulfonyl groups), silyl groups (such as trimethylsilyl and trimethylsilylethoxymethyl groups), and carbamoyl groups (such as Boc and Cbz groups) can be used for protecting NH or OH groups.

For example, when one or more selected from $R^1$ and $R^2$ are a carboxylic acid(s), they can be esterified, amidated, or formylated by a method known in the art, and the ester, amide, or formyl group introduced here can be further subjected to functional group conversion. When one or more selected from $R^1$ and $R^2$ are an amino group(s), they can be, for example, acylated, sulfonamidated, or sulfamidated by a method known in the art. The amino group(s) can also be converted to a halogen group(s) by a method known in the art, for example, the method of Sandmeyer et al. (Chem. Ber., 17. 2650, 1884).

When one or more selected from $R^1$ and $R^2$ are a halogen group(s), a functional group(s) can be introduced by forming a C—C bond using a boron derivative by the method of Suzuki et al. (Chemical Reviews, 95(7), 2457, 1995) or Molander et al. (Org. Lett., 393, 3, 2001). Functional groups that can be introduced include aryl, alkyl, and piperidinyl groups, and corresponding commercially available boron derivatives can be used. A functional group selected from Group Q can be further introduced into the functional group introduced here such as a piperidinyl group, by a method known in the art. If boron derivatives are not commercially available, boron derivatives can be prepared by methods known in the art, for example, the methods of Miyaura et al. (J. Org. Chem., 60, 7508, 1995), Hartwig et al. (Chemical Reviews, 110, 890, 2010. Organic Synthesis, 82, 126, 2005), Vedejs et al. (J. Org. Chem., 3020, 60, 1995), and Chan et al. (Tetrahedron Lett., 44, 3863, 2003), and can be used for functional group conversion.

When one or more selected from $R^1$ and $R^2$ are a halogen group(s), a functional group(s) can be introduced by forming an N—C bond using an amide derivative or an amine derivative by the method of Buchwald et al. (Organic Synthesis, 78, 23; Coll. Vol. 10: 423) or Freudenberg et al. (Chem. Ber., 88, 10, 1955). Amide derivatives that can be introduced include acetamide, tert-butyl carbamate, isothiazoline 1,1-dioxide, morpholine-4-sulfonamide, and methanesulfonamide. Functional groups introduced by those such as acetamide and tert-butyl carbamate can then be deprotected as appropriate and further converted by treating with sulfonyl chloride or the like.

When one or more selected from $R^1$ and $R^2$ are a halogen group(s), a functional group(s) can be introduced by forming a C—S bond by a method such as that of Liu et al. (Tetrahedron, 66, 2119, 2010). The introduced sulfur atom can be converted to a sulfoxide or sulfone by treatment with an oxidizing agent (such as oxone, 3-chloroperbenzoic acid, or hydrogen peroxide). Alternatively, a sulfide compound obtained by a method known in the art, for example, the method of Itoh et al. (Org. Lett., 6, 4587, 2004) can be converted to an SH group by cleavage, then converted to a sulfonyl chloride group, and further converted to a sulfonamide group or the like.

When one or more selected from $R^1$ and $R^2$ are a hydroxyl group(s), a functional group(s) can be introduced by forming a C—O bond by, for example, the method of Mitsunobu et al. (Synthesis, 1, 1981), Freudenberg et al. (Chem. Ber., 88, 10, 1955), or Williamson et al. (J. Chem. Soc., 4, 229, 1852). Functional groups that can be introduced include alkyl, haloalkyl, and aminoalkyl groups.

When one or more selected from $R^1$ and $R^2$ are a hydroxyl group(s), the hydroxyl group(s) can also be converted to trifluoromethanesulfonamide by the method of Huth et al. (Tetrahedron, 45, 6679, 1989), and then used for the C—C bond or C—N bond formation reaction as described above using a transition metal catalyst such as Pd or Cu. In the case of $R^1=R^2=H$, an ester compound of formula 1 where $R^1$=boronic acid pinacol ester can be prepared by a method such as that of Hartwig et al. (Organic Synthesis, 82, 126, 2005) using a protecting group as necessary. The boronic acid ester group can be converted to a cyano group, an alkyl group, an amino group (such as a piperazine group or a morpholine group), a halogen group, or the like by a method known in the art. A functional group selected from Group Q can be further introduced into the functional group introduced here such as a piperazine group, by a method known in the art.

The compound of general formula I can be prepared from a previously described compound of formula 3 or 4 that can be prepared from a compound of formula 1, and a compound of formula 5 (arylhydrazine) by a method known in the art. In formula 5, $Ar^1$ is $C_{6-10}$ arylene or 5- to 10-membered heteroarylene, and $Ar^2$ represents $C_{6-10}$ aryl or 5- to 10-membered heteroaryl, where the $Ar^1$ and $Ar^2$ are each independently an arylhydrazine derivative that may have one or more substituents selected from Group R. General preparation methods for the arylhydrazine derivative of formula 5 are described below.

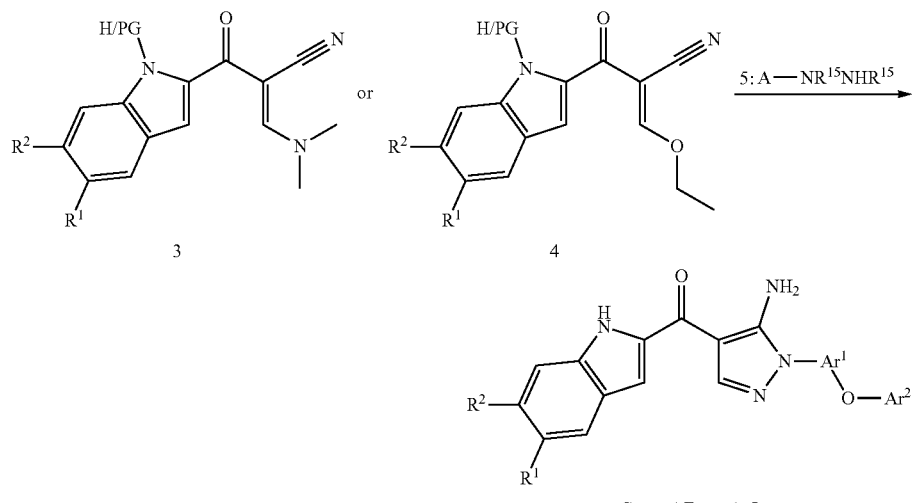

General Formula I (Preparation Method D-1):

An arylhydrazine derivative (formula 5) is commercially available or can be prepared by a method such as that of Freudenberg et al. (Chem. Ber., 88, 10, 1955) from a compound of formula 57 that can be prepared by a method known in the art. A compound of formula 58 can be prepared by subjecting the commercially available compound of formula 57 with a compound of formula 59 in a solvent (such as dimethylformamide, dimethylacetamide, or 1-methyl-2-pyrrolidinone) in the presence of a base (such as potassium carbonate, potassium tert-butoxide, potassium phosphate, or cesium carbonate). The halogen group in formula 59 refers to, for example, fluorine, chlorine, or bromine, and is preferably fluorine or chlorine. $Ar^2$ represents $C_{6-10}$ aryl or 5- to 10-membered heteroaryl substituted with one or more groups selected from Group R (for example, $Ar^2$ represents pyridyl or phenyl which may have a substituent selected from Group R). The compound of formula 5 can be prepared by subjecting the compound of formula 58 with a diazotization reagent (such as sodium nitrite or tert-butyl nitrite) in a solvent (such as methanol, ethanol, acetonitrile, or water) or without a solvent in the presence of an acid (such as hydrochloric acid, sulfuric acid, methanesulfonic acid, or trifluoroacetic acid), and treating the produced diazonium salt with a reducing agent (such as tin chloride). The compound of formula 5 can be prepared both as a free form and as a salt of an appropriate acid (such as hydrochloric acid, sulfuric acid, methanesulfonic acid, or trifluoroacetic acid).

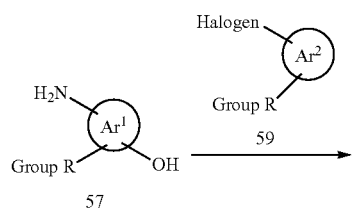

-continued

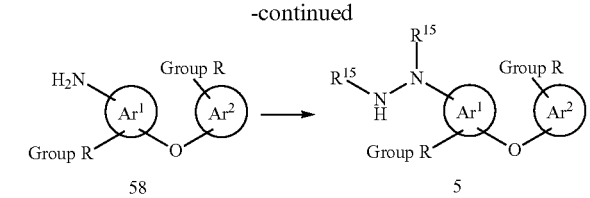

(Preparation Method D-2):

An arylhydrazine derivative (formula 5) can be prepared from a commercially available compound of formula 60 by a method known in the art. The compound of formula 60 can be prepared from a commercially available compound of formula 51 by a method known in the art. The compound of formula 60 can be prepared by treating the compound of formula 51 with a halogenating agent (such as iodine, N-iodosuccinimide, bromine, or N-bromosuccinimide) and, as necessary, a base (such as sodium bicarbonate or pyridine) in a solvent (such as methanol, ethanol, acetonitrile, or tetrahydrofuran). The halogen group in formula 60 is preferably a bromine group or an iodine group. The compound of formula 60 can be converted to a compound of formula 58 by a method such as that of Ullmann et al. (Ber. Dtsch. Chem. Ges., 36, 2389, 1903). The compound of formula 58 can be prepared by subjecting the compound of formula 60 with a compound of formula 61 in a solvent (such as dimethyl sulfoxide, toluene, or 1-methyl-2-pyrrolidinone) in the presence of a catalyst (such as copper iodide or copper chloride) and a catalyst ligand (such as N,N-dimethylglycine, 1-methylimidazole, pyridine-2-carboxylic acid, or ethyl 2-oxocyclohexane-1-carboxylate) and in the presence of a base (such as cesium carbonate, potassium carbonate, potassium tert-butoxide, or potassium phosphate). $Ar^2$ in formula 61 represents $C_{6-10}$ aryl substituted with one or more groups selected from Group R (for example, $Ar^2$ represents phenyl which may have a substituent selected from Group R). The compound of formula 5 can be prepared by subjecting the compound of formula 58 with a diazotization reagent (such as sodium nitrite or tert-butyl nitrite) in a solvent (such as methanol, ethanol, acetonitrile, or water) or without a solvent in the presence of an acid (such as hydrochloric acid, sulfuric acid, methanesulfonic acid, or trifluoroacetic acid), and treating the produced diazonium salt with a reducing agent (such as tin chloride). The compound of formula 5 can be prepared both as a free form and as a salt of an appropriate acid (such as hydrochloric acid, sulfuric acid, methanesulfonic acid, or trifluoroacetic acid).

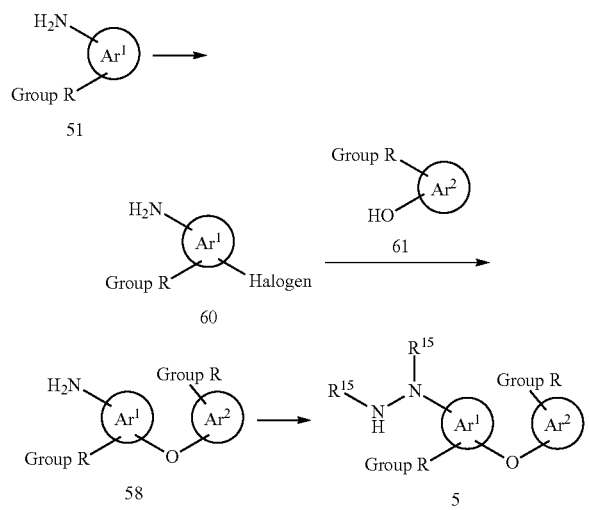

(Preparation Method D-3):

An arylhydrazine derivative (formula 5) can be prepared from a commercially available compound of formula 62 by a method known in the art, for example, the method of Freudenberg et al. (Chem. Ber., 88, 10, 1955). The halogen group in formula 62 refers to a fluorine group, a chlorine group, a bromine group, or an iodine group, and is preferably a fluorine group or a chlorine group. A compound of formula 63 can be prepared by subjecting the compound of formula 62 with a compound of formula 61 in a solvent (such as dimethylformamide, dimethylacetamide, or 1-methyl-2-pyrrolidinone) in the presence of a base (such as cesium carbonate, potassium carbonate, potassium tert-butoxide, or potassium phosphate). $Ar^2$ in formula 61 represents $C_{6-10}$ aryl or 5- to 10-membered heteroaryl substituted with one or more groups selected from Group R (for example, $Ar^2$ represents pyridyl or phenyl which may have a substituent selected from Group R). A compound of formula 58 can be prepared by subjecting the compound of formula 63 with a reducing agent (a method using a reducing agent such as sodium hydrosulfite, zinc, or tin chloride, or a reduction reaction performed using a palladium catalyst or the like in a hydrogen atmosphere) in a solvent (such as methanol, ethanol, tetrahydrofuran, or water, or a mixed solvent thereof). The compound of formula 5 can be prepared by subjecting the compound of formula 58 with a diazotization reagent (such as sodium nitrite or tert-butyl nitrite) in a solvent (such as methanol, ethanol, acetonitrile, or water) or without a solvent in the presence of an acid (such as hydrochloric acid, sulfuric acid, methanesulfonic acid, or trifluoroacetic acid), and treating the produced diazonium salt with a reducing agent (such as tin chloride). The compound of formula 5 can be prepared both as a free form and as a salt of an appropriate acid (such as hydrochloric acid, sulfuric acid, methanesulfonic acid, or trifluoroacetic acid).

(Preparation Method D-4):

An arylhydrazine derivative (formula 5) can be prepared from a commercially available compound of formula 64 by a method known in the art. In formula 64, the halogen A is preferably a fluorine group or a chlorine group, and the halogen B is preferably a bromine group or an iodine group. A compound of formula 65 can be prepared by subjecting the compound of formula 64 with a compound of formula 61 in a solvent (such as dimethylformamide, dimethylacetamide, or 1-methyl-2-pyrrolidinone) in the presence of a base (such as cesium carbonate, potassium carbonate, potassium tert-butoxide, or potassium phosphate). $Ar^2$ in formula 61 represents $C_{6-10}$ aryl or 5- to 10-membered heteroaryl substituted with one or more groups selected from Group R (for example, $Ar^2$ represents pyridyl or phenyl which may have a substituent selected from Group R). The compound of formula 5 (where either or both of $R^{15}$s are Boc or H) can be prepared by treating the compound of formula 65 with a base (such as isopropylmagnesium chloride or butyllithium) in a solvent (such as tetrahydrofuran or 1,4-dioxane), and then treating with a reagent as a hydrazine source (such as di-tert-butyl azodicarboxylate). The compound of formula 5 (where either or both of $R^{15}$s are Boc or H) can also be prepared by subjecting the compound of formula 65 with an appropriate reagent as a hydrazine source (such as tert-butyl carbazate or di-tert-butyl hydrazodicarboxylate) in a solvent (such as N,N-dimethylformamide, N,N-dimethylacetamide, tetrahydrofuran, or 1,4-dioxane) in the presence of a catalyst (such as palladium acetate or copper iodide), a ligand (such as XPhos, tBuXPhos, N,N-dimethylglycine, 1-methylimidazole, pyridine-2-carboxylic acid, or ethyl 2-oxocyclohexane-1-carboxylate), and a base (such as potassium carbonate, cesium carbonate, or potassium phosphate). The obtained compound of formula 5 where one or two $R^{15}$(s) are a Boc group(s) can be used as a salt of formula 5 for preparing the compound of general formula [I] after removing the Boc group(s) with an appropriate acid (such as hydrochloric acid, sulfuric acid, methanesulfonic acid, or trifluoroacetic acid). It can also be used for preparing the compound of general formula [I] without removing the Boc group(s) in this step, and removing the Boc group(s) in the reaction solution in the next step.

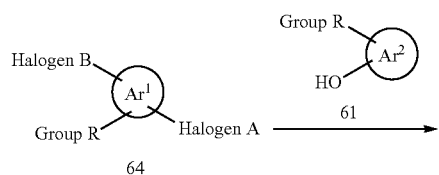

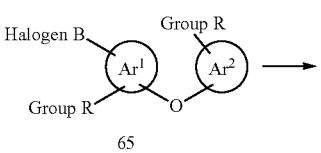

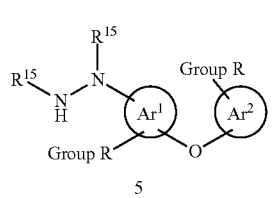

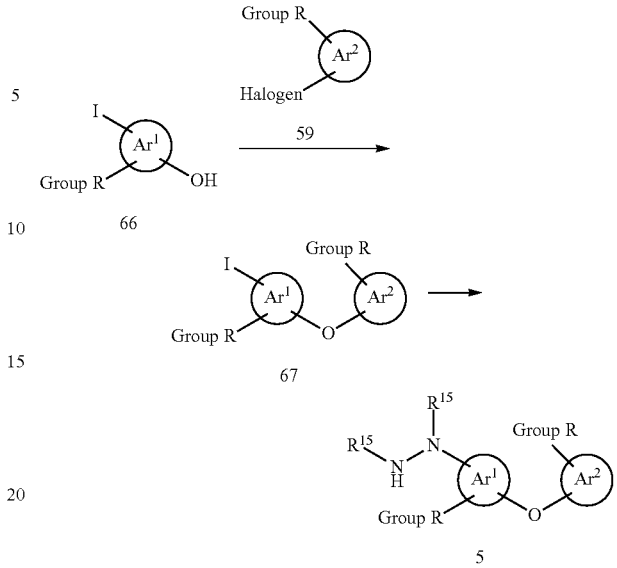

(Preparation Method D-5):

An arylhydrazine derivative (formula 5) can be prepared from a commercially available iodophenol derivative (formula 66) by a method known in the art. A compound of formula 67 can be prepared by subjecting the iodophenol derivative (formula 66) with a compound of formula 59 in a solvent (such as dimethyl sulfoxide, toluene, or 1-methyl-2-pyrrolidinone) in the presence of a base (such as potassium phosphate, cesium carbonate, potassium carbonate, or potassium tert-butoxide) and, as necessary, a catalyst (such as copper iodide or copper chloride) and a catalyst ligand (such as XPhos, tBuXPhos, N,N-dimethylglycine, 1-methylimidazole, pyridine-2-carboxylic acid, or ethyl 2-oxocyclohexane-1-carboxylate). $Ar^2$ in formula 59 represents $C_{6-10}$ aryl or 5- to 10-membered heteroaryl substituted with one or more groups selected from Group R (for example, $Ar^2$ represents pyridyl or phenyl which may have a substituent selected from Group R). The compound of formula 5 (where either or both of $R^{15}$s are Boc or H) can be prepared by subjecting the compound of formula 67 with an appropriate reagent as a hydrazine source (such as tert-butyl carbazate or di-tert-butyl hydrazodicarboxylate) in a solvent (such as tetrahydrofuran or 1,4-dioxane) in the presence of a catalyst (such as palladium acetate or copper iodide), a ligand (such as XPhos, tBuXPhos, N,N-dimethylglycine, 1-methylimidazole, pyridine-2-carboxylic acid, or ethyl 2-oxocyclohexane-1-carboxylate), and a base (such as potassium phosphate, potassium carbonate, or cesium carbonate). The obtained compound of formula 5 where one or two $R^{15}$(s) are a Boc group(s) can be used as a salt of formula 5 for preparing the compound of general formula [I] after removing the Boc group(s) with an appropriate acid (such as hydrochloric acid, sulfuric acid, methanesulfonic acid, or trifluoroacetic acid). It can also be used for preparing the compound of general formula [I] without removing the Boc group(s) in this step and removing the Boc group(s) in the reaction solution in the next step.

(Preparation Method D-6):

An arylhydrazine derivative (formula 5) can be prepared from a commercially available compound of formula 62 by a method known in the art. A compound of formula 63 can be prepared by subjecting the compound of formula 62 with a compound of formula 61 in a solvent (such as dimethylformamide, dimethylacetamide, or 1-methyl-2-pyrrolidinone) in the presence of a base (such as cesium carbonate, potassium carbonate, potassium tert-butoxide, or potassium phosphate). $Ar^2$ in formula 61 represents $C_{6-10}$ aryl or 5- to 10-membered heteroaryl substituted with one or more groups selected from Group R (for example, $Ar^2$ represents phenyl which may have a substituent selected from Group R). A compound of formula 58 can be prepared by treating the compound of formula 63 with a reducing agent (a method using a reducing agent such as sodium hydrosulfite, zinc, or tin chloride, or a reduction reaction performed using a palladium catalyst or the like in a hydrogen atmosphere) in a solvent (such as methanol, ethanol, tetrahydrofuran, or water, or a mixed solvent thereof). A compound of formula 67 can be prepared by subjecting the compound of formula 58 with a diazotization reagent (such as sodium nitrite or tert-butyl nitrite) in a solvent (such as methanol, ethanol, acetonitrile, or water) in the presence of an acid (such as hydrochloric acid, sulfuric acid, methanesulfonic acid, or trifluoroacetic acid), and subjecting the produced diazonium salt with an iodine source (e.g., copper iodide, or an alkali metal iodide salt such as potassium iodide). The compound of formula 5 (where either or both of $R^{15}$s are Boc or H) can be prepared by subjecting the compound of formula 67 with an appropriate reagent as a hydrazine source (such as tert-butyl carbonate or di-tert-butyl hydrazodicarboxylate) in a solvent (such as tetrahydrofuran or 1,4-dioxane) in the presence of a catalyst (such as palladium acetate or copper iodide), a ligand (such as XPhos, tBuXPhos, N,N-dimethylglycine, 1-methylimidazole, pyridine-2-carboxylic acid, or ethyl 2-oxocyclohexane-1-carboxylate), and a base (such as potassium phosphate, potassium carbonate, or cesium carbonate). The obtained compound of formula 5 where one or two $R^{15}$(s) are a Boc group(s) can be used as a salt of formula 5 for preparing the compound of general formula [I] after removing the Boc group(s) with an appropriate acid (such as hydrochloric acid, sulfuric acid, methanesulfonic acid, or trifluoroacetic acid). It can also be used for preparing the compound of general formula [I] without removing the Boc group(s) in this step and removing the Boc group(s) in the reaction solution in the next step.

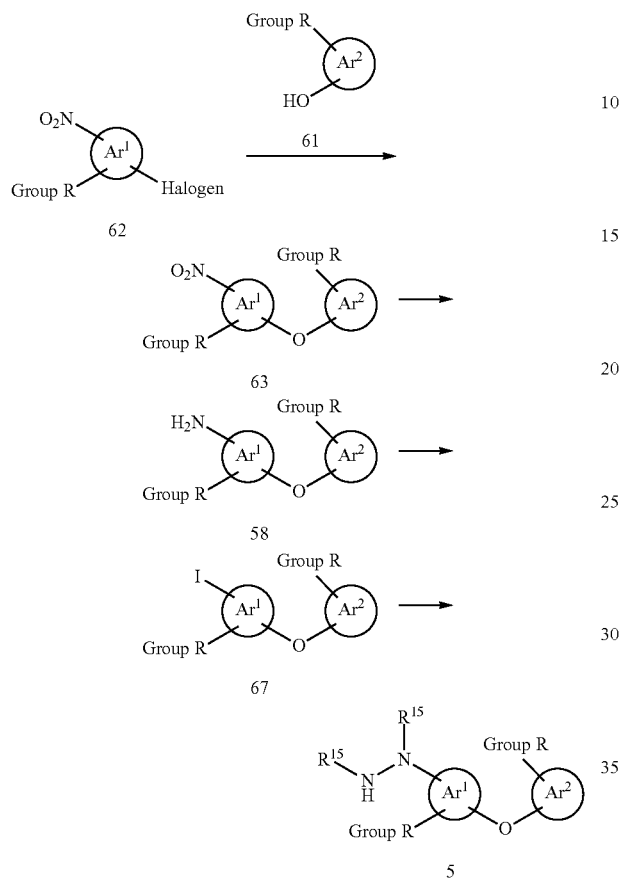

(Preparation Method D-7):

An arylhydrazine derivative (formula 5) can be prepared from a commercially available compound of formula 66 by a method known in the art. A compound of formula 67 can be prepared by subjecting the compound of formula 66 with a compound of formula 59 in a solvent (such as dimethyl sulfoxide, toluene, or 1-methyl-2-pyrrolidinone) in the presence of a base (such as potassium phosphate, cesium carbonate, potassium carbonate, or potassium tert-butoxide) and, as necessary, a catalyst (such as copper iodide or copper chloride) and a catalyst ligand (such as N,N-dimethylglycine, 1-methylimidazole, pyridine-2-carboxylic acid, or ethyl 2-oxocyclohexane-1-carboxylate). $Ar^2$ in formula 59 represents $C_{6-10}$ aryl or 5- to 10-membered heteroaryl substituted with one or more groups selected from Group R (for example, $Ar^2$ represents pyridyl or phenyl which may have a substituent selected from Group R). The halogen group in formula 59 is a fluorine group, a chlorine group, a bromine group, or an iodine group. The compound of formula 5 (where either or both of $R^{15}$s are Boc or H) can be prepared by subjecting the compound of formula 67 with an appropriate reagent as a hydrazine source (such as tert-butyl carbazate or di-tert-butyl hydrazodicarboxylate) in a solvent (such as tetrahydrofuran or 1,4-dioxane) in the presence of a catalyst (such as palladium acetate or copper iodide), a ligand (such as XPhos, tBuXPhos, N,N-dimethylglycine, 1-methylimidazole, pyridine-2-carboxylic acid, or ethyl 2-oxocyclohexane-1-carboxylate), and a base (such as potassium phosphate, potassium carbonate, or cesium carbonate). When the functional group on $Ar^2$ of formula 5, which corresponds to Group R, is a halogen group, the compound of formula 5 can be further subjected to hydrogenation reaction or the like in a solvent (such as methanol or ethanol) in the presence of a metal catalyst such as palladium carbon, to prepare a compound of formula 5 from which the halogen group on $Ar^2$ is removed. The obtained compound of formula 5 where one or two $R^{15}$(s) are a Boc group(s) can be used as a salt of formula 5 for preparing the compound of general formula [I] after removing the Boc group(s) with an appropriate acid (such as hydrochloric acid, sulfuric acid, methanesulfonic acid, or trifluoroacetic acid). It can also be used for preparing the compound of general formula [I] without removing the Boc group(s) in this step and removing the Boc group(s) in the reaction solution in the next step.

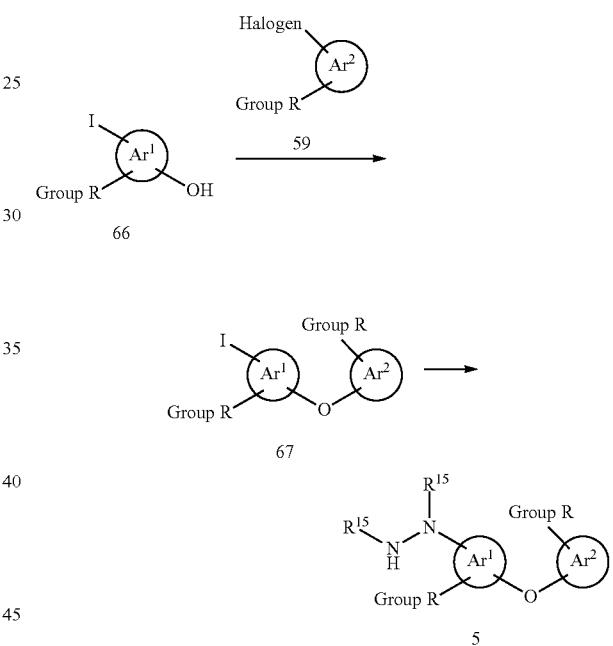

(Preparation Method E-1)

Sulfamidating reagents are commercially available or can be prepared by methods known in the art. For example, a sulfamidating reagent (formula 91) can be prepared by subjecting chlorosulfonyl isocyanate with 2-bromoethanol in a solvent (such as dichloromethane), and then subjecting the prepared compound of formula 90 with a primary amine ($R^{14}$—$NH_2$). Depending on the functional group on the primary amine used here, a protecting group can be used as necessary to prepare the target compound efficiently. Arylsulfonyl groups (such as benzenesulfonyl and toluenesulfonyl groups), silyl groups (such as tert-butyldimethylsilyl, trimethylsilyl, and trimethylsilylethoxymethyl groups), carbamoyl groups (such as Boc and Cbz groups), and the like can be used for protecting the functional group. The sulfamidating reagent (formula 91) may be prepared before use and used as a solution, or may be isolated by a method known in the art and used.

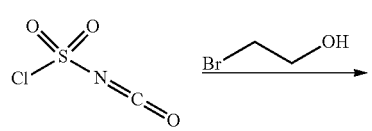

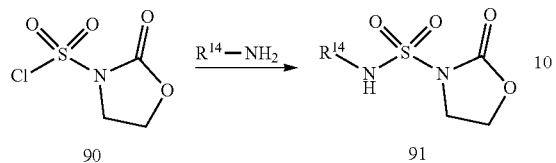

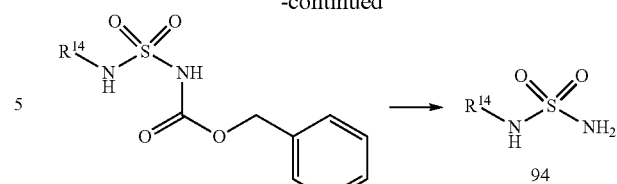

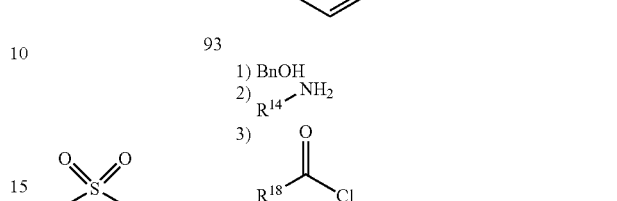

A sulfamidating reagent (formula 92) can also be prepared by subjecting sulfuryl chloride with a secondary amine (R$^{16}$R$^{17}$NH, such as morpholine or piperidine) in a solvent (such as dichloromethane) in the presence of a base (such as triethylamine). Depending on the functional group on the secondary amine used here, a protecting group can be used as necessary to prepare the target compound efficiently. Arylsulfonyl groups (such as benzenesulfonyl and toluenesulfonyl groups), silyl groups (such as tert-butyldimethylsilyl, trimethylsilyl, and trimethylsilylethoxymethyl groups), carbamoyl groups (such as Boc and Cbz groups), and the like can be used for protecting the functional group. The sulfamidating reagent (formula 92) may be prepared before use and used as a solution, or may be isolated by a method known in the art and used.

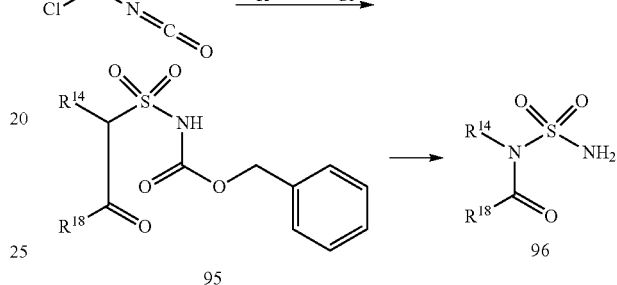

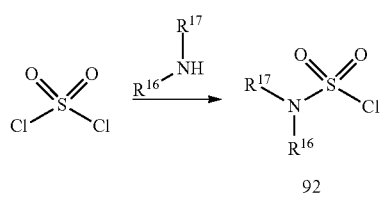

Compounds of formulas 93 and 97 can also be prepared by subjecting chlorosulfonyl isocyanate with benzyl alcohol in a solvent (such as dichloromethane), and then subjecting the prepared benzyl N-chlorosulfonylcarbamate with a primary amine (R$^{14}$—NH$_2$, such as methylamine) or a secondary amine (R$^{16}$R$^{17}$NH, such as morpholine). When a primary amine is allowed to act, a compound of formula 95 can be prepared by further treating with an acylating agent (such as pivaloyl chloride or acetyl chloride). Sulfamidating reagents (formulas 94, 96, and 98) can be prepared by removing the Cbz groups from the compounds of formulas 93, 95, and 97 in a solvent (such as methanol) in the presence of Pd—C in a hydrogen atmosphere. The sulfamidating reagents (formulas 94, 96, and 98) may be prepared before use and used as solutions, or may be isolated by a method known in the art and used.

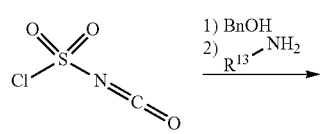

(Preparation Method E-2)

Sulfonamidation can be performed using sulfonyl chloride or sulfonamide. Sulfonamidating reagents are commercially available or can be prepared by a method known in the art. For example, methanesulfonyl chloride and methanesulfonamide are commercially available. As a commercially unavailable sulfonyl chloride, a sulfonamidating reagent (formula 102) can be prepared by subjecting a commercially available compound of formula 99 with a brominating agent (such as carbon tetrabromide or triphenylphosphine) in a solvent (such as tetrahydrofuran) to provide a compound of formula 100, then treating it with thiourea in a solvent such as ethanol to provide a compound of formula 101, and further treating it with N-chlorosuccinimide in a solvent such as acetic acid. The sulfamidating reagent (formula 102) may be prepared before use and used as a solution, or may be isolated by a method known in the art and used.

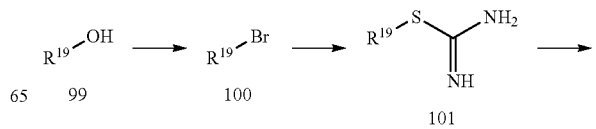

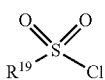

A method of preparing a sulfonyl chloride (formula 107) from a commercially available alkylsulfonyl chloride is known in the art. A compound of formula 105 in which $R^{20}$ is converted to $R^{22}$ can be prepared by converting a commercially available compound of formula 103 to a compound of formula 104 by treatment with a base (such as pyridine) in a solvent (such as 2-propanol), and then introducing a functional group onto the alkylsulfonyl group ($R^{20}$). Next, the sulfonamidating reagent (formula 107) can be prepared by treating the compound of formula 105 with potassium thiocyanate to prepare a compound of formula 106, and then treating it with thionyl chloride. The sulfonamidating reagent (formula 107) may be prepared before use and used as a solution, or may be isolated by a method known in the art and used.

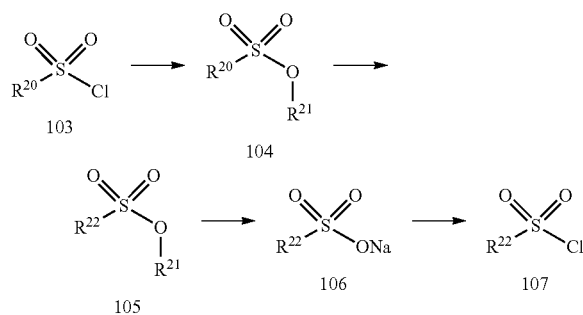

(Preparation Method E-3)

A corresponding sulfonamidating reagent (formula 108 or 109) can be prepared by subjecting a commercially available sulfonyl chloride or a compound of formula 102 or 107 prepared by the preparation method E-2 with a commercially available solvent containing ammonia gas (such as aqueous ammonia) in a solvent (such as tetrahydrofuran or dioxane). The sulfonamidating reagent (formula 108 or 109) may be prepared before use and used as a solution, or may be isolated by a method known in the art and used.

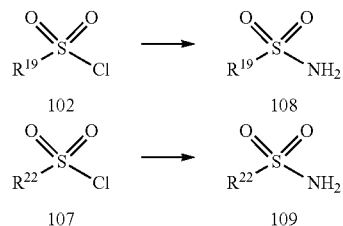

(Preparation Method E-4)

Commercially available sulfonyl chlorides, commercially available sulfamidating reagents, sulfamidating reagents prepared by the preparation method E-1, sulfonamidating reagents prepared by the preparation method E-2, or sulfonamidating reagents prepared by the preparation method E-3 can be used for preparing the compounds of general formula I in which a sulfamide or sulfonamide group is introduced into $R^1$ or $R^2$. Such a functional group conversion may be performed before forming an indole ring, after forming an indole ring, or after converting to the compound of general formula I.

Depending on the functional group on the $R^1$, $R^2$, sulfonamide group, or sulfamide group, a protecting group can be used as necessary to prepare the target compound efficiently. Arylsulfonyl groups (such as benzenesulfonyl and toluenesulfonyl groups), silyl groups (such as trimethylsilyl and trimethylsilylethoxymethyl groups), and carbamoyl groups (such as Boc and Cbz groups) can be used for protecting NH or OH groups.

For example, when one or more functional groups selected from $R^1$ and $R^2$ are an amino group(s) ($NH_2$), the amino group(s) can be sulfonamidated or sulfamidated by a method known in the art. For example, a compound of formula 1 having a sulfonamide group can be prepared using a base (such as pyridine or triethylamine) and a commercially available sulfonamidating reagent, a sulfonamidating reagent prepared by the preparation method E-2, or a commercially available halogenated sulfonamidating reagent such as alkylsulfonyl chloride for a compound of formula 1 in which $R^2$ is an amino group in a solvent (such as dichloromethane). Alternatively, for example, a compound of formula 1 having a sulfamide group can be prepared using a base (such as pyridine or triethylamine) and a commercially available sulfamidating reagent or a sulfamidating reagent prepared by the preparation method E-1 for a compound of formula 1 in which $R^2$ is an amino group in a solvent (such as dichloromethane).

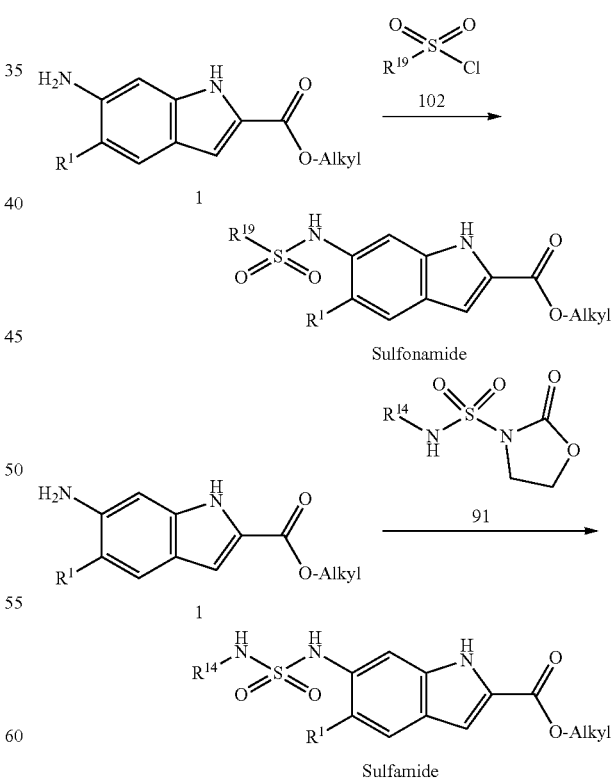

When one or more functional groups selected from $R^1$ and $R^2$ are a halogen group(s), a compound of formula 1 having a sulfonamide or sulfamide group can be prepared using a commercially available sulfonamidating or sulfamidating reagent or using a sulfonamidating or sulfamidating reagent prepared by the preparation method E-1, E-2, or E-3. For example, a compound of formula 1 having a sulfonamide or sulfamide group can be prepared from a compound of formula 1 where $R^2$ is a halogen group by a method known in the art, for example, the method of Buchwald et al. (Organic Synthesis, 78, 23; Coll. Vol. 10: 423, J. Am. Chem. Soc., 124, 6043, 2002). A compound into which a sulfonamide or sulfamide group is introduced can be prepared.

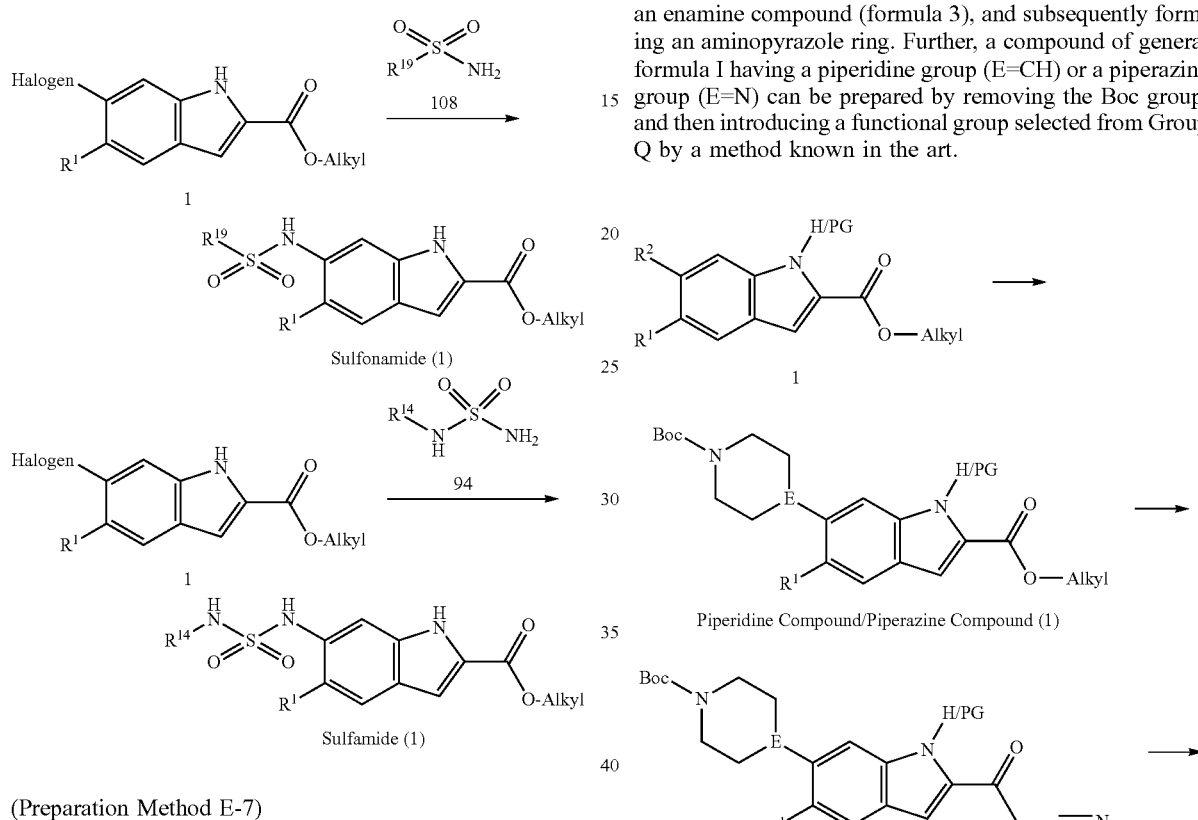

Sulfonamide (1)

Sulfamide (1)

(Preparation Method E-7)

A compound of general formula I in which one or more piperidine groups (E=CH) or piperazine groups (E=N) are introduced into $R^1$ and/or $R^2$ can be prepared from a compound of general formula I in which one or more of $R^1$ and $R^2$ are a halogen group(s). A piperidine group can be introduced into a compound of general formula I in which one or more of $R^1$ and $R^2$ are a halogen group(s) by the method of Suzuki et al. (Chemical Reviews, 95(7), 2457, 1995) or Molander et al. (Org. Lett., 393, 3, 2001) in combination with double bond reduction reaction, using tert-butyl 4-(4,4,5,5-tetramethyl-1,3,2-dioxaborolan-2-yl)-3,6-dihydro-2H-pyridine-1-carboxylate. A piperazine group can be introduced by a method such as that of Chan et al. (Tetrahedron Lett., 44, 3863, 2003) or Buchwald et al. (Organic synthesis, 78, 23; Coll. Vol. 10: 423, J. Am. Chem. Soc., 124, 6043, 2002), using tert-butyl piperazine-1-carboxylate. Such a functional group conversion may be performed before forming an indole ring after forming an indole ring, or after converting to the compound of general formula I.

Depending on the functional group on $R^1$ or $R^2$, a protecting group can be used as necessary to prepare the target compound efficiently. Arylsulfonyl groups (such as benzenesulfonyl and toluenesulfonyl groups), silyl groups (such as trimethylsilyl and trimethylsilylethoxymethyl groups), and carbamoyl groups (such as Boc and Cbz groups) can be used for protecting NH or OH groups.

For example, a compound of formula 1 into which a piperidine or piperazine group is introduced can be prepared by the above method using a compound of formula 1 in which $R^2$ is a halogen group. A protected compound of general formula I where $R^2$ is a piperidine or piperazine group can be prepared by derivatizing a compound of formula 1 into which a piperidine or piperazine group is introduced to a ketonitrile compound (formula 2) and then to an enamine compound (formula 3), and subsequently forming an aminopyrazole ring. Further, a compound of general formula I having a piperidine group (E=CH) or a piperazine group (E=N) can be prepared by removing the Boc group, and then introducing a functional group selected from Group Q by a method known in the art.

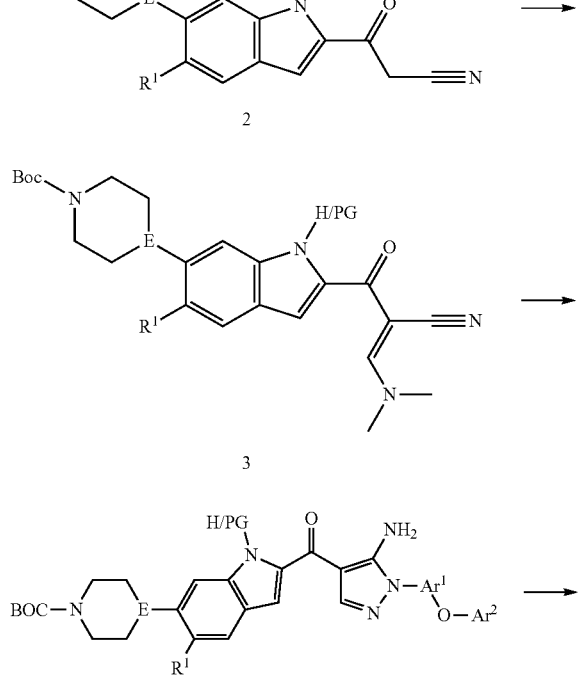

Piperidine Compound/Piperazine Compound (1)

Protected Compound of General Formula I

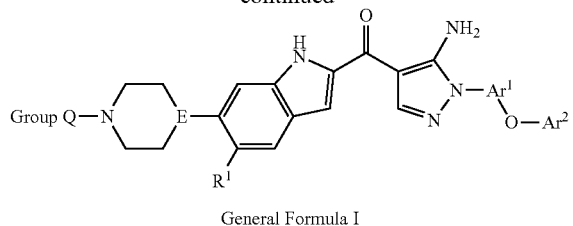

General Formula I (Preparation Method E-8)

A compound of general formula I in which one or more amide groups)(—CONR$^9$R$^{10}$) are introduced into R$^1$ and/or R$^2$ can be prepared using an ester compound in which one or more of R$^1$ and R$^2$ are a carboxyl group(s). R$^{23}$ and R$^{13}$ are preferably those that can be cleaved separately from each other, examples of which include R$^{13}$=methyl and R$^{23}$=tert-butyl. Depending on the functional group on R$^1$ or R$^2$, a protecting group can be used as necessary to prepare the target compound efficiently. Arylsulfonyl groups (such as benzenesulfonyl and toluenesulfonyl groups), silyl groups (such as trimethylsilyl and trimethylsilylethoxymethyl groups), and carbamoyl groups (such as Boc and Cbz groups) can be used for protecting NH or OH groups. For example, after derivatizing a compound of formula 1 where R$^2$ is an ester group (—CO$_2$R$^{23}$) to a ketonitrile compound (formula 2) and then to an enamine compound (formula 3), an aminopyrazole ring can be formed and the ester group (—CO$_2$R$^{23}$) in general formula I can be converted to an amide group) (—CONR$^9$R$^{10}$) by a method known in the art. Further, the protected compound of general formula I prepared using a protecting group can be prepared into a compound of general formula I by removing the protecting group by a method known in the art.

Such a functional group conversion may be performed before forming an indole ring, after forming an indole ring, or after converting to the compound of general formula I.

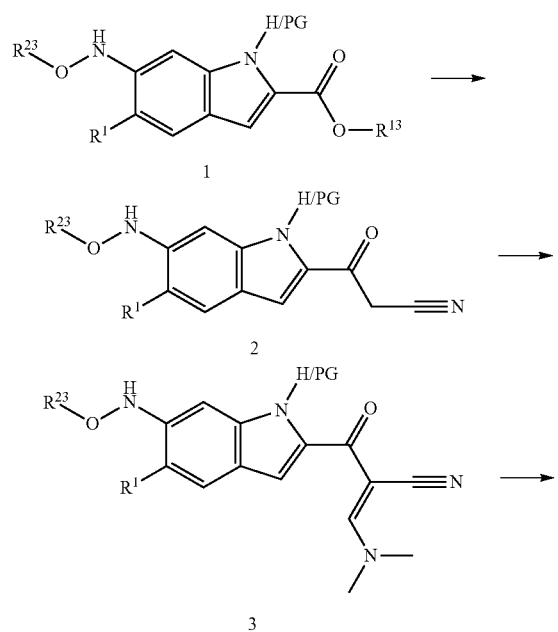

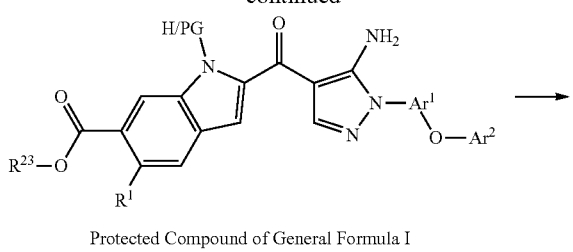

Protected Compound of General Formula I

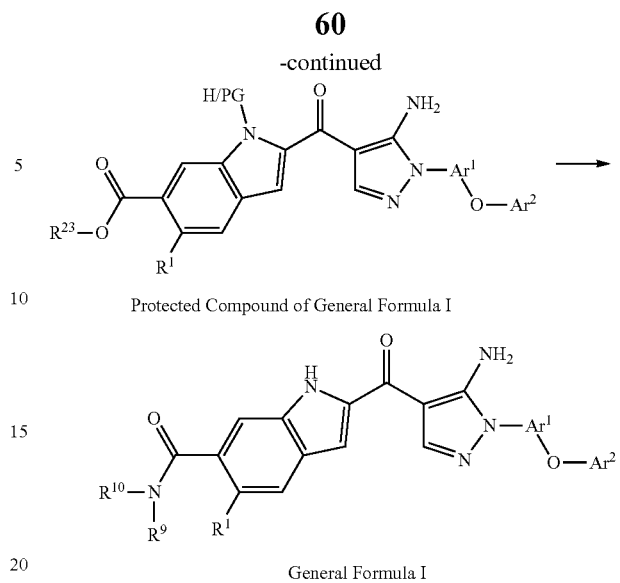

General Formula I (Preparation Method E-11)

A compound of general formula I in which one or more alkylsulfonyl groups (R$^8$SO2-) are introduced into R$^1$ and/or R$^2$ can be prepared using a compound of formula 1 in which one or more of R$^1$ and R$^2$ are a halogen group(s). In this case, the halogen group is preferably a chlorine group, a bromine group, or an iodine group, and more preferably a bromine group or an iodine group. For example, a compound of formula 36 can be prepared by cleaving the sulfide group of a compound of formula 34 obtained using a compound of formula 34 in which R$^2$ in formula 1 is a halogen group by the method of Itoh et al. (Org. Lett., 6, 4587, 2004) to provide a compound of formula 35, and then forming a sulfonyl chloride. A compound of formula 40 can be prepared by subjecting the compound of formula 36 with a reagent represented by R$^5$. Moreover, a compound of formula 38 having a sulfone group on the indole can be prepared by direct introduction of R$^8$SO$_2$— by the method of Barta et al. (WO 2000069821). Depending on the type of the functional group on R$^8$ on formula 38, a compound of formula 38 into which a functional group selected from Group Q is further introduced can be prepared by a method known in the art. After derivatizing the obtained compounds of formulas 40 and 38 to a ketonitrile compound (formula 2) and then to an enamine compound (formula 3), respectively, an aminopyrazole ring can be formed and a compound of general formula I can be prepared. Further, the compound of general formula I prepared using a protecting group can be prepared into a compound of general formula I by removing the protecting group by a method known in the art. Such a functional group conversion may be performed before forming an indole ring, after forming an indole ring, or after converting to the compound of general formula I.

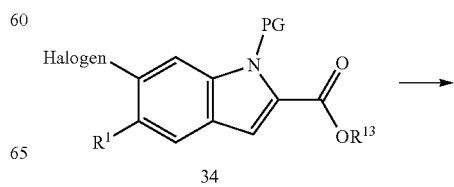

34

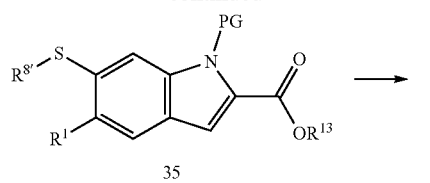
35

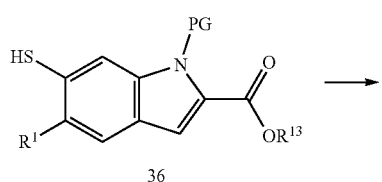
36

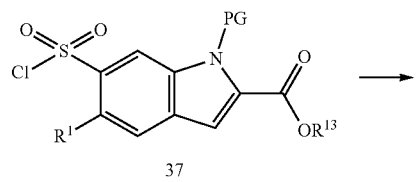
37

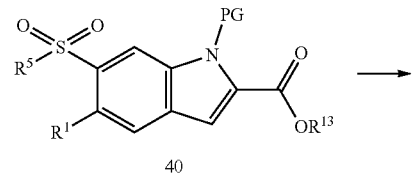
40

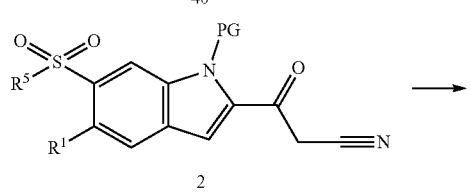
2

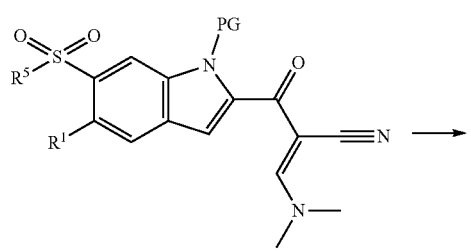
3

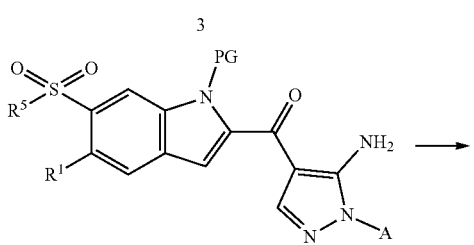
Protected Compound of General Formula I

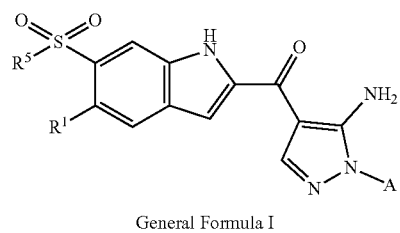
General Formula I

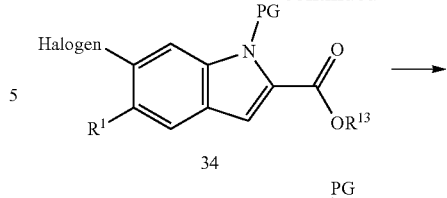
34

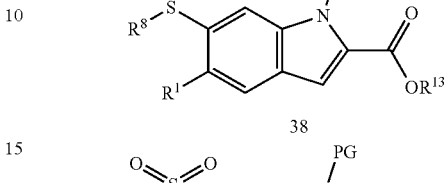
38

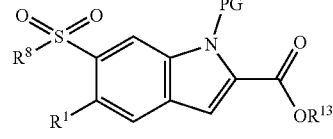
39

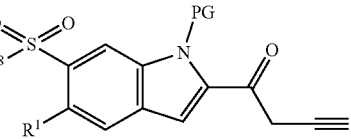
2

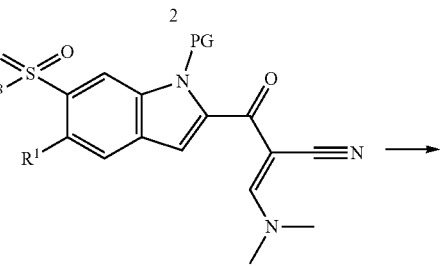
3

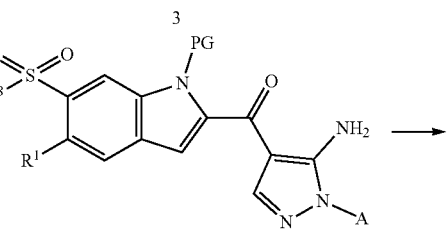
Protected Compound of General Formula I

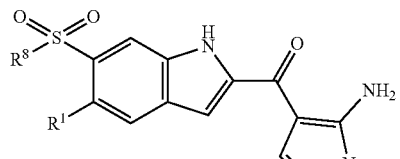
General Formula I (Preparation Method E-12)

A compound of general formula I in which one or more alkoxy groups ($R^7O—$) are introduced into $R^1$ and/or $R^2$ can be prepared using a compound of formula 1 in which one or more of $R^1$ and $R^2$ are a hydroxyl group(s) or $R^7O—$. Depending on the functional group on $R^1$, $R^2$, or $R^7$, a protecting group can be used as necessary to prepare the target compound efficiently. Arylsulfonyl groups (such as benzenesulfonyl and toluenesulfonyl groups), silyl groups (such as trimethylsilyl and trimethylsilylethoxymethyl groups), and carbamoyl groups (such as Boc and Cbz groups) can be used for protecting NH or OH groups. For example, a functional group can be introduced into a compound of formula 41 (where R" is a hydrogen atom) which can be prepared by a method known in the art and in which the O-alkyl in formula 1 is converted to a hydroxyl group, by forming a C—O bond by a method such as that of Mitsunobu et al. (Synthesis, 1, 1981), Mulvihill et al. (WO 2011143645), or Williamson et al. (J. Chem. Soc., 4, 229, 1852). Functional groups that can be introduced include alkyl, haloalkyl, and aminoalkyl groups. After derivatizing the prepared compound of formula 42 to a ketonitrile compound (formula 2) and then to an enamine compound (formula 3), an aminopyrazole ring can be formed and a compound of general formula I can be prepared. Further, the compound of general formula I prepared using a protecting group can be prepared into a compound of general formula I by removing the protecting group by a method known in the art. Such a functional group conversion may be performed before forming an indole ring, after forming an indole ring, or after converting to the compound of general formula I.

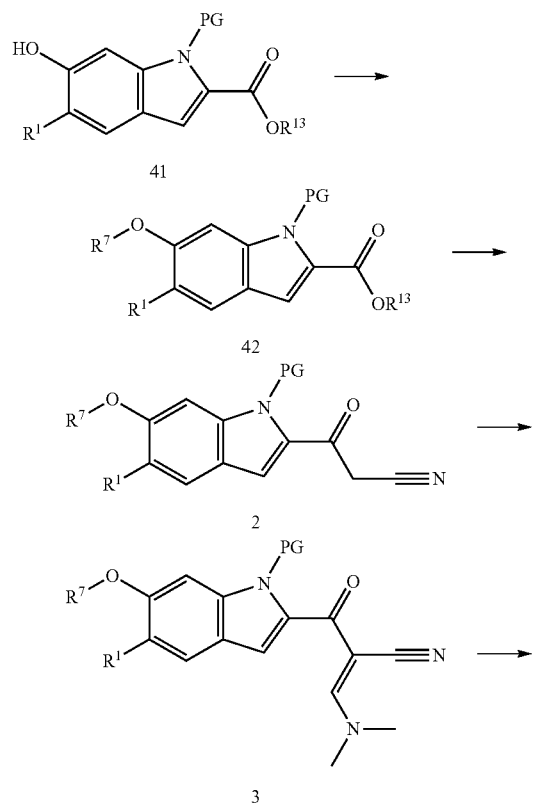

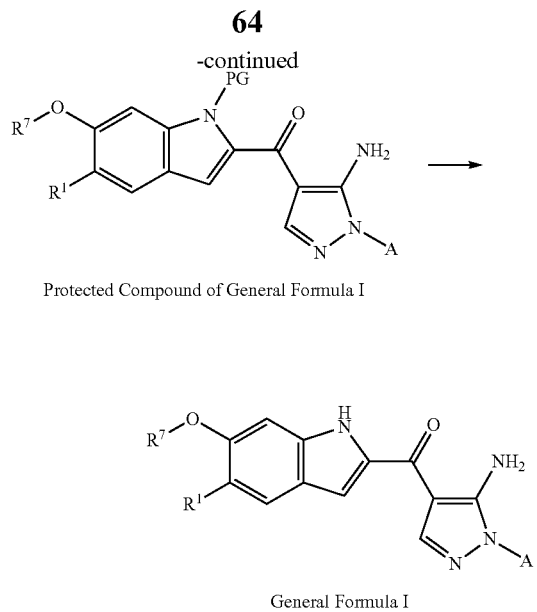

Protected Compound of General Formula I

General Formula I

EXAMPLES

Herein below, the present invention will be described in more detail with reference to Examples, but it is not to be construed as being limited thereto.

Data from mass spectrometry with high performance liquid chromatography (LC-MS) were used for determining the structure and purity of the compound. The data were obtained using a Micromass (SQD) equipped with an Acquity gradient ultra high performance liquid chromatography system (manufactured by Waters Corporation), an SQD2 mass spectrometer equipped with an Acquity gradient ultra high performance liquid chromatography system (manufactured by Waters Corporation), a Micromass (ZQ) equipped with a 2525 gradient high performance liquid chromatography system (manufactured by Waters Corporation), a Micromass (SQD) equipped with a 2524 gradient high performance liquid chromatography system (manufactured by Waters Corporation), a Micromass (SQD) equipped with an Acquity I-Class gradient ultra high performance liquid chromatography system (manufactured by Waters Corporation), or a Micromass (2020) equipped with a Nexera high performance liquid chromatography system (manufactured by Shimadzu Corporation). Any of the conditions in the following table was used for high performance liquid chromatography.

| Measurement Condition | Device Name | Mobile Phase | Gradient Program | Column Name | Column Temperature (° C.) |
|---|---|---|---|---|---|
| A1 | Acquity UPLC-SQD#M08SQD412W | A) 0.1% FA in CH3CN, B) 0.1% FA in H2O | A/B = 5/95 → 100/0 (1 min) | Ascentis Express C18 2.1 mml · D. × 50 mmL, 2.7 um | 35 |
| A1 | Acquity UPLC-SQD#LBA602 | A) 0.1% FA in CH3CN, B) 0.1% FA in H2O | A/B = 5/95 → 100/0 (1 min) | Ascentis Express C18 2.1 mml · D. × 50 mmL, 2.7 um | 35 |
| A2 | Acquity UPLC-SQD2#LCA029 | A) 0.1% FA in CH3CN, B) 0.1% FA in H2O | A/B = 5/95 → 100/0 (1 min) | Ascentis Express C18 2.1 mml · D. × 50 mmL, 2.7 um | 35 |

-continued

| Measurement Condition | Device Name | Mobile Phase | Gradient Program | Column Name | Column Temperature (° C.) |
|---|---|---|---|---|---|
| A3 | Acquity UPLC-SQD#LBA602 | A) 0.05% TFA in MeCN, B) 0.05% TFA in H2O | A/B = 5/95 → 100/0 (1 min) | Ascentis Express C18 2.1 mmI.D. × 50 mmL, 2.7 um | 35 |
| B1 | Acquity UPLC-SQD#M08SQD412W | A) 0.1% FA in CH3CN, B) 0.1% FA in H2O | A/B = 5/95 → 67/33 (3 min) → 100/0 (0.2 min) | ACQUITY UPLC BEH Phenyl 2.1 mmI.D. × 50 mmL, 1.7 um | 35 |
| B1 | Acquity UPLC-SQD#LBA602 | A) 0.1% FA in CH3CN, B) 0.1% FA in H2O | A/B = 5/95 → 67/33 (3 min) → 100/0 (0.2 min) | ACQUITY UPLC BEH Phenyl 2.1 mmI.D. × 50 mmL, 1.7 um | 35 |
| B2 | Acquity UPLC-SQD#M08SQD412W | A) 0.1% FA in CH3CN, B) 0.1% FA in H2O | A/B = 5/95 → 67/33 (3 min) → 100/0 (0.2 min) | ACQUITY UPLC BEH Phenyl 2.1 mmI.D. × 50 mmL, 1.7 um | 35 |
| B3 | Acquity UPLC-SQD#LBA602 | A) 0.05% TFA in MeCN, B) 0.05% TFA in H2O | A/B = 5/95 → 67/33 (3 min) → 100/0 (0.2 min | ACQUITY UPLC BEH Phenyl 2.1 mmI.D. × 50 mmL, 1.7 um | 35 |
| C1 | Acquity UPLC-SQD#M08SQD412W | A) 0.1% FA in CH3CN, B) 0.1% FA in H2O | A/B = 5/95 → 67/33 (4.6 min) → 100/0 (0.4 min) | ACQUITY UPLC BEH Phenyl 2.1 mmI.D. × 50 mmL, 1.7 um | 35 |
| D1 | Acquity UPLC-SQD#M08SQD412W | A) 0.1% FA in CH3CN, B) 0.1% FA in H2O | A/B = 40/60 → 100/0 (1 min) → 100/0 (0.4 min) | Ascentis Express C18 2.1 mmI.D. × 50 mmL, 2.7 um | 35 |
| D1 | Acquity UPLC-SQD#LBA602 | A) 0.1% FA in CH3CN, B) 0.1% FA in H2O | A/B = 40/60 → 100/0 (1 min) → 100/0 (0.4 min) | Ascentis Express C18 2.1 mmI.D. × 50 mmL, 2.7 um | 35 |
| D2 | Acquity UPLC-SQD2#LCA029 | A) 0.1% FA in CH3CN, B) 0.1% FA in H2O | A/B = 40/60 → 100/0 (1 min) → 100/0 (0.4 min) | Ascentis Express C18 2.1 mmI.D. × 50 mmL, 2.7 um | 35 |
| D3 | Acquity UPLC-SQD#LBA602 | A) 0.05% TFA in H2O, B) 0.05% TFA in MeCN | A/B = 40/60 → 100/0 (1 min) → 100/0 (0.4 min) | Ascentis Express C18 2.1 mmI.D. × 50 mmL, 2.7 um | 35 |
| E1 | Acquity UPLC-SQD#M08SQD412W | A) 0.1% FA, CH3CN, B) 0.1% FA, | A/B = 80/20 → 100/0 (1 min) → 100/0 (0.4 min) | Ascentis Express C18 2.1 mmI.D. × 50 mmL, 2.7 um | 35 |
| E1 | Acquity UPLC-SQD#LBA602 | A) 0.1% FA, CH3CN, B) 0.1% FA, | A/B = 80/20 → 100/0 (1 min) → 100/0 (0.4 min) | Ascentis Express C18 2.1 mmI.D. × 50 mmL, 2.7 um | 35 |
| E2 | Acquity UPLC-SQD2#LCA029 | A) 0.1% FA, CH3CN, B) 0.1% FA, | A/B = 80/20 → 100/0 (1 min) → 100/0 (0.4 min) | Ascentis Express C18 2.1 mmI.D. × 50 mmL, 2.7 um | 35 |
| E3 | Acquity UPLC-SQD#LBA602 | A) 0.05% TFA in H2O, B) 0.05% TFA in MeCN | A/B = 80/20 → 100/0 (1 min) → 100/0 (0.4 min) | Ascentis Express C18 2.1 mmI.D. × 50 mmL, 2.7 um | 35 |
| F1 | Acquity UPLC-SQD#M08SQD412W | A) 0.1% FA, CH3CN, B) 0.1% FA, | A/B = 20/80 → 100/0 (3 min) → 100/0 (0.6 min) | ACQUITY UPLC BEH Phenyl 2.1 mmI.D. × 50 mmL, 1.7 um | 35 |
| F1 | Acquity UPLC-SQD#LBA602 | A) 0.1% FA, CH3CN, B) 0.1% FA, | A/B = 20/80 → 100/0 (3 min) → 100/0 (0.6 min) | ACQUITY UPLC BEH Phenyl 2.1 mmI.D. × 50 mmL, 1.7 um | 35 |
| F3 | Acquity UPLC-SQD#LBA602 | A) 0.05% TFA in MeCN, B) 0.05% TFA in H2O | A/B = 20/80 → 100/0 (3 min) → 100/0 (0.6 min) | ACQUITY UPLC BEH Phenyl 2.1 mmI.D. × 50 mmL, 1.7 um | 35 |
| G1 | Acquity UPLC-SQD#LBA602 | A) 0.1% FA, CH3CN, B) 0.1% FA, | A/B = 5/95 → 70/30 (1 min) → 70/30 (0.4 min) | Ascentis Express C18 2.1 mmI.D. × 50 mmL, 2.7 um | 35 |
| G2 | Acquity UPLC-SQD2#LCA029 | A) 0.1% FA, CH3CN, B) 0.1% FA, | A/B = 5/95 → 70/30 (1 min) → 70/30 (0.4 min) | Ascentis Express C18 2.1 mmI.D. × 50 mmL, 2.7 um | 35 |
| G3 | Acquity UPLC-SQD#LBA602 | A) 0.05% TFA in H2O, B) 0.05% TFA in MeCN | A/B = 5/95 → 70/30 (1 min) → 70/30 (0.4 min) | Ascentis Express C18 2.1 mmI.D. × 50 mmL, 2.7 um | 35 |
| H3 | ZQ | A) 0.05% TFA in H2O, B) 0.05% TFA in MeCN | A/B = 10/90 → 95/5 (3.5 min) → 10/90 (1 min) → 10/90 (0.5 min) | SunFire C18 4.6 mmI.D. × 50 mmL, 5 um | 25 |
| A4 | Acquity UPLC-SQD#LBA602 | A) 0.1% FA, CH3CN, B) 0.1% FA, | A/B = 10/90 → 98/2 (1 min) → 100/0 (0.4 min) | Ascentis Express C18 2.1 mmI.D. × 50 mmL, 2.7 um | 35 |
| J1 | Acquity UPLC I-Class/SQD | A) 10 mM AcONH4 in H2O, B) MeOH | A/B = 5/95 → 100/0 (1 min) → 100/0 (0.4 min) | Ascentis Express C18 2.1 mmI.D. × 50 mmL, 2.7 um | 35 |
| J2 | Acquity UPLC I-Class/SQD | A) 10 mM AcONH4 in H2O, B) MeOH | A/B = 5/95 → 100/0 (1 min) → 100/0 (0.4 min) | Ascentis Express C18 2.1 mmI D. × 50 mmL, 5 um | 35 |
| J3 | Acquity UPLC/SQD | A) 10 mM AcONH4 in H2O, B) MeOH | A/B = 5/95 → 100/0 (1 min) → 100/0 (0.4 min) | Ascentis Express C18 2.1 mmI.D. × 50 mmL, 5 um | 35 |

| Measurement Condition | Device Name | Mobile Phase | Gradient Program | Column Name | Column Temperature (° C.) |
|---|---|---|---|---|---|
| J4 | Nexera/2020 | A) 0.05% TFA in H2O, B) 0.05% TFA in MeCN | A/B = 5/95 → 100/0 (1.5 min) → 100/0 (0.5 min) | Kinetex 1.7u C18 2.1 mmI · D. × 50 mmL, 1.7 um | 35 |
| TFA Rev. 5 | Nexera/2020 | A) 0.05% TFA in MeCN, B) 0.05% TFA in H2O | A/B = 5/95 → 100/0 (1.5 min) | Kinetex 1.7u C18 2.1 mmI · D. × 50 mmL, 1.7 um | 35 |
| TFA Rev. 6 | Nexera/2020 | A) 0.05% TFA in MeCN, B) 0.05% TFA in H2O | A/B = 5/95 → 100/0 (1.5 min) | Meteoric Core C18 2.1 mmI · D. × 50 mmL, 2.7 um | 35 |
| TFA Rev. 7 | Nexera/2020 | A) 0.05% TFA in MeCN, B) 0.05% TFA in H2O | A/B = 5/95 → 100/0 (1.5 min) | Ascentis Express C18 2.1 mmI · D. × 50 mmL, 2.7 um | 35 |
| AA Rev. 2 | Acquity UPLC/SQD | A) MeOH B) 10 mM AcONH4 in H2O | A/B = 5/95 → 100/0 (1 min) | Ascentis Express C18 2.1 mmI · D. × 50 mmL, 2.7 um | 35 |
| AA Rev. 3 | Nexera/2020 | A) MeOH B) 10 mM AcONH4 in H2O | A/B = 5/95 → 100/0 (1.5 min) | Ascentis Express C18 2.1 mmI · D. × 50 mmL, 2.7 um | 35 |
| AA Rev. 4 | Acquity UPLC/SQD | A) MeOH B) 10 mM AcONH4 in H2O | A/B = 5/95 → 100/0 (1 min) | Ascentis Express C18 2.1 mmI · D. × 50 mmL, 2.7 um | 35 |
| AA Rev. 5 | Acquity UPLC I-Class/SQD | A) MeOH B) 10 mM AcONH4 in H2O | A/B = 5/95 → 100/0 (1 min) | Ascentis Express C18 2.1 mmI · D. × 50 mmL, 2.7 um | 35 |
| AA Rev. 7 | Acquity UPLC/SQD | A) MeOH B) 10 mM AcONH4 in H2O | A/B = 5/95 → 100/0 (1 min) | Ascentis Express C18 2.1 mmI · D. × 50 mmL, 5 um | 35 |
| AA Rev. 8 | Acquity UPLC I-Class/SQD | A) MeOH B) 10 mM AcONH4 in H2O | A/B = 5/95 → 100/0 (1 min) | Ascentis Express C18 2.1 mmI · D. × 50 mmL, 5 um | 35 |
| AA Rev. 10 | Acquity UPLC I-Class/SQD | A) MeOH B) 10 mM AcONH4 in H2O | A/B = 5/95 → 100/0 (1 min) | Ascentis Express C18 2.1 mmI · D. × 50 mmL, 5 um | 35 |
| AA Rev. 11 | Acquity UPLC I-Class/SQD | A) MeOH B) 10 mM AcONH4 in H2O | A/B = 5/95 → 100/0 (1 min) | Ascentis Express C18 2.1 mmI · D. × 50 mmL, 2.7 um | 35 |

Example 1

Example 1-1-1 (Compound I-A010)

Synthesis of 2-(6-bromo-5-morpholine-1H-indole-2-carbonyl)-3-(dimethylamino)prop-2-enenitrile

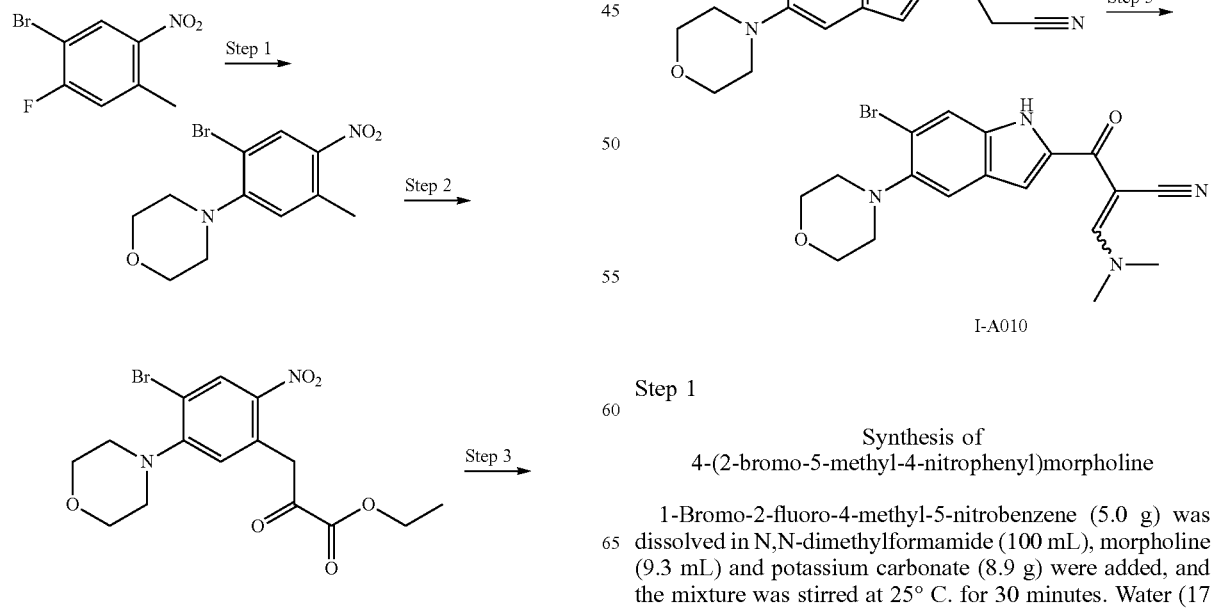

Step 1

Synthesis of 4-(2-bromo-5-methyl-4-nitrophenyl)morpholine

1-Bromo-2-fluoro-4-methyl-5-nitrobenzene (5.0 g) was dissolved in N,N-dimethylformamide (100 mL), morpholine (9.3 mL) and potassium carbonate (8.9 g) were added, and the mixture was stirred at 25° C. for 30 minutes. Water (17 mL) was added to the reaction solution, and the resulting solid was collected by filtration and washed by suspending in hexane to give the target compound (5.7 g).
Step 2

Synthesis of ethyl 3-(4-bromo-5-morpholino-2-nitrophenyl)-2-oxopropanoate 4-(2-Bromo-5-methyl-4-nitrophenyl)morpholine (5.70 g) was dissolved in ethanol (68 mL), a 20% solution of sodium ethoxide in ethanol (37.1 mL) and diethyl oxalate (12.9 mL) were added at 0° C., and the mixture was stirred at 45° C. for 21 hours. Water (100 mL) was added to the reaction solution, and the mixture was neutralized by adding 2 M hydrochloric acid (50 mL). The resulting mixture was extracted with ethyl acetate (200 mL×2). The combined organic layers were washed with saturated saline and dried over anhydrous sodium sulfate. The drying agent was removed by filtration and the filtrate was concentrated under reduced pressure. The resulting residue was washed by suspending in hexane to give the target compound (12.3 g).
Step 3

Synthesis of ethyl 6-bromo-5-morpholino-1H-indole-2-carboxylate

Ethyl 3-(4-bromo-5-morpholino-2-nitrophenyl)-2-oxopropanoate (11.9 g) was dissolved in acetic acid (7.5 mL), iron powder (8.3 g) was added, and the mixture was stirred at 80° C. for one hour. Iron powder (8.3 g) was further added and the mixture was stirred for 2.5 hours. The reaction solution was cooled to 25° C. and the insoluble matter was filtered off by celite filtration. The filtrate was concentrated under reduced pressure, water was added to the resulting residue, and the mixture was extracted with ethyl acetate (300 mL). The organic layer was washed with water (100 mL×3) and a saturated aqueous sodium bicarbonate solution and concentrated under reduced pressure. The resulting residue was purified by column chromatography (hexane/ethyl acetate) to give the target compound (5.1 g).
Step 4

Synthesis of 3-(6-bromo-5-morpholino-1H-indol-2-yl)-3-oxopropanenitrile

Lithium bis(trimethylsilyl)amide (1.0 M solution in tetrahydrofuran, 18.25 mL) was added to a solution of ethyl 6-bromo-5-morpholino-1H-indole-2-carboxylate (3.5 g), tetrahydrofuran (105 mL), and acetonitrile (2.1 mL) at 0° C. and the mixture was stirred for 0.5 hour. Water and 2 M hydrochloric acid (30 mL) were added to the reaction solution and the mixture was extracted with ethyl acetate (500 mL). The organic layer was dried over anhydrous sodium sulfate. The drying agent was removed by filtration and the filtrate was concentrated under reduced pressure to give the target compound (5.1 g).
Step 5

Synthesis of (E)-2-(6-bromo-5-morpholino-1H-indole-2-carbonyl)-3-(dimethylamino)acrylonitrile Triethylamine (2723 mL) and N,N-dimethylformamide dimethylacetal (1.43 mL) were added to a solution of 3-(6-bromo-5-morpholino-1H-indol-2-yl)-3-oxopropanenitrile (3.4 g) in tetrahydrofuran (74 mL) at room temperature and the mixture was stirred for 30 minutes. The reaction solution was concentrated under reduced pressure and washed by suspending in dichloromethane and hexane to give the target compound.

| Example No. | Compound No. | |
|---|---|---|
| 1-1-1 | I-A010 | 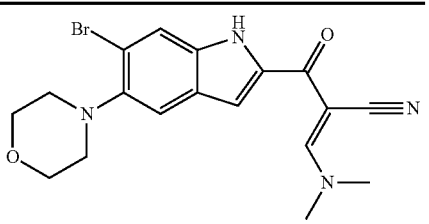 |

Example 1-2-1 (Compound I-H048)

Synthesis of N-{2-[2-cyano-3-(dimethylamino)prop-2-enoyl]-5-methoxy-1H-indol-6-yl}methanesulfonamide

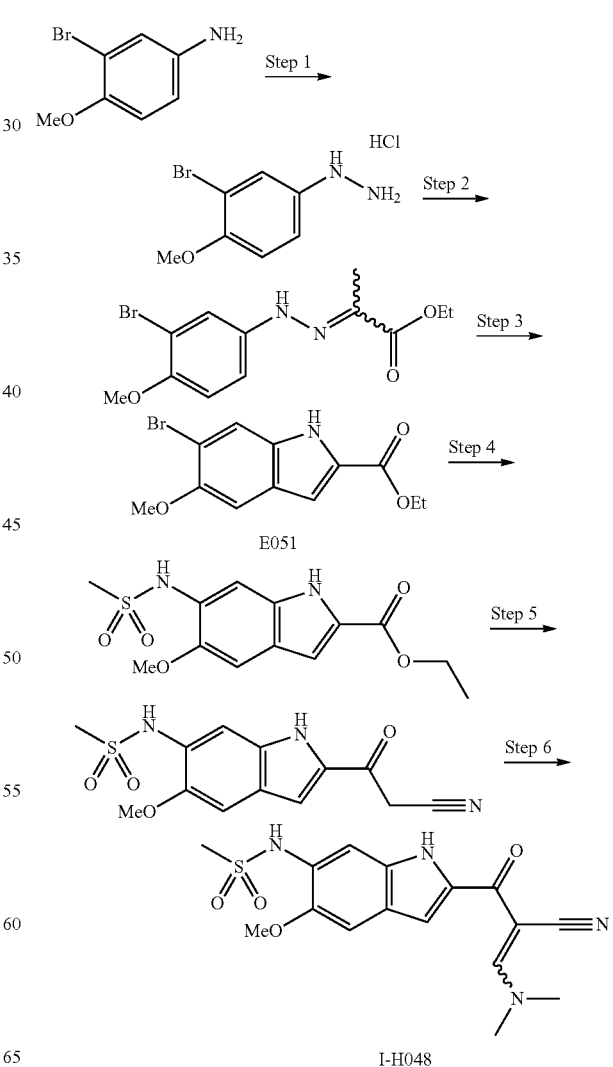

Step 1

Synthesis of (3-bromo-4-methoxyphenyl)hydrazine hydrochloride

3-Bromo-4-methoxyaniline (3.3 g) was suspended in a mixture of concentrated hydrochloric acid (33 mL) and water (4 mL), and sodium nitrite (1.7 g) dissolved in water (6 mL) was added at 0° C. Tin(II) chloride (7.4 g) dissolved in concentrated hydrochloric acid (33 mL) was added at 0° C., and the mixture was stirred at 25° C. for one hour. The precipitated solid was collected by filtration and washed by suspending in ethyl acetate to give the target compound (4.13 g).

Step 2

Synthesis of ethyl (E)-2-(2-(3-bromo-4-methoxyphenyl)hydrazino)propanoate (3-Bromo-4-methoxyphenyl)hydrazine hydrochloride (4.1 g) and ethyl pyruvate (3.8 g) were suspended in ethanol (65 mL) at 25° C. and the mixture was stirred at 25° C. for two hours. The reaction solution was concentrated under reduced pressure (10 mL), ethyl acetate (150 mL) was added, and the mixture was washed with water and saturated saline and dried over anhydrous sodium sulfate. The drying agent was removed by filtration and the filtrate was concentrated under reduced pressure. The resulting residue was purified by column chromatography (hexane/ethyl acetate) to give the target compound (1.46 g).

Step 3

Synthesis of ethyl 6-bromo-5-methoxy-1H-indole-2-carboxylate (E051)

Ethyl [(4-methoxy-3-bromo)hydrazinylidene]propanoate (1.4 g) was dissolved in dichloromethane (8.8 mL), Eaton's reagent (0.89 mL) was added, and the mixture was stirred at 40° C. for two hours in a nitrogen atmosphere. The reaction solution was cooled to 25° C. and concentrated under reduced pressure. The resulting residue was purified by column chromatography (hexane/ethyl acetate) to give the target compound (519 mg).

Step 4

Synthesis of ethyl 5-methoxy-6-(methylsulfonamido)-1H-indole-2-carboxylate

Ethyl 6-bromo-5-methoxy-1H-indole-2-carboxylate (515 mg) was dissolved in dioxane (0.9 mL) in a nitrogen atmosphere, and allylpalladium chloride dimer (44 mg), potassium carbonate (716 mg), methanesulfonamide (246 mg), and tBuXPhos (123 mg) were added. The reaction system was degassed under reduced pressure and the atmosphere therein was then replaced by nitrogen. The mixture was heated at 100° C. for two hours. The reaction solution was cooled to 25° C., diluted with ethyl acetate, and filtered through celite. The ethyl acetate layer was washed with a saturated aqueous sodium bicarbonate solution and saturated saline and dried over anhydrous magnesium sulfate. The drying agent was removed by filtration, and the filtrate was concentrated under reduced pressure, and the resulting residue was washed by suspending in ethyl acetate/hexane to give the target compound (563 mg).

Step 5

Synthesis of N-[2-(2-cyanoacetyl)-1H-indole-5-methoxy-6-yl]methanesulfonamide Ethyl 6-(methanesulfonamido)-5-methoxy-1H-indole-2-carboxylate (480 mg) was suspended in tetrahydrofuran (15 mL) and the suspension was cooled to 0° C., followed by dropwise addition of lithium bis(trimethylsilyl)amide (1.0 M solution in tetrahydrofuran, 5.9 mL). After stirring for 30 minutes, dehydrated acetonitrile (0.24 mL) was added dropwise and the mixture was stirred at 0° C. for one hour. Ethyl acetate (50 mL) was added to the reaction solution, and the mixture was washed with 1 M hydrochloric acid (10 mL×2) and saturated saline (10 mL). It was dried over anhydrous sodium sulfate. The drying agent was removed by filtration and the filtrate was concentrated under reduced pressure to give the target compound (518 mg).

Step 6

Synthesis of N-{2-[2-cyano-3-(dimethylamino)prop-2-enoyl]-5-methoxy-1H-indol-6-yl}methanesulfonamide (I-H048)

N-[2-(2-Cyanoacetyl)-5-methoxy-1H-indol-6-yl]methanesulfonamide (516 mg) was suspended in tetrahydrofuran (3.3 mL), N,N-dimethylformamide dimethylacetal (245 µL) was added, and the mixture was stirred at 25° C. for one hour. The reaction solution was concentrated under reduced pressure to give the target compound (640 mg).

| Example No. | Compound No. | |
|---|---|---|
| 1-2-1 | I-H048 | 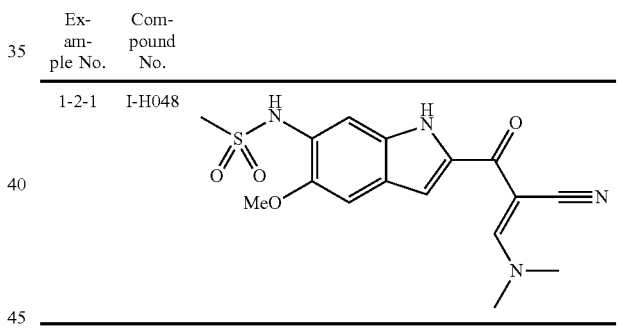 |

Example 1-2-2

The compound of Example 1-2-2 was synthesized from a corresponding bromoaniline by the similar method as in Example 1-2-1.

| Example No. | Compound No. | |
|---|---|---|
| 1-2-2 | I-A009 | 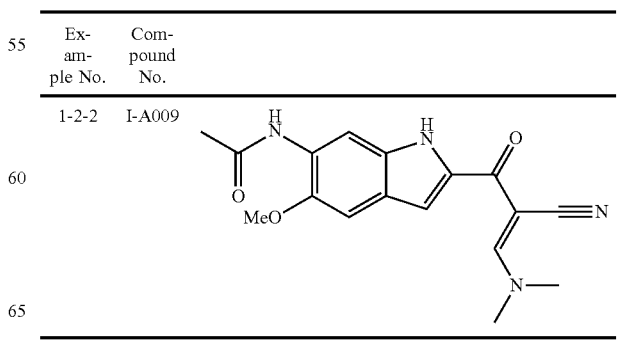 |

Example 1-2-3 (Compound I-H062)

Synthesis of N-{2-[2-cyano-3-(dimethylamino)prop-2-enoyl]-6-methoxy-1H-indol-5-yl}methanesulfonamide

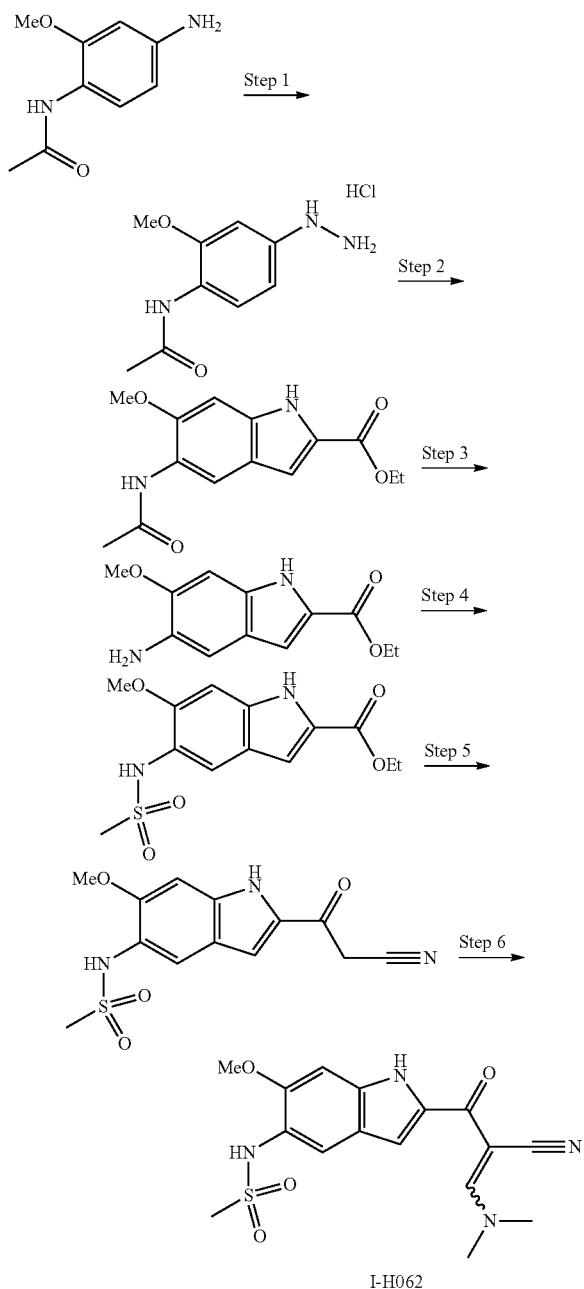

Step 1

Synthesis of N-(4-hydrazinyl-2-methoxyphenyl)acetamide hydrochloride

N-(4-Amino-2-methoxyphenyl)acetamide (387 mg) was suspended in concentrated hydrochloric acid (2.0 mL), and sodium nitrite (202 mg) dissolved in water (2.0 mL) was added at 0° C. Tin(II) chloride (892 mg) dissolved in concentrated hydrochloric acid (2.0 mL) was added at 0° C., and the mixture was stirred at 25° C. for two hours. The precipitated solid was collected by filtration and washed with ethyl acetate to give the target compound (524 mg).

Step 2

Synthesis of ethyl 5-acetamido-6-methoxy-1H-indole-2-carboxylate

N-(4-Hydrazinyl-2-methoxyphenyl)acetamide hydrochloride (523 mg) was suspended in ethanol (5.0 mL), ethyl pyruvate (0.26 mL) was added at 25° C., and the mixture was stirred at 25° C. for two hours. Water (10 mL) was added to the reaction solution and the precipitated solid was collected by filtration to give an arylhydrazone compound (304 mg). A part of the obtained arylhydrazone compound (233 mg) was dissolved in dichloroethane (4.0 mL), Eaton's reagent (0.38 mL) was added, and the mixture was stirred at 70° C. for three hours. The reaction solution was cooled to 25° C., water was added, and the mixture was extracted with ethyl acetate. The organic layer was dried over anhydrous sodium sulfate. The drying agent was removed by filtration and the filtrate was concentrated under reduced pressure to give the target compound (263 mg).

Step 3

Synthesis of ethyl 5-amino-6-methoxy-1H-indole-2-carboxylate

Ethyl 5-acetamido-6-methoxy-1H-indole-2-carboxylate (250 mg) was dissolved in ethanol (7.0 mL), concentrated sulfuric acid (0.48 mL) was added, and the mixture was stirred at 80° C. for six hours. The reaction solution was cooled to 25° C. and concentrated under reduced pressure. Water was added to the resulting residue and the mixture was extracted with ethyl acetate. The organic layer was washed with a saturated aqueous sodium bicarbonate solution and saturated saline and dried over anhydrous sodium sulfate. The drying agent was removed by filtration and the filtrate was concentrated under reduced pressure to give the target compound (208 mg).

Step 4

Synthesis of ethyl 5-(methanesulfonamido)-6-methoxy-1H-indole-2-carboxylate Ethyl 5-amino-6-methoxy-1H-indole-2-carboxylate (185 mg) was dissolved in N,N-dimethylacetamide (2.0 mL), N-methylmorpholine (0.12 mL) and methanesulfonyl chloride (82 µL) were added at 0° C., and the mixture was stirred at 25° C. for one hour. Water (5.0 mL) was added to the reaction solution and the precipitated solid was collected by filtration to give the target compound (203 mg).

Step 5

Synthesis of N-[2-(2-cyanoacetyl)-6-methoxy-1H-indol-5-yl]methanesulfonamide Ethyl 5-(methanesulfonamido)-6-methoxy-1H-indole-2-carboxylate (141 mg) was suspended in tetrahydrofuran (8.0 mL) and the mixture was cooled to 0° C. Dehydrated acetonitrile (50 µL) and lithium bis(trimethylsilyl)amide (1.3 M solution in tetrahydrofuran, 1.75 mL) were added dropwise and the mixture was stirred at 0° C. for 1.5 hours. Water and 5 M hydrochloric acid were added to the reaction solution and the precipitated solid was collected by filtration to give the target compound (122 mg).
Step 6

Synthesis of N-{2-[2-cyano-3-(dimethylamino)prop-2-enoyl]-6-methoxy-1H-indol-5-yl}methanesulfonamide (I-H062)

N-[2-(2-Cyanoacetyl)-6-methoxy-1H-indol-5-yl]methanesulfonamide (111 mg) was suspended in tetrahydrofuran (5.0 mL), N,N-dimethylformamide dimethylacetal (80 μL) was added, and the mixture was stirred at 25° C. for one hour. tert-Butyl methyl ether (10 mL) was added to the reaction solution and the precipitated solid was collected by filtration to give the target compound (134 mg).

| Example No. | Compound No. | |
|---|---|---|
| 1-2-3 | I-H062 | 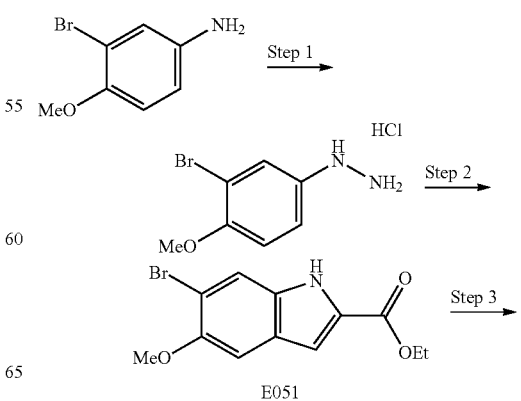 |

Example 1-2-4 (Compound I-H053)

Synthesis of N-{2-[2-cyano-3-(dimethylamino)prop-2-enoyl]-5-methyl-1H-indol-6-yl}methanesulfonamide

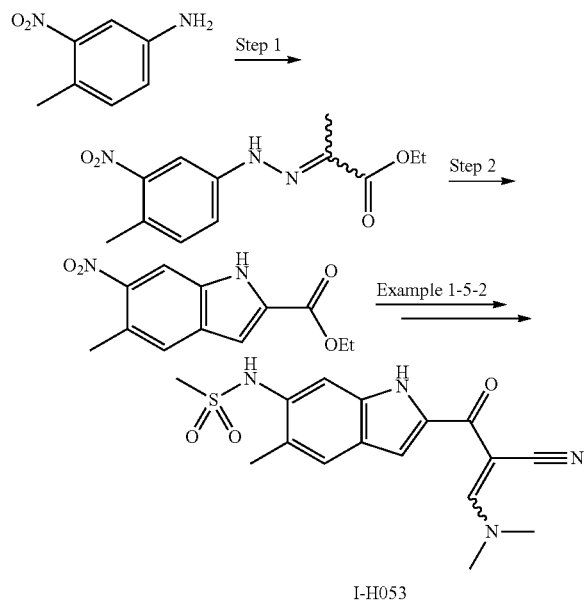

Step 1

Synthesis of ethyl 2-[(4-methyl-3-nitrophenyl)hydrazinylidene]propanoate

4-Methyl-3-nitroaniline (5.00 g) was suspended in water (75 mL), concentrated hydrochloric acid (15 mL) and sodium nitrite (2.5 g) were added at 0° C., and the mixture was stirred for 1.5 hours. Ethyl 2-methylacetoacetate (5.7 mL) and sodium acetate (18.9 g) were added to the reaction solution, and the mixture was stirred at 25° C. for 15 hours. The reaction solution was extracted with ethyl acetate and the organic layer was washed with saturated saline. Concentration under reduced pressure gave a residue which was then purified by column chromatography (hexane/ethyl acetate) to give the target compound (4.75 g).
Step 2

Synthesis of ethyl 5-methyl-6-nitro-1H-indole-2-carboxylate

Ethyl 2-[(4-methyl-3-nitrophenyl)hydrazinylidene]propanoate (3.00 g) was suspended in toluene (30 mL), polyphosphoric acid was added, and the mixture was stirred at 120° C. for two days. The reaction solution was cooled to 25° C., water was added, and the mixture was extracted with ethyl acetate. The organic layer was washed with water and saturated saline. Concentration under reduced pressure gave a residue which was then purified by column chromatography (hexane/ethyl acetate) to give the target compound (872 mg).

| Example No. | Compound No. | |
|---|---|---|
| 1-2-4 | I-H053 | |

Example 1-3-1 (Compound I-H058)

Synthesis of tert-butyl N-{2-[2-cyano-3-(dimethylamino)prop-2-enoyl]-5-methoxy-1-(4-methylphenyl)sulfonylindol-6-yl}carbamate

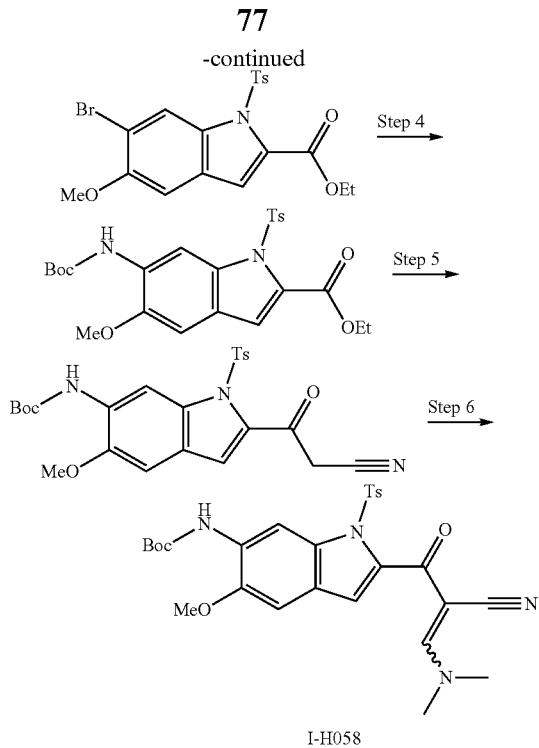

Step 1

Synthesis of (3-bromo-4-methoxyphenyl)hydrazine hydrochloride

3-Bromo-4-methoxyaniline (3.30 g) was suspended in concentrated hydrochloric acid (33 mL), sodium nitrite (1.7 g) dissolved in water (6.0 mL) was added at 0° C., and the mixture was stirred at 0° C. for 30 minutes. Tin(II) chloride (7.4 g) dissolved in concentrated hydrochloric acid (33 mL) was added, and the mixture was stirred at 25° C. for one hour. The precipitated solid was collected by filtration to give the target compound (4.10 g).

Step 2

Synthesis of ethyl 6-bromo-5-methoxy-1H-indole-2-carboxylate (E051)

(3-Bromo-4-methoxyphenyl)hydrazine hydrochloride (4.10 g) was suspended in ethanol (65 mL), ethyl pyruvate (3.8 g) was added at 25° C., and the mixture was stirred for one hour. The reaction solution was concentrated under reduced pressure, water was added to the resulting residue, and the mixture was extracted with ethyl acetate. The organic layer was washed with saturated saline and dried over anhydrous sodium sulfate. The drying agent was removed by filtration, the filtrate was concentrated under reduced pressure, and the resulting residue was purified by column chromatography (hexane/ethyl acetate) to give an arylhydrazone compound (1.50 g). The resulting arylhydrazone compound was dissolved in dichloromethane (8.9 mL), Eaton's reagent (0.89 mL) was added, and the mixture was stirred at 40° C. for two hours in a nitrogen atmosphere. The reaction solution was cooled to 25° C. and concentrated under reduced pressure. The resulting residue was purified by column chromatography (hexane/ethyl acetate) to give the target compound (520 mg).

Step 3

Synthesis of ethyl 6-bromo-5-methoxy-1-(4-methylphenyl)sulfonylindole-2-carboxylate Ethyl 6-bromo-5-methoxy-1H-indole-2-carboxylate (100 mg) was dissolved in N,N-dimethylformamide (2.0 mL), sodium hydride (content: 60%, 20 mg) was added at 0° C., and the mixture was stirred for 20 minutes. p-Toluenesulfonyl chloride (96 mg) was added and the mixture was stirred at 0° C. for 2.5 hours. Water was added to the reaction solution and the precipitated solid was collected by filtration to give the target compound (137 mg).

Step 4

Synthesis of ethyl 5-methoxy-1-(4-methylphenyl)sulfonyl-6-[(2-methylpropan-2-yl)oxycarbonylamino]indole-2-carboxylate Ethyl 6-bromo-5-methoxy-1-(4-methylphenyl)sulfonylindole-2-carboxylate (1.50 g) was dissolved in dioxane (30 mL) in a nitrogen atmosphere, followed by addition of X-Phos (510 mg), cesium carbonate (3.47 g), tert-butyl carbazate (620 mg), and $Pd_2dba_3$ (370 mg). The reaction system was degassed again and the atmosphere therein was replaced by nitrogen. The mixture was heated at 100° C. for three hours. The reaction solution was cooled to 25° C. and the precipitated solid was collected by filtration. The resulting crude solid was purified by column chromatography (petroleum ether/ethyl acetate) to give the target compound (1.20 g).

Step 5

Synthesis of tert-butyl N-[2-(2-cyanoacetyl)-5-methoxy-1-(4-methylphenyl)sulfonylindol-6-yl]carbamate Ethyl 5-methoxy-1-(4-methylphenyl)sulfonyl-6-[(2-methylpropan-2-yl)oxycarbonylamino]indole-2-carboxylate (1.40 g) was suspended in tetrahydrofuran (100 mL), dehydrated acetonitrile (0.5 mL) was added, lithium bis(trimethylsilyl)amide (1.0 M solution in tetrahydrofuran, 16 mL) was added at −78° C., and the mixture was stirred for one hour. A saturated aqueous ammonium chloride solution was added to the reaction solution, and the mixture was extracted with ethyl acetate twice. The organic layers were washed with a saturated aqueous ammonium chloride solution and dried over anhydrous sodium sulfate. The drying agent was removed by filtration and the filtrate was concentrated under reduced pressure to give the target compound (1.50 g).

Step 6

Synthesis of tert-butyl N-{2-[2-cyano-3-(dimethylamino)prop-2-enoyl]-5-methoxy-1-(4-methylphenyl)sulfonylindol-6-yl}carbamate (I-H058)

tert-Butyl N-[2-(2-cyanoacetyl)-5-methoxy-1-(4-methylphenyl)sulfonylindol-6-yl]carbamate (1.50 g) was suspended in tetrahydrofuran (30 mL), N,N-dimethylformamide dimethylacetal (0.43 mL) was added, and the mixture was stirred at 25° C. for two hours. The reaction solution was concentrated under reduced pressure to give the target compound (1.70 g).

| Example No. | Compound No. | |
|---|---|---|
| 1-3-1 | I-H058 | 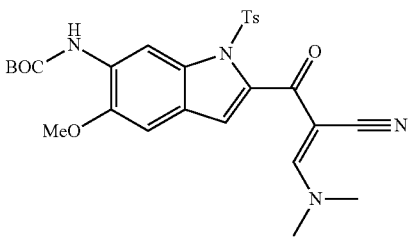 [SMILES: COc1cc2cc(C(=O)/C(C#N)=C/N(C)C)n(S(=O)(=O)c3ccc(C)cc3)c2cc1NC(=O)OC(C)(C)C] |

Example 1-3-2

The compound of Example 1-3-2 was synthesized by the similar method as in Example 1-3-1 using a corresponding amidating reagent or sulfamidating reagent in Step 4.

| Example No. | Compound No. | |
|---|---|---|
| 1-3-2 | I-H059 | 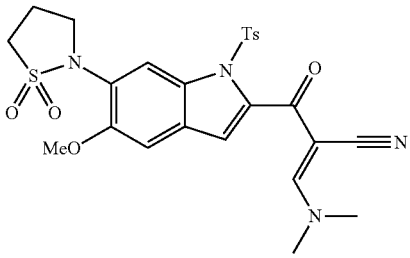 [SMILES: COc1cc2cc(C(=O)/C(C#N)=C/N(C)C)n(S(=O)(=O)c3ccc(C)cc3)c2cc1N1CCCS1(=O)=O] |

Example 1-4-1 (Compound I-H068)

Synthesis of 2-(6-bromo-5-methoxy-1H-indole-2-carbonyl)-3-(dimethylamino)prop-2-enenitrile

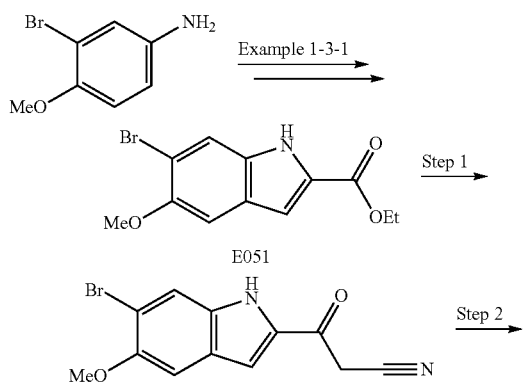

-continued

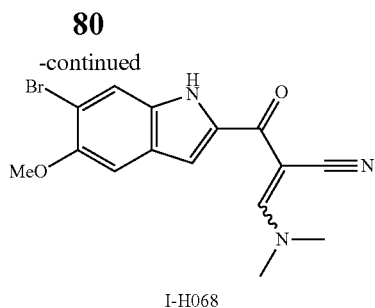

I-H068

Step 1

Synthesis of 3-(6-bromo-5-methoxy-1H-indol-2-yl)-3-oxopropanenitrile

The ester E051 synthesized in Example 1-3-1 (850 mg) was suspended in tetrahydrofuran (28 mL), dehydrated acetonitrile (0.6 mL) was added, lithium bis(trimethylsilyl) amide (1.9 M solution in tetrahydrofuran, 5.3 mL) was added at 0° C., and the mixture was stirred for one hour. 1 M hydrochloric acid (15 mL) was added to the reaction solution and the mixture was extracted with ethyl acetate (50 mL). The organic layer was washed with saturated saline and dried over anhydrous sodium sulfate. The drying agent was removed by filtration and the filtrate was concentrated under reduced pressure to give the target compound (990 mg).

Step 2

Synthesis of 2-(6-bromo-5-methoxy-1H-indole-2-carbonyl)-3-(dimethylamino)prop-2-enenitrile (I-H068)

3-(6-Bromo-5-methoxy-1H-indol-2-yl)-3-oxopropanenitrile (990 mg) was suspended in tetrahydrofuran (34 mL), N,N-dimethylformamide dimethylacetal (0.54 mL) was added, and the mixture was stirred at 25° C. for 1.5 hours. The reaction solution was concentrated under reduced pressure and the resulting residue was washed by suspending in dichloromethane/hexane to give the target compound (990 mg).

| Example No. | Compound No. | |
|---|---|---|
| 1-4-1 | I-H068 | (structure: 6-bromo-5-methoxy-1H-indole with carbonyl-C(CN)=CH-N(CH3) substituent) |

Example 1-4-2 (Compound I-H064)

Synthesis of 2-(6-bromo-5-hydroxy-1H-indole-2-carbonyl)-3-(dimethylamino)prop-2-enenitrile

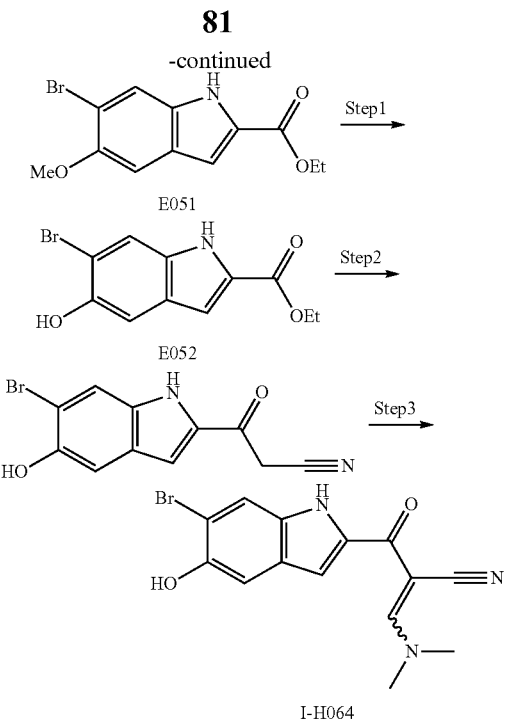

Step 1

Synthesis of ethyl 6-bromo-5-hydroxy-1H-indole-2-carboxylate (E052)

The bromide E051 synthesized in Example 1-3-1 (3.8 g) was dissolved in dichloromethane (106 mL), boron tribromide (1.0 M solution in dichloromethane, 63.7 mL) was added at 0° C., and the mixture was stirred for one hour. Ethanol (15 mL), water (100 mL), and ethyl acetate (100 mL) were added to the reaction solution, and the organic layer was washed with a saturated aqueous sodium bicarbonate solution (100 mL) and then with saturated saline (100 mL) and dried over anhydrous magnesium sulfate. The drying agent was removed by filtration, the filtrate was concentrated under reduced pressure, and the resulting residue was crystallized in dichloromethane (30 mL). The precipitate was collected by filtration and washed with dichloromethane (20 mL) to give the target compound (2.8 g).

Step 2

Synthesis of 3-(6-bromo-5-hydroxy-1H-indol-2-yl)-3-oxopropanenitrile

Ethyl 6-bromo-5-hydroxy-1H-indole-2-carboxylate (50 mg) was suspended in tetrahydrofuran (1.8 mL), dehydrated acetonitrile (28 µL) was added, lithium bis(trimethylsilyl)amide (1.3 M solution in tetrahydrofuran, 1.0 mL) was added at 0° C., and the mixture was stirred for 30 minutes. 1 M hydrochloric acid (1.5 mL) was added to the reaction solution and the mixture was extracted with ethyl acetate. The organic layer was washed with saturated saline and dried over anhydrous sodium sulfate. The drying agent was removed by filtration and the filtrate was concentrated under reduced pressure to give the target compound (53 mg).

Step 3

Synthesis of 2-(6-bromo-5-hydroxy-1H-indole-2-carbonyl)-3-(dimethylamino)prop-2-enenitrile (I-H064)

3-(6-Bromo-5-hydroxy-1H-indol-2-yl)-3-oxopropanenitrile (49 mg) was suspended in tetrahydrofuran (0.88 mL), N,N-dimethylformamide dimethylacetal (35 µL) was added, and the mixture was stirred at 25° C. for 1.5 hours. The precipitated solid was collected by filtration to give the target compound (50 mg).

| Example No. | Compound No. | |
|---|---|---|
| 1-4-2 | I-H064 | 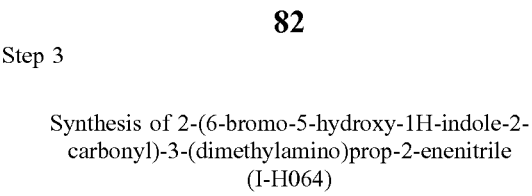 |

Example 1-4-3 (Compound I-A011)

Synthesis of 2-[6-bromo-5-(2,2-difluoroethoxy)-1H-indole-2-carbonyl]-3-(dimethylamino)prop-2-enenitrile

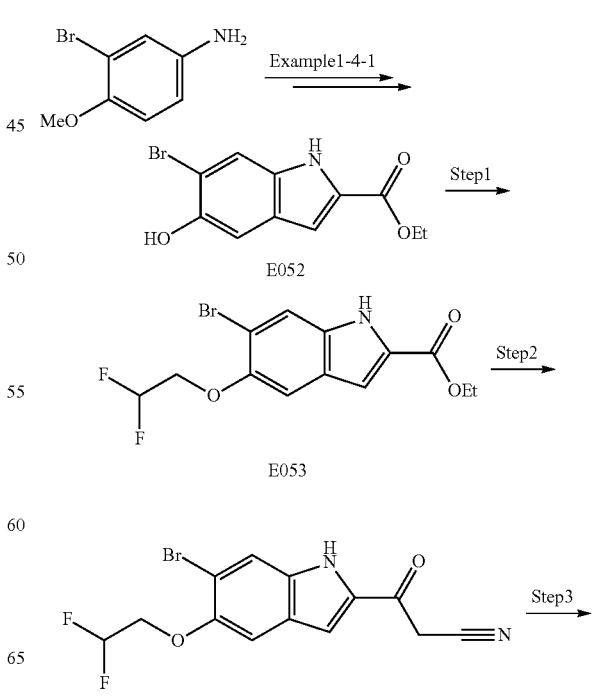

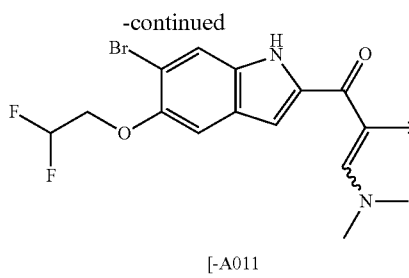

[-A011]

Step 1

Synthesis of ethyl 6-bromo-5-(2,2-difluoroethoxy)-1H-indole-2-carboxylate (E053)

The phenol E052 synthesized in Example 1-4-2 (810 mg) and triphenylphosphine (0.90 g) was dissolved in tetrahydrofuran (16 mL), 2,2-difluoroethanol (0.20 mL) and diisopropyl azodicarboxylate (0.62 mL) were added, and the mixture was stirred at 25° C. for four days. The reaction solution was concentrated under reduced pressure and the resulting residue was purified by column chromatography (hexane/ethyl acetate) to give the target compound (650 mg).

Step 2

Synthesis of 3-[6-bromo-5-(2,2-difluoroethoxy)-1H-indol-2-yl]-3-oxopropanenitrile Ethyl 6-bromo-5-(2,2-difluoroethoxy)-1H-indole-2-carboxylate (650 mg) was dissolved in tetrahydrofuran (13 mL), dehydrated acetonitrile (0.20 mL) was added, lithium bis(trimethylsilyl)amide (1.9 M solution in tetrahydrofuran, 3.9 mL) was added dropwise at 0° C., and the mixture was stirred at 0° C. for one hour. 1 M hydrochloric acid (10 mL) was added to the reaction solution and the mixture was extracted with ethyl acetate (50 mL) four times. The combined organic layers were washed with saturated saline and dried over anhydrous magnesium sulfate. The drying agent was removed by filtration and the filtrate was concentrated under reduced pressure to give the target compound (620 mg).

Step 3

Synthesis of 2-[6-bromo-5-(2,2-difluoroethoxy)-1H-indole-2-carbonyl]-3-(dimethylamino)prop-2-enenitrile 3-[6-Bromo-5-(2,2-difluoroethoxy)-1H-indol-2-yl]-3-oxopropanenitrile (620 mg) was dissolved in tetrahydrofuran (13 mL), TEA (0.51 mL) and N,N-dimethylformamide dimethylacetal (0.27 mL) were added, and the mixture was stirred at 25° C. for one hour. The reaction solution was concentrated under reduced pressure and the resulting residue was recrystallized from hexane/dichloromethane to give the target compound (720 mg).

Example 1-4-4

The compound of Example 1-4-4 was synthesized by the similar method as in Example 1-4-3 using a corresponding aniline and using a corresponding alcohol in Step 1.

| Example No. | Compound No. | |
|---|---|---|
| 1-4-3 | I-A011 | 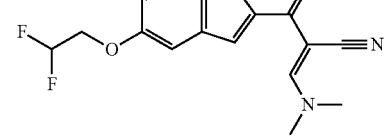 |
| 1-4-4 | I-H044 |  |

Example 1-4-5 (Compound I-H065)

Synthesis of 2-[5-(2,2-difluoroethoxy)-6-morpholin-4-yl-1H-indole-2-carbonyl]-3-(dimethylamino)prop-2-enenitrile

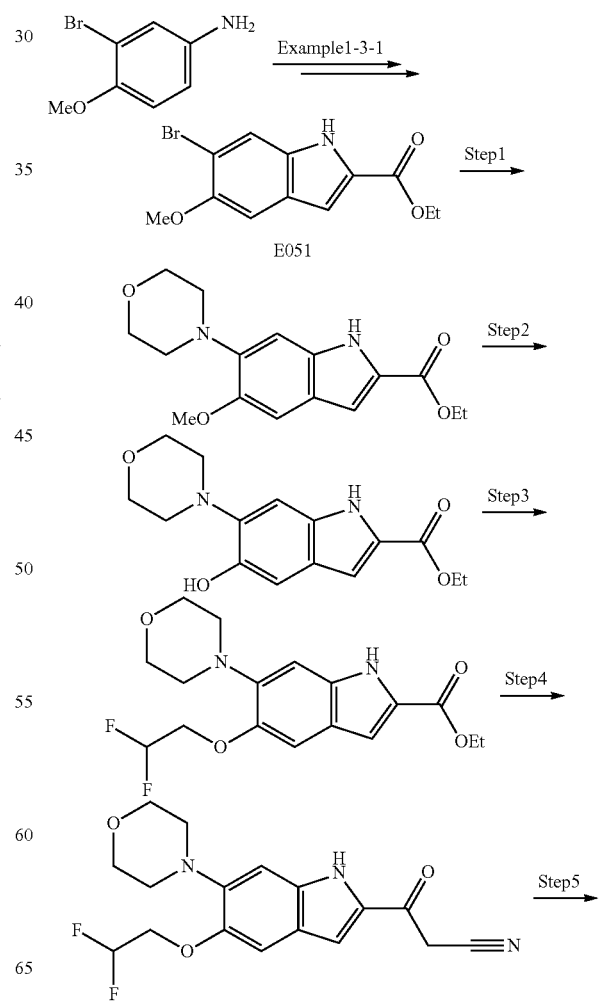

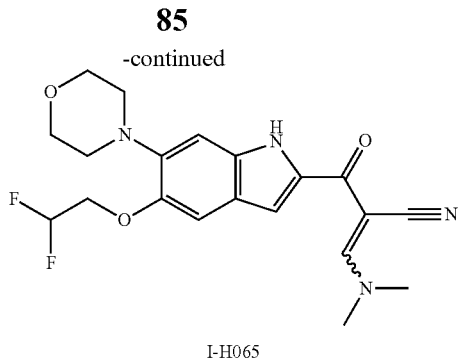

I-H065

Step 1

Synthesis of ethyl 5-methoxy-6-morpholin-4-yl-1H-indole-2-carboxylate

The bromide E051 synthesized in Example 1-3-1 (200 mg) was dissolved in dioxane (3.0 mL) and morpholine (0.29 mL), allylpalladium chloride dimer (49 mg), cesium carbonate (1.75 g), and X-Phos (141 mg) were added. The atmosphere in the reaction system was replaced by nitrogen and the mixture was heated at 80° C. for five hours. The reaction solution was cooled to 25° C., saturated saline was added thereto, and the mixture was extracted with ethyl acetate. The organic layer was washed with saturated saline and dried over anhydrous sodium sulfate. The drying agent was removed by filtration, the filtrate was concentrated under reduced pressure, and the resulting residue was purified by column chromatography (hexane/ethyl acetate) to give the target compound (87 mg).

Step 2

Synthesis of ethyl 5-hydroxy-6-morpholin-4-yl-1H-indole-2-carboxylate

Ethyl 5-methoxy-6-morpholin-4-yl-1H-indole-2-carboxylate (666 mg) was dissolved in dichloromethane (18 mL), boron tribromide (1.0 M solution in dichloromethane, 11 mL) was added at 0° C., and the mixture was stirred at 25° C. for 15 hours. Ethanol (40 mL) and water (13 mL) were added to the reaction solution and the mixture was extracted with ethyl acetate (30 mL). The organic layer was washed with a saturated aqueous sodium bicarbonate solution and saturated saline and dried over anhydrous magnesium sulfate. The drying agent was removed by filtration and the filtrate was concentrated under reduced pressure. The resulting residue was used for the next reaction without purification.

Step 3

Synthesis of ethyl 5-(2,2-difluoroethoxy)-6-morpholin-4-yl-1H-indole-2-carboxylate Ethyl 5-hydroxy-6-morpholin-4-yl-1H-indole-2-carboxylate (183 mg) was suspended in toluene (6.0 mL), 2,2-difluoroethanol (46 μL) and cyanomethylene tri-n-butylphosphorane (215 μL) were added, and the mixture was stirred at 80° C. for eight hours. The reaction solution was concentrated under reduced pressure and the resulting residue was purified by column chromatography (hexane/ethyl acetate) to give the target compound (139 mg).

Step 4

Synthesis of 3-[5-(2,2-difluoroethoxy)-6-morpholin-4-yl-1H-indol-2-yl]-3-oxopropanenitrile Ethyl 5-(2,2-difluoroethoxy)-6-morpholin-4-yl-1H-indole-2-carboxylate (139 mg) was dissolved in tetrahydrofuran (3.9 mL), dehydrated acetonitrile (82 μL) was added, lithium bis(trimethylsilyl)amide (1.9 M solution in tetrahydrofuran, 0.72 mL) was added dropwise at 0° C., and the mixture was stirred at 0° C. for one hour. 1 M hydrochloric acid (4.0 mL) was added to the reaction solution and the mixture was extracted with ethyl acetate (10 mL) three times. The combined organic layers were washed with saturated saline and dried over anhydrous magnesium sulfate. The drying agent was removed by filtration and the filtrate was concentrated under reduced pressure to give the target compound (140 mg).

Step 5

Synthesis of 2-[5-(2,2-difluoroethoxy)-6-morpholin-4-yl-1H-indole-2-carbonyl]-3-(dimethylamino)prop-2-enenitrile (I-H065)

3-[5-(2,2-Difluoroethoxy)-6-morpholin-4-yl-1H-indol-2-yl]-3-oxopropanenitrile (140 mg) was suspended in tetrahydrofuran (4.0 mL), N,N-dimethylformamide dimethylacetal (59 μL) was added, and the mixture was stirred at 25° C. for one hour. The reaction solution was concentrated under reduced pressure and the resulting residue was washed by suspending in dichloromethane/hexane to give the target compound (170 mg).

| Example No. | Compound No. | |
|---|---|---|
| 1-4-5 | I-H065 | 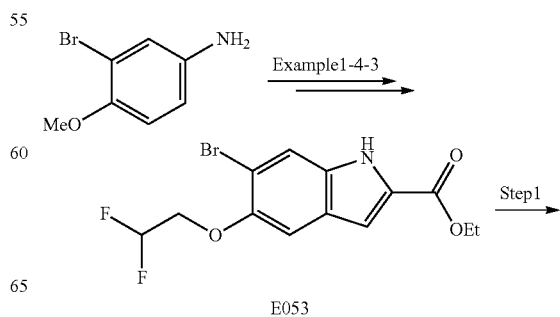 |

Example 1-4-6 (Compound I-H063)

Synthesis of tert-butyl 4-{2-[2-cyano-3-(dimethylamino)prop-2-enoyl]-5-(2,2-difluoroethoxy)-1H-indol-6-yl}piperidine-1-carboxylate

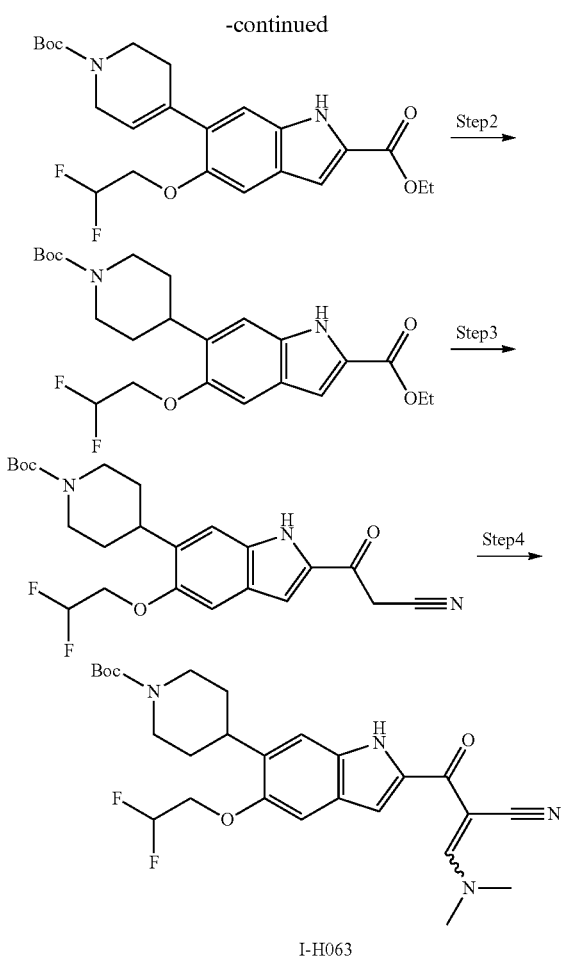

I-H063

Step 1

Synthesis of ethyl 5-(2,2-difluoroethoxy)-6-{1-[(2-methylpropan-2-yl)oxycarbonyl]-3,6-dihydro-2H-pyridin-4-yl}-1H-indole-2-carboxylate The bromide E053 synthesized in Example 1-4-3 (1.00 g) was dissolved in N,N-dimethylformamide (13 mL) and water (1.4 mL), tert-butyl 4-(4,4,5,5-tetramethyl-1,3,2-dioxaborolan-2-yl)-1,2,3,6-tetrahydropyridine-1-carboxylate (1.15 g), PdCl$_2$(dppf) (118 mg), and tripotassium phosphate (915 mg) were added, and the mixture was stirred at 100° C. for 3.5 hours in a nitrogen atmosphere. The reaction solution was cooled to 25° C., water was added, and the mixture was extracted with ethyl acetate. The organic layer was dried over anhydrous sodium sulfate. The drying agent was removed by filtration, the filtrate was concentrated under reduced pressure, and the resulting residue was purified by column chromatography (hexane/ethyl acetate) to give the target compound (1.23 g).

Step 2

Synthesis of ethyl 5-(2,2-difluoroethoxy)-6-{1-[(2-methylpropan-2-yl)oxycarbonyl]piperidin-4-yl}-1-1H-indole-2-carboxylate Ethyl 5-(2,2-difluoroethoxy)-6-{1-[(2-methylpropan-2-yl)oxycarbonyl]-3,6-dihydro-2H-pyridin-4-yl}-1H-indole-2-carboxylate (1.68 g) was dissolved in ethanol, 10% Pd—C (80 mg) was added, and the mixture was stirred at 25° C. for four hours in a hydrogen atmosphere. The insoluble matter was filtered off by celite filtration and the filtrate was concentrated under reduced pressure to give the target compound (1.61 g).

Step 3

Synthesis of tert-butyl 4-[2-(2-cyanoacetyl)-5-(2,2-difluoroethoxy)-1H-indol-6-yl]piperidine-1-carboxylate Ethyl 5-(2,2-difluoroethoxy)-6-{1-[(2-methylpropan-2-yl)oxycarbonyl]piperidin-4-yl}-1H-indole-2-carboxylate (160 mg) was dissolved in tetrahydrofuran (3.5 mL), dehydrated acetonitrile (37 μL) was added, lithium bis(trimethylsilyl)amide (1.9 M solution in tetrahydrofuran, 0.93 mL) was added dropwise at 0° C., and the mixture was stirred at 0° C. for one hour. 1 M hydrochloric acid (4 mL) was added to the reaction solution and the precipitated solid was collected by filtration to give the target compound (85 mg).

Step 4

Synthesis of tert-butyl 4-{2-[2-cyano-3-(dimethylamino)prop-2-enoyl]-5-(2,2-difluoroethoxy)-1H-indol-6-yl}piperidine-1-carboxylate (I-H063)

tert-Butyl 4-[2-(2-cyanoacetyl)-5-(2,2-difluoroethoxy)-1H-indol-6-yl]piperidine-1-carboxylate (85 mg) was suspended in tetrahydrofuran (1.0 mL), N,N-dimethylformamide dimethylacetal (38 μL) was added, and the mixture was stirred at 25° C. for one hour. The reaction solution was concentrated under reduced pressure to give the target compound (79 mg).

| Example No. | Compound No. | |
|---|---|---|
| 1-4-6 | I-H063 | 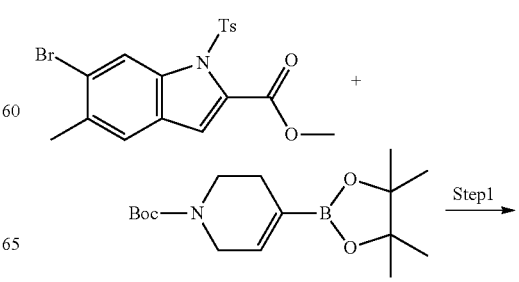 |

Example 1-4-7 (Compound I-H069)

Synthesis of (2E)-3-(dimethylamino)-2-[(E)-[6-(1-methanesulfonylpiperidin-4-yl)-5-methyl-1-[(4-methylbenzene)sulfonyl]-1H-indol-2-yl]carbonyl]prope-2-enenitrile

89

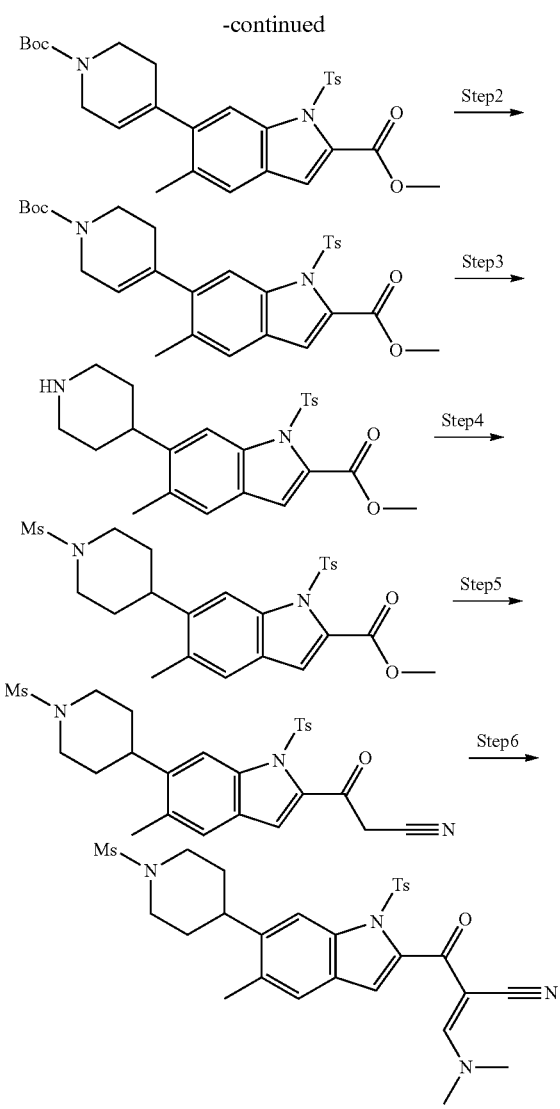

Step 1

Synthesis of methyl 6-[1-[(tert-butoxy)carbonyl]-1,2,3,6-tetrahydropyridin-4-yl]-5-methyl-1-[(4-methylbenzene)sulfonyl]-1H-indole-2-carboxylate Methyl 6-bromo-5-methyl-1-[(4-methylbenzene)sulfonyl]-1H-indole-2-carboxylate (5 g), tetrakis(triphenylphosphane)palladium (1.37 g), tert-butyl 4-(tetramethyl-1,3,2-dioxaborolan-2-yl)-1,2,3,6-tetrahydropyridine-1-carboxylate (4.39 g), and potassium phosphate (5.02 g) were suspended in a mixed solvent of dioxane (100 mL) and water (10 mL), and the mixture was stirred at 100° C. for 16 hours in a nitrogen stream. The insoluble matter was removed by filtration and the filtrate was then concentrated under reduced pressure. The resulting residue was purified by silica gel column chromatography (ethyl acetate/petroleum ether) to give the target compound (6 g).

Step 2

Synthesis of methyl 6-[1-[(tert-butoxy)carbonyl]piperidin-4-yl]-5-methyl-1-[(4-methylbenzene)sulfonyl]-1H-indole-2-carboxylate The compound obtained in Step 1 above (2.7 g) was dissolved in methanol (50 mL), palladium carbon (1.08 g) was added, and the mixture was stirred at 25° C. for five hours in a hydrogen stream. The catalyst was removed by filtration and the filtrate was then concentrated under reduced pressure. The resulting residue was purified by silica gel column chromatography (ethyl acetate/petroleum ether) to give the target compound (1.4 g).

Step 3

Synthesis of methyl 5-methyl-1-[(4-methylbenzene)sulfonyl]-6-(piperidin-4-yl)-1H-indole-2-carboxylate The compound obtained in Step 2 above (1.6 g) was dissolved in dichloromethane (100 mL) and hydrogen chloride gas was introduced into the solution. The reaction solution was stirred at 25° C. for two hours and then concentrated under reduced pressure. The resulting residue was dissolved in a mixed solvent of ethyl acetate (50 mL) and water (50 mL). The aqueous solution was adjusted to pH 8 with a sodium bicarbonate aqueous solution, and the mixture was extracted with ethyl acetate (50 mL×2). After drying the organic layers over sodium sulfate, the drying agent was removed by filtration and the filtrate was then concentrated under reduced pressure to give a crude product (1.4 g).

Step 4

Synthesis of methyl 6-(1-methanesulfonylpiperidin-4-yl)-5-methyl-1-[(4-methylbenzene)sulfonyl]-1H-indole-2-carboxylate The compound obtained in Step 3 above (1.25 g) was dissolved in dichloromethane (30 mL) and triethylamine (444 mg) was added. Methanesulfonyl chloride (1.01 g) was added at 0° C. over five minutes and the reaction solution was stirred at 0° C. for one hour. The reaction solution was concentrated under reduced pressure, and the resulting residue was purified by silica gel column chromatography (ethyl acetate/petroleum ether) to give the target compound (1.1 g).

Step 5

3-[6-(1-Methanesulfonylpiperidin-4-yl)-5-methyl-1-[(4-methylbenzene)sulfonyl]-1H-indol-2-yl]-3-oxo-propanenitrile The compound obtained in Step 4 above (1.2 g) was dissolved in THF (50 mL), and a solution of acetonitrile (290 mg) and LHMDS in THF (1 M, 11.9 mL) was added at −78° C. in a nitrogen stream. After stirring the reaction solution at −78° C. for two hours, the reaction was quenched with an aqueous ammonium chloride solution. The reaction solution was extracted with ethyl acetate (50 mL×2) and the organic layers were dried over sodium sulfate. The drying agent was removed by filtration, the filtrate was concentrated, and the resulting residue was then concentrated under reduced pressure to give a crude product (1.25 g).

Step 6

Synthesis of (2E)-3-(dimethylamino)-2-[(E)-[6-(1-methanesulfonylpiperidin-4-yl)-5-methyl-1-[(4-methylbenzene)sulfonyl]-1H-indol-2-yl]carbonyl]prope-2-enenitrile The compound obtained in Step 5 above (1.25 g) was dissolved in THF (50 mL), dimethylformamide dimethylacetal (320 mg) was added, and the mixture was stirred at 25°

C. for one hour. The reaction solution was concentrated under reduced pressure to give a crude product (1.4 g).

Example 1-4-8 (Compound I-H070)

Synthesis of (2E)-2-[(E)-[6-[1-(cyclopropanesulfonyl)piperidin-4-yl]-5-methyl-1-[(4-methylbenzene)sulfonyl]-1H-indol-2-yl]carbonyl]-3-(dimethylamino)prop-2-enenitrile

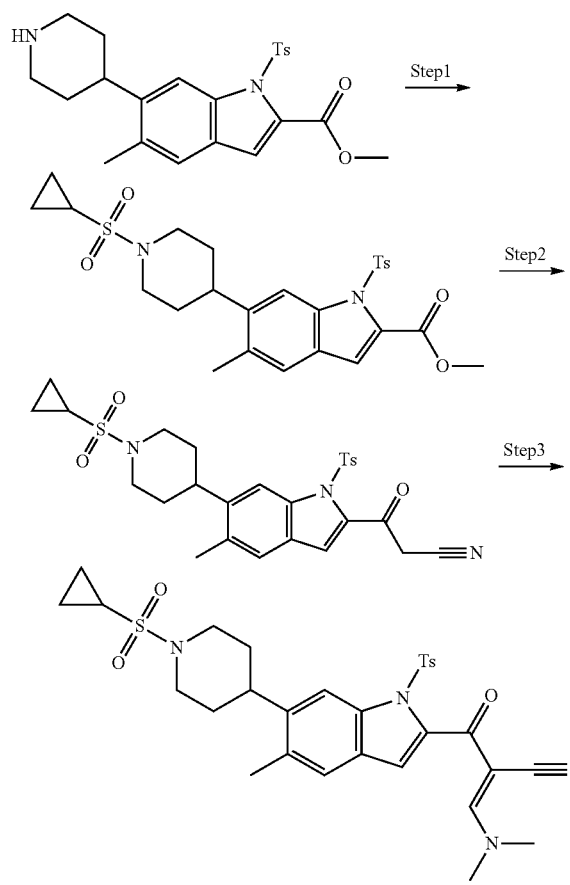

Step 1

Synthesis of methyl 6-[1-(cyclopropanesulfonyl)piperidin-4-yl]-5-methyl-1-[(4-methylbenzene)sulfonyl]-1H-indole-2-carboxylate The compound obtained in Step 3 of Example 1-4-7 (2.5 g) was dissolved in dichloromethane (10 mL) and triethylamine (1.77 g) was added. Cyclopropanesulfonyl chloride (1.24 g) was gradually added at 0° C. and the mixture was then stirred at 25° C. for two hours. The reaction solution was concentrated under reduced pressure and the residue was then purified by silica gel column chromatography (ethyl acetate/petroleum ether) to give the target compound (1.2 g).

Step 2

Synthesis of 3-[6-[1-(cyclopropanesulfonyl)piperidin-4-yl]-5-methyl-1-[(4-methylbenzene)sulfonyl]-1H-indol-2-yl]-3-oxopropanenitrile The compound obtained in Step 1 above (1.6 g) was dissolved in THF (50 mL), acetonitrile (0.37 g) and LHMDS (1 M solution in THF, 15 mL) were added at −78° C., and the mixture was stirred at −78° C. for two hours. The reaction was quenched by adding an aqueous ammonium chloride solution to the reaction solution, and the mixture was extracted with ethyl acetate (50 mL×2). The combined organic layers were washed with an aqueous ammonium chloride solution (50 mL×2) and then dried over sodium sulfate. The drying agent was removed by filtration and the filtrate was concentrated to give the target compound (1.56 g).

Step 3

Synthesis of (2E)-2-[(E)-[6-[1-(cyclopropanesulfonyl)piperidin-4-yl]-5-methyl-1-[(4-methylbenzene)sulfonyl]-1H-indol-2-yl]carbonyl]-3-(dimethylamino)prop-2-enenitrile The compound obtained in Step 2 above (1.56 g) was dissolved in THF (50 mL), dimethylformamide dimethylacetal (0.38 g) was added, and the mixture was stirred at 25° C. for one hour. The reaction solution was concentrated under reduced pressure to give the target compound (1.65 g).

Example 1-4-9 (Compound I-H071)

Synthesis of (2Z)-2-[(Z)-[6-(1-acetylpiperidin-4-yl)-5-methyl-1-[(4-methylbenzene)sulfonyl]-1H-indol-2-yl]carbonyl]-3-(dimethylamino)prop-2-enenitrile

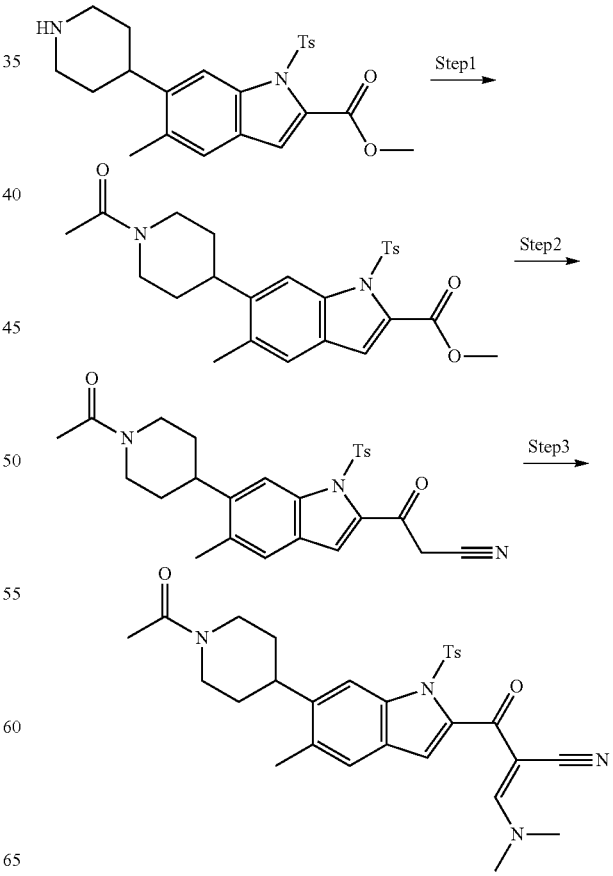

Step 1

Synthesis of methyl 6-(1-acetylpiperidin-4-yl)-5-methyl-1-[(4-methylbenzene)sulfonyl]-1H-indole-2-carboxylate The compound obtained in Step 3 of Example 1-4-7 (1.0 g) was dissolved in dichloromethane (80 mL) and triethylamine (711 mg) was then added. Acetyl chloride (275 mg) was added at 0° C. and the mixture was stirred at 0° C. for 60 minutes. After adding water (100 mL) to the reaction solution, the pH of the reaction solution was adjusted to about 8 to 9 with a 1 M aqueous hydrochloric acid solution at 0° C. The reaction solution was extracted with ethyl acetate (300 mL×3) and the combined organic layers were then dried over sodium sulfate. The drying agent was removed by filtration and the filtrate was concentrated to give the target compound (1.17 g).

Step 2

Synthesis of 3-[6-(1-acetylpiperidin-4-yl)-5-methyl-1-[(4-methylbenzene)sulfonyl]-1H-indol-2-yl]-3-oxopropanenitrile The compound obtained in Step 1 above (1.17 g) was dissolved in THF (50 mL) and acetonitrile (307 mg) was added. LHMDS (1 M solution in THF, 12.5 mL) was added at −78° C. and the mixture was then stirred at −78° C. for 90 minutes. The reaction was quenched by adding an aqueous ammonium chloride solution (300 mL) to the reaction solution, and the mixture was extracted with ethyl acetate (300 mL×2). The combined organic layers were dried over sodium sulfate. The drying agent was removed by filtration and the filtrate was concentrated to give the target compound (1.26 g).

Step 3

Synthesis of (2Z)-2-[(Z)-[6-(1-acetylpiperidin-4-yl)-5-methyl-1-[(4-methylbenzene)sulfonyl]-1H-indol-2-yl]carbonyl]-3-(dimethylamino)prop-2-enenitrile (I-H071)

The compound obtained in Step 2 above (1.26 g) was dissolved in THF (50 mL), dimethylformamide dimethylacetal (0.377 g) was added, and the mixture was stirred at 25° C. for one hour. The reaction solution was concentrated under reduced pressure to give the target compound (1.35 g).

Example 1-4-10

Synthesis of (E)-2-(5-(2,2-difluoroethoxy)-6-(1-(methylsulfonyl)piperidin-4-yl)-1H-indole-2-carbonyl)-3-(dimethylamino)acrylonitrile (I-H073)

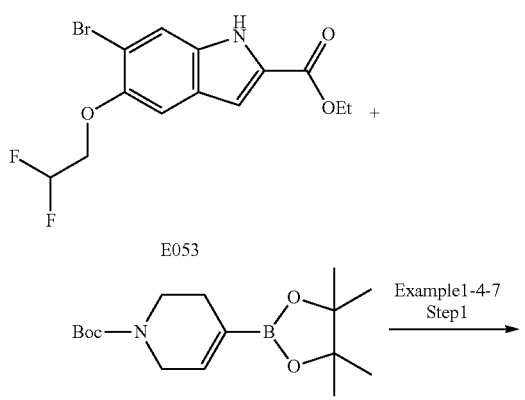

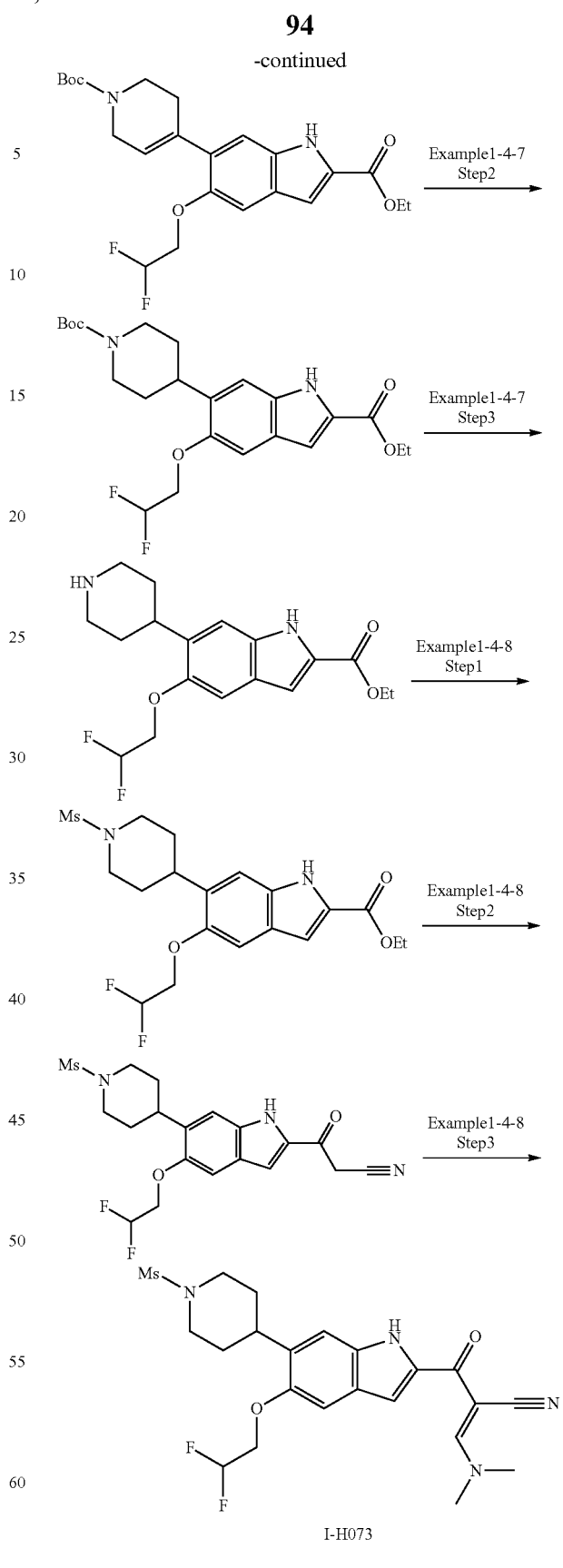

The target compound (I-H073) was obtained by performing Steps 1 to 3 of Example 1-4-7 and Steps 1 to 3 of Example 1-4-8 using E053 obtained in Example 1-4-3.

Example 1-4-11

Synthesis of (E)-2-(6-bromo-5-((1-isopropylpiperidin-4-yl)oxy)-1H-indole-2-carbonyl)-3-(dimethylamino)acrylonitrile (I-H074)

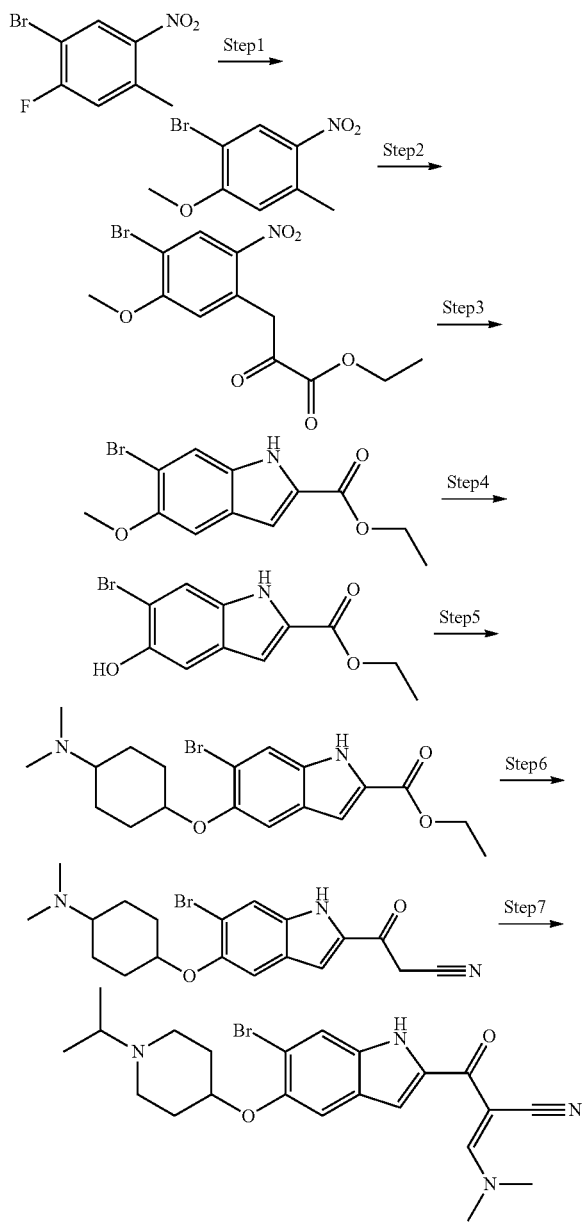

Step 1

Synthesis of 1-bromo-2-methoxy-4-methyl-5-nitrobenzene

Sodium methoxide (28% solution in methanol, 5.73 mL) was added to a solution of 1-bromo-2-fluoro-4-methyl-5-nitrobenzene (7.82 g) in methanol (78 mL) at 25° C., and the mixture was then stirred for 18 hours. Water (78 mL) was added to the reaction solution and the resulting precipitate was collected by filtration and dried to give the target compound (7.55 g).

Step 2

Synthesis of ethyl 3-(4-bromo-5-methoxy-2-nitrophenyl)-2-oxopropanoate

Sodium ethoxide (20% solution in ethanol, 81 mL) was added to a solution of 1-bromo-2-methoxy-4-methyl-5-nitrobenzene (10.2 g) and diethyl oxalate (30.3 g) in ethanol (100 mL) at 25° C., and the mixture was then stirred at 60° C. for two hours. A 5 M aqueous hydrochloric acid solution (40 mL) and water (60 mL) were added to the reaction solution at 0° C. The resulting precipitate was collected by filtration, washed with water (50 mL), and then dried under reduced pressure to give the target compound (10.47 g).

Step 3

Synthesis of ethyl 6-bromo-5-methoxy-1H-indole-2-carboxylate

Ethyl 3-(4-bromo-5-methoxy-2-nitrophenyl)-2-oxopropanoate (10.47 g) was added to acetic acid (101 mL), iron powder (8.45 g) was added, and the mixture was stirred at 80° C. for one hour. After cooling the reaction solution to room temperature, ethyl acetate (100 mL) was added thereto. The insoluble matter was removed by filtration and the filtrate was washed with ethyl acetate (100 mL). Saturated saline (200 mL) was added to the filtrate, and the organic layer was washed with a 5 M aqueous sodium hydroxide solution (200 mL×2) and then further washed with a 5 M aqueous hydrochloric acid solution (200 mL) and saturated saline (200 mL). The organic layer was concentrated under reduced pressure and then azeotropically distilled with toluene. The resulting residue (8.15 g) was used for the next reaction without purification.

Step 4

Synthesis of ethyl 6-bromo-5-hydroxy-1H-indole-2-carboxylate

A solution of boron tribromide in dichloromethane (1 M, 42.7 mL) was added to a solution of ethyl 6-bromo-5-methoxy-1H-indole-2-carboxylate (4.24 g) in dichloromethane (43 mL) at 0° C. and the mixture was stirred for two hours. Ethanol (43 mL) was added to the reaction solution at 0° C., and the reaction solution was then concentrated under reduced pressure. Ethanol (80 mL) was added to the residue which was then dissolved at 80° C. Water (80 mL) was gradually added and the reaction solution was cooled to room temperature. The resulting precipitate was collected by filtration and washed with ethanol-water (1:1, 20 mL). The resulting powder was dried under reduced pressure to give the target compound (3.23 g).

Step 5

Synthesis of ethyl 6-bromo-5-((1-isopropylpiperidin-4-yl)oxy)-1H-indole-2-carboxylate A solution of diisopropyl diazene-1,2-dicarboxylate (1.969 mL) in dichloromethane (5 mL) was added dropwise to a suspension of ethyl 6-bromo-5-hydroxy-1H-indole-2-carboxylate (1421 mg), triphenylphosphine (2623 mg), and 1-isopropylpiperidin-4-ol (1432 mg) in dichloromethane (14 mL) at 0° C. over five minutes. The reaction solution was stirred at 25° C. and then diluted with ethyl acetate (20 mL). The organic layer was washed with saturated saline (20 mL) and then concentrated under reduced pressure. The resulting residue was eluted by silica gel column chromatography (ethyl acetate/methanol, then dichloromethane/methanol) to give the target compound (956 mg).

Step 6

Synthesis of 3-(6-bromo-5-((1-isopropylpiperidin-4-yl)oxy)-1H-indol-2-yl)-3-oxopropanenitrile Ethyl 6-bromo-5-((1-isopropylpiperidin-4-yl)oxy)-1H-indole-2-carboxylate was dissolved in tetrahydrofuran (10 mL), LHMDS (1.3 M, THF solution, 7.2 mL) was added dropwise at −10° C. in a nitrogen atmosphere, and the mixture was further stirred for 15 minutes. A 5 M aqueous hydrochloric acid solution (1.87 mL) was added to the reaction solution at −10° C., and ethyl acetate (10 mL) and water (5 mL) were then added. The organic layer was separated and the aqueous layer was extracted with ethyl acetate (10 mL). The combined organic layers were concentrated under reduced pressure to give the target compound (1341 mg).

Step 7

Synthesis of (E)-2-(6-bromo-5-((1-isopropylpiperidin-4-yl)oxy)-1H-indole-2-carbonyl)-3-(dimethylamino)acrylonitrile (I-H074)

3-(6-Bromo-5-((1-isopropylpiperidin-4-yl)oxy)-1H-indol-2-yl)-3-oxopropanenitrile was suspended in tetrahydrofuran (27 mL), and dimethylformamide dimethylacetal (0.666 mL) was added at 25° C. in a nitrogen atmosphere. The reaction solution was stirred at 25° C. for 18 hours and then concentrated under reduced pressure. THF (6.5 mL) and MTBE (13 mL) were added to the resulting residue. The resulting residue was collected by filtration and washed with MTBE (2 mL), and the powder was then dried under reduced pressure to give the target compound (674 mg).

Example 1-4-12

Synthesis of (E)-tert-butyl 4-((6-bromo-2-(2-cyano-3-(dimethylamino)acryloyl)-1H-indol-5-yl)oxy)piperidine-1-carboxylate (I-H076)

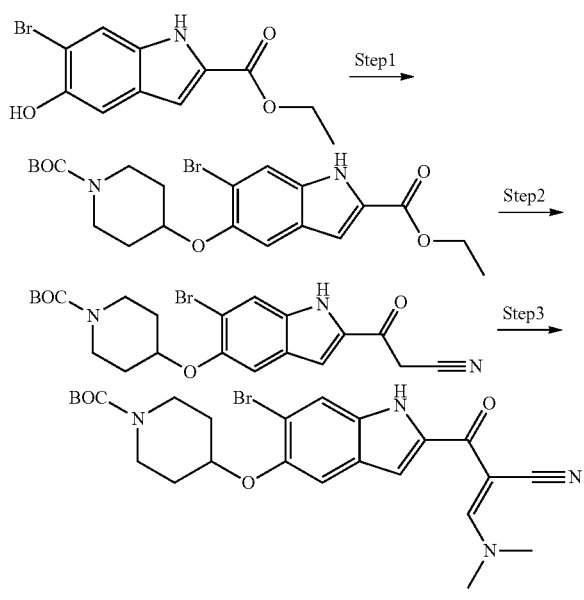

Step 1

Synthesis of ethyl 6-bromo-5-((1-(tert-butoxycarbonyl)piperidin-4-yl)oxy)-1H-indole-2-carboxylate Tributylphosphine (7.9 mL) was added to a suspension of ethyl 6-bromo-5-hydroxy-1H-indole-2-carboxylate obtained in Step 4 of Example 1-4-11 (5.68 g), tert-butyl 4-hydroxypiperidine-1-carboxylate (5.64 g), and ADDP (8.07 g) in toluene (200 mL) at 0° C., and the mixture was stirred at 25° C. for 18 hours. The insoluble matter was removed by filtration. After washing with toluene (100 mL), the filtrate was washed with a 14% aqueous ammonium chloride solution (200 mL) and saturated saline (200 mL) and the organic layer was then dried over sodium sulfate. The drying agent was removed by filtration and the filtrate was concentrated. The resulting residue was then dissolved in ethanol (50 mL) at 50° C. and hexane (80 mL) was added. The resulting precipitate was collected by filtration and washed with hexane (10 mL) to provide a collection. After concentrating the filtrate under reduced pressure, the residue was eluted by silica gel column chromatography (hexane/ethyl acetate) and combined with the collection to provide the target compound (8.42 g).

Step 2

Synthesis of tert-butyl 4-((6-bromo-2-(2-cyanoacetyl)-1H-indol-5-yl)oxy)piperidine-1-carboxylate LHMDS (1.3 M solution in THF, 55.6 mL) was added to a solution of ethyl 6-bromo-5-((1-(tert-butoxycarbonyl)piperidin-4-yl)oxy)-1H-indole-2-carboxylate (5.61 g) and acetonitrile (1.88 mL) in THF (28 mL) at 0° C. and the mixture was stirred for 15 minutes. The reaction was quenched by adding a 10% aqueous acetic acid solution (168 mL) to the reaction solution at 0° C., and the reaction solution was concentrated to about 250 mL under reduced pressure. Methanol (56 mL) was added to the concentrated suspension which was then stirred for 15 minutes. The resulting precipitate was collected by filtration, washed with methanol/water (1/5, 1 mL) and then dried under reduced pressure to give the target compound (5.40 g).

Step 3

Synthesis of (E)-tert-butyl 4-((6-bromo-2-(2-cyano-3-(dimethylamino)acryloyl)-1H-indol-5-yl)oxy)piperidine-1-carboxylate (I-H076)

tert-Butyl 4-((6-bromo-2-(2-cyanoacetyl)-1H-indol-5-yl)oxy)piperidine-1-carboxylate (5.40 g) was suspended in toluene (100 mL), DMF-DMA (1.72 mL) was added at 25° C., and the mixture was stirred for two hours. Hexane (50 mL) was added to the reaction solution to precipitate the target compound. The resulting precipitate was collected by filtration and washed with hexane (10 mL), and the powder was dried under reduced pressure to give the target compound (5.678 g).

Example 1-4-13

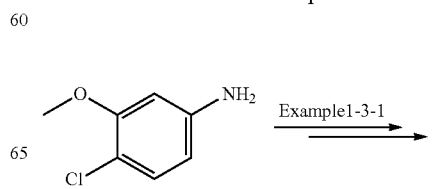

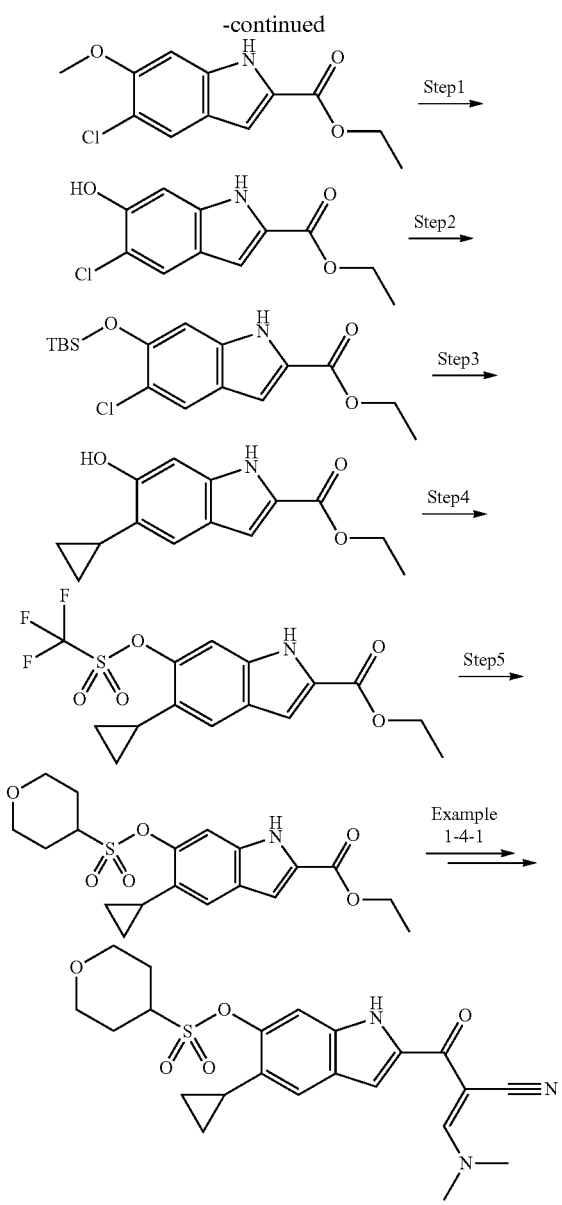

Synthesis of (E)-N-(2-(2-cyano-3-(dimethylamino)acryloyl)-5-cyclopropyl-1H-indol-6-yl)tetrahydro-2H-pyran-4-sulfonamide Step 1

Synthesis of ethyl 5-chloro-6-hydroxy-1H-indole-2-carboxylate

Ethyl 5-chloro-6-methoxy-1H-indole-2-carboxylate (746 mg) obtained by the similar method as in Example 1-3-1 using 4-chloro-3-methoxyaniline was suspended in dichloromethane (14 mL), and a solution of boron tribromide in dichloromethane (1 M, 14.7 mL) was added dropwise at 0° C. The reaction solution was stirred at 0° C. for three hours and further stirred at 25° C. for one hour. The reaction was quenched by adding ethanol (30 mL) at 0° C. and the reaction solution was then concentrated under reduced pressure. The residue was suspended in water (30 mL). After stirring for 10 minutes, the precipitate was collected by filtration and washed (water/ethanol=2/1, 30 mL×4). The powder was dried under reduced pressure to give the target compound (672 mg).

Step 2

Synthesis of ethyl 6-((tert-butyldimethylsilyl)oxy)-5-chloro-1H-indole-2-carboxylate Ethyl 5-chloro-6-hydroxy-1H-indole-2-carboxylate obtained in Step 1 (670 mg) and imidazole (761 mg) were added to dichloromethane (25 mL), tert-butyl-chloro-dimethyl-silane (506 mg) was added at 25° C., and the mixture was stirred 14.5 hours. The reaction solution was concentrated under reduced pressure and the resulting residue was dissolved in a mixture of ethyl acetate and water. The organic layer was washed with a saturated aqueous ammonium chloride solution twice and then dried over sodium sulfate. The drying agent was removed by filtration, the filtrate was concentrated, and the resulting residue was purified by silica gel column chromatography to give the target compound (915 mg).

Step 3

Synthesis of ethyl 5-cyclopropyl-6-hydroxy-1H-indole-2-carboxylate

Ethyl 6-((tert-butyldimethylsilyl)oxy)-5-chloro-1H-indole-2-carboxylate obtained in Step 2 (912 mg), potassium cyclopropyltrifluoroborate (953 mg), allylpalladium(II) chloride dimer (94 mg), Ru-Phos (361 mg), and potassium phosphate (1.643 g) were added to dioxane/(10 mL/1 mL). After the atmosphere in the reaction vessel was replaced by nitrogen, the mixture was stirred at 100° C. for 14.5 hours. The reaction solution was cooled to 25° C. and then made acidic with a 5 M aqueous hydrochloric acid solution. The insoluble matter was removed by filtration. After washing with ethyl acetate, the filtrate was concentrated under reduced pressure and the resulting residue was purified by silica gel column chromatography to give the target compound (342 mg).

Step 4

Synthesis of ethyl 5-cyclopropyl-6-(((trifluoromethyl)sulfonyl)oxy)-1H-indole-2-carboxylate Ethyl 5-cyclopropyl-6-hydroxy-1H-indole-2-carboxylate obtained in Step 3 (340 mg) and pyridine (280 mL) were added to dichloromethane (14 mL), trifluoromethanesulfonic anhydride (0.245 mL) was added at 0° C., and the mixture was then stirred at 0° C. for 15 minutes. The reaction solution was concentrated under reduced pressure and the resulting residue was dissolved in ethyl acetate, washed with a saturated aqueous sodium bicarbonate solution (twice, water, a 1 M aqueous hydrochloric acid solution, and saturated saline, and then dried over sodium sulfate. The drying agent was removed by filtration, the filtrate was concentrated, and the resulting residue was purified by silica gel column chromatography to give the target compound (362 mg).

Step 5

Synthesis of ethyl 5-cyclopropyl-6-((tetrahydro-2H-pyran)-4-sulfonamido)-1H-indole-2-carboxylate A suspension of ethyl 5-cyclopropyl-6-(((trifluoromethyl)sulfonyl)oxy)-1H-indole-2-carboxylate obtained in Step 4

(528 mg), tetrahydro-2H-pyran-4-sulfonamide (289 mg), tris(dibenzylideneacetone)dipalladium-chloroform (145 mg), X-Phos (200 mg), and potassium phosphate (743 mg) in dioxane (14 mL) was added to a reaction vessel. The atmosphere in the reaction vessel was replaced by nitrogen, followed by stirring at 100° C. for 14 hours. After cooling the reaction solution to 25° C., the reaction solution was made acidic by adding a 5 M aqueous hydrochloric acid solution, the insoluble matter was removed by filtration, and the filtrate was washed with ethyl acetate (40 mL×5). After the filtrate was concentrated under reduced pressure, the residue was purified by silica gel column chromatography and then crystallized from hexane/MTBE (6/1) to give the target compound (266 mg).

Synthesis of (E)-N-(2-(2-cyano-3-(dimethylamino) acryloyl)-5-cyclopropyl-1H-indol-6-yl)tetrahydro-2H-pyran-4-sulfonamide The target compound (160 mg) was obtained by performing the similar operation as in Example 1-4-1 using ethyl 5-cyclopropyl-6-((tetrahydro-2H-pyran)-4-sulfonamido)-1H-indole-2-carboxylate obtained in Step 5 (266 mg).

Example 1-4-14

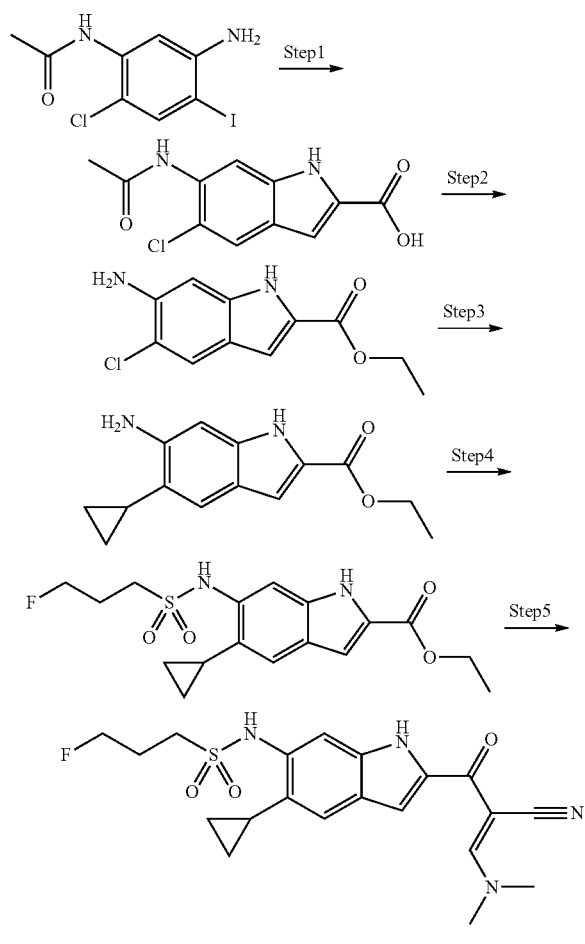

Step 1

Synthesis of 6-acetamido-5-chloro-1H-indole-2-carboxylic acid

The target compound (2.69 g) was obtained by performing the similar operation as in Step 4 of Example 1-5-2 using N-(5-amino-2-chloro-4-iodophenyl)acetamide (3.11 g).

Step 2

Synthesis of ethyl 6-amino-5-chloro-1H-indole-2-carboxylate

Thionyl chloride (4.66 mL) was added dropwise to a solution of 6-acetamido-5-chloro-1H-indole-2-carboxylic acid obtained in Step 1 (2.69 g) in ethanol (53 mL) at 25° C., and the mixture was stirred at 90° C. for five hours. The reaction solution was made basic with a 10% aqueous potassium phosphate solution (200 mL) at 25° C., water (50 mL) was added to the suspension, and the resulting suspension was stirred for 10 minutes. The precipitate was collected by filtration and washed with water (75 mL) and then with hexane (50 mL×2), and the powder was then dried under reduced pressure to give the target compound (2.0 g).

Step 3

Synthesis of ethyl 6-amino-5-cyclopropyl-1H-indole-2-carboxylate

The target compound (1.35 g) was obtained by performing the similar operation as in Step 3 of Example 1-4-13 using ethyl 6-amino-5-chloro-1H-indole-2-carboxylate obtained in Step 2 (1.9 g).

Step 4

Synthesis of ethyl 5-cyclopropyl-6-((3-fluoropropyl) sulfonamido)-1H-indole-2-carboxylate Ethyl 6-amino-5-cyclopropyl-1H-indole-2-carboxylate obtained in Step 3 (672 mg) was added to pyridine (8 mL), 3-fluoropropane-1-sulfonyl chloride (0.427 mL) was added at 25° C., and the mixture was stirred for 2.25 hours. The reaction solution was diluted with a saturated aqueous sodium bicarbonate solution (80 mL). The resulting precipitate was collected by filtration and washed with water (30 mL×4), water/acetonitrile (4/1, 25 mL×3), and hexane/MTBE (3/1, 40 mL×4). The resulting powder was dried under reduced pressure to give the target compound (713 mg).

Step 5

(E)-N-(2-(2-cyano-3-(dimethylamino)acryloyl)-5-cyclopropyl-1H-indol-6-yl)-3-fluoropropane-1-sulfonamide The target compound (727 mg) was obtained by performing the similar operation as in Example 1-4-1 using ethyl 5-cyclopropyl-6-((3-fluoropropyl)sulfonamido)-1H-indole-2-carboxylate obtained in Step 4 (675 mg).

Example 1-4-15

Synthesis of (E)-3-(dimethylamino)-2-(6-fluoro-5-((1-isopropylpiperidin-4-yl)oxy)-1H-indole-2-carbonyl)acrylonitrile -continued

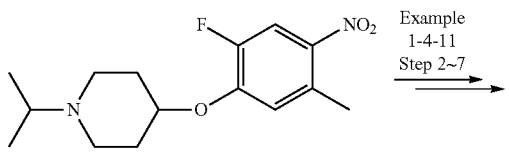
Example 1-4-11
Step 2~7 extracted with ethyl acetate (10 mL×3) and the organic layer was dried over sodium sulfate. The drying agent was removed by filtration, the filtrate was concentrated, and the resulting residue was then concentrated under reduced pressure to give the target compound (1.29 g).

Step 2

Synthesis of (E)-3-(dimethylamino)-2-(6-fluoro-5-((1-isopropylpiperidin-4-yl)oxy)-1H-indole-2-carbonyl)acrylonitrile The target compound (1.65 g) was obtained by performing the similar operation as in Steps 2 to 7 of Example 1-4-11 using 4-(2-fluoro-5-methyl-4-nitrophenoxy)-1-isopropylpiperidine obtained in Step 1.

Example 1-4-16

Synthesis of (E)-2-(6-chloro-5-((1-isopropylpiperidin-4-yl)oxy)-1H-indole-2-carbonyl)-3-(dimethylamino)acrylonitrile The target compound (1.58 g) was obtained by performing the similar operation as in Example 1-4-15 using 1-chloro-2-fluoro-4-methyl-5-nitrobenzene.

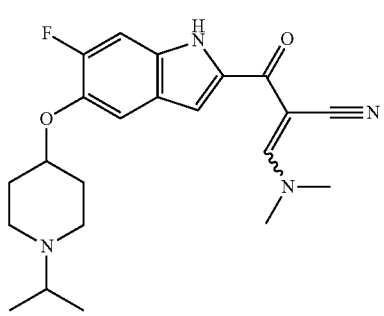

Step 1

Synthesis of 4-(2-fluoro-5-methyl-4-nitrophenoxy)-1-isopropylpiperidine 1,2-Difluoro-4-methyl-5-nitrobenzene (1.0 g) was dissolved in THF (20 mL), a 4 M aqueous potassium hydroxide solution (14.4 mL) was added at 0° C., and the mixture was then stirred at 25° C. for five hours. Ethyl acetate (30 mL) was added to the reaction solution and the mixture was extracted with a 2 M aqueous hydrochloric acid solution (4 mL) and a 0.1 M aqueous hydrochloric acid solution (10 mL×2). The aqueous layer was adjusted to pH 10 with a 4 M aqueous sodium hydroxide solution (4 mL) and then Example 1-4-17

Synthesis of (E)-tert-butyl 4-((2-(2-cyano-3-(dimethylamino)acryloyl)-6-fluoro-1H-indol-5-yl)oxy)piperidine-1-carboxylate The target compound was obtained by performing the similar operation as in Example 1-4-12 using 4-fluoro-3-methoxy-aniline.

Example 1-4-18

Synthesis of (E)-tert-butyl 4-((6-chloro-2-(2-cyano-3-(dimethylamino)acryloyl)-1H-indol-5-yl)oxy)piperidine-1-carboxylate The target compound was obtained by performing the similar operation as in Example 1-4-12 using 4-chloro-3-methoxy-aniline.

| Example No. | Compound No. | |
|---|---|---|
| 1-4-7 | I-H069 | 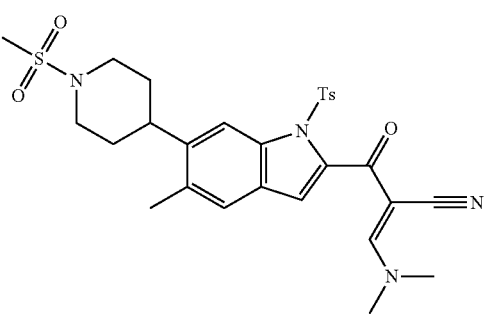 [SMILES: Cc1ccc(S(=O)(=O)n2c(C(=O)/C(C#N)=C/N(C)C)cc3cc(C)c(C4CCN(S(C)(=O)=O)CC4)cc32)cc1] |

-continued
| Example No. | Compound No. | |
|---|---|---|
| 1-4-8 | I-H070 | 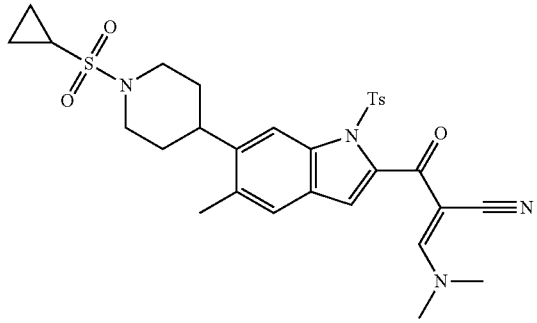 [SMILES: Cc1ccc(S(=O)(=O)n2c(C(=O)/C(C#N)=C/N(C)C)cc3cc(C)c(C4CCN(S(=O)(=O)C5CC5)CC4)cc32)cc1] |
| 1-4-9 | I-H071 | 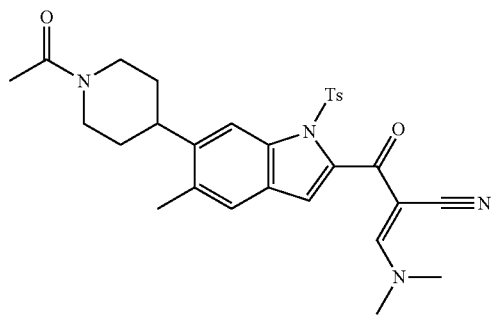 [SMILES: CC(=O)N1CCC(c2cc3c(cc2C)cc(C(=O)/C(C#N)=C/N(C)C)n3S(=O)(=O)c2ccc(C)cc2)CC1] |
| 1-4-10 | I-H073 | 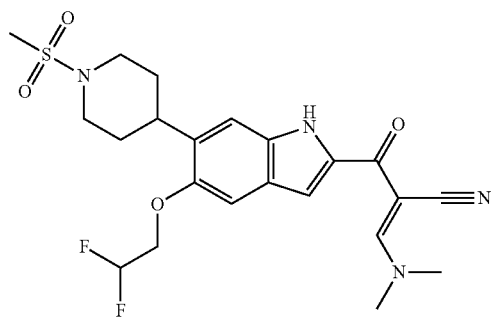 [SMILES: CN(C)/C=C(\C#N)C(=O)c1cc2cc(OCC(F)F)c(C3CCN(S(C)(=O)=O)CC3)cc2[nH]1] |
| 1-4-11 | I-H074 | 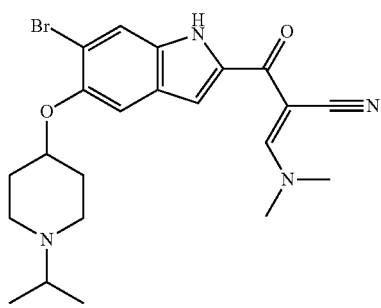 |
| 1-4-12 | I-H076 | 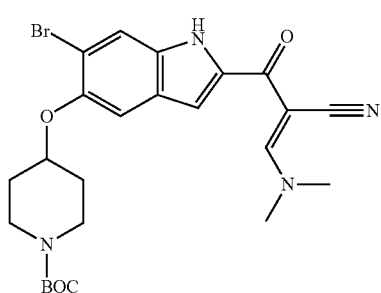 [SMILES: CN(C)/C=C(\C#N)C(=O)c1cc2cc(OC3CCN(C(=O)OC(C)(C)C)CC3)c(Br)cc2[nH]1] |

-continued
| Example No. | Compound No. | |
|---|---|---|
| 1-4-13 | I-H078 | 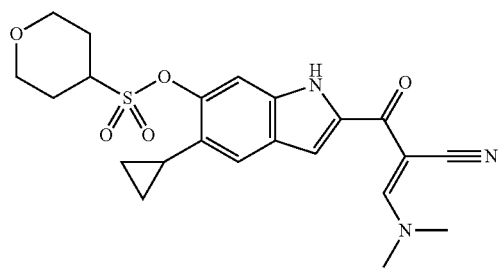 [SMILES: CN(C)/C=C(\C#N)C(=O)c1cc2cc(C3CC3)c(OS(=O)(=O)C3CCOCC3)cc2[nH]1] |
| 1-4-14 | I-H079 | 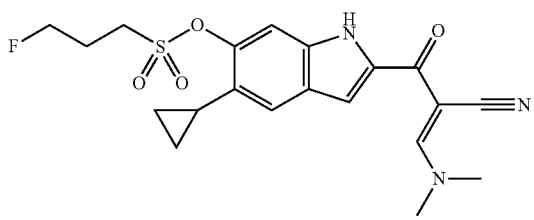 [SMILES: CN(C)/C=C(\C#N)C(=O)c1cc2cc(C3CC3)c(OS(=O)(=O)CCCF)cc2[nH]1] |
| 1-4-15 | I-H080 | 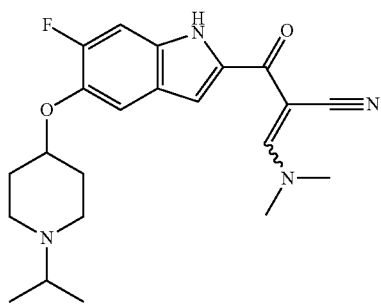 |
| 1-4-16 | I-H081 | 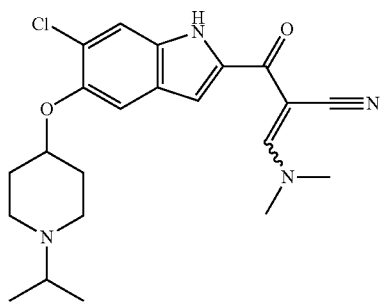 |
| 1-4-17 | I-H082 | 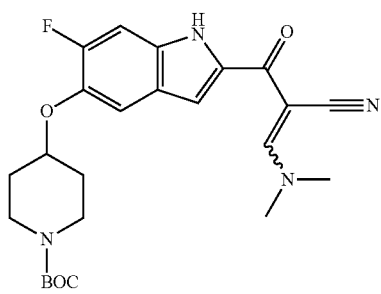 [SMILES: CN(C)C=C(C#N)C(=O)c1cc2cc(OC3CCN(C(=O)OC(C)(C)C)CC3)c(F)cc2[nH]1] |

| Example No. | Compound No. | |
|---|---|---|
| 1-4-18 | I-H083 | 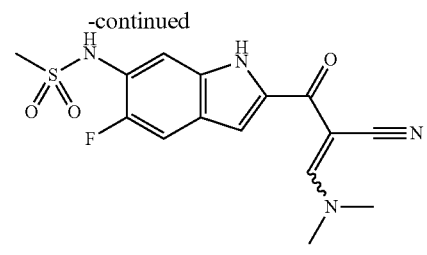 |

Example 1-5-1 (Compound I-H047)

Synthesis of N-{2-[2-cyano-3-(dimethylamino)prop-2-enoyl]-5-fluoro-1H-indol-6-yl}methanesulfonamide

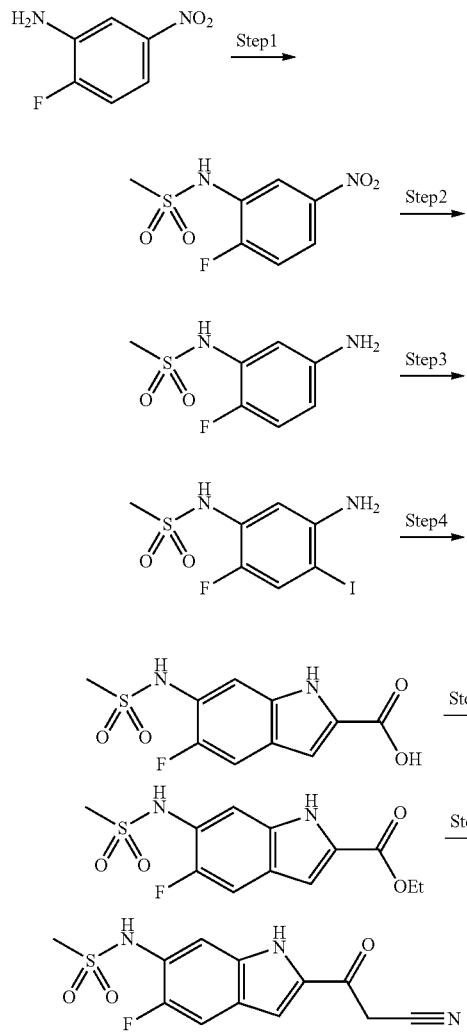

I-H047

Step 1

Synthesis of N-(2-fluoro-5-nitrophenyl)methanesulfonamide

2-Fluoro-5-nitroaniline (3.00 g) was dissolved in tetrahydrofuran (77 mL) and methanesulfonyl chloride (4.5 mL) were added at 0° C., and the mixture was stirred at 0° C. for one hour. DIPEA (9.5 mL) and methanesulfonyl chloride (4.0 mL) were added and the mixture was stirred at 25° C. for two hours. A 5 M aqueous sodium hydroxide solution (15 mL) was added to the reaction solution and the mixture was stirred at 25° C. for three hours. 5 M hydrochloric acid was added to the reaction solution and the mixture was extracted with ethyl acetate. The organic layer was concentrated under reduced pressure and the resulting residue was washed by suspending in tert-butyl methyl ether to give the target compound (4.00 g).

Step 2

Synthesis of N-(5-amino-2-fluorophenyl)methanesulfonamide

N-(2-Fluoro-5-nitrophenyl)methanesulfonamide (2.00 g) was dissolved in methanol (34 mL), 10% Pd—C (45 mg) was added, and the mixture was stirred at 25° C. for three hours in a hydrogen atmosphere. The insoluble matter was filtered off by celite filtration and the filtrate was concentrated under reduced pressure. The resulting residue was crystallized from ethyl acetate/hexane to give the target compound (1.65 g).

Step 3

Synthesis of N-(5-amino-2-fluoro-4-iodophenyl)methanesulfonamide

N-(5-Amino-2-fluorophenyl)methanesulfonamide (1.65 g) was dissolved in dimethyl sulfoxide (8.0 mL), N-iodosuccinimide (1.8 g) was added, and the mixture was stirred at 25° C. for 6.5 hours. Water (32 mL) was added to the reaction solution and the precipitated solid was collected by filtration. The resulting crude solid was purified by column chromatography (dichloromethane/methanol) to give the target compound (1.89 g).
Step 4

Synthesis of 5-fluoro-6-(methanesulfonamido)-1H-indole-2-carboxylic acid

N-(5-Amino-2-fluoro-4-iodophenyl)methanesulfonamide (300 mg) was dissolved in N,N-dimethylformamide (3.6 mL) and DABCO (306 mg) and pyruvic acid (189 µL) were added. The reaction system was degassed under reduced pressure and the atmosphere therein was replaced by nitrogen. X-Phos (48 mg) and allylpalladium chloride dimer (16 mg) were added. The reaction system was degassed again under reduced pressure and the atmosphere therein was replaced by nitrogen. The mixture was heated at 80° C. for three hours. The reaction solution was cooled to 25° C., 1 M hydrochloric acid (15 mL) was added, and the mixture was extracted with ethyl acetate (15 mL). The organic layer was washed with a 5% aqueous N-acetyl-L-cysteine solution (15 mL) and saturated saline (15 mL) and dried over anhydrous sodium sulfate. The drying agent was removed by filtration and the filtrate was concentrated under reduced pressure to give the target compound (466 mg).
Step 5

Synthesis of ethyl 5-fluoro-6-(methanesulfonamido)-1H-indole-2-carboxylate

5-Fluoro-6-(methanesulfonamido)-1H-indole-2-carboxylic acid (247 mg) was suspended in ethanol (3.0 mL), concentrated sulfuric acid (145 µL) was added, and the mixture was stirred at 70° C. for 15 hours. The reaction solution was cooled to 25° C., water (9.0 mL) was added, and the precipitated solid was collected by filtration. The resulting crude solid was washed by suspending in hexane to give the target compound (181 mg).
Step 6

Synthesis of N-[2-(2-cyanoacetyl)-5-fluoro-1H-indol-6-yl]methanesulfonamide

Ethyl 5-fluoro-6-(methanesulfonamido)-1H-indole-2-carboxylate (100 mg) was suspended in tetrahydrofuran (2.2 mL), dehydrated acetonitrile (0.052 mL) was added, sodium bis(trimethylsilyl)amide (1.9 M solution in tetrahydrofuran, 0.18 mL) was added dropwise at 0° C., and the mixture was stirred for 20 minutes. 1 M hydrochloric acid was added to the reaction solution and the mixture was extracted with ethyl acetate. The organic layer was washed with saturated saline and dried over anhydrous sodium sulfate. The drying agent was removed by filtration and the filtrate was concentrated under reduced pressure to give the target compound (95 mg).
Step 7

Synthesis of N-{2-[2-cyano-3-(dimethylamino)prop-2-enoyl]-5-fluoro-1H-indol-6-yl}methanesulfonamide (I-H047)

N-[2-(2-Cyanoacetyl)-5-fluoro-1H-indol-6-yl]methanesulfonamide (95 mg) was suspended in tetrahydrofuran (1.5 mL), N,N-dimethylformamide dimethylacetal (0.043 mL) was added, and the mixture was stirred for one hour. The reaction solution was concentrated under reduced pressure and the resulting residue was washed by suspending in ethyl acetate to give the target compound (96 mg).

| Example No. | Compound No. | |
|---|---|---|
| 1-5-1 | I-H047 | 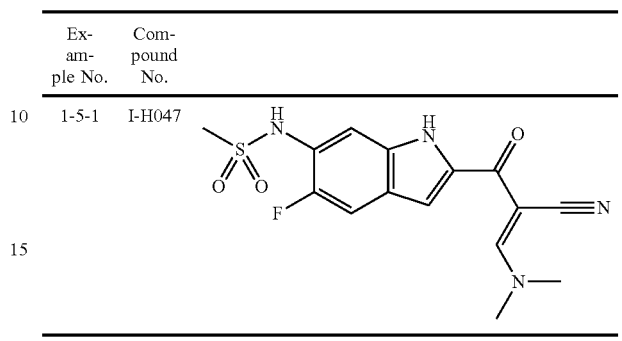 |

Example 1-5-2 (Compound I-H053)

Synthesis of N-{2-[2-cyano-3-(dimethylamino)prop-2-enoyl]-5-methyl-1H-indol-6-yl}methanesulfonamide

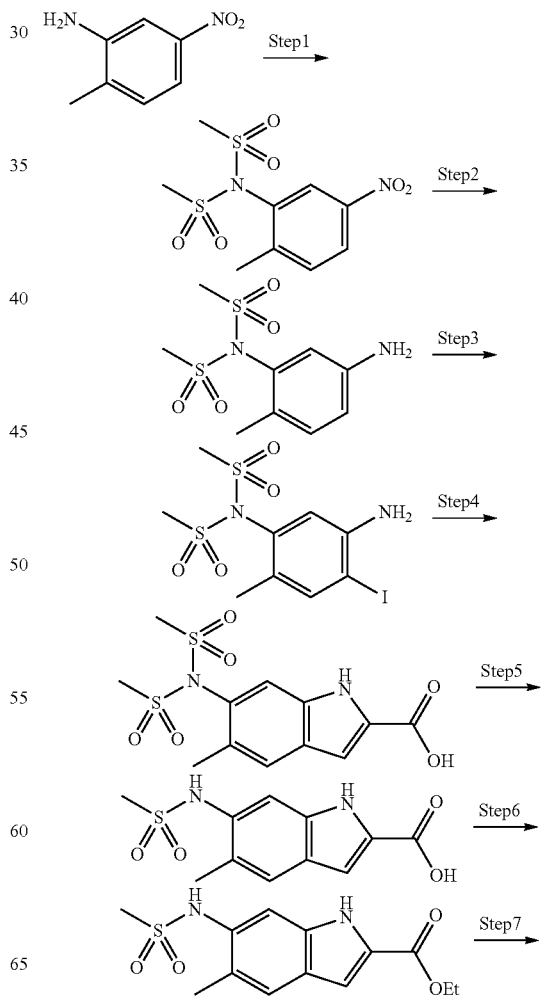

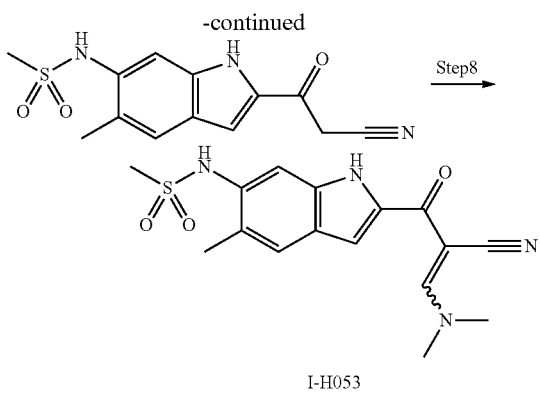

I-H053

Step 1

Synthesis of N-(2-methyl-5-nitrophenyl)-N-methyl-sulfonylmethanesulfonamide

2-Methyl-5-nitroaniline (25.0 g) was dissolved in dichloromethane (250 mL), DIPEA (63 mL) and methanesulfonyl chloride (27 mL) were added at 0° C., and the mixture was stirred at 0° C. for one hour. DIPEA (9.5 mL) and methanesulfonyl chloride (4.0 mL) were added and the mixture was stirred at 0° C. for 20 minutes. 1 M hydrochloric acid (250 mL) was added to the reaction solution, the aqueous layer was discharged, and the organic layer was concentrated to half the volume. The precipitated solid was collected by filtration and washed with hexane to give the target compound (38.0 g).

Step 2

Synthesis of N-(5-amino-2-methylphenyl)-N-methylsulfonylmethanesulfonamide

N-(2-Methyl-5-nitrophenyl)-N-methylsulfonylmethanesulfonamide (38.0 g) was suspended in tetrahydrofuran (150 mL) and water (230 mL), sodium hyposulfite (65.0 g) was added at 25° C., and the mixture was stirred for 10 minutes. Subsequently, concentrated hydrochloric acid (76 mL) was added and the mixture was stirred at 60° C. for three hours. The reaction solution was cooled to 25° C., tripotassium phosphate (180 g) was added, and water (76 mL) was then added. The precipitated solid was collected by filtration and washed with water to give the target compound (22.0 g).

Step 3

Synthesis of N-(5-amino-4-iodo-2-methylphenyl)-N-methylsulfonylmethanesulfonamide N-(5-Amino-2-methylphenyl)-N-methylsulfonylmethanesulfonamide (22.0 g) was dissolved in acetic acid (110 mL), N-iodosuccinimide (18.0 g) was added, and the mixture was stirred at 25° C. for one hour. Sodium sulfite (33.0 g) dissolved in water (330 mL) was added to the reaction solution, and the precipitated solid was collected by filtration and washed with water to give the target compound (28.0 g).

Step 4

Synthesis of 6-[bis(methylsulfonyl)amino]-5-methyl-1H-indole-2-carboxylic acid N-(5-Amino-4-iodo-2-methylphenyl)-N-methylsulfonylmethanesulfonamide (17.0 g) was dissolved in N,N-dimethylformamide (85 mL) and DABCO (14.0 g), pyruvic acid (8.8 mL), and X-Phos (3.0 g) were added. The reaction system was degassed under reduced pressure and the atmosphere therein was replaced by nitrogen. $Pd_2dba_3$ (960 mg) was added. The reaction system was degassed again under reduced pressure and the atmosphere therein was replaced by nitrogen. The mixture was heated at 60° C. for four hours. N-Acetyl-L-cysteine was added to the reaction solution and the mixture was stirred at 60° C. for 30 minutes. The reaction solution was cooled to 25° C., a 5 M aqueous hydrochloric acid solution (85 mL) was added, and the mixture was extracted with ethyl acetate (250 mL) twice. The organic layers were washed with saturated saline (160 mL) twice and dried over anhydrous sodium sulfate. The drying agent was removed by filtration and the filtrate was concentrated under reduced pressure to give the target compound (28.2 g).

Step 5

Synthesis of 6-(methanesulfonamido)-5-methyl-1H-indole-2-carboxylic acid

6-[Bis(methylsulfonyl)amino]-5-methyl-1H-indole-2-carboxylic acid (24.0 g) was suspended in methanol (190 mL), a 8 M aqueous potassium hydroxide solution (43 mL) was added, and the mixture was stirred at 50° C. for 30 minutes. The reaction solution was cooled to 0° C. and neutralized with 5 M hydrochloric acid. Water was added and the precipitated solid was collected by filtration and sequentially washed with methanol/water, 2-propanol, and hexane to give the target compound (18.0 g).

Step 6

Synthesis of ethyl 6-(methanesulfonamido)-5-methyl-1H-indole-2-carboxylate 6-(Methanesulfonamido)-5-methyl-1H-indole-2-carboxylic acid (17.7 g) was suspended in ethanol (270 mL), thionyl chloride (35 mL) was added at 0° C., and the mixture was refluxed for three hours. The reaction solution was cooled to 25° C. and neutralized with a 15% aqueous dipotassium hydrogenphosphate solution. The precipitated solid was collected by filtration and sequentially washed with water, ethanol/water, 2-propanol, and hexane/ethyl acetate to give the target compound (11.4 g).

Step 7

Synthesis of N-[2-(2-cyanoacetyl)-5-methyl-1H-indol-6-yl]methanesulfonamide

Ethyl 6-(methanesulfonamido)-5-methyl-1H-indole-2-carboxylate (18.3 g) was suspended in tetrahydrofuran (280 mL), dehydrated acetonitrile (6.5 mL) was added, lithium bis(trimethylsilyl)amide (1.3 M solution in tetrahydrofuran, 240 mL) was added dropwise at 0° C., and the mixture was stirred for 30 minutes. Water was added to the reaction solution and the aqueous layer was separated. The organic layer was washed with water and the combined aqueous layers were neutralized with 5 M hydrochloric acid. The precipitated solid was collected by filtration and sequentially washed with water, 2-propanol, and ethyl acetate to give the target compound (12.6 g).

Step 8

Synthesis of N-{2-[2-cyano-3-(dimethylamino)prop-2-enoyl]-5-methyl-1H-indol-6-yl}methanesulfonamide (I-H053)

N-[2-(2-Cyanoacetyl)-5-methyl-1H-indol-6-yl]methanesulfonamide (12.5 g) was suspended in tetrahydrofuran (190 mL) and N,N-dimethylformamide (13 mL), N,N-dimethylformamide dimethylacetal (6.0 mL) was added at 0° C., and the mixture was stirred for 30 minutes. 2-Propanol was added to the reaction solution and the precipitated solid was collected by filtration and washed with 2-propanol to give the target compound (14.1 g).

| Example No. | Compound No. | |
|---|---|---|
| 1-5-2 | I-H053 | |

Example 1-5-3 (Compound I-H053)

Synthesis of N-{2-[2-cyano-3-(dimethylamino)prop-2-enoyl]-5-methyl-1H-indol-6-yl}methanesulfonamide

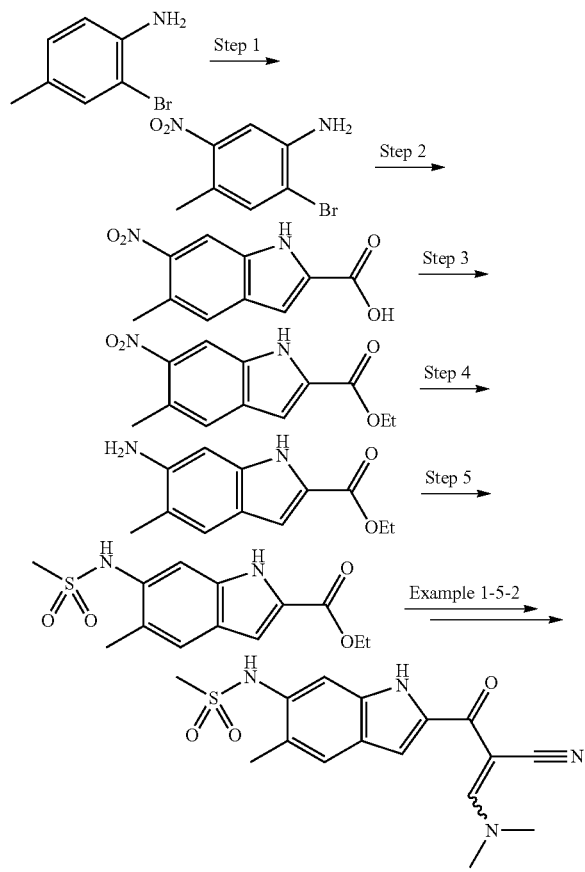

Step 1

Synthesis of 2-bromo-4-methyl-5-nitroaniline

2-Bromo-4-methylaniline (23.8 g) was dissolved in concentrated sulfuric acid (119 mL), urea nitrate (15 g) was added in small portions at 10° C. or lower, and the mixture was stirred at 0° C. for 10 minutes. Water (120 mL) and a 5 M aqueous sodium hydroxide solution (205 mL) were added to the reaction solution and the precipitated solid was collected by filtration to give the target compound (26.3 g).

Step 2

Synthesis of 5-methyl-6-nitro-1H-indole-2-carboxylic acid

2-Bromo-4-methyl-5-nitroaniline (10.0 g) was dissolved in N,N-dimethylformamide (173 mL), tripotassium phosphate (27.6 g), pyruvic acid (9.2 mL), X-Phos (6.2 g), and allylpalladium chloride dimer (1.6 g) were added, and the mixture was heated at 100° C. for 15 hours in a nitrogen atmosphere. The reaction solution was cooled to 25° C., water (350 mL) and a saturated aqueous sodium bicarbonate solution (100 mL) were added, and the mixture was extracted with ethyl acetate (300 mL). 1 M hydrochloric acid was added to the aqueous layer and the precipitated solid was collected by filtration. The resulting crude solid was dissolved in ethyl acetate, water was added, and the mixture was extracted with ethyl acetate. The organic layer was washed with water and concentrated under reduced pressure, and the resulting residue was washed with suspending in ethyl acetate/hexane to give the target compound (7.67 g).

Step 3

Synthesis of ethyl 5-methyl-6-nitro-1H-indole-2-carboxylate

5-Methyl-6-nitro-1H-indole-2-carboxylic acid (6.70 g) was dissolved in ethanol (69 mL), thionyl chloride (6.7 mL) was added, and the mixture was stirred at 90° C. for two hours. The reaction solution was cooled to 25° C., water (51 mL) was added, and the precipitated solid was collected by filtration to give the target compound (6.60 g).

Step 4

Synthesis of ethyl 6-amino-5-methyl-1H-indole-2-carboxylate

Ethyl 5-methyl-6-nitro-1H-indole-2-carboxylate (5.58 g) was dissolved in ethyl acetate (90 mL), tin(II) chloride dihydrate (25.4 g) was added, and the mixture was stirred at 70° C. for three hours. The reaction solution was cooled to 0° C., water (40 mL), a 5 M aqueous sodium hydroxide solution (45 mL), and a saturated aqueous sodium bicarbonate solution (200 mL) were added, and the insoluble matter was filtered off by celite filtration. The filtrate was extracted with ethyl acetate and the organic layer was concentrated under reduced pressure to give the target compound (4.60 g).

Step 5

Synthesis of ethyl 6-(methanesulfonamido)-5-methyl-1H-indole-2-carboxylate

Ethyl 6-amino-5-methyl-1H-indole-2-carboxylate (2.00 g) was dissolved in pyridine (10 mL), methanesulfonyl chloride (0.79 mL) was added at 0° C., and the mixture was stirred at 0° C. for 30 minutes. Water (30 mL) was added to the reaction solution and the precipitated solid was collected by filtration to give the target compound (2.50 g).

| Example No. | Compound No. | |
|---|---|---|
| 1-5-3 | I-H053 | 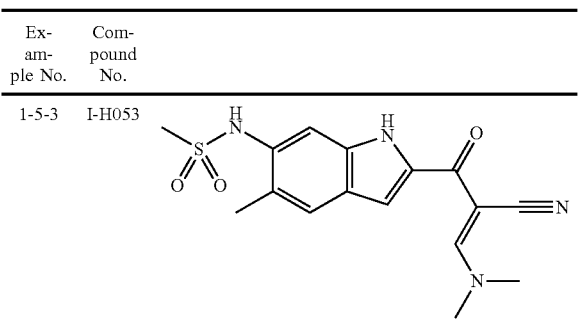 |

Example 1-5-4

Synthesis of (E)-N-(2-(2-cyano-3-(dimethylamino)acryloyl)-5-ethyl-1H-indol-6-yl)methanesulfonamide (I-H072)

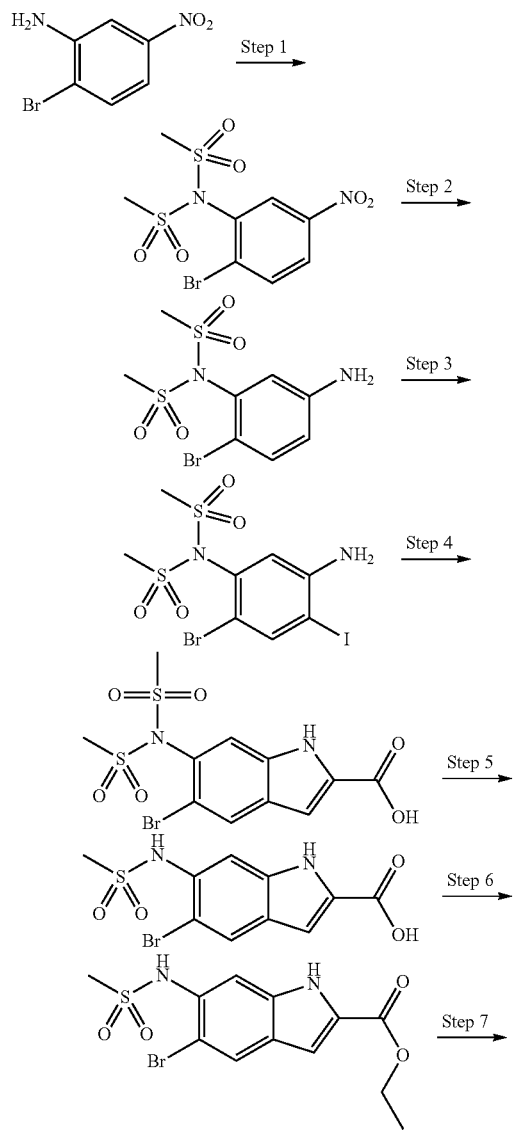

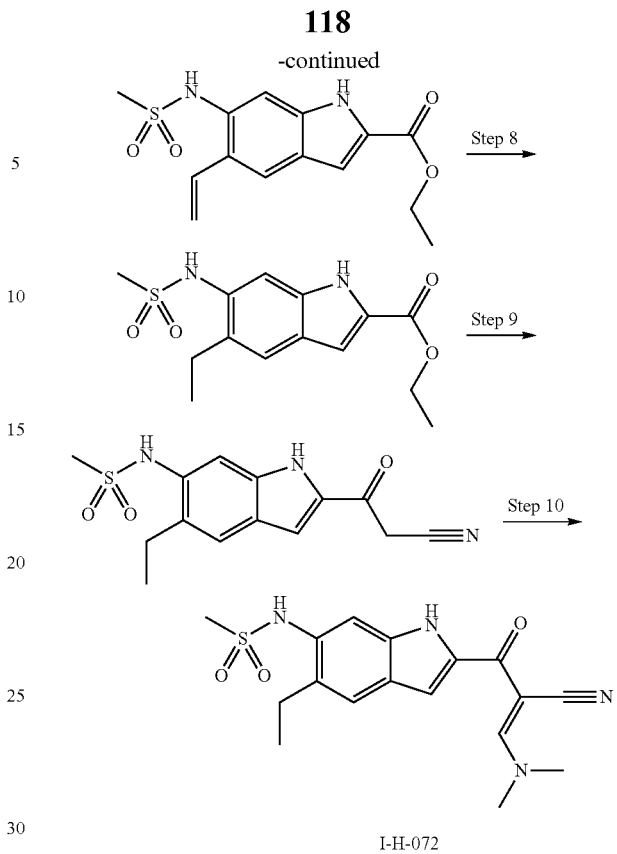

I-H-072

Step 1

Synthesis of N-(2-bromo-5-nitrophenyl)-N-(methylsulfonyl)methanesulfonamide

2-Bromo-5-nitroaniline (5 g) was dissolved in tetrahydrofuran (100 mL) and triethylamine (9.63 mL) was added. Methanesulfonyl chloride (4.49 mL) was added at 25° C. and the mixture was stirred for 90 minutes. A 5 M aqueous hydrochloric acid solution (27.6 mL) and water (75 mL) were added and the mixture was stirred for 10 minutes. The resulting precipitate was collected by filtration and washed with water, and the powder was dried to give the target compound (6.96 g).

Step 2

Synthesis of N-(5-amino-2-bromophenyl)-N-(methylsulfonyl)methanesulfonamide

N-(2-Bromo-5-nitrophenyl)-N-(methylsulfonyl)methanesulfonamide (1 g) was dissolved in a mixed solvent of ethanol (3 mL), tetrahydrofuran (3 mL), and water (6 mL), sodium dithionite (1.4 g) was added, and the mixture was stirred at 25° C. for 30 minutes. Concentrated hydrochloric acid (2 mL) was added and the mixture was then stirred at 65° C. for 90 minutes. Potassium phosphate (4 g) and water (3 mL) were then added at 0° C. and the resulting precipitate was collected by filtration and washed with water. The powder was then dried under reduced pressure to give the target compound (0.537 g).

Step 3

Synthesis of N-(5-amino-2-bromo-4-iodophenyl)-N-(methylsulfonyl)methanesulfonamide N-(5-Amino-2-bromophenyl)-N-(methylsulfonyl)methanesulfonamide (2.12 g) was suspended in acetic acid (12 mL), NIS (1.32 g) was added, and the mixture was then stirred at 25° C. for three hours. The reaction was quenched by adding an aqueous sodium sulfite solution (2.34 g→30 mL), and the resulting precipitate was collected by filtration. The powder was washed with water, and the resulting crude product was purified by silica gel column chromatography (hexane/ethyl acetate) and then crystallized from hexane/ethyl acetate (1/1) to give the target compound (2.21 g).
Step 4

Synthesis of 5-bromo-6-(N-(methylsulfonyl)methylsulfonamido)-1H-indole-2-carboxylic acid N-(5-Amino-2-bromo-4-iodophenyl)-N-(methylsulfonyl)methanesulfonamide (3.6 g), pyruvic acid (3.38 g), 1,4-diazabicyclo[2.2.2]octane (4.3 g), and 1,1'-bis(diphenylphosphino)ferrocene dichloropalladium(II) (0.95 g) were added to dimethylformamide (38 mL), and the mixture was stirred at 65° C. for 15 hours in a nitrogen stream. N-Acetylcysteine (0.626 g) was added to the reaction solution and the mixture was stirred at 65° C. for 30 minutes in a nitrogen stream. A 5 M aqueous hydrochloric acid solution (18 mL) was then added and the mixture was extracted with ethyl acetate (100 mL×2). The combined organic layers were washed with saturated saline (50 mL×2) and then dried over sodium sulfate. The drying agent was removed by filtration and the filtrate was concentrated to give the target compound (3.15 g).
Step 5

Synthesis of 5-bromo-6-(methylsulfonamido)-1H-indole-2-carboxylic acid

5-Bromo-6-(N-(methylsulfonyl)methylsulfonamido)-1H-indole-2-carboxylic acid (3.15 g) was added to 2-propanol (25 mL), a 8 M aqueous potassium hydroxide solution (4.8 mL) was added, and the mixture was then stirred at 65° C. for 2.5 hours. After cooling the reaction solution to 25° C., a 5 M aqueous hydrochloric acid solution (9.2 mL) and water (25 mL) were added and the resulting crystals were collected by filtration. The crystals were washed with ethanol/water (1/1) and then dried under reduced pressure to give the target compound (1.43 g).
Step 6

Synthesis of ethyl 5-bromo-6-(methylsulfonamido)-1H-indole-2-carboxylate

5-Bromo-6-(methylsulfonamido)-1H-indole-2-carboxylic acid (1.43 g) was suspended in ethanol (28.5 mL), and sulfuric acid (13.1 mL) was then added dropwise over five minutes. The reaction solution was refluxed for 22 hours and water (28.5 mL) was then added at room temperature. The precipitate was collected by filtration and washed with water (10 mL×3), and the resulting powder was then dried under reduced pressure to give the target compound (1.31 g).
Step 7

Synthesis of ethyl 6-(methylsulfonamido)-5-vinyl-1H-indole-2-carboxylate

Ethyl 5-bromo-6-(methylsulfonamido)-1H-indole-2-carboxylate (1.0 g), potassium trifluoro(vinyl)borate (1.12 g), 1,1'-bis(diphenylphosphino)ferrocene dichloropalladium(II) (0.171 g), and potassium phosphate (2.60 g) were added to toluene (20 mL) and water (4 mL) and the mixture was refluxed for eight hours in a nitrogen stream. After cooling the reaction solution to 25° C., a 5 M aqueous hydrochloric acid solution (10 mL) was added and the mixture was extracted with ethyl acetate (50 mL). The organic layer was dried over sodium sulfate and the drying agent was then removed by filtration. The filtrate was then concentrated under reduced pressure and the resulting residue was eluted by silica gel column chromatography (hexane/ethyl acetate) to give the target compound (597 mg).
Step 8

Synthesis of ethyl 5-ethyl-6-(methanesulfonamido)-1H-indole-2-carboxylate

Ethyl 6-(methylsulfonamido)-5-vinyl-1H-indole-2-carboxylate (400 mg) was dissolved in methanol (13 mL), Pd—C (160 mg) was suspended, and the suspension was stirred at 25° C. for seven hours and 30 minutes in a hydrogen stream. The insoluble matter was removed by celite filtration and the filtrate was concentrated under reduced pressure. The crude product was purified by reversed phase chromatography (mobile phase: 0.1% formic acid-water-acetonitrile) to give the target compound (245 mg).
Step 9

Synthesis of N-(2-(2-cyanoacetyl)-5-ethyl-1H-indol-6-yl)methanesulfonamide

Ethyl 5-ethyl-6-(methanesulfonamido)-1H-indole-2-carboxylate (245 mg) and acetonitrile (0.082 mL) were added to tetrahydrofuran (6.6 mL) and sodium hexamethyldisilazide (1.9 M, 2.1 mL) was added dropwise at 0° C. in a nitrogen stream. The reaction solution was stirred at 25° C. for 30 minutes, and the reaction was then quenched by adding a 5 M aqueous hydrochloric acid solution (4 mL) and then water (50 mL) at 0° C. The reaction solution was extracted with ethyl acetate (50 mL) and the organic layer was then dried over sodium sulfate. The drying agent was removed by filtration, the filtrate was concentrated, and the resulting residue was then crystallized from MTBE to give the target compound (242 mg).
Step 10

Synthesis of (E)-N-(2-(2-cyano-3-(dimethylamino)acryloyl)-5-ethyl-1H-indol-6-yl)methanesulfonamide N-(2-(2-Cyanoacetyl)-5-ethyl-1H-indol-6-yl)methanesulfonamide (241 mg) was dissolved in tetrahydrofuran (4.4 mL), dimethylformamide dimethylacetal (0.158 mL) was added at 25° C., and the mixture was stirred for 30 minutes. The reaction solution was crystallized by adding MTBE (8 mL) and the precipitate was collected by filtration. The crystals were then washed with MTBE (4 mL×3) and dried under reduced pressure to give the target compound (220 mg).

| Example No. | Compound No. | |
|---|---|---|
| 1-5-4 | I-H072 | (structure) |

Example 1-6-1 (Compound B-B026)

Synthesis of 2-[6-bromo-5-(difluoromethoxy)-1H-indole-2-carbonyl]-3-(dimethylamino)prop-2-enenitrile

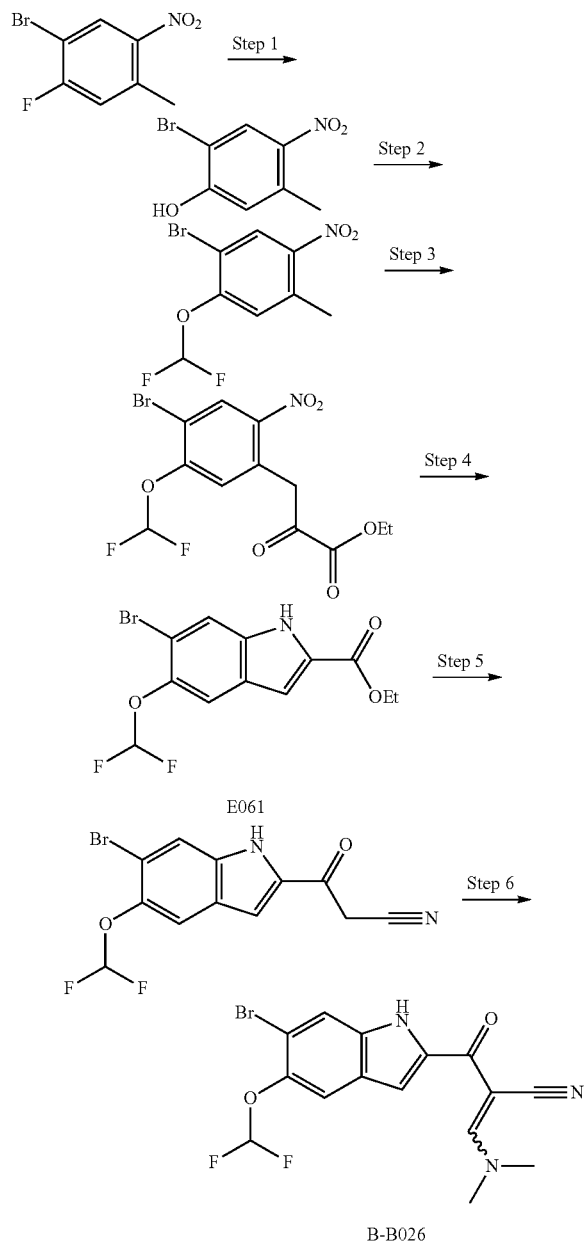

Step 1

Synthesis of 2-bromo-5-methyl-4-nitrophenol

1-Bromo-2-fluoro-4-methyl-5-nitrobenzene (4.57 g) was dissolved in dimethyl sulfoxide (39 mL), a 1 M aqueous sodium hydroxide solution (39 mL) was added, and the mixture was stirred at 100° C. for two hours. The reaction solution was cooled to 25° C., 1 M hydrochloric acid (80 mL) was added, and the mixture was extracted with ethyl acetate. The organic layer was washed with water and saturated saline and dried over anhydrous sodium sulfate. The drying agent was removed by filtration and the filtrate was concentrated under reduced pressure to give the target compound (4.30 g).

Step 2

Synthesis of 1-bromo-2-(difluoromethoxy)-4-methyl-5-nitrobenzene

2-Bromo-5-methyl-4-nitrophenol (5.0 g) was dissolved in N,N-dimethylformamide (72 mL), potassium carbonate (8.9 g) was added, and the mixture was stirred at 25° C. for 15 minutes. Methyl 2-chloro-2,2-difluoroacetate (3.4 mL) was added to the reaction solution and the mixture was further stirred at 100° C. for one hour. The reaction solution was cooled to 25° C., water and 1 M hydrochloric acid were added, and the mixture was extracted with ethyl acetate. The organic layer was washed with water and saturated saline and dried over anhydrous sodium sulfate. The drying agent was removed by filtration, the filtrate was concentrated under reduced pressure, and the resulting residue was purified by column chromatography (hexane/ethyl acetate) to give the target compound (5.1 g).

Step 3

Synthesis of ethyl 3-[4-bromo-5-(difluoromethoxy)-2-nitrophenyl]-2-oxopropanoate 1-Bromo-2-(difluoromethoxy)-4-methyl-5-nitrobenzene (2.73 g) was dissolved in ethanol (48 mL), sodium ethoxide (20% solution in ethanol, 19 mL) and diethyl oxalate (6.6 mL) were added, and the mixture was stirred at 25° C. for 15 hours. 5 M hydrochloric acid was added to the reaction solution, the mixture was concentrated under reduced pressure, and the resulting residue was collected by filtration to give the target compound (3.53 g).

Step 4

Synthesis of ethyl 6-bromo-5-(difluoromethoxy)-1H-indole-2-carboxylate (E061)

Ethyl 3-[4-bromo-5-(difluoromethoxy)-2-nitrophenyl]-2-oxopropanoate (3.50 g) was dissolved in acetic acid (35 mL), iron powder (2.56 g) was added, and the mixture was stirred at 80° C. for one hour. The reaction solution was cooled to 25° C. and the insoluble matter was filtered off by celite filtration. The filtrate was concentrated under reduced pressure, 1 M hydrochloric acid was added to the resulting residue, and the mixture was extracted with ethyl acetate. The organic layer was washed with saturated saline and dried over anhydrous sodium sulfate. The drying agent was removed by filtration, the filtrate was concentrated under reduced pressure, and the resulting residue was purified by column chromatography (hexane/ethyl acetate) to give the target compound (1.40 g).

Step 5

Synthesis of 3-[6-bromo-5-(difluoromethoxy)-1H-indol-2-yl]-3-oxopropanenitrile

Ethyl 6-bromo-5-(difluoromethoxy)-1H-indole-2-carboxylate (470 mg) was suspended in tetrahydrofuran (12 mL), dehydrated acetonitrile (0.15 mL) was added, lithium bis(trimethylsilyl)amide (1.9 M solution in tetrahydrofuran, 3.7 mL) was added dropwise at 0° C., and the mixture was stirred at 0° C. for 20 minutes. Water and 5 M hydrochloric acid were added to the reaction solution, the mixture was extracted with ethyl acetate (20 mL) and dried over anhydrous magnesium sulfate. The drying agent was removed by filtration and the filtrate was concentrated under reduced pressure to give the target compound (440 mg).

Step 6

Synthesis of 2-[6-bromo-5-(difluoromethoxy)-1H-indole-2-carbonyl]-3-(dimethylamino)prop-2-enenitrile (B-B026)

3-[6-Bromo-5-(difluoromethoxy)-1H-indol-2-yl]-3-oxo-propanenitrile (440 mg) was suspended in tetrahydrofuran (9.0 mL), N,N-dimethylformamide dimethylacetal (195 μL) was added, and the mixture was stirred at 25° C. for one hour. tert-Butyl methyl ether (20 mL) was added to the reaction solution and the precipitated solid was collected by filtration to give the target compound (569 mg).

| Example No. | Compound No. | |
|---|---|---|
| 1-6-1 | B-B026 | |

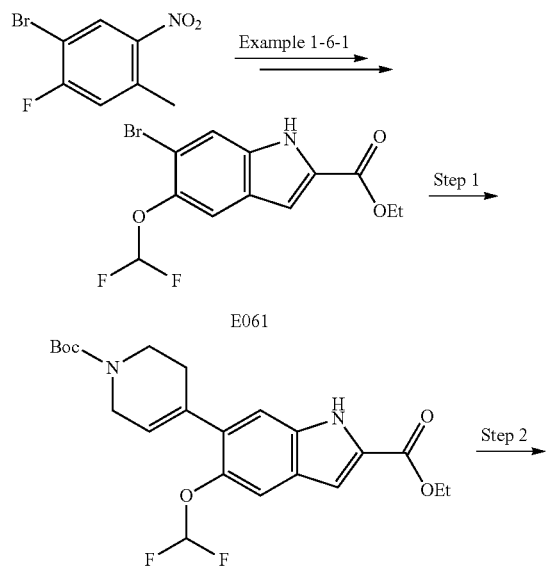

Example 1-6-2 (Compound I-H056)

Synthesis of tert-butyl 4-{2-[2-cyano-3-(dimethylamino)prop-2-enoyl]-5-(difluoromethoxy)-1H-indol-6-yl}piperidine-1-carboxylate

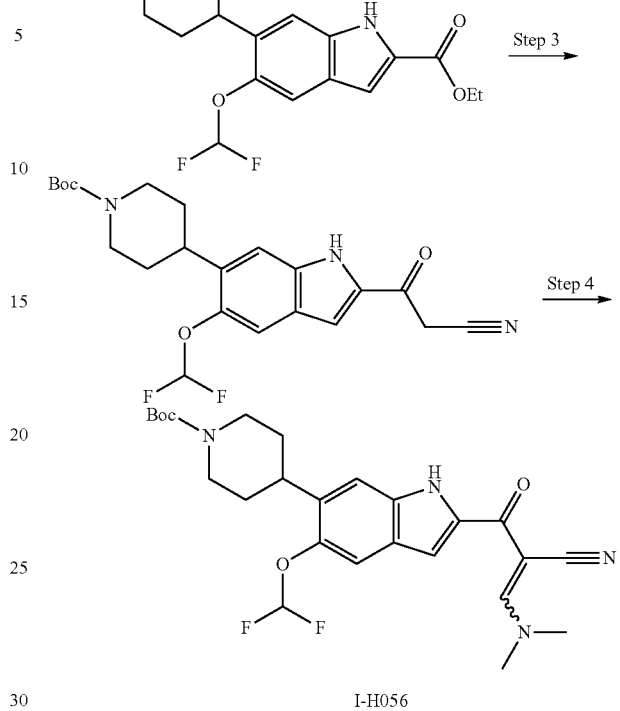

I-H056

Step 1

Synthesis of ethyl 5-(difluoromethoxy)-6-{1-[(2-methylpropan-2-yl)oxycarbonyl]-3,6-dihydro-2H-pyridin-4-yl}-1H-indole-2-carboxylate The bromide E061 synthesized in Example 1-6-1 (250 mg) was dissolved in N,N-dimethylformamide (3.4 mL) and water (0.37 mL), tert-butyl 4-(4,4,5,5-tetramethyl-1,3,2-dioxaborolan-2-yl)-1,2,3,6-tetrahydropyridine-1-carboxylate (301 mg), PdCl$_2$(dppf) (31 mg), and tripotassium phosphate (238 mg) were added, and the mixture was stirred at 100° C. for six hours in a nitrogen atmosphere. The reaction solution was cooled to 25° C., water was added, and the mixture was extracted with ethyl acetate. The organic layer was dried over anhydrous sodium sulfate. The drying agent was removed by filtration, the filtrate was concentrated under reduced pressure, and the resulting residue was purified by column chromatography (hexane/ethyl acetate) to give the target compound (301 mg).

Step 2

Synthesis of ethyl 5-(difluoromethoxy)-6-{1-[(2-methylpropan-2-yl)oxycarbonyl]piperidin-4-yl}-1H-indole-2-carboxylate Ethyl 5-(difluoromethoxy)-6-{1-[(2-methylpropan-2-yl)oxycarbonyl]-3,6-dihydro-2H-pyridin-4-yl}-1H-indole-2-carboxylate (300 mg) was dissolved in ethanol, 10% Pd—C (80 mg) was added, and the mixture was stirred at 25° C. for two hours in a hydrogen atmosphere. Ethyl acetate was added to the reaction solution, the insoluble matter was filtered off by celite filtration, and the filtrate was concentrated under reduced pressure. Water was added to the resulting residue and the mixture was extracted with ethyl acetate. The organic layer was washed with saturated saline and dried over anhydrous magnesium sulfate. The drying agent was removed by filtration and the filtrate was concentrated under reduced pressure to give the target compound (215 mg).

Step 3

Synthesis of tert-butyl 4-[2-(2-cyanoacetyl)-5-(difluoromethoxy)-1H-indol-6-yl]piperidine-1-carboxylate Ethyl 5-(difluoromethoxy)-6-{1-[(2-methylpropan-2-yl)oxycarbonyl]piperidin-4-yl}-1H-indole-2-carboxylate (210 mg) was suspended in tetrahydrofuran (4.8 mL), dehydrated acetonitrile (50 µL) was added, lithium bis(trimethylsilyl)amide (1.0 M solution in tetrahydrofuran, 1.9 mL) was added dropwise at 0° C., and the mixture was stirred at 0° C. for 30 minutes. Water (10 mL) and 1 M hydrochloric acid (10 mL) were added to the reaction solution and the mixture was extracted with ethyl acetate (20 mL). The organic layer was washed with water and saturated saline and dried over anhydrous magnesium sulfate. The drying agent was removed by filtration and the filtrate was concentrated under reduced pressure to give the target compound (234 mg).

Step 4

Synthesis of tert-butyl 4-{2-[2-cyano-3-(dimethylamino)prop-2-enoyl]-5-(difluoromethoxy)-1H-indol-6-yl}piperidine-1-carboxylate (1-H056)

tert-Butyl 4-[2-(2-cyanoacetyl)-5-(difluoromethoxy)-1H-indol-6-yl]piperidine-1-carboxylate (230 mg) was suspended in tetrahydrofuran (3.5 mL), N,N-dimethylformamide dimethylacetal (78 µL) was added, and the mixture was stirred at 25° C. for one hour. The reaction solution was concentrated under reduced pressure and the resulting residue was washed by suspending in tert-butyl methyl ether/hexane to give the target compound (201 mg).

| Example No. | Compound No. | |
|---|---|---|
| 1-6-2 | I-H056 | 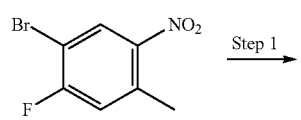 |

Example 1-6-3

Synthesis of (E)-2-(6-bromo-5-((difluoromethyl)thio)-1H-indole-2-carbonyl)-3-(dimethylamino)acrylonitrile (I-H075)

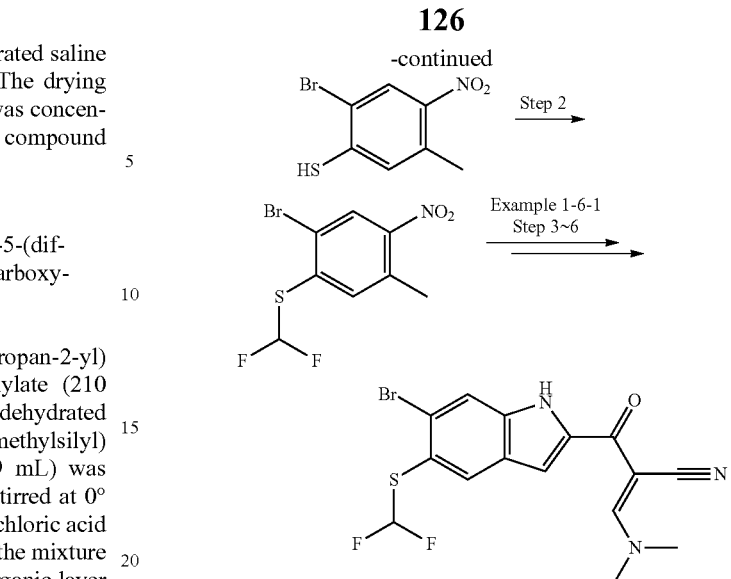

Step 1

Synthesis of 2-bromo-5-methyl-4-nitrobenzenethiol

2-Ethylhexyl 3-mercaptopropanoate (6 mL) was added to a solution of 1-bromo-2-fluoro-4-methyl-5-nitrobenzene (5.61 g) and DBU (8.68 mL) in DMF (51 mL) in a nitrogen atmosphere and the mixture was stirred at 80° C. After cooling the reaction solution to 25° C., a 2 M aqueous hydrochloric acid solution (107 mL) was added and the mixture was stirred for 15 minutes. The reaction solution was filtered and the resulting precipitate was then washed with an aqueous hydrochloric acid solution (20 mL×3). The resulting powder was washed with hexane/ethyl acetate (1/10) to give the target compound (7.7 g).

Step 2

Synthesis of (2-bromo-5-methyl-4-nitrophenyl)(difluoromethyl)sulfane

A solution of 2-bromo-5-methyl-4-nitrobenzenethiol (5.72 g) and sodium 2-chloro-2,2-difluoroacetate (8.41 g) in DMF (50 mL) was added to a suspension of potassium carbonate (5.72 g) in DMF (25 mL) at 80° C. and the mixture was stirred for one hour. The reaction solution was cooled to 25° C. and diluted with water and ethyl acetate (100 mL each). After extracting the aqueous layer with ethyl acetate (100 mL), the combined organic layers were washed with water and saturated saline and then dried over sodium sulfate. The drying agent was removed by filtration and the filtrate was concentrated to give the target compound (6.6 g).

Synthesis of (E)-2-(6-bromo-5-((difluoromethyl)thio)-1H-indole-2-carbonyl)-3-(dimethylamino)acrylonitrile I-H075 was obtained by performing the similar operation as in Steps 3 to 6 of Example 1-6-1 using (2-bromo-5-methyl-4-nitrophenyl) (difluoromethyl)sulfane obtained in Step 2.

| Example No. | Compound No. | |
|---|---|---|
| 1-6-3 | I-H075 | 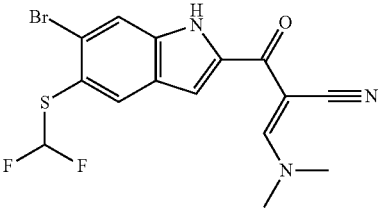 |

Example 1-7-1 (Compound I-A003)

Synthesis of 2-(6-bromo-5-fluoro-1H-indole-2-carbonyl)-3-(dimethylamino)prop-2-enenitrile

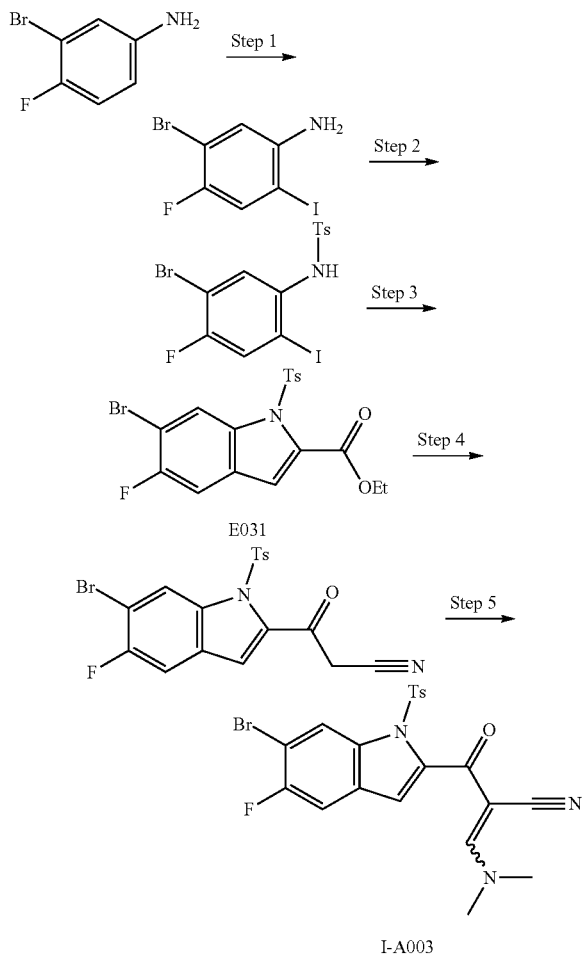

Step 1

Synthesis of 5-bromo-4-fluoro-2-iodoaniline

3-Bromo-4-fluoroaniline (11.0 g) was dissolved in water (220 mL), iodine (16.2 g) was added at 25° C., and the mixture was stirred for three hours. An aqueous sodium thiosulfate solution was added to the reaction solution, the mixture was extracted with ethyl acetate (300 mL), and the organic layer was dried over anhydrous sodium sulfate. The drying agent was removed by filtration, the filtrate was concentrated under reduced pressure, and the resulting residue was purified by column chromatography (hexane/ethyl acetate) to give the target compound (9.10 g).

Step 2

Synthesis of N-(5-bromo-4-fluoro-2-iodophenyl)-4-methylbenzenesulfonamide

5-Bromo-4-fluoro-2-iodoaniline (1.00 g) was dissolved in dichloromethane (12 mL), p-toluenesulfonyl chloride (1.2 g) and pyridine (0.5 mL) were added, and the mixture was stirred at 0° C. for 15 hours. The solid precipitated from the reaction solution was collected by filtration and washed with dichloromethane and hexane to give the target compound (1.23 g).

Step 3

Synthesis of ethyl 6-bromo-5-fluoro-1-(4-methylphenyl)sulfonylindole-2-carboxylate (E031)

N-(5-Bromo-4-fluoro-2-iodophenyl)-4-methylbenzenesulfonamide (120 mg) was dissolved in tetrahydrofuran (2.0 mL) and zinc bromide (172 mg), DIPEA (0.26 mL), and ethyl propiolate (78 μL) were added, after which the reaction system was degassed under reduced pressure and the atmosphere therein was replaced by nitrogen. Pd(PPh$_3$)$_4$ (15 mg) was added. The reaction system was degassed under reduced pressure and the atmosphere therein was replaced by nitrogen. The mixture was stirred at 80° C. for 15 hours. The reaction solution was cooled to 25° C. and the insoluble matter was filtered off by celite filtration. A saturated aqueous sodium bicarbonate solution was added to the filtrate and the mixture was extracted with ethyl acetate. The organic layer was concentrated under reduced pressure and the residue was purified by column chromatography (hexane/ethyl acetate). The resulting solid was washed by suspending in ethyl acetate/hexane=1/1 to give the target compound (41 mg).

Step 4

Synthesis of 3-[6-bromo-5-fluoro-1-(4-methylphenyl)sulfonylindol-2-yl]-3-oxopropanenitrile Ethyl 6-bromo-5-fluoro-1-(4-methylphenyl)sulfonylindole-2-carboxylate (500 mg) was suspended in tetrahydrofuran (6.0 mL), dehydrated acetonitrile (71 μL) was added, an LDA solution (2.2 M solution in tetrahydrofuran, 1.0 mL) was added dropwise at 0° C., and the mixture was stirred for five minutes. Water (1.0 mL) and a saturated aqueous ammonium chloride solution (10 mL) were added to the reaction solution, followed by extraction with ethyl acetate. The organic layer was dried over anhydrous sodium sulfate, the drying agent was removed by filtration, and the filtrate was concentrated under reduced pressure to give the target compound (401 mg).

Step 5

Synthesis of 2-(6-bromo-5-fluoro-1H-indole-2-carbonyl)-3-(dimethylamino)prop-2-enenitrile (I-A003)

3-[6-Bromo-5-fluoro-1-(4-methylphenyl)sulfonylindol-2-yl]-3-oxopropanenitrile (100 mg) was suspended in tetrahydrofuran (2.0 mL), N,N-dimethylformamide dimethylacetal (37 μL) was added, and the mixture was stirred at 25°

C. for 30 minutes. The precipitated solid was collected by filtration to give the target compound (120 mg).

| Example No. | Compound No. | |
|---|---|---|
| 1-7-1 | I-A003 | 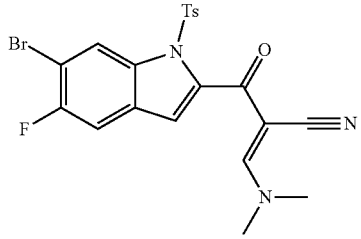 [SMILES: Cc1ccc(S(=O)(=O)n2c(C(=O)/C(C#N)=C/N(C)C)cc3cc(F)c(Br)cc32)cc1] |

Example 1-7-2

Synthesis of (E)-2-(6-bromo-5-isopropyl-1-tosyl-1H-indole-2-carbonyl)-3-(dimethylamino)acrylonitrile (I-A012)

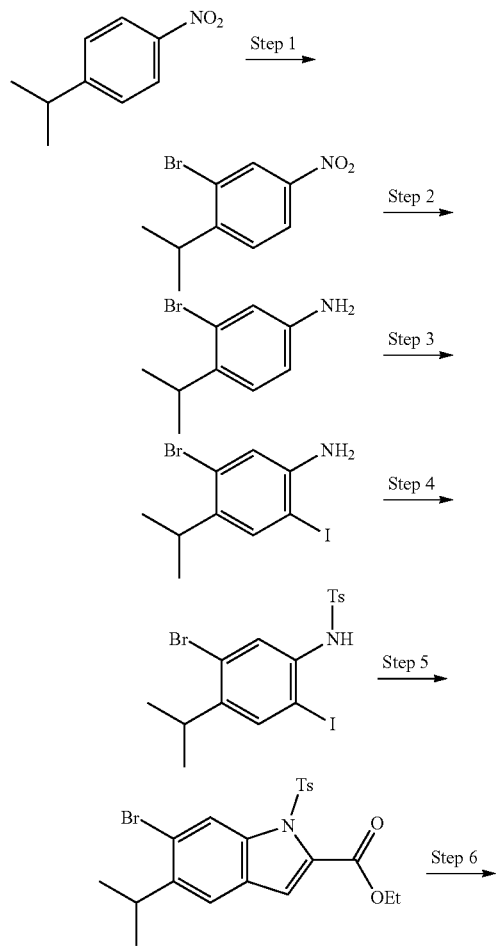

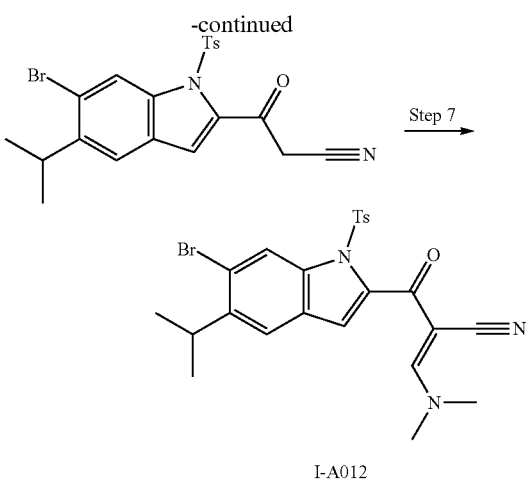

I-A012

Step 1

Synthesis of 2-bromo-1-isopropyl-4-nitrobenzene

1-Isopropyl-4-nitrobenzene (15 g) was added to sulfuric acid (26.7 g), 1,3-dibromo-5,5-dimethylimidazolidine-2,4-dione (13.8 g) was added at 0° C., and the mixture was then stirred for three hours. The reaction solution was poured into ice water and the mixture was extracted with ethyl acetate. The organic layer was washed with an aqueous sodium thiosulfate solution and an aqueous sodium bicarbonate solution and then concentrated under reduced pressure to give the target compound (23.1 g).

Step 2

Synthesis of 3-bromo-4-isopropylaniline

2-Bromo-1-isopropyl-4-nitrobenzene (22.2 g) and ammonium chloride (58.4 g) were added to a mixed solvent of ethanol (445 mL) and water (445 mL). Zinc powder (35.7 g) was gradually added so that the temperature of the reaction solution did not exceed 40° C., after which the mixture was stirred for one hour. The insoluble matter was filtered off through celite, and the filtrate was washed with ethanol and concentrated to about 500 mL under reduced pressure. The residue was extracted with ethyl acetate twice. The combined organic layers were washed with saturated saline and then dried over sodium sulfate. The drying agent was removed by filtration, the filtrate was concentrated, and the resulting residue was purified by silica gel column chromatography to give the target compound (18 g).

Step 3

Synthesis of 5-bromo-2-iodo-4-isopropylaniline

3-Bromo-4-isopropylaniline (18 g) was dissolved in acetic acid (180 mL), N-iodosuccinimide (17 g) was added at 25° C., and the mixture was stirred for 30 minutes. A 1 M aqueous sodium thiosulfate solution (84 mL) and ethyl acetate were added to the reaction solution and the organic layer was washed with an aqueous sodium bicarbonate solution twice. The organic layer was dried over anhydrous sodium sulfate and then the drying agent was removed by filtration. The filtrate was concentrated under reduced pressure and the resulting residue was purified by column chromatography (hexane/ethyl acetate) to give the target compound (23.35 g).

Step 4

Synthesis of N-(5-bromo-2-iodo-4-isopropylphenyl)-4-methylbenzenesulfonamide 5-Bromo-2-iodo-4-isopropylaniline (23.4 g) was dissolved in acetonitrile (229 mL), p-toluenesulfonyl chloride (19.6 g) and pyridine (9.44 mL) were added at 25° C., and the mixture was stirred for 15 hours. Water (230 mL) was added to the reaction solution and the precipitated solid was collected by filtration and washed with water (50 mL×2) and hexane (50 mL×2) to give the target compound (29.14 g).

Step 5

Synthesis of ethyl 6-bromo-5-isopropyl-1-tosyl-1H-indole-2-carboxylate

N-(5-Bromo-2-iodo-4-isopropylphenyl)-4-methylbenzenesulfonamide (6 g) was dissolved in tetrahydrofuran (81 mL) and zinc bromide (8.2 g), DIPEA (12.7 mL), and ethyl propiolate (3.69 mL) were added, after which the reaction system was degassed under reduced pressure and the atmosphere therein was replaced by nitrogen. Pd(PPh3)4 (701 mg) was added. The reaction system was degassed under reduced pressure and the atmosphere therein was replaced by nitrogen. The mixture was stirred at 80° C. for five hours. 2 M hydrochloric acid and ethyl acetate were added to the reaction solution and the organic layer was separated. The organic layer was washed with 2 M hydrochloric acid (twice) and saturated saline and concentrated under reduced pressure. The resulting residue was purified by silica gel column chromatography to give the target compound (3.26 g).

Step 6

Synthesis of 3-(6-bromo-5-isopropyl-1-tosyl-1H-indol-2-yl)-3-oxopropanenitrile Ethyl 6-bromo-5-isopropyl-1-tosyl-1H-indole-2-carboxylate (2.33 g) was added to tetrahydrofuran (20 mL), dehydrated acetonitrile (286 µL) was added, an LHMDS solution (1.3 M solution in tetrahydrofuran, 15.4 mL) was added dropwise at −78° C., and the mixture was stirred for 60 minutes. A 10% aqueous acetic acid solution (70 mL) was added to the reaction solution at −78° C. and the mixture was extracted with ethyl acetate. The organic layer was washed with saturated saline and dried over anhydrous sodium sulfate. The drying agent was removed by filtration, the filtrate was concentrated, and the crystals of the residue were washed with hexane/ethyl acetate (2/1) to give the target compound (2.33 g).

Step 7

Synthesis of (E)-2-(6-bromo-5-isopropyl-1-tosyl-1H-indole-2-carbonyl)-3-(dimethylamino)acrylonitrile (I-A012)

3-(6-Bromo-5-isopropyl-1-tosyl-1H-indol-2-yl)-3-oxopropanenitrile (1.92 g) was suspended in tetrahydrofuran (27.9 mL), N,N-dimethylformamide dimethylacetal (555 µL) was added, and the mixture was stirred at 25° C. for 10 minutes. Hexane (70 mL) was added and the precipitated solid was collected by filtration to give the target compound (2.33 g).

Example 1-7-3

Synthesis of (E)-2-[6-bromo-5-methyl-1-(p-tolylsulfonyl)indole-2-carbonyl]-3-(dimethylamino)prop-2-enenitrile (I-A013)

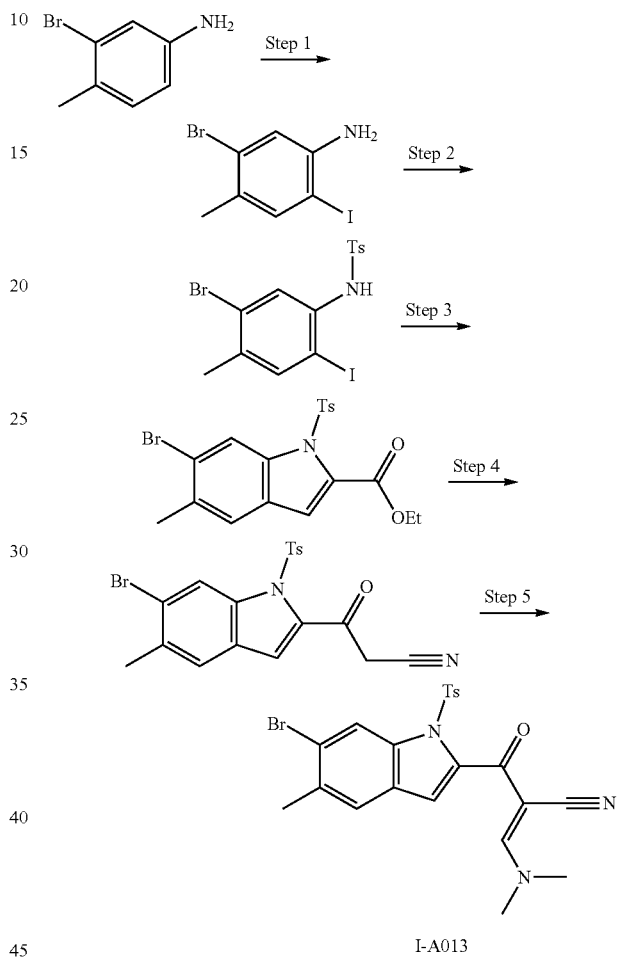

I-A013

The target compound was obtained by performing the similar operation as in Example 1-7-1 using 3-bromo-4-methylaniline instead of 3-bromo-4-fluoroaniline of Example 1-7-1.

| Example No. | Compound No. | |
|---|---|---|
| 1-7-2 | I-A012 | (structure shown) |

| Example No. | Compound No. | |
|---|---|---|
| 1-7-3 | I-A013 | 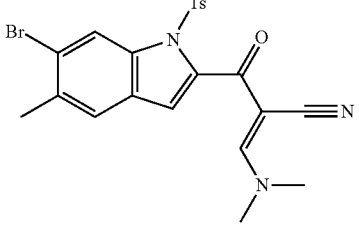 |

Example 1-8-1 (Compound I-E001)

Synthesis of 3-(dimethylamino)-2-[5-fluoro-1-(4-methylphenyl)sulfonyl-6-(1-propan-2-ylpiperidin-4-yl)indole-2-carbonyl]prop-2-enenitrile

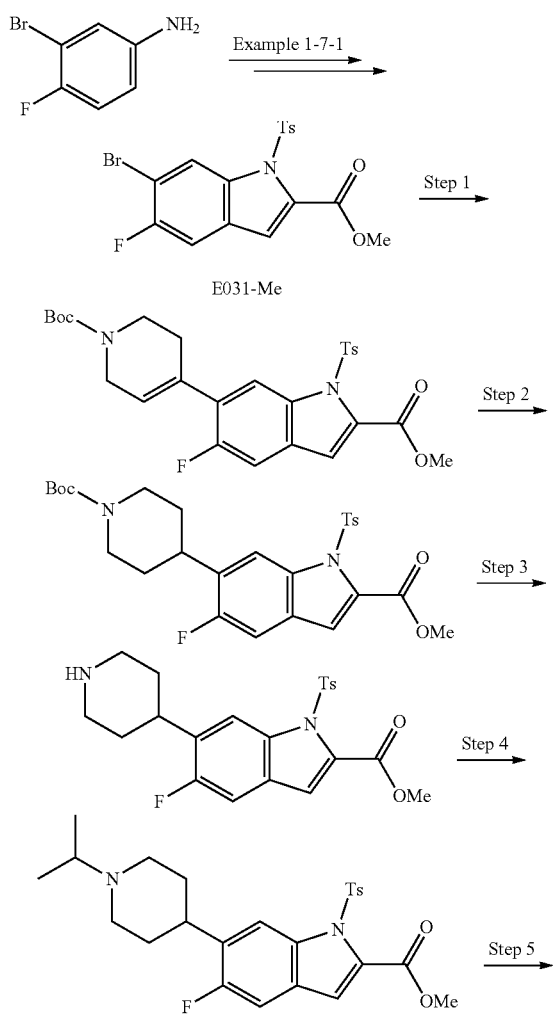

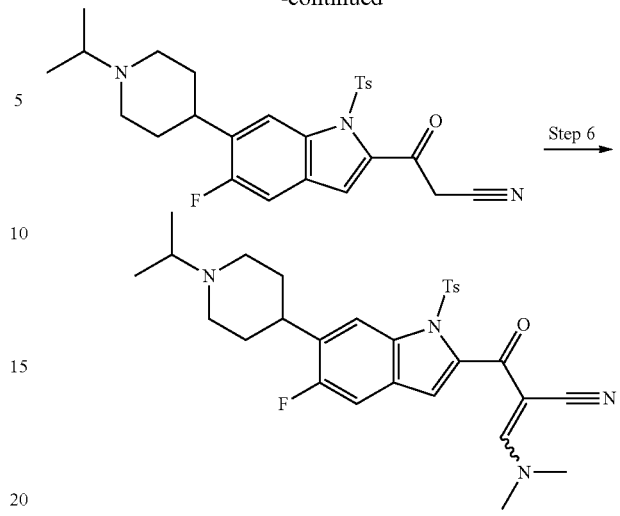

Step 1

Synthesis of ethyl 5-fluoro-1-(4-methylphenyl)sulfonyl-6-{1-[(2-methylpropan-2-yl)oxycarbonyl]-3,6-dihydro-2H-pyridin-4-yl}indole-2-carboxylate The bromide E031-Me synthesized by the similar method as in Example 1-7-1 (4.00 g) was dissolved in dioxane (50 mL) and water (0.5 mL), tert-butyl 4-(4,4,5,5-tetramethyl-1,3,2-dioxaborolan-2-yl)-1,2,3,6-tetrahydropyridine-1-carboxylate (3.48 g), Pd(PPh$_3$)$_4$ (544 mg), and tripotassium phosphate (4.0 g) were added, and the mixture was stirred at 90° C. for 16 hours in a nitrogen atmosphere. The reaction solution was cooled to 25° C. and concentrated under reduced pressure to give the target compound. The resulting residue was used as such for the next reaction without purification.

Step 2

Synthesis of ethyl 5-fluoro-1-(4-methylphenyl)sulfonyl-6-{1-[(2-methylpropan-2-yl)oxycarbonyl]piperidin-4-yl}indole-2-carboxylate Ethyl 5-fluoro-1-(4-methylphenyl)sulfonyl-6-{1-[(2-methylpropan-2-yl)oxycarbonyl]-3,6-dihydro-2H-pyridin-4-yl}indole-2-carboxylate (3.00 g) was dissolved in methanol (200 mL), 10% Pd—C (1.2 g) was added, and the mixture was stirred at 25° C. for 16 hours in a hydrogen atmosphere. The insoluble matter was filtered off and the filtrate was concentrated under reduced pressure to give the target compound (2.50 g).

Step 3

Synthesis of ethyl 5-fluoro-1-(4-methylphenyl)sulfonyl-6-piperidin-4-ylindole-2-carboxylate Ethyl 5-fluoro-1-(4-methylphenyl)sulfonyl-6-{1-[(2-methylpropan-2-yl)oxycarbonyl]piperidin-4-yl}indole-2-carboxylate (9.20 g) was dissolved in tetrahydrofuran (200 mL), trifluoroacetic acid (20 mL) was added, and the mixture was stirred at 25° C. for three hours. The reaction solution was adjusted to pH 8 by adding an aqueous sodium carbonate solution and then extracted with dichloromethane. The organic layer was washed with a saturated aqueous sodium bicarbonate solution and dried over anhydrous sodium sulfate. The drying agent was removed by filtration and the filtrate was concentrated under reduced pressure to give the target compound (6.30 g).
Step 4

Synthesis of ethyl 5-fluoro-1-(4-methylphenyl)sulfonyl-6-(1-propan-2-ylpiperidin-4-yl)indole-2-carboxylate Ethyl 5-fluoro-1-(4-methylphenyl)sulfonyl-6-piperidin-4-ylindole-2-carboxylate (4.50 g) was dissolved in dichloromethane (150 mL), acetone (1.2 mL), sodium triacetoxyborohydride (4.4 g), and acetic acid (3.0 mL) were added, and the mixture was stirred at 25° C. for 16 hours. A saturated aqueous sodium carbonate solution was added to the reaction solution and the mixture was extracted with dichloromethane. The organic layer was washed with a saturated aqueous sodium bicarbonate solution and dried over anhydrous sodium sulfate. The drying agent was removed by filtration and the filtrate was concentrated under reduced pressure to give the target compound (3.80 g).
Step 5

Synthesis of 3-[5-fluoro-1-(4-methylphenyl)sulfonyl-6-(1-propan-2-ylpiperidin-4-yl)indol-2-yl]-3-oxopropanenitrile Ethyl 5-fluoro-1-(4-methylphenyl)sulfonyl-6-(1-propan-2-ylpiperidin-4-yl)indole-2-carboxylate (3.80 g) was suspended in tetrahydrofuran (50 mL), dehydrated acetonitrile (0.85 mL) was added, and a lithium bis(trimethylsilyl)amide solution (1.0 M solution in tetrahydrofuran, 50 mL) was added dropwise at −78° C. After completion of dropwise addition, the mixture was stirred for one hour, diluted with a saturated aqueous ammonium chloride solution (100 mL), and concentrated under reduced pressure. The precipitated solid was collected by filtration to give the target compound (3.80 g).
Step 6

Synthesis of 3-(dimethylamino)-2-[5-fluoro-1-(4-methylphenyl)sulfonyl-6-(1-propan-2-ylpiperidin-4-yl)indole-2-carbonyl]prop-2-enenitrile (I-E001)

3-[5-Fluoro-1-(4-methylphenyl)sulfonyl-6-(1-propan-2-ylpiperidin-4-yl)indol-2-yl]-3-oxopropanenitrile (4.10 g) was suspended in tetrahydrofuran (100 mL), N,N-dimethylformamide dimethylacetal (5.5 mL) was added, and the mixture was stirred at 25° C. for one hour. The reaction solution was concentrated and the precipitated solid was collected by filtration to give the target compound (4.10 g).

| Example No. | Compound No. | |
|---|---|---|
| 1-8-1 | I-E001 | |

Example 1-8-2

A corresponding bromoindole carboxylic acid ester was obtained by the similar method as in Example 1-7-1. The compound of Example 1-8-2 was synthesized by the similar method as in Example 1-8-1.

| Example No. | Compound No. | |
|---|---|---|
| 1-8-2 | I-D001 | 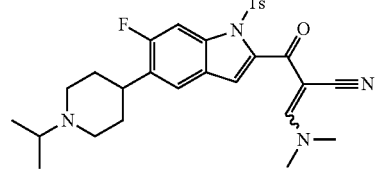 |

Example 1-8-3

A corresponding bromoindole carboxylic acid ester was obtained by the similar method as in Example 1-9-1. The compound of Example 1-8-3 was synthesized by the similar method as in Example 1-8-1.

| Example No. | Compound No. | |
|---|---|---|
| 1-8-3 | I-D002 | 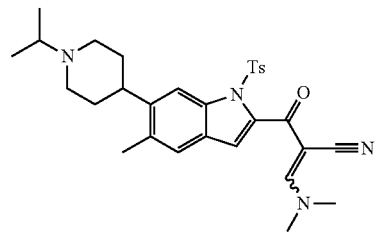 [SMILES: Cc1ccc(S(=O)(=O)n2c(C(=O)C(C#N)=CN(C)C)cc3cc(C)c(C4CCN(C(C)C)CC4)cc32)cc1] |

Example 1-9-1 (Compound I-H016)

Synthesis of N-{2-[2-cyano-3-(dimethylamino)prop-2-enoyl]-5-methyl-1-(4-methylphenyl)sulfonylindol-6-yl}methanesulfonamide

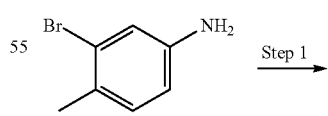

Step 1

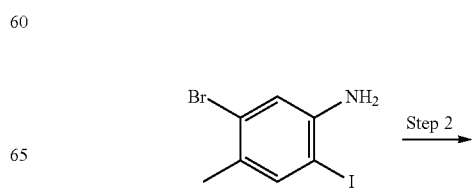

Step 2

-continued

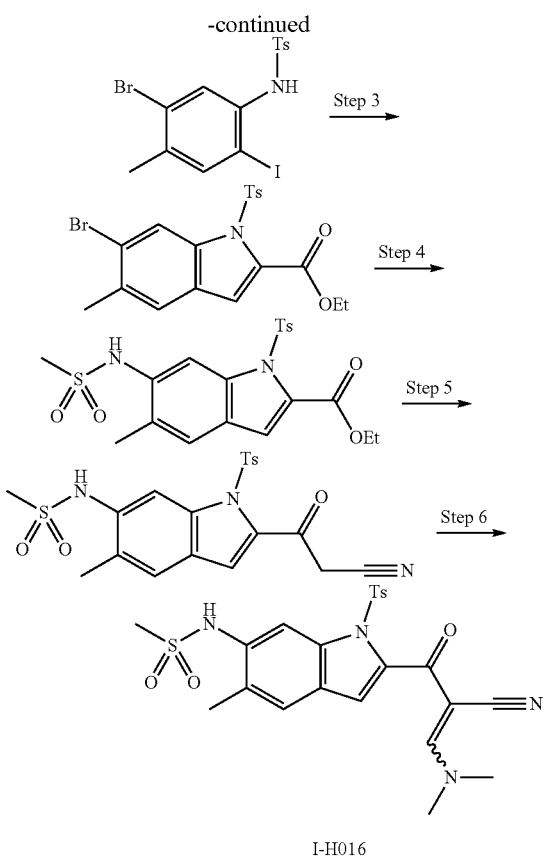

I-H016

Step 1

Synthesis of 5-bromo-2-iodo-4-methylaniline

3-Bromo-4-methylaniline (30.4 g) was dissolved in methanol (210 mL), pyridine (43 mL) and iodine (68.4 g) were added, and the mixture was stirred at 25° C. for two hours. A 20% aqueous sodium thiosulfate solution (150 mL) and water (30 mL) were added to the reaction solution and the mixture was stirred at 25° C. for one hour. Washing with methanol/water (1/1, 100 mL) resulted in the target compound (19.1 g).

Step 2

Synthesis of N-(5-bromo-2-iodo-4-methylphenyl)-4-methylbenzenesulfonamide

5-Bromo-2-iodo-4-methylaniline (8.0 g) was dissolved in an acetonitrile (80 mL), p-toluenesulfonyl chloride (7.3 g) and pyridine (3.5 mL) were added, and the mixture was stirred at 25° C. for 10 hours. Water was added to the reaction solution, and the precipitated solid was collected by filtration and washed with water. This was suspended in hot methanol (102 mL), a 5 M aqueous sodium hydroxide solution (8 mL) was added to and dissolved in the suspension, and the reaction solution was stirred at 50° C. for one hour. Activated carbon (4 g) was added and the mixture was filtered. 5 M hydrochloric acid (8 mL) was added to the filtrate at 50° C. and the mixture was stirred at 25° C. for 30 minutes. Water (93 mL) was further added slowly and the precipitated solid was collected by filtration to give the target compound (7.9 g).

Step 3

Synthesis of ethyl 6-bromo-5-methyl-1-(4-methylphenyl)sulfonylindole-2-carboxylate N-(5-Bromo-2-iodo-4-methylphenyl)-4-methylbenzenesulfonamide (2.0 g) was dissolved in tetrahydrofuran (30 mL) and zinc bromide (2.8 g), DIPEA (4.3 mL), and ethyl propiolate (1.3 mL) were added, after which the reaction system was degassed under reduced pressure and the atmosphere therein was replaced by nitrogen.
Bis(triphenylphosphine)palladium chloride (0.14 g) was added. The reaction system was degassed under reduced pressure and the atmosphere therein was replaced by nitrogen. The mixture was stirred at 80° C. for three hours. The reaction solution was cooled to 25° C. and filtered through celite. The filtrate was concentrated under reduced pressure and the residue was purified by column chromatography (hexane/ethyl acetate). The resulting crude solid was washed by suspending in ethanol/hexane (1/2, 30 mL) to give the target compound (0.85 g).

Step 4

Synthesis of ethyl 5-methyl-6-(methanesulfonamido)-1-(4-methylphenyl)sulfonylindole-2-carboxylate Ethyl 6-bromo-5-methyl-1-(4-methylphenyl)sulfonylindole-2-carboxylate (8.5 g) was dissolved in 1,2-dimethoxyethane (92 mL) in a nitrogen atmosphere and allylpalladium chloride dimer (176 mg), potassium carbonate (4.9 g), methanesulfonamide (2.0 g), and tBuXPhos (620 mg) were added. The reaction system was degassed under reduced pressure and the atmosphere therein was then replaced by nitrogen. The mixture was heated at 80° C. for one hour. The reaction solution was cooled to 25° C., a 1% aqueous N-acetyl-L-cysteine solution (1 L) was added, and the mixture was extracted with ethyl acetate (1 L). The organic layer was washed with a saturated aqueous sodium bicarbonate solution and saturated saline and dried over anhydrous magnesium sulfate. The drying agent was removed by filtration, the filtrate was concentrated under reduced pressure, and the resulting residue was washed by suspending in ethyl acetate/hexane to give the target compound.

Step 5

Synthesis of N-[2-(2-cyanoacetyl)-5-methyl-1-(4-methylphenyl)sulfonylindol-6-yl]methanesulfonamide Ethyl 5-methyl-6-(methanesulfonamido)-1-(4-methylphenyl)sulfonylindole-2-carboxylate (5.93 g) was suspended in tetrahydrofuran (130 mL), sodium bis(trimethylsilyl)amide (1.9 M solution in tetrahydrofuran, 27.7 mL) was added dropwise at −78° C., dehydrated acetonitrile (2.1 mL) was added, and the mixture was stirred for 30 minutes. 1 M hydrochloric acid (200 mL) was added to the reaction solution and the mixture was extracted with ethyl acetate (200 mL). The organic layer was washed with saturated saline and dried over anhydrous sodium sulfate. The drying agent was removed by filtration and the filtrate was concentrated under reduced pressure to give the target compound.

Step 6

Synthesis of N-{2-[2-cyano-3-(dimethylamino)prop-2-enoyl]-5-methyl-1-(4-methylphenyl)sulfonylindol-6-yl}methanesulfonamide (I-H016)

N-[2-(2-Cyanoacetyl)-5-methyl-1-(4-methylphenyl)sulfonylindol-6-yl]methanesulfonamide (11.7 g) was suspended in tetrahydrofuran (130 mL), N,N-dimethylformamide dimethylacetal (3.87 mL) was added, and the mixture was stirred at 25° C. for 30 minutes. The reaction solution was concentrated under reduced pressure and the resulting residue was washed by suspending in methanol to give the target compound (10.1 g).

Examples 1-9-2 to 1-9-10

The compounds of Examples 1-9-2 to 1-9-10 were synthesized by the similar method as in Example 1-9-1 using the corresponding bromoanilines and using the corresponding alkylsulfonamides in Step 4.

| Example No. | Compound No. | |
|---|---|---|
| 1-9-1 | I-H016 | |
| 1-9-2 | I-H005 | |
| 1-9-3 | I-H006 | |
| 1-9-4 | I-H007 | |
| 1-9-5 | I-H067 | |

-continued
| Example No. | Compound No. | |
|---|---|---|
| 1-9-6 | I-H017 | 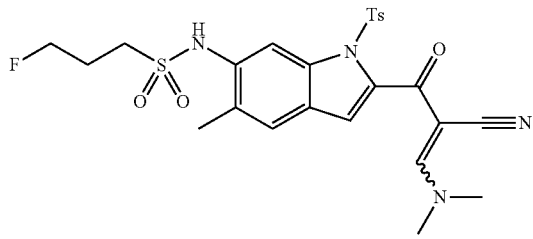 [SMILES: Cc1ccc(S(=O)(=O)n2c(C(=O)C(C#N)=CN(C)C)cc3cc(F)c(NS(=O)(=O)CCCF)cc32)cc1] |
| 1-9-7 | I-H019 | 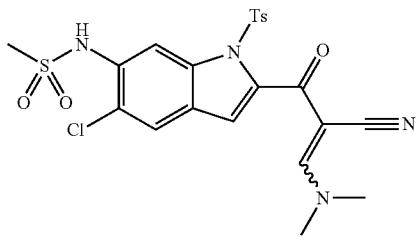 |
| 1-9-8 | I-H021 | 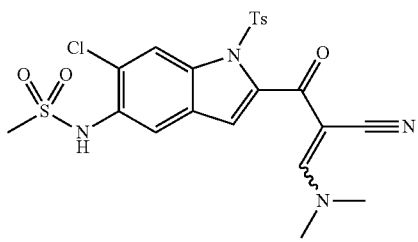 |
| 1-9-9 | I-H023 | 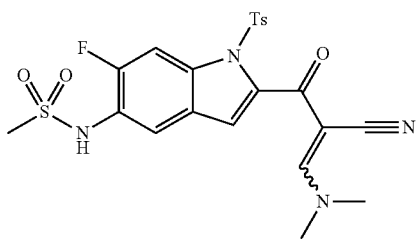 |
| 1-9-10 | I-H014 | 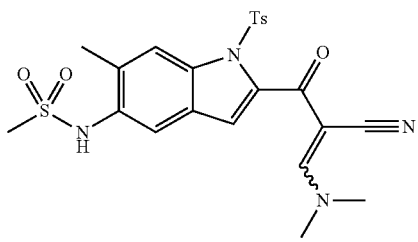 |

Example 1-10-1 (Compound I-A004)

Synthesis of N-{2-[2-cyano-3-(dimethylamino)prop-2-enoyl]-5-fluoro-1-(4-methylphenyl)sulfonylindol-6-yl}acetamide

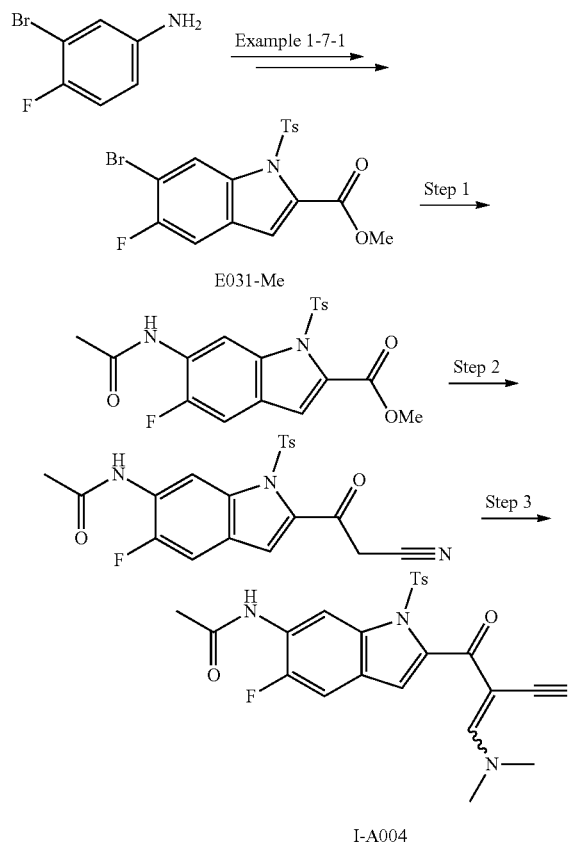

Step 1

Synthesis of ethyl 6-acetamido-5-fluoro-1-(4-methylphenyl)sulfonylindole-2-carboxylate The bromide E031-Me (50.0 g) synthesized by the similar method as in Example 1-7-1 was dissolved in dioxane (500 mL) in a nitrogen atmosphere and XANTPHOS (8.0 g), cesium carbonate (65 g), and acetamide (21 g) were added. The reaction system was degassed under reduced pressure and the atmosphere therein was then replaced by nitrogen. This degassing operation was repeated three times. Pd$_2$dba$_3$.CHCl$_3$ (5.0 g) was added. The reaction system was degassed again and the atmosphere therein was replaced by nitrogen. The mixture was heated at 100° C. for one hour. The reaction solution was cooled to 25° C. and diluted with ethyl acetate, and the insoluble matter was filtered off by celite filtration. The filtrate was washed with water and saturated saline and dried over anhydrous sodium sulfate. The drying agent was removed by filtration, the filtrate was concentrated under reduced pressure, and the resulting residue was crystallized from diethyl ether to give the target compound (40.0 g).

Step 2

Synthesis of N-[2-(2-cyanoacetyl)-5-fluoro-1-(4-methylphenyl)sulfonylindol-6-yl]acetamide Ethyl 6-acetamido-5-fluoro-1-(4-methylphenyl)sulfonylindole-2-carboxylate (270 g) was suspended in tetrahydrofuran (2.0 L), dehydrated acetonitrile (109 mL) was added, LDA (3.0 M solution in tetrahydrofuran, 1.0 L) was added dropwise at −78° C., and the mixture was stirred for 30 minutes. A saturated aqueous ammonium chloride solution (1.5 L) was added to the reaction solution and the mixture was extracted with ethyl acetate. The organic layer was washed with saturated saline and dried over anhydrous sodium sulfate. The drying agent was removed by filtration and the filtrate was concentrated under reduced pressure to give the target compound (180 g).

Step 3

Synthesis of N-{2-[2-cyano-3-(dimethylamino)prop-2-enoyl]-5-fluoro-1-(4-methylphenyl)sulfonylindol-6-yl}acetamide (I-A004)

N-[2-(2-Cyanoacetyl)-5-fluoro-1-(4-methylphenyl)sulfonylindol-6-yl]acetamide (160 g) was suspended in tetrahydrofuran (2.4 L), N,N-dimethylformamide dimethylacetal (70 mL) was added, and the mixture was stirred at 25° C. for one hour. The reaction solution was concentrated and the precipitated solid was then collected by filtration to give the target compound (120 g).

| Example No. | Compound No. | |
|---|---|---|
| 1-10-1 | I-A004 | 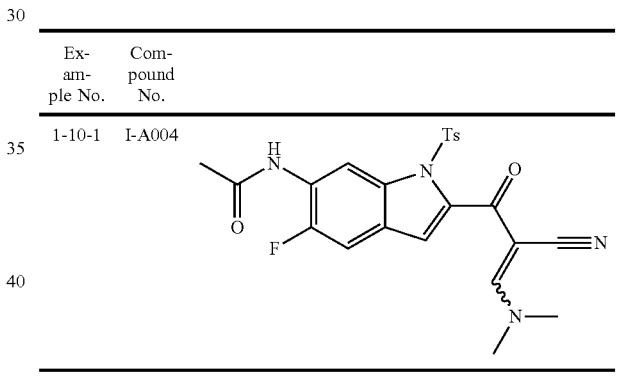 |

Example 1-11-1 (Compound I-H054)

Synthesis of N-{2-[2-cyano-3-(dimethylamino)prop-2-enoyl]-5-methyl-1-(4-methylphenyl)sulfonylindol-6-yl}morpholine-4-sulfonamide

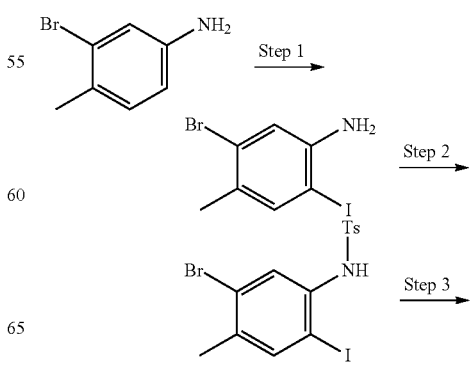

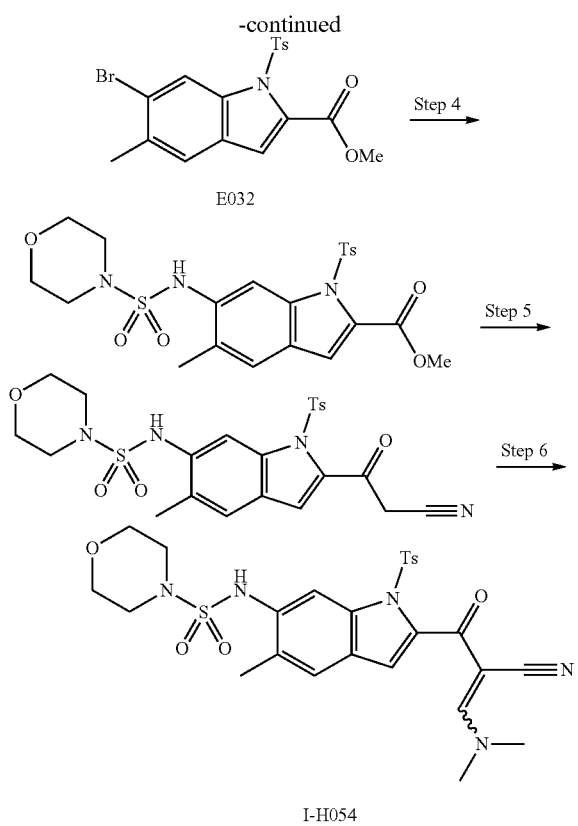

I-H054

Step 1

Synthesis of 5-bromo-2-iodo-4-methylaniline

3-Bromo-4-methylaniline (50.0 g) was dissolved in acetic acid (250 mL), N-iodosuccinimide (59.2 g) was added at 25° C., and the mixture was stirred at 10° C. for three hours. Water (500 mL) was added to the reaction solution and the precipitated solid was collected by filtration to give the target compound (80.0 g).

Step 2

Synthesis of N-(5-bromo-2-iodo-4-methylphenyl)-4-methylbenzenesulfonamide

5-Bromo-2-iodo-4-methylaniline (20.0 g) was dissolved in pyridine (150 mL), p-toluenesulfonyl chloride (14.7 g) was added, and the mixture was stirred at 100° C. for 15 hours. 1 M hydrochloric acid was added to the reaction solution and the mixture was extracted with ethyl acetate. The organic layer was washed with a saturated aqueous sodium carbonate solution and saturated saline and dried over anhydrous sodium sulfate. The drying agent was removed by filtration and the filtrate was concentrated under reduced pressure to give the target compound (27.8 g).

Step 3

Synthesis of methyl 6-bromo-5-methyl-1-(4-methylphenyl)sulfonylindole-2-carboxylate (E032)

N-(5-Bromo-2-iodo-4-methylphenyl)-4-methylbenzenesulfonamide (1.60 g) was dissolved in tetrahydrofuran (15 mL) and zinc bromide (2.3 g), DIPEA (2.7 mL), and methyl propiolate (0.87 mL) were added. The reaction system was degassed under reduced pressure and the atmosphere therein was then replaced by nitrogen. Pd(PPh$_3$)$_4$ (200 mg) was added. The reaction system was degassed under reduced pressure and the atmosphere therein was replaced by nitrogen. The mixture was stirred at 80° C. for 16 hours. The reaction solution was cooled to 25° C. and the insoluble matter was filtered off by celite filtration. Saturated saline was added to the filtrate, the mixture was extracted with ethyl acetate and dried over anhydrous sodium sulfate. The drying agent was removed by filtration, the filtrate was concentrated under reduced pressure, and the resulting residue was purified by column chromatography (petroleum ether/ethyl acetate) to give the target compound (0.12 g).

Step 4

Synthesis of methyl 5-methyl-1-(4-methylphenyl)sulfonyl-6-(morpholin-4-ylsulfonylamino)indole-2-carboxylate Methyl 6-bromo-5-methyl-1-(4-methylphenyl)sulfonylindole-2-carboxylate (1.50 g) was dissolved in 2-methyltetrahydrofuran (50 mL) in a nitrogen atmosphere and allylpalladium chloride (dimer) (65 mg), potassium carbonate (98 mg), morpholine-4-sulfonamide (710 mg), and tBuXPhos (226 mg) were added. The reaction system was degassed under reduced pressure and the atmosphere therein was then replaced by nitrogen. The mixture was heated at 90° C. for 16 hours. The reaction solution was cooled to 25° C., water was added, and the mixture was extracted with ethyl acetate. The organic layer was washed with saturated saline and dried over anhydrous sodium sulfate. The drying agent was removed by filtration and the filtrate was concentrated under reduced pressure to give the target compound (1.70 g).

Step 5

Synthesis of N-[2-(2-cyanoacetyl)-5-methyl-1-(4-methylphenyl)sulfonylindol-6-yl]morpholine-4-sulfonamide Methyl 5-methyl-1-(4-methylphenyl)sulfonyl-6-(morpholin-4-ylsulfonylamino)indole-2-carboxylate (2.30 g) was suspended in tetrahydrofuran (50 mL), dehydrated acetonitrile (0.56 mL) was added, lithium bis(trimethylsilyl)amide (1.0 M solution in tetrahydrofuran, 23 mL) was added dropwise at −78° C., and the mixture was stirred for two hours. A saturated aqueous ammonium chloride solution was added to the reaction solution and the mixture was extracted with ethyl acetate. The organic layer was washed with saturated saline and dried over anhydrous sodium sulfate. The drying agent was removed by filtration and the filtrate was concentrated under reduced pressure to give the target compound (2.20 g).

Step 6

Synthesis of N-{2-[2-cyano-3-(dimethylamino)prop-2-enoyl]-5-methyl-1-(4-methylphenyl)sulfonylindol-6-yl}morpholine-4-sulfonamide (I-H054)

N-[2-(2-Cyanoacetyl)-5-methyl-1-(4-methylphenyl)sulfonylindol-6-yl]morpholine-4-sulfonamide (1.40 g) was suspended in tetrahydrofuran (50 mL), N,N-dimethylformamide dimethylacetal (0.35 mL) was added, and the mixture was stirred at 25° C. for two hours. The reaction solution was concentrated and the precipitated solid was collected by filtration to give the target compound (1.50 g).

| Example No. | Compound No. | |
|---|---|---|
| 1-11-1 | I-H054 | 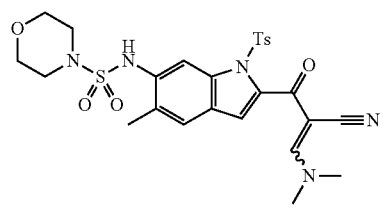 [SMILES: Cc1ccc(S(=O)(=O)n2c(C(=O)C(C#N)=CN(C)C)cc3cc(C)c(NS(=O)(=O)N4CCOCC4)cc32)cc1] |

Example 1-12-1 (Compound I-H057)

Synthesis of tert-butyl N-{2-[2-cyano-3-(dimethylamino)prop-2-enoyl]-5-methyl-1-(4-methylphenyl)sulfonylindol-6-yl}carbamate

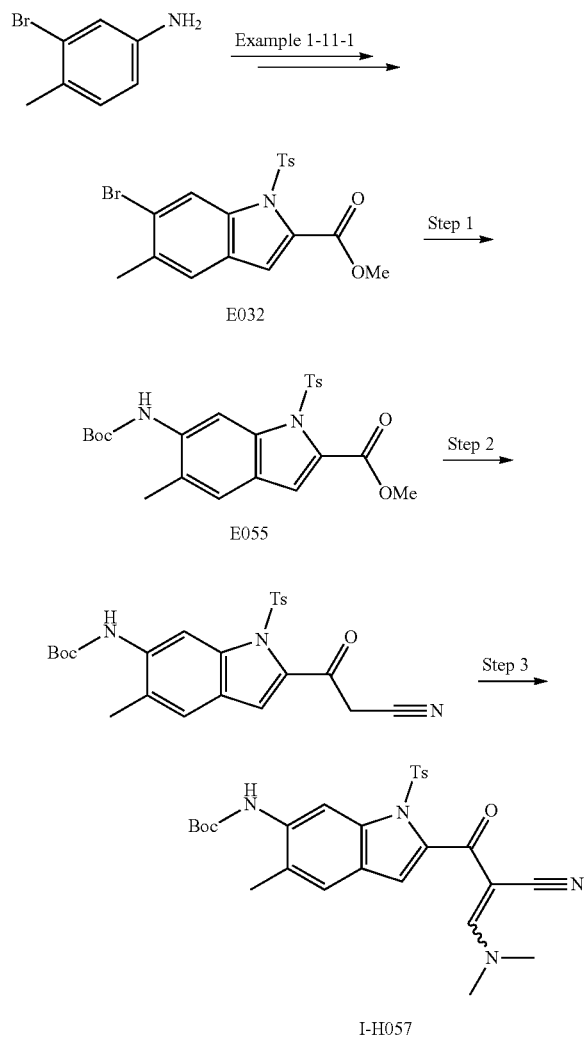

Step 1

Synthesis of methyl 5-methyl-1-(4-methylphenyl)sulfonyl-6-[(2-methylpropan-2-yl)oxycarbonylamino]indole-2-carboxylate (E055)

The bromide E032 synthesized in Example 1-11-1 (2.37 g), tert-butyl carbamate (990 mg), Pd$_2$dba$_3$·CHCl$_3$ (570 mg), X-Phos (790 mg), and cesium carbonate (5.4 g) were dissolved in dioxane (40 mL). Under ultrasonic irradiation, the flask containing the reaction solution was degassed and the atmosphere therein was replaced with nitrogen. The reaction solution was stirred at 100° C. for 16 hours in a nitrogen atmosphere. The reaction solution was cooled to 25° C., water was added thereto, and the mixture was extracted with ethyl acetate. The organic layer was washed with saturated saline and dried over anhydrous sodium sulfate. The drying agent was removed by filtration and the filtrate was concentrated under reduced pressure to give the target compound (4.50 g).

Step 2

Synthesis of tert-butyl N-[2-(2-cyanoacetyl)-5-methyl-1-(4-methylphenyl)sulfonylindol-6-yl]carbamate Methyl 5-methyl-1-(4-methylphenyl)sulfonyl-6-[(2-methylpropan-2-yl)oxycarbonylamino]indole-2-carboxylate (1.20 g) was suspended in tetrahydrofuran (30 mL), dehydrated acetonitrile (0.40 mL) was added, lithium bis(trimethylsilyl)amide (1.0 M solution in tetrahydrofuran, 13 mL) was added dropwise at −78° C., and the mixture was stirred for two hours. A saturated aqueous ammonium chloride solution (75 mL) was added to the reaction solution and the mixture was extracted with ethyl acetate (300 mL). The organic layers were washed with saturated saline (200 mL) and dried over anhydrous sodium sulfate. The drying agent was removed by filtration and the filtrate was concentrated under reduced pressure to give the target compound (1.22 g).

Step 3

Synthesis of tert-butyl N-{2-[2-cyano-3-(dimethylamino)prop-2-enoyl]-5-methyl-1-(4-methylphenyl)sulfonylindol-6-yl}carbamate (I-H057)

tert-Butyl N-[2-(2-cyanoacetyl)-5-methyl-1-(4-methylphenyl)sulfonylindol-6-yl]carbamate (1.22 g) was suspended in tetrahydrofuran (20 mL), N,N-dimethylformamide dimethylacetal (0.37 mL) was added, and the mixture was stirred at 25° C. for 30 minutes. The reaction solution was concentrated under reduced pressure and the precipitated solid was collected by filtration to give the target compound (1.60 g).

Examples 1-12-2 to 1-12-3

The compounds of Examples 1-12-2 to 1-12-3 were synthesized by the similar method as in Example 1-12-1 using the corresponding amines in Step 1.

| Example No. | Compound No. | |
|---|---|---|
| 1-12-1 | I-H057 | 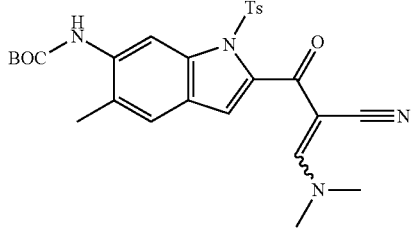 [SMILES: Cc1ccc(S(=O)(=O)n2c(C(=O)C(C#N)=CN(C)C)cc3cc(C)c(NC(=O)OC(C)(C)C)cc32)cc1] |
| 1-12-2 | I-H060 | 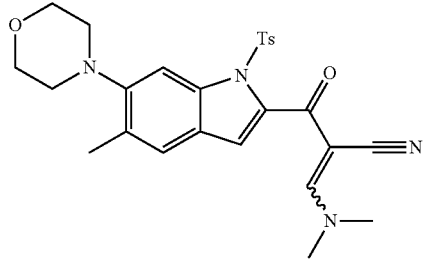 |
| 1-12-3 | I-H061 | 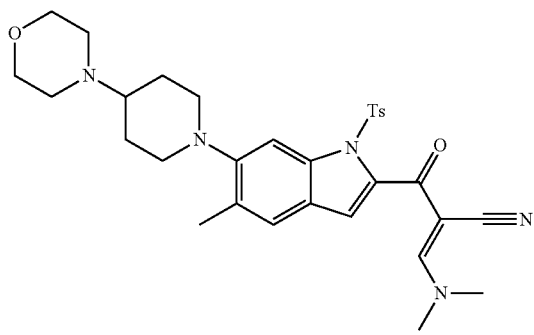 [SMILES: Cc1ccc(S(=O)(=O)n2c(C(=O)/C(C#N)=C/N(C)C)cc3cc(C)c(N4CCC(N5CCOCC5)CC4)cc32)cc1] |
Example 1-12-4 (Compound I-H055)
Synthesis of 3-(dimethylamino)-2-[6-(1,1-dioxo-1,2-thiazolidin-2-yl)-5-fluoro-1-(4-methylphenyl)sulfonylindole-2-carbonyl]prop-2-enenitrile
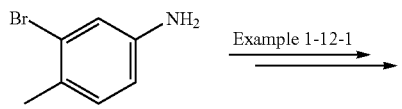
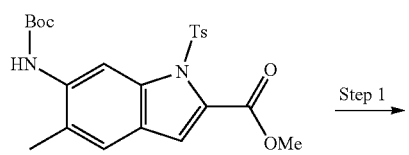
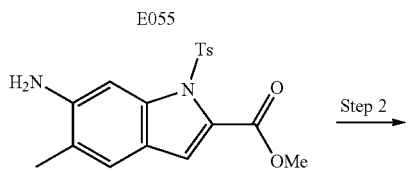
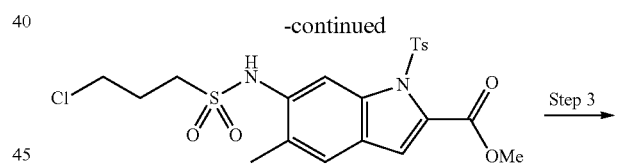
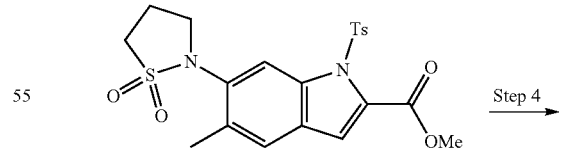
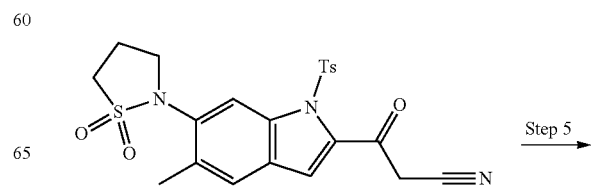

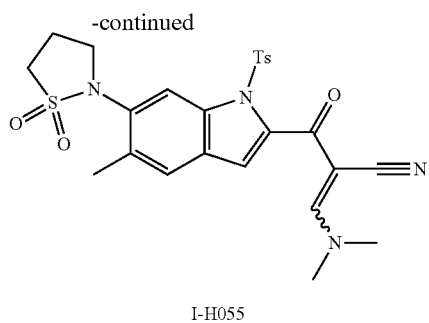

I-H055

Step 1

Synthesis of methyl 6-amino-5-methyl-1-(4-methylphenyl)sulfonylindole-2-carboxylate The Boc compound E055 synthesized in Example 1-12-1 (4.50 g) was dissolved in dichloromethane (100 mL), hydrogen chloride gas was added, and the mixture was stirred at 25° C. for two hours. The precipitated solid was collected by filtration to give the target compound (4.41 g).

Step 2

Synthesis of methyl 6-(3-chloropropylsulfonylamino)-5-fluoro-1-(4-methylphenyl)sulfonylindole-2-carboxylate Methyl 6-amino-5-methyl-1-(4-methylphenyl)sulfonylindole-2-carboxylate (3.00 g) was dissolved in pyridine (30 mL), 3-chloropropyl-1-sulfonyl chloride (2.7 mL) was added, and the mixture was stirred at 25° C. for four hours. 1 M hydrochloric acid (20 mL) was added to the reaction solution and the mixture was extracted with ethyl acetate (50 mL). The organic layer was washed with 1 M hydrochloric acid, a saturated aqueous sodium bicarbonate solution, and saturated saline and dried over anhydrous sodium sulfate. The drying agent was removed by filtration and the filtrate was concentrated under reduced pressure to give the target compound (3.16 g).

Step 3

Synthesis of methyl 6-(1,1-dioxo-1,2-thiazolidin-2-yl)-5-fluoro-1-(4-methylphenyl)sulfonylindole-2-carboxylate Methyl 6-(3-chloropropylsulfonylamino)-5-fluoro-1-(4-methylphenyl)sulfonylindole-2-carboxylate (3.16 g) was dissolved in N,N-dimethylformamide (15 mL), sodium iodide (2.86 g) and potassium carbonate (4.37 g) were added, and the mixture was stirred at 80° C. for 30 minutes. The reaction solution was cooled to 25° C., water was added, and the precipitated solid was collected by filtration to give the target compound (2.15 g).

Step 4

Synthesis of 3-[6-(1,1-dioxo-1,2-thiazolidin-2-yl)-5-fluoro-1-(4-methylphenyl)sulfonylindol-2-yl]-3-oxopropanenitrile Methyl 6-(1,1-dioxo-1,2-thiazolidin-2-yl)-5-fluoro-1-(4-methylphenyl)sulfonylindole-2-carboxylate (2.15 g) was suspended in tetrahydrofuran (50 mL), dehydrated acetonitrile (0.75 mL) was added, lithium bis(trimethylsilyl)amide (1.0 M solution in tetrahydrofuran, 23 mL) was added dropwise at −78° C., and the mixture was stirred for two hours. A saturated aqueous ammonium chloride solution was added to the reaction solution and the mixture was extracted with ethyl acetate. The organic layer was washed with saturated saline and dried over anhydrous sodium sulfate. The drying agent was removed by filtration and the filtrate was concentrated under reduced pressure to give the target compound (2.19 g).

Step 5

Synthesis of 3-(dimethylamino)-2-[6-(1,1-dioxo-1,2-thiazolidin-2-yl)-5-fluoro-1-(4-methylphenyl)sulfonylindole-2-carbonyl]prop-2-enenitrile (1-H055)

3-[6-(1,1-Dioxo-1,2-thiazolidin-2-yl)-5-fluoro-1-(4-methylphenyl)sulfonylindol-2-yl]-3-oxopropanenitrile (2.19 g) was suspended in tetrahydrofuran (30 mL), N,N-dimethylformamide dimethylacetal (0.69 mL) was added, and the mixture was stirred at 25° C. for two hours. The reaction solution was concentrated and the precipitated solid was collected by filtration to give the target compound (2.70 g).

| Example No. | Compound No. | |
|---|---|---|
| 1-12-4 | I-H055 | 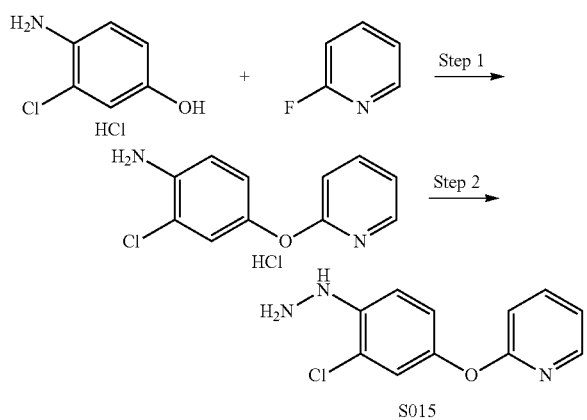 |

Example 2

Example 2-1-1 (Compound S015)

Synthesis of (2-chloro-4-pyridin-2-yloxyphenyl)hydrazine hydrochloride

Step 1

Synthesis of 2-chloro-4-pyridin-2-yloxyaniline hydrochloride

4-Amino-3-chlorophenol (5.40 g) was dissolved in 1-methyl-2-pyrrolidone (76 mL), and potassium tert-butoxide (4.4 g) and potassium carbonate (2.9 g) were added. Then the mixture was stirred at 25° C. for 30 minutes. 2-Fluoropyridine (3.4 mL) was added to the reaction solution and the mixture was stirred at 100° C. for two hours. The reaction solution was cooled to 25° C., water was added, and the mixture was extracted with dichloromethane. The combined organic layers were sequentially washed with a 2 M aqueous sodium hydroxide solution, water, and saturated saline, and dried over anhydrous sodium sulfate. The drying agent was removed by filtration, the filtrate was concentrated under reduced pressure, the resulting residue was dissolved in ethyl acetate (30 mL), and a 4 M hydrochloric acid-ethyl acetate solution (100 mL) was added. The precipitated solid was collected by filtration and sequentially washed with ethyl acetate and hexane to give the target compound (6.10 g).

Step 2

Synthesis of (2-chloro-4-pyridin-2-yloxyphenyl)hydrazine hydrochloride (S015)

2-Chloro-4-pyridin-2-yloxyaniline hydrochloride (1.00 g) was suspended in concentrated hydrochloric acid (10 mL) and the suspension was cooled to 0° C. Sodium nitrite (350 mg) dissolved in water (5.0 mL) was added dropwise and the mixture was stirred at 0° C. for 50 minutes. The reaction solution was filtered and the filtrate was cooled to 0° C. Tin(II) chloride dihydrate (2.2 g) dissolved in concentrated hydrochloric acid (5 mL) was added dropwise thereto and the mixture was stirred at 0° C. for one hour. The reaction solution was diluted with ethyl acetate (100 mL), and a 5 M aqueous sodium hydroxide solution (36 mL) was added. Then the mixture was extracted with ethyl acetate (150 mL) three times. The combined organic layers were washed with saturated saline (100 mL) and dried over anhydrous sodium sulfate. The drying agent was removed by filtration, the filtrate was concentrated to half the volume under reduced pressure, a 4 M Hydrochloric acid-ethyl acetate solution (29 mL) was added, and the mixture was stirred at 0° C. for 30 minutes. The reaction solution was concentrated under reduced pressure and the resulting residue was washed by suspending in methanol/ethyl acetate to give the target compound (900 mg).

| Example No. | Compound No. | |
|---|---|---|
| 2-1-1 | S015 | 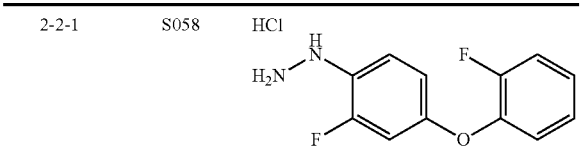 |

Example 2-2-1 (Compound S058)

Synthesis of [2-fluoro-4-(2-fluorophenoxy)phenyl]hydrazine hydrochloride

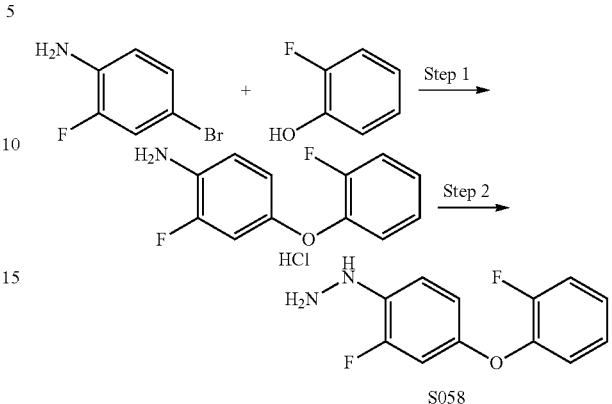

Step 1

Synthesis of 2-fluoro-4-(2-fluorophenoxy)aniline

4-Bromo-2-fluoroaniline (5.00 g) was dissolved in dimethylsulfoxide (100 mL), and 2-fluorophenol (4.10 g), copper(I) bromide (400 mg), cesium carbonate (17 g), and N,N-dimethylglycine (700 mg) were added. Then the mixture was stirred at 120° C. for 15 hours in a nitrogen atmosphere. After cooling the reaction solution to 25° C., water (500 mL) was added and the mixture was extracted with ethyl acetate (300 mL) three times. The combined organic layers were washed with saturated saline (300 mL) five times and dried over anhydrous sodium sulfate. The drying agent was removed by filtration, the filtrate was concentrated under reduced pressure, and the resulting residue was purified by column chromatography (petroleum ether/ethyl acetate) to give the target compound (1.60 g).

Step 2

Synthesis of [2-fluoro-4-(2-fluorophenoxy)phenyl] hydrazine hydrochloride (S058)

2-Fluoro-4-(2-fluorophenoxy)aniline (1.60 g) was dissolved in concentrated hydrochloric acid (50 mL) and the reaction solution was cooled to 0° C. Sodium nitrite (500 mg) dissolved in water (10 mL) was added dropwise and the mixture was stirred at 0° C. for one hour. Tin(II) chloride dihydrate (3.3 g) dissolved in concentrated hydrochloric acid (20 mL) was added dropwise to the reaction solution and the mixture was stirred at 0° C. for two hours. The precipitated solid was collected by filtration to give the target compound (2.00 g).

Examples 2-2-2 to 2-2-4

The compounds of Examples 2-4-2 to 2-2-4 were synthesized from corresponding anilines and phenols by the similar method as in Example 2-2-1.

| Example No. | Compound No. | |
|---|---|---|
| 2-2-1 | S058 | 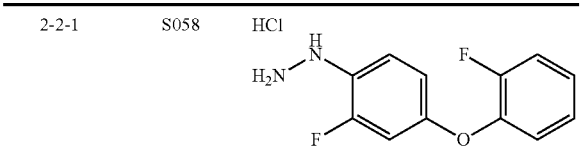 |

| Example No. | Compound No. | |
|---|---|---|
| 2-2-2 | S055 | 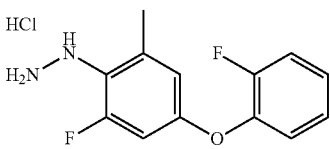 |
| 2-2-3 | S056 | 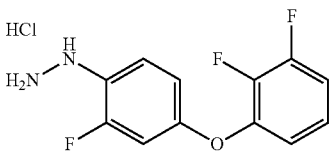 [SMILES: Cl ; NNc1ccc(Oc2cccc(F)c2F)cc1F] |
| 2-2-4 | S057 | 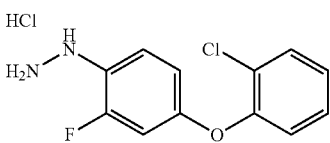 [SMILES: Cl ; NNc1ccc(Oc2ccccc2Cl)cc1F] |

Example 2-3-1 (Compound S038)

Synthesis of [2-fluoro-4-(2-fluorophenoxy)-6-methylphenyl]hydrazine hydrochloride

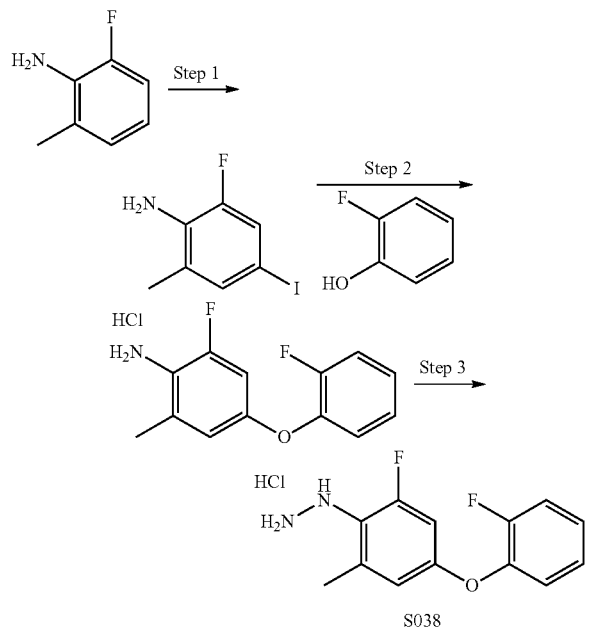

Step 1

Synthesis of 2-fluoro-4-iodo-6-methylaniline

2-Fluoro-6-methylaniline (1.00 g) was dissolved in N,N-dimethylformamide (30 mL) and the reaction solution was cooled to 0° C. N-Iodosuccinimide (1.9 g) was added and the mixture was stirred at 0° C. for 30 minutes. Water was added to the reaction solution and the mixture was extracted with ethyl acetate. The organic layer was sequentially washed with a saturated aqueous sodium bicarbonate solution and saturated saline, and dried over anhydrous magnesium sulfate. The drying agent was removed by filtration, the filtrate was concentrated under reduced pressure, and the resulting residue was purified by column chromatography (hexane/ethyl acetate) to give the target compound (1.60 g).

Step 2

Synthesis of 2-fluoro-4-(2-fluorophenoxy)-6-methylaniline hydrochloride

2-Fluoro-4-iodo-6-methylaniline (1.00 g) was dissolved in toluene (15 mL), and 2-fluorophenol (893 mg), copper(I) chloride (118 mg), potassium carbonate (1.7 g), and 1-methylimidazole (327 mg) were added. Then the mixture was stirred at 130° C. for 15 hours in a nitrogen atmosphere. The reaction solution was cooled to 25° C., water was added, and the mixture was extracted with ethyl acetate. The organic layer was sequentially washed with a saturated aqueous sodium bicarbonate solution and saturated saline, and dried over anhydrous magnesium sulfate. The drying agent was removed by filtration, the filtrate was concentrated under reduced pressure, and the resulting residue was purified by column chromatography (hexane/ethyl acetate). The resulting purified product was dissolved in ethyl acetate (2 mL), and a 4 M hydrochloric acid-ethyl acetate solution (2.0 mL) was added. Then the mixture was stirred at 25° C. for 10 minutes. The precipitated solid was collected by filtration and washed with ethyl acetate to give the target compound (330 mg).

Step 3

Synthesis of [2-fluoro-4-(2-fluorophenoxy)-6-methylphenyl]hydrazine hydrochloride (S038)

2-Fluoro-4-(2-fluorophenoxy)-6-methylaniline hydrochloride (150 mg) was dissolved in concentrated hydrochloric acid (0.7 mL) and water (0.2 mL) and the reaction solution was cooled to 0° C. Sodium nitrite (46 mg) dissolved in water (0.3 mL) was added dropwise and the mixture was stirred at 0° C. for 30 minutes. Tin(II) chloride dihydrate (262 mg) dissolved in concentrated hydrochloric acid (0.7 mL) and water (0.2 mL) was added dropwise to the reaction solution and the mixture was stirred at 0° C. for 30 minutes. The reaction solution was adjusted to pH 11 by adding a 5 M aqueous sodium hydroxide solution, and the mixture was extracted with ethyl acetate. A 4 M Hydrochloric acid-ethyl acetate solution was added to the organic layer, and concentration under reduced pressure gave the target compound (138 mg).

Examples 2-3-2 to 2-3-6

The compounds of Examples 2-3-2 to 2-3-6 were synthesized from corresponding anilines and phenols by the similar method as in Example 2-3-1.

| Example No. | Compound No. | |
|---|---|---|
| 2-3-1 | S038 | (structure) |

| Example No. | Compound No. | |
|---|---|---|
| 2-3-2 | S040 | ![structure] |
| 2-3-3 | S041 | ![structure] |
| 2-3-4 | S042 | ![structure] |
| 2-3-5 | S045 | ![structure] |
| 2-3-6 | S047 | ![structure] |

Example 2-4-1 (Compound Q002)

Synthesis of [4-(2,3-difluorophenoxy)-2-methylphenyl]hydrazine hydrochloride

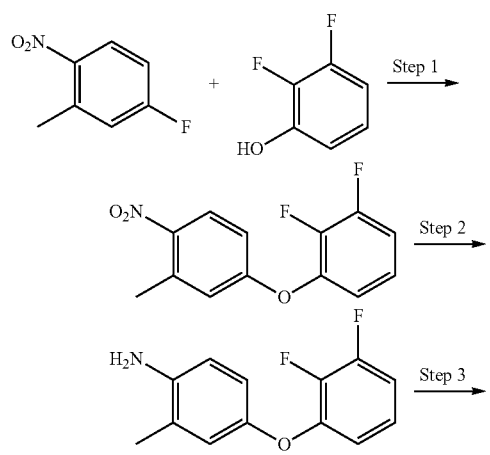

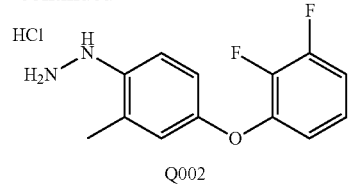

Q002

Step 1

Synthesis of 1,2-difluoro-3-(3-methyl-4-nitrophenoxy)benzene

5-Fluoro-2-nitrotoluene (10.0 g) and 2,3-difluorophenol (10.0 g) were dissolved in N,N-dimethylformamide (200 mL), and potassium carbonate (15 g) was added. Then the mixture was stirred at 100° C. for three hours. The reaction solution was cooled to 0° C. and the precipitated solid was collected by filtration to give the target compound (13.0 g).

Step 2

Synthesis of 4-(2,3-difluorophenoxy)-2-methylaniline 1,2-Difluoro-3-(3-methyl-4-nitrophenoxy)benzene (13.0 g) was dissolved in ethanol (100 mL), and tin(II) chloride dihydrate (33 g) and concentrated hydrochloric acid (20 mL) were added. Then the mixture was stirred at 80° C. for two hours. The reaction solution was cooled to 25° C., diluted with ethyl acetate, and neutralized by adding an ammonia-methanol solution. The insoluble matter was filtered off by celite filtration and the filtrate was concentrated under reduced pressure to give the target compound (13.0 g).

Step 3

Synthesis of [4-(2,3-difluorophenoxy)-2-methylphenyl]hydrazine hydrochloride (Q002)

4-(2,3-Difluorophenoxy)-2-methylaniline (13.0 g) was dissolved in concentrated hydrochloric acid (100 mL) and the reaction solution was cooled to 0° C. Sodium nitrite (4.2 g) dissolved in water (14 mL) was added dropwise, tin(II) chloride dihydrate (25 g) dissolved in 12 M Hydrochloric acid (120 mL) was then added dropwise, and the mixture was stirred at 0° C. for two hours. The precipitated solid was collected by filtration to give the target compound (11.0 g).

Examples 2-4-2 to 2-4-11

The compounds of Examples 2-4-2 to 2-4-11 were synthesized from corresponding nitrobenzenes or nitropyridines and corresponding phenols or hydroxypyridines by the similar method as in Example 2-4-1.

| Example No. | Compound No. | |
|---|---|---|
| 2-4-1 | Q002 | ![structure] |

-continued

| Example No. | Compound No. | |
|---|---|---|
| 2-4-2 | Q001 | HCl, structure |
| 2-4-3 | Q005 | HCl, structure |
| 2-4-4 | Q007 | HCl, structure |
| 2-4-5 | Q019 | HCl, structure |
| 2-4-6 | Q027 | HCl, structure |
| 2-4-7 | Q030 | HCl, structure |
| 2-4-8 | Q031 | HCl, structure |
| 2-4-9 | Q034 | HCl, structure |
| 2-4-10 | S005 | HCl, structure |

-continued

| Example No. | Compound No. | |
|---|---|---|
| 2-4-11 | T009 | HCl, structure |

Example 2-5-1 (Compound T001)

Synthesis of [6-(2-fluorophenoxy)-4-methylpyridin-3-yl]hydrazine hydrochloride

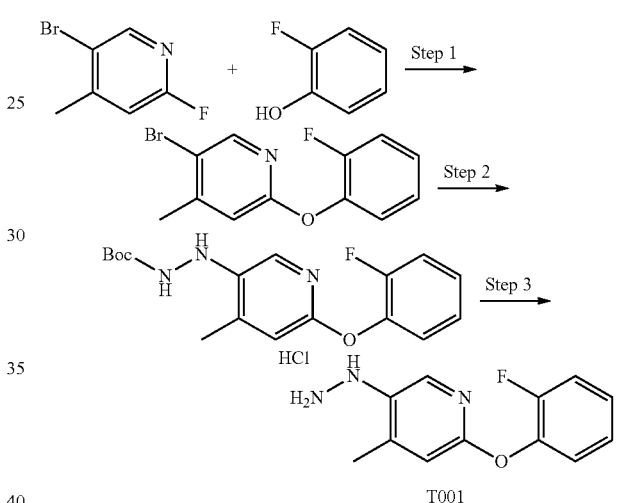

Step 1

Synthesis of 5-bromo-2-(2-fluorophenoxy)-4-methylpyridine

5-Bromo-2-fluoro-4-methylpyridine (20.0 g), 2-fluorophenol (13.0 g), and cesium carbonate (38 g) were dissolved in 1-methyl-2-pyrrolidone (200 mL) and the mixture was stirred at 100° C. for five hours. The reaction solution was cooled to 25° C. and the precipitated solid was collected by filtration and washed with water (100 mL) twice to give the target compound (16.5 g).

Step 2

Synthesis of tert-butyl N-{[6-(2-fluorophenoxy)-4-methylpyridin-3-yl]amino}carbamate 5-Bromo-2-(2-fluorophenoxy)-4-methylpyridine (800 mg), tert-butyl carbazate (450 mg), Pd$_2$dba$_3$·CHCl$_3$ (147 mg), tBuXPhos (181 mg), and potassium carbonate (980 mg) were dissolved in dioxane (30 mL). The flask containing the reaction solution was degassed and the atmosphere therein was replaced by nitrogen. The reaction solution was stirred at 100° C. for 15 hours in a nitrogen atmosphere. Water was added to the reaction solution and the mixture was extracted with ethyl acetate. The organic layer was washed with saturated saline and dried over anhydrous sodium sulfate. The drying agent was removed by filtration, the filtrate was concentrated under reduced pressure, and the resulting residue was purified by column chromatography (hexane/ethyl acetate) to give the target compound (790 mg).

Step 3

Synthesis of [6-(2-fluorophenoxy)-4-methylpyridin-3-yl]hydrazine hydrochloride (T001)

tert-Butyl N-{[6-(2-fluorophenoxy)-4-methylpyridin-3-yl]amino}carbamate (780 mg) was dissolved in 2,2,2-trifluoroethanol (10 mL) and TMSCl (0.76 mL) was added at 0° C. The mixture was stirred at 25° C. for 10 minutes, the reaction solution was concentrated under reduced pressure, and the resulting residue was washed by suspending in ethyl acetate to give the target compound (580 mg).

Examples 2-5-2 to 2-5-9

The compounds of Examples 2-5-2 to 2-5-9 were synthesized from corresponding phenols by the similar method as in Example 2-5-1.

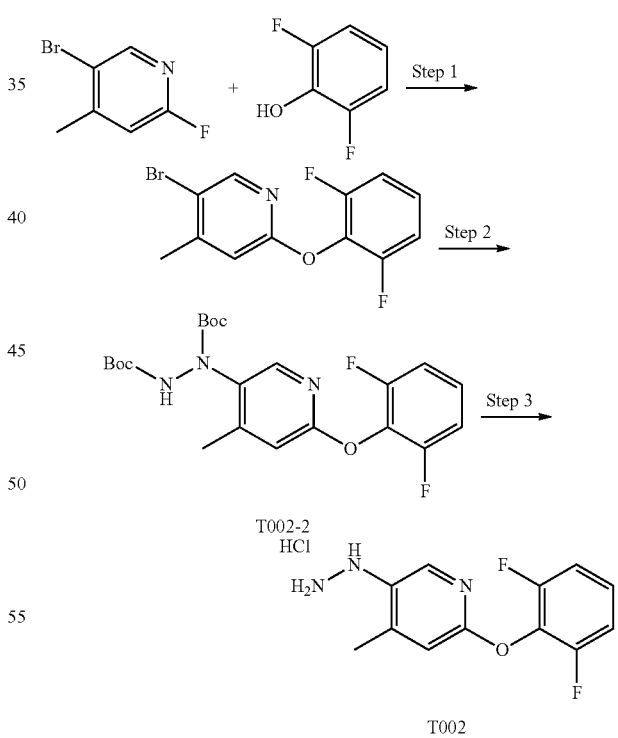

Example 2-6-1 (Compounds T002 and T002-2)

Synthesis of [6-(2,6-difluorophenoxy)-4-methylpyridin-3-yl]hydrazine hydrochloride Step 1

Synthesis of 5-bromo-2-(2,6-difluorophenoxy)-4-methylpyridine 2,6-Difluorophenol (157 g) and 5-bromo-2-fluoro-4-methylpyridine (115 g) were dissolved in N,N-dimethylformamide (345 mL) and cesium carbonate (394 g) was added. The reaction solution was stirred at 120° C. for 24 hours in a nitrogen atmosphere. The reaction solution was cooled to 60° C. and water was added. The precipitated solid was collected by filtration and washed with water to give the target compound (151 g).
Step 2

Synthesis of tert-butyl N-[6-(2,6-difluorophenoxy)-4-methylpyridin-3-yl]-N-[(2-methylpropan-2-yl)oxycarbonylamino]carbamate (T002-2)

5-Bromo-2-(2,6-difluorophenoxy)-4-methylpyridine (149 g) was dissolved in tetrahydrofuran (1.1 L), and iPrMgCl—LiCl (1.3 M solution in tetrahydrofuran, 769 mL) was added at 25° C. in a nitrogen atmosphere. Then the mixture was stirred at 40° C. for two hours. The reaction solution was cooled to −20° C., DBAD (230 g) dissolved in tetrahydrofuran (450 mL) was added, and the mixture was stirred for one hour. 1 M hydrochloric acid (1.2 L) was added to the reaction solution at 0° C. and the mixture was extracted with ethyl acetate (1.2 L). The organic layer was washed with a 20% aqueous sodium chloride solution twice and concentrated under reduced pressure. The resulting residue was crystallized from ethanol/water and washed with ethanol/water to give the target compound (160 g).
Step 3

Synthesis of [6-(2,6-difluorophenoxy)-4-methylpyridin-3-yl]hydrazine hydrochloride (T002)

tert-Butyl N-[6-(2,6-difluorophenoxy)-4-methylpyridin-3-yl]-N-[(2-methylpropan-2-yl)oxycarbonylamino]carbamate (154 g) was dissolved in 2,2,2-trifluoroethanol (1.5 L) and TMSCl (130 mL) was added at 25° C. The mixture was stirred for 24 hours and TMSCl (43 mL) was added. The reaction solution was stirred for one hour and ethyl acetate (770 mL) was added. The precipitated solid was collected by filtration and washed with ethyl acetate to give the target compound (100 g).

| Example No. | Compound No. | |
|---|---|---|
| 2-6-1 | T002 | HCl |

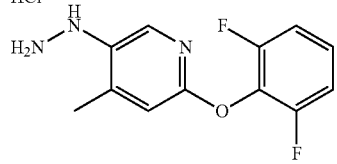

Example 3

Example 3-1-01 (Compound SFA-000)

Synthesis of N-(2-hydroxyethyl)-2-oxo-1,3-oxazolidine-3-sulfonamide

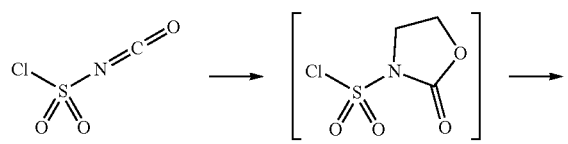

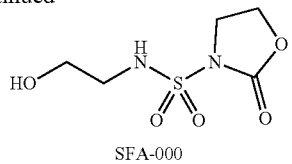

SFA-000

Chlorosulfonyl isocyanate (2.00 g) was dissolved in dichloromethane (20 mL), and 2-bromoethanol (1.0 mL) dissolved in dichloromethane (5.0 mL) was added at 0° C. Then the mixture was stirred at 0° C. for two hours. 2-Aminoethanol (1.1 mL) and TEA (3.6 mL) dissolved in dichloromethane (12 mL) were added to the reaction solution and the mixture was stirred at 25° C. for 15 hours. 1 M hydrochloric acid was added to the reaction solution and the mixture was extracted with ethyl acetate three times. The organic layers were washed with saturated saline and dried over anhydrous magnesium sulfate. The drying agent was removed by filtration, the filtrate was concentrated under reduced pressure, and the resulting residue was purified by column chromatography (dichloromethane/methanol) to give the target compound (1.70 g).

Example 3-1-02 (Compound SFA-002)

Synthesis of N-(2-hydroxyethyl)-2-oxo-1,3-oxazolidine-3-sulfonamide

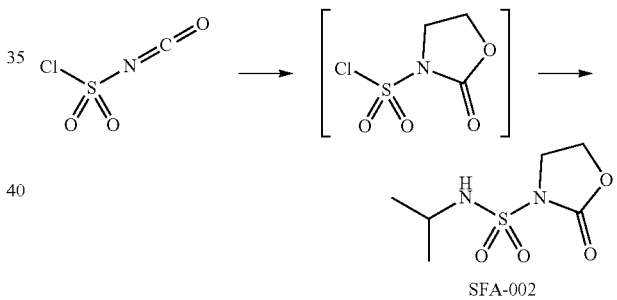

SFA-002

Chlorosulfonyl isocyanate (10.00 g) was dissolved in dichloromethane (20 mL), and 2-bromoethanol (8.8 g) dissolved in dichloromethane (125 mL) was added at 0° C. Then the mixture was stirred at 0° C. for two hours. 2-Aminoethanol (1.1 mL) and TEA (3.6 mL) dissolved in dichloromethane (12 mL) were added to a part of the reaction solution (2.6 g) and the mixture was stirred at 25° C. for 15 hours. 1 M hydrochloric acid was added to the reaction solution and the mixture was extracted with ethyl acetate three times. The organic layers were washed with saturated saline and dried over anhydrous magnesium sulfate. The drying agent was removed by filtration, the filtrate was concentrated under reduced pressure, and the resulting residue was purified by column chromatography (dichloromethane/methanol) to give the target compound (1.70 g).

Examples 3-1-02 to 3-1-08

The compounds of Examples 3-1-02 to 3-1-08 were synthesized by the similar method as in Example 3-1-01 using the corresponding amines.

| Example No. | Compound No. | |
|---|---|---|
| 3-1-01 | SFA-000 | 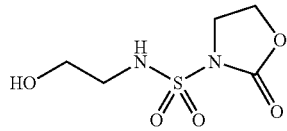 [SMILES: O=C1OCCN1S(=O)(=O)NCCO] |
| 3-1-02 | SFA-002 | 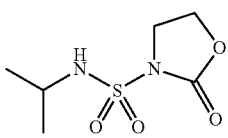 |
| 3-1-03 | SFA-003 | 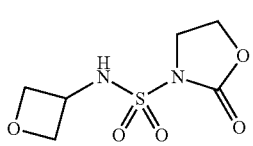 [SMILES: O=C1OCCN1S(=O)(=O)NC1COC1] |
| 3-1-04 | SFA-004 | 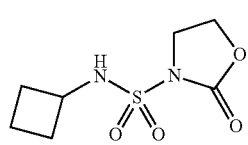 [SMILES: O=C1OCCN1S(=O)(=O)NC1CCC1] |
| 3-1-05 | SFA-005 | 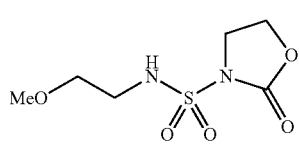 [SMILES: COCCNS(=O)(=O)N1CCOC1=O] |
| 3-1-06 | SFA-006 | 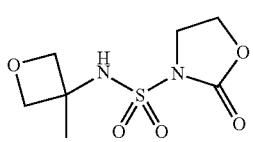 |
| 3-1-07 | SFA-007 | 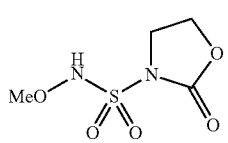 |
| 3-1-08 | SFA-008 | 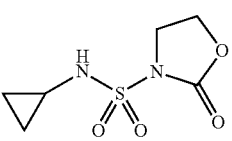 [SMILES: O=C1OCCN1S(=O)(=O)NC1CC1] |

Example 3-2-01 (Compound SFB-001)

Synthesis of N-[2-(tert-butyl dimethylsilyl)oxy-ethyl]-2-oxo-1,3-oxazolidine-3-sulfonamide

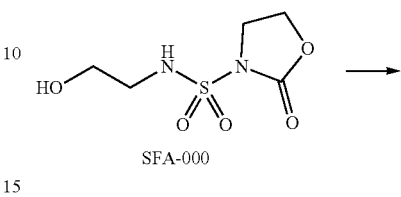

SFA-000

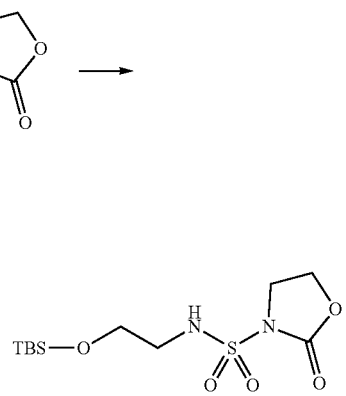

SFB-001

SFA-000 obtained in Example 3-1-01 (1.40 g) was dissolved in N,N-dimethylformamide (15 mL), and imidazole (900 mg) and TBSCl (2.0 g) were added at 0° C. Then the mixture was stirred at 25° C. for 30 minutes. 1 M hydrochloric acid was added to the reaction solution and the mixture was extracted with ethyl acetate twice. The organic layers were washed with saturated saline and dried over anhydrous magnesium sulfate. The drying agent was removed by filtration, the filtrate was concentrated under reduced pressure, and the resulting residue was purified by column chromatography (hexane/ethyl acetate) to give the target compound (2.00 g).

| Example No. | Compound No. | |
|---|---|---|
| 3-2-01 | SFB-001 | 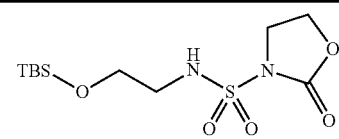 |

Example 3-3-01 (Compound SFC-001)

Synthesis of N-[2-(tert-butyldimethylsilyl)oxy-2-methylpropyl]-2-oxo-1,3-oxazolidine-3-sulfonamide

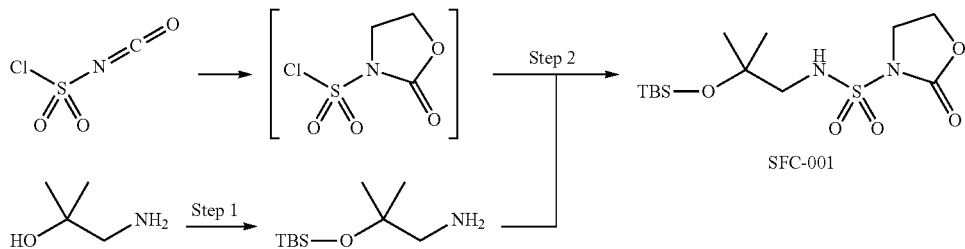

SFC-001

Step 1

Synthesis of 2-(tert-butyldimethylsilyl)oxy-2-methylpropan-1-amine

1-Amino-2-methyl-2-propanol (1.50 g) was dissolved in dichloromethane (50 mL), and DMAP (51 mg), TEA (2.6 mL), and TBSCl (2.7 g) were added. Then the mixture was stirred at 25° C. for three hours. A saturated aqueous sodium bicarbonate solution was added to the reaction solution, the mixture was extracted with ethyl acetate, and the organic layer was dried over anhydrous magnesium sulfate. The drying agent was removed by filtration, the filtrate was concentrated under reduced pressure, and the resulting residue was purified by column chromatography (hexane/ethyl acetate) to give the target compound (1.50 g).

Step 2

Synthesis of N-[2-(tert-butyldimethylsilyl)oxy-2-methylpropyl]-2-oxo-1,3-oxazolidine-3-sulfonamide Chlorosulfonyl isocyanate (1.00 g) was dissolved in dichloromethane (10 mL), and 2-bromoethanol (0.5 mL) dissolved in dichloromethane (2.5 mL) was added at 0° C. Then the mixture was stirred at 0° C. for two hours. 2-(tert-Butyldimethylsilyl)oxy-2-methylpropan-1-amine (1.5 g) and TEA (1.8 mL) dissolved in dichloromethane (12 mL) were added at 0° C. and the mixture was stirred at 25° C. for four hours. 1 M hydrochloric acid was added to the reaction solution and the mixture was extracted with ethyl acetate twice. The organic layers were washed with saturated saline and dried over anhydrous magnesium sulfate. The drying agent was removed by filtration, the filtrate was concentrated under reduced pressure, and the resulting residue was purified by column chromatography (hexane/ethyl acetate) to give the target compound (2.00 g).

Example 3-3-02

The compound of Example 3-3-02 was synthesized from a corresponding aminoalcohol by the similar method as in Example 3-3-01.

| Example No. | Compound No. | |
|---|---|---|
| 3-3-01 | SFC-001 | 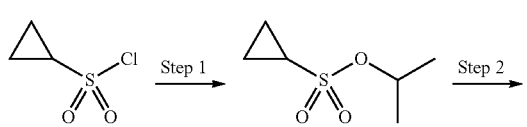 |
| 3-3-02 | SFC-002 | |

Example 3-4-01 (Compound SAA-001)

Synthesis of 1-[2,3-bis(phenylmethoxy)propyl]cyclopropane-1-sulfonyl chloride

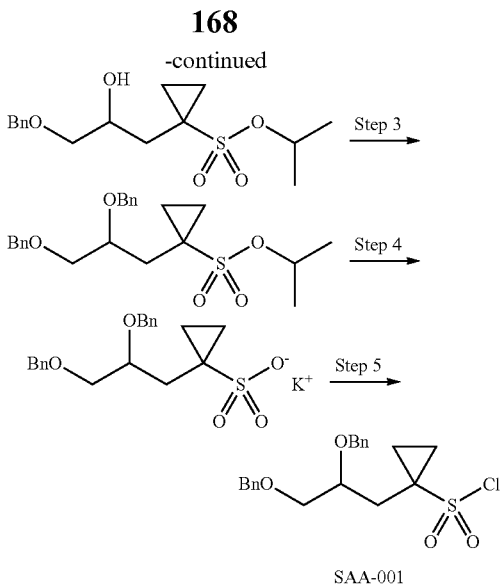

Step 1

Synthesis of propan-2-yl cyclopropanesulfonate

Cyclopentanesulfonyl chloride (5.10 g) was dissolved in 2-propanol (12 mL), and the solution was cooled to 0° C., pyridine (2.9 mL) was added. Then the mixture was stirred at 25° C. for 92 hours. The reaction solution was concentrated under reduced pressure and water was added to the resulting residue. The mixture was extracted with dichloromethane and the organic layer was dried over anhydrous magnesium sulfate. The drying agent was removed by filtration and the filtrate was concentrated under reduced pressure to give the target compound (4.80 g).

Step 2

Synthesis of propan-2-yl 1-(2-hydroxy-3-phenylmethoxypropyl)cyclopropane-1-sulfonate Propan-2-yl cyclopropanesulfonate (3.20 g) was dissolved in tetrahydrofuran (40 mL), the atmosphere in the reaction system was replaced by nitrogen, hexamethylphosphoric triamide (4.4 mL) and n-BuLi (2.7 M solution in hexane, 15 mL) were added dropwise at −78° C., and the mixture was stirred for 30 minutes. Benzyl glycidyl ether (2.5 mL) dissolved in tetrahydrofuran (28 mL) was added dropwise and the mixture was stirred at −40° C. for one hour. The reaction solution was warmed to 25° C., water (50 mL) was added, the mixture was extracted with ethyl acetate (30 mL) twice, and the organic layers were dried over anhydrous sodium sulfate. The drying agent was removed by filtration, the filtrate was concentrated under reduced pressure, and the resulting residue was purified by column chromatography (hexane/ethyl acetate) to give the target compound (3.80 g).

Step 3

Synthesis of propan-2-yl 1-[2,3-bis(phenylmethoxy)propyl]cyclopropane-1-sulfonate Propan-2-yl 1-(2-hydroxy-3-phenylmethoxypropyl)cyclopropane-1-sulfonate (3.60 g) was dissolved in N,N-dimethylformamide (36 mL), and sodium hydride (content: 60%, 520 mg) was added at 0° C. Then the mixture was stirred for 30 minutes. Benzyl bromide (1.6 mL) was added dropwise to the reaction solution and the mixture was stirred at 0° C. for one hour. Water (50 mL) was added to the reaction solution, the mixture was extracted with ethyl acetate (50 mL) twice, and the organic layers were dried over anhydrous sodium sulfate. The drying agent was removed by filtration, the filtrate was concentrated under reduced pressure, and the resulting residue was purified by column chromatography (hexane/ethyl acetate) to give the target compound (3.90 g).

Step 4

Synthesis of potassium 1-[2,3-bis(phenylmethoxy)propyl]cyclopropane-1-sulfonate

Propan-2-yl 1-[2,3-bis(phenylmethoxy)propyl]cyclopropane-1-sulfonate (200 mg) was dissolved in ethanol (2.4 mL), and potassium thiocyanate (49 mg) was added. Then the mixture was stirred at 85° C. for six hours. The reaction solution was cooled to 25° C. and concentrated under reduced pressure. The resulting residue was azeotropically distilled with toluene twice to give the target compound (198 mg).

Step 5

Synthesis of 1-[2,3-bis(phenylmethoxy)propyl]cyclopropane-1-sulfonyl chloride

Potassium 1-[2,3-bis(phenylmethoxy)propyl]cyclopropane-1-sulfonate (198 mg) was dissolved in N,N-dimethylformamide (0.5 mL), and thionyl chloride (3.5 mL) was added. Then the mixture was stirred at 80° C. for one hour. The reaction solution was cooled to 25° C., the precipitated solid was filtered off, and the filtrate was washed with ethyl acetate. The filtrate was concentrated under reduced pressure and the resulting residue was purified by column chromatography (hexane/ethyl acetate) to give the target compound (180 mg).

| Example No. | Compound No. | |
|---|---|---|
| 3-4-01 | SAA-001 | 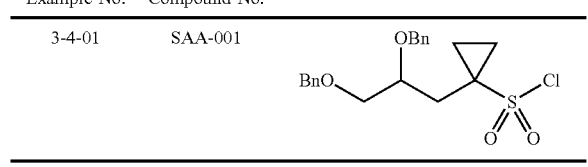 |

Examples 4 and 5

Example 4-1-001

Synthesis of N-{2-{5-amino-1-[6-(2,6-difluorophenoxy)-4-methylpyridin-3-yl]pyrazole-4-carbonyl}-5-methyl-1H-indol-6-yl}methanesulfonamide

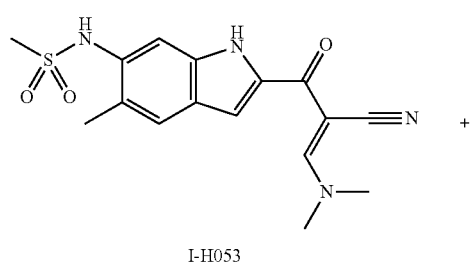

I-H053

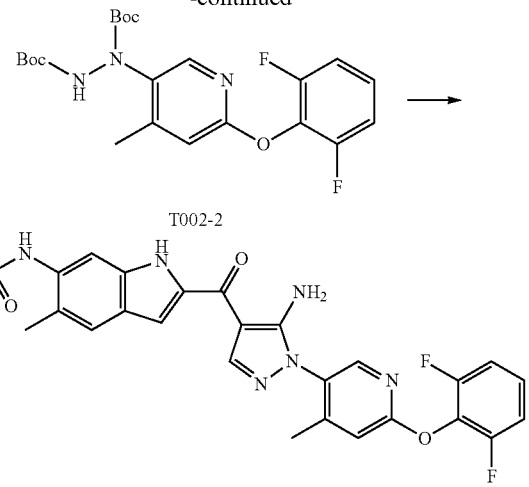

T002-2

Hydrazine T002-2 (260 mg) was dissolved in 1-methyl-2-pyrrolidone (3.0 mL), and methanesulfonic acid (89 μL) was added in a nitrogen atmosphere. Then the mixture was stirred at 100° C. for three hours. The mixture was cooled to 25° C., and enamine I-H053 (200 mg) and N-methylmorpholine (151 μL) were added at 25° C. The reaction system was degassed and the atmosphere therein was replaced by nitrogen. The reaction solution was stirred at 100° C. for 1.5 hours. Water (2.0 mL) was added to the reaction solution at 60° C. and the mixture was cooled to 25° C. The precipitated solid was collected by filtration and washed with ethanol-water and then with 2-propanol to give the target compound (301 mg).

Example 4-1-002

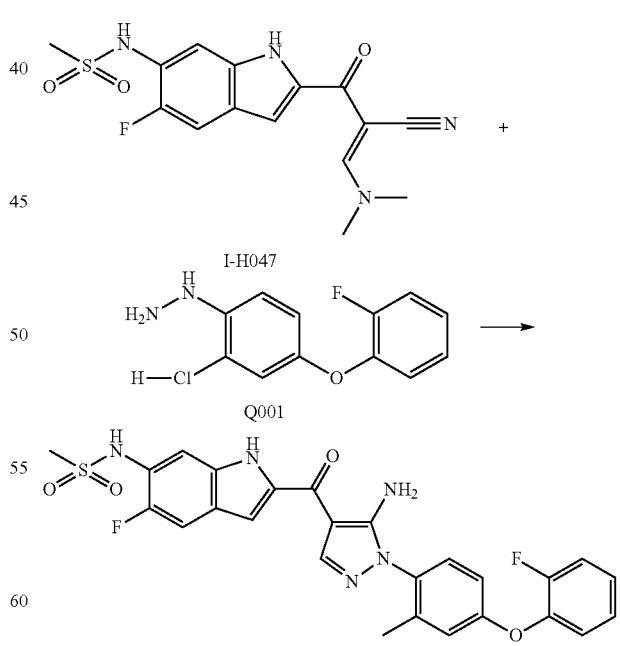

Enamine I-H047 (250 mg) and hydrazine Q001 (700 mg) were added to ethanol (25 mL) and the mixture was stirred at 75° C. for 16 hours. The reaction solution was concentrated under reduced pressure and the resulting residue was purified by Prep HPLC to give the target compound (17 mg).

Examples 4-1-003 to 4-1-017, Example 5-1-070, and the Like

The compounds of Examples 4-1-003 to 4-1-017, Example 5-1-070, and the like shown below were synthesized from the following corresponding enamines and hydrazines by the similar method as in Example 4-1-001 or 4-1-002.

(Corresponding Enamines and Hydrazines)

| Example No. | | Enamine | | Hydrazine |
|---|---|---|---|---|
| 4-1-001 | I-H053 | | T002-2 | |
| 4-1-002 | I-H047 | | Q001 | |
| 4-1-003 | I-H047 | | S015 | |
| 4-1-004 | I-H048 | | Q001 | |
| 4-1-005 | I-H048 | | Q002 | |
| 4-1-006 | I-H048 | | S038 | |

-continued
| Example No. | | Enamine | | Hydrazine |
|---|---|---|---|---|
| 4-1-007 | I-H048 | 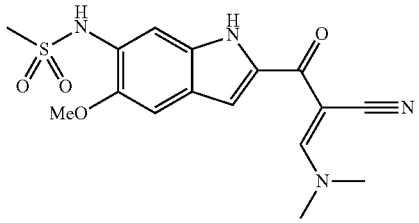 [SMILES: COc1cc2cc(C(=O)/C(C#N)=C/N(C)C)[nH]c2cc1NS(C)(=O)=O] | S047 | 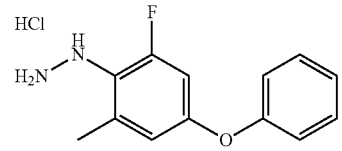 [SMILES: Cl ; Cc1cc(Oc2ccccc2)cc(F)c1NN] |
| 4-1-008 | I-H048 | 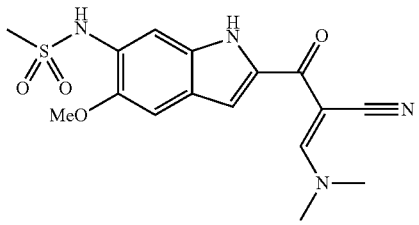 [SMILES: COc1cc2cc(C(=O)/C(C#N)=C/N(C)C)[nH]c2cc1NS(C)(=O)=O] | T001 | 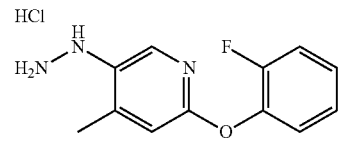 [SMILES: Cl ; Cc1cc(Oc2ccccc2F)ncc1NN] |
| 4-1-009 | I-H048 | 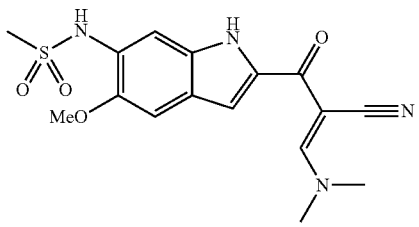 [SMILES: COc1cc2cc(C(=O)/C(C#N)=C/N(C)C)[nH]c2cc1NS(C)(=O)=O] | T002 | 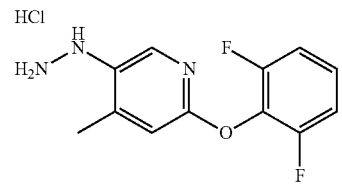 |
| 4-1-010 | I-H048 | 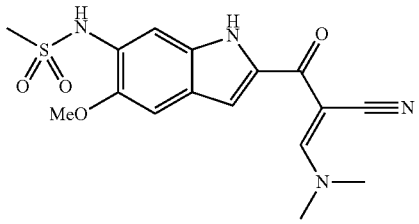 [SMILES: COc1cc2cc(C(=O)/C(C#N)=C/N(C)C)[nH]c2cc1NS(C)(=O)=O] | T007 | 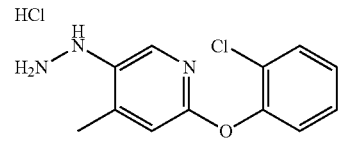 |
| 4-1-011 | I-H048 | 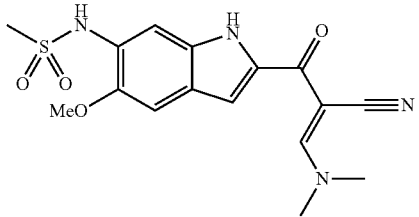 [SMILES: COc1cc2cc(C(=O)/C(C#N)=C/N(C)C)[nH]c2cc1NS(C)(=O)=O] | T011 | 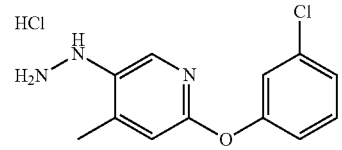 |
| 4-1-012 | I-H056 | 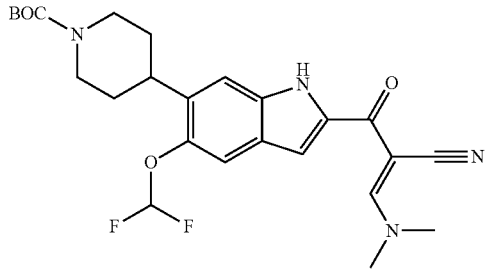 [SMILES: CN(C)/C=C(\C#N)C(=O)c1cc2cc(OC(F)F)c(C3CCN(C(=O)OC(C)(C)C)CC3)cc2[nH]1] | T002 | 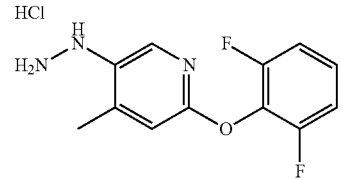 |

| Example No. | | Enamine | Hydrazine | |
|---|---|---|---|---|
| 4-1-013 | I-H062 | [structure: 6-methoxy-5-(methylsulfonamido)-1H-indol-2-yl enamine with cyano and dimethylamino] | Q001 | HCl, H₂N-NH-(2-methyl-4-(2-fluorophenoxy)phenyl) |
| 4-1-014 | I-H062 | [structure: 6-methoxy-5-(methylsulfonamido)-1H-indol-2-yl enamine with cyano and dimethylamino] | T001 | HCl, H₂N-NH-(4-methyl-5-(2-fluorophenoxy)pyridin-... no, 5-hydrazinyl-4-methyl-2-(2-fluorophenoxy)pyridine) |
| 4-1-015 | I-H065 | [structure: 6-morpholino-5-(2,2-difluoroethoxy)-1H-indol-2-yl enamine with cyano and dimethylamino] | Q001 | HCl, H₂N-NH-(2-methyl-4-(2-fluorophenoxy)phenyl) |
| 4-1-016 | I-H065 | [structure: 6-morpholino-5-(2,2-difluoroethoxy)-1H-indol-2-yl enamine with cyano and dimethylamino] | T002 | HCl, 5-hydrazinyl-4-methyl-2-(2,6-difluorophenoxy)pyridine |
| 4-1-017 | I-H067 | [structure: 6-(cyclopropanesulfonamido)-5-methyl-1H-indol-2-yl enamine with cyano and dimethylamino] | T002 | HCl, 5-hydrazinyl-4-methyl-2-(2,6-difluorophenoxy)pyridine |
| 5-1-070 | I-A011 | [structure: 6-bromo-5-(2,2-difluoroethoxy)-1H-indol-2-yl enamine with cyano and dimethylamino] | Q001 | HCl, H₂N-NH-(2-methyl-4-(2-fluorophenoxy)phenyl) |

-continued
| Example No. | | Enamine | Hydrazine | |
|---|---|---|---|---|
| 5-1-169 | I-H065 | 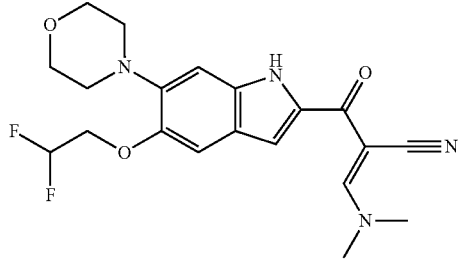 [SMILES: CN(C)/C=C(\C#N)C(=O)c1cc2cc(OCC(F)F)c(N3CCOCC3)cc2[nH]1] | Q019 | HCl 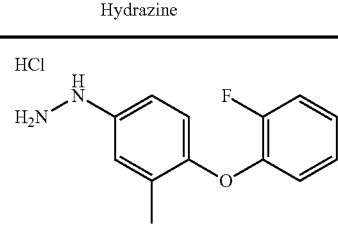 |
| 5-1-198 | I-H053 | 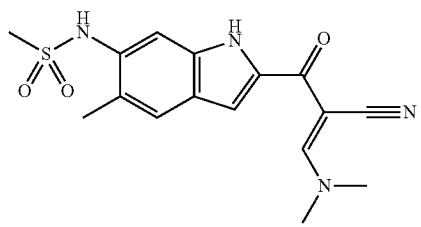 [SMILES: Cc1cc2cc(C(=O)/C(C#N)=C/N(C)C)[nH]c2cc1NS(C)(=O)=O] | Q044 | HCl 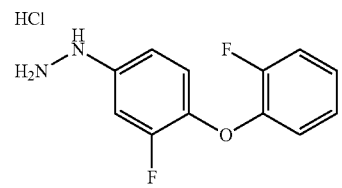 [SMILES: Cl ; NNc1ccc(Oc2ccccc2F)c(F)c1] |
| 5-1-199 | I-H053 | 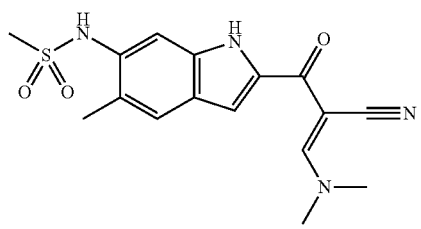 [SMILES: Cc1cc2cc(C(=O)/C(C#N)=C/N(C)C)[nH]c2cc1NS(C)(=O)=O] | Q045 | HCl 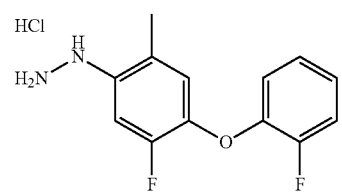 [SMILES: Cl ; Cc1cc(Oc2ccccc2F)c(F)cc1NN] |
| 5-1-200 | I-H053 | 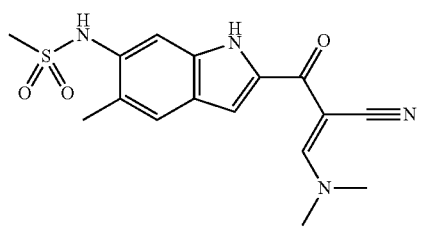 [SMILES: Cc1cc2cc(C(=O)/C(C#N)=C/N(C)C)[nH]c2cc1NS(C)(=O)=O] | S062 | HCl 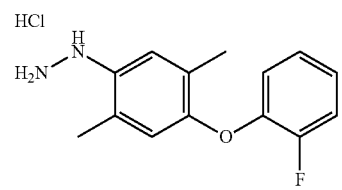 [SMILES: Cl ; Cc1cc(Oc2ccccc2F)c(C)cc1NN] |
| 5-1-260 | I-A012 | 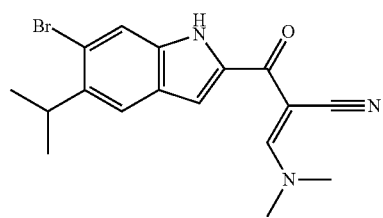 [SMILES: CC(C)c1cc2cc(C(=O)/C(C#N)=C/N(C)C)[nH]c2cc1Br] | Q001 | HCl 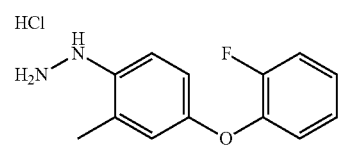 |
| 5-1-307 | I-H053 | 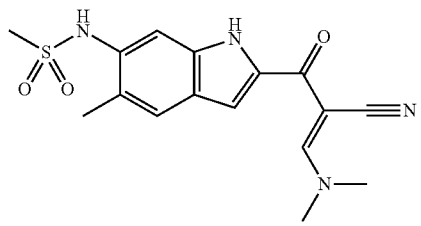 | Q019 | HCl 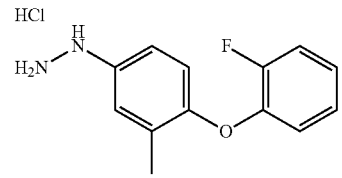 [SMILES: Cl ; Cc1cc(NN)ccc1Oc1ccccc1F] |

-continued
| Example No. | | Enamine | | Hydrazine |
|---|---|---|---|---|
| 5-1-068 | I-H063 | 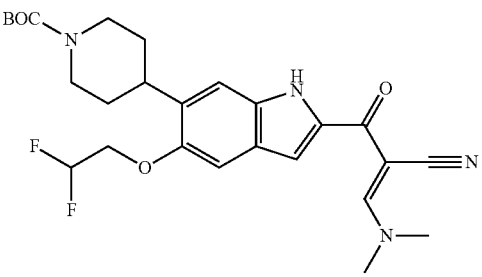 [SMILES: CN(C)/C=C(\C#N)C(=O)c1cc2cc(OCC(F)F)c(C3CCN(C(=O)OC(C)(C)C)CC3)cc2[nH]1] | Q001 | HCl 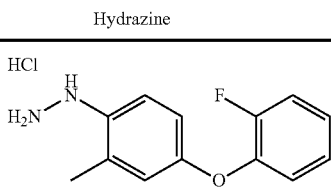 |
| 5-1-069 | I-H063 | 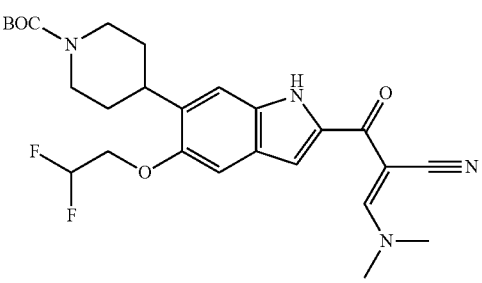 [SMILES: CN(C)/C=C(\C#N)C(=O)c1cc2cc(OCC(F)F)c(C3CCN(C(=O)OC(C)(C)C)CC3)cc2[nH]1] | T002 | HCl 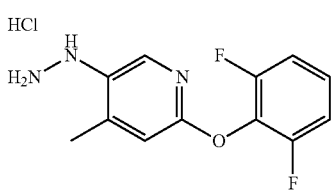 |
| 5-1-131 | I-H070 | 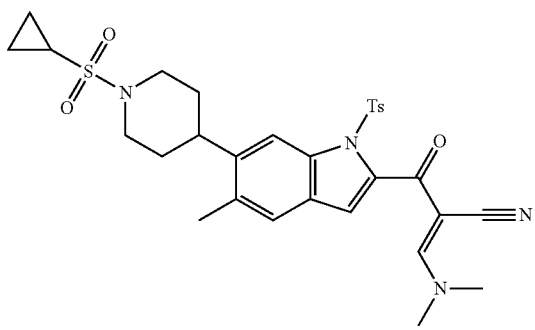 [SMILES: Cc1ccc(S(=O)(=O)n2c(C(=O)/C(C#N)=C/N(C)C)cc3cc(C)c(C4CCN(S(=O)(=O)C5CC5)CC4)cc32)cc1] | Q001 | HCl 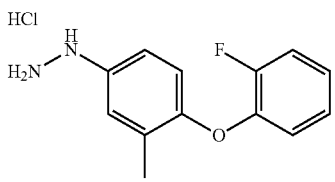 [SMILES: Cl ; Cc1cc(NN)ccc1Oc1ccccc1F] |
| 5-1-217 | I-H073 | 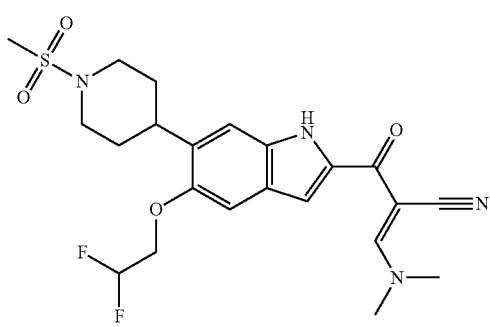 [SMILES: CN(C)/C=C(\C#N)C(=O)c1cc2cc(OCC(F)F)c(C3CCN(S(C)(=O)=O)CC3)cc2[nH]1] | Q019 | HCl 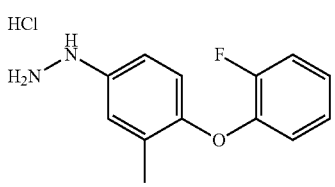 [SMILES: Cl ; Cc1cc(NN)ccc1Oc1ccccc1F] |
| 5-1-134 | I-H074 | 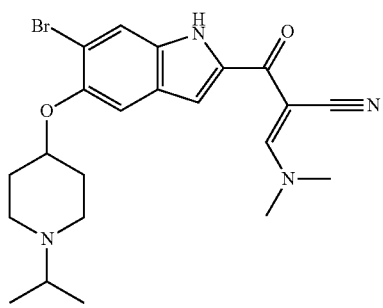 | T002 | HCl 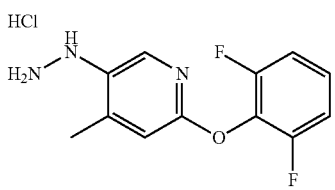 |

-continued
| Example No. | | Enamine | | Hydrazine |
|---|---|---|---|---|
| 5-1-146 | I-H074 | 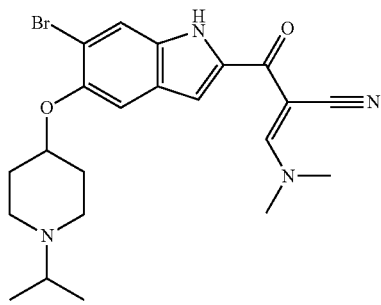 | Q001 HCl | 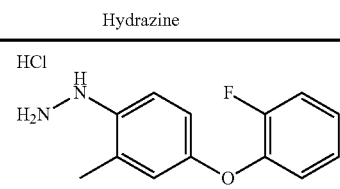 |
| 5-1-148 | I-H074 | 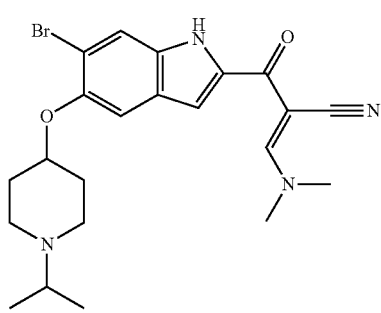 | Q019 HCl | 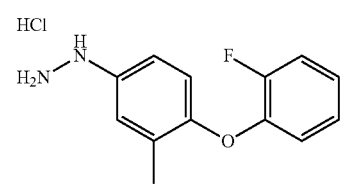 [SMILES: Cl ; Cc1cc(NN)ccc1Oc1ccccc1F] |
| 5-1-153 | I-H074 | 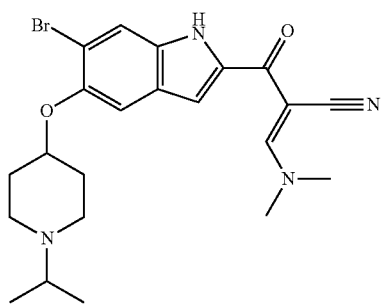 | T001 HCl | 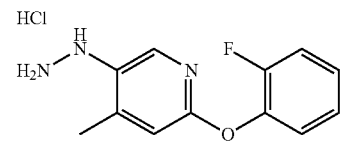 |
| 5-1-154 | I-H074 | 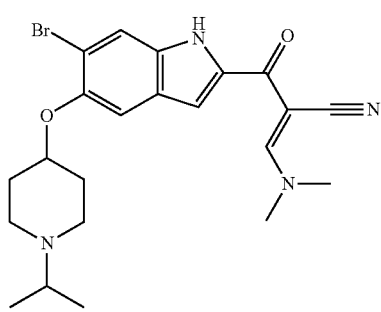 | S038 HCl | 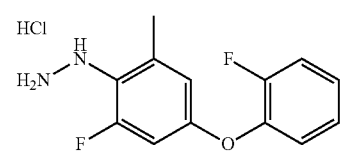 [SMILES: Cl ; Cc1cc(Oc2ccccc2F)cc(F)c1NN] |
| 5-1-195 | I-H080 | 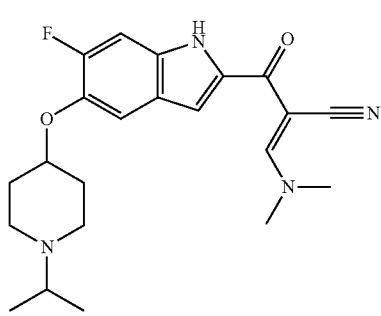 [SMILES: CC(C)N1CCC(Oc2cc3cc(C(=O)/C(C#N)=C/N(C)C)[nH]c3cc2F)CC1] | Q019 HCl | 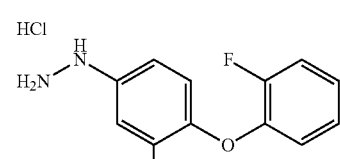 |

| Example No. | | Enamine | | Hydrazine | |
|---|---|---|---|---|---|
| 5-1-196 | I-H081 | 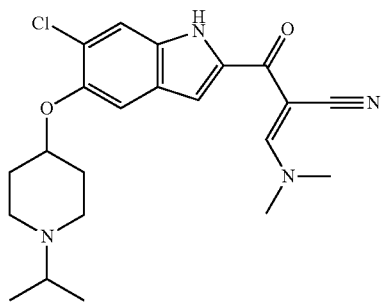 | Q019 | HCl | 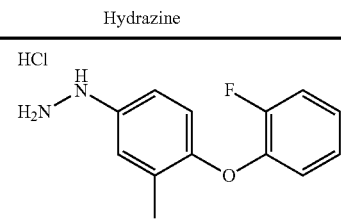 |
| 5-1-197 | I-H081 | 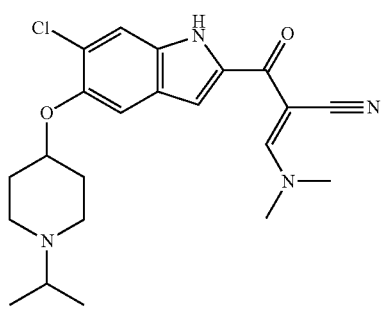 [SMILES: CC(C)N1CCC(Oc2cc3cc(C(=O)/C(C#N)=C/N(C)C)[nH]c3cc2Cl)CC1] | Q001 | HCl | 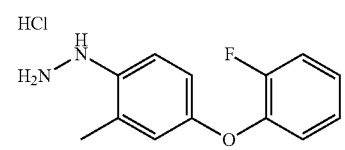 |
| 5-1-203 | I-H080 | 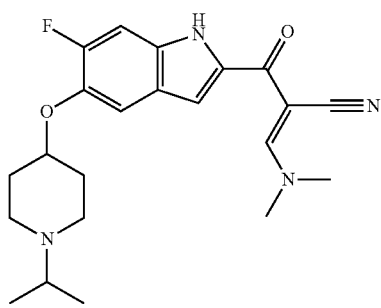 [SMILES: CC(C)N1CCC(Oc2cc3cc(C(=O)/C(C#N)=C/N(C)C)[nH]c3cc2F)CC1] | Q001 | HCl | 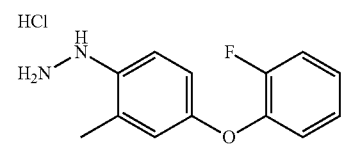 [SMILES: Cl ; Cc1cc(Oc2ccccc2F)ccc1NN] |
| 5-1-204 | I-H080 | 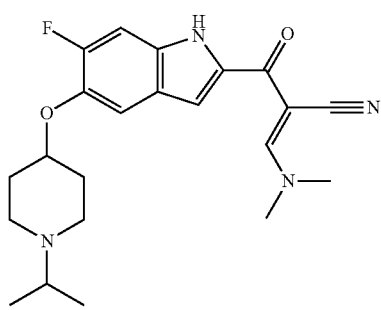 [SMILES: CC(C)N1CCC(Oc2cc3cc(C(=O)/C(C#N)=C/N(C)C)[nH]c3cc2F)CC1] | T002 | HCl | 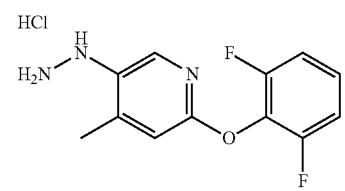 |
| 5-1-205 | I-H081 | 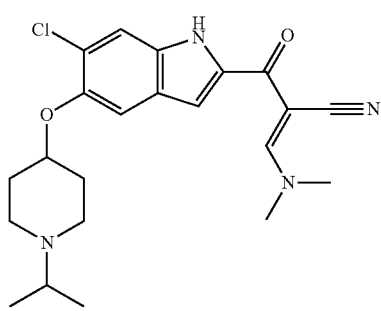 | T002 | HCl | 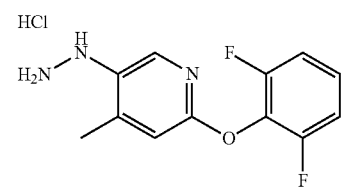 [SMILES: Cl ; Cc1cc(Oc2c(F)cccc2F)ncc1NN] |

-continued
| Example No. | | Enamine | | Hydrazine |
|---|---|---|---|---|
| 5-1-206 | I-H053 | 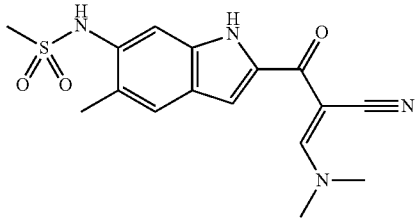 [SMILES: Cc1cc2cc(C(=O)/C(C#N)=C/N(C)C)[nH]c2cc1NS(C)(=O)=O] | S063 | HCl 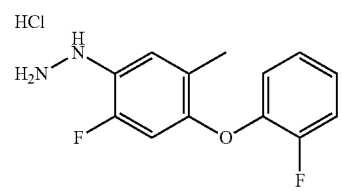 |
| 5-1-207 | I-H053 | 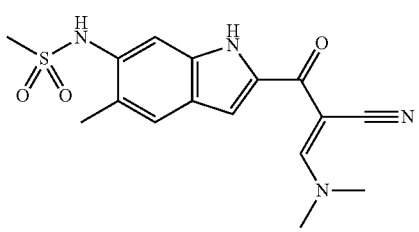 | S064 | HCl 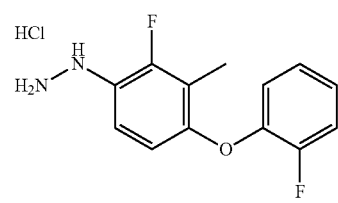 [SMILES: Cl ; Cc1c(Oc2ccccc2F)ccc(NN)c1F] |
| 5-1-208 | I-H080 | 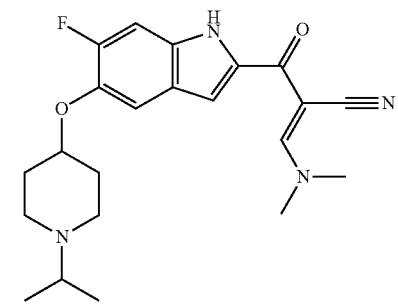 [SMILES: CC(C)N1CCC(Oc2cc3cc(C(=O)/C(C#N)=C/N(C)C)[nH]c3cc2F)CC1] | Q043 | HCl 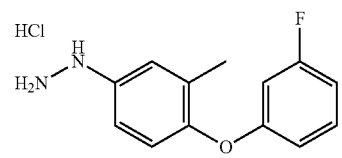 [SMILES: Cl ; Cc1cc(NN)ccc1Oc1cccc(F)c1] |
| 5-1-209 | I-H081 | 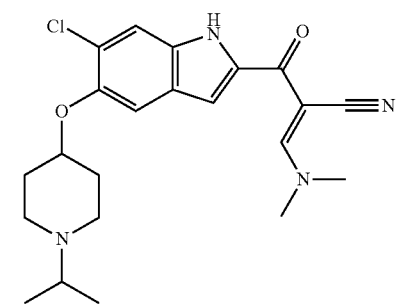 [SMILES: CC(C)N1CCC(Oc2cc3cc(C(=O)/C(C#N)=C/N(C)C)[nH]c3cc2Cl)CC1] | Q043 | HCl 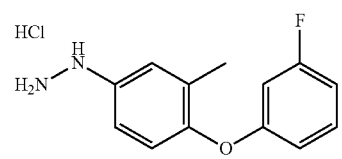 [SMILES: Cl ; Cc1cc(NN)ccc1Oc1cccc(F)c1] |
| 5-1-210 | I-H074 | 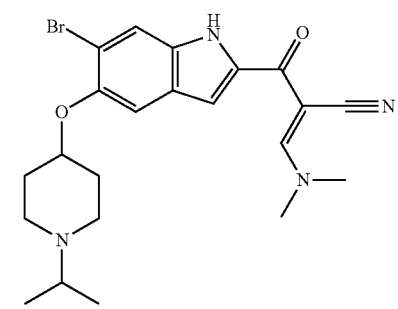 | Q043 | HCl 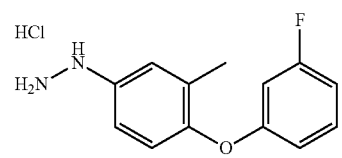 [SMILES: Cl ; Cc1cc(NN)ccc1Oc1cccc(F)c1] |

-continued
| Example No. | | Enamine | | Hydrazine |
|---|---|---|---|---|
| 5-1-211 | I-H053 | 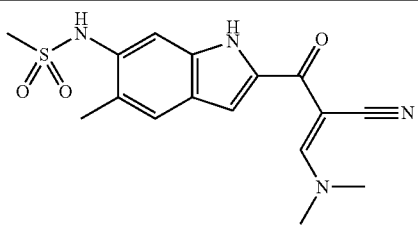 | Q043 | HCl 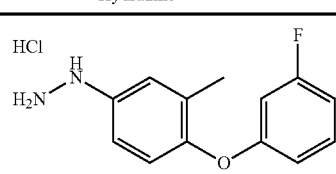 |
| 5-1-212 | I-H074 | 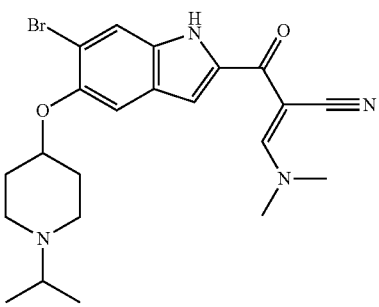 [SMILES: CC(C)N1CCC(Oc2cc3cc(C(=O)/C(C#N)=C/N(C)C)[nH]c3cc2Br)CC1] | S063 | HCl 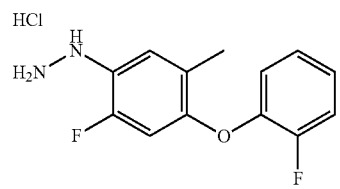 [SMILES: Cl ; Cc1cc(NN)c(F)cc1Oc1ccccc1F] |
| 5-1-213 | I-H053 | 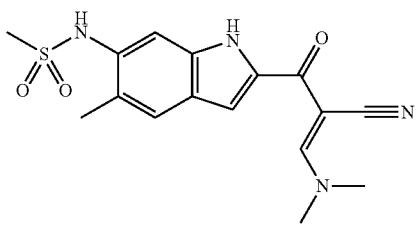 | S065 | HCl 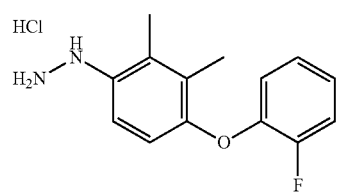 [SMILES: Cl ; Cc1c(NN)ccc(Oc2ccccc2F)c1C] |
| 5-1-214 | I-H053 | 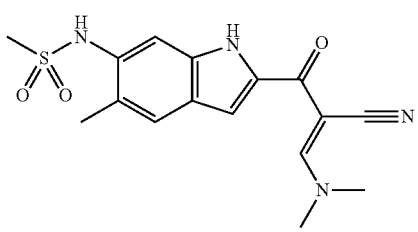 [SMILES: Cc1cc2cc(C(=O)/C(C#N)=C/N(C)C)[nH]c2cc1NS(C)(=O)=O] | S066 | HCl 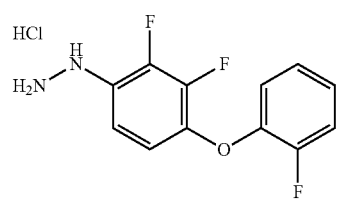 [SMILES: Cl ; NNc1ccc(Oc2ccccc2F)c(F)c1F] |
(Synthesized Compounds)
| Example No. | Compound | m/z (M + H) | Retention Time (Minute) | LCMS Measurement Condition |
|---|---|---|---|---|
| 4-1-001 | 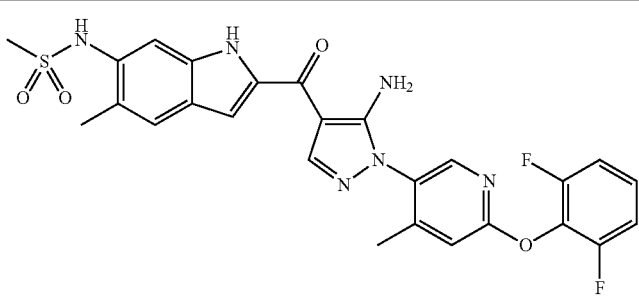 [SMILES: Cc1cc2cc(C(=O)c3cnn(-c4cnc(Oc5c(F)cccc5F)cc4C)c3N)[nH]c2cc1NS(C)(=O)=O] | 553 | 2.32 | B1 |

-continued
| Example No. | Compound | m/z (M + H) | Retention Time (Minute) | LCMS Measurement Condition |
|---|---|---|---|---|
| 4-1-002 | 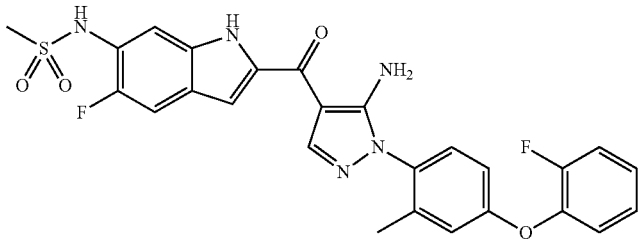 [SMILES: Cc1cc(Oc2ccccc2F)ccc1-n1ncc(C(=O)c2cc3cc(F)c(NS(C)(=O)=O)cc3[nH]2)c1N] | 538 | 0.78 | A1 |
| 4-1-003 | 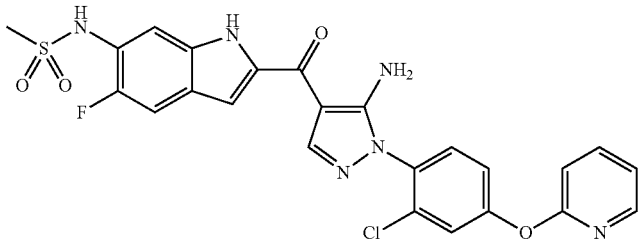 [SMILES: CS(=O)(=O)Nc1cc2[nH]c(C(=O)c3cnn(-c4ccc(Oc5ccccn5)cc4Cl)c3N)cc2cc1F] | 541, 543 | 0.68 | A1 |
| 4-1-004 | 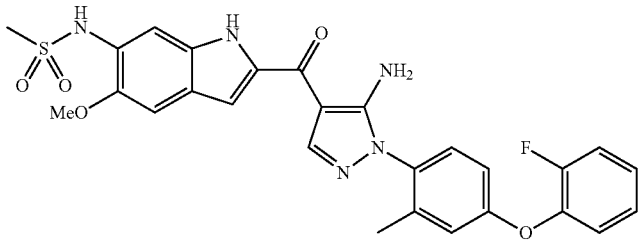 | 550 | 2.42 | B1 |
| 4-1-005 | 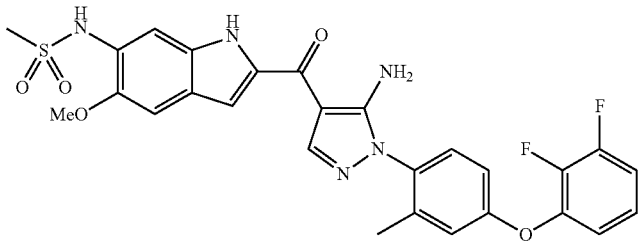 [SMILES: COc1cc2cc(C(=O)c3cnn(-c4ccc(Oc5cccc(F)c5F)cc4C)c3N)[nH]c2cc1NS(C)(=O)=O] | 568 | 2.48 | B1 |
| 4-1-006 | 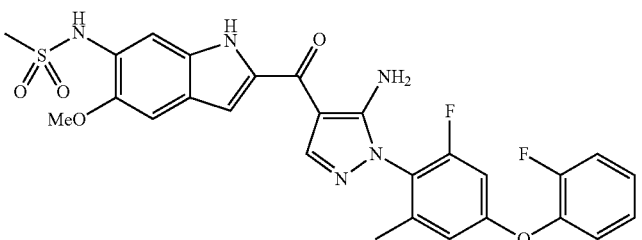 | 568 | 2.44 | B1 |
| 4-1-007 | 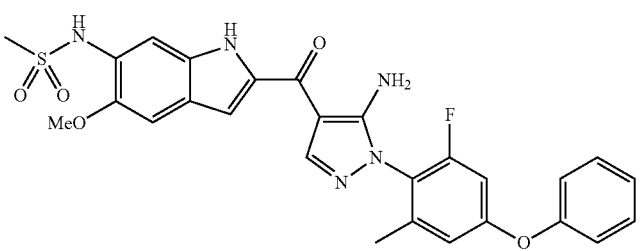 [SMILES: COc1cc2cc(C(=O)c3cnn(-c4c(C)cc(Oc5ccccc5)cc4F)c3N)[nH]c2cc1NS(C)(=O)=O] | 550 | 2.46 | B1 |

-continued

| Example No. | Compound | m/z (M + H) | Retention Time (Minute) | LCMS Measurement Condition |
|---|---|---|---|---|
| 4-1-008 | | 551 | 2.24 | B1 |
| 4-1-009 | | 569 | 2.31 | B1 |
| 4-1-010 | | 567, 569 | 2.33 | B1 |
| 4-1-011 | | 567, 569 | 2.40 | B1 |
| 4-1-012 | | 695 | 1.12 | J2 |

| Example No. | Compound | m/z (M+H) | Retention Time (Minute) | LCMS Measurement Condition |
|---|---|---|---|---|
| 4-1-013 | | 550 | 0.97 | J4 |
| 4-1-014 | | 551 | 0.92 | J1 |
| 4-1-015 | | 592 | 1.04 | J2 |
| 4-1-016 | | 611 | 1.02 | J4 |
| 4-1-017 | | 579 | 0.79 | A1 |

| Example No. | Compound | m/z (M + H) | Retention Time (Minute) | LCMS Measurement Condition |
|---|---|---|---|---|
| 5-1-070 | | 585 | 1.39 | TFA Rev.5 |
| 5-1-169 | | 592 | 1.1 | AA Rev.11 |
| 5-1-198 | | 538 | 1.26 | TFA Rev.5 |
| 5-1-199 | | 552 | 1 | AA Rev.11 |
| 5-1-200 | | 548 | 1.03 | AA Rev.11 |

| Example No. | Compound | m/z (M + H) | Retention Time (Minute) | LCMS Measurement Condition |
|---|---|---|---|---|
| 5-1-260 | | 547 | 1.19 | AA Rev.11 |
| 5-1-307 | | 534 | 1.23 | TFA Rev.7 |
| 5-1-068 | | 690 | 1.13 | TFA Rev.7 |
| 5-1-069 | | 709 | 1.11 | AA Rev.7 |

-continued
| Example No. | Compound | m/z (M + H) | Retention Time (Minute) | LCMS Measurement Condition |
|---|---|---|---|---|
| 5-1-131 | 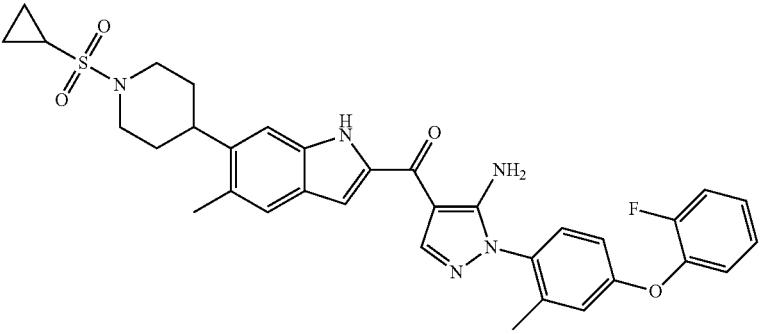 [SMILES: Cc1cc2cc(C(=O)c3cnn(-c4ccc(Oc5ccccc5F)cc4C)c3N)[nH]c2cc1C1CCN(S(=O)(=O)C2CC2)CC1] | 628 | 1.44 | TFA Rev.5 |
| 5-1-217 | 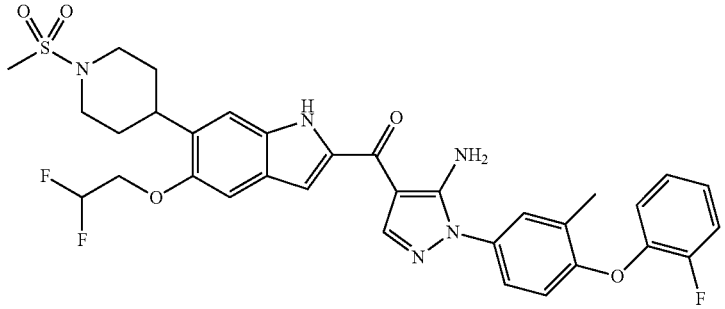 [SMILES: Cc1cc(-n2ncc(C(=O)c3cc4cc(OCC(F)F)c(C5CCN(S(C)(=O)=O)CC5)cc4[nH]3)c2N)ccc1Oc1ccccc1F] | 668 | 1.36 | TFA Rev.6 |
| 5-1-134 | 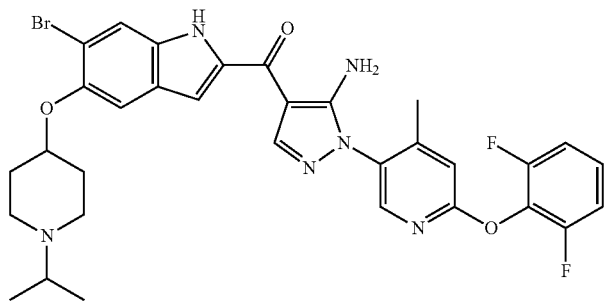 [SMILES: Cc1cc(Oc2c(F)cccc2F)ncc1-n1ncc(C(=O)c2cc3cc(OC4CCN(C(C)C)CC4)c(Br)cc3[nH]2)c1N] | 665 | 0.99 | AA Rev.11 |
| 5-1-146 | 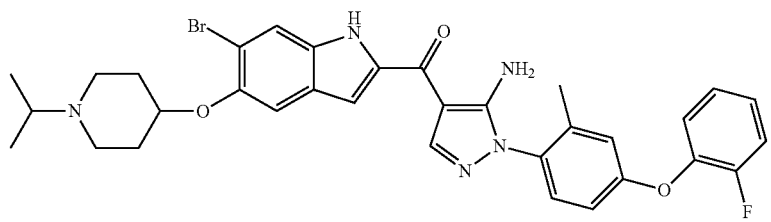 [SMILES: Cc1cc(Oc2ccccc2F)ccc1-n1ncc(C(=O)c2cc3cc(OC4CCN(C(C)C)CC4)c(Br)cc3[nH]2)c1N] | 646 | 1.01 | AA Rev.11 |
| 5-1-148 | 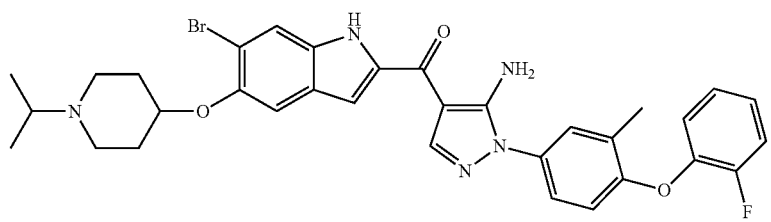 [SMILES: Cc1cc(-n2ncc(C(=O)c3cc4cc(OC5CCN(C(C)C)CC5)c(Br)cc4[nH]3)c2N)ccc1Oc1ccccc1F] | 646 | 1.07 | TFA Rev.6 |

-continued
| Example No. | Compound | m/z (M + H) | Retention Time (Minute) | LCMS Measurement Condition |
|---|---|---|---|---|
| 5-1-153 | 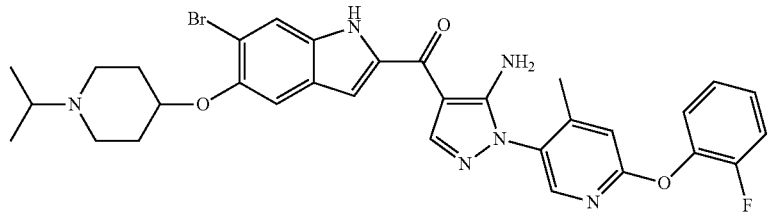 [SMILES: Cc1cc(Oc2ccccc2F)ncc1-n1ncc(C(=O)c2cc3cc(OC4CCN(C(C)C)CC4)c(Br)cc3[nH]2)c1N] | 647 | 0.97 | AA Rev.11 |
| 5-1-154 | 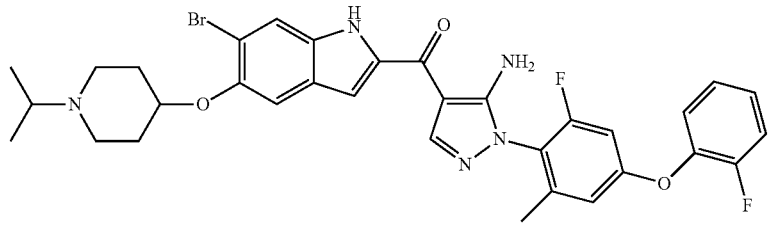 [SMILES: Cc1cc(Oc2ccccc2F)cc(F)c1-n1ncc(C(=O)c2cc3cc(OC4CCN(C(C)C)CC4)c(Br)cc3[nH]2)c1N] | 664 | 1.01 | AA Rev.11 |
| 5-1-195 | 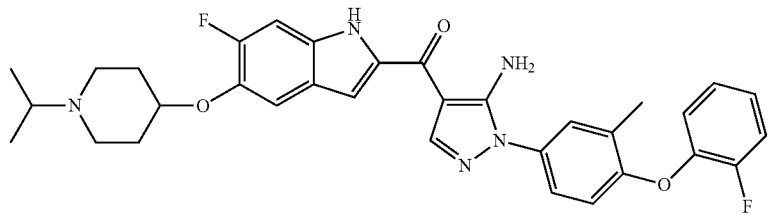 [SMILES: Cc1cc(-n2ncc(C(=O)c3cc4cc(OC5CCN(C(C)C)CC5)c(F)cc4[nH]3)c2N)ccc1Oc1ccccc1F] | 586 | 1.03 | AA Rev.11 |
| 5-1-196 | 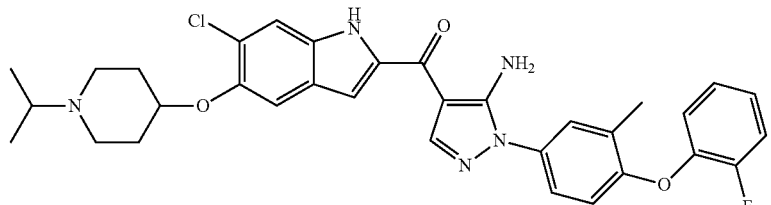 | 602 | 1.18 | TFA Rev.5 |
| 5-1-197 | 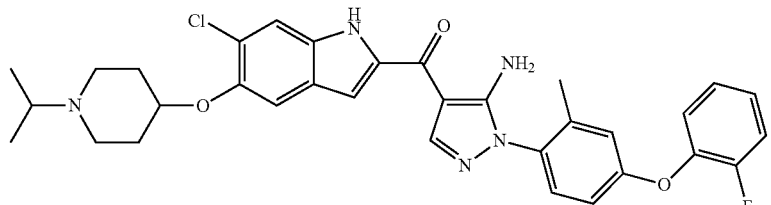 | 602 | 1.01 | AA Rev.11 |
| 5-1-203 | 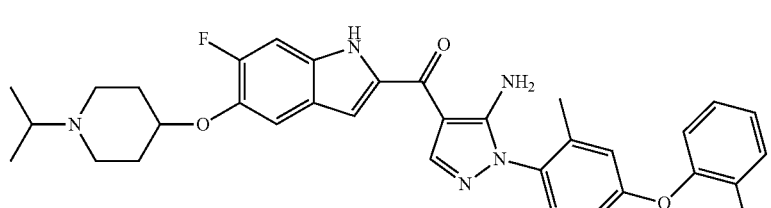 | 586 | 1.11 | TFA Rev.5 |

-continued

| Example No. | Compound | m/z (M + H) | Retention Time (Minute) | LCMS Measurement Condition |
|---|---|---|---|---|
| 5-1-204 | | 605 | 0.97 | AA Rev.11 |
| 5-1-205 | | 621 | 1 | AA Rev.11 |
| 5-1-206 | | 552 | 1.29 | TFA Rev.5 |
| 5-1-207 | | 552 | 1.03 | AA Rev.11 |
| 5-1-208 | | 586 | 1.05 | AA Rev.11 |
| 5-1-209 | | 602 | 1.19 | TFA Rev.5 |

-continued

| Example No. | Compound | m/z (M + H) | Retention Time (Minute) | LCMS Measurement Condition |
|---|---|---|---|---|
| 5-1-210 | | 646 | 1.19 | TFA Rev.5 |
| 5-1-211 | | 534 | 1.06 | AA Rev.11 |
| 5-1-212 | | 664 | 1.17 | TFA Rev.5 |
| 5-1-213 | | 548 | 1.29 | TFA Rev.5 |
| 5-1-214 | | 556 | 1.25 | TFA Rev.5 |

Example 4-2-001

Synthesis of [5-amino-1-[4-(2-fluorophenoxy)-2-methylphenyl]pyrazol-4-yl]-[6-fluoro-5-(1-propan-2-ylpiperidin-4-yl)-1H-indol-2-yl]methanone

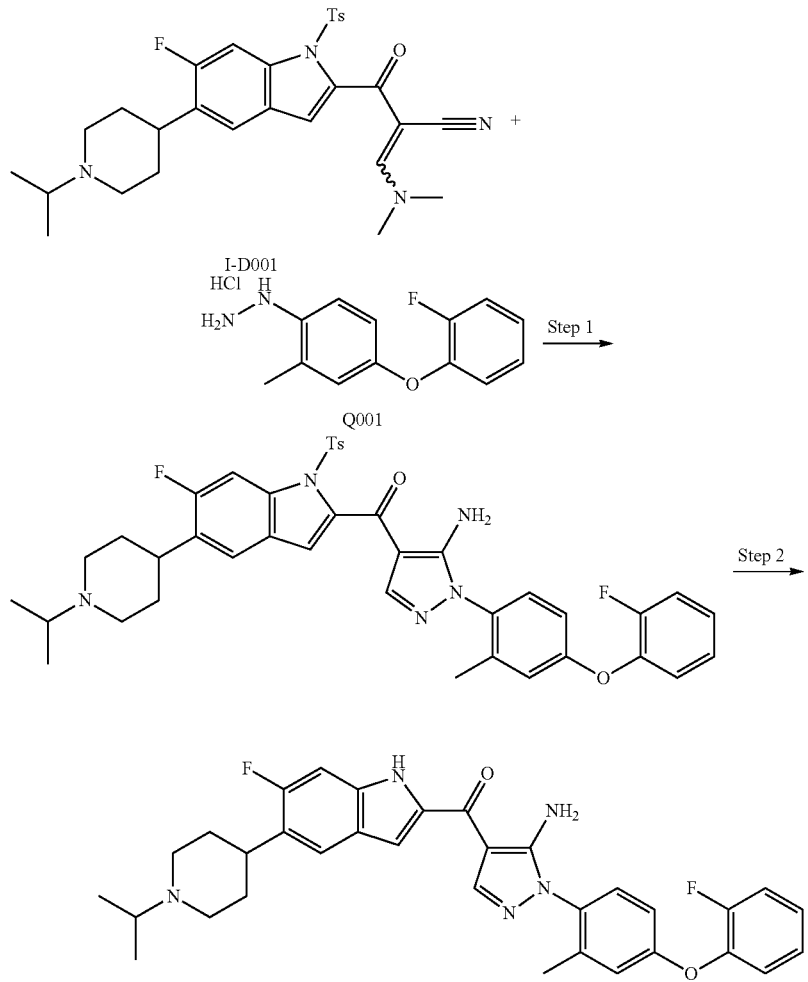

Step 1

Synthesis of (5-amino-1-(4-(2-fluorophenoxy)-2-methylphenyl)-1H-pyrazol-4-yl)(6-fluoro-5-(1-isopropylpiperidin-4-yl)-1-tosyl-1H-indol-2-yl)methanone Enamine I-D001 (200 mg) and hydrazine Q001 (400 mg) were added to ethanol (20 mL) and the mixture was stirred at 80° C. for 18 hours. The reaction solution was concentrated under reduced pressure and the residue was purified by silica gel column chromatography (dichloromethane/methanol=20/1) to give a crude product of the target compound (200 mg).

Step 2

Synthesis of [5-amino-1-[4-(2-fluorophenoxy)-2-methylphenyl]pyrazol-4-yl]-[6-fluoro-5-(1-propan-2-ylpiperidin-4-yl)-1H-indol-2-yl]methanone The crude product of (5-amino-1-(4-(2-fluorophenoxy)-2-methylphenyl)-1H-pyrazol-4-yl) (6-fluoro-5-(1-isopropylpiperidin-4-yl)-1-tosyl-1H-indol-2-yl)methanone (200 mg) was added to ethanol (20 mL), and lithium hydroxide monohydrate (400 mg) was added. Then the mixture was stirred at 50° C. for 18 hours. The reaction solution was concentrated under reduced pressure, the resulting residue was extracted with ethyl acetate (100 mL×4), and the combined organic layers were concentrated under reduced pressure. The resulting residue was purified by HPLC, and the fractions in which the target compound was eluted were adjusted to pH 8 with aqueous ammonia. The combined fractions were extracted with ethyl acetate and the organic layer was concentrated under reduced pressure to give the target compound (80 mg).

Examples 4-2-002 to 4-2-125, Example 5-1-001, and the Like

The compounds of Examples 4-2-002 to 4-2-125, Example 5-1-001, and the like shown below were synthesized from the following corresponding enamines and hydrazines by the similar method as in Example 4-2-001.

(Corresponding Enamines and Hydrazines)

| Example No. | | Enamine | | Hydrazine |
|---|---|---|---|---|
| 4-2-001 | I-D001 | (structure) | Q001 | HCl, 2-fluorophenoxy-methylphenyl hydrazine |
| 4-2-002 | I-D001 | (structure) | Q002 | HCl, 2,3-difluorophenoxy-methylphenyl hydrazine |
| 4-2-003 | I-D001 | (structure) | Q007 | HCl, 3-chlorophenoxy-methylphenyl hydrazine |
| 4-2-004 | I-D001 | (structure) | Q027 | HCl, 2,3-difluorophenoxy-methylphenyl hydrazine |
| 4-2-005 | I-D001 | (structure) | Q030 | HCl, 3-chlorophenoxyphenyl hydrazine |
| 4-2-006 | I-D001 | (structure) | Q031 | HCl, 3-fluorophenoxyphenyl hydrazine |

-continued

| Example No. | | Enamine | | Hydrazine |
|---|---|---|---|---|
| 4-2-007 | I-D001 | | S056 | HCl, H₂N-NH-(2-F,4-(2,3-difluorophenoxy)phenyl) |
| 4-2-008 | I-D001 | | S057 | HCl, H₂N-NH-(2-F,4-(2-chlorophenoxy)phenyl) |
| 4-2-009 | I-D001 | | S058 | HCl, H₂N-NH-(2-F,4-(2-fluorophenoxy)phenyl) |
| 4-2-010 | I-E001 | | Q001 | HCl, H₂N-NH-(2-methyl,4-(2-fluorophenoxy)phenyl) |
| 4-2-011 | I-E001 | | Q002 | HCl, H₂N-NH-(2-methyl,4-(2,3-difluorophenoxy)phenyl) |

-continued
| Example No. | | Enamine | | Hydrazine |
|---|---|---|---|---|
| 4-2-012 | I-E001 | 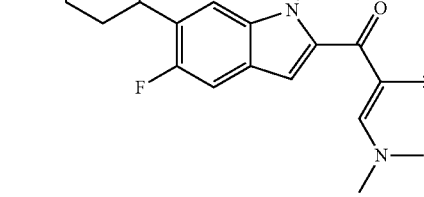 | Q005 | HCl 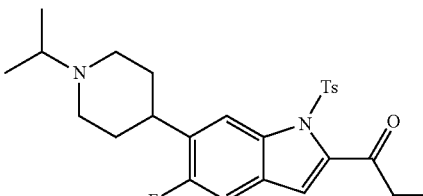 |
| 4-2-013 | I-E001 | 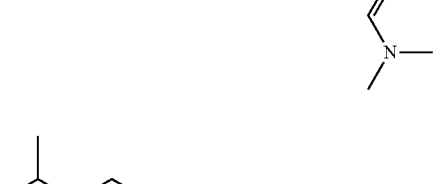 | Q007 | HCl 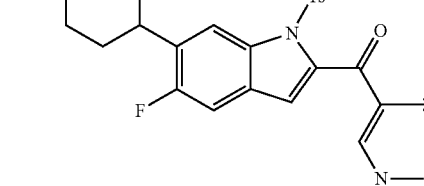 |
| 4-2-014 | I-E001 | 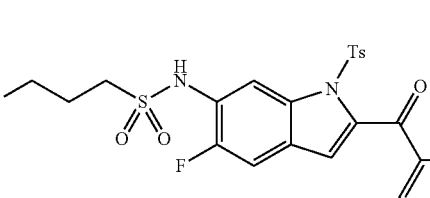 | Q019 | HCl |
| 4-2-015 | I-H005 | | Q001 | HCl |
| 4-2-016 | I-H005 | | Q002 | HCl |

-continued

| Example No. | | Enamine | | Hydrazine |
|---|---|---|---|---|
| 4-2-017 | I-H005 | (structure) | S005 | HCl (structure) |
| 4-2-018 | I-H005 | (structure) | S015 | HCl (structure) |
| 4-2-019 | I-H005 | (structure) | S038 | HCl (structure) |
| 4-2-020 | I-H005 | (structure) | T001 | HCl (structure) |
| 4-2-021 | I-H005 | (structure) | T002 | HCl (structure) |
| 4-2-022 | I-H005 | (structure) | T005 | HCl (structure) |

-continued

| Example No. | | Enamine | | Hydrazine |
|---|---|---|---|---|
| 4-2-023 | I-H005 | (structure) | T007 | HCl, hydrazinyl-methyl-pyridine-(2-chlorophenoxy) |
| 4-2-024 | I-H005 | (structure) | T009 | HCl, hydrazinyl-methyl-pyridine-(2-fluoro-6-chlorophenoxy) |
| 4-2-025 | I-H005 | (structure) | T010 | HCl, hydrazinyl-methyl-pyridine-(2-methylphenoxy) |
| 4-2-026 | I-H005 | (structure) | T011 | HCl, hydrazinyl-methyl-pyridine-(3-chlorophenoxy) |
| 4-2-027 | I-H005 | (structure) | T013 | HCl, hydrazinyl-methyl-pyridine-(4-fluorophenoxy) |
| 4-2-028 | I-H005 | (structure) | T014 | HCl, hydrazinyl-methyl-pyridine-(3,5-difluorophenoxy) |

-continued

| Example No. | | Enamine | Hydrazine | |
|---|---|---|---|---|
| 4-2-029 | I-H006 | | Q002 | HCl |
| 4-2-030 | I-H006 | | Q034 | HCl |
| 4-2-031 | I-H006 | | T002 | HCl |
| 4-2-032 | I-H006 | | T005 | HCl |
| 4-2-033 | I-H006 | | T007 | HCl |
| 4-2-034 | I-H006 | | T008 | HCl |

-continued
| Example No. | | Enamine | | | Hydrazine |
|---|---|---|---|---|---|
| 4-2-035 | I-H006 | 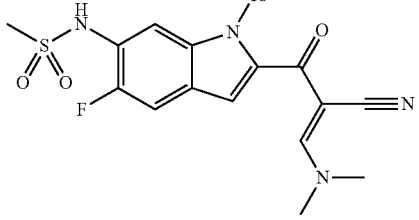 | T009 | HCl | 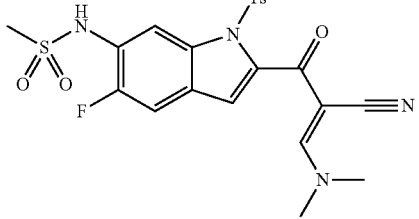 |
| 4-2-036 | I-H006 | 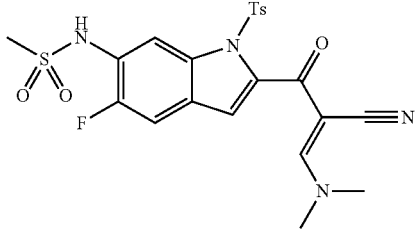 | T010 | HCl | 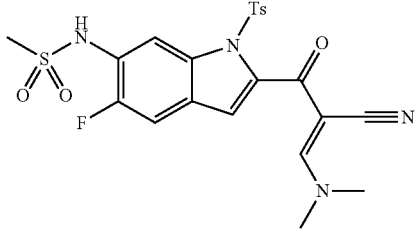 |
| 4-2-037 | I-H006 | 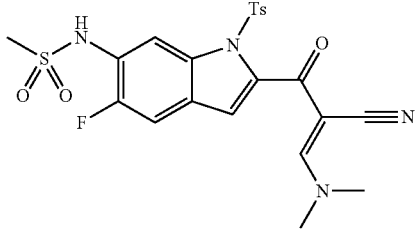 | T011 | HCl | 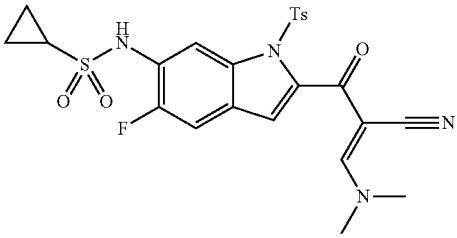 |
| 4-2-038 | I-H006 | 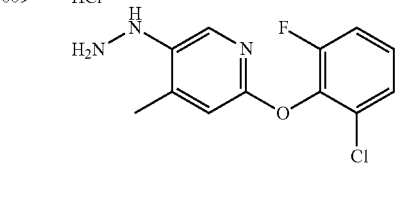 | T012 | HCl | 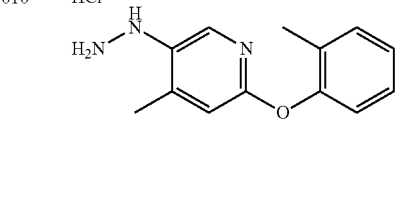 |
| 4-2-039 | I-H006 | 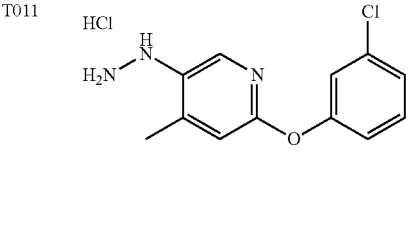 | T013 | HCl | 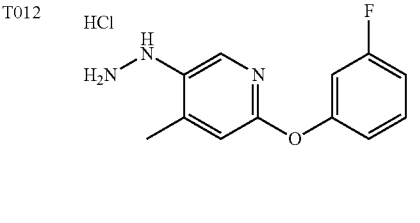 |
| 4-2-040 | I-H007 | 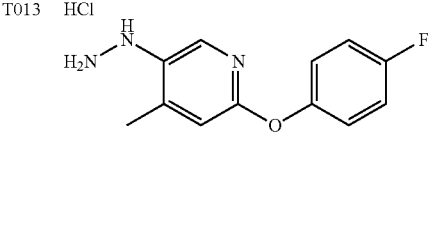 | Q001 | HCl | 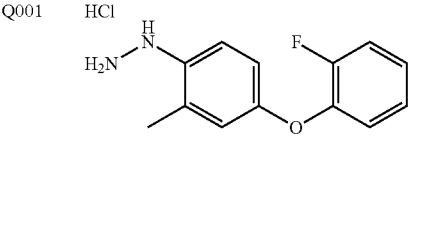 |

-continued

| Example No. | | Enamine | | Hydrazine |
|---|---|---|---|---|
| 4-2-041 | I-H007 | | Q002 | HCl, hydrazine on methylphenyl 2,3-difluorophenyl ether |
| 4-2-042 | I-H007 | | S055 | HCl, hydrazine on 2,6-dimethylphenyl 2-fluorophenyl ether |
| 4-2-043 | I-H007 | | T001 | HCl, hydrazine on methylpyridinyl 2-fluorophenyl ether |
| 4-2-044 | I-H007 | | T002 | HCl, hydrazine on methylpyridinyl 2,6-difluorophenyl ether |
| 4-2-045 | I-H007 | | T005 | HCl, hydrazine on methylpyridinyl 2,3-difluorophenyl ether |
| 4-2-046 | I-H007 | | T009 | HCl, hydrazine on methylpyridinyl 2-fluoro-6-chlorophenyl ether |

-continued

| Example No. | | Enamine | | Hydrazine |
|---|---|---|---|---|
| 4-2-047 | I-H007 | (structure) | T010 | HCl (structure) |
| 4-2-048 | I-H007 | (structure) | T012 | HCl (structure) |
| 4-2-049 | I-H014 | (structure) | Q001 | HCl (structure) |
| 4-2-050 | I-H014 | (structure) | Q002 | HCl (structure) |
| 4-2-051 | I-H014 | (structure) | S038 | HCl (structure) |
| 4-2-052 | I-H014 | (structure) | T001 | HCl (structure) |

-continued

| Example No. | | Enamine | | Hydrazine | |
|---|---|---|---|---|---|
| 4-2-053 | I-H016 | | Q001 | HCl | |
| 4-2-054 | I-H016 | | Q002 | HCl | |
| 4-2-055 | I-H016 | | S038 | HCl | |
| 4-2-056 | I-H016 | | S040 | HCl | |
| 4-2-057 | I-H016 | | S041 | HCl | |
| 4-2-058 | I-H016 | | S042 | HCl | |

| Example No. | | Enamine | | Hydrazine |
|---|---|---|---|---|
| 4-2-059 | I-H016 | 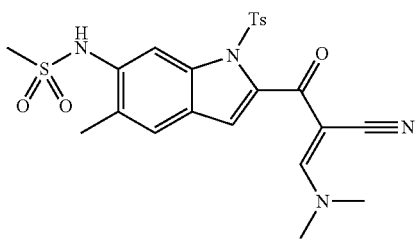 [SMILES: Cc1ccc(S(=O)(=O)n2c(C(=O)/C(C#N)=C/N(C)C)cc3cc(C)c(NS(C)(=O)=O)cc32)cc1] | S045 | 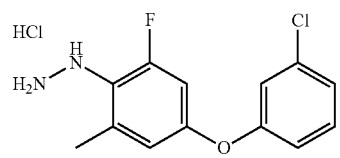 [SMILES: Cl ; Cc1cc(Oc2cccc(Cl)c2)cc(F)c1NN] |
| 4-2-060 | I-H016 | 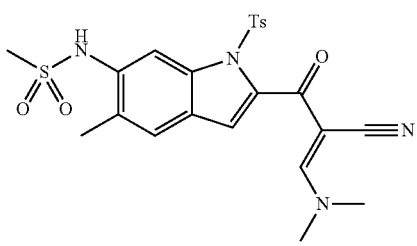 [SMILES: Cc1ccc(S(=O)(=O)n2c(C(=O)/C(C#N)=C/N(C)C)cc3cc(C)c(NS(C)(=O)=O)cc32)cc1] | S047 | 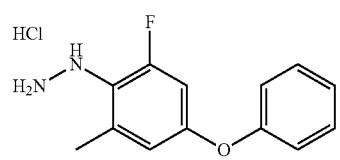 [SMILES: Cl ; Cc1cc(Oc2ccccc2)cc(F)c1NN] |
| 4-2-061 | I-H016 | 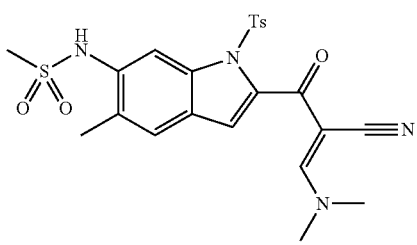 | T001 | 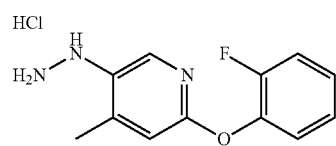 [SMILES: Cl ; Cc1cc(Oc2ccccc2F)ncc1NN] |
| 4-2-062 | I-H016 | 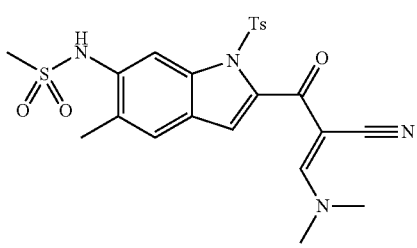 [SMILES: Cc1ccc(S(=O)(=O)n2c(C(=O)/C(C#N)=C/N(C)C)cc3cc(C)c(NS(C)(=O)=O)cc32)cc1] | T005 | 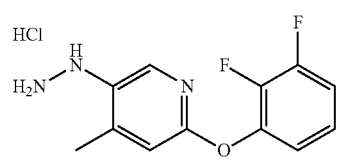 [SMILES: Cl ; Cc1cc(Oc2cccc(F)c2F)ncc1NN] |
| 4-2-063 | I-H016 | 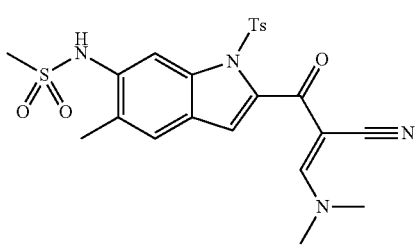 | T007 | 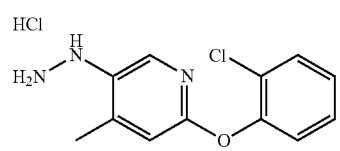 [SMILES: Cl ; Cc1cc(Oc2ccccc2Cl)ncc1NN] |
| 4-2-064 | I-H016 | 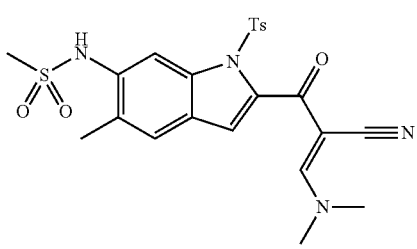 | T009 | 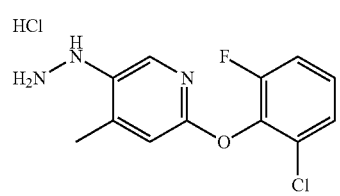 [SMILES: Cl ; Cc1cc(Oc2c(F)cccc2Cl)ncc1NN] |

-continued

| Example No. | | Enamine | Hydrazine | |
|---|---|---|---|---|
| 4-2-065 | I-H016 | | T010 | HCl |
| 4-2-066 | I-H016 | | T011 | HCl |
| 4-2-067 | I-H016 | | T013 | HCl |
| 4-2-068 | I-H017 | | Q001 | HCl |
| 4-2-069 | I-H017 | | Q002 | HCl |
| 4-2-070 | I-H017 | | S038 | HCl |

-continued
| Example No. | | Enamine | | Hydrazine |
|---|---|---|---|---|
| 4-2-071 | I-H017 | 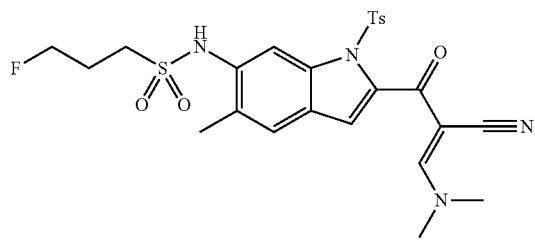 | S040 | 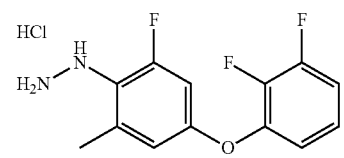 |
| 4-2-072 | I-H017 | 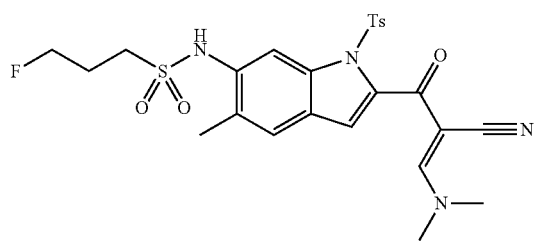 | T001 | 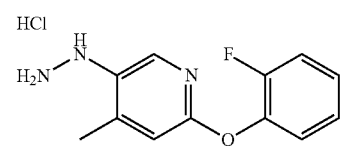 |
| 4-2-073 | I-H017 | 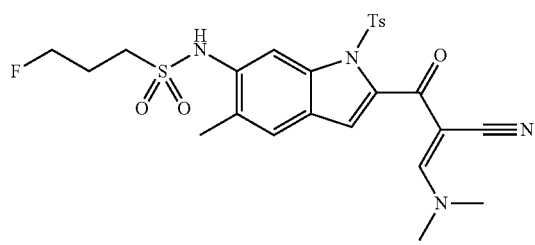 | T002 | 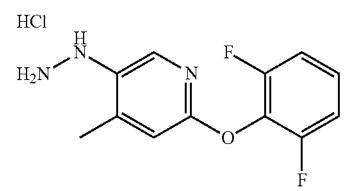 |
| 4-2-074 | I-H017 | 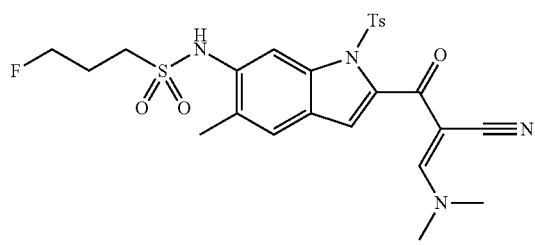 | T007 | 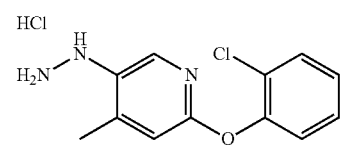 |
| 4-2-075 | I-H017 | 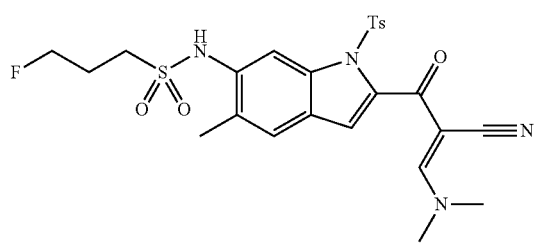 | T011 | 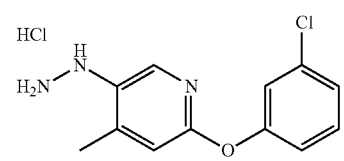 |
| 4-2-076 | I-H017 | 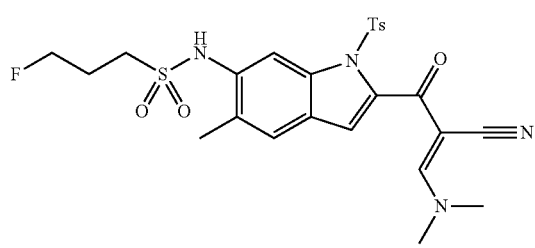 | T013 | 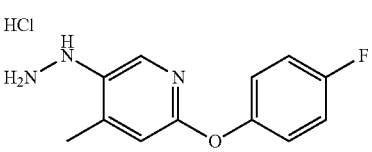 [SMILES: Cl ; Cc1cc(Oc2ccc(F)cc2)ncc1NN] |

-continued

| Example No. | | Enamine | | Hydrazine |
|---|---|---|---|---|
| 4-2-077 | I-H019 | (structure) | Q001 | HCl (structure) |
| 4-2-078 | I-H019 | (structure) | Q002 | HCl (structure) |
| 4-2-079 | I-H019 | (structure) | S038 | HCl (structure) |
| 4-2-080 | I-H019 | (structure) | S040 | HCl (structure) |
| 4-2-081 | I-H019 | (structure) | S041 | HCl (structure) |
| 4-2-082 | I-H019 | (structure) | S042 | HCl (structure) |

-continued

| Example No. | | Enamine | | Hydrazine | |
|---|---|---|---|---|---|
| 4-2-083 | I-H019 | | S045 | HCl | |
| 4-2-084 | I-H019 | | S047 | HCl | |
| 4-2-085 | I-H019 | | T001 | HCl | |
| 4-2-086 | I-H019 | | T002 | HCl | |
| 4-2-087 | I-H019 | | T005 | HCl | |
| 4-2-088 | I-H019 | | T007 | HCl | |

-continued
| Example No. | | Enamine | | Hydrazine |
|---|---|---|---|---|
| 4-2-089 | I-H019 | 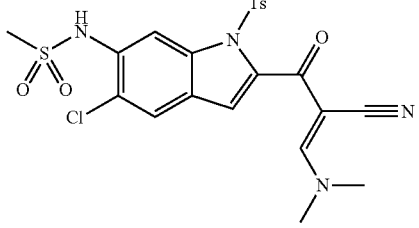 | T009 | 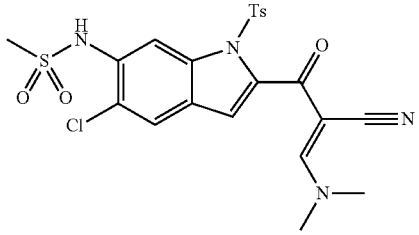 HCl |
| 4-2-090 | I-H019 | 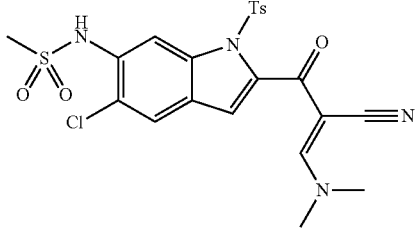 | T010 | 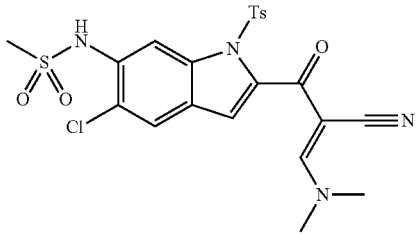 HCl |
| 4-2-091 | I-H019 | 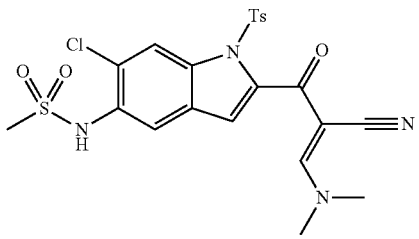 | T011 | 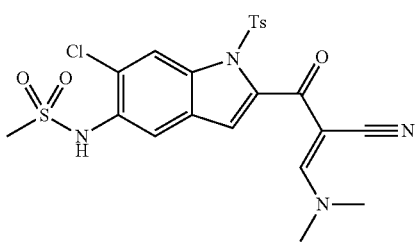 HCl |
| 4-2-092 | I-H019 | 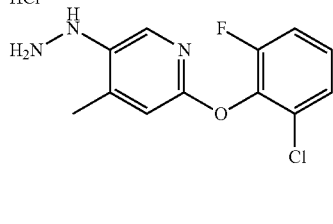 | T013 | 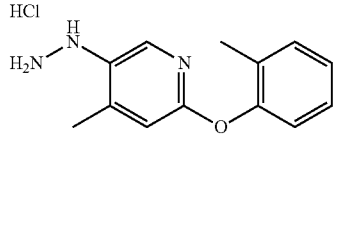 [SMILES: Cl ; Cc1cc(Oc2ccccc2C)ncc1NN] HCl |
| 4-2-093 | I-H021 | 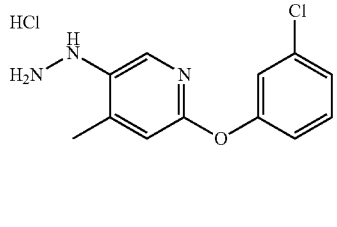 [SMILES: Cl ; Cc1cc(Oc2cccc(Cl)c2)ncc1NN] | S038 | 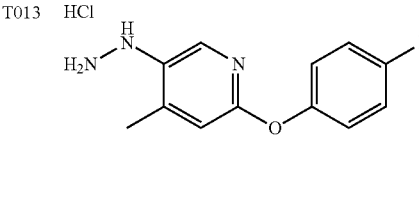 HCl |
| 4-2-094 | I-H021 | 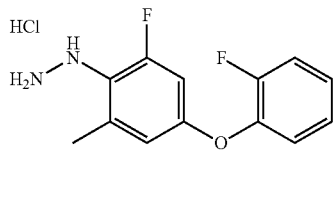 [SMILES: Cl ; Cc1cc(Oc2ccccc2F)cc(F)c1NN] | S040 | 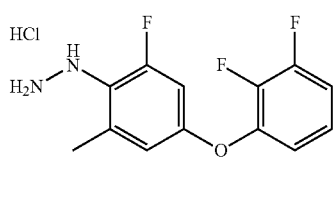 [SMILES: Cl ; Cc1cc(Oc2cccc(F)c2F)cc(F)c1NN] HCl |

-continued

| Example No. | | Enamine | | Hydrazine | |
|---|---|---|---|---|---|
| 4-2-095 | I-H021 | (structure) | S047 | HCl | (structure) |
| 4-2-096 | I-H021 | (structure) | T001 | HCl | (structure) |
| 4-2-097 | I-H023 | (structure) | Q001 | HCl | (structure) |
| 4-2-098 | I-H023 | (structure) | Q002 | HCl | (structure) |
| 4-2-099 | I-H023 | (structure) | S038 | HCl | (structure) |
| 4-2-100 | I-H023 | (structure) | S040 | HCl | (structure) |

-continued
| Example No. | | Enamine | | | Hydrazine | |
|---|---|---|---|---|---|---|
| 4-2-101 | I-H023 |  | | S041 | HCl |  |
| 4-2-102 | I-H023 | 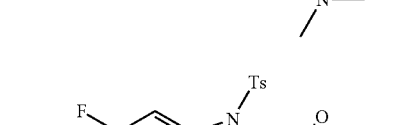 | | S042 | HCl |  |
| 4-2-103 | I-H023 | 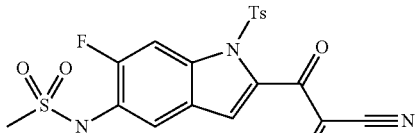 | | S047 | HCl |  |
| 4-2-104 | I-H023 | 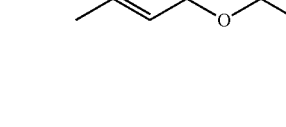 | | T001 | HCl | 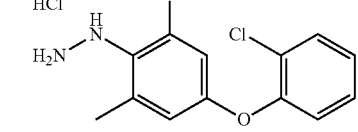 |
| 4-2-105 | I-H054 | 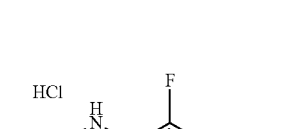 | | Q001 | HCl | 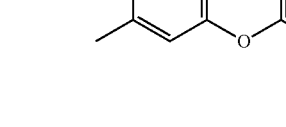 |
| 4-2-106 | I-H054 | 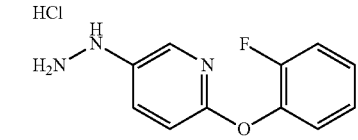 [SMILES: Cl ; NNc1ccc(Oc2ccccc2F)nc1] | | Q002 | HCl |  |

| Example No. | | Enamine | | Hydrazine |
|---|---|---|---|---|
| 4-2-107 | I-H054 | | S038 | HCl, H₂N-NH-(2-F,3-Me-5-(2-fluorophenoxy)phenyl) |
| 4-2-108 | I-H054 | | T001 | HCl, H₂N-NH-(4-methyl-6-(2-fluorophenoxy)pyridin-3-yl) |
| 4-2-109 | I-H054 | | T002 | HCl, H₂N-NH-(4-methyl-6-(2,6-difluorophenoxy)pyridin-3-yl) |
| 4-2-110 | I-H054 | | T007 | HCl, H₂N-NH-(4-methyl-6-(2-chlorophenoxy)pyridin-3-yl) |
| 4-2-111 | I-H054 | | T011 | HCl, H₂N-NH-(4-methyl-6-(3-chlorophenoxy)pyridin-3-yl) |

-continued

| Example No. | | Enamine | | Hydrazine |
|---|---|---|---|---|
| 4-2-112 | I-H055 | [structure: 6-(isothiazolidin-2-yl 1,1-dioxide)-5-methyl-1-Ts-indol-2-yl with 2-cyano-3-(dimethylamino)acryloyl group] | Q001 | HCl; 4-(2-fluorophenoxy)-2-methylphenylhydrazine |
| 4-2-113 | I-H055 | [same enamine structure] | Q002 | HCl; 4-(2,3-difluorophenoxy)-2-methylphenylhydrazine |
| 4-2-114 | I-H055 | [same enamine structure] | S038 | HCl; 2-fluoro-4-(2-fluorophenoxy)-6-methylphenylhydrazine |
| 4-2-115 | I-H055 | [same enamine structure] | S040 | HCl; 4-(2,3-difluorophenoxy)-2-fluoro-6-methylphenylhydrazine |
| 4-2-116 | I-H055 | [same enamine structure] | T002 | HCl; 6-(2,6-difluorophenoxy)-4-methylpyridin-3-yl hydrazine |
| 4-2-117 | I-H055 | [same enamine structure] | T007 | HCl; 6-(2-chlorophenoxy)-4-methylpyridin-3-yl hydrazine |

-continued

| Example No. | | Enamine | | Hydrazine |
|---|---|---|---|---|
| 4-2-118 | I-H055 | (structure) | T011 | (structure) |
| 4-2-119 | I-H055 | (structure) | T013 | (structure) |
| 4-2-120 | I-H059 | (structure) | S038 | (structure) |
| 4-2-121 | I-H059 | (structure) | T002 | (structure) |
| 4-2-122 | I-H060 | (structure) | Q001 | (structure) |

-continued
| Example No. | | Enamine | | Hydrazine |
|---|---|---|---|---|
| 4-2-123 | I-H060 | 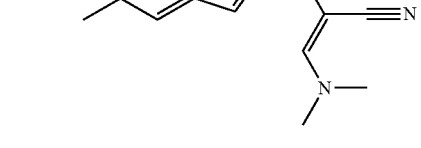 | T001 HCl | 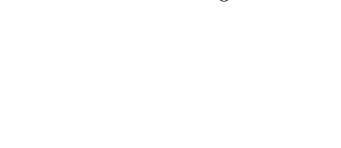 |
| 4-2-124 | I-H060 | 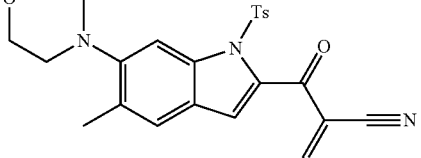 | T002 HCl | 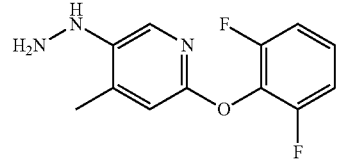 |
| 4-2-125 | I-H061 | 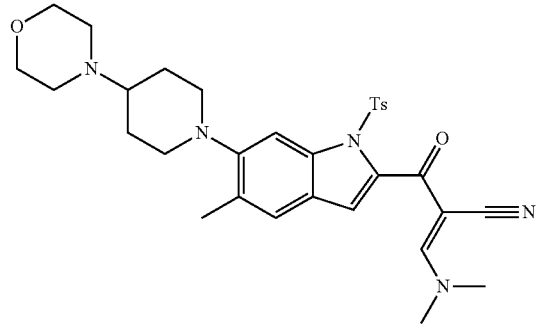 [SMILES: Cc1ccc(S(=O)(=O)n2c(C(=O)/C(C#N)=C/N(C)C)cc3cc(C)c(N4CCC(N5CCOCC5)CC4)cc32)cc1] | T002 HCl | 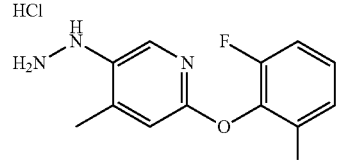 |
| 5-1-001 | I-D001 | 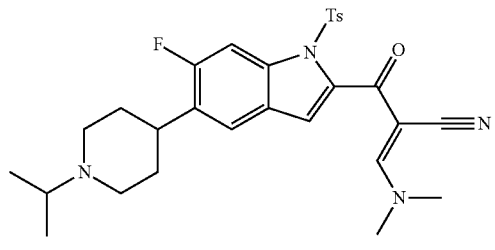 [SMILES: Cc1ccc(S(=O)(=O)n2c(C(=O)/C(C#N)=C/N(C)C)cc3cc(C4CCN(C(C)C)CC4)c(F)cc32)cc1] | Q035 HCl | 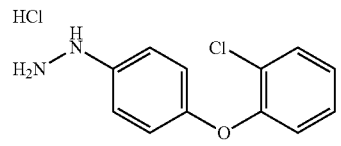 [SMILES: Cl ; NNc1ccc(Oc2ccccc2Cl)cc1] |
| 5-1-002 | I-D001 | 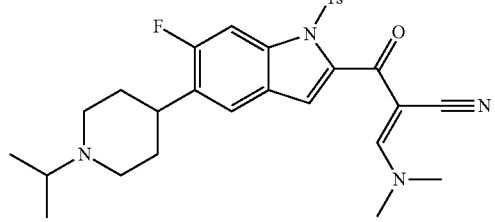 | S060 HCl | 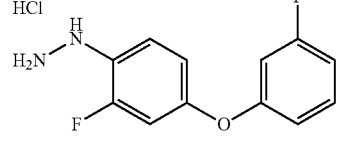 |
| 5-1-003 | I-D001 | 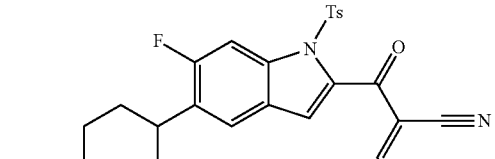 | S059 HCl | 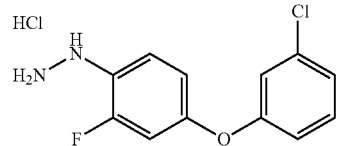 |

-continued

| Example No. | | Enamine | | Hydrazine |
|---|---|---|---|---|
| 5-1-004 | I-D001 | (structure) | Q036 | HCl, H₂N-NH-C₆H₄-O-C₆H₄-F (4-(2-fluorophenoxy)phenylhydrazine hydrochloride) |
| 5-1-005 | I-D001 | (structure) | Q037 | HCl, 2-methyl-4-(3-fluorophenoxy)phenylhydrazine hydrochloride |
| 5-1-006 | I-E001 | (structure) | S060 | HCl, 2-fluoro-4-(3-fluorophenoxy)phenylhydrazine hydrochloride |
| 5-1-007 | I-E001 | (structure) | Q036 | HCl, 4-(2-fluorophenoxy)phenylhydrazine hydrochloride |
| 5-1-008 | I-E001 | (structure) | Q030 | HCl, 4-(3-chlorophenoxy)phenylhydrazine hydrochloride |

-continued

| Example No. | | Enamine | | Hydrazine |
|---|---|---|---|---|
| 5-1-009 | I-E001 | (structure) | Q037 | 2-methyl-4-(3-fluorophenoxy)phenylhydrazine·HCl |
| 5-1-010 | I-E001 | (structure) | S059 | 4-(3-chlorophenoxy)-2-fluorophenylhydrazine·HCl |
| 5-1-011 | I-E001 | (structure) | S056 | 4-(2,3-difluorophenoxy)-2-fluorophenylhydrazine·HCl |
| 5-1-012 | I-D002 | (structure) | Q019 | 4-(2-fluorophenoxy)-3-methylphenylhydrazine·HCl |
| 5-1-013 | I-E001 | (structure) | Q027 | 4-(2,3-difluorophenoxy)phenylhydrazine·HCl |

-continued

| Example No. | | Enamine | Hydrazine | |
|---|---|---|---|---|
| 5-1-014 | I-E001 | (structure) | Q031 | HCl (structure) |
| 5-1-015 | I-E001 | (structure) | Q035 | HCl (structure) |
| 5-1-016 | I-H047 | (structure) | Q011 | HCl (structure) |
| 5-1-017 | I-H047 | (structure) | Q019 | HCl (structure) |
| 5-1-018 | I-H047 | (structure) | Q013 | HCl (structure) |
| 5-1-019 | I-H007 | (structure) | S052 | HCl (structure) |

| Example No. | | Enamine | | Hydrazine |
|---|---|---|---|---|
| 5-1-022 | I-H006 | 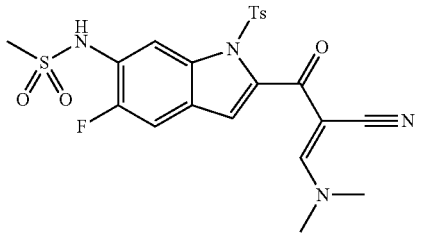 | S052 |  |
| 5-1-023 | I-H006 | 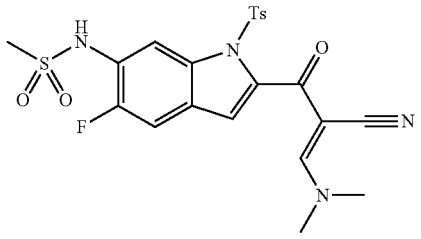 | S061 |  |
| 5-1-024 | I-H006 | 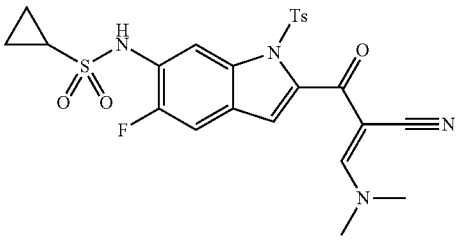 | S049 | 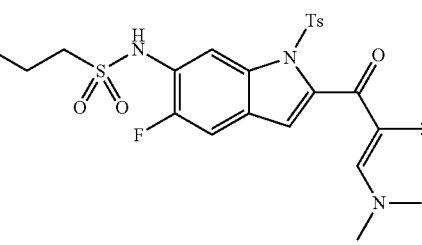 |
| 5-1-025 | I-H007 | | S061 | |
| 5-1-026 | I-H007 | | S049 | |
| 5-1-027 | I-H005 | | S052 | |

-continued

| Example No. | | Enamine | | Hydrazine |
|---|---|---|---|---|
| 5-1-028 | I-H005 | [structure: 3-fluoropropylsulfonamide-fluoroindole-Ts with cyanoenamine] | S049 | HCl, [structure: 2,6-dichloro-4-(2,3-difluorophenoxy)phenylhydrazine] |
| 5-1-030 | I-H006 | [structure: methylsulfonamide-fluoroindole-Ts with cyanoenamine] | S050 | HCl, [structure: 2,6-difluoro-4-(2,3-difluorophenoxy)phenylhydrazine] |
| 5-1-031 | I-H007 | [structure: cyclopropylsulfonamide-fluoroindole-Ts with cyanoenamine] | S050 | HCl, [structure: 2,6-difluoro-4-(2,3-difluorophenoxy)phenylhydrazine] |
| 5-1-032 | I-H006 | [structure: methylsulfonamide-fluoroindole-Ts with cyanoenamine] | S055 | HCl, [structure: 2,6-dimethyl-4-(2-fluorophenoxy)phenylhydrazine] |
| 5-1-033 | I-H005 | [structure: 3-fluoropropylsulfonamide-fluoroindole-Ts with cyanoenamine] | S061 | HCl, [structure: 2,6-dichloro-4-(2-fluorophenoxy)phenylhydrazine] |
| 5-1-034 | I-H005 | [structure: 3-fluoropropylsulfonamide-fluoroindole-Ts with cyanoenamine] | S050 | HCl, [structure: 2,6-difluoro-4-(2,3-difluorophenoxy)phenylhydrazine] |

-continued

| Example No. | | Enamine | | Hydrazine |
|---|---|---|---|---|
| 5-1-035 | I-H005 | (structure) | S026 | HCl (structure) |
| 5-1-036 | I-H005 | (structure) | S025 | HCl (structure) |
| 5-1-037 | I-H005 | (structure) | S016 | HCl (structure) |
| 5-1-038 | I-H006 | (structure) | T014 | HCl (structure) |
| 5-1-039 | I-H006 | (structure) | T017 | HCl (structure) |
| 5-1-040 | I-H005 | (structure) | S055 | HCl (structure) |

| Example No. | | Enamine | | Hydrazine |
|---|---|---|---|---|
| 5-1-041 | I-H006 | 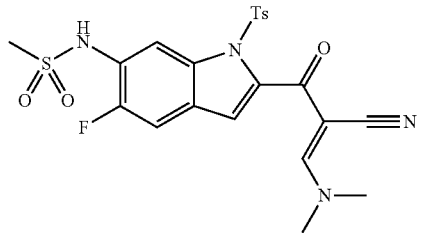 [SMILES: Cc1ccc(S(=O)(=O)n2c(C(=O)/C(C#N)=C/N(C)C)cc3cc(F)c(NS(C)(=O)=O)cc32)cc1] | T020 | 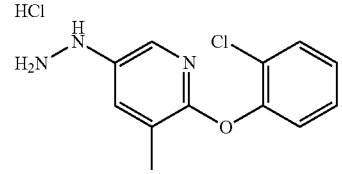 [SMILES: Cl ; Cc1cc(NN)cnc1Oc1ccccc1Cl] HCl |
| 5-1-042 | I-H006 | 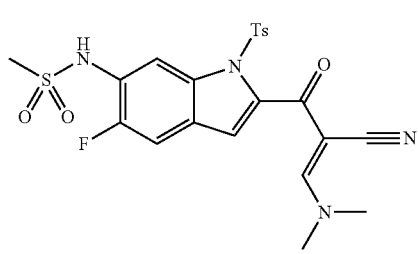 | T021 | 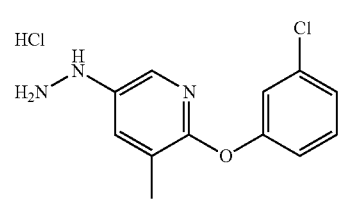 [SMILES: Cl ; Cc1cc(NN)cnc1Oc1cccc(Cl)c1] HCl |
| 5-1-043 | I-H006 | 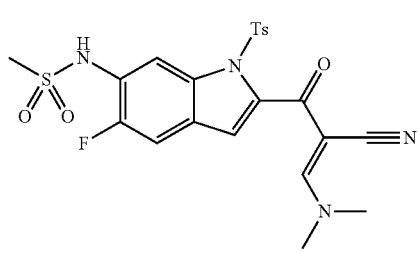 | T022 | 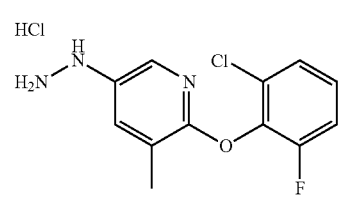 [SMILES: Cl ; Cc1cc(NN)cnc1Oc1c(F)cccc1Cl] HCl |
| 5-1-044 | I-H006 | 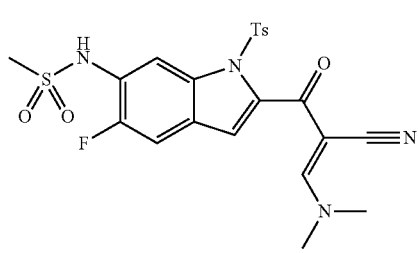 | T018 | 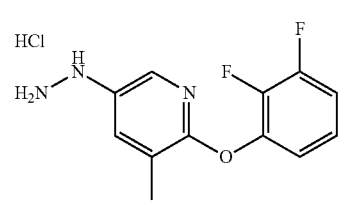 [SMILES: Cl ; Cc1cc(NN)cnc1Oc1cccc(F)c1F] HCl |
| 5-1-045 | I-H006 | 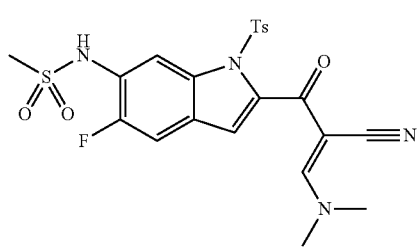 | T019 | 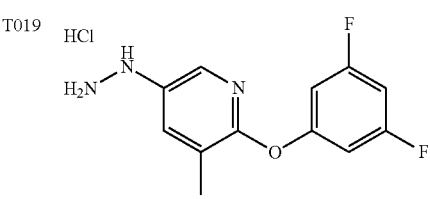 HCl |
| 5-1-046 | I-H007 | 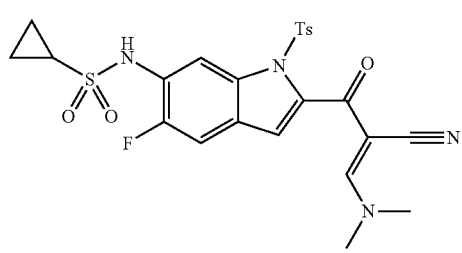 [SMILES: Cc1ccc(S(=O)(=O)n2c(C(=O)/C(C#N)=C/N(C)C)cc3cc(F)c(NS(=O)(=O)C4CC4)cc32)cc1] | T013 | 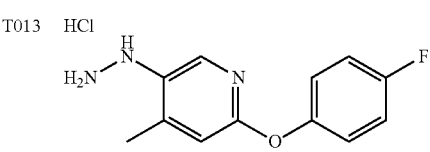 HCl |

-continued

| Example No. | | Enamine | | Hydrazine |
|---|---|---|---|---|
| 5-1-047 | I-H023 | [structure: 6-fluoro-5-(methylsulfonamido)-1-Ts-indol-2-yl with α-cyano-β-dimethylamino enone] | T010 HCl | [structure: 5-hydrazinyl-4-methyl-2-(2-methylphenoxy)pyridine] |
| 5-1-048 | I-H023 | [structure: 6-fluoro-5-(methylsulfonamido)-1-Ts-indol-2-yl with α-cyano-β-dimethylamino enone] | S045 HCl | [structure: hydrazinyl-fluoro-methyl-(3-chlorophenoxy)benzene] |
| 5-1-049 | I-H023 | [structure: 6-fluoro-5-(methylsulfonamido)-1-Ts-indol-2-yl with α-cyano-β-dimethylamino enone] | T005 HCl | [structure: 5-hydrazinyl-4-methyl-2-(2,3-difluorophenoxy)pyridine] |
| 5-1-050 | I-H023 | [structure: 6-fluoro-5-(methylsulfonamido)-1-Ts-indol-2-yl with α-cyano-β-dimethylamino enone] | T007 HCl | [structure: 5-hydrazinyl-4-methyl-2-(2-chlorophenoxy)pyridine] |
| 5-1-051 | I-H006 | [structure: 5-fluoro-6-(methylsulfonamido)-1-Ts-indol-2-yl with α-cyano-β-dimethylamino enone] | T026 HCl | [structure: 3-hydrazinyl-4,6-dimethyl-2-(2-chlorophenoxy)pyridine] |
| 5-1-052 | I-H006 | [structure: 5-fluoro-6-(methylsulfonamido)-1-Ts-indol-2-yl with α-cyano-β-dimethylamino enone] | T027 HCl | [structure: 3-hydrazinyl-4,6-dimethyl-2-(3-chlorophenoxy)pyridine] |

| Example No. | | Enamine | Hydrazine | |
|---|---|---|---|---|
| 5-1-053 | I-H006 | (structure) | T024 | (structure) |
| 5-1-054 | I-H006 | (structure) | T025 | (structure) |
| 5-1-055 | I-H006 | (structure) | T015 | (structure) |
| 5-1-059 | I-H005 | (structure) | T012 | (structure) |
| 5-1-060 | I-H006 | (structure) | T023 | (structure) |
| 5-1-063 | I-H017 | (structure) | S016 | (structure) |

-continued

| Example No. | | Enamine | | Hydrazine |
|---|---|---|---|---|
| 5-1-064 | I-H054 | (tetrahydropyran-4-yl)sulfonamide-N-(5-methyl-1-Ts-indol-6-yl), 2-(2-cyano-3-(dimethylamino)acryloyl) | T013 | HCl; 5-hydrazinyl-6-methyl-2-(4-fluorophenoxy)pyridine |
| 5-1-065 | I-H054 | (tetrahydropyran-4-yl)sulfonamide-N-(5-methyl-1-Ts-indol-6-yl), 2-(2-cyano-3-(dimethylamino)acryloyl) | S016 | HCl; 4-hydrazinyl-2-chloro-1-((3-chloropyridin-2-yl)oxy)benzene |
| 5-1-066 | I-H054 | (tetrahydropyran-4-yl)sulfonamide-N-(5-methyl-1-Ts-indol-6-yl), 2-(2-cyano-3-(dimethylamino)acryloyl) | S040 | HCl; 1-hydrazinyl-2-fluoro-4-(2,3-difluorophenoxy)-6-methylbenzene |
| 5-1-077 | I-H061 | 6-(4-morpholinopiperidin-1-yl)-5-methyl-1-Ts-indol-2-yl, 2-(2-cyano-3-(dimethylamino)acryloyl) | T001 | HCl; 5-hydrazinyl-4-methyl-2-(2-fluorophenoxy)pyridine |
| 5-1-078 | I-H061 | 6-(4-morpholinopiperidin-1-yl)-5-methyl-1-Ts-indol-2-yl, 2-(2-cyano-3-(dimethylamino)acryloyl) | T001 | HCl; 5-hydrazinyl-4-methyl-2-(2-fluorophenoxy)pyridine |

-continued
| Example No. | | Enamine | | Hydrazine |
|---|---|---|---|---|
| 5-1-080 | I-A011 | 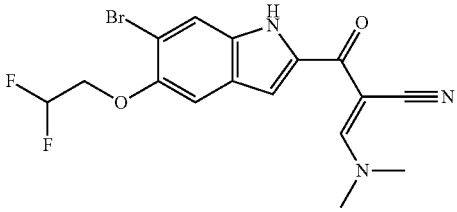 [SMILES: CN(C)/C=C(\C#N)C(=O)c1cc2cc(OCC(F)F)c(Br)cc2[nH]1] | T002 HCl | 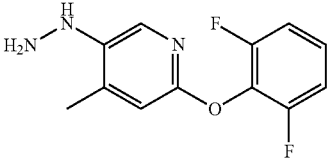 |
| 5-1-081 | I-H053 | 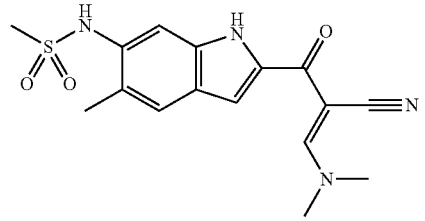 | Q034 HCl | 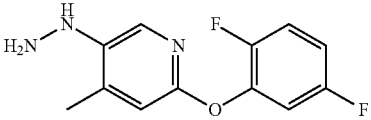 |
| 5-1-082 | B-B026 | 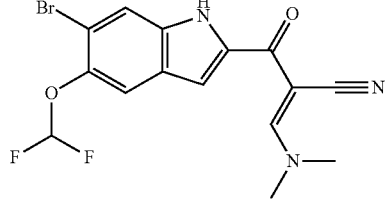 | Q001 HCl | 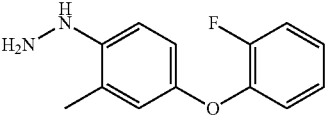 |
| 5-1-084 | I-H060 | 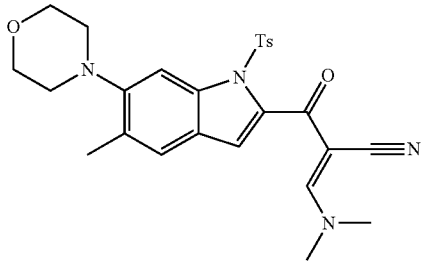 | S038 HCl | 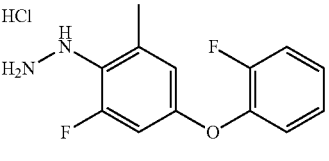 |
| 5-1-085 | I-H061 | 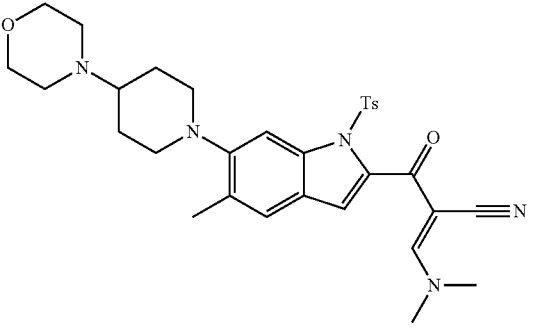 [SMILES: Cc1ccc(S(=O)(=O)n2c(C(=O)/C(C#N)=C/N(C)C)cc3cc(C)c(N4CCC(N5CCOCC5)CC4)cc32)cc1] | S038 HCl | 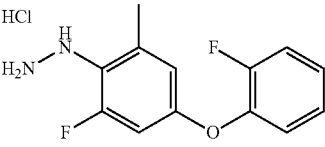 |
| 5-1-086 | I-H069 | 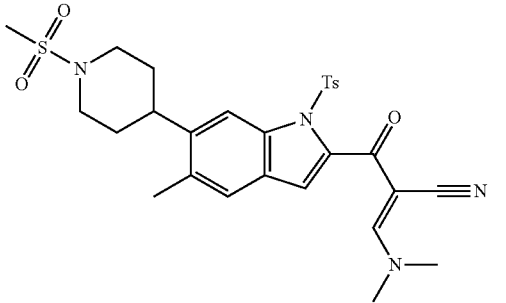 [SMILES: Cc1ccc(S(=O)(=O)n2c(C(=O)/C(C#N)=C/N(C)C)cc3cc(C)c(C4CCN(S(C)(=O)=O)CC4)cc32)cc1] | Q001 HCl | 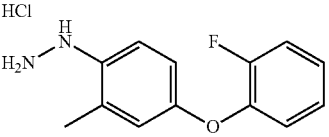 [SMILES: Cl ; Cc1cc(Oc2ccccc2F)ccc1NN] |

-continued

| Example No. | | Enamine | | Hydrazine |
|---|---|---|---|---|
| 5-1-090 | I-H069 | (structure) | T001 | HCl (structure) |
| 5-1-091 | I-H069 | (structure) | T002 | HCl (structure) |
| 5-1-092 | I-H053 | (structure) | Q035 | HCl (structure) |
| 5-1-096 | I-H053 | (structure) | Q040 | HCl (structure) |
| 5-1-107 | I-H053 | (structure) | Q041 | HCl (structure) |
| 5-1-108 | I-H053 | (structure) | Q042 | HCl (structure) |

-continued

| Example No. | | Enamine | | Hydrazine |
|---|---|---|---|---|
| 5-1-109 | I-H053 | (structure) | T016 | HCl (structure) |
| 5-1-111 | I-H069 | (structure) | S038 | HCl (structure) |
| 5-1-123 | I-H070 | (structure) | T001 | HCl (structure) |
| 5-1-132 | I-H071 | (structure) | Q001 | HCl (structure) |
| 5-1-133 | I-H071 | (structure) | T001 | HCl (structure) |

| Example No. | | Enamine | | Hydrazine |
|---|---|---|---|---|
| 5-1-138 | I-H071 | (acetyl-piperidinyl-methylindole-Ts, acyl cyanoenamine NMe2) | S038 | HCl, H2N-NH-(2-methyl-4-(2-fluorophenoxy)-6-fluorophenyl) |
| 5-1-139 | I-H071 | (acetyl-piperidinyl-methylindole-Ts, acyl cyanoenamine NMe2) | T002 | HCl, H2N-NH-(5-(2,6-difluorophenoxy)-4-methylpyridin-2-yl) |
| 5-1-140 | I-H053 | (methanesulfonamido-methylindole, acyl cyanoenamine NMe2) | S038 | HCl, H2N-NH-(2-methyl-4-(2-fluorophenoxy)-6-fluorophenyl) |
| 5-1-141 | I-H072 | (methanesulfonamido-ethylindole, acyl cyanoenamine NMe2) | T002 | HCl, H2N-NH-(5-(2,6-difluorophenoxy)-4-methylpyridin-2-yl) |
| 5-1-142 | I-H053 | (methanesulfonamido-methylindole, acyl cyanoenamine NMe2) | S048 | HCl, H2N-NH-(4-(2-chloro-6-fluorophenoxy)-2-fluoro-6-methylphenyl) |

-continued

| Example No. | | Enamine | | Hydrazine |
|---|---|---|---|---|
| 5-1-144 | I-H070 | [structure: 6-(1-cyclopropylsulfonyl-piperidin-4-yl)-5-methyl-1-Ts-indole-2-yl with acyl-CN-enamine NMe2] | T002 HCl | [structure: 5-hydrazinyl-2-(2,6-difluorophenoxy)-4-methylpyridine] |
| 5-1-145 | I-H068 | [structure: 6-Br-5-MeO-1H-indol-2-yl with acyl-CN-enamine NMe2] | T001 HCl | [structure: 5-hydrazinyl-2-(2-fluorophenoxy)-4-methylpyridine] |
| 5-1-147 | I-A010 | [structure: 6-Br-5-morpholino-1H-indol-2-yl with acyl-CN-enamine NMe2] | Q001 HCl | [structure: 4-(2-fluorophenoxy)-3-methylphenylhydrazine] |
| 5-1-149 | B-B026 | [structure: 6-Br-5-OCHF2-1H-indol-2-yl with acyl-CN-enamine NMe2] | T002 HCl | [structure: 5-hydrazinyl-2-(2,6-difluorophenoxy)-4-methylpyridine] |
| 5-1-150 | I-A011 | [structure: 6-Br-5-(2,2-difluoroethoxy)-1H-indol-2-yl with acyl-CN-enamine NMe2] | Q019 HCl | [structure: 4-(2-fluorophenoxy)-3-methylphenylhydrazine] |
| 5-1-151 | I-A010 | [structure: 6-Br-5-morpholino-1H-indol-2-yl with acyl-CN-enamine NMe2] | Q019 HCl | [structure: 4-(2-fluorophenoxy)-3-methylphenylhydrazine] |

-continued

| Example No. | | Enamine | | Hydrazine |
|---|---|---|---|---|
| 5-1-152 | B-B026 | [6-bromo-5-(difluoromethoxy)-1H-indol-2-yl structure with acryl-nitrile dimethylamino enamine] | Q019 | HCl, [hydrazinyl-3-methyl-4-(2-fluorophenoxy)phenyl] |
| 5-1-155 | I-A010 | [6-bromo-5-morpholino-1H-indol-2-yl structure with acryl-nitrile dimethylamino enamine] | T002 | HCl, [hydrazinyl-4-methyl-6-(2,6-difluorophenoxy)pyridin-3-yl] |

(Synthesized Compounds)

| Example No. | Compound | m/z (M + H) | Retention Time (Minute) | LCMS Measurement Condition |
|---|---|---|---|---|
| 4-2-001 | [5-(1-isopropylpiperidin-4-yl)-6-fluoro-1H-indol-2-yl ketone with 5-amino-1-(4-(2-fluorophenoxy)-2-methylphenyl)-1H-pyrazol-4-yl] | 570 | 0.62 | A1 |
| 4-2-002 | [5-(1-isopropylpiperidin-4-yl)-6-fluoro-1H-indol-2-yl ketone with 5-amino-1-(4-(2,3-difluorophenoxy)-2-methylphenyl)-1H-pyrazol-4-yl] | 588 | 0.63 | A1 |
| 4-2-003 | [5-(1-isopropylpiperidin-4-yl)-6-fluoro-1H-indol-2-yl ketone with 5-amino-1-(4-(3-chlorophenoxy)-2-methylphenyl)-1H-pyrazol-4-yl] | 586, 588 | 0.67 | A1 |

| Example No. | Compound | m/z (M + H) | Retention Time (Minute) | LCMS Measurement Condition |
|---|---|---|---|---|
| 4-2-004 | | 574 | 0.71 | A1 |
| 4-2-005 | | 572, 574 | 0.74 | A1 |
| 4-2-006 | | 556 | 0.63 | A1 |
| 4-2-007 | | 592 | 0.64 | A1 |
| 4-2-008 | | 590, 592 | 0.71 | A1 |
| 4-2-009 | | 574 | 0.59 | A1 |

-continued
| Example No. | Compound | m/z (M + H) | Retention Time (Minute) | LCMS Measurement Condition |
|---|---|---|---|---|
| 4-2-010 | 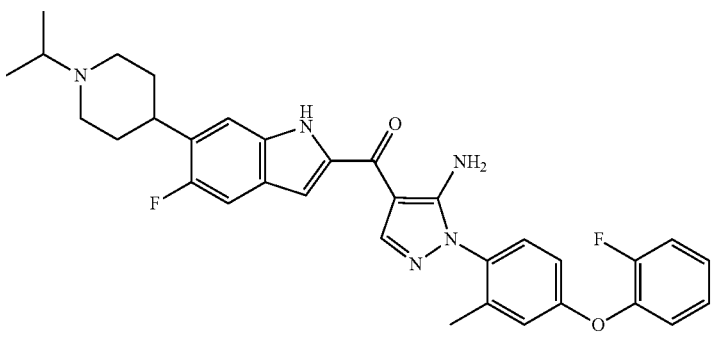 [SMILES: Cc1cc(Oc2ccccc2F)ccc1-n1ncc(C(=O)c2cc3cc(F)c(C4CCN(C(C)C)CC4)cc3[nH]2)c1N] | 570 | 0.66 | A1 |
| 4-2-011 | 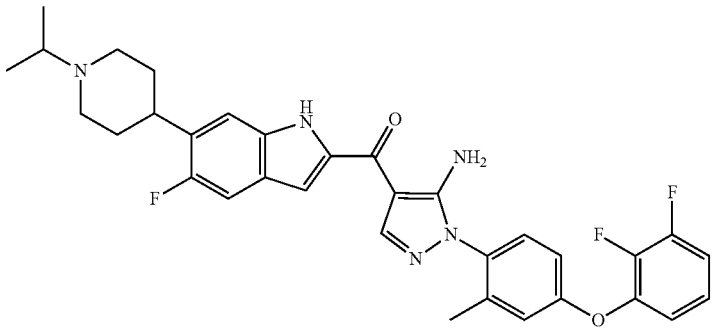 [SMILES: Cc1cc(Oc2cccc(F)c2F)ccc1-n1ncc(C(=O)c2cc3cc(F)c(C4CCN(C(C)C)CC4)cc3[nH]2)c1N] | 588 | 0.68 | A1 |
| 4-2-012 | 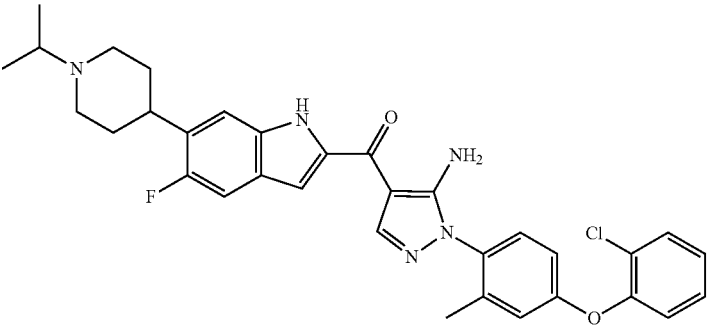 [SMILES: Cc1cc(Oc2ccccc2Cl)ccc1-n1ncc(C(=O)c2cc3cc(F)c(C4CCN(C(C)C)CC4)cc3[nH]2)c1N] | 586, 588 | 0.67 | A1 |
| 4-2-013 | 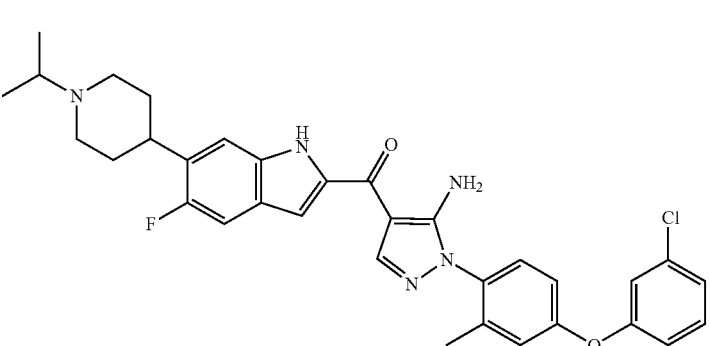 | 586, 588 | 0.71 | A1 |

-continued
| Example No. | Compound | m/z (M + H) | Retention Time (Minute) | LCMS Measurement Condition |
|---|---|---|---|---|
| 4-2-014 | 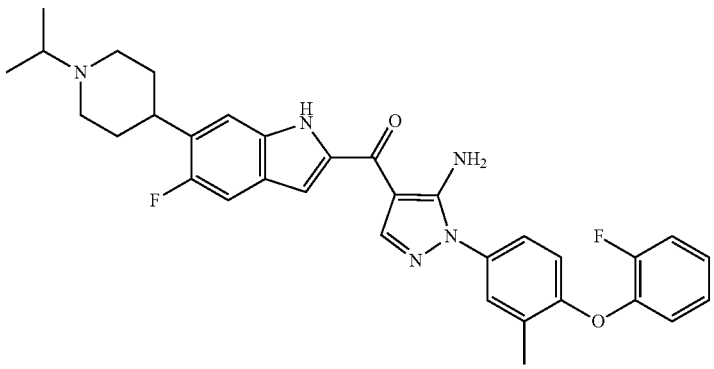 [SMILES: Cc1cc(-n2ncc(C(=O)c3cc4cc(F)c(C5CCN(C(C)C)CC5)cc4[nH]3)c2N)ccc1Oc1ccccc1F] | 570 | 0.70 | A1 |
| 4-2-015 | 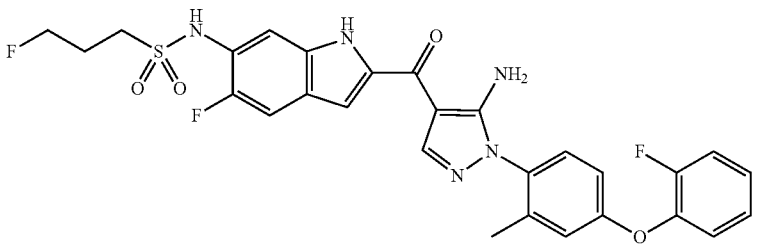 | 584 | 0.84 | A2 |
| 4-2-016 | 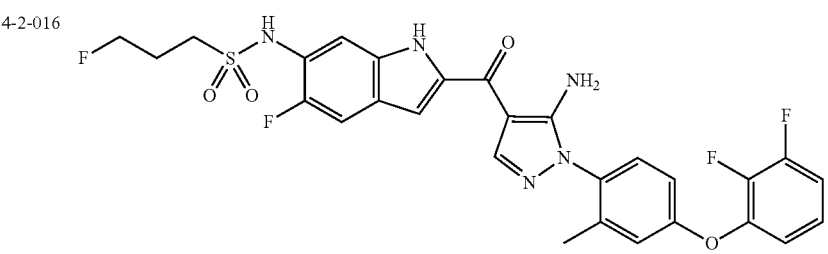 | 602 | 0.85 | A2 |
| 4-2-017 | 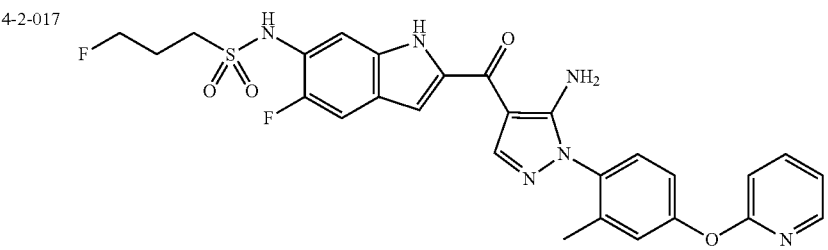 | 567 | 0.74 | A2 |
| 4-2-018 | 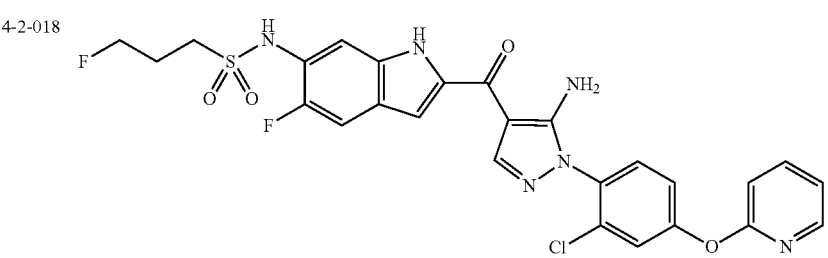 | 587, 589 | 0.75 | A2 |

| Example No. | Compound | m/z (M + H) | Retention Time (Minute) | LCMS Measurement Condition |
|---|---|---|---|---|
| 4-2-019 | | 602 | 0.82 | A1 |
| 4-2-020 | | 585 | 0.79 | A2 |
| 4-2-021 | | 603 | 0.79 | A1 |
| 4-2-022 | | 603 | 0.81 | A2 |
| 4-2-023 | | 601, 603 | 0.82 | A2 |

| Example No. | Compound | m/z (M + H) | Retention Time (Minute) | LCMS Measurement Condition |
|---|---|---|---|---|
| 4-2-024 | 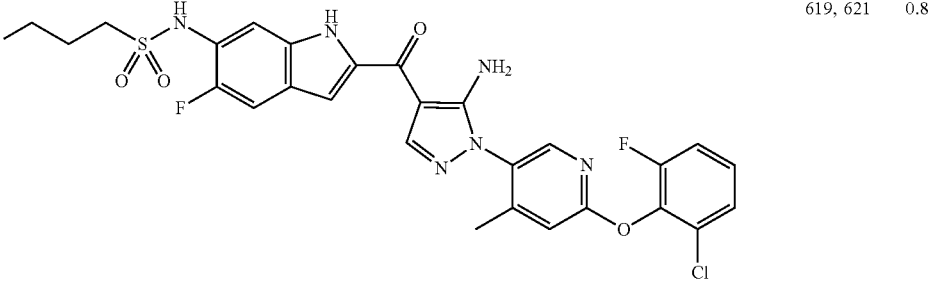 | 619, 621 | 0.81 | A1 |
| 4-2-025 |  | 581 | 2.42 | B1 |
| 4-2-026 | 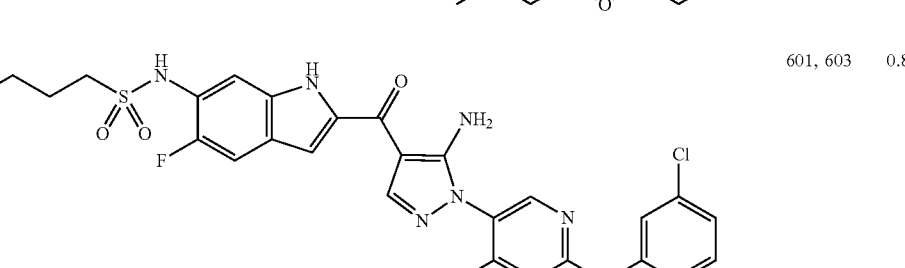 | 601, 603 | 0.84 | A2 |
| 4-2-027 | 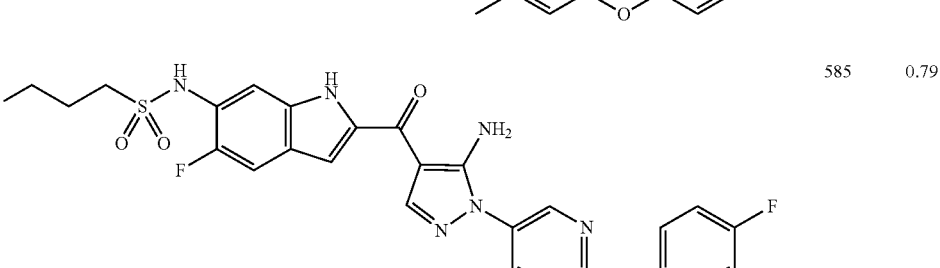 | 585 | 0.79 | A2 |
| 4-2-028 | 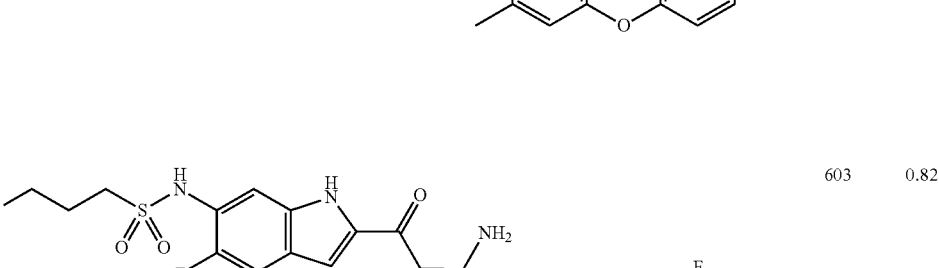 | 603 | 0.82 | A2 |

-continued

| Example No. | Compound | m/z (M + H) | Retention Time (Minute) | LCMS Measurement Condition |
|---|---|---|---|---|
| 4-2-029 | | 556 | 0.79 | A1 |
| 4-2-030 | | 557 | 0.75 | A1 |
| 4-2-031 | | 557 | 0.75 | A1 |
| 4-2-032 | | 557 | 0.75 | A1 |
| 4-2-033 | | 555, 557 | 0.78 | A2 |

| Example No. | Compound | m/z (M + H) | Retention Time (Minute) | LCMS Measurement Condition |
|---|---|---|---|---|
| 4-2-034 | | 573, 575 | 0.78 | A1 |
| 4-2-035 | | 573, 575 | 0.78 | A1 |
| 4-2-036 | | 535 | 0.75 | A1 |
| 4-2-037 | | 555, 557 | 0.81 | A2 |
| 4-2-038 | | 539 | 0.73 | A1 |

-continued
| Example No. | Compound | m/z (M + H) | Retention Time (Minute) | LCMS Measurement Condition |
|---|---|---|---|---|
| 4-2-039 | 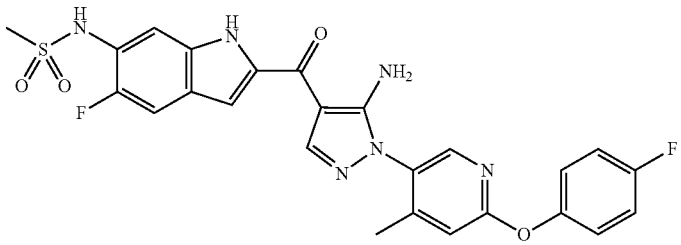 [SMILES: Cc1cc(Oc2ccc(F)cc2)ncc1-n1ncc(C(=O)c2cc3cc(F)c(NS(C)(=O)=O)cc3[nH]2)c1N] | 539 | 0.75 | A2 |
| 4-2-040 | 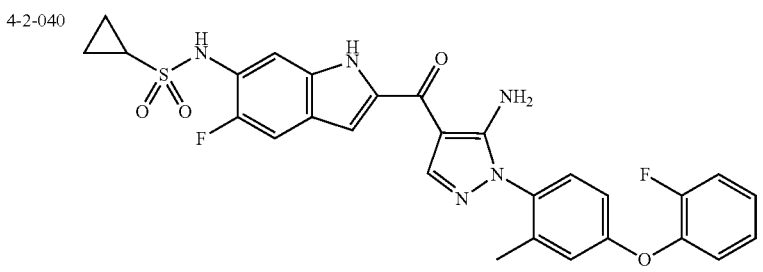 | 564 | 0.81 | A1 |
| 4-2-041 | 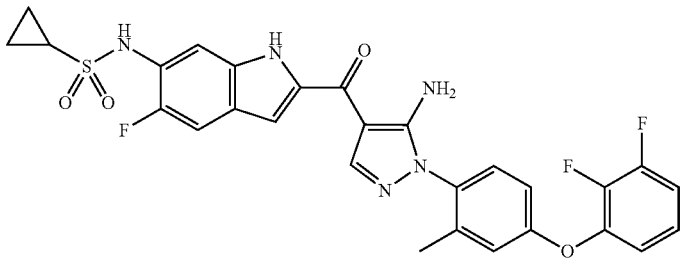 [SMILES: Cc1cc(Oc2cccc(F)c2F)ccc1-n1ncc(C(=O)c2cc3cc(F)c(NS(=O)(=O)C4CC4)cc3[nH]2)c1N] | 582 | 0.85 | A2 |
| 4-2-042 | 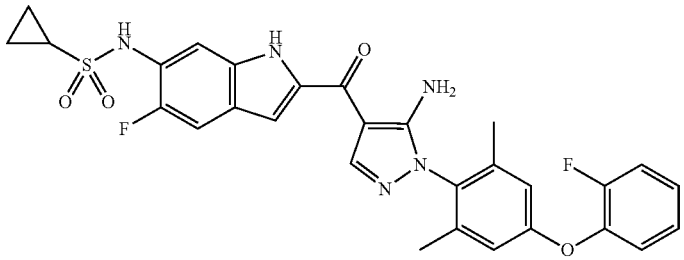 [SMILES: Cc1cc(Oc2ccccc2F)cc(C)c1-n1ncc(C(=O)c2cc3cc(F)c(NS(=O)(=O)C4CC4)cc3[nH]2)c1N] | 578 | 0.83 | A1 |
| 4-2-043 | 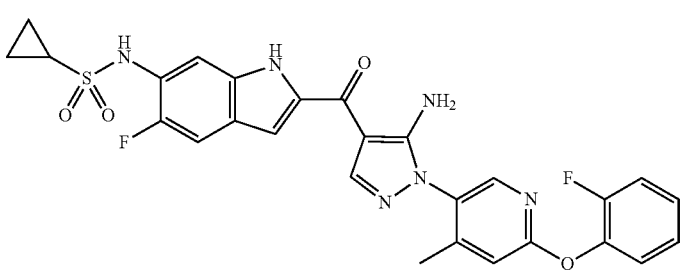 [SMILES: Cc1ccccc1Oc1cc(C)c(-n2ncc(C(=O)c3cc4cc(F)c(NS(=O)(=O)C5CC5)cc4[nH]3)c2N)cn1] | 565 | 0.77 | A1 |

-continued

| Example No. | Compound | m/z (M + H) | Retention Time (Minute) | LCMS Measurement Condition |
|---|---|---|---|---|
| 4-2-044 | | 583 | 0.79 | A1 |
| 4-2-045 | | 583 | 0.79 | A1 |
| 4-2-046 | | 599, 601 | 0.81 | A1 |
| 4-2-047 | | 561 | 0.79 | A1 |
| 4-2-048 | | 565 | 0.77 | A1 |

-continued

| Example No. | Compound | m/z (M + H) | Retention Time (Minute) | LCMS Measurement Condition |
|---|---|---|---|---|
| 4-2-049 | | 534 | 0.75 | A1 |
| 4-2-050 | | 552 | 2.38 | B1 |
| 4-2-051 | | 552 | 2.33 | B1 |
| 4-2-052 | | 535 | 2.12 | B1 |
| 4-2-053 | | 534 | 0.79 | A1 |
| 4-2-054 | | 552 | 2.48 | B1 |

| Example No. | Compound | m/z (M + H) | Retention Time (Minute) | LCMS Measurement Condition |
|---|---|---|---|---|
| 4-2-055 | | 552 | 1.44 | F1 |
| 4-2-056 | | 570 | 2.50 | B1 |
| 4-2-057 | | 570 | 2.48 | B1 |
| 4-2-058 | | 568, 570 | 0.83 | A1 |
| 4-2-059 | | 568, 570 | 0.86 | A1 |
| 4-2-060 | | 534 | 2.47 | B1 |

-continued

| Example No. | Compound | m/z (M + H) | Retention Time (Minute) | LCMS Measurement Condition |
|---|---|---|---|---|
| 4-2-061 | | 535 | 0.74 | A1 |
| 4-2-062 | | 553 | 0.76 | A1 |
| 4-2-063 | | 551, 553 | 2.33 | B1 |
| 4-2-064 | | 569, 571 | 2.41 | B1 |
| 4-2-065 | | 531 | 2.30 | B1 |

-continued

| Example No. | Compound | m/z (M + H) | Retention Time (Minute) | LCMS Measurement Condition |
|---|---|---|---|---|
| 4-2-066 | | 551, 553 | 2.39 | B1 |
| 4-2-067 | | 535 | 0.74 | A1 |
| 4-2-068 | | 580 | 0.83 | A1 |
| 4-2-069 | | 598 | 0.84 | A1 |
| 4-2-070 | | 598 | 0.83 | A1 |
| 4-2-071 | | 616 | 0.84 | A1 |

-continued
| Example No. | Compound | m/z (M + H) | Retention Time (Minute) | LCMS Measurement Condition |
|---|---|---|---|---|
| 4-2-072 | 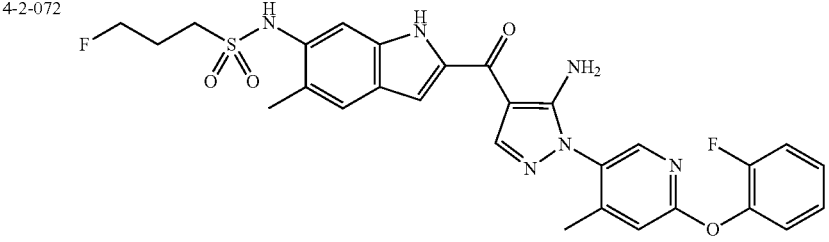 | 581 | 0.78 | A1 |
| 4-2-073 | 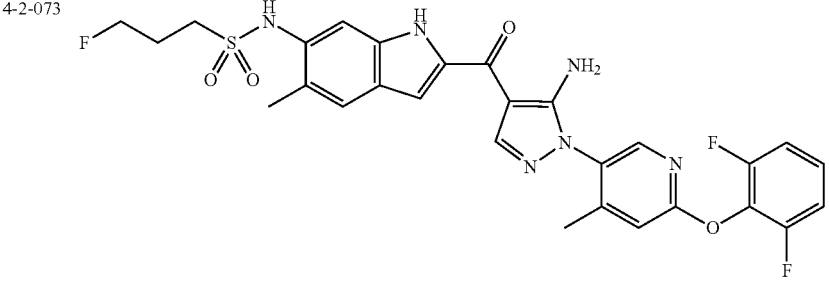 | 599 | 0.80 | A1 |
| 4-2-074 | 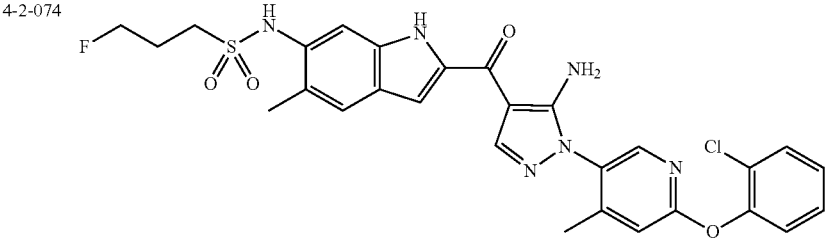 | 597, 599 | 0.54 | D1 |
| 4-2-075 | 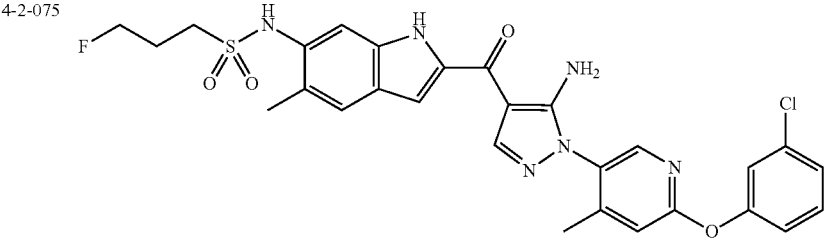 | 597, 599 | 0.57 | D1 |
| 4-2-076 | 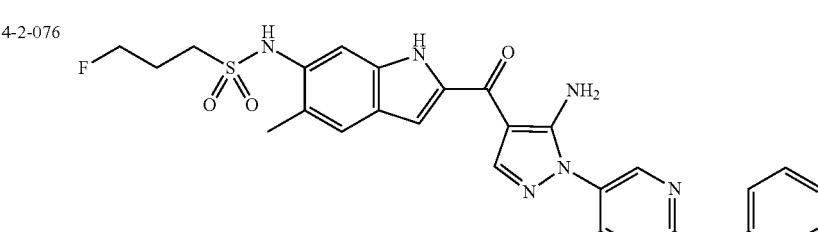 | 581 | 0.78 | A1 |

-continued

| Example No. | Compound | m/z (M + H) | Retention Time (Minute) | LCMS Measurement Condition |
|---|---|---|---|---|
| 4-2-077 | | 554, 556 | 2.49 | B1 |
| 4-2-078 | | 572, 574 | 2.58 | H3 |
| 4-2-079 | | 572, 574 | 2.52 | B1 |
| 4-2-080 | | 590, 592 | 0.84 | A1 |
| 4-2-081 | | 590, 592 | 0.83 | A1 |
| 4-2-082 | | 588, 590, 592 | 0.86 | A1 |

-continued

| Example No. | Compound | m/z (M + H) | Retention Time (Minute) | LCMS Measurement Condition |
|---|---|---|---|---|
| 4-2-083 | | 588, 590, 592 | 0.89 | A1 |
| 4-2-084 | | 554, 556 | 0.83 | A1 |
| 4-2-085 | | 555, 557 | 2.32 | B1 |
| 4-2-086 | | 573, 575 | 0.79 | A1 |
| 4-2-087 | | 573, 575 | 2.40 | B1 |

-continued

| Example No. | Compound | m/z (M + H) | Retention Time (Minute) | LCMS Measurement Condition |
|---|---|---|---|---|
| 4-2-088 | | 571, 573, 575 | 0.80 | A1 |
| 4-2-089 | | 589, 591, 593 | 0.82 | A1 |
| 4-2-090 | | 551, 553 | 0.80 | A1 |
| 4-2-091 | | 571, 573, 575 | 0.82 | A1 |
| 4-2-092 | | 555, 557 | 2.31 | B1 |

-continued

| Example No. | Compound | m/z (M + H) | Retention Time (Minute) | LCMS Measurement Condition |
|---|---|---|---|---|
| 4-2-093 | | 572, 574 | 2.40 | B1 |
| 4-2-094 | | 590, 592 | 2.45 | B1 |
| 4-2-095 | | 554, 556 | 2.41 | B1 |
| 4-2-096 | | 555, 557 | 0.73 | A1 |
| 4-2-097 | | 538 | 0.75 | A1 |
| 4-2-098 | | 556 | 0.77 | A1 |

-continued

| Example No. | Compound | m/z (M + H) | Retention Time (Minute) | LCMS Measurement Condition |
|---|---|---|---|---|
| 4-2-099 | | 556 | 0.76 | A1 |
| 4-2-100 | | 574 | 2.37 | B1 |
| 4-2-101 | | 574 | 2.36 | B1 |
| 4-2-102 | | 572, 574 | 2.43 | B1 |
| 4-2-103 | | 538 | 2.33 | B1 |
| 4-2-104 | | 539 | 2.11 | B1 |

-continued
| Example No. | Compound | m/z (M + H) | Retention Time (Minute) | LCMS Measurement Condition |
|---|---|---|---|---|
| 4-2-105 | 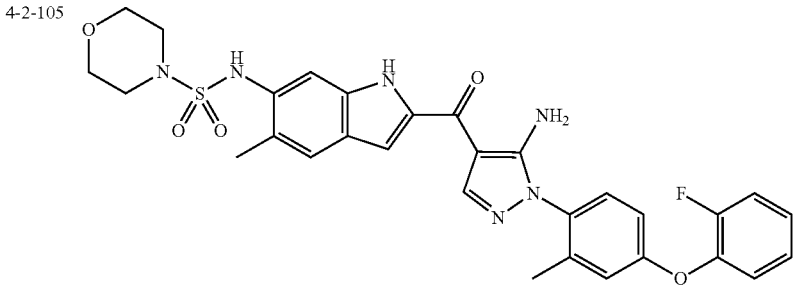 | 605 | 0.82 | A1 |
| 4-2-106 | 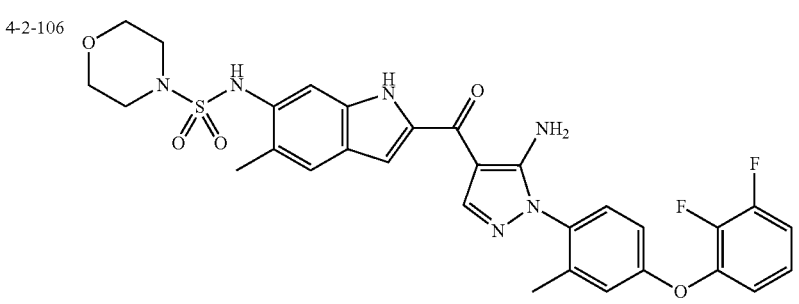 | 623 | 0.83 | A1 |
| 4-2-107 |  | 623 | 0.82 | A1 |
| 4-2-108 | 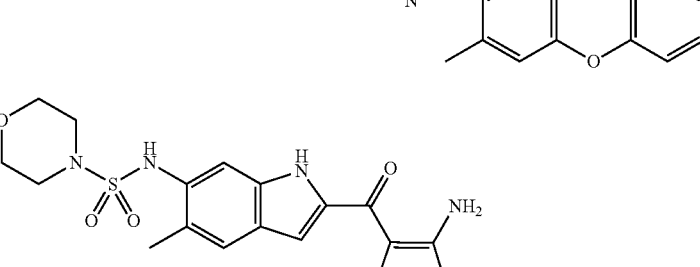 | 606 | 2.37 | B1 |
| 4-2-109 | 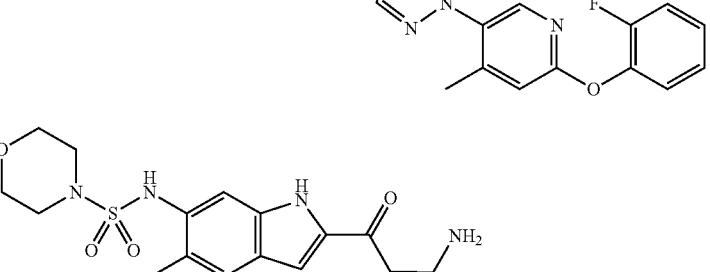 | 624 | 0.79 | A1 |

-continued

| Example No. | Compound | m/z (M + H) | Retention Time (Minute) | LCMS Measurement Condition |
|---|---|---|---|---|
| 4-2-110 | | 622, 624 | 0.80 | A1 |
| 4-2-111 | | 622, 624 | 0.82 | A1 |
| 4-2-112 | | 560 | 0.83 | A1 |
| 4-2-113 | | 578 | 0.84 | A1 |
| 4-2-114 | | 578 | 0.83 | A1 |

-continued
| Example No. | Compound | m/z (M + H) | Retention Time (Minute) | LCMS Measurement Condition |
|---|---|---|---|---|
| 4-2-115 | 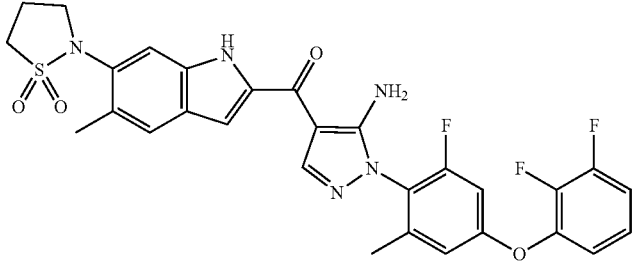 [SMILES: Cc1cc2cc(C(=O)c3cnn(-c4c(C)cc(Oc5cccc(F)c5F)cc4F)c3N)[nH]c2cc1N1CCCS1(=O)=O] | 596 | 0.84 | A1 |
| 4-2-116 | 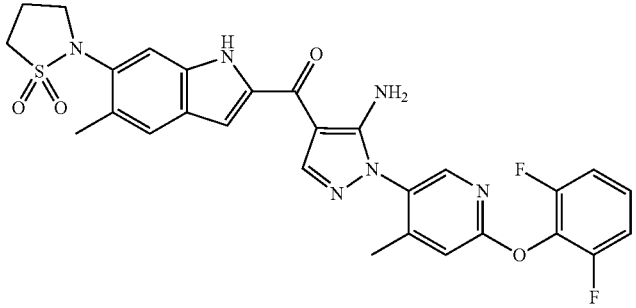 [SMILES: Cc1cc2cc(C(=O)c3cnn(-c4cnc(Oc5c(F)cccc5F)cc4C)c3N)[nH]c2cc1N1CCCS1(=O)=O] | 579 | 0.80 | A1 |
| 4-2-117 | 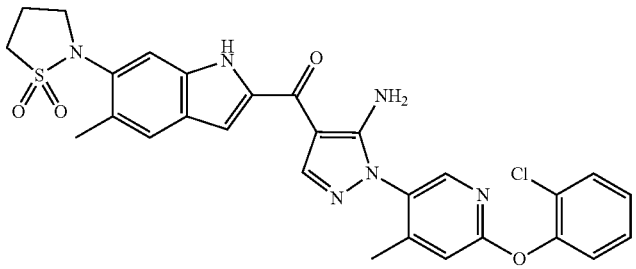 [SMILES: Cc1cc2cc(C(=O)c3cnn(-c4cnc(Oc5ccccc5Cl)cc4C)c3N)[nH]c2cc1N1CCCS1(=O)=O] | 577, 579 | 0.81 | A1 |
| 4-2-118 | 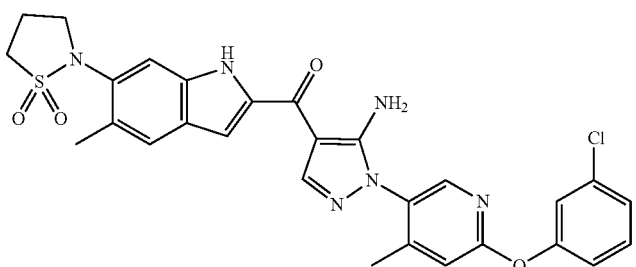 | 577, 579 | 0.83 | A1 |
| 4-2-119 | 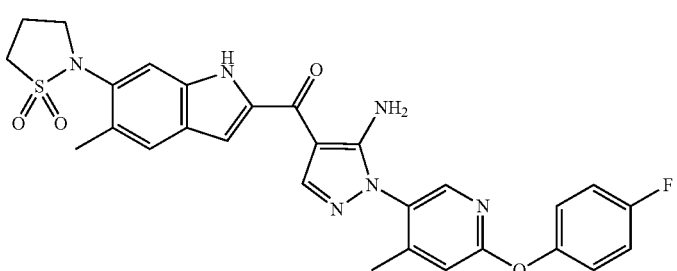 | 561 | 0.78 | A1 |

-continued

| Example No. | Compound | m/z (M + H) | Retention Time (Minute) | LCMS Measurement Condition |
|---|---|---|---|---|
| 4-2-120 | | 594 | 0.97 | J2 |
| 4-2-121 | | 595 | 0.94 | J3 |
| 4-2-122 | | 526 | 1.09 | J4 |
| 4-2-123 | | 527 | 1.06 | J2 |
| 4-2-124 | | 545 | 1.10 | J1 |

-continued

| Example No. | Compound | m/z (M + H) | Retention Time (Minute) | LCMS Measurement Condition |
|---|---|---|---|---|
| 4-2-125 | | 528 | 1.11 | J1 |
| 5-1-001 | | 572 | 1.11 | TFA Rev.5 |
| 5-1-002 | | 574 | 1.08 | TFA Rev.5 |
| 5-1-003 | | 590 | 1.13 | TFA Rev.5 |

| Example No. | Compound | m/z (M + H) | Retention Time (Minute) | LCMS Measurement Condition |
|---|---|---|---|---|
| 5-1-004 | | 556 | 0.97 | AA Rev.2 |
| 5-1-005 | | 570 | 1.1 | TFA Rev.5 |
| 5-1-006 | | 574 | 1.04 | AA Rev.2 |
| 5-1-007 | | 556 | 1.04 | AA Rev.2 |

-continued
| Example No. | Compound | m/z (M + H) | Retention Time (Minute) | LCMS Measurement Condition |
|---|---|---|---|---|
| 5-1-008 | 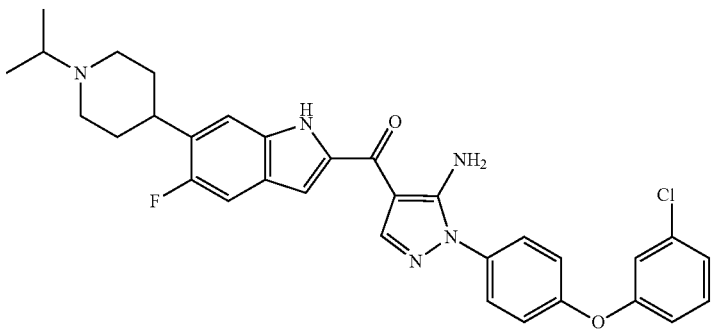 | 572 | 1.11 | AA Rev.2 |
| 5-1-009 | 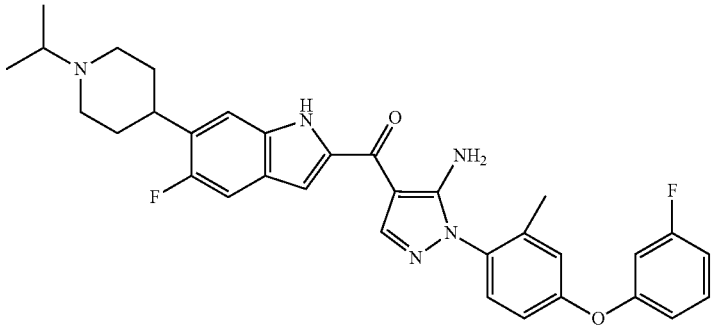 [SMILES: Cc1cc(Oc2cccc(F)c2)ccc1-n1ncc(C(=O)c2cc3cc(F)c(C4CCN(C(C)C)CC4)cc3[nH]2)c1N] | 570 | 1.06 | AA Rev.2 |
| 5-1-010 | 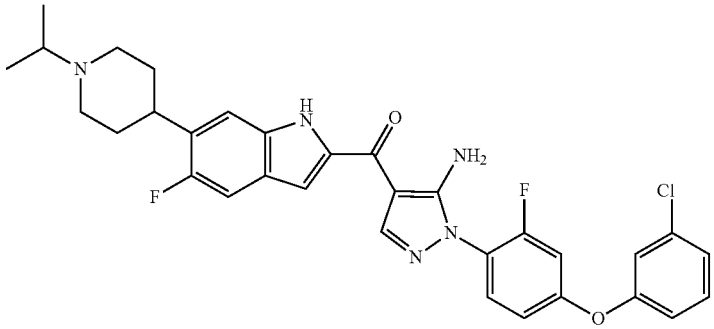 [SMILES: CC(C)N1CCC(c2cc3[nH]c(C(=O)c4cnn(-c5ccc(Oc6cccc(Cl)c6)cc5F)c4N)cc3cc2F)CC1] | 590 | 1.08 | AA Rev.2 |
| 5-1-011 | 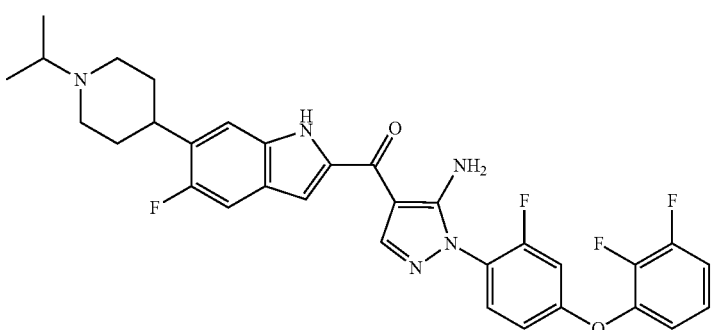 | 592 | 1.12 | TFA Rev.5 |

| Example No. | Compound | m/z (M + H) | Retention Time (Minute) | LCMS Measurement Condition |
|---|---|---|---|---|
| 5-1-012 | 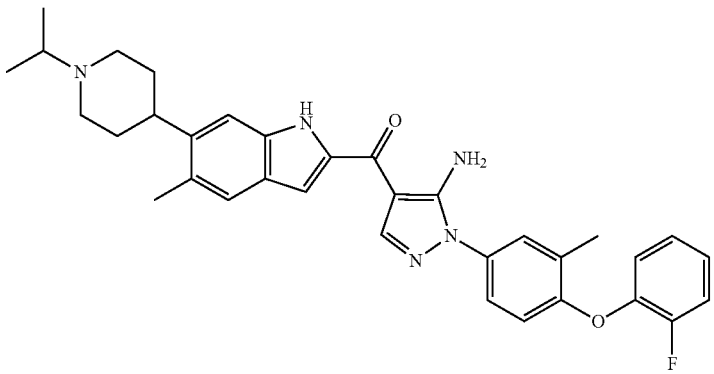 [SMILES: Cc1cc(-n2ncc(C(=O)c3cc4cc(C)c(C5CCN(C(C)C)CC5)cc4[nH]3)c2N)ccc1Oc1ccccc1F] | 566 | 1.06 | AA Rev.2 |
| 5-1-013 | 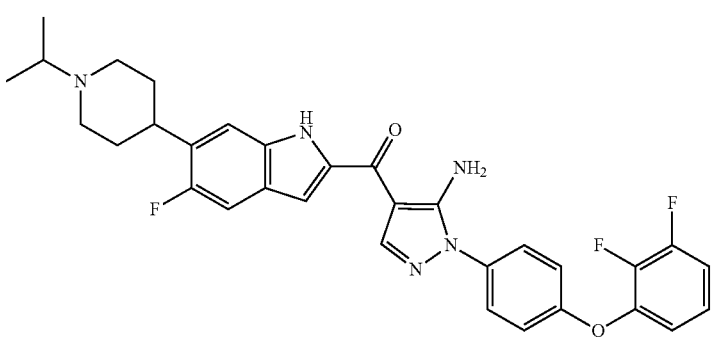 [SMILES: CC(C)N1CCC(c2cc3[nH]c(C(=O)c4cnn(-c5ccc(Oc6cccc(F)c6F)cc5)c4N)cc3cc2F)CC1] | 574 | 1.04 | AA Rev.2 |
| 5-1-014 | 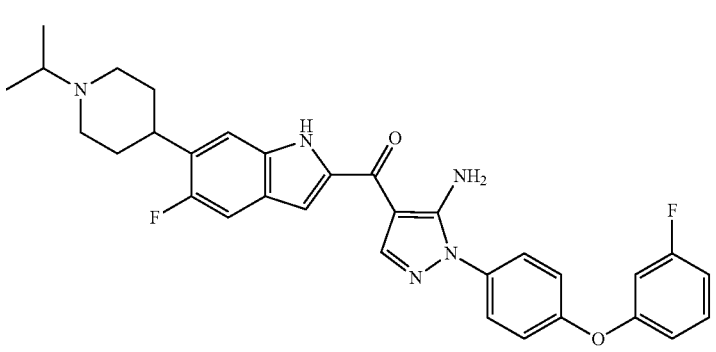 [SMILES: CC(C)N1CCC(c2cc3[nH]c(C(=O)c4cnn(-c5ccc(Oc6cccc(F)c6)cc5)c4N)cc3cc2F)CC1] | 556 | 1.05 | AA Rev.2 |
| 5-1-015 | 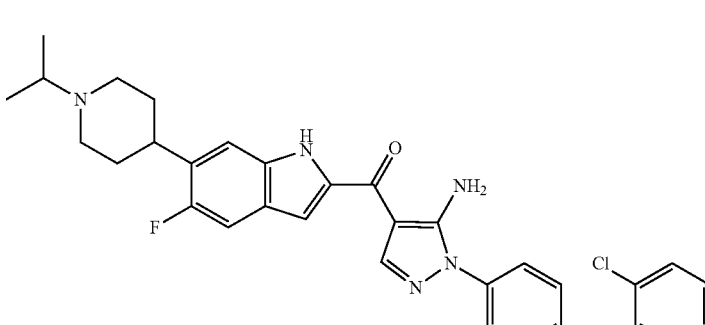 | 572 | 1.06 | AA Rev.2 |

-continued

| Example No. | Compound | m/z (M + H) | Retention Time (Minute) | LCMS Measurement Condition |
|---|---|---|---|---|
| 5-1-016 | | 576 | 1.42 | AA Rev.3 |
| 5-1-017 | | 538 | 1.45 | AA Rev.3 |
| 5-1-018 | | 558 | 1.39 | AA Rev.3 |
| 5-1-019 | | 586 | 1.4 | AA Rev.3 |
| 5-1-022 | | 560 | 0.98 | AA Rev.11 |

-continued

| Example No. | Compound | m/z (M + H) | Retention Time (Minute) | LCMS Measurement Condition |
|---|---|---|---|---|
| 5-1-023 | | 592 | 1.42 | AA Rev.3 |
| 5-1-024 | | 610 | 1.44 | AA Rev.3 |
| 5-1-025 | | 618 | 1.45 | AA Rev.3 |
| 5-1-026 | | 636 | 1.47 | AA Rev.3 |
| 5-1-027 | | 606 | 1.41 | AA Rev.3 |
| 5-1-028 | | 656 | 1.3 | TFA Rev.5 |

| Example No. | Compound | m/z (M + H) | Retention Time (Minute) | LCMS Measurement Condition |
|---|---|---|---|---|
| 5-1-030 | | 578 | 0.99 | AA Rev.11 |
| 5-1-031 | | 604 | 1.43 | AA Rev.3 |
| 5-1-032 | | 552 | 0.99 | AA Rev.4 |
| 5-1-033 | | 638 | 1.29 | TFA Rev.5 |
| 5-1-034 | | 624 | 1.01 | AA Rev.11 |

| Example No. | Compound | m/z (M + H) | Retention Time (Minute) | LCMS Measurement Condition |
|---|---|---|---|---|
| 5-1-035 | | 589 | 1.14 | TFA Rev.5 |
| 5-1-036 | | 605 | 0.98 | AA Rev.11 |
| 5-1-037 | | 621 | 0.97 | AA Rev.4 |
| 5-1-038 | | 557 | 0.96 | AA Rev.4 |
| 5-1-039 | | 539 | 1.19 | TFA Rev.5 |

| Example No. | Compound | m/z (M + H) | Retention Time (Minute) | LCMS Measurement Condition |
|---|---|---|---|---|
| 5-1-040 | 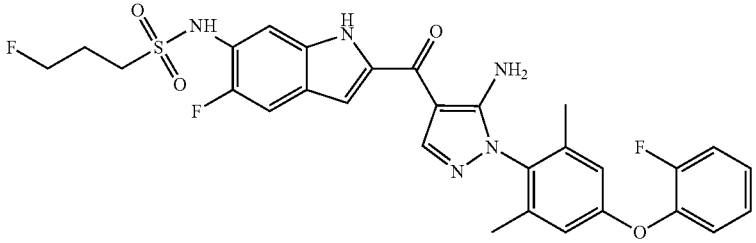 | 598 | 1 | AA Rev.4 |
| 5-1-041 | 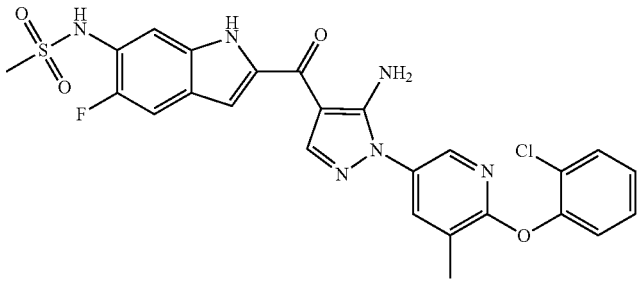 [SMILES: Cc1cc(-n2ncc(C(=O)c3cc4cc(F)c(NS(C)(=O)=O)cc4[nH]3)c2N)cnc1Oc1ccccc1F] | 555 | 1.23 | TFA Rev.5 |
| 5-1-042 | 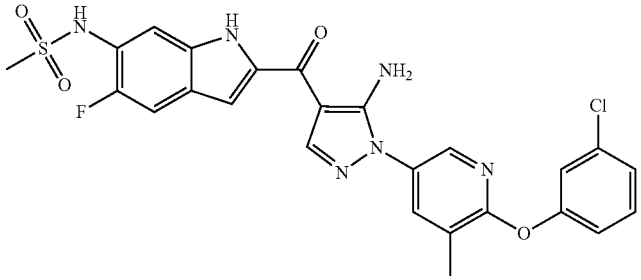 [SMILES: Cc1cc(-n2ncc(C(=O)c3cc4cc(F)c(NS(C)(=O)=O)cc4[nH]3)c2N)cnc1Oc1cccc(Cl)c1] | 555 | 1.02 | AA Rev.4 |
| 5-1-043 | 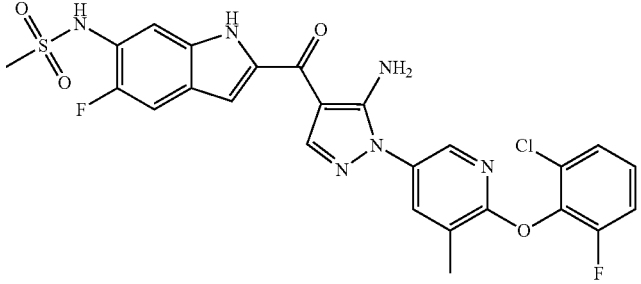 [SMILES: Cc1cc(-n2ncc(C(=O)c3cc4cc(F)c(NS(C)(=O)=O)cc4[nH]3)c2N)cnc1Oc1c(F)cccc1Cl] | 573 | 1 | AA Rev.4 |
| 5-1-044 | 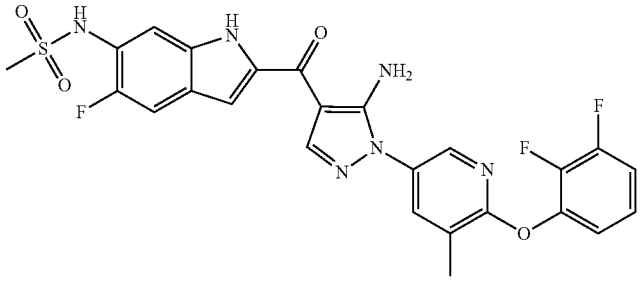 [SMILES: Cc1cc(-n2ncc(C(=O)c3cc4cc(F)c(NS(C)(=O)=O)cc4[nH]3)c2N)cnc1Oc1cccc(F)c1F] | 557 | 0.98 | AA Rev.4 |

-continued
| Example No. | Compound | m/z (M + H) | Retention Time (Minute) | LCMS Measurement Condition |
|---|---|---|---|---|
| 5-1-045 | 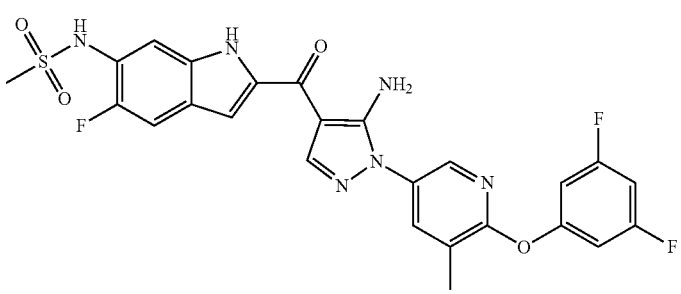 [SMILES: Cc1cc(-n2ncc(C(=O)c3cc4cc(F)c(NS(C)(=O)=O)cc4[nH]3)c2N)cnc1Oc1cc(F)cc(F)c1] | 557 | 1 | AA Rev.4 |
| 5-1-046 | 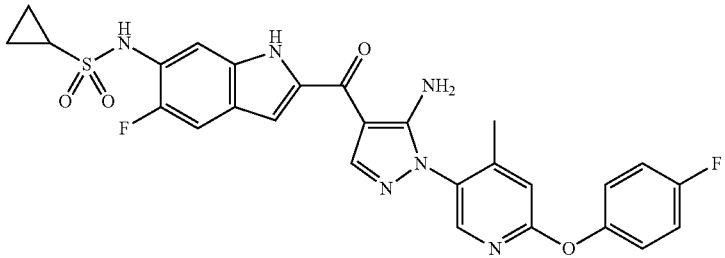 [SMILES: Cc1cc(Oc2ccc(F)cc2)ncc1-n1ncc(C(=O)c2cc3cc(F)c(NS(=O)(=O)C4CC4)cc3[nH]2)c1N] | 565 | 1.18 | TFA Rev.5 |
| 5-1-047 | 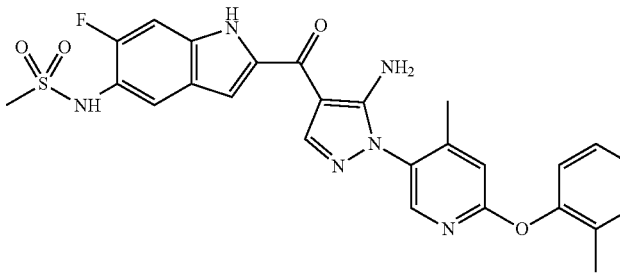 | 535 | 1.12 | TFA Rev.5 |
| 5-1-048 | 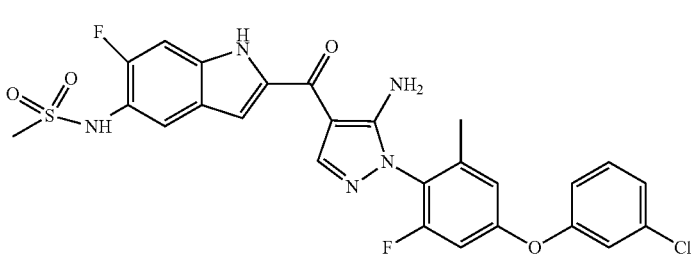 [SMILES: Cc1cc(Oc2cccc(Cl)c2)cc(F)c1-n1ncc(C(=O)c2cc3cc(NS(C)(=O)=O)c(F)cc3[nH]2)c1N] | 572 | 1.24 | TFA Rev.5 |
| 5-1-049 | 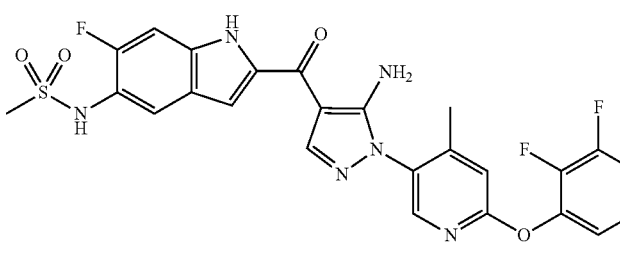 | 557 | 0.91 | AA Rev.4 |

-continued

| Example No. | Compound | m/z (M + H) | Retention Time (Minute) | LCMS Measurement Condition |
|---|---|---|---|---|
| 5-1-050 | | 555 | 1.13 | TFA Rev.5 |
| 5-1-051 | | 569 | 0.99 | AA Rev.5 |
| 5-1-052 | | 569 | 1.22 | TFA Rev.5 |
| 5-1-053 | | 571 | 0.99 | AA Rev.5 |
| 5-1-054 | | 571 | 1 | AA Rev.5 |
| 5-1-055 | | 589 | 1.24 | TFA Rev.5 |

-continued

| Example No. | Compound | m/z (M + H) | Retention Time (Minute) | LCMS Measurement Condition |
|---|---|---|---|---|
| 5-1-059 | | 585 | 0.98 | AA Rev.5 |
| 5-1-060 | | 553 | 0.96 | AA Rev.5 |
| 5-1-063 | | 617 | 1.01 | AA Rev.5 |
| 5-1-064 | | 606 | 0.99 | AA Rev.5 |
| 5-1-065 | | 642 | 1.01 | AA Rev.5 |
| 5-1-066 | | 641 | 1.03 | AA Rev.5 |

-continued
| Example No. | Compound | m/z (M + H) | Retention Time (Minute) | LCMS Measurement Condition |
|---|---|---|---|---|
| 5-1-077 | 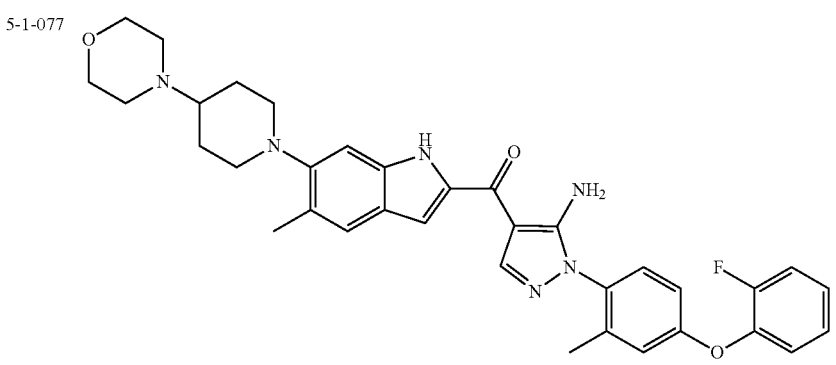 | 609 | 1.1 | AA Rev.10 |
| 5-1-078 | 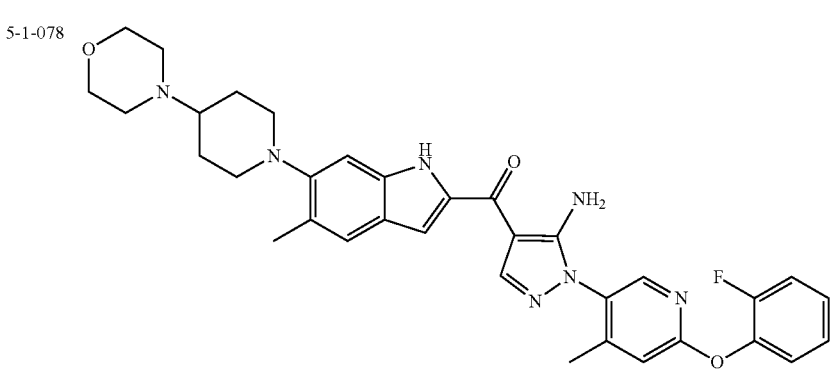 | 610 | 1.07 | AA Rev.10 |
| 5-1-080 | 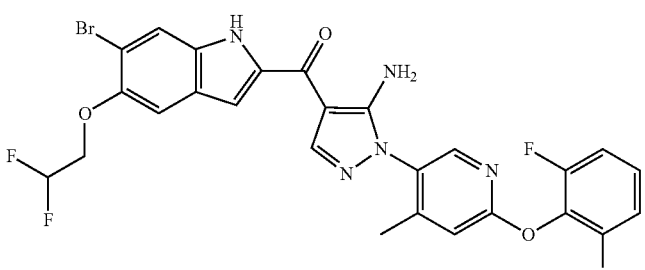 | 604 | 1.07 | AA Rev.11 |
| 5-1-081 | 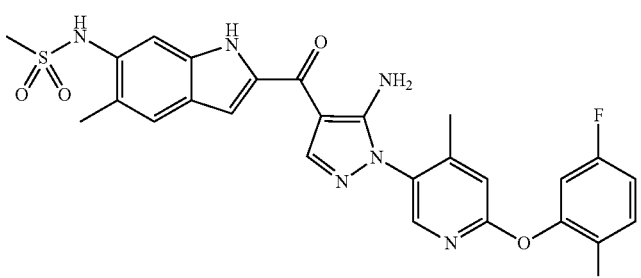 | 553 | 0.98 | AA Rev.11 |

-continued

| Example No. | Compound | m/z (M + H) | Retention Time (Minute) | LCMS Measurement Condition |
|---|---|---|---|---|
| 5-1-082 | | 571 | 1.1 | AA Rev.11 |
| 5-1-084 | | 544 | 1.12 | AA Rev.11 |
| 5-1-085 | | 627 | 1.11 | TFA Rev.5 |
| 5-1-086 | | 602 | 1.36 | TFA Rev.5 |

-continued

| Example No. | Compound | m/z (M + H) | Retention Time (Minute) | LCMS Measurement Condition |
|---|---|---|---|---|
| 5-1-090 | | 603 | 1.04 | AA Rev.11 |
| 5-1-091 | | 621 | 1.05 | AA Rev.11 |
| 5-1-092 | | 552 | 1 | AA Rev.11 |
| 5-1-096 | | 568 | 1.03 | AA Rev.11 |

-continued

| Example No. | Compound | m/z (M + H) | Retention Time (Minute) | LCMS Measurement Condition |
|---|---|---|---|---|
| 5-1-107 | | 552 | 1.01 | AA Rev.11 |
| 5-1-108 | | 516 | 1.02 | AA Rev.11 |
| 5-1-109 | | 517 | 0.95 | AA Rev.11 |
| 5-1-111 | | 620 | 1.07 | AA Rev.11 |
| 5-1-123 | | 629 | 1.37 | TFA Rev.5 |

| Example No. | Compound | m/z (M + H) | Retention Time (Minute) | LCMS Measurement Condition |
|---|---|---|---|---|
| 5-1-132 | | 566 | 1.33 | TFA Rev.5 |
| 5-1-133 | | 567 | 1.06 | AA Rev.11 |
| 5-1-138 | | 584 | 1.08 | AA Rev.11 |
| 5-1-139 | | 585 | 1.06 | AA Rev.11 |

| Example No. | Compound | m/z (M + H) | Retention Time (Minute) | LCMS Measurement Condition |
|---|---|---|---|---|
| 5-1-140 | | 570 | 1.3 | TFA Rev.5 |
| 5-1-141 | | 567 | 1.3 | TFA Rev.5 |
| 5-1-142 | | 586 | 1.27 | TFA Rev.5 |
| 5-1-144 | | 647 | 1.08 | AA Rev.11 |

-continued

| Example No. | Compound | m/z (M + H) | Retention Time (Minute) | LCMS Measurement Condition |
|---|---|---|---|---|
| 5-1-145 | | 536 | 1.06 | AA Rev.11 |
| 5-1-147 | | 590 | 1.11 | AA Rev.11 |
| 5-1-149 | | 590 | 1.08 | AA Rev.11 |
| 5-1-150 | | 585 | 1.42 | TFA Rev.5 |
| 5-1-151 | | 590 | 1.14 | AA Rev.11 |

| Example No. | Compound | m/z (M + H) | Retention Time (Minute) | LCMS Measurement Condition |
|---|---|---|---|---|
| 5-1-152 | | 571 | 1.45 | TFA Rev.5 |
| 5-1-155 | | 609 | 1.09 | AA Rev.11 |

Example 4-2-126

Synthesis of N-{5-amino-1-[4-(2,6-difluorophenoxy)-2-methylphenyl]pyrazole-4-carbonyl}-5-fluoro-1H-indol-6-yl}-N-ethylmethanesulfonamide

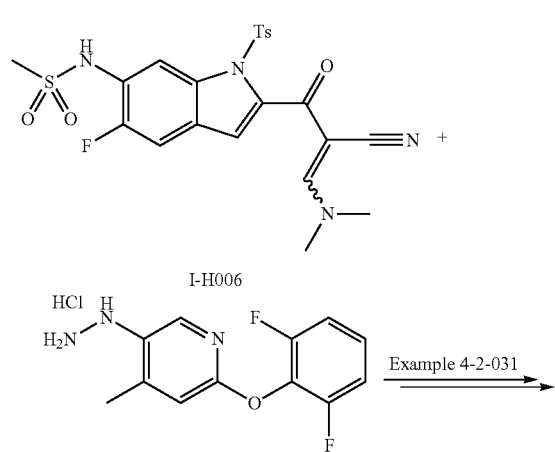

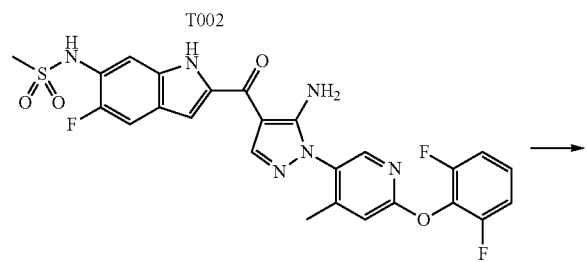

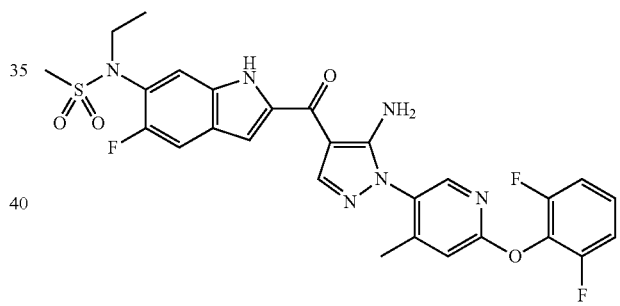

The methanesulfonamide synthesized in Example 4-2-031 (50 mg) was suspended in toluene (0.9 mL), and cyanomethylenetri-n-butylphosphorane (35 μL) and ethanol (8 μL) were added. Then the mixture was stirred at 100° C. for one hour. The reaction solution was purified by silica gel column chromatography (hexane/ethyl acetate) to give the target compound (34 mg).

Examples 4-2-127 to 4-2-128 and Example 5-1-067

The compounds of Examples 4-2-127 to Example 4-2-128 and Example 5-1-067 shown below were synthesized by the similar method as in Example 4-2-126 using the corresponding alcohols shown below.

(Corresponding Enamines, Hydrazines, and Alcohols (Alkylating Reagents))
| Example No. | Enamine | Hydrazine | Alkylating Reagent |
|---|---|---|---|
| 4-2-126 | I-H006 | T002 HCl | |
| 4-2-127 | I-H006 | T002 HCl | |
| 4-2-128 | I-H006 | T002 HCl | |
| 5-1-067 | I-H006 | T002 HCl | |
(Synthesized Compounds)
| Example No. | Compound | m/z (M + H) | Retention Time (Minute) | LCMS Measurement Condition |
|---|---|---|---|---|
| 4-2-126 | | 585 | 1.02 | J4 |

-continued

| Example No. | Compound | m/z (M + H) | Retention Time (Minute) | LCMS Measurement Condition |
|---|---|---|---|---|
| 4-2-127 | | 641 | 1.00 | J1 |
| 4-2-128 | | 670 | 1.00 | J1 |
| 5-1-067 | | 599 | 1.04 | AA Rev.5 |

Examples 4-2-129 and 4-2-130
Synthesis of N-{2-{5-amino-1-[4-(2,6-difluorophenoxy)-2-methylphenyl]pyrazole-4-carbonyl}-6-(2-morpholin-4-ylethoxy)-1H-indol-5-yl}methanesulfonamide and N-{2-{5-amino-1-[4-(2,6-difluorophenoxy)-2-methylphenyl]pyrazole-4-carbonyl}-6-hydroxy-1H-indol-5-yl}-N-(2-morpholin-4-ylethyl)methanesulfonamide
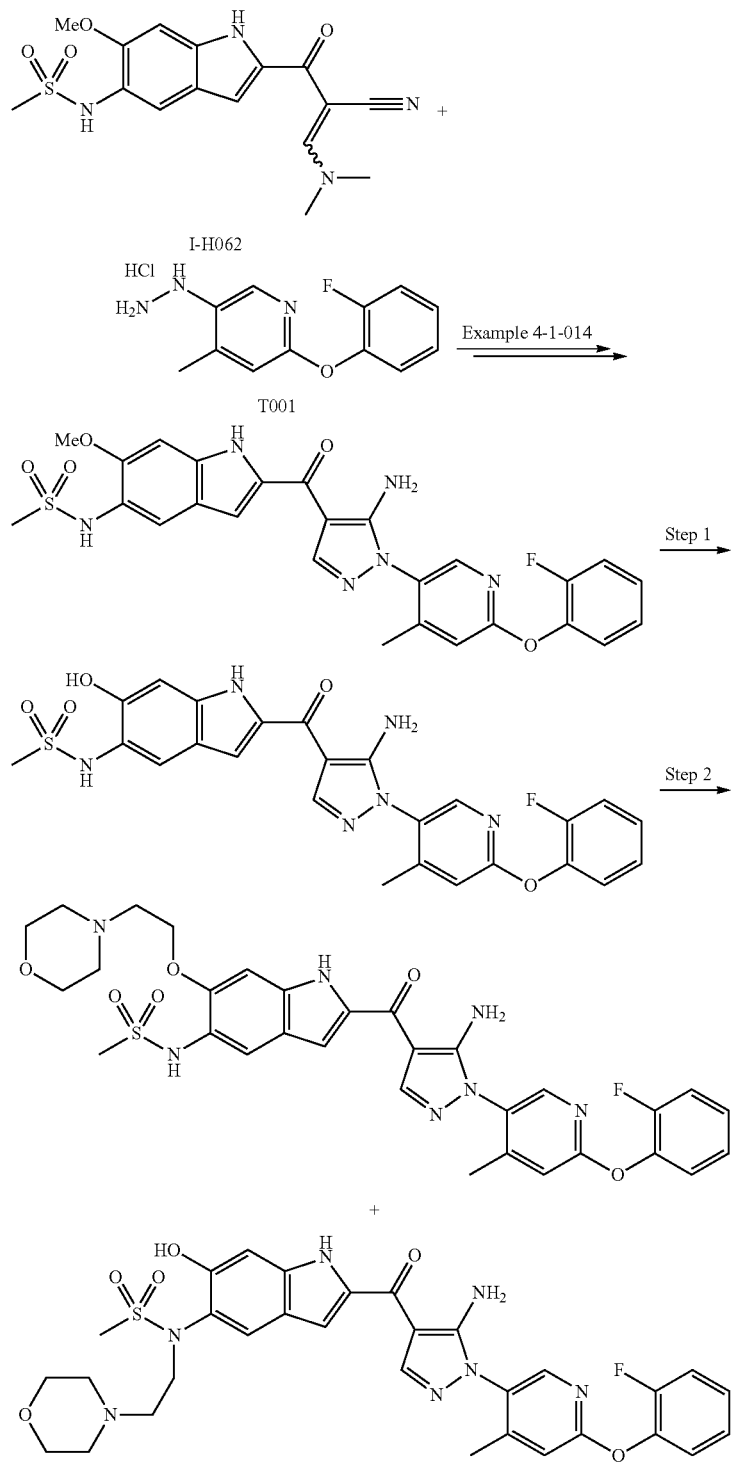

Step 1

Synthesis of N-{2-{5-amino-1-[4-(2,6-difluorophenoxy)-2-methylphenyl]pyrazole-4-carbonyl}-6-hydroxy-1H-indol-5-yl}methanesulfonamide The methanesulfonamide synthesized in Example 4-1-014 (41 mg) was suspended in dichloromethane (1.5 mL), and boron tribromide (1.0 M solution in dichloromethane, 0.8 mL) was added at 0° C. Then the mixture was stirred at 25° C. for 24 hours. A 5% aqueous sodium bicarbonate solution was added to the reaction solution, the mixture was extracted with ethyl acetate, and the organic layer was dried over sodium sulfate. The drying agent was removed by filtration, the filtrate was then concentrated under reduced pressure, and the resulting residue was purified by column chromatography (ethyl acetate) to give the target compound (32 mg).

Step 2

Synthesis of N-{2-{5-amino-1-[4-(2,6-difluorophenoxy)-2-methylphenyl]pyrazole-4-carbonyl}-6-(2-morpholin-4-ylethoxy)-1H-indol-5-yl}methanesulfonamide and N-{2-{5-amino-1-[4-(2,6-difluorophenoxy)-2-methylphenyl]pyrazole-4-carbonyl}-6-hydroxy-1H-indol-5-yl}-N-(2-morpholin-4-ylethyl)methanesulfonamide N-{2-{5-Amino-1-[4-(2,6-difluorophenoxy)-2-methylphenyl]pyrazole-4-carbonyl}-6-hydroxy-1H-indol-5-yl}methanesulfonamide (32 mg) and triphenylphosphine (17 mg) were dissolved in tetrahydrofuran (1.0 mL), and 4-(2-hydroxyethyl)morpholine (8 μL) and diisopropyl azodicarboxylate (13 μL) were added. Then the mixture was stirred at 25° C. for 3.5 hours. A 1 M aqueous sodium hydroxide solution was added to the reaction solution and the mixture was extracted with ethyl acetate. The organic layer was washed with saturated saline and dried over sodium sulfate. The drying agent was removed by filtration and the filtrate was then concentrated under reduced pressure. The resulting residue was purified by Prep-HPLC and then by column chromatography (hexane/ethyl acetate) to give the target compounds, an O-alkylated compound (5.1 mg) and an N-alkylated compound (4.4 mg).

(Corresponding Enamines and Hydrazines)

| Example No. | | Enamine | | Hydrazine |
|---|---|---|---|---|
| 4-2-129 | I-H062 | | T001 | HCl |
| 4-2-130 | I-H062 | | T001 | HCl |

(Synthesized Compounds)

| Example No. | Compound | m/z (M + H) | Retention Time (Minute) | LCMS Measurement Condition |
|---|---|---|---|---|
| 4-2-129 | | 650 | 0.91 | J4 |
| 4-2-130 | | 650 | 0.90 | J4 |

Example 4-3-001

Synthesis of {5-amino-1-[4-(2,3-difluorophenoxy)-2-fluoro-6-methylphenyl]pyrazol-4-yl}-(6-amino-5-fluoro-1H-indol-2-yl)methanone

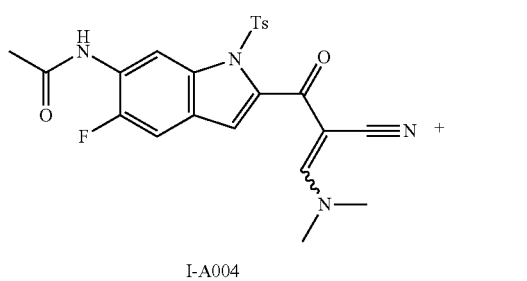

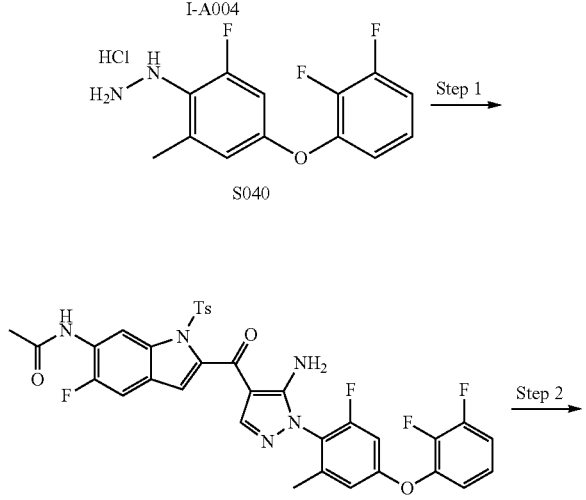

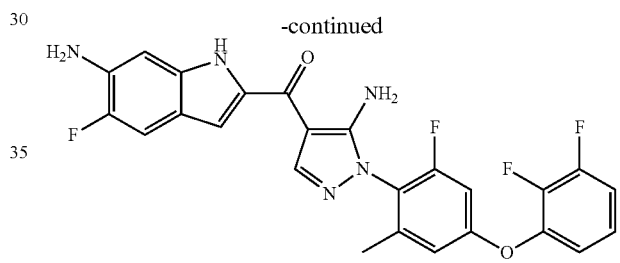

Step 1

Synthesis of N-{2-{5-amino-1-[4-(2,3-difluorophenoxy)-2-fluoro-6-methylphenyl]pyrazole-4-carbonyl}-5-fluoro-1-(4-methylphenyl)sulfonylindol-6-yl}acetamide Enamine I-A004 (317 mg) and hydrazine S040 (172 mg) were dissolved in 1-methyl-2-pyrrolidone (0.5 mL), and N-methylmorpholine (186 μL) was added. Then the atmosphere in the flask was replaced by nitrogen, and the mixture was stirred at 100° C. The reaction solution was cooled to 25° C., water (3.0 mL) was added, and the mixture was extracted with ethyl acetate. The organic layer was washed with water (10 mL) three times and dried over sodium sulfate. The drying agent was removed by filtration and the filtrate was then concentrated under reduced pressure to give the target compound (390 mg).

Step 2

Synthesis of {5-amino-1-[4-(2,3-difluorophenoxy)-2-fluoro-6-methylphenyl]pyrazol-4-yl}-(6-amino-5-fluoro-1H-indol-2-yl)methanone N-{2-{5-Amino-1-[4-(2,3-difluorophenoxy)-2-fluoro-6-methylphenyl]pyrazole-4-carbonyl}-5-fluoro-1-(4-methylphenyl)sulfonylindol-6-yl}acetamide (390 mg) was dissolved in methanesulfonic acid (1.6 mL), and water (0.5 mL)

was added. Then the mixture was stirred at 100° C. for 20 hours. The reaction solution was cooled to 0° C., and water (3 ml), a 5 M aqueous sodium hydroxide solution (4.7 mL), and a saturated aqueous sodium bicarbonate solution (10 mL) were added. Then the mixture was extracted with ethyl acetate (10 mL) twice. The combined organic layers were dried over sodium sulfate. The drying agent was removed by filtration, the filtrate was then concentrated under reduced pressure, and the resulting residue was purified by column chromatography (hexane/ethyl acetate) to give the target compound (207 mg).

(Corresponding Enamine and Hydrazine)

| Example No. | Enamine | Hydrazine |
|---|---|---|
| 4-3-001 | I-A004 | S040 |

(Synthesized Compound)

| Example No. | Compound | m/z (M + H) | Retention Time (Minute) | LCMS Measurement Condition |
|---|---|---|---|---|
| 4-3-001 | | 496 | 0.81 | A1 |

Example 4-4-001

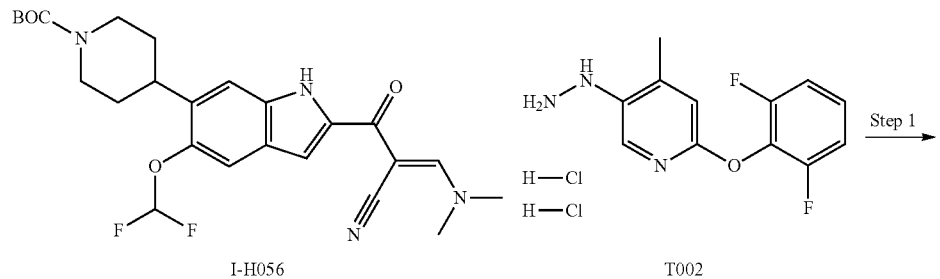

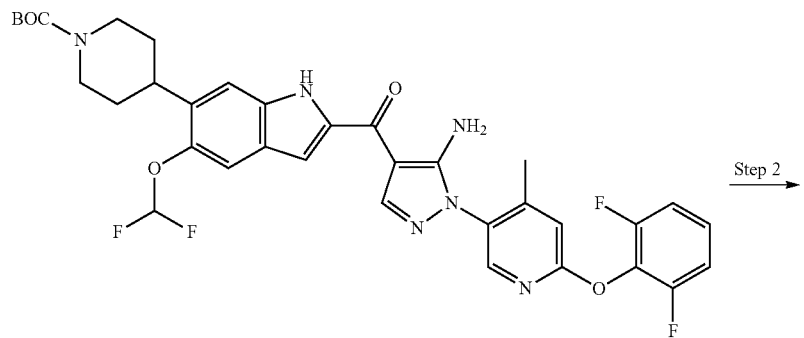

-continued

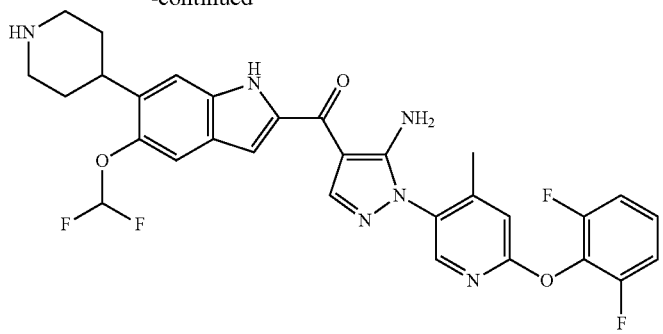

Step 1

Synthesis of tert-butyl 4-(2-(5-amino-1-(6-(2,6-difluorophenoxy)-4-methylpyridin-3-yl)-1H-pyrazole-4-carbonyl)-5-(difluoromethoxy)-1H-indol-6-yl)piperidine-1-carboxylate Enamine I-H056 (500 mg) and hydrazine T002 (172 mg) were dissolved in 1-methyl-2-pyrrolidone (0.52 mL), and N-methylmorpholine (293 μL) was added. Then the atmosphere in the flask was replaced by nitrogen, and the mixture was stirred at 100° C. for one hour. The reaction solution was cooled to 25° C., water (6.0 mL) was added, and the resulting precipitate was collected by filtration, washed with water (10 mL), and washed with hexane (5 mL). The powder was purified by silica gel column chromatography (hexane/ethyl acetate, 2%→55%) to give the target compound (589 mg).

Step 2

Synthesis of (5-amino-1-(6-(2,6-difluorophenoxy)-4-methylpyridin-3-yl)-1H-pyrazol-4-yl)(5-(difluoromethoxy)-6-(piperidin-4-yl)-1H-indol-2-yl)methanone tert-Butyl 4-(2-(5-amino-1-(6-(2,6-difluorophenoxy)-4-methylpyridin-3-yl)-1H-pyrazole-4-carbonyl)-5-(difluoromethoxy)-1H-indol-6-yl)piperidine-1-carboxylate (589 mg) was added to trifluoroethanol (11.8 mL), and TMSCl (1.08 mL) was added at 25° C. Then the mixture was stirred for one hour. The reaction solution was concentrated under reduced pressure and the resulting residue was crystallized from ethanol/hexane (1/5, 5 mL). The crystals were collected by filtration and washed with ethanol/hexane (1/5, 10 mL) to give the target compound (459 mg).
(Corresponding Enamine and Hydrazine)

| Example No. | Enamine | | Hydrazine | |
|---|---|---|---|---|
| 4-4-001 | I-H056 | [structure: Boc-piperidine-indole with difluoromethoxy, acryl nitrile enamine] | T002 | HCl [structure: hydrazinyl-methylpyridine with 2,6-difluorophenoxy] |

(Synthesized Compound)

| Example No. | Compound | m/z (M + H) | Retention Time (Minute) | LCMS Measurement Condition |
|---|---|---|---|---|
| 4-4-001 | [structure of final compound] | 595 | 0.93 | J4 |

Example 4-5-001

Synthesis of N-{2-{5-amino-1-[6-(2-fluorophenoxy)-4-methylpyridin-3-yl]pyrazole-4-carbonyl}-5-fluoro-1H-indol-6-yl}morpholine-4-sulfonamide

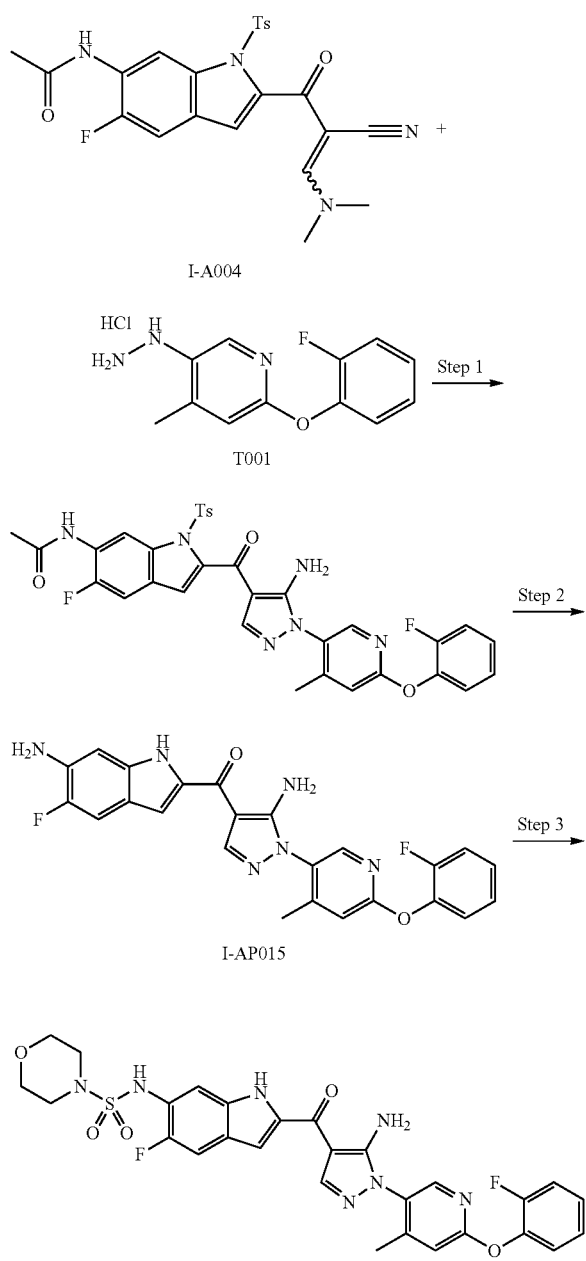

Step 1

Synthesis of N-{2-{5-amino-1-[6-(2-fluorophenoxy)-4-methylpyridin-3-yl]pyrazole-4-carbonyl}-5-fluoro-1-(4-methylphenyl)sulfonylindol-6-yl}acetamide Enamine I-A004 (3.31 g), hydrazine T001 (2.6 g), and N-methylmorpholine (1.86 mL) were dissolved in 1-methyl-2-pyrrolidone (33 mL) and the reaction solution was stirred at 100° C. for three hours in a nitrogen atmosphere. The reaction solution was cooled to 25° C., water (40 mL) was added, and the mixture was suspended in ethyl acetate/hexane/t-butyl methyl ether. The precipitate was collected by filtration and then washed with tert-butyl methyl ether and then with ethyl acetate/hexane (1/5) to provide a powder of the target compound. The filtrate was concentrated under reduced pressure, and the resulting residue was purified by silica gel column chromatography (hexane/ethyl acetate=30%→100%) and combined with the previously obtained precipitate to provide the target compound (5.57 g).

Step 2

Synthesis of (6-amino-5-fluoro-1H-indol-2-yl)-{5-amino-1-[6-(2-fluorophenoxy)-4-methylpyridin-3-yl]pyrazol-4-yl}methanone (I-AP015)

N-{2-{5-Amino-1-[6-(2-fluorophenoxy)-4-methylpyridin-3-yl]pyrazole-4-carbonyl}-5-fluoro-1-(4-methylphenyl)sulfonylindol-6-yl}acetamide (1.98 g) was dissolved in methanesulfonic acid (6.0 mL), and water (2.0 mL) was added. Then the mixture was stirred at 95° C. for six hours. The reaction solution was cooled to 0° C. and adjusted to pH 8 to 9 with a 5 M aqueous NaOH solution, after which the mixture was extracted with ethyl acetate (100 mL) twice, and the combined organic layers were dried over sodium sulfate. The drying agent was removed by filtration, the filtrate was then concentrated under reduced pressure, and the resulting residue was purified by silica gel column chromatography (hexane/ethyl acetate=0%→85%) to give the target compound (1.04 g).

Step 3

Synthesis of N-{2-{5-amino-1-[6-(2-fluorophenoxy)-4-methylpyridin-3-yl]pyrazole-4-carbonyl}-5-fluoro-1H-indol-6-yl}morpholine-4-sulfonamide (6-Amino-5-fluoro-1H-indol-2-yl)-{5-amino-1-[6-(2-fluorophenoxy)-4-methylpyridin-3-yl]pyrazol-4-yl}methanone (70 mg) was dissolved in pyridine (1.2 mL), and morpholine-4-sulfonyl chloride (230 mg) was added. Then the mixture was stirred at 25° C. for 15 hours. 0.1 M hydrochloric acid was added to the reaction solution and the mixture was extracted with ethyl acetate twice. The organic layers were washed with a saturated aqueous sodium chloride solution and dried over sodium sulfate. The drying agent was removed by filtration, the filtrate was then concentrated under reduced pressure, and the resulting residue was purified by chromatography (hexane/ethyl acetate). The eluate containing the target compound was concentrated under reduced pressure and the resulting residue was crystallized from hexane/dichloromethane to give the target compound (58 mg).

Examples 4-5-002 to 4-5-012, Example 5-1-057, and the Like

The compounds of Examples 4-5-002 to 4-5-012, Example 5-1-057, and the like were synthesized from corresponding hydrazines and from corresponding sulfamidating reagents in Step 3 by the similar method as in Example 4-5-001.

(Corresponding Enamines, Hydrazines, and Sulfamidating Reagents)

| Example No. | Enamine | | Hydrazine | | Sulfamidating Reagent | |
|---|---|---|---|---|---|---|
| 4-5-001 | I-A004 | [structure] | T001 | HCl [structure] | 1828-66-6 | [structure] |
| 4-5-002 | I-A004 | [structure] | Q001 | HCl [structure] | 1828-66-6 | [structure] |
| 4-5-003 | I-A004 | [structure] | Q001 | HCl [structure] | SFA-001 | [structure] |
| 4-5-004 | I-A004 | [structure] | Q001 | HCl [structure] | SFA-002 | [structure] |
| 4-5-005 | I-A004 | [structure] | Q001 | HCl [structure] | SFA-003 | [structure] |
| 4-5-006 | I-A004 | [structure] | Q001 | HCl [structure] | SFA-004 | [structure] |
| 4-5-007 | I-A004 | [structure] | Q001 | HCl [structure] | SFA-005 | [structure] |
| 4-5-008 | I-A004 | [structure] | Q001 | HCl [structure] | SFA-006 | [structure] |

-continued
| Example No. | Enamine | Hydrazine | Sulfamidating Reagent |
|---|---|---|---|
| 4-5-009 | I-A004 | Q001 HCl | SFA-007 |
| 4-5-010 | I-A004 | Q001 HCl | SFA-008 |
| 4-5-011 | I-A004 | S040 HCl | 1828-66-6 |
| 4-5-012 | I-A004 | T001 HCl | SFA-001 |
| 5-1-057 | I-H057 | T001 HCl | SFA-001 |
| 5-1-029 | I-A004 | Q001 HCl | By-product of 4-5-007 |
(Synthesized Compounds)
| Example No. | Compound | m/z (M + H) | Retention Time (Minute) | LCMS Measurement Condition |
|---|---|---|---|---|
| 4-5-001 |  | 610 | 2.32 | B1 |

| Example No. | Compound | m/z (M + H) | Retention Time (Minute) | LCMS Measurement Condition |
|---|---|---|---|---|
| 4-5-002 | | 609 | 2.49 | B1 |
| 4-5-003 | | 623 | 3.45 | B2 |
| 4-5-004 | | 581 | 0.84 | A1 |
| 4-5-005 | | 595 | 2.34 | B1 |
| 4-5-006 | | 593 | 2.66 | B1 |
| 4-5-007 | | 597 | 2.45 | 81 |
| 4-5-008 | | 609 | 2.40 | B1 |
| 4-5-009 | | 569 | 2.50 | B1 |

-continued

| Example No. | Compound | m/z (M + H) | Retention Time (Minute) | LCMS Measurement Condition |
|---|---|---|---|---|
| 4-5-010 | | 579 | 0.82 | A1 |
| 4-5-011 | | 645 | 3.69 | B2 |
| 4-5-012 | | 624 | 2.25 | B1 |
| 5-1-057 | | 620 | 0.98 | AA Rev.5 |
| 5-1-029 | | 556 | 1.48 | AA Rev.3 |

Example 4-6-001

Synthesis of {5-amino-1-[6-(2-fluorophenoxy)-4-methylpyridin-3-yl]pyrazol-4-yl}-[5-fluoro-6-(2-hydroxyethylsulfamoylamino)-1H-indol-2-yl]methanone

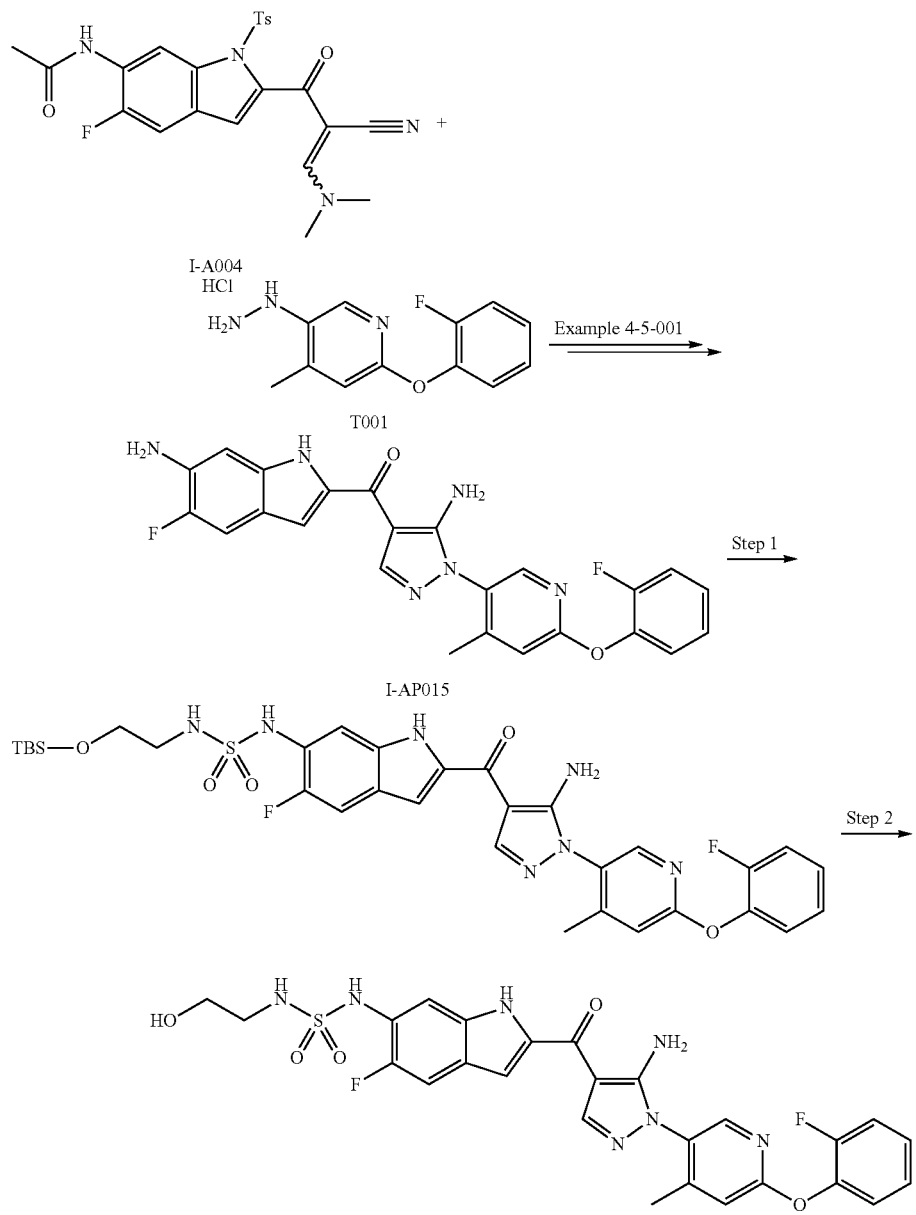

Step 1

Synthesis of {5-amino-1-[6-(2-fluorophenoxy)-4-methylpyridin-3-yl]pyrazol-4-yl}-{6-[2-(tert-butyldimethylsilyl)oxyethylsulfamoylamino]-5-fluoro-1H-indol-2-yl}methanone Aniline I-AP015 synthesized in Example 4-5-001 (51 mg) was dissolved in acetonitrile (1.0 mL), and TEA (44 μL) and N-[2-(tert-butyldimethylsilyl)oxyethyl]-2-oxo-1,3-oxazolidine-3-sulfonamide SFB-001 (70 mg) were added. Then the mixture was stirred at 80° C. for three hours. TEA (444) was added and the mixture was further stirred at 80° C. for eight hours. N-[2-(tert-Butyldimethylsilyl)oxyethyl]-2-oxo-1,3-oxazolidine-3-sulfonamide SFB-001 (27 mg) was added and the mixture was further stirred at 80° C. for five hours. N-[2-(tert-Butyldimethylsilyl)oxyethyl]-2-oxo-1,3-oxazolidine-3-sulfonamide SFB-001 (27 mg) was added and the mixture was further stirred at 80° C. for two hours. The reaction solution was cooled to 25° C. and concentrated under reduced pressure. The resulting residue was purified by chromatography (hexane/ethyl acetate) to give the target compound (103 mg).

Step 2

Synthesis of {5-amino-1-[6-(2-fluorophenoxy)-4-methylpyridin-3-yl]pyrazol-4-yl}-[5-fluoro-6-(2-hydroxyethylsulfamoylamino)-1H-indol-2-yl]methanone {5-Amino-1-[6-(2-fluorophenoxy)-4-methylpyridin-3-yl]pyrazol-4-yl}-{6-[2-(tert-butyldimethylsilyl)oxyethylsulfamoylamino]-5-fluoro-1H-indol-2-yl}methanone (97 mg) was dissolved in 2,2,2-trifluoroethanol (2.0 mL), and TMSCl (394) was added. Then the mixture was stirred at 0° C. for 1.5 hours. A saturated aqueous sodium bicarbonate solution (20 mL) was added to the reaction solution, the mixture was extracted with ethyl acetate (100 mL) twice, and the organic layers were dried over sodium sulfate. The drying agent was removed by filtration and the filtrate was concentrated under reduced pressure. The resulting residue was crystallized from hexane/ethyl acetate to give the target compound (57 mg).

Examples 4-6-002 to 4-6-004

The compounds of Examples 4-6-002 to 4-6-004 were synthesized by the similar method as in Example 4-6-001 using the corresponding hydrazines and using the corresponding sulfamidating reagents in Step 1.

(Corresponding Enamines, Hydrazines, and Sulfamidating Reagents)

| Example No. | Enamine | Hydrazine | Sulfamidating Reagent |
|---|---|---|---|
| 4-6-001 | I-A004 | T001 | SFB-001 |
| 4-6-002 | I-A004 | Q001 | SFB-001 |
| 4-6-003 | I-A004 | Q001 | SFC-002 |
| 4-6-004 | I-A004 | Q001 | SFC-001 |

(Synthesized Compounds)

| Example No. | Compound | m/z (M + H) | Retention Time (Minute) | LCMS Measurement Condition |
|---|---|---|---|---|
| 4-6-001 | | 584 | 0.68 | A1 |

| Example No. | Compound | m/z (M + H) | Retention Time (Minute) | LCMS Measurement Condition |
|---|---|---|---|---|
| 4-6-002 | | 583 | 2.23 | B1 |
| 4-6-003 | | 611 | 2.39 | B1 |
| 4-6-004 | | 611 | 2.36 | B1 |

Example 4-7-001

Synthesis of N-{2-{5-amino-1-[6-(2-fluorophenoxy)-4-methylpyridin-3-yl]pyrazole-4-carbonyl}-5-fluoro-1H-indol-6-yl}methanesulfonamide

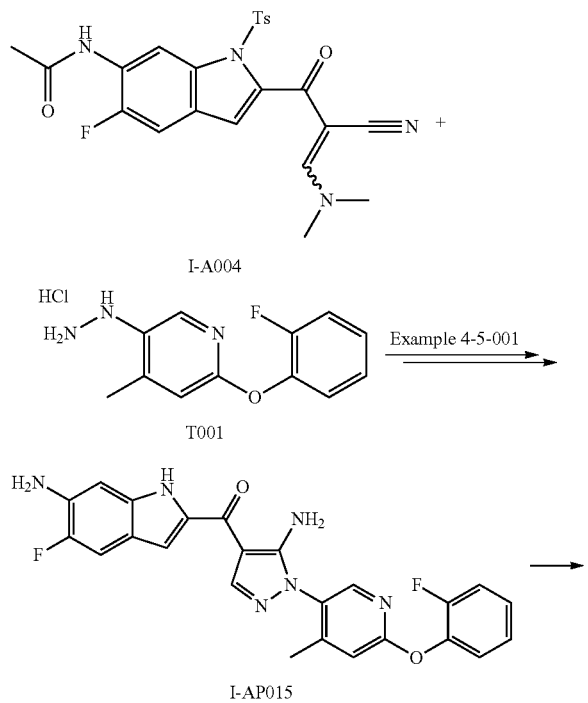

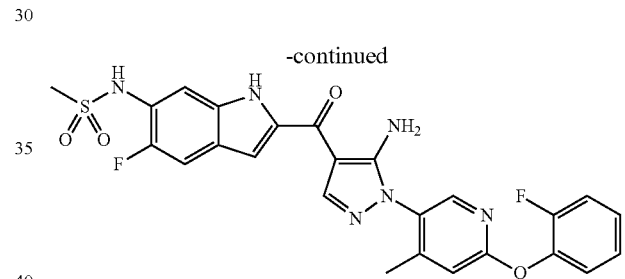

Aniline I-AP015 synthesized in Example 4-5-001 (344 mg) was dissolved in pyridine (5.0 mL), and methanesulfonyl chloride (87 μL) was added. Then the mixture was stirred at 25° C. for one hour. Water (10 mL) was added to the reaction solution and the mixture was extracted with ethyl acetate (50 mL). The organic layer was washed with 1 M hydrochloric acid (10 mL) twice and with saturated saline (10 mL) and dried over sodium sulfate. The drying agent was removed by filtration, the filtrate was then concentrated under reduced pressure, and the resulting residue was purified by column chromatography (hexane/ethyl acetate). The eluate containing the target compound was concentrated under reduced pressure and the resulting residue was then crystallized from hexane/dichloromethane to give the target compound (276 mg).

Examples 4-7-002 to 4-7-016, Example 5-1-266, and the Like

The compounds of Examples 4-7-002 to 4-7-016, Example 5-1-266, and the like were synthesized by the similar method as in Example 4-7-001 using the corresponding enamines, hydrazines, and sulfonamidating reagents.

(Corresponding Enamines, Hydrazines, and Sulfonamidating Reagents)

| Example No. | | Enamine | | Hydrazine | Sulfonamidating Reagent |
|---|---|---|---|---|---|
| 4-7-001 | I-A004 | (structure) | T001 | HCl (structure) | (structure) |
| 4-7-002 | I-A004 | (structure) | Q001 | HCl (structure) | (structure) |
| 4-7-003 | I-A004 | (structure) | S038 | HCl (structure) | (structure) |
| 4-7-004 | I-A004 | (structure) | S038 | HCl (structure) | (structure) |
| 4-7-005 | I-A004 | (structure) | S040 | HCl (structure) | (structure) |
| 4-7-006 | I-A004 | (structure) | S040 | HCl (structure) | (structure) |
| 4-7-007 | I-A004 | (structure) | S041 | HCl (structure) | (structure) |
| 4-7-008 | I-A004 | (structure) | S041 | HCl (structure) | (structure) |

-continued

| Example No. | | Enamine | | Hydrazine | | Sulfonamidating Reagent |
|---|---|---|---|---|---|---|
| 4-7-009 | I-A004 | (enamine structure with acetamido-fluoro-indole-Ts, C(O), C=CH-N(CH3)2, CN) | S042 | (same enamine structure) | | methanesulfonyl chloride |
| 4-7-010 | I-A004 | (same enamine structure) | S042 | HCl, H2N-NH-aryl (F, 2-chlorophenoxy, methyl) | | cyclopropanesulfonyl chloride |
| 4-7-011 | I-A004 | (same enamine structure) | S045 | HCl, H2N-NH-aryl (F, 3-chlorophenoxy, methyl) | | methanesulfonyl chloride |
| 4-7-012 | I-A004 | (same enamine structure) | S045 | HCl, H2N-NH-aryl (F, 3-chlorophenoxy, methyl) | | cyclopropanesulfonyl chloride |
| 4-7-013 | I-A004 | (same enamine structure) | S047 | HCl, H2N-NH-aryl (F, phenoxy, methyl) | | methanesulfonyl chloride |
| 4-7-014 | I-A004 | (same enamine structure) | S047 | HCl, H2N-NH-aryl (F, phenoxy, methyl) | | cyclopropanesulfonyl chloride |
| 4-7-015 | I-A004 | (same enamine structure) | T007 | HCl, H2N-NH-pyridyl (Cl, 2-chlorophenoxy, methyl) | | cyclopropanesulfonyl chloride |
| 4-7-016 | I-A004 | (same enamine structure) | T011 | HCl, H2N-NH-pyridyl (3-chlorophenoxy, methyl) | | cyclopropanesulfonyl chloride |

-continued
| Example No. | Enamine | | Hydrazine | | Sulfonamidating Reagent |
|---|---|---|---|---|---|
| 5-1-266 | I-A012 | 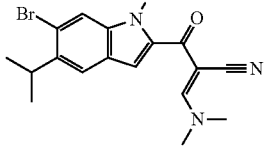 | Q001 | HCl 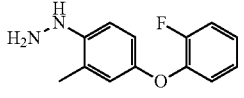 | No Reagent |
| 5-1-267 | I-A012 | 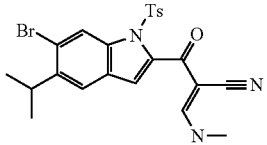 | Q001 | HCl 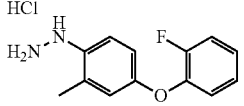 [SMILES: Cl ; Cc1cc(Oc2ccccc2F)ccc1NN] |  |
| 5-1-269 | I-H057 | 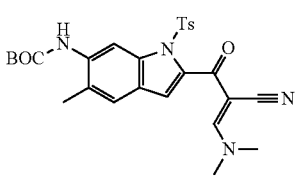 [SMILES: Cc1ccc(S(=O)(=O)n2c(C(=O)/C(C#N)=C/N(C)C)cc3cc(C)c(NC(=O)OC(C)(C)C)cc32)cc1] | T002 | HCl 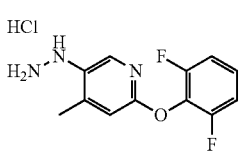 [SMILES: Cl ; Cc1cc(Oc2c(F)cccc2F)ncc1NN] | 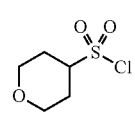 |
| 5-1-280 | I-A012 | 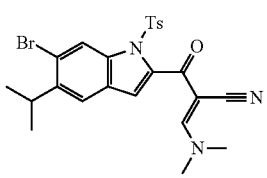 [SMILES: Cc1ccc(S(=O)(=O)n2c(C(=O)/C(C#N)=C/N(C)C)cc3cc(C(C)C)c(Br)cc32)cc1] | Q001 | HCl 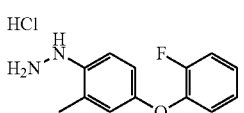 |  |
| 5-1-281 | I-H067 | 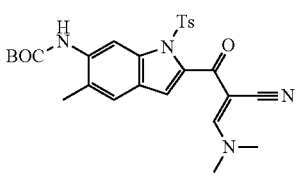 [SMILES: Cc1ccc(S(=O)(=O)n2c(C(=O)/C(C#N)=C/N(C)C)cc3cc(C)c(NC(=O)OC(C)(C)C)cc32)cc1] | T002 | HCl 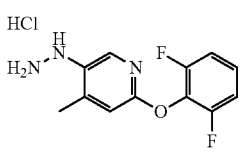 [SMILES: Cl ; Cc1cc(Oc2c(F)cccc2F)ncc1NN] | 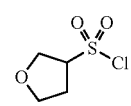 |
| 5-1-282 | I-A012 | 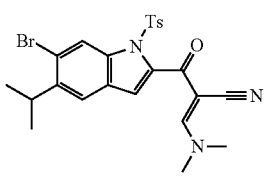 [SMILES: Cc1ccc(S(=O)(=O)n2c(C(=O)/C(C#N)=C/N(C)C)cc3cc(C(C)C)c(Br)cc32)cc1] | Q001 | HCl 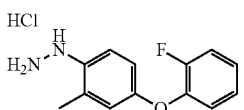 | 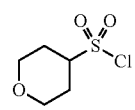 |
| 5-1-296 | I-A011 | 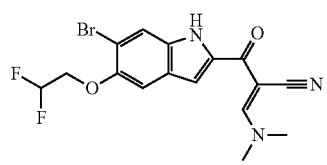 [SMILES: CN(C)/C=C(\C#N)C(=O)c1cc2cc(OCC(F)F)c(Br)cc2[nH]1] | T002 | HCl 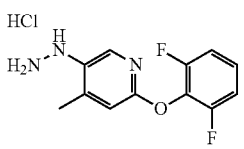 [SMILES: Cl ; Cc1cc(Oc2c(F)cccc2F)ncc1NN] | 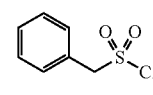 |
| 5-1-297 | I-A011 | 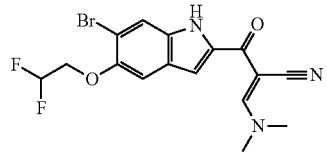 [SMILES: CN(C)/C=C(\C#N)C(=O)c1cc2cc(OCC(F)F)c(Br)cc2[nH]1] | T002 | HCl 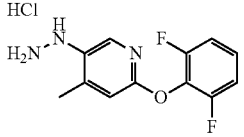 [SMILES: Cl ; Cc1cc(Oc2c(F)cccc2F)ncc1NN] | 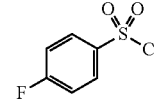 |
| 5-1-298 | I-A011 | 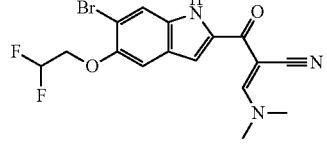 | T002 | HCl 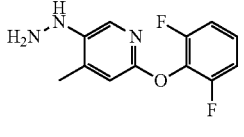 | 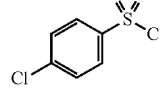 |

-continued

| Example No. | | Enamine | Hydrazine | | Sulfonamidating Reagent |
|---|---|---|---|---|---|
| 5-1-299 | I-A011 | (structure) | T002 | (structure) | (structure) |
| 5-1-300 | I-A011 | (structure) | T002 | (structure) | (structure) |
| 5-1-301 | I-A011 | (structure) | T002 | (structure) | (structure) |
| 5-1-304 | I-A012 | (structure) | T002 | (structure) | (structure) |
| 5-1-305 | I-A012 | (structure) | T002 | (structure) | (structure) |
| 5-1-305 | I-A012 | (structure) | T002 | (structure) | (structure) |
| 5-1-314 | I-H057 | (structure) | T002 | (structure) | (structure) |
| 5-1-315 | I-A011 | (structure) | T002 | (structure) | (structure) |
| 5-1-317 | I-H057 | (structure) | T002 | (structure) | (structure) |

-continued

| Example No. | Enamine | | Hydrazine | | Sulfonamidating Reagent |
|---|---|---|---|---|---|
| 5-1-318 | I-A011 | | T002 | | |
| 5-1-319 | I-A011 | | T002 | | |
| 5-1-320 | I-H075 | | T002 | | |
| 5-1-325 | I-A011 | | Q001 | | |
| 5-1-326 | I-A011 | | T001 | | |
| 5-1-327 | I-A011 | | T002 | | |
| 5-1-328 | I-A011 | | T002 | | |
| 5-1-329 | I-A011 | | T002 | | |
| 5-1-330 | I-A011 | | T002 | | |

-continued
| Example No. | | Enamine | | Hydrazine | | Sulfonamidating Reagent |
|---|---|---|---|---|---|---|
| 5-1-331 | I-A011 | 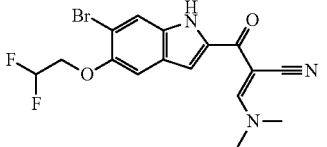 [SMILES: CN(C)/C=C(\C#N)C(=O)c1cc2cc(OCC(F)F)c(Br)cc2[nH]1] | Q001 | 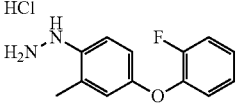 [SMILES: Cl ; Cc1cc(Oc2ccccc2F)ccc1NN] | | 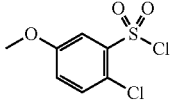 |
| 5-1-333 | I-H057 | 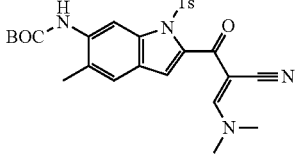 | T001 |  | | 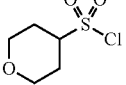 |
| 5-1-339 | I-H075 | 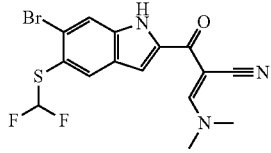 | T001 | 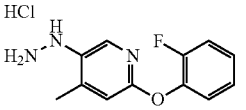 [SMILES: Cl ; Cc1cc(Oc2ccccc2F)ncc1NN] | | 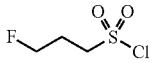 |
| 5-1-346 | I-H075 | 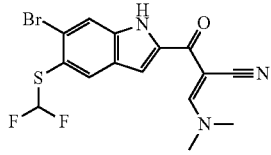 | T002 | 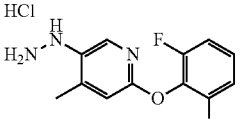 | | 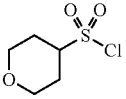 |
| 5-1-347 | I-H057 | 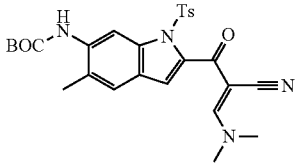 [SMILES: Cc1ccc(S(=O)(=O)n2c(C(=O)/C(C#N)=C/N(C)C)cc3cc(C)c(NC(=O)OC(C)(C)C)cc32)cc1] | Q001 | 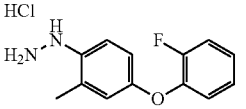 [SMILES: Cl ; Cc1cc(Oc2ccccc2F)ccc1NN] | | 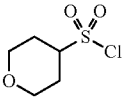 |
| 5-1-378 | I-A004 | 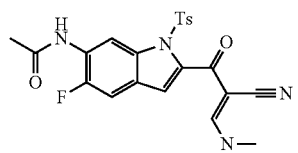 | T001 | 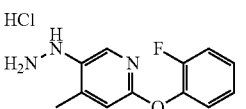 | | 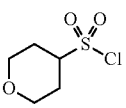 |
| 5-1-380 | B-B026 | 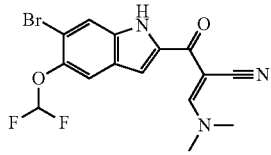 [SMILES: CN(C)/C=C(\C#N)C(=O)c1cc2cc(OC(F)F)c(Br)cc2[nH]1] | T002 | 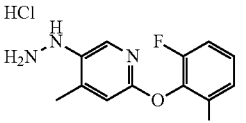 | | 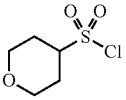 |
| 5-1-381 | I-A004 | 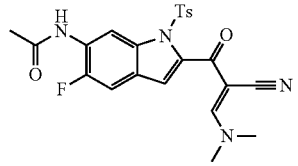 [SMILES: CC(=O)Nc1cc2c(cc1F)cc(C(=O)/C(C#N)=C/N(C)C)n2S(=O)(=O)c1ccc(C)cc1] | T002 | 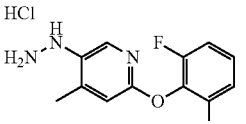 | | 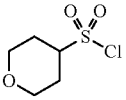 |
| 5-1-382 | I-A011 | 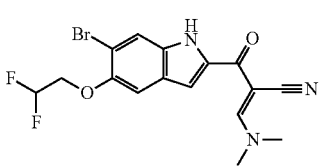 [SMILES: CN(C)/C=C(\C#N)C(=O)c1cc2cc(OCC(F)F)c(Br)cc2[nH]1] | T002 | 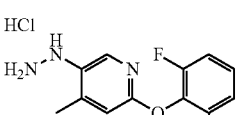 | | 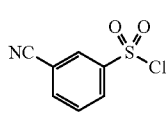 |

-continued

| Example No. | | Enamine | | Hydrazine | Sulfonamidating Reagent |
|---|---|---|---|---|---|
| 5-1-383 | I-A011 | (structure) | T002 | HCl (structure) | (3-chlorobenzenesulfonyl chloride) |
| 5-1-384 | I-A011 | (structure) | T002 | HCl (structure) | (pyridine-3-sulfonyl chloride) |
| 5-1-389 | I-A004 | (structure) | Q001 | HCl (structure) | (tetrahydropyran-4-sulfonyl chloride) |
| 5-1-390 | B-B026 | (structure) | Q001 | HCl (structure) | (tetrahydropyran-4-sulfonyl chloride) |
| 5-1-395 | I-H078 | (structure) | T002 | HCl (structure) | No Reagent |
| 5-1-396 | I-H078 | (structure) | T001 | HCl (structure) | No Reagent |
| 5-1-397 | I-H078 | (structure) | Q001 | HCl (structure) | No Reagent |
| 5-1-401 | B-B026 | (structure) | T001 | HCl (structure) | (tetrahydropyran-4-sulfonyl chloride) |

-continued

| Example No. | Enamine | | Hydrazine | | Sulfonamidating Reagent |
|---|---|---|---|---|---|
| 5-1-414 | I-A011 | [structure: 6-bromo-5-(2,2-difluoroethoxy)indole enamine] | Q001 | HCl, [structure: 4-(2-fluorophenoxy)-2-methylphenyl hydrazine] | [structure: 3-methoxybenzenesulfonyl chloride] |
| 5-1-415 | I-A011 | [structure: 6-bromo-5-(2,2-difluoroethoxy)indole enamine] | Q001 | HCl, [structure: 4-(2-fluorophenoxy)-2-methylphenyl hydrazine] | [structure: 3,5-difluorobenzenesulfonyl chloride] |
| 5-1-416 | I-A011 | [structure: 6-bromo-5-(2,2-difluoroethoxy)indole enamine] | Q001 | HCl, [structure: 4-(2-fluorophenoxy)-2-methylphenyl hydrazine] | [structure: 3-cyanobenzenesulfonyl chloride] |
| 5-1-417 | I-A011 | [structure: 6-bromo-5-(2,2-difluoroethoxy)indole enamine] | Q001 | HCl, [structure: 4-(2-fluorophenoxy)-2-methylphenyl hydrazine] | [structure: 3-chlorobenzenesulfonyl chloride] |
| 5-1-418 | I-A011 | [structure: 6-bromo-5-(2,2-difluoroethoxy)indole enamine] | Q001 | HCl, [structure: 4-(2-fluorophenoxy)-2-methylphenyl hydrazine] | [structure: pyridine-3-sulfonyl chloride] |
| 5-1-419 | I-A011 | [structure: 6-bromo-5-(2,2-difluoroethoxy)indole enamine] | T001 | HCl, [structure: 5-hydrazinyl-6-(2-fluorophenoxy)-4-methylpyridine] | [structure: 3-methoxybenzenesulfonyl chloride] |
| 5-1-420 | I-A011 | [structure: 6-bromo-5-(2,2-difluoroethoxy)indole enamine] | T001 | HCl, [structure: 5-hydrazinyl-6-(2-fluorophenoxy)-4-methylpyridine] | [structure: 3,5-difluorobenzenesulfonyl chloride] |
| 5-1-422 | I-A011 | [structure: 6-bromo-5-(2,2-difluoroethoxy)indole enamine] | T001 | HCl, [structure: 5-hydrazinyl-6-(2-fluorophenoxy)-4-methylpyridine] | [structure: 3-cyanobenzenesulfonyl chloride] |
| 5-1-424 | I-A011 | [structure: 6-bromo-5-(2,2-difluoroethoxy)indole enamine] | T001 | HCl, [structure: 5-hydrazinyl-6-(2-fluorophenoxy)-4-methylpyridine] | [structure: 3-chlorobenzenesulfonyl chloride] |

-continued

| Example No. | | Enamine | | Hydrazine | | Sulfonamidating Reagent |
|---|---|---|---|---|---|---|
| 5-1-425 | I-A011 | (structure) | T001 | HCl | (structure) | (structure) |
| 5-1-426 | I-H079 | (structure) | Q001 | HCl | (structure) | No Reagent |
| 5-1-427 | I-H079 | (structure) | T002 | HCl | (structure) | No Reagent |
| 5-1-428 | I-H079 | (structure) | T001 | HCl | (structure) | No Reagent |
| 5-1-439 | I-H057 | (structure) | T001 | HCl | (structure) | (structure) |
| 5-1-440 | I-H057 | (structure) | T001 | HCl | (structure) | (structure) |
| 5-1-441 | I-H057 | (structure) | T001 | HCl | (structure) | (structure) |
| 5-1-460 | I-H057 | (structure) | T001 | HCl | (structure) | (structure) |
| 5-1-461 | I-H057 | (structure) | T001 | HCl | (structure) | (structure) |

-continued

| Example No. | | Enamine | Hydrazine | | Sulfonamidating Reagent |
|---|---|---|---|---|---|
| 5-1-462 | I-H057 | (structure) | T001 | (structure) HCl | (structure) |
| 5-1-463 | I-H057 | (structure) | T001 | (structure) HCl | (structure) |
| 5-1-464 | I-H057 | (structure) | T001 | (structure) HCl | (structure) |
| 5-1-465 | I-H057 | (structure) | T001 | (structure) HCl | (structure) |
| 5-1-466 | I-H057 | (structure) | T001 | (structure) HCl | (structure) |
| 5-1-467 | I-H057 | (structure) | T001 | (structure) HCl | (structure) |
| 5-1-477 | I-H057 | (structure) | T001 | (structure) HCl | (structure) |
| 5-1-478 | I-H057 | (structure) | T001 | (structure) HCl | (structure) |

-continued

| Example No. | Enamine | | Hydrazine | | Sulfonamidating Reagent |
|---|---|---|---|---|---|
| 5-1-479 | I-H057 | [structure] | T001 | [structure] | [structure] |
| 5-1-480 | I-H057 | [structure] | T001 | [structure] | [structure] |
| 5-1-481 | I-H057 | [structure] | T001 | [structure] | [structure] |
| 5-1-482 | I-H057 | [structure] | T001 | [structure] | [structure] |
| 5-1-483 | I-H057 | [structure] | T001 | [structure] | [structure] |
| 5-1-484 | I-H057 | [structure] | T001 | [structure] | [structure] |
| 5-1-485 | I-H057 | [structure] | T001 | [structure] | [structure] |
| 5-1-486 | I-H057 | [structure] | T001 | [structure] | [structure] |

| Example No. | Enamine | | Hydrazine | | Sulfonamidating Reagent |
|---|---|---|---|---|---|
| 5-1-487 | I-H057 | (structure) | T001 | (structure) | (structure) |
| 5-1-488 | I-H057 | (structure) | T001 | (structure) | (structure) |
| 5-1-489 | I-A004 | (structure) | Q001 | (structure) | (structure) |
| 5-1-490 | I-A004 | (structure) | Q001 | (structure) | (structure) |
| 5-1-491 | I-A004 | (structure) | T002 | (structure) | (structure) |
| 5-1-492 | I-A004 | (structure) | T002 | (structure) | (structure) |
| 5-1-493 | I-A004 | (structure) | Q019 | (structure) | (structure) |
| 5-1-494 | I-H051 | (structure) | T001 | (structure) | (structure) |

-continued

| Example No. | | Enamine | Hydrazine | | Sulfonamidating Reagent |
|---|---|---|---|---|---|
| 5-1-495 | I-H057 | | T001 | | |
| 5-1-496 | I-H057 | | T001 | | |
| 5-1-497 | I-H057 | | T001 | | |
| 5-1-498 | I-H057 | | T001 | | |
| 5-1-499 | I-H057 | | T001 | | |
| 5-1-500 | I-H057 | | T001 | | |
| 5-1-501 | I-H057 | | T001 | | |
| 5-1-502 | I-H057 | | T001 | | |

-continued

| Example No. | Enamine | Hydrazine | Sulfonamidating Reagent |
|---|---|---|---|
| 5-1-504 | I-H057 | T001 | |
| 5-1-505 | I-H057 | T001 | |
| 5-1-506 | I-H057 | T001 | |
| 5-1-507 | I-H057 | T001 | |
| 5-1-508 | I-H057 | T001 | |
| 5-1-509 | I-H057 | T001 | |
| 5-1-510 | I-H057 | Q001 | |
| 5-1-511 | I-H057 | T002 | |

| Example No. | Enamine | | Hydrazine | | Sulfonamidating Reagent |
|---|---|---|---|---|---|
| 5-1-512 | I-A004 | [structure] | Q001 | HCl, [structure] | [structure] |
| 5-1-513 | I-A004 | [structure] | T002 | HCl, [structure] | [structure] |
| 5-1-514 | I-A004 | [structure] | T001 | HCl, [structure] | [structure] |
| 5-1-515 | I-H057 | [structure] | Q001 | HCl, [structure] | [structure] |
| 5-1-516 | I-H057 | [structure] | T002 | HCl, [structure] | [structure] |
| 5-1-517 | I-A004 | [structure] | Q001 | HCl, [structure] | [structure] |
| 5-1-518 | I-A004 | [structure] | T002 | HCl, [structure] | [structure] |
| 5-1-519 | I-A004 | [structure] | T001 | HCl, [structure] | [structure] |

-continued

| Example No. | | Enamine | | Hydrazine | Sulfonamidating Reagent |
|---|---|---|---|---|---|
| 5-1-520 | I-H057 | | Q001 | HCl, H₂N-NH-(4-(2-fluorophenoxy)-2-methylphenyl) | 5-methyl-2-fluoropyridine-3-sulfonyl chloride |
| 5-1-521 | I-H057 | | T002 | HCl, H₂N-NH-(5-(2,6-difluorophenoxy)-4-methylpyridin-2-yl) | 5-methyl-2-fluoropyridine-3-sulfonyl chloride |
| 5-1-522 | I-A004 | | Q001 | HCl, H₂N-NH-(4-(2-fluorophenoxy)-2-methylphenyl) | 5-methyl-2-fluoropyridine-3-sulfonyl chloride |
| 5-1-523 | I-A004 | | T002 | HCl, H₂N-NH-(5-(2,6-difluorophenoxy)-4-methylpyridin-2-yl) | 5-methyl-2-fluoropyridine-3-sulfonyl chloride |
| 5-1-524 | I-A004 | | T001 | HCl, H₂N-NH-(5-(2-fluorophenoxy)-4-methylpyridin-2-yl) | 5-methyl-2-fluoropyridine-3-sulfonyl chloride |
| 5-1-525 | I-H057 | | Q001 | HCl, H₂N-NH-(4-(2-fluorophenoxy)-2-methylphenyl) | 6-chloropyridine-2-sulfonyl chloride |
| 5-1-526 | I-H057 | | T002 | HCl, H₂N-NH-(5-(2,6-difluorophenoxy)-4-methylpyridin-2-yl) | 6-chloropyridine-2-sulfonyl chloride |
| 5-1-527 | I-A004 | | Q001 | HCl, H₂N-NH-(4-(2-fluorophenoxy)-2-methylphenyl) | 6-chloropyridine-2-sulfonyl chloride |

-continued

| Example No. | | Enamine | | Hydrazine | | Sulfonamidating Reagent |
|---|---|---|---|---|---|---|
| 5-1-528 | I-A004 | [structure: 6-acetamido-5-fluoro-1-Ts-indole with enamine-CN] | T002 | HCl, H₂N-NH-[5-methyl-pyridyl-O-(2,6-difluorophenyl)] | | [6-chloropyridine-2-sulfonyl chloride] |
| 5-1-529 | I-A004 | [structure: 6-acetamido-5-fluoro-1-Ts-indole with enamine-CN] | T001 | HCl, H₂N-NH-[methylpyridyl-O-(2-fluorophenyl)] | | [6-chloropyridine-2-sulfonyl chloride] |
| 5-1-530 | I-H057 | [structure: 6-BOC-NH-5-methyl-1-Ts-indole with enamine-CN] | Q001 | HCl, H₂N-NH-[methylphenyl-O-(2-fluorophenyl)] | | [6-methylpyridine-2-sulfonyl chloride] |
| 5-1-531 | I-H057 | [structure: 6-BOC-NH-5-methyl-1-Ts-indole with enamine-CN] | T002 | HCl, H₂N-NH-[methylpyridyl-O-(2,6-difluorophenyl)] | | [6-methylpyridine-2-sulfonyl chloride] |
| 5-1-532 | I-A004 | [structure: 6-acetamido-5-fluoro-1-Ts-indole with enamine-CN] | Q001 | HCl, H₂N-NH-[methylphenyl-O-(2-fluorophenyl)] | | [6-methylpyridine-2-sulfonyl chloride] |
| 5-1-533 | I-A004 | [structure: 6-acetamido-5-fluoro-1-Ts-indole with enamine-CN] | T002 | HCl, H₂N-NH-[methylpyridyl-O-(2,6-difluorophenyl)] | | [6-methylpyridine-2-sulfonyl chloride] |
| 5-1-534 | I-A004 | [structure: 6-acetamido-5-fluoro-1-Ts-indole with enamine-CN] | T001 | HCl, H₂N-NH-[methylpyridyl-O-(2-fluorophenyl)] | | [6-methylpyridine-2-sulfonyl chloride] |
| 5-1-535 | I-H057 | [structure: 6-BOC-NH-5-methyl-1-Ts-indole with enamine-CN] | Q001 | HCl, H₂N-NH-[methylphenyl-O-(2-fluorophenyl)] | | [6-cyanopyridine-2-sulfonyl chloride] |

| Example No. | | Enamine | Hydrazine | | Sulfonamidating Reagent |
|---|---|---|---|---|---|
| 5-1-536 | I-H057 | [structure: BOC-NH, methyl, indole-Ts, C(O), CN, =CH-N(CH₃)₂ enamine] | T002 | HCl, H₂N-NH-[5-(2,6-difluorophenoxy)-4-methylpyridin-3-yl] | 6-cyanopyridine-2-sulfonyl chloride |
| 5-1-537 | I-A004 | [structure: AcNH, F, indole-Ts, C(O), CN, enamine] | Q001 | HCl, H₂N-NH-[4-(2-fluorophenoxy)-3-methylphenyl] | 6-cyanopyridine-2-sulfonyl chloride |
| 5-1-538 | I-A004 | [structure: AcNH, F, indole-Ts, C(O), CN, enamine] | T002 | HCl, H₂N-NH-[5-(2,6-difluorophenoxy)-4-methylpyridin-3-yl] | 6-cyanopyridine-2-sulfonyl chloride |
| 5-1-539 | I-A004 | [structure: AcNH, F, indole-Ts, C(O), CN, enamine] | T001 | HCl, H₂N-NH-[5-(2-fluorophenoxy)-4-methylpyridin-3-yl] | 6-cyanopyridine-2-sulfonyl chloride |
| 5-1-540 | I-H057 | [structure: BOC-NH, methyl, indole-Ts, C(O), CN, enamine] | Q001 | HCl, H₂N-NH-[4-(2-fluorophenoxy)-3-methylphenyl] | 5-chloropyridine-3-sulfonyl chloride |
| 5-1-541 | I-H057 | [structure: BOC-NH, methyl, indole-Ts, C(O), CN, enamine] | T002 | HCl, H₂N-NH-[5-(2,6-difluorophenoxy)-4-methylpyridin-3-yl] | 5-chloropyridine-3-sulfonyl chloride |
| 5-1-542 | I-A004 | [structure: AcNH, F, indole-Ts, C(O), CN, enamine] | Q001 | HCl, H₂N-NH-[4-(2-fluorophenoxy)-3-methylphenyl] | 5-chloropyridine-3-sulfonyl chloride |
| 5-1-543 | I-A004 | [structure: AcNH, F, indole-Ts, C(O), CN, enamine] | T002 | HCl, H₂N-NH-[5-(2,6-difluorophenoxy)-4-methylpyridin-3-yl] | 5-chloropyridine-3-sulfonyl chloride |

| Example No. | | Enamine | Hydrazine | | Sulfonamidating Reagent |
|---|---|---|---|---|---|
| 5-1-544 | I-A004 | acetamido-fluoro-indole-Ts with cyanoenamine-NMe2 | T001 | HCl, H2N-NH-(5-methyl-6-(2-fluorophenoxy)pyridin-3-yl) | 5-chloropyridine-3-sulfonyl chloride |
| 5-1-545 | I-H057 | BOC-amino-methyl-indole-Ts with cyanoenamine-NMe2 | Q001 | HCl, H2N-NH-(4-(2-fluorophenoxy)-3-methylphenyl) | 5-fluoropyridine-3-sulfonyl chloride |
| 5-1-546 | I-H057 | BOC-amino-methyl-indole-Ts with cyanoenamine-NMe2 | T002 | HCl, H2N-NH-(5-methyl-6-(2,6-difluorophenoxy)pyridin-3-yl) | 5-fluoropyridine-3-sulfonyl chloride |
| 5-1-547 | I-A004 | acetamido-fluoro-indole-Ts with cyanoenamine-NMe2 | Q001 | HCl, H2N-NH-(4-(2-fluorophenoxy)-3-methylphenyl) | 5-fluoropyridine-3-sulfonyl chloride |
| 5-1-548 | I-A004 | acetamido-fluoro-indole-Ts with cyanoenamine-NMe2 | T002 | HCl, H2N-NH-(5-methyl-6-(2,6-difluorophenoxy)pyridin-3-yl) | 5-fluoropyridine-3-sulfonyl chloride |
| 5-1-549 | I-A004 | acetamido-fluoro-indole-Ts with cyanoenamine-NMe2 | T001 | HCl, H2N-NH-(5-methyl-6-(2-fluorophenoxy)pyridin-3-yl) | 5-fluoropyridine-3-sulfonyl chloride |
| 5-1-550 | I-H057 | BOC-amino-methyl-indole-Ts with cyanoenamine-NMe2 | Q001 | HCl, H2N-NH-(4-(2-fluorophenoxy)-3-methylphenyl) | 3-fluorobenzenesulfonyl chloride |
| 5-1-551 | I-H057 | BOC-amino-methyl-indole-Ts with cyanoenamine-NMe2 | T002 | HCl, H2N-NH-(5-methyl-6-(2,6-difluorophenoxy)pyridin-3-yl) | 3-fluorobenzenesulfonyl chloride |

-continued

| Example No. | | Enamine | Hydrazine | | Sulfonamidating Reagent |
|---|---|---|---|---|---|
| 5-1-552 | I-A004 | [structure] | Q001 | [structure, HCl] | [structure] |
| 5-1-553 | I-A004 | [structure] | T002 | [structure, HCl] | [structure] |
| 5-1-554 | I-A004 | [structure] | T001 | [structure, HCl] | [structure] |
| 5-1-555 | I-H057 | [structure] | T002 | [structure, HCl] | [structure] |
| 5-1-556 | I-A004 | [structure] | T001 | [structure, HCl] | [structure] |
| 5-1-557 | I-H057 | [structure] | T002 | [structure, HCl] | [structure] |
| 5-1-558 | I-A004 | [structure] | Q001 | [structure, HCl] | [structure] |
| 5-1-559 | I-A004 | [structure] | T002 | [structure, HCl] | [structure] |

-continued

| Example No. | | Enamine | | Hydrazine | | Sulfonamidating Reagent |
|---|---|---|---|---|---|---|
| 5-1-560 | I-A004 | | T001 | HCl | | |
| 5-1-561 | I-H057 | | T002 | HCl | | |
| 5-1-562 | I-A004 | | Q001 | HCl | | |
| 5-1-563 | I-A004 | | T002 | HCl | | |
| 5-1-564 | I-A004 | | T001 | HCl | | |
| 5-1-565 | I-H057 | | T002 | HCl | | |
| 5-1-566 | I-A004 | | Q001 | HCl | | |
| 5-1-567 | I-A004 | | T002 | HCl | | |

| Example No. | | Enamine | Hydrazine | | Sulfonamidating Reagent |
|---|---|---|---|---|---|
| 5-1-568 | I-A004 | (structure) | T001 | (structure) | (structure) |
| 5-1-569 | I-A011 | (structure) | T002 | (structure) | (structure) |
| 5-1-570 | I-A011 | (structure) | T002 | (structure) | (structure) |
| 5-1-571 | I-A011 | (structure) | T002 | (structure) | (structure) |
| 5-1-572 | I-A011 | (structure) | T002 | (structure) | (structure) |
| 5-1-573 | I-A011 | (structure) | T002 | (structure) | (structure) |
| 5-1-574 | I-A011 | (structure) | T002 | (structure) | (structure) |
| 5-1-575 | I-A011 | (structure) | T002 | (structure) | (structure) |
| 5-1-576 | I-A011 | (structure) | T002 | (structure) | (structure) |

-continued

| Example No. | Enamine | | Hydrazine | | Sulfonamidating Reagent |
|---|---|---|---|---|---|
| 5-1-577 | I-H057 | [structure: BOC-NH-methylindole-Ts with acyl cyanoenamine] | T001 | [structure: H2N-NH-methylpyridine-O-fluorophenyl, HCl] | [structure: dimethylaminopyrimidine sulfonyl chloride] |

(Synthesized Compounds)

| Example No. | Compound | m/z (M + H) | Retention Time (Minute) | LCMS Measurement Condition |
|---|---|---|---|---|
| 4-7-001 | [structure] | 539 | 0.73 | A1 |
| 4-7-002 | [structure] | 624 | 2.46 | B1 |
| 4-7-003 | [structure] | 556 | 0.78 | A1 |
| 4-7-004 | [structure] | 582 | 0.87 | A1 |

| Example No. | Compound | m/z (M + H) | Retention Time (Minute) | LCMS Measurement Condition |
|---|---|---|---|---|
| 4-7-005 | | 574 | 2.48 | H3 |
| 4-7-006 | | 600 | 2.58 | H3 |
| 4-7-007 | | 574 | 0.79 | A1 |
| 4-7-008 | | 600 | 0.82 | A1 |
| 4-7-009 | | 572, 574 | 0.87 | A1 |
| 4-7-010 | | 598, 600 | 0.9 | A1 |

-continued
| Example No. | Compound | m/z (M + H) | Retention Time (Minute) | LCMS Measurement Condition |
|---|---|---|---|---|
| 4-7-011 | 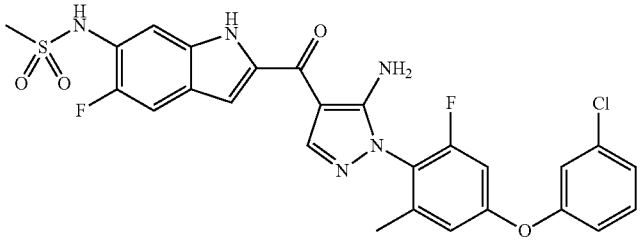 [SMILES: Cc1cc(Oc2cccc(Cl)c2)cc(F)c1-n1ncc(C(=O)c2cc3cc(F)c(NS(C)(=O)=O)cc3[nH]2)c1N] | 572, 574 | 1.56 | F1 |
| 4-7-012 | 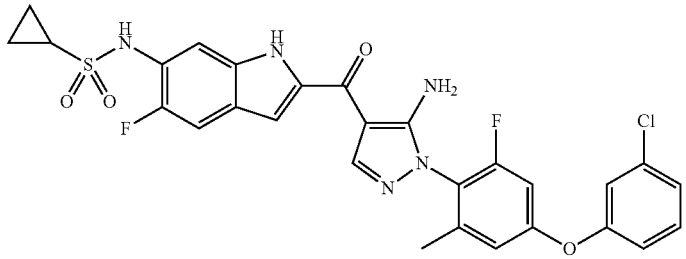 [SMILES: Cc1cc(Oc2cccc(Cl)c2)cc(F)c1-n1ncc(C(=O)c2cc3cc(F)c(NS(=O)(=O)C4CC4)cc3[nH]2)c1N] | 598, 600 | 1.66 | F1 |
| 4-7-013 | 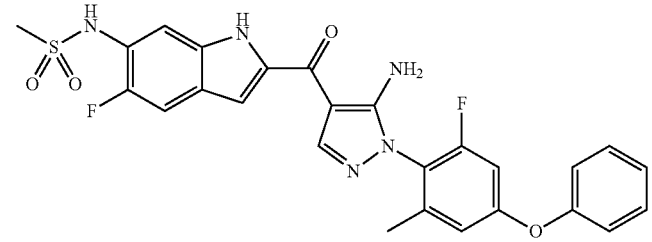 [SMILES: Cc1cc(Oc2ccccc2)cc(F)c1-n1ncc(C(=O)c2cc3cc(F)c(NS(C)(=O)=O)cc3[nH]2)c1N] | 538 | 1.43 | F1 |
| 4-7-014 | 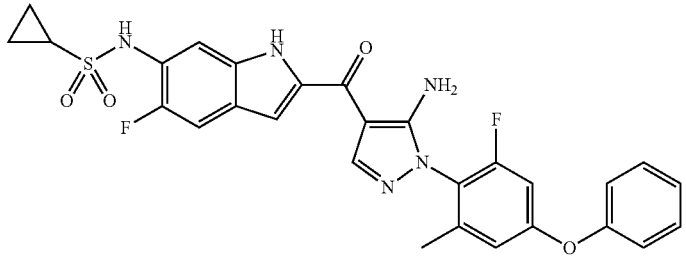 [SMILES: Cc1cc(Oc2ccccc2)cc(F)c1-n1ncc(C(=O)c2cc3cc(F)c(NS(=O)(=O)C4CC4)cc3[nH]2)c1N] | 564 | 1.53 | F1 |
| 4-7-015 | 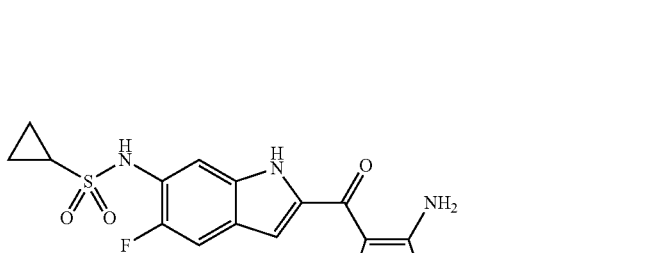 | 581, 583 | 0.84 | A1 |

| Example No. | Compound | m/z (M + H) | Retention Time (Minute) | LCMS Measurement Condition |
|---|---|---|---|---|
| 4-7-016 | | 581, 583 | 0.87 | A1 |
| 5-1-266 | | 484 | 1.05 | AA Rev.11 |
| 5-1-267 | | 562 | 1.03 | AA Rev.11 |
| 5-1-269 | | 623 | 1 | AA Rev.11 |

-continued

| Example No. | Compound | m/z (M + H) | Retention Time (Minute) | LCMS Measurement Condition |
|---|---|---|---|---|
| 5-1-280 | | 608 | 1.07 | AA Rev.11 |
| 5-1-281 | | 609 | 1 | AA Rev.11 |
| 5-1-282 | | 632 | 1.28 | TFA Rev.7 |
| 5-1-296 | | 695 | 1.31 | TFA Rev.7 |

-continued

| Example No. | Compound | m/z (M + H) | Retention Time (Minute) | LCMS Measurement Condition |
|---|---|---|---|---|
| 5-1-297 | | 699 | 1.3 | TFA Rev.7 |
| 5-1-298 | | 715 | 1.35 | TFA Rev.7 |
| 5-1-299 | | 711 | 1.29 | TFA Rev.7 |

-continued
| Example No. | Compound | m/z (M + H) | Retention Time (Minute) | LCMS Measurement Condition |
|---|---|---|---|---|
| 5-1-300 | 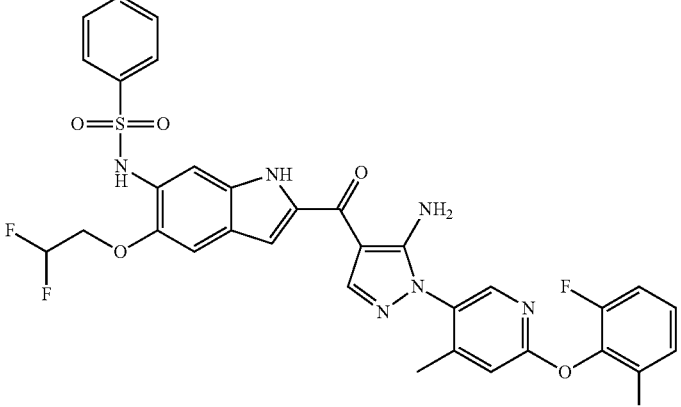 | 695 | 1.32 | TFA Rev.7 |
| 5-1-301 | 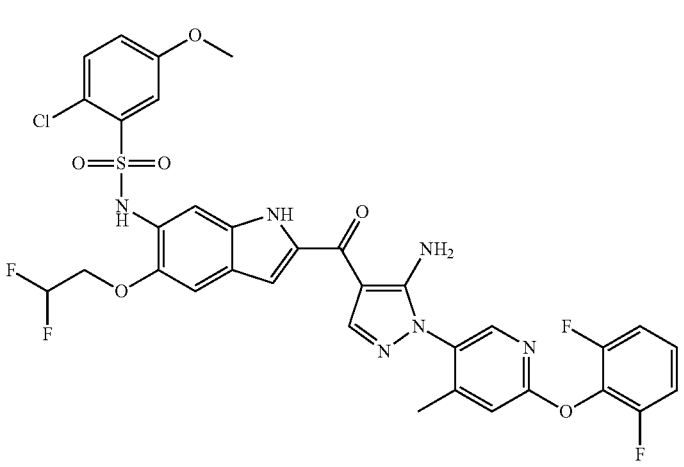 [SMILES: COc1ccc(Cl)c(S(=O)(=O)Nc2cc3[nH]c(C(=O)c4cnn(-c5cnc(Oc6c(F)cccc6F)cc5C)c4N)cc3cc2OCC(F)F)c1] | 745 | 1.34 | TFA Rev.7 |
| 5-1-304 |  | 649 | 1.4 | TFA Rev.7 |

| Example No. | Compound | m/z (M + H) | Retention Time (Minute) | LCMS Measurement Condition |
|---|---|---|---|---|
| 5-1-305 | | 627 | 1.28 | TFA Rev.7 |
| 5-1-306 | | 635 | 1.07 | AA Rev.11 |
| 5-1-314 | | 621 | 1.06 | AA Rev.11 |
| 5-1-315 | | 687 | 1.06 | AA Rev.11 |

| Example No. | Compound | m/z (M + H) | Retention Time (Minute) | LCMS Measurement Condition |
|---|---|---|---|---|
| 5-1-317 | | 607 | 1.28 | TFA Rev.7 |
| 5-1-318 | | 673 | 1.3 | TFA Rev.7 |
| 5-1-319 | | 689 | 1.2 | TFA Rev.7 |
| 5-1-320 | | 667 | 1.28 | TFA Rev.7 |

-continued

| Example No. | Compound | m/z (M + H) | Retention Time (Minute) | LCMS Measurement Condition |
|---|---|---|---|---|
| 5-1-325 | | 670 | 1.02 | AA Rev.11 |
| 5-1-326 | | 671 | 0.97 | AA Rev.11 |
| 5-1-327 | | 711 | 1.3 | TFA Rev.7 |
| 5-1-328 | | 715 | 1.33 | TFA Rev.7 |

-continued
| Example No. | Compound | m/z (M + H) | Retention Time (Minute) | LCMS Measurement Condition |
|---|---|---|---|---|
| 5-1-329 | 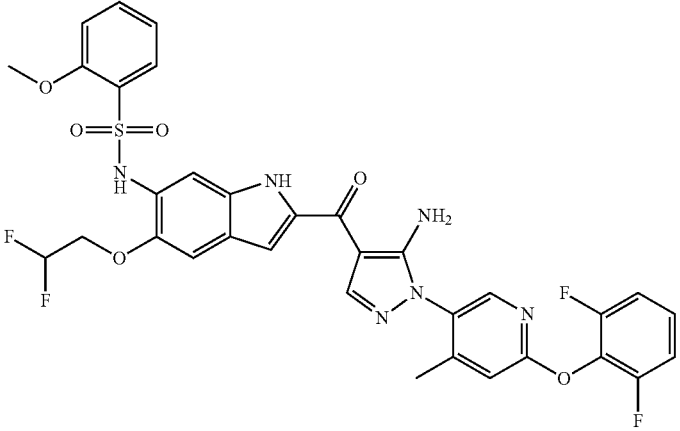 | 711 | 1.29 | TFA Rev.7 |
| 5-1-330 | 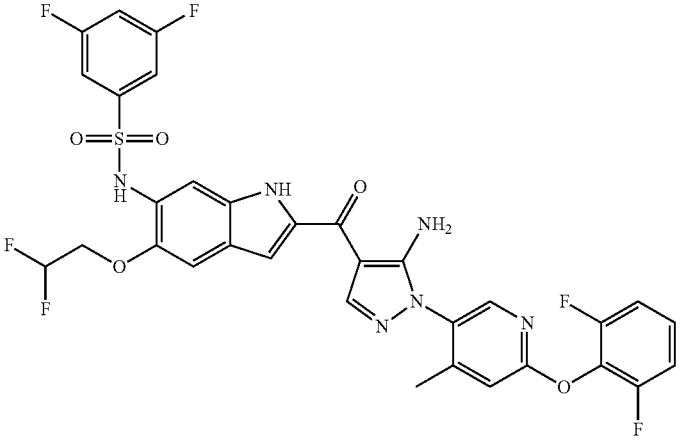 | 717 | 1.32 | TFA Rev.7 |
| 5-1-331 | 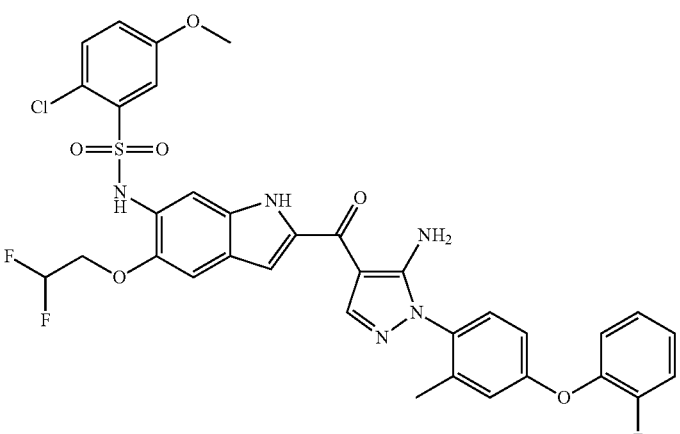 | 726 | 1.37 | TFA Rev.7 |

| Example No. | Compound | m/z (M + H) | Retention Time (Minute) | LCMS Measurement Condition |
|---|---|---|---|---|
| 5-1-333 | | 605 | 0.96 | AA Rev.11 |
| 5-1-339 | | 649 | 1 | AA Rev.11 |
| 5-1-346 | | 691 | 1.02 | AA Rev.11 |
| 5-1-347 | | 604 | 1.2 | TFA Rev.7 |

-continued

| Example No. | Compound | m/z (M + H) | Retention Time (Minute) | LCMS Measurement Condition |
|---|---|---|---|---|
| 5-1-378 | | 609 | 1.11 | TFA Rev.7 |
| 5-1-380 | | 675 | 0.99 | AA Rev.11 |
| 5-1-381 | | 627 | 1.14 | TFA Rev.7 |
| 5-1-382 | | 706 | 1.26 | TFA Rev.7 |

-continued

| Example No. | Compound | m/z (M + H) | Retention Time (Minute) | LCMS Measurement Condition |
|---|---|---|---|---|
| 5-1-383 | | 715 | 1.34 | TFA Rev.7 |
| 5-1-384 | | 682 | 0.96 | AA Rev.11 |
| 5-1-389 | | 608 | 1.18 | TFA Rev.7 |
| 5-1-390 | | 656 | 1.01 | AA Rev.11 |

| Example No. | Compound | m/z (M + H) | Retention Time (Minute) | LCMS Measurement Condition |
|---|---|---|---|---|
| 5-1-395 | | 649 | 1.02 | AA Rev.11 |
| 5-1-396 | | 631 | 1.22 | TFA Rev.7 |
| 5-1-397 | | 630 | 1.04 | AA Rev.11 |
| 5-1-401 | | 657 | 0.97 | AA Rev.11 |

| Example No. | Compound | m/z (M + H) | Retention Time (Minute) | LCMS Measurement Condition |
|---|---|---|---|---|
| 5-1-414 | 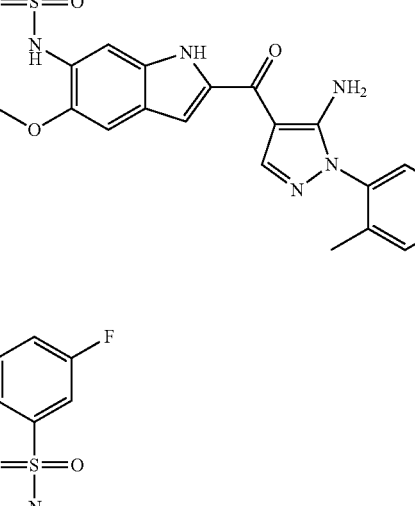 | 692 | 1.33 | TFA Rev.7 |
| 5-1-415 | 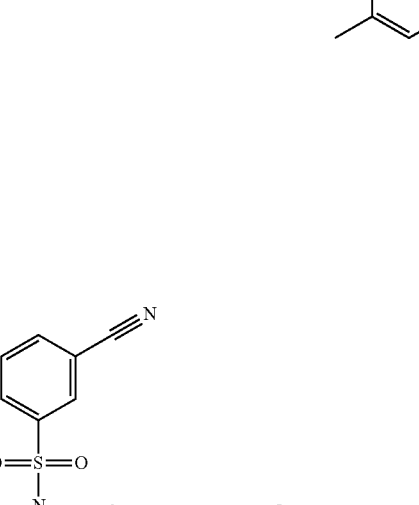 | 698 | 1.35 | TFA Rev.7 |
| 5-1-416 | 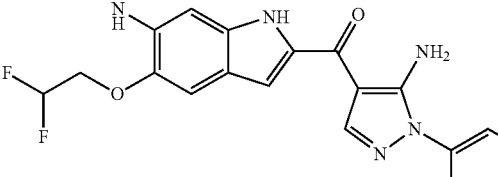 | 687 | 1.29 | TFA Rev.7 |

| Example No. | Compound | m/z (M + H) | Retention Time (Minute) | LCMS Measurement Condition |
|---|---|---|---|---|
| 5-1-417 | | 696 | 1.37 | TFA Rev.7 |
| 5-1-418 | | 663 | 1.21 | TFA Rev.7 |
| 5-1-419 | | 693 | 1.27 | TFA Rev.7 |

-continued

| Example No. | Compound | m/z (M + H) | Retention Time (Minute) | LCMS Measurement Condition |
|---|---|---|---|---|
| 5-1-420 | | 699 | 1.3 | TFA Rev.7 |
| 5-1-422 | | 688 | 1.24 | TFA Rev.7 |
| 5-1-424 | | 697 | 1.32 | TFA Rev.7 |

-continued

| Example No. | Compound | m/z (M + H) | Retention Time (Minute) | LCMS Measurement Condition |
|---|---|---|---|---|
| 5-1-425 | | 664 | 1.15 | TFA Rev.7 |
| 5-1-426 | | 606 | 1.04 | AA Rev.11 |
| 5-1-427 | | 625 | 1.02 | AA Rev.11 |
| 5-1-428 | | 607 | 1.01 | AA Rev.11 |

| Example No. | Compound | m/z (M + H) | Retention Time (Minute) | LCMS Measurement Condition |
|---|---|---|---|---|
| 5-1-439 | | 627 | 1.03 | AA Rev.11 |
| 5-1-440 | | 622 | 1.23 | TFA Rev.7 |
| 5-1-441 | | 598 | 0.98 | AA Rev.11 |

| Example No. | Compound | m/z (M + H) | Retention Time (Minute) | LCMS Measurement Condition |
|---|---|---|---|---|
| 5-1-460 | | 633 | 1.29 | TFA Rev.7 |
| 5-1-461 | | 639 | 1.09 | AA Rev.11 |
| 5-1-462 | | 611 | 1.28 | TFA Rev.7 |

-continued

| Example No. | Compound | m/z (M + H) | Retention Time (Minute) | LCMS Measurement Condition |
|---|---|---|---|---|
| 5-1-463 | | 665 | 1.33 | TFA Rev.7 |
| 5-1-464 | | 631 | 1.31 | TFA Rev.7 |
| 5-1-465 | | 647 | 1.32 | TFA Rev.7 |

-continued

| Example No. | Compound | m/z (M + H) | Retention Time (Minute) | LCMS Measurement Condition |
|---|---|---|---|---|
| 5-1-466 | | 647 | 1.32 | TFA Rev.7 |
| 5-1-467 | | 653 | 1.32 | TFA Rev.7 |
| 5-1-477 | | 598 | 1.16 | TFA Rev.7 |

-continued

| Example No. | Compound | m/z (M + H) | Retention Time (Minute) | LCMS Measurement Condition |
|---|---|---|---|---|
| 5-1-478 | | 623 | 1.19 | TFA Rev.7 |
| 5-1-479 | | 623 | 0.96 | AA Rev.11 |
| 5-1-480 | | 623 | 1.19 | TFA Rev.7 |

-continued

| Example No. | Compound | m/z (M + H) | Retention Time (Minute) | LCMS Measurement Condition |
|---|---|---|---|---|
| 5-1-481 | | 637 | 1.22 | TFA Rev.7 |
| 5-1-482 | | 628 | 1.17 | TFA Rev.7 |
| 5-1-483 | | 628 | 1.24 | TFA Rev.7 |

-continued

| Example No. | Compound | m/z (M + H) | Retention Time (Minute) | LCMS Measurement Condition |
|---|---|---|---|---|
| 5-1-484 | | 628 | 0.99 | AA Rev.11 |
| 5-1-485 | | 666 | 1.27 | TFA Rev.7 |
| 5-1-486 | | 666 | 1.27 | TFA Rev.7 |

-continued

| Example No. | Compound | m/z (M + H) | Retention Time (Minute) | LCMS Measurement Condition |
|---|---|---|---|---|
| 5-1-487 | | 666 | 1.28 | TFA Rev.7 |
| 5-1-488 | | 612 | 0.99 | AA Rev.11 |
| 5-1-489 | | 601 | 0.98 | AA Rev.11 |

| Example No. | Compound | m/z (M + H) | Retention Time (Minute) | LCMS Measurement Condition |
|---|---|---|---|---|
| 5-1-490 | | 625 | 1 | AA Rev.11 |
| 5-1-491 | | 620 | 0.95 | AA Rev.11 |
| 5-1-492 | | 644 | 0.98 | AA Rev.11 |

-continued

| Example No. | Compound | m/z (M + H) | Retention Time (Minute) | LCMS Measurement Condition |
|---|---|---|---|---|
| 5-1-493 | | 608 | 1.23 | TFA Rev.7 |
| 5-1-494 | | 616 | 1.2 | TFA Rev.7 |
| 5-1-495 | | 632 | 1.25 | TFA Rev.7 |

-continued

| Example No. | Compound | m/z (M + H) | Retention Time (Minute) | LCMS Measurement Condition |
|---|---|---|---|---|
| 5-1-496 | | 645 | 1.29 | TFA Rev.7 |
| 5-1-497 | | 640 | 1.26 | TFA Rev.7 |
| 5-1-498 | | 656 | 1.3 | TFA Rev.7 |

| Example No. | Compound | m/z (M + H) | Retention Time (Minute) | LCMS Measurement Condition |
|---|---|---|---|---|
| 5-1-499 | | 690 | 1.32 | TFA Rev.7 |
| 5-1-500 | | 615 | 1.02 | AA Rev.11 |
| 5-1-501 | | 651 | 1.01 | AA Rev.11 |

-continued

| Example No. | Compound | m/z (M + H) | Retention Time (Minute) | LCMS Measurement Condition |
|---|---|---|---|---|
| 5-1-502 | | 616 | 0.97 | AA Rev.11 |
| 5-1-504 | | 630 | 0.99 | AA Rev.11 |
| 5-1-505 | | 616 | 1.2 | TFA Rev.7 |

-continued

| Example No. | Compound | m/z (M + H) | Retention Time (Minute) | LCMS Measurement Condition |
|---|---|---|---|---|
| 5-1-506 | | 612 | 0.98 | AA Rev.11 |
| 5-1-507 | | 612 | 0.98 | AA Rev.11 |
| 5-1-508 | | 632 | 0.99 | AA Rev.11 |

-continued

| Example No. | Compound | m/z (M + H) | Retention Time (Minute) | LCMS Measurement Condition |
|---|---|---|---|---|
| 5-1-509 | | 632 | 1.01 | AA Rev.11 |
| 5-1-510 | | 627 | 1.24 | TFA Rev.7 |
| 5-1-511 | | 646 | 0.99 | AA Rev.11 |

| Example No. | Compound | m/z (M + H) | Retention Time (Minute) | LCMS Measurement Condition |
|---|---|---|---|---|
| 5-1-512 | | 631 | 1.22 | TFA Rev.7 |
| 5-1-513 | | 650 | 0.96 | AA Rev.11 |
| 5-1-514 | | 632 | 1.15 | TFA Rev.7 |

-continued

| Example No. | Compound | m/z (M + H) | Retention Time (Minute) | LCMS Measurement Condition |
|---|---|---|---|---|
| 5-1-515 | | 615 | 1.01 | AA Rev.11 |
| 5-1-516 | | 634 | 0.98 | AA Rev.11 |
| 5-1-517 | | 619 | 0.98 | AA Rev.11 |

-continued

| Example No. | Compound | m/z (M + H) | Retention Time (Minute) | LCMS Measurement Condition |
|---|---|---|---|---|
| 5-1-518 | | 638 | 0.95 | AA Rev.11 |
| 5-1-519 | | 620 | 0.94 | AA Rev.11 |
| 5-1-520 | | 629 | 1.03 | AA Rev.11 |

-continued

| Example No. | Compound | m/z (M + H) | Retention Time (Minute) | LCMS Measurement Condition |
|---|---|---|---|---|
| 5-1-521 | | 648 | 1 | AA Rev.11 |
| 5-1-522 | | 633 | 1 | AA Rev.11 |
| 5-1-523 | | 652 | 0.97 | AA Rev.11 |

-continued

| Example No. | Compound | m/z (M + H) | Retention Time (Minute) | LCMS Measurement Condition |
|---|---|---|---|---|
| 5-1-524 | | 634 | 0.96 | AA Rev.11 |
| 5-1-525 | | 631 | 1.31 | TFA Rev.7 |
| 5-1-526 | | 650 | 1 | AA Rev.11 |

-continued
| Example No. | Compound | m/z (M + H) | Retention Time (Minute) | LCMS Measurement Condition |
|---|---|---|---|---|
| 5-1-527 | 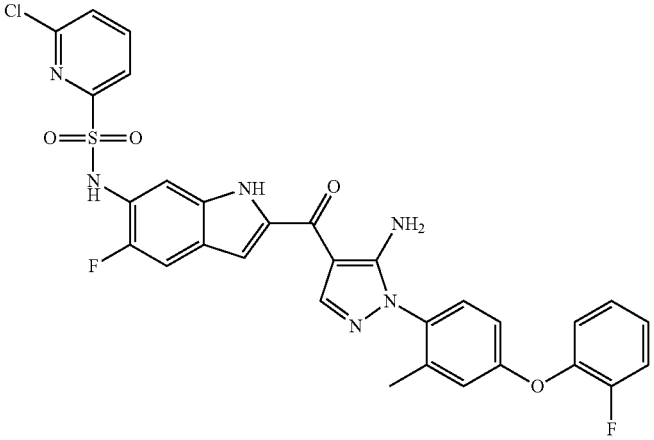 | 635 | 1 | AA Rev.11 |
| 5-1-528 | 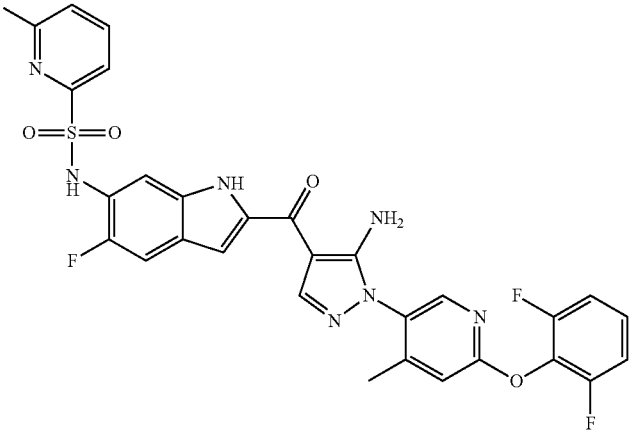 | 654 | 0.98 | AA Rev.11 |
| 5-1-529 | 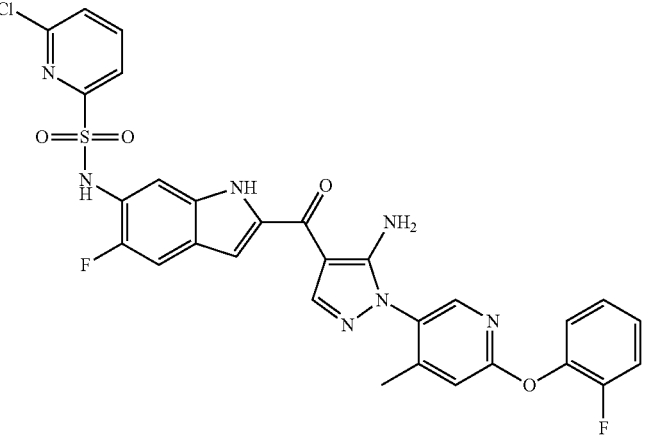 | 636 | 0.96 | AA Rev.11 |

-continued

| Example No. | Compound | m/z (M + H) | Retention Time (Minute) | LCMS Measurement Condition |
|---|---|---|---|---|
| 5-1-530 | | 611 | 1.27 | TFA Rev.7 |
| 5-1-531 | | 630 | 1.23 | TFA Rev.7 |
| 5-1-532 | | 615 | 1.24 | TFA Rev.7 |

-continued

| Example No. | Compound | m/z (M + H) | Retention Time (Minute) | LCMS Measurement Condition |
|---|---|---|---|---|
| 5-1-533 | | 634 | 0.97 | AA Rev.11 |
| 5-1-534 | | 616 | 0.96 | AA Rev.11 |
| 5-1-535 | | 622 | 1.26 | TFA Rev.7 |

| Example No. | Compound | m/z (M + H) | Retention Time (Minute) | LCMS Measurement Condition |
|---|---|---|---|---|
| 5-1-536 | 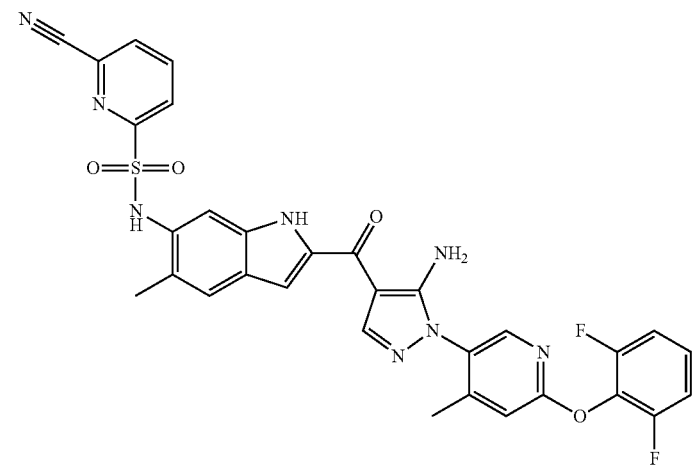 | 641 | 1.23 | TFA Rev.7 |
| 5-1-537 | 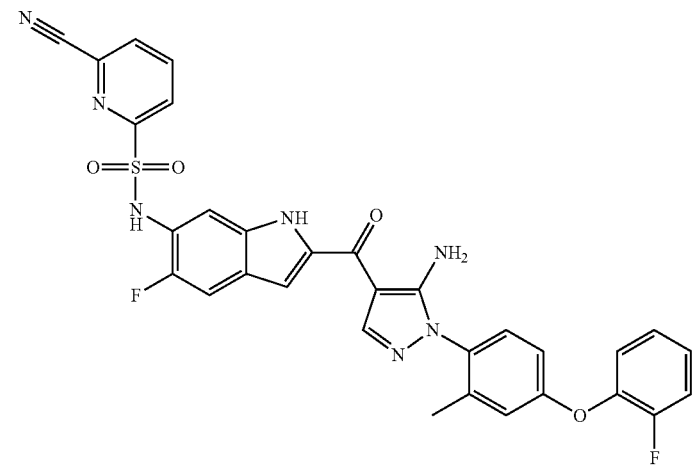 | 626 | 1.23 | TFA Rev.7 |
| 5-1-538 | 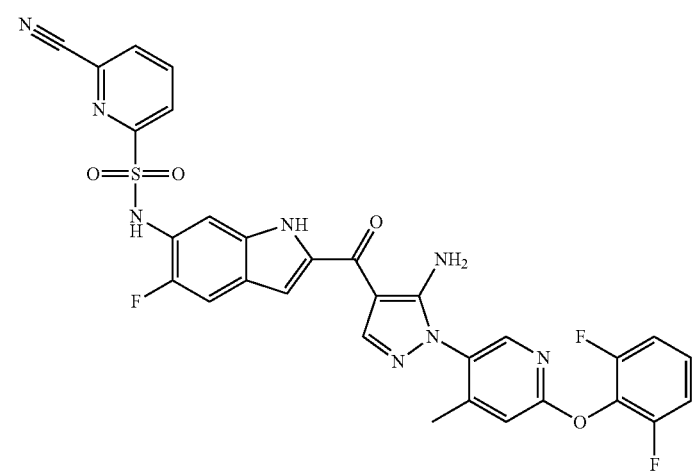 | 645 | 1.19 | TFA Rev.7 |

-continued

| Example No. | Compound | m/z (M + H) | Retention Time (Minute) | LCMS Measurement Condition |
|---|---|---|---|---|
| 5-1-539 | | 627 | 1.17 | TFA Rev.7 |
| 5-1-540 | | 631 | 1.31 | TFA Rev.7 |
| 5-1-541 | | 650 | 1.28 | TFA Rev.7 |

| Example No. | Compound | m/z (M + H) | Retention Time (Minute) | LCMS Measurement Condition |
|---|---|---|---|---|
| 5-1-542 | 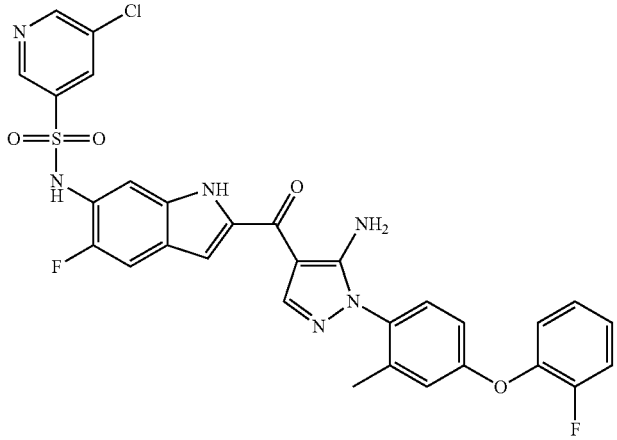 | 635 | 1.02 | AA Rev.11 |
| 5-1-543 | 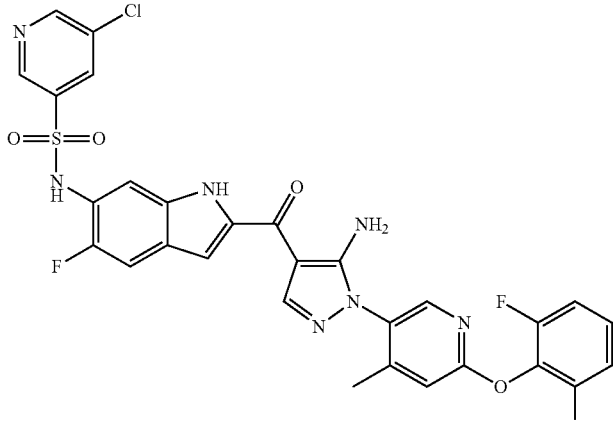 | 654 | 1.24 | TFA Rev.7 |
| 5-1-544 | 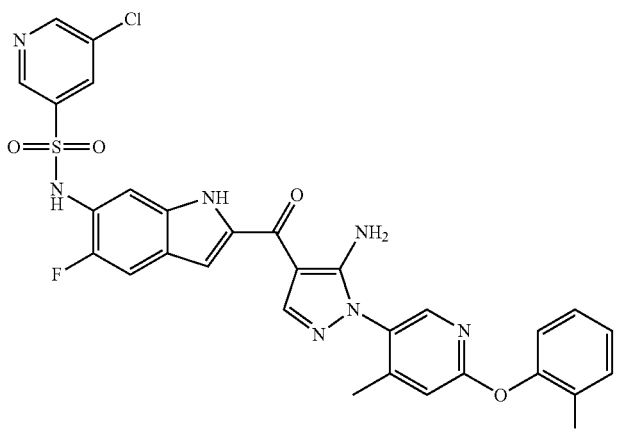 | 636 | 1.22 | TFA Rev.7 |

| Example No. | Compound | m/z (M + H) | Retention Time (Minute) | LCMS Measurement Condition |
|---|---|---|---|---|
| 5-1-545 | | 615 | 1.27 | TFA Rev.7 |
| 5-1-546 | | 634 | 1.23 | TFA Rev.7 |
| 5-1-547 | | 619 | 1 | AA Rev.11 |

| Example No. | Compound | m/z (M + H) | Retention Time (Minute) | LCMS Measurement Condition |
|---|---|---|---|---|
| 5-1-548 | | 638 | 1.2 | TFA Rev.7 |
| 5-1-549 | | 620 | 1.18 | TFA Rev.7 |
| 5-1-550 | | 614 | 1.33 | TFA Rev.7 |

-continued
| Example No. | Compound | m/z (M + H) | Retention Time (Minute) | LCMS Measurement Condition |
|---|---|---|---|---|
| 5-1-551 | 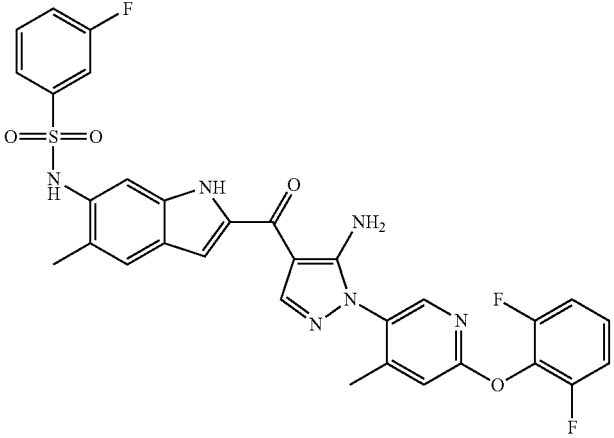 [SMILES: Cc1cc2cc(C(=O)c3cnn(-c4cnc(Oc5c(F)cccc5F)cc4C)c3N)[nH]c2cc1NS(=O)(=O)c1cccc(F)c1] | 633 | 1.29 | TFA Rev.7 |
| 5-1-552 | 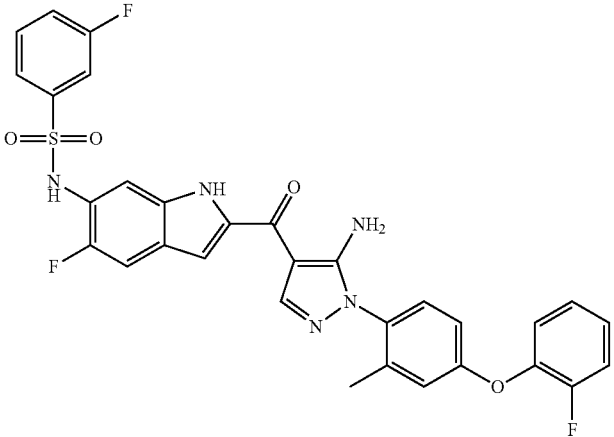 | 618 | 1.03 | AA Rev.11 |
| 5-1-553 | 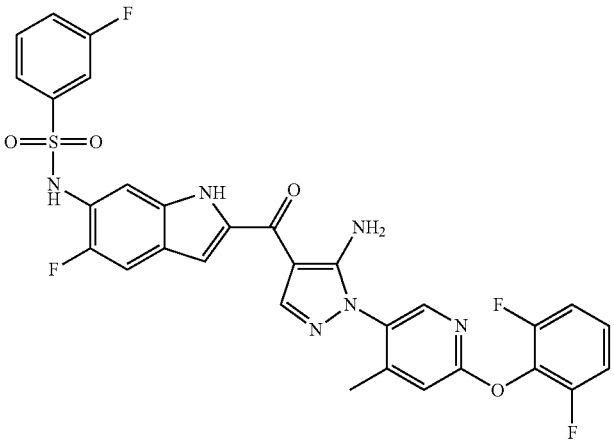 [SMILES: Cc1cc(Oc2c(F)cccc2F)ncc1-n1ncc(C(=O)c2cc3cc(F)c(NS(=O)(=O)c4cccc(F)c4)cc3[nH]2)c1N] | 637 | 1.01 | AA Rev.11 |

| Example No. | Compound | m/z (M + H) | Retention Time (Minute) | LCMS Measurement Condition |
|---|---|---|---|---|
| 5-1-554 | | 619 | 1.24 | TFA Rev.7 |
| 5-1-555 | | 640 | 1 | AA Rev.11 |
| 5-1-556 | | 626 | 0.96 | AA Rev.11 |

-continued
| Example No. | Compound | m/z (M + H) | Retention Time (Minute) | LCMS Measurement Condition |
|---|---|---|---|---|
| 5-1-557 | 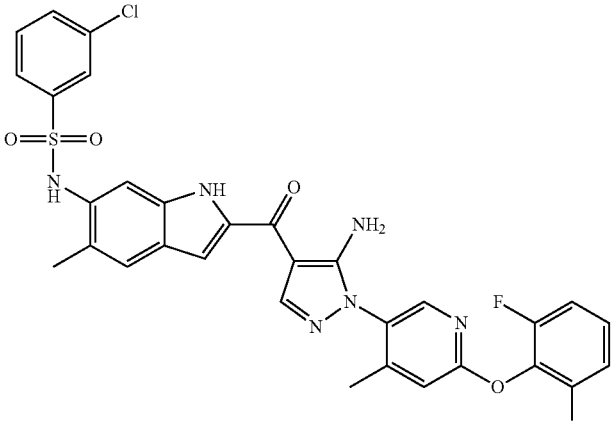 | 649 | 1.34 | TFA Rev.7 |
| 5-1-558 | 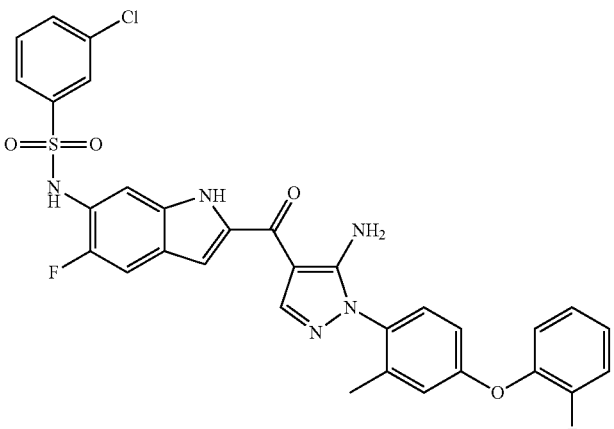 | 634 | 1.05 | AA Rev.11 |
| 5-1-559 | 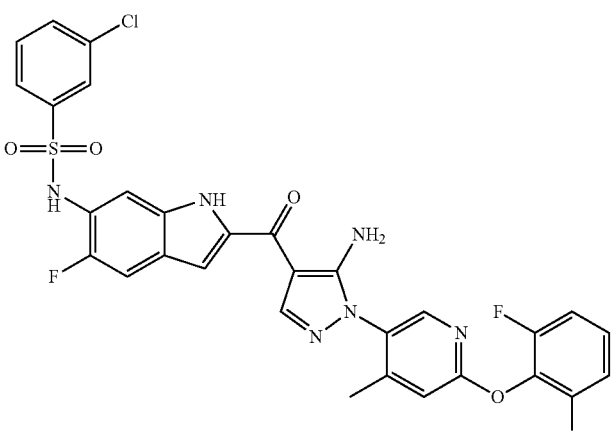 | 653 | 1.03 | AA Rev.11 |

-continued

| Example No. | Compound | m/z (M + H) | Retention Time (Minute) | LCMS Measurement Condition |
|---|---|---|---|---|
| 5-1-560 | | 635 | 1.29 | TFA Rev.7 |
| 5-1-561 | | 651 | 1.33 | TFA Rev.7 |
| 5-1-562 | | 636 | 1.05 | AA Rev.11 |

-continued

| Example No. | Compound | m/z (M + H) | Retention Time (Minute) | LCMS Measurement Condition |
|---|---|---|---|---|
| 5-1-563 | | 655 | 1.03 | AA Rev.11 |
| 5-1-564 | | 637 | 1.02 | AA Rev.11 |
| 5-1-565 | | 669 | 1.29 | TFA Rev.7 |

| Example No. | Compound | m/z (M + H) | Retention Time (Minute) | LCMS Measurement Condition |
|---|---|---|---|---|
| 5-1-566 | 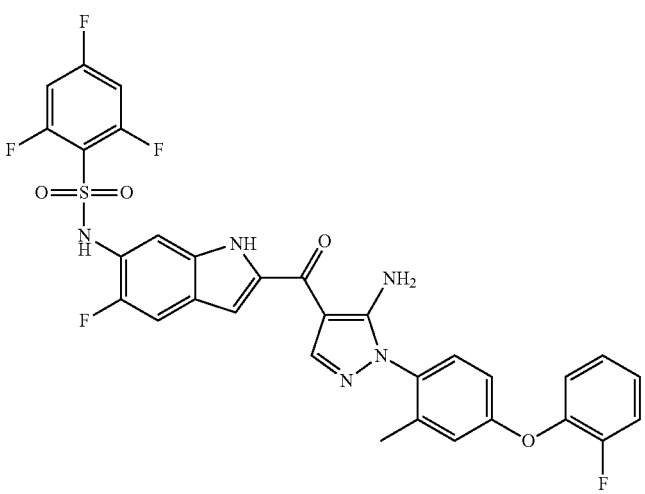 | 654 | 1.02 | AA Rev.11 |
| 5-1-567 | 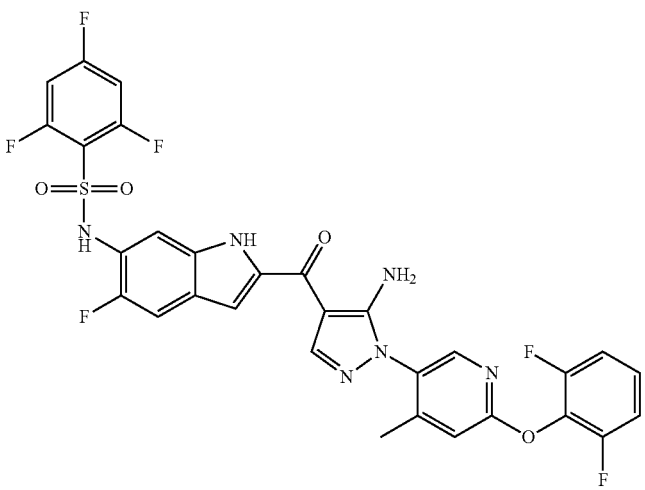 [SMILES: Cc1cc(Oc2c(F)cccc2F)ncc1-n1ncc(C(=O)c2cc3cc(F)c(NS(=O)(=O)c4c(F)cc(F)cc4F)cc3[nH]2)c1N] | 673 | 0.99 | AA Rev.11 |
| 5-1-568 | 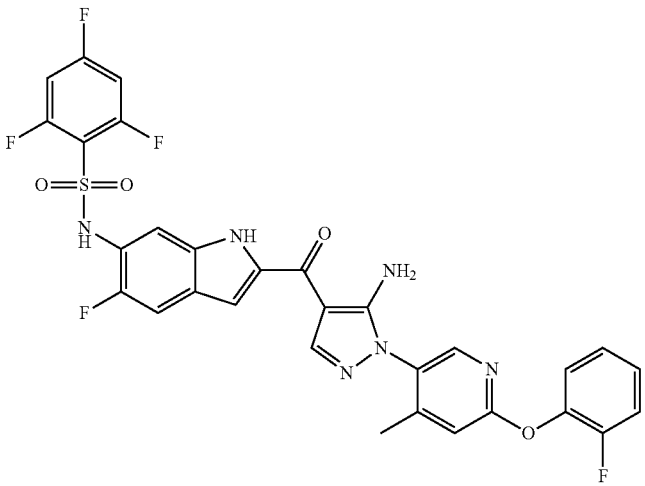 [SMILES: Cc1cc(Oc2ccccc2F)ncc1-n1ncc(C(=O)c2cc3cc(F)c(NS(=O)(=O)c4c(F)cc(F)cc4F)cc3[nH]2)c1N] | 655 | 0.98 | AA Rev.11 |

-continued

| Example No. | Compound | m/z (M + H) | Retention Time (Minute) | LCMS Measurement Condition |
|---|---|---|---|---|
| 5-1-569 | | 712 | 1.23 | TFA Rev.7 |
| 5-1-570 | | 700 | 1.25 | TFA Rev.7 |
| 5-1-571 | | 714 | 1.28 | TFA Rev.7 |

| Example No. | Compound | m/z (M + H) | Retention Time (Minute) | LCMS Measurement Condition |
|---|---|---|---|---|
| 5-1-572 | | 716 | 1.28 | TFA Rev.7 |
| 5-1-573 | | 696 | 1.25 | TFA Rev.7 |
| 5-1-574 | | 707 | 0.96 | AA Rev.11 |

-continued

| Example No. | Compound | m/z (M + H) | Retention Time (Minute) | LCMS Measurement Condition |
|---|---|---|---|---|
| 5-1-575 | | 716 | 1.28 | TFA Rev.7 |
| 5-1-576 | | 700 | 1.24 | TFA Rev.7 |
| 5-1-577 | | 642 | 1.24 | TFA Rev.7 |

Example 4-8-001
Synthesis of N-{2-{5-amino-1-[4-(2-fluorophenoxy)-2-methylphenyl]pyrazole-4-carbonyl}-5-fluoro-1H-indol-6-yl}-1-(2,3-dihydroxypropyl)cyclopropane-1-sulfonamide
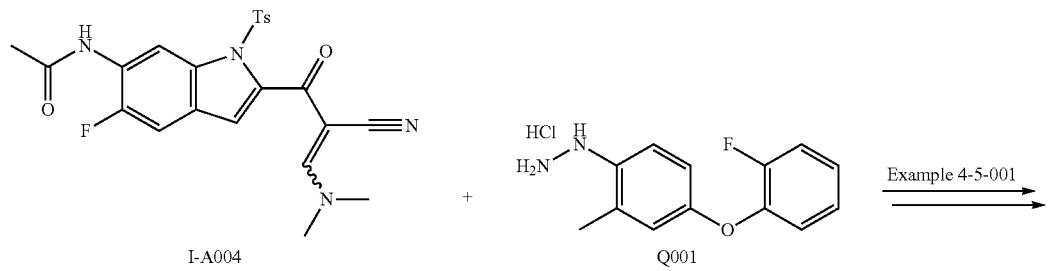
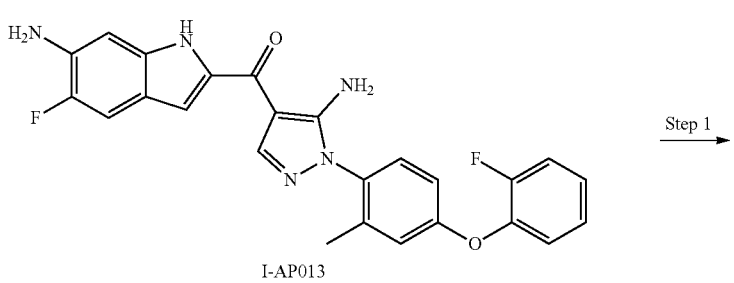
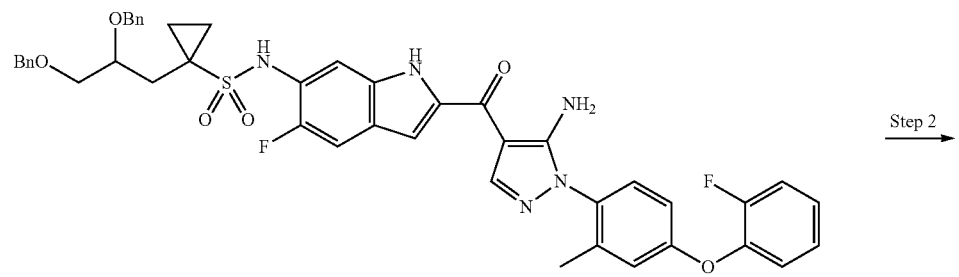
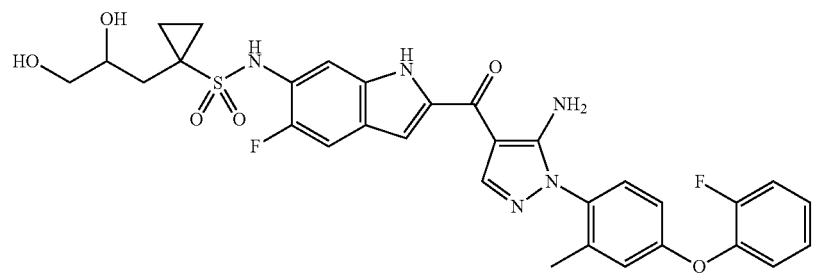 [SMILES: Cc1cc(Oc2ccccc2F)ccc1-n1ncc(C(=O)c2cc3cc(F)c(NS(=O)(=O)C4(CC(O)CO)CC4)cc3[nH]2)c1N]

Step 1

Synthesis of N-{2-{5-amino-1-[4-(2-fluorophenoxy)-2-methylphenyl]pyrazole-4-carbonyl}-5-fluoro-1H-indol-6-yl}-1-[2,3-bis(phenylmethoxy)propyl]cyclopropane-1-sulfonamide Aniline I-AP013 (70 mg) synthesized from enamine I-A004 and hydrazine Q001 by the similar method for aniline I-AP015 synthesized in Example 4-5-001 was dissolved in dichloromethane (1.5 mL) and pyridine (1.5 mL). 1-[2,3-Bis(phenylmethoxy)propyl]cyclopropane-1-sulfonyl chloride SAA-001 (126 mg), TEA (47 μL), and DMAP (1.8 mg) were added and the mixture was stirred at 25° C. for 15 hours. The reaction solution was purified by column chromatography (hexane/ethyl acetate) to give the target compound (60 mg).

Step 2

Synthesis of N-{2-{5-amino-1-[4-(2-fluorophenoxy)-2-methylphenyl]pyrazole-4-carbonyl}-5-fluoro-1H-indol-6-yl}-1-(2,3-dihydroxypropyl)cyclopropane-1-sulfonamide N-{2-{5-Amino-1-[4-(2-fluorophenoxy)-2-methylphenyl]pyrazole-4-carbonyl}-5-fluoro-1H-indol-6-yl}-1-[2,3-bis(phenylmethoxy)propyl]cyclopropane-1-sulfonamide (58 mg) was dissolved in dichloromethane (3.0 mL), and trimethylsilyl iodide (71 μL) was added at 0° C. Then the mixture was stirred at 0° C. for five hours. Trimethylsilyl iodide (10 μL) was added, and the mixture was warmed to 25° C. and stirred for four hours. A saturated aqueous sodium bicarbonate solution (5.0 mL) was added to the reaction solution, the mixture was extracted with ethyl acetate (100 mL), and the organic layer was dried over sodium sulfate. The drying agent was removed by filtration, the filtrate was then concentrated under reduced pressure, and the resulting residue was purified by Prep-HPLC to give the target compound (13 mg).

(Corresponding Enamine, Hydrazine, and Sulfamidating Reagent)

| Example No. | Enamine | | Hydrazine | | Sulfamidating Reagent | |
|---|---|---|---|---|---|---|
| 4-8-001 | I-A004 | [structure] | Q001 | [structure] | SAA-001 | [structure] |

(Synthesized Compound)

| Example No. | Compound | m/z (M + H) | Retention Time (Minute) | LCMS Measurement Condition |
|---|---|---|---|---|
| 4-8-001 | [structure] | 638 | 2.25 | B1 |

Example 4-9-001

Synthesis of {5-amino-1-[6-(2-fluorophenoxy)-4-methylpyridin-3-yl]pyrazol-4-yl}-[6-(1,1-dioxo-1,2-thiazolidin-2-yl)-5-fluoro-1H-indol-2-yl]methanone

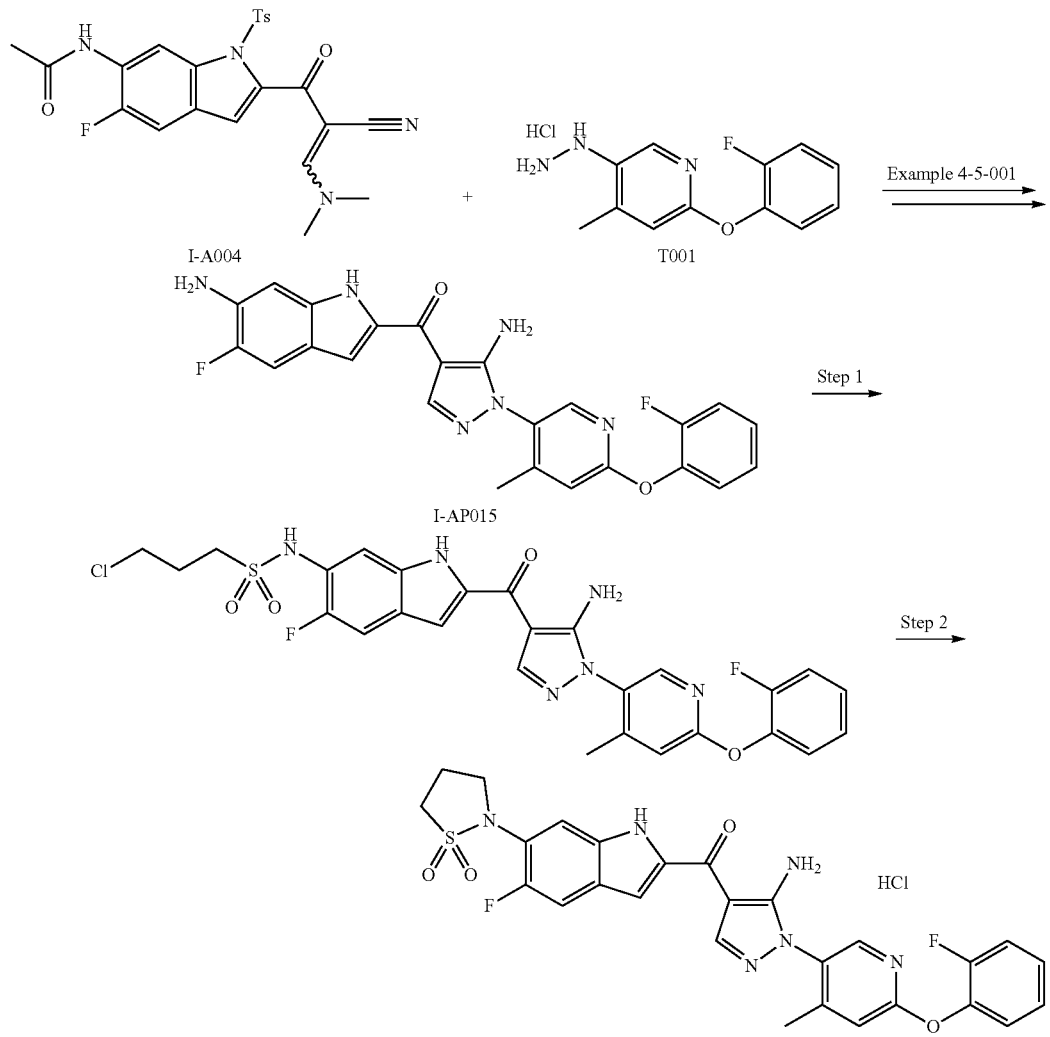

Step 1

Synthesis of N-{2-{5-amino-1-[6-(2-fluorophenoxy)-4-methylpyridin-3-yl]pyrazole-4-carbonyl}-5-fluoro-1H-indol-6-yl}-3-chloropropane-1-sulfonamide Aniline I-AP015 synthesized in Example 4-5-001 (79 mg) was dissolved in pyridine (1.6 mL), and 3-chloropropanesulfonyl chloride (41 µL) was added at 0° C. Then the mixture was stirred at 25° C. for three hours. 1 M hydrochloric acid (30 mL) was added to the reaction solution and the mixture was extracted with ethyl acetate (20 mL) three times. The organic layers were washed with 1 M hydrochloric acid (20 mL) and dried over sodium sulfate. The drying agent was removed by filtration, the filtrate was then concentrated under reduced pressure, and the resulting residue was purified by column chromatography (hexane/ethyl acetate) to give the target compound (87 mg).

Step 2

Synthesis of {5-amino-1-[6-(2-fluorophenoxy)-4-methylpyridin-3-yl]pyrazol-4-yl}-[6-(1,1-dioxo-1,2-thiazolidin-2-yl)-5-fluoro-1H-indol-2-yl]methanone N-{2-{5-Amino-1-[6-(2-fluorophenoxy)-4-methylpyridin-3-yl]pyrazole-4-carbonyl}-5-fluoro-1H-indol-6-yl}-3-chloropropane-1-sulfonamide (88 mg) was dissolved in N,N-dimethylformamide (1.8 mL), and sodium iodide (66 mg) and potassium carbonate (101 mg) were added. Then the mixture was stirred at 80° C. for 15 minutes. The reaction solution was cooled to 25° C., and water (15 ml) and 2 M hydrochloric acid (2.0 mL) were added. Then the precipitated solid was collected by filtration to give the target compound (63 mg).

Example 4-9-002
The compound of Example 4-9-002 was synthesized from a corresponding enamine and a corresponding hydrazine by the similar method as in Example 4-9-001.
(Corresponding Enamines and Hydrazines)
| Example No. | Enamine | | Hydrazine | |
|---|---|---|---|---|
| 4-9-001 | I-A004 | 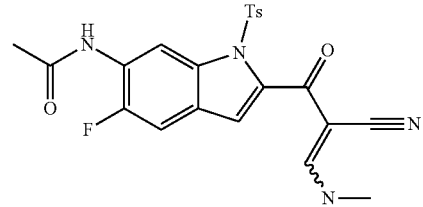 | T001 | HCl |
| 4-9-002 | I-A004 | | T002 | HCl |
(Synthesized Compounds)
| Example No. | Compound | m/z (M + H) | Retention Time (Minute) | LCMS Measurement Condition |
|---|---|---|---|---|
| 4-9-001 | 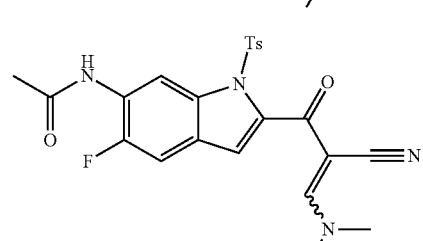 | 565 | 0.81 | A1 |
| 4-9-002 | | 583 | 0.87 | A1 |

Example 4-10-001

Synthesis of 2-{{2-{5-amino-1-[6-(2-fluorophenoxy)-4-methylpyridin-3-yl]pyrazole-4-carbonyl}-5-fluoro-1H-indol-6-yl}sulfamoyl}-N,N-diethylacetamide

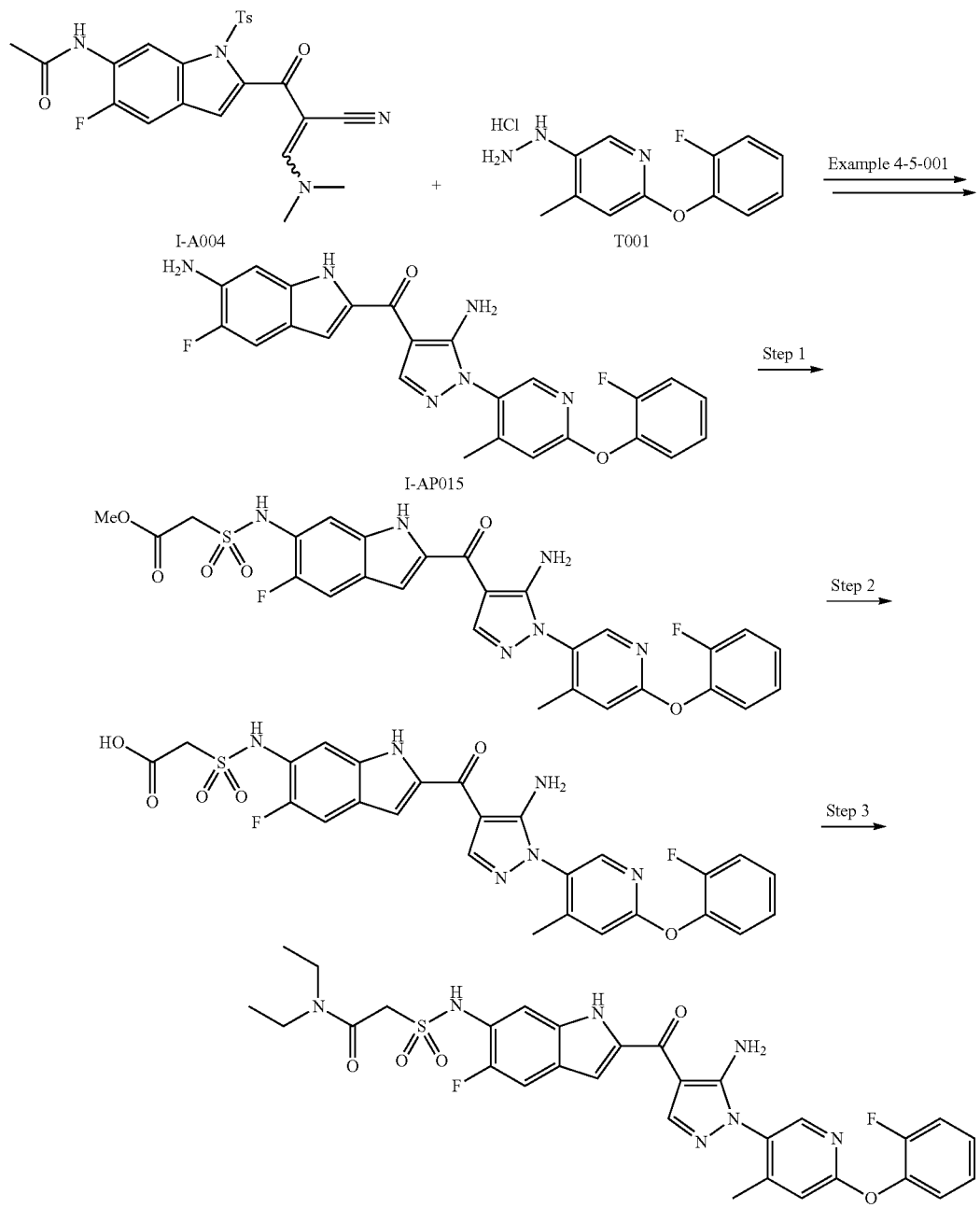

Step 1

Synthesis of methyl 2-{{2-{5-amino-1-[6-(2-fluorophenoxy)-4-methylpyridin-3-yl]pyrazole-4-carbonyl}-5-fluoro-1H-indol-6-yl}sulfamoyl}acetate Aniline I-AP015 synthesized in Example 4-5-001 (300 mg) was dissolved in dichloromethane (6.0 mL), and TEA (0.3 mL) and methyl chlorosulfonylacetate (0.4 M solution in tetrahydrofuran, 2.0 mL) were added at 0° C. Then the mixture was stirred at 25° C. for one hour. 0.1 M hydrochloric acid (25 mL) was added to the reaction solution, the mixture was extracted with dichloromethane (25 mL), and the organic layer was dried over the sodium sulfate. The drying agent was removed by filtration, the filtrate was then concentrated under reduced pressure, and the resulting residue was purified by column chromatography (dichloromethane/ethyl acetate) to give the target compound (327 mg).

Step 2

Synthesis of 2-{{2-{5-amino-1-[6-(2-fluorophenoxy)-4-methylpyridin-3-yl]pyrazole-4-carbonyl}-5-fluoro-1H-indol-6-yl}sulfamoyl}acetic acid Methyl 2-{{2-{5-amino-1-[6-(2-fluorophenoxy)-4-methylpyridin-3-yl]pyrazole-4-carbonyl}-5-fluoro-1H-indol-6-yl}sulfamoyl}acetate (237 mg) was dissolved in methanol (4.0 mL), and a 4 M aqueous sodium hydroxide solution (0.5 mL) was added. Then the mixture was stirred at 50° C. for two hours. 1 M hydrochloric acid was added to the reaction solution until it became acidic. The mixture was extracted with ethyl acetate three times and the organic layers were dried over sodium sulfate. The drying agent was removed by filtration and the filtrate was then concentrated under reduced pressure to give the target compound (217 mg).

Step 3

Synthesis of 2-{{2-{5-amino-1-[6-(2-fluorophenoxy)-4-methylpyridin-3-yl]pyrazole-4-carbonyl}-5-fluoro-1H-indol-6-yl}sulfamoyl}-N,N-diethylacetamide 2-{{2-{5-Amino-1-[6-(2-fluorophenoxy)-4-methylpyridin-3-yl]pyrazole-4-carbonyl}-5-fluoro-1H-indol-6-yl}sulfamoyl}acetic acid (90 mg) and HATU (76 mg) were suspended in dichloromethane (3.0 mL), and diethylamine (21 μL) and DIPEA (81 μL) were added. Then the mixture was stirred at 25° C. for four hours. 0.1 M hydrochloric acid was added to the reaction solution, the mixture was extracted with ethyl acetate, and the organic layer was dried over the sodium sulfate. The drying agent was removed by filtration, the filtrate was then concentrated under reduced pressure, and the residue was purified by column chromatography (dichloromethane/ethyl acetate) to give the target compound (38 mg).

Examples 4-10-002 to 4-10-006

The compounds of Examples 4-10-002 to 4-10-006 were synthesized by the similar method as in Example 4-10-001 using the corresponding hydrazines and using the corresponding amines in Step 3.

(Corresponding Enamines, Hydrazines, and Amines)

| Example No. | Enamine | | Hydrazine | | Amine |
|---|---|---|---|---|---|
| 4-10-001 | I-A004 | [structure] | T001 | HCl [structure] | [structure] |
| 4-10-002 | I-A004 | [structure] | Q001 | HCl [structure] | [structure] |
| 4-10-003 | I-A004 | [structure] | Q001 | HCl [structure] | [structure] |

-continued

| Example No. | Enamine | Hydrazine | Amine |
|---|---|---|---|
| 4-10-004 | I-A004 | Q001 HCl | morpholine |
| 4-10-005 | I-A004 | T001 HCl | pyrrolidine |
| 4-10-006 | I-A004 | T001 HCl | morpholine |

(Synthesized Compounds)

| Example No. | Compound | m/z (M + H) | Retention Time (Minute) | LCMS Measurement Condition |
|---|---|---|---|---|
| 4-10-001 | | 638 | 0.82 | A1 |
| 4-10-002 | | 623 | 2.42 | B1 |

-continued
| Example No. | Compound | m/z (M + H) | Retention Time (Minute) | LCMS Measurement Condition |
|---|---|---|---|---|
| 4-10-003 | 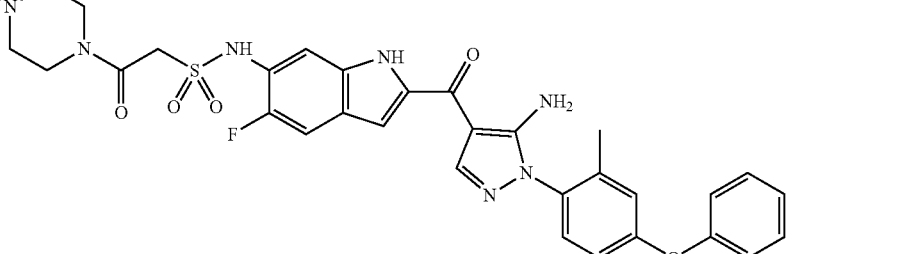 | 692 | 1.97 | B1 |
| 4-10-004 | 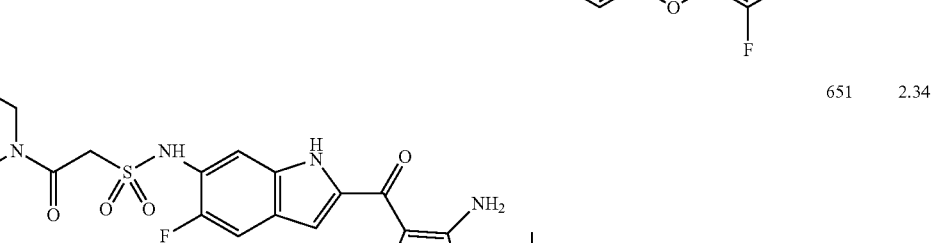 | 651 | 2.34 | B1 |
| 4-10-005 | 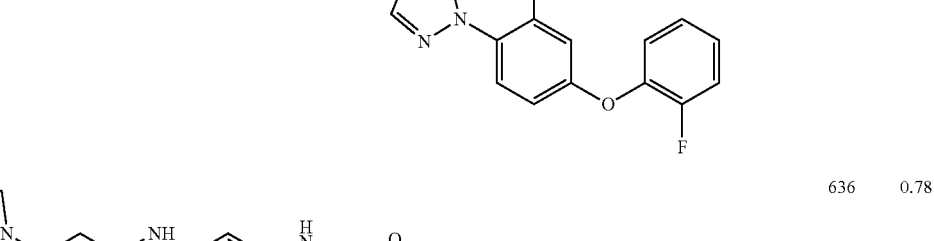 | 636 | 0.78 | A1 |
| 4-10-006 | 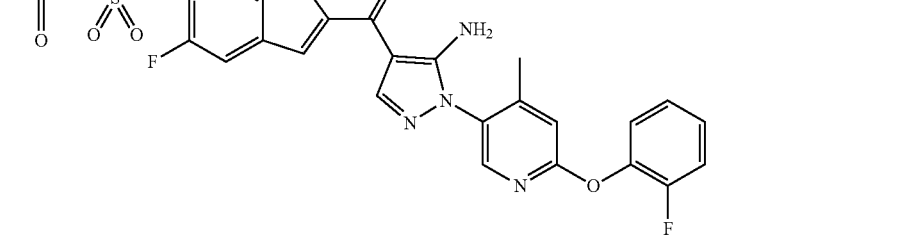 | 652 | 2.15 | B1 |

Example 4-10-007
Synthesis of N-{2-{5-amino-1-[4-(2-fluorophenoxy)-2-methylphenyl]pyrazole-4-carbonyl}-5-methyl-1H-indol-6-yl}-2-morpholin-4-yl-2-oxoethanesulfonamide
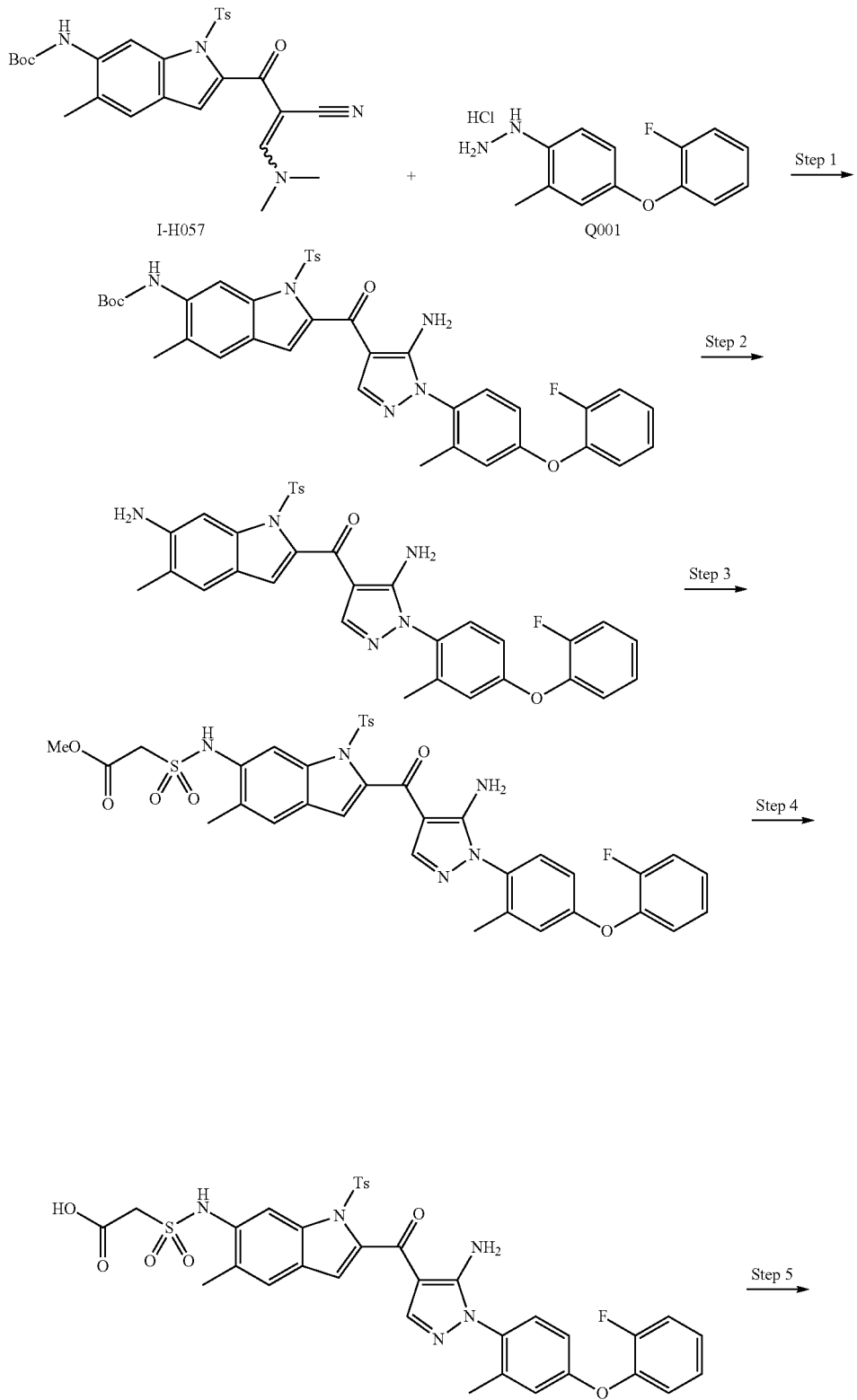

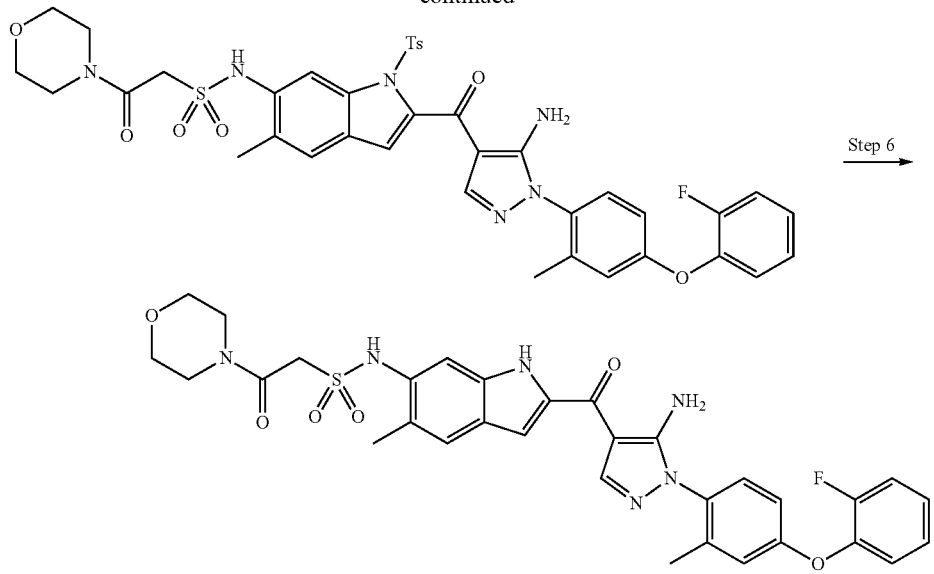

Step 6 →

Step 1

Synthesis of tert-butyl N-{2-{5-amino-1-[4-(2-fluorophenoxy)-2-methylphenyl]pyrazole-4-carbonyl}-5-methyl-1-(4-methylphenyl)sulfonylindol-6-yl}carbamate Enamine I-H057 (1.60 g) and hydrazine Q001 (1.60 g) were dissolved in ethanol (30 mL) and the reaction solution was stirred at 75° C. for 16 hours. The reaction solution was concentrated under reduced pressure to give the target compound (2.00 g).

Step 2

Synthesis of {5-amino-1-[4-(2-fluorophenoxy)-2-methylphenyl]pyrazol-4-yl}-[6-amino-5-methyl-1-(4-methylphenyl)sulfonylindol-2-yl]methanone tert-Butyl N-{2-{5-amino-1-[4-(2-fluorophenoxy)-2-methylphenyl]pyrazole-4-carbonyl}-5-methyl-1-(4-methylphenyl)sulfonylindol-6-yl}carbamate (2.00 g) was dissolved in dichloromethane (150 mL) and the reaction solution was bubbled with hydrogen chloride gas and stirred at 25° C. for two hours. The reaction solution was concentrated under reduced pressure, a 10% aqueous ammonia solution was added to the resulting residue, and the mixture was extracted with ethyl acetate. The organic layer was washed with saturated saline and dried over sodium sulfate. The drying agent was removed by filtration, the filtrate was then concentrated under reduced pressure, and the resulting residue was purified by column chromatography (petroleum ether/ethyl acetate) to give the target compound (1.25 g).

Step 3

Synthesis of methyl 2-{{2-{5-amino-1-[4-(2-fluorophenoxy)-2-methylphenyl]pyrazole-4-carbonyl}-5-methyl-1-(4-methylphenyl)sulfonylindol-6-yl}sulfamoyl}acetate {5-Amino-1-[4-(2-fluorophenoxy)-2-methylphenyl]pyrazol-4-yl}-[6-amino-5-methyl-1-(4-methylphenyl)sulfonylindol-2-yl]methanone (1.25 g) and TEA (20 mL) were dissolved in tetrahydrofuran (30 mL), and methyl chlorosulfonylacetate (1.76 g) was added at 0° C. Then the mixture was stirred at 25° C. for two hours. The reaction solution was concentrated under reduced pressure, 1 M hydrochloric acid was added to the resulting residue, and the mixture was extracted with ethyl acetate. The organic layer was washed with saturated saline and dried over sodium sulfate. The drying agent was removed by filtration, the filtrate was then concentrated under reduced pressure, and the resulting residue was purified by column chromatography (petroleum ether/ethyl acetate) to give the target compound (1.20 g).

Step 4

Synthesis of 2-{{2-{5-amino-1-[4-(2-fluorophenoxy)-2-methylphenyl]pyrazole-4-carbonyl}-5-methyl-1-(4-methylphenyl)sulfonylindol-6-yl}sulfamoyl}acetic acid Methyl 2-{{2-{5-amino-1-[4-(2-fluorophenoxy)-2-methylphenyl]pyrazole-4-carbonyl}-5-methyl-1-(4-methylphenyl)sulfonylindol-6-yl}sulfamoyl}acetate (50 mg) was suspended in methanol (10 mL), and a 1 M aqueous sodium hydroxide solution (3.3 mL) was added. Then the mixture was stirred at 25° C. for two hours. The reaction solution was concentrated under reduced pressure, 1 M hydrochloric acid was added to the resulting residue, and the mixture was extracted with ethyl acetate. The organic layer was washed with saturated saline and dried over sodium sulfate. The drying agent was removed by filtration and the filtrate was then concentrated under reduced pressure to give the target compound (55 mg).

Step 5

Synthesis of N-{2-{5-amino-1-[4-(2-fluorophenoxy)-2-methylphenyl]pyrazole-4-carbonyl}-5-methyl-1-(4-methylphenyl)sulfonylindol-6-yl}-2-morpholin-4-yl-2-oxoethanesulfonamide 2-{{12-{5-Amino-1-[4-(2-fluorophenoxy)-2-methylphenyl]pyrazole-4-carbonyl}-5-methyl-1-(4-methylphenyl)sulfonylindol-6-yl}sulfamoyl}acetic acid (200 mg) was suspended in dichloromethane (20 mL), and morpholine (47

μL), DIPEA (70 μL), 1-ethyl-3-(3-dimethylaminopropyl) carbodiimide hydrochloride (105 mg), and HOBt (37 mg) were added. Then the mixture was stirred at 25° C. for 16 hours. The reaction solution was concentrated under reduced pressure to give the target compound (210 mg).
Step 6

Synthesis of N-{2-{5-amino-1-[4-(2-fluorophenoxy)-2-methylphenyl]pyrazole-4-carbonyl}-5-methyl-1H-indol-6-yl}-2-morpholin-4-yl-2-oxoethanesulfonamide N-{2-{5-Amino-1-[4-(2-fluorophenoxy)-2-methylphenyl]pyrazole-4-carbonyl}-5-methyl-1-(4-methylphenyl)sulfonylindol-6-yl}-2-morpholin-4-yl-2-oxoethanesulfonamide (120 mg) was suspended in dichloromethane (15 mL), and methanesulfonic acid (1.5 mL) was added. Then the mixture was stirred at 25° C. for two hours. The reaction solution was concentrated under reduced pressure, a 10% aqueous ammonia solution was added to the resulting residue, and the mixture was extracted with ethyl acetate. The organic layer was washed with saturated saline and dried over sodium sulfate. The drying agent was removed by filtration, the filtrate was then concentrated under reduced pressure, and the resulting residue was purified by Prep-HPLC to give the target compound (22 mg).

Examples 4-10-008 to 4-10-017, Example 5-1-056, and the Like

The compounds of Examples 4-10-008 to 4-10-017, Example 5-1-056, and the like shown below were synthesized by the similar method as in 4-10-007 using the corresponding enamines and hydrazines and using the corresponding amines in Step 5.
(Corresponding Enamines, Hydrazines, and Amines)

| Example No. | Enamine | | Hydrazine | | Amine |
|---|---|---|---|---|---|
| 4-10-007 | I-H057 | [structure] | Q001 | [structure] | [morpholine structure] |
| 4-10-008 | I-H057 | [structure] | Q001 | [structure] | [isopropylamine structure] |
| 4-10-009 | I-H057 | [structure] | S038 | [structure] | [morpholine structure] |
| 4-10-010 | I-H057 | [structure] | T002 | [structure] | [morpholine structure] |

-continued

| Example No. | | Enamine | | Hydrazine | Amine |
|---|---|---|---|---|---|
| 4-10-011 | I-H058 | (Boc-NH, MeO-indole-Ts, C(O)-C(CN)=CH-NMe2) | Q001 | HCl, H2N-NH-(4-(2-fluorophenoxy)-3-methylphenyl) | isopropylamine |
| 4-10-012 | I-H058 | (Boc-NH, MeO-indole-Ts, C(O)-C(CN)=CH-NMe2) | Q001 | HCl, H2N-NH-(4-(2-fluorophenoxy)-3-methylphenyl) | morpholine |
| 4-10-013 | I-H058 | (Boc-NH, MeO-indole-Ts, C(O)-C(CN)=CH-NMe2) | S038 | HCl, H2N-NH-(2-fluoro-4-(2-fluorophenoxy)-6-methylphenyl) | morpholine |
| 4-10-014 | I-H058 | (Boc-NH, MeO-indole-Ts, C(O)-C(CN)=CH-NMe2) | T001 | HCl, H2N-NH-(6-(2-fluorophenoxy)-4-methylpyridin-3-yl) | pyrrolidine |
| 4-10-015 | I-H058 | (Boc-NH, MeO-indole-Ts, C(O)-C(CN)=CH-NMe2) | T001 | HCl, H2N-NH-(6-(2-fluorophenoxy)-4-methylpyridin-3-yl) | isopropylamine |
| 4-10-016 | I-H058 | (Boc-NH, MeO-indole-Ts, C(O)-C(CN)=CH-NMe2) | T001 | HCl, H2N-NH-(6-(2-fluorophenoxy)-4-methylpyridin-3-yl) | morpholine |

-continued

| Example No. | | Enamine | Hydrazine | Amine |
|---|---|---|---|---|
| 4-10-017 | I-H058 | (structure) | T002 (structure) | (pyrrolidine) |
| 5-1-056 | I-A004 | (structure) | T001 (structure) | (isopropylamine) |
| 5-1-058 | I-H057 | (structure) | T001 (structure) | (isopropylamine) |
| 5-1-088 | I-H057 | (structure) | T002 (structure) | (pyrrolidine) |
| 5-1-089 | I-H057 | (structure) | S038 (structure) | (isopropylamine) |
| 5-1-110 | I-H057 | (structure) | S038 (structure) | (pyrrolidine) |

US 10,479,780 B2

583 584

-continued

| Example No. | | Enamine | | Hydrazine | | Amine |
|---|---|---|---|---|---|---|
| 5-1-121 | I-H057 | BOC-NH, 5-methyl-6-NH, N-Ts indole, 2-(CO-C(CN)=CH-NMe2) | T001 | HCl, H2N-NH-(5-pyridyl with 4-methyl, 2-(2-fluorophenoxy)) | | pyrrolidine (NH) |
| 5-1-122 | I-H058 | BOC-NH, 5-MeO-6-NH, N-Ts indole, 2-(CO-C(CN)=CH-NMe2) | Q001 | HCl, H2N-NH-(4-(2-fluorophenoxy)-3-methylphenyl) | | pyrrolidine (NH) |
| 5-1-130 | I-H058 | BOC-NH, 5-MeO-6-NH, N-Ts indole, 2-(CO-C(CN)=CH-NMe2) | S038 | HCl, H2N-NH-(2-methyl-6-fluoro-4-(2-fluorophenoxy)phenyl) | | pyrrolidine (NH) |
| 5-1-136 | I-H057 | BOC-NH, 5-methyl-6-NH, N-Ts indole, 2-(CO-C(CN)=CH-NMe2) | T002 | HCl, H2N-NH-(5-pyridyl with 4-methyl, 2-(2,6-difluorophenoxy)) | | isopropylamine (NH2) |
| 5-1-137 | I-H058 | BOC-NH, 5-MeO-6-NH, N-Ts indole, 2-(CO-C(CN)=CH-NMe2) | S038 | HCl, H2N-NH-(2-methyl-6-fluoro-4-(2-fluorophenoxy)phenyl) | | isopropylamine (NH2) |
| 5-1-143 | I-H058 | BOC-NH, 5-MeO-6-NH, N-Ts indole, 2-(CO-C(CN)=CH-NMe2) | T002 | HCl, H2N-NH-(5-pyridyl with 4-methyl, 2-(2,6-difluorophenoxy)) | | morpholine (NH) |

(Synthesized Compounds)
| Example No. | Compound | m/z (M + H) | Retention Time (Minute) | LCMS Measurement Condition |
|---|---|---|---|---|
| 4-10-007 | 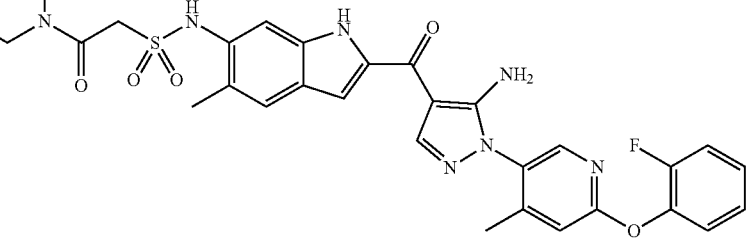 | 647 | 0.98 | J4 |
| 4-10-008 | 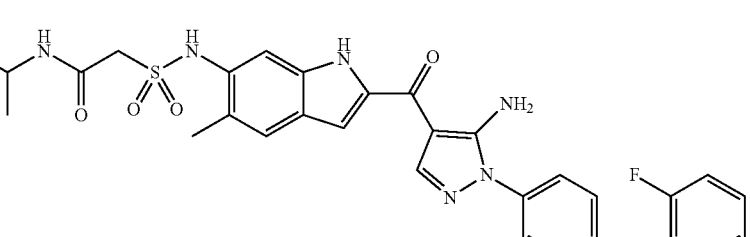 | 619 | 1.00 | J4 |
| 4-10-009 | 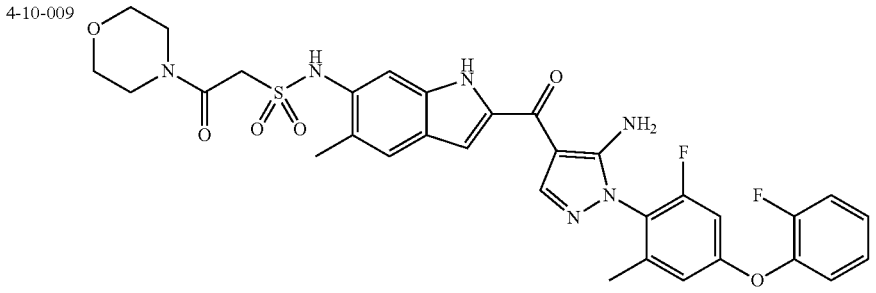 | 665 | 0.98 | J4 |
| 4-10-010 |  | 666 | 0.98 | J1 |
| 4-10-011 | 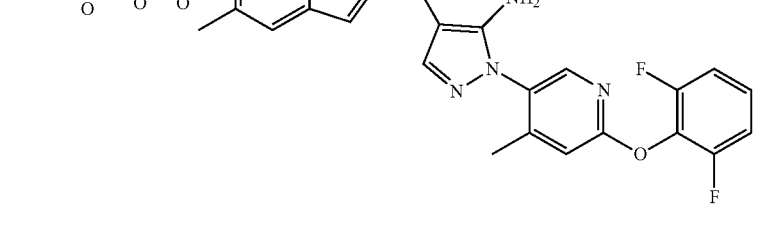 | 635 | 0.98 | J2 |

-continued
| Example No. | Compound | m/z (M + H) | Retention Time (Minute) | LCMS Measurement Condition |
|---|---|---|---|---|
| 4-10-012 | 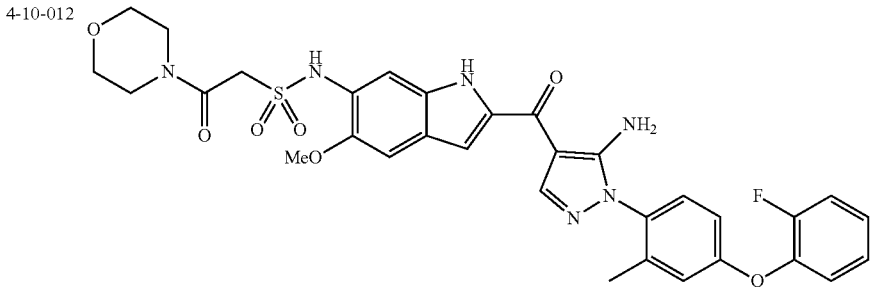 | 663 | 0.96 | J3 |
| 4-10-013 | 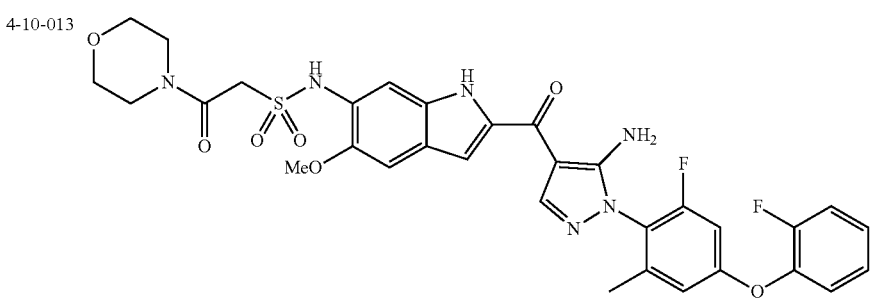 | 681 | 0.95 | J3 |
| 4-10-014 | 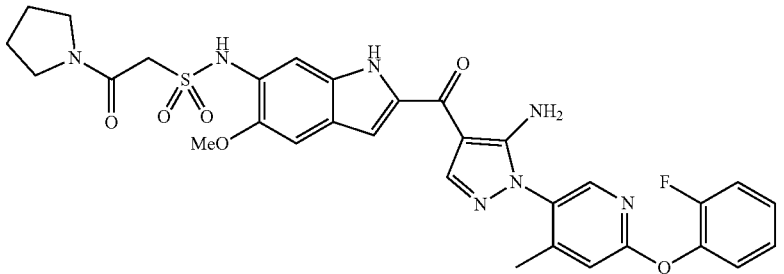 [SMILES: COc1cc2cc(C(=O)c3cnn(-c4cnc(Oc5ccccc5F)cc4C)c3N)[nH]c2cc1NS(=O)(=O)CC(=O)N1CCCC1] | 648 | 0.92 | J2 |
| 4-10-015 | 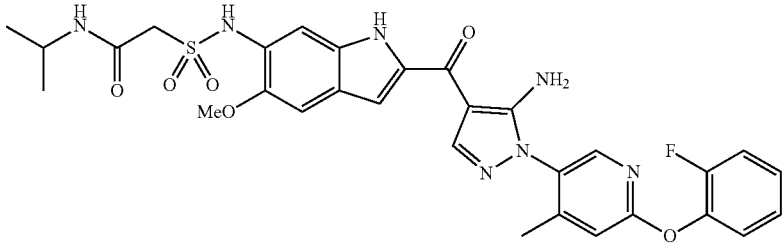 [SMILES: COc1cc2cc(C(=O)c3cnn(-c4cnc(Oc5ccccc5F)cc4C)c3N)[nH]c2cc1NS(=O)(=O)CC(=O)NC(C)C] | 636 | 0.94 | J2 |
| 4-10-016 | 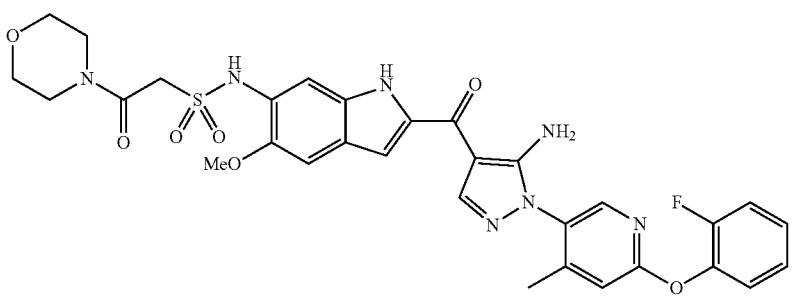 [SMILES: COc1cc2cc(C(=O)c3cnn(-c4cnc(Oc5ccccc5F)cc4C)c3N)[nH]c2cc1NS(=O)(=O)CC(=O)N1CCOCC1] | 664 | 0.91 | J3 |

-continued

| Example No. | Compound | m/z (M + H) | Retention Time (Minute) | LCMS Measurement Condition |
|---|---|---|---|---|
| 4-10-017 | | 666 | 0.94 | J2 |
| 5-1-056 | | 624 | 0.96 | AA Rev.5 |
| 5-1-058 | | 620 | 0.99 | AA Rev.5 |
| 5-1-088 | | 650 | 1.0 | AA Rev.11 |

| Example No. | Compound | m/z (M + H) | Retention Time (Minute) | LCMS Measurement Condition |
|---|---|---|---|---|
| 5-1-089 | | 637 | 1.03 | AA Rev.11 |
| 5-1-110 | | 649 | 1.02 | AA Rev.11 |
| 5-1-121 | | 632 | 0.98 | AA Rev.11 |
| 5-1-122 | | 647 | 1.23 | TFA Rev.5 |

-continued

| Example No. | Compound | m/z (M + H) | Retention Time (Minute) | LCMS Measurement Condition |
|---|---|---|---|---|
| 5-1-130 | | 665 | 1.25 | TFA Rev.5 |
| 5-1-136 | | 638 | 1.0 | AA Rev.11 |
| 5-1-137 | | 653 | 1.0 | AA Rev.11 |
| 5-1-143 | | 682 | 0.95 | AA Rev.11 |

Example 4-11-001

Synthesis of N-{2-{5-amino-1-[6-(2-fluorophenoxy)-4-methylpyridin-3-yl]pyrazole-4-carbonyl}-5-methoxy-1H-indol-6-yl}acetamide

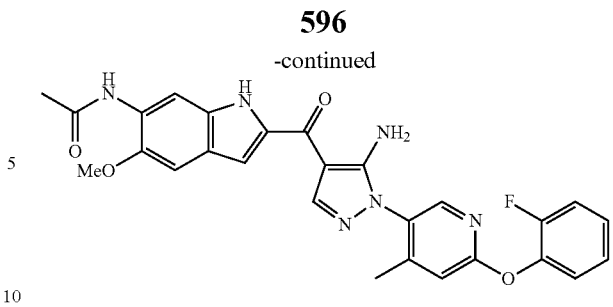

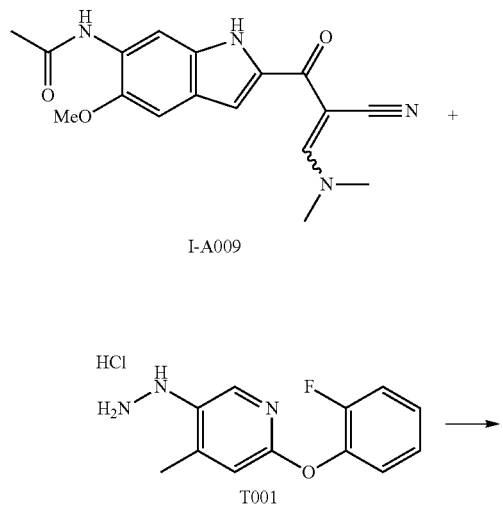

Enamine I-A009 (450 mg) and hydrazine T001 (549 mg) were dissolved in 1-methyl-2-pyrrolidone (5.5 mL), and N-methylmorpholine (758 μL) was added. Then the atmosphere in the flask was replaced by nitrogen, and the mixture was stirred at 100° C. for one hour. The reaction solution was cooled to 25° C., a saturated aqueous ammonium chloride solution (50 mL) was added, and the precipitated solid was collected by filtration and purified by column chromatography (hexane/ethyl acetate, dichloromethane/methanol) to give the target compound (774 mg).

(Corresponding Enamine and Hydrazine)

(Synthesized Compound)

| Example No. | Compound | m/z (M + H) | Retention Time (Minute) | LCMS Measurement Condition |
|---|---|---|---|---|
| 4-11-001 | | 515 | 0.73 | A1 |

Example 4-12-001

Synthesis of N-{2-{5-amino-1-[6-(2-fluorophenoxy)-4-methylpyridin-3-yl]pyrazole-4-carbonyl}-5-methoxy-1H-indol-6-yl}morpholine-4-sulfonamide

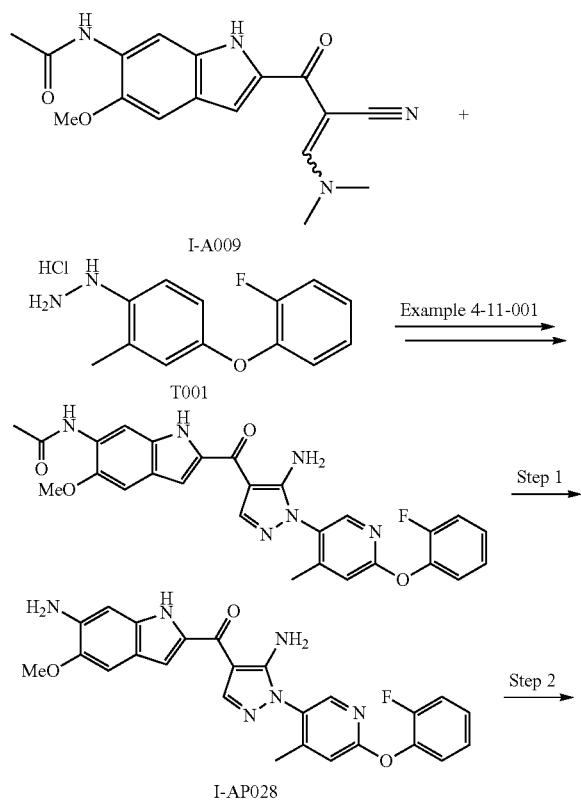

Step 1

Synthesis of {5-amino-1-[6-(2-fluorophenoxy)-4-methylpyridin-3-yl]pyrazol-4-yl}-(6-amino-5-methoxy-1H-indol-2-yl)methanone (I-AP028)

The acetamide synthesized in Example 4-11-001 (543 mg) was dissolved in ethanol (10 mL), and concentrated sulfuric acid (563 µL) was added. Then the mixture was refluxed for 66 hours. The reaction solution was cooled to 25° C. and a saturated aqueous sodium bicarbonate solution (20 mL) was added. The precipitated solid was collected by filtration and washed with water (20 mL) to give the target compound (583 mg).

Step 2

Synthesis of N-{2-{5-amino-1-[6-(2-fluorophenoxy)-4-methylpyridin-3-yl]pyrazole-4-carbonyl}-5-methoxy-1H-indol-6-yl}morpholine-4-sulfonamide {5-Amino-1-[6-(2-fluorophenoxy)-4-methylpyridin-3-yl]pyrazol-4-yl}-(6-amino-5-methoxy-1H-indol-2-yl)methanone (90 mg) was dissolved in pyridine (1.0 mL), and morpholine-4-sulfonyl chloride (354 mg) was added. Then the mixture was stirred at 25° C. for four hours. The reaction solution was purified by Prep-HPLC to give the target compound (47 mg).

Examples 4-12-002 to 4-12-003

The compounds of Examples 4-12-002 to 4-12-003 were synthesized by the similar method as in Example 4-12-001 using the corresponding hydrazines and using the corresponding amidating reagents in Step 2.

(Corresponding Enamines, Hydrazines, and Amidating Reagents)

| Example No. | | Enamine | Hydrazine | | Amidating Reagent |
|---|---|---|---|---|---|
| 4-12-001 | I-A009 | (structure) | T001 | (structure) | 1828-66-6 (structure) |

-continued
| Example No. | | Enamine | Hydrazine | | Amidating Reagent |
|---|---|---|---|---|---|
| 4-12-002 | I-A009 | 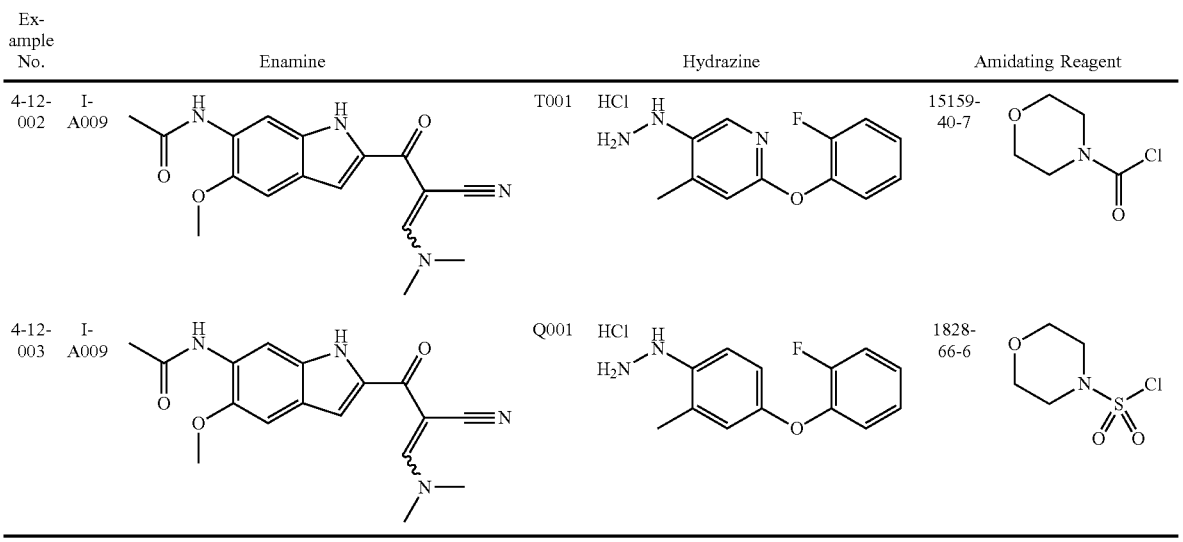 | T001 HCl | | 15159-40-7 |
| 4-12-003 | I-A009 | | Q001 HCl | | 1828-66-6 |
(Synthesized Compounds)
| Example No. | Compound | m/z (M + H) | Retention Time (Minute) | LCMS Measurement Condition |
|---|---|---|---|---|
| 4-12-001 | | 622 | 0.77 | A1 |
| 4-12-002 | | 586 | 0.74 | A1 |
| 4-12-003 | | 621 | 0.82 | A1 |

Example 4-13-001

Synthesis of N-{2-{5-amino-1-[6-(2-fluorophenoxy)-4-methylpyridin-3-yl]pyrazole-4-carbonyl}-5-methoxy-1H-indol-6-yl}-3-fluoropropane-1-sulfonamide

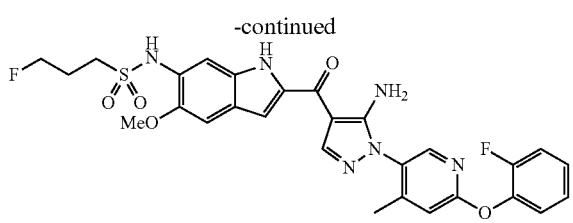

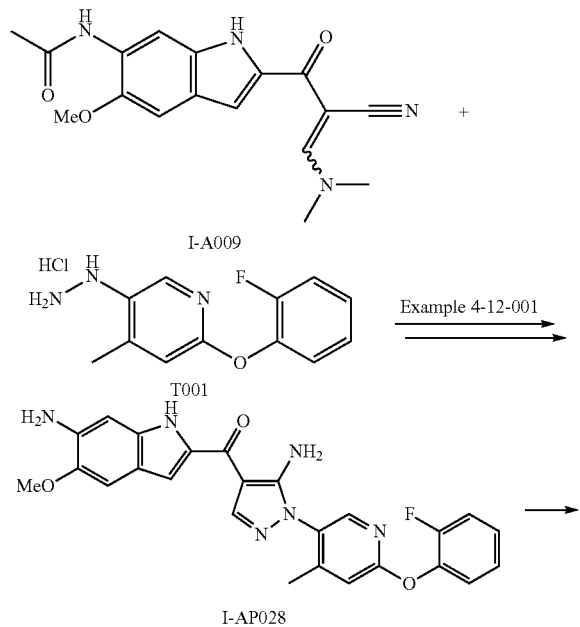

Aniline I-AP028 synthesized in Example 4-12-001 (100 mg) was dissolved in pyridine (0.5 mL), and 3-fluoropropanesulfonyl chloride (35 μL) was added. Then the mixture was stirred at 25° C. for one hour. 1 M hydrochloric acid (5.0 mL) was added to the reaction solution and the mixture was extracted with ethyl acetate (20 mL). The organic layer was washed with 1 M hydrochloric acid (5.0 mL) and saturated saline (5.0 mL), and dried over sodium sulfate.

The drying agent was removed by filtration, the filtrate was then concentrated under reduced pressure, and the resulting residue was purified by Prep-HPLC to give the target compound (42 mg).

Example 4-13-002

The compound of Example 4-13-002 was synthesized from a corresponding hydrazine by the similar method as in Example 4-13-001.

(Corresponding Enamine and Hydrazine)

(Synthesized Compound)
| Example No. | Compound | m/z (M + H) | Retention Time (Minute) | LCMS Measurement Condition |
|---|---|---|---|---|
| 4-13-001 | | 597 | 0.78 | A1 |
| 4-13-002 | | 596 | 0.83 | A1 |
Example 4-14-001
Synthesis of {5-amino-1-[6-(2-fluorophenoxy)-4-methylpyridin-3-yl]pyrazol-4-yl}-[6-(1,1-dioxo-1,2-thiazolidin-2-yl)-5-methoxy-1H-indol-2-yl]methanone
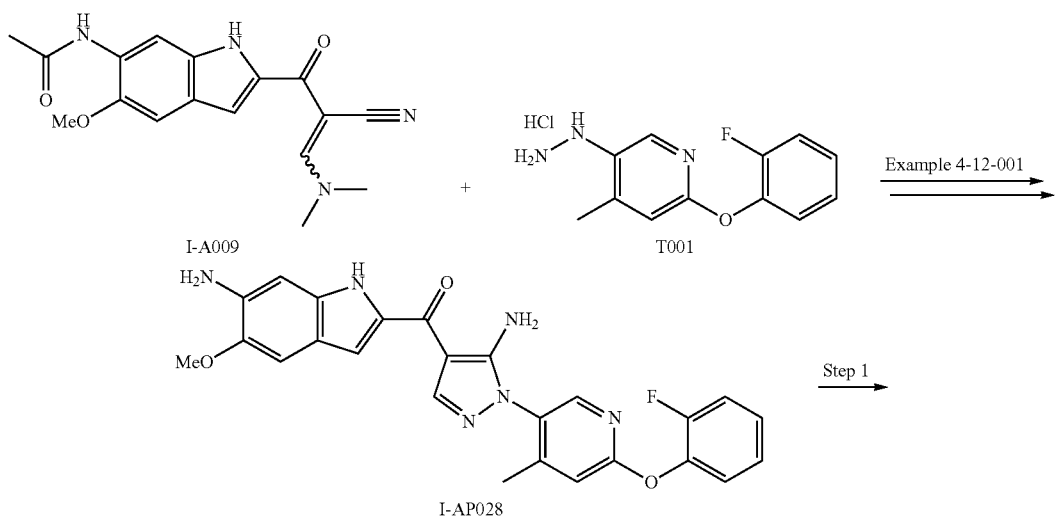
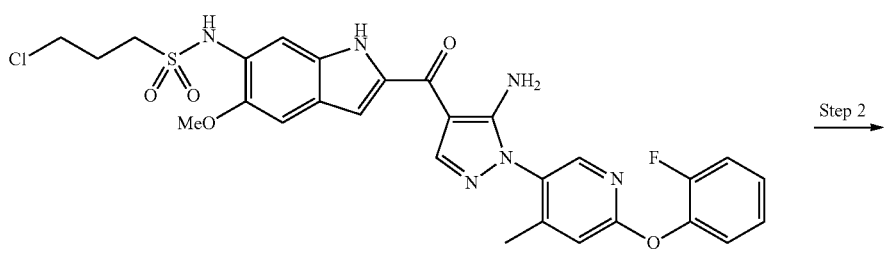

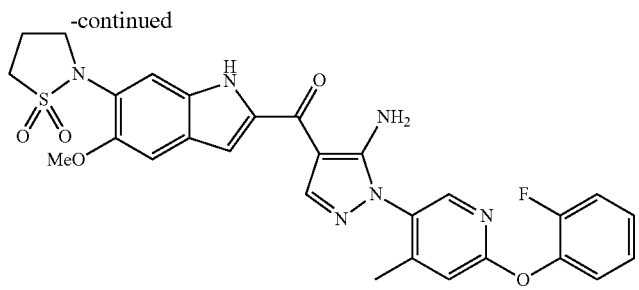

Step 1

Synthesis of N-{2-{5-amino-1-[6-(2-fluorophenoxy)-4-methylpyridin-3-yl]pyrazole-4-carbonyl}-5-methoxy-1H-indol-6-yl}-3-chloropropane-1-sulfonamide Aniline I-AP028 synthesized in Example 4-12-001 (100 mg) was dissolved in pyridine (1.0 mL), and 3-chloropropanesulfonyl chloride (52 μL) was added. Then the mixture was stirred at 25° C. for 30 minutes. 1 M hydrochloric acid (10 mL) was added to the reaction solution and the mixture was extracted with ethyl acetate (30 mL). The organic layer was washed with 1 M hydrochloric acid (10 mL) and saturated saline (10 mL), and dried over sodium sulfate. The drying agent was removed by filtration and the filtrate was then concentrated under reduced pressure. The resulting residue was used as such for the next reaction without purification.

Step 2

Synthesis of {5-amino-1-[6-(2-fluorophenoxy)-4-methylpyridin-3-yl]pyrazol-4-yl}-[6-(1,1-dioxo-1,2-thiazolidin-2-yl)-5-methoxy-1H-indol-2-yl]methanone N-{2-{5-Amino-1-[6-(2-fluorophenoxy)-4-methylpyridin-3-yl]pyrazole-4-carbonyl}-5-methoxy-1H-indol-6-yl}-3-chloropropane-1-sulfonamide (80 mg) was dissolved in N,N-dimethylformamide (0.8 mL), and sodium iodide (95 mg) and potassium carbonate (146 mg) were added. Then the mixture was stirred at 80° C. for one hour. The reaction solution was cooled to 25° C., water (20 mL) was added, and the mixture was extracted with ethyl acetate (30 mL). The organic layer was washed with water (20 mL) and saturated saline (10 mL), and dried over sodium sulfate. The drying agent was removed by filtration, the filtrate was then concentrated under reduced pressure, and the resulting residue was purified by Prep-HPLC to give the target compound (38 mg).

Example 4-14-002

The compound of Example 4-14-002 was synthesized from a corresponding enamine and a corresponding hydrazine by the similar method as in Example 4-14-001.

(Corresponding Enamines and Hydrazines)

| Example No. | Enamine | | Hydrazine | |
|---|---|---|---|---|
| 4-14-001 | I-A009 | [structure] | T001 | HCl [structure] |
| 4-14-002 | I-A009 | [structure] | Q001 | HCl [structure] |

(Synthesized Compounds)
| Example No. | Compound | m/z (M + H) | Retention Time (Minute) | LCMS Measurement Condition |
|---|---|---|---|---|
| 4-14-001 | | 577 | 0.74 | A1 |
| 4-14-002 | | 576 | 0.79 | A1 |
Example 4-15-001
Synthesis of N-{2-{5-amino-1-[4-(2,3-difluorophenoxy)-2-methylphenyl]pyrazole-4-carbonyl}-1H-indol-4-yl}-2-morpholin-4-yl-2-oxoethanesulfonamide
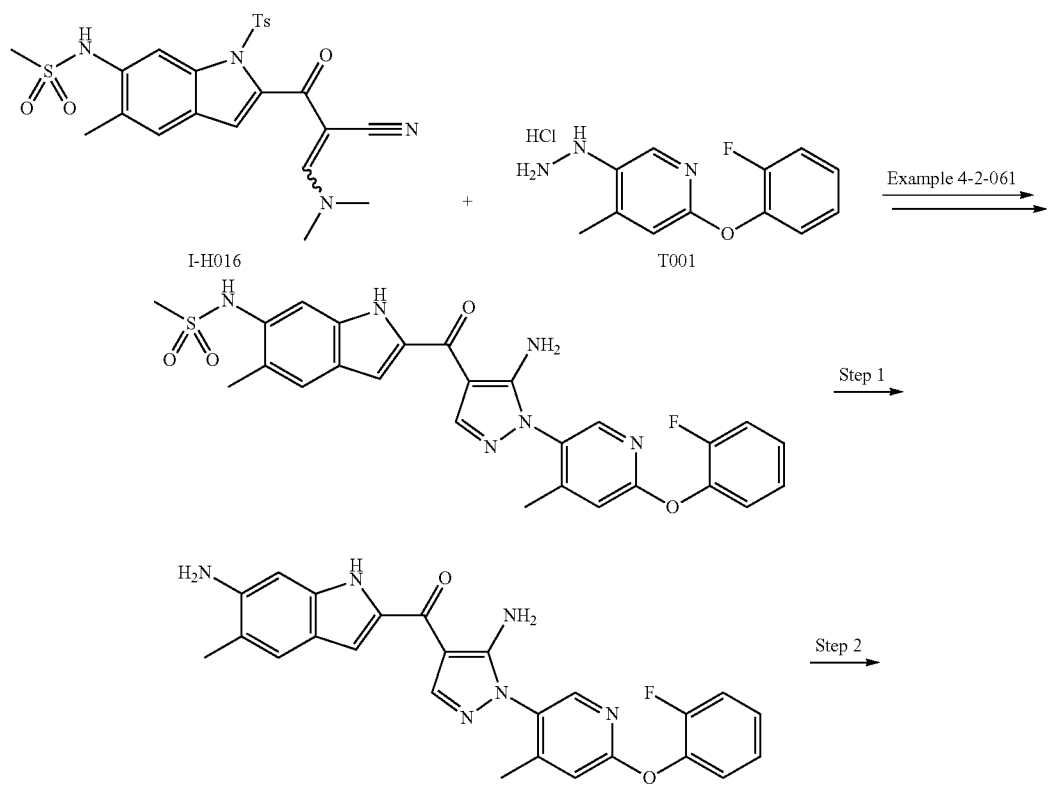

-continued

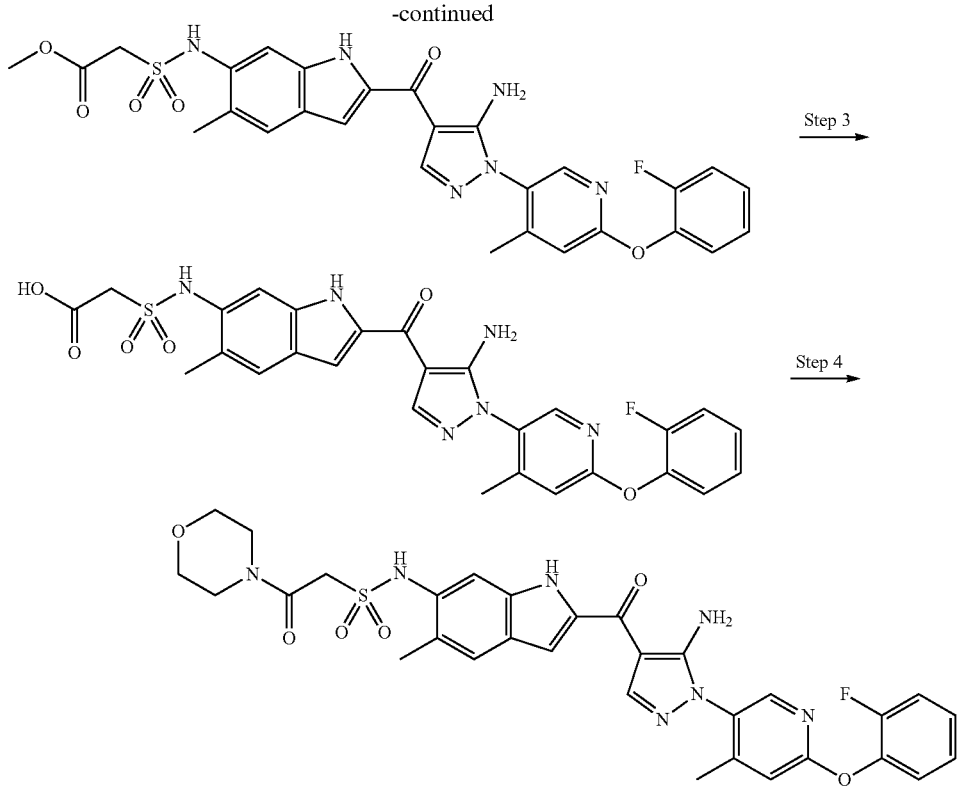

Step 1

Synthesis of (5-amino-1-(6-(2-fluorophenoxy)-4-methylpyridin-3-yl)-1H-pyrazol-4-yl)(6-amino-5-methyl-1H-indol-2-yl)methanone N-(2-(5-Amino-1-(6-(2-fluorophenoxy)-4-methylpyridin-3-yl)-1H-pyrazole-4-carbonyl)-5-methyl-1H-indol-6-yl)methanesulfonamide synthesized in Example 4-2-061 (1.24 g) was suspended in water (1.5 mL), and methanesulfonic acid (7.5 mL) was added. Then the mixture was stirred at 50° C. After confirming disappearance of the raw material, the reaction solution was neutralized with a 2 M aqueous sodium hydroxide solution. The reaction solution was extracted with dichloromethane (50 mL) three times, and the combined organic layers were washed with saturated saline and then dried over sodium sulfate. The drying agent was removed by filtration, the filtrate was concentrated, and the resulting residue was purified by silica gel column chromatography (ethyl acetate/hexane) to give the target compound (385 mg).

Step 2

Synthesis of methyl 2-(N-(2-(5-amino-1-(6-(2-fluorophenoxy)-4-methylpyridin-3-yl)-1H-pyrazole-4-carbonyl)-5-methyl-1H-indol-6-yl)sulfamoyl)acetate (5-Amino-1-(6-(2-fluorophenoxy)-4-methyl pyridin-3-yl)-1H-pyrazol-4-yl)(6-amino-5-methyl-1H-indol-2-yl) methanone (224 mg) and triethylamine (0.47 mL) were added to dichloromethane (5 mL), and a solution of methyl 2-(chlorosulfonyl)acetate (225 mg) in THF (3.3 mL) was added at 0° C. Then the mixture was stirred at 25° C. for four hours. The reaction solution was diluted with ethyl acetate (about 10 mL) and then washed with 0.1 M hydrochloric acid (about 10 mL). After extracting the aqueous layer with ethyl acetate (about 10 mL), the combined organic layers were washed with saturated saline (about 30 mL) and then dried over sodium sulfate. The drying agent was removed by filtration, the filtrate was concentrated, and the resulting residue was purified by silica gel column chromatography (ethyl acetate/hexane, 30%→75%) to give the target compound (186 mg).

Step 3

Synthesis of 2-(N-(2-(5-amino-1-(6-(2-fluorophenoxy)-4-methylpyridin-3-yl)-1H-pyrazole-4-carbonyl)-5-methyl-1H-indol-6-yl)sulfamoyl)acetic acid Methyl 2-(N-(2-(5-amino-1-(6-(2-fluorophenoxy)-4-methylpyridin-3-yl)-1H-pyrazole-4-carbonyl)-5-methyl-1H-indol-6-yl)sulfamoyl)acetate (186 mg) was added to methanol (3 mL), and a 4 M aqueous sodium hydroxide solution (0.39 mL) was added at 25° C. The reaction solution was stirred at 50° C. for two hours and then made acidic with 1 M hydrochloric acid. The reaction solution was extracted with ethyl acetate (about 5 mL) three times and the combined organic layers were then dried over sodium sulfate. The drying agent was removed by filtration and the filtrate was concentrated to give the target compound (169 mg).

Step 4

Synthesis of N-(2-(5-amino-1-(6-(2-fluorophenoxy)-4-methylpyridin-3-yl)-1H-pyrazole-4-carbonyl)-5-methyl-1H-indol-6-yl)-2-morpholino-2-oxoethanesulfonamide 2-(N-(2-(5-Amino-1-(6-(2-fluorophenoxy)-4-methylpyridin-3-yl)-1H-pyrazole-4-carbonyl)-5-methyl-1H-indol-6- yl)sulfamoyl)acetic acid (115 mg) and morpholine (27 μL) were dissolved in N,N-dimethylformamide (1.5 mL), and HATU (118 mg) and N,N-diisopropylethylamine (81 μL) were added at 25° C. Then the mixture was stirred for one hour. The reaction solution was diluted with ethyl acetate (about 10 mL) and washed with 1 M hydrochloric acid (about 10 mL). The aqueous layer was further extracted with ethyl acetate (about 10 mL) twice, and the combined organic layers were washed with saturated saline (about 10 mL) and then dried over sodium sulfate. The drying agent was removed by filtration and the filtrate was concentrated. The resulting residue was then purified by silica gel column chromatography (ethyl acetate/hexane, 70%→100%), and the eluate containing the target compound was concentrated under reduced pressure. The resulting residue was crystallized from dichloromethane/hexane (2/1) and the resulting crystals were collected by filtration and washed with dichloromethane/hexane (1/1) to give the target compound (64 mg).

(Corresponding Enamine and Hydrazine)

| Example No. | Enamine | Hydrazine |
|---|---|---|
| 4-15-001 | I-H016 | T001 |

(Synthesized Compound)

| Example No. | Compound | m/z (M + H) | Retention Time (Minute) | LCMS Measurement Condition |
|---|---|---|---|---|
| 4-15-001 | | 648 | 2.24 | B1 |

Examples 4-16-001 and 5-1-062

Synthesis of {5-amino-1-[6-(2-fluorophenoxy)-4-methylpyridin-3-yl]pyrazol-4-yl}-[6-(1,1-dioxo-1,2-thiazolidin-2-yl)-5-methyl-1H-indol-2-yl]methanone

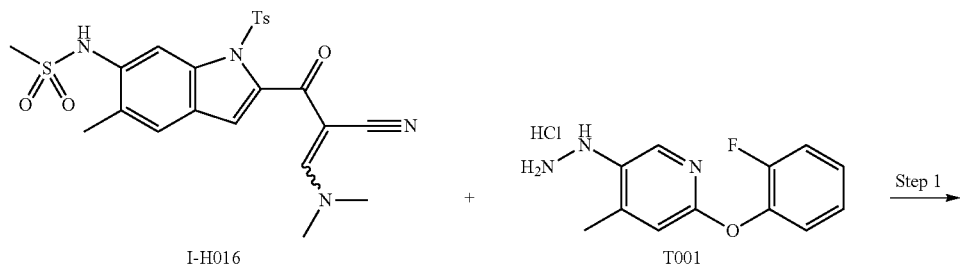

-continued

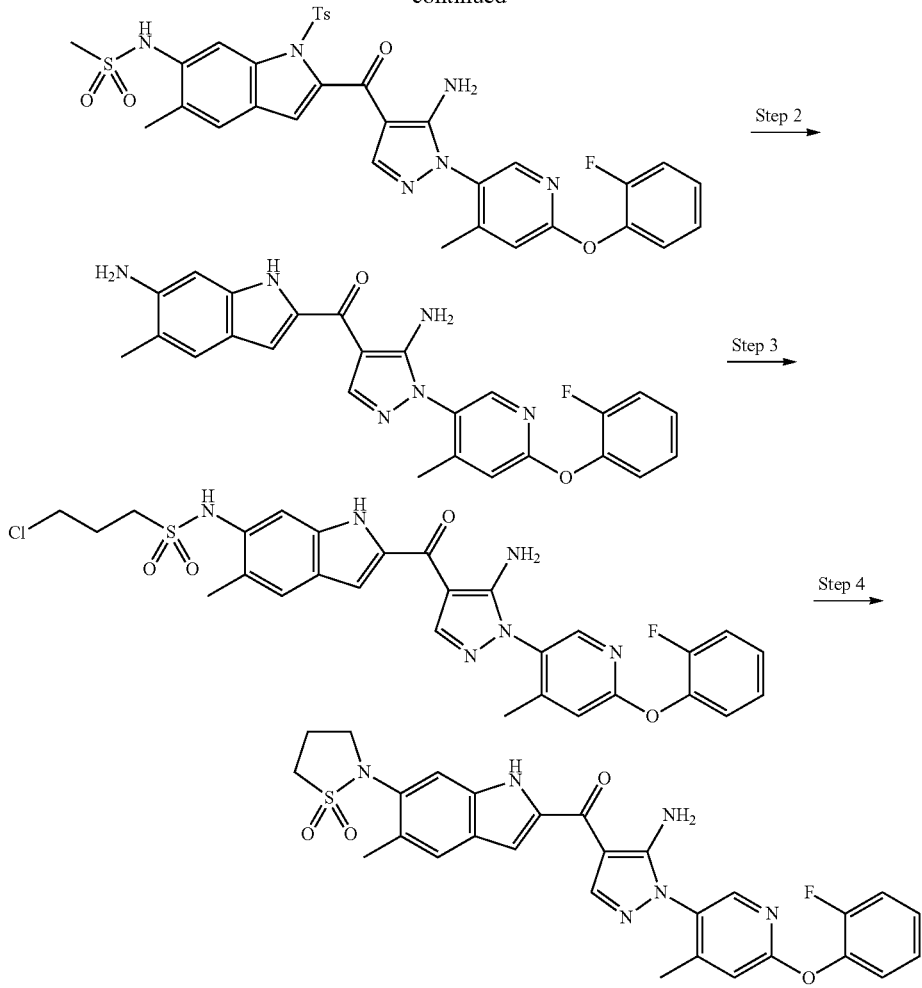

Step 1

Synthesis of N-{2-{5-amino-1-[6-(2-fluorophenoxy)-4-methylpyridin-3-yl]pyrazole-4-carbonyl}-5-methyl-1-(4-methylphenyl)sulfonylindol-6-yl}methanesulfonamide Enamine I-H016 (1.12 g) and hydrazine T001 (894 mg) were dissolved in 1-methyl-2-pyrrolidone (10 mL), and N-methylmorpholine (642 μL) was added. Then the atmosphere in the flask was replaced by nitrogen, and the mixture was stirred at 100° C. for three hours. The reaction solution was cooled to 25° C., water was added, the mixture was extracted with ethyl acetate, and the organic layer was dried over sodium sulfate. The drying agent was removed by filtration, the filtrate was then concentrated under reduced pressure, and the resulting residue was purified by column chromatography (ethyl acetate/hexane). The fractions containing the target compound were concentrated under reduced pressure and the resulting residue was crystallized from tert-butyl methyl ether to give the target compound (1.43 g).

Step 2

Synthesis of {5-amino-1-[6-(2-fluorophenoxy)-4-methylpyridin-3-yl]pyrazol-4-yl}-(6-amino-5-methyl-1H-indol-2-yl)methanone Methanesulfonic acid (0.48 mL) and water (0.16 mL) were added to N-{2-{5-amino-1-[6-(2-fluorophenoxy)-4-methylpyridin-3-yl]pyrazole-4-carbonyl}-5-methyl-1-(4-methylphenyl)sulfonylindol-6-yl}methanesulfonamide (100 mg) and the mixture was stirred at 100° C. for six hours. The reaction solution was cooled to 25° C., neutralized with a 2 M aqueous sodium hydroxide solution, and extracted with ethyl acetate, and the organic layer was dried over sodium sulfate. The drying agent was removed by filtration, the filtrate was then concentrated under reduced pressure, and the resulting residue was purified by column chromatography (ethyl acetate/hexane) to give the target compound (35 mg).

Step 3

Synthesis of N-{2-{5-amino-1-[6-(2-fluorophenoxy)-4-methylpyridin-3-yl]pyrazole-4-carbonyl}-5-methyl-1H-indol-6-yl}-3-chloropropane-1-sulfonamide {5-Amino-1-[6-(2-fluorophenoxy)-4-methylpyridin-3-yl]pyrazol-4-yl}-(6-amino-5-methyl-1H-indol-2-yl)methanone (83 mg) was dissolved in pyridine (1.7 mL), and 3-chloropropanesulfonyl chloride (44 μL) was added. Then the mixture was stirred at 25° C. for two hours. 3-Chloropropanesulfonyl chloride (44 μL) was added and the mixture was further stirred at 25° C. for 30 minutes. 1 M hydrochloric acid (30 mL) was added to the reaction solution and the mixture was extracted with ethyl acetate (20 mL) three times. The organic layers were washed with 1 M hydrochloric acid (20 mL) twice and dried over magnesium sulfate. The drying agent was removed by filtration, the filtrate was then concentrated under reduced pressure, and the resulting residue was purified by column chromatography (ethyl acetate/hexane) to give the target compound (96 mg).

Step 4

Synthesis of {5-amino-1-[6-(2-fluorophenoxy)-4-methylpyridin-3-yl]pyrazol-4-yl}-[6-(1,1-dioxo-1,2-thiazolidin-2-yl)-5-methyl-1H-indol-2-yl]methanone N-{2-{5-Amino-1-[6-(2-fluorophenoxy)-4-methylpyridin-3-yl]pyrazole-4-carbonyl}-5-methyl-1H-indol-6-yl}-3-chloropropane-1-sulfonamide (96 mg) was dissolved in N,N-dimethylformamide (1.9 mL), and sodium iodide (72 mg) and potassium carbonate (111 mg) were added. Then the mixture was stirred at 25° C. for 30 minutes. Water (15 mL) and 2 M hydrochloric acid (2.0 mL) were added to the reaction solution and the precipitated solid was collected by filtration. The resulting solid was purified by column chromatography (hexane/ethyl acetate) to give the target compound (72 mg).

The compound of Example 5-1-062 shown below was synthesized by the similar method as above using the corresponding enamine and hydrazine shown below.

(Corresponding Enamines and Hydrazines)

| Example No. | | Enamine | | Hydrazine |
| --- | --- | --- | --- | --- |
| 4-16-001 | I-H016 | [structure] | T001 HCl | [structure] |
| 5-1-062 | I-H055 | [structure] | S016 HCl | [structure] |

(Synthesized Compounds)

| Example No. | Compound | m/z (M + H) | Retention Time (Minute) | LCMS Measurement Condition |
| --- | --- | --- | --- | --- |
| 4-16-001 | [structure] | 561 | 0.83 | A1 |

| Example No. | Compound | m/z (M + H) | Retention Time (Minute) | LCMS Measurement Condition |
|---|---|---|---|---|
| 5-1-062 | | 597 | 1.01 | AA Rev. 5 |
Example 4-17-001
Synthesis of 1-{4-{2-{5-amino-1-{6-(2,6-difluorophenoxy)-4-methylpyridin-3-yl}pyrazole-4-carbonyl}-5-(2,2-difluoroethoxy)-1H-indol-6-yl}piperidin-1-yl}ethanone
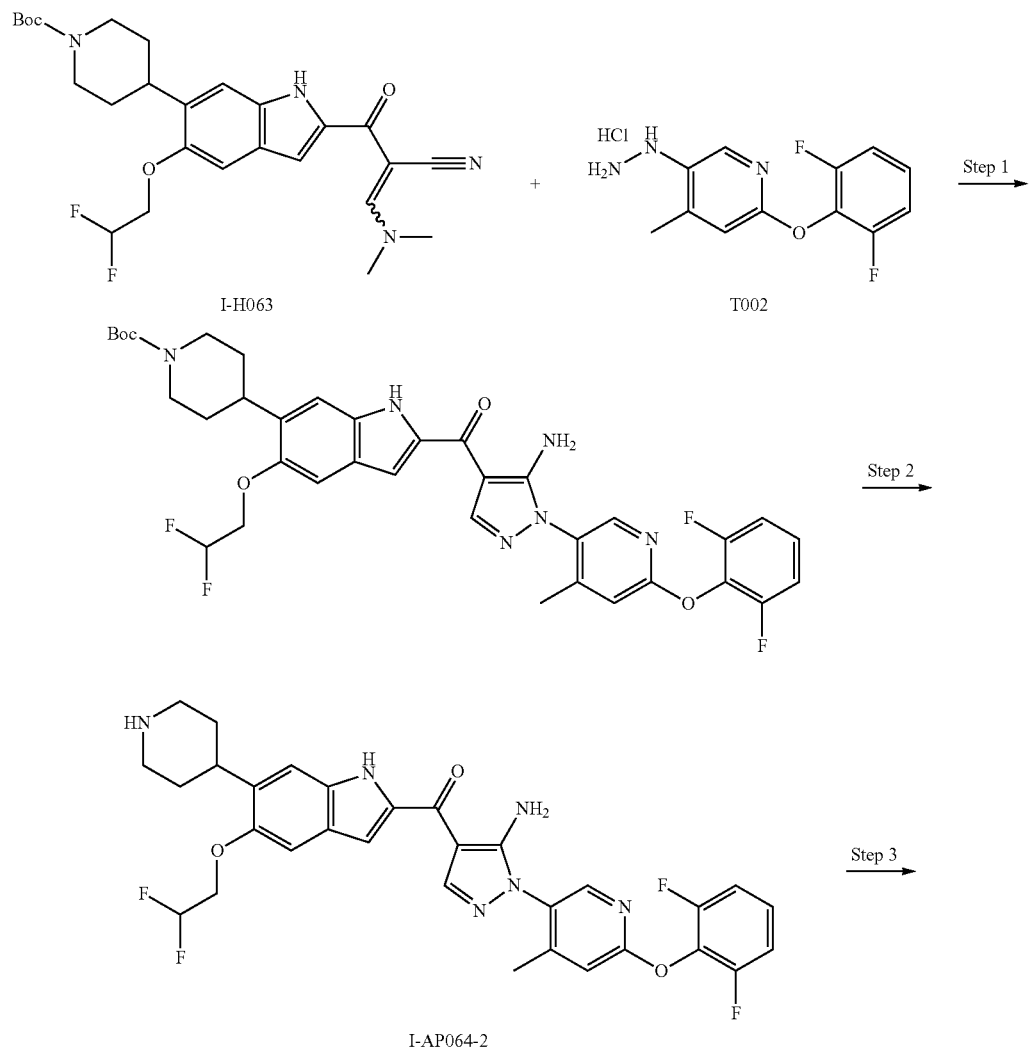

-continued

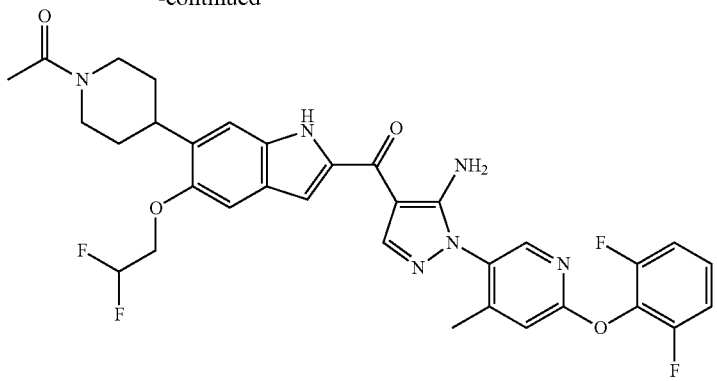

Step 1

Synthesis of tert-butyl 4-{2-{5-amino-1-[6-(2,6-difluorophenoxy)-4-methylpyridin-3-yl]pyrazole-4-carbonyl}-5-(2,2-difluoroethoxy)-1H-indol-6-yl}piperidine-1-carboxylate Enamine I-H063 (320 mg) and hydrazine T002 (268 mg) were dissolved in 1-methyl-2-pyrrolidone (3.2 mL), and N-methylmorpholine (0.18 mL) was added. Then the atmosphere in the flask was replaced by nitrogen, and the mixture was stirred at 100° C. for two hours. The reaction solution was cooled to 25° C., water was added, and the precipitated solid was collected by filtration to give the target compound (366 mg).

Step 2

Synthesis of {5-amino-1-[6-(2,6-difluorophenoxy)-4-methylpyridin-3-yl]pyrazol-4-yl}-[5-(2,2-difluoroethoxy)-6-piperidin-4-yl-1H-indol-2-yl]methanone (I-AP064-2)

tert-Butyl 4-{2-{5-amino-1-[6-(2,6-difluorophenoxy)-4-methylpyridin-3-yl]pyrazole-4-carbonyl}-5-(2,2-difluoroethoxy)-1H-indol-6-yl}piperidine-1-carboxylate (306 mg) was dissolved in 2,2,2-trifluoroethanol (3.0 mL), and TMSCl (0.17 mL) was added at 0° C. Then the mixture was stirred at 25° C. for 1.5 hours. A saturated aqueous sodium bicarbonate solution was added to the reaction solution and the mixture was extracted with ethyl acetate. The organic layer was washed with saturated saline and dried over sodium sulfate. The drying agent was removed by filtration and the filtrate was concentrated under reduced pressure. The resulting residue was washed by suspending in tert-butyl methyl ether/hexane to give the target compound (350 mg).

Step 3

Synthesis of 1-{4-{2-{5-amino-1-{6-(2,6-difluorophenoxy)-4-methylpyridin-3-yl}pyrazole-4-carbonyl}-5-(2,2-difluoroethoxy)-1H-indol-6-yl}piperidin-1-yl}ethanone {5-Amino-1-[6-(2,6-difluorophenoxy)-4-methylpyridin-3-yl]pyrazol-4-yl}-[5-(2,2-difluoroethoxy)-6-piperidin-4-yl-1H-indol-2-yl]methanone (85 mg) was dissolved in pyridine (1.4 mL), and acetic anhydride (26 μL) was added. Then the mixture was stirred at 25° C. for two hours. 1 M hydrochloric acid was added to the reaction solution and the mixture was extracted with ethyl acetate. The organic layer was washed with a saturated aqueous sodium bicarbonate solution and saturated saline, and dried over sodium sulfate. The drying agent was removed by filtration, the filtrate was then concentrated under reduced pressure, and the resulting residue was purified by column chromatography (ethyl acetate/methanol) to give the target compound (76 mg).

Examples 4-17-002 to 4-17-024 and Examples 5-1-071 and 5-1-073

The compounds of Examples 4-17-002 to 4-17-024 were synthesized by the similar method as in Example 4-17-001 using the corresponding enamines and hydrazines and using the corresponding amidating reagents in Step 3.

(Corresponding Enamines, Hydrazines, and Amidating Reagents)

| Example No. | Enamine | | Hydrazine | | Amidating Reagent |
|---|---|---|---|---|---|
| 4-17-001 | I-H063 | [enamine structure] | T002 HCl | [hydrazine structure] | [acetic anhydride] |
| 4-17-002 | I-H056 | [enamine structure] | Q001 HCl | [hydrazine structure] | [acetic anhydride] |
| 4-17-003 | I-H056 | [enamine structure] | Q001 HCl | [hydrazine structure] | [methanesulfonyl chloride] |
| 4-17-004 | I-H056 | [enamine structure] | Q001 HCl | [hydrazine structure] | [cyclopropanesulfonyl chloride] |
| 4-17-005 | I-H056 | [enamine structure] | S038 HCl | [hydrazine structure] | [acetic anhydride] |

| Example No. | | Enamine | Hydrazine | | Amidating Reagent |
|---|---|---|---|---|---|
| 4-17-006 | I-H056 | 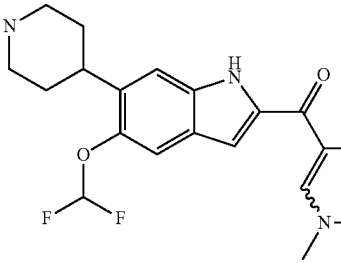 | S038 | 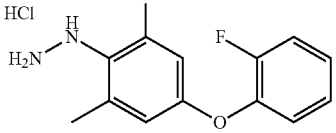 | 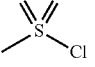 |
| 4-17-007 | I-H056 | 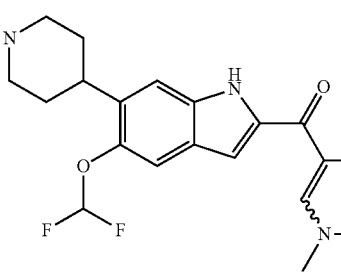 | S038 | 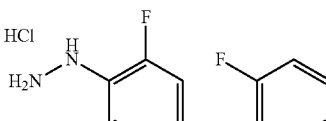 | 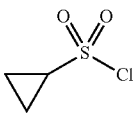 |
| 4-17-008 | I-H056 | 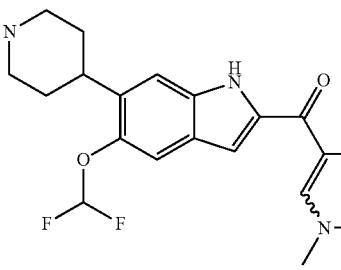 | T001 | 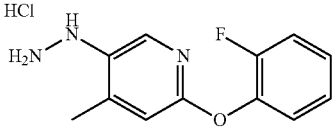 | 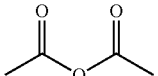 |
| 4-17-009 | I-H056 | 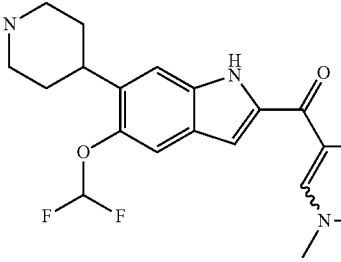 | T001 | 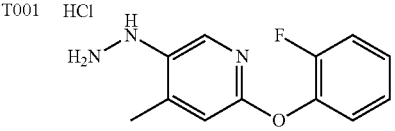 |  |
| 4-17-010 | I-H056 | 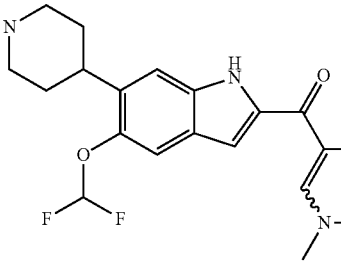 | T001 | 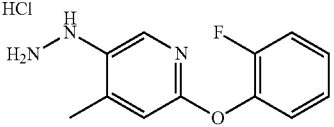 | 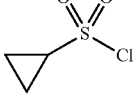 |

-continued

| Example No. | Enamine | Hydrazine | Amidating Reagent |
|---|---|---|---|
| 4-17-011 | I-H056 | T002 HCl | |
| 4-17-012 | I-H056 | T002 HCl | |
| 4-17-013 | I-H056 | T002 HCl | |
| 4-17-014 | I-H063 | Q001 HCl | |
| 4-17-015 | I-H063 | Q001 HCl | |

-continued
| Example No. | Enamine | | Hydrazine | | Amidating Reagent |
|---|---|---|---|---|---|
| 4-17-016 | I-H063 | 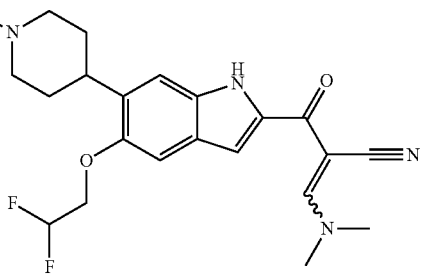 | Q001 HCl | 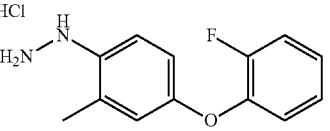 | 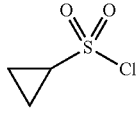 |
| 4-17-017 | I-H063 | 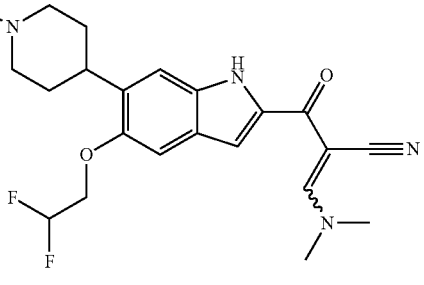 | S038 HCl | 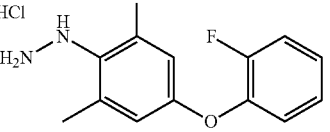 | 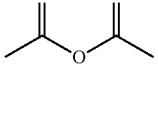 |
| 4-17-018 | I-H063 | 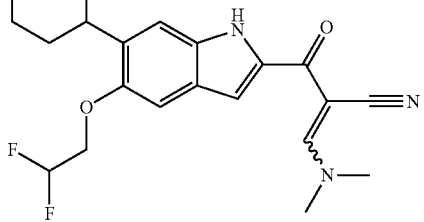 | S038 HCl | 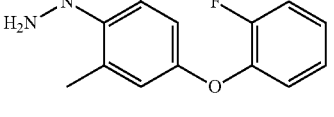 | 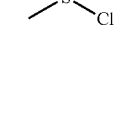 |
| 4-17-019 | I-H063 | 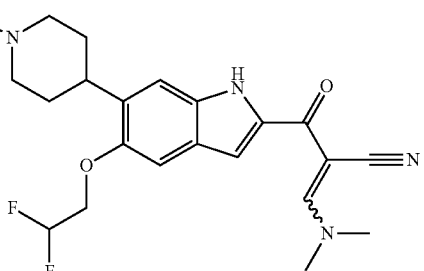 | S038 HCl | 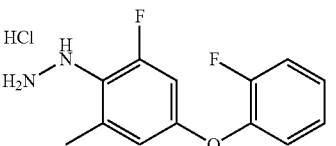 | 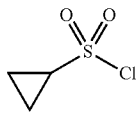 |
| 4-17-020 | I-H063 | 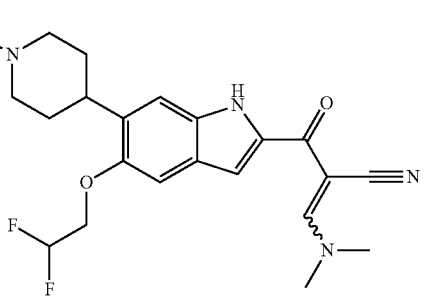 | T001 HCl | 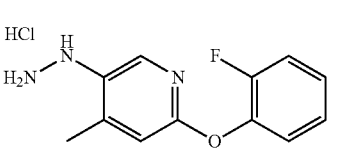 [SMILES: Cl ; Cc1cc(Oc2ccccc2F)ncc1NN] | 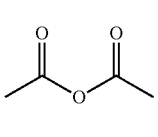 |

-continued

| Example No. | | Enamine | Hydrazine | Amidating Reagent |
|---|---|---|---|---|
| 4-17-021 | I-H063 | (structure) | T001 HCl (structure) | (methanesulfonyl chloride) |
| 4-17-022 | I-H063 | (structure) | T001 HCl (structure) | (cyclopropanesulfonyl chloride) |
| 4-17-023 | I-H063 | (structure) | T002 HCl (structure) | (methanesulfonyl chloride) |
| 4-17-024 | I-H063 | (structure) | T002 HCl (structure) | (cyclopropanesulfonyl chloride) |

(Synthesized Compounds)
| Example No. | Compound | m/z (M + H) | Retention Time (Minute) | LCMS Measurement Condition |
|---|---|---|---|---|
| 4-17-001 | 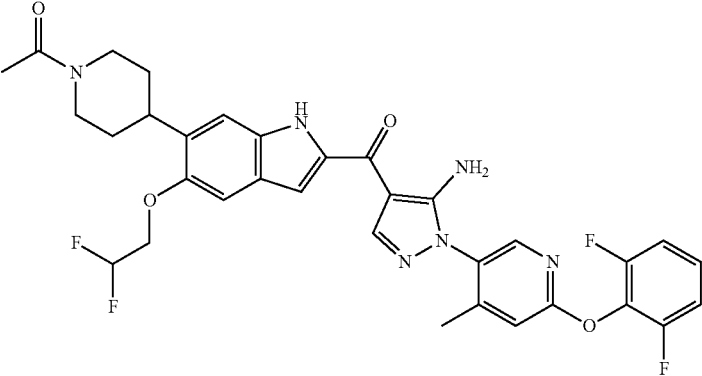 [SMILES: CC(=O)N1CCC(c2cc3[nH]c(C(=O)c4cnn(-c5cnc(Oc6c(F)cccc6F)cc5C)c4N)cc3cc2OCC(F)F)CC1] | 651 | 1.02 | J4 |
| 4-17-002 | 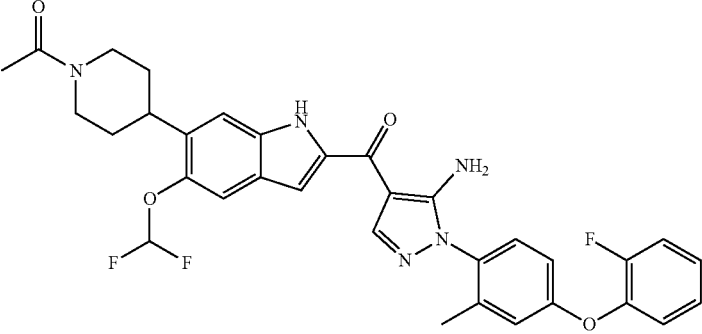 [SMILES: CC(=O)N1CCC(c2cc3[nH]c(C(=O)c4cnn(-c5ccc(Oc6ccccc6F)cc5C)c4N)cc3cc2OC(F)F)CC1] | 618 | 1.04 | J4 |
| 4-17-003 | 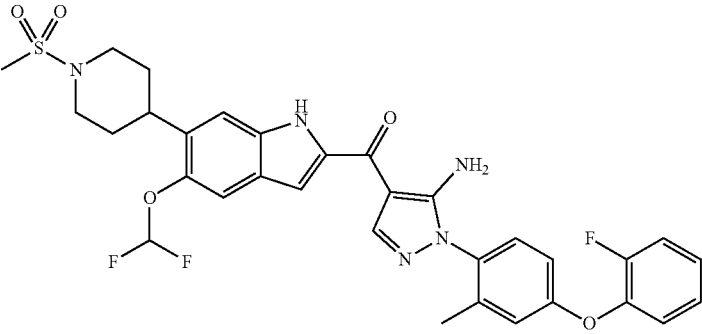 [SMILES: Cc1cc(Oc2ccccc2F)ccc1-n1ncc(C(=O)c2cc3cc(OC(F)F)c(C4CCN(S(C)(=O)=O)CC4)cc3[nH]2)c1N] | 654 | 1.03 | J2 |
| 4-17-004 | 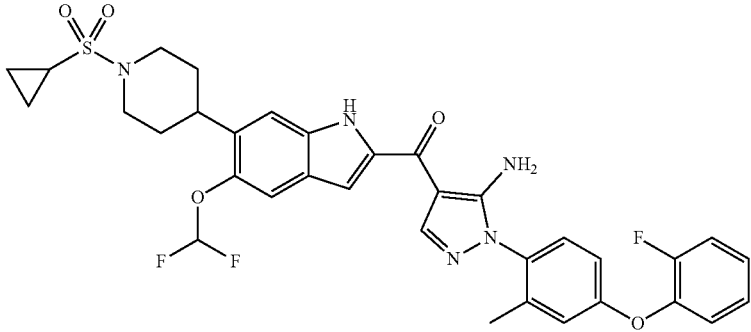 [SMILES: Cc1cc(Oc2ccccc2F)ccc1-n1ncc(C(=O)c2cc3cc(OC(F)F)c(C4CCN(S(=O)(=O)C5CC5)CC4)cc3[nH]2)c1N] | 680 | 1.06 | J4 |

-continued

| Example No. | Compound | m/z (M + H) | Retention Time (Minute) | LCMS Measurement Condition |
|---|---|---|---|---|
| 4-17-005 | | 636 | 1.04 | J4 |
| 4-17-006 | | 672 | 1.03 | J4 |
| 4-17-007 | | 698 | 1.05 | J4 |
| 4-17-008 | | 619 | 1.01 | J2 |

-continued

| Example No. | Compound | m/z (M + H) | Retention Time (Minute) | LCMS Measurement Condition |
|---|---|---|---|---|
| 4-17-009 | | 655 | 1.00 | J4 |
| 4-17-010 | | 681 | 1.03 | J4 |
| 4-17-011 | | 637 | 1.02 | J4 |
| 4-17-012 | | 673 | 1.01 | J4 |

-continued
| Example No. | Compound | m/z (M + H) | Retention Time (Minute) | LCMS Measurement Condition |
|---|---|---|---|---|
| 4-17-013 | 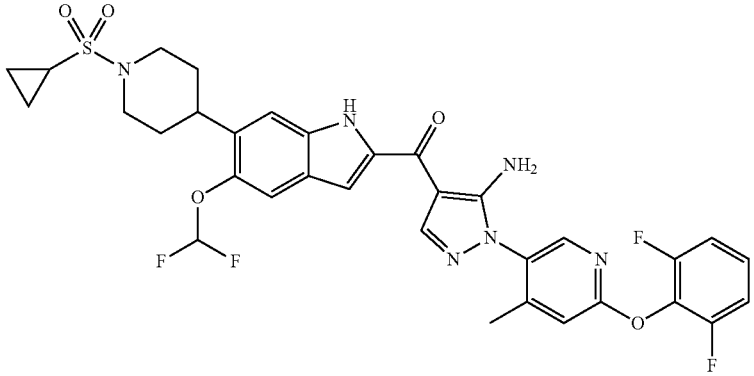 [SMILES: Cc1cc(Oc2c(F)cccc2F)ncc1-n1ncc(C(=O)c2cc3cc(OC(F)F)c(C4CCN(S(=O)(=O)C5CC5)CC4)cc3[nH]2)c1N] | 699 | 1.04 | J4 |
| 4-17-014 | 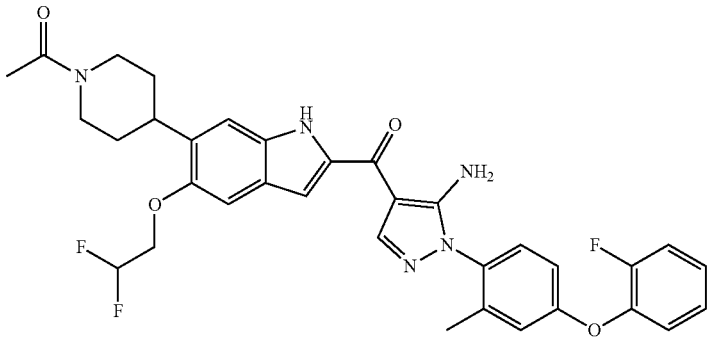 [SMILES: CC(=O)N1CCC(c2cc3[nH]c(C(=O)c4cnn(-c5ccc(Oc6ccccc6F)cc5C)c4N)cc3cc2OCC(F)F)CC1] | 632 | 1.04 | J3 |
| 4-17-015 | 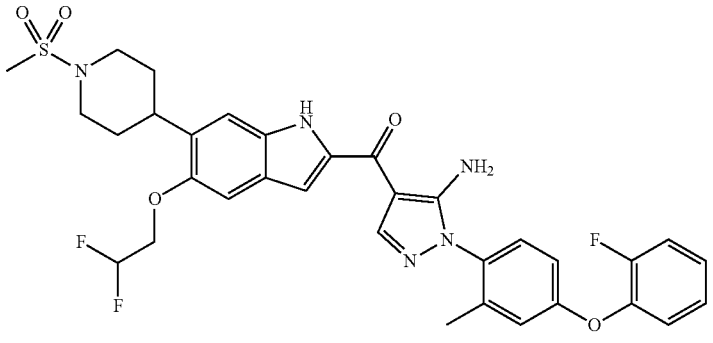 [SMILES: Cc1cc(Oc2ccccc2F)ccc1-n1ncc(C(=O)c2cc3cc(OCC(F)F)c(C4CCN(S(C)(=O)=O)CC4)cc3[nH]2)c1N] | 668 | 1.03 | J3 |
| 4-17-016 | 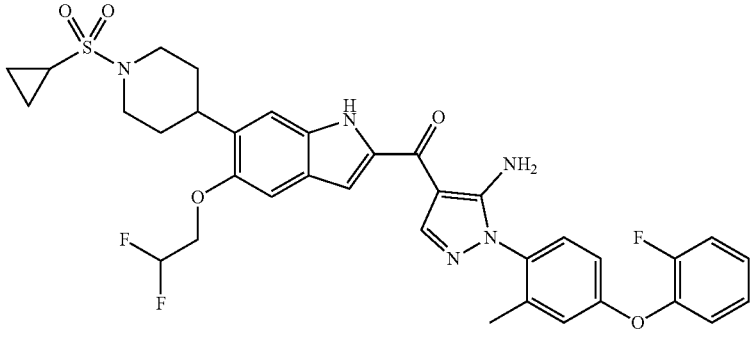 [SMILES: Cc1cc(Oc2ccccc2F)ccc1-n1ncc(C(=O)c2cc3cc(OCC(F)F)c(C4CCN(S(=O)(=O)C5CC5)CC4)cc3[nH]2)c1N] | 694 | 1.05 | J3 |

| Example No. | Compound | m/z (M + H) | Retention Time (Minute) | LCMS Measurement Condition |
|---|---|---|---|---|
| 4-17-017 | | 650 | 1.03 | J4 |
| 4-17-018 | | 686 | 1.02 | J2 |
| 4-17-019 | | 712 | 1.04 | J2 |
| 4-17-020 | | 633 | 1.00 | J4 |

-continued

| Example No. | Compound | m/z (M + H) | Retention Time (Minute) | LCMS Measurement Condition |
|---|---|---|---|---|
| 4-17-021 | | 669 | 0.99 | J2 |
| 4-17-022 | | 695 | 1.02 | J2 |
| 4-17-023 | | 687 | 1.01 | J4 |
| 4-17-024 | | 713 | 1.04 | J3 |

The compounds of the following table were obtained as by-products from Examples 4-17-003 and 4-17-004.
| Example No. | Compound | m/z (M + H) | Retention Time (Minute) | LCMS Measurement Condition |
|---|---|---|---|---|
| 5-1-073 | | 632 | 1.05 | AA Rev. 8 |
| 5-1-071 | | 658 | 1.08 | AA Rev. 8 |
Example 4-18-001
Synthesis of 2-amino-1-{4-{2-{5-amino-1-[6-(2,6-difluorophenoxy)-4-methyl pyridin-3-yl]pyrazole-4-carbonyl}-5-(2,2-difluoroethoxy)-1H-indol-6-yl}piperidin-1-yl}ethanone
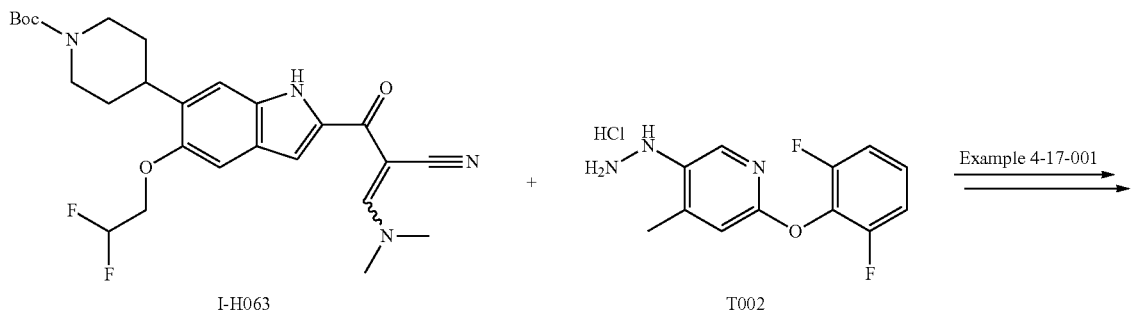

-continued

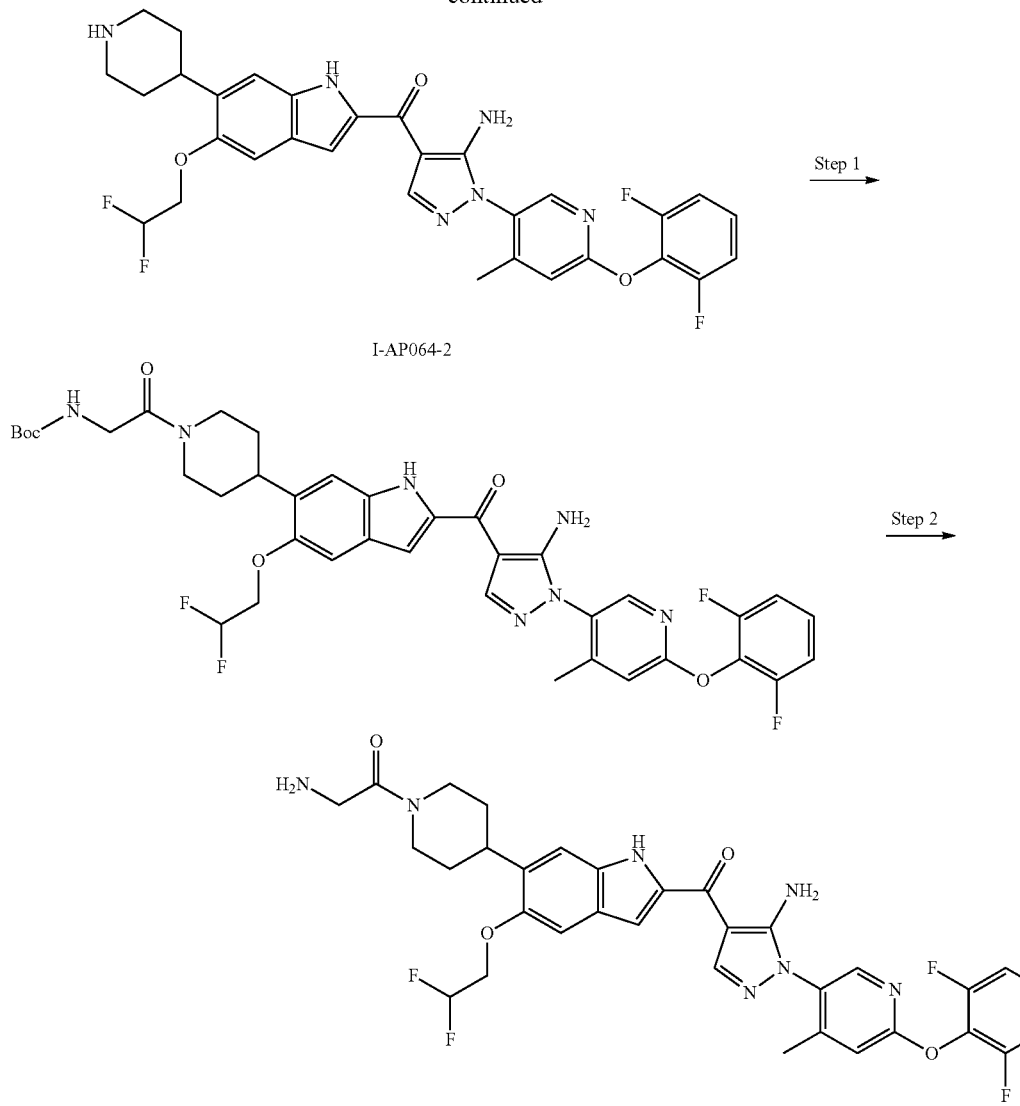

Step 1

Synthesis of tert-butyl N-{2-{4-{2-{5-amino-1-[6-(2,6-difluorophenoxy)-4-methylpyridin-3-yl]pyrazole-4-carbonyl}-5-(2,2-difluoroethoxy)-1H-indol-6-yl}piperidin-1-yl}-2-oxoethyl}carbamate Amine I-AP064-2 synthesized in Example 4-17-001 (85 mg) was dissolved in N,N-dimethylformamide (1.4 mL), and DIPEA (54 μL), HATU (80 mg), and N-(tert-butoxycarbonyl)glycine (32 mg) were added. Then the mixture was stirred at 0° C. for one hour. Saturated saline (5 mL) was added to the reaction solution and the mixture was extracted with ethyl acetate. The organic layer was washed with 0.5 M hydrochloric acid and saturated saline, and dried over sodium sulfate. The drying agent was removed by filtration, the filtrate was then concentrated under reduced pressure, and the resulting residue was purified by column chromatography (hexane/ethyl acetate) to give the target compound (90 mg).

Step 2

Synthesis of 2-amino-1-{4-{2-{5-amino-1-[6-(2,6-difluorophenoxy)-4-methylpyridin-3-yl]pyrazole-4-carbonyl}-5-(2,2-difluoroethoxy)-1H-indol-6-yl}piperidin-1-yl}ethanone tert-Butyl N-{2-{4-{2-{5-amino-1-[6-(2,6-difluorophenoxy)-4-methylpyridin-3-yl]pyrazole-4-carbonyl}-5-(2,2-difluoroethoxy)-1H-indol-6-yl}piperidin-1-yl}-2-oxoethyl}carbamate (78 mg) was dissolved in 2,2,2-trifluoroethanol (2.0 mL), and TMSCl (40 μL) was added at 0° C. Then the mixture was stirred at 25° C. for 3.5 hours. A saturated aqueous sodium bicarbonate solution was added to the reaction solution and the mixture was extracted with ethyl acetate. The organic layer was washed with saturated saline and dried over sodium sulfate. The drying agent was removed by filtration and the filtrate was concentrated under reduced pressure. The resulting residue was washed by suspending in tert-butyl methyl ether to give the target compound (67 mg).

Examples 4-18-002 to 4-18-004
The compounds of Examples 4-18-002 to 4-18-004 were synthesized from corresponding enamines and hydrazines by the similar method as in Example 4-18-001.
(Corresponding Enamines and Hydrazines)
| Example No. | | Enamine | | Hydrazine |
|---|---|---|---|---|
| 4-18-001 | I-H063 | 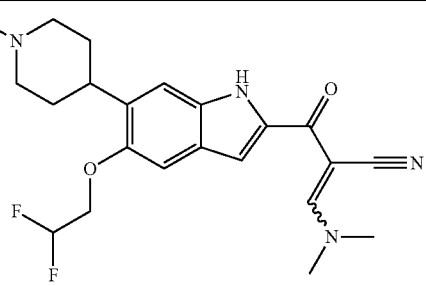 | T002 HCl | 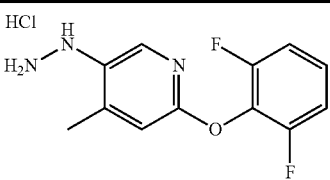 |
| 4-18-002 | I-H056 | 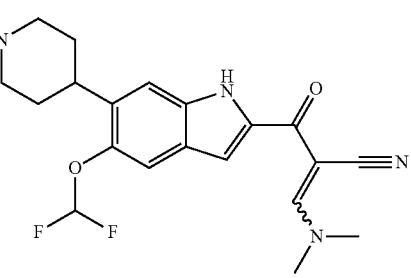 | Q001 HCl | 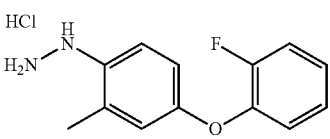 [SMILES: Cl ; Cc1cc(Oc2ccccc2F)ccc1NN] |
| 4-18-003 | I-H056 | 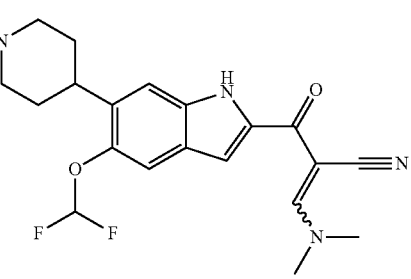 | T002 HCl | 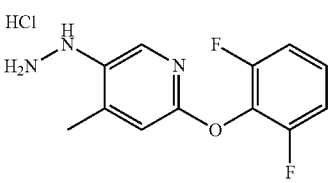 [SMILES: Cl ; Cc1cc(Oc2c(F)cccc2F)ncc1NN] |
| 4-18-004 | I-H063 | 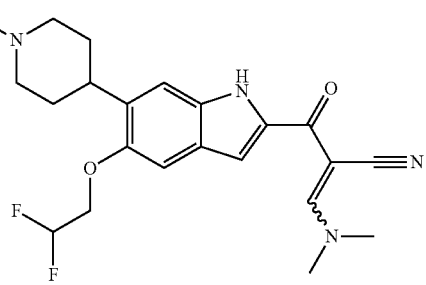 | Q001 HCl | 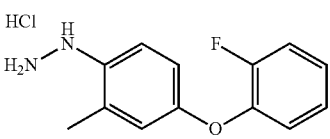 [SMILES: Cl ; Cc1cc(Oc2ccccc2F)ccc1NN] |

(Synthesized Compounds)

| Example No. | Compound | m/z (M + H) | Retention Time (Minute) | LCMS Measurement Condition |
|---|---|---|---|---|
| 4-18-001 | | 666 | 0.96 | J4 |
| 4-18-002 | | 633 | 0.99 | J4 |
| 4-18-003 | | 652 | 0.97 | J4 |
| 4-18-004 | | 647 | 0.98 | J3 |

Example 4-19-001
Synthesis of N-(2-(5-amino-1-(6-(2,6-difluorophenoxy)-4-methylpyridin-3-yl)-1H-pyrazole-4-carbonyl)-5-methoxy-1H-indol-6-yl)-3-fluoropropane-1-sulfonamide
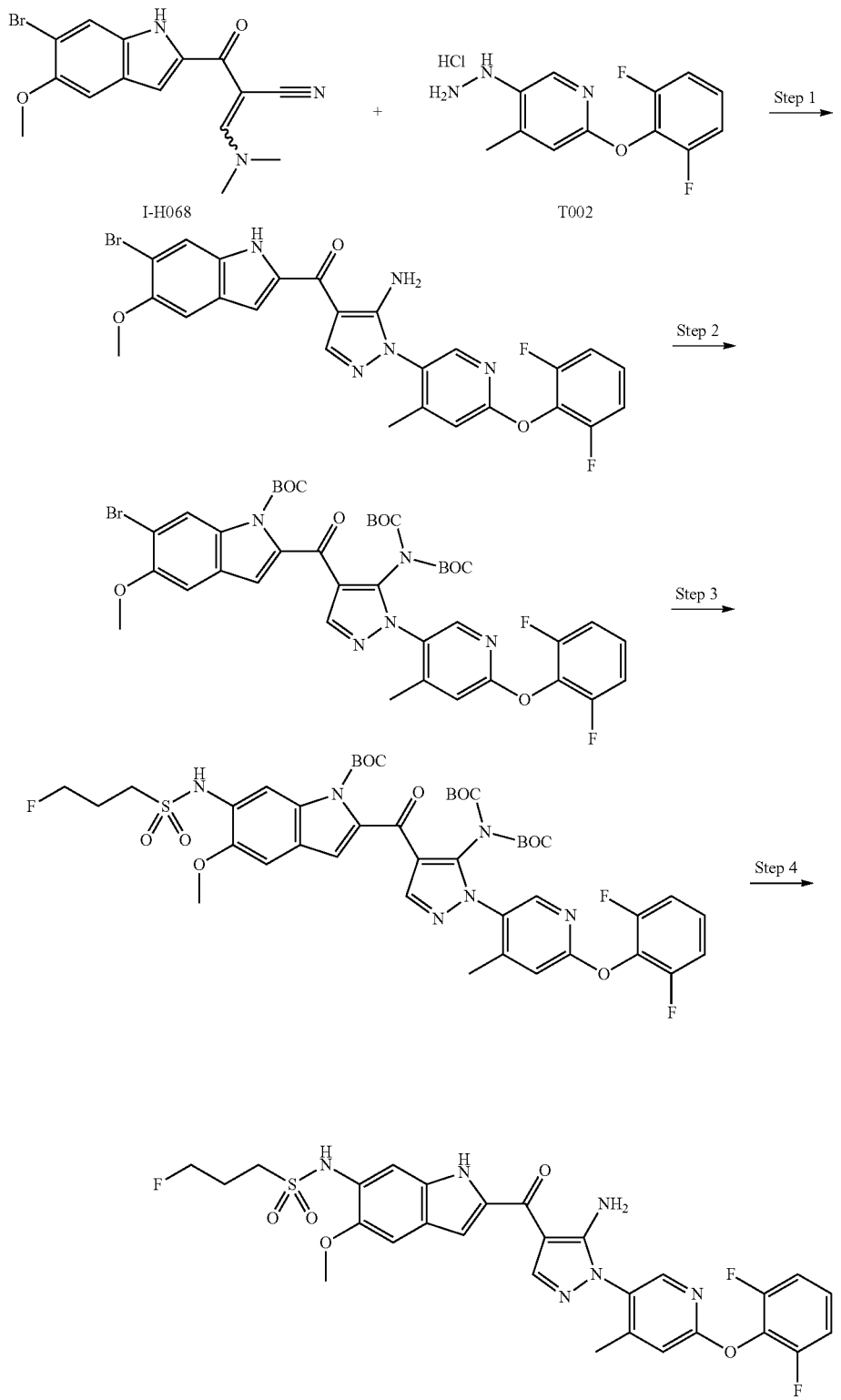

Step 1

Synthesis of (5-amino-1-(6-(2,6-difluorophenoxy)-4-methylpyridin-3-yl)-1H-pyrazol-4-yl)(6-bromo-5-methoxy-1H-indol-2-yl)methanone Enamine I-H068 (342 mg) and hydrazine T002 (414 mg) were dissolved in 1-methyl-2-pyrrolidone (6 mL), and N-methylmorpholine (0.281 mL) was added. Then the atmosphere in the flask was replaced by nitrogen, and the mixture was stirred at 100° C. for four hours. The reaction solution was cooled to 25° C., water (3 mL) was added, and the mixture was extracted with ethyl acetate (30 mL). The organic layer was washed with water (20 mL) and saturated saline (20 mL×2) and then dried over sodium sulfate. The drying agent was removed by filtration and the filtrate was concentrated. The resulting crude product of the target compound (682 mg) was then used for the next reaction without purification.

Step 2

Synthesis of Boc-protected compound of (5-amino-1-(6-(2,6-difluorophenoxy)-4-methylpyridin-3-yl)-1H-pyrazol-4-yl)(6-bromo-5-methoxy-1H-indol-2-yl)methanone (5-Amino-1-(6-(2,6-difluorophenoxy)-4-methylpyridin-3-yl)-1H-pyrazol-4-yl)(6-bromo-5-methoxy-1H-indol-2-yl)methanone (642 mg) was dissolved in THF (4.9 mL), and DMAP (12 mg) and $Boc_2O$ (0.91 mL) were added at 25° C. Then the mixture was stirred for four hours. The reaction solution was concentrated under reduced pressure and the resulting residue was then purified by silica gel column chromatography (ethyl acetate/hexane) to give the target compound (631 mg).

Step 3

Synthesis of Boc-protected compound of N-(2-(5-amino-1-(6-(2,6-difluorophenoxy)-4-methylpyridin-3-yl)-1H-pyrazole-4-carbonyl)-5-methoxy-1H-indol-6-yl)-3-fluoropropane-1-sulfonamide The Boc-protected compound of (5-amino-1-(6-(2,6-difluorophenoxy)-4-methylpyridin-3-yl)-1H-pyrazol-4-yl)(6-bromo-5-methoxy-1H-indol-2-yl)methanone obtained in Step 2 (100 mg), allylpalladium chloride dimer (4.2 mg), tBuXPhos (11 mg), potassium carbonate (35 mg), and 3-fluoropropane-1-sulfonamide (21 mg) were dissolved in dioxane (1 mL) and the mixture was stirred at 100° C. for two hours in a nitrogen stream. The reaction solution was cooled to 25° C. and then filtered through celite. The resulting filtrate was concentrated under reduced pressure to give a crude product of the target compound (132 mg). The crude product was used for the next reaction without purification.

Step 4

Synthesis of N-(2-(5-amino-1-(6-(2,6-difluorophenoxy)-4-methylpyridin-3-yl)-1H-pyrazole-4-carbonyl)-5-methoxy-1H-indol-6-yl)-3-fluoropropane-1-sulfonamide The Boc-protected compound of N-(2-(5-amino-1-(6-(2,6-difluorophenoxy)-4-methylpyridin-3-yl)-1H-pyrazole-4-carbonyl)-5-methoxy-1H-indol-6-yl)-3-fluoropropane-1-sulfonamide obtained in Step 3 was dissolved in 2,2,2-trifluoroethanol (2 mL), and TMSCl (0.075 mL) was added at 25° C. Then the mixture was stirred for three hours. The reaction solution was concentrated under reduced pressure and the resulting residue was purified by silica gel column chromatography (ethyl acetate/hexane) and further purified by PrepHPLC to give the target compound (36 mg).

(Corresponding Enamine and Hydrazine)

| Example No. | Enamine | | Hydrazine | |
|---|---|---|---|---|
| 4-19-001 | I-H068 | [structure] | T002 | [structure] |

(Synthesized Compound)

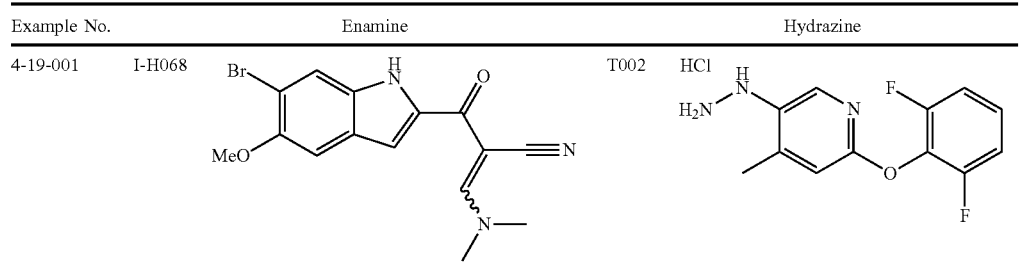

| Example No. | Compound | m/z (M + H) | Retention Time (Minute) | LCMS Measurement Condition |
|---|---|---|---|---|
| 4-19-001 | [structure] | 615 | 0.85 | A1 |

Example 4-20-001

Synthesis of 2-[5-amino-1-[4-(2-fluorophenoxy)-2-methylphenyl]pyrazole-4-carbonyl]-5-fluoro-6-(sulfamoylamino)-1H-indole

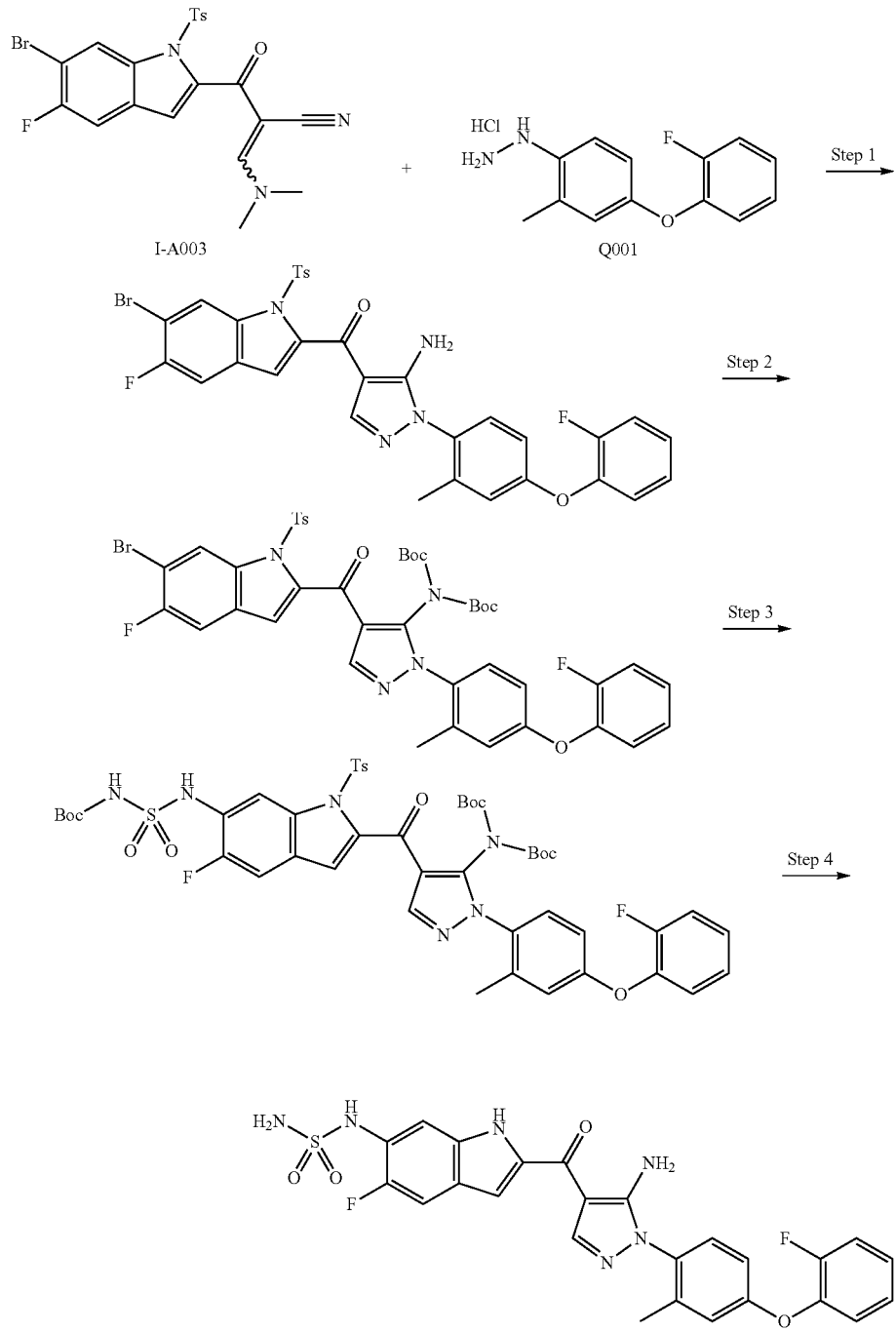

Step 1

Synthesis of 4-([6-bromo-5-fluoro-1-[(4-methylbenzene)sulfonyl]-1H-indol-2-yl]carbonyl)-1-[4-(2-fluorophenoxy)-2-methylphenyl]-1H-pyrazole-5-amine Enamine I-A003 (350 mg) and hydrazine Q001 (288 mg) were dissolved in ethanol (20 mL), the atmosphere in the flask was replaced by nitrogen, and the mixture was stirred at 75° C. for 16 hours. The reaction solution was extracted with ethyl acetate (80 mL) twice and the combined organic layers were concentrated under reduced pressure to give a crude product of the target compound (320 mg). The crude product was used for the next reaction without purification.

Step 2

Synthesis of tert-butyl N-[4-([6-bromo-5-fluoro-1-[(4-methylbenzene)sulfonyl]-1H-indol-2-yl]carbonyl)-1-[4-(2-fluorophenoxy)-2-methylphenyl]-1H-pyrazol-5-yl]-N-[tert-butoxy)carbonyl]carbamate 4-([6-Bromo-5-fluoro-1-[(4-methylbenzene)sulfonyl]-1H-indol-2-yl]carbonyl)-1-[4-(2-fluorophenoxy)-2-methylphenyl]-1H-pyrazole-5-amine obtained in Step 1 (320 mg) was dissolved in THF (30 mL), and Boc$_2$O (309 mg), DMAP (28 mg), and triethylamine (143 mg) were added. Then the mixture was stirred at 50° C. for 16 hours. The reaction solution was extracted with ethyl acetate (100 mL) and the organic layer was washed with 0.5 M hydrochloric acid (80 mL), a saturated aqueous sodium bicarbonate solution (80 mL), and then saturated saline (80 mL). The organic layer was concentrated under reduced pressure to give a crude product of the target compound (380 mg). The crude product was used for the next reaction without purification.

Step 3

The crude product obtained in Step 2 (380 mg), tert-butyl N-sulfamoylcarbamate (849 mg), allylpalladium chloride dimer (16 mg), tBuXPhos (55 mg), and potassium carbonate (179 mg) were added to 2-methyltetrahydrofuran (30 mL) and the mixture was stirred at 90° C. for five hours in a nitrogen atmosphere. The reaction solution was extracted with ethyl acetate (80 mL) twice and the combined organic layers were washed with a saturated aqueous sodium bicarbonate solution (80 mL) twice and saturated saline (80 mL) twice. The organic layer was concentrated under reduced pressure to give a crude product of the target compound (350 mg). The crude product was used for the next reaction without purification.

Step 4

Synthesis of 2-[5-amino-1-[4-(2-fluorophenoxy)-2-methylphenyl]pyrazole-4-carbonyl]-5-fluoro-6-(sulfamoylamino)-1H-indole The crude product obtained in Step 3 (350 mg) and methanesulfonic acid (2 mL) were added to dichloromethane (20 mL) at 25° C. and the mixture was then stirred at 50° C. for three hours. The reaction solution was adjusted to pH 7 to 8 with a saturated aqueous sodium bicarbonate solution and then extracted with ethyl acetate (100 mL). The organic layer was washed with saturated saline (80 mL) twice and then concentrated under reduced pressure, and the resulting residue was purified by PrepHPLC to give the target compound (33 mg).

Examples 4-20-002 to 4-20-003, Example 5-1-291, and the Like

The compounds of Examples 4-20-002 to 4-20-003, Example 5-1-291, and the like were synthesized by the similar method as in Example 4-20-001 using the corresponding enamines and hydrazines and using the corresponding sulfamidating or sulfonamidating reagents in Step 3.

(Corresponding Enamines, Hydrazines, and Sulfamidating Reagents or Sulfonamidating Reagents)

| Example No. | Enamine | | Hydrazine | | Sulfamidating/Sulfonamidating Reagent | |
|---|---|---|---|---|---|---|
| 4-20-001 | I-A003 | [structure] | Q001 | [structure] | 148017-28-1 | [structure] |
| 4-20-002 | I-A003 | [structure] | Q002 | [structure] | 148017-28-1 | [structure] |
| 4-20-003 | I-A003 | [structure] | Q019 | [structure] | 148017-28-1 | [structure] |

-continued

| Example No. | Enamine | Hydrazine | Sulfamidating Reagent |
|---|---|---|---|
| 5-1-291 | I-A013 | T002 HCl | |
| 5-1-292 | I-A013 | T002 HCl | |
| 5-1-303 | I-A012 | T002 HCl | |

(Synthesized Compounds)

| Example No. | Compound | m/z (M + H) | Retention Time (Minute) | LCMS Measurement Condition |
|---|---|---|---|---|
| 4-20-001 | | 539 | 0.76 | A2 |
| 4-20-002 | | 557 | 0.75 | A1 |

-continued

| Example No. | Compound | m/z (M + H) | Retention Time (Minute) | LCMS Measurement Condition |
|---|---|---|---|---|
| 4-20-003 | | 539 | 0.76 | A2 |
| 5-1-291 | | 650 | 1.02 | AA Rev. 11 |
| 5-1-292 | | 638 | 1.02 | AA Rev. 11 |
| 5-1-303 | | 678 | 1.31 | TFA Rev. 7 |

Example 4-21-001
Synthesis of 1-{2-{5-amino-1-[6-(2,6-difluorophenoxy)-4-methylpyridin-3-yl]pyrazole-4-carbonyl}-5-(2,2-difluoroethoxy)-1H-indol-6-yl}pyrrolidin-2-one
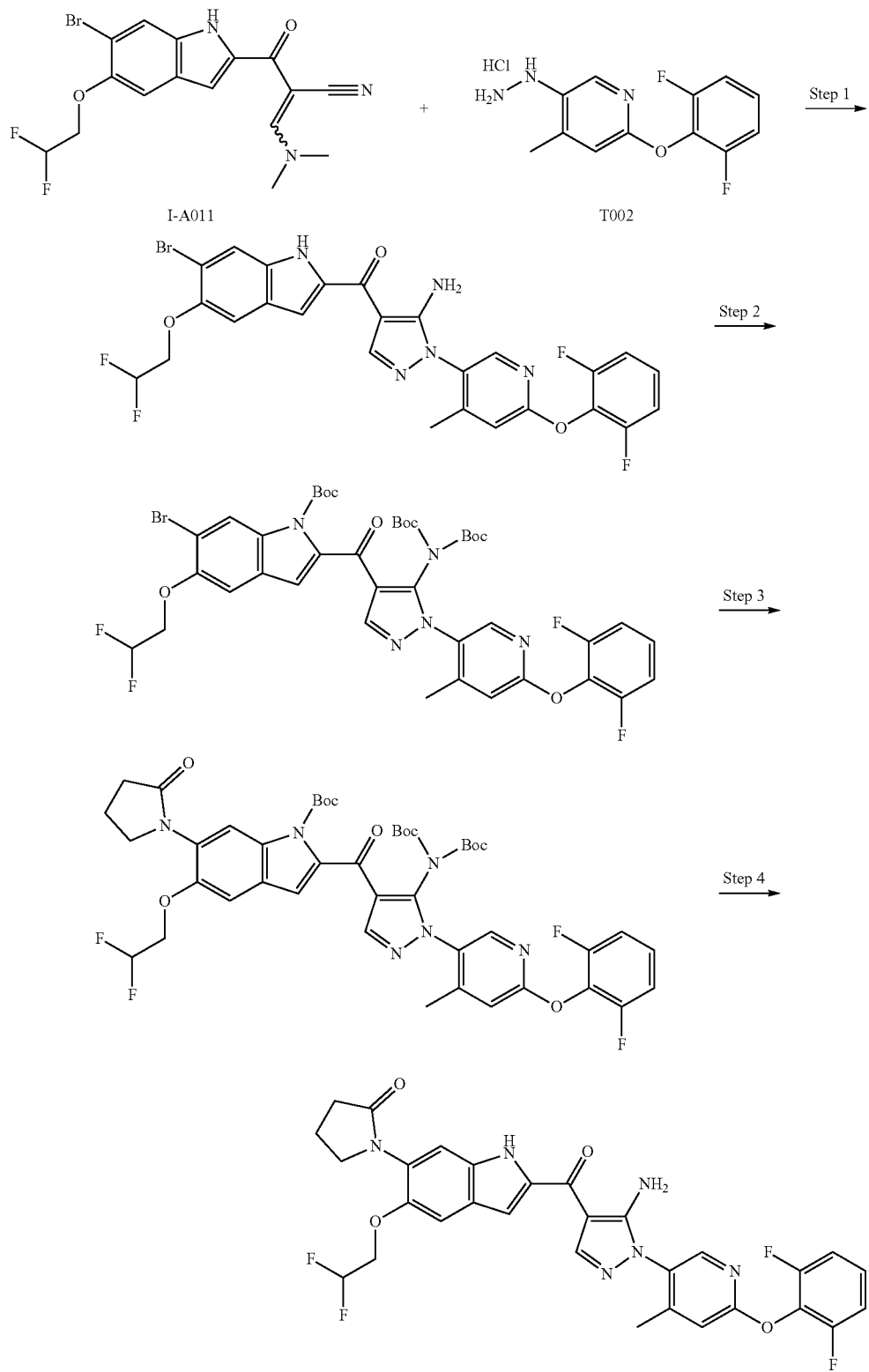

Step 1

Synthesis of {5-amino-1-[6-(2,6-difluorophenoxy)-4-methylpyridin-3-yl]pyrazol-4-yl}-[6-bromo-5-(2,2-difluoroethoxy)-1H-indol-2-yl]methanone Enamine I-A011 (1.39 g) and hydrazine T002 (1.47 g) were suspended in N,N-dimethylacetamide (13 mL), the atmosphere in the flask was replaced by nitrogen, and the suspension was stirred at 100° C. for one hour. The reaction solution was cooled to 25° C., water (50 mL) was added, and the precipitated solid was collected by filtration and washed by suspending in hexane/ethyl acetate to give the target compound (2.30 g).

Step 2

Synthesis of tert-butyl 2-{5-{bis[(2-methylpropan-2-yl)oxycarbonyl]amino}-1-[6-(2,6-difluorophenoxy)-4-methylpyridin-3-yl]pyrazole-4-carbonyl}-6-bromo-5-(2,2-difluoroethoxy)indole-1-carboxylate {5-Amino-1-[6-(2,6-difluorophenoxy)-4-methylpyridin-3-yl]pyrazol-4-yl}-[6-bromo-5-(2,2-difluoroethoxy)-1H-indol-2-yl]methanone obtained in Step 1 (500 mg) was dissolved in tetrahydrofuran (7.0 mL), and Boc$_2$O (722 mg) and DMAP (10 mg) were added. Then the mixture was stirred at 25° C. for 30 minutes. The reaction solution was concentrated under reduced pressure and the resulting residue was purified by column chromatography (hexane/ethyl acetate) to give the target compound (360 mg).

Step 3

Synthesis of tert-butyl 2-{5-{bis[(2-methylpropan-2-yl)oxycarbonyl]amino}-1-[6-(2,6-difluorophenoxy)-4-methylpyridin-3-yl]pyrazole-4-carbonyl}-5-(2,2-difluoroethoxy)-6-(2-oxopyrrolidin-1-yl)indole-1-carboxylate tert-Butyl 2-{5-{bis[(2-methylpropan-2-yl)oxycarbonyl]amino}-1-[6-(2,6-difluorophenoxy)-4-methylpyridin-3-yl]pyrazole-4-carbonyl}-6-bromo-5-(2,2-difluoroethoxy)indole-1-carboxylate obtained in Step 2 (125 mg) was dissolved in dioxane (2.0 mL), and 2-pyrrolidone (53 μL), Pd$_2$dba$_3$ (14 mg), XANTPHOS (24 mg), and cesium carbonate (135 mg) were added. Then the mixture was stirred at 100° C. for one hour. The reaction solution was cooled to 25° C., the insoluble matter was filtered off by celite filtration, and the filtrate was concentrated under reduced pressure. The resulting residue was used as such for the next reaction without purification.

Step 4

Synthesis of 1-{2-{5-amino-1-[6-(2,6-difluorophenoxy)-4-methylpyridin-3-yl]pyrazole-4-carbonyl}-5-(2,2-difluoroethoxy)-1H-indol-6-yl}pyrrolidin-2-one Trifluoroacetic acid (4.5 mL) was added to tert-butyl 2-{5-{bis[(2-methylpropan-2-yl)oxycarbonyl]amino}-1-[6-(2,6-difluorophenoxy)-4-methylpyridin-3-yl]pyrazole-4-carbonyl}-5-(2,2-difluoroethoxy)-6-(2-oxopyrrolidin-1-yl)indole-1-carboxylate (151 mg) and the mixture was stirred at 25° C. for one hour. The reaction solution was concentrated under reduced pressure, a saturated aqueous sodium bicarbonate solution was added to the resulting residue, and the mixture was extracted with ethyl acetate. The organic layer was washed with saturated saline and dried over sodium sulfate. The drying agent was removed by filtration, the filtrate was then concentrated under reduced pressure, and the resulting residue was purified by column chromatography (hexane/ethyl acetate) to give the target compound (48 mg).

Examples 4-21-002 to 4-21-009, Example 5-1-244, and the Like

The compounds of Examples 4-21-002 to 4-21-009, Example 5-1-244, and the like were synthesized by the similar method as in Example 4-21-001 using the corresponding enamines and hydrazines and using the corresponding amidating reagents in Step 3.

(Corresponding Enamines, Hydrazines, and Amidating Reagents)

| Example No. | Enamine | | Hydrazine | | Amidating Reagent |
|---|---|---|---|---|---|
| 4-21-001 | I-A011 | [structure] | T002 | [structure] | [structure] |
| 4-21-002 | I-A011 | [structure] | Q001 | [structure] | [structure] |

-continued

| Example No. | | Enamine | | Hydrazine | Amidating Reagent |
|---|---|---|---|---|---|
| 4-21-003 | I-A011 | (6-bromo-5-(2,2-difluoroethoxy)-1H-indol-2-yl) enamine with CN and NMe₂ | Q001 | HCl H₂N-NH-C₆H₃(Me)-O-C₆H₄-F | oxazolidin-2-one |
| 4-21-004 | I-A011 | (6-bromo-5-(2,2-difluoroethoxy)-1H-indol-2-yl) enamine with CN and NMe₂ | S038 | HCl H₂N-NH-C₆H₂(F)(Me)-O-C₆H₄-F | pyrrolidin-2-one |
| 4-21-005 | I-A011 | (6-bromo-5-(2,2-difluoroethoxy)-1H-indol-2-yl) enamine with CN and NMe₂ | T002 | HCl H₂N-NH-pyridyl(Me)-O-C₆H₃F₂ | oxazolidin-2-one |
| 4-21-006 | B-B026 | (6-bromo-5-(difluoromethoxy)-1H-indol-2-yl) enamine with CN and NMe₂ | Q001 | HCl H₂N-NH-C₆H₃(Me)-O-C₆H₄-F | pyrrolidin-2-one |
| 4-21-007 | B-B026 | (6-bromo-5-(difluoromethoxy)-1H-indol-2-yl) enamine with CN and NMe₂ | Q001 | HCl H₂N-NH-C₆H₃(Me)-O-C₆H₄-F | oxazolidin-2-one |
| 4-21-008 | B-B026 | (6-bromo-5-(difluoromethoxy)-1H-indol-2-yl) enamine with CN and NMe₂ | T002 | HCl H₂N-NH-pyridyl(Me)-O-C₆H₃F₂ | pyrrolidin-2-one |

-continued

| Example No. | | Enamine | Hydrazine | | Amidating Reagent |
|---|---|---|---|---|---|
| 4-21-009 | B-B026 | [structure: 6-bromo-5-(difluoromethoxy)-1H-indol-2-yl with acyl-cyanoenamine] | T002 HCl | [structure: 5-hydrazinyl-2-(2,6-difluorophenoxy)-4-methylpyridine] | [structure: oxazolidin-2-one] |
| 5-1-244 | I-A011 | [structure: 6-bromo-5-(2,2-difluoroethoxy)-1H-indol-2-yl with acyl-cyanoenamine] | Q001 HCl | [structure: 4-hydrazinyl-2-(2-fluorophenoxy)-3-methylbenzene] | [structure: (4S)-4-benzyloxazolidin-2-one] |
| 5-1-245 | I-A011 | [structure: 6-bromo-5-(2,2-difluoroethoxy)-1H-indol-2-yl with acyl-cyanoenamine] | Q001 HCl | [structure: 4-hydrazinyl-2-(2-fluorophenoxy)-3-methylbenzene] | [structure: (4R)-4-benzyloxazolidin-2-one] |

(Synthesized Compounds)

| Example No. | Compound | m/z (M + H) | Retention Time (Minute) | LCMS Measurement Condition |
|---|---|---|---|---|
| 4-21-001 | [structure] | 609 | 0.98 | J4 |
| 4-21-002 | [structure] | 590 | 1.00 | J2 |

-continued
| Example No. | Compound | m/z (M + H) | Retention Time (Minute) | LCMS Measurement Condition |
|---|---|---|---|---|
| 4-21-003 | 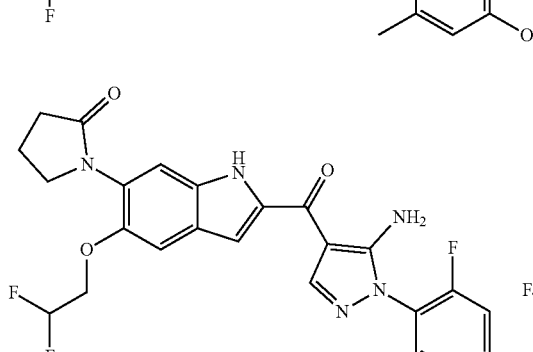 | 592 | 0.97 | J2 |
| 4-21-004 | 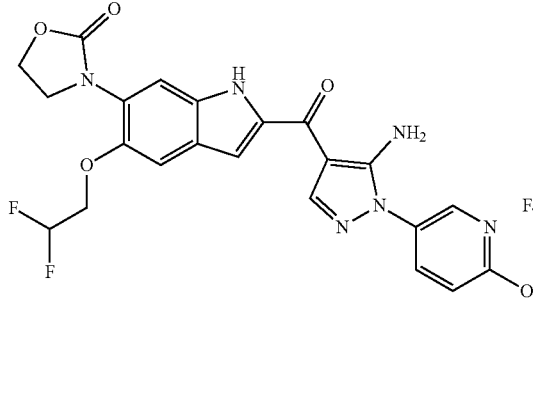 | 608 | 1.03 | J4 |
| 4-21-005 | 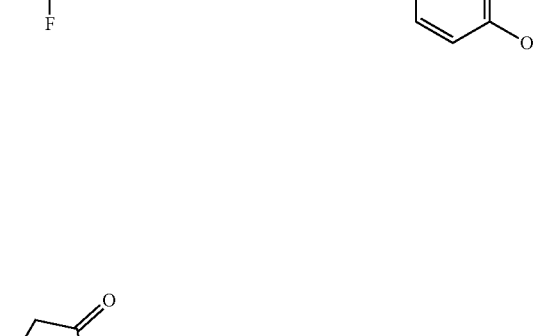 | 611 | 0.94 | J2 |
| 4-21-006 | 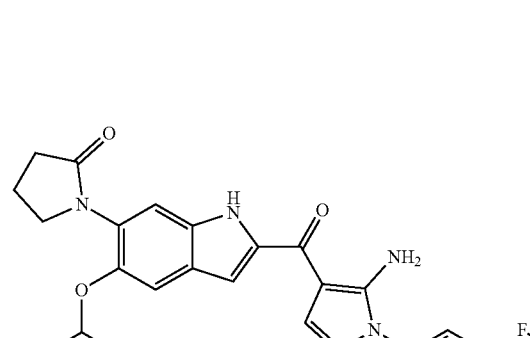 | 576 | 1.01 | J4 |

-continued

| Example No. | Compound | m/z (M + H) | Retention Time (Minute) | LCMS Measurement Condition |
|---|---|---|---|---|
| 4-21-007 | | 578 | 0.98 | J4 |
| 4-21-008 | | 595 | 0.99 | J4 |
| 4-21-009 | | 597 | 0.96 | J4 |
| 5-1-244 | | 682 | 1.42 | TFA Rev. 7 |

| Example No. | Compound | m/z (M + H) | Retention Time (Minute) | LCMS Measurement Condition |
|---|---|---|---|---|
| 5-2-245 | 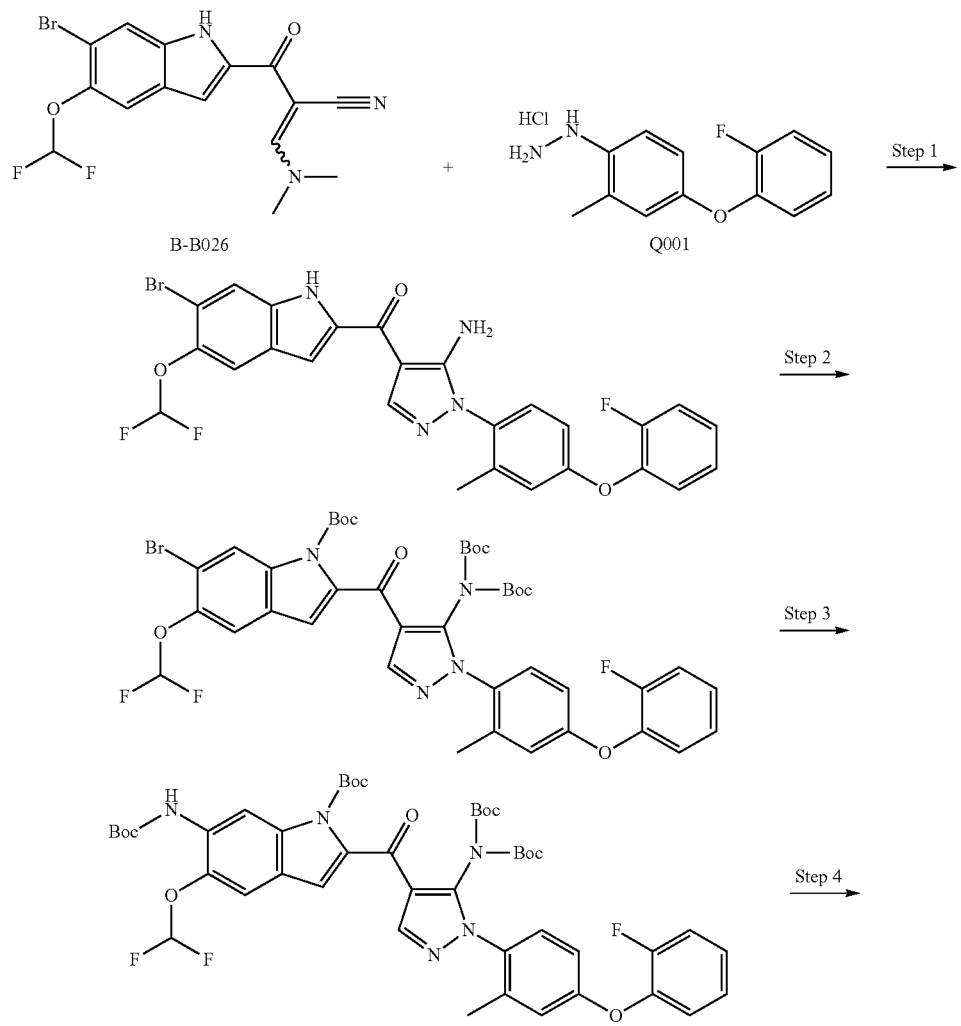 | 682 | 1.42 | TFA Rev. 7 |
Example 4-22-001
Synthesis of N-(2-(5-amino-1-(4-(2-fluorophenoxy)-2-methylphenyl)-1H-pyrazole-4-carbonyl)-5-(difluoromethoxy)-1H-indol-6-yl)morpholine-4-sulfonamide -continued

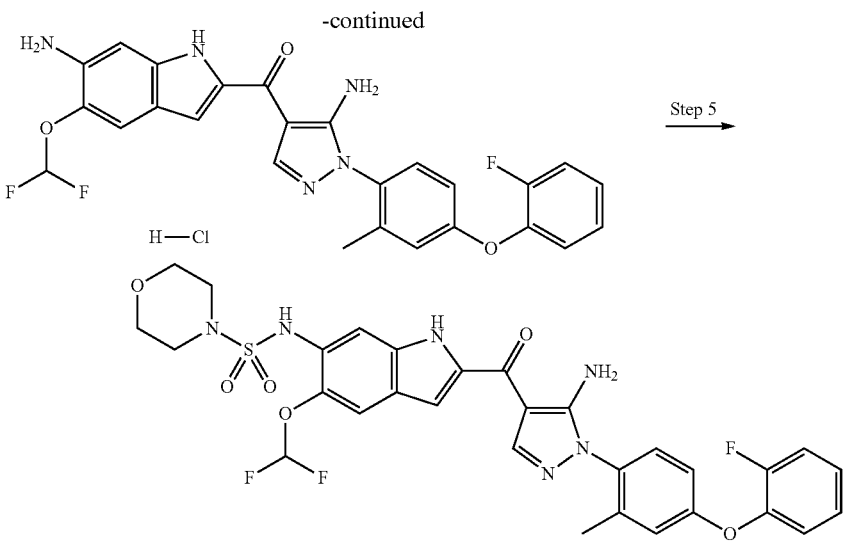

Step 1

Synthesis of (5-amino-1-(4-(2-fluorophenoxy)-2-methylphenyl)-1H-pyrazol-4-yl)(6-bromo-5-(difluoromethoxy)-1H-indol-2-yl)methanone Enamine B-B026 (511 mg) and hydrazine Q001 (392 mg) were dissolved in 1-methyl-2-pyrrolidone (6.6 mL), and N-methylmorpholine (161 μL) was added. Then the atmosphere in the flask was replaced by nitrogen, and the mixture was stirred at 100° C. for two hours. The reaction solution was cooled to 25° C., water (20 mL) was added, and the mixture was extracted with ethyl acetate (30 mL) three times. The combined organic layers were dried over magnesium sulfate, the drying agent was then removed by filtration, and the filtrate was concentrated. The resulting residue was then purified by silica gel column chromatography (ethyl acetate/hexane, 10%→40%), and the eluate containing the target compound was concentrated under reduced pressure. The resulting residue was crystallized from dichloromethane/hexane (1/3, 5 mL), and the solid was collected by filtration and washed with hexane to give the target compound (535 mg).

Step 2

Synthesis of Boc-protected compound of (5-amino-1-(4-(2-fluorophenoxy)-2-methylphenyl)-1H-pyrazol-4-yl)(6-bromo-5-(difluoromethoxy)-1H-indol-2-yl)methanone (5-Amino-1-(4-(2-fluorophenoxy)-2-methylphenyl)-1H-pyrazol-4-yl)(6-bromo-5-(difluoromethoxy)-1H-indol-2-yl)methanone obtained in Step 1 (530 mg), Boc$_2$O (0.768 mL), triethylamine (0.464 mL), and DMAP (11 mg) were added to dichloromethane (7.7 mL) and the mixture was stirred at 25° C. for two hours. The reaction solution was concentrated under reduced pressure, and the resulting residue was dissolved in ethyl acetate (50 mL) and washed with 0.5 M hydrochloric acid (30 mL) and then with saturated saline (30 mL). The organic layer was dried over magnesium sulfate, the drying agent was then removed by filtration, and the filtrate was concentrated. The resulting residue was then purified by silica gel column chromatography (ethyl acetate/hexane, 0%→45%) to give the target compound (803 mg).

Step 3

Synthesis of tert-butyl 2-(5-(bis(tert-butoxy carbonyl)amino)-1-(4-(2-fluorophenoxy)-2-methylphenyl)-1H-pyrazole-4-carbonyl)-6-((tert-butoxycarbonyl)amino)-5-(difluoromethoxy)-1H-indole-1-carboxylate The target compound obtained in Step 2 (750 mg), potassium carbonate (357 mg), O-tert-butyl carbamate (151 mg), XPhos (61 mg), and Pd$_2$dba$_3$ (39 mg) were added to dioxane (8.6 mL) and the mixture was stirred at 100° C. for five hours in a nitrogen atmosphere. The reaction solution was cooled to 25° C. and then filtered through celite. The filtrate was washed with ethyl acetate and concentrated under reduced pressure. The resulting residue was purified by silica gel column chromatography (ethyl acetate/hexane, 0%→35%) to give the target compound (809 mg).

Step 4

Synthesis of (5-amino-1-(4-(2-fluorophenoxy)-2-methylphenyl)-1H-pyrazol-4-yl)(6-amino-5-(difluoromethoxy)-1H-indol-2-yl)methanone hydrochloride tert-Butyl 2-(5-(bis(tert-butoxycarbonyl)amino)-1-(4-(2-fluorophenoxy)-2-methylphenyl)-1H-pyrazole-4-carbonyl)-6-((tert-butoxycarbonyl)amino)-5-(difluoromethoxy)-1H-indole-1-carboxylate obtained in Step 3 (800 mg) and TMSCl (1.12 mL) were added to 2,2,2-trifluoroethanol (16 mL) at 25° C. and the mixture was stirred for one hour. The reaction solution was concentrated under reduced pressure and the resulting residue was crystallized from ethanol/hexane (2/1, 8 mL). The resulting solid was collected by filtration and washed with ethanol/hexane (1/2, 10 mL) to give the target compound (401 mg).

Step 5

Synthesis of N-(2-(5-amino-1-(4-(2-fluorophenoxy)-2-methylphenyl)-1H-pyrazole-4-carbonyl)-5-(difluoromethoxy)-1H-indol-6-yl)morpholine-4-sulfonamide (5-Amino-1-(4-(2-fluorophenoxy)-2-methylphenyl)-1H-pyrazol-4-yl)(6-amino-5-(difluoromethoxy)-1H-indol-2-yl)

methanone hydrochloride obtained in Step 4 (100 mg) and morpholine-4-sulfonyl chloride (205 mg) were added to pyridine (0.91 mL) at 0° C. and the mixture was stirred at 25° C. for 18 hours. The reaction solution was diluted with ethyl acetate (5 mL) and then washed with 1 M hydrochloric acid (5 mL) and saturated saline (5 mL), and the organic layer was dried over magnesium sulfate. The drying agent was removed by filtration, the filtrate was concentrated, and the resulting residue was purified by silica gel column chromatography (ethyl acetate/hexane, 12%→100%) to give the target compound (27 mg).

Examples 4-22-002 to 4-22-006, Example 5-1-020, and the Like

The compounds of Examples 4-22-002 to 4-22-006, Example 5-1-020, and the like were synthesized by the similar method as in Example 4-22-001 using the corresponding enamines and hydrazines and using the corresponding sulfamidating reagents in Step 5.

(Corresponding Enamines, Hydrazines, and Sulfamidating Reagents)

| Example No. | Enamine | | Hydrazine | | Sulfamidating Reagent | |
|---|---|---|---|---|---|---|
| 4-22-001 | B-B026 | [structure] | Q001 | [structure] | 1828-66-6 | [structure] |
| 4-22-002 | B-B026 | [structure] | T001 | [structure] | 1828-66-6 | [structure] |
| 4-22-003 | B-B026 | [structure] | T002 | [structure] | 1828-66-6 | [structure] |
| 4-22-004 | I-A010 | [structure] | T001 | [structure] | 1828-66-6 | [structure] |
| 4-22-005 | I-A011 | [structure] | Q001 | [structure] | 1828-66-6 | [structure] |
| 4-22-006 | I-A011 | [structure] | T001 | [structure] | 1828-66-6 | [structure] |

-continued
| Example No. | Enamine | Hydrazine | Sulfamidating Reagent |
|---|---|---|---|
| 5-1-020 | I-A003 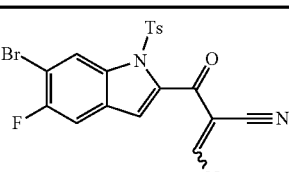 | T001 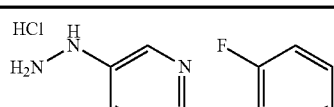 | SFA-008 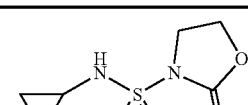 |
| 5-1-021 | I-A003 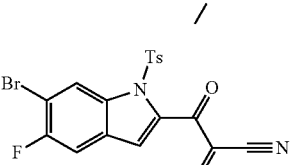 | T001 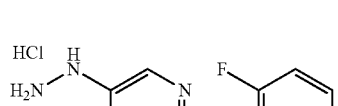 | SFA-002 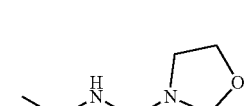 |
(Synthesized Compounds)
| Example No. | Compound | m/z (M + H) | Retention Time (Minute) | LCMS Measurement Condition |
|---|---|---|---|---|
| 4-22-001 | | 657 | 2.63 | B1 |
| 4-22-002 | | 658 | 0.79 | A1 |
| 4-22-003 | | 676 | 0.81 | A1 |

-continued
| Example No. | Compound | m/z (M + H) | Retention Time (Minute) | LCMS Measurement Condition |
|---|---|---|---|---|
| 4-22-004 | 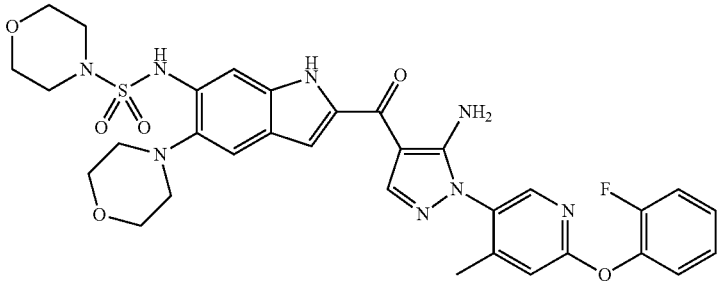 [SMILES: Cc1cc(Oc2ccccc2F)ncc1-n1ncc(C(=O)c2cc3cc(N4CCOCC4)c(NS(=O)(=O)N4CCOCC4)cc3[nH]2)c1N] | 677 | 0.85 | A1 |
| 4-22-005 | 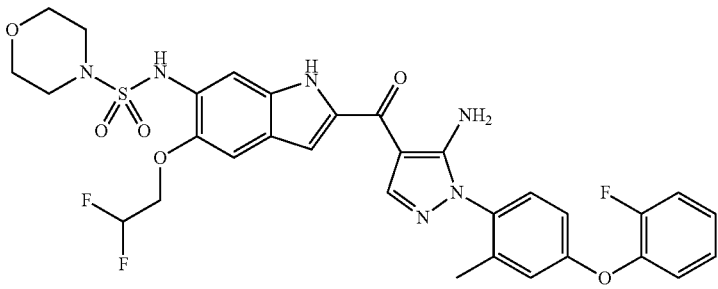 [SMILES: Cc1cc(Oc2ccccc2F)ccc1-n1ncc(C(=O)c2cc3cc(OCC(F)F)c(NS(=O)(=O)N4CCOCC4)cc3[nH]2)c1N] | 671 | 0.90 | A1 |
| 4-22-006 | 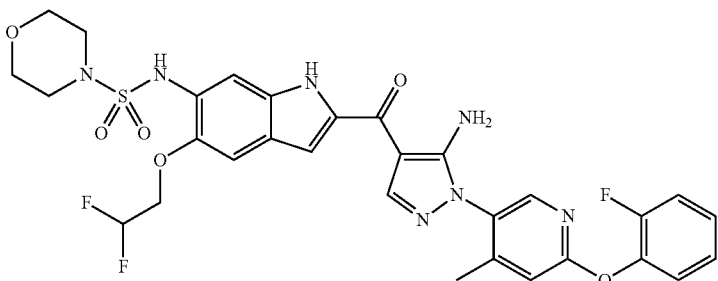 | 672 | 0.85 | A1 |
| 5-1-020 | 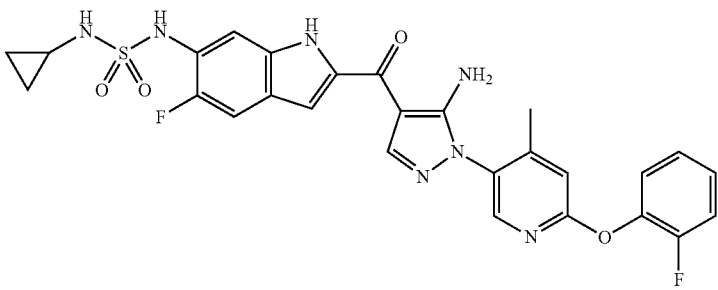 [SMILES: Cc1cc(Oc2ccccc2F)ncc1-n1ncc(C(=O)c2cc3cc(F)c(NS(=O)(=O)NC4CC4)cc3[nH]2)c1N] | 580 | 1.20 | TFA Rev.5 |
| 5-1-021 | 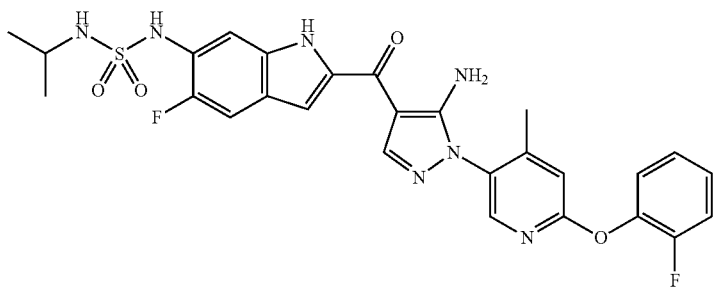 [SMILES: Cc1cc(Oc2ccccc2F)ncc1-n1ncc(C(=O)c2cc3cc(F)c(NS(=O)(=O)NC(C)C)cc3[nH]2)c1N] | 582 | 1.41 | AA Rev.3 |

Example 5-1-074

The target compound was obtained by performing Steps 1 to 4 of 4-22-003 using enamine (B-B026) and hydrazine (T002) as starting materials. The target compounds shown in the following table were also obtained by performing the similar operation using respective enamines and hydrazines. (Corresponding Enamines and Hydrazines)

| Example No. | Enamine | | Hydrazine | |
| --- | --- | --- | --- | --- |
| 5-1-074 | B-B026 | [structure] | T002 HCl | [structure] |
| 5-1-083 | B-B026 | [structure] | Q001 HCl | [structure] |
| 5-1-161 | B-B026 | [structure] | Q019 HCl | [structure] |
| 5-1-162 | I-A011 | [structure] | Q019 HCl | [structure] |

(Synthesized Compounds)

| Example No. | Compound | m/z (M + H) | Retention Time (Minute) | LCMS Measurement Condition |
| --- | --- | --- | --- | --- |
| 5-1-074 | [structure] | 527 | 0.97 | AA Rev.10 |

| Example No. | Compound | m/z (M + H) | Retention Time (Minute) | LCMS Measurement Condition |
|---|---|---|---|---|
| 5-1-083 | | 508 | 1.01 | AA Rev.11 |
| 5-1-161 | | 508 | 1.05 | AA Rev.11 |
| 5-1-162 | | 522 | 1.04 | AA Rev.11 |

Example 4-23-001

Synthesis of {5-amino-1-[6-(2,6-difluorophenoxy)-4-methylpyridin-3-yl]pyrazol-4-yl}-[5-(2,2-difluoroethoxy)-6-(4-methylsulfonylpiperazin-1-yl)-1H-indol-2-yl]methanone

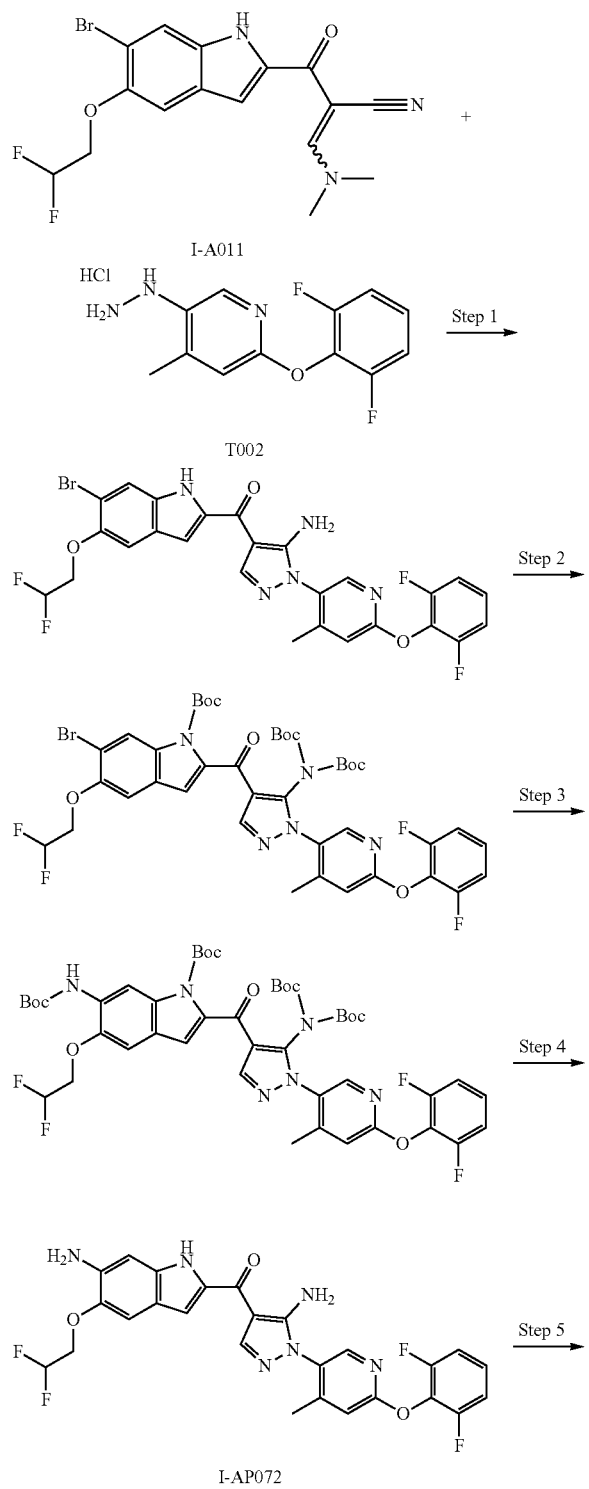

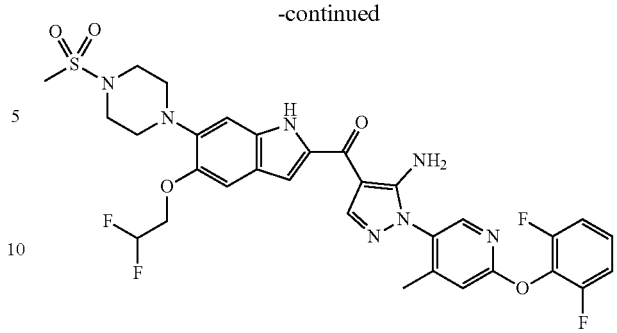

Step 1

Synthesis of {5-amino-1-[6-(2,6-difluorophenoxy)-4-methylpyridin-3-yl]pyrazol-4-yl}-[6-bromo-5-(2,2-difluoroethoxy)-1H-indol-2-yl]methanone Enamine I-A011 (1.39 g) and hydrazine T002 (1.47 g) were suspended in N,N-dimethylacetamide (13 mL), the atmosphere in the flask was replaced by nitrogen, and the suspension was stirred at 100° C. for one hour. The reaction solution was cooled to 25° C., water (50 mL) was added, and the precipitated solid was collected by filtration and washed by suspending in hexane/ethyl acetate to give the target compound (2.30 g).

Step 2

Synthesis of tert-butyl 2-{5-{bis[(2-methylpropan-2-yl)oxycarbonyl]amino}-1-[6-(2,6-difluorophenoxy)-4-methylpyridin-3-yl]pyrazole-4-carbonyl}-6-bromo-5-(2,2-difluoroethoxy)indole-1-carboxylate {5-Amino-1-[6-(2,6-difluorophenoxy)-4-methylpyridin-3-yl]pyrazol-4-yl}-[6-bromo-5-(2,2-difluoroethoxy)-1H-indol-2-yl]methanone (500 mg) was dissolved in tetrahydrofuran (7.0 mL), and Boc$_2$O (722 mg) and DMAP (10 mg) were added. Then the mixture was stirred at 25° C. for 30 minutes. The reaction solution was concentrated under reduced pressure and the resulting residue was purified by column chromatography (hexane/ethyl acetate) to give the target compound (360 mg).

Step 3

Synthesis of tert-butyl 2-{5-{bis[(2-methylpropan-2-yl)oxycarbonyl]amino}-1-[6-(2,6-difluorophenoxy)-4-methylpyridin-3-yl]pyrazole-4-carbonyl}-5-(2,2-difluoroethoxy)-6-[(2-methylpropan-2-yl)oxycarbonylamino]indole-1-carboxylate tert-Butyl 2-{5-{bis[(2-methylpropan-2-yl)oxycarbonyl]amino}-1-[6-(2,6-difluorophenoxy)-4-methylpyridin-3-yl]pyrazole-4-carbonyl}-6-bromo-5-(2,2-difluoroethoxy)indole-1-carboxylate (820 mg) was dissolved in dioxane (8.2 mL), and tert-butyl carbamate (159 mg), Pd$_2$dba$_3$ (83 mg), X-Phos (130 mg), and cesium carbonate (886 mg) were added. Then the mixture was stirred at 100° C. for 3.5 hours in a nitrogen atmosphere. The reaction solution was cooled to 25° C., ethyl acetate was added, and the insoluble matter was filtered off. The filtrate was concentrated under reduced pressure and the resulting residue was used as such for the next reaction without purification.

Step 4

Synthesis of [6-amino-5-(2,2-difluoroethoxy)-1H-indol-2-yl]-{5-amino-1-[6-(2,6-difluorophenoxy)-4-methylpyridin-3-yl]pyrazol-4-yl}methanone
(I-AP072)

Trifluoroacetic acid (8.5 mL) was added to tert-butyl 2-{5-{bis[(2-methylpropan-2-yl)oxycarbonyl]amino}-1-[6-(2,6-difluorophenoxy)-4-methylpyridin-3-yl]pyrazole-4-carbonyl}-5-(2,2-difluoroethoxy)-6-[(2-methylpropan-2-yl)oxycarbonylamino]indole-1-carboxylate (852 mg), and the mixture was stirred at 25° C. for one hour. The reaction solution was concentrated under reduced pressure, a saturated aqueous sodium bicarbonate solution (80 mL) was added to the resulting residue, and the mixture was extracted with ethyl acetate (80 mL). The organic layer was washed with a saturated aqueous sodium bicarbonate solution (80 mL) and saturated saline (80 mL), and dried over sodium sulfate. The drying agent was removed by filtration, the filtrate was then concentrated under reduced pressure, and the resulting residue was purified by column chromatography (hexane/ethyl acetate) to give the target compound (410 mg).

Step 5

Synthesis of {5-amino-1-[6-(2,6-difluorophenoxy)-4-methylpyridin-3-yl]pyrazol-4-yl}-[5-(2,2-difluoroethoxy)-6-(4-methylsulfonylpiperazin-1-yl)-1H-indol-2-yl]methanone

[6-Amino-5-(2,2-difluoroethoxy)-1H-indol-2-yl]-{5-amino-1-[6-(2,6-difluorophenoxy)-4-methylpyridin-3-yl]pyrazol-4-yl}methanone (70 mg) was dissolved in 1-methyl-2-pyrrolidone (4 mL), and N,N-bis(2-chloroethyl)methanesulfonamide (143 mg), potassium carbonate (179 mg), and sodium iodide (194 mg) were added. Then the mixture was stirred at 100° C. for 8.5 hours. The reaction solution was cooled to 25° C., water (30 mL) was added, and the mixture was extracted with ethyl acetate (50 mL). The organic layer was washed with saturated saline (20 mL) and dried over sodium sulfate. The drying agent was removed by filtration, the filtrate was then concentrated under reduced pressure, and the resulting residue was purified by Prep-HPLC to give the target compound (47 mg).

Examples 4-23-002 to 4-23-007, Example 5-1-075, and the Like

The compounds of Examples 4-23-002 to 4-23-007, Example 5-1-075, and the like were synthesized from corresponding enamines and hydrazines by the similar method as in Example 4-23-001.
(Corresponding Enamines and Hydrazines)

| Example No. | | Enamine | | Hydrazine |
|---|---|---|---|---|
| 4-23-001 | I-A011 | [structure] | T002 HCl | [structure] |
| 4-23-002 | B-026 | [structure] | Q001 HCl | [structure] |
| 4-23-003 | B-026 | [structure] | S0308 HCl | [structure] |

-continued

| Example No. | | Enamine | | Hydrazine |
|---|---|---|---|---|
| 4-23-004 | B-026 | [6-bromo-5-(difluoromethoxy)-1H-indol-2-yl with 2-cyano-3-(dimethylamino)acryloyl] | T001 HCl | [5-hydrazinyl-2-(2-fluorophenoxy)-4-methylpyridine] |
| 4-23-005 | I-A011 | [6-bromo-5-(2,2-difluoroethoxy)-1H-indol-2-yl with 2-cyano-3-(dimethylamino)acryloyl] | Q001 HCl | [4-(2-fluorophenoxy)-2-methylphenylhydrazine] |
| 4-23-006 | I-A011 | [6-bromo-5-(2,2-difluoroethoxy)-1H-indol-2-yl with 2-cyano-3-(dimethylamino)acryloyl] | S038 HCl | [2-fluoro-4-(2-fluorophenoxy)-6-methylphenylhydrazine] |
| 4-23-007 | I-A011 | [6-bromo-5-(2,2-difluoroethoxy)-1H-indol-2-yl with 2-cyano-3-(dimethylamino)acryloyl] | T001 HCl | [5-hydrazinyl-2-(2-fluorophenoxy)-4-methylpyridine] |
| 5-1-075 | B-B026 | [6-bromo-5-(difluoromethoxy)-1H-indol-2-yl with 2-cyano-3-(dimethylamino)acryloyl] | T002 HCl | [5-hydrazinyl-2-(2,6-difluorophenoxy)-4-methylpyridine] |
| 5-1-093 | I-A010 | [6-bromo-5-(morpholin-4-yl)-1H-indol-2-yl with 2-cyano-3-(dimethylamino)acryloyl] | Q001 HCl | [4-(2-fluorophenoxy)-2-methylphenylhydrazine] |
| 5-1-099 | I-A004 | [6-acetamido-5-fluoro-1-tosyl-1H-indol-2-yl with 2-cyano-3-(dimethylamino)acryloyl] | T002 HCl | [5-hydrazinyl-2-(2,6-difluorophenoxy)-4-methylpyridine] |

| Example No. | | Enamine | | Hydrazine |
|---|---|---|---|---|
| 5-1-125 | I-A004 | (structure) | Q001 HCl | (structure) |
| 5-1-158 | I-A010 | (structure) | Q019 HCl | (structure) |
| 5-1-171 | I-A011 | (structure) | Q019 HCl | (structure) |
| 5-1-175 | B-B026 | (structure) | Q019 HCl | (structure) |
| 5-1-176 | I-H074 | (structure) | Q019 HCl | (structure) |
| 5-1-187 | I-H074 | (structure) | T002 HCl | (structure) |

-continued
| Example No. | Enamine | | Hydrazine | |
|---|---|---|---|---|
| 5-1-191 | I-H074 |  | Q001 HCl | 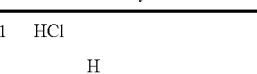 |
(Synthesized Compounds)
| Example No. | Compound | m/z (M + H) | Retention Time (Minute) | LCMS Measurement Condition |
|---|---|---|---|---|
| 4-23-001 | 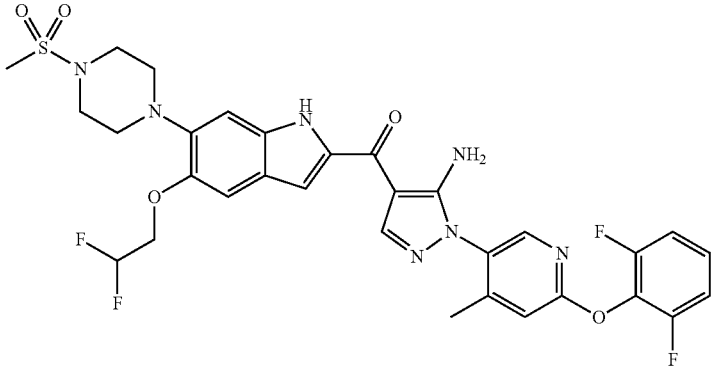 [SMILES: Cc1cc(Oc2c(F)cccc2F)ncc1-n1ncc(C(=O)c2cc3cc(OCC(F)F)c(N4CCN(S(C)(=O)=O)CC4)cc3[nH]2)c1N] | 688 | 1.02 | J4 |
| 4-23-002 | 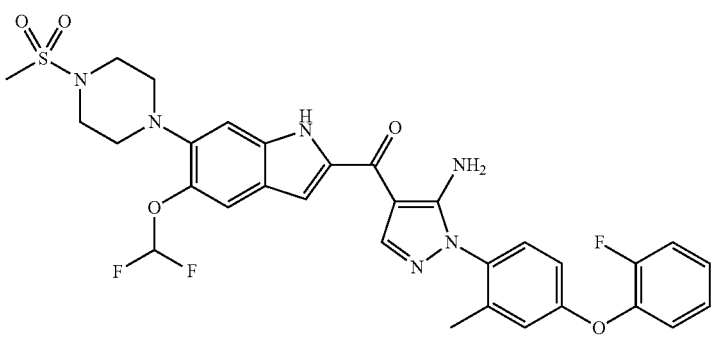 [SMILES: Cc1cc(Oc2ccccc2F)ccc1-n1ncc(C(=O)c2cc3cc(OC(F)F)c(N4CCN(S(C)(=O)=O)CC4)cc3[nH]2)c1N] | 655 | 1.04 | J4 |
| 4-23-003 | 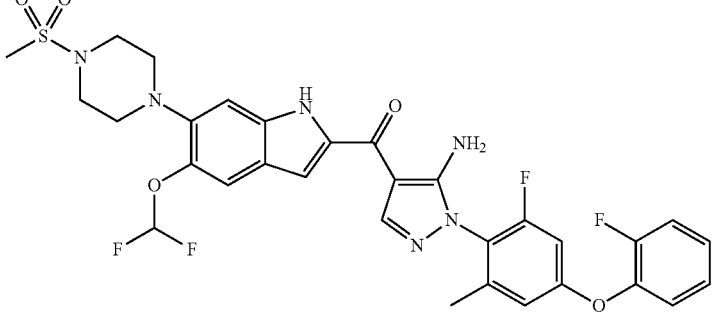 | 673 | 1.06 | J4 |

-continued
| Example No. | Compound | m/z (M + H) | Retention Time (Minute) | LCMS Measurement Condition |
|---|---|---|---|---|
| 4-23-004 | 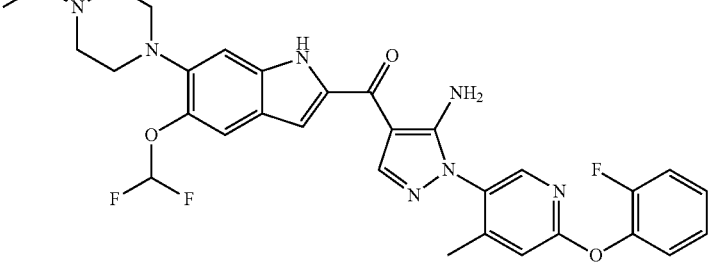 | 656 | 1.03 | J1 |
| 4-23-005 | 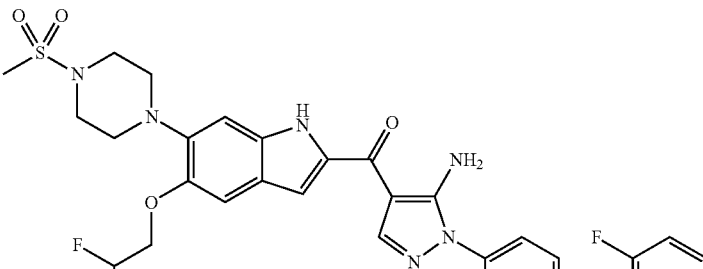 | 669 | 1.04 | J4 |
| 4-23-006 | 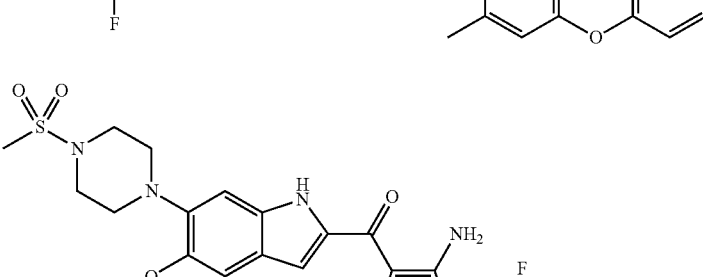 | 687 | 1.04 | J4 |
| 4-23-007 | 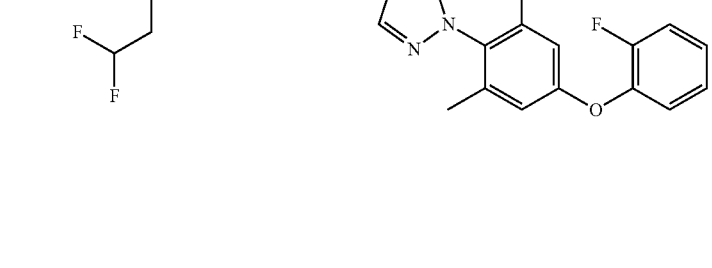 | 670 | 1.00 | J4 |

-continued
| Example No. | Compound | m/z (M + H) | Retention Time (Minute) | LCMS Measurement Condition |
|---|---|---|---|---|
| 5-1-075 | 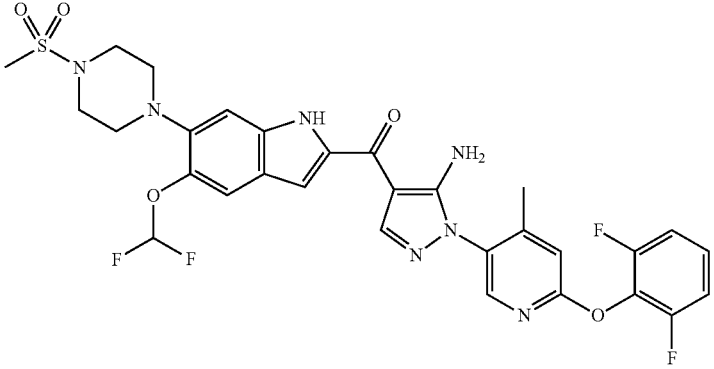 [SMILES: Cc1cc(Oc2c(F)cccc2F)ncc1-n1ncc(C(=O)c2cc3cc(OC(F)F)c(N4CCN(S(C)(=O)=O)CC4)cc3[nH]2)c1N] | 674 | 1.01 | AA Rev.10 |
| 5-1-093 | 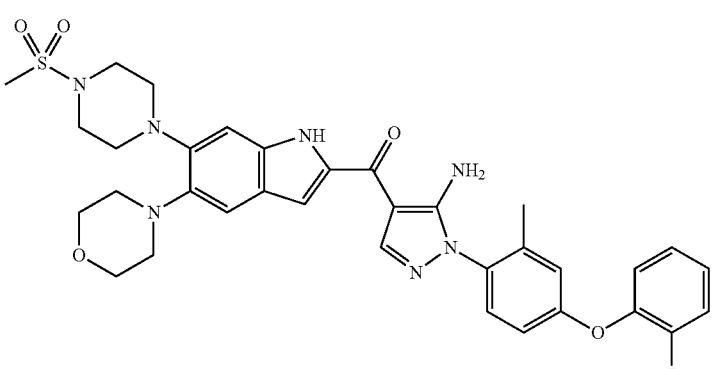 | 674 | 1.06 | AA Rev.11 |
| 5-1-099 | 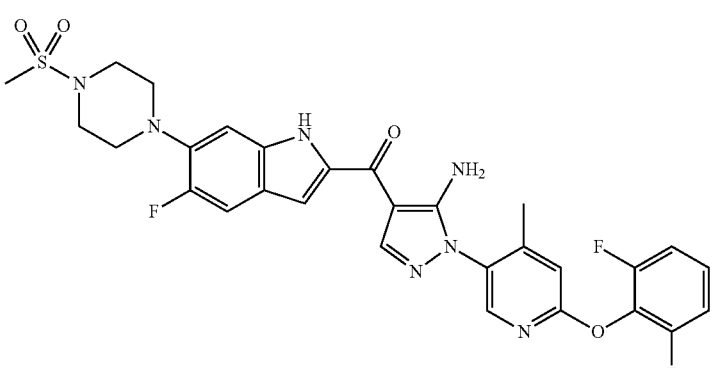 | 626 | 1.02 | AA Rev.11 |
| 5-1-125 | 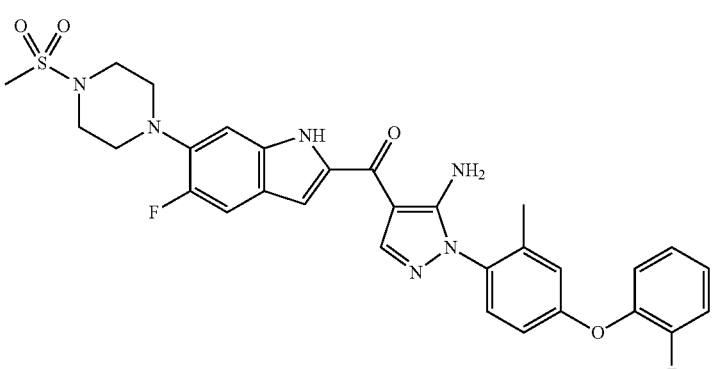 | 607 | 1.05 | AA Rev.11 |

-continued

| Example No. | Compound | m/z (M + H) | Retention Time (Minute) | LCMS Measurement Condition |
|---|---|---|---|---|
| 5-1-158 | | 674 | 1.17 | TFA Rev.5 |
| 5-1-171 | | 669 | 1.31 | TFA Rev.6 |
| 5-1-175 | | 655 | 1.08 | AA Rev.11 |
| 5-1-176 | | 730 | 1.12 | TFA Rev.5 |

| Example No. | Compound | m/z (M + H) | Retention Time (Minute) | LCMS Measurement Condition |
|---|---|---|---|---|
| 5-1-187 | | 749 | 1.05 | TFA Rev.5 |
| 5-1-191 | | 730 | 1.08 | TFA Rev.5 |

Example 4-23-008

Synthesis of {5-amino-1-[6-(2,6-difluorophenoxy)-4-methylpyridin-3-yl]pyrazol-4-yl}-[5-(2,2-difluoroethoxy)-6-(oxetan-3-ylamino)-1H-indol-2-yl]methanone

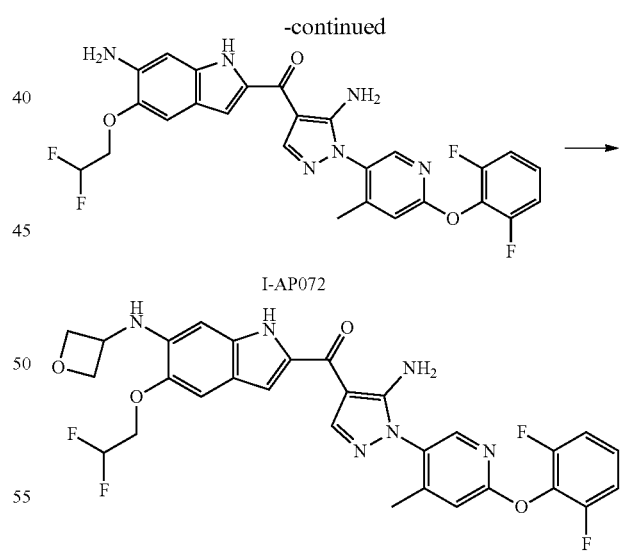

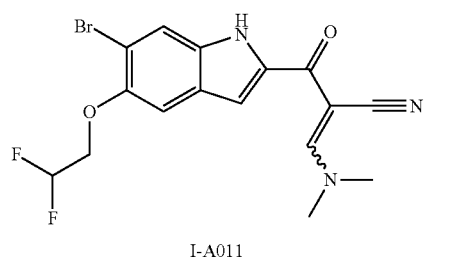

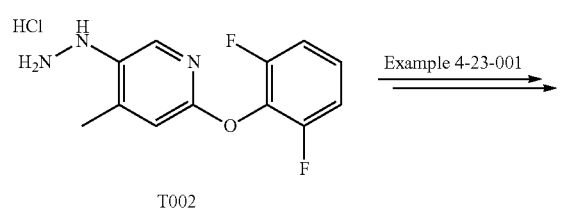

Aniline I-AP072 synthesized in Example 4-23-001 (70 mg) was suspended in dichloromethane (3.0 mL), and acetic acid (74 μL), oxetan-3-one (83 μL), and then sodium triacetoxyborohydride (137 mg) were added. Then the mixture was stirred at 25° C. for one hour. A saturated aqueous sodium bicarbonate solution was added to the reaction solution and the mixture was extracted with dichloromethane. The organic layer was washed with water and dried over sodium sulfate. The drying agent was removed by filtration, the filtrate was then concentrated under reduced pressure, and the resulting residue was purified by column chromatography (hexane/ethyl acetate). The eluate containing the target compound was concentrated under reduced pressure and the resulting residue was washed by suspending in ethyl acetate/hexane to give the target compound (49 mg).

Examples 4-23-009 to 4-23-021, Example 5-1-079, and the Like

The compounds of Examples 4-23-009 to 4-23-021, Example 5-1-079, and the like were synthesized by the similar method as in Example 4-23-008 using the corresponding enamines, hydrazines, and ketones.
(Corresponding Enamines, Hydrazines, and Ketones)

| Example No. | | Enamine | Hydrazine | | Ketone |
|---|---|---|---|---|---|
| 4-23-008 | I-A011 | | T002 | HCl | |
| 4-23-009 | B-B026 | | Q001 | HCl | |
| 4-23-010 | B-B026 | | Q001 | HCl | |
| 4-23-011 | B-B026 | | S038 | HCl | |
| 4-23-012 | B-B026 | | S038 | HCl | |

-continued

| Example No. | | Enamine | Hydrazine | | Ketone |
|---|---|---|---|---|---|
| 4-23-013 | B-B026 | | T001 | HCl | |
| 4-23-014 | B-B026 | | T002 | HCl | |
| 4-23-015 | B-B026 | | T002 | HCl | |
| 4-23-016 | I-A011 | | Q001 | HCl | |
| 4-23-017 | I-A011 | | Q001 | HCl | |
| 4-23-018 | I-A011 | | Q001 | HCl | |

-continued

| Example No. | | Enamine | Hydrazine | | Ketone |
|---|---|---|---|---|---|
| 4-23-019 | I-A011 | | S038 | HCl | |
| 4-23-020 | I-A011 | | T001 | HCl | |
| 4-23-021 | I-A011 | | T002 | HCl | |
| 5-1-079 | I-A011 | | T002 | HCl | |
| 5-1-102 | I-A004 | | T002 | HCl | |
| 5-1-113 | I-A004 | | T002 | HCl | |

-continued
| Example No. | | Enamine | Hydrazine | | Ketone |
|---|---|---|---|---|---|
| 5-1-118 | I-A004 | | Q001 | HCl | |
| 5-1-129 | I-A010 | | Q001 | HCl | |
| 5-1-135 | I-A004 | | Q001 | HCl | |
(Synthesized Compounds)
| Example No. | Compound | m/z (M + H) | Retention Time (Minute) | LCMS Measurement Condition |
|---|---|---|---|---|
| 4-23-008 | | 597 | 0.99 | J3 |
| 4-23-009 | | 564 | 1.01 | J4 |
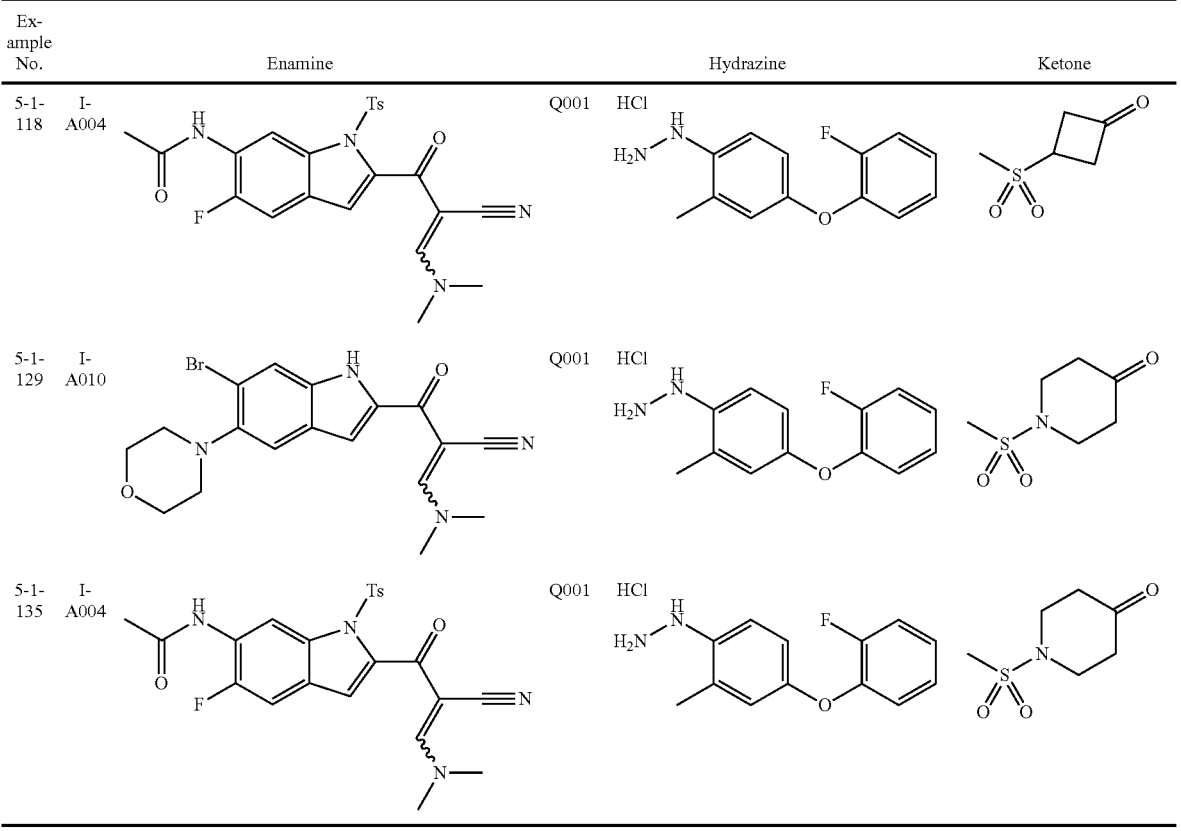

-continued

| Example No. | Compound | m/z (M + H) | Retention Time (Minute) | LCMS Measurement Condition |
|---|---|---|---|---|
| 4-23-010 | | 669 | 1.02 | J4 |
| 4-23-011 | | 582 | 1.04 | J1 |
| 4-23-012 | | 687 | 1.04 | J1 |
| 4-23-013 | | 565 | 1.01 | J1 |
| 4-23-014 | | 583 | 1.00 | J4 |

-continued

| Example No. | Compound | m/z (M + H) | Retention Time (Minute) | LCMS Measurement Condition |
|---|---|---|---|---|
| 4-23-015 | | 688 | 1.00 | J3 |
| 4-23-016 | | 578 | 1.04 | J1 |
| 4-23-017 | | 683 | 1.01 | J4 |
| 4-23-018 | | 655 | 1.02 | J1 |
| 4-23-019 | | 596 | 1.03 | J1 |
| 4-23-020 | | 579 | 1.00 | J1 |

-continued

| Example No. | Compound | m/z (M + H) | Retention Time (Minute) | LCMS Measurement Condition |
|---|---|---|---|---|
| 4-23-021 | | 7.02 | 0.99 | J4 |
| 5-1-079 | | 660 | 0.97 | AA Rev.10 |
| 5-1-102 | | 612 | 1.21 | TFA Rev.5 |
| 5-1-113 | | 640 | 1.02 | AA Rev.11 |
| 5-1-118 | | 593 | 1.01 | AA Rev.11 |

| Example No. | Compound | m/z (M + H) | Retention Time (Minute) | LCMS Measurement Condition |
|---|---|---|---|---|
| 5-1-129 | | 688 | 1.05 | AA Rev.11 |
| 5-1-135 | | 621 | 1.04 | AA Rev.11 |
Example 4-23-022
Synthesis of {5-amino-1-[6-(2,6-difluorophenoxy)-4-methylpyridin-3-yl]pyrazol-4-yl}-[5-(2,2-difluoroethoxy)-6-[(1-methylsulfonylazetidin-3-yl)amino]-1H-indol-2-yl]methanone
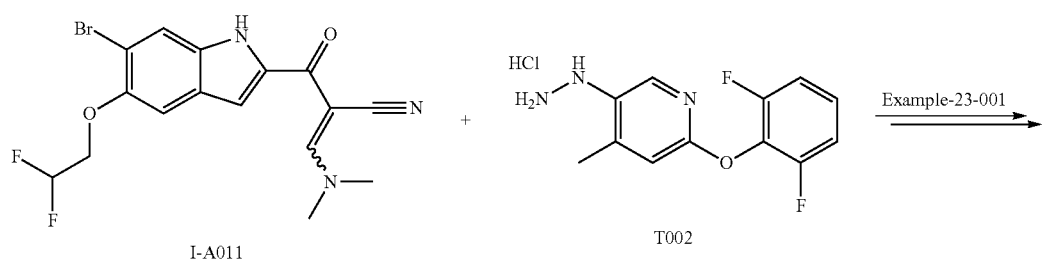
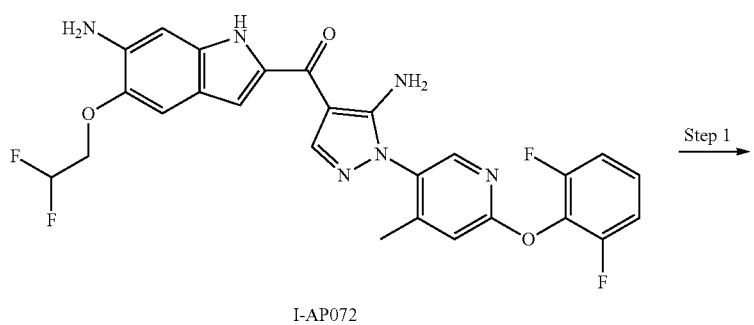

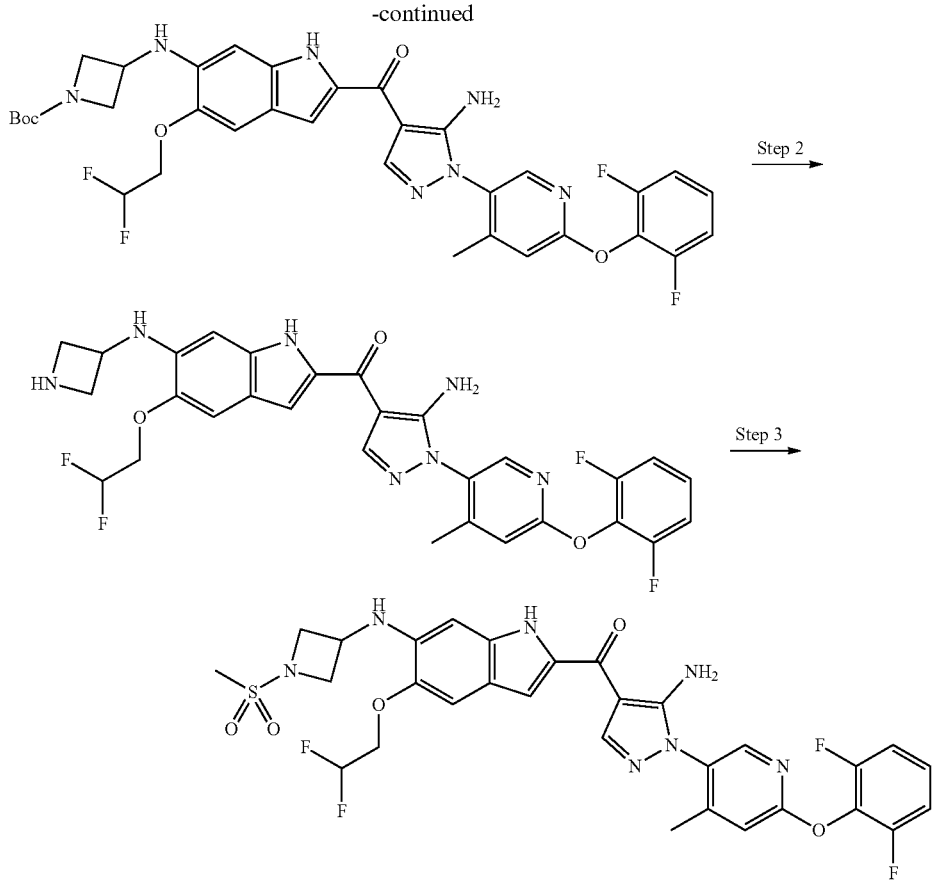

Step 1

Synthesis of tert-butyl 3-{{2-{5-amino-1-[6-(2,6-difluorophenoxy)-4-methylpyridin-3-yl]pyrazole-4-carbonyl}-5-(2,2-difluoroethoxy)-1H-indol-6-yl}amino}azetidine-1-carboxylate Aniline I-AP072 synthesized in Example 4-23-001 (70 mg) was suspended in dichloromethane (0.7 mL), and acetic acid (148 µL), tert-butyl 3-oxoazetidine-1-carboxylate (89 mg), and then sodium triacetoxyborohydride (137 mg) were added. Then the mixture was stirred at 25° C. for 1.5 hours. Ethyl acetate was added to the reaction solution and the insoluble matter was filtered off by celite filtration. A saturated aqueous sodium bicarbonate solution was added to the filtrate and the mixture was extracted with dichloromethane. The organic layer was washed with saturated saline and dried over sodium sulfate. The drying agent was removed by filtration and the filtrate was then concentrated under reduced pressure. The resulting residue was used as such for the next reaction without purification.

Step 2

Synthesis of {5-amino-1-[6-(2,6-difluorophenoxy)-4-methylpyridin-3-yl]pyrazol-4-yl}-[6-(azetidin-3-ylamino)-5-(2,2-difluoroethoxy)-1H-indol-2-yl]methanone tert-Butyl 3-{{2-{5-amino-1-[6-(2,6-difluorophenoxy)-4-methylpyridin-3-yl]pyrazole-4-carbonyl}-5-(2,2-difluoroethoxy)-1H-indol-6-yl}amino}azetidine-1-carboxylate (90 mg) was suspended in a 4 M hydrochloric acid-ethyl acetate solution (2.7 mL) and the mixture was stirred at 25° C. for 1.5 hours. The reaction solution was concentrated under reduced pressure, a saturated aqueous sodium bicarbonate solution (30 mL) was added to the resulting residue, and the mixture was extracted with ethyl acetate (30 mL). The organic layer was washed with saturated saline (20 mL) and dried over sodium sulfate. The drying agent was removed by filtration and the filtrate was then concentrated under reduced pressure. The resulting residue was used as such for the next reaction without purification.

Step 3

Synthesis of {5-amino-1-[6-(2,6-difluorophenoxy)-4-methylpyridin-3-yl]pyrazol-4-yl}-[5-(2,2-difluoroethoxy)-6-[(1-methylsulfonylazetidin-3-yl)amino]-1H-indol-2-yl]methanone {5-Amino-1-[6-(2,6-difluorophenoxy)-4-methylpyridin-3-yl]pyrazol-4-yl}-[6-(azetidin-3-ylamino)-5-(2,2-difluoroethoxy)-1H-indol-2-yl]methanone (77 mg) was dissolved in dichloromethane (1.3 mL), and TEA (36 µL) and methanesulfonyl chloride (20 µL) were added. Then the mixture was stirred at 80° C. for one hour. Saturated saline (20 mL) was added to the reaction solution, the mixture was extracted with ethyl acetate (30 mL), and the organic layer was dried over sodium sulfate. The drying agent was removed by filtration, the filtrate was then concentrated under reduced pressure, and the resulting residue was purified by Prep-HPLC to give the target compound (41 mg).

Examples 4-23-023 to 4-23-028

The compounds of Examples 4-23-023 to 4-23-028 were synthesized by the similar method as in Example 4-23-022 using the corresponding enamines and hydrazines and using the corresponding ketones in Step 1.
(Corresponding Enamines, Hydrazines, and Ketones)

| Example No. | Enamine | | Hydrazine | | Ketone |
|---|---|---|---|---|---|
| 4-23-022 | I-A011 | | T002 | HCl | |
| 4-23-023 | B-B026 | | Q001 | HCl | |
| 4-23-024 | B-B026 | | S038 | HCl | |
| 4-23-025 | B-B026 | | T001 | HCl | |
| 4-23-026 | B-B026 | | T11 | HCl | |
| 4-23-027 | I-A011 | | S038 | HCl | |

-continued
| Example No. | Enamine | Hydrazine | Ketone |
|---|---|---|---|
| 4-23-028 | I-A011 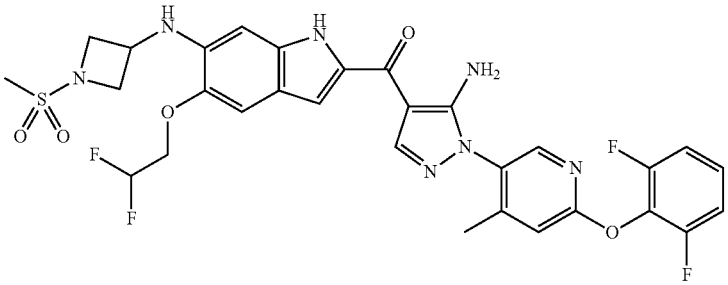 | S038 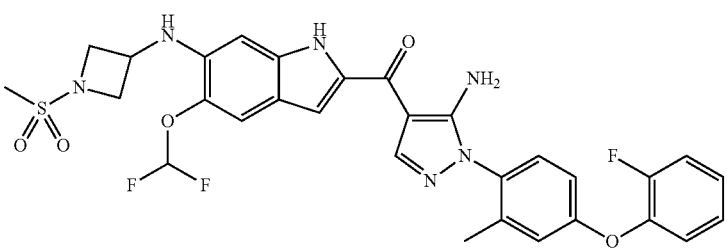 | 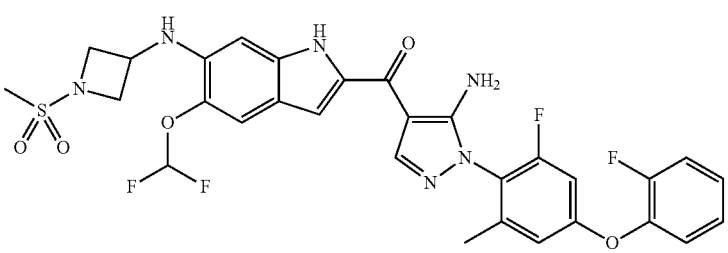 |
(Synthesized Compounds)
| Example No. | Compound | m/z (M + H) | Retention Time (Minute) | LCMS Measurement Condition |
|---|---|---|---|---|
| 4-23-022 | 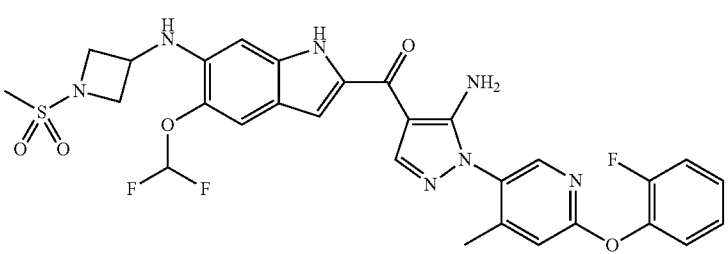 [SMILES: Cc1cc(Oc2ccccc2F)ccc1-n1ncc(C(=O)c2cc3cc(OC(F)F)c(NC4CN(S(C)(=O)=O)C4)cc3[nH]2)c1N] | 674 | 1.00 | J1 |
| 4-23-023 | | 641 | 0.99 | J4 |
| 4-23-024 | | 659 | 1.02 | J4 |
| 4-23-025 | | 642 | 0.99 | J4 |

| Example No. | Compound | m/z (M + H) | Retention Time (Minute) | LCMS Measurement Condition |
|---|---|---|---|---|
| 4-23-026 | | 670 | 1.02 | J1 |
| 4-23-027 | | 673 | 1.01 | J1 |
| 4-23-028 | | 701 | 1.03 | J1 |
Example 4-23-029
Synthesis of 1-{2-{5-amino-1-[6-(2,6-difluorophenoxy)-4-methyl pyridin-3-yl]pyrazole-4-carbonyl}-5-(2,2-difluoroethoxy)-1H-indol-6-yl}-6-methylpyrimidine-2,4-dione
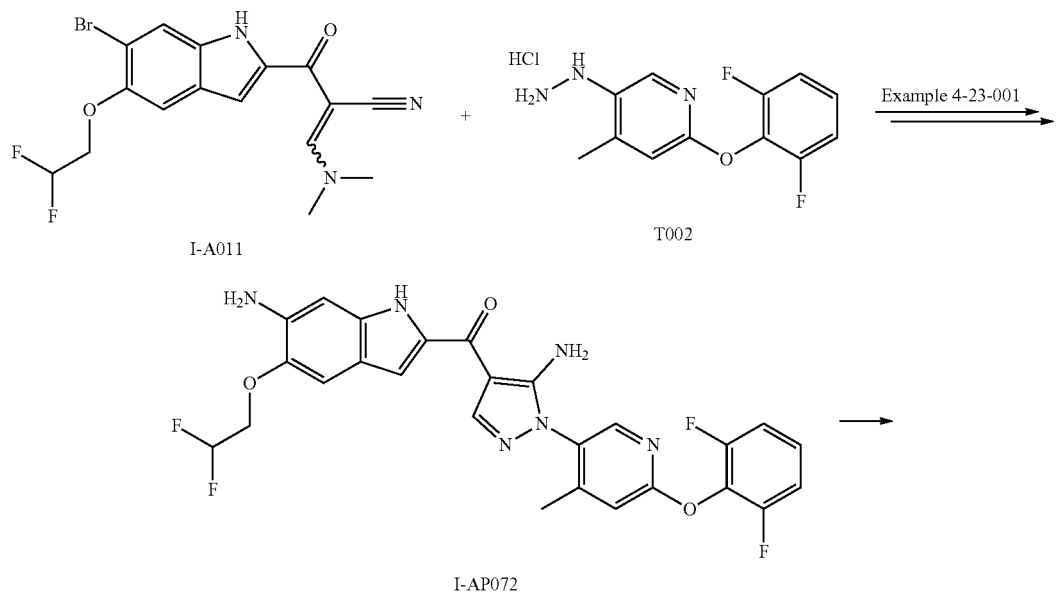

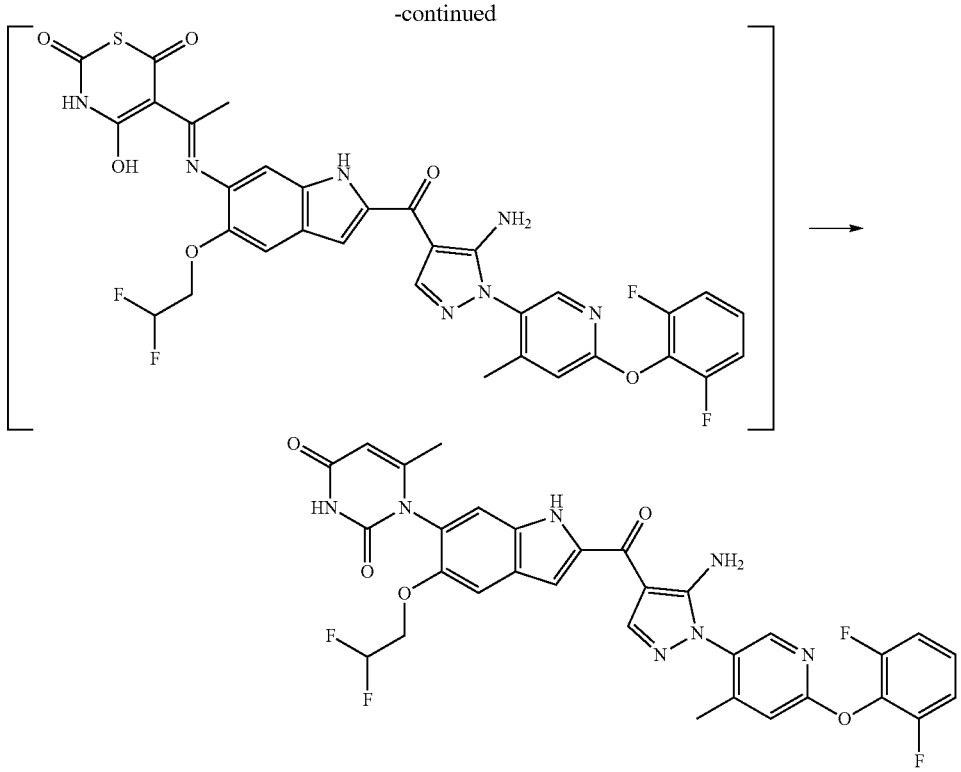

Aniline I-AP072 synthesized in Example 4-23-001 (60 mg) was dissolved in ethanol (2.0 mL), and 5-acetyl-4-hydroxy-3H-1,3-thiazine-2,6-dione (42 mg) was added. Then the mixture was stirred at 80° C. for 1.5 hours. The reaction solution was concentrated under reduced pressure, N,N-dimethylformamide (2.0 mL) was added to the resulting residue, and the mixture was stirred at 150° C. for 3.5 hours. The reaction solution was cooled to 25° C., water was added, and the mixture was extracted with ethyl acetate. The organic layer was washed with saturated saline and dried over sodium sulfate. The drying agent was removed by filtration and the filtrate was concentrated under reduced pressure. The resulting residue was washed by suspending in ethyl acetate/hexane to give the target compound (69 mg).

Examples 4-23-030 to 4-23-031, Example 5-1-072, and the Like

The compounds of Examples 4-23-030 to 4-23-031, Example 5-1-072, and the like were synthesized from corresponding enamines and hydrazines by the similar method as in Example 4-23-029.

(Corresponding Enamines and Hydrazines)

-continued

| Example No. | | Enamine | | Hydrazine |
|---|---|---|---|---|
| 4-23-031 | B-B026 | (6-bromo-5-(difluoromethoxy)-1H-indol-2-yl) enamine with CN and NMe2 | Q001 HCl | 4-(2-fluorophenoxy)-2-methylphenyl hydrazine |
| 5-1-072 | B-B026 | (6-bromo-5-(difluoromethoxy)-1H-indol-2-yl) enamine with CN and NMe2 | T002 HCl | 6-(2,6-difluorophenoxy)-4-methylpyridin-3-yl hydrazine |
| 5-1-101 | I-A004 | N-acetyl, 5-fluoro, N-Ts indol-2-yl enamine with CN and NMe2 | T002 HCl | 6-(2,6-difluorophenoxy)-4-methylpyridin-3-yl hydrazine |
| 5-1-104 | I-A004 | N-acetyl, 5-fluoro, N-Ts indol-2-yl enamine with CN and NMe2 | Q001 HCl | 4-(2-fluorophenoxy)-2-methylphenyl hydrazine |
| 5-1-116 | I-A010 | 6-bromo-5-morpholino-1H-indol-2-yl enamine with CN and NMe2 | Q001 HCl | 4-(2-fluorophenoxy)-2-methylphenyl hydrazine |

(Synthesized Compounds)

| Example No. | Compound | m/z (M + H) | Retention Time (Minute) | LCMS Measurement Condition |
|---|---|---|---|---|
| 4-23-029 | | 650 | 0.93 | J2 |
| 4-23-030 | | 631 | 0.96 | J4 |
| 4-23-031 | | 617 | 0.97 | J2 |
| 5-1-072 | | 636 | 0.95 | AA Rev.8 |

| Example No. | Compound | m/z (M + H) | Retention Time (Minute) | LCMS Measurement Condition |
|---|---|---|---|---|
| 5-1-101 | 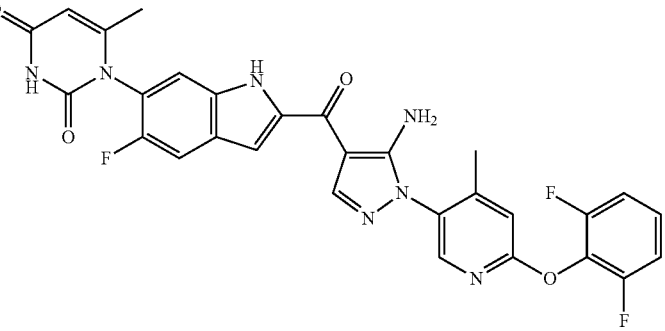 | 588 | 1.13 | TFA Rev.5 |
| 5-1-104 | 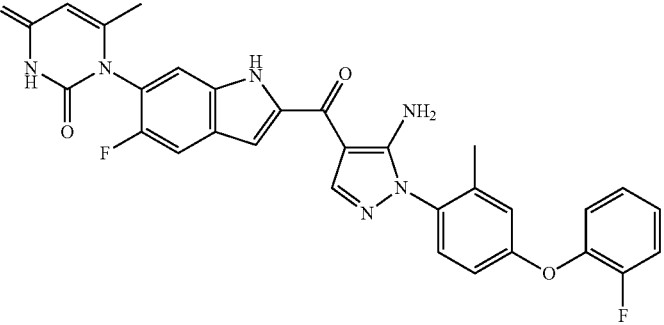 | 569 | 1.00 | AA Rev.11 |
| 5-1-116 | 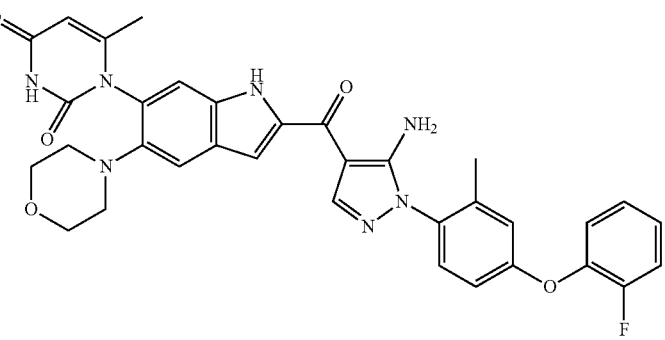 | 636 | 1.15 | TFA Rev.5 |
Example 4-23-032
Synthesis of 3-{2-{5-amino-1-[6-(2,6-difluorophenoxy)-4-methylpyridin-3-yl]pyrazole-4-carbonyl}-5-(2,2-difluoroethoxy)-1H-indol-6-yl}-5,5-dimethylimidazolidine-2,4-dione
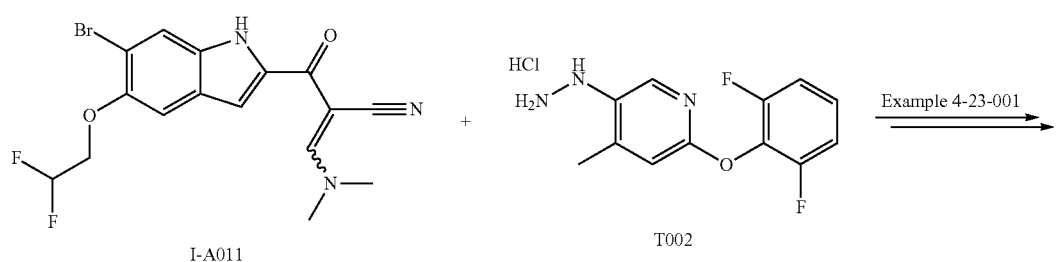

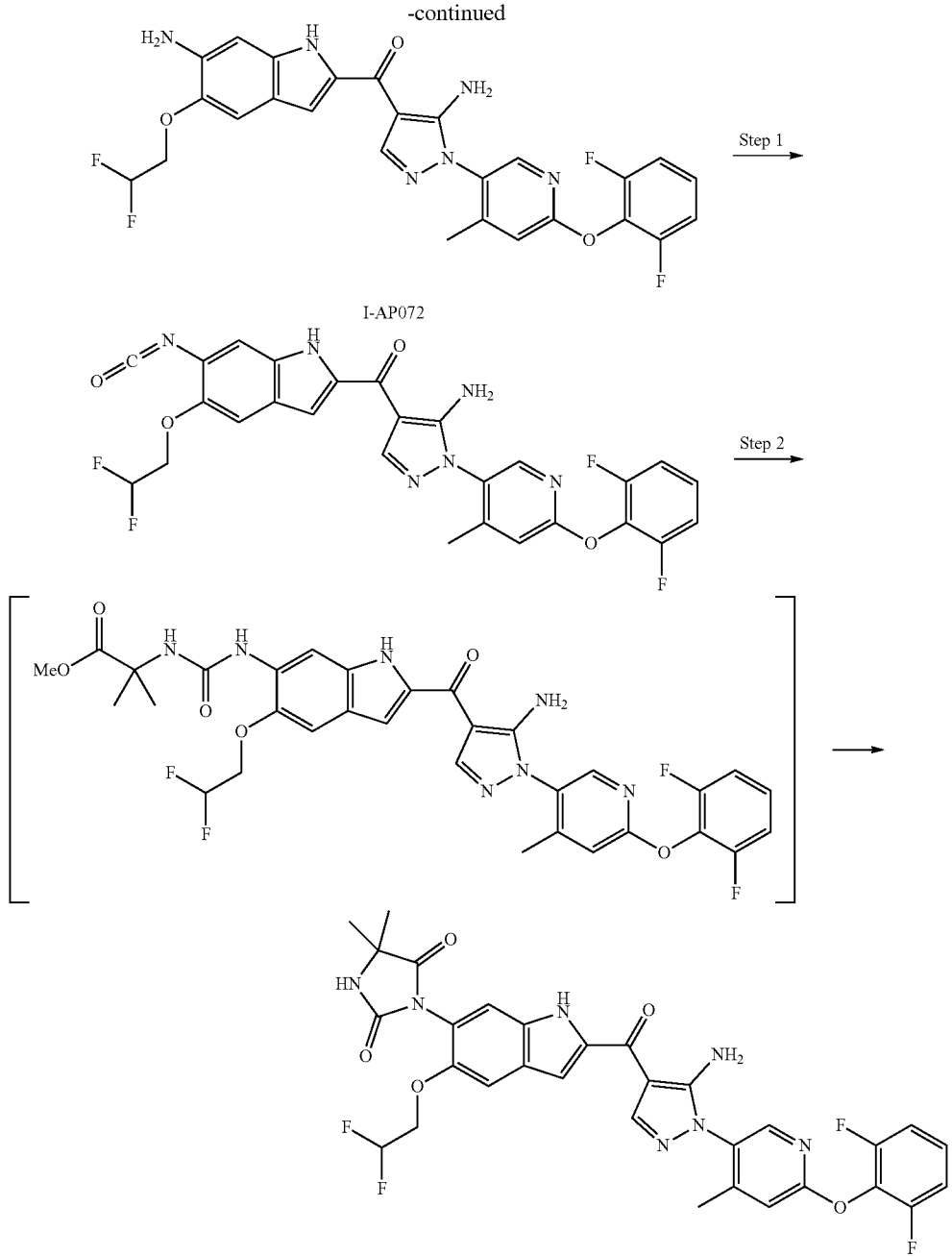

Step 1

Synthesis of {5-amino-1-[6-(2,6-difluorophenoxy)-4-methylpyridin-3-yl]pyrazol-4-yl}-[5-(2,2-difluoroethoxy)-6-isocyanato-1H-indol-2-yl]methanone Aniline I-AP072 synthesized in Example 4-23-001 (91 mg) was suspended in dichloromethane (4.0 mL) and water (4.0 mL), and triphosgene (18 mg) was added. Then the mixture was stirred at 25° C. for one hour. Water (30 mL) was added to the reaction solution, the mixture was extracted with dichloromethane (70 mL), and the organic layer was dried over sodium sulfate. The drying agent was removed by filtration and the filtrate was then concentrated under reduced pressure. The resulting residue was used as such for the next reaction without purification.

Step 2

Synthesis of 3-{2-{5-amino-1-[6-(2,6-difluorophenoxy)-4-methylpyridin-3-yl]pyrazole-4-carbonyl}-5-(2,2-difluoroethoxy)-1H-indol-6-yl}-5,5-dimethyl-imidazolidine-2,4-dione {5-Amino-1-[6-(2,6-difluorophenoxy)-4-methylpyridin-3-yl]pyrazol-4-yl}-[5-(2,2-difluoroethoxy)-6-isocyanato-1H-indol-2-yl]methanone (95 mg) was dissolved in tetrahydrofuran (1.7 mL), and methyl α-amino-isobutyrate hydrochloride (34 mg) and TEA (61 μL) were added. Then the mixture was stirred at 60° C. for 1.5 hours. Concentrated hydrochloric acid (1.0 mL) was added to the reaction solution and the mixture was further stirred at 60° C. for 2.5 hours. The reaction solution was cooled to 25° C., water (50 mL) was added, and the mixture was extracted with ethyl acetate (30 mL) three times. The organic layers were washed with a saturated aqueous sodium bicarbonate solution (30 mL) and saturated saline (20 mL), and dried over sodium sulfate. The drying agent was removed by filtration, the filtrate was then concentrated under reduced pressure, and the resulting residue was purified by Prep-HPLC to give the target compound (39 mg).

Examples 4-23-033 to 4-23-035

The compounds of Examples 4-23-033 to 4-23-035 were synthesized from corresponding enamines and hydrazines by the similar method as in Example 4-23-032.

(Corresponding Enamines and Hydrazines)

| Example No. | | Enamine | | Hydrazine |
|---|---|---|---|---|
| 4-23-032 | I-A011 | | T002 HCl | |
| 4-23-033 | I-A011 | | Q001 HCl | |
| 4-23-034 | B-B026 | | T002 HCl | |
| 4-23-035 | B-B026 | | Q001 HCl | |

(Synthesized Compounds)
| Example No. | Compound | m/z (M + H) | Retention Time (Minute) | LCMS Measurement Condition |
|---|---|---|---|---|
| 4-23-032 | 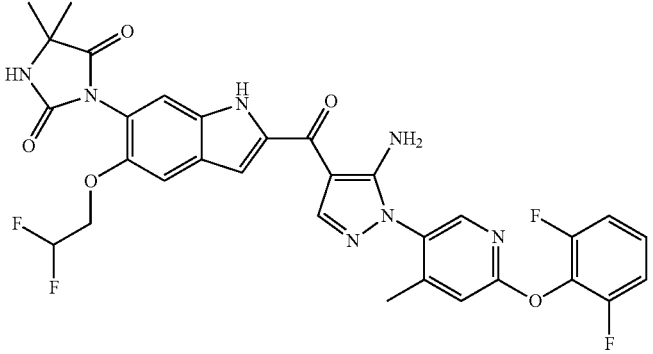 [SMILES: Cc1cc(Oc2c(F)cccc2F)ncc1-n1ncc(C(=O)c2cc3cc(OCC(F)F)c(N4C(=O)NC(C)(C)C4=O)cc3[nH]2)c1N] | 652 | 0.97 | J1 |
| 4-23-033 | 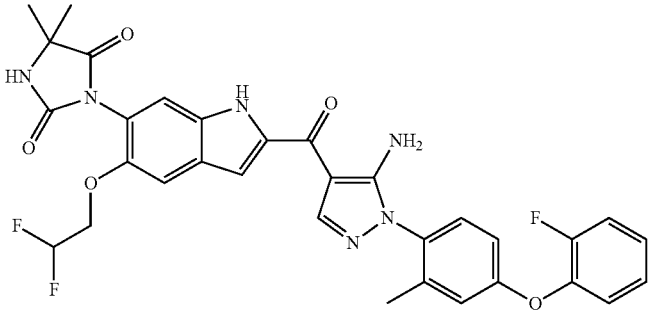 [SMILES: Cc1cc(Oc2ccccc2F)ccc1-n1ncc(C(=O)c2cc3cc(OCC(F)F)c(N4C(=O)NC(C)(C)C4=O)cc3[nH]2)c1N] | 633 | 0.99 | J1 |
| 4-23-034 | 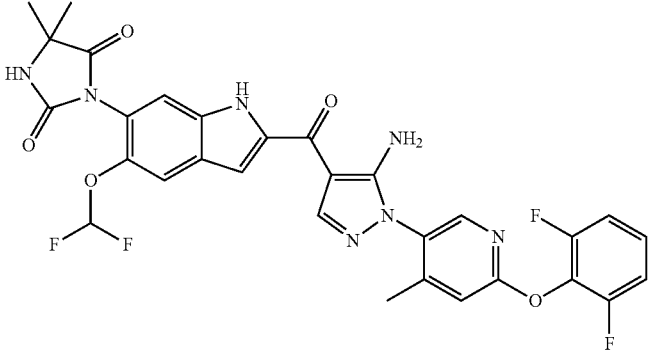 [SMILES: Cc1cc(Oc2c(F)cccc2F)ncc1-n1ncc(C(=O)c2cc3cc(OC(F)F)c(N4C(=O)NC(C)(C)C4=O)cc3[nH]2)c1N] | 638 | 0.96 | J2 |
| 4-23-035 | 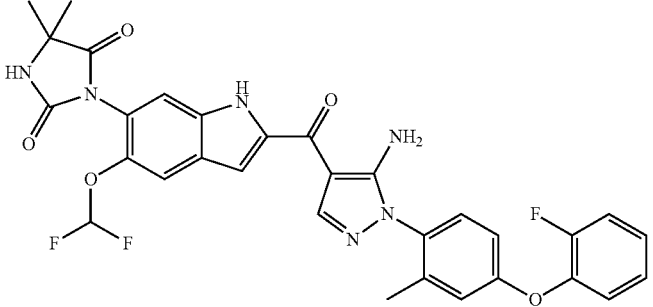 [SMILES: Cc1cc(Oc2ccccc2F)ccc1-n1ncc(C(=O)c2cc3cc(OC(F)F)c(N4C(=O)NC(C)(C)C4=O)cc3[nH]2)c1N] | 619 | 0.98 | J4 |

Example 5-1-233

Synthesis of 3-(2-(5-amino-1-(4-(2-fluorophenoxy)-3-methylphenyl)-1H-pyrazole-4-carbonyl)-5-((1-cyclobutylpiperidin-4-yl)oxy)-1H-indol-6-yl)-5,5-dimethylimidazolidine-2,4-dione

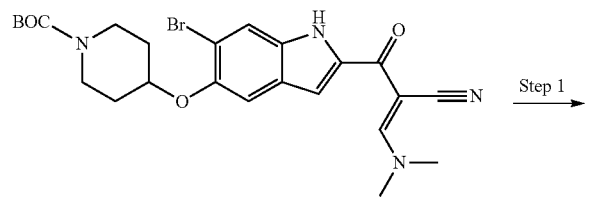

Step 1

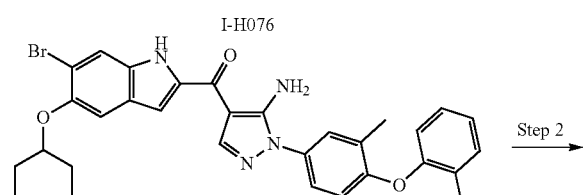

Step 2

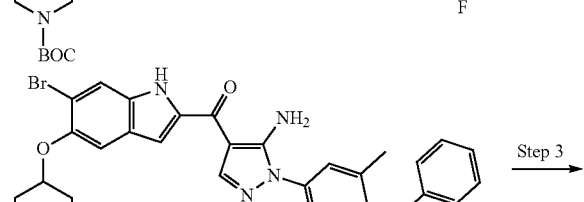

Step 3

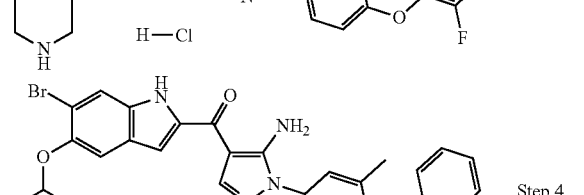

Step 4

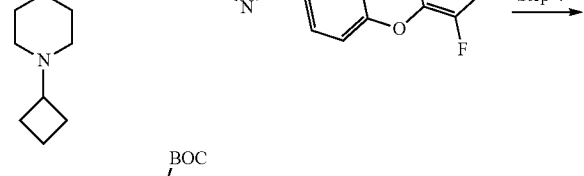

Step 5

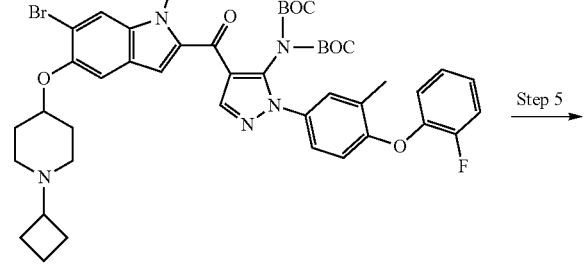

Step 6

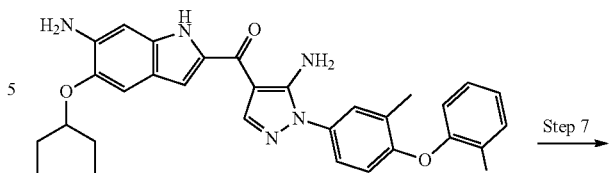

Step 7

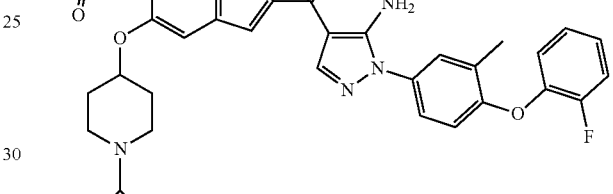

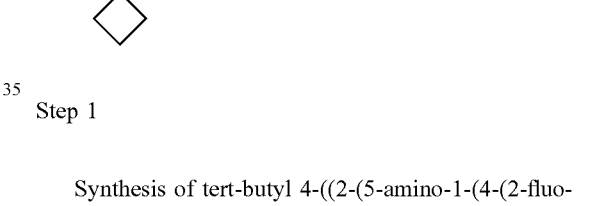

Step 1

Synthesis of tert-butyl 4-((2-(5-amino-1-(4-(2-fluorophenoxy)-3-methylphenyl)-1H-pyrazole-4-carbonyl)-6-bromo-1H-indol-5-yl)oxy)piperidine-1-carboxylate (4-(2-Fluorophenoxy)-3-methylphenyl)hydrazine hydrochloride (0.70 g) and 4-methylmorpholine (0.574 mL) were added at room temperature to a flask containing a solution of (E)-tert-butyl 4-((6-bromo-2-(2-cyano-3-(dimethylamino)acryloyl)-1H-indol-5-yl)oxy)piperidine-1-carboxylate obtained in Example 1-4-12 (I-H076, 0.9 g) in NMP (9 mL). The atmosphere in the flask was replaced by nitrogen. The reaction solution was stirred at 80° C. for two hours, water was then added, and the mixture was extracted with ethyl acetate. The organic layer was washed with water and saturated saline and dried over sodium sulfate. The drying agent was removed by filtration, the filtrate was concentrated, and the resulting residue was purified by silica gel column chromatography (ethyl acetate/hexane) to give the target compound (844 mg).

Step 2

Synthesis of (5-amino-1-(4-(2-fluorophenoxy)-3-methylphenyl)-1H-pyrazol-4-yl)(6-bromo-5-(piperidin-4-yloxy)-1H-indol-2-yl)methanone hydrochloride tert-Butyl 4-((2-(5-amino-1-(4-(2-fluorophenoxy)-3-methylphenyl)-1H-pyrazole-4-carbonyl)-6-bromo-1H-indol-5-yl)oxy)piperidine-1-carboxylate obtained in Step 1 (844 mg) was added to 2,2,2-trifluoroethanol (16 mL), and TMSCl (0.455 mL) was added at 25° C. After concentrating the reaction solution under reduced pressure, the residue was dissolved in DMSO-water and the reaction solution was purified by C18 column (TFA-water-acetonitrile). The organic solvent component was evaporated from the fractions containing the target compound under reduced pressure. The precipitate in the residual aqueous solution was collected by filtration and dried to give the target compound (647 mg).

Step 3

Synthesis of (5-amino-1-(4-(2-fluorophenoxy)-3-methylphenyl)-1H-pyrazol-4-yl)(6-bromo-5-((1-cyclobutylpiperidin-4-yl)oxy)-1H-indol-2-yl)methanone (5-Amino-1-(4-(2-fluorophenoxy)-3-methylphenyl)-1H-pyrazol-4-yl)(6-bromo-5-(piperidin-4-yloxy)-1H-indol-2-yl)methanone hydrochloride obtained in Step 2 (488 mg) was suspended in dichloromethane (7.6 mL) and cyclobutanone (0.085 mL), triethylamine (0.233 mL), acetic acid (0.131 mL), and sodium triacetoxyborohydride (484 mg) were added at 25° C. The reaction solution was stirred for three days and ethanol was then added. The reaction solution was purified by Prep HPLC (0.05% TFA-water-acetonitrile), after which the eluate of the target compound was neutralized with a saturated aqueous sodium bicarbonate solution and then extracted with ethyl acetate. The solvent was concentrated under reduced pressure and the resulting residue was crystallized from dichloromethane/hexane to give the target compound (470 mg).

Step 4

Synthesis of tert-butyl 2-[5-[bis(tert-butoxycarbonyl)amino]-1-[4-(2-fluorophenoxy)-3-methyl-phenyl]pyrazole-4-carbonyl]-6-bromo-5-[(1-cyclobutyl-4-piperidyl)oxy]indole-1-carboxylate (5-Amino-1-(4-(2-fluorophenoxy)-3-methylphenyl)-1H-pyrazol-4-yl)(6-bromo-5-((1-cyclobutylpiperidin-4-yl)oxy)-1H-indol-2-yl)methanone obtained in Step 3 (420 mg) was added to tetrahydrofuran (6.4 mL), and di-tert-butyl dicarbonate (0.807 mL) and DMAP (6.2 mg) were added at 25° C. The reaction solution was stirred at 25° C. for one hour and then purified by silica gel column chromatography (dichloromethane/methanol) to give the target compound (534 mg).

Step 5

Synthesis of tert-butyl 2-(5-(bis(tert-butoxycarbonyl)amino)-1-(4-(2-fluorophenoxy)-3-methylphenyl)-1H-pyrazole-4-carbonyl)-6-((tert-butoxycarbonyl)amino)-5-((1-cyclobutylpiperidin-4-yl)oxy)-1H-indole-1-carboxylate tert-Butyl 2-[5-[bis(tert-butoxycarbonyl)amino]-1-[4-(2-fluorophenoxy)-3-methyl-phenyl]pyrazole-4-carbonyl]-6-bromo-5-[(1-cyclobutyl-4-piperidyl)oxy]indole-1-carboxylate obtained in Step 4 (120 mg), X-Phos (9 mg), tert-butyl carbamate (22 mg), [Pd(allyl)Cl]2 (2.3 mg), and cesium carbonate (122 mg) were added to dioxane (1.2 mL) and the mixture was stirred at 80° C. for 18 hours in a nitrogen stream. SiliametS DMT (120 mg) was added to the reaction solution and the solid was removed by celite filtration. The filtrate was concentrated under reduced pressure to give the target compound. The target compound was used for the next reaction without purification.

Step 6

Synthesis of (5-amino-1-(4-(2-fluorophenoxy)-3-methylphenyl)-1H-pyrazol-4-yl)(6-amino-5-((1-cyclobutylpiperidin-4-yl)oxy)-1H-indol-2-yl)methanone Chlorotrimethylsilane (0.253 mL) was added to tert-butyl 2-(5-(bis(tert-butoxycarbonyl)amino)-1-(4-(2-fluorophenoxy)-3-methylphenyl)-1H-pyrazole-4-carbonyl)-6-((tert-butoxycarbonyl)amino)-5-((1-cyclobutylpiperidin-4-yl)oxy)-1H-indole-1-carboxylate obtained in Step 5 (124 mg) in 2,2,2-trifluoroethanol (3.7 mL) at 25° C. and the mixture was stirred. The reaction solution was diluted with DMSO and then purified by C18 column (0.05% TFA-water-acetonitrile), and the fractions of the target compound were neutralized with a saturated aqueous sodium bicarbonate solution. The solvent (about 3 mL) was evaporated and the resulting solid was collected by filtration, washed with water, and dried under reduced pressure to give the target compound (81 mg).

Step 7

Synthesis of 3-(2-(5-amino-1-(4-(2-fluorophenoxy)-3-methylphenyl)-1H-pyrazole-4-carbonyl)-5-((1-cyclobutylpiperidin-4-yl)oxy)-1H-indol-6-yl)-5,5-dimethylimidazolidine-2,4-dione A solution of (5-amino-1-(4-(2-fluorophenoxy)-3-methylphenyl)-1H-pyrazol-4-yl)(6-amino-5-((1-cyclobutylpiperidin-4-yl)oxy)-1H-indol-2-yl)methanone obtained in Step 6 (30 mg) in dichloromethane (0.5 mL) was added to a solution of bis(trichloromethyl) carbonate (5.4 mg) in dichloromethane/water (1/1, 1 mL) at 25° C. After 30 minutes, 2-amino-2-methylpropanoic acid hydrochloride (19 mg) was added and the mixture was stirred for 30 minutes. After concentrating the reaction solution under reduced pressure, THF (0.3 mL) and concentrated hydrochloric acid (0.3 mL) were added and the mixture was stirred at 80° C. for two hours. The mixture was purified by C18 column (0.05% TFA-water-acetonitrile). A saturated aqueous sodium bicarbonate solution was added to the eluate containing the target compound. The resulting precipitate was collected by filtration, washed with water, and dried to give the target compound (17 mg).

The compounds shown in the following tables could be obtained by respectively using the corresponding enamines, hydrazines, and the like.

(Corresponding Enamines and Hydrazines)

| Example No. | | Enamine | | Hydrazine |
| --- | --- | --- | --- | --- |
| 5-1-233 | I-H076 | | Q019 | HCl |
| 5-1-114 | I-A004 | | T002 | HCl |
| 5-1-117 | I-A010 | | Q001 | HCl |
| 5-1-127 | I-A004 | | Q001 | HCl |
| 5-1-164 | I-A010 | | Q019 | HCl |
| 5-1-170 | I-A011 | | Q019 | HCl |

US 10,479,780 B2

751                                                                 752

-continued

| Example No. | | Enamine | Hydrazine | |
|---|---|---|---|---|
| 5-1-179 | B-B026 | 6-bromo-5-(difluoromethoxy)-1H-indol-2-yl with 2-cyano-3-(dimethylamino)acryloyl | Q019 HCl | 4-(2-fluorophenoxy)-3-methylphenylhydrazine |
| 5-1-180 | I-H074 | 6-bromo-5-((1-isopropylpiperidin-4-yl)oxy)-1H-indol-2-yl with 2-cyano-3-(dimethylamino)acryloyl | Q019 HCl | 4-(2-fluorophenoxy)-3-methylphenylhydrazine |
| 5-1-188 | I-H074 | 6-bromo-5-((1-isopropylpiperidin-4-yl)oxy)-1H-indol-2-yl with 2-cyano-3-(dimethylamino)acryloyl | T002 HCl | 6-(2,6-difluorophenoxy)-4-methylpyridin-3-yl hydrazine |
| 5-1-193 | I-H074 | 6-bromo-5-((1-isopropylpiperidin-4-yl)oxy)-1H-indol-2-yl with 2-cyano-3-(dimethylamino)acryloyl | Q001 HCl | 4-(2-fluorophenoxy)-2-methylphenylhydrazine |
| 5-1-243 | I-A011 | 6-bromo-5-(2,2-difluoroethoxy)-1H-indol-2-yl with 2-cyano-3-(dimethylamino)acryloyl | Q001 HCl | 4-(2-fluorophenoxy)-2-methylphenylhydrazine |
| 5-1-250 | I-A011 | 6-bromo-5-(2,2-difluoroethoxy)-1H-indol-2-yl with 2-cyano-3-(dimethylamino)acryloyl | Q001 HCl | 4-(2-fluorophenoxy)-2-methylphenylhydrazine |

-continued
| Example No. | | Enamine | Hydrazine | |
|---|---|---|---|---|
| 5-1-251 | I-A011 | 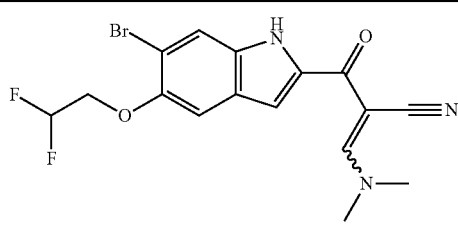 | Q001 HCl | 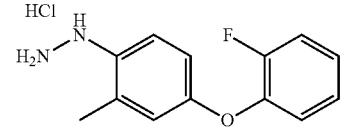 [SMILES: Cl ; Cc1cc(Oc2ccccc2F)ccc1NN] |
| 5-1-252 | I-A011 | 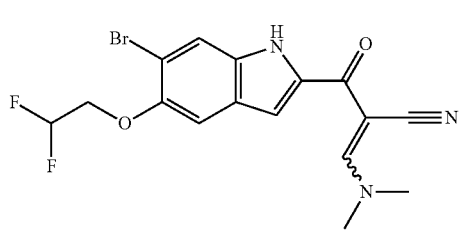 | Q001 HCl | 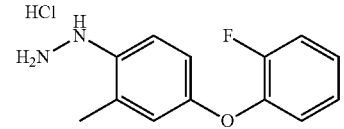 [SMILES: Cl ; Cc1cc(Oc2ccccc2F)ccc1NN] |
| 5-1-253 | I-A011 | 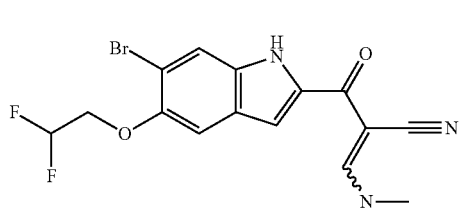 | Q001 HCl | 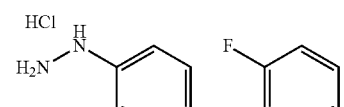 |
| 5-1-265 | I-A004 | 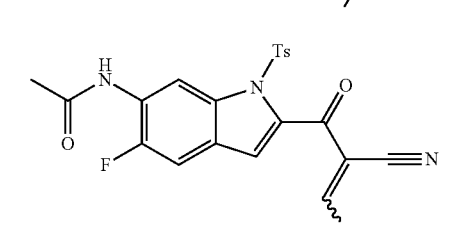 | Q001 HCl | 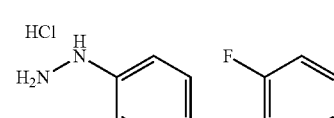 |
| 5-1-268 | I-H057 | 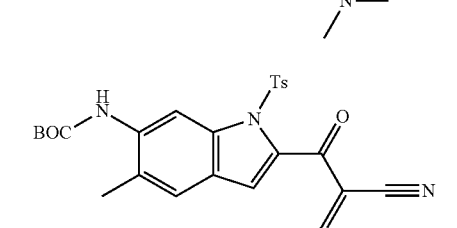 | Q001 HCl | 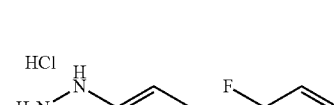 |
| 5-1-270 | I-A011 | 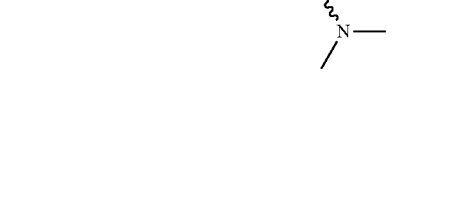 | Q001 HCl |  |

-continued
| Example No. | | Enamine | Hydrazine | |
|---|---|---|---|---|
| 5-1-286 | I-H057 | 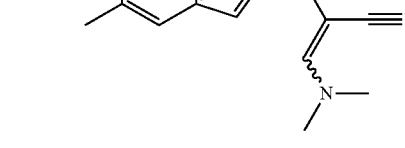 | T002 HCl | 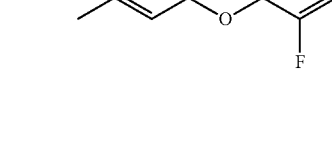 |
| 5-1-287 | I-H074 | 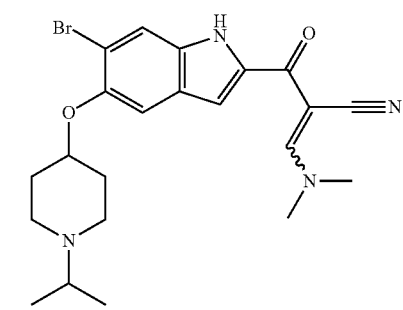 | Q019 HCl | 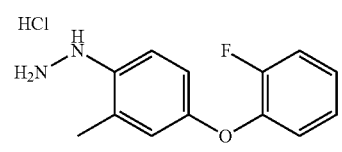 [SMILES: Cl ; Cc1cc(Oc2ccccc2F)ccc1NN] |
| 5-1-293 | I-H074 | 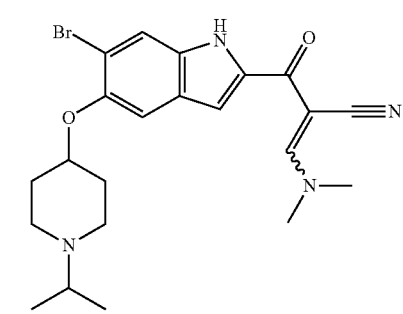 | Q019 HCl | 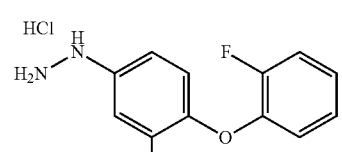 |
| 5-1-294 | I-H074 | 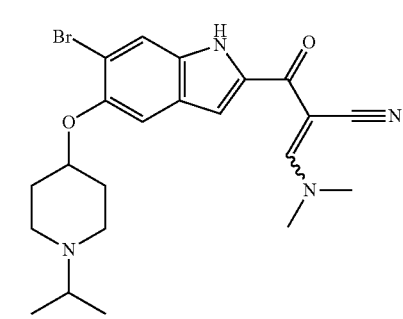 | Q019 HCl | 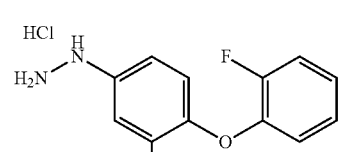 |
| 5-1-295 | I-H074 | 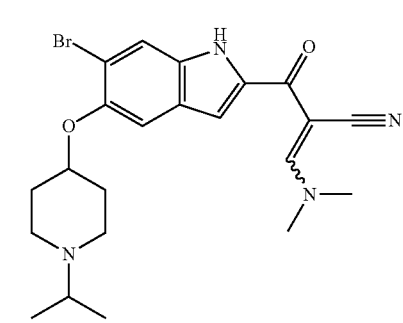 | Q019 HCl | 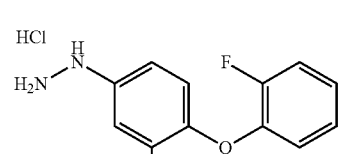 |

| Example No. | | Enamine | | Hydrazine |
|---|---|---|---|---|
| 5-1-312 | I-A004 | | T002 HCl | |
| 5-1-316 | I-H057 | | T002 HCl | |
| 5-1-324 | I-H075 | | T002 HCl | |
| 5-1-334 | I-H057 | | T001 HCl | |
| 5-1-341 | I-H057 | | T002 HCl | |
| 5-1-342 | I-H057 | | T002 HCl | |

-continued
| Example No. | | Enamine | Hydrazine | |
|---|---|---|---|---|
| 5-1-343 | I-A004 | 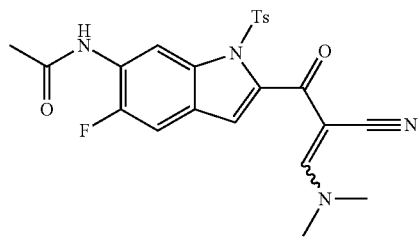 [SMILES: CC(=O)Nc1cc2c(cc1F)cc(C(=O)C(C#N)=CN(C)C)n2S(=O)(=O)c1ccc(C)cc1] | T002 HCl | 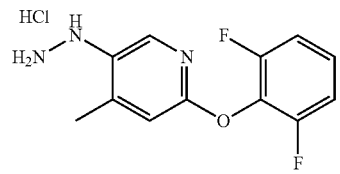 [SMILES: Cl ; Cc1cc(Oc2c(F)cccc2F)ncc1NN] |
| 5-1-344 | I-A004 | 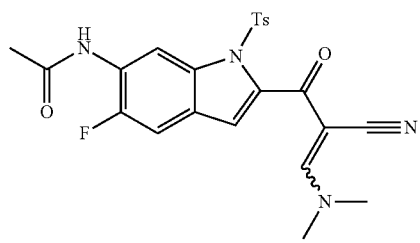 [SMILES: CC(=O)Nc1cc2c(cc1F)cc(C(=O)C(C#N)=CN(C)C)n2S(=O)(=O)c1ccc(C)cc1] | T002 HCl | 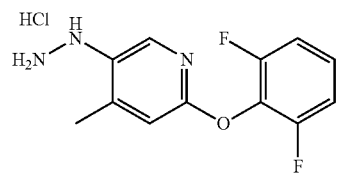 [SMILES: Cl ; Cc1cc(Oc2c(F)cccc2F)ncc1NN] |
| 5-1-345 | I-A004 | 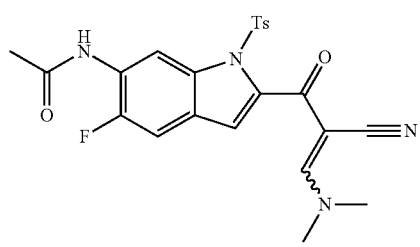 [SMILES: CC(=O)Nc1cc2c(cc1F)cc(C(=O)C(C#N)=CN(C)C)n2S(=O)(=O)c1ccc(C)cc1] | T002 HCl | 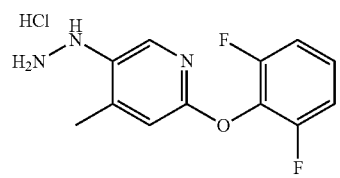 [SMILES: Cl ; Cc1cc(Oc2c(F)cccc2F)ncc1NN] |
| 5-1-356 | I-H057 | 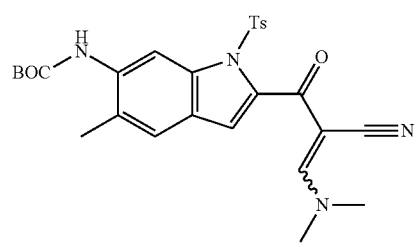 | Q001 HCl | 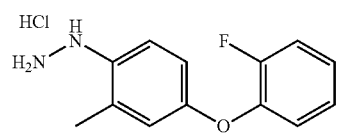 [SMILES: Cl ; Cc1cc(Oc2ccccc2F)ccc1NN] |
| 5-1-359 | I-H075 | 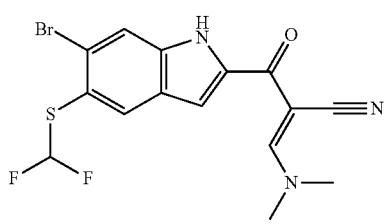 [SMILES: CN(C)/C=C(\C#N)C(=O)c1cc2cc(SC(F)F)c(Br)cc2[nH]1] | T001 HCl | 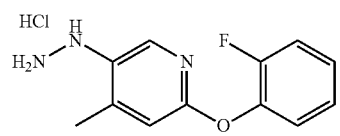 [SMILES: Cl ; Cc1cc(Oc2ccccc2F)ncc1NN] |
| 5-1-366 | I-H057 | 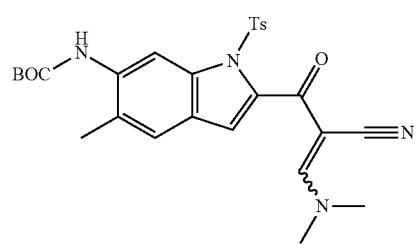 | T002 HCl | 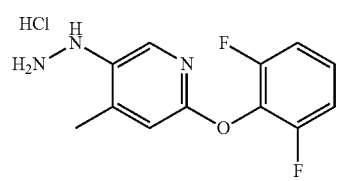 [SMILES: Cl ; Cc1cc(Oc2c(F)cccc2F)ncc1NN] |

-continued

| Example No. | | Enamine | Hydrazine | |
|---|---|---|---|---|
| 5-1-367 | I-H057 | | T002 HCl | |
| 5-1-368 | I-A004 | | T002 HCl | |
| 5-1-369 | I-A004 | | T002 HCl | |
| 5-1-370 | I-A004 | | T002 HCl | |
| 5-1-371 | I-H057 | | Q001 HCl | |
| 5-1-372 | I-H057 | | Q001 HCl | |

-continued

| Example No. | | Enamine | | Hydrazine |
|---|---|---|---|---|
| 5-1-373 | I-H057 | | Q001 HCl | |
| 5-1-374 | I-A004 | | Q001 HCl | |
| 5-1-375 | I-A004 | | Q001 HCl | |
| 5-1-376 | I-A004 | | Q001 HCl | |
| 5-1-377 | I-A011 | | T001 HCl | |
| 5-1-379 | I-A004 | | T001 HCl | |

-continued

| Example No. | | Enamine | | Hydrazine |
|---|---|---|---|---|
| 5-1-402 | B-B026 | (6-bromo-5-(difluoromethoxy)-1H-indol-2-yl with acrylonitrile-dimethylamino enamine) | T001 HCl | 5-hydrazinyl-2-(2-fluorophenoxy)-4-methylpyridine |
| 5-1-404 | I-H057 | (N-Boc-6-amino-5-methyl-1-Ts-indol-2-yl with acrylonitrile-dimethylamino enamine) | T002 HCl | 5-hydrazinyl-2-(2,6-difluorophenoxy)-4-methylpyridine |
| 5-1-405 | I-A004 | (6-acetamido-5-fluoro-1-Ts-indol-2-yl with acrylonitrile-dimethylamino enamine) | T002 HCl | 5-hydrazinyl-2-(2,6-difluorophenoxy)-4-methylpyridine |
| 5-1-406 | I-A004 | (6-acetamido-5-fluoro-1-Ts-indol-2-yl with acrylonitrile-dimethylamino enamine) | T002 HCl | 5-hydrazinyl-2-(2,6-difluorophenoxy)-4-methylpyridine |
| 5-1-407 | I-A004 | (6-acetamido-5-fluoro-1-Ts-indol-2-yl with acrylonitrile-dimethylamino enamine) | T002 HCl | 5-hydrazinyl-2-(2,6-difluorophenoxy)-4-methylpyridine |
| 5-1-408 | I-H057 | (N-Boc-6-amino-5-methyl-1-Ts-indol-2-yl with acrylonitrile-dimethylamino enamine) | Q001 HCl | 4-(2-fluorophenoxy)-3-methylphenylhydrazine |

-continued

| Example No. | | Enamine | Hydrazine | |
|---|---|---|---|---|
| 5-1-409 | I-H057 | | Q001 | HCl, 2-fluorophenoxy-methylphenyl hydrazine |
| 5-1-410 | I-H057 | | Q001 | HCl, 2-fluorophenoxy-methylphenyl hydrazine |
| 5-1-411 | I-A004 | | Q001 | HCl, 2-fluorophenoxy-methylphenyl hydrazine |
| 5-1-412 | I-A004 | | Q001 | HCl, 2-fluorophenoxy-methylphenyl hydrazine |
| 5-1-429 | I-H057 | | T002 | HCl, 2,6-difluorophenoxy-methylpyridyl hydrazine |
| 5-1-430 | I-A004 | | T002 | HCl, 2,6-difluorophenoxy-methylpyridyl hydrazine |

-continued

| Example No. | | Enamine | Hydrazine | |
|---|---|---|---|---|
| 5-1-431 | I-A004 | | T002 | HCl |
| 5-1-432 | I-A004 | | T002 | HCl |
| 5-1-433 | I-A004 | | T002 | HCl |
| 5-1-434 | I-H057 | | Q001 | HCl |
| 5-1-435 | I-H057 | | Q001 | HCl |
| 5-1-436 | I-A004 | | Q001 | HCl |

-continued

| Example No. | | Enamine | Hydrazine | |
|---|---|---|---|---|
| 5-1-437 | I-A004 | (structure) | Q001 HCl | (structure) |
| 5-1-438 | I-A004 | (structure) | Q001 HCl | (structure) |
| 5-1-442 | I-H057 | (structure) | T002 HCl | (structure) |
| 5-1-443 | I-H057 | (structure) | T002 HCl | (structure) |
| 5-1-444 | I-H057 | (structure) | Q001 HCl | (structure) |
| 5-1-445 | I-A004 | (structure) | Q001 HCl | (structure) |

-continued
| Example No. | | Enamine | Hydrazine |
|---|---|---|---|
| 5-1-446 | I-A004 | 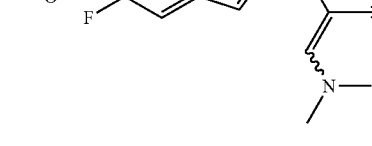 | Q001 HCl 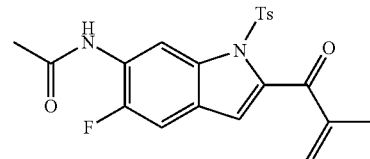 |
| 5-1-447 | I-A004 | 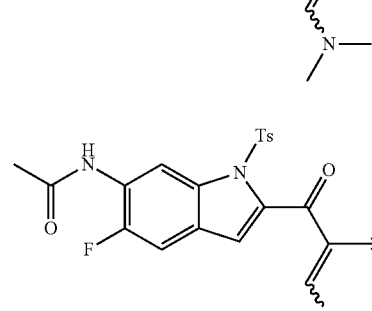 | Q001 HCl 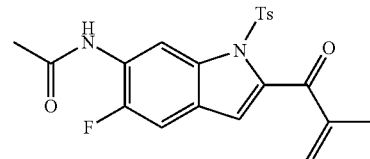 |
| 5-1-448 | I-A004 | 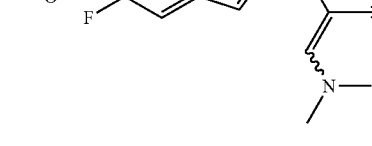 | Q001 HCl 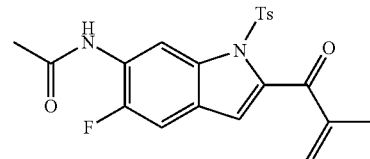 |
| 5-1-449 | I-A004 | 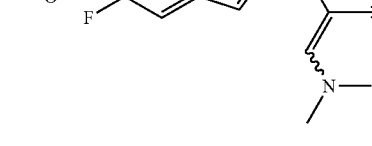 | Q001 HCl 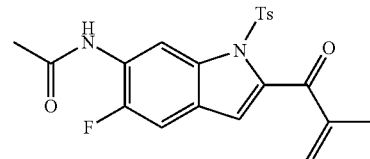 |
| 5-1-450 | I-A004 | 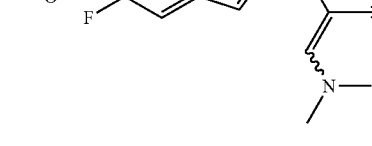 | Q001 HCl 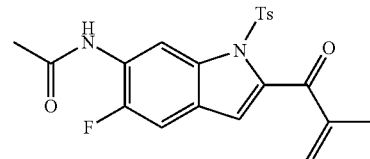 |
| 5-1-451 | I-H057 | 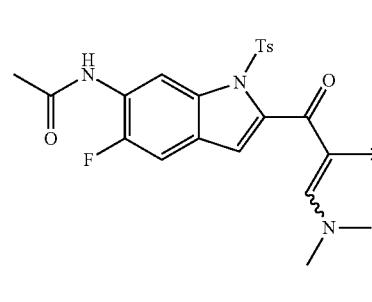 | T002 HCl 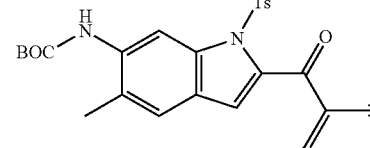 |

-continued

| Example No. | | Enamine | Hydrazine | |
|---|---|---|---|---|
| 5-1-452 | I-H057 | [structure: BOC-NH-indole(5-Me, N-Ts)-C(O)-C(CN)=CH-N(Me)2] | T002 HCl | [structure: H2N-NH-pyridine(4-Me)-O-(2,6-difluorophenyl)] |
| 5-1-453 | I-H057 | [structure: BOC-NH-indole(5-Me, N-Ts)-C(O)-C(CN)=CH-N(Me)2] | T002 HCl | [structure: H2N-NH-pyridine(4-Me)-O-(2,6-difluorophenyl)] |
| 5-1-454 | I-H057 | [structure: BOC-NH-indole(5-Me, N-Ts)-C(O)-C(CN)=CH-N(Me)2] | T002 HCl | [structure: H2N-NH-pyridine(4-Me)-O-(2,6-difluorophenyl)] |
| 5-1-455 | I-H057 | [structure: BOC-NH-indole(5-Me, N-Ts)-C(O)-C(CN)=CH-N(Me)2] | T002 HCl | [structure: H2N-NH-pyridine(4-Me)-O-(2,6-difluorophenyl)] |
| 5-1-456 | I-H057 | [structure: BOC-NH-indole(5-Me, N-Ts)-C(O)-C(CN)=CH-N(Me)2] | Q001 HCl | [structure: H2N-NH-phenyl(3-Me)-O-(2-fluorophenyl)] |
| 5-1-457 | I-H057 | [structure: BOC-NH-indole(5-Me, N-Ts)-C(O)-C(CN)=CH-N(Me)2] | Q001 HCl | [structure: H2N-NH-phenyl(3-Me)-O-(2-fluorophenyl)] |

-continued
| Example No. | | Enamine | Hydrazine | |
|---|---|---|---|---|
| 5-1-458 | I-H057 | 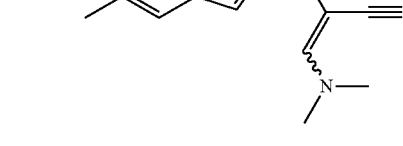 | Q001 HCl | 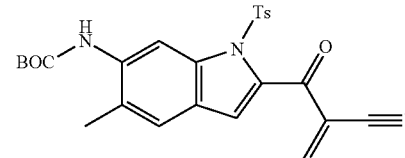 |
| 5-1-459 | I-H057 |  | Q001 HCl | 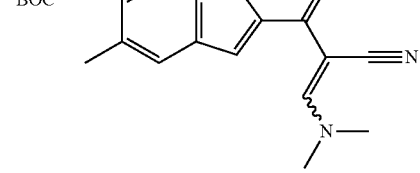 |
| 5-1-468 | I-H057 | 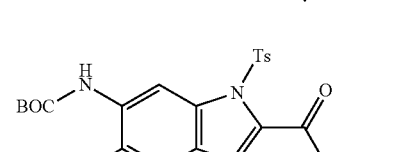 | Q019 HCl |  |
| 5-1-469 | I-H057 |  | Q019 HCl |  |
| 5-1-470 | I-H057 |  | Q019 HCl |  |
| 5-1-472 | I-H057 |  | Q019 HCl |  |

-continued

| Example No. | | Enamine | Hydrazine | |
|---|---|---|---|---|
| 5-1-469 | I-H057 | (structure) | Q019 HCl | (structure) |
| 5-1-470 | I-H057 | (structure) | Q019 HCl | (structure) |
| 5-1-472 | I-H057 | (structure) | Q-19 HCl | (structure) |
| 5-1-473 | I-H057 | (structure) | Q-19 HCl | (structure) |
| 5-1-474 | I-H057 | (structure) | Q019 HCl | (structure) |
| 5-1-475 | I-H057 | (structure) | Q-19 HCl | (structure) |

-continued

| Example No. | | Enamine | | Hydrazine |
|---|---|---|---|---|
| 5-1-476 | I-H057 | [structure: BOC-NH on methylindole with Ts group, bearing acyl group with CN and dimethylaminomethylene] | Q001 HCl | [structure: 4-(2-fluorophenoxy)-2-methylphenyl hydrazine·HCl] |
| 5-1-246 | I-A011 | [structure: 6-bromo-5-(2,2-difluoroethoxy)-1H-indole-2-yl with acyl CN dimethylaminomethylene] | Q001 HCl | [structure: 4-(2-fluorophenoxy)-2-methylphenyl hydrazine·HCl] |

(Synthesized Compounds)

| Example No. | Compound | m/z (M + H) | Retention Time (Minute) | LCMS Measurement Condition |
|---|---|---|---|---|
| 5-1-233 | [structure: hydantoin-substituted indole with 1-cyclobutylpiperidin-4-yloxy group, linked via carbonyl to 5-amino-1-(3-methyl-4-(2-fluorophenoxy)phenyl)pyrazol-4-yl] | 706 | 1.04 | AA Rev.11 |
| 5-1-114 | [structure: 5,5-dimethylhydantoin-substituted 5-fluoro-1H-indole-2-yl carbonyl linked to 5-amino-1-(6-(2,6-difluorophenoxy)-4-methylpyridin-3-yl)pyrazol-4-yl] | 590 | 1.18 | TFA Rev.5 |

-continued

| Example No. | Compound | m/z (M + H) | Retention Time (Minute) | LCMS Measurement Condition |
|---|---|---|---|---|
| 5-1-117 | | 638 | 1 | AA Rev.11 |
| 5-1-127 | | 571 | 1.22 | TFA Rev.5 |
| 5-1-164 | | 638 | 1.03 | AA Rev.11 |
| 5-1-170 | | 633 | 1.25 | TFA Rev.5 |

-continued
| Example No. | Compound | m/z (M + H) | Retention Time (Minute) | LCMS Measurement Condition |
|---|---|---|---|---|
| 5-1-179 | 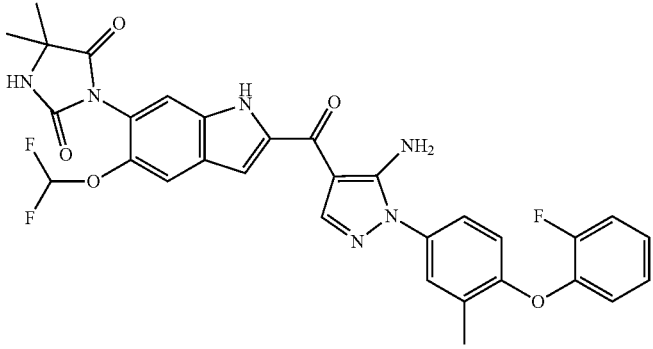 [SMILES: Cc1cc(-n2ncc(C(=O)c3cc4cc(OC(F)F)c(N5C(=O)NC(C)(C)C5=O)cc4[nH]3)c2N)ccc1Oc1ccccc1F] | 619 | 1.28 | TFA Rev.5 |
| 5-1-180 | 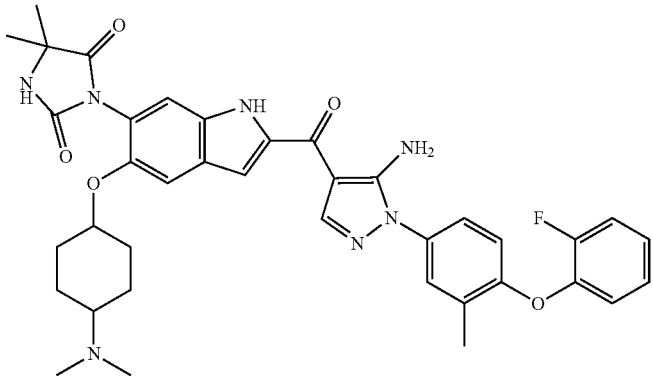 [SMILES: Cc1cc(-n2ncc(C(=O)c3cc4cc(OC5CCC(N(C)C)CC5)c(N5C(=O)NC(C)(C)C5=O)cc4[nH]3)c2N)ccc1Oc1ccccc1F] | 694 | 1.07 | TFA Rev.5 |
| 5-1-188 | 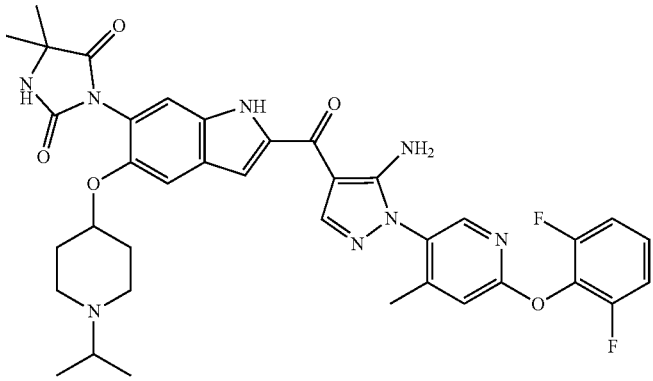 [SMILES: Cc1cc(Oc2c(F)cccc2F)ncc1-n1ncc(C(=O)c2cc3cc(OC4CCN(C(C)C)CC4)c(N4C(=O)NC(C)(C)C4=O)cc3[nH]2)c1N] | 713 | 1.01 | TFA Rev.5 |
| 5-1-193 | 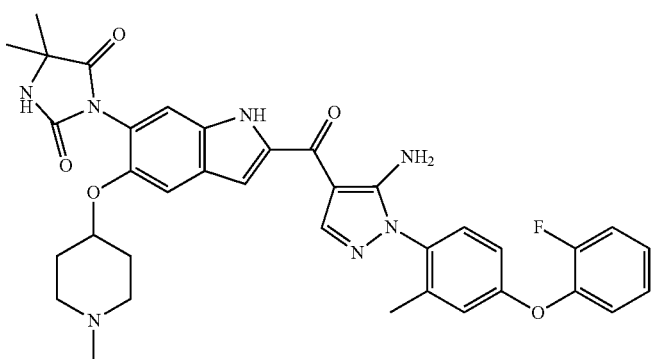 | 694 | 1.03 | TFA Rev.5 |

-continued

| Example No. | Compound | m/z (M + H) | Retention Time (Minute) | LCMS Measurement Condition |
|---|---|---|---|---|
| 5-1-243 | | 685 | 0.95 | AA Rev.11 |
| 5-1-250 | | 661 | 0.95 | AA Rev.11 |
| 5-1-251 | | 711 | 0.98 | AA Rev.11 |
| 5-1-252 | | 645 | 0.99 | AA Rev.11 |

| Example No. | Compound | m/z (M + H) | Retention Time (Minute) | LCMS Measurement Condition |
|---|---|---|---|---|
| 5-1-253 | 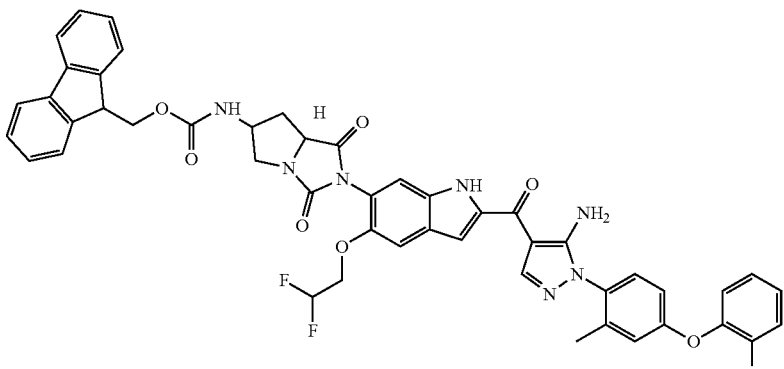 | 882 | 1.41 | TFA Rev.7 |
| 5-1-265 | 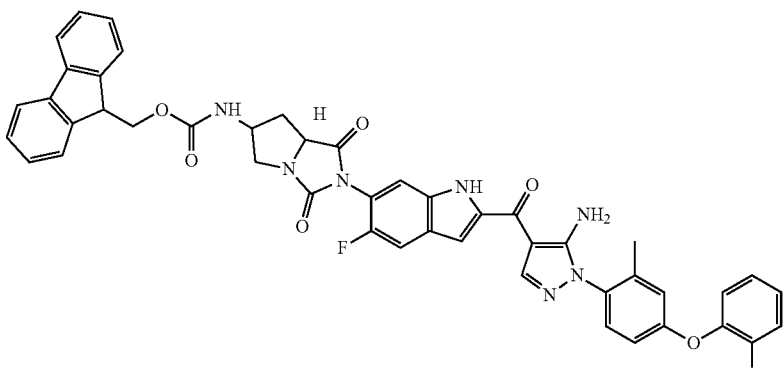 | 820 | 1.11 | AA Rev.11 |
| 5-1-268 | 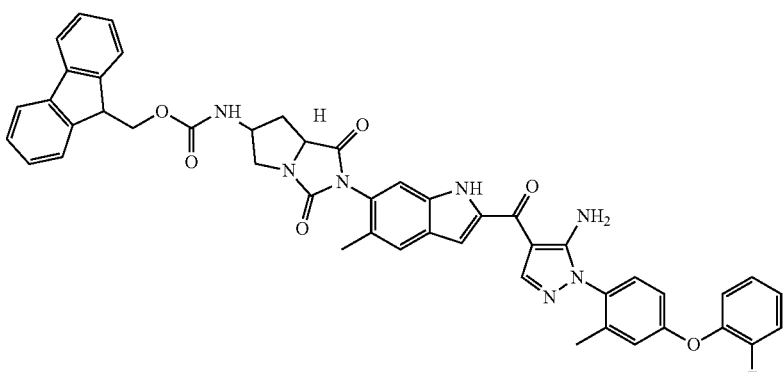 | 816 | 1.12 | AA Rev.11 |
| 5-1-270 | 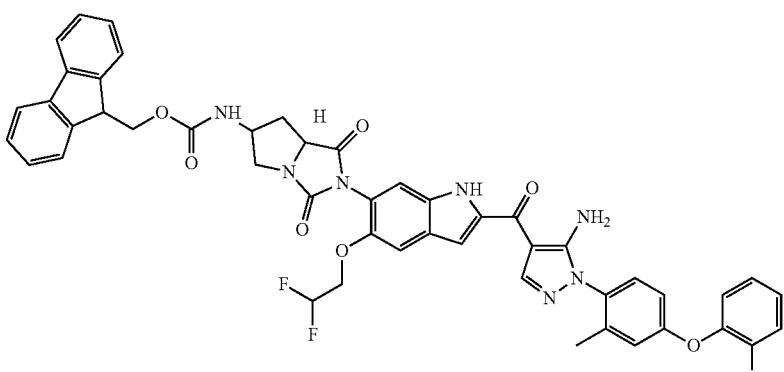 | 882 | 1.41 | TFA Rev.7 |

-continued

| Example No. | Compound | m/z (M + H) | Retention Time (Minute) | LCMS Measurement Condition |
|---|---|---|---|---|
| 5-1-286 | | 586 | 1.13 | TFA Rev.7 |
| 5-1-287 | | 680 | 0.96 | TFA Rev.7 |
| 5-1-293 | | 696 | 0.92 | TFA Rev.7 |

-continued

| Example No. | Compound | m/z (M + H) | Retention Time (Minute) | LCMS Measurement Condition |
|---|---|---|---|---|
| 5-1-294 | | 756 | 1.04 | TFA Rev.7 |
| 5-1-295 | | 708 | 0.99 | TFA Rev.7 |
| 5-1-312 | | 602 | 0.98 | AA Rev.11 |

-continued

| Example No. | Compound | m/z (M + H) | Retention Time (Minute) | LCMS Measurement Condition |
|---|---|---|---|---|
| 5-1-316 | | 626 | 1.24 | TFA Rev.7 |
| 5-1-324 | | 654 | 1.01 | AA Rev.11 |
| 5-1-334 | | 568 | 1.1 | TFA Rev.7 |
| 5-1-341 | | 598 | 0.99 | AA Rev.11 |

-continued

| Example No. | Compound | m/z (M + H) | Retention Time (Minute) | LCMS Measurement Condition |
|---|---|---|---|---|
| 5-1-342 | | 628 | 0.96 | AA Rev.11 |
| 5-1-343 | | 588 | 1.09 | TFA Rev.7 |
| 5-1-344 | | 616 | 1.18 | TFA Rev.7 |
| 5-1-345 | | 604 | 1.06 | TFA Rev.7 |

-continued

| Example No. | Compound | m/z (M + H) | Retention Time (Minute) | LCMS Measurement Condition |
|---|---|---|---|---|
| 5-1-356 | | 567 | 0.99 | AA Rev.11 |
| 5-1-359 | | 636 | 1.16 | TFA Rev.7 |
| 5-1-366 | | 584 | 1.1 | TFA Rev.7 |
| 5-1-367 | | 612 | 1.19 | TFA Rev.7 |

-continued
| Example No. | Compound | m/z (M + H) | Retention Time (Minute) | LCMS Measurement Condition |
|---|---|---|---|---|
| 5-1-368 | 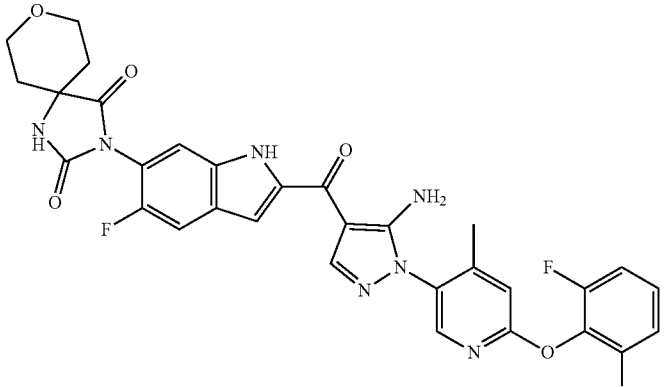 | 632 | 1.09 | TFA Rev.7 |
| 5-1-369 | 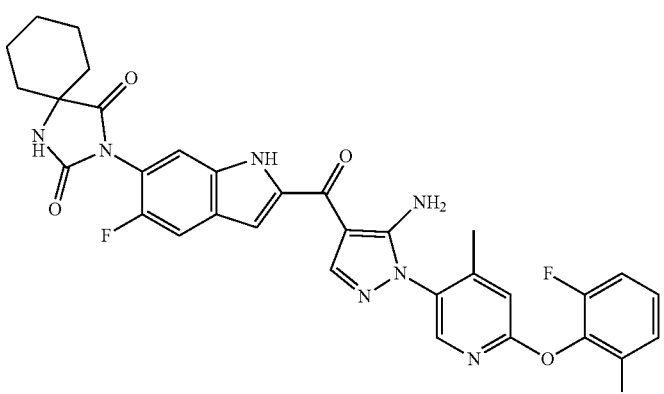 | 630 | 1.02 | AA Rev.11 |
| 5-1-370 | 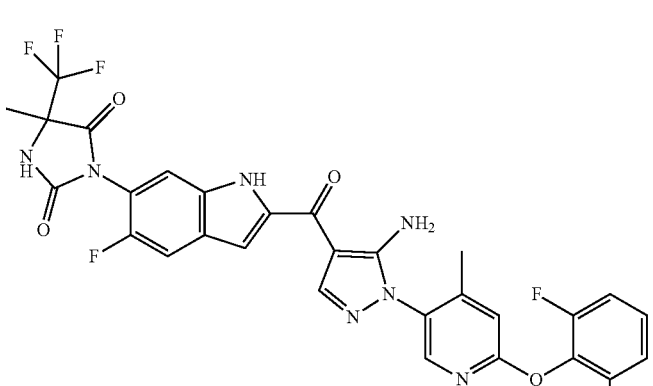 | 644 | 1.22 | TFA Rev.7 |

-continued

| Example No. | Compound | m/z (M + H) | Retention Time (Minute) | LCMS Measurement Condition |
|---|---|---|---|---|
| 5-1-371 | | 579 | 1.19 | TFA Rev.7 |
| 5-1-372 | | 565 | 1.13 | TFA Rev.7 |
| 5-1-373 | | 593 | 1.22 | TFA Rev.7 |
| 5-1-374 | | 583 | 1 | AA Rev.11 |

-continued

| Example No. | Compound | m/z (M + H) | Retention Time (Minute) | LCMS Measurement Condition |
|---|---|---|---|---|
| 5-1-375 | | 569 | 0.98 | AA Rev.11 |
| 5-1-376 | | 585 | 0.96 | AA Rev.11 |
| 5-1-377 | | 634 | 1.1 | TFA Rev.7 |
| 5-1-379 | | 572 | 1.09 | TFA Rev.7 |

-continued

| Example No. | Compound | m/z (M + H) | Retention Time (Minute) | LCMS Measurement Condition |
|---|---|---|---|---|
| 5-1-402 | | 620 | 0.96 | AA Rev.11 |
| 5-1-404 | | 600 | 0.94 | AA Rev.11 |
| 5-1-405 | | 562 | 1.04 | TFA Rev.7 |
| 5-1-406 | | 576 | 0.94 | AA Rev.11 |

-continued

| Example No. | Compound | m/z (M + H) | Retention Time (Minute) | LCMS Measurement Condition |
|---|---|---|---|---|
| 5-1-407 | | 592 | 0.9 | AA Rev.11 |
| 5-1-408 | | 609 | 1.13 | TFA Rev.7 |
| 5-1-409 | | 607 | 1.27 | TFA Rev.7 |

-continued

| Example No. | Compound | m/z (M + H) | Retention Time (Minute) | LCMS Measurement Condition |
| --- | --- | --- | --- | --- |
| 5-1-410 | | 581 | 1.11 | TFA Rev.7 |
| 5-1-411 | | 557 | 0.97 | AA Rev.11 |
| 5-1-412 | | 625 | 1.25 | TFA Rev.7 |
| 5-1-429 | | 640 | 1.03 | AA Rev.11 |

-continued

| Example No. | Compound | m/z (M + H) | Retention Time (Minute) | LCMS Measurement Condition |
| --- | --- | --- | --- | --- |
| 5-1-430 | | 652 | 1.21 | TFA Rev.7 |
| 5-1-431 | | 604 | 1.17 | TFA Rev.7 |
| 5-1-432 | | 602 | 1.17 | TFA Rev.7 |
| 5-1-433 | | 618 | 1.06 | TFA Rev.7 |

-continued

| Example No. | Compound | m/z (M + H) | Retention Time (Minute) | LCMS Measurement Condition |
|---|---|---|---|---|
| 5-1-434 | | 539 | 1.08 | TFA Rev.7 |
| 5-1-435 | | 621 | 1.05 | AA Rev.11 |
| 5-1-436 | | 633 | 1.03 | AA Rev.11 |
| 5-1-437 | | 613 | 1.13 | TFA Rev.7 |

-continued

| Example No. | Compound | m/z (M + H) | Retention Time (Minute) | LCMS Measurement Condition |
|---|---|---|---|---|
| 5-1-438 | | 597 | 1.21 | TFA Rev.7 |
| 5-1-442 | | 558 | 0.95 | AA Rev.11 |
| 5-1-443 | | 572 | 1.09 | TFA Rev.7 |
| 5-1-444 | | 553 | 1.13 | TFA Rev.7 |

| Example No. | Compound | m/z (M + H) | Retention Time (Minute) | LCMS Measurement Condition |
|---|---|---|---|---|
| 5-1-445 | | 543 | 0.97 | AA Rev.11 |
| 5-1-446 | | 573 | 0.95 | AA Rev.11 |
| 5-1-447 | | 585 | 1.03 | AA Rev.11 |
| 5-1-448 | | 583 | 1.01 | AA Rev.11 |

-continued

| Example No. | Compound | m/z (M + H) | Retention Time (Minute) | LCMS Measurement Condition |
|---|---|---|---|---|
| 5-1-449 | | 599 | 0.98 | AA Rev.11 |
| 5-1-450 | | 611 | 1.26 | TFA Rev.7 |
| 5-1-451 | | 588 | 0.95 | AA Rev.11 |

-continued

| Example No. | Compound | m/z (M + H) | Retention Time (Minute) | LCMS Measurement Condition |
|---|---|---|---|---|
| 5-1-452 | | 648 | 1.04 | AA Rev.11 |
| 5-1-453 | | 600 | 1.03 | AA Rev.11 |
| 5-1-454 | | 598 | 1.17 | TFA Rev.7 |
| 5-1-455 | | 614 | 1.06 | TFA Rev.7 |

-continued
| Example No. | Compound | m/z (M + H) | Retention Time (Minute) | LCMS Measurement Condition |
| --- | --- | --- | --- | --- |
| 5-1-456 |  | 569 | 1.02 | TFA Rev.7 |
| 5-1-457 | 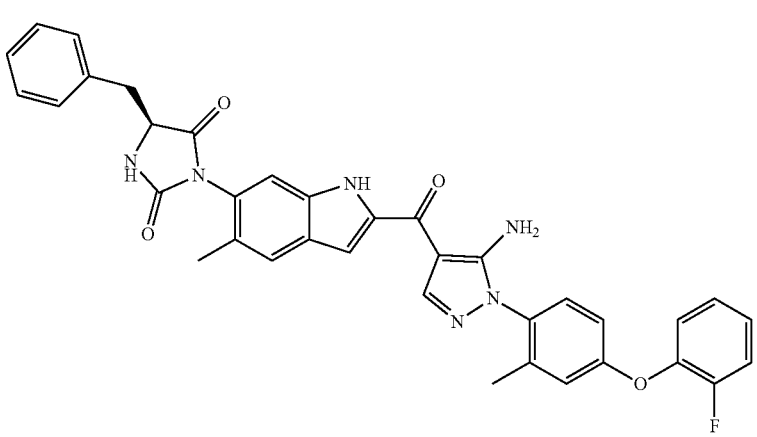 | 629 | 1.26 | TFA Rev.7 |
| 5-1-458 | 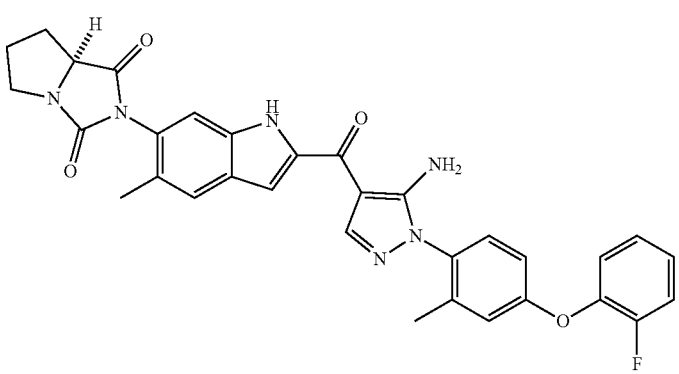 [SMILES: Cc1cc(Oc2ccccc2F)ccc1-n1ncc(C(=O)c2cc3cc(F)c(N4C(=O)[C@@H]5CCCN5C4=O)cc3[nH]2)c1N] | 579 | 1.21 | TFA Rev.7 |
| 5-1-459 | 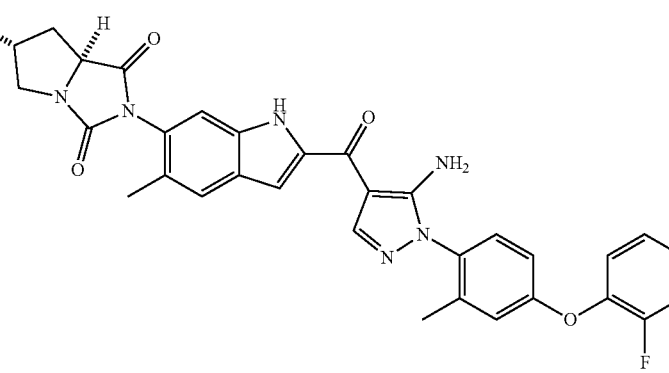 | 595 | 1.1 | TFA Rev.7 |

-continued

| Example No. | Compound | m/z (M + H) | Retention Time (Minute) | LCMS Measurement Condition |
| --- | --- | --- | --- | --- |
| 5-1-468 | | 579 | 1.24 | TFA Rev.7 |
| 5-1-469 | | 609 | 1.18 | TFA Rev.7 |
| 5-1-470 | | 607 | 1.08 | AA Rev.11 |
| 5-1-472 | | 621 | 1.33 | TFA Rev.7 |

-continued

| Example No. | Compound | m/z (M + H) | Retention Time (Minute) | LCMS Measurement Condition |
|---|---|---|---|---|
| 5-1-473 | | 565 | 1.03 | AA Rev.11 |
| 5-1-474 | | 593 | 1.27 | TFA Rev.7 |
| 5-1-475 | | 581 | 1.16 | TFA Rev.7 |
| 5-1-476 | | 581 | 1.23 | TFA Rev.7 |

| Example No. | Compound | m/z (M + H) | Retention Time (Minute) | LCMS Measurement Condition |
|---|---|---|---|---|
| 5-1-246 | | 717 | 1.00 | AA Rev.11 |

Example 4-23-036

Synthesis of 3-{2-{5-amino-1-[6-(2,6-difluorophenoxy)-4-methylpyridin-3-yl]pyrazole-4-carbonyl}-5-(2,2-difluoroethoxy)-1H-indol-6-yl}-5,5-dimethyl-2-sulfanylideneimidazolidin-4-one

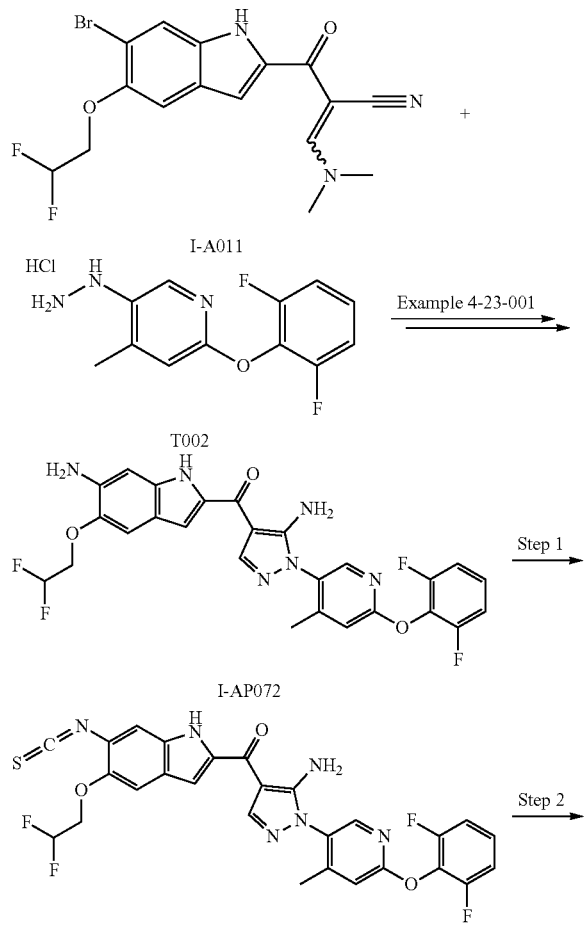

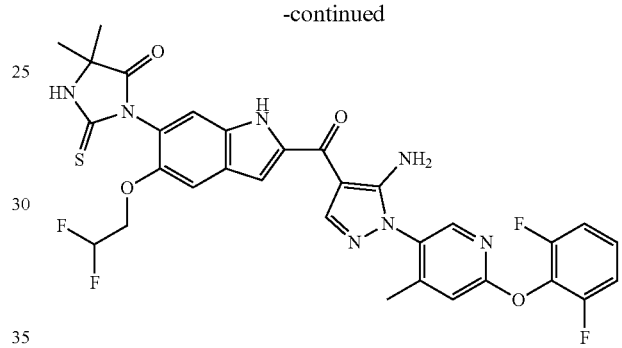

Step 1

Synthesis of {5-amino-1-[6-(2,6-difluorophenoxy)-4-methylpyridin-3-yl]pyrazol-4-yl}-[5-(2,2-difluoroethoxy)-6-isothiocyanato-1H-indol-2-yl]methanone Aniline I-AP072 synthesized in Example 4-23-001 (91 mg) was suspended in dichloromethane (4.0 mL) and water (4.0 mL), thiophosgene (23 mg) was added, and the mixture was stirred at 25° C. for one hour. Water (30 mL) was added to the reaction solution, the mixture was extracted with dichloromethane (70 mL), and the organic layer was dried over sodium sulfate. The drying agent was removed by filtration and the filtrate was then concentrated under reduced pressure. The resulting residue was used as such for the next reaction without purification.

Step 2

Synthesis of 3-{2-{5-amino-1-[6-(2,6-difluorophenoxy)-4-methylpyridin-3-yl]pyrazole-4-carbonyl}-5-(2,2-difluoroethoxy)-1H-indol-6-yl}-5,5-dimethyl-2-sulfanylideneimidazolidin-4-one {5-Amino-1-[6-(2,6-difluorophenoxy)-4-methylpyridin-3-yl]pyrazol-4-yl}-[5-(2,2-difluoroethoxy)-6-isothiocyanato-1H-indol-2-yl]methanone (98 mg) was dissolved in tetrahydrofuran (1.7 mL), methyl α-amino-isobutyrate hydrochloride (34 mg) and TEA (61 µL) were added, and the mixture was stirred at 60° C. for three hours. After cooling the reaction solution to 25° C., water (30 mL) was added and the mixture was extracted with ethyl acetate (50 mL). The organic layer was dried over sodium sulfate. After removing drying agent by filtration, the filtrate was concentrated under reduced pressure, and the resulting residue was purified by Prep-HPLC to give the target compound (28 mg).

Examples 4-23-037 to 4-23-039, Example 5-1-115, and the Like

The compounds of Examples 4-23-037 to 4-23-039, Example 5-1-115, and the like were synthesized from corresponding enamines and hydrazines by the similar method as in Example 4-23-036.

(Corresponding Enamines and Hydrazines)

| Example No. | | Enamine | | Hydrazine |
|---|---|---|---|---|
| 4-23-036 | I-A011 | | T002 | HCl |
| 4-23-037 | I-A011 | | Q001 | HCl |
| 4-23-038 | B-B026 | | T002 | HCl |
| 4-23-039 | B-B026 | | Q001 | HCl |
| 5-1-115 | I-A004 | | T002 | HCl |

-continued

| Example No. | | Enamine | | Hydrazine |
|---|---|---|---|---|
| 5-1-120 | I-A010 | (structure) | Q001 HCl | (structure) |
| 5-1-126 | I-A004 | (structure) | Q001 HCl | (structure) |

(Synthesized Compounds)

| Example No. | Compound | m/z (M + H) | Retention Time (Minute) | LCMS Measurement Condition |
|---|---|---|---|---|
| 4-23-036 | (structure) | 668 | 0.98 | J4 |
| 4-23-037 | (structure) | 649 | 1.01 | J1 |

-continued
| Example No. | Compound | m/z (M + H) | Retention Time (Minute) | LCMS Measurement Condition |
|---|---|---|---|---|
| 4-23-038 | 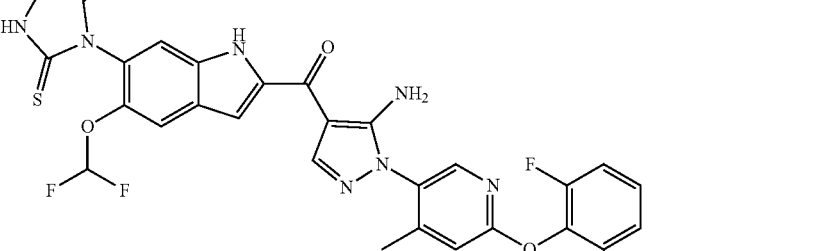 | 654 | 0.98 | J4 |
| 4-23-039 | 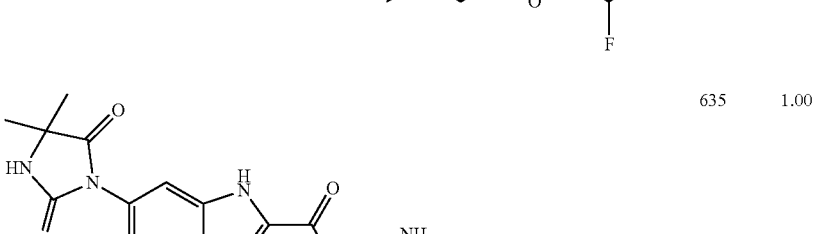 | 635 | 1.00 | J4 |
| 5-1-115 | 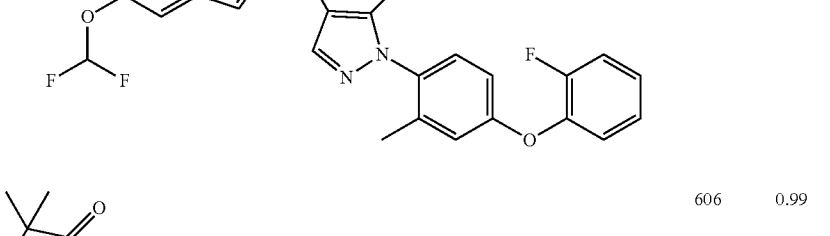 | 606 | 0.99 | AA Rev.11 |
| 5-1-120 | 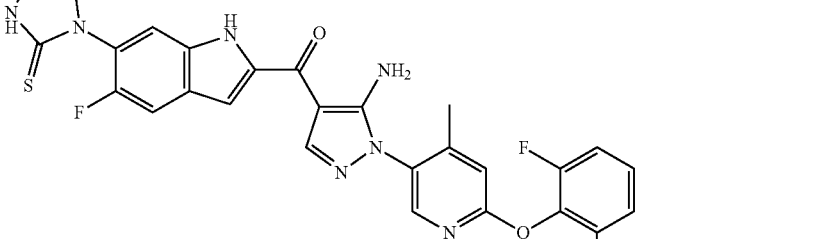 | 654 | 1.03 | AA Rev.11 |

| Example No. Compound | m/z (M + H) | Retention Time (Minute) | LCMS Measurement Condition |
|---|---|---|---|
| 5-1-126 | 587 | 1.02 | AA Rev.11 |

Example 4-24-001

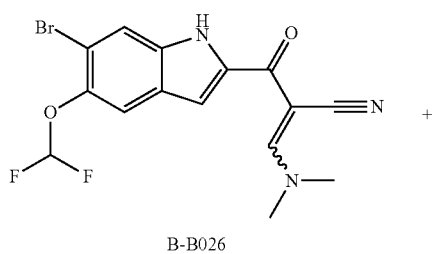

B-B026

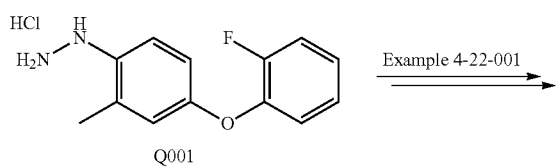

Q001

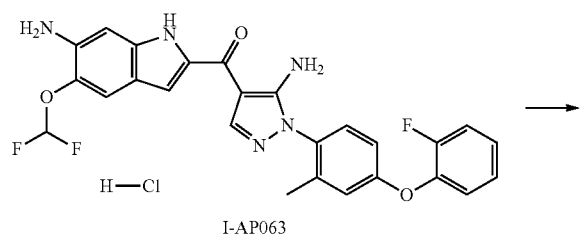

I-AP063

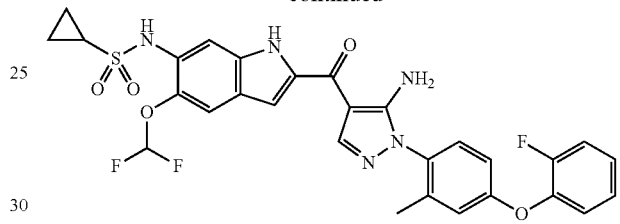

Aniline I-AP063 synthesized in Example 4-22-001 (70 mg) and cyclopropanesulfonyl chloride (0.018 mL) were added to pyridine (0.6 mL) at 0° C. and the mixture was stirred at 25° C. for three hours. The reaction solution was diluted with ethyl acetate (5 mL), washed with 1 M hydrochloric acid (5 mL) and saturated saline (5 mL) and then dried over magnesium sulfate. The drying agent was removed by filtration, the filtrate was concentrated, and the resulting residue was then crystallized from ethanol/t-butyl methyl ether (1/5, 10 mL). The resulting solid was collected by filtration and then washed with hexane to give the target compound (37 mg).

Examples 4-24-002 to 4-24-035, Example 5-1-076, and the Like

The compounds of Examples 4-24-002 to 4-24-035, Example 5-1-076, and the like were synthesized by the similar method as in Example 4-24-001 using the corresponding enamines, hydrazines, and sulfonamidating reagents.

(Corresponding Enamines, Hydrazines, and Sulfonamidating Reagents)

| Example No. | | Enamine | Hydrazine | | Sulfonamidating Reagent |
|---|---|---|---|---|---|
| 4-24-001 | B-B026 | | Q001 | HCl | |
| 4-24-002 | B-B026 | | Q001 | HCl | |
| 4-24-003 | B-B026 | | Q001 | HCl | |
| 4-24-004 | B-B026 | | Q001 | HCl | |
| 4-24-005 | B-B026 | | S038 | HCl | |
| 4-24-006 | B-B026 | | S038 | HCl | |

-continued

| | | | | | |
|---|---|---|---|---|---|
| 4-24-007 | B-B026 | (6-bromo-5-(difluoromethoxy)-1H-indol-2-yl with acryloyl-CN-dimethylaminomethylene) | T001 HCl | 5-hydrazinyl-6-(2-fluorophenoxy)-4-methylpyridine | cyclopropanesulfonyl chloride |
| 4-24-008 | B-B026 | (6-bromo-5-(difluoromethoxy)-1H-indol-2-yl with acryloyl-CN-dimethylaminomethylene) | T001 HCl | 5-hydrazinyl-6-(2-fluorophenoxy)-4-methylpyridine | methanesulfonyl chloride |
| 4-24-009 | B-B026 | (6-bromo-5-(difluoromethoxy)-1H-indol-2-yl with acryloyl-CN-dimethylaminomethylene) | T001 HCl | 5-hydrazinyl-6-(2-fluorophenoxy)-4-methylpyridine | 3-fluoropropane-1-sulfonyl chloride |
| 4-24-010 | B-B026 | (6-bromo-5-(difluoromethoxy)-1H-indol-2-yl with acryloyl-CN-dimethylaminomethylene) | T002 HCl | 5-hydrazinyl-6-(2,6-difluorophenoxy)-4-methylpyridine | cyclopropanesulfonyl chloride |
| 4-24-011 | B-B026 | (6-bromo-5-(difluoromethoxy)-1H-indol-2-yl with acryloyl-CN-dimethylaminomethylene) | T002 HCl | 5-hydrazinyl-6-(2,6-difluorophenoxy)-4-methylpyridine | methanesulfonyl chloride |
| 4-24-012 | B-B026 | (6-bromo-5-(difluoromethoxy)-1H-indol-2-yl with acryloyl-CN-dimethylaminomethylene) | T002 HCl | 5-hydrazinyl-6-(2,6-difluorophenoxy)-4-methylpyridine | 3-fluoropropane-1-sulfonyl chloride |
| 4-24-013 | I-A010 | (6-bromo-5-morpholino-1H-indol-2-yl with acryloyl-CN-dimethylaminomethylene) | Q001 HCl | 4-hydrazinyl-2-methyl-1-(2-fluorophenoxy)benzene | methanesulfonyl chloride |

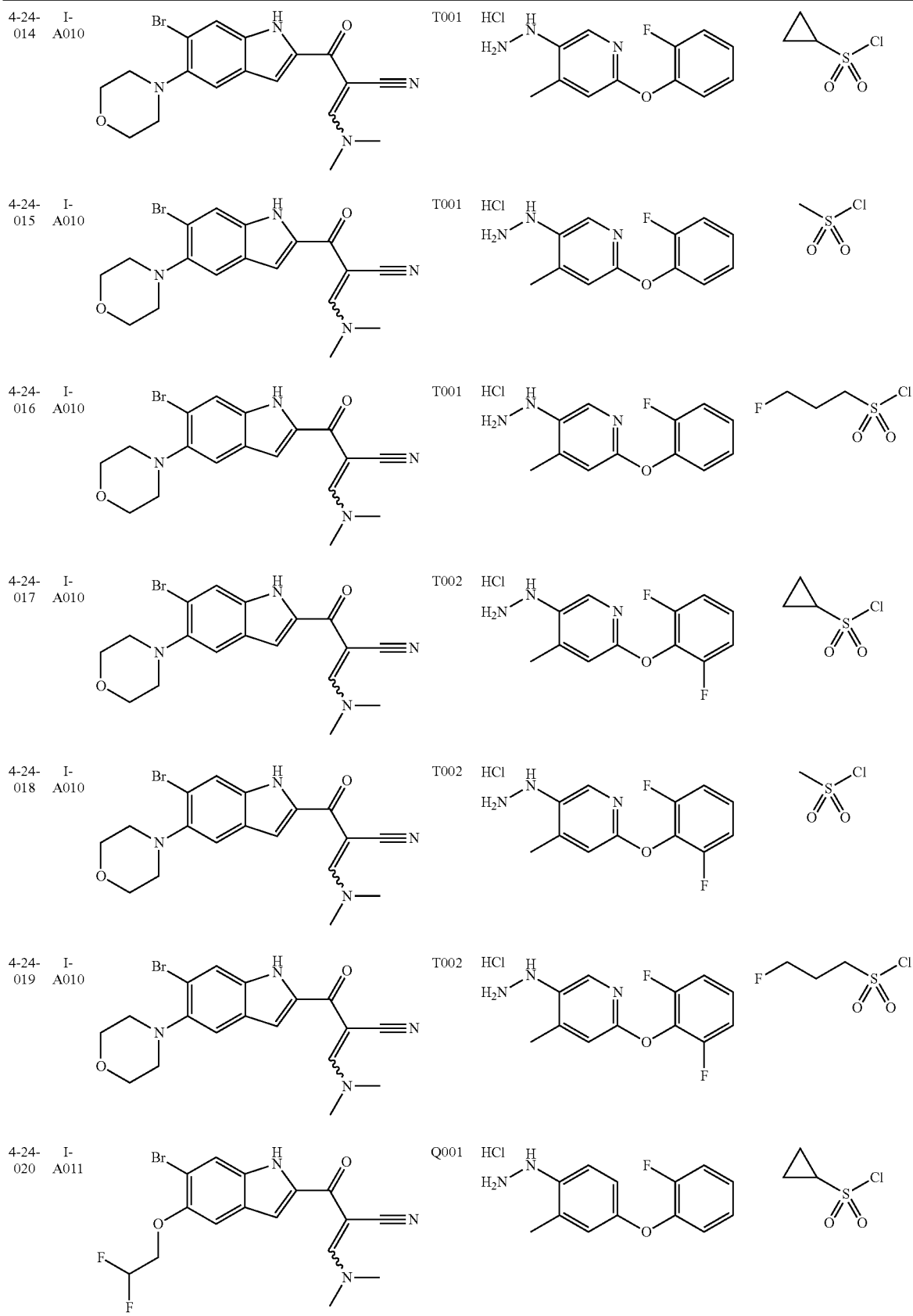

| | | | | | |
|---|---|---|---|---|---|
| 4-24-021 | I-A011 | (6-bromo-5-(2,2-difluoroethoxy)-1H-indol-2-yl) with acyl cyanide dimethylaminomethylene | Q001 HCl | H₂N-NH-(4-(2-fluorophenoxy)-2-methylphenyl) | methanesulfonyl chloride |
| 4-24-022 | I-A011 | (6-bromo-5-(2,2-difluoroethoxy)-1H-indol-2-yl) with acyl cyanide dimethylaminomethylene | Q001 HCl | H₂N-NH-(4-(2-fluorophenoxy)-2-methylphenyl) | 3-fluoropropane-1-sulfonyl chloride |
| 4-24-023 | I-A011 | (6-bromo-5-(2,2-difluoroethoxy)-1H-indol-2-yl) with acyl cyanide dimethylaminomethylene | Q001 HCl | H₂N-NH-(4-(2-fluorophenoxy)-2-methylphenyl) | 3,3-difluoropropane-1-sulfonyl chloride |
| 4-24-024 | I-A011 | (6-bromo-5-(2,2-difluoroethoxy)-1H-indol-2-yl) with acyl cyanide dimethylaminomethylene | S038 HCl | H₂N-NH-(2-fluoro-4-(2-fluorophenoxy)-6-methylphenyl) | cyclopropanesulfonyl chloride |
| 4-24-025 | I-A011 | (6-bromo-5-(2,2-difluoroethoxy)-1H-indol-2-yl) with acyl cyanide dimethylaminomethylene | S038 HCl | H₂N-NH-(2-fluoro-4-(2-fluorophenoxy)-6-methylphenyl) | methanesulfonyl chloride |
| 4-24-026 | I-A011 | (6-bromo-5-(2,2-difluoroethoxy)-1H-indol-2-yl) with acyl cyanide dimethylaminomethylene | S038 HCl | H₂N-NH-(2-fluoro-4-(2-fluorophenoxy)-6-methylphenyl) | 3-fluoropropane-1-sulfonyl chloride |
| 4-24-027 | I-A011 | (6-bromo-5-(2,2-difluoroethoxy)-1H-indol-2-yl) with acyl cyanide dimethylaminomethylene | T001 HCl | H₂N-NH-(6-(2-fluorophenoxy)-4-methylpyridin-3-yl) | cyclopropanesulfonyl chloride |

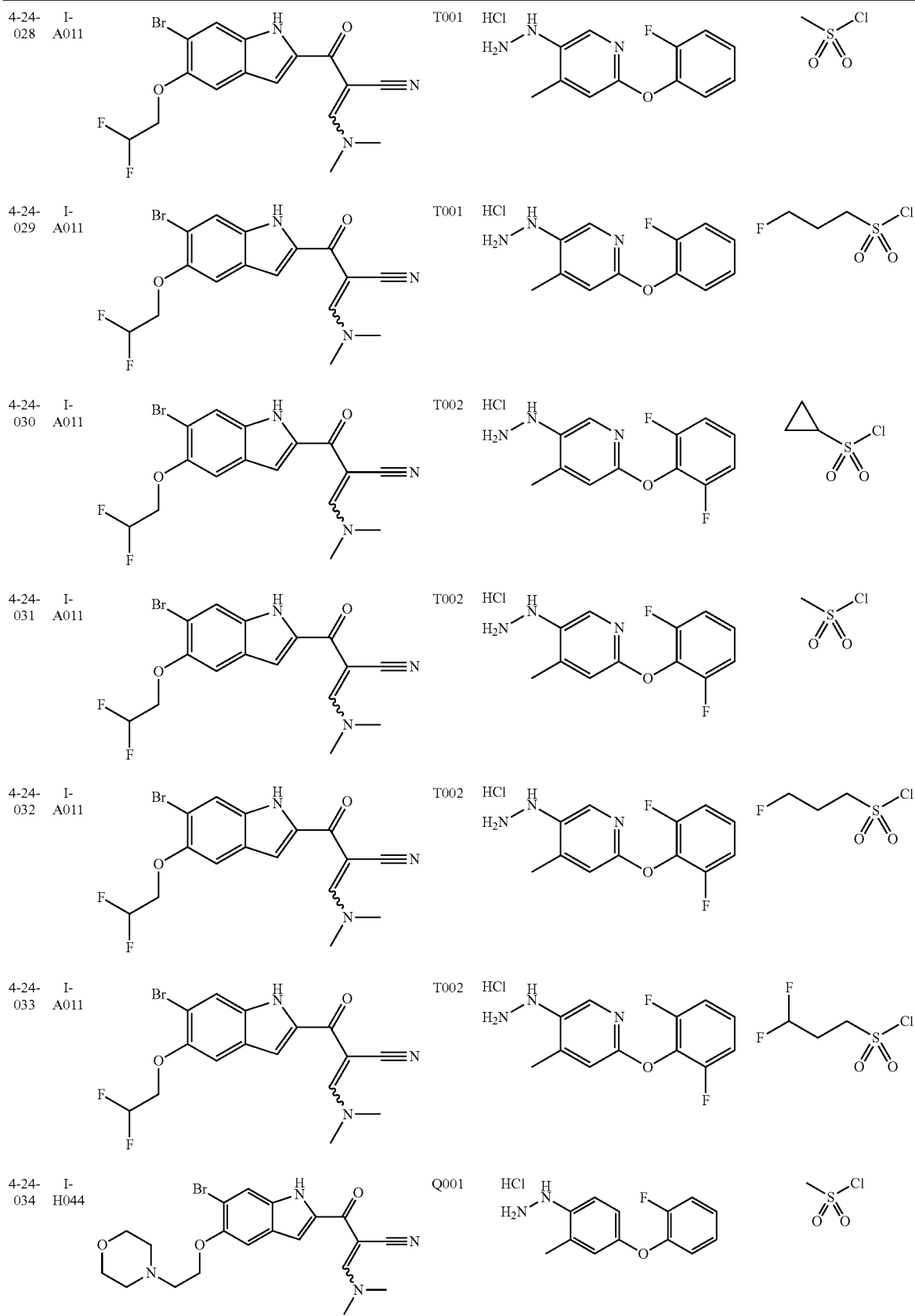

-continued
| | | | | | | |
|---|---|---|---|---|---|---|
| 4-24-035 | I-H068 | 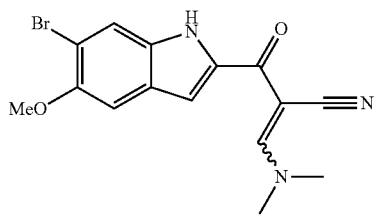 [SMILES: COc1cc2cc(C(=O)C(C#N)=CN(C)C)[nH]c2cc1Br] | T002 | HCl | 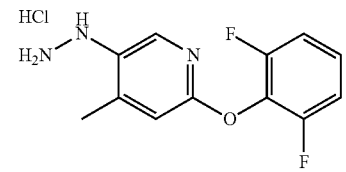 [SMILES: Cl ; Cc1cc(Oc2c(F)cccc2F)ncc1NN] | 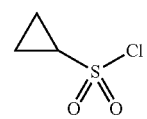 |
| Example No. | | Enamine | | | Hydrazine | Chloride Reagent |
|---|---|---|---|---|---|---|
| 5-1-076 | B-B026 | 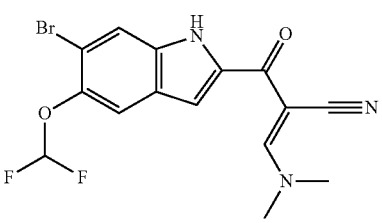 | S038 | HCl | 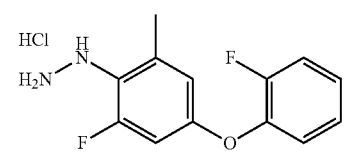 [SMILES: Cl ; Cc1cc(Oc2ccccc2F)cc(F)c1NN] |  |
| 5-1-157 | I-A010 | 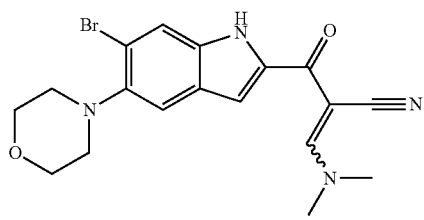 [SMILES: CN(C)C=C(C#N)C(=O)c1cc2cc(N3CCOCC3)c(Br)cc2[nH]1] | Q019 | HCl | 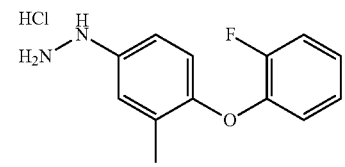 [SMILES: Cl ; Cc1cc(NN)ccc1Oc1ccccc1F] |  |
| 5-1-166 | I-A011 | 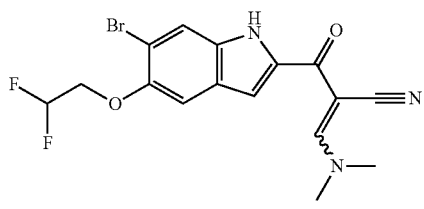 [SMILES: CN(C)C=C(C#N)C(=O)c1cc2cc(OCC(F)F)c(Br)cc2[nH]1] | Q019 | HCl | 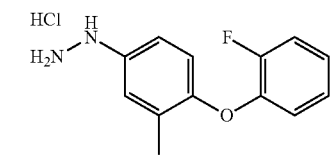 [SMILES: Cl ; Cc1cc(NN)ccc1Oc1ccccc1F] |  |
| 5-1-167 | B-B026 | 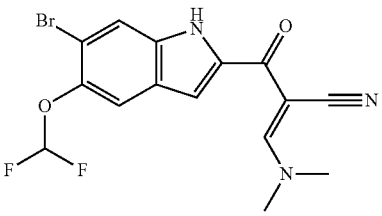 [SMILES: CN(C)/C=C(\C#N)C(=O)c1cc2cc(OC(F)F)c(Br)cc2[nH]1] | Q019 | HCl | 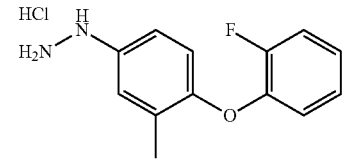 [SMILES: Cl ; Cc1cc(NN)ccc1Oc1ccccc1F] |  |
| 5-1-279 | I-A011 | 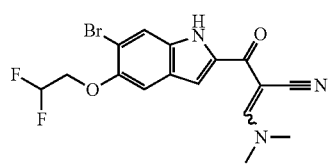 [SMILES: CN(C)C=C(C#N)C(=O)c1cc2cc(OCC(F)F)c(Br)cc2[nH]1] | Q001 | HCl | 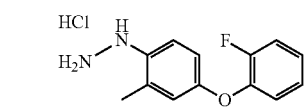 [SMILES: Cl ; Cc1cc(Oc2ccccc2F)ccc1NN] | 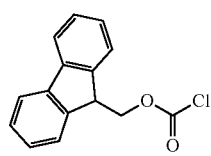 [SMILES: O=C(Cl)OCC1c2ccccc2-c2ccccc21] |

(Synthesized Compounds)

| Example No. | Compound | m/z (M + H) | Retention Time (Minute) | LCMS Measurement Condition |
|---|---|---|---|---|
| 4-24-001 | | 612 | 2.65 | B1 |
| 4-24-002 | | 586 | 2.53 | B1 |
| 4-24-003 | | 632 | 2.66 | B1 |
| 4-24-004 | | 650 | 1.00 | J4 |
| 4-24-005 | | 630 | 1.00 | J4 |

-continued

| Example No. | Compound | m/z (M + H) | Retention Time (Minute) | LCMS Measurement Condition |
|---|---|---|---|---|
| 4-24-006 | | 650 | 0.99 | J4 |
| 4-24-007 | | 613 | 0.80 | A1 |
| 4-24-008 | | 587 | 0.77 | A1 |
| 4-24-009 | | 633 | 0.80 | A1 |
| 4-24-010 | | 631 | 0.82 | A1 |

-continued

| Example No. | Compound | m/z (M + H) | Retention Time (Minute) | LCMS Measurement Condition |
|---|---|---|---|---|
| 4-24-011 | | 605 | 0.79 | A1 |
| 4-24-012 | | 651 | 0.82 | A1 |
| 4-24-013 | | 605 | 0.87 | A1 |
| 4-24-014 | | 632 | 0.86 | A1 |
| 4-24-015 | | 606 | 0.82 | A1 |

| Example No. | Compound | m/z (M + H) | Retention Time (Minute) | LCMS Measurement Condition |
|---|---|---|---|---|
| 4-24-016 | 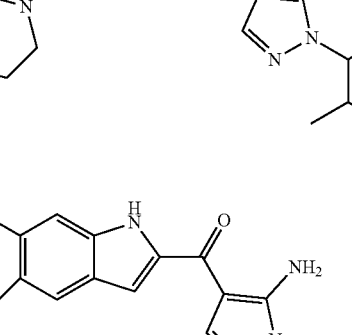 | 652 | 0.86 | A1 |
| 4-24-017 |  | 650 | 0.88 | A1 |
| 4-24-018 |  | 624 | 0.84 | A1 |
| 4-24-019 | 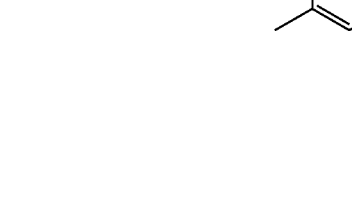 | 670 | 0.88 | A1 |
| 4-24-020 |  | 626 | 0.90 | A1 |

-continued

| Example No. | Compound | m/z (M + H) | Retention Time (Minute) | LCMS Measurement Condition |
|---|---|---|---|---|
| 4-24-021 | | 600 | 0.87 | A1 |
| 4-24-022 | | 646 | 0.90 | A1 |
| 4-24-023 | | 664 | 1.00 | J4 |
| 4-24-024 | | 644 | 1.02 | J4 |
| 4-24-025 | | 618 | 1.00 | J1 |

-continued

| Example No. | Compound | m/z (M + H) | Retention Time (Minute) | LCMS Measurement Condition |
|---|---|---|---|---|
| 4-24-026 | | 664 | 1.02 | J4 |
| 4-24-027 | | 627 | 0.86 | A1 |
| 4-24-028 | | 601 | 0.83 | A1 |
| 4-24-029 | | 647 | 0.86 | A1 |
| 4-24-030 | | 645 | 1.00 | J1 |

-continued

| Example No. | Compound | m/z (M + H) | Retention Time (Minute) | LCMS Measurement Condition |
|---|---|---|---|---|
| 4-24-031 | | 619 | 0.95 | J4 |
| 4-24-032 | | 665 | 1.00 | J1 |
| 4-24-033 | | 683 | 1.00 | J4 |
| 4-24-034 | | 649 | 1.85 | B1 |
| 4-24-035 | | 595 | 0.85 | A1 |

-continued

| Example No. | Compound | m/z (M + H) | Retention Time (Minute) | LCMS Measurement Condition |
|---|---|---|---|---|
| 5-1-076 | | 604 | 1.26 | TFA Rev. 5 |
| 5-1-157 | | 605 | 1.03 | AA Rev. 11 |
| 5-1-166 | | 600 | 1.31 | TFA Rev. 5 |
| 5-1-167 | | 586 | 1.31 | TFA Rev. 5 |

| Example No. | Compound | m/z (M + H) | Retention Time (Minute) | LCMS Measurement Condition |
|---|---|---|---|---|
| 5-1-279 | 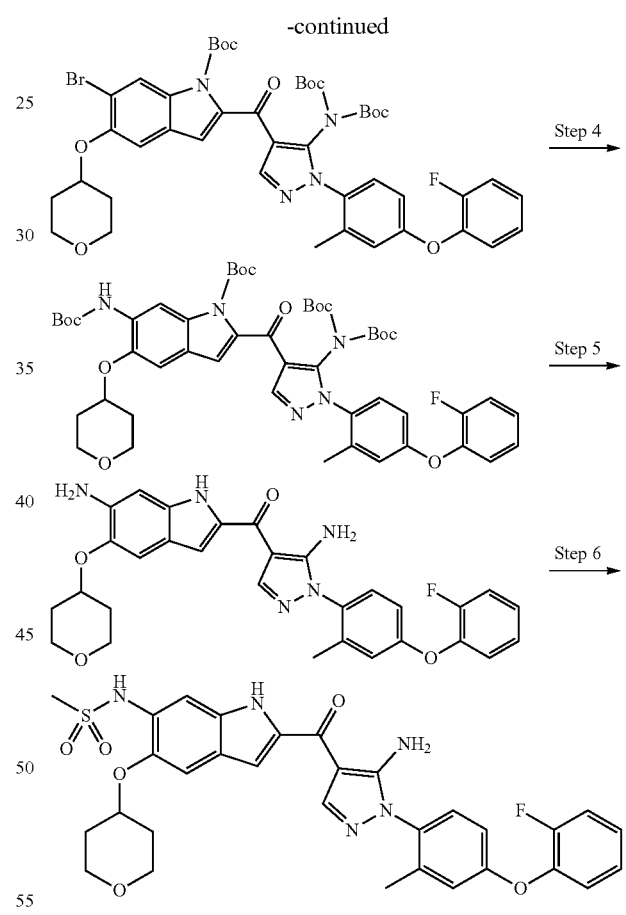 | 744 | 1.19 | AA Rev. 11 |

Example 4-24-036

Synthesis of N-{2-{5-amino-1-[4-(2-fluorophenoxy)-2-methylphenyl]pyrazole-4-carbonyl}-5-(oxan-4-yloxy)-1H-indol-6-yl}methanesulfonamide

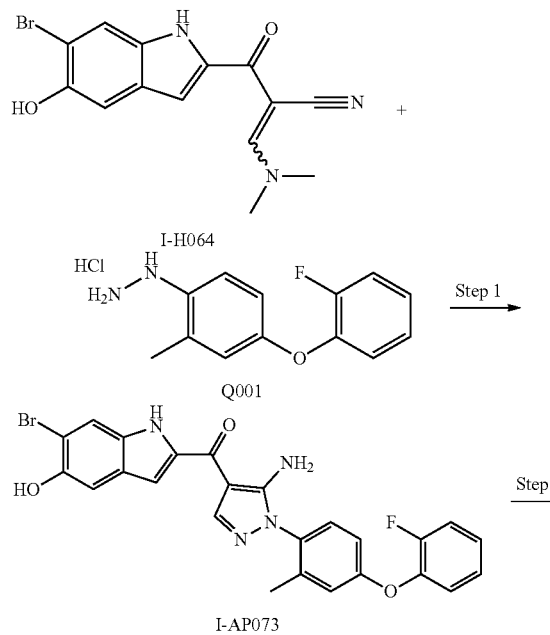

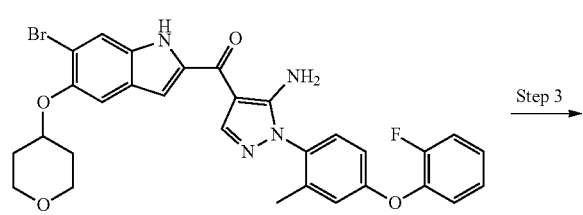

Step 1

Synthesis of {5-amino-1-[4-(2-fluorophenoxy)-2-methylphenyl]pyrazol-4-yl}-(6-bromo-5-hydroxy-1H-indol-2-yl)methanone (I-AP073)

Enamine I-H064 (50 mg) and hydrazine Q001 (60 mg) were dissolved in 1-methyl-2-pyrrolidone (1.5 mL), N-methylmorpholine (74 µL) was added, and the mixture was stirred at 100° C. for five hours. After cooling the reaction solution to 25° C., a 20% aqueous formic acid solution was added, the mixture was extracted with ethyl acetate, and the organic layer was dried over sodium sulfate. After removing the drying agent by filtration, the filtrate was then concentrated under reduced pressure, and the resulting residue was purified by Prep-HPLC to give the target compound (68 mg).
Step 2

Synthesis of {5-amino-1-[4-(2-fluorophenoxy)-2-methylphenyl]pyrazol-4-yl}-[6-bromo-5-(oxan-4-yloxy)-1H-indol-2-yl]methanone {5-Amino-1-[4-(2-fluorophenoxy)-2-methylphenyl]pyrazol-4-yl}-(6-bromo-5-hydroxy-1H-indol-2-yl)methanone (10 mg) was dissolved in tetrahydrofuran (0.2 mL), tetrahydro-2H-pyran-4-ol (2.4 mg), triphenylphosphine (6.0 mg), and diisopropyl azodicarboxylate (4.7 mg) were added, and the mixture was stirred at 25° C. for 72 hours. The reaction solution was purified by Prep-HPLC to give the target compound (5.5 mg).
Step 3

Synthesis of tert-butyl 2-{5-{bis[(2-methylpropan-2-yl)oxycarbonyl]amino}-1-[4-(2-fluorophenoxy)-2-methylphenyl]pyrazole-4-carbonyl}-6-bromo-5-(oxan-4-yloxy)indole-1-carboxylate {5-Amino-1-[4-(2-fluorophenoxy)-2-methylphenyl]pyrazol-4-yl}-[6-bromo-5-(oxan-4-yloxy)-1H-indol-2-yl]methanone (5.5 mg) was dissolved in dichloromethane (1.8 mL), Boc$_2$O (7.5 µL), DMAP (0.10 mg), and TEA (4.6 µL) were added, and the mixture was stirred at 25° C. for 15 hours. Water was added to the reaction solution, the mixture was extracted with ethyl acetate, and the organic layer was dried over sodium sulfate. After removing the drying agent by filtration, the filtrate was then concentrated under reduced pressure, and the resulting residue was purified by column chromatography (hexane/ethyl acetate) to give the target compound (4.6 mg).
Step 4

Synthesis of tert-butyl 2-{5-{bis[(2-methylpropan-2-yl)oxycarbonyl]amino}-1-[4-(2-fluorophenoxy)-2-methylphenyl]pyrazole-4-carbonyl}-6-[(2-methylpropan-2-yl)oxycarbonylamino]-5-(oxan-4-yloxy)indole-1-carboxylate tert-Butyl 2-{5-{bis[(2-methylpropan-2-yl)oxycarbonyl]amino}-1-[4-(2-fluorophenoxy)-2-methylphenyl]pyrazole-4-carbonyl}-6-bromo-5-(oxan-4-yloxy)indole-1-carboxylate (4.6 mg), tert-butyl carbamate (1.8 mg), Pd$_2$dba$_3$ (1.0 mg), X-Phos (1.5 mg), and cesium carbonate (10 mg) were dissolved in dioxane (1.0 mL), and the mixture was stirred at 100° C. for 3.5 hours in a nitrogen atmosphere. Water was added to the reaction solution, the mixture was extracted with ethyl acetate, and the organic layer was dried over sodium sulfate. After removing the drying agent by filtration, the filtrate was concentrated under reduced pressure. The resulting residue was used for the next reaction without purification.
Step 5

Synthesis of {5-amino-1-[4-(2-fluorophenoxy)-2-methylphenyl]pyrazol-4-yl}-[6-amino-5-(oxan-4-yloxy)-1H-indol-2-yl]methanone tert-Butyl 2-{5-{bis[(2-methylpropan-2-yl)oxy carbonyl]amino}-1-[4-(2-fluorophenoxy)-2-methylphenyl]pyrazole-4-carbonyl}-6-[(2-methylpropan-2-yl)oxycarbonylamino]-5-(oxan-4-yloxy)indole-1-carboxylate (5.0 mg) was dissolved in dichloromethane (1.0 mL), trifluoroacetic acid (250 µL) was added, and the mixture was stirred at 25° C. for five hours. The reaction solution was concentrated under reduced pressure, a saturated aqueous sodium bicarbonate solution was added to the resulting residue, the mixture was extracted with ethyl acetate, and the organic layer was dried over sodium sulfate. After removing the drying agent by filtration, the filtrate was then concentrated under reduced pressure. The resulting residue was used as such for the next reaction without purification.
Step 6

Synthesis of N-{2-{5-amino-1-[4-(2-fluorophenoxy)-2-methylphenyl]pyrazole-4-carbonyl}-5-(oxan-4-yloxy)-1H-indol-6-yl}methanesulfonamide {5-Amino-1-[4-(2-fluorophenoxy)-2-methylphenyl]pyrazol-4-yl}-[6-amino-5-(oxan-4-yloxy)-1H-indol-2-yl]methanone (2.8 mg) was dissolved in pyridine (0.5 mL), methanesulfonyl chloride (1.24) was added, and the mixture was stirred at 25° C. for 30 minutes. After adding water to the reaction solution, the mixture was extracted with ethyl acetate, and the organic layer was dried over sodium sulfate. After removing the drying agent by filtration, the filtrate was concentrated under reduced pressure, and the resulting residue was purified by Prep-HPLC to give the target compound (0.6 mg).

Example 4-24-037

Synthesis of N-{2-{5-amino-1-[4-(2-fluorophenoxy)-2-methylphenyl]pyrazole-4-carbonyl}-5-[2-(3,5-dimethyl-4-methylsulfonylpiperazin-1-yl)ethoxy]-1H-indol-6-yl}methanesulfonamide

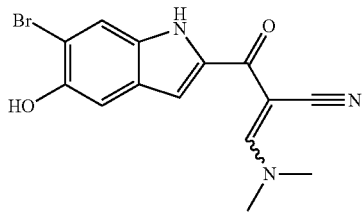

I-H064

+

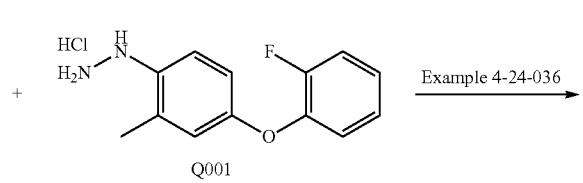

Q001

Example 4-24-036 →

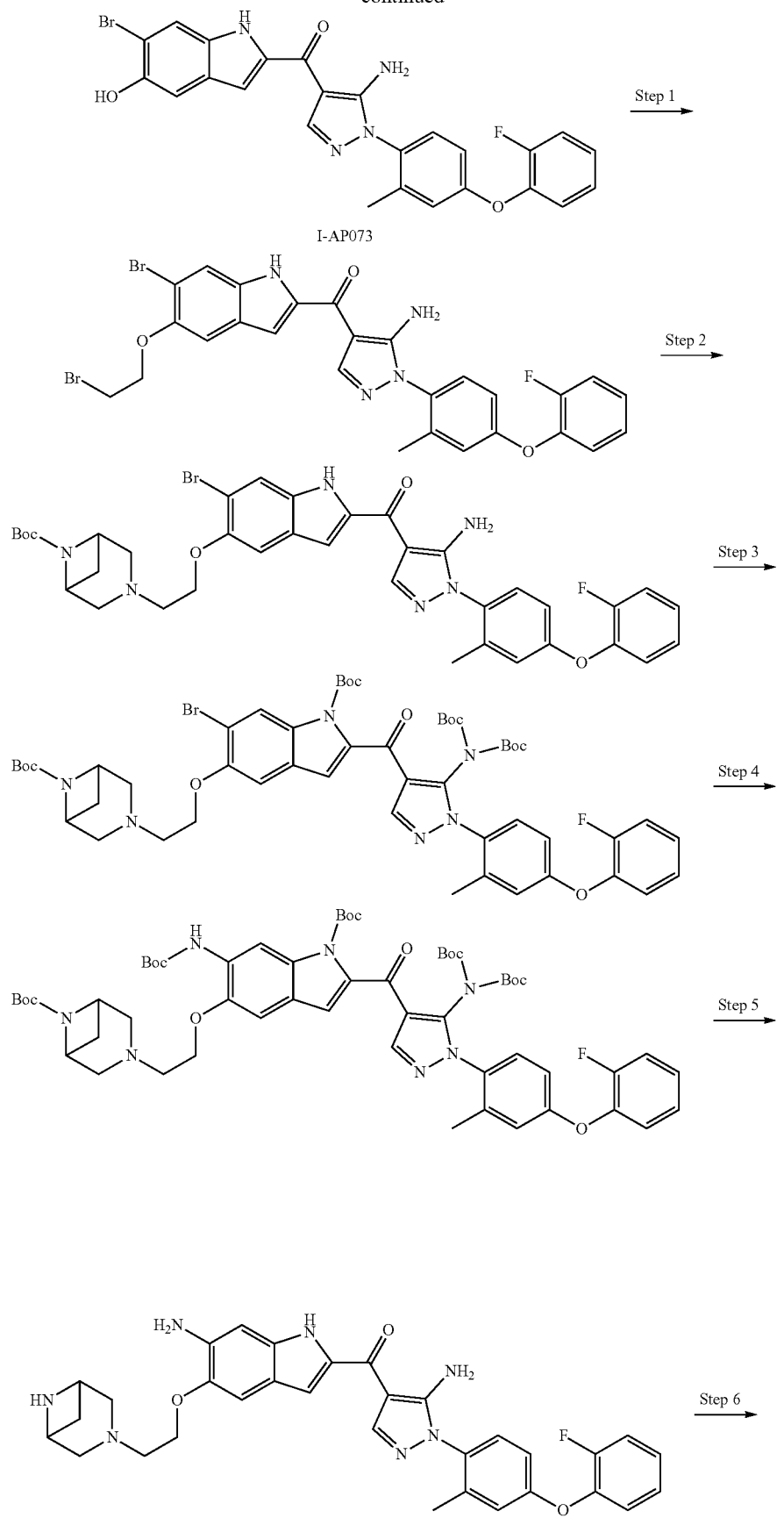

-continued

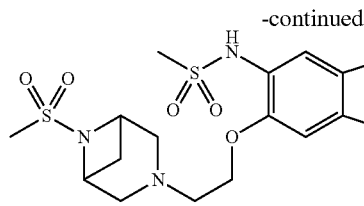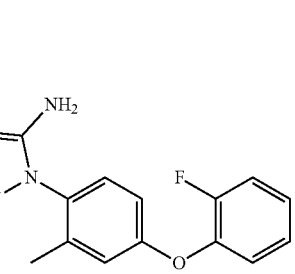

Step 1

Synthesis of {5-amino-1-[4-(2-fluorophenoxy)-2-methylphenyl]pyrazol-4-yl}-[6-bromo-5-(2-bromoethoxy)-1H-indol-2-yl]methanone Bromide I-AP073 synthesized in Example 4-24-036 (873 mg) was suspended in acetonitrile (10 mL), 1,2-dibromoethane (6.3 g) and cesium carbonate (1.64 g) were added, and the mixture was stirred at 60° C. for one hour. Water was added to the reaction solution, the mixture was extracted with ethyl acetate, and the organic layer was dried over sodium sulfate. After removing the drying agent by filtration, the filtrate was then concentrated under reduced pressure, and the resulting residue was purified by column chromatography (hexane/ethyl acetate) to give the target compound (865 mg).

Step 2

Synthesis of tert-butyl 3-{2-{{2-{5-amino-1-[4-(2-fluorophenoxy)-2-methylphenyl]pyrazole-4-carbonyl}-6-bromo-1H-indol-5-yl}oxy}ethyl}-3,6-diazabicyclo[3.1.1]heptane-6-carboxylate {5-Amino-1-[4-(2-fluorophenoxy)-2-methylphenyl]pyrazol-4-yl}-[6-bromo-5-(2-bromoethoxy)-1H-indol-2-yl]methanone (100 mg) was suspended in acetonitrile (1.0 mL), tert-butyl 3,6-diazabicyclo[3.1.1]heptane-6-carboxylate (63 mg) and cesium carbonate (130 mg) were added, and the mixture was stirred at 70° C. for three hours. Water was added to the reaction solution, the mixture was extracted with ethyl acetate, and the organic layer was dried over sodium sulfate. After removing the drying agent by filtration, the filtrate was concentrated under reduced pressure, and the resulting residue was purified by column chromatography (hexane/ethyl acetate) to give the target compound (79 mg).

Step 3

Synthesis of tert-butyl 2-{5-{bis[(2-methylpropan-2-yl)oxycarbonyl]amino}-1-[4-(2-fluorophenoxy)-2-methylphenyl]pyrazole-4-carbonyl}-6-bromo-5-{2-{6-[(2-methylpropan-2-yl)oxycarbonyl]-3,6-diazabicyclo[3.1.1]heptan-3-yl}ethoxy}indole-1-carboxylate tert-Butyl 3-{2-{{2-{5-amino-1-[4-(2-fluorophenoxy)-2-methylphenyl]pyrazole-4-carbonyl}-6-bromo-1H-indol-5-yl}oxy}ethyl}-3,6-diazabicyclo[3.1.1]heptane-6-carboxylate (79 mg) was dissolved in dichloromethane (2.1 mL), Boc$_2$O (98 µL), DMAP (1.3 mg), and TEA (59 µL) were added, and the mixture was stirred at 25° C. for 15 hours. Water was added to the reaction solution, the mixture was extracted with ethyl acetate, and the organic layer was dried over sodium sulfate. After removing the drying agent by filtration, the filtrate was concentrated under reduced pressure, and the resulting residue was purified by column chromatography (hexane/ethyl acetate) to give the target compound (75 mg).

Step 4

Synthesis of tert-butyl 2-{5-{bis[(2-methylpropan-2-yl)oxycarbonyl]amino}-1-[4-(2-fluorophenoxy)-2-methylphenyl]pyrazole-4-carbonyl}-5-{2-{3,5-dimethyl-4-[(2-methylpropan-2-yl)oxycarbonyl]piperazin-1-yl}ethoxy}-6-[(2-methylpropan-2-yl)oxycarbonylamino]indole-1-carboxylate tert-Butyl 2-{5-{bis[(2-methylpropan-2-yl)oxycarbonyl]amino}-1-[4-(2-fluorophenoxy)-2-methylphenyl]pyrazole-4-carbonyl}-6-bromo-5-{2-{6-[(2-methylpropan-2-yl)oxycarbonyl]-3,6-diazabicyclo[3.1.1]heptan-3-yl}ethoxy}indole-1-carboxylate (75 mg), tert-butyl carbamate (25 mg), Pd$_2$dba$_3$ (15 mg), X-Phos (21 mg), and cesium carbonate (141 mg) were dissolved in dioxane (1.4 mL), and the mixture was stirred at 100° C. for five hours in a nitrogen atmosphere. Water was added to the reaction solution, the mixture was extracted with ethyl acetate, and the organic layer was dried over sodium sulfate. After removing the drying agent d by filtration, the filtrate was concentrated under reduced pressure, and the resulting residue was purified by column chromatography (hexane/ethyl acetate) to give the target compound (42 mg).

Step 5

Synthesis of {6-amino-5-[2-(3,5-dimethylpiperazin-1-yl)ethoxy]-1H-indol-2-yl}-{5-amino-1-[4-(2-fluorophenoxy)-2-methylphenyl]pyrazol-4-yl}methanone tert-Butyl 2-{5-{bis[(2-methylpropan-2-yl)oxycarbonyl]amino}-1-[4-(2-fluorophenoxy)-2-methylphenyl]pyrazole-4-carbonyl}-5-{2-{3,5-dimethyl-4-[(2-methylpropan-2-yl)oxycarbonyl]piperazin-1-yl}ethoxy}-6-[(2-methylpropan-2-yl)oxy carbonyl amino]indole-1-carboxylate (42 mg) was dissolved in dichloromethane (1.0 mL), trifluoroacetic acid (250 µL) was added, and the mixture was stirred at 25° C. for one hour. The reaction solution was concentrated under reduced pressure, a saturated aqueous sodium bicarbonate solution was added to the resulting residue, the mixture was extracted with ethyl acetate, and the organic layer was dried over sodium sulfate. After removing the drying agent by filtration, the filtrate was concentrated under reduced pressure. The resulting residue was used as such for the next reaction without purification.

Step 6

Synthesis of N-{2-{5-amino-1-[4-(2-fluorophenoxy)-2-methylphenyl]pyrazole-4-carbonyl}-5-[2-(3,5-dimethyl-4-methylsulfonylpiperazin-1-yl)ethoxy]-1H-indol-6-yl}methanesulfonamide {6-Amino-5-[2-(3,5-dimethylpiperazin-1-yl)ethoxy]-1H-indol-2-yl}-{5-amino-1-[4-(2-fluorophenoxy)-2-methylphenyl]pyrazol-4-yl}methanone (23 mg) was dissolved in pyridine (0.4 mL), methanesulfonyl chloride (12 μL) was added, and the mixture was stirred at 25° C. for one hour. Water was added to the reaction solution, the mixture was extracted with ethyl acetate, and the organic layer was dried over sodium sulfate. After removing the drying agent by filtration, the filtrate was concentrated under reduced pressure, and the resulting residue was purified by Prep-HPLC to give the target compound (2.5 mg).

Examples 4-24-038 to 4-24-039 and Examples 5-1-237 and 5-1-242

The compounds of Examples 4-24-038 to 4-24-039 were synthesized by the similar method as in Examples 4-24-036 and 4-24-037 using the corresponding amines in Step 1.
The compounds of Examples 5-1-237 and 5-1-242 were also synthesized as described below.

Example 5-1-237

Synthesis of (R)-(5-amino-1-(4-(2-fluorophenoxy)-3-methylphenyl)-1H-pyrazol-4-yl)(6-bromo-5-(2,3-dihydroxypropoxy)-1H-indol-2-yl)methanone

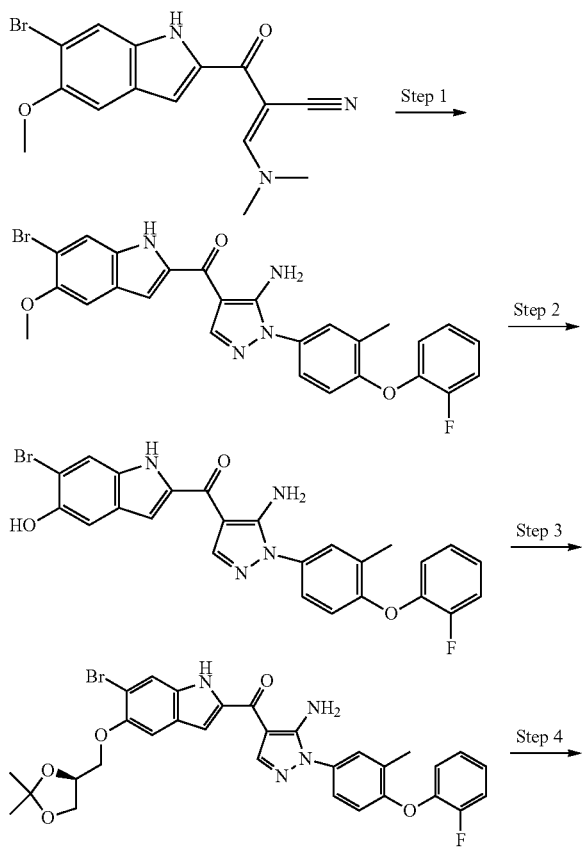

Step 1

Synthesis of (5-amino-1-(4-(2-fluorophenoxy)-3-methylphenyl)-1H-pyrazol-4-yl)(6-bromo-5-methoxy-1H-indol-2-yl)methanone Enamine (I-H068, 990 mg), hydrazine (Q019, 1146 mg), and 4-methylmorpholine (0.938 mL) were added to NMP (10 mL), and the mixture was stirred at 90° C. for four hours in a nitrogen atmosphere. Water and ethyl acetate were added to the reaction solution and the aqueous layer was extracted with ethyl acetate four times. The combined organic layers were washed with saturated saline and then dried over sodium sulfate. After removing the drying agent by filtration, the filtrate was concentrated, and the resulting residue was crystallized from ethyl acetate/MTBE (1/1). The precipitate was collected by filtration and washed with MTBE. The resulting powder was dried under reduced pressure to give the target compound (989 mg).

Step 2

Synthesis of (5-amino-1-(4-(2-fluorophenoxy)-3-methylphenyl)-1H-pyrazol-4-yl)(6-bromo-5-hydroxy-1H-indol-2-yl)methanone (5-amino-1-(4-(2-fluorophenoxy)-3-methylphenyl)-1H-pyrazol-4-yl)(6-bromo-5-methoxy-1H-indol-2-yl)methanone obtained in Step 1 (964 mg) was suspended in dichloroethane (18 mL) and boron tribromide (1.0 M solution in dichloromethane, 9 mL) was added at 25° C. The reaction solution was stirred at 25° C. for 1.5 hours in a nitrogen atmosphere, after which the reaction was quenched with methanol (30 mL) and the reaction solution was then concentrated under reduced pressure. The resulting residue was crystallized from methanol/water (4/1) and the crystals were collected by filtration, washed with MTBE, and then dried under reduced pressure to give the target compound (699 mg).

Step 3

Synthesis of (S)-(5-amino-1-(4-(2-fluorophenoxy)-3-methylphenyl)-1H-pyrazol-4-yl)(6-bromo-5-((2,2-dimethyl-1,3-dioxolan-4-yl)methoxy)-1H-indol-2-yl)methanone (5-Amino-1-(4-(2-fluorophenoxy)-3-methylphenyl)-1H-pyrazol-4-yl)(6-bromo-5-hydroxy-1H-indol-2-yl)methanone obtained in Step 2 (100 mg), triphenylphosphine (202 mg), and [(4S)-2,2-dimethyl-1,3-dioxolan-4-yl]methanol (0.094 mL) were added to THF (2.4 mL), diisopropyl azodicarboxylate (0.15 mL) was then added at 25° C., and the reaction solution was stirred at 25° C. for 18 hours in a nitrogen atmosphere. The reaction solution was concentrated under reduced pressure and the residue was purified by C18 column (formic acid-water-acetonitrile). The frac-

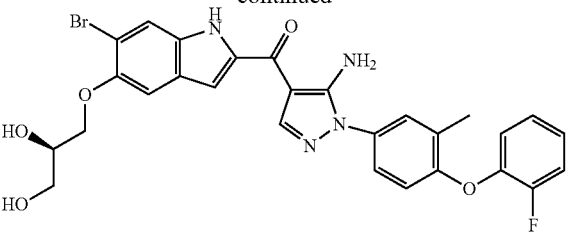

tions of the target compound were added to ethyl acetate/5% saturated aqueous sodium bicarbonate solution and the organic layer was dried over sodium sulfate. After removing the drying agent by filtration, the filtrate was concentrated to give the target compound (69 mg).

Step 4

Synthesis of (R)-(5-amino-1-(4-(2-fluorophenoxy)-3-methylphenyl)-1H-pyrazol-4-yl)(6-bromo-5-(2,3-dihydroxypropoxy)-1H-indol-2-yl)methanone (S)-(5-Amino-1-(4-(2-fluorophenoxy)-3-methylphenyl)-1H-pyrazol-4-yl)(6-bromo-5-((2,2-dimethyl-1,3-dioxolan-4-yl)methoxy)-1H-indol-2-yl)methanone obtained in Step 3 (68 mg) and a 2 M aqueous hydrochloric acid solution (0.268 mL) were added to methanol (2 mL) and the mixture was stirred at 60° C. for two hours. After cooling the reaction solution to 25° C., the resulting precipitate was collected by filtration, washed with solvents (methanol, ethyl acetate, and then dichloromethane), and dried under reduced pressure to give the target compound (50 mg).

Example 5-1-242

Synthesis of (R)—N-(2-(5-amino-1-(4-(2-fluorophenoxy)-3-methylphenyl)-1H-pyrazole-4-carbonyl)-5-(2,3-dihydroxypropoxy)-1H-indol-6-yl)methanesulfonamide

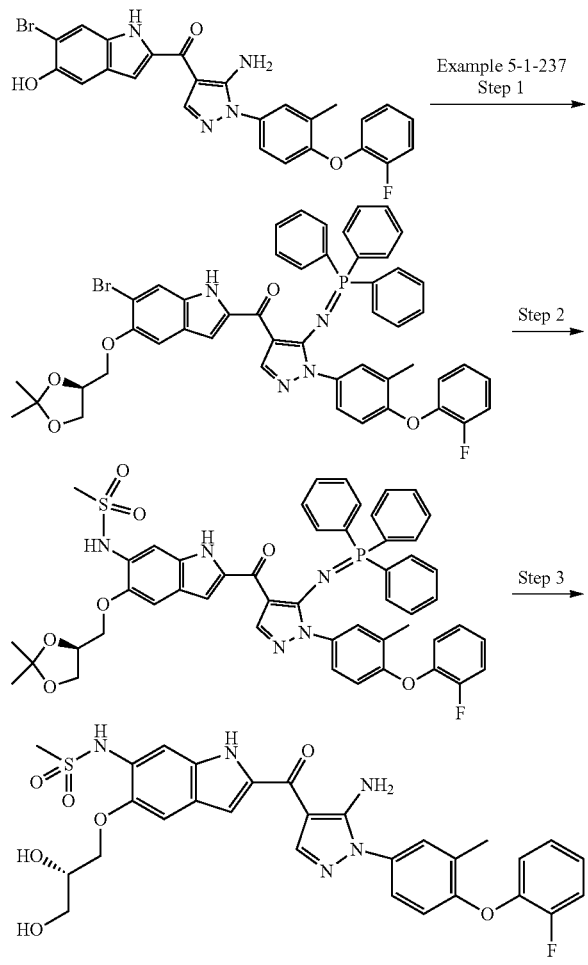

Step 1

Synthesis of (S)-(6-bromo-5-((2,2-dimethyl-1,3-dioxolan-4-yl)methoxy)-1H-indol-2-yl)(1-(4-(2-fluorophenoxy)-3-methylphenyl)-5-((triphenylphosphoranylidene)amino)-1H-pyrazol-4-yl)methanone The target compound (73 mg) was obtained by the reaction of Example 5-1-237.

Step 2

Synthesis of (S)—N-(5-((2,2-dimethyl-1,3-dioxolan-4-yl)methoxy)-2-(1-(4-(2-fluorophenoxy)-3-methylphenyl)-5-((triphenylphosphoranylidene)amino)-1H-pyrazole-4-carbonyl)-1H-indol-6-yl)methanesulfonamide (S)-(6-Bromo-5-((2,2-dimethyl-1,3-dioxolan-4-yl)methoxy)-1H-indol-2-yl)(1-(4-(2-fluorophenoxy)-3-methylphenyl)-5-((triphenylphosphoranylidene)amino)-1H-pyrazol-4-yl)methanone obtained in Step 1 (89 mg), methanesulfonamide (14 mg), cesium carbonate (99 mg), di-μ-chlorobis[η-allyl] palladium(II)] (3.7 mg), and tBu-X-Phos (11 mg) were added to dioxane (1 mL) and the mixture was stirred at 90° C. for two hours in a nitrogen atmosphere. The reaction mixture was purified by C18 column (formic acid-water-acetonitrile). The fractions of the target compound were added to ethyl acetate/5% saturated aqueous sodium bicarbonate solution and the organic layer was dried over sodium sulfate. After removing the drying agent by filtration and the filtrate was concentrated to give the target compound (80 mg).

Step 3

Synthesis of (R)—N-(2-(5-amino-1-(4-(2-fluorophenoxy)-3-methylphenyl)-1H-pyrazole-4-carbonyl)-5-(2,3-dihydroxypropoxy)-1H-indol-6-yl)methanesulfonamide (S)—N-(5-((2,2-Dimethyl-1,3-dioxolan-4-yl)methoxy)-2-(1-(4-(2-fluorophenoxy)-3-methylphenyl)-5-((triphenylphosphoranylidene)amino)-1H-pyrazole-4-carbonyl)-1H-indol-6-yl)methanesulfonamide obtained in Step 2 (79 mg) and a 5 M aqueous hydrochloric acid solution (0.55 mL) were added to THF (2 mL) and the mixture was stirred at 60° C. for 18 hours. The reaction solution was concentrated under reduced pressure and the residue was then crystallized from ethyl acetate, collected by filtration, and then dried to give the target compound (32 mg).

(Corresponding Enamines, Hydrazines, and Reagents)

| Example No. | | Enamine | | Hydrazine | Reagent |
|---|---|---|---|---|---|
| 4-24-036 | I-H064 | (6-bromo-5-hydroxy-1H-indol-2-yl with cyano enamine) | Q001 HCl | (1-hydrazinyl-4-(2-fluorophenoxy)-2-methylbenzene) | (tetrahydro-2H-pyran-4-ol) |
| 4-24-037 | I-H064 | (6-bromo-5-hydroxy-1H-indol-2-yl with cyano enamine) | Q001 HCl | (1-hydrazinyl-4-(2-fluorophenoxy)-2-methylbenzene) | (BOC-protected diazabicyclic amine) |
| 4-24-038 | I-H064 | (6-bromo-5-hydroxy-1H-indol-2-yl with cyano enamine) | Q001 HCl | (1-hydrazinyl-4-(2-fluorophenoxy)-2-methylbenzene) | (Boc-protected diazabicyclic amine with stereochemistry) |
| 4-24-039 | I-H064 | (6-bromo-5-hydroxy-1H-indol-2-yl with cyano enamine) | Q001 HCl | (1-hydrazinyl-4-(2-fluorophenoxy)-2-methylbenzene) | (oxa-azabicyclic amine) |
| 5-1-237 | I-H068 | (6-bromo-5-methoxy-1H-indol-2-yl with cyano enamine) | Q019 HCl | (1-hydrazinyl-4-(2-fluorophenoxy)-3-methylbenzene) | |
| 5-1-242 | I-H068 | (6-bromo-5-methoxy-1H-indol-2-yl with cyano enamine) | Q019 HCl | (1-hydrazinyl-4-(2-fluorophenoxy)-3-methylbenzene) | |

(Synthesized Compounds)

| Example No. | Compound | m/z (M + H) | Retention Time (Minute) | LCMS Measurement Condition |
|---|---|---|---|---|
| 4-24-036 | | 620 | 0.98 | J2 |
| 4-24-037 | | 738 | 0.97 | J2 |
| 4-24-038 | | 738 | 0.95 | J2 |
| 4-24-039 | | 675 | 1.00 | J2 |
| 5-1-237 | | 595 | 1.01 | AA Rev. 11 |

| Example No. | Compound | m/z (M + H) | Retention Time (Minute) | LCMS Measurement Condition |
|---|---|---|---|---|
| 5-1-242 | | 610 | 0.95 | AA Rev. 11 |

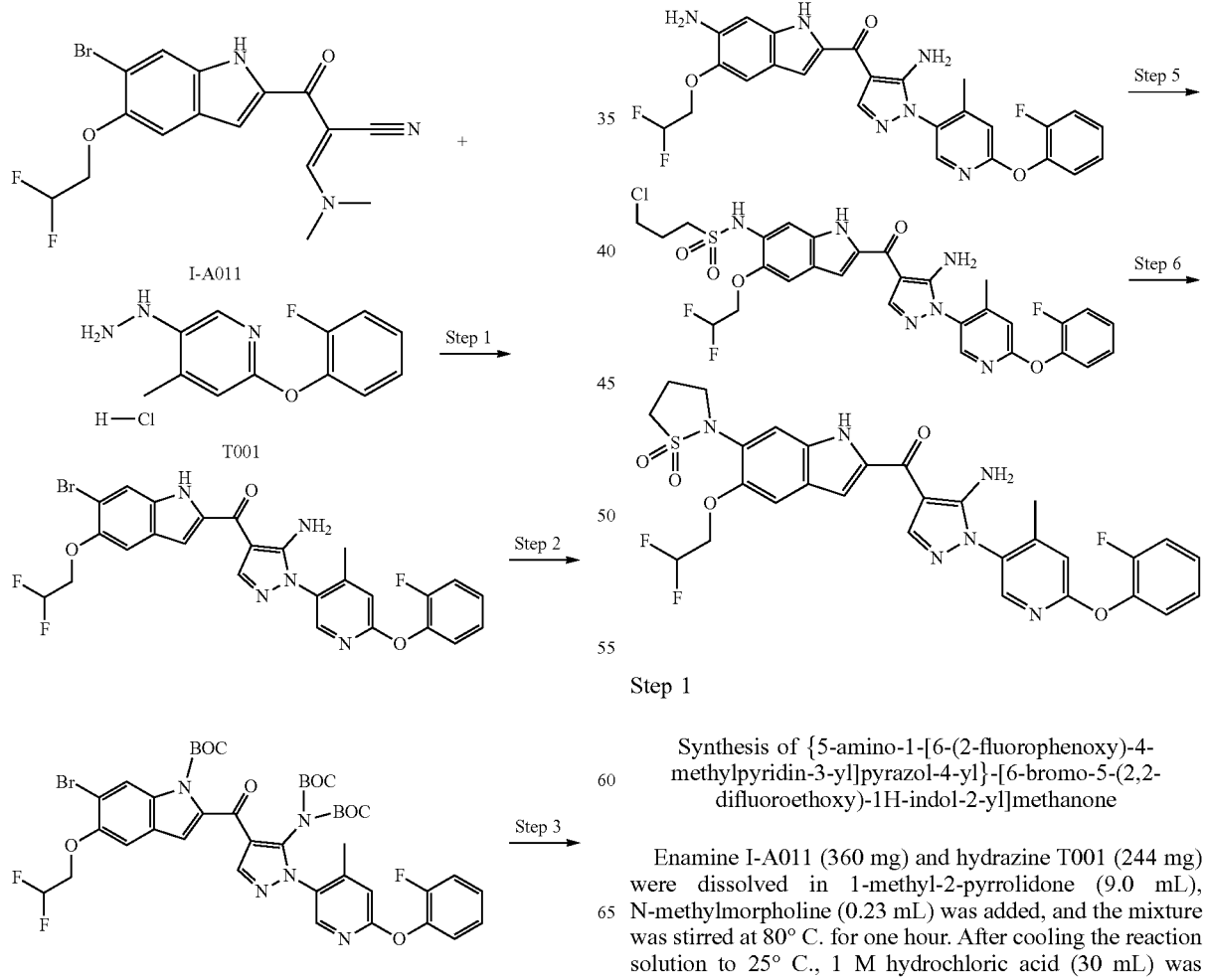

Example 4-25-001

Synthesis of {5-amino-1-[6-(2-fluorophenoxy)-4-methylpyridin-3-yl]pyrazol-4-yl}-[5-(2,2-difluoroethoxy)-6-(1,1-dioxo-1,2-thiazolidin-2-yl)-1H-indol-2-yl]methanone Step 1

Synthesis of {5-amino-1-[6-(2-fluorophenoxy)-4-methylpyridin-3-yl]pyrazol-4-yl}-[6-bromo-5-(2,2-difluoroethoxy)-1H-indol-2-yl]methanone Enamine I-A011 (360 mg) and hydrazine T001 (244 mg) were dissolved in 1-methyl-2-pyrrolidone (9.0 mL), N-methylmorpholine (0.23 mL) was added, and the mixture was stirred at 80° C. for one hour. After cooling the reaction solution to 25° C., 1 M hydrochloric acid (30 mL) was added, and the precipitated solid was collected by filtration to give the target compound (576 mg).
Step 2

Synthesis of tert-butyl 2-{5-{bis[(2-methylpropan-2-yl)oxycarbonyl]amino}-1-[6-(2-fluorophenoxy)-4-methylpyridin-3-yl]pyrazole-4-carbonyl}-6-bromo-5-(2,2-difluoroethoxy)indole-1-carboxylate {5-Amino-1-[6-(2-fluorophenoxy)-4-methylpyridin-3-yl]pyrazol-4-yl}-[6-bromo-5-(2,2-difluoroethoxy)-1H-indol-2-yl]methanone (576 mg) was dissolved in tetrahydrofuran (12 mL), Boc$_2$O (1.0 mL) and DMAP (48 mg) were added, and the mixture was stirred at 25° C. for 30 minutes. The reaction solution was concentrated under reduced pressure and the resulting residue was purified by column chromatography (hexane/ethyl acetate) to give the target compound (629 mg).
Step 3

Synthesis of tert-butyl 2-{5-{bis[(2-methylpropan-2-yl)oxycarbonyl]amino}-1-[6-(2-fluorophenoxy)-4-methylpyridin-3-yl]pyrazole-4-carbonyl}-5-(2,2-difluoroethoxy)-6-[(2-methylpropan-2-yl)oxycarbonylamino]indole-1-carboxylate tert-Butyl 2-{5-{bis[(2-methylpropan-2-yl)oxycarbonyl]amino}-1-[6-(2-fluorophenoxy)-4-methylpyridin-3-yl]pyrazole-4-carbonyl}-6-bromo-5-(2,2-difluoroethoxy)indole-1-carboxylate (629 mg), tert-butyl carbamate (125 mg), Pd$_2$dba$_3$ (73 mg), X-Phos (101 mg), and cesium carbonate (693 mg) were dissolved in dioxane (13 mL) and the mixture was stirred at 100° C. for two hours in a nitrogen atmosphere. Water was added to the reaction solution, the mixture was extracted with ethyl acetate, and the organic layer was dried over magnesium sulfate. After removing the drying agent by filtration, the filtrate was then concentrated under reduced pressure to give the target compound (956 mg).
Step 4

Synthesis of [6-amino-5-(2,2-difluoroethoxy)-1H-indol-2-yl]-{5-amino-1-[6-(2-fluorophenoxy)-4-methylpyridin-3-yl]pyrazol-4-yl}methanone (I-AP031)

tert-Butyl 2-{5-{bis[(2-methylpropan-2-yl)oxycarbonyl]amino}-1-[6-(2-fluorophenoxy)-4-methylpyridin-3-yl]pyrazole-4-carbonyl}-5-(2,2-difluoroethoxy)-6-[(2-methylpropan-2-yl)oxycarbonylamino]indole-1-carboxylate (956 mg) was dissolved in 2,2,2-trifluoroethanol (19 mL), TMSCl (1.2 mL) was added, and the mixture was stirred at 25° C. for 1.5 hours. The reaction solution was concentrated under reduced pressure and the resulting residue was purified by column chromatography (dichloromethane/methanol) to give the target compound (460 mg).
Step 5

Synthesis of N-{2-{5-amino-1-[6-(2-fluorophenoxy)-4-methylpyridin-3-yl]pyrazole-4-carbonyl}-5-(2,2-difluoroethoxy)-1H-indol-6-yl}-3-chloropropane-1-sulfonamide

[6-Amino-5-(2,2-difluoroethoxy)-1H-indol-2-yl]-{5-amino-1-[6-(2-fluorophenoxy)-4-methylpyridin-3-yl]pyrazol-4-yl}methanone (70 mg) was dissolved in pyridine (1.6 mL), 3-chloropropane-1-sulfonyl chloride (49 μL) was added, and the mixture was stirred at 25° C. for three hours. The reaction solution was purified by Prep-HPLC. Eluate containing the target compound was concentrated under reduced pressure and the resulting residue was washed by suspending in dichloromethane/hexane to give the target compound (37 mg).
Step 6

Synthesis of {5-amino-1-[6-(2-fluorophenoxy)-4-methylpyridin-3-yl]pyrazol-4-yl}-[5-(2,2-difluoroethoxy)-6-(1,1-dioxo-1,2-thiazolidin-2-yl)-1H-indol-2-yl]methanone N-{2-{5-Amino-1-[6-(2-fluorophenoxy)-4-methylpyridin-3-yl]pyrazole-4-carbonyl}-5-(2,2-difluoroethoxy)-1H-indol-6-yl}-3-chloropropane-1-sulfonamide (37 mg) was dissolved in N,N-dimethylformamide (0.7 mL), sodium iodide (25 mg) and potassium carbonate (39 mg) were added, and the mixture was stirred at 80° C. for one hour. After cooling the reaction solution to 25° C., water (15 mL) and 2 M hydrochloric acid (2.0 mL) were added, and the precipitated solid was collected by filtration to give the target compound (30 mg).

Examples 4-25-002 to 4-25-012

The compounds of Examples 4-25-002 to 4-25-012 were synthesized from corresponding enamines and hydrazines by the similar method as in Example 4-25-001.
(Corresponding Enamines and Hydrazines)

| Example No. | | Enamine | | Hydrazine |
|---|---|---|---|---|
| 4-25-001 | I-A011 | 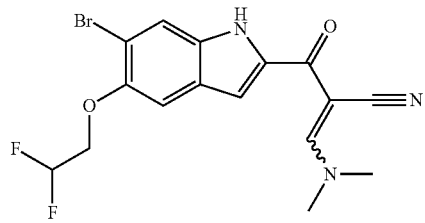 [SMILES: CN(C)C=C(C#N)C(=O)c1cc2cc(OCC(F)F)c(Br)cc2[nH]1] | T001 | HCl 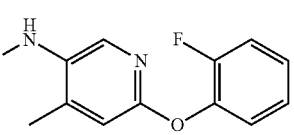 |

-continued

| Example No. | | Enamine | | Hydrazine |
|---|---|---|---|---|
| 4-25-002 | B-B026 | [6-bromo-5-(difluoromethoxy)-1H-indol-2-yl structure with dimethylaminomethylene cyanoketone] | Q001 | HCl; [2-fluorophenoxy-methylphenyl hydrazine] |
| 4-25-003 | B-B026 | [6-bromo-5-(difluoromethoxy)-1H-indol-2-yl structure with dimethylaminomethylene cyanoketone] | S038 | HCl; [fluoro-(2-fluorophenoxy)-methylphenyl hydrazine] |
| 4-25-004 | B-B026 | [6-bromo-5-(difluoromethoxy)-1H-indol-2-yl structure with dimethylaminomethylene cyanoketone] | T001 | HCl; [6-(2-fluorophenoxy)-4-methylpyridin-3-yl hydrazine] |
| 4-25-005 | B-B026 | [6-bromo-5-(difluoromethoxy)-1H-indol-2-yl structure with dimethylaminomethylene cyanoketone] | T002 | HCl; [6-(2,6-difluorophenoxy)-4-methylpyridin-3-yl hydrazine] |
| 4-25-006 | I-A010 | [6-bromo-5-morpholino-1H-indol-2-yl structure with dimethylaminomethylene cyanoketone] | Q001 | HCl; [2-fluorophenoxy-methylphenyl hydrazine] |
| 4-25-007 | I-A010 | [6-bromo-5-morpholino-1H-indol-2-yl structure with dimethylaminomethylene cyanoketone] | T001 | HCl; [6-(2-fluorophenoxy)-4-methylpyridin-3-yl hydrazine] |
| 4-25-008 | I-A010 | [6-bromo-5-morpholino-1H-indol-2-yl structure with dimethylaminomethylene cyanoketone] | T002 | HCl; [6-(2,6-difluorophenoxy)-4-methylpyridin-3-yl hydrazine] |

-continued

| Example No. | | Enamine | | Hydrazine |
|---|---|---|---|---|
| 4-25-009 | I-A011 | [structure: 6-bromo-5-(2,2-difluoroethoxy)-1H-indol-2-yl ketone with cyanoenamine NMe2] | Q001 | HCl, [structure: 4-(2-fluorophenoxy)-2-methylphenyl hydrazine] |
| 4-25-010 | I-A011 | [structure: 6-bromo-5-(2,2-difluoroethoxy)-1H-indol-2-yl ketone with cyanoenamine NMe2] | S038 | HCl, [structure: 2-fluoro-4-(2-fluorophenoxy)-6-methylphenyl hydrazine] |
| 4-25-011 | I-A011 | [structure: 6-bromo-5-(2,2-difluoroethoxy)-1H-indol-2-yl ketone with cyanoenamine NMe2] | T002 | HCl, [structure: 6-(2,6-difluorophenoxy)-4-methylpyridin-3-yl hydrazine] |
| 4-25-012 | I-H044 | [structure: 6-bromo-5-(2-morpholinoethoxy)-1H-indol-2-yl ketone with cyanoenamine NMe2] | Q001 | HCl, [structure: 4-(2-fluorophenoxy)-2-methylphenyl hydrazine] |

(Synthesized Compounds)

| Example No. | Compound | m/z (M + H) | Retention Time (Minute) | LCMS Measurement Condition |
|---|---|---|---|---|
| 4-25-001 | [structure of synthesized compound with isothiazolidine dioxide, indole, aminopyrazole, fluorophenoxy-methylpyridine, and difluoroethoxy substituents] | 627 | 0.84 | A1 |

-continued

| Example No. | Compound | m/z (M + H) | Retention Time (Minute) | LCMS Measurement Condition |
|---|---|---|---|---|
| 4-25-002 | | 612 | 2.65 | B1 |
| 4-25-003 | | 630 | 1.00 | J2 |
| 4-25-004 | | 613 | 0.80 | A1 |
| 4-25-005 | | 631 | 0.82 | A1 |
| 4-25-006 | | 631 | 0.84 | A1 |

-continued

| Example No. | Compound | m/z (M + H) | Retention Time (Minute) | LCMS Measurement Condition |
| --- | --- | --- | --- | --- |
| 4-25-007 | | 632 | 0.81 | A1 |
| 4-25-008 | | 650 | 0.83 | A1 |
| 4-25-009 | | 626 | 0.88 | A1 |
| 4-25-010 | | 644 | 1.01 | J1 |
| 4-25-011 | | 645 | 0.97 | J4 |

| Example No. | Compound | m/z (M + H) | Retention Time (Minute) | LCMS Measurement Condition |
|---|---|---|---|---|
| 4-25-012 |  | 675 | 1.91 | B1 |
Example 4-25-013
Synthesis of 1-{2-{5-amino-1-[6-(2-fluorophenoxy)-4-methylpyridin-3-yl]pyrazole-4-carbonyl}-5-(2,2-difluoroethoxy)-1H-indol-6-yl}-pyrrolidin-2-one
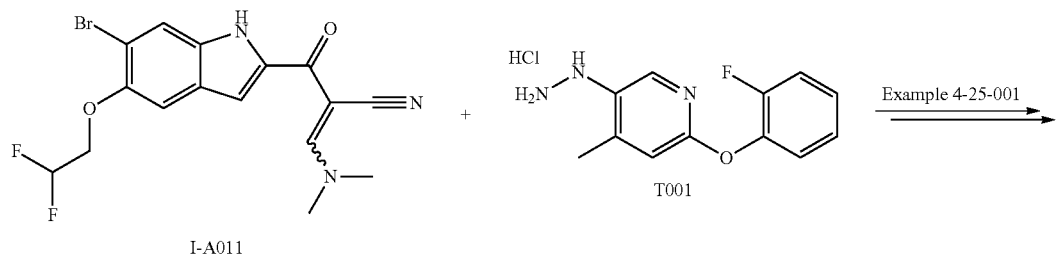
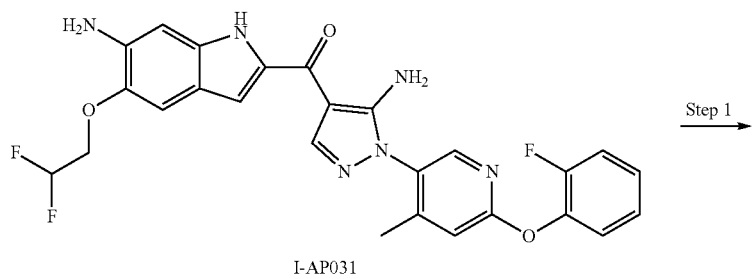
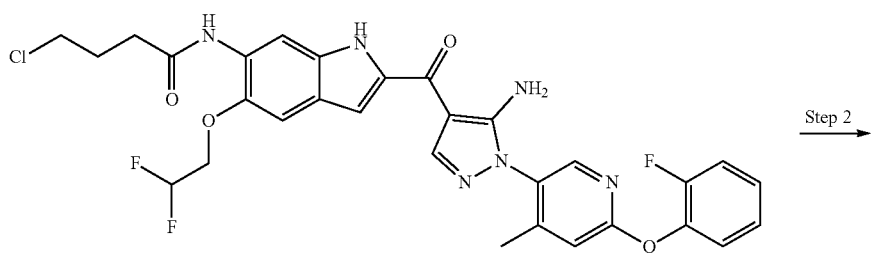

-continued

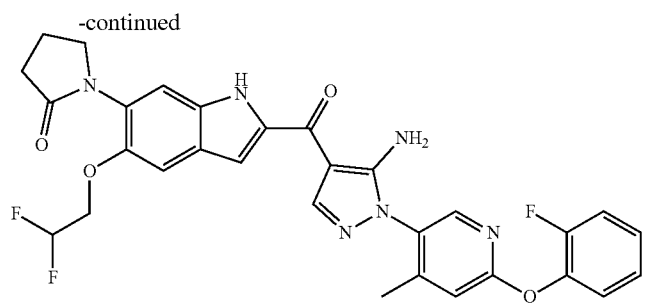

Step 1

Synthesis of N-{2-{5-amino-1-[6-(2-fluorophenoxy)-4-methylpyridin-3-yl]pyrazole-4-carbonyl}-5-(2,2-difluoroethoxy)-1H-indol-6-yl}-4-chlorobutanamide Aniline I-AP031 synthesized in Example 4-25-001 (100 mg) was dissolved in pyridine (1.9 mL), 4-chlorobutyryl chloride (42 μL) was added, and the mixture was stirred at 25° C. for five hours. Water (10 mL) was added to the reaction solution and the mixture was extracted with ethyl acetate (20 mL). The organic layer was washed with water and dried over sodium sulfate. After removing the drying agent by filtration, the filtrate was concentrated under reduced pressure. The resulting residue was used as such for the next reaction without purification.

Step 2

Synthesis of 1-{2-{5-amino-1-[6-(2-fluorophenoxy)-4-methylpyridin-3-yl]pyrazole-4-carbonyl}-5-(2,2-difluoroethoxy)-1H-indol-6-yl}pyrrolidin-2-one N-{2-{5-Amino-1-[6-(2-fluorophenoxy)-4-methylpyridin-3-yl]pyrazole-4-carbonyl}-5-(2,2-difluoroethoxy)-1H-indol-6-yl}-4-chlorobutanamide (120 mg) was dissolved in N,N-dimethylformamide (2.0 mL), sodium iodide (57 mg) and potassium carbonate (79 mg) were added, and the mixture was stirred at 80° C. for 15 hours. After cooling the reaction solution to 25° C., water was added, the mixture was extracted with ethyl acetate, and the organic layer was dried over sodium sulfate. After removing the drying agent by filtration, the filtrate was concentrated under reduced pressure, and the resulting residue was purified by Prep-HPLC to give the target compound (12 mg).

Examples 4-25-014 to 4-25-015, Example 5-1-098, and the Like

The compounds of Examples 4-25-014 to 4-25-015, Example 5-1-098, and the like were synthesized from corresponding enamines and hydrazines by the similar method as in Example 4-25-013.

(Corresponding Enamines and Hydrazines)

| Example No. | | Enamine | | Hydrazine |
|---|---|---|---|---|
| 4-25-013 | I-A011 | 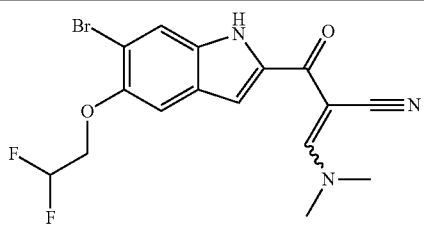 | T001 | 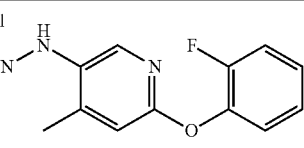 |
| 4-25-014 | B-B026 | 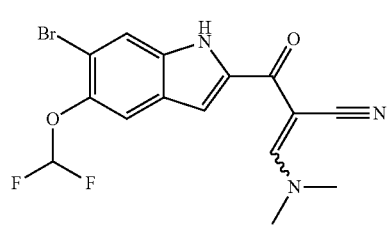 [SMILES: CN(C)C=C(C#N)C(=O)c1cc2cc(OC(F)F)c(Br)cc2[nH]1] | T001 | 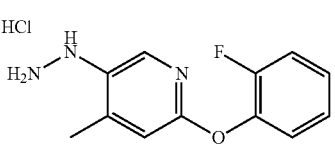 |
| 4-25-015 | B-B026 | 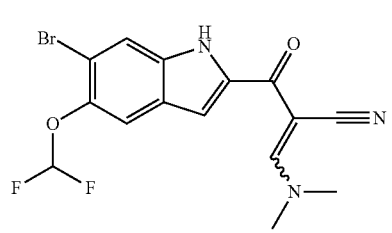 [SMILES: CN(C)C=C(C#N)C(=O)c1cc2cc(OC(F)F)c(Br)cc2[nH]1] | S038 | 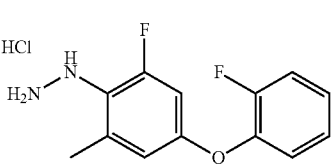 [SMILES: Cl ; Cc1cc(Oc2ccccc2F)cc(F)c1NN] |

-continued

| Example No. | Enamine | | Hydrazine | |
|---|---|---|---|---|
| 5-1-098 | I-H047 | (structure) | T002 | HCl (structure) |
| 5-1-103 | I-H047 | (structure) | Q001 | HCl (structure) |
| 5-1-105 | I-A010 | (structure) | Q001 | HCl (structure) |

(Synthesized Compounds)

| Example No. | Compound | m/z (M + H) | Retention Time (Minute) | LCMS Measurement Condition |
|---|---|---|---|---|
| 4-25-013 | (structure) | 591 | 1.00 | J4 |
| 4-25-014 | (structure) | 577 | 1.01 | J4 |

-continued

| Example No. | Compound | m/z (M + H) | Retention Time (Minute) | LCMS Measurement Condition |
|---|---|---|---|---|
| 4-25-015 | | 594 | 1.04 | J1 |
| 5-1-098 | | 547 | 1.01 | AA Rev. 11 |
| 5-1-103 | | 528 | 1.23 | TFA Rev. 5 |
| 5-1-105 | | 595 | 1.04 | AA Rev. 11 |

Example 4-25-016

Synthesis of 3-{2-{5-amino-1-[6-(2-fluorophenoxy)-4-methylpyridin-3-yl]pyrazole-4-carbonyl}-5-(2,2-difluoroethoxy)-1H-indol-6-yl}-1,3-oxazolidin-2-one

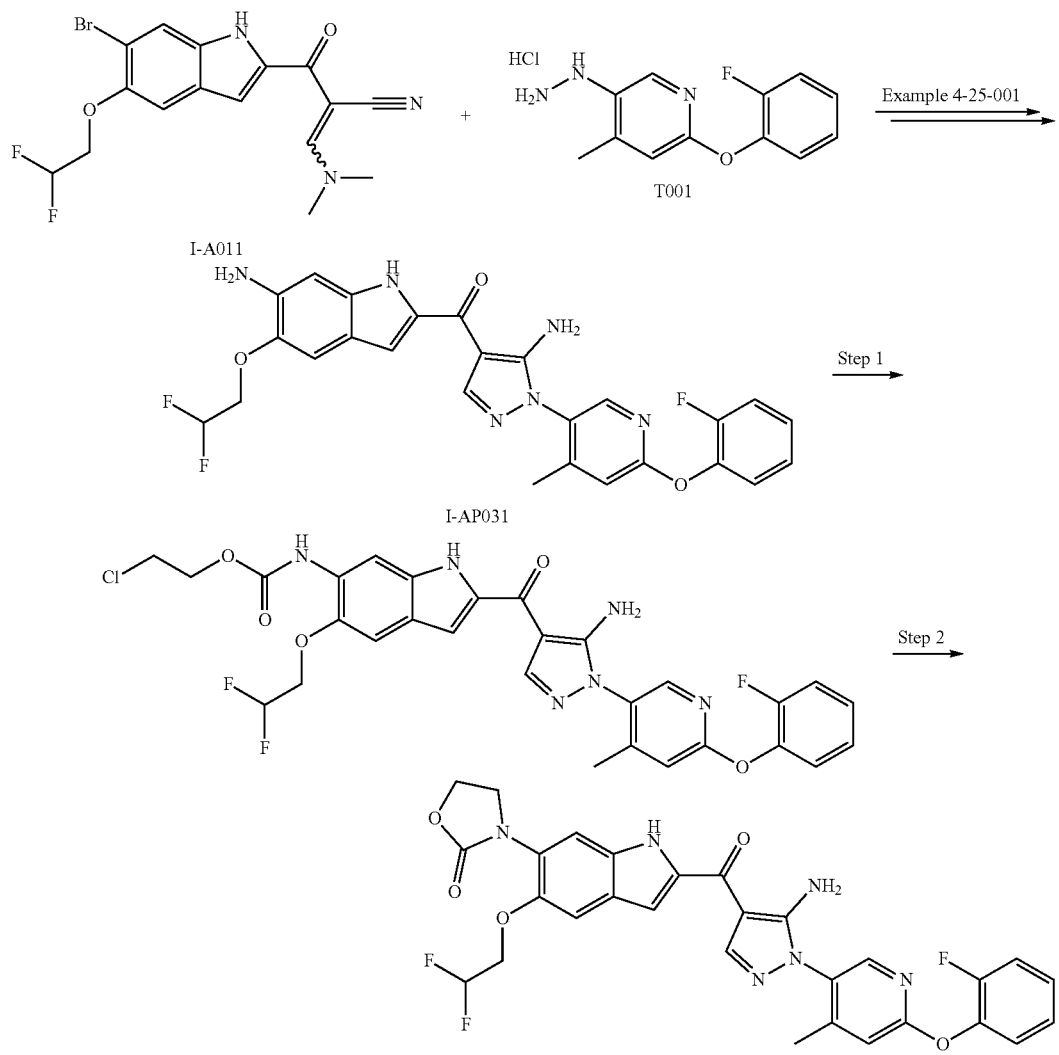

Step 1

Synthesis of 2-chloroethyl N-{2-{5-amino-1-[6-(2-fluorophenoxy)-4-methylpyridin-3-yl]pyrazole-4-carbonyl}-5-(2,2-difluoroethoxy)-1H-indol-6-yl}carbamate Aniline I-AP031 synthesized in Example 4-25-001 (100 mg) was dissolved in pyridine (1.9 mL), 2-chloroethyl chloroformate (304) was added, and the mixture was stirred at 25° C. for five hours. Water (10 mL) was added to the reaction solution and the precipitated solid was collected by filtration to give the target compound (94 mg).

Step 2

Synthesis of 3-{2-{5-amino-1-[6-(2-fluorophenoxy)-4-methylpyridin-3-yl]pyrazole-4-carbonyl}-5-(2,2-difluoroethoxy)-1H-indol-6-yl}-1,3-oxazolidin-2-one 2-Chloroethyl N-{2-{5-amino-1-[6-(2-fluorophenoxy)-4-methylpyridin-3-yl]pyrazole-4-carbonyl}-5-(2,2-difluoroethoxy)-1H-indol-6-yl}carbamate (120 mg) was dissolved in N,N-dimethylformamide (1.9 mL), sodium iodide (57 mg) and potassium carbonate (79 mg) were added, and the mixture was stirred at 80° C. for 30 minutes. After cooling the reaction solution to 25° C., water was added, and the precipitated solid was collected by filtration and then washed by suspending in dichloromethane/hexane to give the target compound (58 mg).

Examples 4-25-017 to 4-25-019

The compounds of Examples 4-25-017 to 4-25-019 were synthesized from corresponding enamines and hydrazines by the similar method as in Example 4-25-016.
(Corresponding Enamines and Hydrazines)

| Example No. | Enamine | | Hydrazine | |
|---|---|---|---|---|
| 4-25-016 | I-A011 | (structure) | T001 | HCl (structure) |
| 4-25-017 | I-A011 | (structure) | S038 | HCl (structure) |
| 4-25-018 | B-B026 | (structure) | T001 | HCl (structure) |
| 4-25-019 | B-B026 | (structure) | S038 | HCl (structure) |

(Synthesized Compounds)

| Example No. | Compound | m/z (M + H) | Retention Time (Minute) | LCMS Measurement Condition |
|---|---|---|---|---|
| 4-25-016 | (structure) | 593 | 0.96 | J1 |

| Example No. | Compound | m/z (M + H) | Retention Time (Minute) | LCMS Measurement Condition |
|---|---|---|---|---|
| 4-25-017 | | 610 | 1.00 | J1 |
| 4-25-018 | | 579 | 0.97 | J4 |
| 4-25-019 | | 596 | 1.01 | J4 |
Example 4-25-020
Synthesis of {5-amino-1-[6-(2-fluorophenoxy)-4-methylpyridin-3-yl]pyrazol-4-yl}-[5-(2,2-difluoroethoxy)-6-morpholin-4-yl-1H-indol-2-yl]methanone
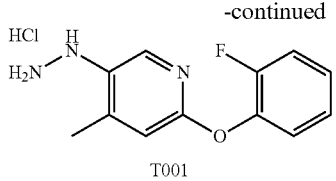
T001
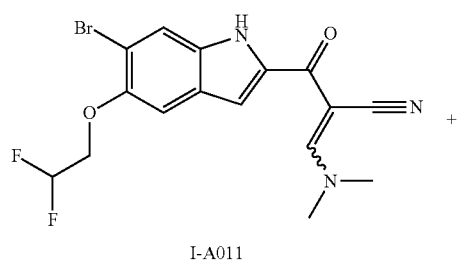
I-A011
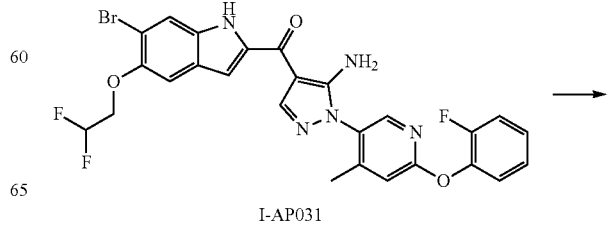
I-AP031

-continued

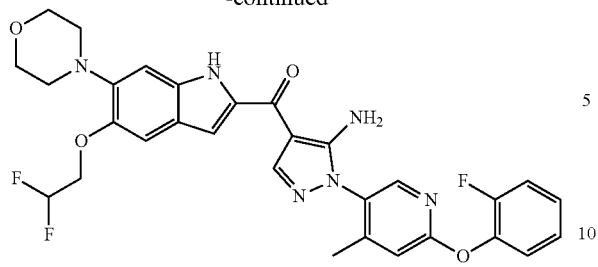

Aniline I-AP031 synthesized in Example 4-25-001 (100 mg) was dissolved in 1-methyl-2-pyrrolidone (1.9 mL), and bis(2-bromoethyl) ether (48 μL), sodium iodide (57 mg), and potassium carbonate (106 mg) were added. Then, the mixture was stirred at 80° C. for 15 hours. A saturated aqueous sodium bicarbonate solution was added to the reaction solution, the mixture was extracted with ethyl acetate, and the organic layer was dried over magnesium sulfate. After removing the drying agent by filtration, the filtrate was concentrated under reduced pressure, and the resulting residue was purified by column chromatography (hexane/ethyl acetate) to give the target compound (33 mg).

Examples 4-25-021 to 4-50-025, Example 5-1-087, and the Like

The compounds of Examples 4-25-021 to 4-50-025, Example 5-1-087, and the like were synthesized from corresponding enamines and hydrazines by the similar method as in Example 4-25-020.

(Corresponding Enamines and Hydrazines)

| Example No. | | Enamine | Hydrazine |
|---|---|---|---|
| 4-25-020 | I-A011 | | T001 |
| 4-25-021 | I-A011 | | S038 |
| 4-25-022 | B-B026 | | T001 |
| 4-25-023 | B-B026 | | T002 |
| 4-25-024 | B-B026 | | Q001 |

-continued
| Example No. | | Enamine | | Hydrazine |
|---|---|---|---|---|
| 4-25-025 | B-B026 | 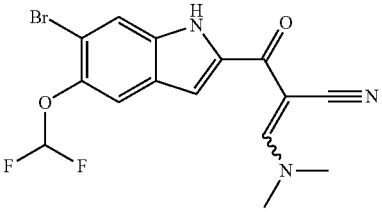 [SMILES: CN(C)C=C(C#N)C(=O)c1cc2cc(OC(F)F)c(Br)cc2[nH]1] | S038 | 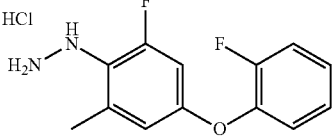 |
| 5-1-087 | I-A011 | 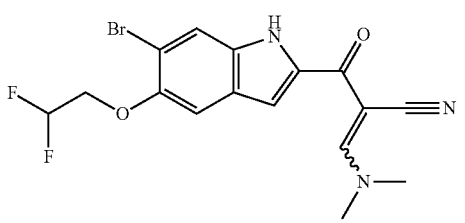 [SMILES: CN(C)C=C(C#N)C(=O)c1cc2cc(OCC(F)F)c(Br)cc2[nH]1] | Q001 | 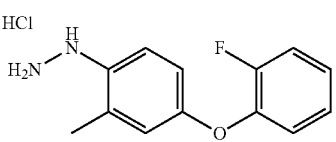 [SMILES: Cl ; Cc1cc(Oc2ccccc2F)ccc1NN] |
| 5-1-112 | I-A004 | 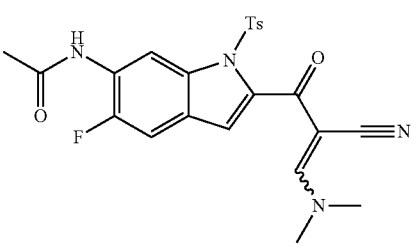 [SMILES: CC(=O)Nc1cc2c(cc1F)cc(C(=O)C(C#N)=CN(C)C)n2S(=O)(=O)c1ccc(C)cc1] | T002 | 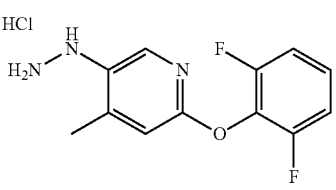 [SMILES: Cl ; Cc1cc(Oc2c(F)cccc2F)ncc1NN] |
| 5-1-124 | I-A010 | 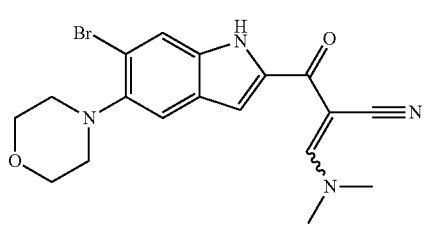 | Q001 | 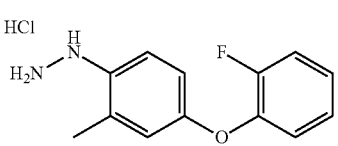 |
| 5-1-128 | I-A004 | 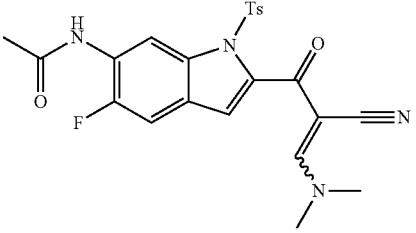 [SMILES: CC(=O)Nc1cc2c(cc1F)cc(C(=O)C(C#N)=CN(C)C)n2S(=O)(=O)c1ccc(C)cc1] | Q001 | 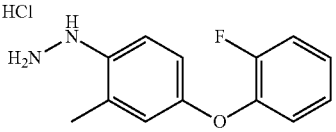 |
| 5-1-165 | I-A010 | 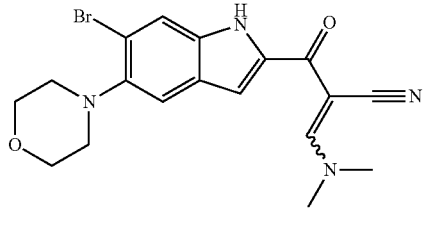 [SMILES: CN(C)C=C(C#N)C(=O)c1cc2cc(N3CCOCC3)c(Br)cc2[nH]1] | Q019 | 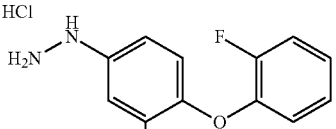 |
| 5-1-172 | I-A011 | 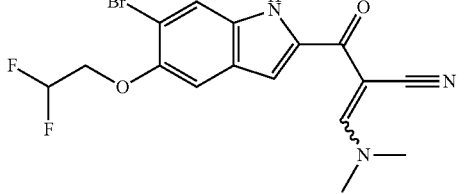 | Q019 | 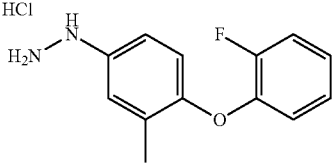 [SMILES: Cl ; Cc1cc(NN)ccc1Oc1ccccc1F] |

-continued

| Example No. | | Enamine | | Hydrazine | |
|---|---|---|---|---|---|
| 5-1-181 | B-B026 | (structure) | Q019 | HCl | (structure) |
| 5-1-182 | I-H074 | (structure) | Q019 | HCl | (structure) |
| 5-1-194 | I-H074 | (structure) | Q001 | HCl | (structure) |
| 5-1-201 | I-H074 | (structure) | T002 | HCl | (structure) |
| 5-1-202 | I-H074 | (structure) | T002 | HCl | (structure) |

-continued
| Example No. | Enamine | | Hydrazine |
|---|---|---|---|
| 5-1-215 | I-H074 | 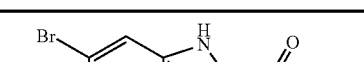 | S063 HCl  |
(Synthesized Compounds)
| Example No. | Compound | m/z (M + H) | Retention Time (Minute) | LCMS Measurement Condition |
|---|---|---|---|---|
| 4-25-020 | | 593 | 1.04 | J1 |
| 4-25-021 | | 610 | 1.07 | J4 |
| 4-25-022 | | 579 | 1.08 | J1 |

-continued

| Example No. | Compound | m/z (M + H) | Retention Time (Minute) | LCMS Measurement Condition |
|---|---|---|---|---|
| 4-25-023 | | 597 | 1.05 | J2 |
| 4-25-024 | | 578 | 1.08 | J4 |
| 4-25-025 | | 596 | 1.10 | J4 |
| 5-1-087 | | 606 | 1.05 | AA Rev. 11 |

-continued
| Example No. | Compound | m/z (M + H) | Retention Time (Minute) | LCMS Measurement Condition |
|---|---|---|---|---|
| 5-1-112 | 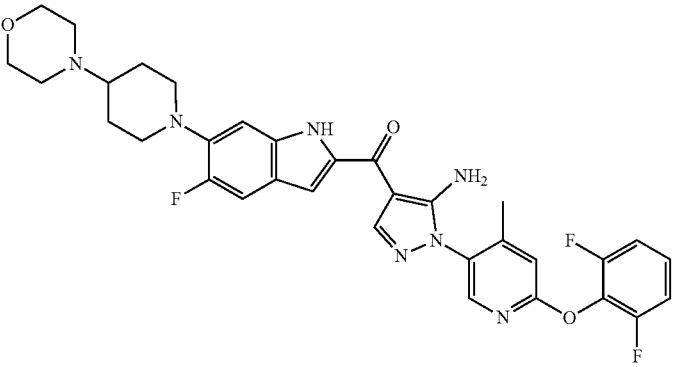 [SMILES: Cc1cc(Oc2c(F)cccc2F)ncc1-n1ncc(C(=O)c2cc3cc(F)c(N4CCC(N5CCOCC5)CC4)cc3[nH]2)c1N] | 632 | 1.07 | AA Rev. 11 |
| 5-1-124 | 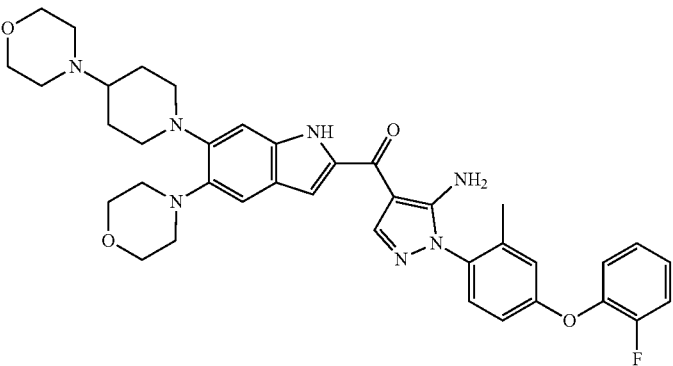 [SMILES: Cc1cc(Oc2ccccc2F)ccc1-n1ncc(C(=O)c2cc3cc(N4CCOCC4)c(N4CCC(N5CCOCC5)CC4)cc3[nH]2)c1N] | 680 | 1.11 | AA Rev. 11 |
| 5-1-128 | 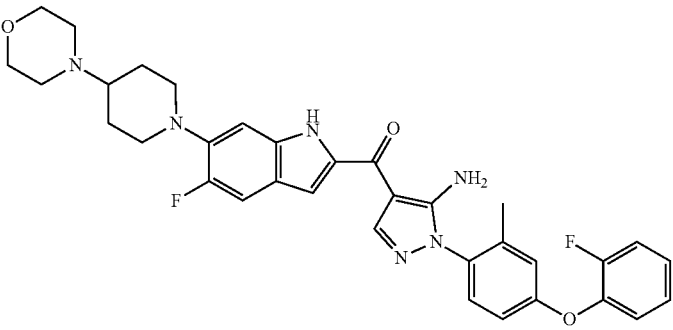 [SMILES: Cc1cc(Oc2ccccc2F)ccc1-n1ncc(C(=O)c2cc3cc(F)c(N4CCC(N5CCOCC5)CC4)cc3[nH]2)c1N] | 613 | 1.10 | TFA Rev. 5 |
| 5-1-165 | 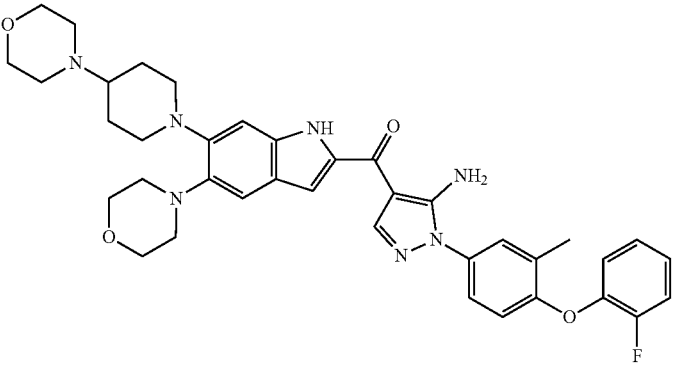 [SMILES: Cc1cc(-n2ncc(C(=O)c3cc4cc(N5CCOCC5)c(N5CCC(N6CCOCC6)CC5)cc4[nH]3)c2N)ccc1Oc1ccccc1F] | 680 | 1.14 | AA Rev. 11 |

-continued

| Example No. | Compound | m/z (M + H) | Retention Time (Minute) | LCMS Measurement Condition |
|---|---|---|---|---|
| 5-1-172 | | 675 | 1.11 | TFA Rev. 5 |
| 5-1-181 | | 661 | 1.14 | AA Rev. 11 |
| 5-1-182 | | 736 | 1.03 | AA Rev. 11 |
| 5-1-194 | | 736 | 1.02 | AA Rev. 11 |

-continued

| Example No. | Compound | m/z (M + H) | Retention Time (Minute) | LCMS Measurement Condition |
|---|---|---|---|---|
| 5-1-201 | | 755 | 1.00 | AA Rev. 11 |
| 5-1-202 | | 686 | 0.95 | AA Rev. 11 |
| 5-1-215 | | 754 | 1.03 | AA Rev. 11 |

Example 4-25-026

Synthesis of {5-amino-1-[6-(2-fluorophenoxy)-4-methylpyridin-3-yl]pyrazol-4-yl}-[5-(2,2-difluoroethoxy)-6-(4-morpholin-4-ylpiperidin-1-yl)-1H-indol-2-yl]methanone

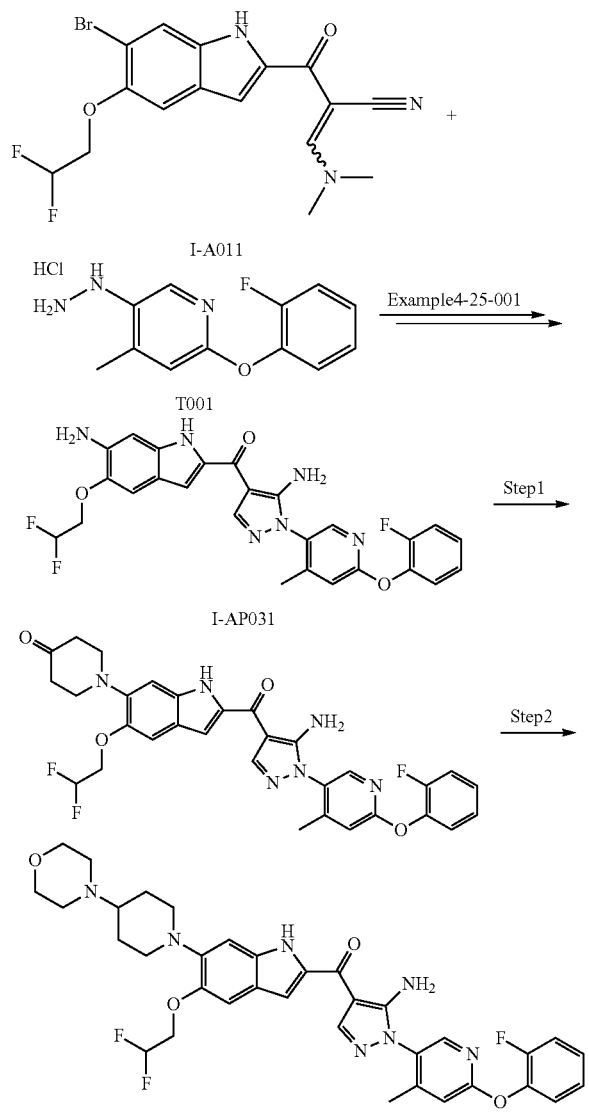

Step 1

Synthesis of 1-{2-{5-amino-1-[6-(2-fluorophenoxy)-4-methylpyridin-3-yl]pyrazole-4-carbonyl}-5-(2,2-difluoroethoxy)-1H-indol-6-yl}piperidin-4-one Aniline I-AP031 synthesized in Example 4-25-001 (100 mg) was suspended in ethanol (2.6 mL) and water (1.3 mL), and 1-benzyl-1-methyl-4-oxopiperidin-1-ium iodide (76 mg) and potassium carbonate (4 mg) were added. Then, the mixture was stirred at 80° C. for 4.5 hours. After cooling the reaction solution to 25° C., water was added, and the precipitated solid was collected by filtration to give the target compound (115 mg).

Step 2

Synthesis of {5-amino-1-[6-(2-fluorophenoxy)-4-methylpyridin-3-yl]pyrazol-4-yl}-[5-(2,2-difluoroethoxy)-6-(4-morpholin-4-ylpiperidin-1-yl)-1H-indol-2-yl]methanone 1-{2-{5-Amino-1-[6-(2-fluorophenoxy)-4-methylpyridin-3-yl]pyrazole-4-carbonyl}-5-(2,2-difluoroethoxy)-1H-indol-6-yl}piperidin-4-one (115 mg) was suspended in dichloromethane (1.0 mL), and morpholine (83 μL), acetic acid (109 μL), and then sodium triacetoxyborohydride (202 mg) were added. Then, the mixture was stirred at 25° C. for two hours. After adding water to the reaction solution, the mixture was extracted with ethyl acetate, and the organic layer was dried over magnesium sulfate. After removing the drying agent by filtration, the filtrate was concentrated under reduced pressure, and the resulting residue was purified by reversed phase column chromatography (water/acetonitrile) to give the target compound (41 mg).

Examples 4-25-027 to 4-50-032

The compounds of Examples 4-25-027 to 4-50-032 were synthesized from corresponding enamines and hydrazines by the similar method as in Example 4-25-026.

(Corresponding Enamines and Hydrazines)

| Example No. | | Enamine | | Hydrazine |
|---|---|---|---|---|
| 4-25-026 | I-A011 | (structure) | T001 | (structure) |

-continued

| Example No. | | Enamine | | Hydrazine |
|---|---|---|---|---|
| 4-25-027 | I-A011 | (6-bromo-5-(2,2-difluoroethoxy)-1H-indol-2-yl) enamine with CN and N(CH₃)₂ | T002 | HCl, H₂N-NH-(5-(2,6-difluorophenoxy)-4-methylpyridin-3-yl) |
| 4-25-028 | I-A011 | (6-bromo-5-(2,2-difluoroethoxy)-1H-indol-2-yl) enamine with CN and N(CH₃)₂ | Q001 | HCl, H₂N-NH-(4-(2-fluorophenoxy)-2-methylphenyl) |
| 4-25-029 | I-A011 | (6-bromo-5-(2,2-difluoroethoxy)-1H-indol-2-yl) enamine with CN and N(CH₃)₂ | S038 | HCl, H₂N-NH-(2-fluoro-4-(2-fluorophenoxy)-6-methylphenyl) |
| 4-25-030 | B-B026 | (6-bromo-5-(difluoromethoxy)-1H-indol-2-yl) enamine with CN and N(CH₃)₂ | T001 | HCl, H₂N-NH-(6-(2-fluorophenoxy)-4-methylpyridin-3-yl) |
| 4-25-031 | B-B026 | (6-bromo-5-(difluoromethoxy)-1H-indol-2-yl) enamine with CN and N(CH₃)₂ | T002 | HCl, H₂N-NH-(6-(2,6-difluorophenoxy)-4-methylpyridin-3-yl) |
| 4-25-032 | B-B026 | (6-bromo-5-(difluoromethoxy)-1H-indol-2-yl) enamine with CN and N(CH₃)₂ | Q001 | HCl, H₂N-NH-(4-(2-fluorophenoxy)-2-methylphenyl) |

(Synthesized Compounds)

| Example No. | Compound | m/z (M + H) | Retention Time (Minute) | LCMS Measurement Condition |
|---|---|---|---|---|
| 4-25-026 | | 676 | 1.05 | J4 |
| 4-25-027 | | 694 | 1.03 | J4 |
| 4-25-028 | | 675 | 1.09 | J1 |
| 4-25-029 | | 693 | 1.08 | J4 |

-continued

| Example No. | Compound | m/z (M + H) | Retention Time (Minute) | LCMS Measurement Condition |
|---|---|---|---|---|
| 4-25-030 | | 662 | 1.09 | J1 |
| 4-25-031 | | 680 | 1.06 | J2 |
| 4-25-032 | | 661 | 1.08 | J4 |

Example 4-26-001
Synthesis of N-(2-(5-amino-1-(4-(2-fluorophenoxy)-2-methylphenyl)-1H-pyrazole-4-carbonyl)-5-fluoro-1H-indol-6-yl)-2-oxo-2-(pyrrolidin-1-yl)ethanesulfonamide
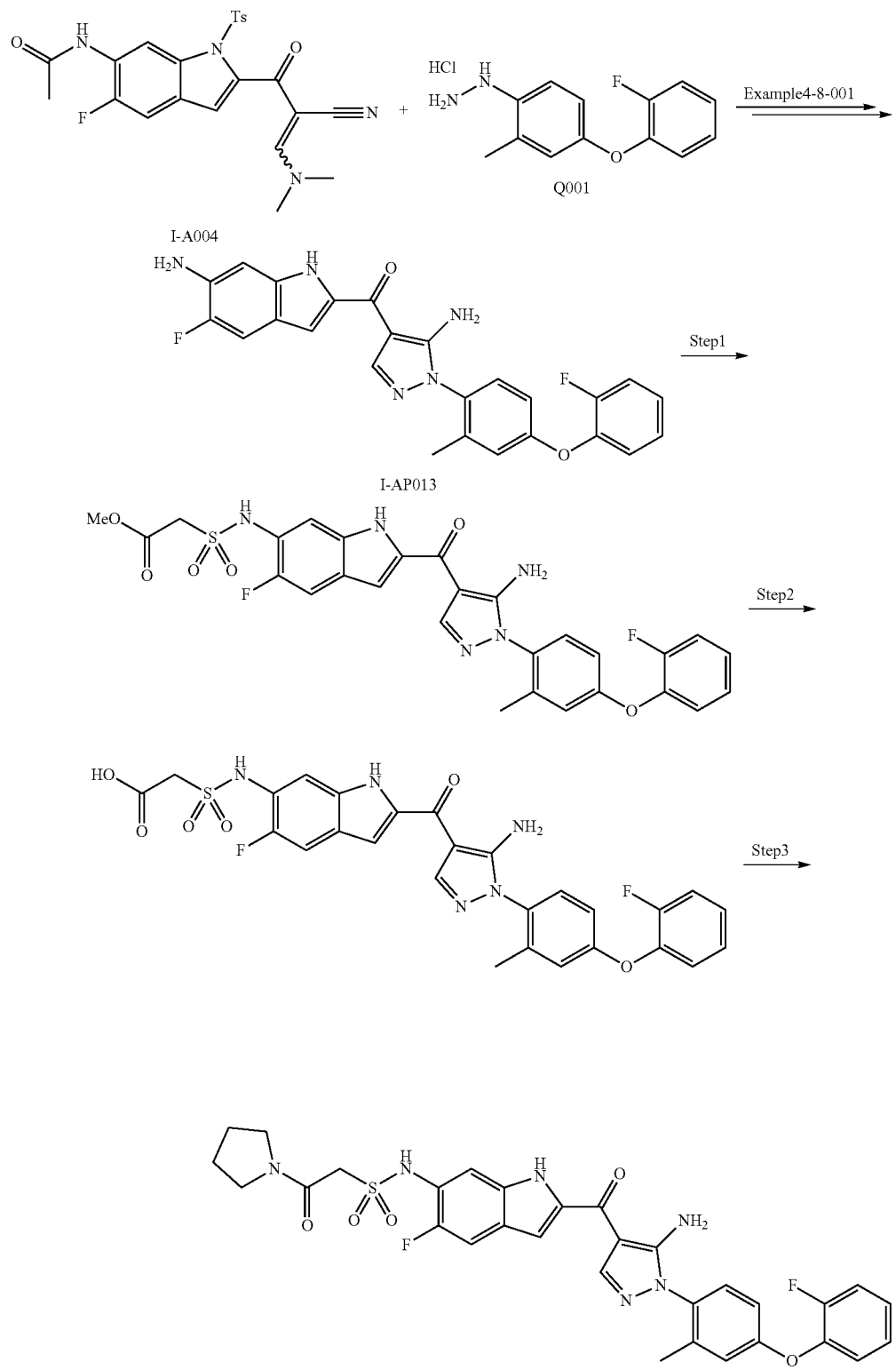

Step 1

Synthesis of methyl 2-(N-(2-(5-amino-1-(4-(2-fluorophenoxy)-2-methylphenyl)-1H-pyrazole-4-carbonyl)-5-fluoro-1H-indol-6-yl)sulfamoyl)acetate Aniline I-AP013 synthesized in Example 4-8-001 (194 mg) was dissolved in dichloromethane (2 mL), and triethylamine (0.146 mL) and methyl 2-chlorosulfonylacetate (0.42 M solution in tetrahydrofuran, 1 mL) were added at 0° C. Then, the mixture was stirred at 25° C. for one hour. The reaction solution was diluted with dichloromethane (20 mL) and washed with 1 M hydrochloric acid (20 mL) and the organic layer was then dried over magnesium sulfate. After removing the drying agent by filtration, the filtrate was concentrated, and the resulting residue was purified by silica gel column chromatography (ethyl acetate/hexane, 0%→60%) to give the target compound (82 mg).

Step 2

Synthesis of 2-(N-(2-(5-amino-1-(4-(2-fluorophenoxy)-2-methylphenyl)-1H-pyrazole-4-carbonyl)-5-fluoro-1H-indol-6-yl)sulfamoyl)acetic acid Methyl 2-(N-(2-(5-amino-1-(4-(2-fluorophenoxy)-2-methylphenyl)-1H-pyrazole-4-carbonyl)-5-fluoro-1H-indol-6-yl)sulfamoyl)acetate obtained in Step 1 (80 mg) and a 4 M aqueous sodium hydroxide solution (0.168 mL) were added to methanol (1.5 mL) and the mixture was stirred at 50° C. for two hours. 1 M hydrochloric acid (5 mL) was added to the reaction solution and the mixture was extracted with ethyl acetate (10 mL). The organic layer was dried over magnesium sulfate, the drying agent was removed by filtration, and the filtrate was concentrated to give the target compound (71 mg).

Step 3

Synthesis of N-(2-(5-amino-1-(4-(2-fluorophenoxy)-2-methylphenyl)-1H-pyrazole-4-carbonyl)-5-fluoro-1H-indol-6-yl)-2-oxo-2-(pyrrolidin-1-yl)ethanesulfonamide 2-(N-(2-(5-Amino-1-(4-(2-fluorophenoxy)-2-methylphenyl)-1H-pyrazole-4-carbonyl)-5-fluoro-1H-indol-6-yl)sulfamoyl)acetic acid obtained in Step 2 (70 mg), pyrrolidine (0.020 mL), 1-(3-dimethylaminopropyl)-3-ethylcarbodiimide hydrochloride (46 mg), diisopropylethylamine (0.042 mL), and HOBt (18 mg) were added to dichloromethane (1.5 mL) at 25° C. and the reaction solution was stirred at 25° C. for 18 hours. The reaction solution was purified by PrepHPLC, and the eluate containing the target compound was desalted by PL-HCO3 MP SPE. The eluate after desalting was concentrated under reduced pressure to give the target compound (23 mg).

(Corresponding Enamine, Hydrazine, and Amine)

| Example No. | Enamine | Hydrazine | Amine |
|---|---|---|---|
| 4-26-001 | I-A004 | Q001 | |

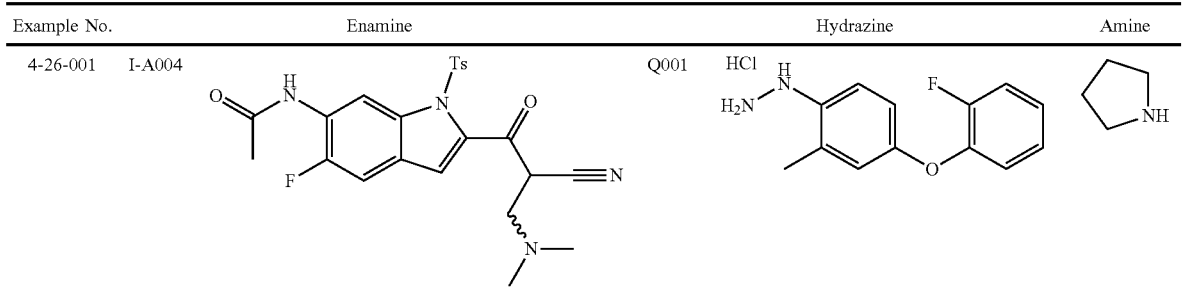

(Synthesized Compound)

| Example No. | Compound | m/z (M + H) | Retention Time (Minute) | LCMS Measurement Condition |
|---|---|---|---|---|
| 4-26-001 | | 635 | 2.46 | B1 |

Example 5-1-061

Synthesis of N-[2-[5-amino-1-[4-(2-fluorophenoxy)-2-methylphenyl]pyrazole-4-carbonyl]-5-hydroxy-1H-indol-6-yl]methanesulfonamide

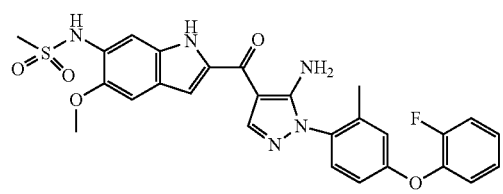

→

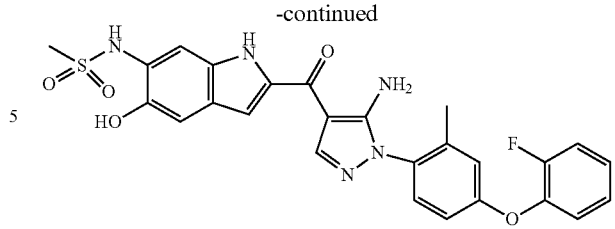

N-[2-[5-Amino-1-[4-(2-fluorophenoxy)-2-methylphenyl]pyrazole-4-carbonyl]-5-methoxy-1H-indol-6-yl]methanesulfonamide obtained in Example 4-1-004 (75 mg) was dissolved in dichloromethane (2 mL) and a boron tribromide-dichloromethane solution (1.0 M) was added at 0° C. The reaction solution was concentrated under reduced pressure and the resulting residue was purified by reversed phase chromatography (0.05% TFA-MeCN—H$_2$O) to give the target compound (26 mg).

(Corresponding Enamine and Hydrazine)

| Example No. | | Enamine | | Hydrazine |
|---|---|---|---|---|
| 5-1-061 | I-H048 | 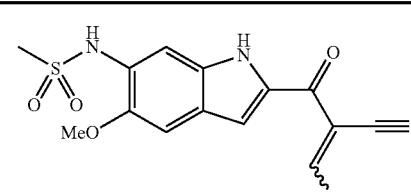 | Q001 HCl | 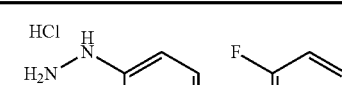 |

(Synthesized Compound)

| Example No. | Compound | m/z (M + H) | Retention Time (Minute) | LCMS Measurement Condition |
|---|---|---|---|---|
| 5-1-061 |  | 536 | 0.95 | AA Rev.5 |

Example 5-1-163

Synthesis of (5-amino-1-(4-(2-fluorophenoxy)-3-methylphenyl)-1H-pyrazol-4-yl)(6-amino-5-((1-isopropylpiperidin-4-yl)oxy)-1H-indol-2-yl)methanone

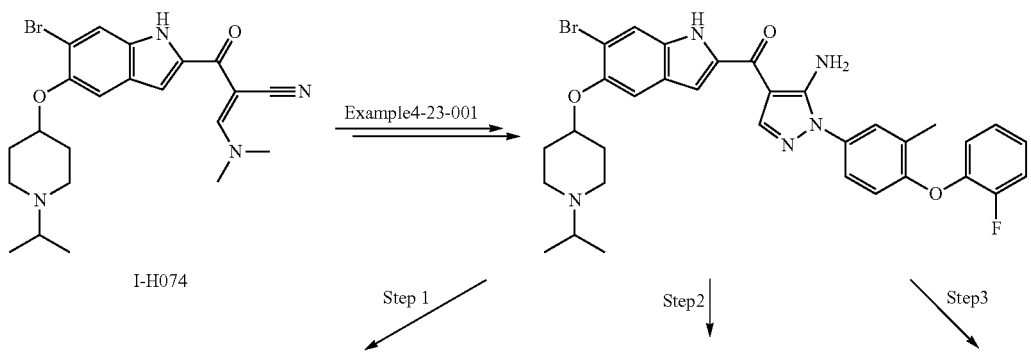

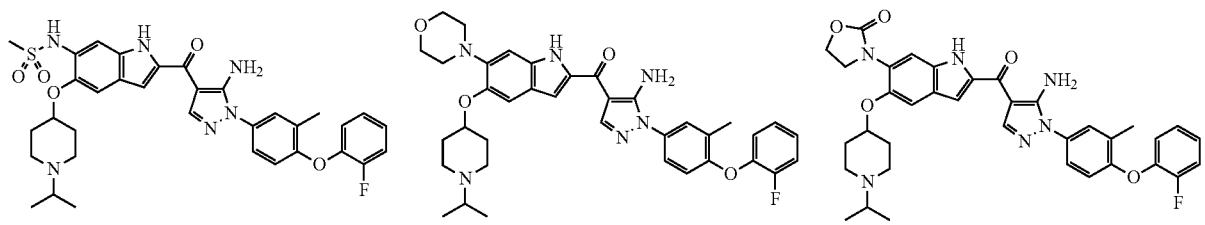

The compound of Example 5-1-163 was obtained by performing the similar operation as in Example 4-23-001 using Enamine I-H074 and hydrazine (Q019).

Step 1

Synthesis of N-(2-(5-amino-1-(4-(2-fluorophenoxy)-3-methylphenyl)-1H-pyrazole-4-carbonyl)-5-((1-isopropylpiperidin-4-yl)oxy)-1H-indol-6-yl)methanesulfonamide Methanesulfonyl chloride (11 mg) was allowed to act on the compound of Example 5-1-163 (40 mg) in pyridine (0.8 mL) at 25° C. for two hours, and the resulting reaction mixture was purified by PrepHPLC to give the target compound (3 mg).

Step 2

Synthesis of (5-amino-1-(4-(2-fluorophenoxy)-3-methylphenyl)-1H-pyrazol-4-yl)(5-((1-isopropylpiperidin-4-yl)oxy)-6-morpholino-1H-indol-2-yl)methanone The compound of Example 5-1-163 (40 mg), bis(2-bromoethyl) ether (64 mg), sodium iodide (82 mg), and potassium carbonate (57 mg) were allowed to act on each other in NMP (1.6 mL) at 100° C. for two hours and the resulting reaction mixture was purified by PrepHPLC to give the target compound (41 mg).

Step 3

Synthesis of 3-(2-(5-amino-1-(4-(2-fluorophenoxy)-3-methylphenyl)-1H-pyrazole-4-carbonyl)-5-((1-isopropylpiperidin-4-yl)oxy)-1H-indol-6-yl)oxazolidin-2-one Chloroethyl chloroformate (14 mg) was allowed to act on the compound of Example 5-1-163 (40 mg) in pyridine (1.6 mL) at 25° C. for 30 minutes. The reaction solution was concentrated under reduced pressure. After diluting the resulting residue with DMF (2 mL), potassium carbonate (47 mg) and sodium iodide (21 mg) were added and the mixture was stirred at 80° C. The reaction mixture was purified by MPLC (0.05% TFA-water-acetonitrile) using C18 column to give the target compound (46 mg).

The compounds shown in the following tables could be obtained by respectively using the corresponding enamines, hydrazines and the like.

(Corresponding Enamines, Hydrazines, and Reagents)

| Example No. | | Enamine | | Hydrazine | Reagent Reacted with Aniline |
|---|---|---|---|---|---|
| 5-1-163 | I-H074 | (bromo-indole-piperidine enamine with CN and N-dimethyl) | Q019 | HCl, H2N-NH-(3-methyl-4-(2-fluorophenoxy)phenyl) | No Reagent |
| 5-1-156 | I-H074 | (same enamine) | Q019 | HCl, same hydrazine | methanesulfonyl chloride |
| 5-1-174 | I-H074 | (same enamine) | Q019 | HCl, same hydrazine | 1-bromo-2-(2-bromoethoxy)ethane |
| 5-1-178 | I-H074 | (same enamine) | Q019 | HCl, same hydrazine | 2-chloroethyl chloroformate |
| 5-1-183 | I-H074 | (same enamine) | T002 | HCl, H2N-NH-(4-methyl-6-(2,6-difluorophenoxy)pyridin-3-yl) | No Reagent |

-continued

| Example No. | | Enamine | Hydrazine | Reagent Reacted with Aniline |
|---|---|---|---|---|
| 5-1-184 | I-H074 | (enamine structure: 6-bromo-5-((1-isopropylpiperidin-4-yl)oxy)-1H-indole with dimethylaminomethylene cyanoketone) | T002 HCl (5-hydrazinyl-2-(2,6-difluorophenoxy)-4-methylpyridine) | methanesulfonyl chloride |
| 5-1-185 | I-H074 | (same enamine) | T002 HCl (same hydrazine) | 1-bromo-2-(2-bromoethoxy)ethane |
| 5-1-186 | I-H074 | (same enamine) | T002 HCl (same hydrazine) | 2-chloroethyl carbonochloridate |
| 5-1-189 | I-H074 | (same enamine) | Q001 HCl (4-(2-fluorophenoxy)-2-methylphenylhydrazine) | methanesulfonyl chloride |
| 5-1-190 | I-H074 | (same enamine) | Q001 HCl (same hydrazine) | 1-bromo-2-(2-bromoethoxy)ethane |

-continued

| Example No. | | Enamine | Hydrazine | | Reagent Reacted with Aniline |
|---|---|---|---|---|---|
| 5-1-192 | I-H074 | [structure: 6-bromo-5-(1-isopropylpiperidin-4-yloxy)-1H-indol-2-yl enamine with CN and NMe2] | Q001 HCl | [structure: 2-methyl-4-(2-fluorophenoxy)phenylhydrazine] | [structure: 2-chloroethyl chloroformate] |
| 5-1-232 | I-H076 | [structure: 6-bromo-5-(1-BOC-piperidin-4-yloxy)-1H-indol-2-yl enamine with CN and NMe2] | Q019 HCl | [structure: 3-methyl-4-(2-fluorophenoxy)phenylhydrazine] | No Reagent |
| 5-1-231 | I-H076 | [structure: 6-bromo-5-(1-BOC-piperidin-4-yloxy)-1H-indol-2-yl enamine with CN and NMe2] | Q019 HCl | [structure: 3-methyl-4-(2-fluorophenoxy)phenylhydrazine] | [structure: methanesulfonyl chloride] |
| 5-1-095 | I-A004 | [structure: 6-acetamido-5-fluoro-1-tosyl-1H-indol-2-yl enamine with CN and NMe2] | Q001 HCl | [structure: 2-methyl-4-(2-fluorophenoxy)phenylhydrazine] | [structure: 2-chloroethyl chloroformate] |
| 5-1-097 | I-A004 | [structure: 6-acetamido-5-fluoro-1-tosyl-1H-indol-2-yl enamine with CN and NMe2] | T002 HCl | [structure: 5-(2,6-difluorophenoxy)-4-methylpyridin-2-yl hydrazine] | [structure: 2-chloroethyl chloroformate] |

-continued

| Example No. | | Enamine | | Hydrazine | | Reagent Reacted with Aniline |
|---|---|---|---|---|---|---|
| 5-1-106 | I-A010 | (structure) | Q001 | (structure) | | (structure) |
| 5-1-160 | I-A010 | (structure) | Q019 | (structure) | | (structure) |
| 5-1-168 | I-A011 | (structure) | Q019 | (structure) | | (structure) |
| 5-1-177 | B-B026 | (structure) | Q019 | (structure) | | (structure) |
| 5-1-094 | I-A010 | (structure) | Q001 | (structure) | | (structure) |
| 5-1-159 | I-A010 | (structure) | Q019 | (structure) | | (structure) |
| 5-1-100 | I-A004 | (structure) | T002 | (structure) | | (structure) |

-continued

| Example No. | Enamine | Hydrazine | Reagent Reacted with Aniline |
|---|---|---|---|
| 5-1-119 | I-A004 | Q001 | |
| 5-1-173 | B-B026 | Q019 | |

(Synthesized Compounds)

| Example No. | Compound | m/z (M + H) | Retention Time (Minute) | LCMS Measurement Condition |
|---|---|---|---|---|
| 5-1-163 | | 583 | 0.96 | AA Rev.11 |
| 5-1-156 | | 661 | 0.97 | AA Rev.11 |

-continued

| Example No. | Compound | m/z (M + H) | Retention Time (Minute) | LCMS Measurement Condition |
|---|---|---|---|---|
| 5-1-174 | | 653 | 1.02 | AA Rev.11 |
| 5-1-178 | | 653 | 0.94 | AA Rev.11 |
| 5-1-183 | | 602 | 0.9 | AA Rev.11 |
| 5-1-184 | | 680 | 1.02 | TFA Rev.5 |

-continued

| Example No. | Compound | m/z (M + H) | Retention Time (Minute) | LCMS Measurement Condition |
|---|---|---|---|---|
| 5-1-185 | | 672 | 1 | TFA Rev.5 |
| 5-1-186 | | 672 | 1 | TFA Rev.5 |
| 5-1-189 | | 661 | 0.92 | AA Rev.11 |
| 5-1-190 | | 653 | 1.03 | TFA Rev.5 |

-continued

| Example No. | Compound | m/z (M + H) | Retention Time (Minute) | LCMS Measurement Condition |
|---|---|---|---|---|
| 5-1-192 | | 653 | 0.93 | AA Rev.11 |
| 5-1-232 | | 595 | 0.92 | TFA Rev.7 |
| 5-1-231 | | 673 | 1.07 | AA Rev.11 |
| 5-1-095 | | 530 | 1 | AA Rev.11 |

-continued
| Example No. | Compound | m/z (M + H) | Retention Time (Minute) | LCMS Measurement Condition |
|---|---|---|---|---|
| 5-1-097 | 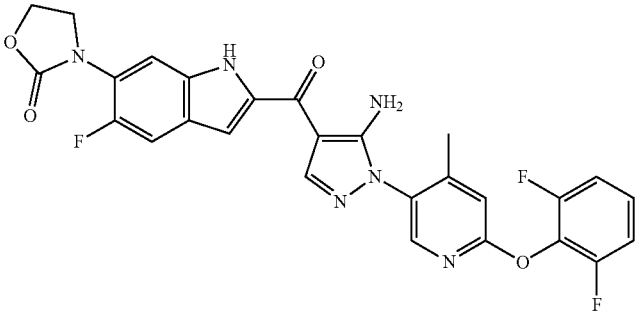 [SMILES: Cc1cc(Oc2c(F)cccc2F)ncc1-n1ncc(C(=O)c2cc3cc(F)c(N4CCOC4=O)cc3[nH]2)c1N] | 549 | 0.97 | AA Rev.11 |
| 5-1-106 | 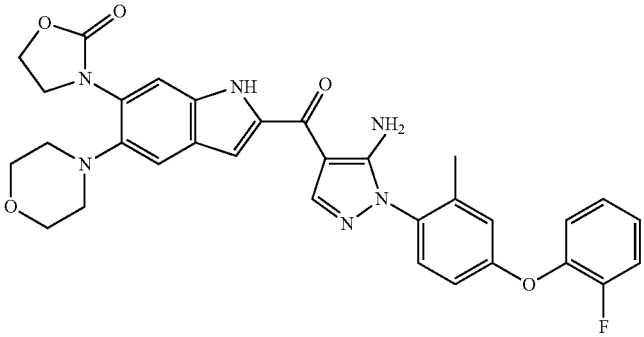 [SMILES: Cc1cc(Oc2ccccc2F)ccc1-n1ncc(C(=O)c2cc3cc(N4CCOCC4)c(N4CCOC4=O)cc3[nH]2)c1N] | 597 | 1 | AA Rev.11 |
| 5-1-160 | 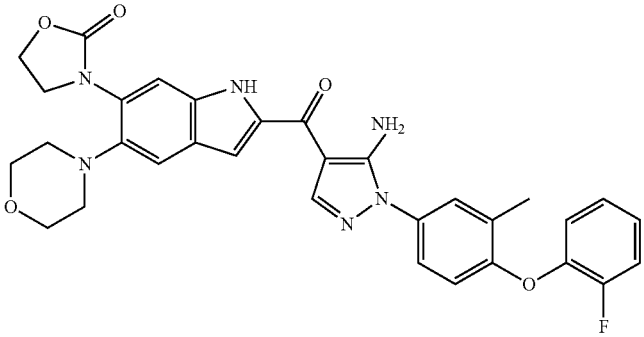 [SMILES: Cc1cc(-n2ncc(C(=O)c3cc4cc(N5CCOCC5)c(N5CCOC5=O)cc4[nH]3)c2N)ccc1Oc1ccccc1F] | 597 | 1.24 | TFA Rev.5 |
| 5-1-168 | 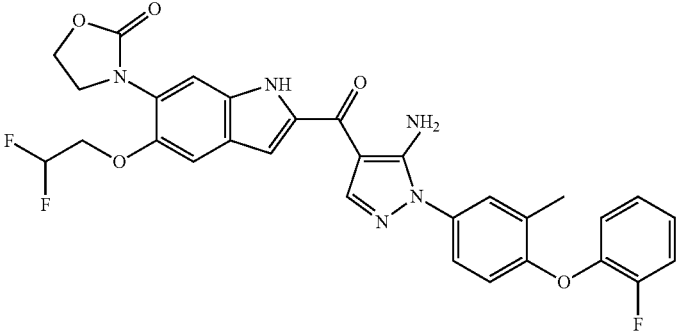 [SMILES: Cc1cc(-n2ncc(C(=O)c3cc4cc(OCC(F)F)c(N5CCOC5=O)cc4[nH]3)c2N)ccc1Oc1ccccc1F] | 592 | 1.28 | TFA Rev.5 |

-continued

| Example No. | Compound | m/z (M + H) | Retention Time (Minute) | LCMS Measurement Condition |
|---|---|---|---|---|
| 5-1-177 | | 578 | 1.3 | TFA Rev.5 |
| 5-1-094 | | 597 | 1.1 | AA Rev.11 |
| 5-1-159 | | 597 | 1.11 | AA Rev.11 |
| 5-1-100 | | 549 | 1.07 | AA Rev.11 |

| Example No. | Compound | m/z (M + H) | Retention Time (Minute) | LCMS Measurement Condition |
|---|---|---|---|---|
| 5-1-119 | | 530 | 1.32 | TFA Rev.5 |
| 5-1-173 | | 578 | 1.42 | TFA Rev.5 |

Example 5-1-220

Synthesis of (5-amino-1-(4-(2-fluorophenoxy)-3-methylphenyl)-1H-pyrazol-4-yl)(6-bromo-5-((1-(oxetan-3-yl)piperidin-4-yl)oxy)-1H-indol-2-yl)methanone

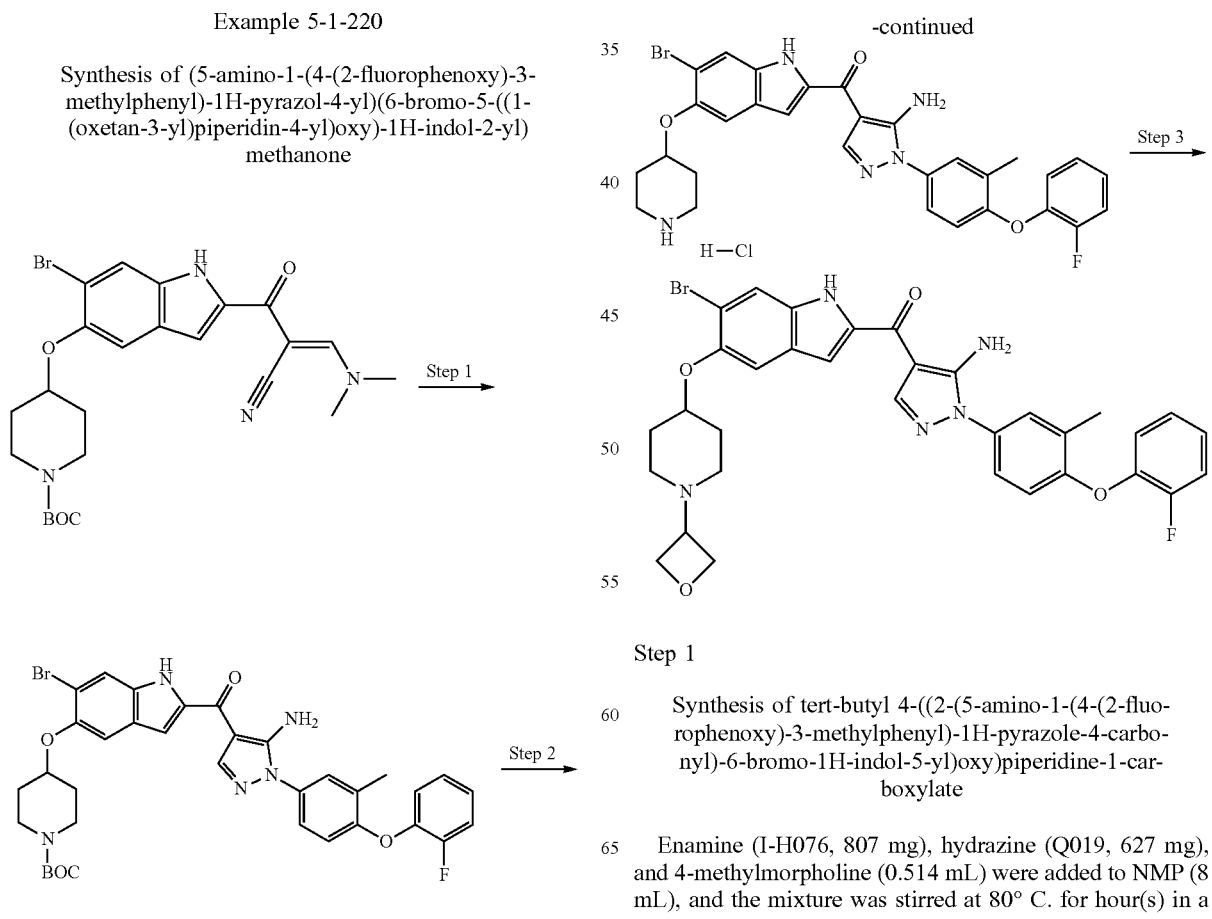

Step 1

Synthesis of tert-butyl 4-((2-(5-amino-1-(4-(2-fluorophenoxy)-3-methylphenyl)-1H-pyrazole-4-carbonyl)-6-bromo-1H-indol-5-yl)oxy)piperidine-1-carboxylate Enamine (I-H076, 807 mg), hydrazine (Q019, 627 mg), and 4-methylmorpholine (0.514 mL) were added to NMP (8 mL), and the mixture was stirred at 80° C. for hour(s) in a nitrogen atmosphere. The mixture was purified by C18 column (0.1% formic acid-water-acetonitrile) and a silica gel column (hexane/ethyl acetate) to give the target compound (841 mg).

Step 2

Synthesis of (5-amino-1-(4-(2-fluorophenoxy)-3-methylphenyl)-1H-pyrazol-4-yl)(6-bromo-5-(piperidin-4-yloxy)-1H-indol-2-yl)methanone hydrochloride tert-Butyl 4-((2-(5-amino-1-(4-(2-fluorophenoxy)-3-methylphenyl)-1H-pyrazole-4-carbonyl)-6-bromo-1H-indol-5-yl)oxy)piperidine-1-carboxylate obtained in Step 1 (697 mg) was suspended in ethyl acetate (15 mL), a 4 M hydrochloric acid-ethyl acetate solution (15 mL) was added at 25° C. and the mixture was stirred at 25° C. for one hour. After adding ethyl acetate (15 mL) to the reaction solution, the precipitate was collected by filtration and washed with ethyl acetate (5 mL). The resulting powder was dried under reduced pressure to give the target compound (616 mg).

Step 3

Synthesis of (5-amino-1-(4-(2-fluorophenoxy)-3-methylphenyl)-1H-pyrazol-4-yl)(6-bromo-5-((1-(oxetan-3-yl)piperidin-4-yl)oxy)-1H-indol-2-yl)methanone (5-Amino-1-(4-(2-fluorophenoxy)-3-methylphenyl)-1H-pyrazol-4-yl)(6-bromo-5-(piperidin-4-yloxy)-1H-indol-2-yl)methanone hydrochloride obtained in Step 2 (96 mg), oxetan-3-one (32 mg), triethylamine (66 mg), sodium triacetoxyborohydride (191 mg), and acetic acid (54 mg) were suspended in dichloromethane (2 mL) and the mixture was stirred at 25° C. for two days. The solvent was evaporated and the residue was then purified by C18 column (0.1% formic acid-water-acetonitrile) to give the target compound (96 mg).

The following compounds were synthesized by the similar method as in Example 5-1-220 using the corresponding enamines and hydrazines.
(Corresponding Enamines, Hydrazines, and Amines)

| Example No. | Enamine | | Hydrazine | | Reagent Reacted with Amine |
|---|---|---|---|---|---|
| 5-1-220 | I-H076 | [structure] | Q019 | [structure] | [structure] |
| 5-1-222 | I-H076 | [structure] | T002 | [structure] | [structure] |
| 5-1-219 | I-H076 | [structure] | Q019 | [structure] | [structure] |

| Example No. | Enamine | | Hydrazine | Reagent Reacted with Amine |
|---|---|---|---|---|
| 5-1-224 | I-H076 | 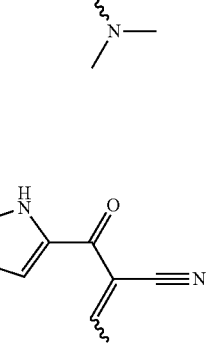 | T002 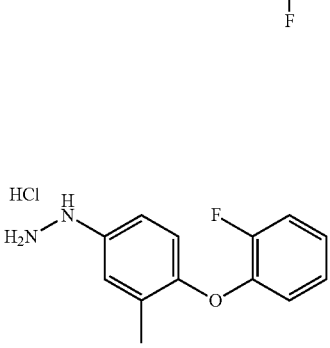 | 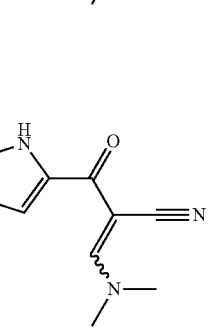 |
| 5-1-218 | I-H076 | 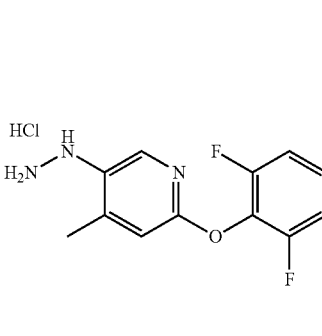 | Q019 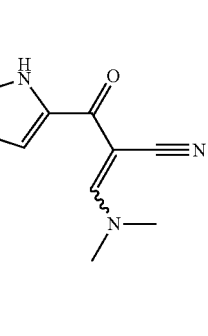 | 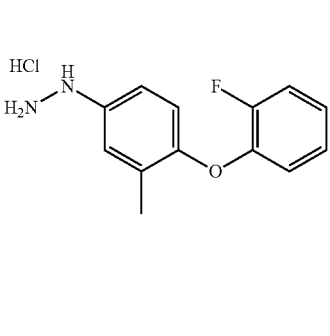 [SMILES: Cl ; Cc1cc(NN)ccc1Oc1ccccc1F] |
| 5-1-221 | I-H076 | 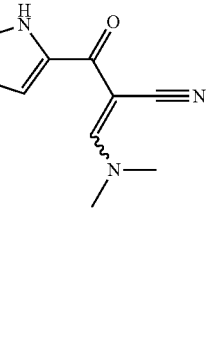 | T002 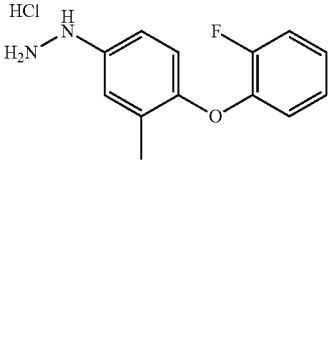 |  |
| 5-1-234 | I-H082 |  | Q019 | |
| 5-1-235 | I-H083 | | Q019 | |

-continued

| Example No. | | Enamine | | Hydrazine | Reagent Reacted with Amine |
|---|---|---|---|---|---|
| 5-1-216 | I-H076 | | Q019 | HCl, H2N-NH-(3-methyl-4-(2-fluorophenoxy)phenyl) | cyclopentanone |
| 5-1-223 | I-H076 | | T002 | HCl, H2N-NH-(4-methyl-6-(2,6-difluorophenoxy)pyridin-3-yl) | cyclopentanone |
| 5-1-225 | I-H076 | | Q019 | HCl, H2N-NH-(3-methyl-4-(2-fluorophenoxy)phenyl) | TBS-O-CH2-CHO |
| 5-1-226 | I-H076 | | T002 | HCl, H2N-NH-(4-methyl-6-(2,6-difluorophenoxy)pyridin-3-yl) | TBS-O-CH2-CHO |
| 5-1-227 | I-H076 | | Q019 | HCl, H2N-NH-(3-methyl-4-(2-fluorophenoxy)phenyl) | 3-oxothietane 1,1-dioxide |

-continued

| Example No. | Enamine | Hydrazine | Reagent Reacted with Amine |
|---|---|---|---|
| 5-1-228 | I-H076 | T002 HCl | |

(Synthesized Compounds)

| Example No. | Compound | m/z (M + H) | Retention Time (Minute) | LCMS Measurement Condition |
|---|---|---|---|---|
| 5-1-220 | | 660 | 1.11 | AA Rev.11 |
| 5-1-222 | | 679 | 1.05 | AA Rev.11 |
| 5-1-219 | | 644 | 1.06 | TFA Rev.6 |

-continued

| Example No. | Compound | m/z (M + H) | Retention Time (Minute) | LCMS Measurement Condition |
|---|---|---|---|---|
| 5-1-224 | | 663 | 1.12 | AA Rev.11 |
| 5-1-218 | | 658 | 1.14 | AA Rev.11 |
| 5-1-221 | | 677 | 1.09 | AA Rev.11 |
| 5-1-234 | | 598 | 1.09 | TFA Rev.7 |

-continued

| Example No. | Compound | m/z (M + H) | Retention Time (Minute) | LCMS Measurement Condition |
|---|---|---|---|---|
| 5-1-235 | | 614 | 1.14 | AA Rev.11 |
| 5-1-216 | | 672 | 1.12 | AA Rev.11 |
| 5-1-223 | | 691 | 1.07 | AA Rev.11 |
| 5-1-225 | | 648 | 1.01 | TFA Rev.6 |

| Example No. | Compound | m/z (M + H) | Retention Time (Minute) | LCMS Measurement Condition |
|---|---|---|---|---|
| 5-1-226 | 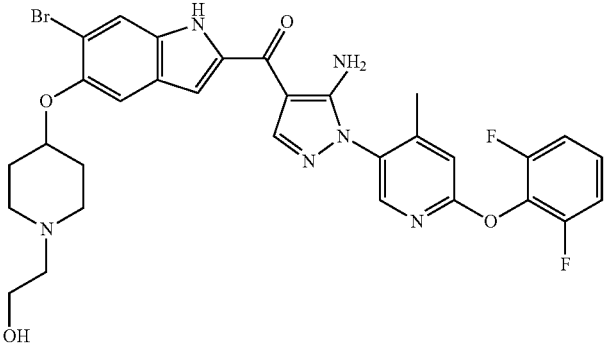 [SMILES: Cc1cc(Oc2c(F)cccc2F)ncc1-n1ncc(C(=O)c2cc3cc(OC4CCN(CCO)CC4)c(Br)cc3[nH]2)c1N] | 667 | 0.95 | TFA Rev.6 |
| 5-1-227 | 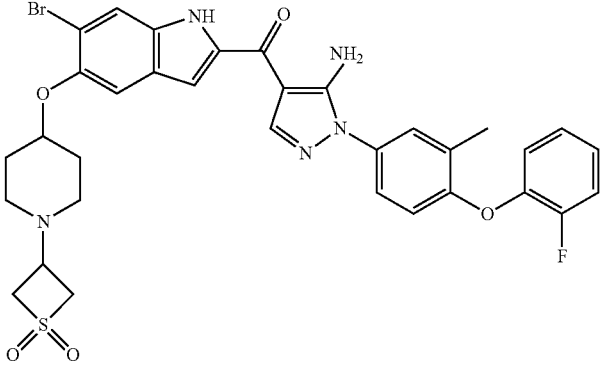 [SMILES: Cc1cc(-n2ncc(C(=O)c3cc4cc(OC5CCN(C6CS(=O)(=O)C6)CC5)c(Br)cc4[nH]3)c2N)ccc1Oc1ccccc1F] | 708 | 1.07 | AA Rev.11 |
| 5-1-228 | 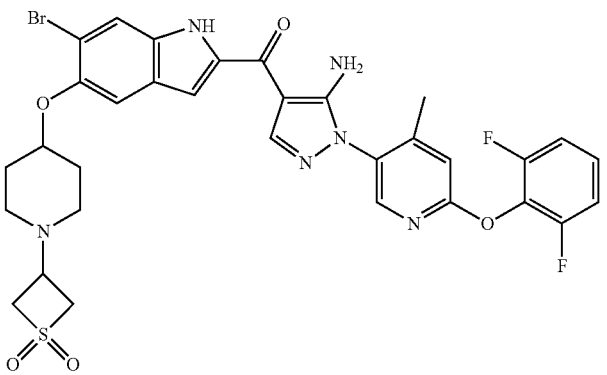 [SMILES: Cc1cc(Oc2c(F)cccc2F)ncc1-n1ncc(C(=O)c2cc3cc(OC4CCN(C5CS(=O)(=O)C5)CC4)c(Br)cc3[nH]2)c1N] | 727 | 1.02 | AA Rev.11 |

Example 5-1-229
Synthesis of (5-amino-1-(6-(2,6-difluorophenoxy)-4-methylpyridin-3-yl)-1H-pyrazol-4-yl)(5-((1-isopropylpiperidin-4-yl)oxy)-6-(1-(methylsulfonyl)piperidin-4-yl)-1H-indol-2-yl)methanone
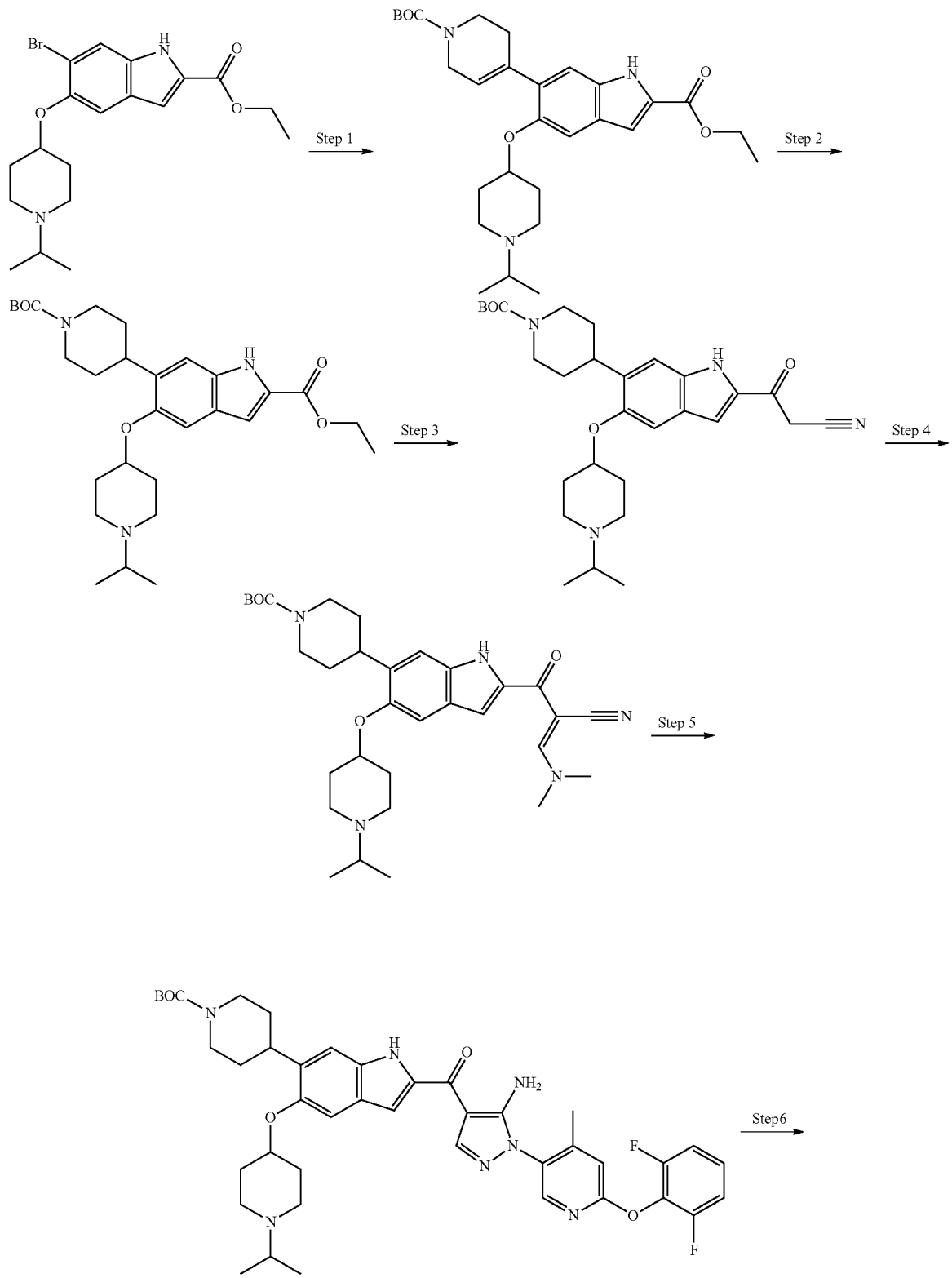

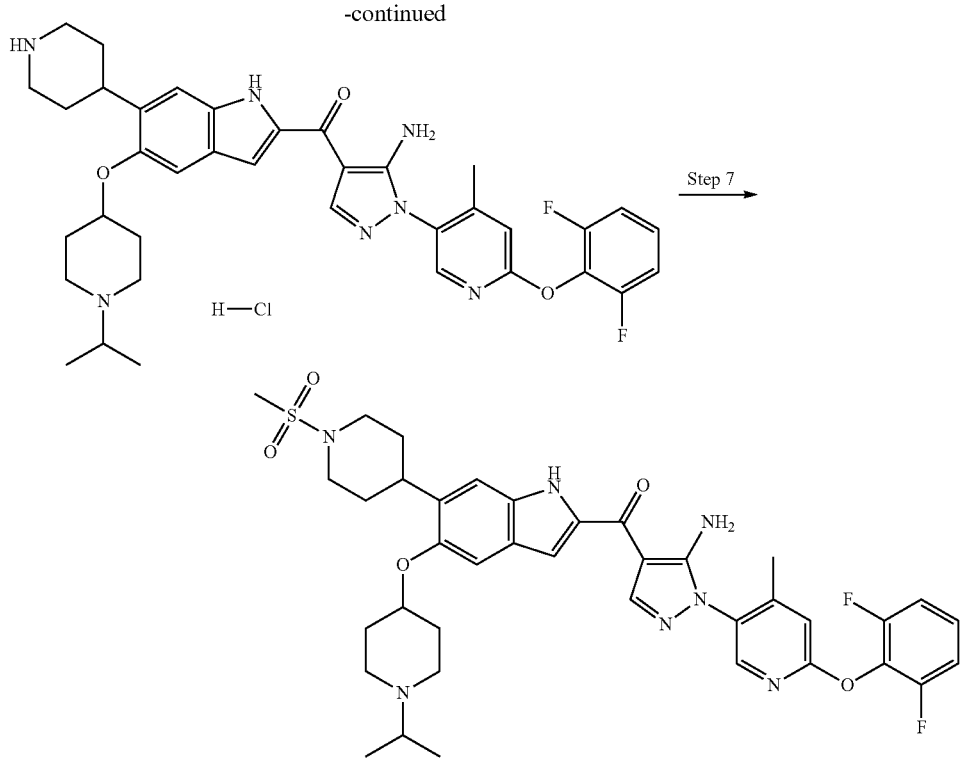

-continued

Step 1

Synthesis of ethyl 6-(1-(tert-butoxycarbonyl)-1,2,3,6-tetrahydropyridin-4-yl)-5-((1-isopropylpiperidin-4-yl)oxy)-1H-indole-2-carboxylate 6-Bromo-5-((1-isopropylpiperidin-4-yl)oxy)-1H-indole-2-carboxylic acid obtained in Step 5 of Example 1-4-11 (1.38 g), tert-butyl 4-(4,4,5,5-tetramethyl-1,3,2-dioxaborolan-2-yl)-1,2,3,6-tetrahydropyridine-1-carboxylate (1.59 g), X-Phos (0.246 g), palladium acetate (58 mg), and potassium phosphate (1.37 g) were stirred in DMF/water (17.5 mL/2.0 mL) at 100° C. for two hours. After purifying the reaction mixture by C18 column (formic acid/water/acetonitrile), the fractions of the target compound were desalted and then concentrated under reduced pressure to give the target compound (1.4 g).

Step 2

Synthesis of ethyl 6-(1-(tert-butoxycarbonyl)piperidin-4-yl)-5-((1-isopropylpiperidin-4-yl)oxy)-1H-indole-2-carboxylate Ethyl 6-(1-(tert-butoxycarbonyl)-1,2,3,6-tetrahydropyridin-4-yl)-5-((1-isopropylpiperidin-4-yl)oxy)-1H-indole-2-carboxylate obtained in Step 1 (1.35 g) and palladium carbon (3.09 g) were added to ethanol (1 mL) and the mixture was stirred for one hour in a hydrogen stream. After removing the insoluble matter by filtration, the filtrate was washed with ethyl acetate and then concentrated under reduced pressure to give the target compound (1.05 g).

Step 3

Synthesis of tert-butyl 4-(2-(2-cyanoacetyl)-5-((1-isopropylpiperidin-4-yl)oxy)-1H-indol-6-yl)piperidine-1-carboxylate Ethyl 6-(1-(tert-butoxycarbonyl)piperidin-4-yl)-5-((1-isopropylpiperidin-4-yl)oxy)-1H-indole-2-carboxylate obtained in Step 2 (990 mg) and acetonitrile (0.302 mL) were added to THF (20 mL), LHMDS (1 M, 11.6 mL) was added at 0° C., and the mixture was stirred for one hour. A 10% aqueous acetic acid solution (26.5 mL) and then water (20 mL) was added at 0° C., after which the mixture was extracted with ethyl acetate (20 mL×3). The combined organic layers were washed with saturated saline and then dried over sodium sulfate. After removing the drying agent by filtration, the filtrate was concentrated under reduced pressure to give the target compound (1.46 g).

Step 4

Synthesis of (E)-tert-butyl 4-(2-(2-cyano-3-(dimethylamino)acryloyl)-5-((1-isopropylpiperidin-4-yl)oxy)-1H-indol-6-yl)piperidine-1-carboxylate tert-Butyl 4-(2-(2-cyanoacetyl)-5-((1-isopropylpiperidin-4-yl)oxy)-1H-indol-6-yl)piperidine-1-carboxylate obtained in Step 3 (1.46 g) was added to THF (29 mL), DMF-DMA (0.576 mL) was then added, and the mixture was stirred at 25° C. for one hour. The reaction solution was concentrated under reduced pressure to give the target compound (1.5 g).

Step 5

Synthesis of tert-butyl 4-(2-(5-amino-1-(6-(2,6-difluorophenoxy)-4-methylpyridin-3-yl)-1H-pyrazole-4-carbonyl)-5-((1-isopropylpiperidin-4-yl)oxy)-1H-indol-6-yl)piperidine-1-carboxylate (E)-tert-Butyl 4-(2-(2-cyano-3-(dimethylamino)acryloyl)-5-((1-isopropylpiperidin-4-yl)oxy)-1H-indol-6-yl)piperidine-1-carboxylate obtained in Step 4 (100 mg), 4-methylmorpholine (0.059 mL), and hydrazine (T002, 77 mg) were added to NMP (3 mL) and the mixture was stirred at 100° C. for one hour in a nitrogen atmosphere. The reaction mixture was purified by C18 column (formic acid/water/acetonitrile) to give the target compound (60 mg).

Step 6

Synthesis of (5-amino-1-(6-(2,6-difluorophenoxy)-4-methylpyridin-3-yl)-1H-pyrazol-4-yl)(5-((1-isopropylpiperidin-4-yl)oxy)-6-(piperidin-4-yl)-1H-indol-2-yl)methanone Chlorotrimethylsilane (0.189 mL) was added to a solution of tert-butyl 4-(2-(5-amino-1-(6-(2,6-difluorophenoxy)-4-methylpyridin-3-yl)-1H-pyrazole-4-carbonyl)-5-isopropylpiperidin-4-yl)oxy)-1H-indol-6-yl)piperidine-1-carboxylate obtained in Step 5 (57 mg) in 2,2,2-trifluoroethanol (1.7 mL) at 25° C. and the mixture was stirred for 1.5 hours. The reaction solution was concentrated under reduced pressure to give the target compound (75 mg).

Step 7

Synthesis of (5-amino-1-(6-(2,6-difluorophenoxy)-4-methylpyridin-3-yl)-1H-pyrazol-4-yl)(5-((1-isopropylpiperidin-4-yl)oxy)-6-(1-(methylsulfonyl)piperidin-4-yl)-1H-indol-2-yl)methanone (5-Amino-1-(6-(2,6-difluorophenoxy)-4-methylpyridin-3-yl)-1H-pyrazol-4-yl)(5-isopropylpiperidin-4-yl)oxy)-6-(piperidin-4-yl)-1H-indol-2-yl)methanone obtained in Step 6 (50 mL) was dissolved in pyridine (2 mL) and after adding methanesulfonyl chloride (0.058 mL) at 25° C., the mixture was stirred for five hours. The reaction mixture was purified by C18 column (formic acid/water/acetonitrile) to give the target compound (40 mg).

Example 5-1-230

The compound of Example 5-1-230 was obtained by using hydrazine Q019 instead of T002 in Step 5 of Example 5-1-229 and performing the operations of Steps 6 and 7 of Example 5-1-229.

(Corresponding Enamines and Hydrazines)

| Example No. | | Enamine | | Hydrazine |
|---|---|---|---|---|
| 5-1-229 | I-H074 | 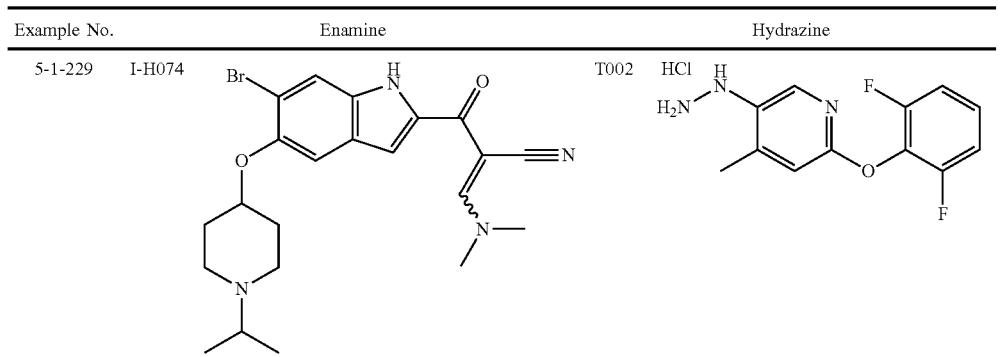 | T002 | |
| 5-1-230 | I-H074 | 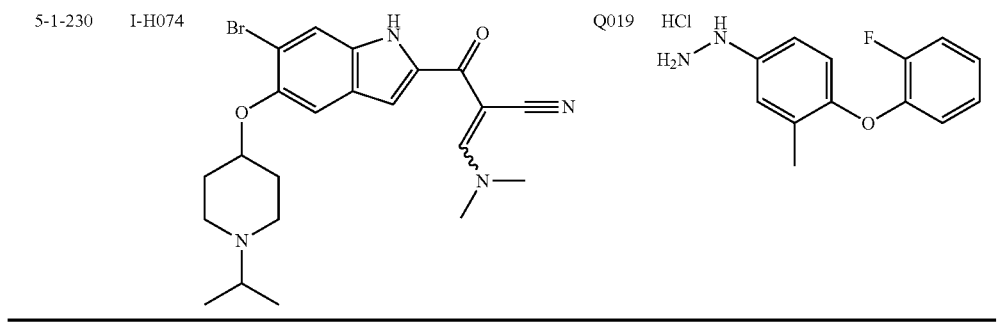 | Q019 | |

(Synthesized Compounds)

| Example No. | Compound | m/z (M + H) | Retention Time (Minute) | LCMS Measurement Condition |
|---|---|---|---|---|
| 5-1-229 | | 748 | 0.97 | AA Rev.11 |
| 5-1-230 | | 729 | 1.08 | TFA Rev.6 |

Example 5-1-236

Synthesis of (5-amino-1-(4-(2-fluorophenoxy)-3-methylphenyl)-1H-pyrazol-4-yl)(5-((1-isopropylpiperidin-4-yl)oxy)-6-(1-methyl-1H-pyrazol-4-yl)-1H-indol-2-yl)methanone

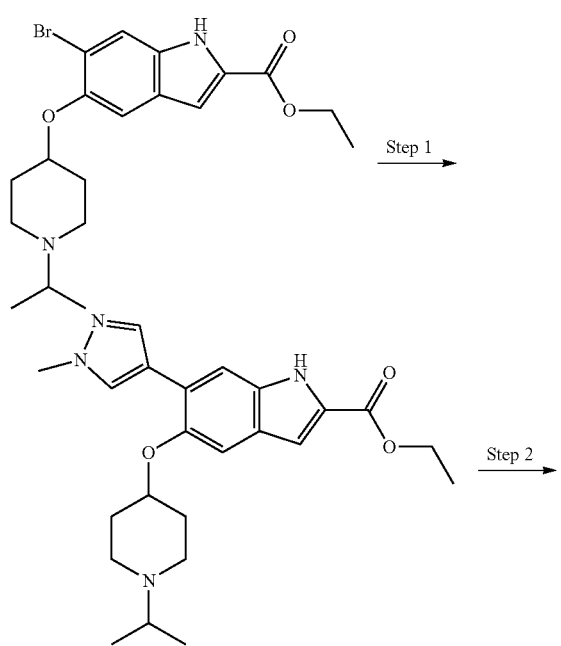

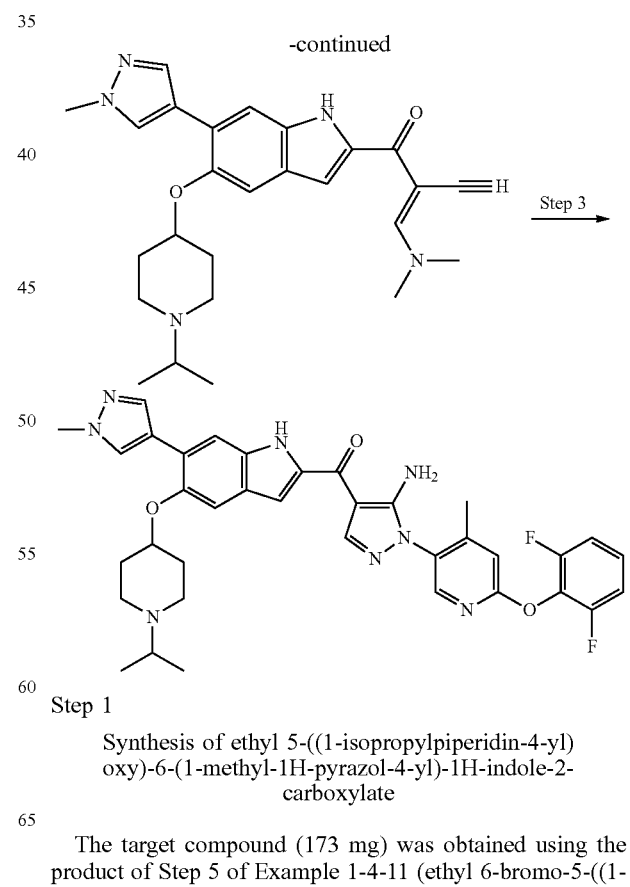

Step 1

Synthesis of ethyl 5-((1-isopropylpiperidin-4-yl)oxy)-6-(1-methyl-1H-pyrazol-4-yl)-1H-indole-2-carboxylate The target compound (173 mg) was obtained using the product of Step 5 of Example 1-4-11 (ethyl 6-bromo-5-((1- isopropylpiperidin-4-yl)oxy)-1H-indole-2-carboxylate, 500 mg) and using 1-methyl-4-(4,4,5,5-tetramethyl-1,3,2-dioxaborolan-2-yl)-1H-pyrazole instead of tert-butyl 4-(4,4,5,5-tetramethyl-1,3,2-dioxaborolan-2-yl)-1,2,3,6-tetrahydropyridine-1-carboxylate of Step 1 of Example 5-1-229.

Step 2

Synthesis of (E)-3-(dimethylamino)-2-(5-((1-isopropylpiperidin-4-yl)oxy)-6-(1-methyl-1H-pyrazol-4-yl)-1H-indole-2-carbonyl)acrylonitrile The target compound (148 mg) was obtained by performing the similar operations as in Steps 3 and 4 of Example 5-1-229 for ethyl 5-((1-isopropylpiperidin-4-yl)oxy)-6-(1-methyl-1H-pyrazol-4-yl)-1H-indole-2-carboxylate obtained in Step 1 (143 mg).

Step 3

Synthesis of (5-amino-1-(4-(2-fluorophenoxy)-3-methylphenyl)-1H-pyrazol-4-yl)(5-((1-isopropylpiperidin-4-yl)oxy)-6-(1-methyl-1H-pyrazol-4-yl)-1H-indol-2-yl)methanone (E)-3-(dimethylamino)-2-(5-((1-isopropylpiperidin-4-yl)oxy)-6-(1-methyl-1H-pyrazol-4-yl)-1H-indole-2-carbonyl)acrylonitrile obtained in Step 2 (75 mg), hydrazine (Q019, 65 mg), and 4-methylmorpholine (49 mg) were stirred in NMP (1.8 mL) at 100° C. for two hours in a nitrogen atmosphere. The reaction mixture was purified by C18 column (TFA-water-acetonitrile) to give the target compound (39 mg).

The following compounds were obtained by performing the similar operation as in Example 5-1-236 using the boronate esters and hydrazines in the table.
(Corresponding Enamines, Hydrazines, and Boronate Esters)

| Example No. | | | Hydrazine | Boronate Ester |
|---|---|---|---|---|
| 5-1-236 | Q019 | HCl | (structure) | (structure) |
| 5-1-249 | T002 | HCl | (structure) | (structure) |
| 5-1-240 | Q019 | HCl | (structure) | (structure) |
| 5-1-241 | T002 | HCl | (structure) | (structure) |
| 5-1-238 | Q019 | HCl | (structure) | (structure) |
| 5-1-239 | T002 | HCl | (structure) | (structure) |

(Synthesized Compounds)

| Example No. | Compound | m/z (M + H) | Retention Time (Minute) | LCMS Measurement Condition |
|---|---|---|---|---|
| 5-1-236 | | 648 | 1.08 | TFA Rev.7 |
| 5-1-249 | | 667 | 0.94 | AA Rev.11 |
| 5-1-240 | | 646 | 1.06 | TFA Rev.7 |
| 5-1-241 | | 665 | 0.95 | AA Rev.11 |

-continued
| Example No. | Compound | m/z (M + H) | Retention Time (Minute) | LCMS Measurement Condition |
|---|---|---|---|---|
| 5-1-238 | 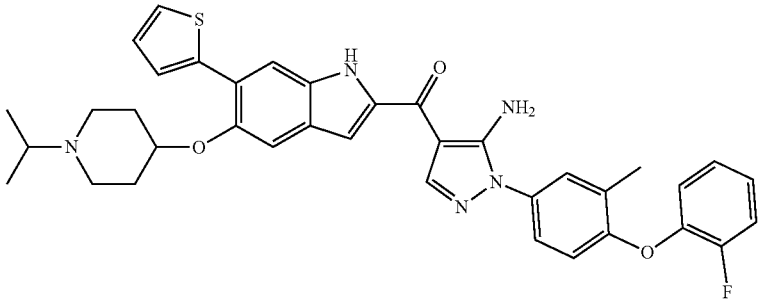 [SMILES: Cc1cc(-n2ncc(C(=O)c3cc4cc(OC5CCN(C(C)C)CC5)c(-c5cccs5)cc4[nH]3)c2N)ccc1Oc1ccccc1F] | 650 | 1.19 | TFA Rev.7 |
| 5-1-239 | 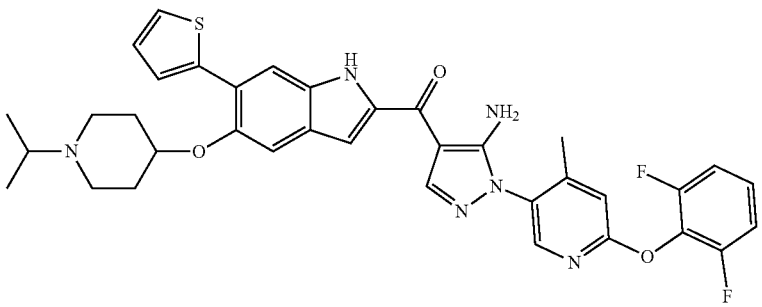 [SMILES: Cc1cc(Oc2c(F)cccc2F)ncc1-n1ncc(C(=O)c2cc3cc(OC4CCN(C(C)C)CC4)c(-c4cccs4)cc3[nH]2)c1N] | 669 | 1.12 | TFA Rev.7 |

Example 5-1-247

Synthesis of (5-amino-1-(4-(2-fluorophenoxy)-3-methylphenyl)-1H-pyrazol-4-yl)(5-((1-isopropylpiperidin-4-yl)oxy)-6-(tetrahydro-2H-pyran-4-yl)-1H-indol-2-yl)methanone

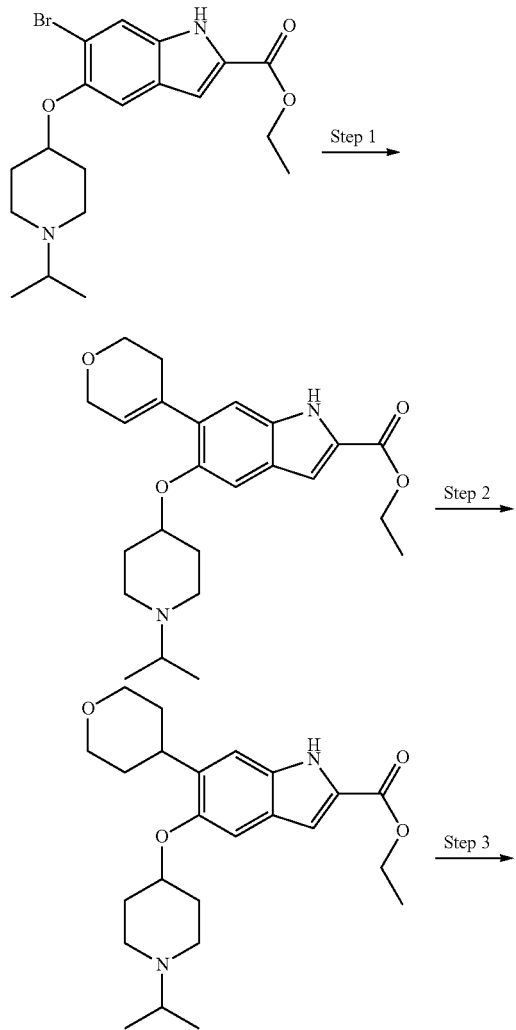

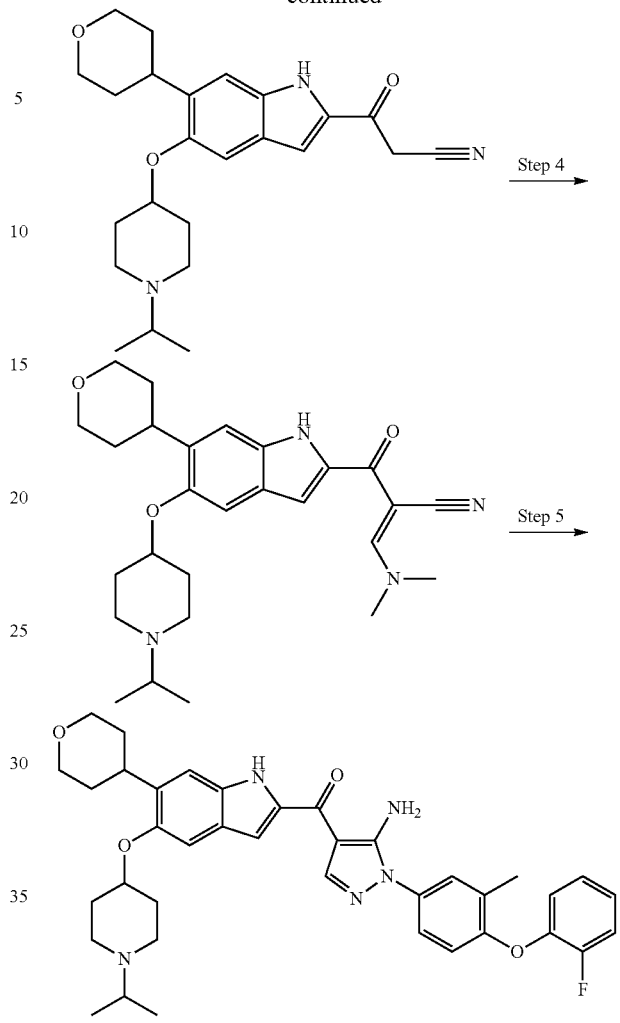

The target compound (Example 5-1-247) was obtained by using 3,6-dihydro-2H-pyran-4-boronic acid pinacol ester in Step 1 of Example 5-1-229 and further performing the similar operations as in Steps 2 to 5 of Example 5-1-229.

The compound of Example 5-1-248 was obtained using hydrazine T002 instead of hydrazine Q019 in Step 5 of Example 5-1-229.

| Example No. | Compound | Hydrazine | | m/z (M + H) | Retention Time (Minute) | LCMS Measurement Condition |
|---|---|---|---|---|---|---|
| 5-1-247 | | Q019 | HCl | 652 | 1.06 | AA Rev.11 |

-continued

| Example No. | Compound | Hydrazine | m/z (M + H) | Retention Time (Minute) | LCMS Measurement Condition |
|---|---|---|---|---|---|
| 5-1-248 | (structure) | T002 (structure) | 671 | 0.99 | AA Rev.11 |

Example 5-1-256 and the Like

The target compounds shown in the following tables were obtained by using ethyl 6-bromo-5-(2,2-difluoroethoxy)-1H-indole-2-carboxylate as a starting material, and by performing the similar treatment as in Example 5-1-247 by respectively using the boronate esters and hydrazines shown in the tables.

(Corresponding Hydrazines and Boronate Esters)

| Example No. | | Hydrazine | Boronate Ester |
|---|---|---|---|
| 5-1-256 | Q019 | (structure) | (structure) |
| 5-1-258 | Q019 | (structure) | (structure) |
| 5-1-257 | T002 | (structure) | (structure) |
| 5-1-259 | T002 | (structure) | (structure) |
| 5-1-261 | Q019 | (structure) | (structure) |

-continued
| Example No. | | | Hydrazine | Boronate Ester |
|---|---|---|---|---|
| 5-1-262 | T002 | HCl | 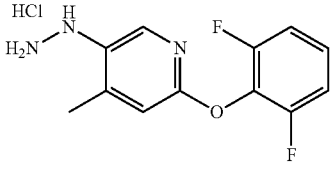 [SMILES: Cl ; Cc1cc(Oc2c(F)cccc2F)ncc1NN] | 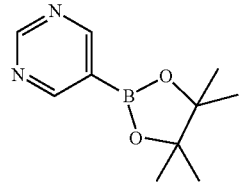 |
| 5-1-263 | Q019 | HCl | 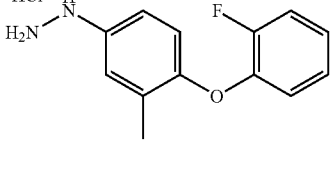 | 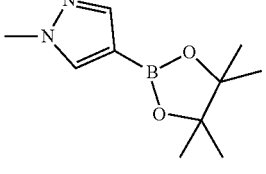 |
| 5-1-264 | T002 | HCl | 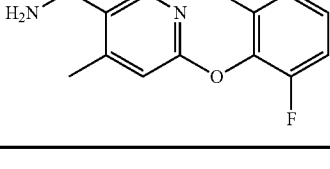 | 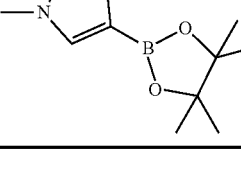 |
(Synthesized Compounds)
| Example No. | Compound | m/z (M + H) | Retention Time (Minute) | LCMS Measurement Condition |
|---|---|---|---|---|
| 5-1-256 | 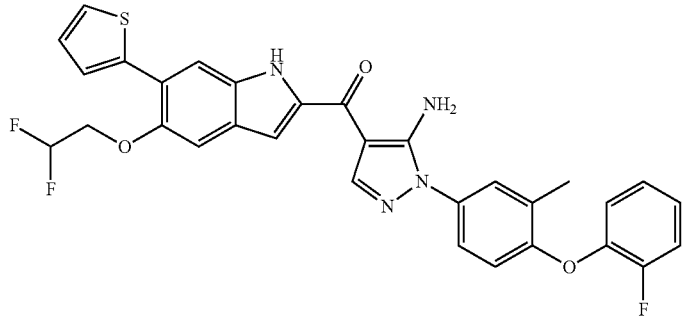 [SMILES: Cc1cc(-n2ncc(C(=O)c3cc4cc(OCC(F)F)c(-c5cccs5)cc4[nH]3)c2N)ccc1Oc1ccccc1F] | 589 | 1.47 | TFA Rev.7 |
| 5-1-258 | 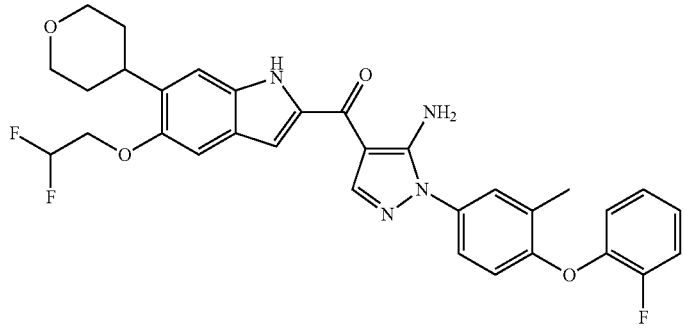 [SMILES: Cc1cc(-n2ncc(C(=O)c3cc4cc(OCC(F)F)c(C5CCOCC5)cc4[nH]3)c2N)ccc1Oc1ccccc1F] | 591 | 1.39 | TFA Rev.7 |

| Example No. | Compound | m/z (M + H) | Retention Time (Minute) | LCMS Measurement Condition |
|---|---|---|---|---|
| 5-1-257 | 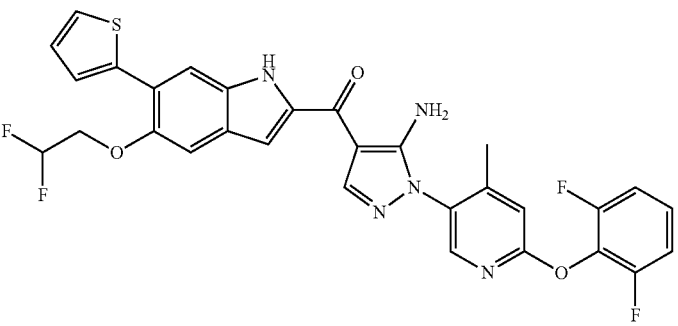 [SMILES: Cc1cc(Oc2c(F)cccc2F)ncc1-n1ncc(C(=O)c2cc3cc(OCC(F)F)c(-c4cccs4)cc3[nH]2)c1N] | 608 | 1.39 | TFA Rev.7 |
| 5-1-259 | 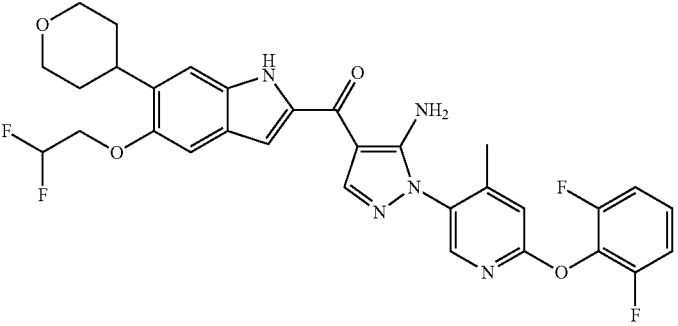 [SMILES: Cc1cc(Oc2c(F)cccc2F)ncc1-n1ncc(C(=O)c2cc3cc(OCC(F)F)c(C4CCOCC4)cc3[nH]2)c1N] | 610 | 1.31 | TFA Rev.7 |
| 5-1-261 | 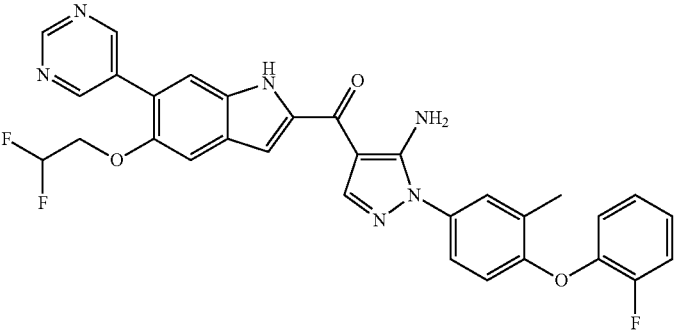 [SMILES: Cc1cc(-n2ncc(C(=O)c3cc4cc(OCC(F)F)c(-c5cncnc5)cc4[nH]3)c2N)ccc1Oc1ccccc1F] | 585 | 1.07 | AA Rev.11 |
| 5-1-262 | 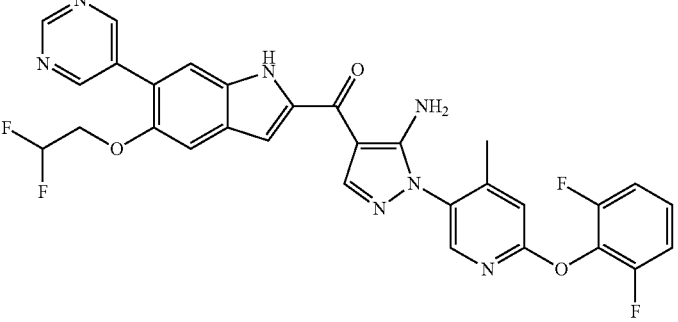 | 604 | 1.01 | AA Rev.11 |

-continued
| Example No. | Compound | m/z (M + H) | Retention Time (Minute) | LCMS Measurement Condition |
|---|---|---|---|---|
| 5-1-263 | | 587 | 1.29 | TFA Rev.7 |
| 5-1-264 | | 606 | 1.02 | AA Rev.11 |
Example 5-1-302
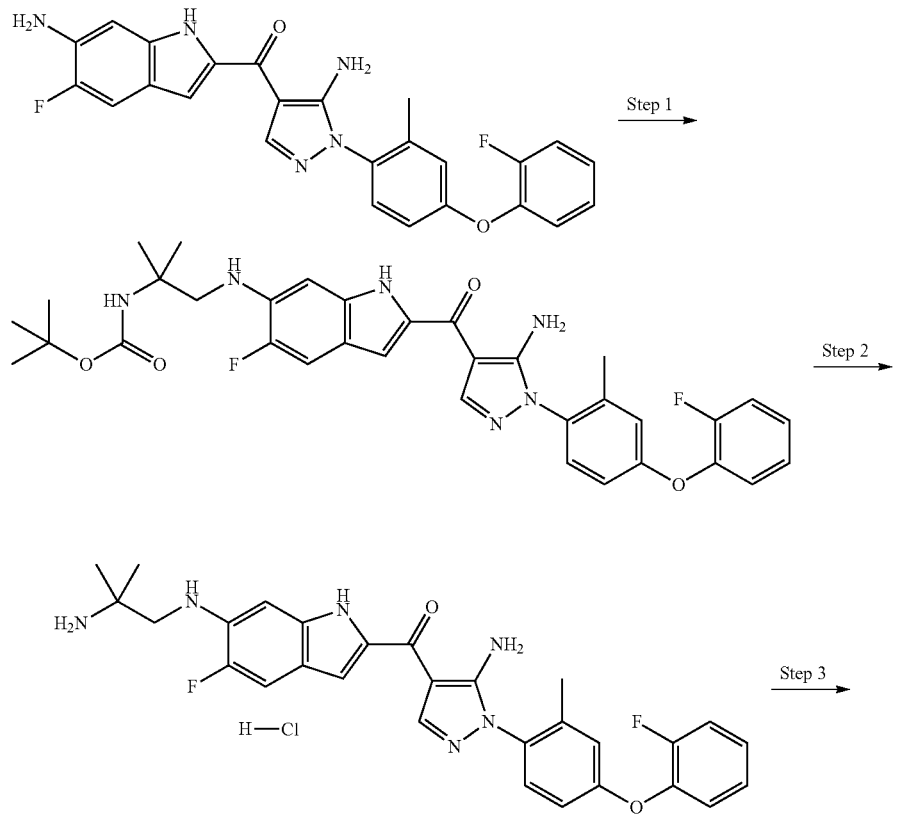

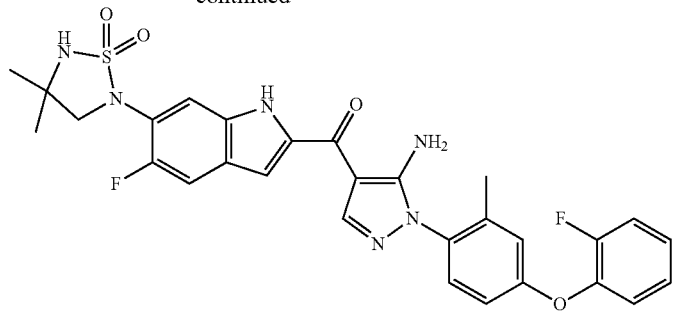

Step 1

Synthesis of tert-butyl (1-((2-(5-amino-1-(4-(2-fluorophenoxy)-2-methylphenyl)-1H-pyrazole-4-carbonyl)-5-fluoro-1H-indol-6-yl)amino)-2-methylpropan-2-yl)carbamate Aniline I-AP013 synthesized in Example 4-8-001 (100 mg), tert-butyl (2-methyl-1-oxopropan-2-yl)carbamate (86 mg), and acetic acid (0.062 mL) were added to dichloromethane (2 mL) and sodium triacetoxyborohydride (138 mg) was then added at 0° C. In a nitrogen stream, the mixture was stirred at 25° C. for three hours, after which an aqueous sodium bicarbonate solution and ethyl acetate were added and the organic layer was separated. The organic layer was washed with 20% saline solution and then dried over sodium sulfate. After removing the drying agent by filtration, the filtrate was concentrated, and the resulting residue was purified by silica gel column chromatography (ethyl acetate/hexane) to give the target compound (208 mg).

Step 2

Synthesis of (5-amino-1-(4-(2-fluorophenoxy)-2-methylphenyl)-1H-pyrazol-4-yl)(6-((2-amino-2-methylpropyl)amino)-5-fluoro-1H-indol-2-yl)methanone hydrochloride tert-Butyl (1-((2-(5-amino-1-(4-(2-fluorophenoxy)-2-methylphenyl)-1H-pyrazole-4-carbonyl)-5-fluoro-1H-indol-6-yl)amino)-2-methylpropan-2-yl)carbamate obtained in Step 1 (129 mg) was dissolved in 2,2,2-trifluoroethanol and chloro(trimethyl)silane (0.156 mL) was added at 25° C. The reaction solution was stirred at 25° C. for four hours and then concentrated under reduced pressure. The crude product was used for the next reaction without purification.

Step 3

Synthesis of (5-amino-1-(4-(2-fluorophenoxy)-2-methylphenyl)-1H-pyrazol-4-yl)(6-(4,4-dimethyl-1,1-dioxido-1,2,5-thiadiazolidin-2-yl)-5-fluoro-1H-indol-2-yl)methanone (5-Amino-1-(4-(2-fluorophenoxy)-2-methylphenyl)-1H-pyrazol-4-yl)(6-((2-amino-2-methylpropyl)amino)-5-fluoro-1H-indol-2-yl)methanone hydrochloride obtained in Step 2 (75 mg) and sulfamide (39 mg) were added to pyridine (2 mL) and the mixture was stirred in a sealed tube at 110° C. for four hours. The reaction solution was concentrated under reduced pressure and the resulting residue was purified by silica gel column chromatography (hexane/ethyl acetate) to give the target compound (21 mg).

The compounds shown in the following tables could be obtained by respectively using the corresponding enamines and hydrazines and the like.

(Corresponding Enamines, Hydrazines, and Thiazolidine-Forming Reagents)

| Example No. | Enamine | Hydrazine | Thiazoazolidine Cyclization Reagent |
|---|---|---|---|
| 5-1-302 I-A004 | | Q001 | |
| 5-1-313 I-H057 | | T002 | |

-continued

| Example No. | | Enamine | Hydrazine | Thiazoazolidine Cyclization Reagent |
|---|---|---|---|---|
| 5-1-321 | I-A011 | | T002 | |
| 5-1-322 | I-A011 | | Q001 | |
| 5-1-323 | I-A011 | | Q001 | |
| 5-1-340 | B-B026 | | Q001 | |
| 5-1-398 | I-A004 | | T002 | |
| 5-1-399 | I-A004 | | T002 | |
| 5-1-400 | I-A004 | | T002 | |
| 5-1-403 | I-A004 | | Q001 | |

-continued

| Example No. | Enamine | | Hydrazine | | Thiazoazolidine Cyclization Reagent |
|---|---|---|---|---|---|
| 5-1-413 | I-A004 | | T001 | HCl | |
| 5-1-421 | I-A004 | | T001 | HCl | |
| 5-1-423 | B-8026 | | Q001 | HCl | |

(Synthesized Compounds)

| Example No. | Compound | m/z (M + H) | Retention Time (Minute) | LCMS Measurement Condition |
|---|---|---|---|---|
| 5-1-302 | | 593 | 1.04 | AA Rev.11 |
| 5-1-313 | | 608 | 1.02 | AA Rev.11 |

-continued

| Example No. | Compound | m/z (M + H) | Retention Time (Minute) | LCMS Measurement Condition |
|---|---|---|---|---|
| 5-1-321 | | 674 | 1.24 | TFA Rev.7 |
| 5-1-322 | | 655 | 1.28 | TFA Rev.7 |
| 5-1-323 | | 681 | 1.08 | AA Rev.11 |
| 5-1-340 | | 641 | 1.3 | TFA Rev.7 |

-continued

| Example No. | Compound | m/z (M + H) | Retention Time (Minute) | LCMS Measurement Condition |
|---|---|---|---|---|
| 5-1-398 | | 612 | 1.22 | TFA Rev.7 |
| 5-1-399 | | 638 | 1.29 | TFA Rev.7 |
| 5-1-400 | | 654 | 1.15 | TFA Rev.7 |
| 5-1-403 | | 635 | 1 | AA Rev.11 |

| Example No. | Compound | m/z (M + H) | Retention Time (Minute) | LCMS Measurement Condition |
|---|---|---|---|---|
| 5-1-413 | | 636 | 0.96 | AA Rev.11 |
| 5-1-421 | | 594 | 0.99 | AA Rev.11 |
| 5-1-423 | | 667 | 1.09 | AA Rev.11 |
Example 5-1-353
Synthesis of 3-(2-(5-amino-1-(4-(2-fluorophenoxy)-2-methylphenyl)-1H-pyrazole-4-carbonyl)-5-(2,2-difluoro ethoxy)-1H-indol-6-yl)-7-(oxetan-3-yl)-1,3,7-triazaspiro[4.4]nonane-2,4-dione
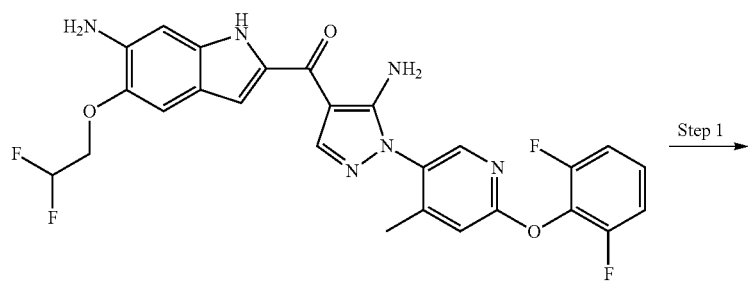
Step 1

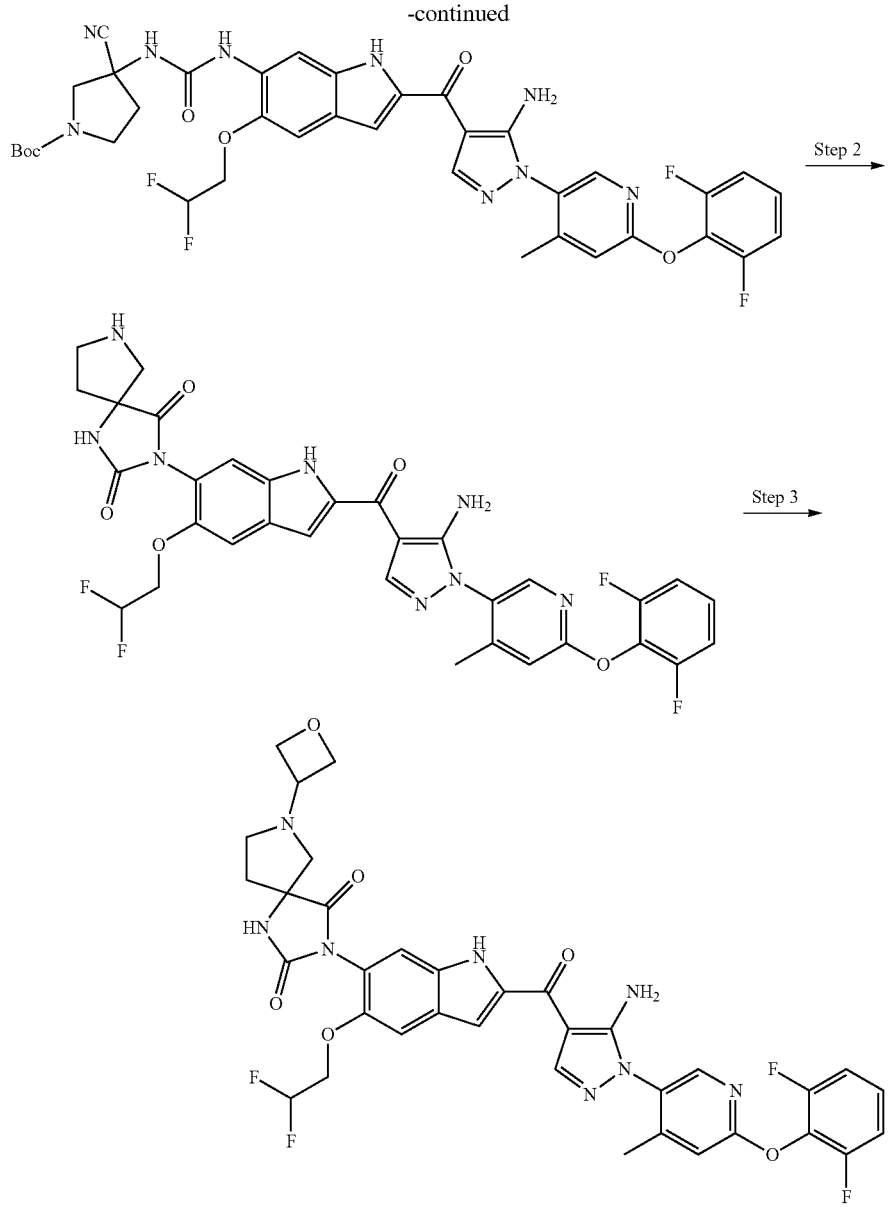

Step 1

Synthesis of tert-butyl 3-(3-(2-(5-amino-1-(6-(2,6-difluorophenoxy)-4-methylpyridin-3-yl)-1H-pyrazole-4-carbonyl)-5-(2,2-difluoroethoxy)-1H-indol-6-yl)ureido)-3-cyanopyrrolidine-1-carboxylate Triphosgene (180 mg) was added to a solution of (5-amino-1-(6-(2,6-difluorophenoxy)-4-methylpyridin-3-yl)-1H-pyrazol-4-yl)(6-amino-5-(2,2-difluoroethoxy)-1H-indol-2-yl)methanone hydrochloride (350 mg) obtained from enamine (I-A011) and hydrazine (Q001) in THF (8 mL), and the mixture was stirred at 25° C. for 30 minutes. After concentrating the reaction solution under reduced pressure, dichloromethane/hexane was added and the reaction solution was concentrated under reduced pressure. Triethylamine (0.388 mL) was added to a solution of the resulting residue and 3-amino-3-cyanopyrrolidine-1-carboxylic acid (256 mL) in THF (8 mL), and the mixture was stirred at 60° C. for five hours. After filtrating the reaction solution and washing with THF, the filtrate was concentrated under reduced pressure. The residue was crystallized from ethyl acetate/hexane to give the target compound (530 mg).

Step 2

Synthesis of 3-(2-(5-amino-1-(6-(2,6-difluorophenoxy)-4-methylpyridin-3-yl)-1H-pyrazole-4-carbonyl)-5-(2,2-difluoroethoxy)-1H-indol-6-yl)-1,3,7-triazaspiro[4.4]nonane-2,4-dione tert-Butyl 3-(3-(2-(5-amino-1-(6-(2,6-difluorophenoxy)-4-methylpyridin-3-yl)-1H-pyrazole-4-carbonyl)-5-(2,2-difluoroethoxy)-1H-indol-6-yl)ureido)-3-cyanopyrrolidine-1-carboxylate obtained in Step 1 (404 mg) was added to dioxane/methanol (4 mL/1 mL), concentrated hydrochloric acid (0.1 mL) was added, and the mixture was stirred at 100° C. for 18 hours. After concentrating the reaction solution under reduced pressure, the residue was diluted with a saturated aqueous sodium bicarbonate solution and the mixture was extracted with ethyl acetate. The organic layer was washed with saturated saline and then dried over sodium sulfate. After removing the drying agent by filtration, the filtrate was concentrated, and the resulting residue was purified by silica gel column chromatography (ethyl acetate/methanol) to give the target compound (178 mg).

Step 3

Synthesis of 3-(2-(5-amino-1-(4-(2-fluorophenoxy)-2-methylphenyl)-1H-pyrazole-4-carbonyl)-5-(2,2-difluoroethoxy)-1H-indol-6-yl)-7-(oxetan-3-yl)-1,3,7-triazaspiro[4.4]nonane-2,4-dione 3-(2-(5-Amino-1-(6-(2,6-difluorophenoxy)-4-methylpyridin-3-yl)-1H-pyrazole-4-carbonyl)-5-(2,2-difluoroethoxy)-1H-indol-6-yl)-1,3,7-triazaspiro[4.4]nonane-2,4-dione obtained in Step 2 (90 mg) and oxetan-3-one (0.052 mL) were added to THF/DMA (1 mL/1 mL), acetic acid (0.078 mL) and sodium triacetoxyborohydride (145 mg) were added, and the mixture was stirred at 25° C. for one hour. After diluting the reaction solution with ethyl acetate and a saturated aqueous sodium bicarbonate solution, the organic layer was washed with saturated saline and then dried over sodium sulfate. After removing the drying agent by filtration, the filtrate was concentrated, and the resulting residue was then crystallized from dichloromethane/hexane to give the target compound (57 mg).

The compounds shown in the following tables could be obtained by respectively using the enamines, the hydrazines, and the carbonyl compounds used in Step 3 in the tables. (Corresponding Enamines, Hydrazines, and Carbonyl Compounds)

| Example No. | Enamine | | Hydrazine | | Carbonyl Compound |
|---|---|---|---|---|---|
| 5-1-349 | I-A011 | [structure] | Q001 | HCl [structure] | [structure] |
| 5-1-353 | I-A011 | [structure] | Q001 | HCl [structure] | [structure] |
| 5-1-355 | I-A011 | [structure] | Q001 | HCl [structure] | [structure] |
| 5-1-348 | I-A011 | [structure] | T002 | HCl [structure] | [structure] |
| 5-1-352 | I-A011 | [structure] | T002 | HCl [structure] | [structure] |
| 5-1-354 | I-A011 | [structure] | T002 | HCl [structure] | [structure] |

-continued
| Example No. | | Enamine | | Hydrazine | Carbonyl Compound |
|---|---|---|---|---|---|
| 5-1-365 | I-H057 | 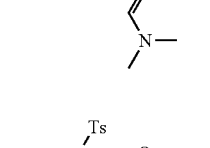 | Q001 | HCl 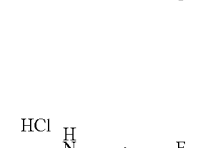 | |
| 5-1-393 | I-H057 | 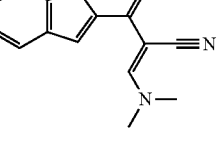 | Q001 | HCl 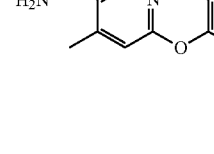 |  |
| 5-1-394 | I-H057 | 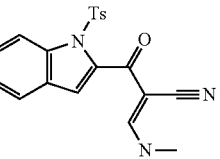 | Q001 | HCl 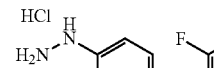 | 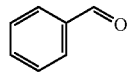 |
| 5-1-358 | I-H057 | 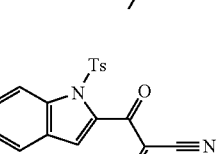 | T002 | HCl  | |
| 5-1-362 | I-H057 | 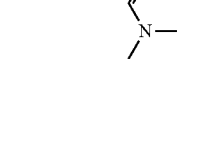 | T002 | HCl  |  |
| 5-1-363 | I-H057 | 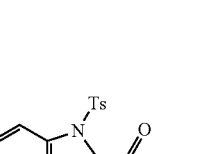 | T002 | HCl  |  |

(Synthesized Compounds)

| Example No. | Compound | m/z (M + H) | Retention Time (Minute) | LCMS Measurement Condition |
|---|---|---|---|---|
| 5-1-349 | | 660 | 0.94 | AA Rev.11 |
| 5-1-353 | | 716 | 0.96 | TFA Rev.7 |
| 5-1-355 | | 750 | 1.04 | TFA Rev.7 |
| 5-1-348 | | 679 | 0.92 | TFA Rev.7 |

-continued
| Example No. | Compound | m/z (M + H) | Retention Time (Minute) | LCMS Measurement Condition |
|---|---|---|---|---|
| 5-1-352 | 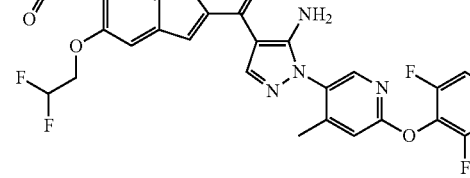 | 735 | 0.93 | TFA Rev.7 |
| 5-1-354 | 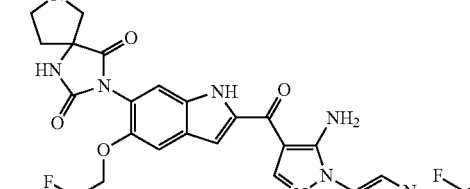 | 769 | 1.02 | TFA Rev.7 |
| 5-1-365 | 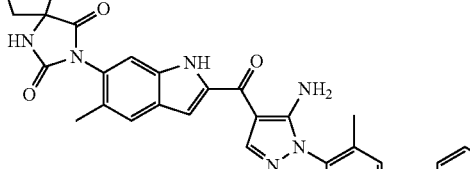 | 594 | 0.94 | TFA Rev.7 |
| 5-1-393 | 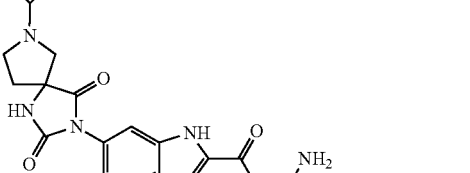 | 650 | 0.95 | TFA Rev.7 |

-continued

| Example No. | Compound | m/z (M + H) | Retention Time (Minute) | LCMS Measurement Condition |
|---|---|---|---|---|
| 5-1-394 | | 684 | 1.04 | TFA Rev.7 |
| 5-1-358 | | 613 | 0.91 | TFA Rev.7 |
| 5-1-362 | | 669 | 0.92 | TFA Rev.7 |
| 5-1-363 | | 703 | 1.07 | AA Rev.11 |

Example 5-1-385

Synthesis of (5-amino-1-(4-(2-fluorophenoxy)-3-methylphenyl)-1H-pyrazol-4-yl)(5-((1-cyclopentylpiperidin-4-yl)oxy)-6-(2-(trifluoromethyl)phenyl)-1H-indol-2-yl)methanone

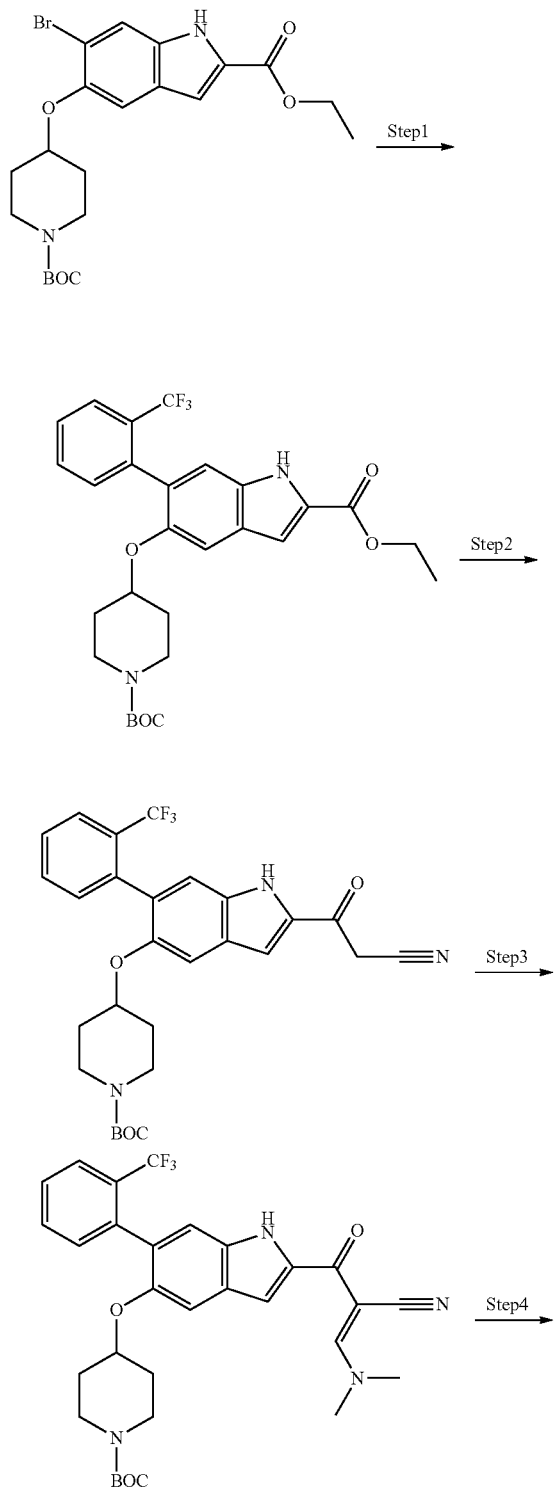

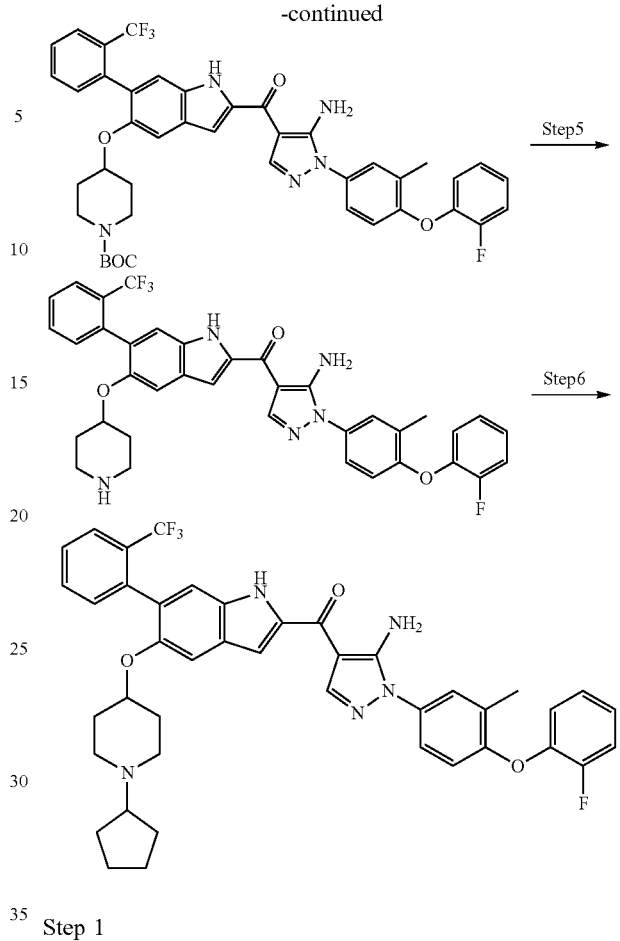

Step 1

Synthesis of ethyl 5-((1-(tert-butoxycarbonyl)piperidin-4-yl)oxy)-6-(2-(trifluoromethyl)phenyl)-1H-indole-2-carboxylate Ethyl 6-bromo-5-((1-(tert-butoxycarbonyl)piperidin-4-yl)oxy)-1H-indole-2-carboxylate obtained in Step 1 of Example 1-4-12 (650 mg), (2-trifluoromethyl)phenylboronic acid (977 mg), X-Phos (663 mg), palladium acetate (156 mg), and potassium phosphate (886 mg) were added to DMF/water (13 mL/1.3 mL), and the mixture was stirred at 100° C. for three hours in a nitrogen stream. The reaction mixture was purified by C18 column (TFA-water-acetonitrile) to give the target compound (695 mg).

Step 2

Synthesis of tert-butyl 4-((2-(2-cyanoacetyl)-6-(2-(trifluoromethyl)phenyl)-1H-indol-5-yl)oxy)piperidine-1-carboxylate Ethyl 5-((1-(tert-butoxycarbonyl)piperidin-4-yl)oxy)-6-(2-(trifluoromethyl)phenyl)-1H-indole-2-carboxylate obtained in Step 1 (638 mg) and acetonitrile (0.188 mg) were dissolved in THF (19 mL) and NaHMDS (1.9 M solution in THF, 3.15 mL) was added at 0° C. After 30 minutes, the reaction was quenched by adding a 1 M aqueous hydrochloric acid solution (30 mL), the mixture was extracted with ethyl acetate (30 mL×3), and the combined organic layers were dried over sodium sulfate. After removing the drying agent by filtration, the filtrate was concentrated, and the resulting residue was then purified by C18 column (0.05% TFA-water-acetonitrile) to give the target compound (558 mg).

Step 3

Synthesis of tert-butyl (E)-4-((2-(2-cyano-3-(dimethylamino)acryloyl)-6-(2-(trifluoromethyl)phenyl)-1H-indol-5-yl)oxy)piperidine-1-carboxylate tert-Butyl 4-42-(2-cyanoacetyl)-6-(2-(trifluoromethyl)phenyl)-1H-indol-5-yl)oxy)piperidine-1-carboxylate obtained in Step 2 (458 mg) was dissolved in THF (9.1 mL), DMF-DMA (0.209 mL) was added, and the mixture was stirred at 25° C. for one hour. The reaction solution was concentrated under reduced pressure to give the target compound (616 mg).

Step 4

Synthesis of tert-butyl 4-((2-(5-amino-1-(4-(2-fluorophenoxy)-3-methylphenyl)-1H-pyrazole-4-carbonyl)-6-(2-(trifluoromethyl)phenyl)-1H-indol-5-yl)oxy)piperidine-1-carboxylate tert-Butyl (E)-4-42-(2-cyano-3-(dimethylamino)acryloyl)-6-(2-(trifluoromethyl)phenyl)-1H-indol-5-yl)oxy)piperidine-1-carboxylate obtained in Step 3 (330 mg), 4-methylmorpholine (0.187 mL), and hydrazine (Q019, 274 mg) were added to NMP (9 mL), and the mixture was stirred at 100° C. for 30 minutes in a nitrogen atmosphere. The reaction mixture was purified by C18 column (TFA-water-acetonitrile), the resulting fractions were poured into ethyl acetate/saturated saline, and the organic layer was dried over sodium sulfate. The drying agent was removed by filtration and the filtrate was concentrated to give the target compound (488 mg).

Step 5

Synthesis of (5-amino-1-(4-(2-fluorophenoxy)-3-methylphenyl)-1H-pyrazol-4-yl)(5-(piperidin-4-yloxy)-6-(2-(trifluoromethyl)phenyl)-1H-indol-2-yl)methanone tert-Butyl 4-((2-(5-amino-1-(4-(2-fluorophenoxy)-3-methylphenyl)-1H-pyrazole-4-carbonyl)-6-(2-(trifluoromethyl)phenyl)-1H-indol-5-yl)oxy)piperidine-1-carboxylate obtained in Step 4 (436 mg) was dissolved in 2,2,2-trifluoroethanol (0.96 mL), chlorotrimethylsilane (0.724 mL) was added at 25° C., and the mixture was stirred for 30 minutes. The reaction solution was concentrated under reduced pressure and the residue was then purified by C18 column (formic acid-water-acetonitrile) to give the target compound (339 mg).

Step 6

Synthesis of (5-amino-1-(4-(2-fluorophenoxy)-3-methylphenyl)-1H-pyrazol-4-yl)(5-((1-cyclopentylpiperidin-4-yl)oxy)-6-(2-(trifluoromethyl)phenyl)-1H-indol-2-yl)methanone (5-Amino-1-(4-(2-fluorophenoxy)-3-methylphenyl)-1H-pyrazol-4-yl)(5-(piperidin-4-yloxy)-6-(2-(trifluoromethyl)phenyl)-1H-indol-2-yl)methanone obtained in Step 5 (75 mg), cyclopentanone (0.040 mL), triethylamine (0.034 mL), and acetic acid (0.038 mL) were added to dichloromethane (1.5 mL), sodium triacetoxyborohydride (119 mg) was added, and the mixture was stirred for 20 hours. After evaporating the solvent, the resulting residue was purified by C18 column (TFA-water-acetonitrile) to give the target compound (86 mg).

The compounds shown in the following tables could be obtained by respectively using the phenylboronate derivatives and hydrazines in Example 5-1-385.
(Corresponding Enamines, Hydrazines, and Phenylboronate Derivatives)

| Example No. | Phenylboronate Derivative | Hydrazine |
|---|---|---|
| 5-1-385 | 2-(trifluoromethyl)phenylboronic acid | Q019 HCl (H₂N-NH-(4-(2-fluorophenoxy)-3-methylphenyl)) |
| 5-1-387 | 2-(trifluoromethyl)phenylboronic acid | T002 HCl (H₂N-NH-(5-(2,6-difluorophenoxy)-4-methylpyridin-2-yl)) |
| 5-1-285 | 2-chlorophenylboronic acid | Q019 HCl (H₂N-NH-(4-(2-fluorophenoxy)-3-methylphenyl)) |

-continued
| Example No. | Phenylboronate Derivative | Hydrazine | | |
|---|---|---|---|---|
| 5-1-288 | 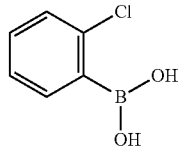 | T002 | HCl | 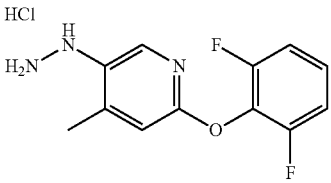 |
| 5-1-308 | 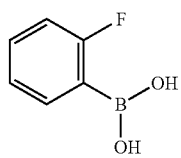 | Q019 | HCl | 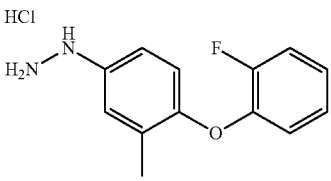 [SMILES: Cl ; Cc1cc(NN)ccc1Oc1ccccc1F] |
| 5-1-310 | 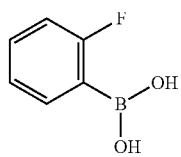 | T002 | HCl | 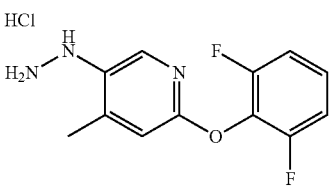 [SMILES: Cl ; Cc1cc(Oc2c(F)cccc2F)ncc1NN] |
| 5-1-335 | 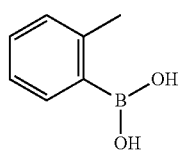 | Q019 | HCl | 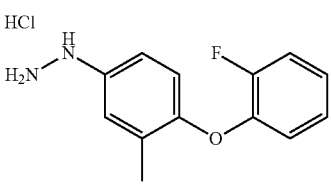 [SMILES: Cl ; Cc1cc(NN)ccc1Oc1ccccc1F] |
| 5-1-337 | 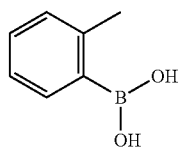 | T002 | HCl | 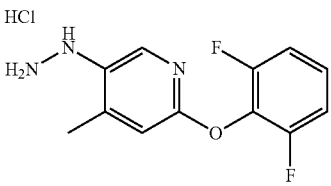 |
| 5-1-503 | 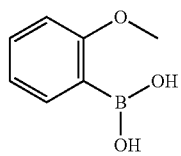 | T002 | HCl | 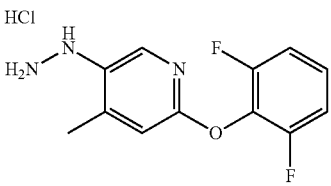 |

(Synthesized Compounds)
| Example No. | Compound | m/z (M + H) | Retention Time (Minute) | LCMS Measurement Condition |
|---|---|---|---|---|
| 5-1-385 | 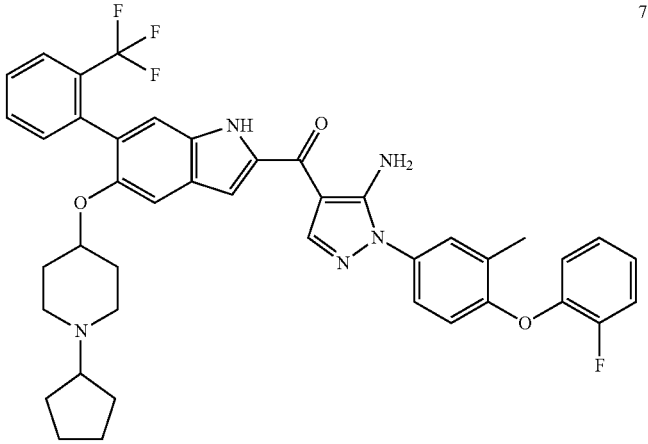 | 738 | 1.13 | AA Rev.11 |
| 5-1-387 | 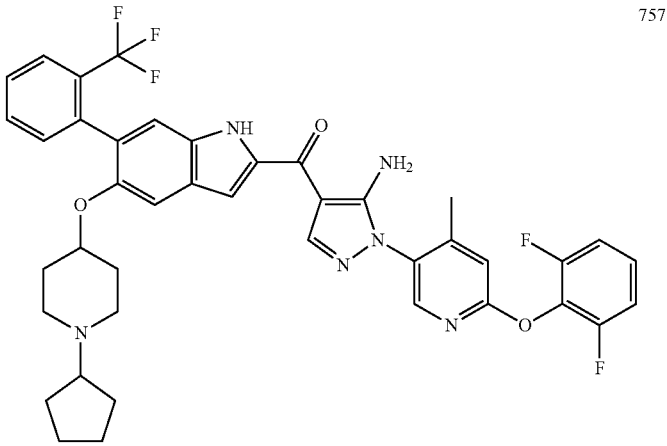 | 757 | 1.12 | TFA Rev.7 |
| 5-1-285 | 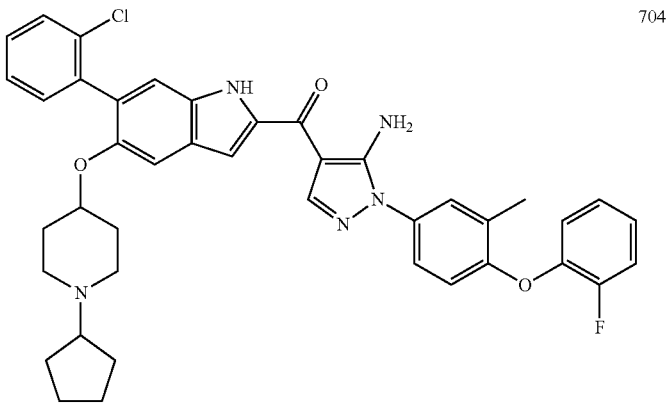 | 704 | 1.14 | AA Rev.11 |

-continued

| Example No. | Compound | m/z (M + H) | Retention Time (Minute) | LCMS Measurement Condition |
|---|---|---|---|---|
| 5-1-288 | | 723 | 1.11 | TFA Rev.7 |
| 5-1-308 | | 688 | 1.15 | TFA Rev.7 |
| 5-1-310 | | 707 | 1.08 | TFA Rev.7 |

-continued
| Example No. | Compound | m/z (M + H) | Retention Time (Minute) | LCMS Measurement Condition |
|---|---|---|---|---|
| 5-1-335 | 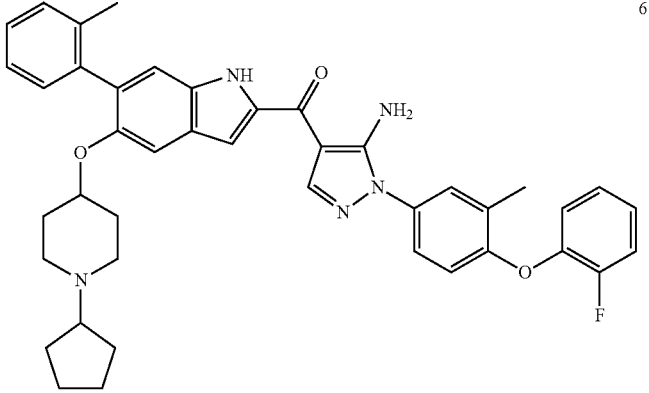 | 684 | 1.19 | TFA Rev.7 |
| 5-1-337 | 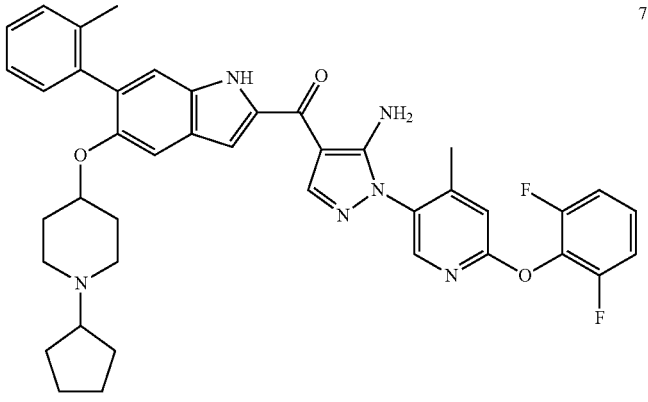 | 703 | 1.12 | TFA Rev.7 |
| 5-1-503 | 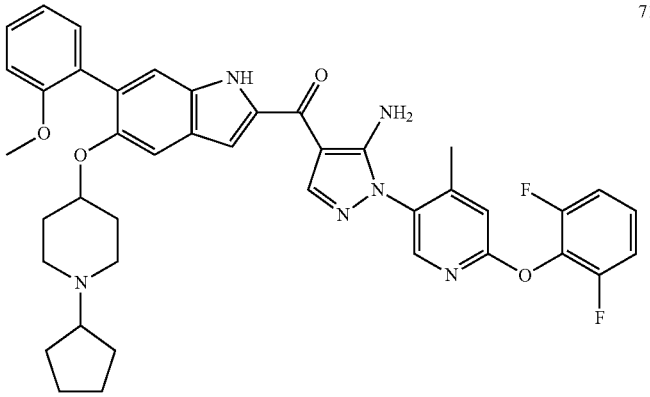 | 719 | 1.08 | TFA Rev.7 |

Example 5-1-386

Synthesis of (5-amino-1-(4-(2-fluorophenoxy)-3-methylphenyl)-1H-pyrazol-4-yl)(5-((1-(1,1-dioxidothietan-3-yl)piperidin-4-yl)oxy)-6-(2-(trifluoromethyl)phenyl)-1H-indol-2-yl)methanone

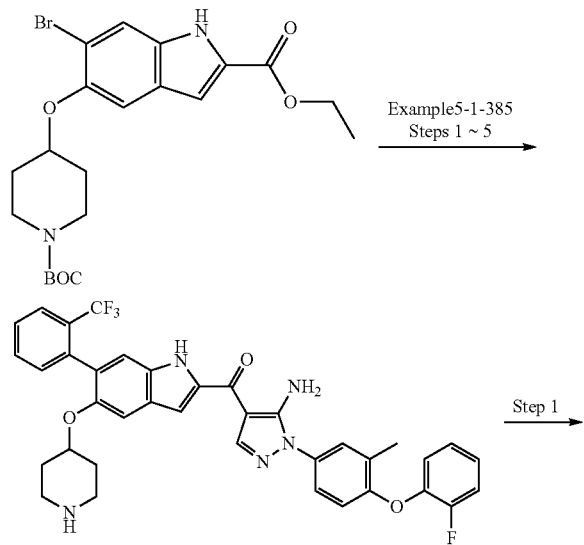

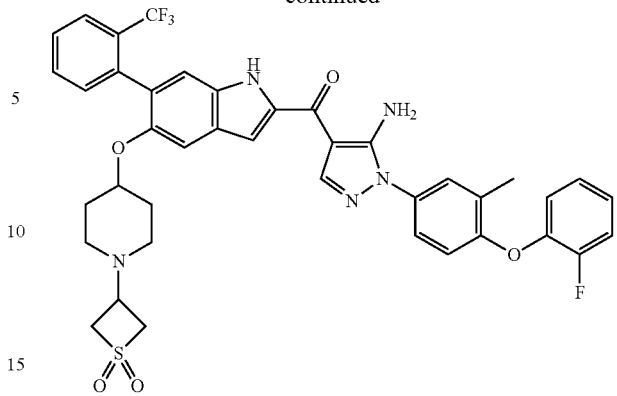

Step 1

(5-Amino-1-(4-(2-fluorophenoxy)-3-methylphenyl)-1H-pyrazol-4-yl)(5-(piperidin-4-yloxy)-6-(2-(trifluoromethyl)phenyl)-1H-indol-2-yl)methanone obtained in Step 5 of Example 5-1-385 (75 mg), 3-bromothietane 1,1-dioxide (83 mg), N,N-diisopropylethylamine (0.117 mL), and potassium iodide (93 mg) were added to THF (0.75 mL) and DMF (0.75 mL) and the mixture was stirred at 25° C. for 20 hours. The reaction mixture was purified by C18 column (TFA-water-acetonitrile) to give the target compound (86 mg).

The compounds shown in the following tables could be obtained by respectively using the phenylboronate derivatives and hydrazines of Example 5-1-386.
(Corresponding Phenylboronate Derivatives and Hydrazines)

| Example No. | Phenylboronate Derivative | Hydrazine | |
|---|---|---|---|
| 5-1-386 | (2-(trifluoromethyl)phenyl)boronic acid | Q019 HCl | 1-(4-(2-fluorophenoxy)-3-methylphenyl)hydrazine |
| 5-1-388 | (2-(trifluoromethyl)phenyl)boronic acid | T002 HCl | 1-(6-(2,6-difluorophenoxy)-4-methylpyridin-3-yl)hydrazine |
| 5-1-289 | (2-chlorophenyl)boronic acid | Q019 HCl | 1-(4-(2-fluorophenoxy)-3-methylphenyl)hydrazine |
| 5-1-290 | (2-chlorophenyl)boronic acid | T002 HCl | 1-(6-(2,6-difluorophenoxy)-4-methylpyridin-3-yl)hydrazine |

-continued
| Example No. | Phenylboronate Derivative | Hydrazine | | |
|---|---|---|---|---|
| 5-1-309 | 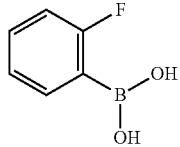 | Q019 | HCl | 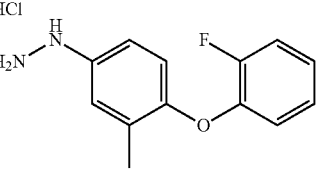 |
| 5-1-311 | 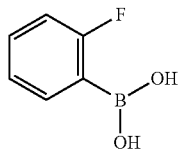 | T002 | HCl | 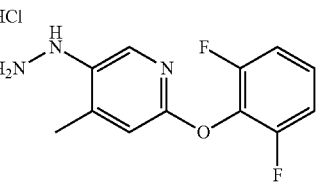 |
| 5-1-336 | 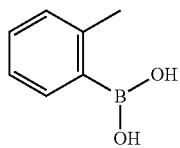 | Q019 | HCl | 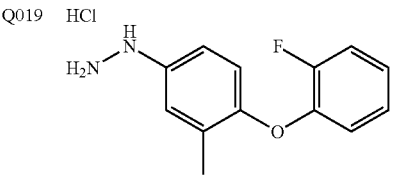 |
| 5-1-338 | 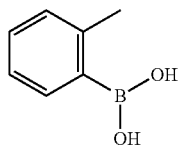 | T002 | HCl | 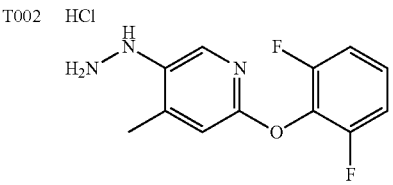 |
| 5-1-283 | 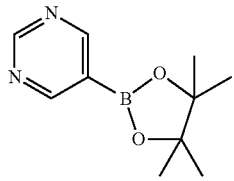 | Q019 | HCl | 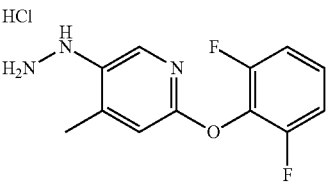 |
| 5-1-284 | 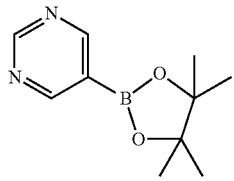 | T002 | HCl | 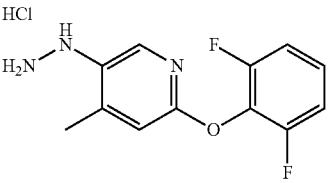 |

(Synthesized Compounds)
| Example No. | Compound | m/z (M+H) | Retention Time (Minute) | LCMS Measurement Condition |
|---|---|---|---|---|
| 5-1-386 | 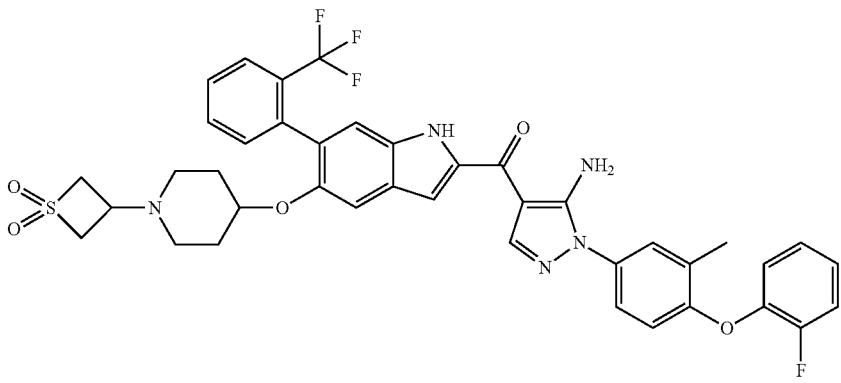 [SMILES: Cc1cc(-n2ncc(C(=O)c3cc4cc(OC5CCN(C6CS(=O)(=O)C6)CC5)c(-c5ccccc5C(F)(F)F)cc4[nH]3)c2N)ccc1Oc1ccccc1F] | 774 | 1.13 | TFA Rev.7 |
| 5-1-388 | 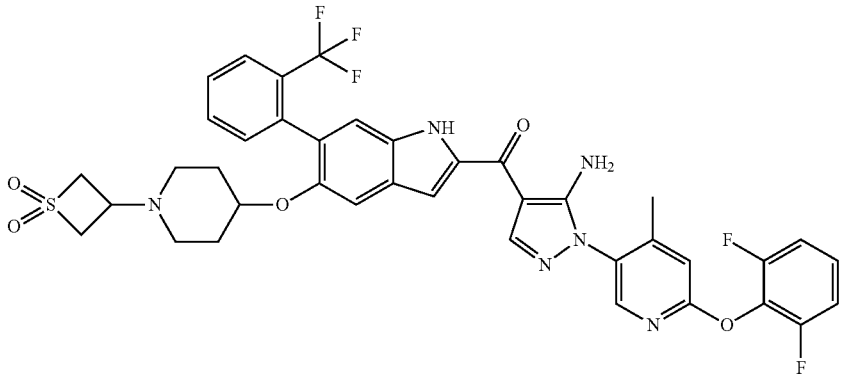 [SMILES: Cc1cc(Oc2c(F)cccc2F)ncc1-n1ncc(C(=O)c2cc3cc(OC4CCN(C5CS(=O)(=O)C5)CC4)c(-c4ccccc4C(F)(F)F)cc3[nH]2)c1N] | 793 | 1.07 | TFA Rev.7 |
| 5-1-289 | 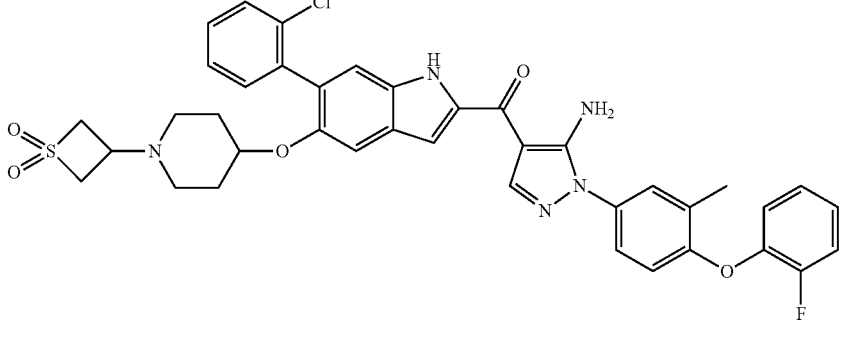 | 740 | 1.12 | TFA Rev.7 |
| 5-1-290 | 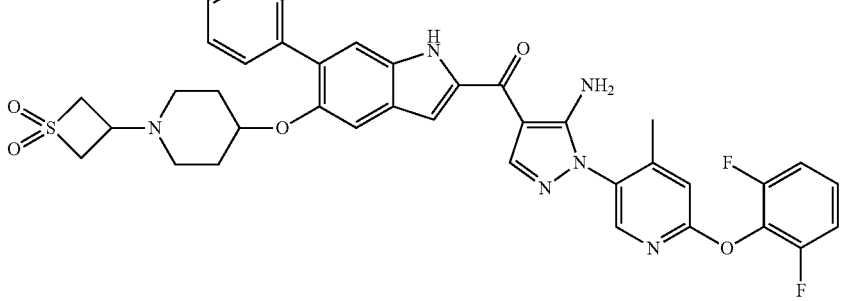 | 759 | 1.05 | TFA Rev.7 |

| Example No. | Compound | m/z (M + H) | Retention Time (Minute) | LCMS Measurement Condition |
|---|---|---|---|---|
| 5-1-309 | 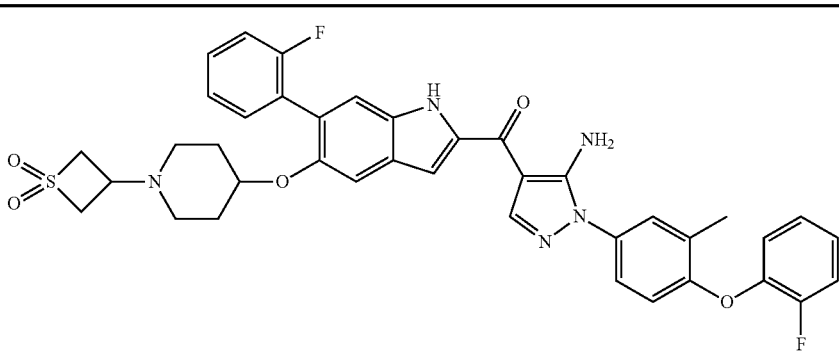 | 724 | 1.1 | TFA Rev.7 |
| 5-1-311 | 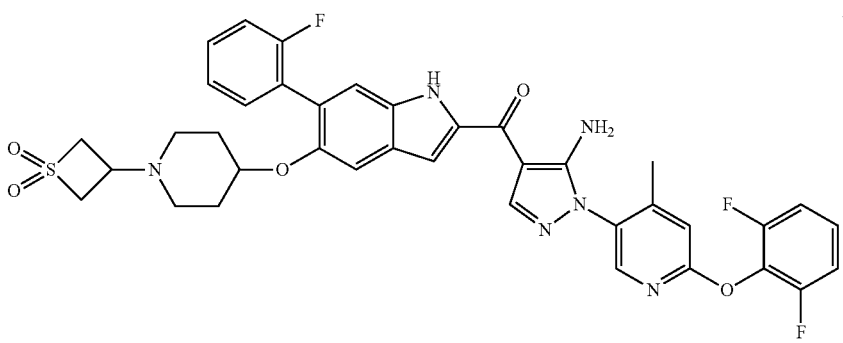 | 743 | 1.03 | TFA Rev.7 |
| 5-1-336 | 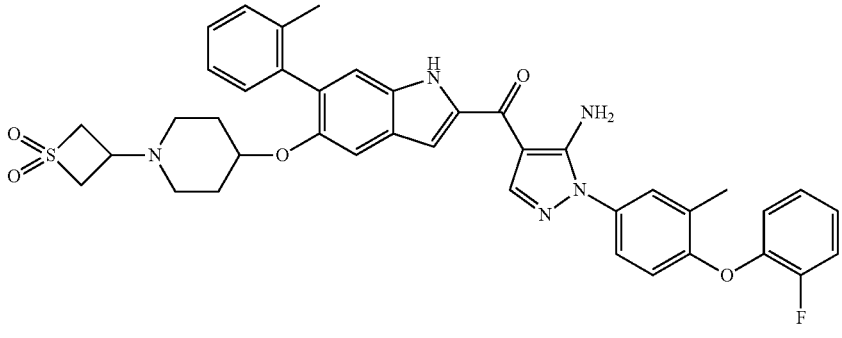 [SMILES: Cc1cc(-n2ncc(C(=O)c3cc4cc(OC5CCN(C6CS(=O)(=O)C6)CC5)c(-c5ccccc5C)cc4[nH]3)c2N)ccc1Oc1ccccc1F] | 720 | 1.12 | TFA Rev.7 |
| 5-1-338 | 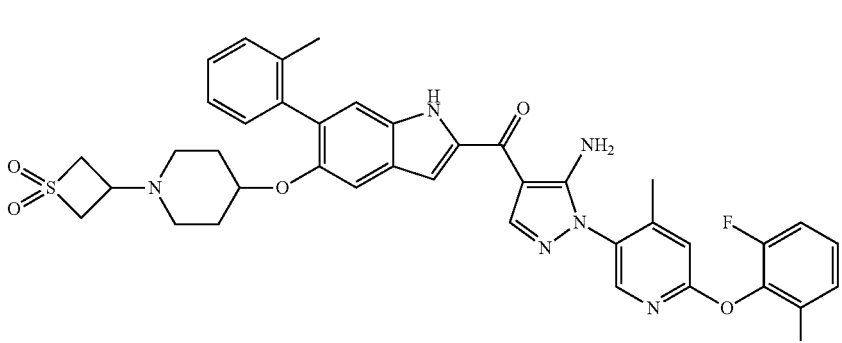 | 739 | 1.05 | TFA Rev.7 |

| Example No. | Compound | m/z (M + H) | Retention Time (Minute) | LCMS Measurement Condition |
|---|---|---|---|---|
| 5-1-283 | | 708 | 0.98 | TFA Rev.7 |
| 5-1-284 | | 727 | 1 | AA Rev.11 |
Example 5-1-391
Synthesis of 3-(2-(5-amino-1-(4-(2-fluorophenoxy)-2-methylphenyl)-1H-pyrazole-4-carbonyl)-5-methyl-1H-indol-6-yl)-8-(oxetan-3-yl)-1,3,8-triazaspiro[4.5]decane-2,4-dione
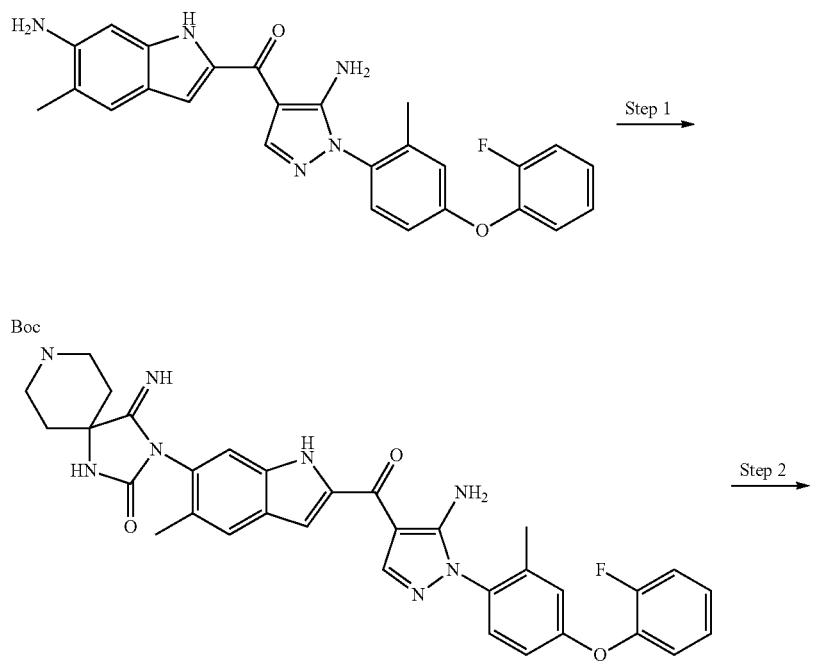

-continued

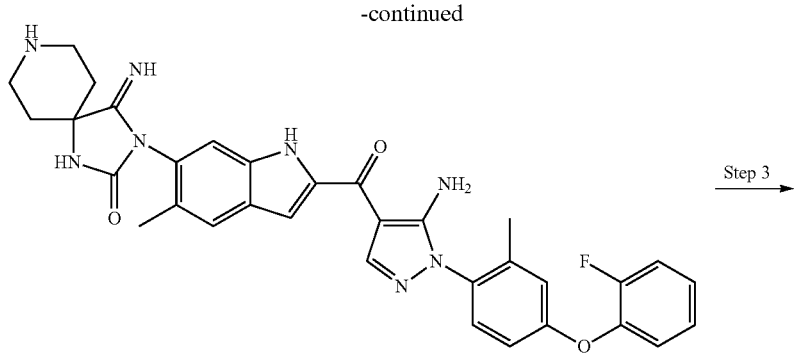

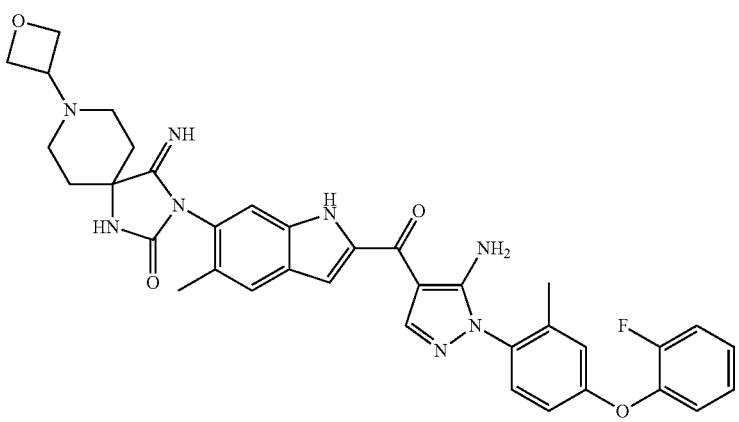

Step 1

Synthesis of tert-butyl 3-[2-[5-amino-1-[4-(2-fluorophenoxy)-2-methylphenyl]pyrazole-4-carbonyl]-5-methyl-1H-indol-6-yl]-4-imino-2-oxo-1,3,8-triazaspiro[4.5]decane-8-carboxylate (5-Amino-1-(4-(2-fluorophenoxy)-2-methylphenyl)-1H-pyrazol-4-yl)(6-amino-5-methyl-1H-indol-2-yl)methanone (267 mg) obtained from enamine (I-H057) and hydrazine (Q001) and triphosgene (267 mg) were added to THF (3.5 mL) and the mixture was stirred at 25° C. for one hour. The reaction solution was concentrated under reduced pressure and then crystallized by adding hexane/ethyl acetate (2 mL/0.5 mL). The resulting solid, tert-butyl 4-amino-4-cyanopiperidine-1-carboxylate (264 mg), and triethylamine (0.327 mL) were added to THF (3.5 mL) and the mixture was stirred at 25° C. for two hours. The reaction solution was concentrated under reduced pressure and then crystallized from hexane/ethyl acetate (15 mL/2 mL) to give the target compound (530 mg).

Step 2

Synthesis of 3-(2-(5-amino-1-(4-(2-fluorophenoxy)-2-methylphenyl)-1H-pyrazole-4-carbonyl)-5-methyl-1H-indol-6-yl)-1,3,8-triazaspiro[4.5]decane-2,4-dione tert-Butyl 3-[2-[5-amino-1-[4-(2-fluorophenoxy)-2-methylphenyl]pyrazole-4-carbonyl]-5-methyl-1H-indol-6-yl]-4-imino-2-oxo-1,3,8-triazaspiro[4.5]decane-8-carboxylate obtained in Step 1 (414 mg) was added to methanol/dioxane (1 mL/5 mL), and after adding concentrated hydrochloric acid (0.1 mL), the mixture was stirred at 100° C. for three hours. After concentrating the reaction solution under reduced pressure, a saturated aqueous sodium bicarbonate solution (20 mL) and ethyl acetate (20 mL) were added to the resulting residue. The organic layer was washed with 13% saline (10 mL) and then dried over sodium sulfate. After removing the drying agent by filtration, the filtrate was concentrated and the resulting residue was purified by amino column chromatography (ethyl acetate/methanol) to give the target compound (121 mg).

Step 3

Synthesis of 3-(2-(5-amino-1-(4-(2-fluorophenoxy)-2-methylphenyl)-1H-pyrazole-4-carbonyl)-5-methyl-1H-indol-6-yl)-8-(oxetan-3-yl)-1,3,8-triazaspiro[4.5]-decane-2,4-dione The target compound (30 mg) was obtained by performing the similar operation as in Example 5-1-353 using 3-(2-(5-amino-1-(4-(2-fluorophenoxy)-2-methylphenyl)-1H-pyrazole-4-carbonyl)-5-methyl-1H-indol-6-yl)-1,3,8-triazaspiro[4.5]decane-2,4-dione obtained in Step 2 (59 mg).

The compounds shown in the following tables could be obtained by respectively using the enamines, the hydrazines, and the carbonyl compounds used in Step 3 in the table.

(Corresponding Enamines, Hydrazines, and Carbonyl Compounds)

| Example No. | | Enamine | | Hydrazine | Carbonyl Compound |
|---|---|---|---|---|---|
| 5-1-364 | I-H057 | (structure) | Q001 | HCl (structure) | |
| 5-1-391 | I-H057 | (structure) | Q001 | HCl (structure) | (oxetanone) |
| 5-1-392 | I-H057 | (structure) | Q001 | HCl (structure) | (benzaldehyde) |
| 5-1-471 | I-H057 | (structure) | Q019 | HCl (structure) | Boc20 |
| 5-1-357 | I-H057 | (structure) | T002 | HCl (structure) | |
| 5-1-360 | I-H057 | (structure) | T002 | HCl (structure) | (oxetanone) |
| 5-1-361 | I-H057 | (structure) | T002 | HCl (structure) | (benzaldehyde) |
| 5-1-271 | I-A011 | (structure) | Q001 | HCl (structure) | |

-continued
| Example No. | | Enamine | | Hydrazine | Carbonyl Compound |
|---|---|---|---|---|---|
| 5-1-272 | I-A011 | (structure) | Q001 | (structure) | (structure) |
| 5-1-277 | I-A011 | (structure) | Q001 | (structure) | (structure) |
| 5-1-332 | I-A011 | (structure) | T002 | (structure) | (structure) |
| 5-1-350 | I-A011 | (structure) | T002 | (structure) | (structure) |
| 5-1-351 | I-A011 | (structure) | T002 | (structure) | (structure) |
(Synthesized Compounds)
| Example No. | Compound | m/z (M + H) | Retention Time (Minute) | LCMS Measurement Condition |
|---|---|---|---|---|
| 5-1-364 | 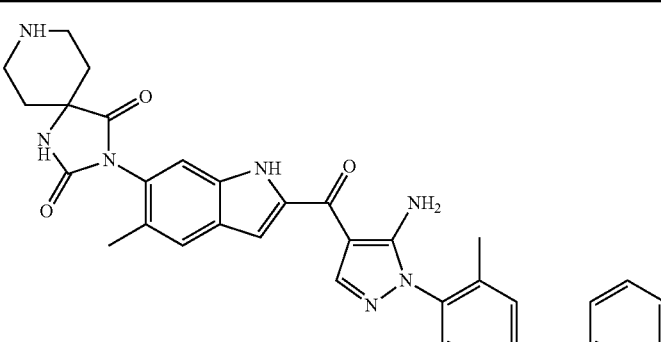 | 608 | 0.94 | TFA Rev.7 |

-continued
| Example No. | Compound | m/z (M + H) | Retention Time (Minute) | LCMS Measurement Condition |
|---|---|---|---|---|
| 5-1-391 | 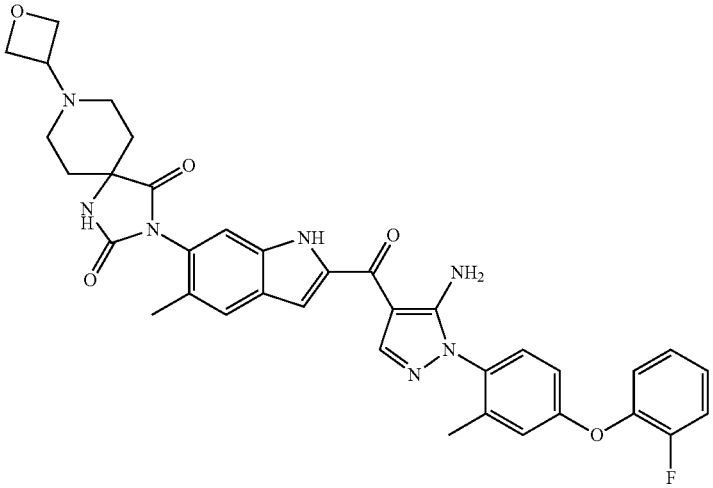 [SMILES: Cc1cc2cc(C(=O)c3cnn(-c4ccc(Oc5ccccc5F)cc4C)c3N)[nH]c2cc1N1C(=O)NC2(CCN(C3COC3)CC2)C1=O] | 664 | 0.94 | TFA Rev.7 |
| 5-1-392 | 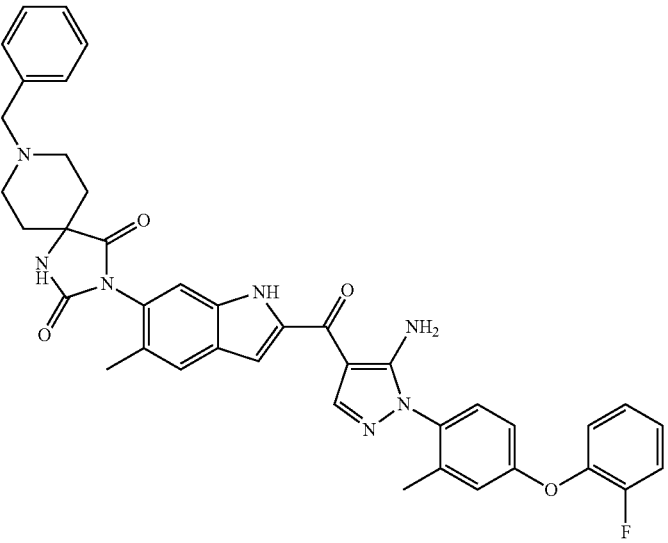 [SMILES: Cc1cc2cc(C(=O)c3cnn(-c4ccc(Oc5ccccc5F)cc4C)c3N)[nH]c2cc1N1C(=O)NC2(CCN(Cc3ccccc3)CC2)C1=O] | 698 | 1.02 | TFA Rev.7 |
| 5-1-471 | 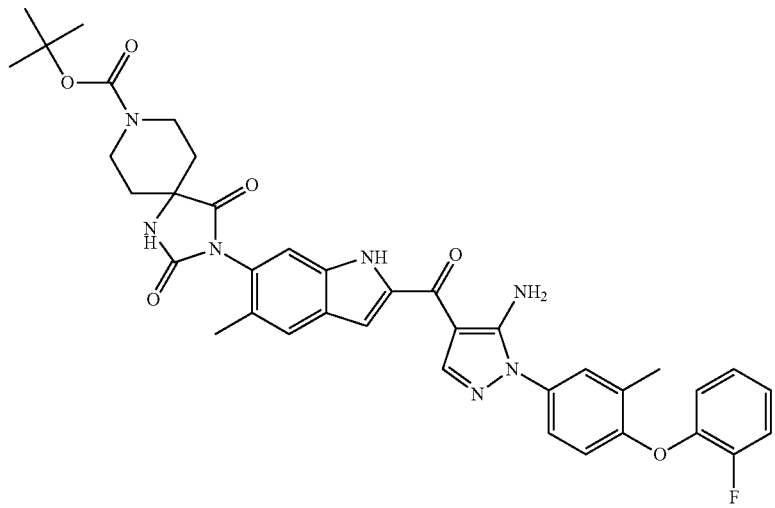 [SMILES: Cc1cc(-n2ncc(C(=O)c3cc4cc(C)c(N5C(=O)NC6(CCN(C(=O)OC(C)(C)C)CC6)C5=O)cc4[nH]3)c2N)ccc1Oc1ccccc1F] | 708 | 1.36 | TFA Rev.7 |

-continued
| Example No. | Compound | m/z (M + H) | Retention Time (Minute) | LCMS Measurement Condition |
|---|---|---|---|---|
| 5-1-357 | 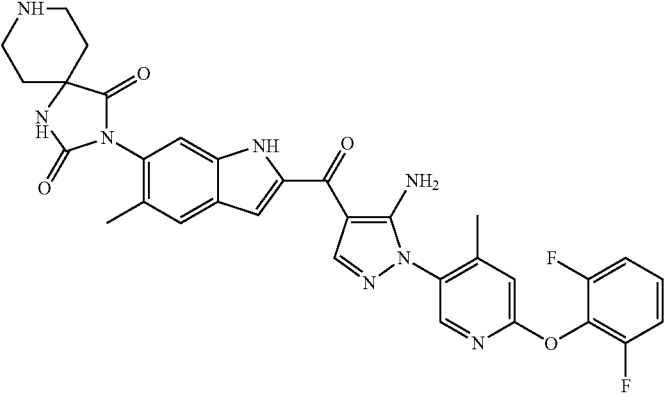 [SMILES: Cc1cc2cc(C(=O)c3cnn(-c4cnc(Oc5c(F)cccc5F)cc4C)c3N)[nH]c2cc1N1C(=O)NC2(CCNCC2)C1=O] | 627 | 0.91 | TFA Rev.7 |
| 5-1-360 | 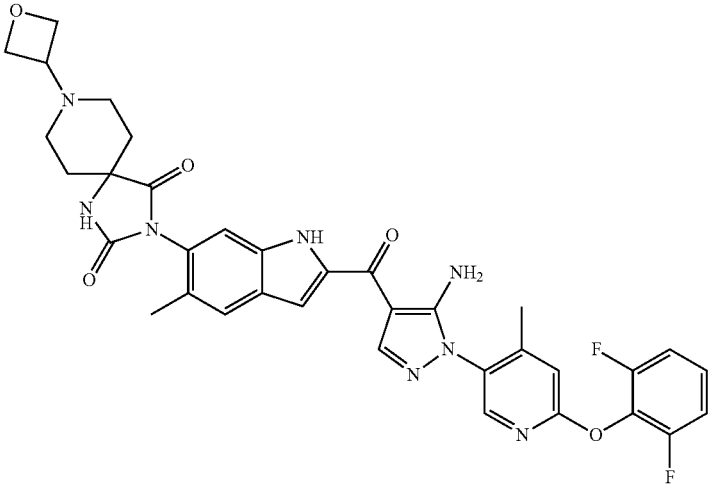 [SMILES: Cc1cc2cc(C(=O)c3cnn(-c4cnc(Oc5c(F)cccc5F)cc4C)c3N)[nH]c2cc1N1C(=O)NC2(CCN(C3COC3)CC2)C1=O] | 683 | 0.92 | TFA Rev.7 |
| 5-1-361 | 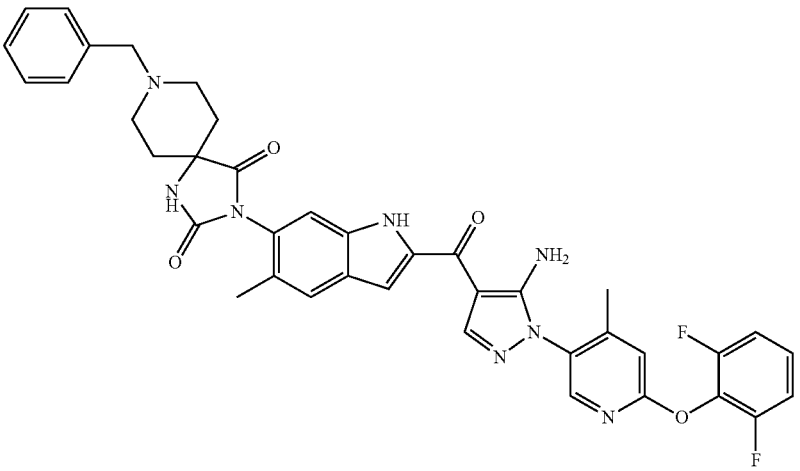 [SMILES: Cc1cc2cc(C(=O)c3cnn(-c4cnc(Oc5c(F)cccc5F)cc4C)c3N)[nH]c2cc1N1C(=O)NC2(CCN(Cc3ccccc3)CC2)C1=O] | 717 | 1.00 | TFA Rev.7 |

-continued
| Example No. | Compound | m/z (M + H) | Retention Time (Minute) | LCMS Measurement Condition |
|---|---|---|---|---|
| 5-1-271 | 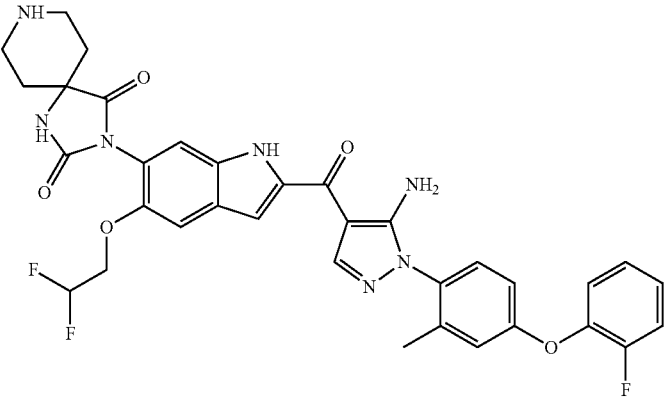 [SMILES: Cc1cc(Oc2ccccc2F)ccc1-n1ncc(C(=O)c2cc3cc(OCC(F)F)c(N4C(=O)NC5(CCNCC5)C4=O)cc3[nH]2)c1N] | 674 | 0.93 | AA Rev.11 |
| 5-1-272 | 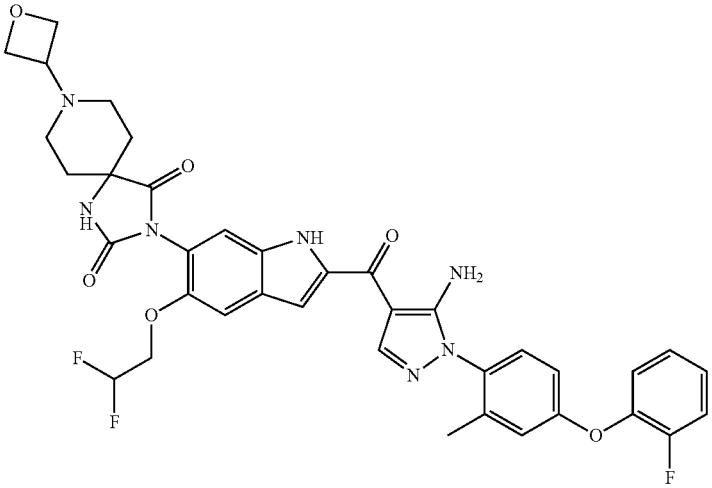 [SMILES: Cc1cc(Oc2ccccc2F)ccc1-n1ncc(C(=O)c2cc3cc(OCC(F)F)c(N4C(=O)NC5(CCN(C6COC6)CC5)C4=O)cc3[nH]2)c1N] | 730 | 0.98 | AA Rev.11 |
| 5-1-277 | 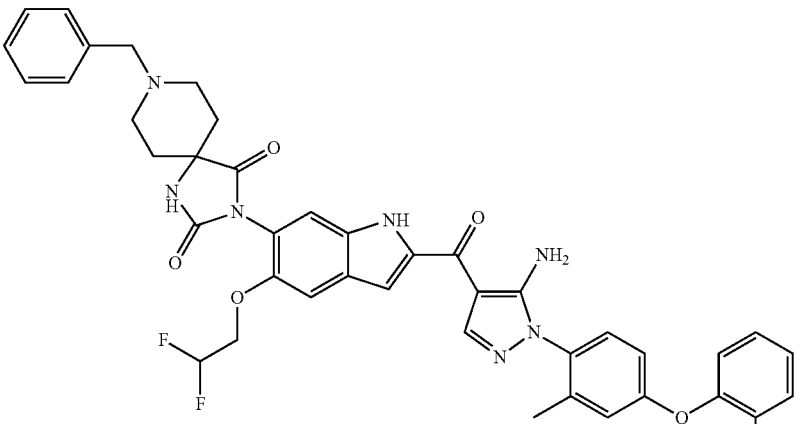 | 764 | 1.06 | TFA Rev.7 |

-continued

| Example No. | Compound | m/z (M + H) | Retention Time (Minute) | LCMS Measurement Condition |
|---|---|---|---|---|
| 5-1-332 | | 693 | 0.92 | TFA Rev.7 |
| 5-1-350 | | 749 | 0.93 | TFA Rev.7 |
| 5-1-351 | | 783 | 1.01 | TFA Rev.7 |

Example 5-1-254
Synthesis of N-((6S,7aS)-2-(2-(5-amino-1-(4-(2-fluorophenoxy)-2-methylphenyl)-1H-pyrazole-4-carbonyl)-5-(2,2-difluoroethoxy)-1H-indol-6-yl)-1,3-dioxohexahydro-1H-pyrrolo[1,2-c]imidazol-6-yl)methanesulfonamide
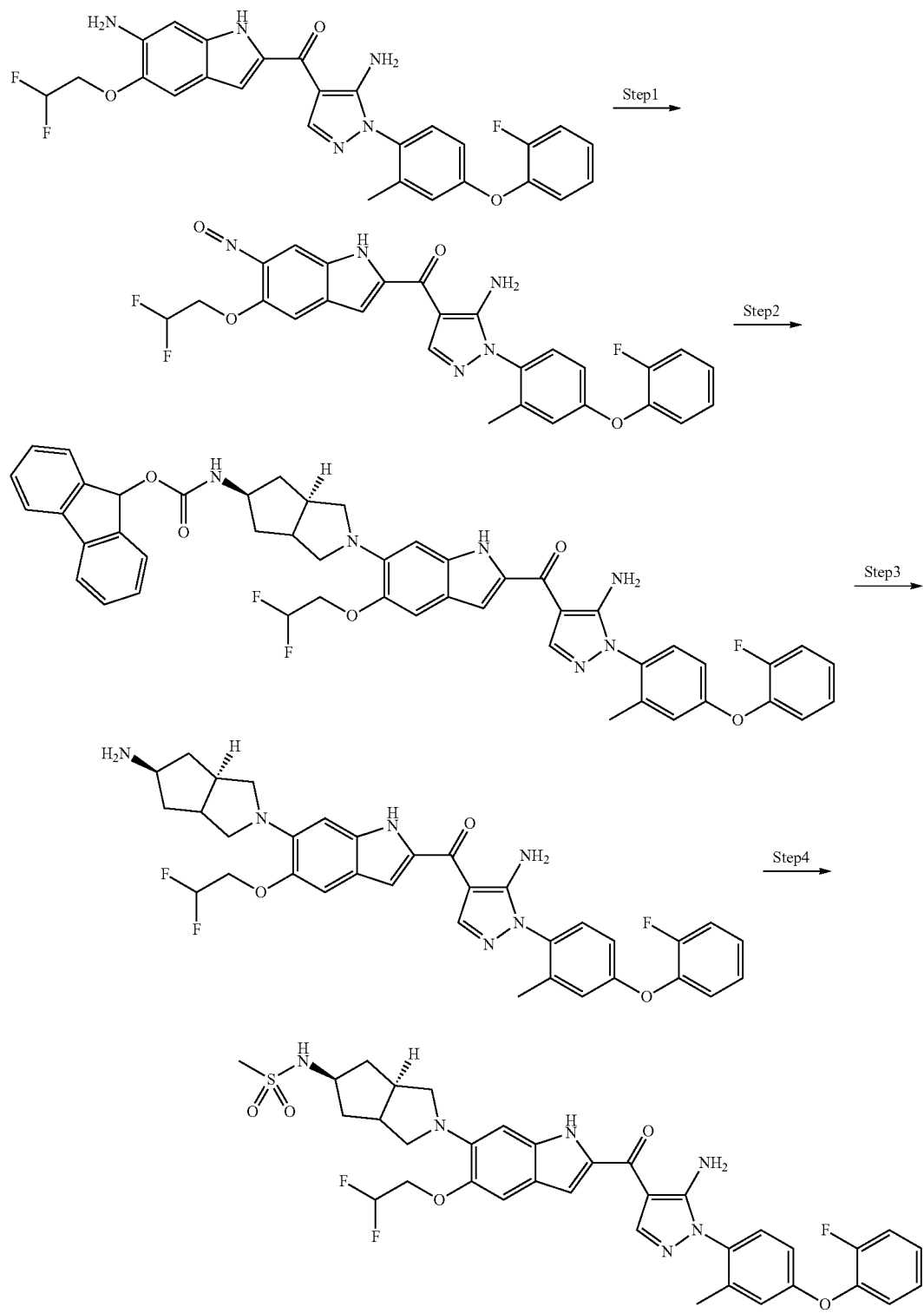

Step 1

Synthesis of (5-amino-1-(4-(2-fluorophenoxy)-2-methylphenyl)-1H-pyrazol-4-yl)(5-(2,2-difluoroethoxy)-6-isocyanato-1H-indol-2-yl)methanone

[6-Amino-5-(2,2-difluoroethoxy)-1H-indol-2-yl]-[5-amino-1-[4-(2-fluorophenoxy)-2-methylphenyl]pyrazol-4-yl]methanone used for synthesis in Example 5-1-569 (750 mg) and bis(trichloromethyl) carbonate (427 mg) were added to THF (7.2 mL) and the mixture was stirred at 25° C. for 15 minutes. After concentrating the reaction solution under reduced pressure, the residue was suspended in MTBE and the precipitate was collected by filtration and dried to give the target compound (770 mg).

Step 2

Synthesis of (9H-fluoren-9-yl)methyl ((6S,7aS)-2-(2-(5-amino-1-(4-(2-fluorophenoxy)-2-methylphenyl)-1H-pyrazole-4-carbonyl)-5-(2,2-difluoroethoxy)-1H-indol-6-yl)-1,3-dioxohexahydro-1H-pyrrolo[1,2-c]imidazol-6-yl)carbamate (5-Amino-1-(4-(2-fluorophenoxy)-2-methylphenyl)-1H-pyrazol-4-yl)(5-(2,2-difluoroethoxy)-6-isocyanato-1H-indol-2-yl)methanone obtained in Step 1 (300 mg) and (2S,4S)-4-((((9H-fluoren-9-yl)methoxy)carbonyl)amino)pyrrolidine-2-carboxylic acid hydrochloride (256 mg) were suspended in THF (10 mL), triethylamine (0.306 mL) was added, and the mixture was then stirred at 25° C. for 40 minutes. The insoluble matter was removed by filtration and the filtrate was then concentrated under reduced pressure. The resulting residue was diluted with THF (10 mL), concentrated hydrochloric acid (0.3 mL) was added, and the mixture was stirred at 70° C. for 18 hours. After concentrating the reaction solution under reduced pressure, the residue was diluted with ethyl acetate/saturated aqueous sodium bicarbonate solution and the organic layer was washed with water and saturated saline and then dried over sodium sulfate. After removing the drying agent by filtration, the filtrate was concentrated to give the target compound (483 mg).

Step 3

Synthesis of (6S,7aS)-6-amino-2-(2-(5-amino-1-(4-(2-fluorophenoxy)-2-methylphenyl)-1H-pyrazole-4-carbonyl)-5-(2,2-difluoroethoxy)-1H-indol-6-yl)tetrahydro-1H-pyrrolo[1,2-c]imidazole-1,3(2H)-dione (9H-Fluoren-9-yl)methyl ((6S,7aS)-2-(2-(5-amino-1-(4-(2-fluorophenoxy)-2-methylphenyl)-1H-pyrazole-4-carbonyl)-5-(2,2-difluoroethoxy)-1H-indol-6-yl)-1,3-dioxohexahydro-1H-pyrrolo[1,2-c]imidazol-6-yl)carbamate obtained in Step 2 (483 mg) was dissolved in THF (5 mL), piperidine (0.5 mL) was added, and the mixture was stirred at 25° C. for two hours. The reaction solution was concentrated under reduced pressure and the resulting residue was then purified by NH2 column chromatography (ethyl acetate/methanol) to give the target compound (190 mg).

Step 4

Synthesis of N-((6S,7aS)-2-(2-(5-amino-1-(4-(2-fluorophenoxy)-2-methylphenyl)-1H-pyrazole-4-carbonyl)-5-(2,2-difluoroethoxy)-1H-indol-6-yl)-1,3-dioxohexahydro-1H-pyrrolo[1,2-c]imidazol-6-yl)methanesulfonamide (6S,7aS)-6-Amino-2-(2-(5-amino-1-(4-(2-fluorophenoxy)-2-methylphenyl)-1H-pyrazole-4-carbonyl)-5-(2,2-difluoroethoxy)-1H-indol-6-yl)tetrahydro-1H-pyrrolo[1,2-c]imidazole-1,3(2H)-dione obtained in Step 3 (60 mg) was dissolved in pyridine (1 mL), methanesulfonyl chloride (0.014 mL) was added, and the mixture was then stirred at 25° C. for four hours. The reaction solution was diluted with ethyl acetate and a saturated aqueous sodium bicarbonate solution and the organic layer was washed with a saturated aqueous sodium bicarbonate solution, a 2 M aqueous hydrochloric acid solution, and saturated saline and then dried over sodium sulfate. After removing the drying agent by filtration, the filtrate was concentrated and the resulting residue was purified by silica gel column chromatography (ethyl acetate/hexane) to give the target compound (44 mg).

Example 5-1-278

Synthesis of furan-2-ylmethyl ((6S,7aS)-2-(2-(5-amino-1-(4-(2-fluorophenoxy)-2-methylphenyl)-1H-pyrazole-4-carbonyl)-5-(2,2-difluoroethoxy)-1H-indol-6-yl)-1,3-dioxohexahydro-1H-pyrrolo[1,2-c]imidazol-6-yl)carbamate

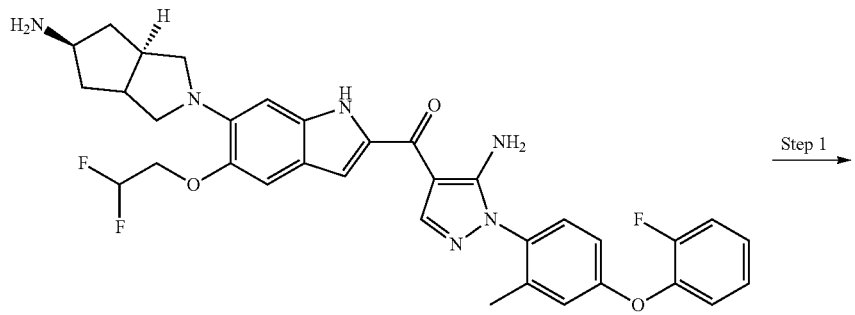

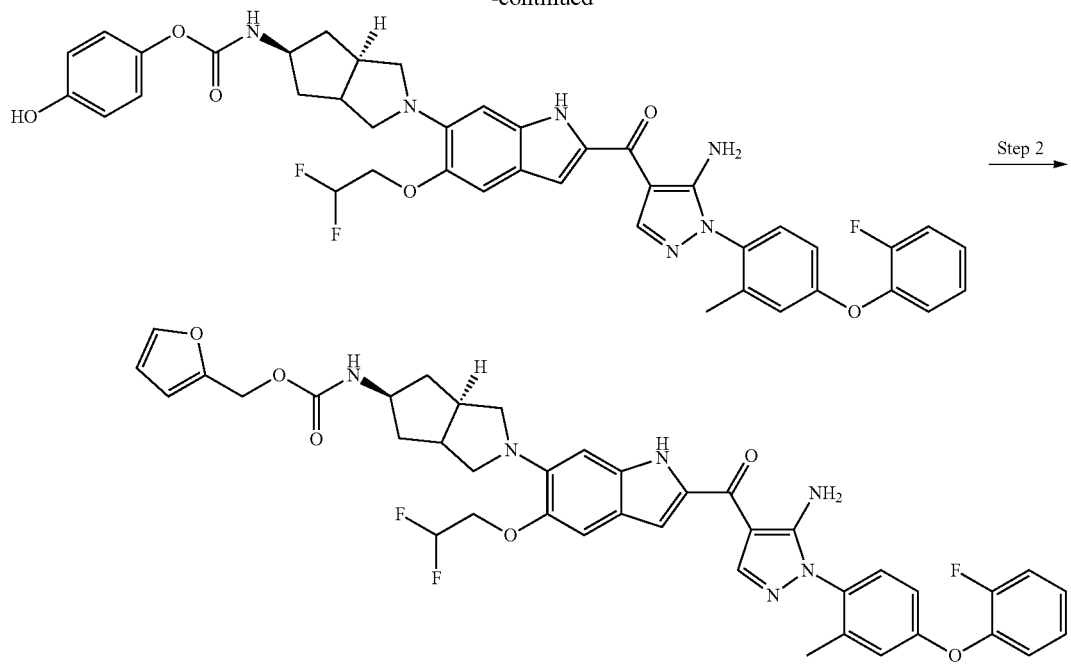

Step 1

Synthesis of 4-nitrophenyl ((6S,7aS)-2-(2-(5-amino-1-(4-(2-fluorophenoxy)-2-methylphenyl)-1H-pyrazole-4-carbonyl)-5-(2,2-difluoroethoxy)-1H-indol-6-yl)-1,3-dioxohexahydro-1H-pyrrolo[1,2-c]imidazol-6-yl)carbamate (6S,7aS)-6-Amino-2-(2-(5-amino-1-(4-(2-fluorophenoxy)-2-methylphenyl)-1H-pyrazole-4-carbonyl)-5-(2,2-difluoroethoxy)-1H-indol-6-yl)tetrahydro-1H-pyrrolo[1,2-c]imidazole-1,3(2H)-dione obtained in Step 3 of Example 5-1-254 (30 mg) was dissolved in THF (2 mL), a solution of bis(4-nitrophenyl) carbonate (13 mg) in THF (1.0 mL) was added, and the mixture was stirred at 25° C. for 30 minutes. After concentrating the reaction solution under reduced pressure, the resulting residue was purified by silica gel column chromatography (hexane/ethyl acetate) to give the target compound (24 mg).

Step 2

Synthesis of furan-2-ylmethyl ((6S,7aS)-2-(2-(5-amino-1-(4-(2-fluorophenoxy)-2-methylphenyl)-1H-pyrazole-4-carbonyl)-5-(2,2-difluoroethoxy)-1H-indol-6-yl)-1,3-dioxohexahydro-1H-pyrrolo[1,2-c]imidazol-6-yl)carbamate 4-Nitrophenyl ((6S,7aS)-2-(2-(5-amino-1-(4-(2-fluorophenoxy)-2-methylphenyl)-1H-pyrazole-4-carbonyl)-5-(2,2-difluoroethoxy)-1H-indol-6-yl)-1,3-dioxohexahydro-1H-pyrrolo[1,2-c]imidazol-6-yl)carbamate obtained in Step 1 (24 mg) was dissolved in THF, furan-2-ylmethanol (0.013 mL) and triethylamine (0.008 mL) were added, and the mixture was stirred at 70° C. for four hours. After concentrating the reaction solution under reduced pressure, the resulting residue was purified by silica gel column chromatography (hexane/ethyl acetate) to give the target compound (6.3 mg).

The compounds shown in the following table could be obtained by respectively using the enamines, the hydrazine, and the chloride reagents used in Step 4 in the table.

The compounds shown in the following table could be obtained by respectively using the corresponding enamines and hydrazines and the like.

(Corresponding Enamines, Hydrazines, and Chloride Reagents)

| Example | Enamine | Hydrazine | Chloride Reagent |
|---|---|---|---|
| 5-1-254 I-A011 | (structure) | Q001 (structure) | (structure) |

-continued

| Example | | Enamine | Hydrazine | Chloride Reagent |
|---|---|---|---|---|
| 5-1-255 | I-A011 | [structure: 6-bromo-5-(2,2-difluoroethoxy)indole with dimethylaminomethylene cyanoketone] | Q001 HCl [4-(2-fluorophenoxy)-2-methylphenyl hydrazine] | [3-fluoropropanesulfonyl chloride] |
| 5-1-273 | I-A011 | [structure: 6-bromo-5-(2,2-difluoroethoxy)indole with dimethylaminomethylene cyanoketone] | Q001 HCl [4-(2-fluorophenoxy)-2-methylphenyl hydrazine] | [benzyl chloroformate] |
| 5-1-274 | I-A011 | [structure: 6-bromo-5-(2,2-difluoroethoxy)indole with dimethylaminomethylene cyanoketone] | Q001 HCl [4-(2-fluorophenoxy)-2-methylphenyl hydrazine] | [isobutyl chloroformate] |
| 5-1-275 | I-A011 | [structure: 6-bromo-5-(2,2-difluoroethoxy)indole with dimethylaminomethylene cyanoketone] | Q001 HCl [4-(2-fluorophenoxy)-2-methylphenyl hydrazine] | [benzylsulfonyl chloride] |
| 5-1-276 | I-A011 | [structure: 6-bromo-5-(2,2-difluoroethoxy)indole with dimethylaminomethylene cyanoketone] | Q001 HCl [4-(2-fluorophenoxy)-2-methylphenyl hydrazine] | [naphthalene-2-sulfonyl chloride] |
| 5-1-278 | I-A011 | [structure: 6-bromo-5-(2,2-difluoroethoxy)indole with dimethylaminomethylene cyanoketone] | Q001 HCl [4-(2-fluorophenoxy)-2-methylphenyl hydrazine] | |

(Synthesized Compounds)

| Example No. | Compound | m/z (M + H) | Retention Time (Minute) | LCMS Measurement Condition |
|---|---|---|---|---|
| 5-1-254 | [complex structure with methanesulfonamido-pyrrolidine-imidazolidinedione fused to difluoroethoxyindole-aminopyrazole-(fluorophenoxy)methylphenyl] | 738 | 1.14 | TFA Rev.7 |

-continued

| Example No. | Compound | m/z (M + H) | Retention Time (Minute) | LCMS Measurement Condition |
|---|---|---|---|---|
| 5-1-255 | | 784 | 0.97 | AA Rev.11 |
| 5-1-273 | | 794 | 1.29 | TFA Rev.7 |
| 5-1-274 | | 760 | 1.28 | TFA Rev.7 |
| 5-1-275 | | 814 | 1.02 | AA Rev.11 |
| 5-1-276 | | 850 | 1.32 | TFA Rev.7 |

-continued
| Example No. | Compound | m/z (M + H) | Retention Time (Minute) | LCMS Measurement Condition |
|---|---|---|---|---|
| 5-1-278 | 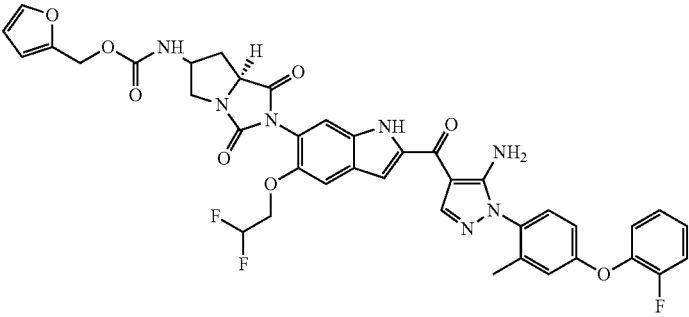 [SMILES: Cc1cc(Oc2ccccc2F)ccc1-n1ncc(C(=O)c2cc3cc(OCC(F)F)c(N4C(=O)[C@@H]5CC(NC(=O)OCc6ccco6)CN5C4=O)cc3[nH]2)c1N] | 784 | 1.24 | TFA Rev.7 |
The compounds in Example No. 5 (Example Nos. (5-1-001) to (5-1-577)) were synthesized by the general synthesis methods described above and/or the synthesis methods in Examples. These compounds in Example No. 5 are listed as described below.

| Example No. | Chemical Structure | Compound Name | m/z (M + H) | Reaction Time (Minute) | LCMS Measurement Condition |
|---|---|---|---|---|---|
| 5-1-001 | 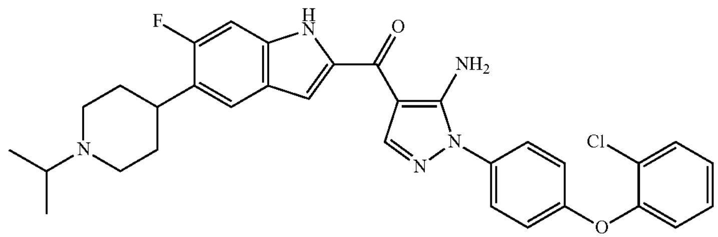 [SMILES: CC(C)N1CCC(c2cc3cc(C(=O)c4cnn(-c5ccc(Oc6ccccc6Cl)cc5)c4N)[nH]c3cc2F)CC1] | [5-amino-1-[4-(2-chlorophenoxy)phenyl]pyrazol-4-yl]-[6-fluoro-5-(1-propan-2-ylpiperidin-4-yl)-1H-indol-2-yl]methanone | 572, 574 | 1.11 | TFA Rev.5 |
| 5-1-002 | 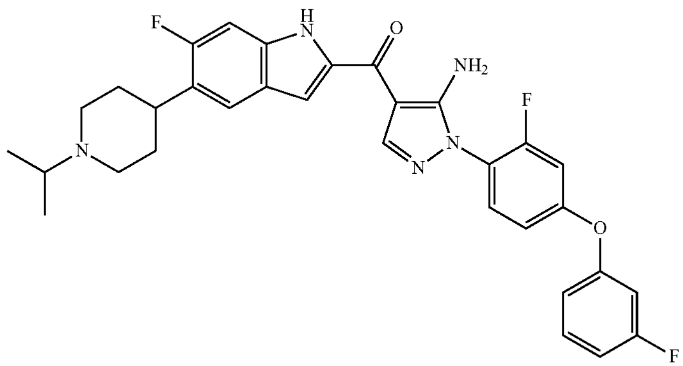 [SMILES: CC(C)N1CCC(c2cc3cc(C(=O)c4cnn(-c5ccc(Oc6cccc(F)c6)cc5F)c4N)[nH]c3cc2F)CC1] | [5-amino-1-[2-fluoro-4-(3-fluorophenoxy)phenyl]pyrazol-4-yl]-[6-fluoro-5-(1-propan-2-ylpiperidin-4-yl)-1H-indol-2-yl]methanone | 574 | 1.08 | TFA Rev.5 |
| 5-1-003 | 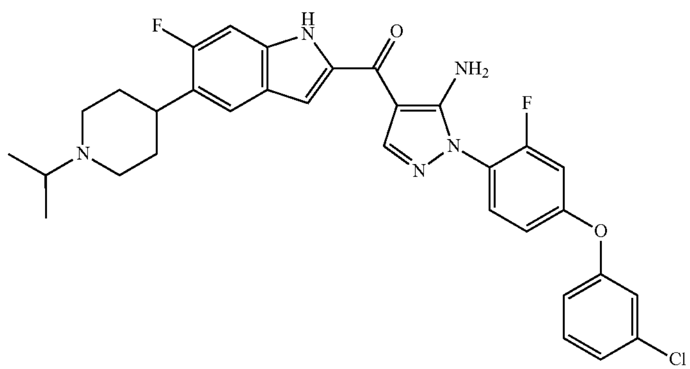 [SMILES: CC(C)N1CCC(c2cc3cc(C(=O)c4cnn(-c5ccc(Oc6cccc(Cl)c6)cc5F)c4N)[nH]c3cc2F)CC1] | [5-amino-1-[4-(3-chlorophenoxy)-2-fluorophenyl]pyrazol-4-yl]-[6-fluoro-5-(1-propan-2-ylpiperidin-4-yl)-1H-indol-2-yl]methanone | 590, 592 | 1.13 | TFA Rev.5 |

-continued

| Example No. | Chemical Structure | Compound Name | m/z (M + H) | Reaction Time (Minute) | LCMS Measurement Condition |
|---|---|---|---|---|---|
| 5-1-004 | 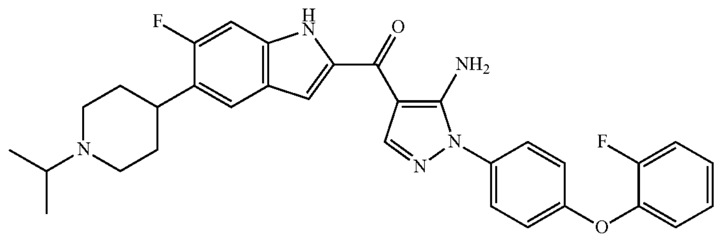 [SMILES: CC(C)N1CCC(c2cc3cc(C(=O)c4cnn(-c5ccc(Oc6ccccc6F)cc5)c4N)[nH]c3cc2F)CC1] | [5-amino-1-[4-(2-fluorophenoxy)phenyl]pyrazol-4-yl]-[6-fluoro-5-(1-propan-2-ylpiperidin-4-yl)-1H-indol-2-yl]methanone | 556 | 0.97 | AA Rev.2 |
| 5-1-005 | 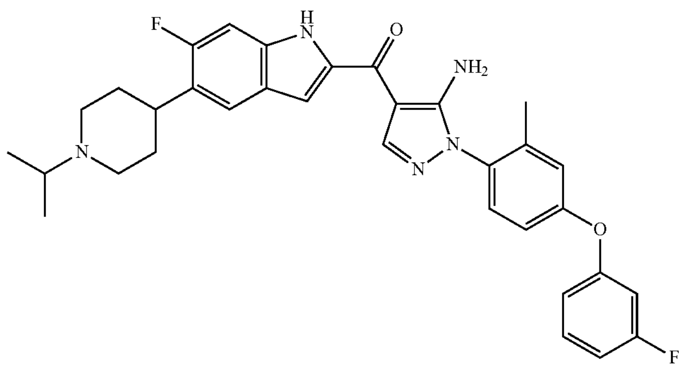 | [5-amino-1-[4-(3-fluorophenoxy)-2-methylphenyl]pyrazol-4-yl]-[6-fluoro-5-(1-propan-2-ylpiperidin-4-yl)-1H-indol-2-yl]methanone | 570 | 1.10 | TFA Rev.5 |
| 5-1-006 | 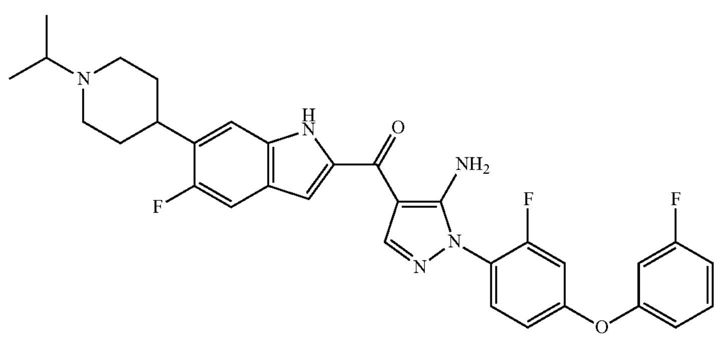 [SMILES: CC(C)N1CCC(c2cc3[nH]c(C(=O)c4cnn(-c5ccc(Oc6cccc(F)c6)cc5F)c4N)cc3cc2F)CC1] | [5-amino-1-[2-fluoro-4-(3-fluorophenoxy)phenyl]pyrazol-4-yl]-[5-fluoro-6-(1-propan-2-ylpiperidin-4-yl)-1H-indol-2-yl]methanone | 574 | 1.04 | AA Rev.2 |

-continued

| Example No. | Chemical Structure | Compound Name | m/z (M + H) | Reaction Time (Minute) | LCMS Measurement Condition |
|---|---|---|---|---|---|
| 5-1-007 | 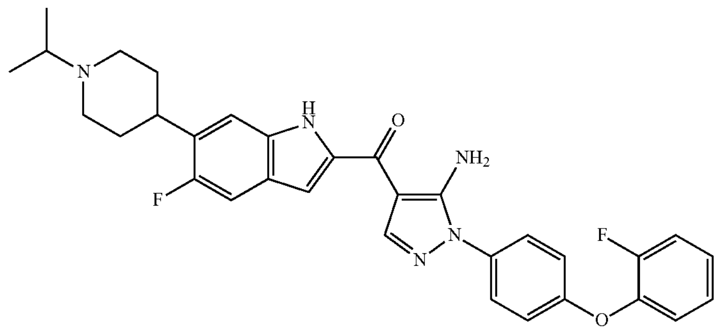 [SMILES: CC(C)N1CCC(c2cc3[nH]c(C(=O)c4cnn(-c5ccc(Oc6ccccc6F)cc5)c4N)cc3cc2F)CC1] | [5-amino-1-[4-(2-fluorophenoxy)phenyl]pyrazol-4-yl]-[5-fluoro-6-(1-propan-2-ylpiperidin-4-yl)-1H-indol-2-yl]methanone | 556 | 1.04 | AA Rev.2 |
| 5-1-008 | 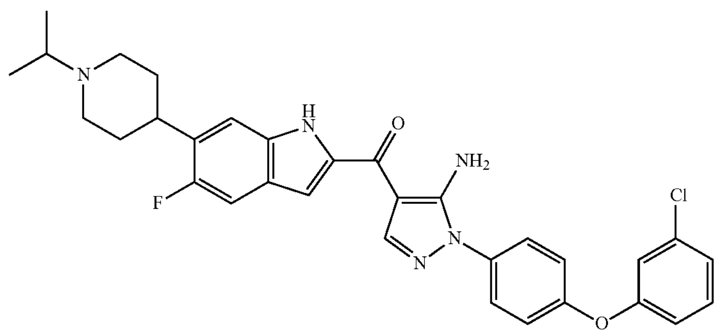 [SMILES: CC(C)N1CCC(c2cc3[nH]c(C(=O)c4cnn(-c5ccc(Oc6cccc(Cl)c6)cc5)c4N)cc3cc2F)CC1] | [5-amino-1-[4-(3-chlorophenoxy)phenyl]pyrazol-4-yl]-[5-fluoro-6-(1-propan-2-ylpiperidin-4-yl)-1H-indol-2-yl]methanone | 572, 574 | 1.11 | AA Rev.2 |
| 5-1-009 | 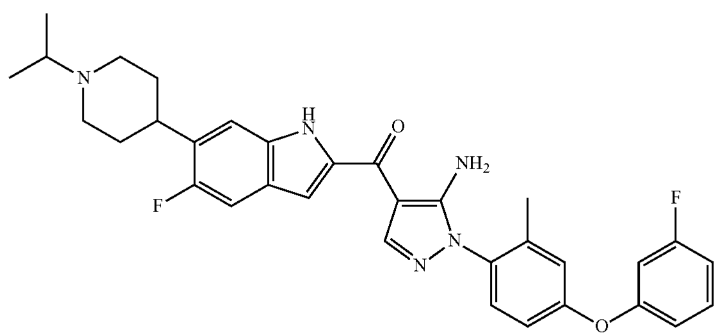 [SMILES: Cc1cc(Oc2cccc(F)c2)ccc1-n1ncc(C(=O)c2cc3cc(F)c(C4CCN(C(C)C)CC4)cc3[nH]2)c1N] | [5-amino-1-[4-(3-fluorophenoxy)-2-methylphenyl]pyrazol-4-yl]-[5-fluoro-6-(1-propan-2-ylpiperidin-4-yl)-1H-indol-2-yl]methanone | 570 | 1.06 | AA Rev.2 |

-continued

| Example No. | Chemical Structure | Compound Name | m/z (M + H) | Reaction Time (Minute) | LCMS Measurement Condition |
|---|---|---|---|---|---|
| 5-1-010 | 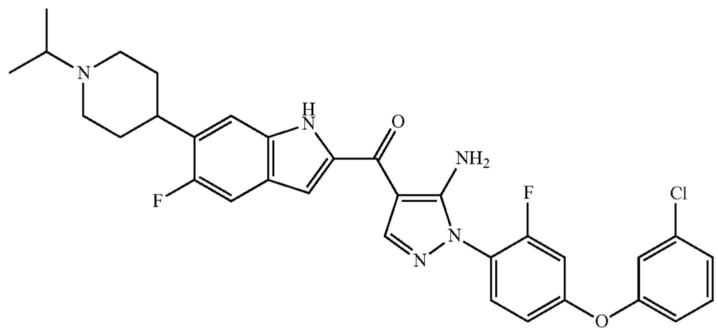 | [5-amino-1-[4-(3-chlorophenoxy)-2-fluorophenyl]pyrazol-4-yl]-[5-fluoro-6-(1-propan-2-yl)piperidin-4-yl)-1H-indol-2-yl]methanone | 590, 592 | 1.08 | AA Rev.2 |
| 5-1-011 | 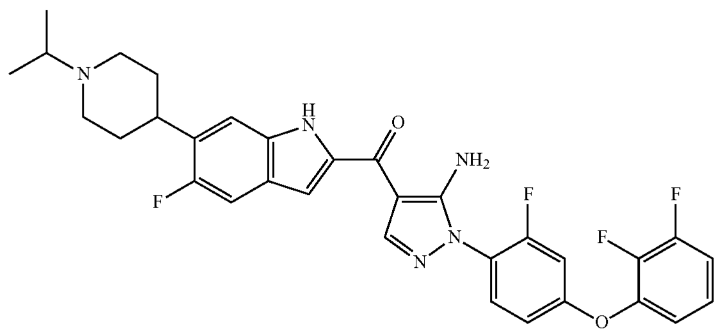 [SMILES: CC(C)N1CCC(c2cc3[nH]c(C(=O)c4cnn(-c5ccc(Oc6cccc(F)c6F)cc5F)c4N)cc3cc2F)CC1] | [5-amino-1-[4-(2,3-difluorophenoxy)-2-fluorophenyl]pyrazol-4-yl]-[5-fluoro-6-(1-propan-2-yl)piperidin-4-yl)-1H-indol-2-yl]methanone | 592 | 1.12 | TFA Rev.5 |

-continued

| Example No. | Chemical Structure | Compound Name | m/z (M + H) | Reaction Time (Minute) | LCMS Measurement Condition |
|---|---|---|---|---|---|
| 5-1-012 | 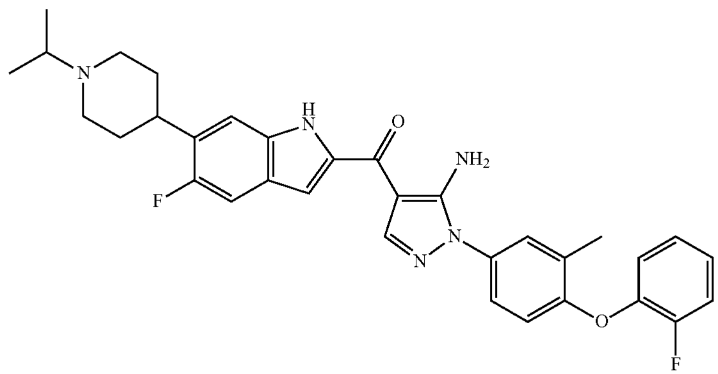 [SMILES: Cc1cc(-n2ncc(C(=O)c3cc4cc(F)c(C5CCN(C(C)C)CC5)cc4[nH]3)c2N)ccc1Oc1ccccc1F] | [5-amino-1-[4-(2-fluorophenoxy)-3-methylphenyl]pyrazol-4-yl]-[5-methyl-6-(1-propan-2-ylpiperidin-4-yl)-1H-indol-2-yl]methanone | 566 | 1.06 | AA Rev.2 |
| 5-1-013 | 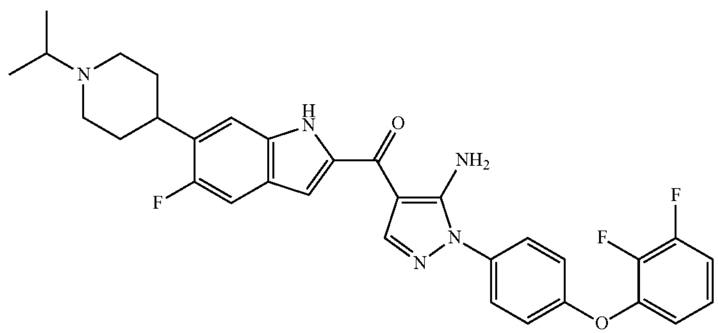 [SMILES: CC(C)N1CCC(c2cc3[nH]c(C(=O)c4cnn(-c5ccc(Oc6cccc(F)c6F)cc5)c4N)cc3cc2F)CC1] | [5-amino-1-[4-(2,3-difluorophenoxy)phenyl]pyrazol-4-yl]-[5-fluoro-6-(1-propan-2-ylpiperidin-4-yl)-1H-indol-2-yl]methanone | 574 | 1.04 | AA Rev.2 |

| Example No. | Chemical Structure | Compound Name | m/z (M + H) | Reaction Time (Minute) | LCMS Measurement Condition |
|---|---|---|---|---|---|
| 5-1-014 | 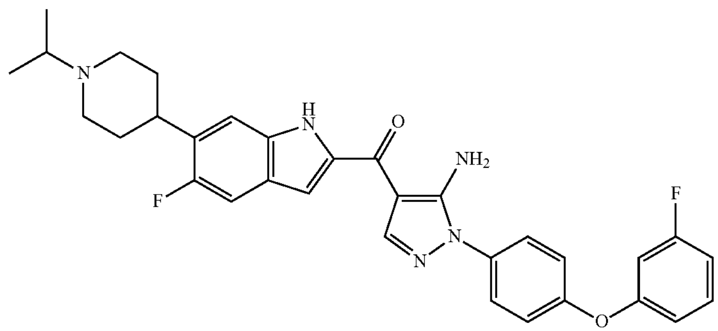 [SMILES: CC(C)N1CCC(c2cc3[nH]c(C(=O)c4cnn(-c5ccc(Oc6cccc(F)c6)cc5)c4N)cc3cc2F)CC1] | [5-amino-1-[4-(3-fluorophenoxy)phenyl]pyrazol-4-yl]-[5-fluoro-6-(1-propan-2-ylpiperidin-4-yl)-1H-indol-2-yl]methanone | 556 | 1.05 | AA Rev.2 |
| 5-1-015 | 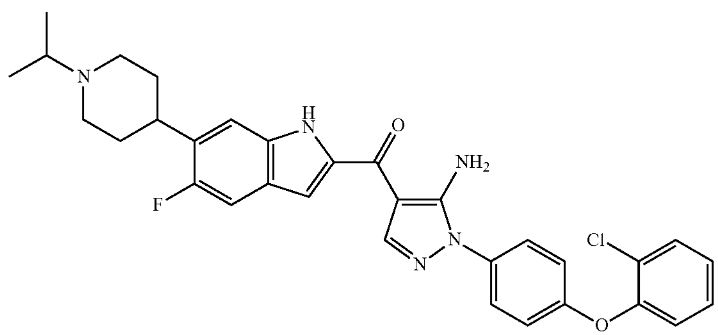 | [5-amino-1-[4-(2-chlorophenoxy)phenyl]pyrazol-4-yl]-[5-fluoro-6-(1-propan-2-ylpiperidin-4-yl)-1H-indol-2-yl]methanone | 572, 574 | 1.06 | AA Rev.2 |
| 5-1-016 | 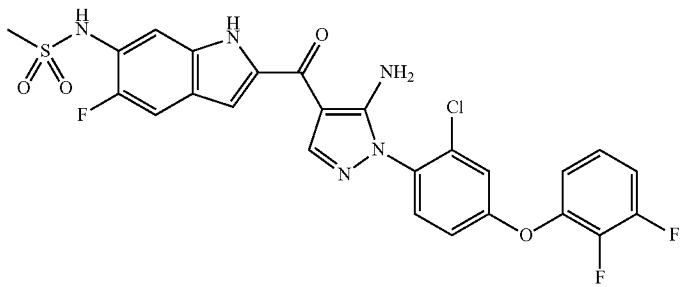 [SMILES: CS(=O)(=O)Nc1cc2[nH]c(C(=O)c3cnn(-c4ccc(Oc5cccc(F)c5F)cc4Cl)c3N)cc2cc1F] | N-[2-[5-amino-1-[2-chloro-4-(2,3-difluorophenoxy)phenyl]pyrazole-4-carbonyl]-5-fluoro-1H-indol-6-yl]methanesulfonamide | 576, 578 | 1.42 | AA Rev.3 |

| Example No. | Chemical Structure | Compound Name | m/z (M + H) | Reaction Time (Minute) | LCMS Measurement Condition |
|---|---|---|---|---|---|
| 5-1-017 | 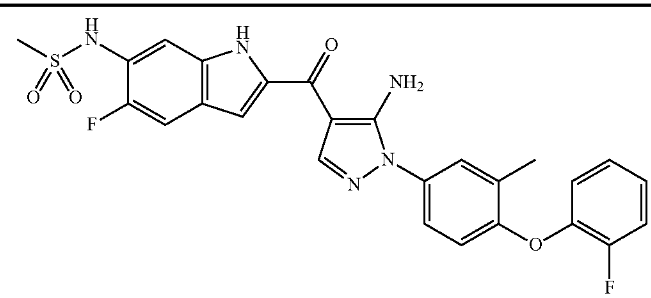 | N-[2-[5-amino-1-[4-(2-fluorophenoxy)-3-methylphenyl]pyrazole-4-carbonyl]-5-fluoro-1H-indol-6-yl]methanesulfonamide | 538 | 1.45 | AA Rev.3 |
| 5-1-018 | 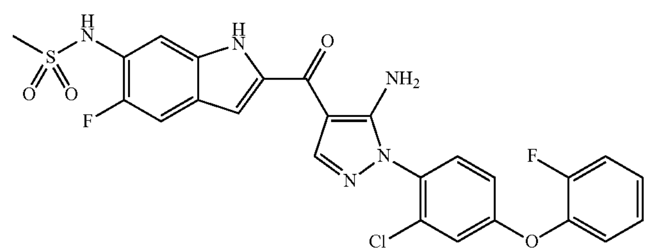 [SMILES: CS(=O)(=O)Nc1cc2[nH]c(C(=O)c3cnn(-c4ccc(Oc5ccccc5F)cc4Cl)c3N)cc2cc1F] | N-[2-[5-amino-1-[2-chloro-4-(2-fluorophenoxy)phenyl]pyrazole-4-carbonyl]-5-fluoro-1H-indol-6-yl]methanesulfonamide | 558, 560 | 1.39 | AA Rev.3 |
| 5-1-019 | 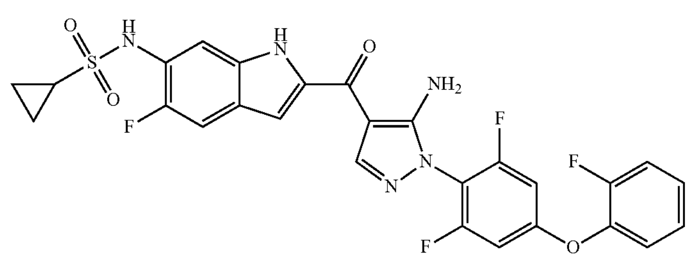 | N-[2-[5-amino-1-[2,6-difluoro-4-(2-fluorophenoxy)phenyl]pyrazole-4-carbonyl]-5-fluoro-1H-indol-6-yl]cyclopropanesulfonamide | 586 | 1.40 | AA Rev.3 |

| Example No. | Chemical Structure | Compound Name | m/z (M + H) | Reaction Time (Minute) | LCMS Measurement Condition |
|---|---|---|---|---|---|
| 5-1-020 | 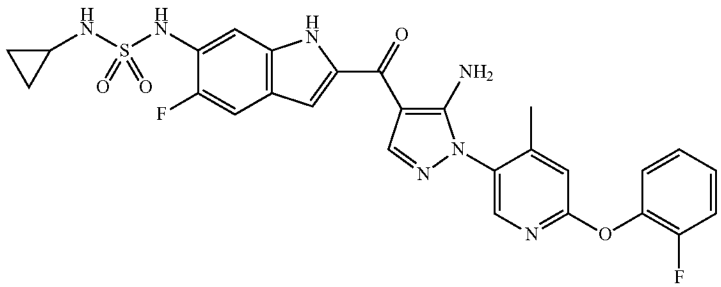 [SMILES: Cc1cc(Oc2ccccc2F)ncc1-n1ncc(C(=O)c2cc3cc(F)c(NS(=O)(=O)NC4CC4)cc3[nH]2)c1N] | [5-amino-1-[6-(2-fluorophenoxy)-4-methylpyridin-3-yl]pyrazol-4-yl]-[6-(cyclopropylsulfamoylamino)-5-fluoro-1H-indol-2-yl]methanone | 580 | 1.20 | TFA Rev.5 |
| 5-1-021 | 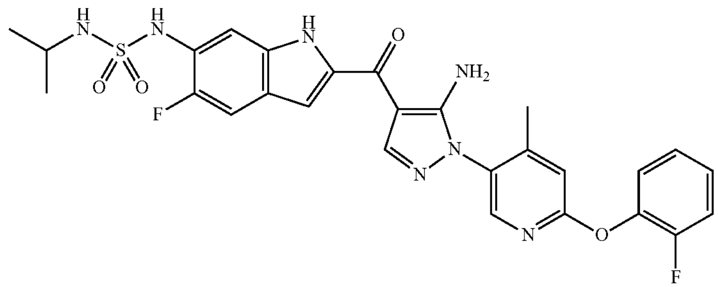 [SMILES: Cc1cc(Oc2ccccc2F)ncc1-n1ncc(C(=O)c2cc3cc(F)c(NS(=O)(=O)NC(C)C)cc3[nH]2)c1N] | [5-amino-1-[6-(2-fluorophenoxy)-4-methylpyridin-3-yl]pyrazol-4-yl]-[5-fluoro-6-(propan-2-ylsulfamoylamino)-1H-indol-2-yl]methanone | 582 | 1.41 | AA Rev.3 |
| 5-1-022 | 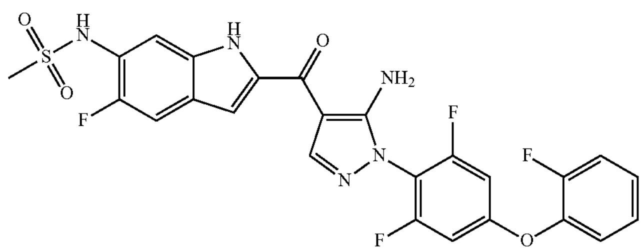 [SMILES: CS(=O)(=O)Nc1cc2[nH]c(C(=O)c3cnn(-c4c(F)cc(Oc5ccccc5F)cc4F)c3N)cc2cc1F] | N-[2-[5-amino-1-[2,6-difluoro-4-(2-fluorophenoxy)phenyl]pyrazole-4-carbonyl]-5-fluoro-1H-indol-6-yl]methanesulfonamide | 560 | 0.98 | AA Rev.11 |

| Example No. | Chemical Structure | Compound Name | m/z (M + H) | Reaction Time (Minute) | LCMS Measurement Condition |
|---|---|---|---|---|---|
| 5-1-023 | 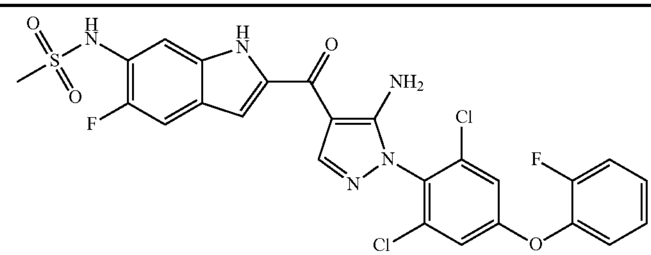 | N-[2-[5-amino-1-[2,6-dichloro-4-(2-fluorophenoxy)phenyl]pyrazole-4-carbonyl]-5-fluoro-1H-indol-6-yl]methanesulfonamide | 592, 594, 596 | 1.42 | AA Rev.3 |
| 5-1-024 | 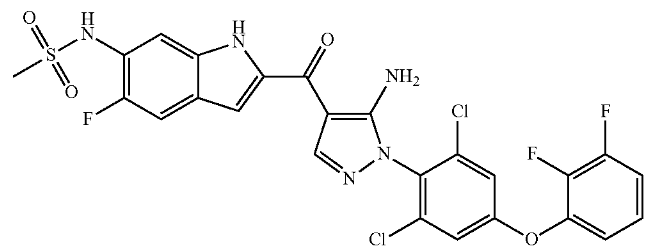 | N-[2-[5-amino-1-[2,6-dichloro-4-(2,3-difluorophenoxy)phenyl]pyrazole-4-carbonyl]-5-fluoro-1H-indol-6-yl]methanesulfonamide | 610, 612, 614 | 1.44 | AA Rev.3 |
| 5-1-025 | 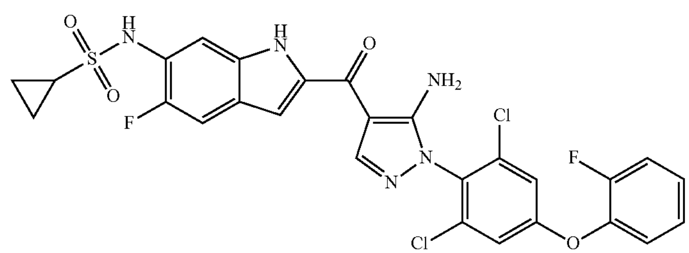 [SMILES: Nc1c(C(=O)c2cc3cc(F)c(NS(=O)(=O)C4CC4)cc3[nH]2)cnn1-c1c(Cl)cc(Oc2ccccc2F)cc1Cl] | N-[2-[5-amino-1-[2,6-dichloro-4-(2-fluorophenoxy)phenyl]pyrazole-4-carbonyl]-5-fluoro-1H-indol-6-yl]cyclopropanesulfonamide | 618, 620, 622 | 1.45 | AA Rev.3 |
| 5-1-026 | 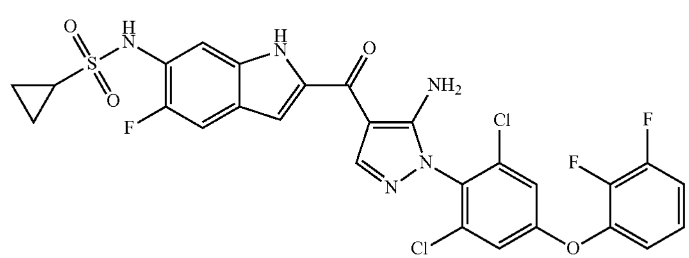 | N-[2-[5-amino-1-[2,6-dichloro-4-(2,3-difluorophenoxy)phenyl]pyrazole-4-carbonyl]-5-fluoro-1H-indol-6-yl]cyclopropanesulfonamide | 636, 638, 640 | 1.47 | AA Rev.3 |

-continued

| Example No. | Chemical Structure | Compound Name | m/z (M + H) | Reaction Time (Minute) | LCMS Measurement Condition |
|---|---|---|---|---|---|
| 5-1-027 | 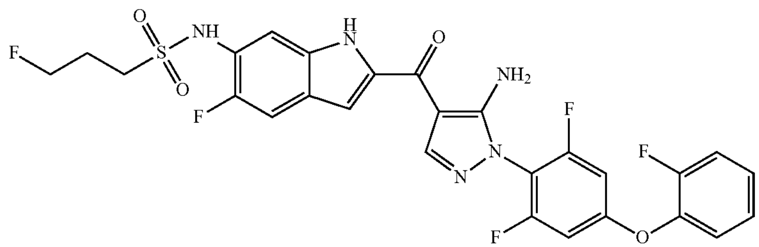 | N-[2-[5-amino-1-[2,6-difluoro-4-(2-fluorophenoxy)phenyl]pyrazole-4-carbonyl]-5-fluoro-1H-indol-6-yl]-3-fluoropropane-1-sulfonamide | 606 | 1.41 | AA Rev.3 |
| 5-1-028 | 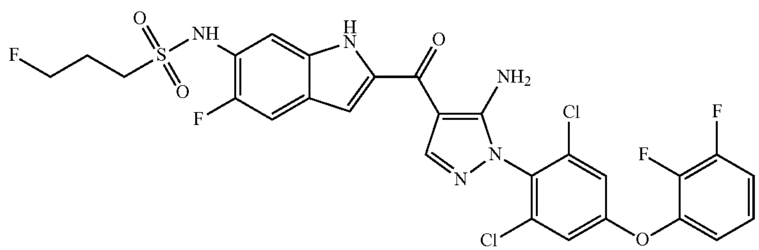 | N-[2-[5-amino-1-[2,6-dichloro-4-(2,3-difluorophenoxy)phenyl]pyrazole-4-carbonyl]-5-fluoro-1H-indol-6-yl]-3-fluoropropane-1-sulfanamide | 656, 658, 660 | 1.30 | TFA Rev.5 |
| 5-1-029 | 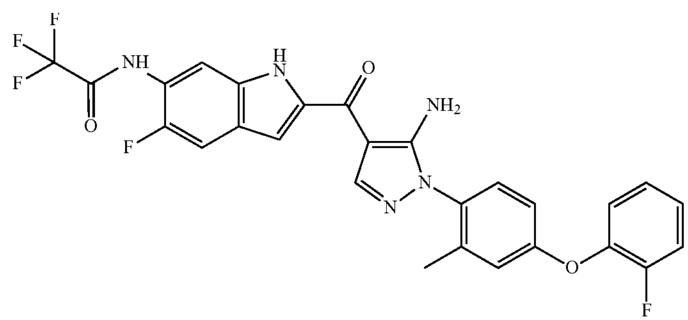 [SMILES: Cc1cc(Oc2ccccc2F)ccc1-n1ncc(C(=O)c2cc3cc(F)c(NC(=O)C(F)(F)F)cc3[nH]2)c1N] | N-[2-[5-amino-1-[4-(2-fluorophenoxy)-2-methylphenyl]pyrazole-4-carbonyl]-5-fluoro-1H-indol-6-yl]-2,2,2-trifluoroacetamide | 556 | 1.48 | AA Rev.3 |

| Example No. | Chemical Structure | Compound Name | m/z (M + H) | Reaction Time (Minute) | LCMS Measurement Condition |
|---|---|---|---|---|---|
| 5-1-030 | 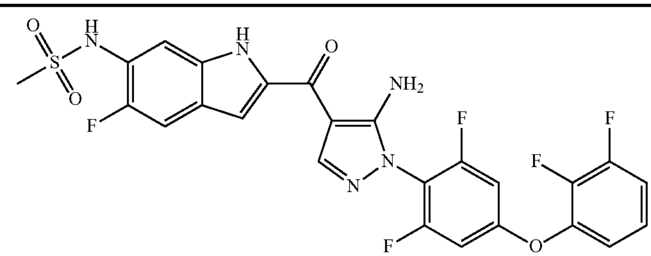 | N-[2-[5-amino-1-[4-(2,3-difluorophenoxy)-2,6-difluorophenyl]pyrazole-4-carbonyl]-5-fluoro-1H-indol-6-yl]methanesulfonamide | 578 | 0.99 | AA Rev.11 |
| 5-1-031 | 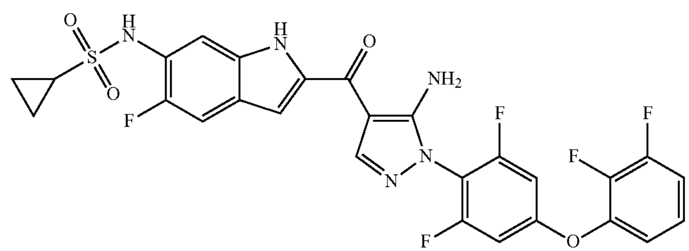 [SMILES: Nc1c(C(=O)c2cc3cc(F)c(NS(=O)(=O)C4CC4)cc3[nH]2)cnn1-c1c(F)cc(Oc2cccc(F)c2F)cc1F] | N-[2-[5-amino-1-[4-(2,3-difluorophenoxy)-2,6-difluorophenyl]pyrazole-4-carbonyl]-5-fluoro-1H-indol-6-yl]cyclopropanesulfonamide | 604 | 1.43 | AA Rev.3 |
| 5-1-032 | 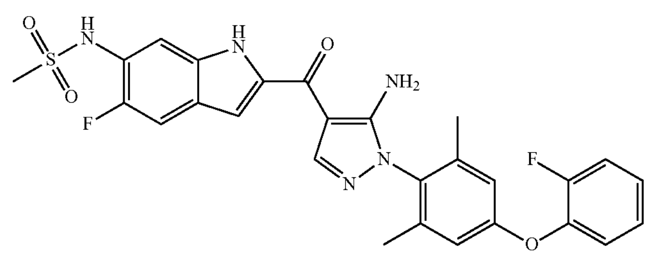 [SMILES: Cc1cc(Oc2ccccc2F)cc(C)c1-n1ncc(C(=O)c2cc3cc(F)c(NS(C)(=O)=O)cc3[nH]2)c1N] | N-[2-[5-amino-1-[4-(2-fluorophenoxy)-2,6-dimethylphenyl]pyrazole-4-carbonyl]-5-fluoro-1H-indol-6-yl]methanesulfonamide | 552 | 0.99 | AA Rev.4 |
| 5-1-033 | 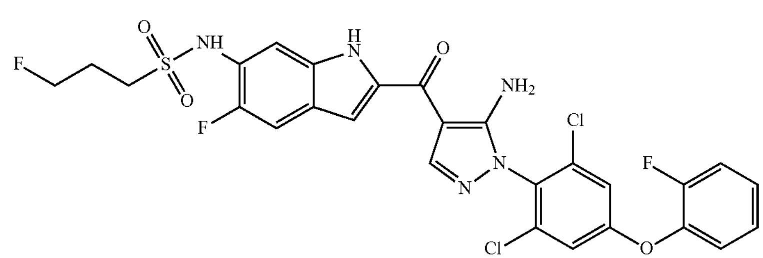 [SMILES: Nc1c(C(=O)c2cc3cc(F)c(NS(=O)(=O)CCCF)cc3[nH]2)cnn1-c1c(Cl)cc(Oc2ccccc2F)cc1Cl] | N-[2-[5-amino-1-[2,6-dichloro-4-(2-fluorophenoxy)phenyl]pyrazole-4-carbonyl]-5-fluoro-1H-indol-6-yl]-3-fluoropropane-1-sulfonamide | 638, 640, 642 | 1.29 | TFA Rev.5 |

-continued

| Example No. | Chemical Structure | Compound Name | m/z (M + H) | Reaction Time (Minute) | LCMS Measurement Condition |
|---|---|---|---|---|---|
| 5-1-034 | 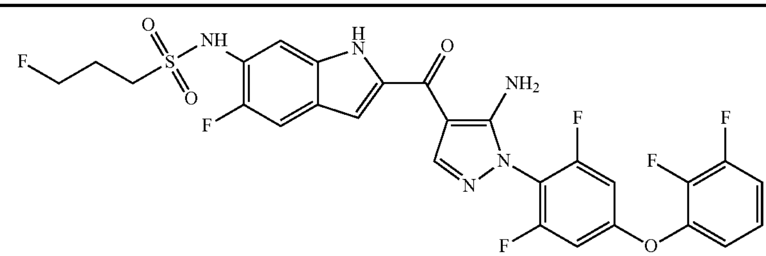 | N-[2-[5-amino-1-[4-(2,3-difluorophenoxy)-2,6-difluorophenyl]pyrazole-4-carbonyl]-5-fluoro-1H-indol-6-yl]-3-fluoropropane-1-sulfonamide | 624 | 1.01 | AA Rev.11 |
| 5-1-035 | 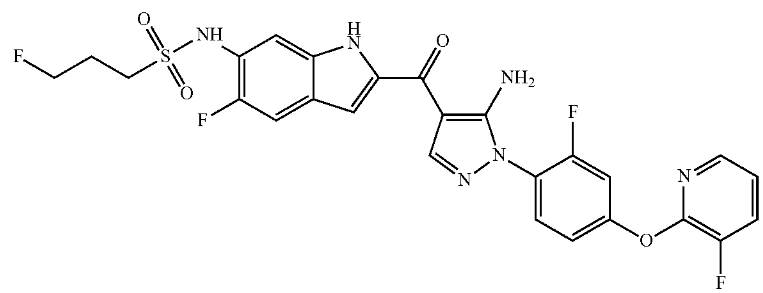 | N-[2-[5-amino-1-[2-fluoro-4-(3-fluoropyridin-2-yl)oxyphenyl]pyrazole-4-carbonyl]-5-fluoro-1H-indol-6-yl]-3-fluoropropane-1-sulfonamide | 589 | 1.14 | TFA Rev.5 |
| 5-1-036 | 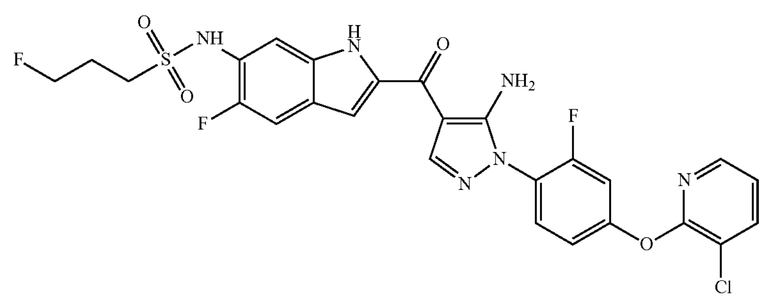 [SMILES: Nc1c(C(=O)c2cc3cc(F)c(NS(=O)(=O)CCCF)cc3[nH]2)cnn1-c1ccc(Oc2ncccc2F)cc1F] | N-[2-[5-amino-1-[4-(3-chloropyridin-2-yl)oxy-2-fluorophenyl]pyrazole-4-carbonyl]-5-fluoro-1H-indol-6-yl]-3-fluoropropane-1-sulfonamide | 605, 607 | 0.98 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-037 | 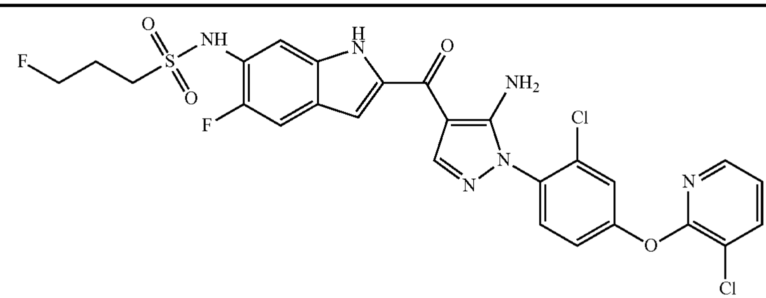 | N-[2-[5-amino-1-[2-chloro-4-(3-chloropyridin-2-yl)oxyphenyl]pyrazole-4-carbonyl]-5-fluoro-1H-indol-6-yl]-3-fluoropropane-1-sulfonamide | 621, 623, 625 | 0.97 | AA Rev.4 |
| 5-1-038 | 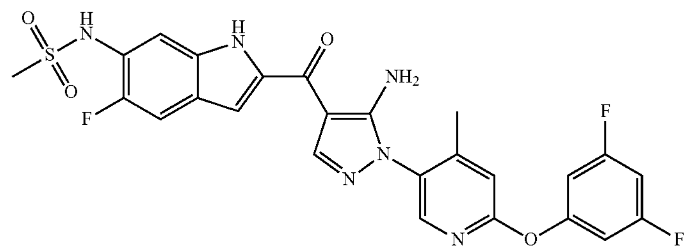 [SMILES: Cc1cc(Oc2cc(F)cc(F)c2)ncc1-n1ncc(C(=O)c2cc3cc(F)c(NS(C)(=O)=O)cc3[nH]2)c1N] | N-[2-[5-amino-1-[6-(3,5-difluorophenoxy)-4-methylpyridin-3-yl]pyrazole-4-carbonyl]-5-fluoro-1H-indol-6-yl]methanesulfonamide | 557 | 0.96 | AA Rev.4 |
| 5-1-039 | 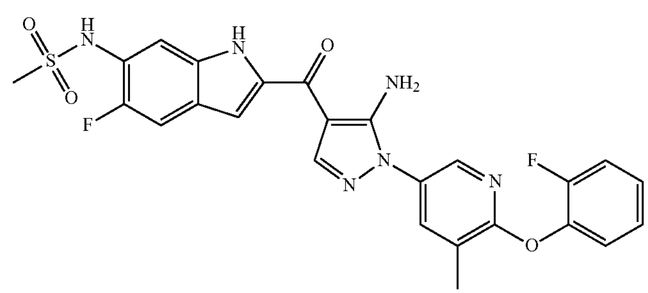 | N-[2-[5-amino-1-[6-(2-fluorophenoxy)-5-methylpyridin-3-yl]pyrazole-4-carbonyl]-5-fluoro-1H-indol-6-yl]methanesulfonamide | 539 | 1.19 | TFA Rev.5 |

-continued

| Example No. | Chemical Structure | Compound Name | m/z (M + H) | Reaction Time (Minute) | LCMS Measurement Condition |
|---|---|---|---|---|---|
| 5-1-040 | 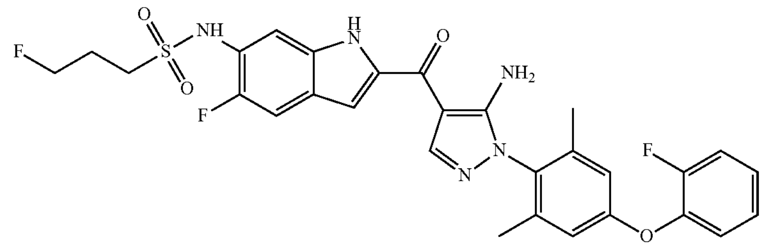 | N-[2-[5-amino-1-[4-(2-fluorophenoxy)-2,6-dimethylphenyl]pyrazole-4-carbonyl]-5-fluoro-1H-indol-6-yl]-3-fluoropropane-1-sulfonamide | 598 | 1.00 | AA Rev.4 |
| 5-1-041 | 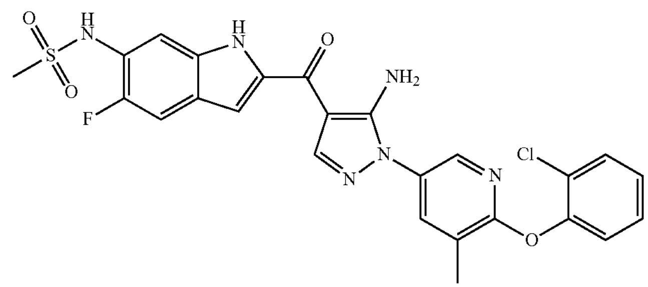 [SMILES: Cc1cc(-n2ncc(C(=O)c3cc4cc(F)c(NS(C)(=O)=O)cc4[nH]3)c2N)cnc1Oc1ccccc1Cl] | N-[2-[5-amino-1-[6-(2-chlorophenoxy)-5-methylpyridin-3-yl]pyrazole-4-carbonyl]-5-fluoro-1H-indol-6-yl]methanesulfonamide | 555, 557 | 1.23 | TFA Rev.5 |
| 5-1-042 | 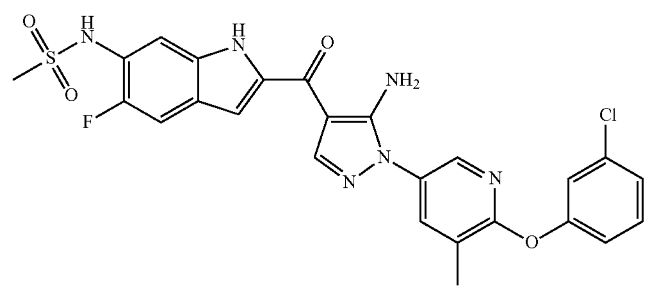 [SMILES: Cc1cc(-n2ncc(C(=O)c3cc4cc(F)c(NS(C)(=O)=O)cc4[nH]3)c2N)cnc1Oc1cccc(Cl)c1] | N-[2-[5-amino-1-[6-(3-chlorophenoxy)-5-methylpyridin-3-yl]pyrazole-4-carbonyl]-5-fluoro-1H-indol-6-yl]methanesulfonamide | 555, 557 | 1.02 | AA Rev.4 |

| Example No. | Chemical Structure | Compound Name | m/z (M + H) | Reaction Time (Minute) | LCMS Measurement Condition |
|---|---|---|---|---|---|
| 5-1-043 | 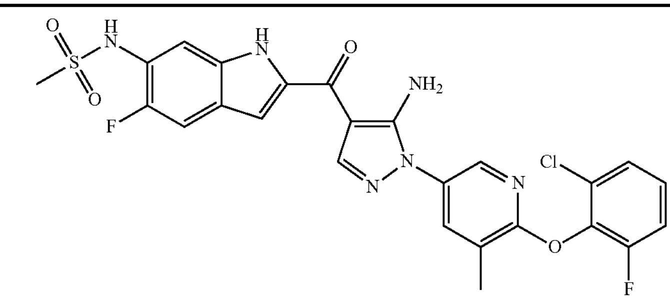 | N-[2-[5-amino-1-[6-(2-chloro-6-fluorophenoxy)-5-methylpyridin-3-yl]pyrazole-4-carbonyl]-5-fluoro-1H-indol-6-yl]methanesulfonamide | 573, 575 | 1.00 | AA Rev.4 |
| 5-1-044 | 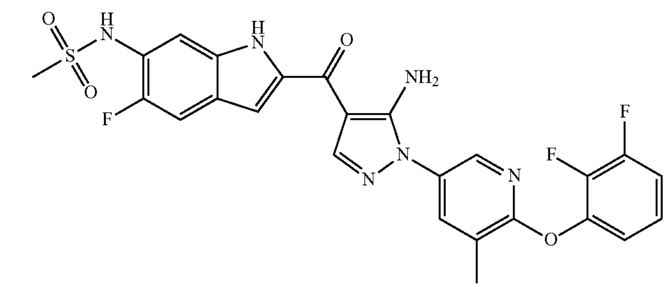 [SMILES: Cc1cc(-n2ncc(C(=O)c3cc4cc(F)c(NS(C)(=O)=O)cc4[nH]3)c2N)cnc1Oc1cccc(F)c1F] | N-[2-[5-amino-1-[6-(2,3-difluorophenoxy)-5-methylpyridin-3-yl]pyrazole-4-carbonyl]-5-fluoro-1H-indol-6-yl]methanesulfonamide | 557 | 0.98 | AA Rev.4 |
| 5-1-045 | 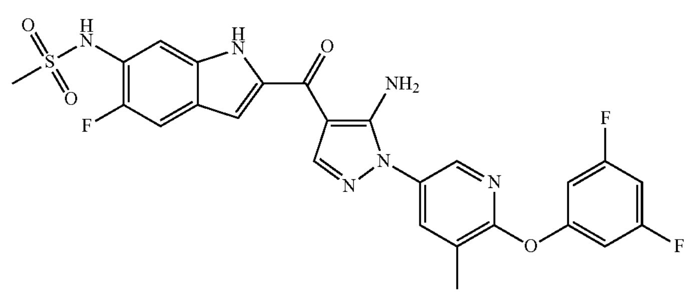 [SMILES: Cc1cc(-n2ncc(C(=O)c3cc4cc(F)c(NS(C)(=O)=O)cc4[nH]3)c2N)cnc1Oc1cc(F)cc(F)c1] | N-[2-[5-amino-1-[6-(3,5-difluorophenoxy)-5-methylpyridin-3-yl]pyrazole-4-carbonyl]-5-fluoro-1H-indol-6-yl]methanesulfonamide | 557 | 1.00 | AA Rev.4 |

| Example No. | Chemical Structure | Compound Name | m/z (M + H) | Reaction Time (Minute) | LCMS Measurement Condition |
|---|---|---|---|---|---|
| 5-1-046 | 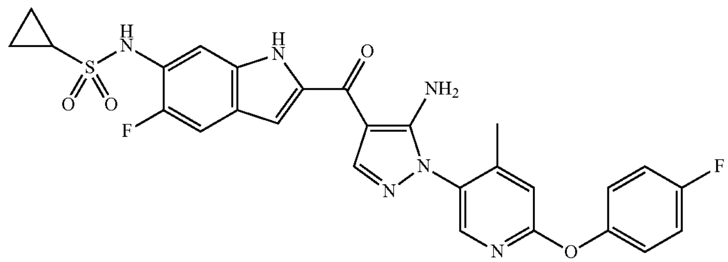 [SMILES: Cc1cc(Oc2ccc(F)cc2)ncc1-n1ncc(C(=O)c2cc3cc(F)c(NS(=O)(=O)C4CC4)cc3[nH]2)c1N] | N-[2-[5-amino-1-[6-(4-fluorophenoxy)-4-methylpyridin-3-yl]pyrazole-4-carbonyl]-5-fluoro-1H-indol-6-yl]cyclopropanesulfonamide | 565 | 1.18 | TFA Rev.5 |
| 5-1-047 | 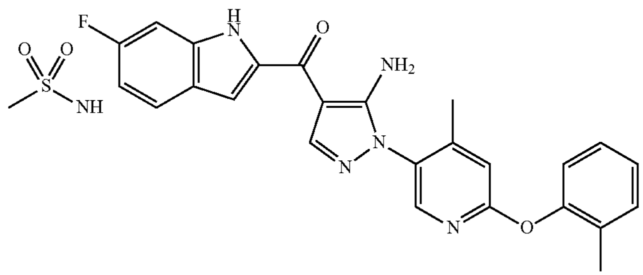 | N-[2-[5-amino-1-[4-methyl-6-(2-methylphenoxy)pyridin-3-yl]pyrazole-4-carbonyl]-6-fluoro-1H-indol-5-yl]methanesulfonamide | 535 | 1.12 | TFA Rev.5 |
| 5-1-048 | 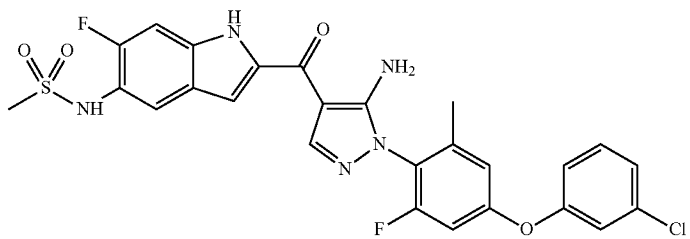 [SMILES: Cc1cc(Oc2cccc(Cl)c2)cc(F)c1-n1ncc(C(=O)c2cc3cc(NS(C)(=O)=O)c(F)cc3[nH]2)c1N] | N-[2-[5-amino-1-[4-(3-chlorophenoxy)-2-fluoro-6-methylphenyl]pyrazole-4-carbonyl]-6-fluoro-1H-indol-5-yl]methanesulfonamide | 572, 574 | 1.24 | TFA Rev.5 |

| Example No. | Chemical Structure | Compound Name | m/z (M+H) | Reaction Time (Minute) | LCMS Measurement Condition |
|---|---|---|---|---|---|
| 5-1-049 | 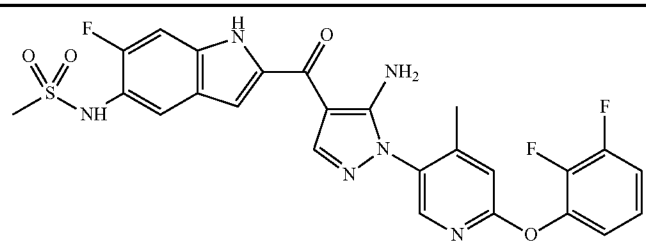 | N-[2-[5-amino-1-[6-(2,3-difluorophenoxy)-4-methylpyridin-3-yl]pyrazole-4-carbonyl]-6-fluoro-1H-indol-5-yl]methanesulfonamide | 557 | 0.91 | AA Rev.4 |
| 5-1-050 | 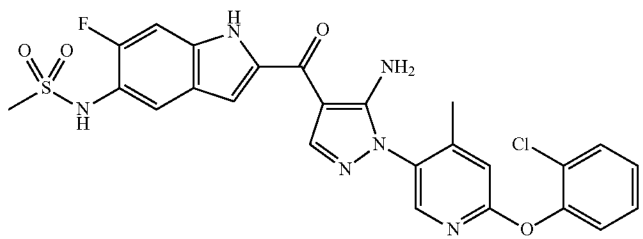 [SMILES: Cc1cc(Oc2ccccc2Cl)ncc1-n1ncc(C(=O)c2cc3cc(NS(C)(=O)=O)c(F)cc3[nH]2)c1N] | N-[2-[5-amino-1-[6-(2-chlorophenoxy)-4-methylpyridin-3-yl]pyrazole-4-carbonyl]-6-fluoro-1H-indol-5-yl]methanesulfonamide | 555, 557 | 1.13 | TFA Rev.5 |
| 5-1-051 | 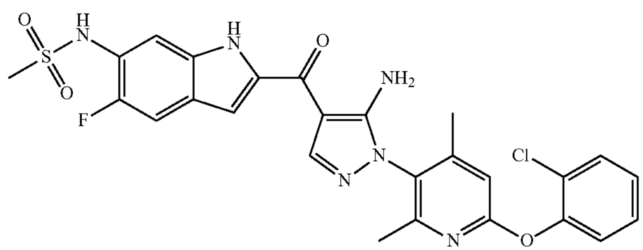 | N-[2-[5-amino-1-[6-(2-chlorophenoxy)-2,4-dimethylpyridin-3-yl]pyrazole-4-carbonyl]-5-fluoro-1H-indol-6-yl]methanesulfonamide | 569, 571 | 0.99 | AA Rev.5 |
| 5-1-052 | 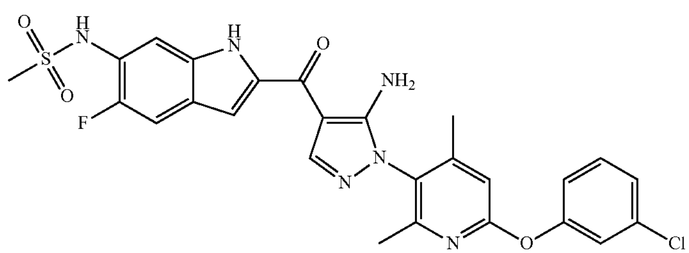 [SMILES: Cc1cc(Oc2cccc(Cl)c2)nc(C)c1-n1ncc(C(=O)c2cc3cc(F)c(NS(C)(=O)=O)cc3[nH]2)c1N] | N-[2-[5-amino-1-[6-(3-chlorophenoxy)-2,4-dimethylpyridin-3-yl]pyrazole-4-carbonyl]-5-fluoro-1H-indol-6-yl]methanesulfonamide | 569, 571 | 1.22 | TFA Rev.5 |

-continued

| Example No. | Chemical Structure | Compound Name | m/z (M + H) | Reaction Time (Minute) | LCMS Measurement Condition |
|---|---|---|---|---|---|
| 5-1-053 | 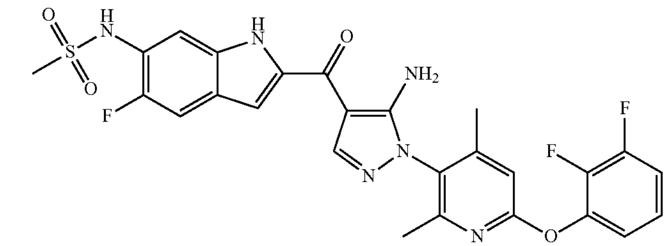 | N-[2-[5-amino-1-[6-(2,3-difluorophenoxy)-2,4-dimethylpyridin-3-yl]pyrazole-4-carbonyl]-5-fluoro-1H-indol-6-yl]methanesulfonamide | 571 | 0.99 | AA Rev.5 |
| 5-1-054 | 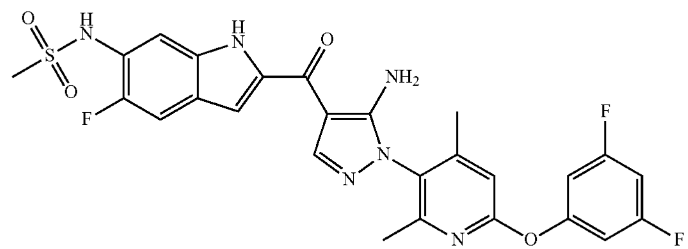 [SMILES: Cc1cc(Oc2cc(F)cc(F)c2)nc(C)c1-n1ncc(C(=O)c2cc3cc(F)c(NS(C)(=O)=O)cc3[nH]2)c1N] | N-[2-[5-amino-1-[6-(3,5-difluorophenoxy)-2,4-dimethylpyridin-3-yl]pyrazole-4-carbonyl]-5-fluoro-1H-indol-6-yl]methanesulfonamide | 571 | 1.00 | AA Rev.5 |
| 5-1-055 | 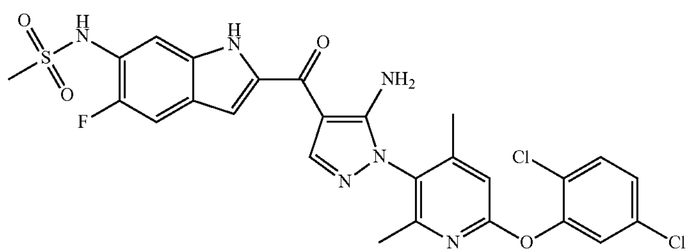 [SMILES: Cc1cc(Oc2cc(Cl)ccc2Cl)nc(C)c1-n1ncc(C(=O)c2cc3cc(F)c(NS(C)(=O)=O)cc3[nH]2)c1N] | N-[2-[5-amino-1-[6-(2,5-dichlorophenoxy)-4-methylpyridin-3-yl]pyrazole-4-carbonyl]-5-fluoro-1H-indol-6-yl]methanesulfonamide | 589, 591, 593 | 1.24 | TFA Rev.5 |

| Example No. | Chemical Structure | Compound Name | m/z (M + H) | Reaction Time (Minute) | LCMS Measurement Condition |
|---|---|---|---|---|---|
| 5-1-056 | 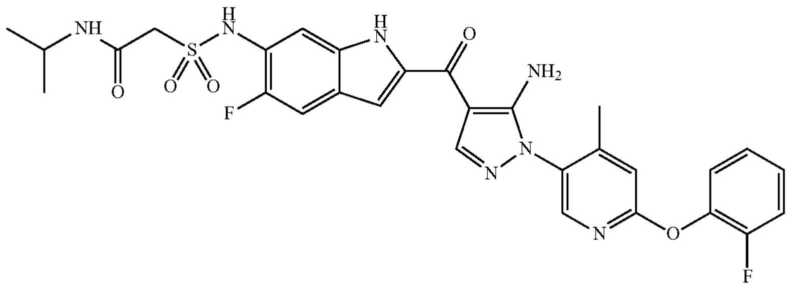 [SMILES: Cc1cc(Oc2ccccc2F)ncc1-n1ncc(C(=O)c2cc3cc(F)c(NS(=O)(=O)CC(=O)NC(C)C)cc3[nH]2)c1N] | 2-[[2-[5-amino-1-[6-(2-fluorophenoxy)-4-methylpyridin-3-yl]pyrazole-4-carbonyl]-5-fluoro-1H-indol-6-yl]sulfamoyl]-N-propan-2-ylacetamide | 624 | 0.96 | AA Rev.5 |
| 5-1-057 | 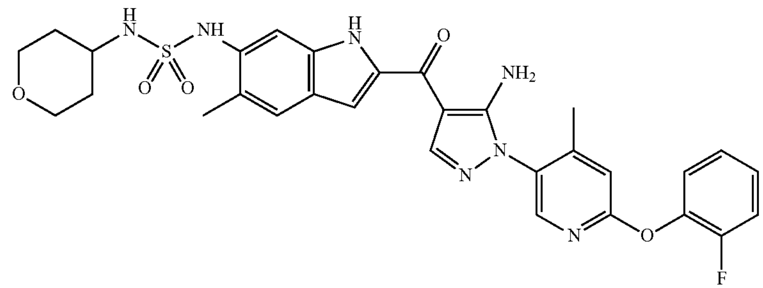 [SMILES: Cc1cc2cc(C(=O)c3cnn(-c4cnc(Oc5ccccc5F)cc4C)c3N)[nH]c2cc1NS(=O)(=O)NC1CCOCC1] | [5-amino-1-[6-(2-fluorophenoxy)-4-methylpyridin-3-yl]pyrazol-4-yl]-[5-methyl-6-(oxan-4-ylsulfamoylamino)-1H-indol-2-yl]methanone | 620 | 0.98 | AA Rev.5 |
| 5-1-058 | 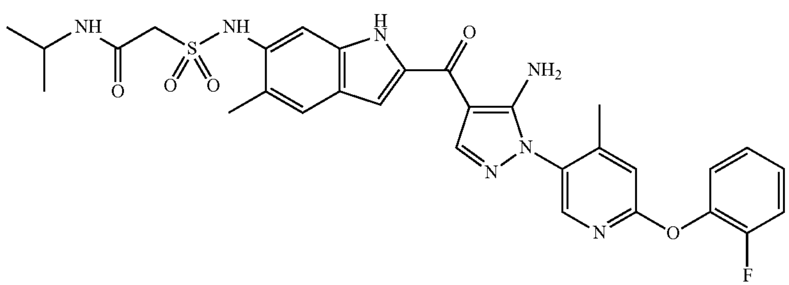 [SMILES: Cc1cc2cc(C(=O)c3cnn(-c4cnc(Oc5ccccc5F)cc4C)c3N)[nH]c2cc1NS(=O)(=O)CC(=O)NC(C)C] | 2-[[2-[5-amino-1-[6-(2-fluorophenoxy)-4-methylpyridin-3-yl]pyrazole-4-carbonyl]-5-methyl-1H-indol-6-yl]sulfamoyl]-N-propan-2-ylacetamide | 620 | 0.99 | AA Rev.5 |

-continued

| Example No. | Chemical Structure | Compound Name | m/z (M + H) | Reaction Time (Minute) | LCMS Measurement Condition |
|---|---|---|---|---|---|
| 5-1-059 | 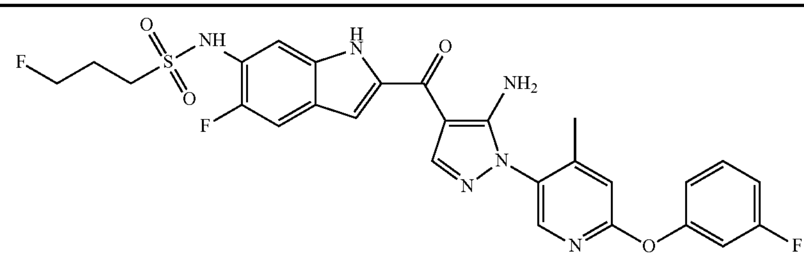 | N-[2-[5-amino-1-[6-(3-fluorophenoxy)-4-methylpyridin-3-yl]pyrazole-4-carbonyl]-5-fluoro-1H-indol-6-yl]-3-fluoropropane-1-sulfonamide | 585 | 0.98 | AA Rev.5 |
| 5-1-060 | 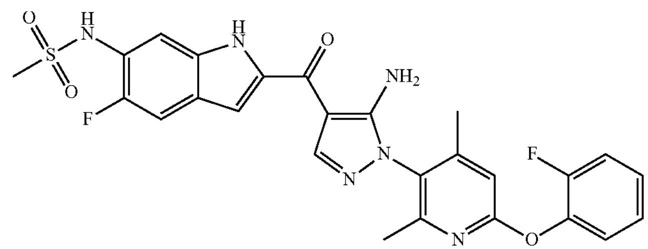 | N-[2-[5-amino-1-[6-(2-fluorophenoxy)-2,4-dimethylpyridin-3-yl]pyrazole-4-carbonyl]-5-fluoro-1H-indol-6-yl]methanesulfonamide | 553 | 0.96 | AA Rev.5 |
| 5-1-061 | 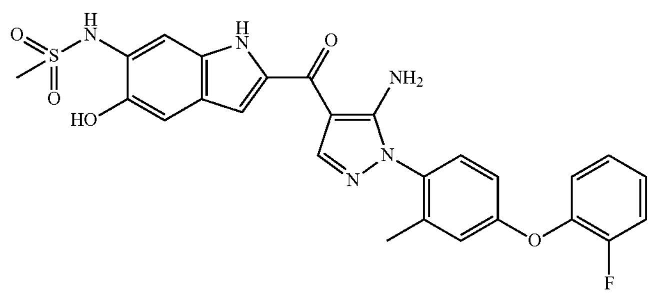 [SMILES: Cc1cc(Oc2ccccc2F)ccc1-n1ncc(C(=O)c2cc3cc(O)c(NS(C)(=O)=O)cc3[nH]2)c1N] | N-[2-[5-amino-1-[4-(2-fluorophenoxy)-2-methylphenyl]pyrazole-4-carbonyl]-5-hydroxy-1H-indol-6-yl]methanesulfonamide | 536 | 0.95 | AA Rev.5 |

| Example No. | Chemical Structure | Compound Name | m/z (M + H) | Reaction Time (Minute) | LCMS Measurement Condition |
|---|---|---|---|---|---|
| 5-1-062 | 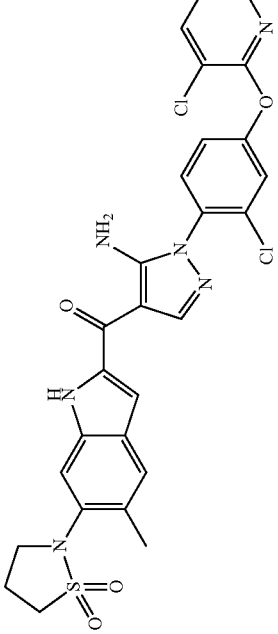 | [5-amino-1-[2-chloro-4-(3-chloropyridin-2-yl)oxyphenyl]pyrazol-4-yl]-[6-(1,1-dioxo-1,2-thiazolidin-2-yl)-5-methyl-1H-indol-2-yl]methanone | 597, 599, 601 | 1.01 | AA Rev.5 |
| 5-1-063 | 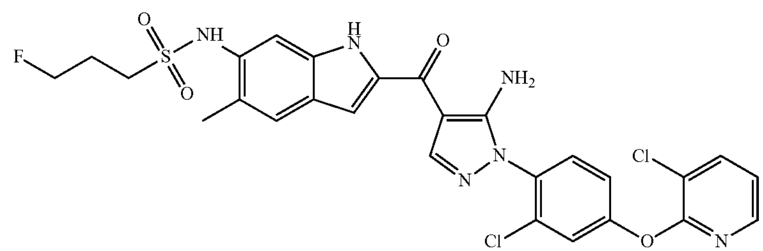 [SMILES: Cc1cc2cc(C(=O)c3cnn(-c4ccc(Oc5ncccc5Cl)cc4Cl)c3N)[nH]c2cc1NS(=O)(=O)CCCF] | N-[2-[5-amino-1-[2-chloro-4-(3-chloropyridin-2-yl)oxyphenyl]pyrazole-4-carbonyl]-5-methyl-1H-indol-6-yl]-3-fluoropropane-1-sulfonamide | 617, 619, 621 | 1.01 | AA Rev.5 |
| 5-1-064 | 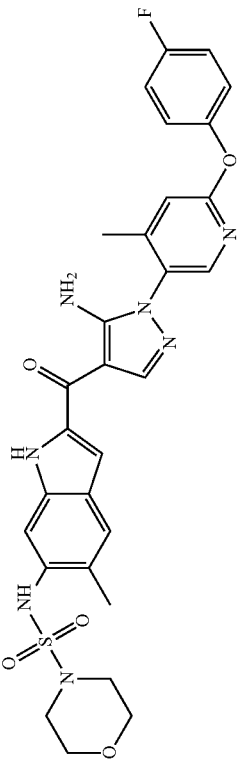 | N-[2-[5-amino-1-[6-(4-fluorophenoxy)-4-methylpyridin-3-yl]pyrazole-4-carbonyl]-5-methyl-1H-indol-6-yl]morpholine-4-sulfonamide | 606 | 0.99 | AA Rev.5 |

| Example No. | Chemical Structure | Compound Name | m/z (M + H) | Reaction Time (Minute) | LCMS Measurement Condition |
|---|---|---|---|---|---|
| 5-1-065 | 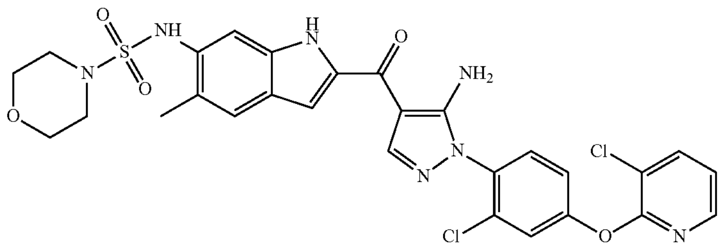 [SMILES: Cc1cc2cc(C(=O)c3cnn(-c4ccc(Oc5ncccc5Cl)cc4Cl)c3N)[nH]c2cc1NS(=O)(=O)N1CCOCC1] | N-[2-[5-amino-1-[2-chloro-4-(3-chloropyridin-2-yl)oxyphenyl]pyrazole-4-carbonyl]-5-methyl-1H-indol-6-yl]morpholine-4-sulfonamide | 642, 644, 646 | 1.01 | AA Rev.5 |
| 5-1-066 | 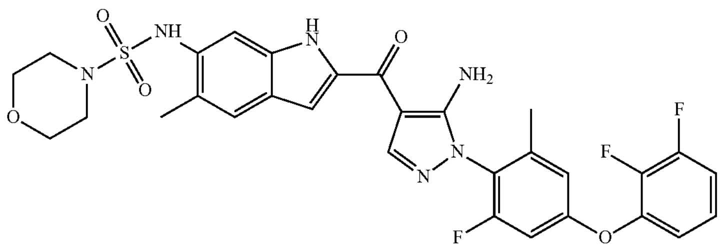 [SMILES: Cc1cc2cc(C(=O)c3cnn(-c4c(C)cc(Oc5cccc(F)c5F)cc4F)c3N)[nH]c2cc1NS(=O)(=O)N1CCOCC1] | N-[2-[5-amino-1-[4-(2,3-difluorophenoxy)-2-fluoro-6-methylphenyl]pyrazole-4-carbonyl]-5-methyl-1H-indol-6-yl]morpholine-4-sulfonamide | 641 | 1.03 | AA Rev.5 |
| 5-1-067 | 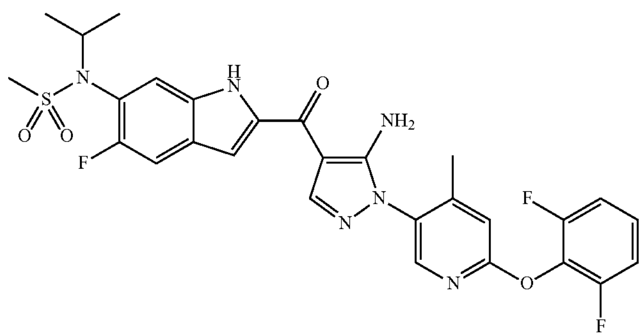 [SMILES: Cc1cc(Oc2c(F)cccc2F)ncc1-n1ncc(C(=O)c2cc3cc(F)c(N(C(C)C)S(C)(=O)=O)cc3[nH]2)c1N] | N-[2-[5-amino-1-[6-(2,6-difluorophenoxy)-4-methylpyridin-3-yl]pyrazole-4-carbonyl]-5-fluoro-1H-indol-6-yl]-N-propan-2-ylmethanesulfonamide | 599 | 1.04 | AA Rev.5 |

| Example No. | Chemical Structure | Compound Name | m/z (M + H) | Reaction Time (Minute) | LCMS Measurement Condition |
|---|---|---|---|---|---|
| 5-1-068 | 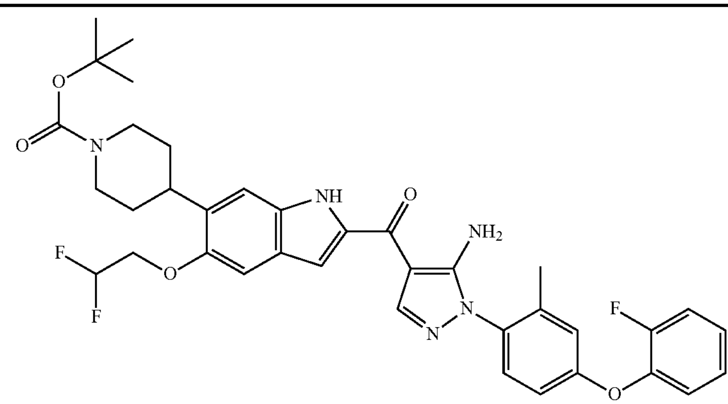 | tert-Butyl 4-[2-[5-amino-1-[4-(2-fluorophenoxy)-2-methylphenyl]pyrazole-4-carbonyl]-5-(2,2-difluoroethoxy)-1H-indol-6-yl]piperidine-1-carboxylate | 690 | 1.13 | AA Rev.7 |
| 5-1-069 | 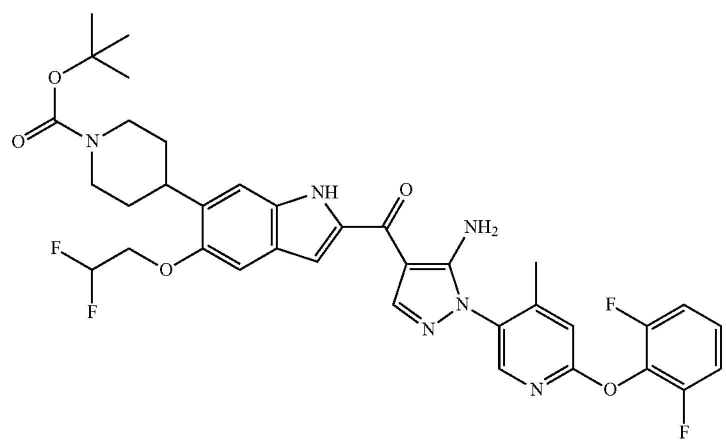 [SMILES: Cc1cc(Oc2c(F)cccc2F)ncc1-n1ncc(C(=O)c2cc3cc(OCC(F)F)c(C4CCN(C(=O)OC(C)(C)C)CC4)cc3[nH]2)c1N] | tert-Butyl 4-[2-[5-amino-1-[6-(2,6-difluorophenoxy)-4-methylpyridin-3-yl]pyrazole-4-carbonyl]-5-(2,2-difluoroethoxy)-1H-indol-6-yl]piperidine-1-carboxylate | 709 | 1.11 | AA Rev.7 |

| Example No. | Chemical Structure | Compound Name | m/z (M + H) | Reaction Time (Minute) | LCMS Measurement Condition |
|---|---|---|---|---|---|
| 5-1-070 | 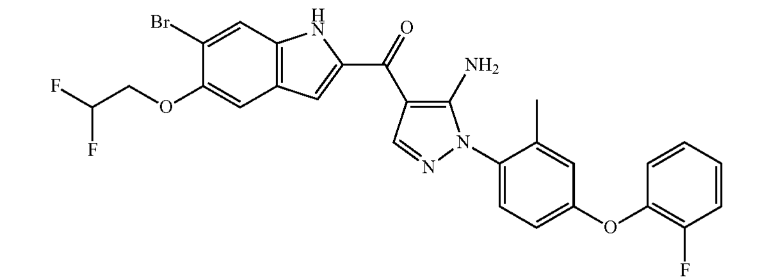 [SMILES: Cc1cc(Oc2ccccc2F)ccc1-n1ncc(C(=O)c2cc3cc(OCC(F)F)c(Br)cc3[nH]2)c1N] | [5-amino-1-[4-(2-fluorophenoxy)-2-methylphenyl]pyrazol-4-yl]-[6-bromo-5-(2,2-difluoroethoxy)-1H-indol-2-yl]methanone | 585, 587 | 1.39 | AA Rev.5 |
| 5-1-071 | 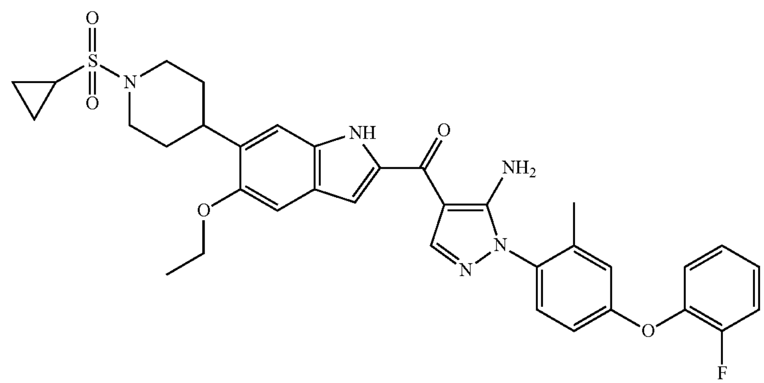 [SMILES: CCOc1cc2cc(C(=O)c3cnn(-c4ccc(Oc5ccccc5F)cc4C)c3N)[nH]c2cc1C1CCN(S(=O)(=O)C2CC2)CC1] | [5-amino-1-[4-(2-fluorophenoxy)-2-methylphenyl]pyrazol-4-yl]-[6-(1-cyclopropylsulfonylpiperidin-4-yl)-5-ethoxy-1H-indol-2-yl]methanone | 658 | 1.08 | AA Rev.8 |
| 5-1-072 | 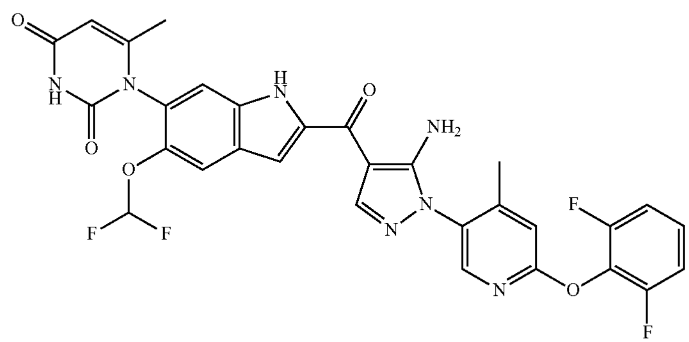 [SMILES: Cc1cc(Oc2c(F)cccc2F)ncc1-n1ncc(C(=O)c2cc3cc(OC(F)F)c(-n4c(C)cc(=O)[nH]c4=O)cc3[nH]2)c1N] | 1-[2-[5-amino-1-[6-(2,6-difluorophenoxy)-4-methylpyridin-3-yl]pyrazole-4-carbonyl]-5-(difluoromethoxy)-1H-indol-6-yl]-6-methylpyrimidine-2,4-dione | 636 | 0.95 | AA Rev.8 |

-continued

| Example No. | Chemical Structure | Compound Name | m/z (M + H) | Reaction Time (Minute) | LCMS Measurement Condition |
|---|---|---|---|---|---|
| 5-1-073 | 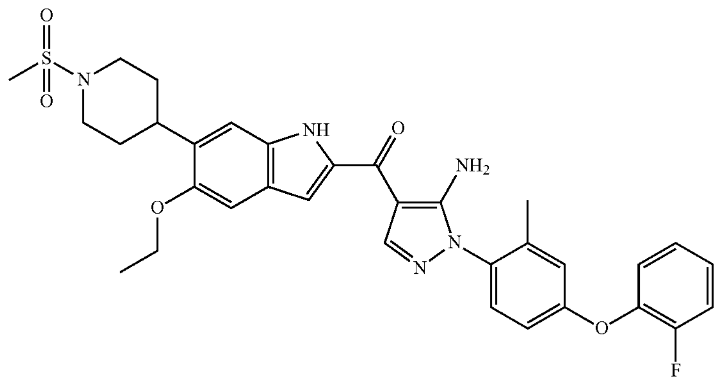 [SMILES: CCOc1cc2cc(C(=O)c3cnn(-c4ccc(Oc5ccccc5F)cc4C)c3N)[nH]c2cc1C1CCN(S(C)(=O)=O)CC1] | [5-amino-1-[4-(2-fluorophenoxy)-2-methylphenyl]pyrazol-4-yl]-[5-ethoxy-6-(1-methylsulfonylpiperidin-4-yl)-1H-indol-2-yl]methanone | 632 | 1.05 | AA Rev.8 |
| 5-1-074 | 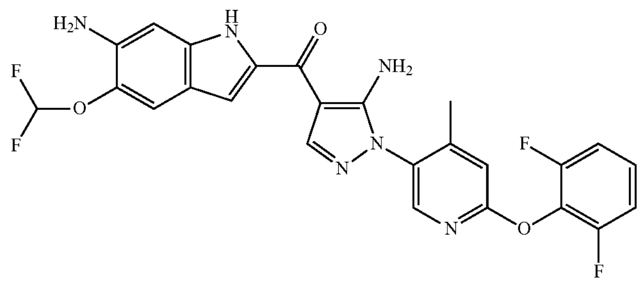 [SMILES: Cc1cc(Oc2c(F)cccc2F)ncc1-n1ncc(C(=O)c2cc3cc(OC(F)F)c(N)cc3[nH]2)c1N] | [6-amino-5-(difluoromethoxy)-1H-indol-2-yl]-[5-amino-1-[6-(2,6-difluorophenoxy)-4-methylpyridin-3-yl]pyrazol-4-yl]methanone | 527 | 0.97 | AA Rev.10 |

| Example No. | Chemical Structure | Compound Name | m/z (M + H) | Reaction Time (Minute) | LCMS Measurement Condition |
|---|---|---|---|---|---|
| 5-1-075 | 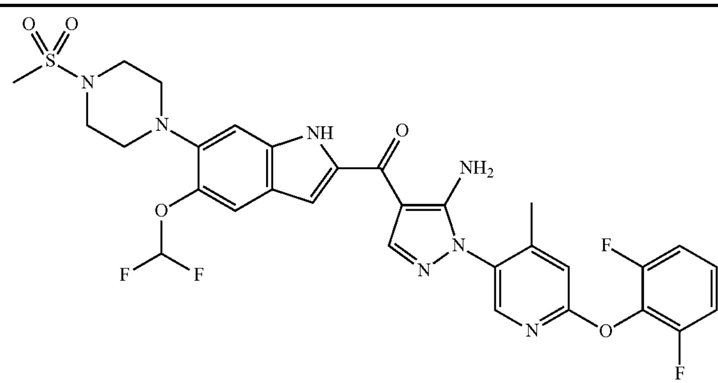 | [5-amino-1-[6-(2,6-difluorophenoxy)-4-methylpyridin-3-yl]pyrazol-4-yl]-[5-(difluoromethoxy)-6-(4-methylsulfonylpiperazin-1-yl)-1H-indol-2-yl]methanone | 674 | 1.01 | AA Rev.10 |
| 5-1-076 | 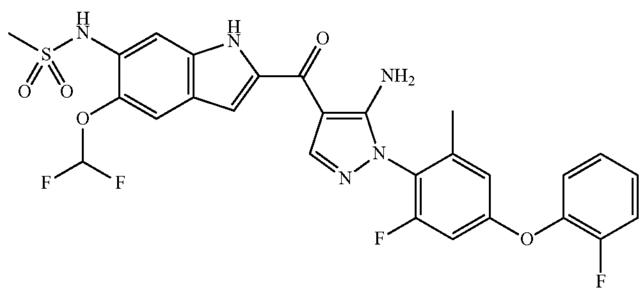 [SMILES: Cc1cc(Oc2ccccc2F)cc(F)c1-n1ncc(C(=O)c2cc3cc(OC(F)F)c(NS(C)(=O)=O)cc3[nH]2)c1N] | N-[2-[5-amino-1-[2-fluoro-4-(2-fluorophenoxy)-6-methylphenyl]pyrazole-4-carbonyl]-5-(difluoromethoxy)-1H-indol-6-yl]methanesulfonamine | 604 | 1.26 | TFA Rev.5 |
| 5-1-077 | 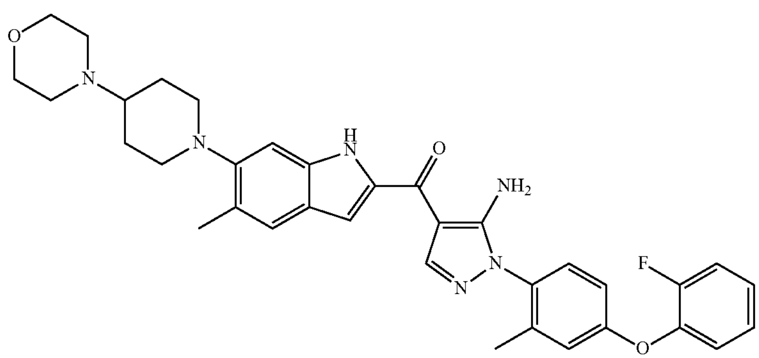 [SMILES: Cc1cc2cc(C(=O)c3cnn(-c4ccc(Oc5ccccc5F)cc4C)c3N)[nH]c2cc1N1CCC(N2CCOCC2)CC1] | [5-amino-1-[4-(2-fluorophenoxy)-2-methylphenyl]pyrazol-4-yl]-[5-methyl-6-(4-morpholin-4-ylpiperidin-1-yl)-1H-indol-2-yl]methanone | 609 | 1.10 | AA Rev.10 |

-continued

| Example No. | Chemical Structure | Compound Name | m/z (M + H) | Reaction Time (Minute) | LCMS Measurement Condition |
|---|---|---|---|---|---|
| 5-1-078 | 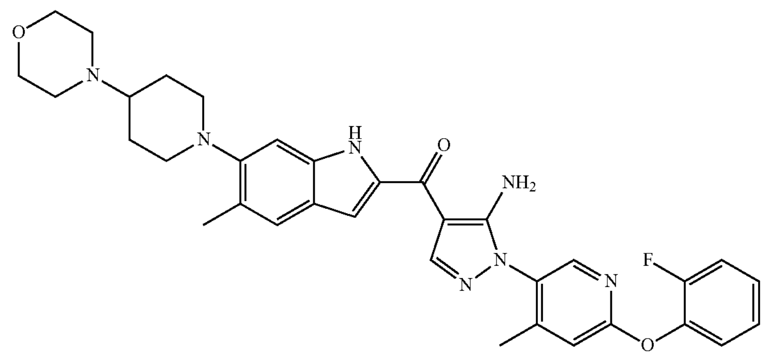 [SMILES: Cc1cc2cc(C(=O)c3cnn(-c4cnc(Oc5ccccc5F)cc4C)c3N)[nH]c2cc1N1CCC(N2CCOCC2)CC1] | [5-amino-1-[6-(2-fluorophenoxy)-4-methylpyridin-3-yl]pyrazol-4-yl]-[5-methyl-6-(4-morpholin-4-ylpiperidin-1-yl)-1H-indol-2-yl]methanone | 610 | 1.07 | AA Rev.10 |
| 5-1-079 | 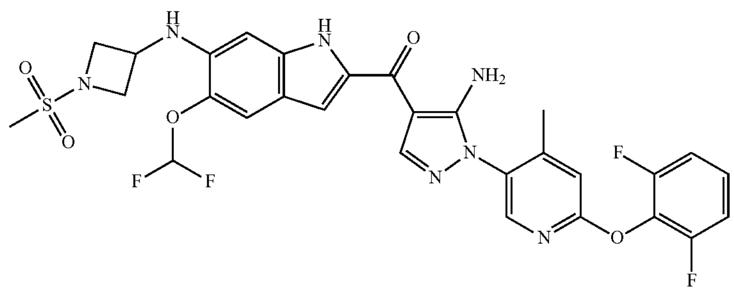 [SMILES: Cc1cc(Oc2c(F)cccc2F)ncc1-n1ncc(C(=O)c2cc3cc(OC(F)F)c(NC4CN(S(C)(=O)=O)C4)cc3[nH]2)c1N] | [5-amino-1-[6-(2,6-difluorophenoxy)-4-methylpyridin-3-yl]pyrazol-4-yl]-[5-(difluoromethoxy)-6-[(1-methylsulfonylazetidin-3-yl)amino]-1H-indol-2-yl]methanone | 660 | 0.97 | AA Rev.10 |
| 5-1-080 | 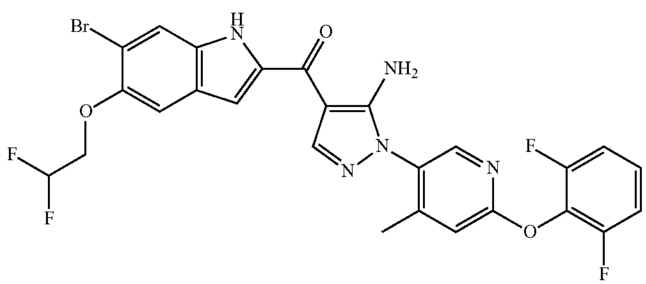 [SMILES: Cc1cc(Oc2c(F)cccc2F)ncc1-n1ncc(C(=O)c2cc3cc(OCC(F)F)c(Br)cc3[nH]2)c1N] | [5-amino-1-[6-(2,6-difluorophenoxy)-4-methylpyridin-3-yl]pyrazol-4-yl]-[6-bromo-5-(2,2-difluoroethoxy)-1H-indol-2-yl]methanone | 604, 606 | 1.07 | AA Rev.11 |

| Example No. | Chemical Structure | Compound Name | m/z (M + H) | Reaction Time (Minute) | LCMS Measurement Condition |
|---|---|---|---|---|---|
| 5-1-081 | 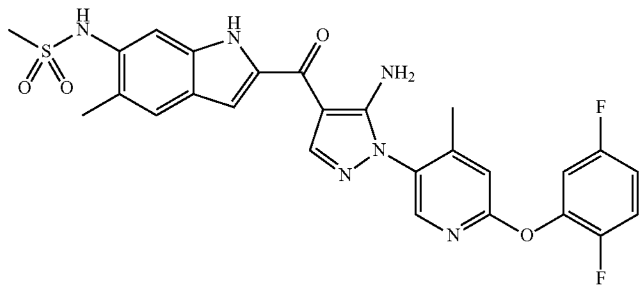 [SMILES: Cc1cc2cc(C(=O)c3cnn(-c4cnc(Oc5cc(F)ccc5F)cc4C)c3N)[nH]c2cc1NS(C)(=O)=O] | N-[2-[5-amino-1-[6-(2,5-difluorophenoxy)-4-methylpyridin-3-yl]pyrazole-4-carbonyl]-5-methyl-1H-indol-6-yl]methanesulfonamide | 553 | 0.98 | AA Rev.11 |
| 5-1-082 | 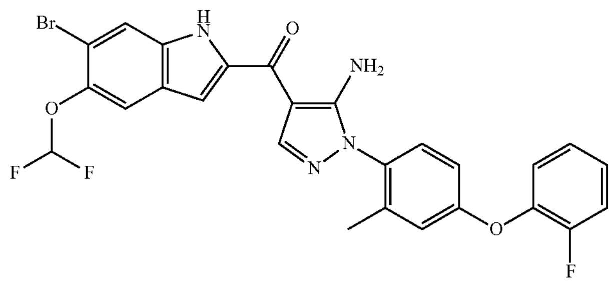 [SMILES: Cc1cc(Oc2ccccc2F)ccc1-n1ncc(C(=O)c2cc3cc(OC(F)F)c(Br)cc3[nH]2)c1N] | [5-amino-1-[4-(2-fluorophenoxy)-2-methylphenyl]pyrazol-4-yl]-[6-bromo-5-(difluoromethoxy)-1H-indol-2-yl]methanone | 571, 573 | 1.10 | AA Rev.11 |
| 5-1-083 | 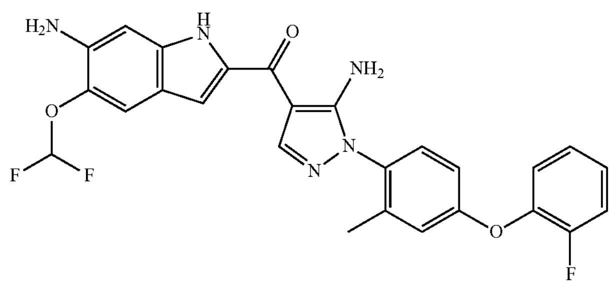 [SMILES: Cc1cc(Oc2ccccc2F)ccc1-n1ncc(C(=O)c2cc3cc(OC(F)F)c(N)cc3[nH]2)c1N] | [6-amino-5-(difluoromethoxy)-1H-indol-2-yl]-[5-amino-1-[4-(2-fluorophenoxy)-2-methylphenyl]pyrazol-4-yl]methanone | 508 | 1.01 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-084 | 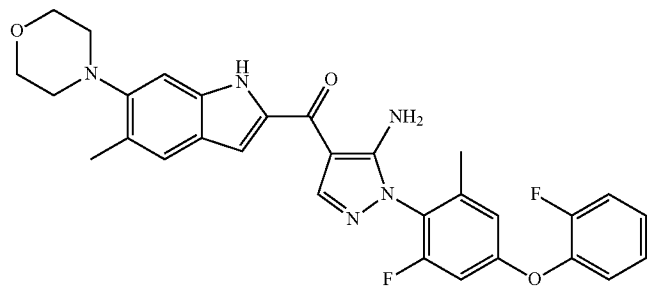 [SMILES: Cc1cc2cc(C(=O)c3cnn(-c4c(C)cc(Oc5ccccc5F)cc4F)c3N)[nH]c2cc1N1CCOCC1] | [5-amino-1-[2-fluoro-4-(2-fluorophenoxy)-6-methylphenyl]pyrazol-4-yl]-(5-methyl-6-morpholin-4-yl-1H-indol-2-yl)methanone | 544 | 1.12 | AA Rev.11 |
| 5-1-085 | 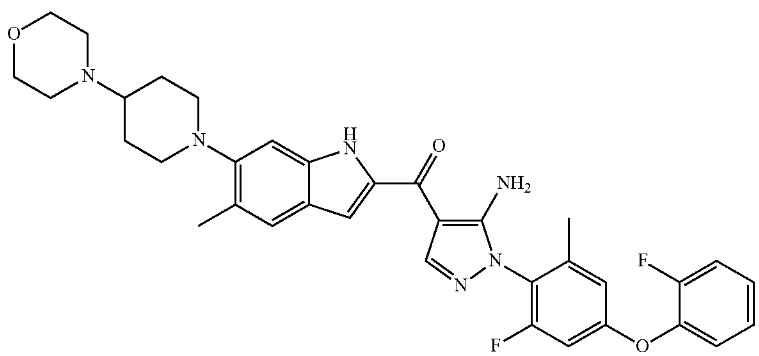 [SMILES: Cc1cc2cc(C(=O)c3cnn(-c4c(C)cc(Oc5ccccc5F)cc4F)c3N)[nH]c2cc1N1CCC(N2CCOCC2)CC1] | [5-amino-1-[2-fluoro-4-(2-fluorophenoxy)-6-methylphenyl]pyrazol-4-yl]-[5-methyl-6-(4-morpholin-4-ylpiperidin-1-yl)-1H-indol-2-yl]methanone | 627 | 1.11 | TFA Rev.5 |
| 5-1-086 | 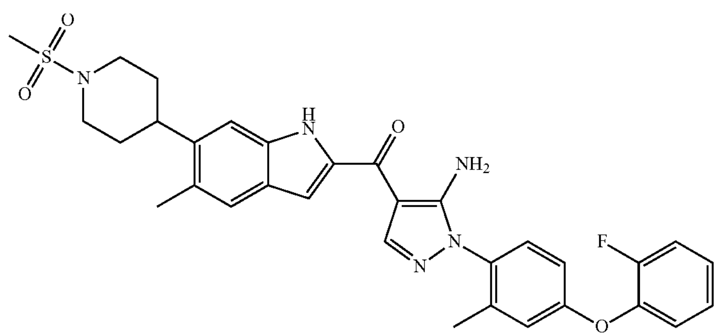 | [5-amino-1-[4-(2-fluorophenoxy)-2-methylphenyl]pyrazol-4-yl]-[5-methyl-6-(1-methylsulfonylpiperidin-4-yl)-1H-indol-2-yl]methanone | 602 | 1.36 | TFA Rev.5 |

| Example No. | Chemical Structure | Compound Name | m/z (M + H) | Reaction Time (Minute) | LCMS Measurement Condition |
|---|---|---|---|---|---|
| 5-1-087 | 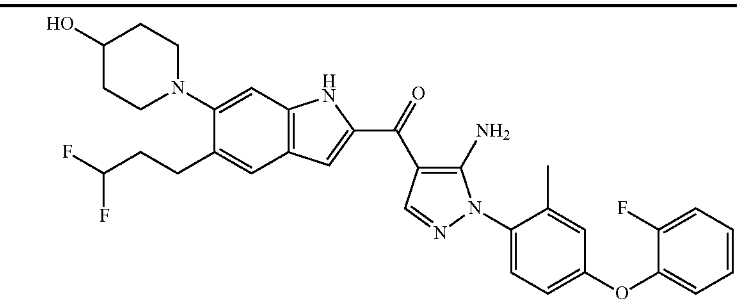 | [5-amino-1-[4-(2-fluorophenoxy)-2-methylphenyl]pyrazol-4-yl]-[5-(2,2-difluoroethoxy)-6-(4-hydroxypiperidin-1-yl)-1H-indol-2-yl]methanone | 606 | 1.05 | AA Rev.11 |
| 5-1-088 | 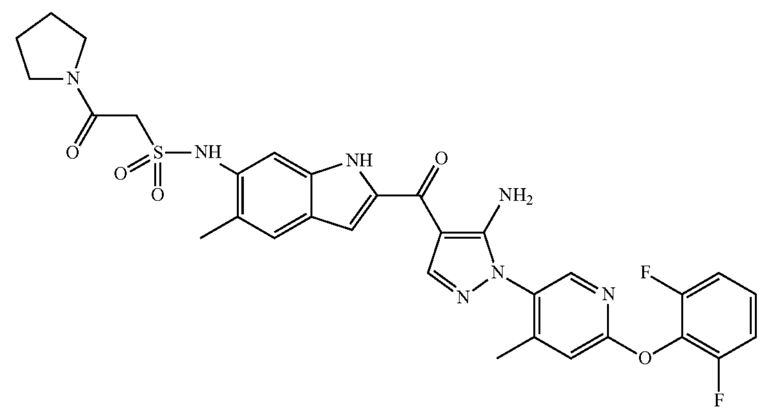 [SMILES: Cc1cc2cc(C(=O)c3cnn(-c4cnc(Oc5c(F)cccc5F)cc4C)c3N)[nH]c2cc1NS(=O)(=O)CC(=O)N1CCCC1] | N-[2-[5-amino-1-[6-(2,6-difluorophenoxy)-4-methylpyridin-3-yl]pyrazole-4-carbonyl]-5-methyl-1H-indol-6-yl]-2-oxo-2-pyrrolidin-1-ylethanesulfonamide | 650 | 1.00 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-089 | 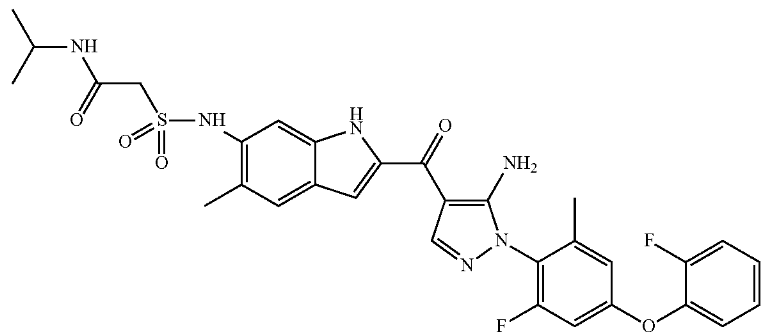 [SMILES: Cc1cc2cc(C(=O)c3cnn(-c4c(C)cc(Oc5ccccc5F)cc4F)c3N)[nH]c2cc1NS(=O)(=O)CC(=O)NC(C)C] | 2-[[2-[5-amino-1-[2-fluoro-4-(2-fluorophenoxy)-6-methylphenyl]pyrazole-4-carbonyl]-5-methyl-1H-indol-6-yl]sulfamoyl]-N-propan-2-ylacetamide | 637 | 1.03 | AA Rev.11 |
| 5-1-090 | 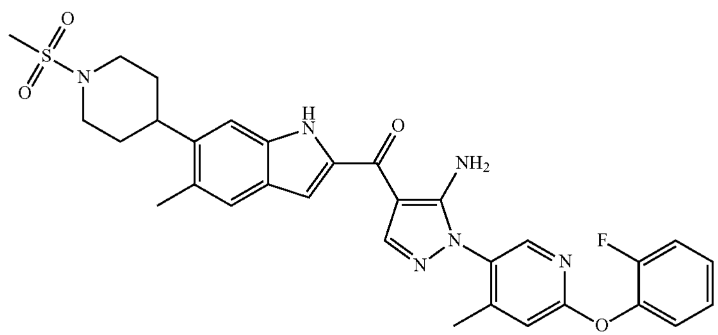 | [5-amino-1-[6-(2-fluorophenoxy)-4-methylpyridin-3-yl]pyrazol-4-yl]-[5-methyl-6-(1-methylsulfonylpiperidin-4-yl)-1H-indol-2-yl]methanone | 603 | 1.04 | AA Rev.11 |

| Example No. | Chemical Structure | Compound Name | m/z (M + H) | Reaction Time (Minute) | LCMS Measurement Condition |
|---|---|---|---|---|---|
| 5-1-091 | 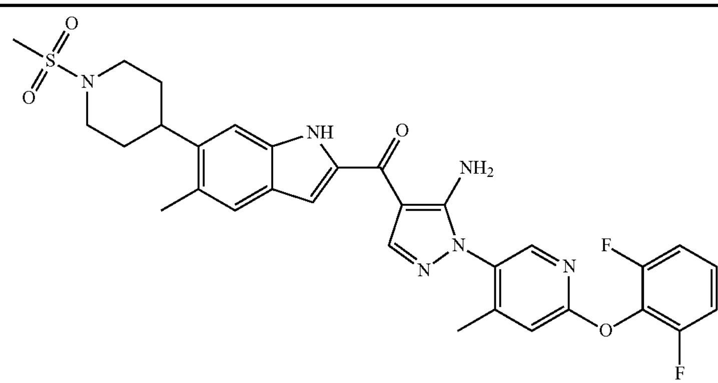 | [5-amino-1-[6-(2,6-difluorophenoxy)-4-methylpyridin-3-yl]pyrazol-4-yl]-[5-methyl-6-(1-methylsulfonylpiperidin-4-yl)-1H-indol-2-yl]methanone | 621 | 1.05 | AA Rev.11 |
| 5-1-092 | 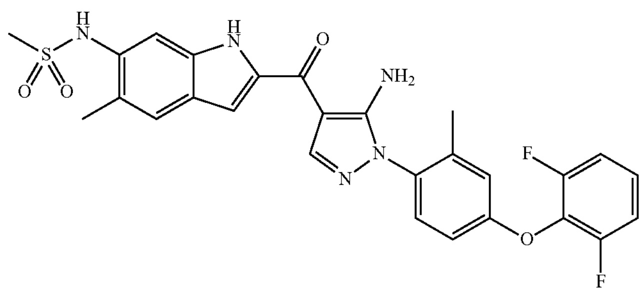 [SMILES: Cc1cc2cc(C(=O)c3cnn(-c4ccc(Oc5c(F)cccc5F)cc4C)c3N)[nH]c2cc1NS(C)(=O)=O] | N-[2-[5-amino-1-[4-(2,6-difluorophenoxy)-2-methylphenyl]pyrazole-4-carbonyl]-5-methyl-1H-indol-6-yl]methanesulfonamide | 552 | 1.00 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-093 | 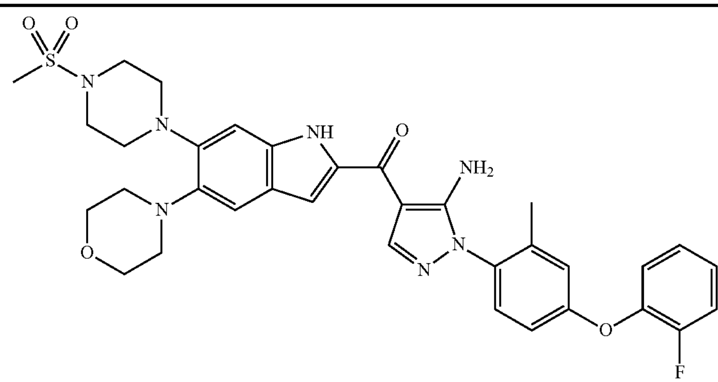 | [5-amino-1-[4-(2-fluorophenoxy)-2-methylphenyl]pyrazol-4-yl]-[6-(4-methylsulfonylpiperazin-1-yl)-5-morpholin-4-yl-1H-indol-2-yl]methanone | 674 | 1.06 | AA Rev.11 |
| 5-1-094 | 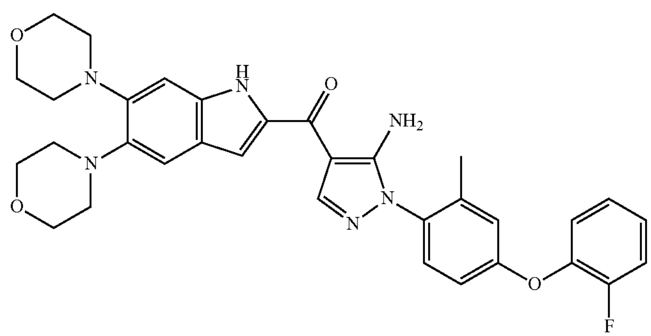 [SMILES: Cc1cc(Oc2ccccc2F)ccc1-n1ncc(C(=O)c2cc3cc(N4CCOCC4)c(N4CCOCC4)cc3[nH]2)c1N] | [5-amino-1-[4-(2-fluorophenoxy)-2-methylphenyl]pyrazol-4-yl]-(5,6-dimorpholin-4-yl-1H-indol-2-yl)methanone | 597 | 1.10 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-095 | 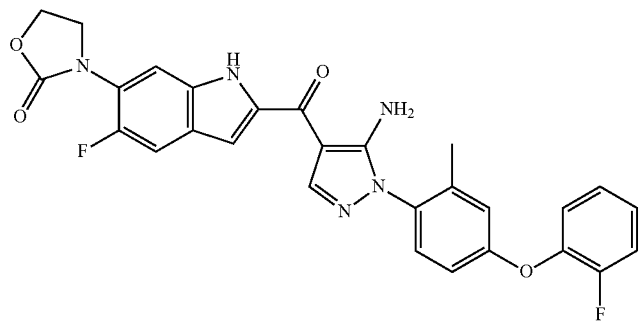 [SMILES: Cc1cc(Oc2ccccc2F)ccc1-n1ncc(C(=O)c2cc3cc(F)c(N4CCOC4=O)cc3[nH]2)c1N] | 3-[2-[5-amino-1-[4-(2-fluorophenoxy)-2-methylphenyl]pyrazole-4-carbonyl]-5-fluoro-1H-indol-6-yl]-1,3-oxazolidin-2-one | 530 | 1.00 | AA Rev.11 |
| 5-1-096 | 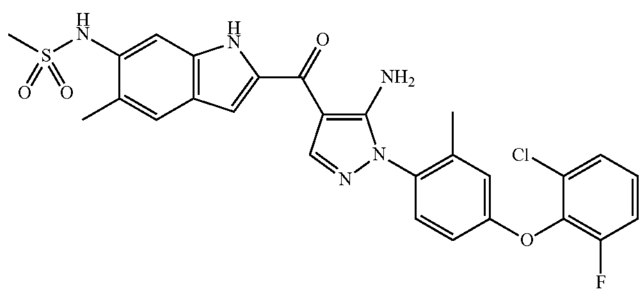 [SMILES: Cc1cc2cc(C(=O)c3cnn(-c4ccc(Oc5c(F)cccc5Cl)cc4C)c3N)[nH]c2cc1NS(C)(=O)=O] | N-[2-[5-amino-1-[4-(2-chloro-6-fluorophenoxy)-2-methylphenyl]pyrazole-4-carbonyl]-5-methyl-1H-indol-6-yl]methanesulfonamide | 568, 570 | 1.03 | AA Rev.11 |
| 5-1-097 | 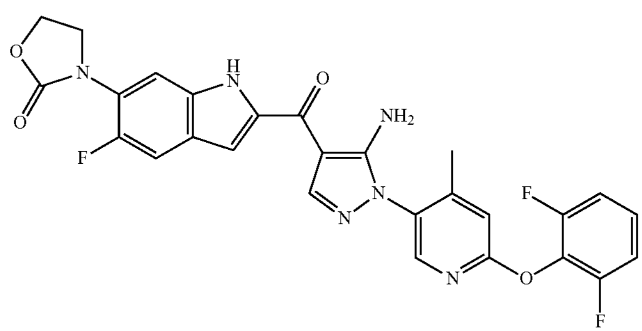 [SMILES: Cc1cc(Oc2c(F)cccc2F)ncc1-n1ncc(C(=O)c2cc3cc(F)c(N4CCOC4=O)cc3[nH]2)c1N] | 3-[2-[5-amino-1-[6-(2,6-difluorophenoxy)-4-methylpyridin-3-yl]pyrazole-4-carbonyl]-5-fluoro-1H-indol-6-yl]-1,3-oxazolidin-2-one | 549 | 0.97 | AA Rev.11 |

| Example No. | Chemical Structure | Compound Name | m/z (M + H) | Reaction Time (Minute) | LCMS Measurement Condition |
|---|---|---|---|---|---|
| 5-1-098 | 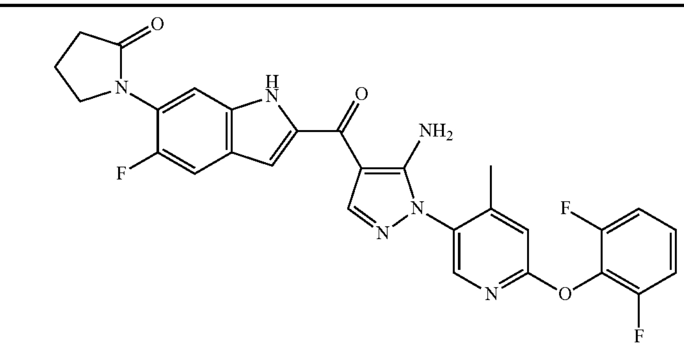 | 1-[2-[5-amino-1-[6-(2,6-difluorophenoxy)-4-methylpyridin-3-yl]pyrazole-4-carbonyl]-5-fluoro-1H-indol-6-yl]pyrrolidin-2-one | 547 | 1.01 | AA Rev.11 |
| 5-1-099 | 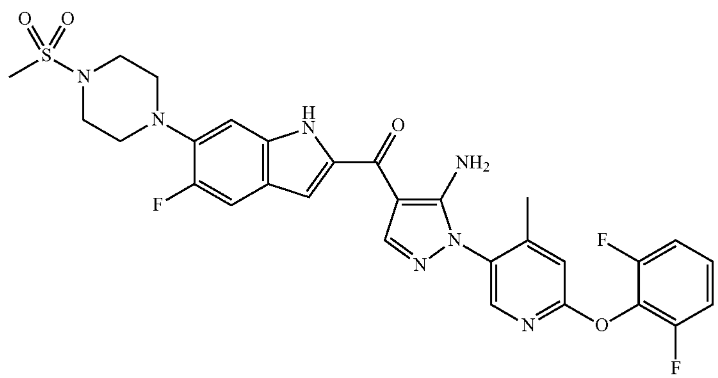 [SMILES: Cc1cc(Oc2c(F)cccc2F)ncc1-n1ncc(C(=O)c2cc3cc(F)c(N4CCN(S(C)(=O)=O)CC4)cc3[nH]2)c1N] | [5-amino-1-[5-(2,6-difluorophenoxy)-4-methylpyridin-3-yl]pyrazol-4-yl]-[5-fluoro-6-(4-methylsulfonylpiperazin-1-yl)-1H-indol-2-yl]methanone | 626 | 1.02 | AA Rev.11 |

| Example No. | Chemical Structure | Compound Name | m/z (M + H) | Reaction Time (Minute) | LCMS Measurement Condition |
|---|---|---|---|---|---|
| 5-1-100 | 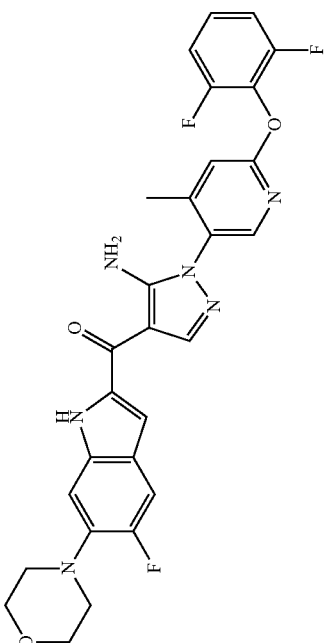 | [5-amino-1-[6-(2,6-difluorophenoxy)-4-methylpyridin-3-yl]pyrazol-4-yl]-(5-fluoro-6-morpholin-4-yl-1H-indol-2-yl)methanone | 549 | 1.07 | AA Rev.11 |
| 5-1-101 | 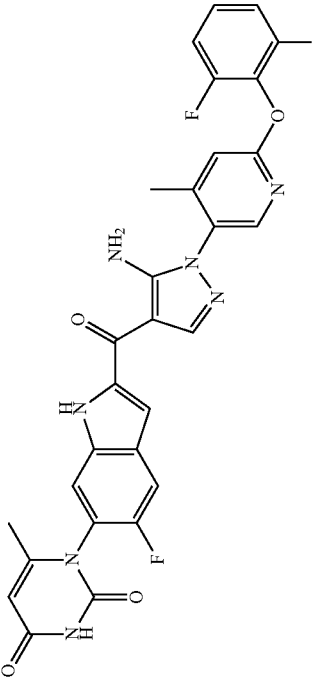 | 1-[2-[5-amino-1-[6-(2,6-difluorophenoxy)-4-methylpyridin-3-yl]pyrazole-4-carbonyl]-5-fluoro-1H-indol-6-yl]-6-methylpyrimidine-2,4-dione | 588 | 1.13 | TFA Rev.5 |
| 5-1-102 | 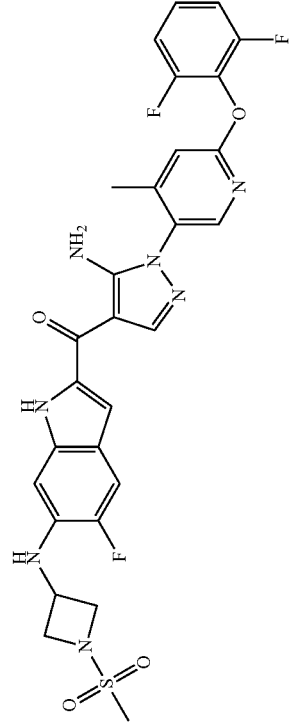 | [5-amino-1-[6-(2,6-difluorophenoxy)-4-methylpyridin-3-yl]pyrazol-4-yl]-[5-fluoro-6-[(1-methylsulfonylazetidin-3-yl)amino]-1H-indol-2-yl]methanone | 612 | 1.21 | TFA Rev.5 |

| Example No. | Chemical Structure | Compound Name | m/z (M + H) | Reaction Time (Minute) | LCMS Measurement Condition |
|---|---|---|---|---|---|
| 5-1-103 | 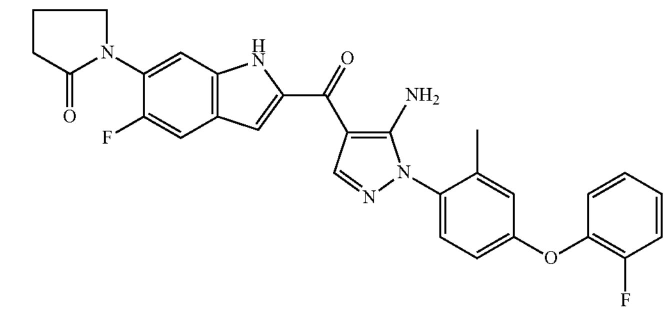 [SMILES: Cc1cc(Oc2ccccc2F)ccc1-n1ncc(C(=O)c2cc3cc(F)c(N4CCCC4=O)cc3[nH]2)c1N] | 1-[2-[5-amino-1-[4-(2-fluorophenoxy)-2-methylphenyl]pyrazole-4-carbonyl]-5-fluoro-1H-indol-6-yl]pyrrolidin-2-one | 528 | 1.23 | TFA Rev.5 |
| 5-1-104 | 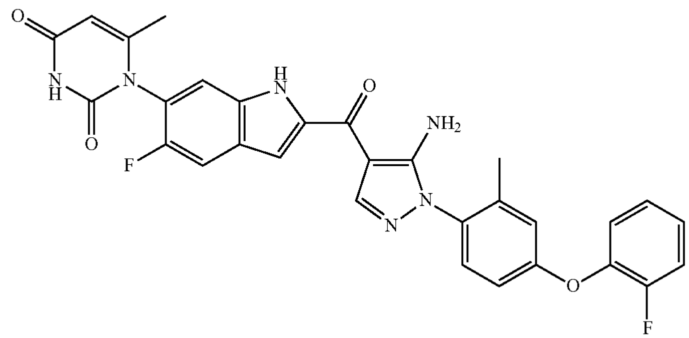 [SMILES: Cc1cc(Oc2ccccc2F)ccc1-n1ncc(C(=O)c2cc3cc(F)c(-n4c(C)cc(=O)[nH]c4=O)cc3[nH]2)c1N] | 1-[2-[5-amino-1-[4-(2-fluorophenoxy)-2-methylphenyl]pyrazole-4-carbonyl]-5-fluoro-1H-indol-6-yl]-6-methylpyrimidine-2,4-dione | 569 | 1.00 | AA Rev.11 |
| 5-1-105 | 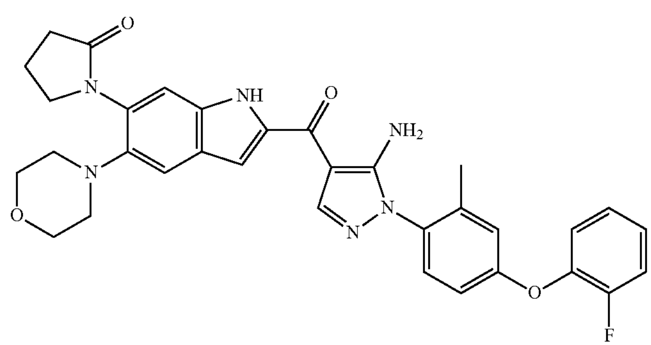 [SMILES: Cc1cc(Oc2ccccc2F)ccc1-n1ncc(C(=O)c2cc3cc(N4CCOCC4)c(N4CCCC4=O)cc3[nH]2)c1N] | 1-[2-[5-amino-1-[4-(2-fluorophenoxy)-2-methylphenyl]pyrazole-4-carbonyl]-5-morpholin-4-yl-1H-indol-6-yl]pyrrolidin-2-one | 595 | 1.04 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-106 | 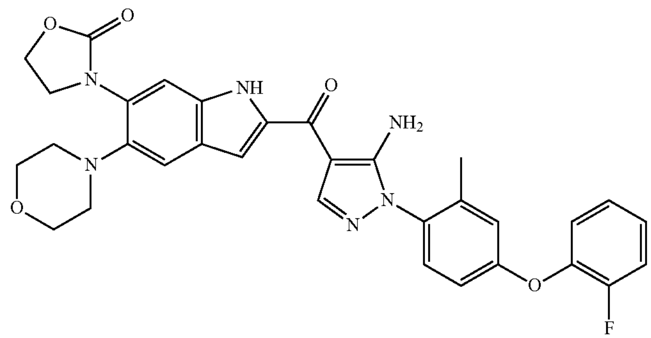 [SMILES: Cc1cc(Oc2ccccc2F)ccc1-n1ncc(C(=O)c2cc3cc(N4CCOCC4)c(N4CCOC4=O)cc3[nH]2)c1N] | 3-[2-[5-amino-1-[4-(2-fluorophenoxy)-2-methylphenyl]pyrazole-4-carbonyl]-5-morpholin-4-yl-1H-indol-6-yl]-1,3-oxazolidin-2-one | 597 | 1.00 | AA Rev.11 |
| 5-1-107 | 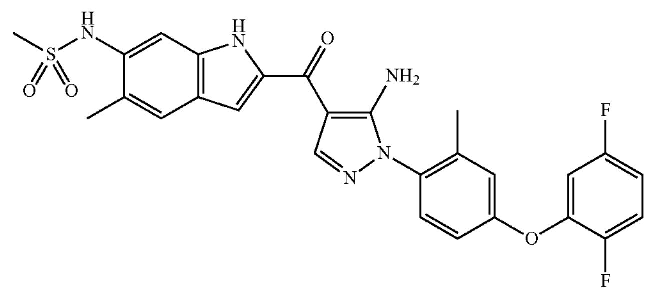 [SMILES: Cc1cc2cc(C(=O)c3cnn(-c4ccc(Oc5cc(F)ccc5F)cc4C)c3N)[nH]c2cc1NS(C)(=O)=O] | N-[2-[5-amino-1-[4-(2,5-difluorophenoxy)-2-methylphenyl]pyrazole-4-carbonyl]-5-methyl-1H-indol-6-yl]methanesulfonamide | 552 | 1.01 | AA Rev.11 |
| 5-1-108 | 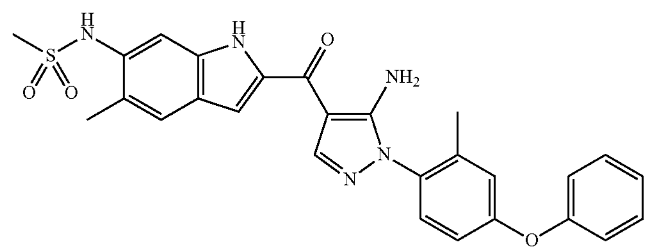 [SMILES: Cc1cc2cc(C(=O)c3cnn(-c4ccc(Oc5ccccc5)cc4C)c3N)[nH]c2cc1NS(C)(=O)=O] | N-[2-[5-amino-1-(2-methyl-4-phenoxyphenyl)pyrazole-4-carbonyl]-5-methyl-1H-indol-6-yl]methanesulfonamide | 516 | 1.02 | AA Rev.11 |

| Example No. | Chemical Structure | Compound Name | m/z (M + H) | Reaction Time (Minute) | LCMS Measurement Condition |
|---|---|---|---|---|---|
| 5-1-109 | 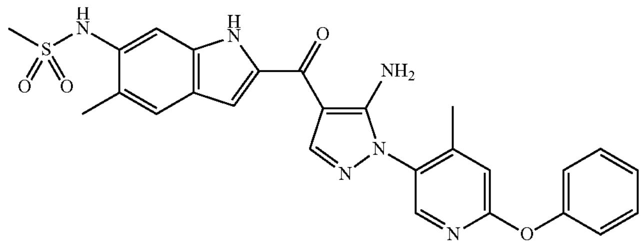 [SMILES: Cc1cc2cc(C(=O)c3cnn(-c4cnc(Oc5ccccc5)cc4C)c3N)[nH]c2cc1NS(C)(=O)=O] | N-[2-[5-amino-1-(4-methyl-6-phenoxypyridin-3-yl)pyrazole-4-carbonyl]-5-methyl-1H-indol-6-yl]methanesulfonamide | 517 | 0.95 | AA Rev.11 |
| 5-1-110 | 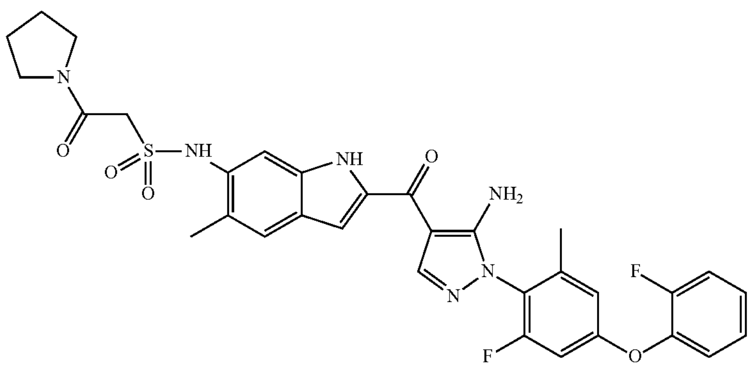 [SMILES: Cc1cc2cc(C(=O)c3cnn(-c4c(C)cc(Oc5ccccc5F)cc4F)c3N)[nH]c2cc1NS(=O)(=O)CC(=O)N1CCCC1] | N-[2-[5-amino-1-[2-fluoro-4-(2-fluorophenoxy)-6-methylphenyl]pyrazole-4-carbonyl]-5-methyl-1H-indol-6-yl]-2-oxo-2-pyrrolidin-1-ylethanesulfonamide | 649 | 1.02 | AA Rev.11 |
| 5-1-111 | 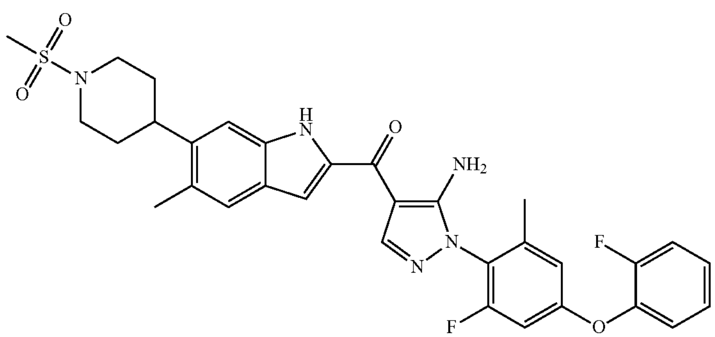 | [5-amino-1-[2-fluoro-4-(2-fluorophenoxy)-6-methylphenyl]pyrazol-4-yl]-[5-methyl-6-(1-methylsulfonylpiperidin-4-yl)-1H-indol-2-yl]methanone | 620 | 1.07 | AA Rev.11 |

| Example No. | Chemical Structure | Compound Name | m/z (M + H) | Reaction Time (Minute) | LCMS Measurement Condition |
|---|---|---|---|---|---|
| 5-1-112 | 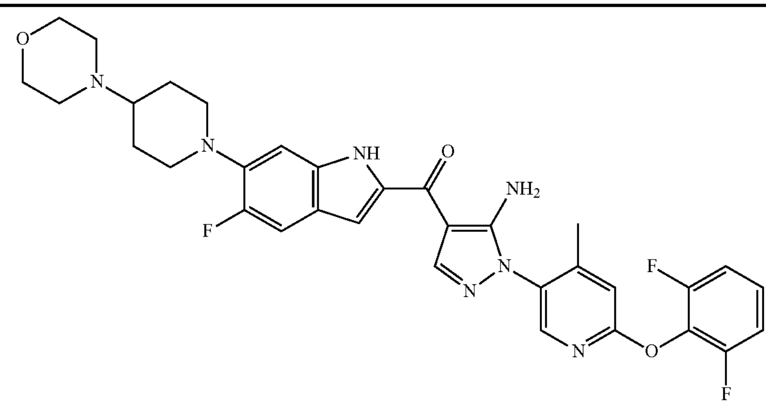 | [5-amino-1-[6-(2,6-difluorophenoxy)-4-methylpyridin-3-yl]pyrazol-4-yl]-[5-fluoro-6-(4-morpholin-4-ylpiperidin-1-yl)-1H-indol-2-yl]methanone | 632 | 1.07 | AA Rev.11 |
| 5-1-113 | 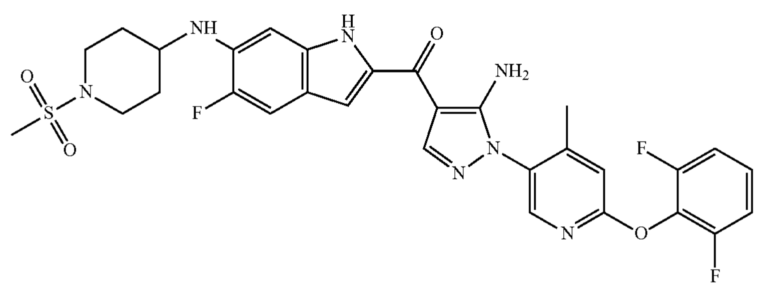 [SMILES: Cc1cc(Oc2c(F)cccc2F)ncc1-n1ncc(C(=O)c2cc3cc(F)c(NC4CCN(S(C)(=O)=O)CC4)cc3[nH]2)c1N] | [5-amino-1-[6-(2,6-difluorophenoxy)-4-methylpyridin-3-yl]pyrazol-4-yl]-[5-fluoro-6-[(1-methylsulfonylpiperidin-4-yl)amino]-1H-indol-2-yl]methanone | 640 | 1.02 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-114 | 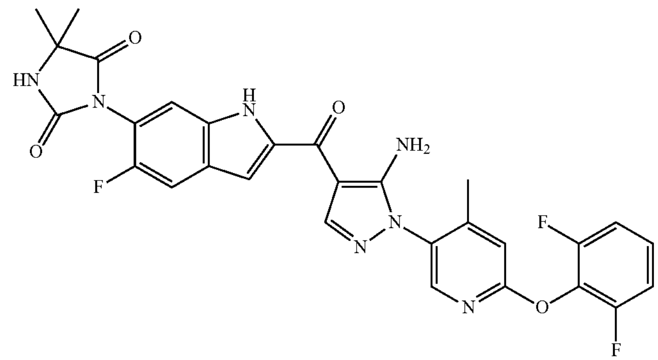 [SMILES: Cc1cc(Oc2c(F)cccc2F)ncc1-n1ncc(C(=O)c2cc3cc(F)c(N4C(=O)NC(C)(C)C4=O)cc3[nH]2)c1N] | 3-[2-[5-amino-1-[6-(2,6-difluorophenoxy)-4-methylpyridin-3-yl]pyrazole-4-carbonyl]-5-fluoro-1H-indol-6-yl]-5,5-dimethylimidazolidine-2,4-dione | 590 | 1.18 | TFA Rev.5 |
| 5-1-115 | 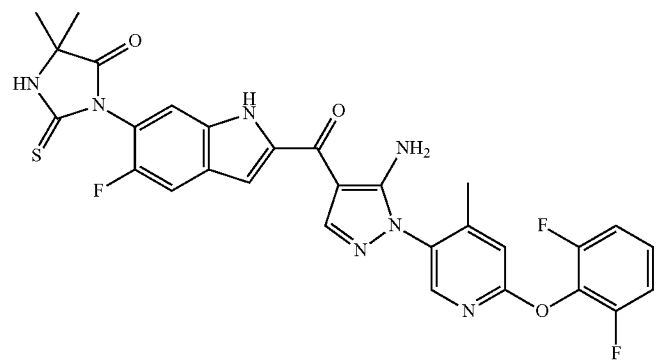 [SMILES: Cc1cc(Oc2c(F)cccc2F)ncc1-n1ncc(C(=O)c2cc3cc(F)c(N4C(=O)C(C)(C)NC4=S)cc3[nH]2)c1N] | 3-[2-[5-amino-1-[6-(2,6-difluorophenoxy)-4-methylpyridin-3-yl]pyrazole-4-carbonyl]-5-fluoro-1H-indol-6-yl]-5,5-dimethyl-2-sulfanylideneimidazolidin-4-one | 606 | 0.99 | AA Rev.11 |

| Example No. | Chemical Structure | Compound Name | m/z (M + H) | Reaction Time (Minute) | LCMS Measurement Condition |
|---|---|---|---|---|---|
| 5-1-116 | 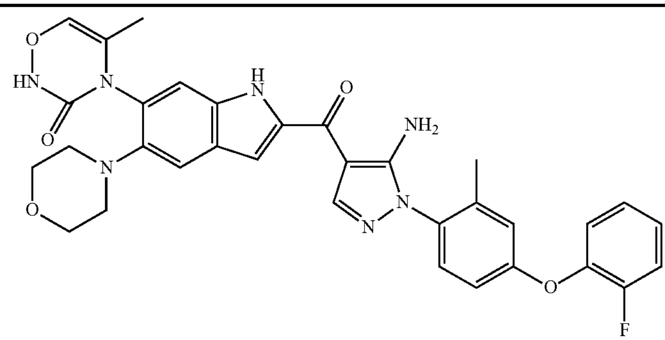 | 1-[2-[5-amino-1-[4-(2-fluorophenoxy)-2-methylphenyl]pyrazole-4-carbonyl]-5-morpholin-4-yl-1H-indol-6-yl]-6-methylpyrimidine-2,4-dione | 636 | 1.15 | TFA Rev.5 |
| 5-1-117 | 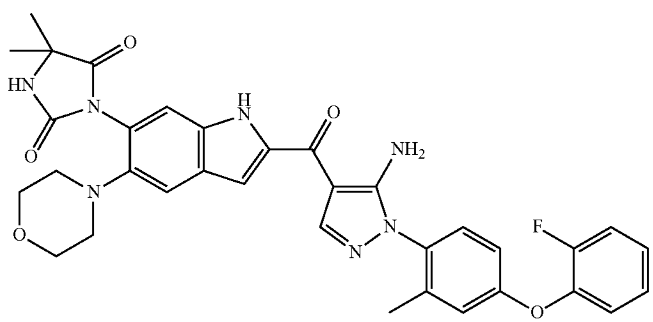 [SMILES: Cc1cc(Oc2ccccc2F)ccc1-n1ncc(C(=O)c2cc3cc(N4CCOCC4)c(N4C(=O)NC(C)(C)C4=O)cc3[nH]2)c1N] | 3-[2-[5-amino-1-[4-(2-fluorophenoxy)-2-methylphenyl]pyrazole-4-carbonyl]-5-morpholin-4-yl-1H-indol-6-yl]-5,5-dimethylimidazolidine-2,4-dione | 638 | 1.00 | AA Rev.11 |
| 5-1-118 | 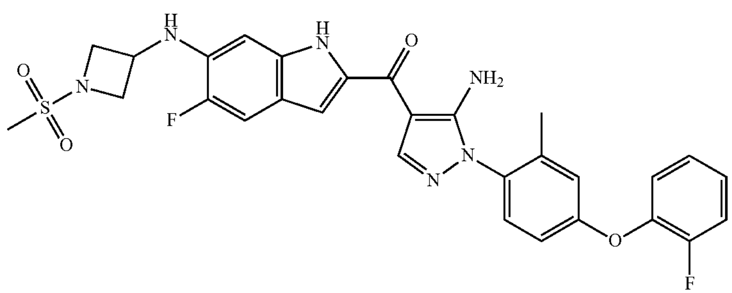 [SMILES: Cc1cc(Oc2ccccc2F)ccc1-n1ncc(C(=O)c2cc3cc(F)c(NC4CN(S(C)(=O)=O)C4)cc3[nH]2)c1N] | [5-amino-1-[4-(2-fluorophenoxy)-2-methylphenyl]pyrazol-4-yl]-[5-fluoro-5-[(1-methylsulfonylazetidin-3-yl)amino]-1H-indol-2-yl]methanone | 593 | 1.01 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-119 | 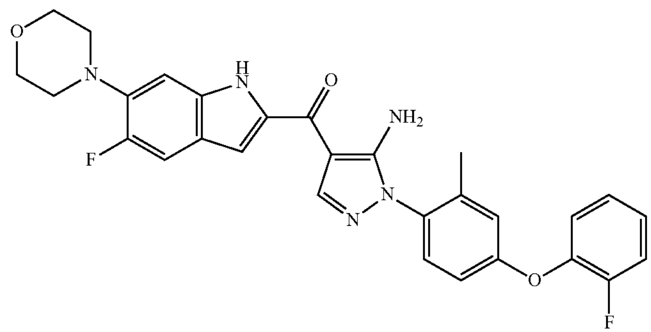 [SMILES: Cc1cc(Oc2ccccc2F)ccc1-n1ncc(C(=O)c2cc3cc(F)c(N4CCOCC4)cc3[nH]2)c1N] | [5-amino-1-[4-(2-fluorophenoxy)-2-methylphenyl]pyrazol-4-yl]-(5-fluoro-6-morpholin-4-yl-1H-indol-2-yl)methanone | 530 | 1.32 | TFA Rev.5 |
| 5-1-120 | 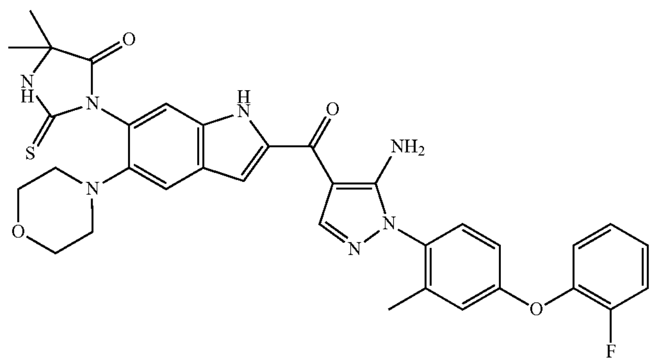 [SMILES: Cc1cc(Oc2ccccc2F)ccc1-n1ncc(C(=O)c2cc3cc(N4CCOCC4)c(N4C(=O)C(C)(C)NC4=S)cc3[nH]2)c1N] | 3-[2-[5-amino-1-[4-(2-fluorophenoxy)-2-methylphenyl]pyrazole-4-carbonyl]-5-morpholin-4-yl-1H-indol-6-yl]-5,5-dimethyl-2-sulfanylideneimidazolidin-4-one | 654 | 1.03 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-121 | 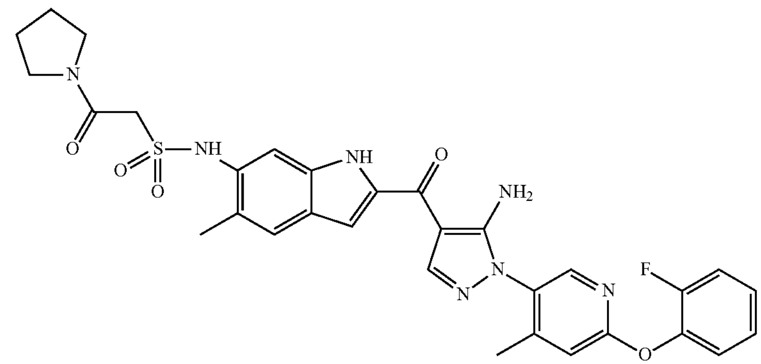 [SMILES: Cc1cc2cc(C(=O)c3cnn(-c4cnc(Oc5ccccc5F)cc4C)c3N)[nH]c2cc1NS(=O)(=O)CC(=O)N1CCCC1] | N-[2-[5-amino-1-[6-(2-fluorophenoxy)-4-methylpyridin-3-yl]pyrazole-4-carbonyl]-5-methyl-1H-indol-6-yl]-2-oxo-2-pyrrolidin-1-ylethanesulfonamide | 632 | 0.98 | AA Rev.11 |
| 5-1-122 | 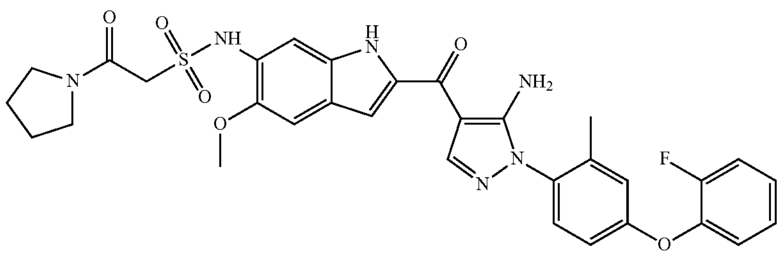 [SMILES: COc1cc2cc(C(=O)c3cnn(-c4ccc(Oc5ccccc5F)cc4C)c3N)[nH]c2cc1NS(=O)(=O)CC(=O)N1CCCC1] | N-[2-[5-amino-1-[4-(2-fluorophenoxy)-2-methylphenyl]pyrazole-4-carbonyl]-5-methoxy-1H-indol-6-yl]-2-oxo-2-pyrrolidin-1-ylethanesulfonamide | 647 | 1.23 | TFA Rev.5 |
| 5-1-123 | 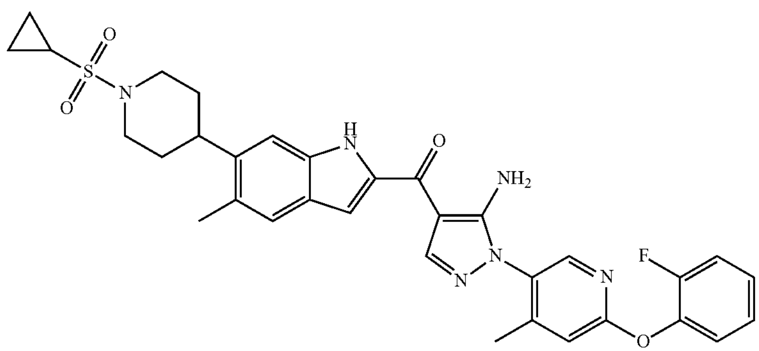 [SMILES: Cc1cc2cc(C(=O)c3cnn(-c4cnc(Oc5ccccc5F)cc4C)c3N)[nH]c2cc1C1CCN(S(=O)(=O)C2CC2)CC1] | [5-amino-1-[6-(2-fluorophenoxy)-4-methylpyridin-3-yl]pyrazol-4-yl]-[6-(1-cyclopropylsulfonylpiperidin-4-yl)-5-methyl-1H-indol-2-yl]methanone | 629 | 1.37 | TFA Rev.5 |

| Example No. | Chemical Structure | Compound Name | m/z (M + H) | Reaction Time (Minute) | LCMS Measurement Condition |
|---|---|---|---|---|---|
| 5-1-124 | 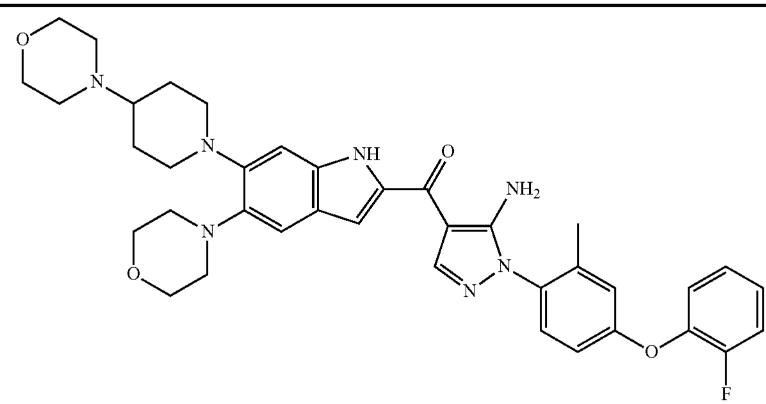 | [5-amino-1-[4-(2-fluorophenoxy)-2-methylphenyl]pyrazol-4-yl]-[5-morpholin-4-yl-6-(4-morpholin-4-ylpiperidin-1-yl)-1H-indol-2-yl]methanone | 680 | 1.11 | AA Rev.11 |
| 5-1-125 | 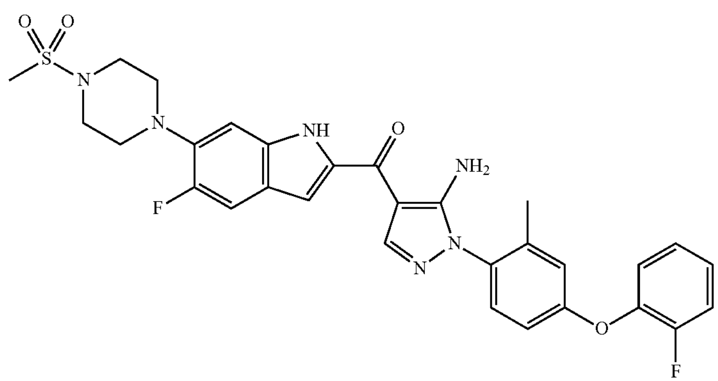 [SMILES: Cc1cc(Oc2ccccc2F)ccc1-n1ncc(C(=O)c2cc3cc(F)c(N4CCN(S(C)(=O)=O)CC4)cc3[nH]2)c1N] | [5-amino-1-[4-(2-fluorophenoxy)-2-methylphenyl]pyrazol-4-yl]-[5-fluoro-6-(4-methylsulfonylpiperazin-1-yl)-1H-indol-2-yl]methanone | 607 | 1.05 | AA Rev.11 |

| Example No. | Chemical Structure | Compound Name | m/z (M + H) | Reaction Time (Minute) | LCMS Measurement Condition |
|---|---|---|---|---|---|
| 5-1-126 | 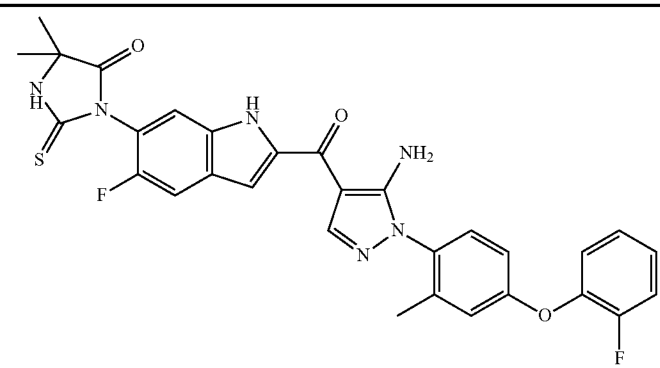 | 3-[2-[5-amino-1-[4-(2-fluorophenoxy)-2-methylphenyl]pyrazole-4-carbonyl]-5-fluoro-1H-indol-6-yl]-5,5-dimethyl-2-sulfanylideneimidazolidin-4-one | 587 | 1.02 | AA Rev.11 |
| 5-1-127 | 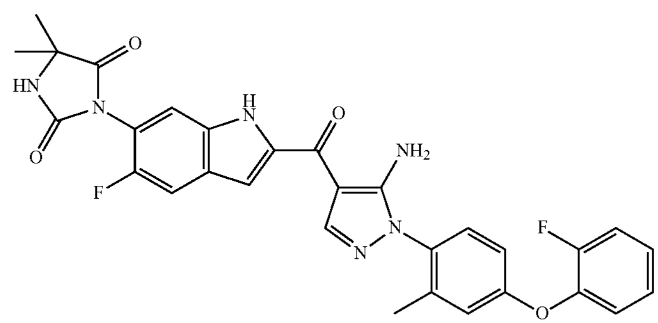 [SMILES: Cc1cc(Oc2ccccc2F)ccc1-n1ncc(C(=O)c2cc3cc(F)c(N4C(=O)NC(C)(C)C4=O)cc3[nH]2)c1N] | 3-[2-[5-amino-1-[4-(2-fluorophenoxy)-2-methylphenyl]pyrazole-4-carbonyl]-5-fluoro-1H-indol-6-yl]-5,5-dimethylimidazolidine-2,4-dione | 571 | 1.22 | TFA Rev.5 |

-continued

| Example No. | Chemical Structure | Compound Name | m/z (M + H) | Reaction Time (Minute) | LCMS Measurement Condition |
|---|---|---|---|---|---|
| 5-1-128 | 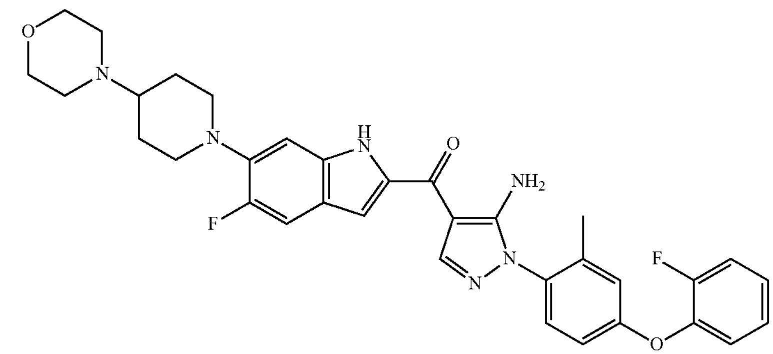 [SMILES: Cc1cc(Oc2ccccc2F)ccc1-n1ncc(C(=O)c2cc3cc(F)c(N4CCC(N5CCOCC5)CC4)cc3[nH]2)c1N] | [5-amino-1-[4-(2-fluorophenoxy)-2-methylphenyl]pyrazol-4-yl]-[5-fluoro-6-(4-morpholin-4-ylpiperidin-1-yl)-1H-indol-2-yl]methanone | 613 | 1.10 | TFA Rev.5 |
| 5-1-129 | 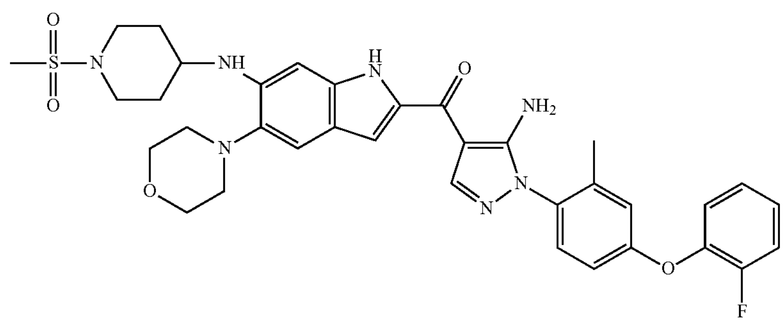 [SMILES: Cc1cc(Oc2ccccc2F)ccc1-n1ncc(C(=O)c2cc3cc(N4CCOCC4)c(NC4CCN(S(C)(=O)=O)CC4)cc3[nH]2)c1N] | [5-amino-1-[4-(2-fluorophenoxy)-2-methylphenyl]pyrazol-4-yl]-[6-[(1-methylsulfonylpiperidin-4-yl)amino]-5-morpholin-4-yl-1H-indol-2-yl]methanone | 688 | 1.05 | AA Rev.11 |
| 5-1-130 | 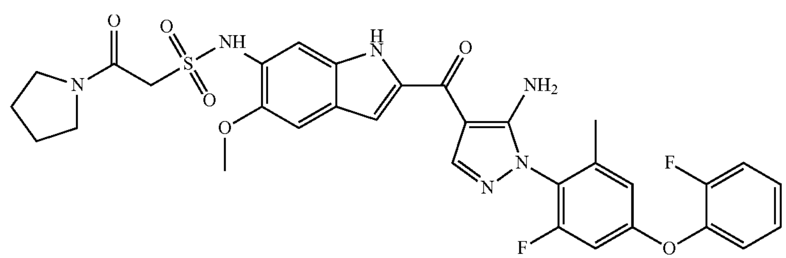 [SMILES: COc1cc2cc(C(=O)c3cnn(-c4c(C)cc(Oc5ccccc5F)cc4F)c3N)[nH]c2cc1NS(=O)(=O)CC(=O)N1CCCC1] | N-[2-[5-amino-1-[2-fluoro-4-(2-fluorophenoxy)-6-methylphenyl]pyrazole-4-carbonyl]-5-methoxy-1H-indol-6-yl]-2-oxo-2-pyrrolidin-1-ylethanesulfonamide | 665 | 1.25 | TFA Rev.5 |

-continued

| Example No. | Chemical Structure | Compound Name | m/z (M + H) | Reaction Time (Minute) | LCMS Measurement Condition |
|---|---|---|---|---|---|
| 5-1-131 | 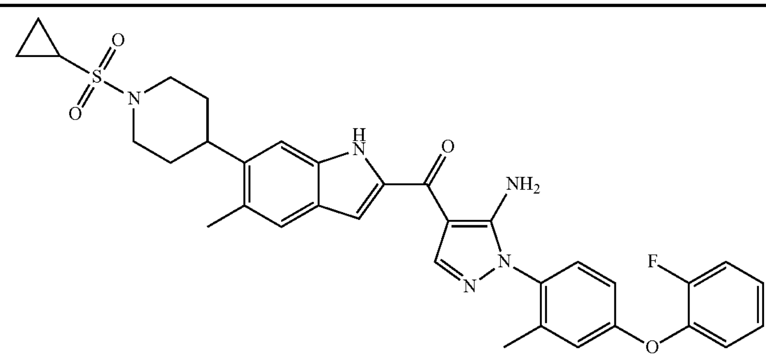 | [5-amino-1-[4-(2-fluorophenoxy)-2-methylphenyl]pyrazol-4-yl]-[6-(1-cyclopropylsulfonylpiperidin-4-yl)-5-methyl-1H-indol-2-yl]methanone | 628 | 1.44 | TFA Rev.5 |
| 5-1-132 | 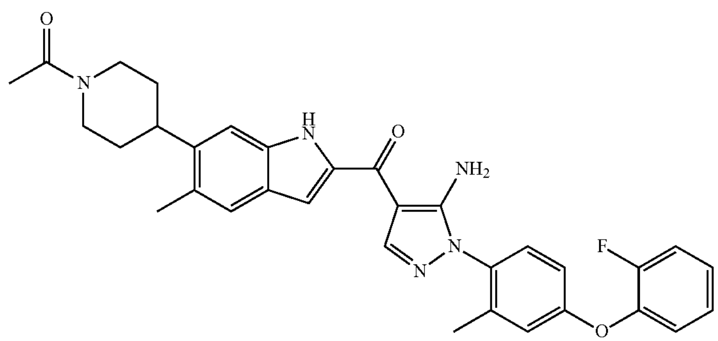 [SMILES: CC(=O)N1CCC(c2cc3[nH]c(C(=O)c4cnn(-c5ccc(Oc6ccccc6F)cc5C)c4N)cc3cc2C)CC1] | 1-[4-[2-[5-amino-1-[4-(2-fluorophenoxy)-2-methylphenyl]pyrazole-4-carbonyl]-5-methyl-1H-indol-6-yl]piperidin-1-yl]ethanone | 566 | 1.33 | TFA Rev.5 |
| 5-1-133 | 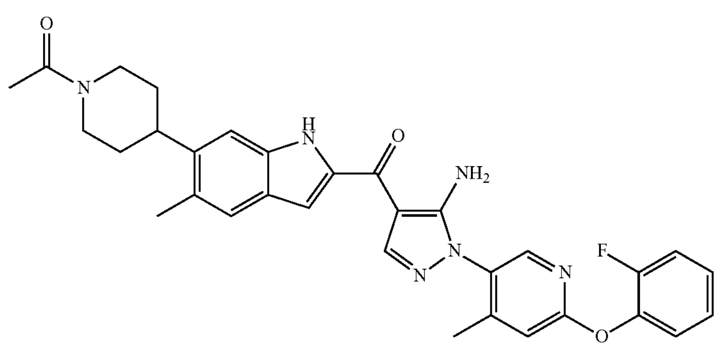 [SMILES: CC(=O)N1CCC(c2cc3[nH]c(C(=O)c4cnn(-c5cnc(Oc6ccccc6F)cc5C)c4N)cc3cc2C)CC1] | 1-[4-[2-[5-amino-1-[6-(2-fluorophenoxy)-4-methylpyridin-3-yl]pyrazole-4-carbonyl]-5-methyl-1H-indol-6-yl]piperidin-1-yl]ethanone | 567 | 1.06 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-134 | 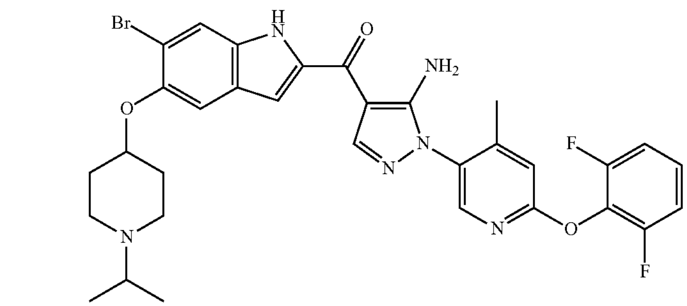 [SMILES: Cc1cc(Oc2c(F)cccc2F)ncc1-n1ncc(C(=O)c2cc3cc(OC4CCN(C(C)C)CC4)c(Br)cc3[nH]2)c1N] | [5-amino-1-[6-(2,6-difluorophenoxy)-4-methylpyridin-3-yl]pyrazol-4-yl]-[6-bromo-5-(1-propan-2-ylpiperidin-4-yl)oxy-1H-indol-2-yl]methanone | 665, 667 | 0.99 | AA Rev.11 |
| 5-1-135 | 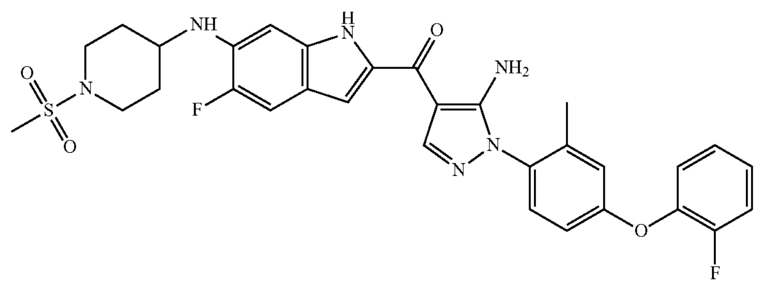 [SMILES: Cc1cc(Oc2ccccc2F)ccc1-n1ncc(C(=O)c2cc3cc(F)c(NC4CCN(S(C)(=O)=O)CC4)cc3[nH]2)c1N] | [5-amino-1-[4-(2-fluorophenoxy)-2-methylphenyl]pyrazol-4-yl]-[5-fluoro-6-[(1-methylsulfonylpiperidin-4-yl)amino]-1H-indol-2-yl]methanone | 621 | 1.04 | AA Rev.11 |
| 5-1-136 | 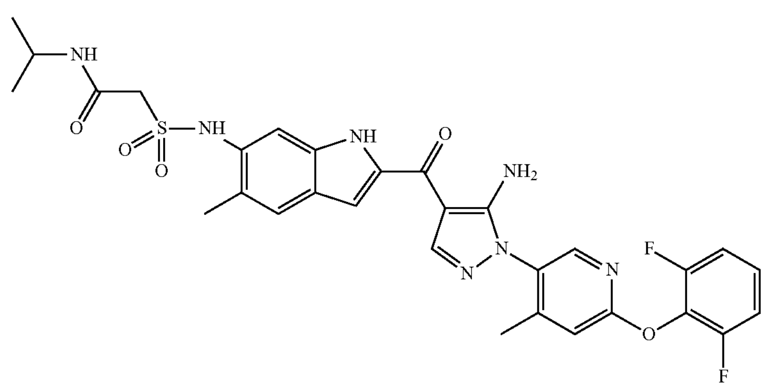 [SMILES: Cc1cc2cc(C(=O)c3cnn(-c4cnc(Oc5c(F)cccc5F)cc4C)c3N)[nH]c2cc1NS(=O)(=O)CC(=O)NC(C)C] | 2-[[2-[5-amino-1-[6-(2,6-difluorophenoxy)-4-methylpyridin-3-yl]pyrazole-4-carbonyl]-5-methyl-1H-indol-6-yl]sulfamoyl]-N-propan-2-ylacetamide | 638 | 1.00 | AA Rev.11 |

| Example No. | Chemical Structure | Compound Name | m/z (M + H) | Reaction Time (Minute) | LCMS Measurement Condition |
|---|---|---|---|---|---|
| 5-1-137 | 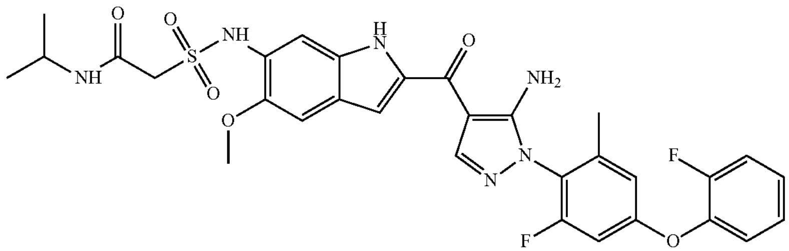 [SMILES: COc1cc2cc(C(=O)c3cnn(-c4c(C)cc(Oc5ccccc5F)cc4F)c3N)[nH]c2cc1NS(=O)(=O)CC(=O)NC(C)C] | 2-[[2-[5-amino-1-[2-fluoro-4-(2-fluorophenoxy)-6-methylphenyl]pyrazole-4-carbonyl]-5-methoxy-1H-indol-6-yl]sulfamoyl]-N-propan-2-ylacetamide | 653 | 1.00 | AA Rev.11 |
| 5-1-138 | 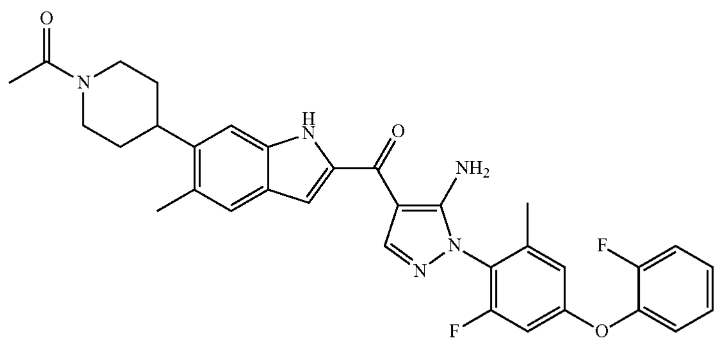 [SMILES: CC(=O)N1CCC(c2cc3[nH]c(C(=O)c4cnn(-c5c(C)cc(Oc6ccccc6F)cc5F)c4N)cc3cc2C)CC1] | 1-[4-[2-[5-amino-1-[2-fluoro-4-(2-fluorophenoxy)-6-methylphenyl]pyrazole-4-carbonyl]-5-methyl-1H-indol-6-yl]piperidin-1-yl]ethanone | 584 | 1.08 | AA Rev.11 |
| 5-1-139 | 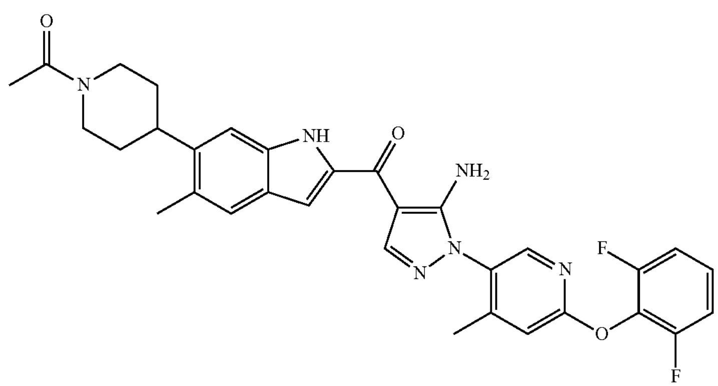 [SMILES: CC(=O)N1CCC(c2cc3[nH]c(C(=O)c4cnn(-c5cnc(Oc6c(F)cccc6F)cc5C)c4N)cc3cc2C)CC1] | 1-[4-[2-[5-amino-1-[6-(2,6-difluorophenoxy)-4-methylpyridin-3-yl]pyrazole-4-carbonyl]-5-methyl-1H-indol-6-yl]piperidin-1-yl]ethanone | 585 | 1.06 | AA Rev.11 |

| Example No. | Chemical Structure | Compound Name | m/z (M + H) | Reaction Time (Minute) | LCMS Measurement Condition |
|---|---|---|---|---|---|
| 5-1-140 | 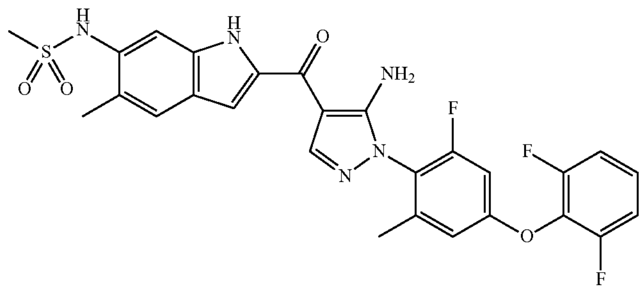 [SMILES: Cc1cc2cc(C(=O)c3cnn(-c4c(C)cc(Oc5c(F)cccc5F)cc4F)c3N)[nH]c2cc1NS(C)(=O)=O] | N-[2-[5-amino-1-[4-(2,6-difluorophenoxy)-2-fluoro-6-methylphenyl]pyrazole-4-carbonyl]-5-methyl-1H-indol-6-yl]methanesulfonamide | 570 | 1.30 | TFA Rev.5 |
| 5-1-141 | 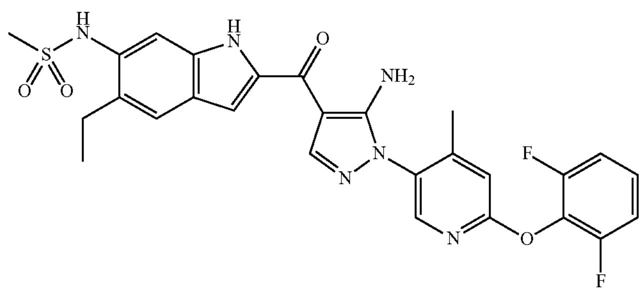 [SMILES: CCc1cc2cc(C(=O)c3cnn(-c4cnc(Oc5c(F)cccc5F)cc4C)c3N)[nH]c2cc1NS(C)(=O)=O] | N-[2-[5-amino-1-[6-(2,6-difluorophenoxy)-4-methylpyridin-3-yl]pyrazole-4-carbonyl]-5-ethyl-1H-indol-6-yl]methanesulfonamide | 567 | 1.30 | TFA Rev.5 |
| 5-1-142 | 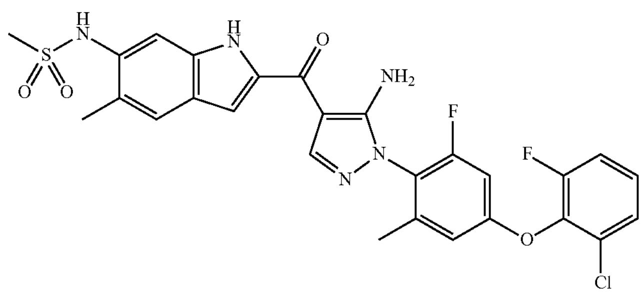 | N-[2-[5-amino-1-[4-(2-chloro-6-fluorophenoxy)-2-fluoro-6-methylphenyl]pyrazole-4-carbonyl]-5-methyl-1H-indol-6-yl]methanesulfonamide | 586, 588 | 1.27 | TFA Rev.5 |

| Example No. | Chemical Structure | Compound Name | m/z (M + H) | Reaction Time (Minute) | LCMS Measurement Condition |
|---|---|---|---|---|---|
| 5-1-143 | 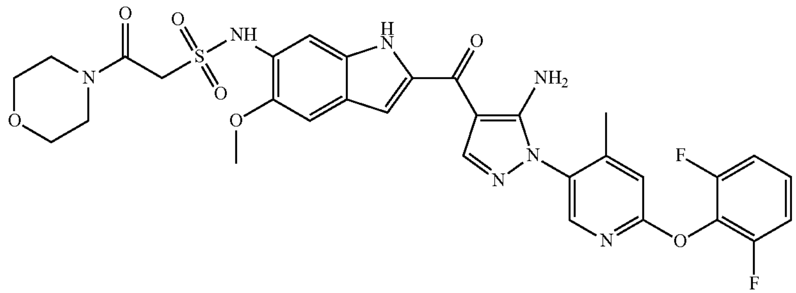 [SMILES: COc1cc2cc(C(=O)c3cnn(-c4cnc(Oc5c(F)cccc5F)cc4C)c3N)[nH]c2cc1NS(=O)(=O)CC(=O)N1CCOCC1] | N-[2-[5-amino-1-[6-(2,6-difluorophenoxy)-4-methylpyridin-3-yl]pyrazole-4-carbonyl]-5-methoxy-1H-indol-6-yl]-2-morpholin-4-yl-2-oxoethanesulfonamide | 682 | 0.95 | AA Rev.11 |
| 5-1-144 | 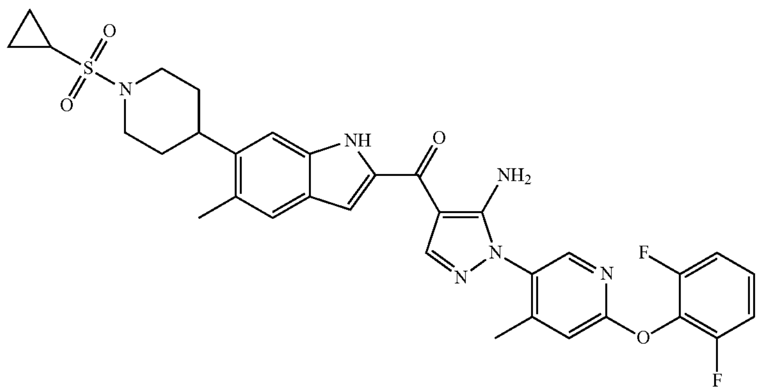 [SMILES: Cc1cc2cc(C(=O)c3cnn(-c4cnc(Oc5c(F)cccc5F)cc4C)c3N)[nH]c2cc1C1CCN(S(=O)(=O)C2CC2)CC1] | [5-amino-1-[6-(2,6-difluorophenoxy)-4-methylpyridin-3-yl]pyrazol-4-yl]-[6-(1-cyclopropylsulfonylpiperidin-4-yl)-5-methyl-1H-indol-2-yl]methanone | 647 | 1.08 | AA Rev.11 |
| 5-1-145 | 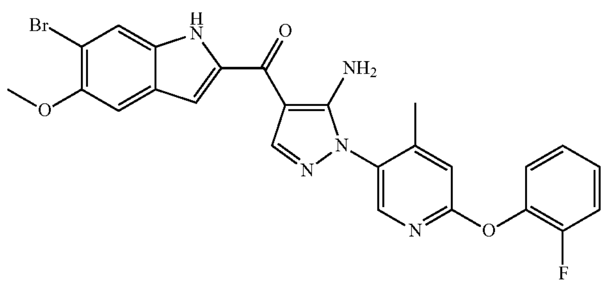 [SMILES: COc1cc2cc(C(=O)c3cnn(-c4cnc(Oc5ccccc5F)cc4C)c3N)[nH]c2cc1Br] | [5-amino-1-[6-(2-fluorophenoxy)-4-methylpyridin-3-yl]pyrazol-4-yl]-(6-bromo-5-methoxy-1H-indol-2-yl)methanone | 536, 538 | 1.06 | AA Rev.11 |

| Example No. | Chemical Structure | Compound Name | m/z (M + H) | Reaction Time (Minute) | LCMS Measurement Condition |
|---|---|---|---|---|---|
| 5-1-146 | 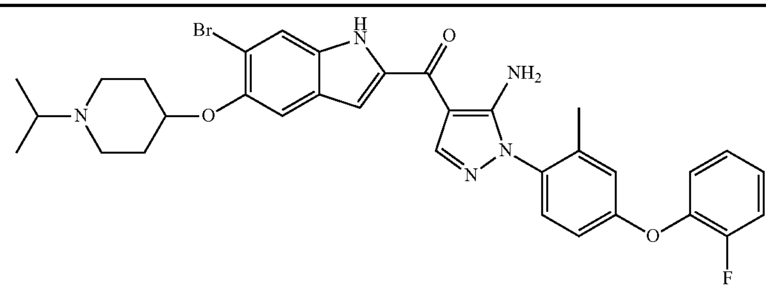 | [5-amino-1-[4-(2-fluorophenoxy)-2-methylphenyl]pyrazol-4-yl]-[6-bromo-5-(1-propan-2-ylpiperidin-4-yl)oxy-1H-indol-2-yl]methanone | 646, 648 | 1.01 | AA Rev.11 |
| 5-1-147 | 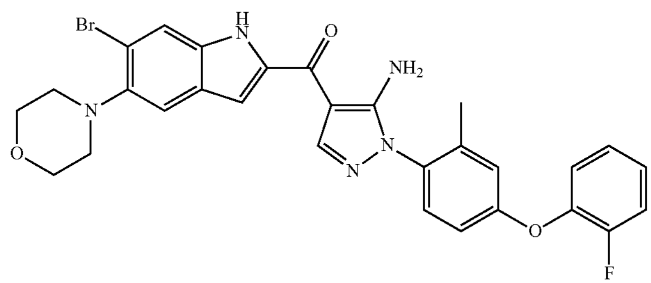 [SMILES: Cc1cc(Oc2ccccc2F)ccc1-n1ncc(C(=O)c2cc3cc(N4CCOCC4)c(Br)cc3[nH]2)c1N] | [5-amino-1-[4-(2-fluorophenoxy)-2-methylphenyl]pyrazol-4-yl]-(6-bromo-5-morpholin-4-yl-1H-indol-2-yl)methanone | 590, 592 | 1.11 | AA Rev.11 |
| 5-1-148 | 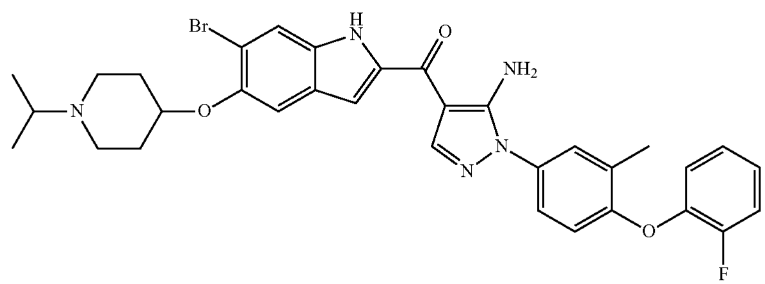 [SMILES: Cc1cc(-n2ncc(C(=O)c3cc4cc(OC5CCN(C(C)C)CC5)c(Br)cc4[nH]3)c2N)ccc1Oc1ccccc1F] | [5-amino-1-[4-(2-fluorophenoxy)-3-methylphenyl]pyrazol-4-yl]-[6-bromo-5-(1-propan-2-ylpiperidin-4-yl)oxy-1H-indol-2-yl]methanone | 646, 648 | 1.07 | TFA Rev.6 |

-continued

| Example No. | Chemical Structure | Compound Name | m/z (M + H) | Reaction Time (Minute) | LCMS Measurement Condition |
|---|---|---|---|---|---|
| 5-1-149 | 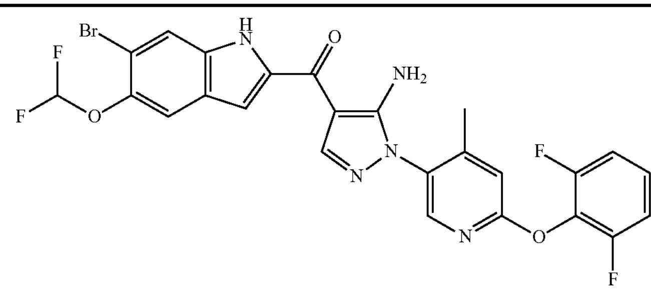 | [5-amino-1-[6-(2,6-difluorophenoxy)-4-methylpyridin-3-yl]pyrazol-4-yl]-[6-bromo-5-(difluoromethoxy)-1H-indol-2-yl]methanone | 590, 592 | 1.08 | AA Rev.11 |
| 5-1-150 | 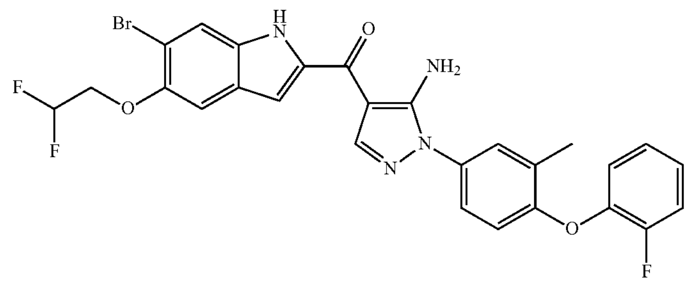 [SMILES: Cc1cc(-n2ncc(C(=O)c3cc4cc(OCC(F)F)c(Br)cc4[nH]3)c2N)ccc1Oc1ccccc1F] | [5-amino-1-[4-(2-fluorophenoxy)-3-methylphenyl]pyrazol-4-yl]-[6-bromo-5-(2,2-difluoroethoxy)-1H-indol-2-yl]methanone | 585, 587 | 1.42 | TFA Rev.5 |
| 5-1-151 | 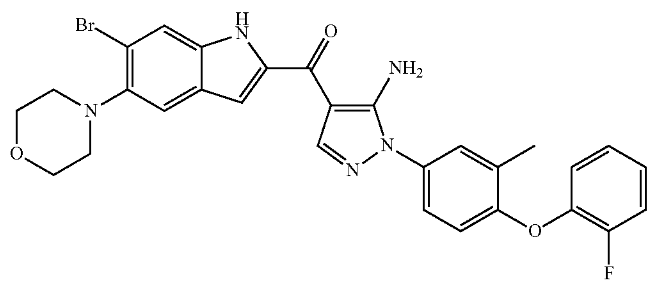 [SMILES: Cc1cc(-n2ncc(C(=O)c3cc4cc(N5CCOCC5)c(Br)cc4[nH]3)c2N)ccc1Oc1ccccc1F] | [5-amino-1-[4-(2-fluorophenoxy)-3-methylphenyl]pyrazol-4-yl]-(6-bromo-5-morpholin-4-yl-1H-indol-2-yl)methanone | 590, 592 | 1.14 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-152 | 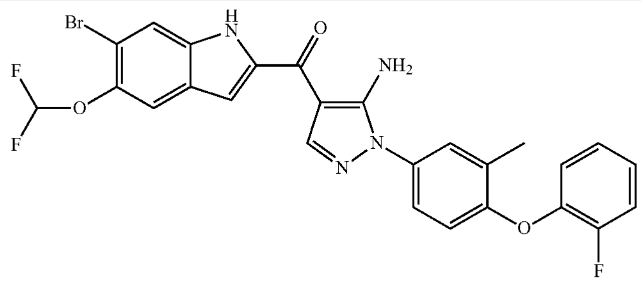 [SMILES: Cc1cc(-n2ncc(C(=O)c3cc4cc(OC(F)F)c(Br)cc4[nH]3)c2N)ccc1Oc1ccccc1F] | [5-amino-1-[4-(2-fluorophenoxy)-3-methylphenyl]pyrazol-4-yl]-[6-bromo-5-(difluoromethoxy)-1H-indol-2-yl]methanone | 571, 573 | 1.45 | TFA Rev.5 |
| 5-1-153 | 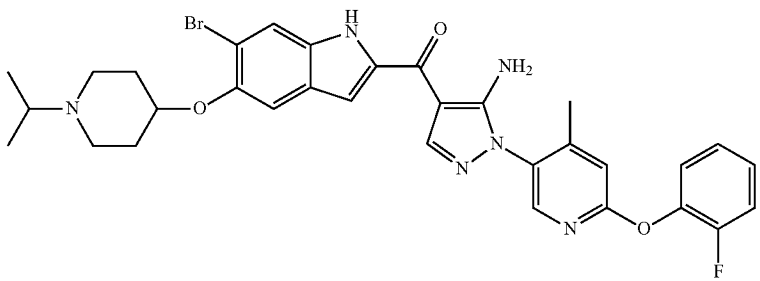 [SMILES: Cc1cc(Oc2ccccc2F)ncc1-n1ncc(C(=O)c2cc3cc(OC4CCN(C(C)C)CC4)c(Br)cc3[nH]2)c1N] | [5-amino-1-[6-(2-fluorophenoxy)-4-methylpyridin-3-yl]pyrazol-4-yl]-[6-bromo-5-(1-propan-2-ylpiperidin-4-yl)oxy-1H-indol-2-yl]methanone | 647, 649 | 0.97 | AA Rev.11 |
| 5-1-154 | 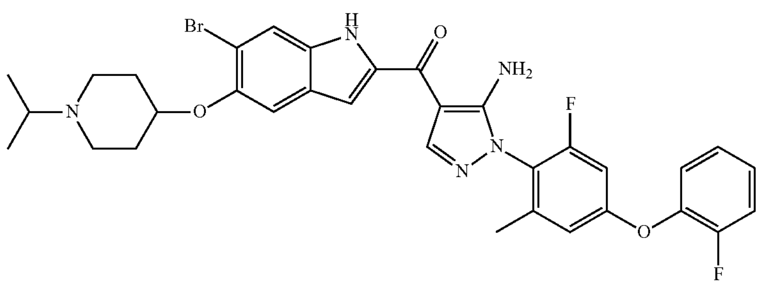 [SMILES: Cc1cc(Oc2ccccc2F)cc(F)c1-n1ncc(C(=O)c2cc3cc(OC4CCN(C(C)C)CC4)c(Br)cc3[nH]2)c1N] | [5-amino-1-[2-fluoro-4-(2-fluorophenoxy)-6-methylphenyl]pyrazol-4-yl]-[6-bromo-5-(1-propan-2-ylpipendin-4-yl)oxy-1H-indol-2-yl]methanone | 664, 666 | 1.01 | AA Rev.11 |

| Example No. | Chemical Structure | Compound Name | m/z (M + H) | Reaction Time (Minute) | LCMS Measurement Condition |
|---|---|---|---|---|---|
| 5-1-155 | 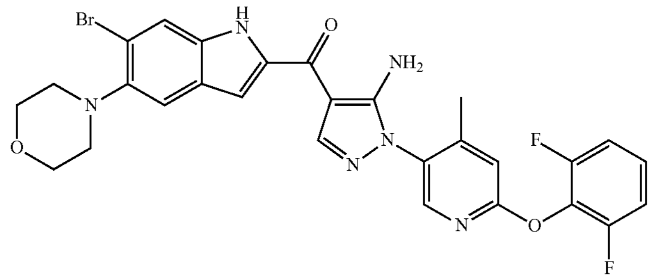 [SMILES: Cc1cc(Oc2c(F)cccc2F)ncc1-n1ncc(C(=O)c2cc3cc(N4CCOCC4)c(Br)cc3[nH]2)c1N] | [5-amino-1-[6-(2,6-difluorophenoxy)-4-methylpyridin-3-yl]pyrazol-4-yl]-(6-bromo-5-morpholin-4-yl-1H-indol-2-yl)methanone | 609, 611 | 1.09 | AA Rev.11 |
| 5-1-156 | 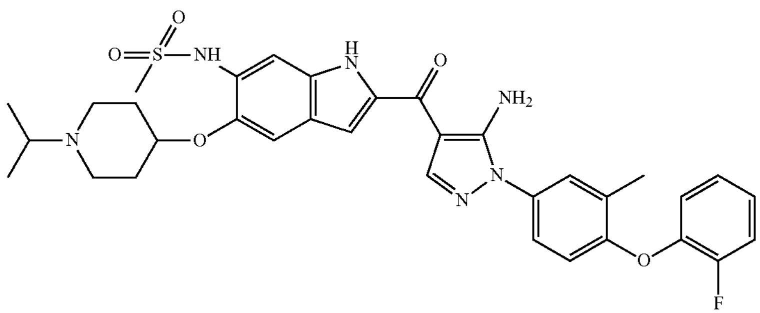 [SMILES: Cc1cc(-n2ncc(C(=O)c3cc4cc(OC5CCN(C(C)C)CC5)c(NS(C)(=O)=O)cc4[nH]3)c2N)ccc1Oc1ccccc1F] | N-[2-[5-amino-1-[4-(2-fluorophenoxy)-3-methylphenyl]pyrazole-4-carbonyl]-5-(1-propan-2-ylpiperidin-4-yl)oxy-1H-indol-6-yl]methanesulfonamide | 661 | 0.97 | AA Rev.11 |
| 5-1-157 | 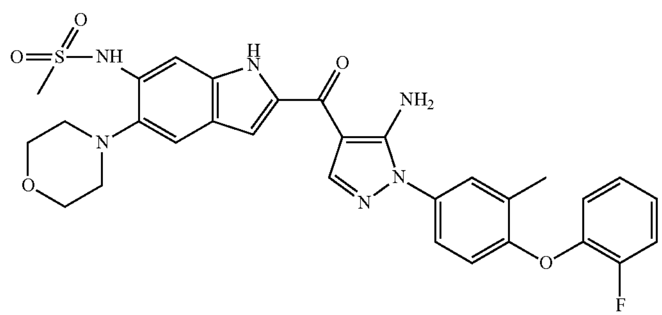 [SMILES: Cc1cc(-n2ncc(C(=O)c3cc4cc(N5CCOCC5)c(NS(C)(=O)=O)cc4[nH]3)c2N)ccc1Oc1ccccc1F] | N-[2-[5-amino-1-[4-(2-fluorophenoxy)-3-methylphenyl]pyrazole-4-carbonyl]-5-morpholin-4-yl-1H-indol-6-yl]methanesulfonamide | 605 | 1.03 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-158 | 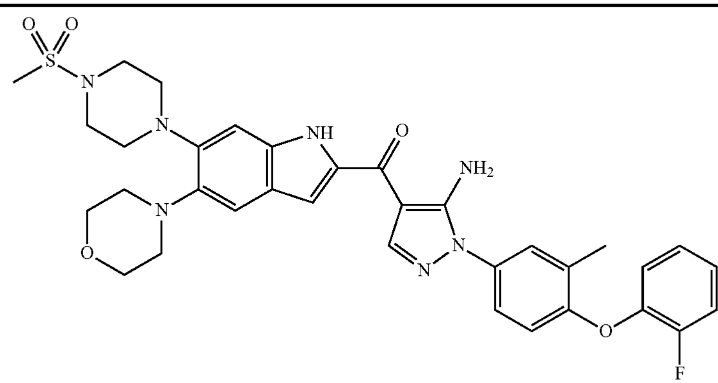 | [5-amino-1-[4-(2-fluorophenoxy)-3-methylphenyl]pyrazol-4-yl]-[6-(4-methylsulfonylpiperazin-1-yl)-5-morpholin-4-yl-1H-indol-2-yl]methanone | 674 | 1.17 | TFA Rev.5 |
| 5-1-159 | 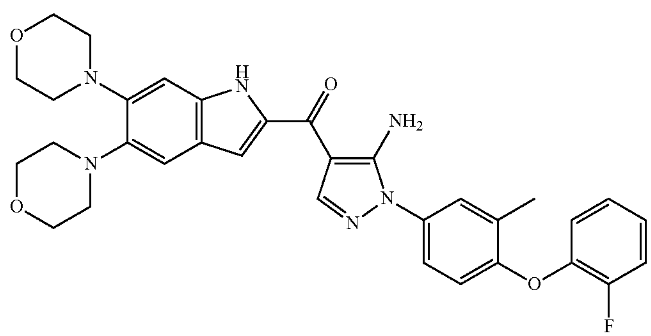 [SMILES: Cc1cc(-n2ncc(C(=O)c3cc4cc(N5CCOCC5)c(N5CCOCC5)cc4[nH]3)c2N)ccc1Oc1ccccc1F] | [5-amino-1-[4-(2-fluorophenoxy)-3-methylphenyl]pyrazol-4-yl]-(5,6-dimorpholin-4-yl-1H-indol-2-yl)methanone | 597 | 1.11 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-160 | 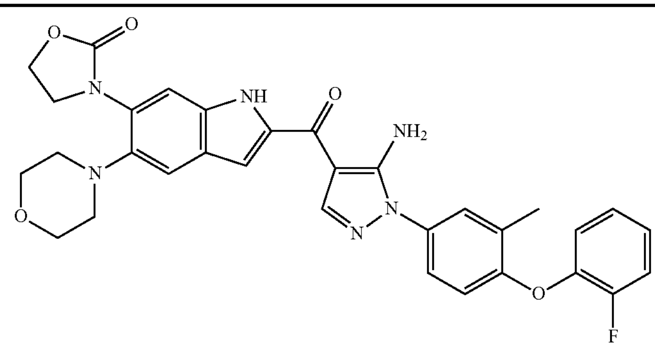 | 3-[2-[5-amino-1-[4-(2-fluorophenoxy)-3-methylphenyl]pyrazole-4-carbonyl]-5-morpholin-4-yl-1H-indol-6-yl]-1,3-oxazolidin-2-one | 597 | 1.24 | TFA Rev.5 |
| 5-1-161 | 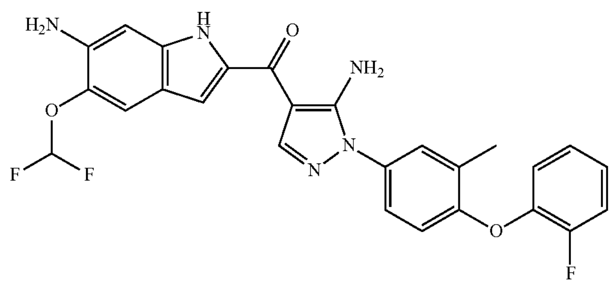 [SMILES: Cc1cc(-n2ncc(C(=O)c3cc4cc(OC(F)F)c(N)cc4[nH]3)c2N)ccc1Oc1ccccc1F] | [6-amino-5-(difluoromethoxy)-1H-indol-2-yl]-[5-amino-1-[4-(2-fluorophenoxy)-3-methylphenyl]pyrazol-4-yl]methanone | 508 | 1.05 | AA Rev.11 |
| 5-1-162 | 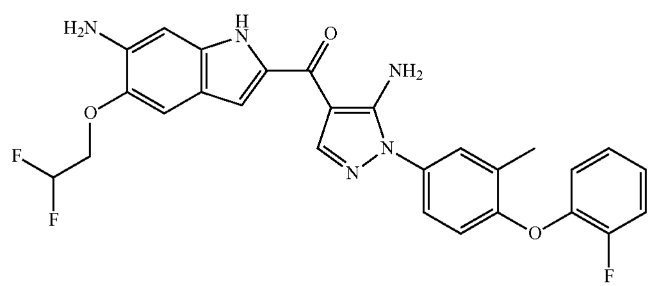 [SMILES: Cc1cc(-n2ncc(C(=O)c3cc4cc(OCC(F)F)c(N)cc4[nH]3)c2N)ccc1Oc1ccccc1F] | [6-amino-5-(2,2-difluoroethoxy)-1H-indol-2-yl]-[5-amino-1-[4-(2-fluorophenoxy)-3-methylphenyl]pyrazol-4-yl]methanone | 522 | 1.04 | AA Rev.11 |

| Example No. | Chemical Structure | Compound Name | m/z (M + H) | Reaction Time (Minute) | LCMS Measurement Condition |
|---|---|---|---|---|---|
| 5-1-163 | 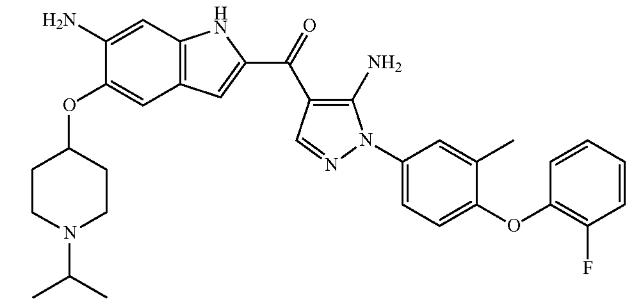 [SMILES: Cc1cc(-n2ncc(C(=O)c3cc4cc(OC5CCN(C(C)C)CC5)c(N)cc4[nH]3)c2N)ccc1Oc1ccccc1F] | [5-amino-1-[4-(2-fluorophenoxy)-3-methylphenyl]pyrazol-4-yl]-[6-amino-5-(1-propan-2-ylpiperidin-4-yl)oxy-1H-indol-2-yl]methanone | 583 | 0.96 | AA Rev.11 |
| 5-1-164 | 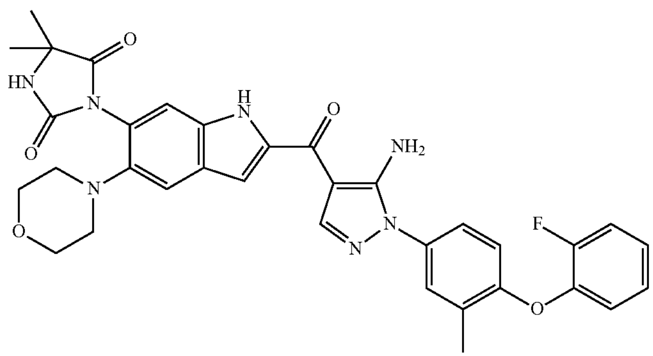 [SMILES: Cc1cc(-n2ncc(C(=O)c3cc4cc(N5CCOCC5)c(N5C(=O)NC(C)(C)C5=O)cc4[nH]3)c2N)ccc1Oc1ccccc1F] | 3-[2-[5-amino-1-[4-(2-fluorophenoxy)-3-methylphenyl]pyrazole-4-carbonyl]-5-morpholin-4-yl-1H-indol-6-yl]-5,5-dimethylimidazolidine-2,4-dione | 638 | 1.03 | AA Rev.11 |

| Example No. | Chemical Structure | Compound Name | m/z (M + H) | Reaction Time (Minute) | LCMS Measurement Condition |
|---|---|---|---|---|---|
| 5-1-165 | 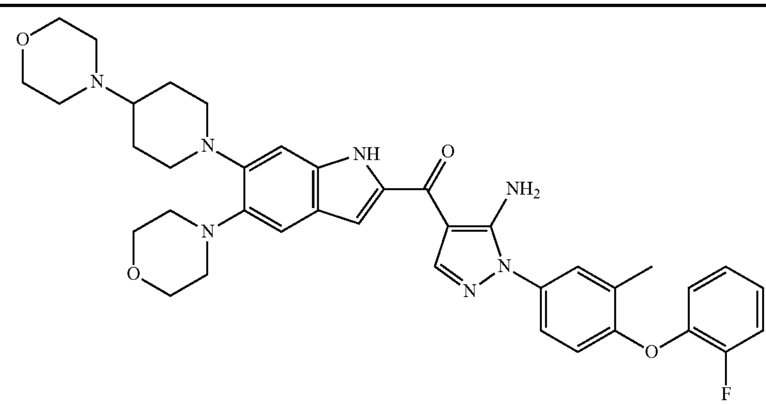 | [5-amino-1-[4-(2-fluorophenoxy)-3-methylphenyl]pyrazol-4-yl]-[5-morpholin-4-yl-6-(4-morpholin-4-ylpiperidin-1-yl)-1H-indol-2-yl]methanone | 680 | 1.14 | AA Rev.11 |
| 5-1-166 | 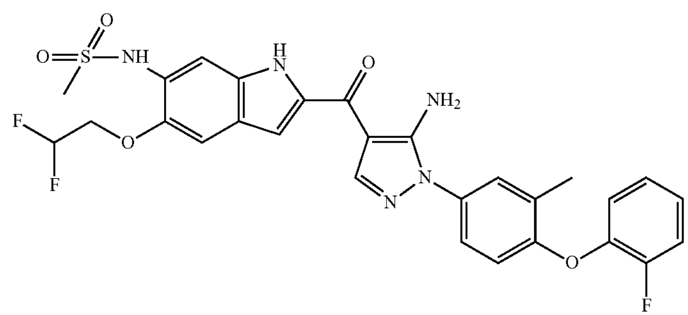 [SMILES: Cc1cc(-n2ncc(C(=O)c3cc4cc(OCC(F)F)c(NS(C)(=O)=O)cc4[nH]3)c2N)ccc1Oc1ccccc1F] | N-[2-[5-amino-1-[4-(2-fluorophenoxy)-3-methylphenyl]pyrazole-4-carbonyl]-5-(2,2-difluoroethoxy)-1H-indol-6-yl]methanesulfonamide | 600 | 1.31 | TFA Rev.5 |
| 5-1-167 | 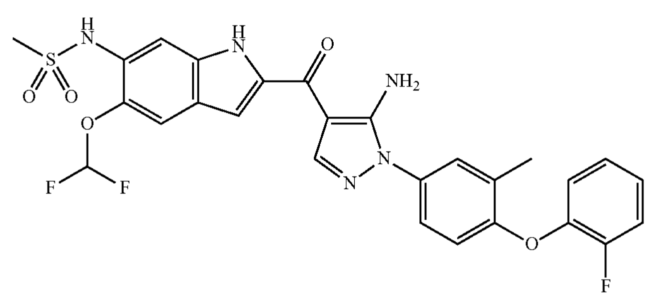 [SMILES: Cc1cc(-n2ncc(C(=O)c3cc4cc(OC(F)F)c(NS(C)(=O)=O)cc4[nH]3)c2N)ccc1Oc1ccccc1F] | N-[2-[5-amino-1-[4-(2-fluorophenoxy)-3-methylphenyl]pyrazole-4-carbonyl]-5-(difluoromethoxy)-1H-indol-6-yl]methanesulfonamide | 586 | 1.31 | TFA Rev.5 |

| Example No. | Chemical Structure | Compound Name | m/z (M + H) | Reaction Time (Minute) | LCMS Measurement Condition |
|---|---|---|---|---|---|
| 5-1-168 | 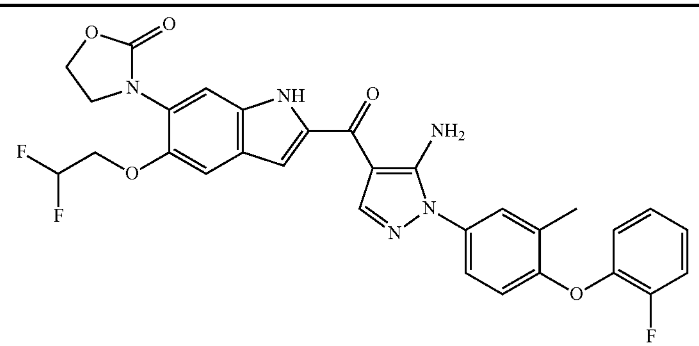 | 3-[2-[5-amino-1-[4-(2-fluorophenoxy)-3-methylphenyl]pyrazole-4-carbonyl]-5-(2,2-difluoroethoxy)-1H-indol-6-yl]-1,3-oxazolidin-2-one | 592 | 1.28 | TFA Rev.5 |
| 5-1-169 | 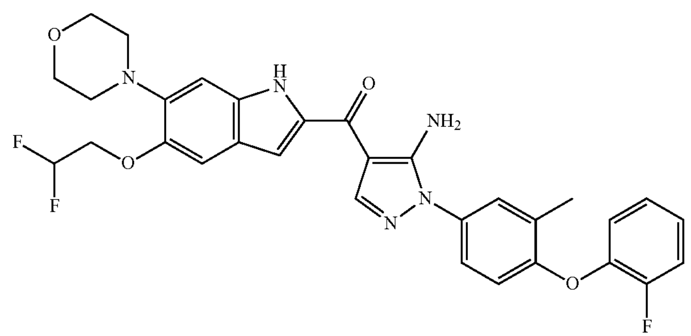 [SMILES: Cc1cc(-n2ncc(C(=O)c3cc4cc(OCC(F)F)c(N5CCOCC5)cc4[nH]3)c2N)ccc1Oc1ccccc1F] | [5-amino-1-[4-(2-fluorophenoxy)-3-methylphenyl]pyrazol-4-yl]-[5-(2,2-difluoroethoxy)-6-morpholin-4-yl-1H-indol-2-yl]methanone | 592 | 1.10 | AA Rev.11 |
| 5-1-170 | 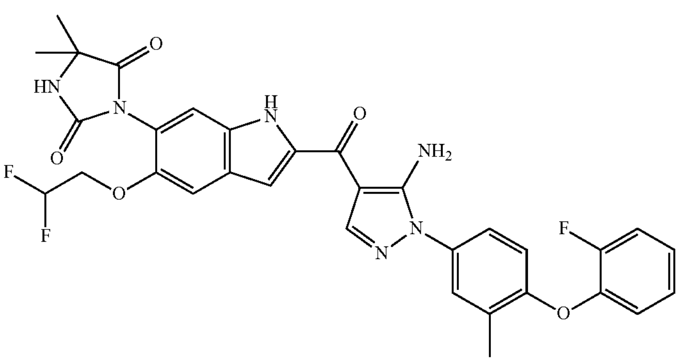 [SMILES: Cc1cc(-n2ncc(C(=O)c3cc4cc(OCC(F)F)c(N5C(=O)NC(C)(C)C5=O)cc4[nH]3)c2N)ccc1Oc1ccccc1F] | 3-[2-[5-amino-1-[4-(2-fluorophenoxy)-3-methylphenyl]pyrazole-4-carbonyl]-5-(2,2-difluoroethoxy)-1H-indol-6-yl]-5,5-dimethylimidazolidine-2,4-dione | 633 | 1.25 | TFA Rev.5 |

| Example No. | Chemical Structure | Compound Name | m/z (M + H) | Reaction Time (Minute) | LCMS Measurement Condition |
|---|---|---|---|---|---|
| 5-1-171 | 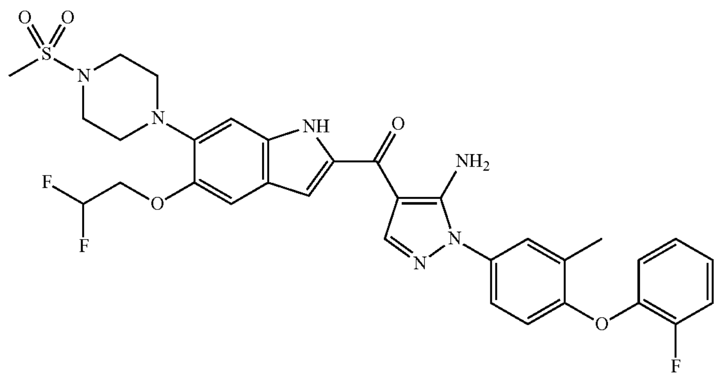 [SMILES: Cc1cc(-n2ncc(C(=O)c3cc4cc(OCC(F)F)c(N5CCN(S(C)(=O)=O)CC5)cc4[nH]3)c2N)ccc1Oc1ccccc1F] | [5-amino-1-[4-(2-fluorophenoxy)-3-methylphenyl]pyrazol-4-yl]-[5-(2,2-difluoroethoxy)-6-(4-methylsulfonylpiperazin-1-yl)-1H-indol-2-yl]methanone | 669 | 1.31 | TFA Rev.6 |
| 5-1-172 | 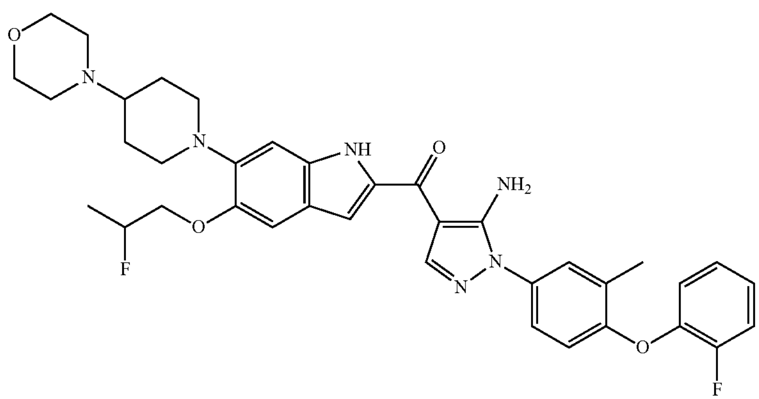 [SMILES: Cc1cc(-n2ncc(C(=O)c3cc4cc(OCC(C)F)c(N5CCC(N6CCOCC6)CC5)cc4[nH]3)c2N)ccc1Oc1ccccc1F] | [5-amino-1-[4-(2-fluorophenoxy)-3-methylphenyl]pyrazol-4-yl]-[5-(2,2-difluoroethoxy)-6-(4-morpholin-4-ylpiperidin-1-yl)-1H-indol-2-yl]methanone | 675 | 1.11 | TFA Rev.5 |

| Example No. | Chemical Structure | Compound Name | m/z (M + H) | Reaction Time (Minute) | LCMS Measurement Condition |
|---|---|---|---|---|---|
| 5-1-173 | 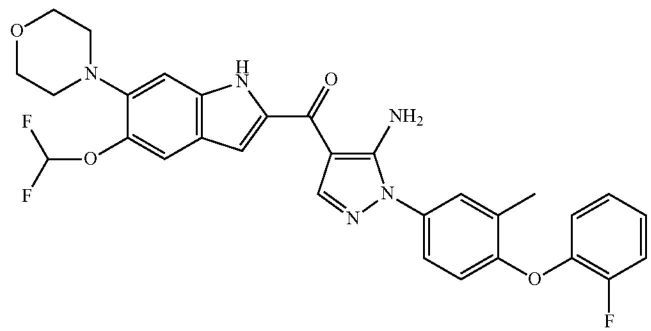 [SMILES: Cc1cc(-n2ncc(C(=O)c3cc4cc(OC(F)F)c(N5CCOCC5)cc4[nH]3)c2N)ccc1Oc1ccccc1F] | [5-amino-1-[4-(2-fluorophenoxy)-3-methylphenyl]pyrazol-4-yl]-[5-(difluoromethoxy)-6-morpholin-4-yl-1H-indol-2-yl]methanone | 578 | 1.42 | TFA Rev.5 |
| 5-1-174 | 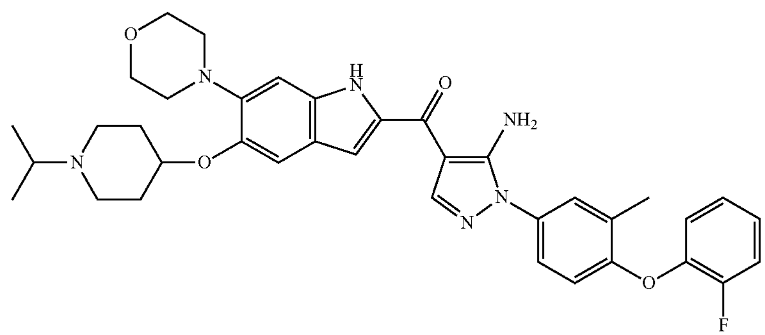 [SMILES: Cc1cc(-n2ncc(C(=O)c3cc4cc(OC5CCN(C(C)C)CC5)c(N5CCOCC5)cc4[nH]3)c2N)ccc1Oc1ccccc1F] | [5-amino-1-[4-(2-fluorophenoxy)-3-methylphenyl]pyrazol-4-yl]-[6-morpholin-4-yl-5-(1-propan-2-ylpiperidin-4-yl)oxy-1H-indol-2-yl]methanone | 653 | 1.02 | AA Rev.11 |

| Example No. | Chemical Structure | Compound Name | m/z (M + H) | Reaction Time (Minute) | LCMS Measurement Condition |
|---|---|---|---|---|---|
| 5-1-175 | 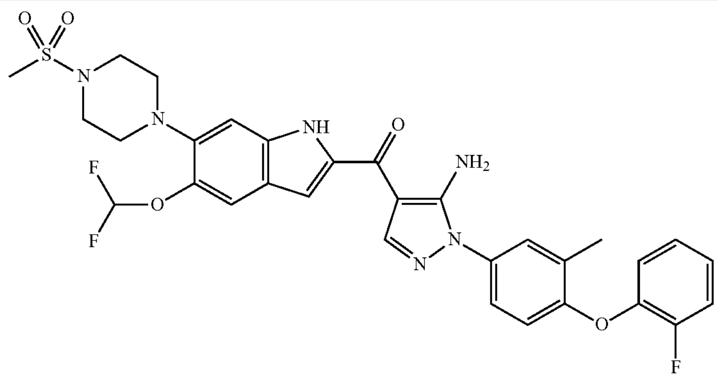 [SMILES: Cc1cc(-n2ncc(C(=O)c3cc4cc(OC(F)F)c(N5CCN(S(C)(=O)=O)CC5)cc4[nH]3)c2N)ccc1Oc1ccccc1F] | [5-amino-1-[4-(2-fluorophenoxy)-3-methylphenyl]pyrazol-4-yl]-[5-(difluoromethoxy)-6-(4-methylsulfoNylpiperazin-1-yl)-1H-indol-2-yl]methanone | 655 | 1.08 | AA Rev.11 |
| 5-1-176 | 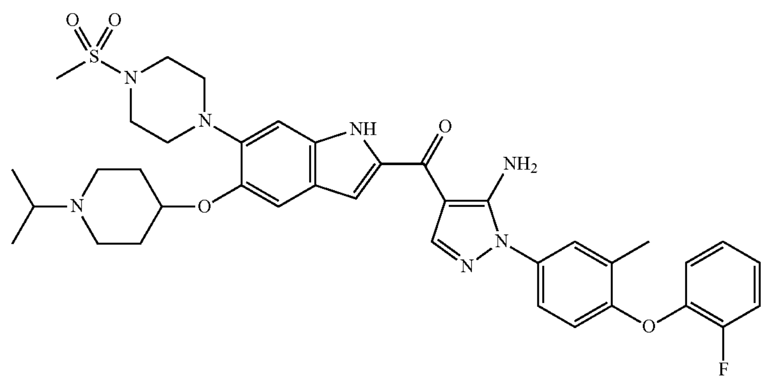 [SMILES: Cc1cc(-n2ncc(C(=O)c3cc4cc(OC5CCN(C(C)C)CC5)c(N5CCN(S(C)(=O)=O)CC5)cc4[nH]3)c2N)ccc1Oc1ccccc1F] | [5-amino-1-[4-(2-fluorophenoxy)-3-methylphenyl]pyrazol-4-yl]-[6-(4-methylsulfonylpiperazin-1-yl)-5-(1-propan-2-ylpiperidin-4-yl)oxy-1H-indol-2-yl]methanone | 730 | 1.12 | TFA Rev.5 |

| Example No. | Chemical Structure | Compound Name | m/z (M + H) | Reaction Time (Minute) | LCMS Measurement Condition |
|---|---|---|---|---|---|
| 5-1-177 | 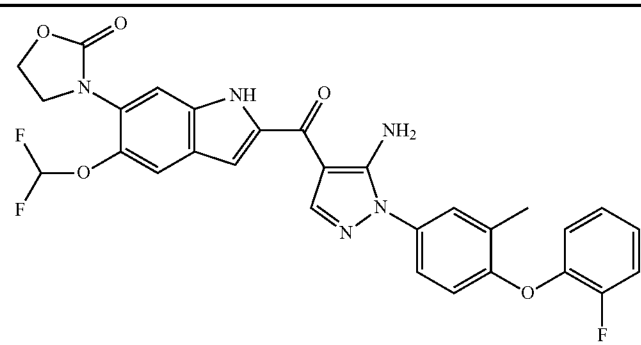 | 3-[2-[5-amino-1-[4-(2-fluorophenoxy)-3-methylphenyl]pyrazole-4-carbonyl]-5-(difluoromethoxy)-1H-indol-6-yl]-1,3-oxazolidin-2-one | 578 | 1.30 | TFA Rev.5 |
| 5-1-178 | 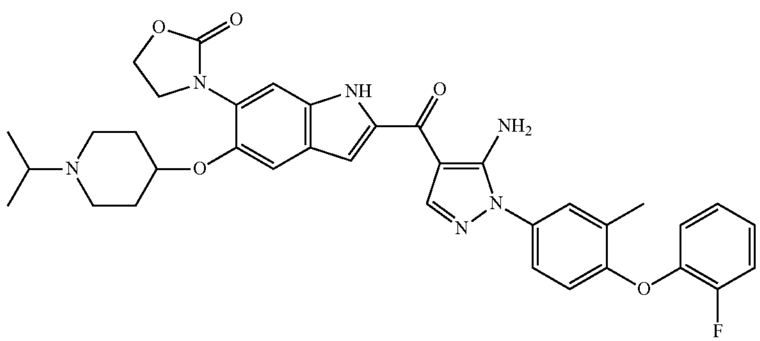 [SMILES: Cc1cc(-n2ncc(C(=O)c3cc4cc(OC5CCN(C(C)C)CC5)c(N5CCOC5=O)cc4[nH]3)c2N)ccc1Oc1ccccc1F] | 3-[2-[5-amino-1-[4-(2-fluorophenoxy)-3-methylphenyl]pyrazole-4-carbonyl]-5-(1-propan-2-ylpiperidin-4-yl)oxy-1H-indol-6-yl]-1,3-oxazolidin-2-one | 653 | 0.94 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-179 | 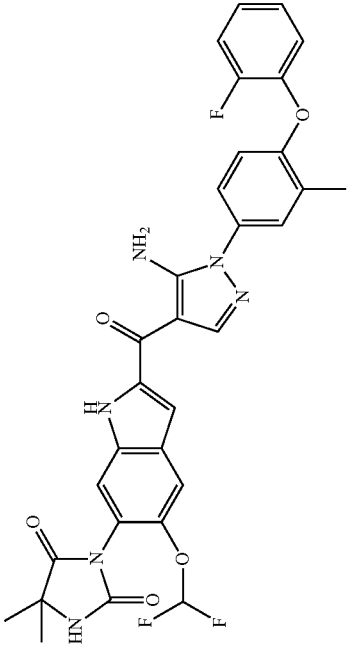 | 3-[2-[5-amino-1-[4-(2-fluorophenoxy)-3-methylphenyl]pyrazole-4-carbonyl]-5-(difluoromethoxy)-1H-indol-6-yl]-5,5-dimethylimidazolidine-2,4-dione | 619 | 1.28 | TFA Rev.5 |
| 5-1-180 | 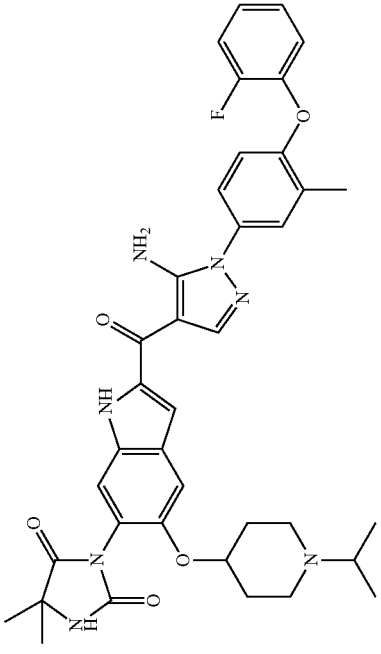 | 3-[2-[5-amino-1-[4-(2-fluorophenoxy)-3-methylphenyl]pyrazole-4-carbonyl]-5-(1-propan-2-ylpiperidin-4-yl)oxy-1H-indol-6-yl]-5,5-dimethylimidazolidine-2,4-dione | 694 | 1.07 | TFA Rev.5 |

| Example No. | Chemical Structure | Compound Name | m/z (M + H) | Reaction Time (Minute) | LCMS Measurement Condition |
|---|---|---|---|---|---|
| 5-1-181 | 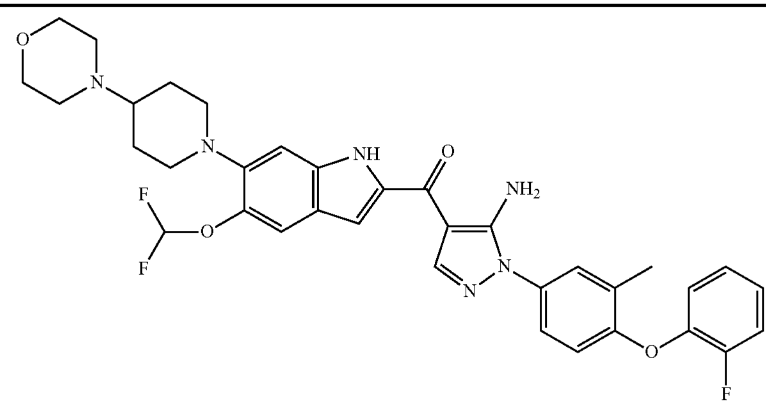 | [5-amino-1-[4-(2-fluorophenoxy)-3-methylphenyl]pyrazol-4-yl]-[5-(difluoromethoxy)-6-(4-morpholin-4-ylpiperidin-1-yl)-1H-indol-2-yl]methanone | 661 | 1.14 | AA Rev.11 |
| 5-1-182 | 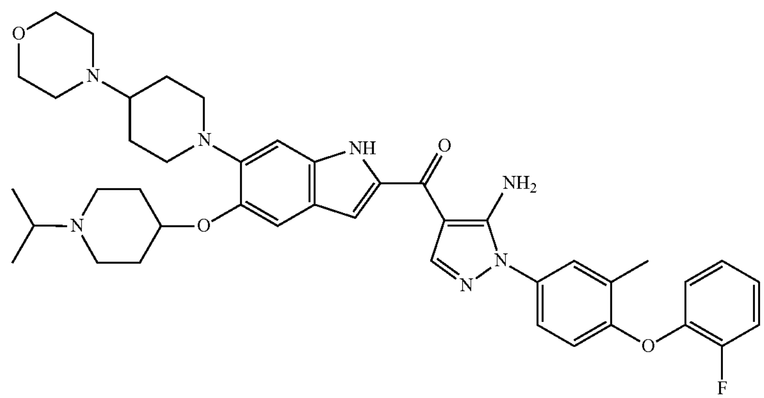 [SMILES: Cc1cc(-n2ncc(C(=O)c3cc4cc(OC5CCN(C(C)C)CC5)c(N5CCC(N6CCOCC6)CC5)cc4[nH]3)c2N)ccc1Oc1ccccc1F] | [5-amino-1-[4-(2-fluorophenoxy)-3-methylphenyl]pyrazol-4-yl]-[6-(4-morpholin-4-ylpiperidin-1-yl)-5-(1-propan-2-ylpiperidin-4-yl)oxy-1H-indol-2-yl]methanone | 736 | 1.03 | AA Rev.11 |

| Example No. | Chemical Structure | Compound Name | m/z (M + H) | Reaction Time (Minute) | LCMS Measurement Condition |
|---|---|---|---|---|---|
| 5-1-183 | 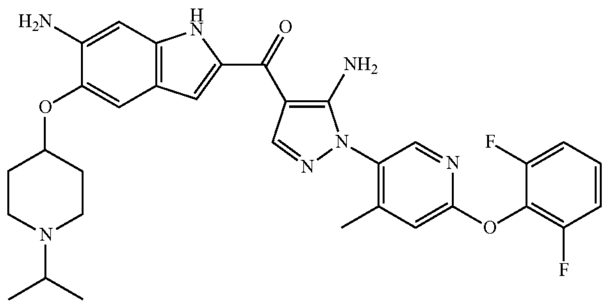 [SMILES: Cc1cc(Oc2c(F)cccc2F)ncc1-n1ncc(C(=O)c2cc3cc(OC4CCN(C(C)C)CC4)c(N)cc3[nH]2)c1N] | [5-amino-1-[6-(2,6-difluorophenoxy)-4-methylpyridin-3-yl]pyrazol-4-yl]-[6-amino-5-(1-propan-2-ylpiperidin-4-yl)oxy-1H-indol-2-yl]methanone | 602 | 0.90 | AA Rev.11 |
| 5-1-184 | 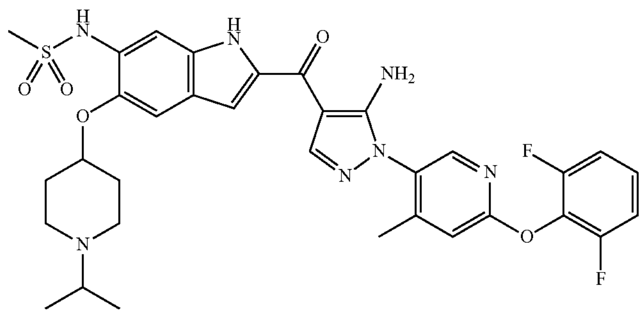 [SMILES: Cc1cc(Oc2c(F)cccc2F)ncc1-n1ncc(C(=O)c2cc3cc(OC4CCN(C(C)C)CC4)c(NS(C)(=O)=O)cc3[nH]2)c1N] | N-[2-[5-amino-1-[6-(2,6-difluorophenoxy)-4-methylpyridin-3-yl]pyrazole-4-carbonyl]-5-(1-propan-2-ylpiperidin-4-yl)oxy-1H-indol-6-yl]methanesulfonamide | 680 | 1.02 | TFA Rev.5 |
| 5-1-185 | 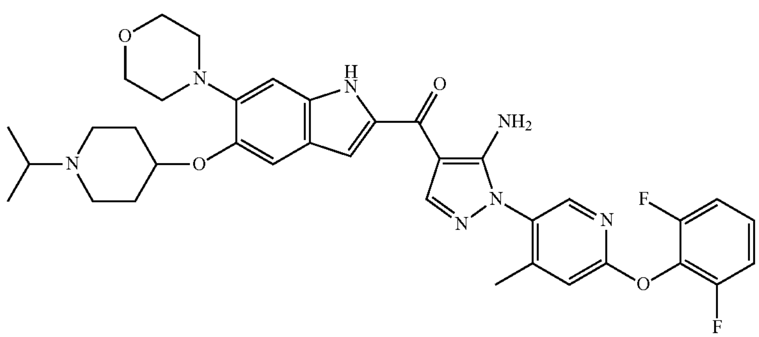 [SMILES: Cc1cc(Oc2c(F)cccc2F)ncc1-n1ncc(C(=O)c2cc3cc(OC4CCN(C(C)C)CC4)c(N4CCOCC4)cc3[nH]2)c1N] | [5-amino-1-[6-(2,6-difluorophenoxy)-4-methylpyridin-3-yl]pyrazol-4-yl]-[6-morpholin-4-yl-5-(1-propan-2-ylpiperidin-4-yl)oxy-1H-indol-2-yl]methanone | 672 | 1.00 | TFA Rev.5 |

| Example No. | Chemical Structure | Compound Name | m/z (M + H) | Reaction Time (Minute) | LCMS Measurement Condition |
|---|---|---|---|---|---|
| 5-1-186 | 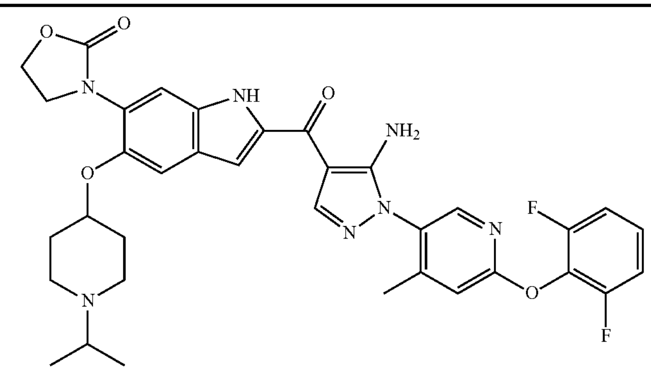 | 3-[2-[5-amino-1-[6-(2,6-difluorophenoxy)-4-methylpyridin-3-yl]pyrazole-4-carbonyl]-5-(1-propan-2-ylpiperidin-4-yl)oxy-1H-indol-6-yl]-1,3-oxazolidin-2-one | 672 | 1.00 | TFA Rev.5 |
| 5-1-187 | 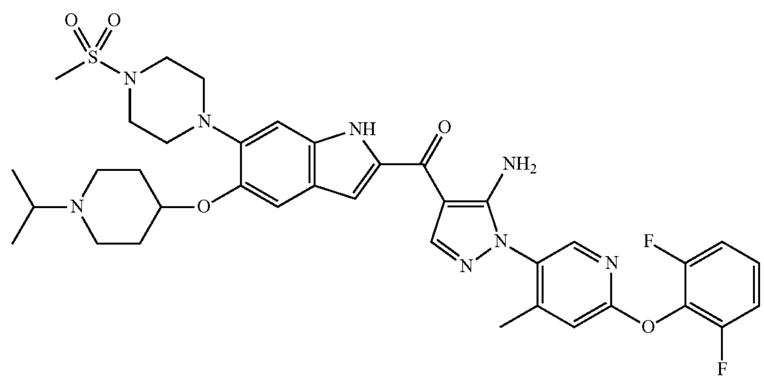 [SMILES: Cc1cc(Oc2c(F)cccc2F)ncc1-n1ncc(C(=O)c2cc3cc(OC4CCN(C(C)C)CC4)c(N4CCN(S(C)(=O)=O)CC4)cc3[nH]2)c1N] | [5-amino-1-[6-(2,6-difluorophenoxy)-4-methylpyridin-3-yl]pyrazol-4-yl]-[6-(4-methylsulfonylpiperazin-1-yl)-5-(1-propan-2-ylpiperidin-4-yl)oxy-1H-indol-2-yl]methanone | 749 | 1.05 | TFA Rev.5 |

| Example No. | Chemical Structure | Compound Name | m/z (M + H) | Reaction Time (Minute) | LCMS Measurement Condition |
|---|---|---|---|---|---|
| 5-1-188 | 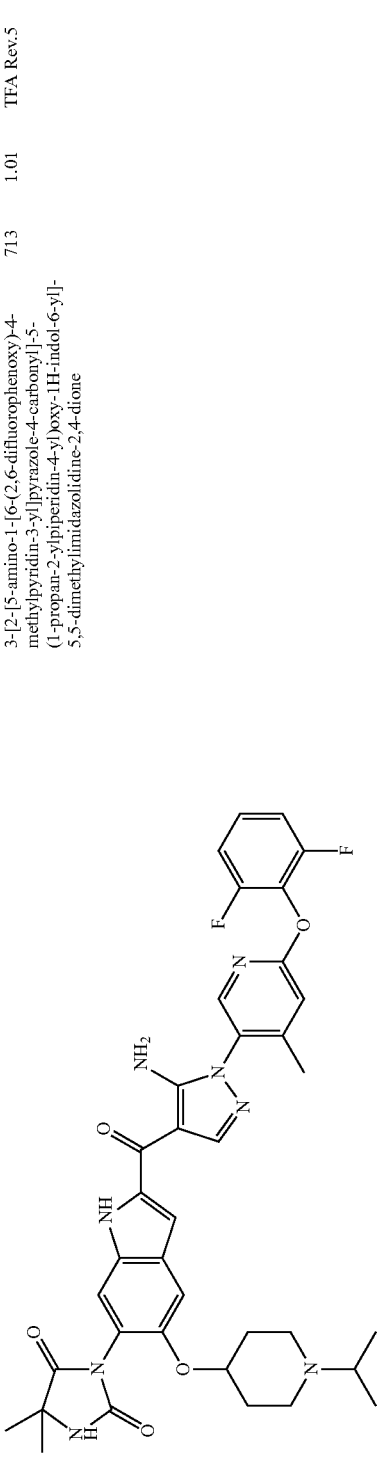 | 3-[2-[5-amino-1-[6-(2,6-difluorophenoxy)-4-methylpyridin-3-yl]pyrazole-4-carbonyl]-5-(1-propan-2-ylpiperidin-4-yl)oxy-1H-indol-6-yl]-5,5-dimethylimidazolidine-2,4-dione | 713 | 1.01 | TFA Rev.5 |
| 5-1-189 | 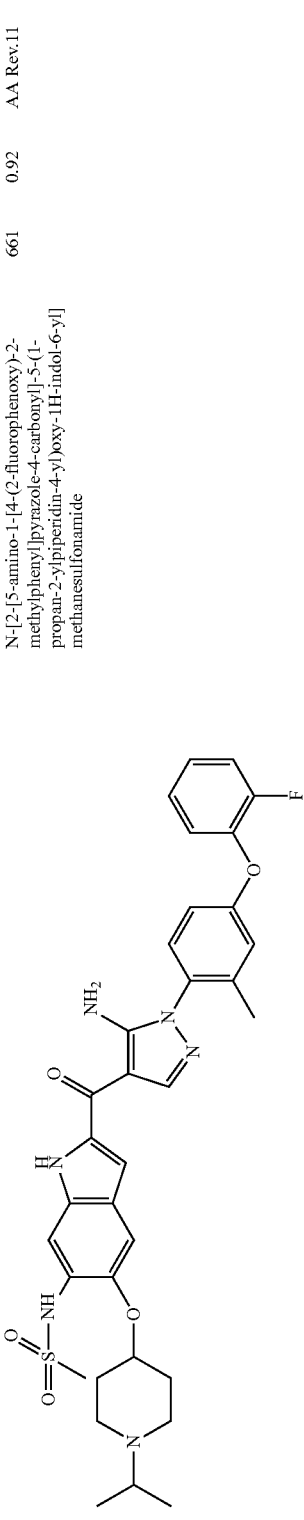 | N-[2-[5-amino-1-[4-(2-fluorophenoxy)-2-methylphenyl]pyrazole-4-carbonyl]-5-(1-propan-2-ylpiperidin-4-yl)oxy-1H-indol-6-yl]methanesulfonamide | 661 | 0.92 | AA Rev.11 |
| 5-1-190 | 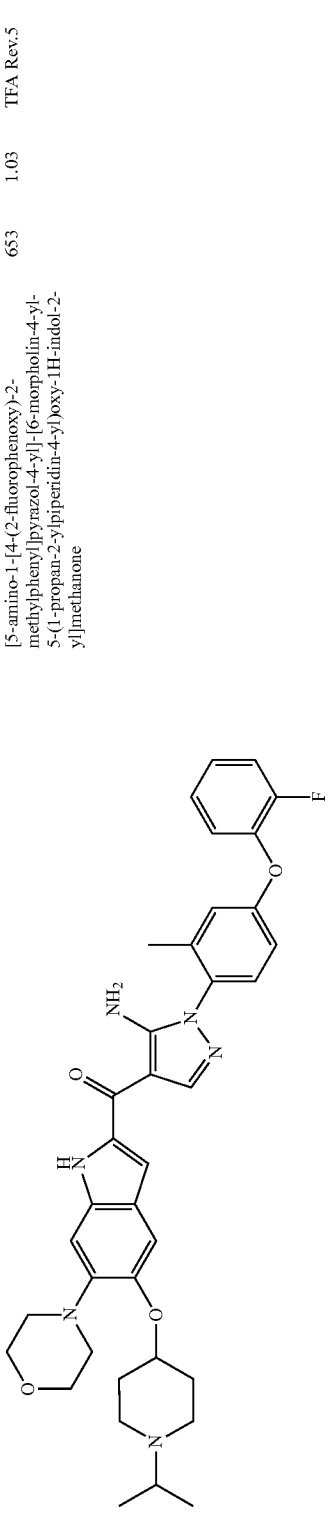 | [5-amino-1-[4-(2-fluorophenoxy)-2-methylphenyl]pyrazol-4-yl]-[6-morpholin-4-yl-5-(1-propan-2-ylpiperidin-4-yl)oxy-1H-indol-2-yl]methanone | 653 | 1.03 | TFA Rev.5 |

| Example No. | Chemical Structure | Compound Name | m/z (M + H) | Reaction Time (Minute) | LCMS Measurement Condition |
|---|---|---|---|---|---|
| 5-1-191 | 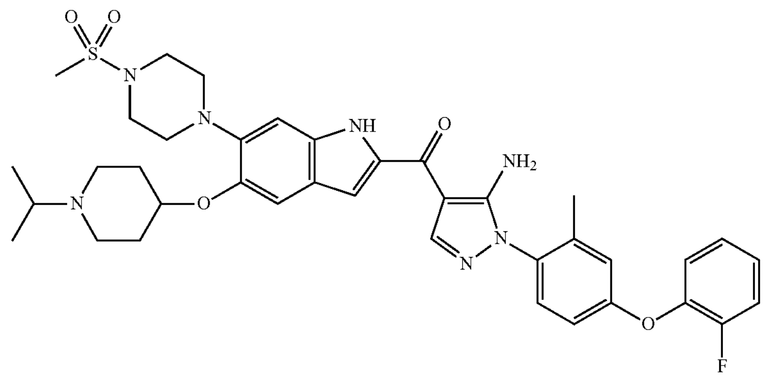 [SMILES: Cc1cc(Oc2ccccc2F)ccc1-n1ncc(C(=O)c2cc3cc(OC4CCN(C(C)C)CC4)c(N4CCN(S(C)(=O)=O)CC4)cc3[nH]2)c1N] | [5-amino-1-[4-(2-fluorophenoxy)-2-methylphenyl]pyrazol-4-yl]-[6-(4-methylsulfonylpiperazin-1-yl)-5-(1-propan-2-ylpiperidin-4-yl)oxy-1H-indol-2-yl]methanone | 730 | 1.08 | TFA Rev.5 |
| 5-1-192 | 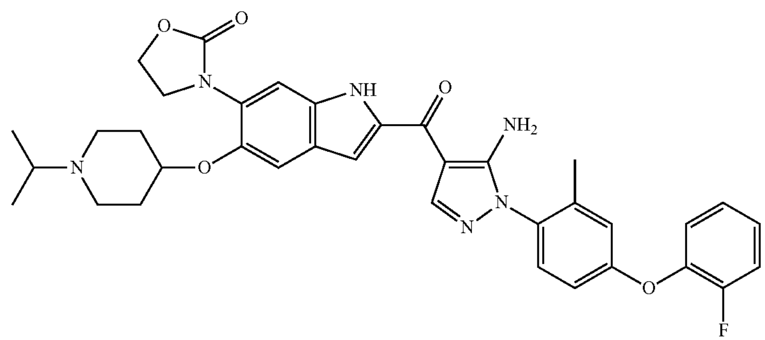 [SMILES: Cc1cc(Oc2ccccc2F)ccc1-n1ncc(C(=O)c2cc3cc(OC4CCN(C(C)C)CC4)c(N4CCOC4=O)cc3[nH]2)c1N] | 3-[2-[5-amino-1-[4-(2-fluorophenoxy)-2-methylphenyl]pyrazole-4-carbonyl]-5-(1-propan-2-ylpiperidin-4-yl)oxy-1H-indol-6-yl]-1,3-oxazolidin-2-one | 653 | 0.93 | AA Rev.11 |

| Example No. | Chemical Structure | Compound Name | m/z (M + H) | Reaction Time (Minute) | LCMS Measurement Condition |
|---|---|---|---|---|---|
| 5-1-193 | 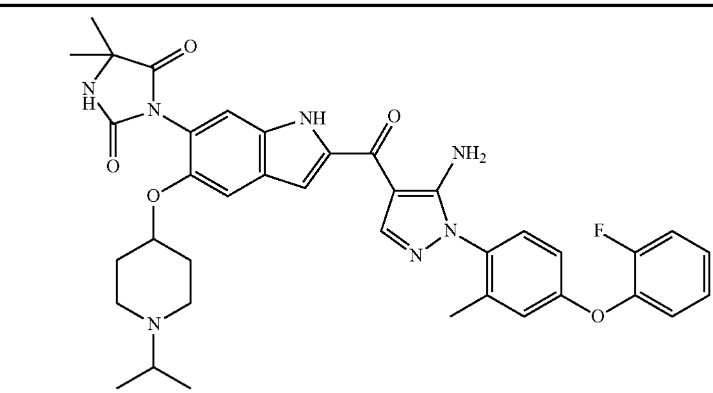 | 3-[2-[5-amino-1-[4-(2-fluorophenoxy)-2-methylphenyl]pyrazole-4-carbonyl]-5-(1-propan-2-ylpiperidin-4-yl)oxy-1H-indol-6-yl]-6,5-dimethylimidazolidine-2,4-dione | 694 | 1.03 | TFA Rev.5 |
| 5-1-194 | 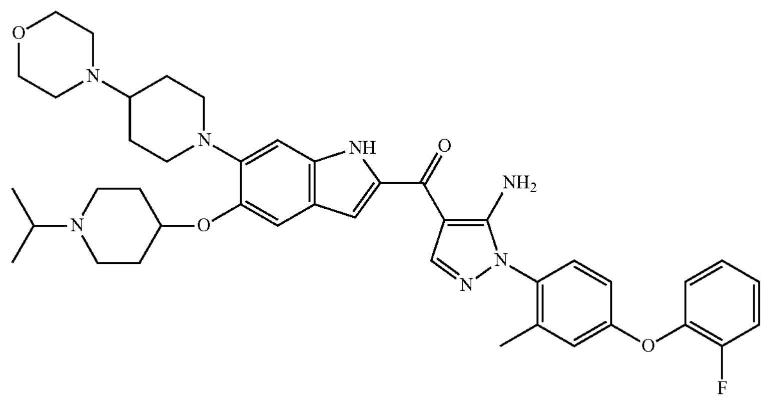 | [5-amino-1-[4-(2-fluorophenoxy)-2-methylphenyl]pyrazol-4-yl]-[6-(4-morpholin-4-ylpiperidin-1-yl)-5-(1-propan-2-ylpiperidin-4-yl)oxy-1H-indol-2-yl]methanone | 736 | 1.02 | AA Rev.11 |

| Example No. | Chemical Structure | Compound Name | m/z (M + H) | Reaction Time (Minute) | LCMS Measurement Condition |
|---|---|---|---|---|---|
| 5-1-195 | 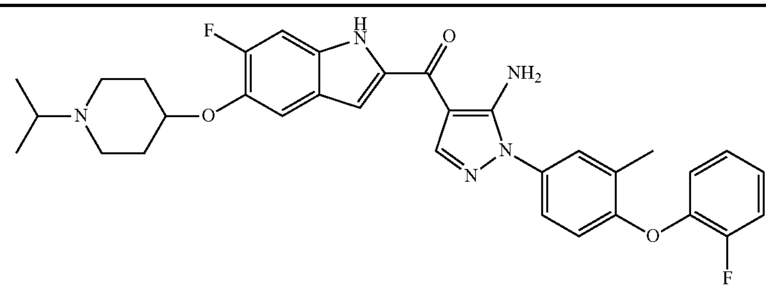 | [5-amino-1-[4-(2-fluorophenoxy)-3-methylphenyl]pyrazol-4-yl]-[6-fluoro-5-(1-propan-2-ylpiperidin-4-yl)oxy-1H-indol-2-yl]methanone | 586 | 1.03 | AA Rev.11 |
| 5-1-196 | 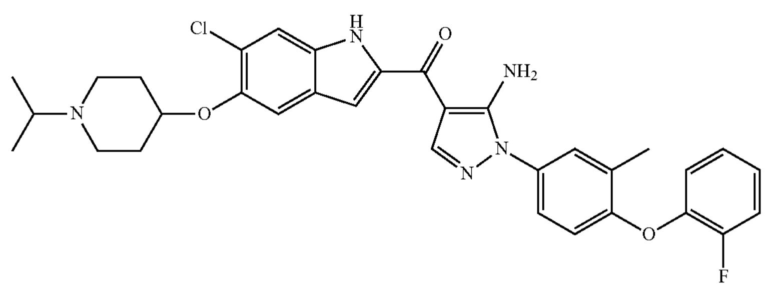 | [5-amino-1-[4-(2-fluorophenoxy)-3-methylphenyl]pyrazol-4-yl]-[6-chloro-5-(1-propan-2-ylpiperidin-4-yl)oxy-1H-indol-2-yl]methanone | 602, 604 | 1.18 | TFA Rev.5 |
| 5-1-197 | 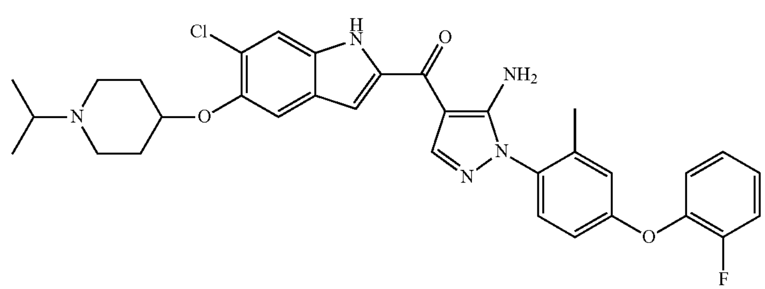 | [5-amino-1-[4-(2-fluorophenoxy)-2-methylphenyl]pyrazol-4-yl]-[6-chloro-5-(1-propan-2-ylpiperidin-4-yl)oxy-1H-indol-2-yl]methanone | 602, 604 | 1.01 | AA Rev.11 |

| Example No. | Chemical Structure | Compound Name | m/z (M + H) | Reaction Time (Minute) | LCMS Measurement Condition |
|---|---|---|---|---|---|
| 5-1-198 | 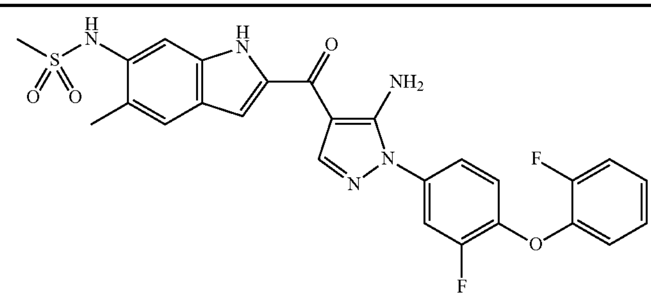 | N-[2-[5-amino-1-[3-fluoro-4-(2-fluorophenoxy)phenyl]pyrazole-4-carbonyl]-5-methyl-1H-indol-6-yl]methanesulfonamide | 538 | 1.26 | TFA Rev.5 |
| 5-1-199 | 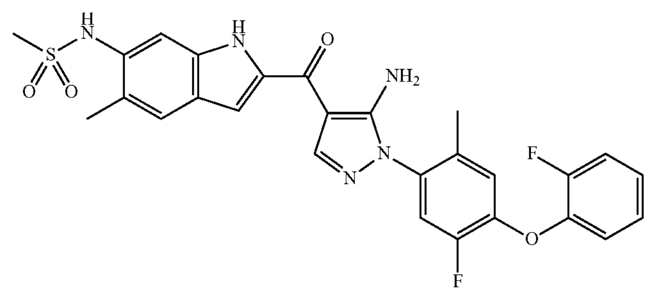 [SMILES: Cc1cc2cc(C(=O)c3cnn(-c4cc(F)c(Oc5ccccc5F)cc4C)c3N)[nH]c2cc1NS(C)(=O)=O] | N-[2-[5-amino-1-[5-fluoro-4-(2-fluorophenoxy)-2-methylphenyl]pyrazole-4-carbonyl]-5-methyl-1H-indol-6-yl]methanesulfonamide | 552 | 1.00 | AA Rev.11 |
| 5-1-200 | 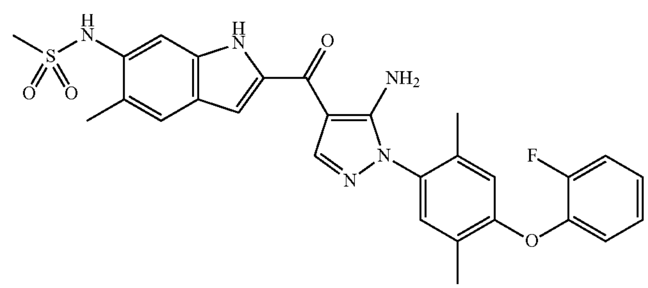 [SMILES: Cc1cc2cc(C(=O)c3cnn(-c4cc(C)c(Oc5ccccc5F)cc4C)c3N)[nH]c2cc1NS(C)(=O)=O] | N-[2-[5-amino-1-[4-(2-fluorophenoxy)-2,5-dimethylphenyl]pyrazole-4-carbonyl]-5-methyl-1H-indol-6-yl]methanesulfonamide | 548 | 1.03 | AA Rev.11 |

| Example No. | Chemical Structure | Compound Name | Reaction Time (Minute) | m/z (M + H) | LCMS Measurement Condition |
|---|---|---|---|---|---|
| 5-1-201 | 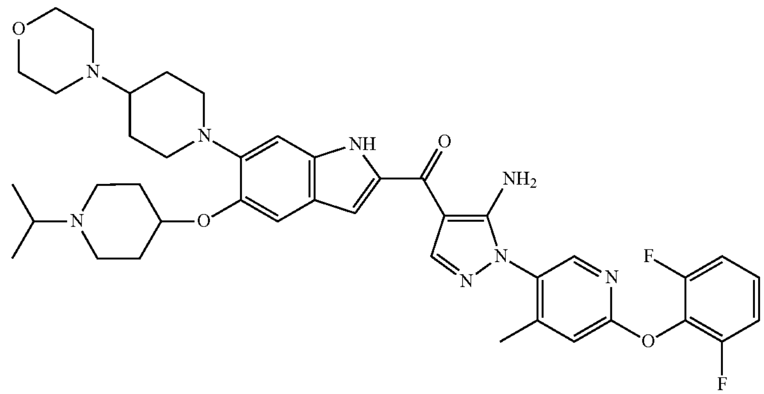 [SMILES: Cc1cc(Oc2c(F)cccc2F)ncc1-n1ncc(C(=O)c2cc3cc(OC4CCN(C(C)C)CC4)c(N4CCC(N5CCOCC5)CC4)cc3[nH]2)c1N] | [5-amino-1-[6-(2,6-difluorophenoxy)-4-methylpyridin-3-yl]pyrazol-4-yl]-[6-(4-morpholin-4-ylpiperidin-1-yl)-5-(1-propan-2-ylpiperidin-4-yl)oxy-1H-indol-2-yl]methanone | 1.00 | 755 | AA Rev.11 |
| 5-1-202 | 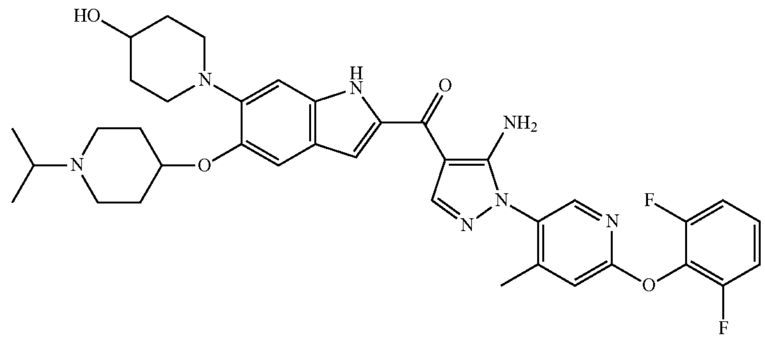 [SMILES: Cc1cc(Oc2c(F)cccc2F)ncc1-n1ncc(C(=O)c2cc3cc(OC4CCN(C(C)C)CC4)c(N4CCC(O)CC4)cc3[nH]2)c1N] | [5-amino-1-[6-(2,6-difluorophenoxy)-4-methylpyridin-3-yl]pyrazol-4-yl]-[6-(4-hydroxypiperidin-1-yl)-5-(1-propan-2-ylpiperidin-4-yl)oxy-1H-indol-2-yl]methanone | 0.95 | 686 | AA Rev.11 |
| 5-1-203 | 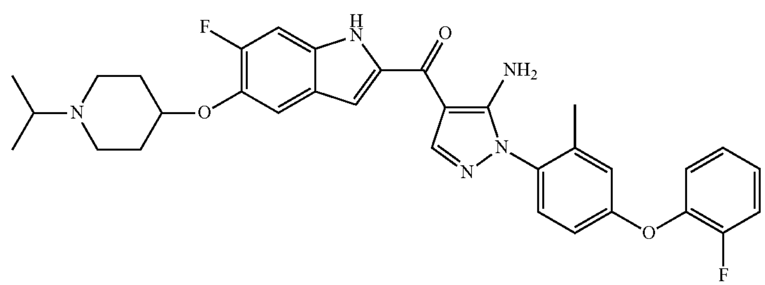 | [5-amino-1-[4-(2-fluorophenoxy)-2-methylphenyl]pyrazol-4-yl]-[6-fluoro-5-(1-propan-2-ylpiperidin-4-yl)oxy-1H-indol-2-yl]methanone | 1.11 | 586 | TFA Rev.5 |

| Example No. | Chemical Structure | Compound Name | m/z (M + H) | Reaction Time (Minute) | LCMS Measurement Condition |
|---|---|---|---|---|---|
| 5-1-204 | 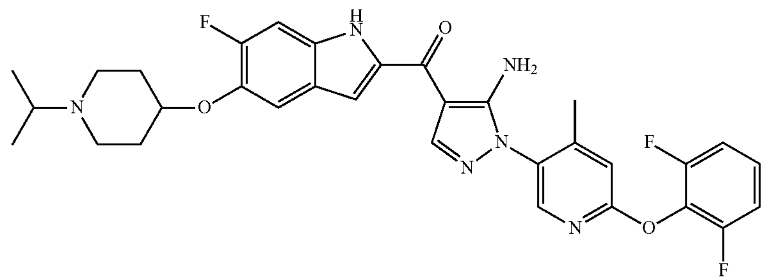 [SMILES: Cc1cc(Oc2c(F)cccc2F)ncc1-n1ncc(C(=O)c2cc3cc(OC4CCN(C(C)C)CC4)c(F)cc3[nH]2)c1N] | [5-amino-1-[6-(2,6-difluorophenoxy)-4-methylpyridin-3-yl]pyrazol-4-yl]-[6-fluoro-5-(1-propan-2-yl)piperidin-4-yl)oxy-1H-indol-2-yl]methanone | 605 | 0.97 | AA Rev.11 |
| 5-1-205 | 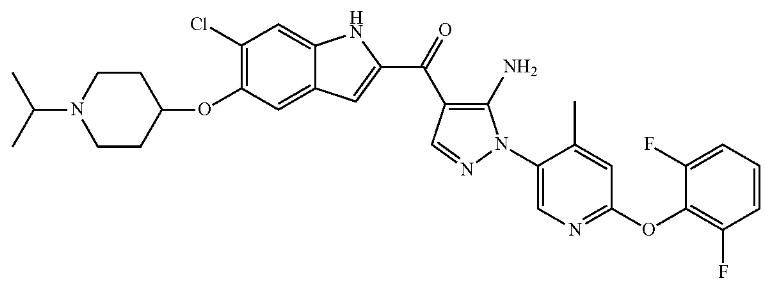 [SMILES: Cc1cc(Oc2c(F)cccc2F)ncc1-n1ncc(C(=O)c2cc3cc(OC4CCN(C(C)C)CC4)c(Cl)cc3[nH]2)c1N] | [5-amino-1-[6-(2,6-difluorophenoxy)-4-methylpyridin-3-yl]pyrazol-4-yl]-[6-chloro-5-(1-propan-2-yl)piperidin-4-yl)oxy-1H-indol-2-yl]methanone | 621, 623 | 1.00 | AA Rev.11 |
| 5-1-206 | 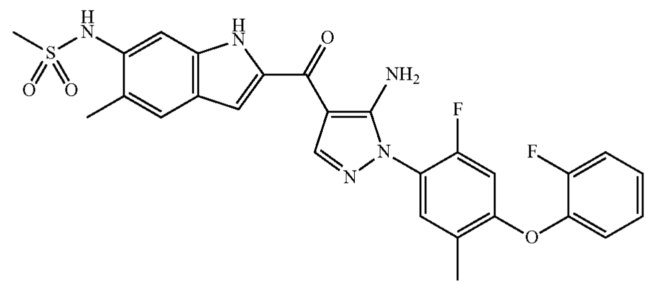 | N-[2-[5-amino-1-[2-fluoro-4-(2-fluorophenoxy)-5-methylphenyl]pyrazole-4-carbonyl]-5-methyl-1H-indol-6-yl]methanesulfonamide | 552 | 1.29 | TFA Rev.5 |

-continued

| Example No. | Chemical Structure | Compound Name | m/z (M + H) | Reaction Time (Minute) | LCMS Measurement Condition |
|---|---|---|---|---|---|
| 5-1-207 | 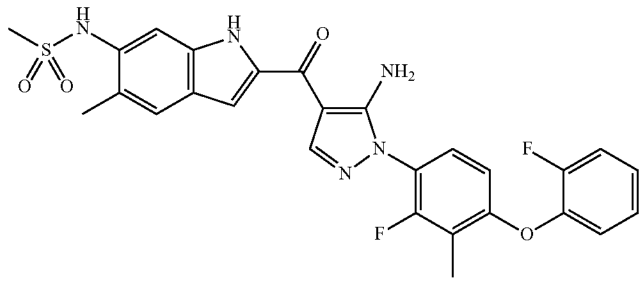 [SMILES: Cc1cc2cc(C(=O)c3cnn(-c4ccc(Oc5ccccc5F)c(C)c4F)c3N)[nH]c2cc1NS(C)(=O)=O] | N-[2-[5-amino-1-[2-fluoro-4-(2-fluorophenoxy)-3-methylphenyl]pyrazole-4-carbonyl]-5-methyl-1H-indol-6-yl]methanesulfonamide | 552 | 1.03 | AA Rev.11 |
| 5-1-208 | 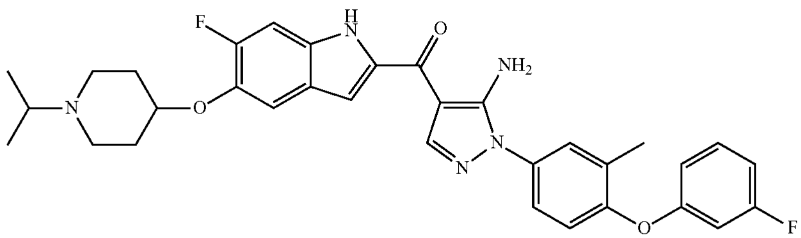 [SMILES: Cc1cc(-n2ncc(C(=O)c3cc4cc(OC5CCN(C(C)C)CC5)c(Cl)cc4[nH]3)c2N)ccc1Oc1cccc(F)c1] | [5-amino-1-[4-(3-fluorophenoxy)-3-methylphenyl]pyrazol-4-yl]-[6-fluoro-5-(1-propan-2-ylpiperidin-4-yl)oxy-1H-indol-2-yl]methanone | 586 | 1.05 | AA Rev.11 |
| 5-1-209 | 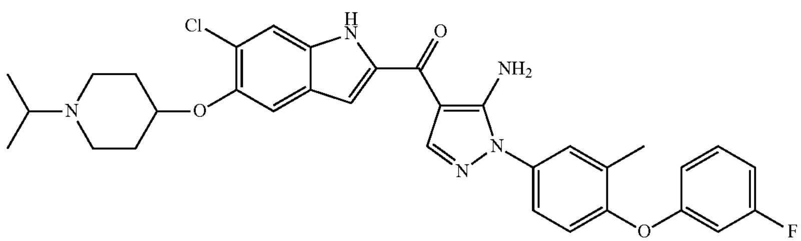 | [5-amino-1-[4-(3-fluorophenoxy)-3-methylphenyl]pyrazol-4-yl]-[6-chloro-5-(1-propan-2-ylpiperidin-4-yl)oxy-1H-indol-2-yl]methanone | 602, 604 | 1.19 | TFA Rev.5 |
| 5-1-210 | 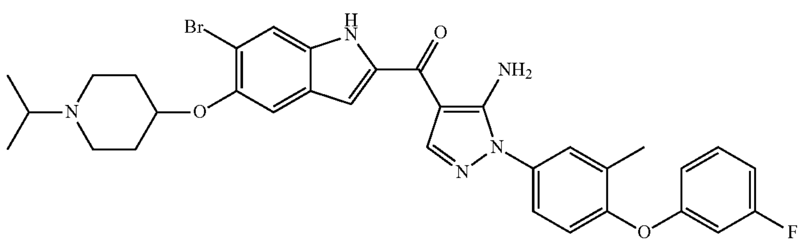 | [5-amino-1-[4-(3-fluorophenoxy)-3-methylphenyl]pyrazol-4-yl]-[6-bromo-5-(1-propan-2-ylpiperidin-4-yl)oxy-1H-indol-2-yl]methanone | 646, 648 | 1.19 | TFA Rev.5 |

-continued

| Example No. | Chemical Structure | Compound Name | m/z (M + H) | Reaction Time (Minute) | LCMS Measurement Condition |
|---|---|---|---|---|---|
| 5-1-211 | 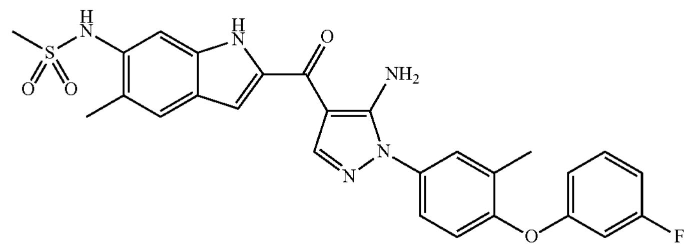 [SMILES: Cc1cc2cc(C(=O)c3cnn(-c4ccc(Oc5cccc(F)c5)c(C)c4)c3N)[nH]c2cc1NS(C)(=O)=O] | N-[2-[5-amino-1-[4-(3-fluorophenoxy)-3-methylphenyl]pyrazole-4-carbonyl]-5-methyl-1H-indol-6-yl]methanesulfonamide | 534 | 1.06 | AA Rev.11 |
| 5-1-212 | 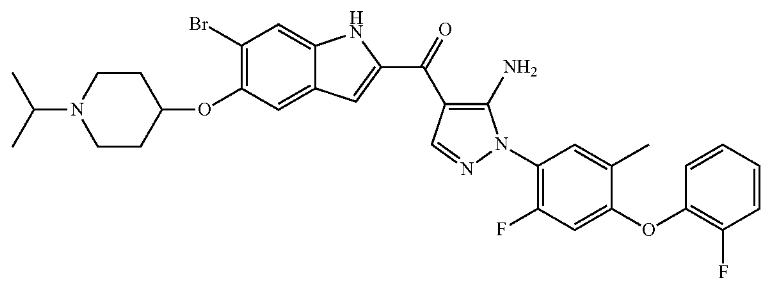 [SMILES: Cc1cc(-n2ncc(C(=O)c3cc4cc(OC5CCN(C(C)C)CC5)c(Br)cc4[nH]3)c2N)c(F)cc1Oc1ccccc1F] | [5-amino-1-[2-fluoro-4-(2-fluorophenoxy)-5-methylphenyl]pyrazol-4-yl]-[6-bromo-5-(1-propan-2-ylpiperidin-4-yl)oxy-1H-indol-2-yl]methanone | 664, 666 | 1.17 | TFA Rev.5 |
| 5-1-213 | 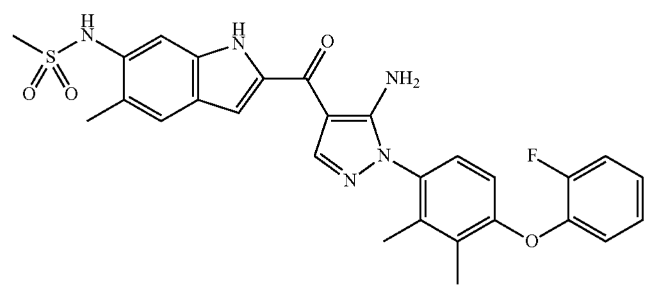 | N-[2-[5-amino-1-[4-(2-fluorophenoxy)-2,3-dimethylphenyl]pyrazole-4-carbonyl]-5-methyl-1H-indol-6-yl]methanesulfonamide | 548 | 1.29 | TFA Rev.5 |

| Example No. | Chemical Structure | Compound Name | m/z (M + H) | Reaction Time (Minute) | LCMS Measurement Condition |
|---|---|---|---|---|---|
| 5-1-214 | 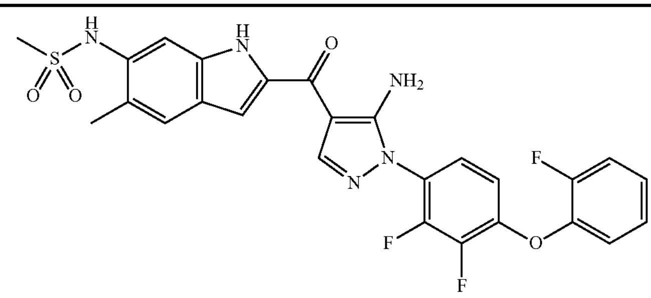 | N-[2-[5-amino-1-[2,3-difluoro-4-(2-fluorophenoxy)phenyl]pyrazole-4-carbonyl]-5-methyl-1H-indol-6-yl]methanesulfonamide | 556 | 1.25 | TFA Rev.5 |
| 5-1-215 | 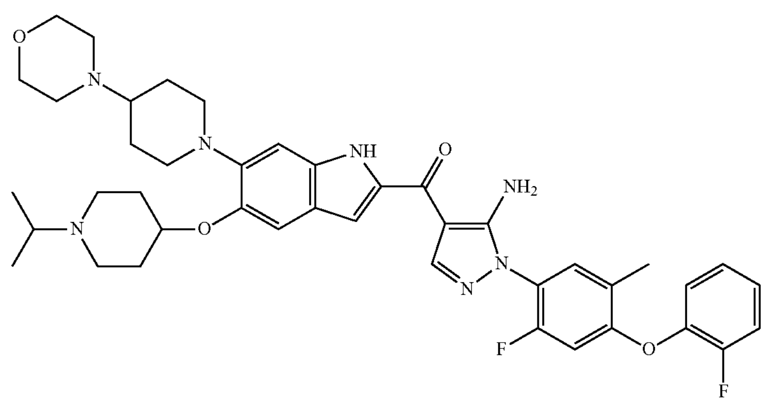 [SMILES: Cc1cc(-n2ncc(C(=O)c3cc4cc(OC5CCN(C(C)C)CC5)c(N5CCC(N6CCOCC6)CC5)cc4[nH]3)c2N)c(F)cc1Oc1ccccc1F] | [5-amino-1-[2-fluoro-4-(2-fluorophenoxy)-5-methylphenyl]pyrazol-4-yl]-[6-(4-morpholin-4-ylpiperidin-1-yl)-5-(1-propan-2-ylpiperidin-4-yl)oxy-1H-indol-2-yl]methanone | 754 | 1.03 | AA Rev.11 |

| Example No. | Chemical Structure | Compound Name | m/z (M + H) | Reaction Time (Minute) | LCMS Measurement Condition |
|---|---|---|---|---|---|
| 5-1-216 | 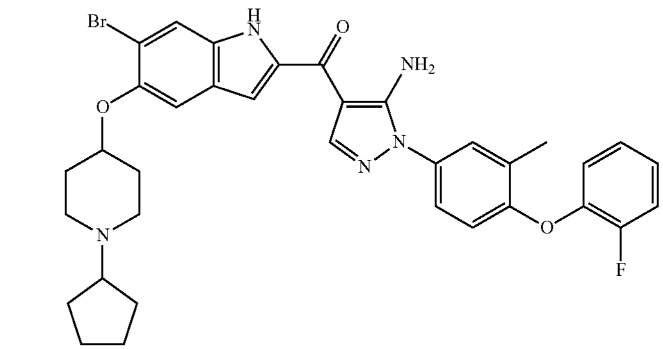 [SMILES: Cc1cc(-n2ncc(C(=O)c3cc4cc(OC5CCN(C6CCCC6)CC5)c(Br)cc4[nH]3)c2N)ccc1Oc1ccccc1F] | [5-amino-1-[4-(2-fluorophenoxy)-3-methylphenyl]pyrazol-4-yl]-[6-bromo-5-(1-cyclopentylpiperidin-4-yl)oxy-1H-indol-2-yl]methanone | 672, 674 | 1.12 | AA Rev.11 |
| 5-1-217 | 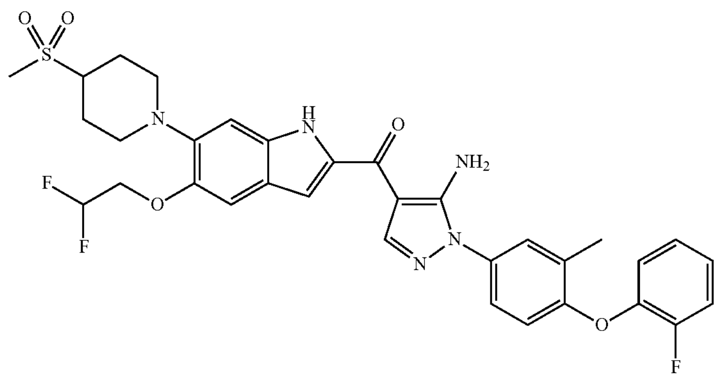 [SMILES: Cc1cc(-n2ncc(C(=O)c3cc4cc(OCC(F)F)c(N5CCC(S(C)(=O)=O)CC5)cc4[nH]3)c2N)ccc1Oc1ccccc1F] | [5-amino-1-[4-(2-fluorophenoxy)-3-methylphenyl]pyrazol-4-yl]-[5-(2,2-difluoroethoxy)-6-(1-methylsulfonylpiperidin-4-yl)-1H-indol-2-yl]methanone | 668 | 1.36 | TFA Rev.6 |

-continued

| Example No. | Chemical Structure | Compound Name | m/z (M + H) | Reaction Time (Minute) | LCMS Measurement Condition |
|---|---|---|---|---|---|
| 5-1-218 | 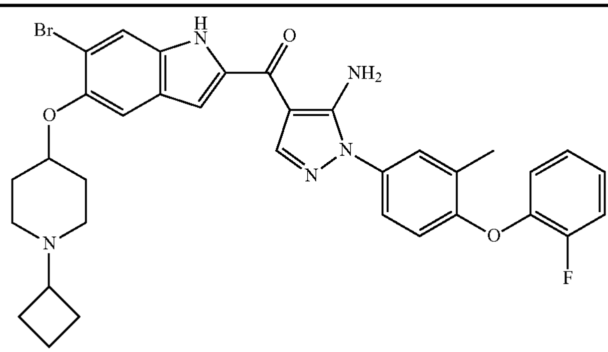 | [5-amino-1-[4-(2-fluorophenoxy)-3-methylphenyl]pyrazol-4-yl]-[6-bromo-5-(1-cyclobutylpiperidin-4-yl)oxy-1H-indol-2-yl]methanone | 658, 660 | 1.14 | AA Rev.11 |
| 5-1-219 | 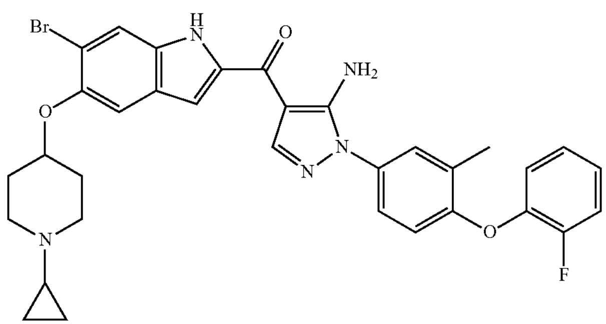 [SMILES: Cc1cc(-n2ncc(C(=O)c3cc4cc(OC5CCN(C6CC6)CC5)c(Br)cc4[nH]3)c2N)ccc1Oc1ccccc1F] | [5-amino-1-[4-(2-fluorophenoxy)-3-methylphenyl]pyrazol-4-yl]-[6-bromo-5-(1-cyclopropylpiperidin-4-yl)oxy-1H-indol-2-yl]methanone | 644, 646 | 1.06 | TFA Rev.6 |
| 5-1-220 | 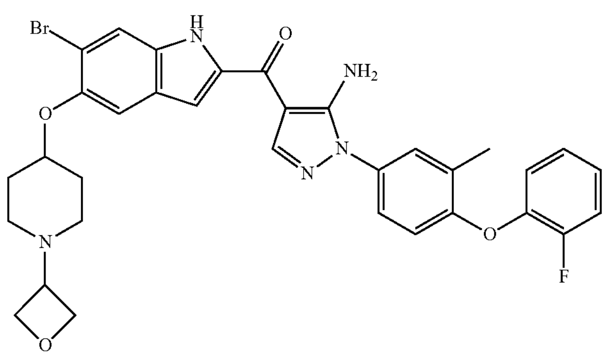 [SMILES: Cc1cc(-n2ncc(C(=O)c3cc4cc(OC5CCN(C6COC6)CC5)c(Br)cc4[nH]3)c2N)ccc1Oc1ccccc1F] | [5-amino-1-[4-(2-fluorophenoxy)-3-methylphenyl]pyrazol-4-yl]-[6-bromo-5-[1-(oxetan-3-yl)piperidin-4-yl]oxy-1H-indol-2-yl]methanone | 660, 662 | 1.11 | AA Rev.11 |

| Example No. | Chemical Structure | Compound Name | m/z (M + H) | Reaction Time (Minute) | LCMS Measurement Condition |
|---|---|---|---|---|---|
| 5-1-221 | 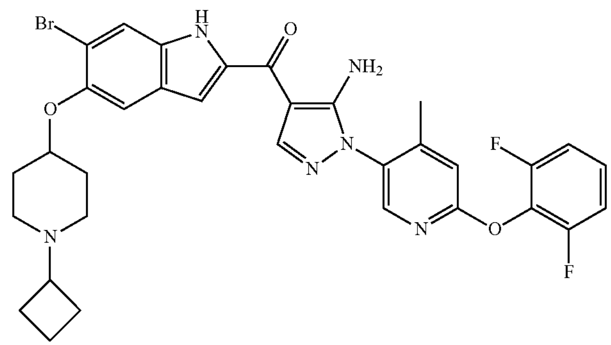 [SMILES: Cc1cc(Oc2c(F)cccc2F)ncc1-n1ncc(C(=O)c2cc3cc(OC4CCN(C5CCC5)CC4)c(Br)cc3[nH]2)c1N] | [5-amino-1-[6-(2,6-difluorophenoxy)-4-methylpyridin-3-yl]pyrazol-4-yl]-[6-bromo-5-(1-cyclobutylpiperidin-4-yl)oxy-1H-indol-2-yl]methanone | 677, 679 | 1.09 | AA Rev.11 |
| 5-1-222 | 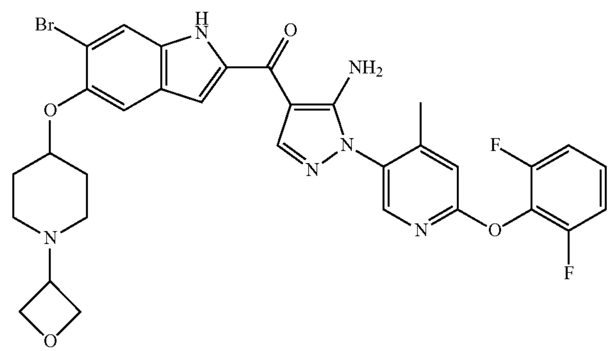 [SMILES: Cc1cc(Oc2c(F)cccc2F)ncc1-n1ncc(C(=O)c2cc3cc(OC4CCN(C5COC5)CC4)c(Br)cc3[nH]2)c1N] | [5-amino-1-[6-(2,6-difluorophenoxy)-4-methylpyridin-3-yl]pyrazol-4-yl]-[6-bromo-5-[1-(oxetan-3-yl)piperidin-4-yl]oxy-1H-indol-2-yl]methanone | 679, 681 | 1.05 | AA Rev.11 |

| Example No. | Chemical Structure | Compound Name | m/z (M + H) | Reaction Time (Minute) | LCMS Measurement Condition |
|---|---|---|---|---|---|
| 5-1-223 | 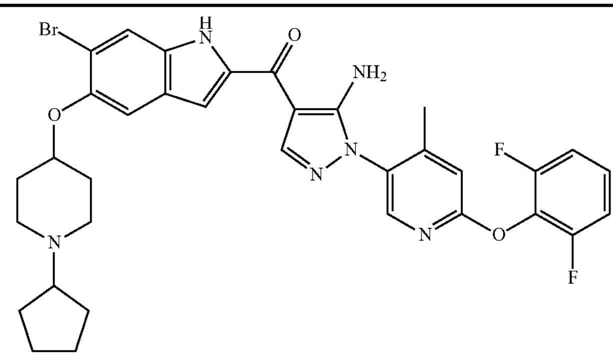 | [5-amino-1-[6-(2,6-difluorophenoxy)-4-methylpyridin-3-yl]pyrazol-4-yl]-[6-bromo-5-(1-cyclopentylpiperidin-4-yl)oxy-1H-indol-2-yl]methanone | 691, 693 | 1.07 | AA Rev.11 |
| 5-1-224 | 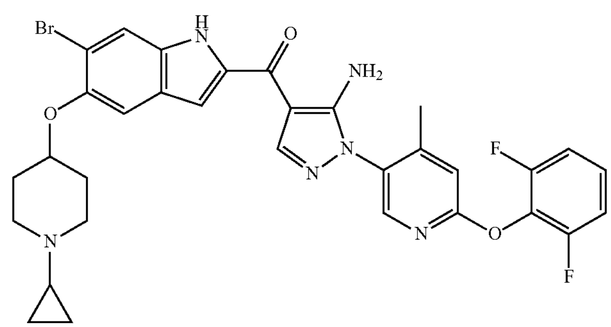 [SMILES: Cc1cc(Oc2c(F)cccc2F)ncc1-n1ncc(C(=O)c2cc3cc(OC4CCN(C5CC5)CC4)c(Br)cc3[nH]2)c1N] | [5-amino-1-[6-(2,6-difluorophenoxy)-4-methylpyridin-3-yl]pyrazol-4-yl]-[6-bromo-5-(1-cyclopropylpiperidin-4-yl)oxy-1H-indol-2-yl]methanone | 663, 665 | 1.12 | AA Rev.11 |
| 5-1-225 | 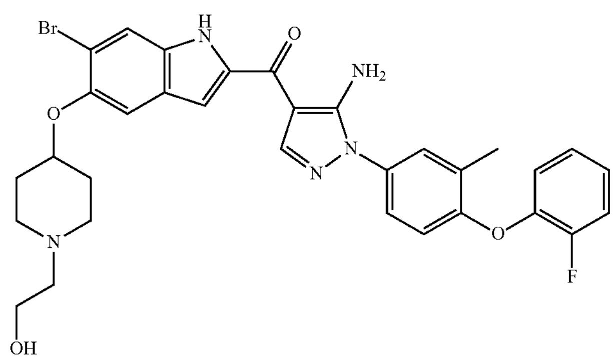 [SMILES: Cc1cc(-n2ncc(C(=O)c3cc4cc(OC5CCN(CCO)CC5)c(Br)cc4[nH]3)c2N)ccc1Oc1ccccc1F] | [5-amino-1-[4-(2-fluorophenoxy)-3-methylphenyl]pyrazol-4-yl]-[6-bromo-5-[1-(2-hydroxyethyl)piperidin-4-yl]oxy-1H-indol-2-yl]methanone | 648, 650 | 1.01 | TFA Rev.6 |

| Example No. | Chemical Structure | Compound Name | m/z (M + H) | Reaction Time (Minute) | LCMS Measurement Condition |
|---|---|---|---|---|---|
| 5-1-226 | 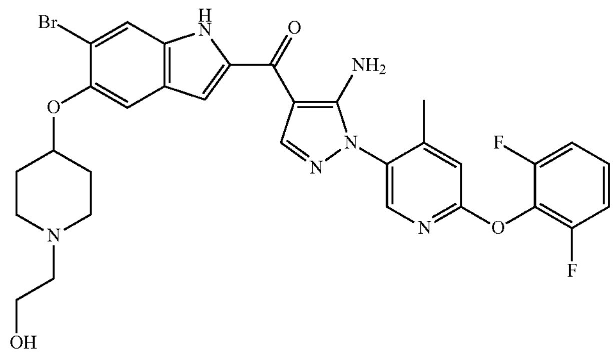 [SMILES: Cc1cc(Oc2c(F)cccc2F)ncc1-n1ncc(C(=O)c2cc3cc(OC4CCN(CCO)CC4)c(Br)cc3[nH]2)c1N] | [5-amino-1-[6-(2,6-difluorophenoxy)-4-methylpyridin-3-yl]pyrazol-4-yl]-[6-bromo-5-[1-(2-hydroxyethyl)piperidin-4-yl]oxy-1H-indol-2-yl]methanone | 667, 669 | 0.95 | TFA Rev.6 |
| 5-1-227 | 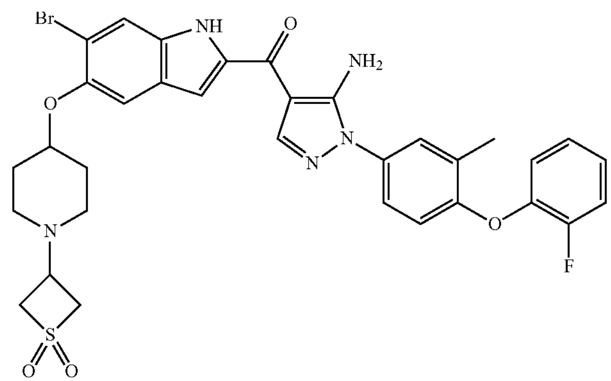 [SMILES: Cc1cc(-n2ncc(C(=O)c3cc4cc(OC5CCN(C6CS(=O)(=O)C6)CC5)c(Br)cc4[nH]3)c2N)ccc1Oc1ccccc1F] | [5-amino-1-[4-(2-fluorophenoxy)-3-methylphenyl]pyrazol-4-yl]-[6-bromo-5-[1-(1,1-dioxothietan-3-yl)piperidin-4-yl]oxy-1H-indol-2-yl]methanone | 708, 710 | 1.07 | AA Rev.11 |

| Example No. | Chemical Structure | Compound Name | m/z (M + H) | Reaction Time (Minute) | LCMS Measurement Condition |
|---|---|---|---|---|---|
| 5-1-228 | 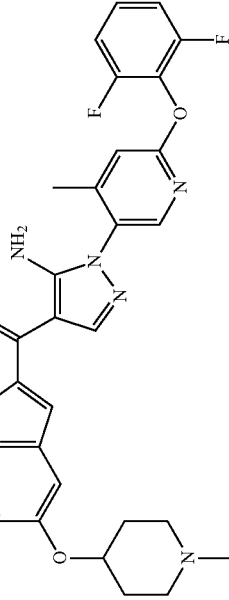 | [5-amino-1-[6-(2,6-difluorophenoxy)-4-methylpyridin-3-yl]pyrazol-4-yl]-[6-bromo-5-[1-(1,1-dioxothietan-3-yl)piperidin-4-yl]oxy-1H-indol-2-yl]methanone | 727, 729 | 1.02 | AA Rev.11 |
| 5-1-229 | 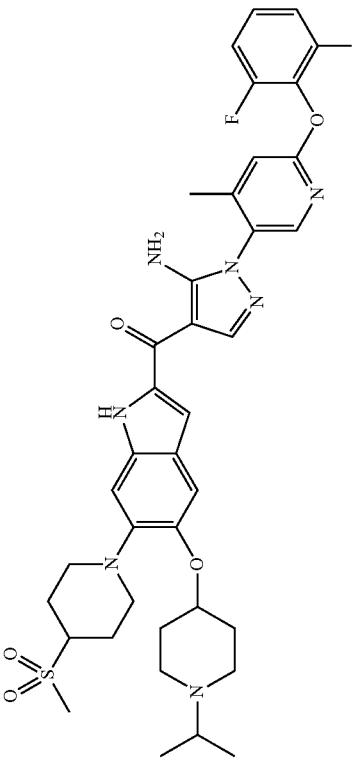 | [5-amino-1-[6-(2,6-difluorophenoxy)-4-methylpyridin-3-yl]pyrazol-4-yl]-[6-(1-methylsulfonylpiperidin-4-yl)-5-(1-propan-2-ylpiperidin-4-yl)oxy-1H-indol-2-yl]methanone | 748 | 0.97 | AA Rev.11 |

| Example No. | Chemical Structure | Compound Name | m/z (M + H) | Reaction Time (Minute) | LCMS Measurement Condition |
|---|---|---|---|---|---|
| 5-1-230 | 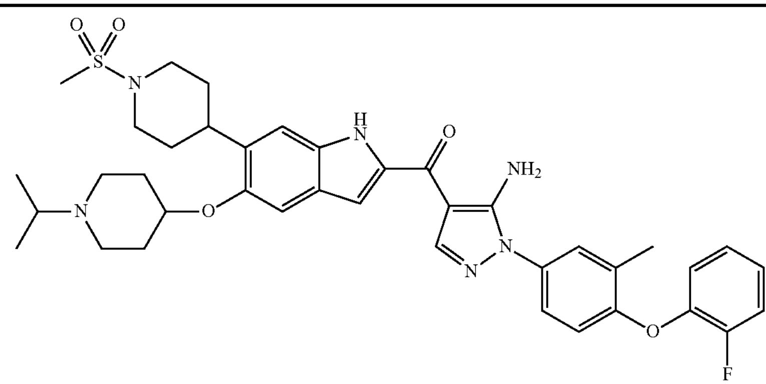 | [5-amino-1-[4-(2-fluorophenoxy)-3-methylphenyl]pyrazol-4-yl]-[6-(1-methylsulfonylpiperidin-4-yl)-5-(1-propan-2-yl)piperidin-4-yl)oxy-1H-indol-2-yl]methanone | 729 | 1.08 | TFA Rev.6 |
| 5-1-231 | 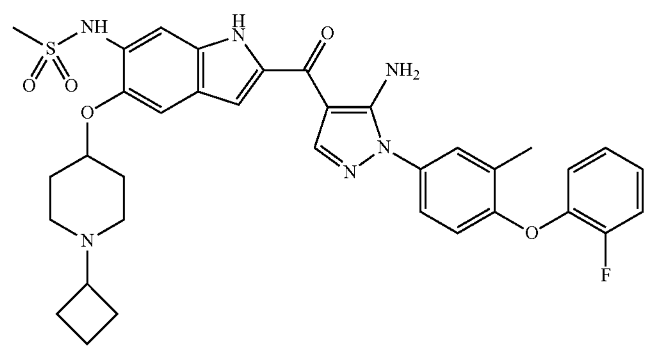 [SMILES: Cc1cc(-n2ncc(C(=O)c3cc4cc(OC5CCN(C6CCC6)CC5)c(NS(C)(=O)=O)cc4[nH]3)c2N)ccc1Oc1ccccc1F] | N-[2-[5-amino-1-[4-(2-fluorophenoxy)-3-methylphenyl]pyrazole-4-carbonyl]-5-(1-cyclobutylpiperidin-4-yl)oxy-1H-indol-6-yl]methanesulfonamide | 673 | 1.07 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-232 | 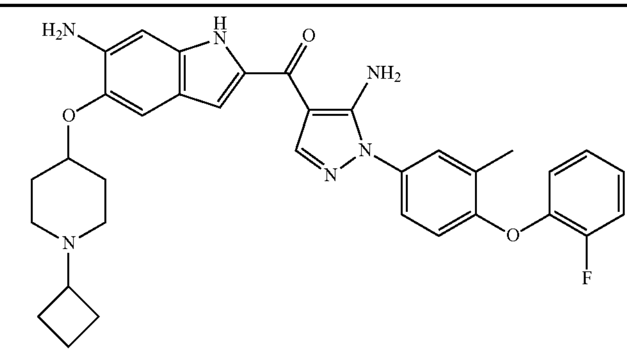 | [6-amino-5-(1-cyclobutylpiperidin-4-yl)oxy-1H-indol-2-yl]-[5-amino-1-[4-(2-fluorophenoxy)-3-methylphenyl]pyrazol-4-yl]methanone | 595 | 0.92 | TFA Rev.7 |
| 5-1-233 | 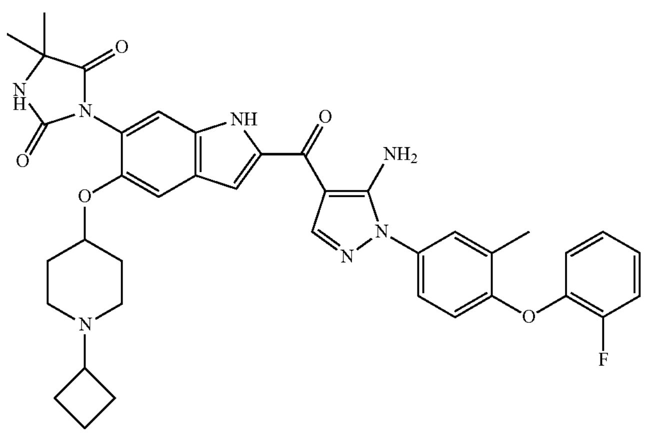 [SMILES: Cc1cc(-n2ncc(C(=O)c3cc4cc(OC5CCN(C6CCC6)CC5)c(N5C(=O)NC(C)(C)C5=O)cc4[nH]3)c2N)ccc1Oc1ccccc1F] | 3-[2-[5-amino-1-[4-(2-fluorophenoxy)-3-methylphenyl]pyrazole-4-carbonyl]-5-(1-cyclobutylpiperidin-4-yl)oxy-1H-indol-6-yl]-5,5-dimethylimidazolidine-2,4-dione | 706 | 1.04 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-234 | 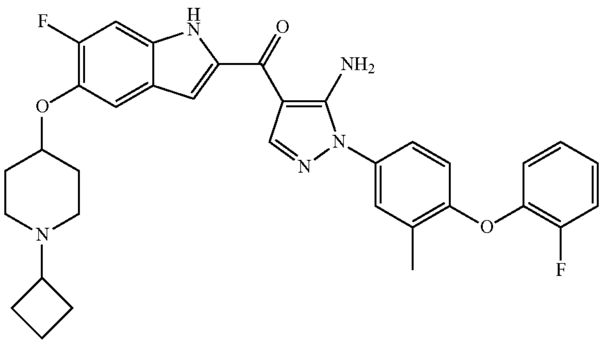 | [5-amino-1-[4-(2-fluorophenoxy)-3-methylphenyl]pyrazol-4-yl]-[5-(1-cyclobutylpiperidin-4-yl)oxy-6-fluoro-1H-indol-2-yl]methanone | 598 | 1.09 | TFA Rev.7 |
| 5-1-235 | 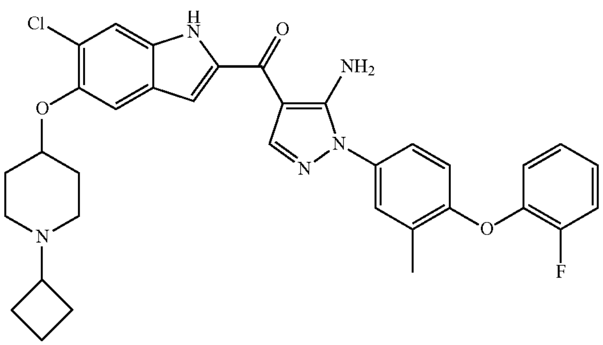 [SMILES: Cc1cc(-n2ncc(C(=O)c3cc4cc(OC5CCN(C6CCC6)CC5)c(Cl)cc4[nH]3)c2N)ccc1Oc1ccccc1F] | [5-amino-1-[4-(2-fluorophenoxy)-3-methylphenyl]pyrazol-4-yl]-[6-chloro-5-(1-cyclobutylpiperidin-4-yl)oxy-1H-indol-2-yl]methanone | 614, 616 | 1.14 | AA Rev.11 |
| 5-1-236 | 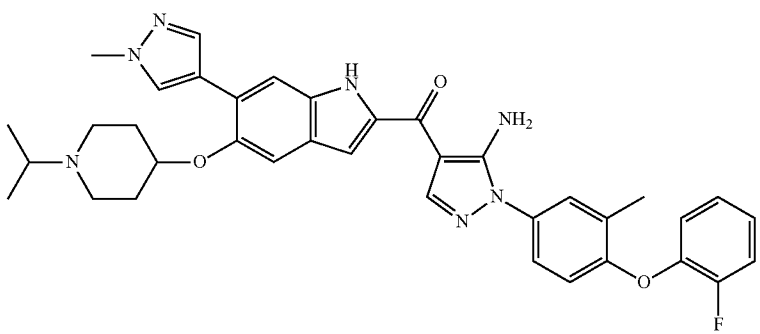 [SMILES: Cc1cc(-n2ncc(C(=O)c3cc4cc(OC5CCN(C(C)C)CC5)c(-c5cnn(C)c5)cc4[nH]3)c2N)ccc1Oc1ccccc1F] | [5-amino-1-[4-(2-fluorophenoxy)-3-methylphenyl]pyrazol-4-yl]-[6-(1-methylpyrazol-4-yl)-5-(1-propan-2-ylpiperidin-4-yl)oxy-1H-indol-2-yl]methanone | 648 | 1.08 | TFA Rev.7 |

| Example No. | Chemical Structure | Compound Name | m/z (M + H) | Reaction Time (Minute) | LCMS Measurement Condition |
|---|---|---|---|---|---|
| 5-1-237 | 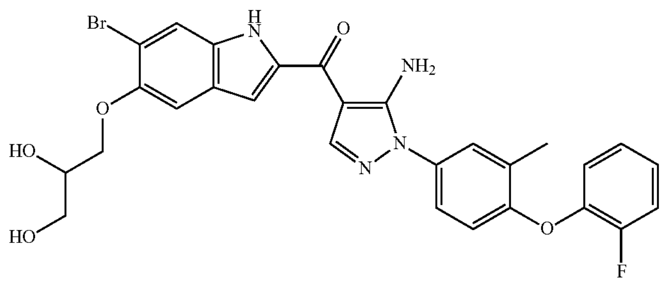 [SMILES: Cc1cc(-n2ncc(C(=O)c3cc4cc(OCC(O)CO)c(Br)cc4[nH]3)c2N)ccc1Oc1ccccc1F] | [5-amino-1-[4-(2-fluorophenoxy)-3-methylphenyl]pyrazol-4-yl]-[6-bromo-5-[(2R)-2,3-dihydroxypropoxy]-1H-indol-2-yl]methanone | 595, 597 | 1.01 | AA Rev.11 |
| 5-1-238 | 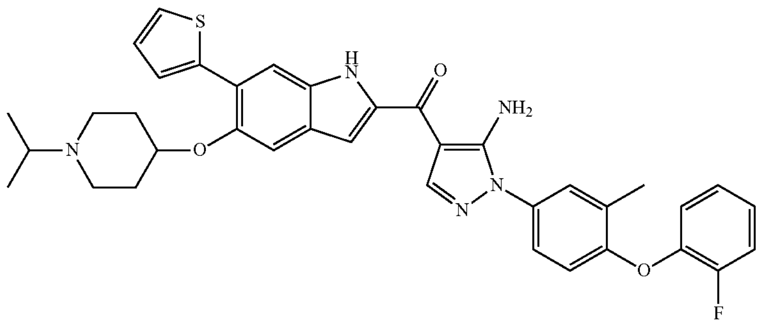 [SMILES: Cc1cc(-n2ncc(C(=O)c3cc4cc(OC5CCN(C(C)C)CC5)c(-c5cccs5)cc4[nH]3)c2N)ccc1Oc1ccccc1F] | [5-amino-1-[4-(2-fluorophenoxy)-3-methylphenyl]pyrazol-4-yl]-[5-(1-propan-2-yl)piperidin-4-yl)oxy-6-thiophen-2-yl-1H-indol-2-yl]]methanone | 650 | 1.19 | TFA Rev.7 |
| 5-1-239 | 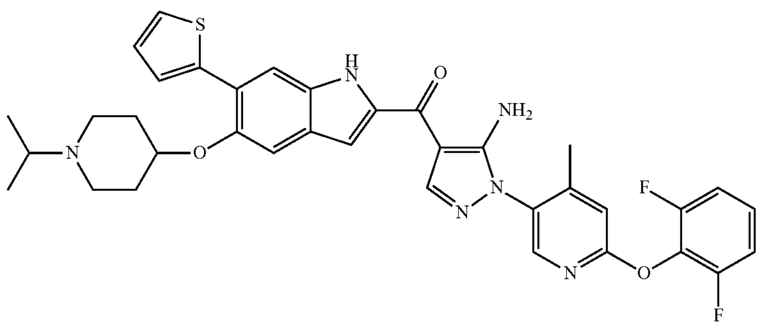 [SMILES: Cc1cc(Oc2c(F)cccc2F)ncc1-n1ncc(C(=O)c2cc3cc(OC4CCN(C(C)C)CC4)c(-c4cccs4)cc3[nH]2)c1N] | [5-amino-1-[6-(2,6-difluorophenoxy)-4-methylpyridin-3-yl]pyrazol-4-yl]-[5-(1-propan-2-yl)piperidin-4-yl)oxy-6-thiophen-2-yl-1H-indol-2-yl]]methanone | 669 | 1.12 | TFA Rev.7 |

| Example No. | Chemical Structure | Compound Name | m/z (M + H) | Reaction Time (Minute) | LCMS Measurement Condition |
|---|---|---|---|---|---|
| 5-1-240 | 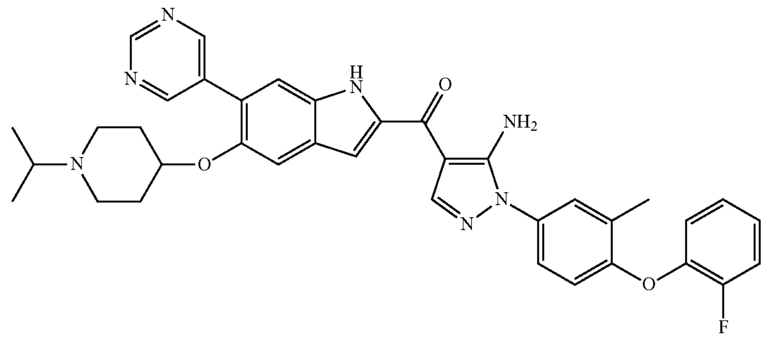 [SMILES: Cc1cc(-n2ncc(C(=O)c3cc4cc(OC5CCN(C(C)C)CC5)c(-c5cncnc5)cc4[nH]3)c2N)ccc1Oc1ccccc1F] | [5-amino-1-[4-(2-fluorophenoxy)-3-methylphenyl]pyrazol-4-yl]-[5-(1-propan-2-ylpiperidin-4-yl)oxy-6-pyrimidin-5-yl-1H-indol-2-yl]methanone | 646 | 1.06 | TFA Rev.7 |
| 5-1-241 | 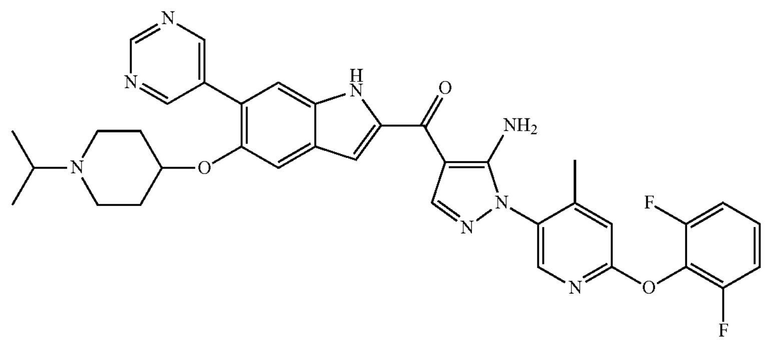 [SMILES: Cc1cc(Oc2c(F)cccc2F)ncc1-n1ncc(C(=O)c2cc3cc(OC4CCN(C(C)C)CC4)c(-c4cncnc4)cc3[nH]2)c1N] | [5-amino-1-[6-(2,6-difluorophenoxy)-4-methylpyridin-3-yl]pyrazol-4-yl]-[5-(1-propan-2-ylpiperidin-4-yl)oxy-6-pyrimidin-5-yl-1H-indol-2-yl]methanone | 665 | 0.95 | AA Rev.11 |
| 5-1-242 | 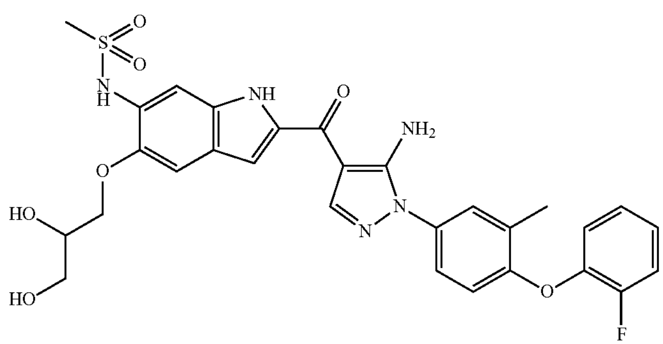 [SMILES: Cc1cc(-n2ncc(C(=O)c3cc4cc(OCC(O)CO)c(NS(C)(=O)=O)cc4[nH]3)c2N)ccc1Oc1ccccc1F] | N-[2-[5-amino-1-[4-(2-fluorophenoxy)-3-methylphenyl]pyrazole-4-carbonyl]-5-[(2R)-2,3-dihydroxypropoxy]-1H-indol-6-yl]methanesulfonamide | 610 | 0.95 | AA Rev.11 |

| Example No. | Chemical Structure | Compound Name | m/z (M + H) | Reaction Time (Minute) | LCMS Measurement Condition |
|---|---|---|---|---|---|
| 5-1-243 | 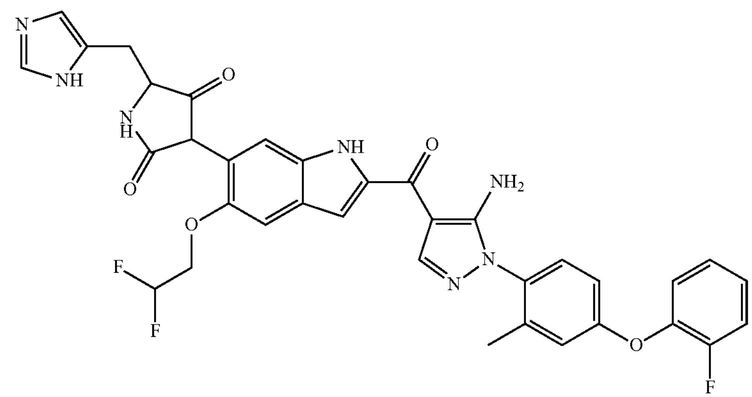 [SMILES: Cc1cc(Oc2ccccc2F)ccc1-n1ncc(C(=O)c2cc3cc(OCC(F)F)c(C4C(=O)NC(Cc5cnc[nH]5)C4=O)cc3[nH]2)c1N] | (5S)-3-[2-[5-amino-1-[4-(2-fluorophenoxy)-2-methylphenyl]pyrazole-4-carbonyl]-5-(2,2-difluoroethoxy)-1H-indol-6-yl]-5-(1H-imidazol-5-ylmethyl)imidazolidine-2,4-dione | 685 | 0.95 | AA Rev.11 |
| 5-1-244 | 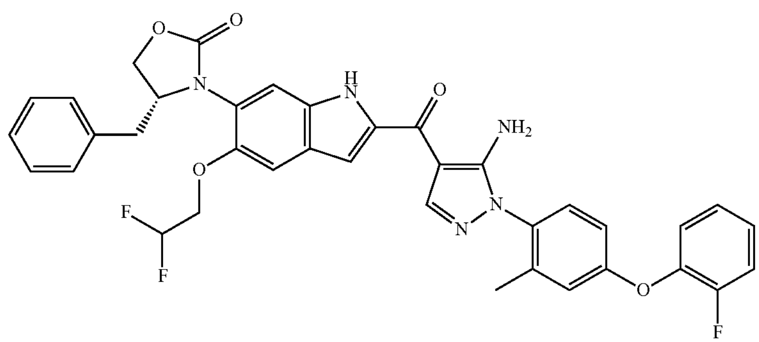 [SMILES: Cc1cc(Oc2ccccc2F)ccc1-n1ncc(C(=O)c2cc3cc(OCC(F)F)c(N4C(=O)OC[C@H]4Cc4ccccc4)cc3[nH]2)c1N] | (4R)-3-[2-[5-amino-1-[4-(2-fluorophenoxy)-2-methylphenyl]pyrazole-4-carbonyl]-1H-indol-6-yl]-5-(2,2-difluoroethoxy)-1H-indol-6-yl]-4-benzyl-1,3-oxazolidin-2-one | 682 | 1.42 | TFA Rev.7 |

| Example No. | Chemical Structure | Compound Name | m/z (M + H) | Reaction Time (Minute) | LCMS Measurement Condition |
|---|---|---|---|---|---|
| 5-1-245 | 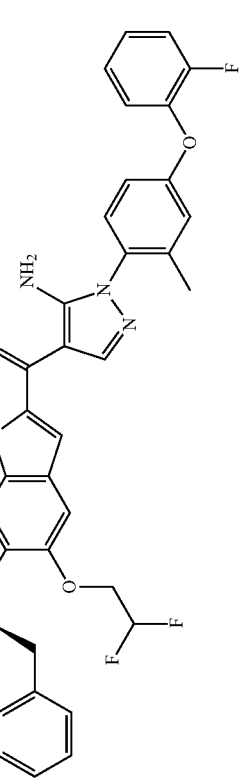 | (4S)-3-[2-[5-amino-1-[4-(2-fluorophenoxy)-2-methylphenyl]pyrazole-4-carbonyl]-5-(2,2-difluoroethoxy)-1H-indol-6-yl]-4-benzyl-1,3-oxazolidin-2-one | 682 | 1.42 | TFA Rev.7 |
| 5-1-246 | 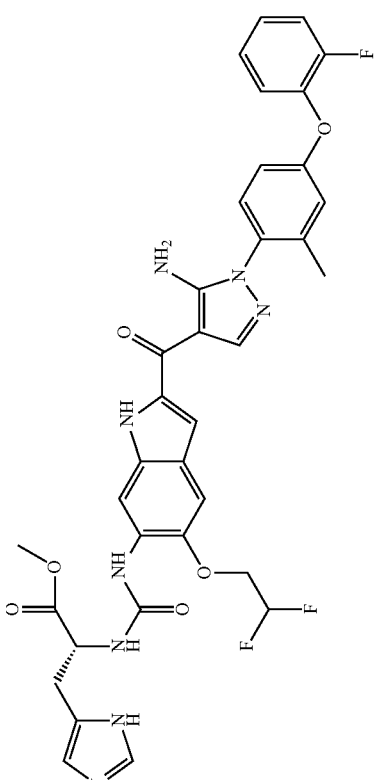 | Methyl (2S)-2-[[2-[5-amino-1-[4-(2-fluorophenoxy)-2-methylphenyl]pyrazole-4-carbonyl]-5-(2,2-difluoroethoxy)-1H-indol-6-yl]carbamoyl]amino]-3-(1H-imidazol-5-yl)propanoate | 717 | 1.00 | AA Rev.11 |

| Example No. | Chemical Structure | Compound Name | m/z (M + H) | Reaction Time (Minute) | LCMS Measurement Condition |
|---|---|---|---|---|---|
| 5-1-247 | 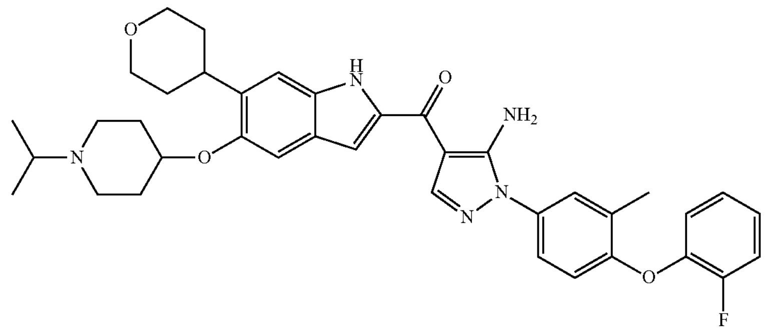 [SMILES: Cc1cc(-n2ncc(C(=O)c3cc4cc(OC5CCN(C(C)C)CC5)c(C5CCOCC5)cc4[nH]3)c2N)ccc1Oc1ccccc1F] | [5-amino-1-[4-(2-fluorophenoxy)-3-methylphenyl]pyrazol-4-yl]-[6-(oxan-4-yl)-5-(1-propan-2-ylpiperidin-4-yl)oxy-1H-indol-2-yl]methanone | 652 | 1.06 | AA Rev.11 |
| 5-1-248 | 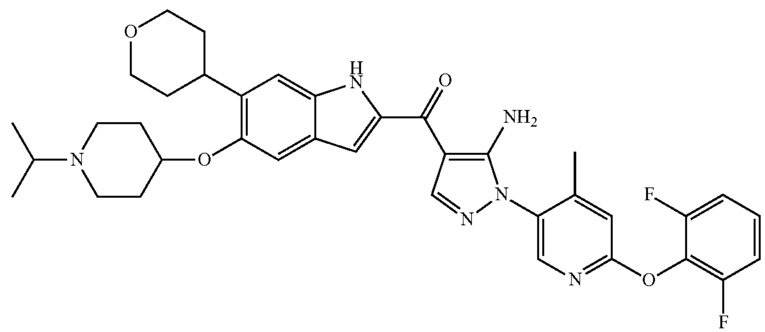 [SMILES: Cc1cc(Oc2c(F)cccc2F)ncc1-n1ncc(C(=O)c2cc3cc(OC4CCN(C(C)C)CC4)c(C4CCOCC4)cc3[nH]2)c1N] | [5-amino-1-[6-(2,6-difluorophenoxy)-4-methylpyridin-3-yl]pyrazol-4-yl]-[6-(oxan-4-yl)-5-(1-propan-2-ylpiperidin-4-yl)oxy-1H-indol-2-yl]methanone | 671 | 0.99 | AA Rev.11 |
| 5-1-249 | 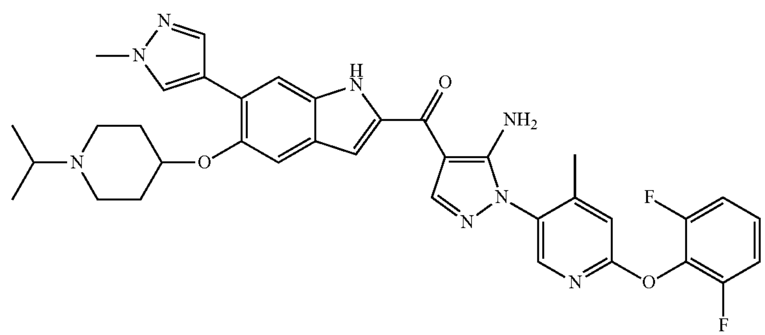 [SMILES: Cc1cc(Oc2c(F)cccc2F)ncc1-n1ncc(C(=O)c2cc3cc(OC4CCN(C(C)C)CC4)c(-c4cnn(C)c4)cc3[nH]2)c1N] | [5-amino-1-[6-(2,6-difluorophenoxy)-4-methylpyridin-3-yl]pyrazol-4-yl]-[6-(1-methylpyrazol-4-yl)-5-(1-propan-2-ylpiperidin-4-yl)oxy-1H-indol-2-yl]methanone | 667 | 0.94 | AA Rev.11 |

| Example No. | Chemical Structure | Compound Name | m/z (M + H) | Reaction Time (Minute) | LCMS Measurement Condition |
|---|---|---|---|---|---|
| 5-1-250 | 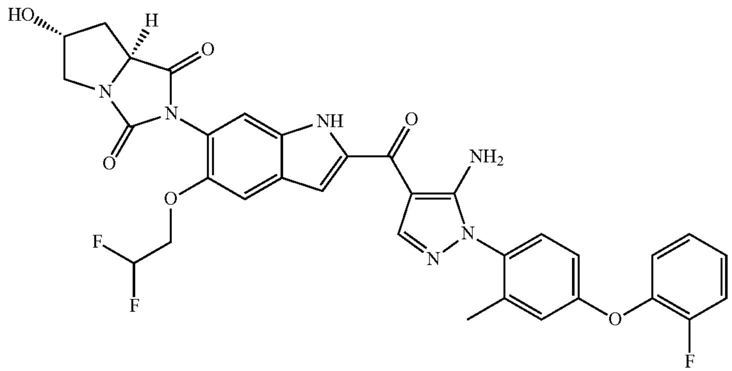 [SMILES: Cc1cc(Oc2ccccc2F)ccc1-n1ncc(C(=O)c2cc3cc(OCC(F)F)c(N4C(=O)[C@@H]5C[C@@H](O)CN5C4=O)cc3[nH]2)c1N] | [(6R,7aS)-2-[2-[5-amino-1-[4-(2-fluorophenoxy)-2-methylphenyl]pyrazole-4-carbonyl]-5-(2,2-difluoroethoxy)-1H-indol-6-yl]-6-hydroxy-5,6,7,7a-tetrahydropyrrolo[1,2-c]imidazole-1,3-dione | 661 | 0.95 | AA Rev.11 |
| 5-1-251 | 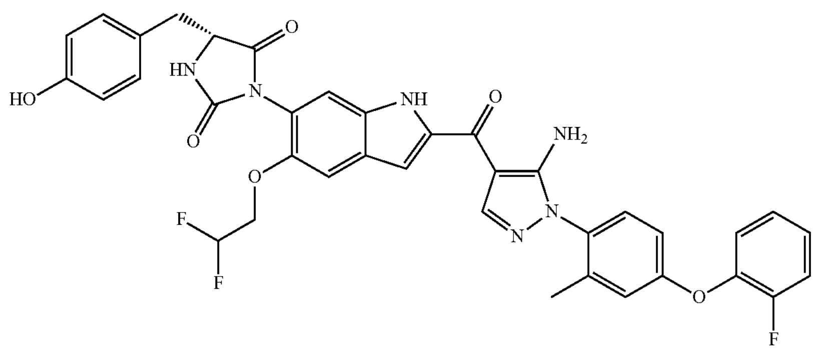 [SMILES: Cc1cc(Oc2ccccc2F)ccc1-n1ncc(C(=O)c2cc3cc(OCC(F)F)c(N4C(=O)N[C@H](Cc5ccc(O)cc5)C4=O)cc3[nH]2)c1N] | (5S)-3-[2-[5-amino-1-[4-(2-fluorophenoxy)-2-methylphenyl]pyrazole-4-carbonyl]-5-(2,2-difluoroethoxy)-1H-indol-6-yl]-5-[(4-hydroxyphenyl)methyl]imidazolidine-2,4-dione | 711 | 0.98 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-252 | 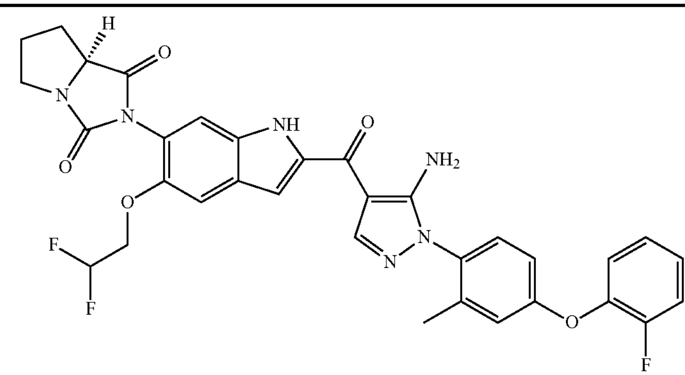 | (7aS)-2-[2-[5-amino-1-[4-(2-fluorophenoxy)-2-methylphenyl]pyrazole-4-carbonyl]-5-(2,2-difluoroethoxy)-1H-indol-6-yl]-5,6,7,7a-tetrahydropyrrolo[1,2-c]imidazole-1,3-dione | 645 | 0.99 | AA Rev.11 |
| 5-1-253 | 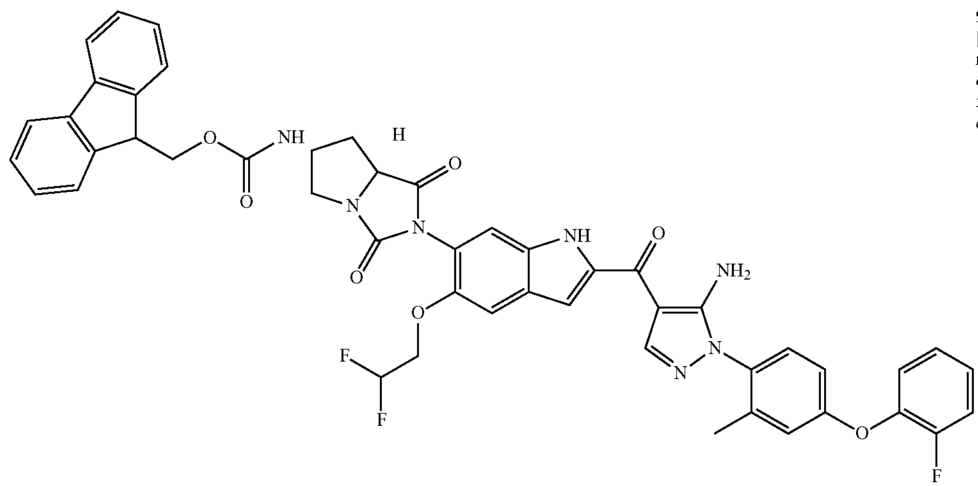 | 9H-fluoren-9-ylmethyl N-[(6S,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]carbamate | 882 | 1.41 | TFA Rev.7 |

| Example No. | Chemical Structure | Compound Name | m/z (M + H) | Reaction Time (Minute) | LCMS Measurement Condition |
|---|---|---|---|---|---|
| 5-1-254 | 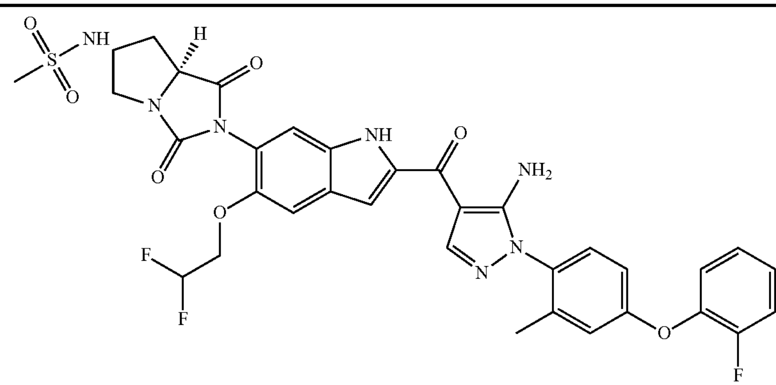 | [N-[(6S,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-5-yl]methanesulfonamide | 738 | 1.14 | TFA Rev.7 |
| 5-1-255 | 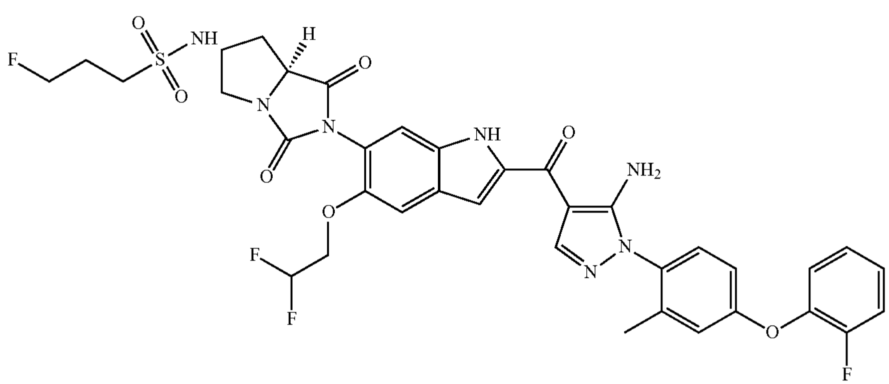 | N-[(6S,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]-3-fluoropropane-1-sulfonamide | 784 | 0.97 | AA Rev.11 |

| Example No. | Chemical Structure | Compound Name | m/z (M + H) | Reaction Time (Minute) | LCMS Measurement Condition |
|---|---|---|---|---|---|
| 5-1-256 | 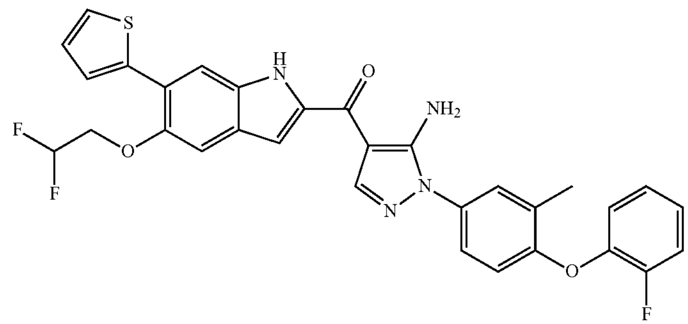 [SMILES: Cc1cc(-n2ncc(C(=O)c3cc4cc(OCC(F)F)c(-c5cccs5)cc4[nH]3)c2N)ccc1Oc1ccccc1F] | [5-amino-1-[4-(2-fluorophenoxy)-3-methylphenyl]pyrazol-4-yl]-[5-(2,2-difluoroethoxy)-6-thiophen-2-yl-1H-indol-2-yl]methanone | 589 | 1.47 | TFA Rev.7 |
| 5-1-257 | 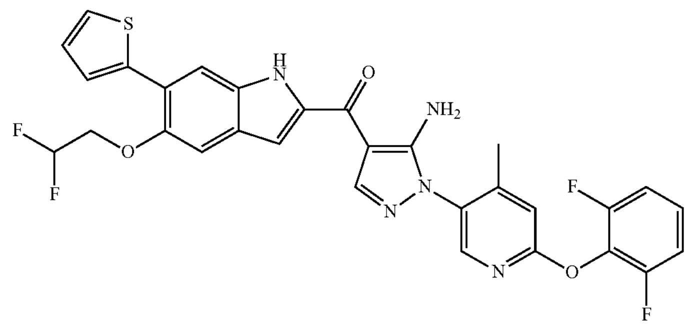 [SMILES: Cc1cc(Oc2c(F)cccc2F)ncc1-n1ncc(C(=O)c2cc3cc(OCC(F)F)c(-c4cccs4)cc3[nH]2)c1N] | [5-amino-1-[6-(2,6-difluorophenoxy)-4-methylpyridin-3-yl]pyrazol-4-yl]-[5-(2,2-difluoroethoxy)-6-thiophen-2-yl-1H-indol-2-yl]methanone | 608 | 1.39 | TFA Rev.7 |
| 5-1-258 | 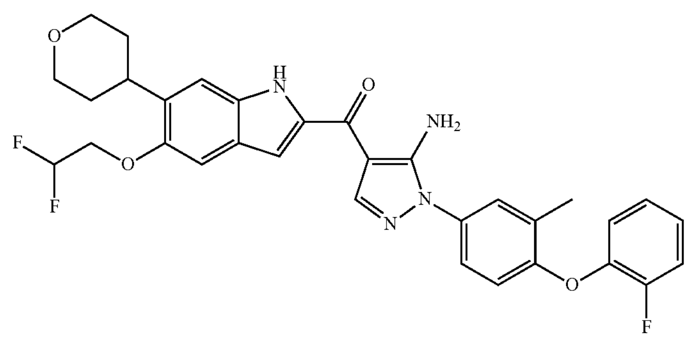 [SMILES: Cc1cc(-n2ncc(C(=O)c3cc4cc(OCC(F)F)c(C5CCOCC5)cc4[nH]3)c2N)ccc1Oc1ccccc1F] | [5-amino-1-[4-(2-fluorophenoxy)-3-methylphenyl]pyrazol-4-yl]-[5-(2,2-difluoroethoxy)-6-(oxan-4-yl)-1H-indol-2-yl]methanone | 591 | 1.39 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-259 | 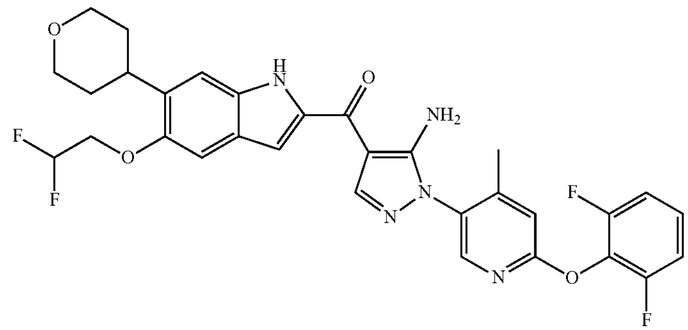 [SMILES: Cc1cc(Oc2c(F)cccc2F)ncc1-n1ncc(C(=O)c2cc3cc(OCC(F)F)c(C4CCOCC4)cc3[nH]2)c1N] | [5-amino-1-[6-(2,6-difluorophenoxy)-4-methylpyridin-3-yl]pyrazol-4-yl]-[5-(2,2-difluoroethoxy)-6-(oxan-4-yl)-1H-indol-2-yl]methanone | 610 | 1.31 | TFA Rev.7 |
| 5-1-260 | 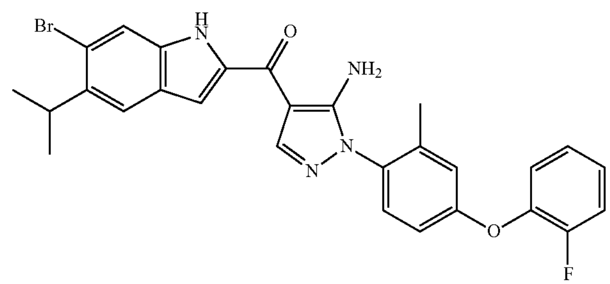 [SMILES: Cc1cc(Oc2ccccc2F)ccc1-n1ncc(C(=O)c2cc3cc(C(C)C)c(Br)cc3[nH]2)c1N] | [5-amino-1-[4-(2-fluorophenyl)pyrazol-4-yl]-(6-bromo-5-propan-2-yl-1H-indol-2-yl)methanone | 547, 549 | 1.19 | AA Rev.11 |
| 5-1-261 | 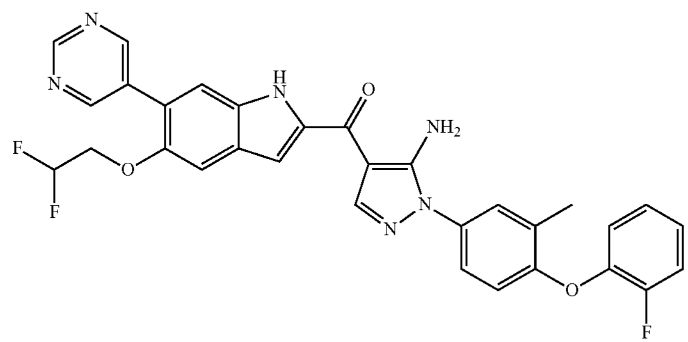 [SMILES: Cc1cc(-n2ncc(C(=O)c3cc4cc(OCC(F)F)c(-c5cncnc5)cc4[nH]3)c2N)ccc1Oc1ccccc1F] | [5-amino-1-[4-(2-fluorophenoxy)-3-methylphenyl]pyrazol-4-yl]-[5-(2,2-difluoroethoxy)-6-pyrimidin-5-yl-1H-indol-2-yl]methanone | 585 | 1.07 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-262 | 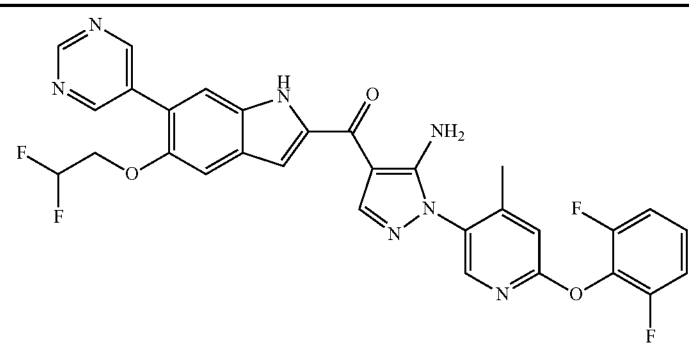 | [5-amino-1-[6-(2,6-difluorophenoxy)-4-methylpyridin-3-yl]pyrazol-4-yl]-[5-(2,2-difluoroethoxy)-6-pyrimidin-5-yl-1H-indol-2-yl]methanone | 604 | 1.01 | AA Rev.11 |
| 5-1-263 | 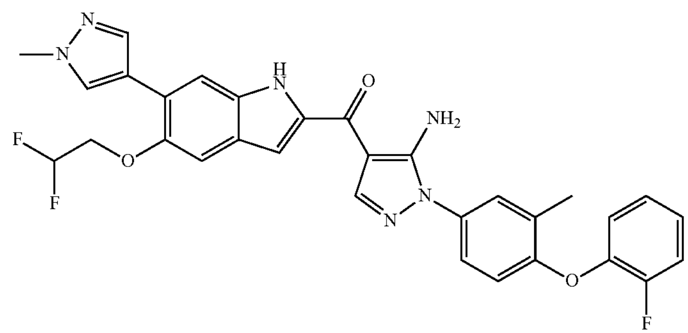 [SMILES: Cc1cc(-n2ncc(C(=O)c3cc4cc(OCC(F)F)c(-c5cnn(C)c5)cc4[nH]3)c2N)ccc1Oc1ccccc1F] | [5-amino-1-[4-(2-fluorophenoxy)-3-methylphenyl]pyrazol-4-yl]-[5-(2,2-difluoroethoxy)-6-(1-methylpyrazol-4-yl)-1H-indol-2-yl]methanone | 587 | 1.29 | TFA Rev.7 |
| 5-1-264 | 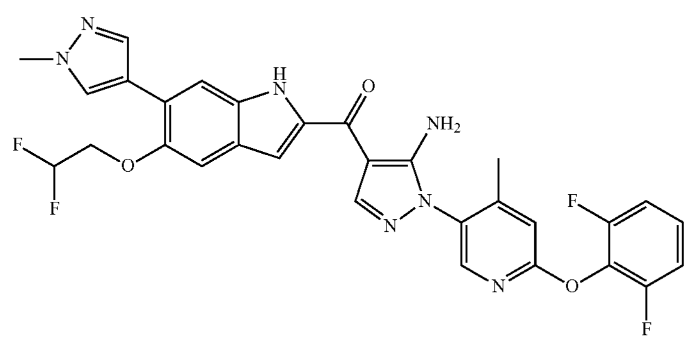 [SMILES: Cc1cc(Oc2c(F)cccc2F)ncc1-n1ncc(C(=O)c2cc3cc(OCC(F)F)c(-c4cnn(C)c4)cc3[nH]2)c1N] | [5-amino-1-[6-(2,6-difluorophenoxy)-4-methylpyridin-3-yl]pyrazol-4-yl]-[5-(2,2-difluoroethoxy)-6-(1-methylpyrazol-4-yl)-1H-indol-2-yl]methanone | 606 | 1.02 | AA Rev.11 |

| Example No. | Compound Name | Chemical Structure | m/z (M + H) | Reaction Time (Minute) | LCMS Measurement Condition |
|---|---|---|---|---|---|
| 5-1-265 | 9H-fluoren-9-ylmethyl N-[(6S,7aS)-2-[2-[5-amino-1-[4-(2-fluorophenoxy)-2-methylphenyl]pyrazole-4-carbonyl]-5-fluoro-1H-indol-6-yl]-1,3-dioxo-5,6,7,7a-tetrahydropyrrolo[1,2-c]imidazol-6-yl]carbamate | 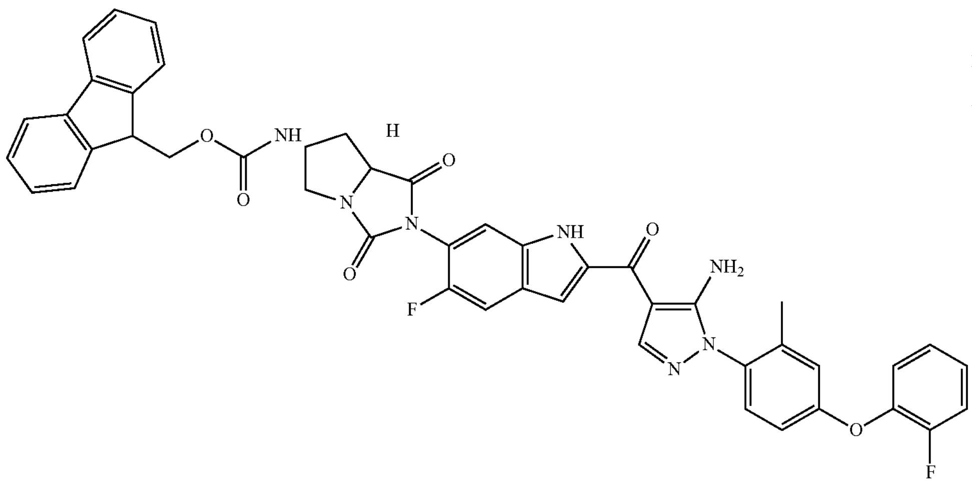 | 820 | 1.11 | AA Rev.11 |
| 5-1-266 | [5-amino-1-[4-(2-fluorophenoxy)-2-methylphenyl]pyrazol-4-yl]-(6-amino-5-propan-2-yl-1H-indol-2-yl)methanone | 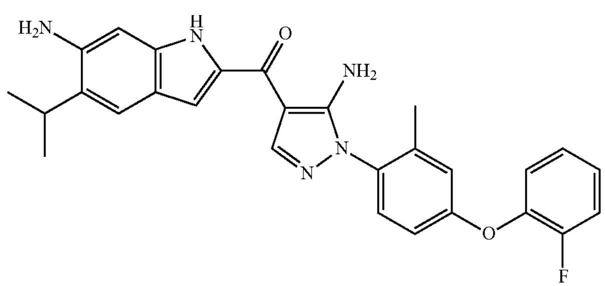 [SMILES: Cc1cc(Oc2ccccc2F)ccc1-n1ncc(C(=O)c2cc3cc(C(C)C)c(N)cc3[nH]2)c1N] | 484 | 1.05 | AA Rev.11 |

| Example No. | Chemical Structure | Compound Name | m/z (M + H) | Reaction Time (Minute) | LCMS Measurement Condition |
|---|---|---|---|---|---|
| 5-1-267 | 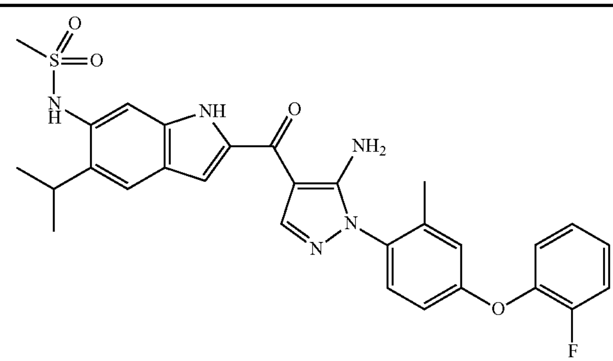 | N-[2-[5-amino-1-[4-(2-fluorophenoxy)-2-methylphenyl]pyrazole-4-carbonyl]-5-propan-2-yl-1H-indol-6-yl]methanesulfonamide | 562 | 1.03 | AA Rev.11 |
| 5-1-268 | 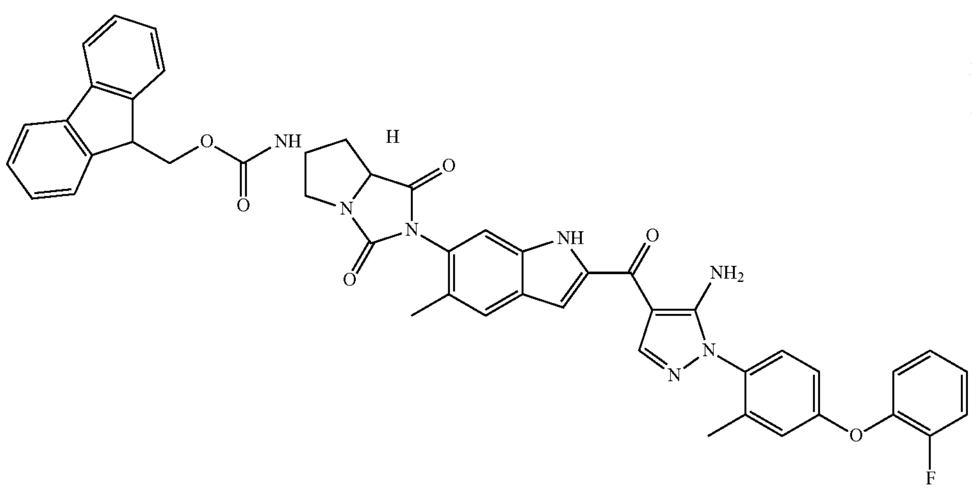 | 9H-fluoren-9-ylmethyl N-[(6S,7aS)-2-[2-[5-amino-1-[4-(2-fluorophenoxy)-2-methylphenyl]pyrazole-4-carbonyl]-5-methyl-1H-indol-6-yl]-1,3-dioxo-5,6,7,7a-tetrahydropyrrolo[1,2-c]imidazol-6-yl]carbamate | 816 | 1.12 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-269 | 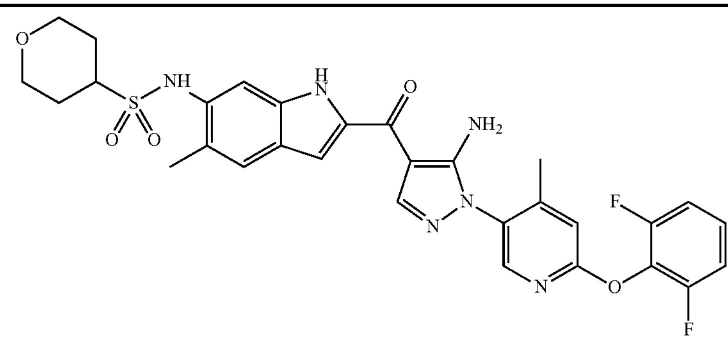 | N-[2-[5-amino-1-[6-(2,6-difluorophenoxy)-4-methylpyridin-3-yl]pyrazole-4-carbonyl]-5-methyl-1H-indol-6-yl]oxane-4-sulfonamide | 623 | 1.00 | AA Rev.11 |
| 5-1-270 | 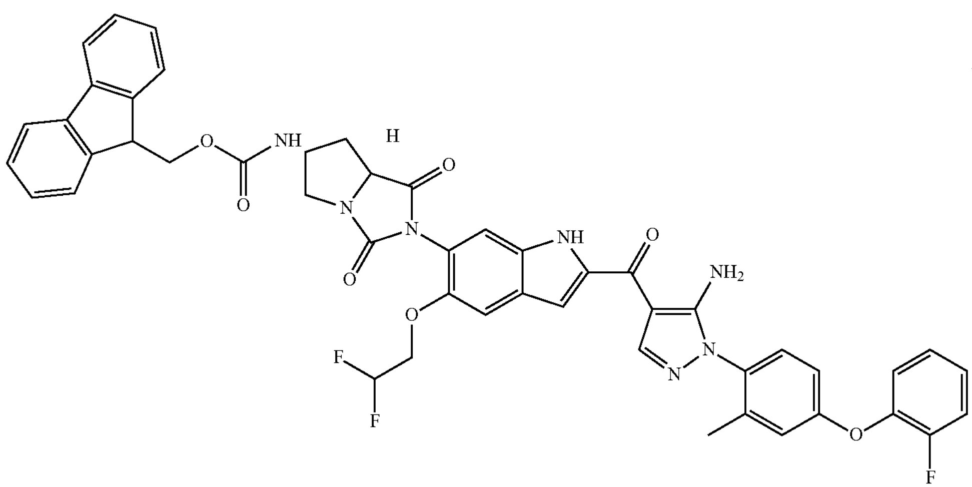 | 9H-fluoren-9-ylmethyl N-[(6R,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]carbamate | 882 | 1.41 | TFA Rev.7 |

| Example No. | Chemical Structure | Compound Name | m/z (M + H) | Reaction Time (Minute) | LCMS Measurement Condition |
|---|---|---|---|---|---|
| 5-1-271 | 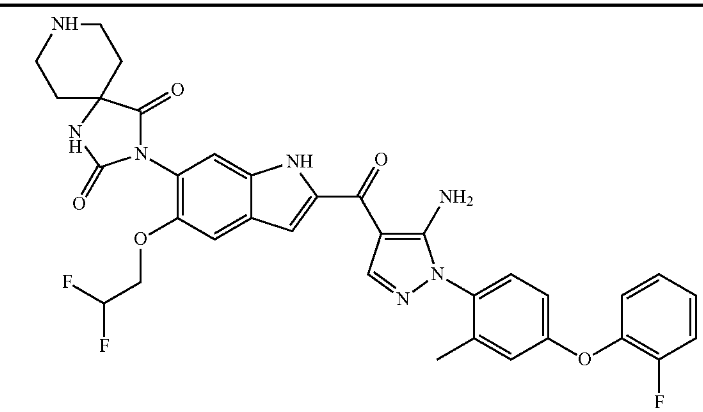 | 3-[2-[5-amino-1-[4-(2-fluorophenoxy)-2-methylphenyl]pyrazole-4-carbonyl]-5-(2,2-difluoroethoxy)-1H-indol-6-yl]-1,3,8-triazaspiro[4.5]decane-2,4-dione | 674 | 0.93 | AA Rev.11 |
| 5-1-272 | 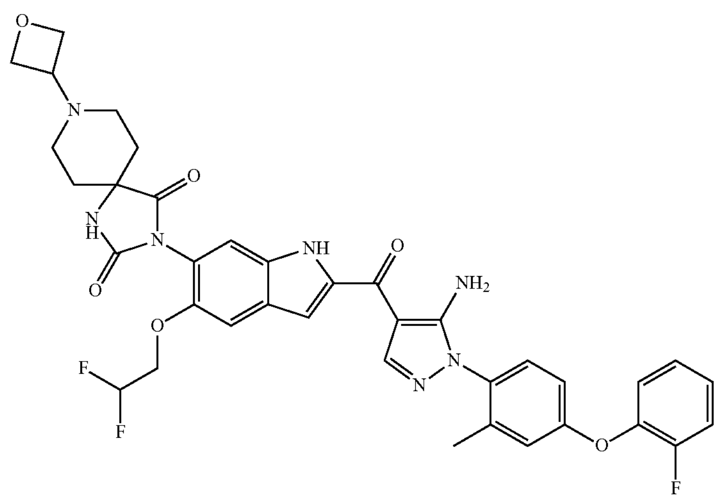 [SMILES: Cc1cc(Oc2ccccc2F)ccc1-n1ncc(C(=O)c2cc3cc(OCC(F)F)c(N4C(=O)NC5(CCN(C6COC6)CC5)C4=O)cc3[nH]2)c1N] | 3-[2-[5-amino-1-[4-(2-fluorophenoxy)-2-methylphenyl]pyrazole-4-carbonyl]-5-(2,2-difluoroethoxy)-1H-indol-6-yl]-8-(oxetan-3-yl)-1,3,8-triazaspiro[4.5]decane-2,4-dione | 730 | 0.98 | AA Rev.11 |

| Example No. | Chemical Structure | Compound Name | m/z (M + H) | Reaction Time (Minute) | LCMS Measurement Condition |
|---|---|---|---|---|---|
| 5-1-273 | 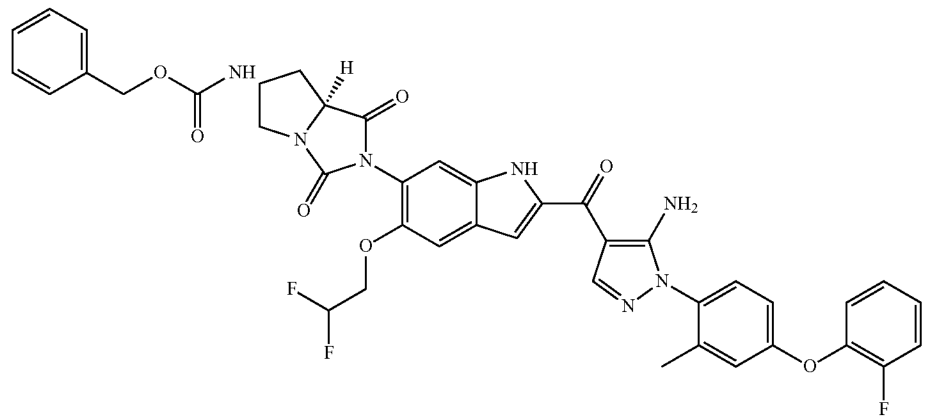 | Benzyl N-[(6S,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]carbamate | 794 | 1.29 | TFA Rev.7 |
| 5-1-274 | 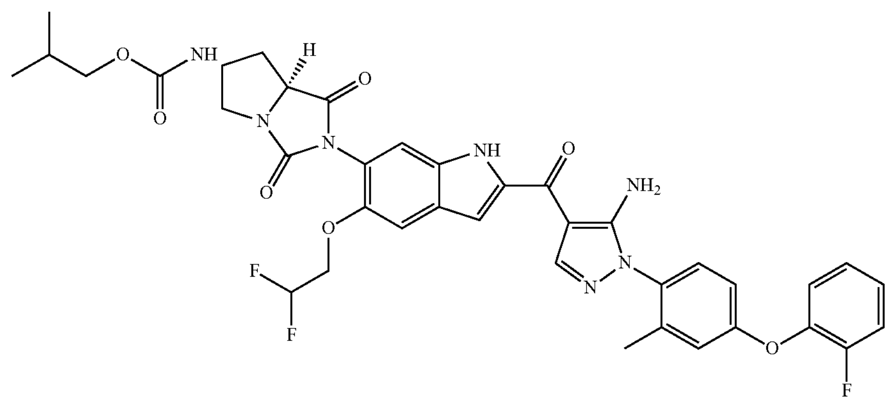 | 2-methylpropyl N-[(6S,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]carbamate | 760 | 1.28 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-275 | 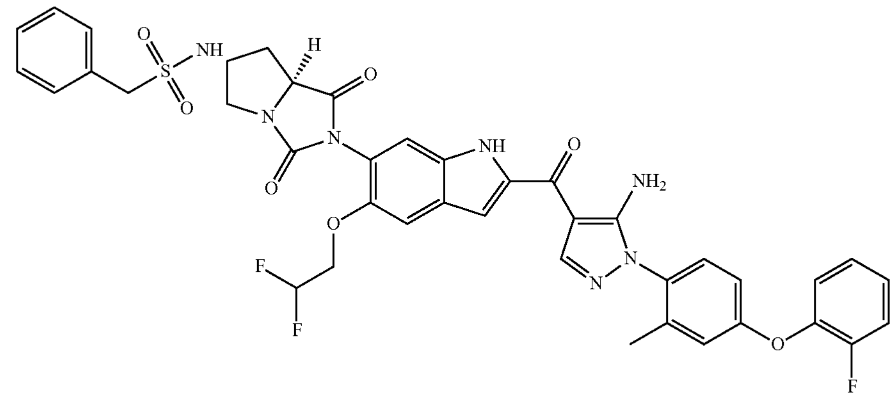 | N-[(6S,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]-1-phenylmethanesulfonamide | 814 | 1.02 | AA Rev.11 |
| 5-1-276 | 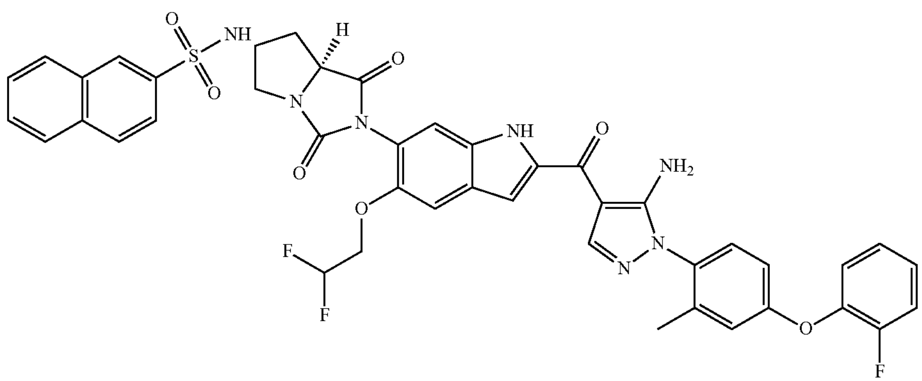 | N-[(6S,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]naphthalene-2-sulfonamide | 850 | 1.32 | TFA Rev.7 |

| Example No. | Chemical Structure | Compound Name | m/z (M + H) | Reaction Time (Minute) | LCMS Measurement Condition |
|---|---|---|---|---|---|
| 5-1-277 | 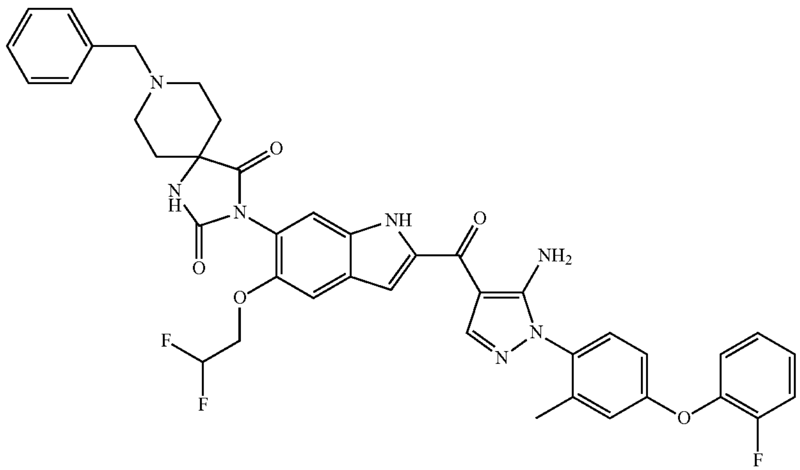 [SMILES: Cc1cc(Oc2ccccc2F)ccc1-n1ncc(C(=O)c2cc3cc(OCC(F)F)c(N4C(=O)NC5(CCN(Cc6ccccc6)CC5)C4=O)cc3[nH]2)c1N] | 3-[2-[5-amino-1-[4-(2-fluorophenoxy)-2-methylphenyl]pyrazole-4-carbonyl]-5-(2,2-difluoroethoxy)-1H-indol-6-yl]-8-benzyl-1,3,8-triazaspiro[4.5]decane-2,4-dione | 764 | 1.06 | TFA Rev.7 |
| 5-1-278 | 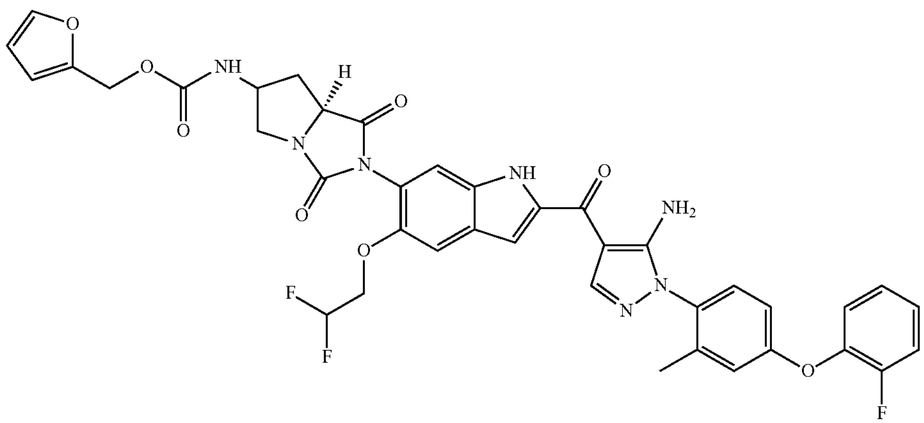 [SMILES: Cc1cc(Oc2ccccc2F)ccc1-n1ncc(C(=O)c2cc3cc(OCC(F)F)c(N4C(=O)[C@@H]5CC(NC(=O)OCc6ccco6)CN5C4=O)cc3[nH]2)c1N] | Furan-2-ylmethyl N-[(6S,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]carbamate | 784 | 1.24 | TFA Rev.7 |

| Example No. | Chemical Structure | Compound Name | m/z (M + H) | Reaction Time (Minute) | LCMS Measurement Condition |
|---|---|---|---|---|---|
| 5-1-279 | 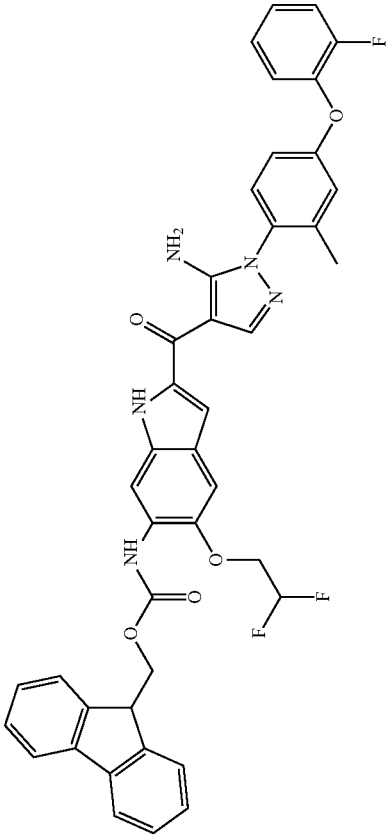 | 9H-fluoren-9-ylmethyl N-[2-[5-amino-1-[4-(2-fluorophenoxy)-2-methylphenyl]pyrazole-4-carbonyl]-5-(2,2-difluoroethoxy)-1H-indol-6-yl] carbamate | 744 | 1.19 | AA Rev.11 |
| 5-1-280 | 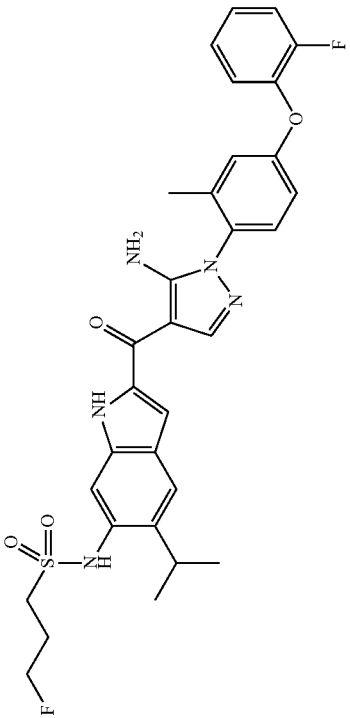 | N-[2-[5-amino-1-[4-(2-fluorophenoxy)-2-methylphenyl]pyrazole-4-carbonyl]-5-propan-2-yl-1H-indol-6-yl]-3-fluoropropane-1-sulfonamide | 608 | 1.07 | AA Rev.11 |

| Example No. | Chemical Structure | Compound Name | m/z (M + H) | Reaction Time (Minute) | LCMS Measurement Condition |
|---|---|---|---|---|---|
| 5-1-281 | 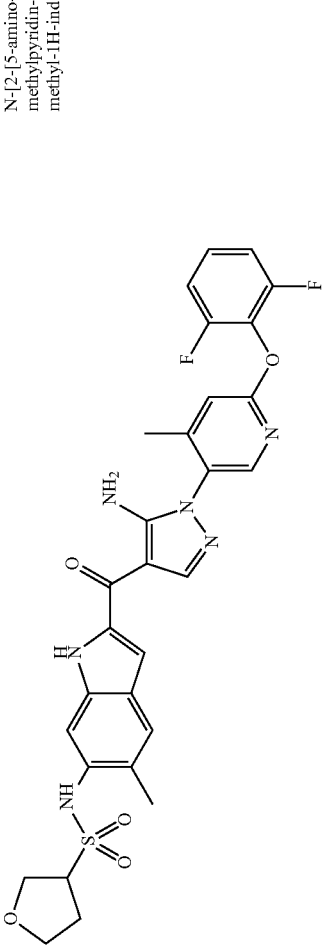 | N-[2-[5-amino-1-[6-(2,6-difluorophenoxy)-4-methylpyridin-3-yl]pyrazole-4-carbonyl]-5-methyl-1H-indol-6-yl]oxolane-3-sulfonamide | 609 | 1.00 | AA Rev.11 |
| 5-1-282 | 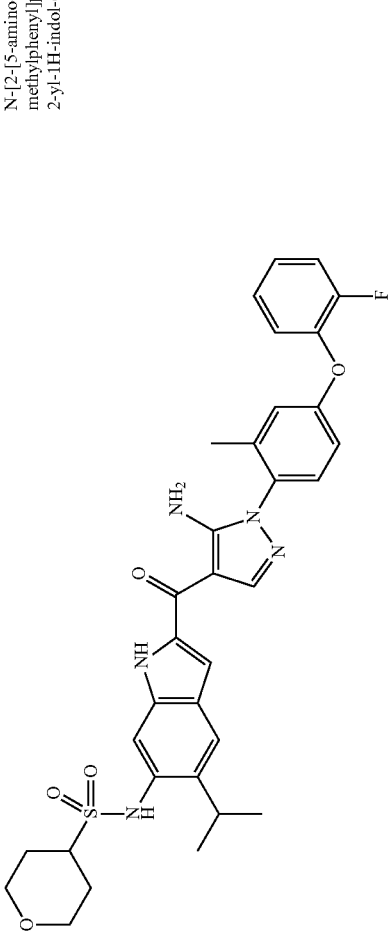 | N-[2-[5-amino-1-[4-(2-fluorophenoxy)-2-methylphenyl]pyrazole-4-carbonyl]-5-propan-2-yl-1H-indol-6-yl]oxane-4-sulfonamide | 632 | 1.28 | TFA Rev.7 |

| Example No. | Chemical Structure | Compound Name | m/z (M + H) | Reaction Time (Minute) | LCMS Measurement Condition |
|---|---|---|---|---|---|
| 5-1-283 | 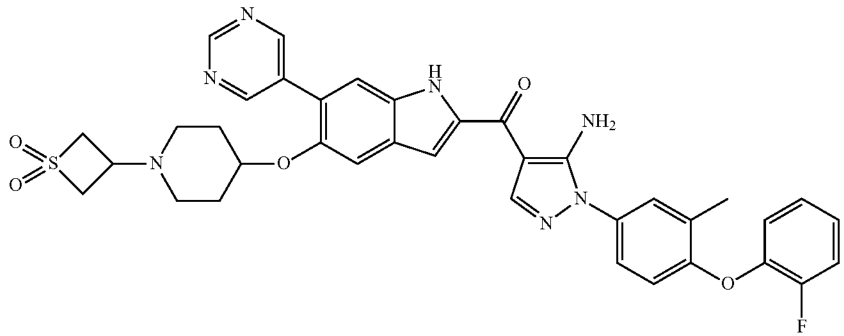 [SMILES: Cc1cc(-n2ncc(C(=O)c3cc4cc(OC5CCN(C6CS(=O)(=O)C6)CC5)c(-c5cncnc5)cc4[nH]3)c2N)ccc1Oc1ccccc1F] | [5-amino-1-[4-(2-fluorophenoxy)-3-methylphenyl]pyrazol-4-yl]-[5-[1-(1,1-dioxothietan-3-yl)piperidin-4-yl]oxy-6-pyrimidin-5-yl-1H-indol-2-yl]methanone | 708 | 0.98 | TFA Rev.7 |
| 5-1-284 | 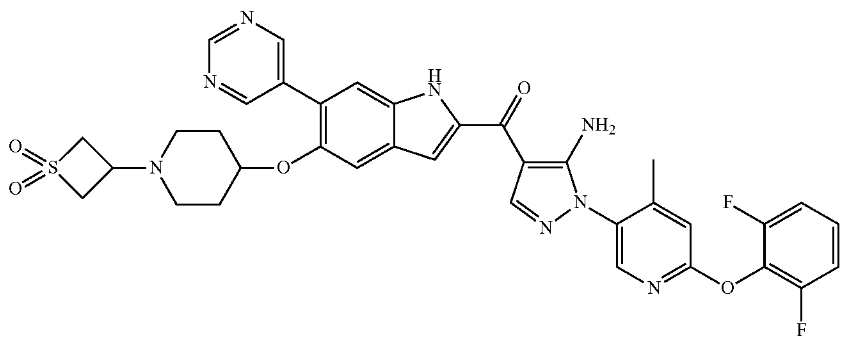 | [5-amino-1-[6-(2,6-difluorophenoxy)-4-methylpyridin-3-yl]pyrazol-4-yl]-[5-[1-(1,1-dioxothietan-3-yl)piperidin-4-yl]oxy-5-pyrimidin-5-yl-1H-indol-2-yl]methanone | 727 | 1.00 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-285 | 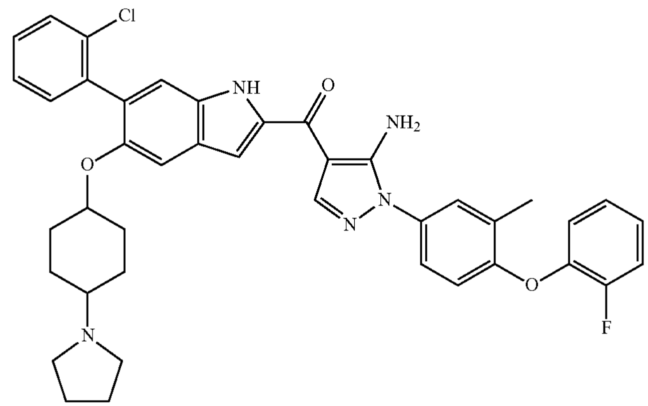 [SMILES: Cc1cc(-n2ncc(C(=O)c3cc4cc(OC5CCC(N6CCCC6)CC5)c(-c5ccccc5Cl)cc4[nH]3)c2N)ccc1Oc1ccccc1F] | [5-amino-1-[4-(2-fluorophenoxy)-3-methylphenyl]pyrazol-4-yl]-[6-(2-chlorophenyl)-5-(1-cyclopentylpiperidin-4-yl)oxy-1H-indol-2-yl]methanone | 704, 706 | 1.14 | AA Rev.11 |
| 5-1-286 | 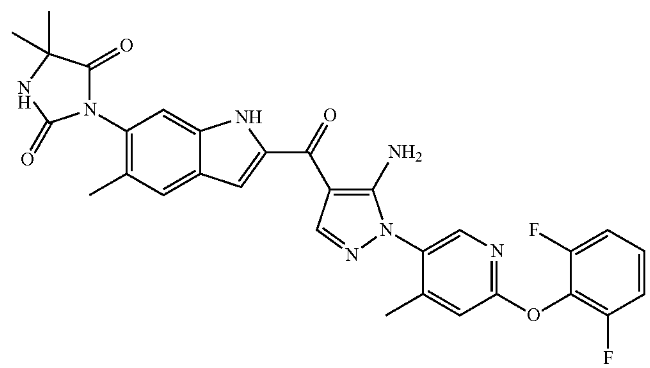 [SMILES: Cc1cc2cc(C(=O)c3cnn(-c4cnc(Oc5c(F)cccc5F)cc4C)c3N)[nH]c2cc1N1C(=O)NC(C)(C)C1=O] | 3-[2-[5-amino-1-[6-(2,6-difluorophenoxy)-4-methylpyridin-3-yl]pyrazole-4-carbonyl]-5-methyl-1H-indol-6-yl]-5,5-dimethylimidazolidine-2,4-dione | 586 | 1.13 | TFA Rev.7 |

| Example No. | Chemical Structure | Compound Name | m/z (M + H) | Reaction Time (Minute) | LCMS Measurement Condition |
|---|---|---|---|---|---|
| 5-1-287 | 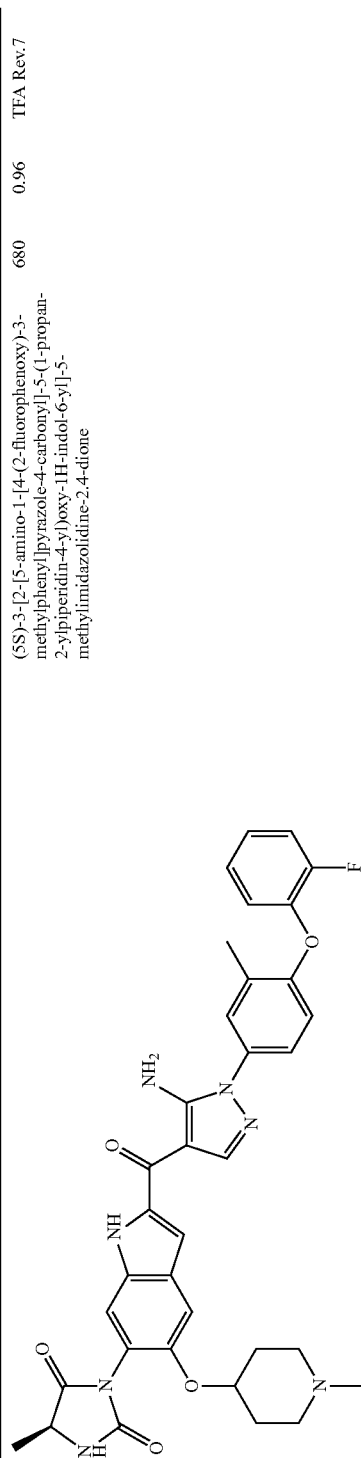 | (5S)-3-[2-[5-amino-1-[4-(2-fluorophenoxy)-3-methylphenyl]pyrazole-4-carbonyl]-5-(1-propan-2-ylpiperidin-4-yl)oxy-1H-indol-6-yl]-5-methylimidazolidine-2,4-dione | 680 | 0.96 | TFA Rev.7 |
| 5-1-288 | 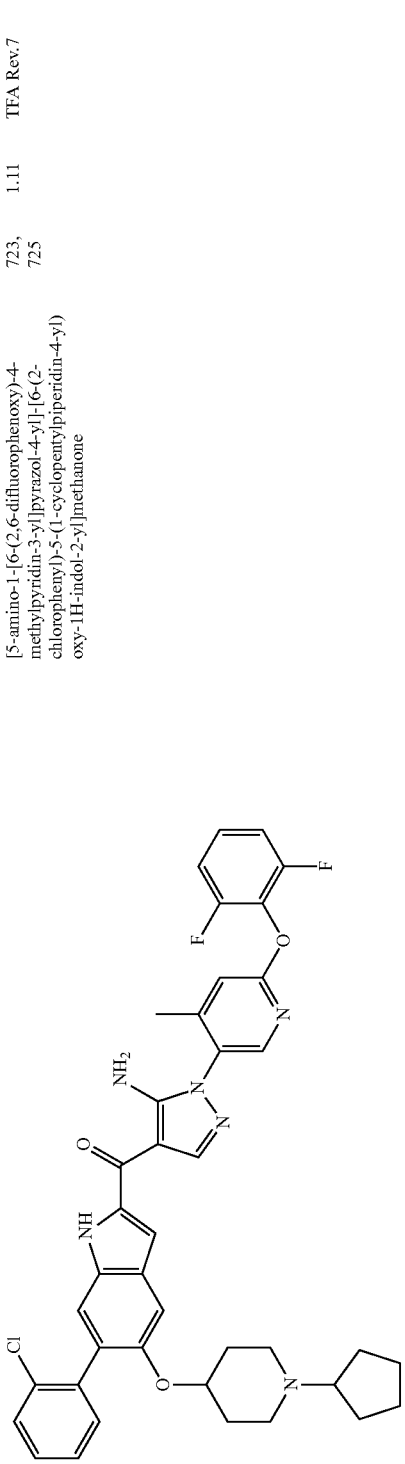 | [5-amino-1-[6-(2,6-difluorophenoxy)-4-methylpyridin-3-yl]pyrazol-4-yl]-[6-(2-chlorophenyl)-5-(1-cyclopentylpiperidin-4-yl)oxy-1H-indol-2-yl]methanone | 723, 725 | 1.11 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-289 | 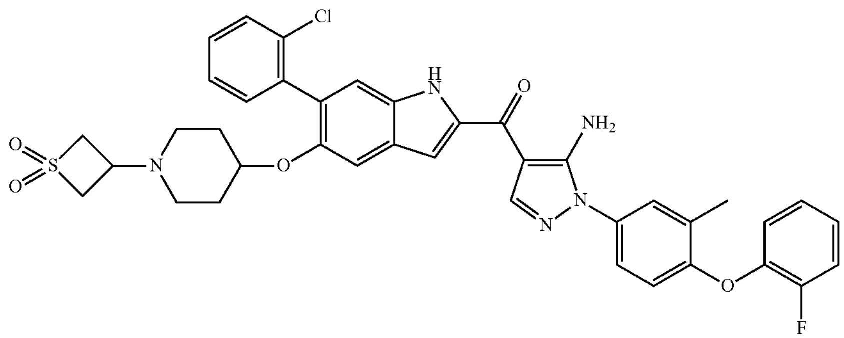 [SMILES: Cc1cc(-n2ncc(C(=O)c3cc4cc(OC5CCN(C6CS(=O)(=O)C6)CC5)c(-c5ccccc5Cl)cc4[nH]3)c2N)ccc1Oc1ccccc1F] | [5-amino-1-[4-(2-fluorophenoxy)-3-methylphenyl]pyrazol-4-yl]-[6-(2-chlorophenyl)-5-[1-(1,1-dioxothietan-3-yl)piperidin-4-yl]oxy-1H-indol-2-yl]methanone | 740, 742 | 1.12 | TFA Rev.7 |
| 5-1-290 | 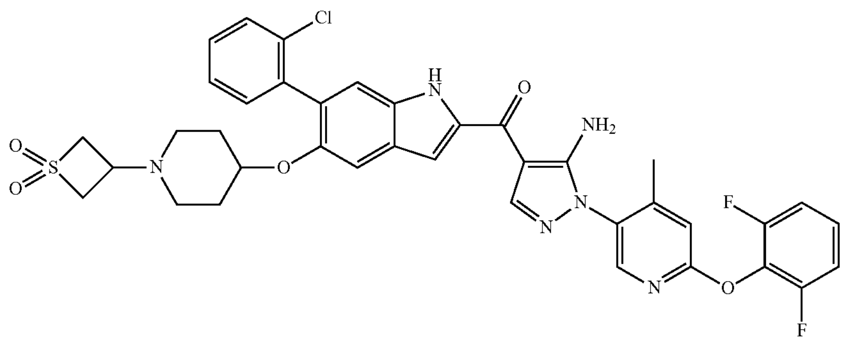 [SMILES: Cc1cc(Oc2c(F)cccc2F)ncc1-n1ncc(C(=O)c2cc3cc(OC4CCN(C5CS(=O)(=O)C5)CC4)c(-c4ccccc4Cl)cc3[nH]2)c1N] | [5-amino-1-[6-(2,6-difluorophenoxy)-4-methylpyridin-3-yl]pyrazol-4-yl]-[6-(2-chlorophenyl)-5-[1-(1,1-dioxothietan-3-yl)piperidin-4-yl]oxy-1H-indol-2-yl]methanone | 759, 761 | 1.05 | TFA Rev.7 |
| 5-1-291 | 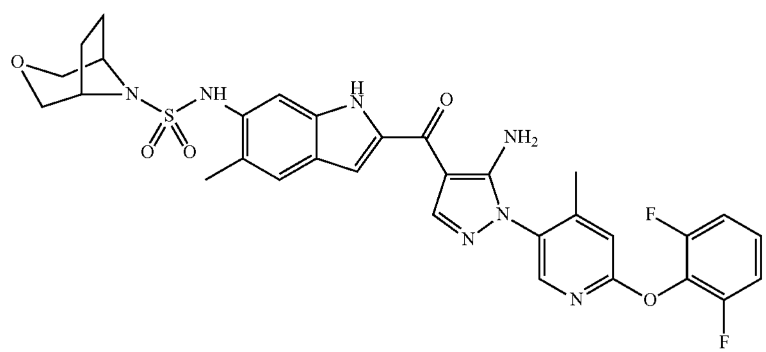 [SMILES: Cc1cc2cc(C(=O)c3cnn(-c4cnc(Oc5c(F)cccc5F)cc4C)c3N)[nH]c2cc1NS(=O)(=O)N1C2CCC1COC2] | N-[2-[5-amino-1-[6-(2,6-difluorophenoxy)-4-methylpyridin-3-yl]pyrazole-4-carbonyl]-5-methyl-1H-indol-6-yl]-3-oxa-8-azabicyclo[3.2.1]octane-8-sulfonamide | 650 | 1.02 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-292 | 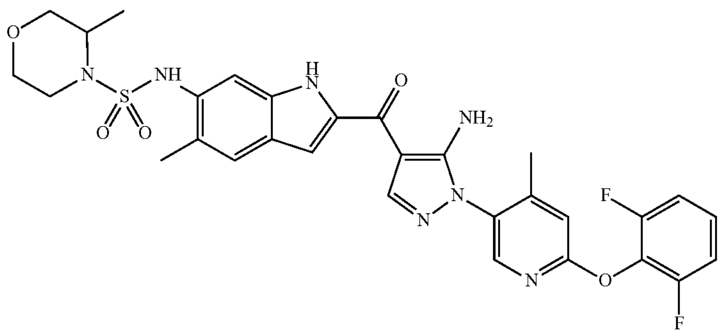 [SMILES: Cc1cc2cc(C(=O)c3cnn(-c4cnc(Oc5c(F)cccc5F)cc4C)c3N)[nH]c2cc1NS(=O)(=O)N1CCOCC1C] | (3R)-N-[2-[5-amino-1-[6-(2,6-difluorophenoxy)-4-methylpyridin-3-yl]pyrazole-4-carbonyl]-5-methyl-1H-indol-6-yl]-3-methylmorpholine-4-sulfonamide | 638 | 1.02 | AA Rev.11 |
| 5-1-293 | 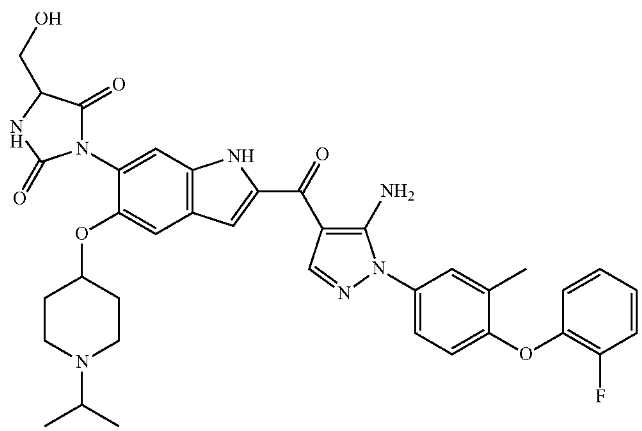 [SMILES: Cc1cc(-n2ncc(C(=O)c3cc4cc(OC5CCN(C(C)C)CC5)c(N5C(=O)NC(CO)C5=O)cc4[nH]3)c2N)ccc1Oc1ccccc1F] | (5S)-3-[2-[5-amino-1-[4-(2-fluorophenoxy)-3-methylphenyl]pyrazole-4-carbonyl]-5-(1-propan-2-ylpiperidin-4-yl)oxy-1H-indol-6-yl]-5-(hydroxymethyl)imidazolidine-2,4-dione | 696 | 0.92 | TFA Rev.7 |

| Example No. | Chemical Structure | Compound Name | m/z (M + H) | Reaction Time (Minute) | LCMS Measurement Condition |
|---|---|---|---|---|---|
| 5-1-294 | 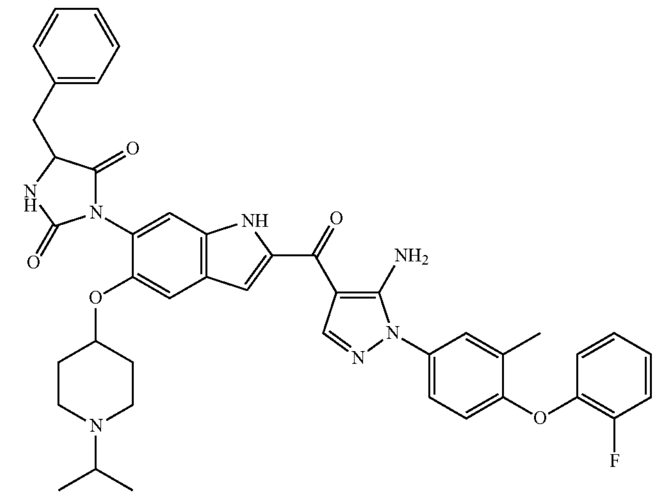 [SMILES: Cc1cc(-n2ncc(C(=O)c3cc4cc(OC5CCN(C(C)C)CC5)c(N5C(=O)NC(Cc6ccccc6)C5=O)cc4[nH]3)c2N)ccc1Oc1ccccc1F] | (5S)-3-[2-[5-amino-1-[4-(2-fluorophenoxy)-3-methylphenyl]pyrazole-4-carbonyl]-5-(1-propan-2-ylpiperidin-4-yl)oxy-1H-indol-6-yl]-5-benzylimidazolidine-2,4-dione | 756 | 1.04 | TFA Rev.7 |
| 5-1-295 | 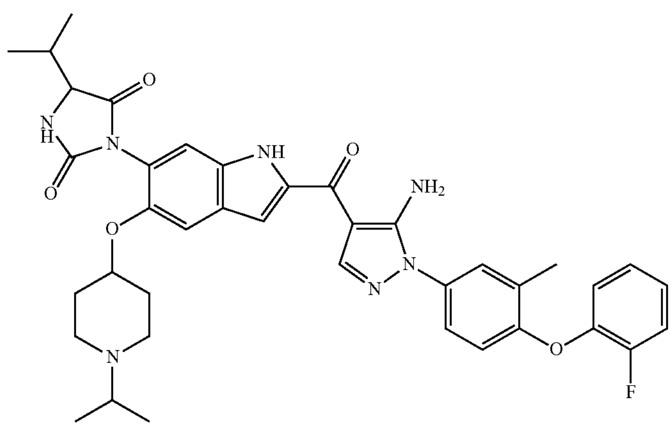 [SMILES: Cc1cc(-n2ncc(C(=O)c3cc4cc(OC5CCN(C(C)C)CC5)c(N5C(=O)NC(C(C)C)C5=O)cc4[nH]3)c2N)ccc1Oc1ccccc1F] | (5S)-3-[2-[5-amino-1-[4-(2-fluorophenoxy)-3-methylphenyl]pyrazole-4-carbonyl]-5-(1-propan-2-ylpiperidin-4-yl)oxy-1H-indol-6-yl]-5-propan-2-ylimidazolidine-2,4-dione | 708 | 0.99 | TFA Rev.7 |

| Example No. | Chemical Structure | Compound Name | m/z (M + H) | Reaction Time (Minute) | LCMS Measurement Condition |
|---|---|---|---|---|---|
| 5-1-296 | 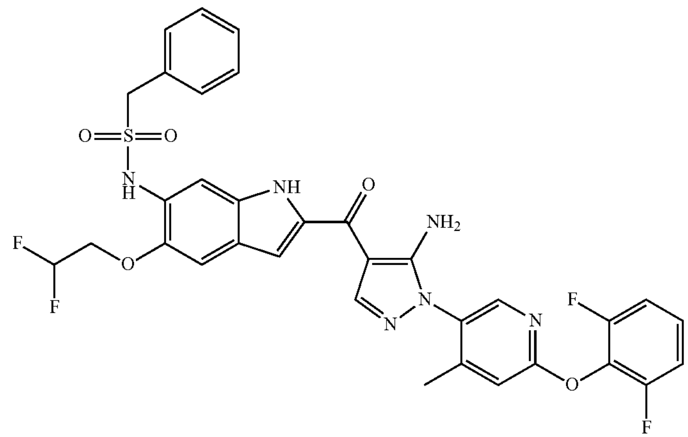 [SMILES: Cc1cc(Oc2c(F)cccc2F)ncc1-n1ncc(C(=O)c2cc3cc(OCC(F)F)c(NS(=O)(=O)Cc4ccccc4)cc3[nH]2)c1N] | N-[2-[5-amino-1-[6-(2,6-difluorophenoxy)-4-methylpyridin-3-yl]pyrazole-4-carbonyl]-5-(2,2-difluoroethoxy)-1H-indol-6-yl]-1-phenylmethanesulfonamide | 695 | 1.31 | TFA Rev.7 |
| 5-1-297 | 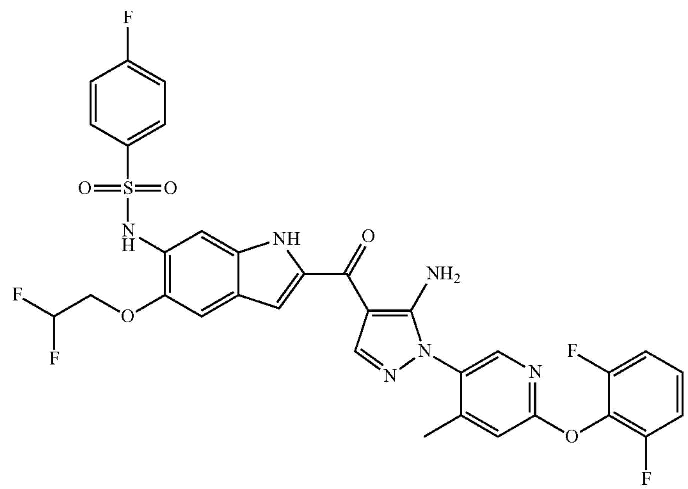 | N-[2-[5-amino-1-[6-(2,6-difluorophenoxy)-4-methylpyridin-3-yl]pyrazole-4-carbonyl]-5-(2,2-difluoroethoxy)-1H-indol-6-yl]-4-fluorobenzenesulfonamide | 699 | 1.30 | TFA Rev.7 |

| Example No. | Chemical Structure | Compound Name | m/z (M + H) | Reaction Time (Minute) | LCMS Measurement Condition |
|---|---|---|---|---|---|
| 5-1-298 | 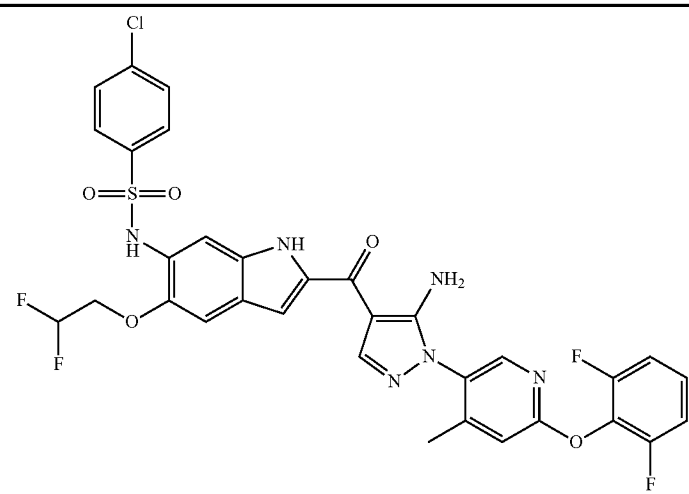 | N-[2-[5-amino-1-[6-(2,6-difluorophenoxy)-4-methylpyridin-3-yl]pyrazole-4-carbonyl]-5-(2,2-difluoroethoxy)-1H-indol-6-yl]-4-chlorobenzenesulfonamide | 715, 717 | 1.35 | TFA Rev.7 |
| 5-1-299 | 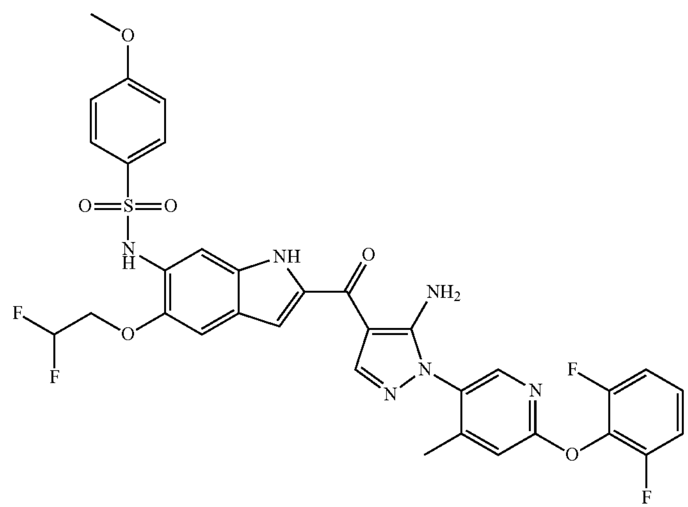 [SMILES: COc1ccc(S(=O)(=O)Nc2cc3[nH]c(C(=O)c4cnn(-c5cnc(Oc6c(F)cccc6F)cc5C)c4N)cc3cc2OCC(F)F)cc1] | N-[2-[5-amino-1-[6-(2,6-difluorophenoxy)-4-methylpyridin-3-yl]pyrazole-4-carbonyl]-5-(2,2-difluoroethoxy)-1H-indol-6-yl]-4-methoxybenzenesulfonamide | 711 | 1.29 | TFA Rev.7 |

| Example No. | Chemical Structure | Compound Name | m/z (M + H) | Reaction Time (Minute) | LCMS Measurement Condition |
|---|---|---|---|---|---|
| 5-1-300 | 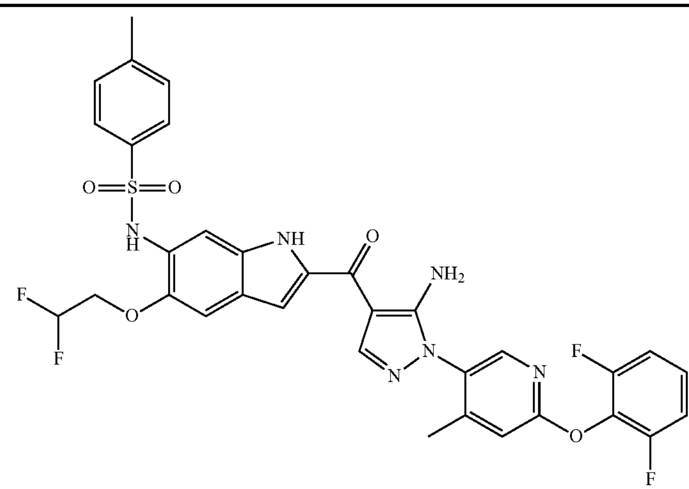 | N-[2-[5-amino-1-[6-(2,6-difluorophenoxy)-4-methylpyridin-3-yl]pyrazole-4-carbonyl]-5-(2,2-difluoroethoxy)-1H-indol-6-yl]-4-methylbenzenesulfonamide | 695 | 1.32 | TFA Rev.7 |
| 5-1-301 | 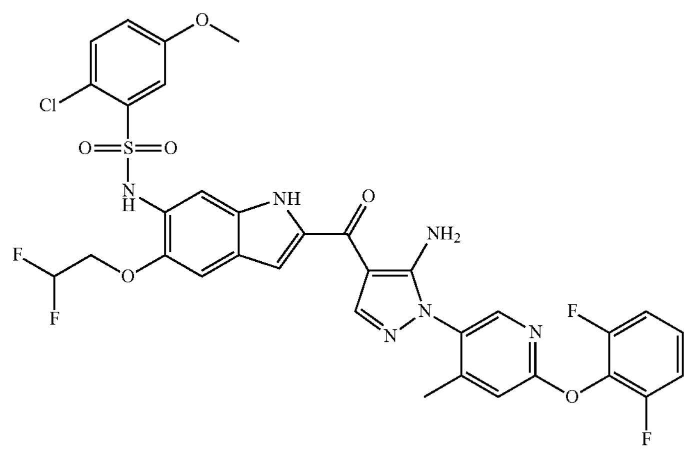 [SMILES: COc1ccc(Cl)c(S(=O)(=O)Nc2cc3[nH]c(C(=O)c4cnn(-c5cnc(Oc6c(F)cccc6F)cc5C)c4N)cc3cc2OCC(F)F)c1] | N-[2-[5-amino-1-[6-(2,6-difluorophenoxy)-4-methylpyridin-3-yl]pyrazole-4-carbonyl]-5-(2,2-difluoroethoxy)-1H-indol-6-yl]-2-chloro-5-methoxybenzenesulfonamide | 745, 747 | 1.34 | TFA Rev.7 |

| Example No. | Chemical Structure | Compound Name | m/z (M + H) | Reaction Time (Minute) | LCMS Measurement Condition |
|---|---|---|---|---|---|
| 5-1-302 | 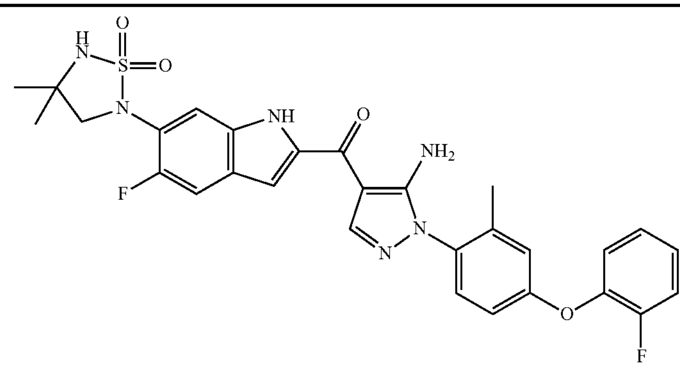 | [5-amino-1-[4-(2-fluorophenoxy)-2-methylphenyl]pyrazol-4-yl]-[6-(4,4-dimethyl-1,1-dioxo-1,2,5-thiadiazolidin-2-yl)-5-fluoro-1H-indol-2-yl]methanone | 593 | 1.04 | AA Rev.11 |
| 5-1-303 | 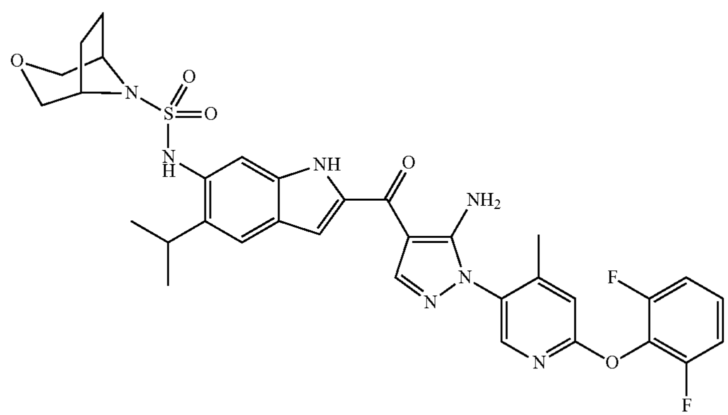 [SMILES: Cc1cc(Oc2c(F)cccc2F)ncc1-n1ncc(C(=O)c2cc3cc(C(C)C)c(NS(=O)(=O)N4C5CCC4COC5)cc3[nH]2)c1N] | N-[2-[5-amino-1-[6-(2,6-difluorophenoxy)-4-methylpyridin-3-yl]pyrazole-4-carbonyl]-5-propan-2-yl-1H-indol-6-yl]-3-oxa-8-azabicyclo[3.2.1]octane-8-sulfonamide | 678 | 1.31 | TFA Rev.7 |

| Example No. | Chemical Structure | Compound Name | m/z (M + H) | Reaction Time (Minute) | LCMS Measurement Condition |
|---|---|---|---|---|---|
| 5-1-304 | 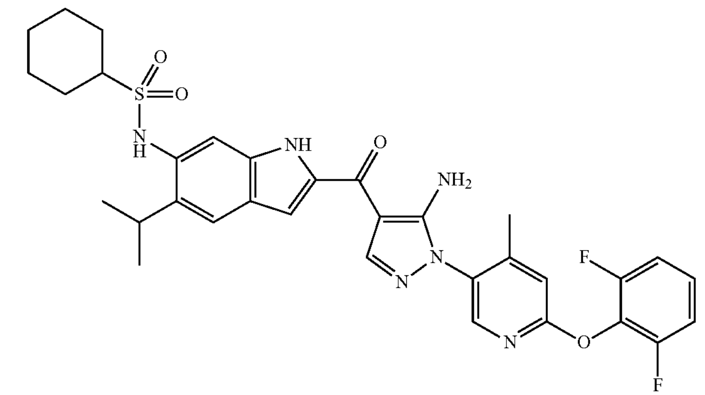 [SMILES: Cc1cc(Oc2c(F)cccc2F)ncc1-n1ncc(C(=O)c2cc3cc(C(C)C)c(NS(=O)(=O)C4CCCCC4)cc3[nH]2)c1N] | N-[2-[5-amino-1-[6-(2,6-difluorophenoxy)-4-methylpyridin-3-yl]pyrazole-4-carbonyl]-5-propan-2-yl-1H-indol-6-yl]cyclohexanesulfonamide | 649 | 1.40 | TFA Rev.7 |
| 5-1-305 | 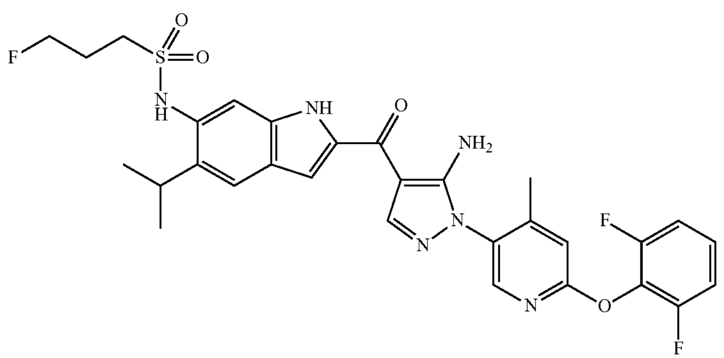 [SMILES: Cc1cc(Oc2c(F)cccc2F)ncc1-n1ncc(C(=O)c2cc3cc(C(C)C)c(NS(=O)(=O)CCCF)cc3[nH]2)c1N] | N-[2-[5-amino-1-[6-(2,6-difluorophenoxy)-4-methylpyridin-3-yl]pyrazole-4-carbonyl]-5-propan-2-yl-1H-indol-6-yl]-3-fluoropropane-1-sulfonamide | 627 | 1.28 | TFA Rev.7 |

| Example No. | Chemical Structure | Compound Name | m/z (M + H) | Reaction Time (Minute) | LCMS Measurement Condition |
|---|---|---|---|---|---|
| 5-1-306 | 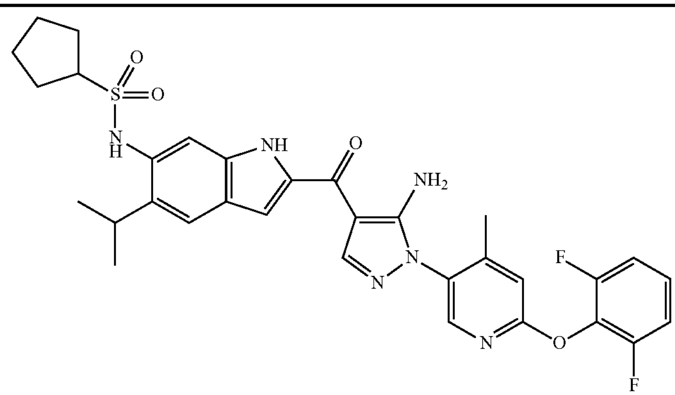 | N-[2-[5-amino-1-[6-(2,6-difluorophenoxy)-4-methylpyridin-3-yl]pyrazole-4-carbonyl]-5-propan-2-yl-1H-indol-6-yl]cyclopentanesulfonamide | 635 | 1.07 | AA Rev.11 |
| 5-1-307 | 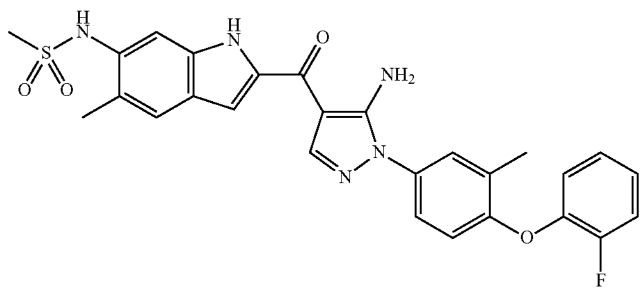 [SMILES: Cc1cc2cc(C(=O)c3cnn(-c4ccc(Oc5ccccc5F)c(C)c4)c3N)[nH]c2cc1NS(C)(=O)=O] | N-[2-[5-amino-1-[4-(2-fluorophenoxy)-3-methylphenyl]pyrazole-4-carbonyl]-5-methyl-1H-indol-6-yl]methanesulfonamide | 534 | 1.23 | TFA Rev.7 |

| Example No. | Chemical Structure | Compound Name | m/z (M + H) | Reaction Time (Minute) | LCMS Measurement Condition |
|---|---|---|---|---|---|
| 5-1-308 | 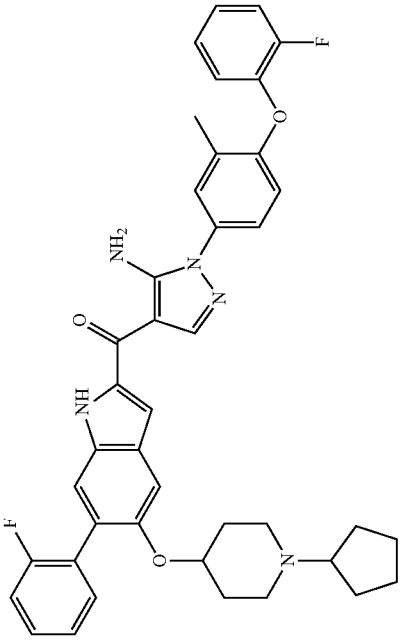 | [5-amino-1-[4-(2-fluorophenoxy)-3-methylphenyl]pyrazol-4-yl]-[5-(1-cyclopentylpiperidin-4-yl)oxy-6-(2-fluorophenyl)-1H-indol-2-yl]methanone | 688 | 1.15 | TFA Rev.7 |
| 5-1-309 | 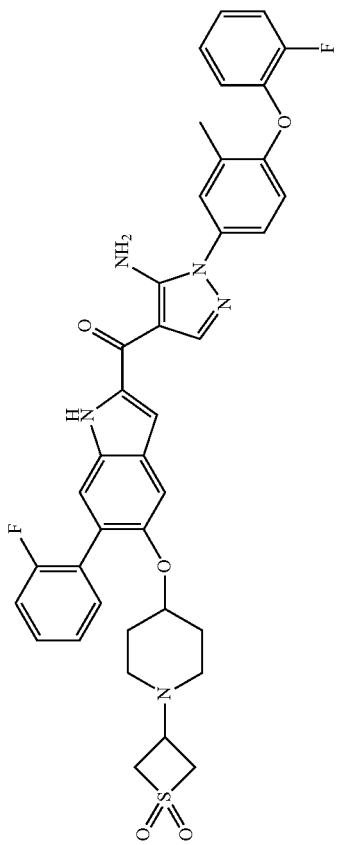 | [5-amino-1-[4-(2-fluorophenoxy)-3-methylphenyl]pyrazol-4-yl]-[5-[1-(1,1-dioxothietan-3-yl)piperidin-4-yl]oxy-6-(2-fluorophenyl)-1H-indol-2-yl]methanone | 724 | 1.10 | TFA Rev.7 |

| Example No. | Chemical Structure | Compound Name | m/z (M + H) | Reaction Time (Minute) | LCMS Measurement Condition |
|---|---|---|---|---|---|
| 5-1-310 | 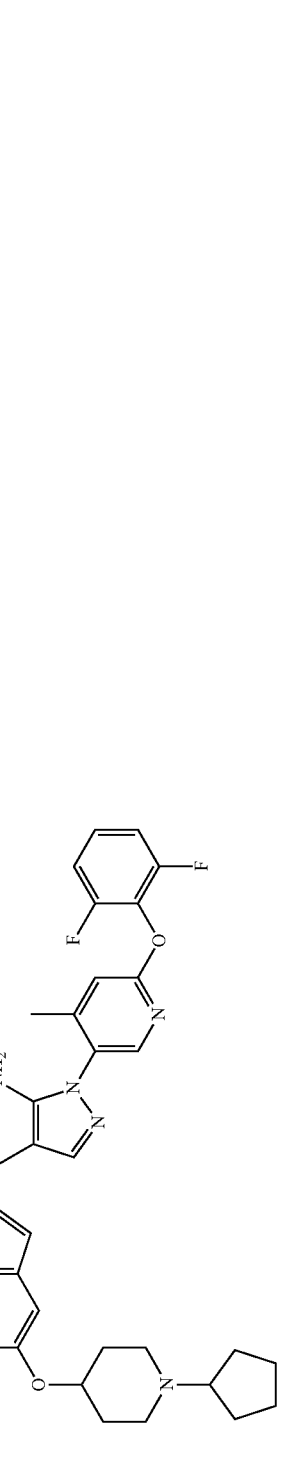 | [5-amino-1-[6-(2,6-difluorophenoxy)-4-methylpyridin-3-yl]pyrazol-4-yl]-[5-(1-cyclopentylpiperidin-4-yl)oxy-6-(2-fluorophenyl)-1H-indol-2-yl]methanone | 707 | 1.08 | TFA Rev.7 |
| 5-1-311 | 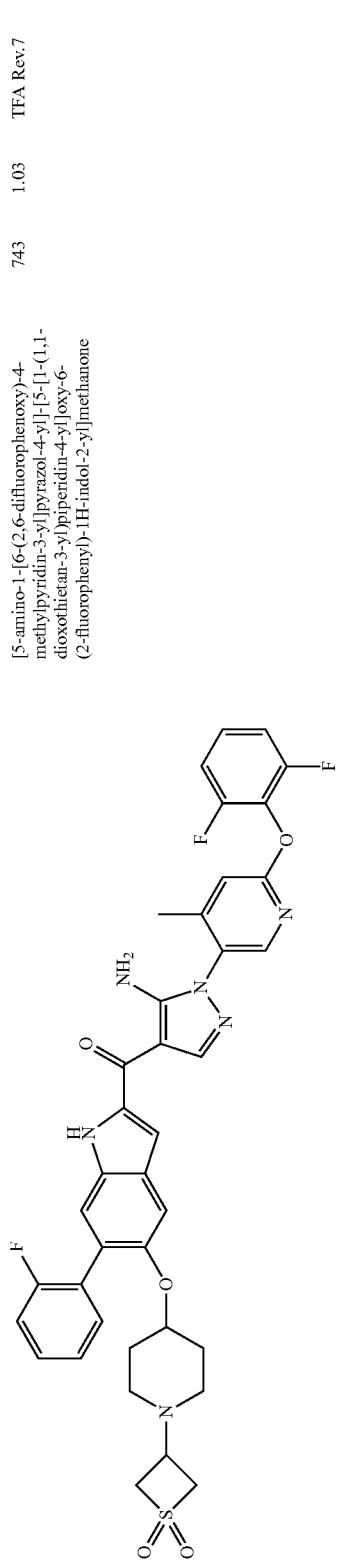 | [5-amino-1-[6-(2,6-difluorophenoxy)-4-methylpyridin-3-yl]pyrazol-4-yl]-[5-[1-(1,1-dioxothietan-3-yl)piperidin-4-yl]oxy-6-(2-fluorophenyl)-1H-indol-2-yl]methanone | 743 | 1.03 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-312 | 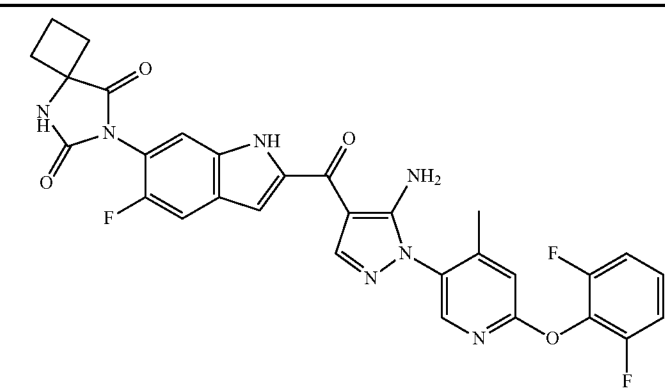 | 7-[2-[5-amino-1-[6-(2,6-difluorophenoxy)-4-methylpyridin-3-yl]pyrazole-4-carbonyl]-5-fluoro-1H-indol-6-yl]-5,7-diazaspiro[3.4]octane-6,8-dione | 602 | 0.98 | AA Rev.11 |
| 5-1-313 | 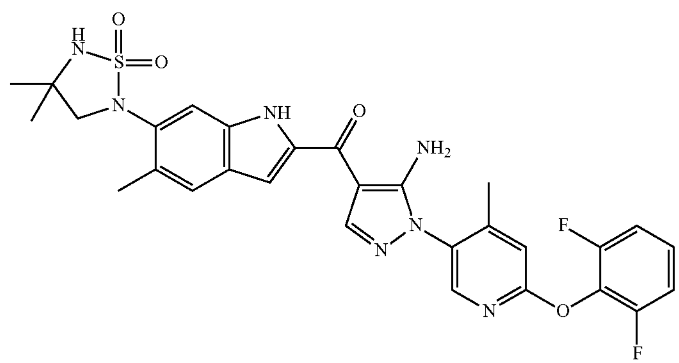 | [5-amino-1-[6-(2,6-difluorophenoxy)-4-methylpyridin-3-yl]pyrazol-4-yl]-[6-(4,4-dimethyl-1,1-dioxo-1,2,5-thiadiazolidin-2-yl)-5-methyl-1H-indol-2-yl]methanone | 608 | 1.02 | AA Rev.11 |

| Example No. | Chemical Structure | Compound Name | m/z (M + H) | Reaction Time (Minute) | LCMS Measurement Condition |
|---|---|---|---|---|---|
| 5-1-314 | 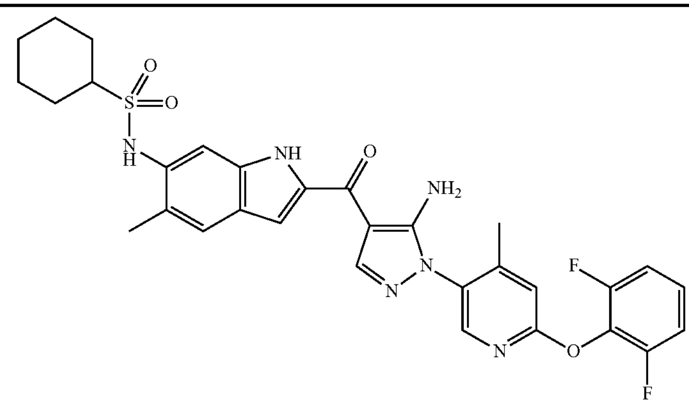 | N-[2-[5-amino-1-[6-(2,6-difluorophenoxy)-4-methylpyridin-3-yl]pyrazole-4-carbonyl]-5-methyl-1H-indol-6-yl]cyclohexanesulfonamide | 621 | 1.06 | AA Rev.11 |
| 5-1-315 | 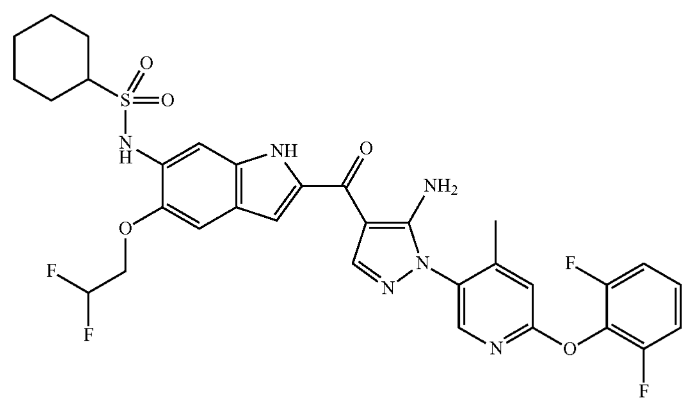 [SMILES: Cc1cc(Oc2c(F)cccc2F)ncc1-n1ncc(C(=O)c2cc3cc(OCC(F)F)c(NS(=O)(=O)C4CCCCC4)cc3[nH]2)c1N] | N-[2-[5-amino-1-[6-(2,6-difluorophenoxy)-4-methylpyridin-3-yl]pyrazole-4-carbonyl]-5-(2,2-difluoroethoxy)-1H-indol-6-yl]cyclohexanesulfonamide | 687 | 1.06 | AA Rev.11 |

| Example No. | Chemical Structure | Compound Name | m/z (M + H) | Reaction Time (Minute) | LCMS Measurement Condition |
|---|---|---|---|---|---|
| 5-1-316 | 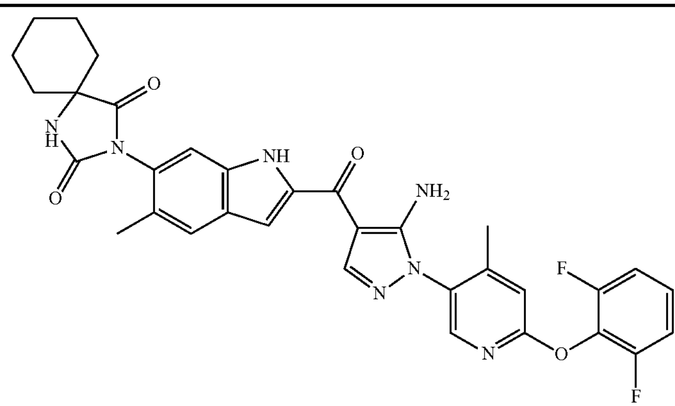 | 3-[2-[5-amino-1-[6-(2,6-difluorophenoxy)-4-methylpyridin-3-yl]pyrazole-4-carbonyl]-5-methyl-1H-indol-6-yl]-1,3-diazaspiro[4.5]decane-2,4-dione | 626 | 1.24 | TFA Rev.7 |
| 5-1-317 | 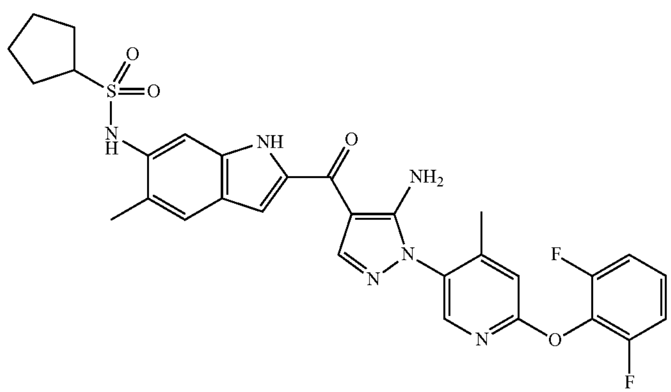 [SMILES: Cc1cc2cc(C(=O)c3cnn(-c4cnc(Oc5c(F)cccc5F)cc4C)c3N)[nH]c2cc1NS(=O)(=O)C1CCCC1] | N-[2-[5-amino-1-[6-(2,6-difluorophenoxy)-4-methylpyridin-3-yl]pyrazole-4-carbonyl]-5-methyl-1H-indol-6-yl]cyclopentanesulfonamide | 607 | 1.28 | TFA Rev.7 |

| Example No. | Chemical Structure | Compound Name | m/z (M + H) | Reaction Time (Minute) | LCMS Measurement Condition |
|---|---|---|---|---|---|
| 5-1-318 | 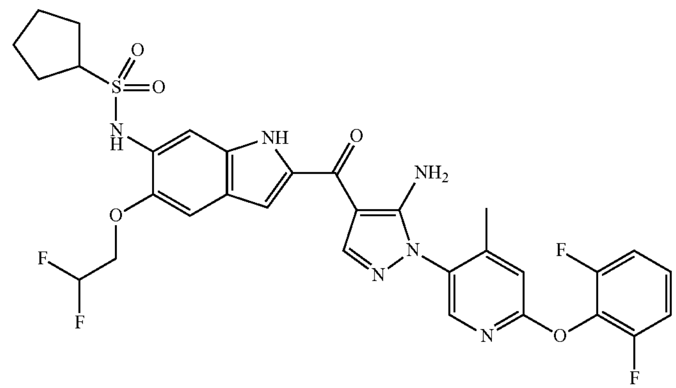 [SMILES: Cc1cc(Oc2c(F)cccc2F)ncc1-n1ncc(C(=O)c2cc3cc(OCC(F)F)c(NS(=O)(=O)C4CCCC4)cc3[nH]2)c1N] | N-[2-[5-amino-1-[6-(2,6-difluorophenoxy)-4-methylpyridin-3-yl]pyrazole-4-carbonyl]-5-(2,2-difluoroethoxy)-1H-indol-6-yl]cyclopentanesulfonamide | 673 | 1.30 | TFA Rev.7 |
| 5-1-319 | 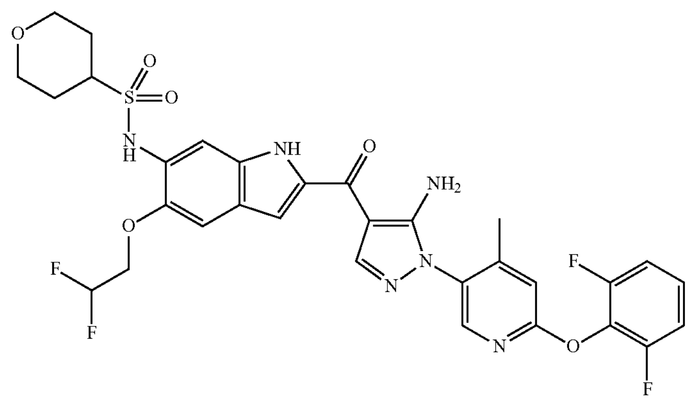 [SMILES: Cc1cc(Oc2c(F)cccc2F)ncc1-n1ncc(C(=O)c2cc3cc(OCC(F)F)c(NS(=O)(=O)C4CCOCC4)cc3[nH]2)c1N] | N-[2-[5-amino-1-[6-(2,6-difluorophenoxy)-4-methylpyridin-3-yl]pyrazole-4-carbonyl]-5-(2,2-difluoroethoxy)-1H-indol-6-yl]oxane-4-sulfonamide | 689 | 1.20 | TFA Rev.7 |

| Example No. | Chemical Structure | Compound Name | m/z (M + H) | Reaction Time (Minute) | LCMS Measurement Condition |
|---|---|---|---|---|---|
| 5-1-320 | 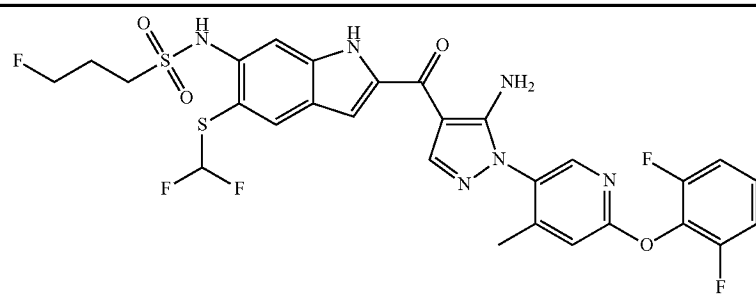 | N-[2-[5-amino-1-[6-(2,6-difluorophenoxy)-4-methylpyridin-3-yl]pyrazole-4-carbonyl]-5-(difluoromethylsulfanyl)-1H-indol-6-yl]-3-fluoropropane-1-sulfonamide | 667 | 1.28 | TFA Rev.7 |
| 5-1-321 | 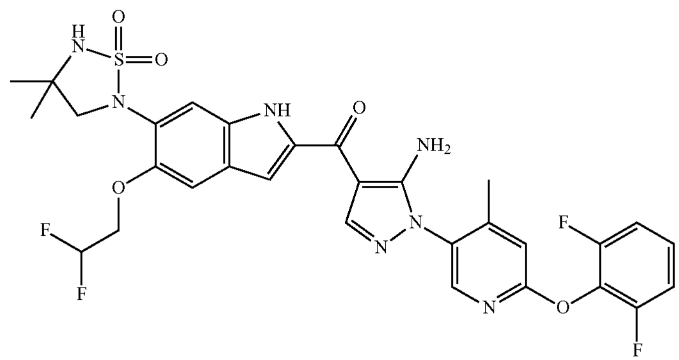 [SMILES: Cc1cc(Oc2c(F)cccc2F)ncc1-n1ncc(C(=O)c2cc3cc(OCC(F)F)c(N4CC(C)(C)NS4(=O)=O)cc3[nH]2)c1N] | [5-amino-1-[6-(2,6-difluorophenoxy)-4-methylpyridin-3-yl]pyrazol-4-yl]-[5-(2,2-difluoroethoxy)-6-(4,4-dimethyl-1,1-dioxo-1,2,5-thiadiazolidin-2-yl)-1H-indol-2-yl]methanone | 674 | 1.24 | TFA Rev.7 |
| 5-1-322 | 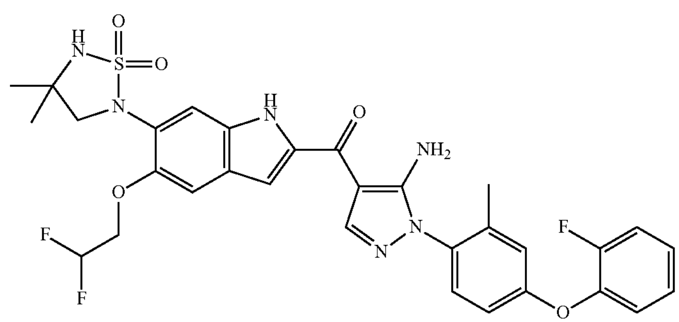 [SMILES: Cc1cc(Oc2ccccc2F)ccc1-n1ncc(C(=O)c2cc3cc(OCC(F)F)c(N4CC(C)(C)NS4(=O)=O)cc3[nH]2)c1N] | [5-amino-1-[4-(2-fluorophenoxy)-2-methylphenyl]pyrazol-4-yl]-[5-(2,2-difluoroethoxy)-6-(4,4-dimethyl-1,1-dioxo-1,2,5-thiadiazolidin-2-yl)-1H-indol-2-yl]methanone | 655 | 1.28 | TFA Rev.7 |

| Example No. | Chemical Structure | Compound Name | m/z (M + H) | Reaction Time (Minute) | LCMS Measurement Condition |
|---|---|---|---|---|---|
| 5-1-323 | 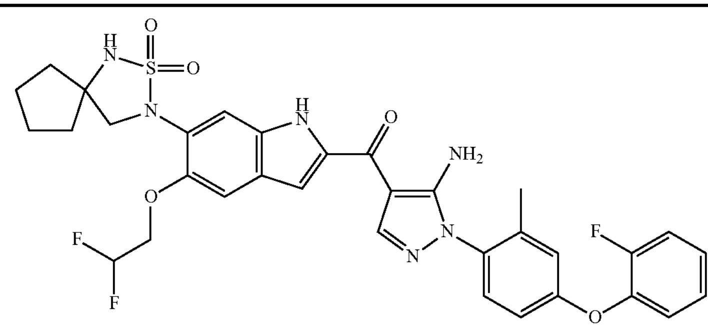 | [5-amino-1-[4-(2-fluorophenoxy)-2-methylphenyl]pyrazol-4-yl]-[5-(2,2-difluoroethoxy)-6-(2,2-dioxo-2λ6-thia-1,3-diazaspiro[4.4]nonan-3-yl)-1H-indol-2-yl]methanone | 681 | 1.08 | AA Rev.11 |
| 5-1-324 | 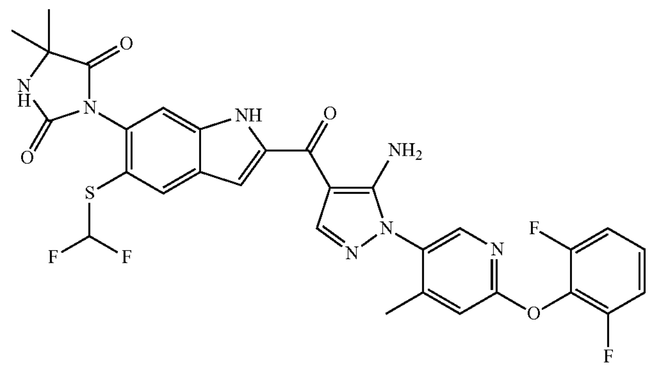 [SMILES: Cc1cc(Oc2c(F)cccc2F)ncc1-n1ncc(C(=O)c2cc3cc(SC(F)F)c(N4C(=O)NC(C)(C)C4=O)cc3[nH]2)c1N] | 3-[2-[5-amino-1-[6-(2,6-difluorophenoxy)-4-methylpyridin-3-yl]pyrazole-4-carbonyl]-5-(difluoromethylsulfanyl)-1H-indol-6-yl]-6,5-dimethylimidazolidine-2,4-dione | 654 | 1.01 | AA Rev.11 |
| 5-1-325 | 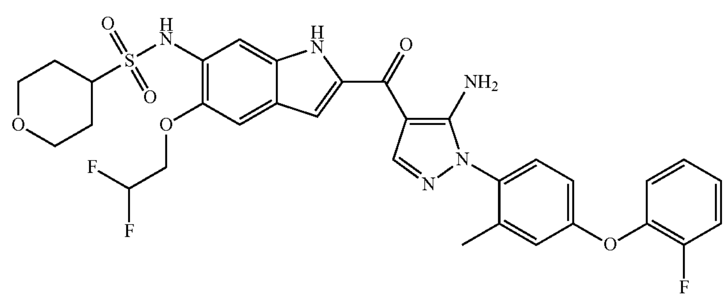 [SMILES: Cc1cc(Oc2ccccc2F)ncc1-n1ncc(C(=O)c2cc3cc(OCC(F)F)c(NS(=O)(=O)C4CCOCC4)cc3[nH]2)c1N] | N-[2-[5-amino-1-[4-(2-fluorophenoxy)-2-methylphenyl]pyrazole-4-carbonyl]-5-(2,2-difluoroethoxy)-1H-indol-6-yl]oxane-4-sulfonamide | 670 | 1.02 | AA Rev.11 |

| Example No. | Chemical Structure | Compound Name | m/z (M + H) | Reaction Time (Minute) | LCMS Measurement Condition |
|---|---|---|---|---|---|
| 5-1-326 | 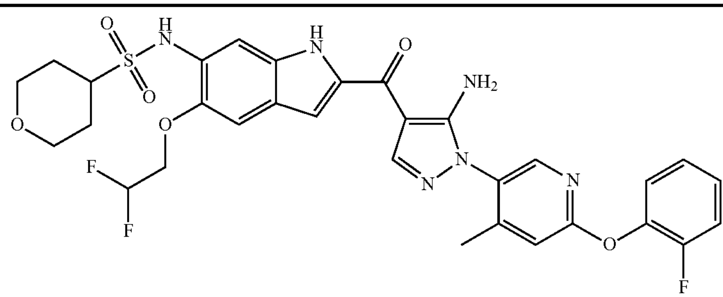 | N-[2-[5-amino-1-[6-(2-fluorophenoxy)-4-methylpyridin-3-yl]pyrazole-4-carbonyl]-5-(2,2-difluoroethoxy)-1H-indol-6-yl]oxane-4-sulfonamide | 671 | 0.97 | AA Rev.11 |
| 5-1-327 | 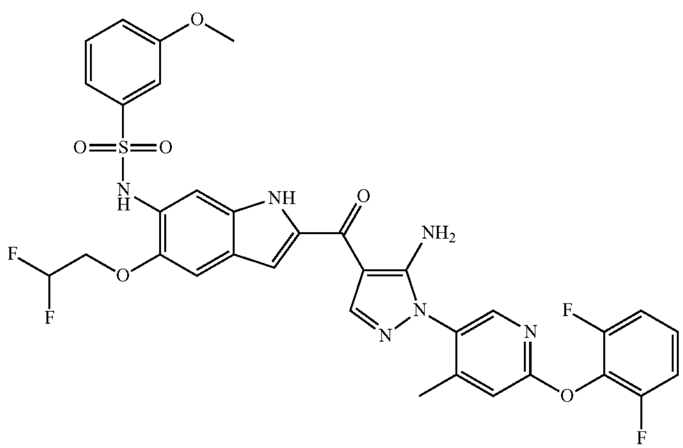 [SMILES: COc1cccc(S(=O)(=O)Nc2cc3[nH]c(C(=O)c4cnn(-c5cnc(Oc6c(F)cccc6F)cc5C)c4N)cc3cc2OCC(F)F)c1] | N-[2-[5-amino-1-[6-(2,6-difluorophenoxy)-4-methylpyridin-3-yl]pyrazole-4-carbonyl]-5-(2,2-difluoroethoxy)-1H-indol-6-yl]-3-methoxybenzenesulfonamide | 711 | 1.30 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-328 | 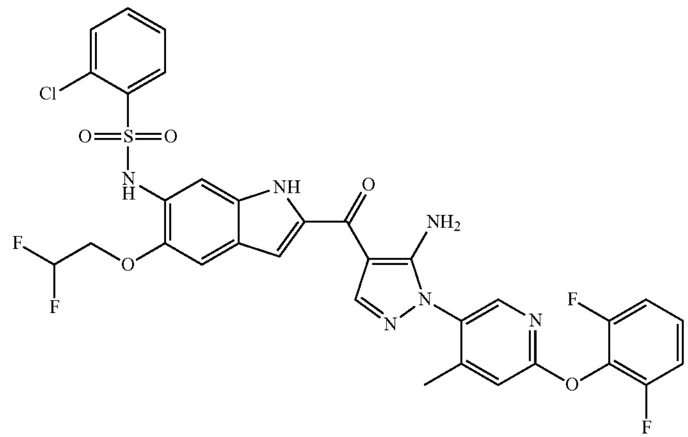 [SMILES: Cc1cc(Oc2c(F)cccc2F)ncc1-n1ncc(C(=O)c2cc3cc(OCC(F)F)c(NS(=O)(=O)c4ccccc4Cl)cc3[nH]2)c1N] | N-[2-[5-amino-1-[6-(2,6-difluorophenoxy)-4-methylpyridin-3-yl]pyrazole-4-carbonyl]-5-(2,2-difluoroethoxy)-1H-indol-6-yl]-2-chlorobenzenesulfonamide | 715, 717 | 1.33 | TFA Rev.7 |
| 5-1-329 | 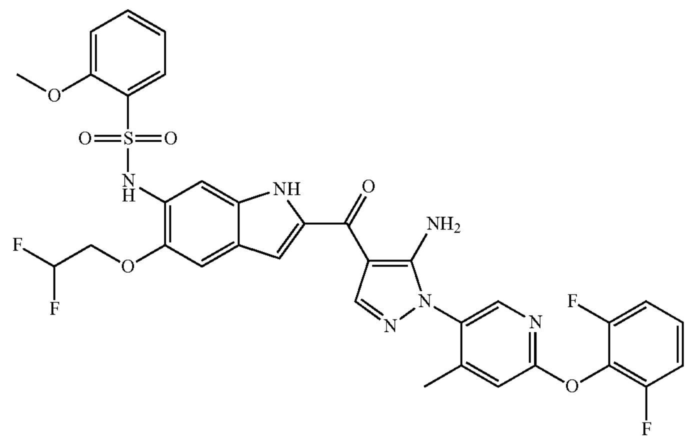 [SMILES: COc1ccccc1S(=O)(=O)Nc1cc2[nH]c(C(=O)c3cnn(-c4cnc(Oc5c(F)cccc5F)cc4C)c3N)cc2cc1OCC(F)F] | N-[2-[5-amino-1-[6-(2,6-difluorophenoxy)-4-methylpyridin-3-yl]pyrazole-4-carbonyl]-5-(2,2-difluoroethoxy)-1H-indol-6-yl]-2-methoxybenzenesulfonamide | 711 | 1.29 | TFA Rev.7 |

| Example No. | Chemical Structure | Compound Name | m/z (M + H) | Reaction Time (Minute) | LCMS Measurement Condition |
|---|---|---|---|---|---|
| 5-1-330 | 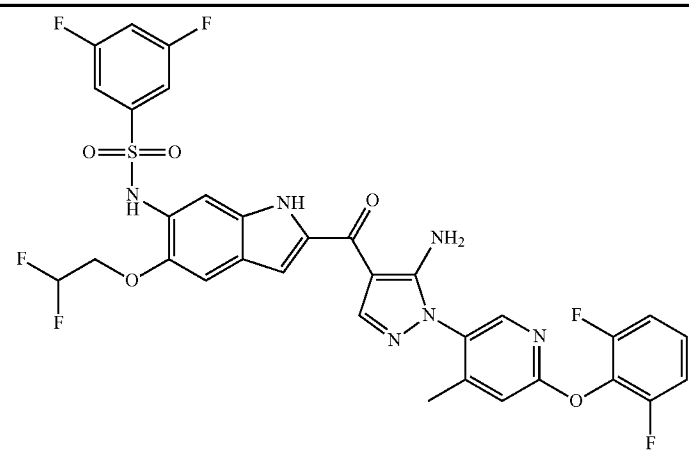 | N-[2-[5-amino-1-[6-(2,6-difluorophenoxy)-4-methylpyridin-3-yl]pyrazole-4-carbonyl]-5-(2,2-difluoroethoxy)-1H-indol-6-yl]-3,5-difluorobenzenesulfonamide | 717 | 1.32 | TFA Rev.7 |
| 5-1-331 | 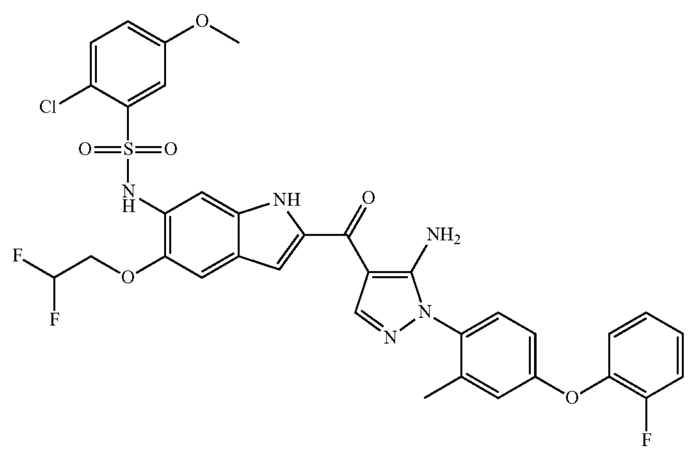 [SMILES: COc1ccc(Cl)c(S(=O)(=O)Nc2cc3[nH]c(C(=O)c4cnn(-c5ccc(Oc6ccccc6F)cc5C)c4N)cc3cc2OCC(F)F)c1] | N-[2-[5-amino-1-[4-(2-fluorophenoxy)-2-methylphenyl]pyrazole-4-carbonyl]-5-(2,2-difluoroethoxy)-1H-indol-6-yl]-2-chloro-5-methoxybenzenesulfonamide | 726, 728 | 1.37 | TFA Rev.7 |

| Example No. | Chemical Structure | Compound Name | m/z (M + H) | Reaction Time (Minute) | LCMS Measurement Condition |
|---|---|---|---|---|---|
| 5-1-332 | 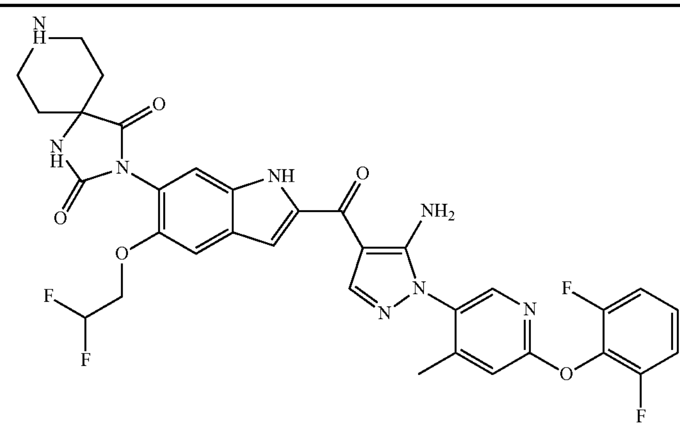 | 3-[2-[5-amino-1-[6-(2,6-difluorophenoxy)-4-methylpyridin-3-yl]pyrazole-4-carbonyl]-5-(2,2-difluoroethoxy)-1H-indol-6-yl]-1,3,8-triazaspiro[4.5]decane-2,4-dione | 693 | 0.92 | TFA Rev.7 |
| 5-1-333 | 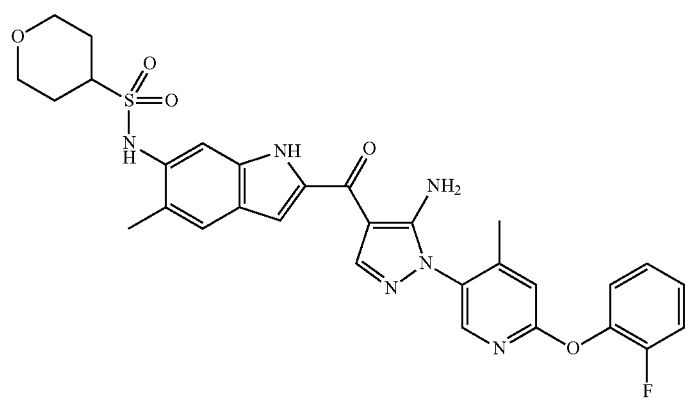 [SMILES: Cc1cc2cc(C(=O)c3cnn(-c4cnc(Oc5ccccc5F)cc4C)c3N)[nH]c2cc1NS(=O)(=O)C1CCOCC1] | N-[2-[5-amino-1-[6-(2-fluorophenoxy)-4-methylpyridin-3-yl]pyrazole-4-carbonyl]-5-methyl-1H-indol-6-yl]oxane-4-sulfonamide | 605 | 0.96 | AA Rev.11 |

| Example No. | Chemical Structure | Compound Name | m/z (M + H) | Reaction Time (Minute) | LCMS Measurement Condition |
|---|---|---|---|---|---|
| 5-1-334 | 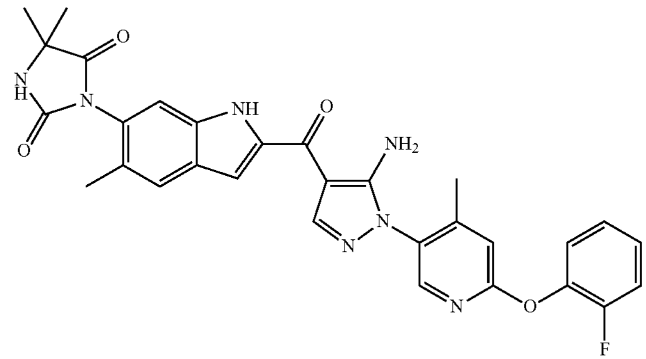 [SMILES: Cc1cc2cc(C(=O)c3cnn(-c4cnc(Oc5ccccc5F)cc4C)c3N)[nH]c2cc1N1C(=O)NC(C)(C)C1=O] | 3-[2-[5-amino-1-[6-(2-fluorophenoxy)-4-methylpyridin-3-yl]pyrazole-4-carbonyl]-5-methyl-1H-indol-6-yl]-5,5-dimethylimidazolidine-2,4-dione | 568 | 1.10 | TFA Rev.7 |
| 5-1-335 | 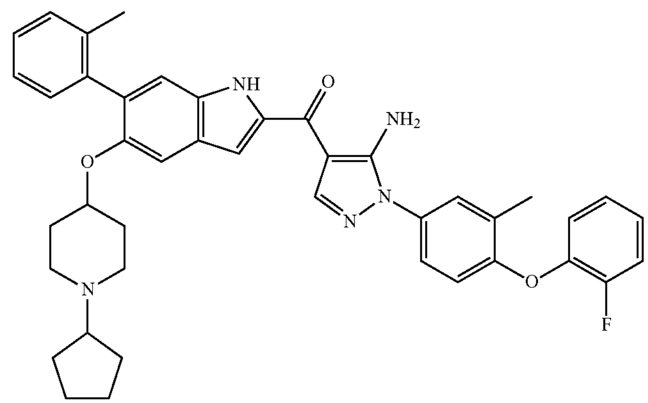 [SMILES: Cc1cc(-n2ncc(C(=O)c3cc4cc(OC5CCN(C6CCCC6)CC5)c(-c5ccccc5C)cc4[nH]3)c2N)ccc1Oc1ccccc1F] | [5-amino-1-[4-(2-fluorophenoxy)-3-methylphenyl]pyrazol-4-yl]-[5-(1-cyclopentylpiperidin-4-yl)oxy-6-(2-methylphenyl)-1H-indol-2-yl]methanone | 684 | 1.19 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-336 | 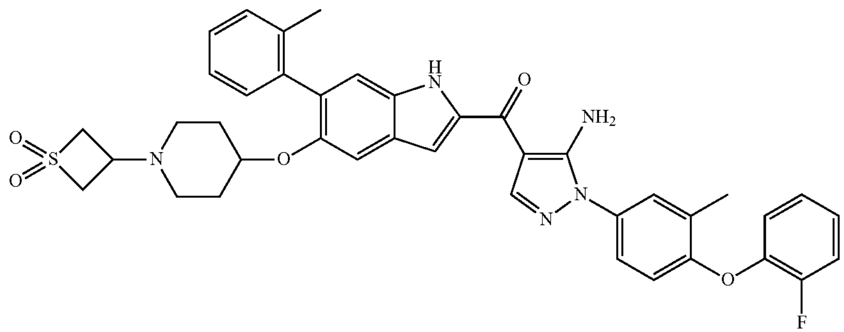 [SMILES: Cc1cc(-n2ncc(C(=O)c3cc4cc(OC5CCN(C6CS(=O)(=O)C6)CC5)c(-c5ccccc5C)cc4[nH]3)c2N)ccc1Oc1ccccc1F] | [5-amino-1-[4-(2-fluorophenoxy)-3-methylphenyl]pyrazol-4-yl]-[5-[1-(1,1-dioxothietan-3-yl)piperidin-4-yl]oxy-6-(2-methylphenyl)-1H-indol-2-yl]methanone | 720 | 1.12 | TFA Rev.7 |
| 5-1-337 | 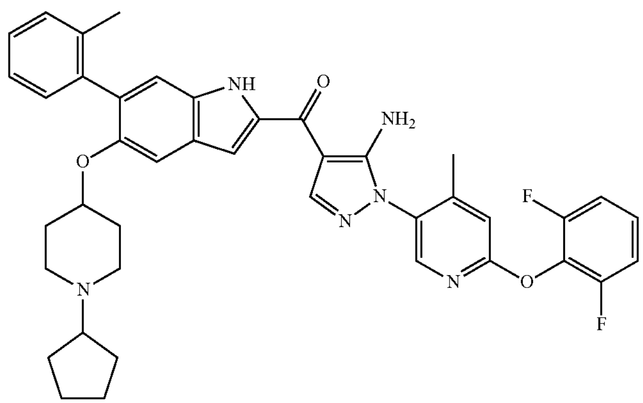 [SMILES: Cc1ccccc1-c1cc2[nH]c(C(=O)c3cnn(-c4cnc(Oc5c(F)cccc5F)cc4C)c3N)cc2cc1OC1CCN(C2CCCC2)CC1] | [5-amino-1-[6-(2,6-difluorophenoxy)-4-methylpyridin-3-yl]pyrazol-4-yl]-[5-(1-cyclopentylpiperidin-4-yl)oxy-6-(2-methylphenyl)-1H-indol-2-yl]methanone | 703 | 1.12 | TFA Rev.7 |

| Example No. | Chemical Structure | Compound Name | m/z (M + H) | Reaction Time (Minute) | LCMS Measurement Condition |
|---|---|---|---|---|---|
| 5-1-338 | 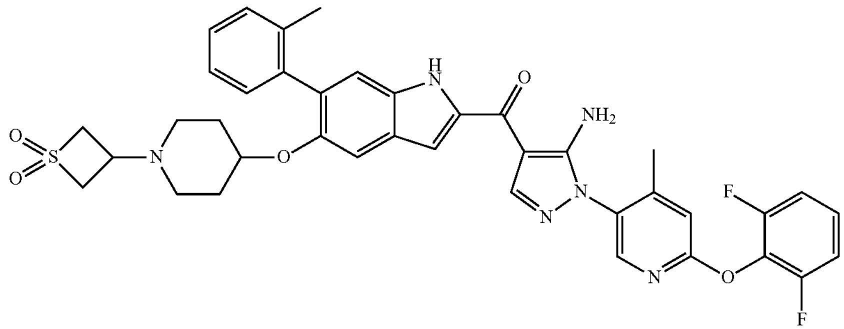 [SMILES: Cc1ccccc1-c1cc2[nH]c(C(=O)c3cnn(-c4cnc(Oc5c(F)cccc5F)cc4C)c3N)cc2cc1OC1CCN(C2CS(=O)(=O)C2)CC1] | [5-amino-1-[6-(2,6-difluorophenoxy)-4-methylpyridin-3-yl]pyrazol-4-yl]-[5-[1-(1,1-dioxothietan-3-yl)piperidin-4-yl]oxy-6-(2-methylphenyl)-1H-indol-2-yl]methanone | 739 | 1.05 | TFA Rev.7 |
| 5-1-339 | 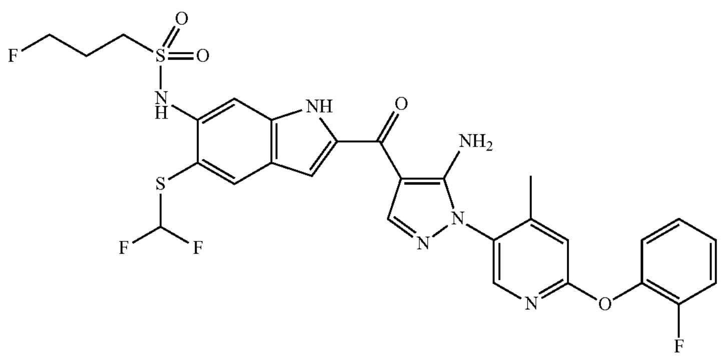 [SMILES: Cc1cc(Oc2ccccc2F)ncc1-n1ncc(C(=O)c2cc3cc(SC(F)F)c(NS(=O)(=O)CCCF)cc3[nH]2)c1N] | N-[2-[5-amino-1-[6-(2-fluorophenoxy)-4-methylpyridin-3-yl]pyrazole-4-carbonyl]-5-(difluoromethylsulfanyl)-1H-indol-6-yl]-3-fluoropropane-1-sulfonamide | 649 | 1.00 | AA Rev.11 |
| 5-1-340 | 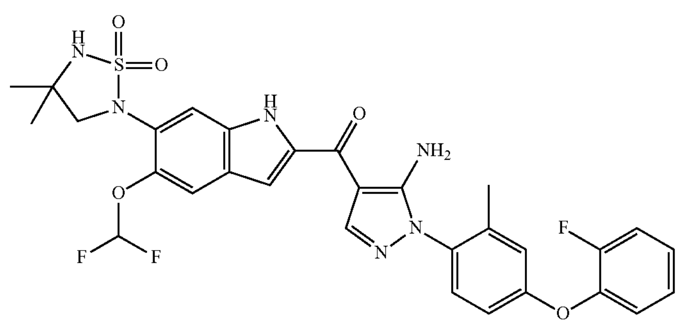 [SMILES: Cc1cc(Oc2ccccc2F)ccc1-n1ncc(C(=O)c2cc3cc(OC(F)F)c(N4CC(C)(C)NS4(=O)=O)cc3[nH]2)c1N] | [5-amino-1-[4-(2-fluorophenoxy)-2-methylphenyl]pyrazol-4-yl]-[5-(difluoromethoxy)-6-(4,4-dimethyl-1,1-dioxo-1,2,5-thiadiazolidin-2-yl)-1H-indol-2-yl]methanone | 641 | 1.30 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-341 | 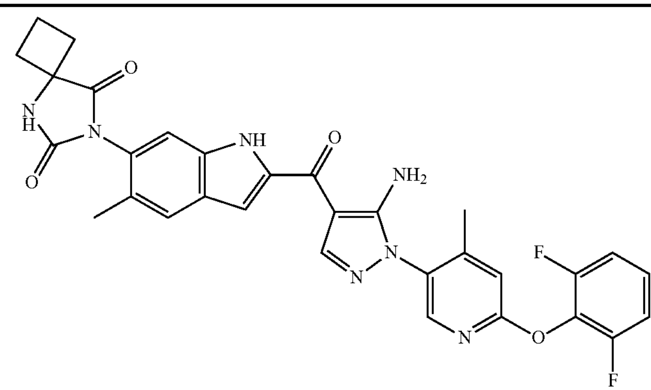 | 7-[2-[5-amino-1-[6-(2,6-difluorophenoxy)-4-methylpyridin-3-yl]pyrazole-4-carbonyl]-5-methyl-1H-indol-6-yl]-5,7-diazaspiro[3.4]octane-6,8-dione | 598 | 0.99 | AA Rev.11 |
| 5-1-342 | 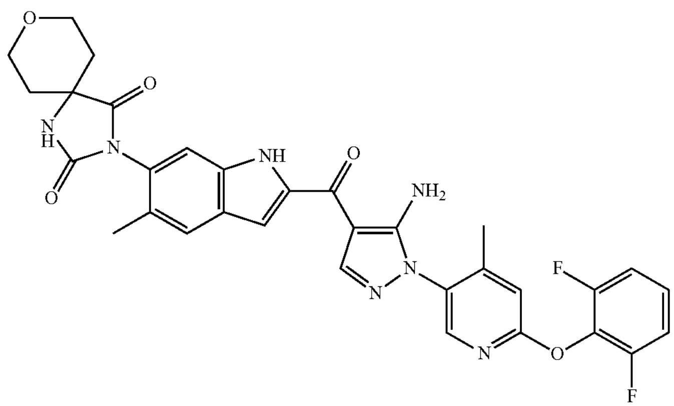 | 3-[2-[5-amino-1-[6-(2,6-difluorophenoxy)-4-methylpyridin-3-yl]pyrazole-4-carbonyl]-5-methyl-1H-indol-6-yl]-8-oxa-1,3-diazaspiro[4.5]decane-2,4-dione | 628 | 0.96 | AA Rev.11 |

| Example No. | Chemical Structure | Compound Name | m/z (M + H) | Reaction Time (Minute) | LCMS Measurement Condition |
|---|---|---|---|---|---|
| 5-1-343 | 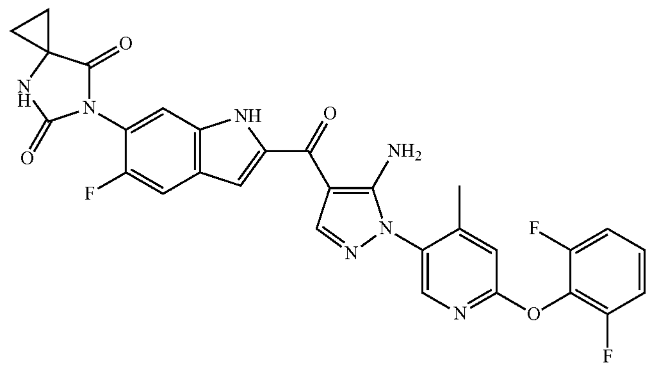 | 6-[2-[5-amino-1-[6-(2,6-difluorophenoxy)-4-methylpyridin-3-yl]pyrazole-4-carbonyl]-5-fluoro-1H-indol-6-yl]-4,6-diazaspiro[2.4]heptane-5,7-dione | 588 | 1.09 | TFA Rev.7 |
| 5-1-344 | 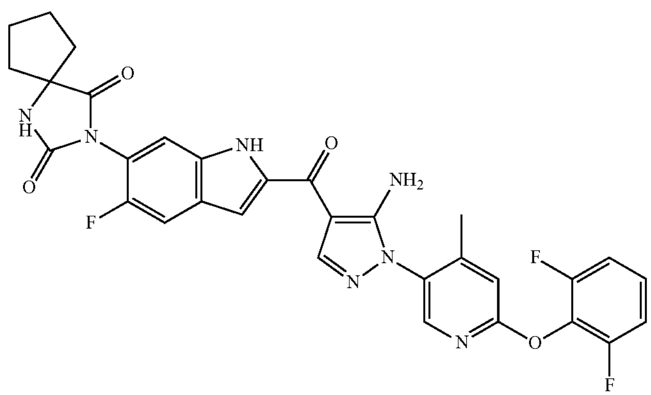 [SMILES: Cc1cc(Oc2c(F)cccc2F)ncc1-n1ncc(C(=O)c2cc3cc(F)c(N4C(=O)NC5(CCCC5)C4=O)cc3[nH]2)c1N] | 3-[2-[5-amino-1-[6-(2,6-difluorophenoxy)-4-methylpyridin-3-yl]pyrazole-4-carbonyl]-5-fluoro-1H-indol-6-yl]-1,3-diazaspiro[4.4]nonane-2,4-dione | 616 | 1.18 | TFA Rev.7 |

| Example No. | Chemical Structure | Compound Name | m/z (M + H) | Reaction Time (Minute) | LCMS Measurement Condition |
|---|---|---|---|---|---|
| 5-1-345 | 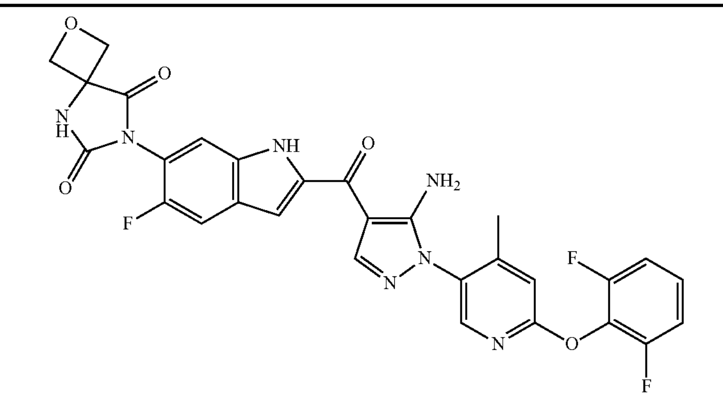 | 7-[2-[5-amino-1-[6-(2,6-difluorophenoxy)-4-methylpyridin-3-yl]pyrazole-4-carbonyl]-5-fluoro-1H-indol-6-yl]-2-oxa-5,7-diazaspiro[3.4]octane-6,8-dione | 604 | 1.06 | TFA Rev.7 |
| 5-1-346 | 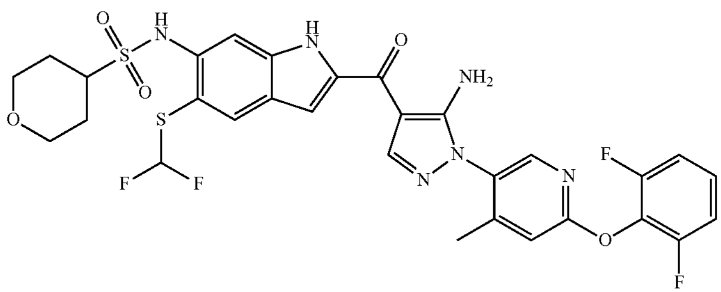 [SMILES: Cc1cc(Oc2c(F)cccc2F)ncc1-n1ncc(C(=O)c2cc3cc(SC(F)F)c(NS(=O)(=O)C4CCOCC4)cc3[nH]2)c1N] | N-[2-[5-amino-1-[6-(2,6-difluorophenoxy)-4-methylpyridin-3-yl]pyrazole-4-carbonyl]-5-(difluoromethylsulfanyl)-1H-indol-6-yl]oxane-4-sulfonamide | 691 | 1.02 | AA Rev.11 |
| 5-1-347 | 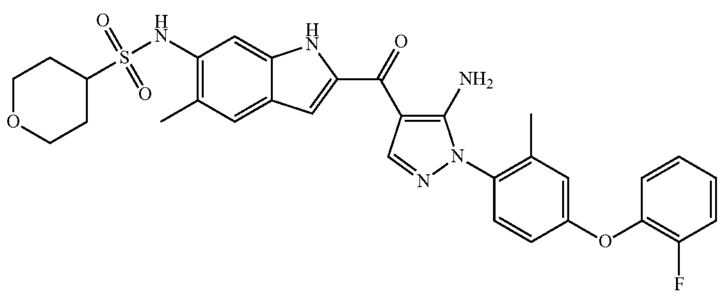 | N-[2-[5-amino-1-[4-(2-fluorophenoxy)-2-methylphenyl]pyrazole-4-carbonyl]-5-methyl-1H-indol-6-yl]oxane-4-sulfonamide | 604 | 1.20 | TFA Rev.7 |

| Example No. | Chemical Structure | Compound Name | m/z (M + H) | Reaction Time (Minute) | LCMS Measurement Condition |
|---|---|---|---|---|---|
| 5-1-348 | 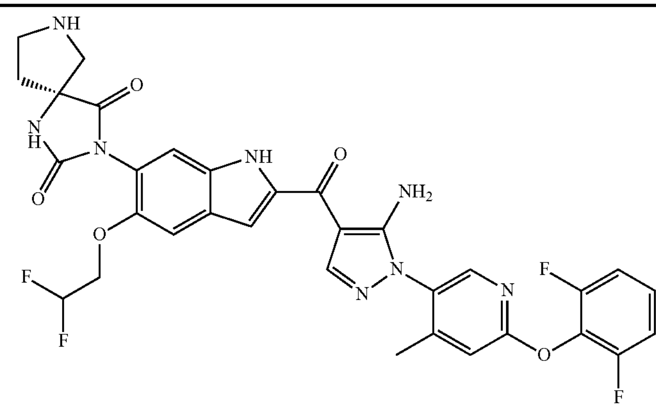 | (5S)-3-[2-[5-amino-1-[6-(2,6-difluorophenoxy)-4-methylpyridin-3-yl]pyrazole-4-carbonyl]-5-(2,2-difluoroethoxy)-1H-indol-6-yl]-1,3,7-triazaspiro[4.4]nonane-2,4-dione | 679 | 0.92 | TFA Rev.7 |
| 5-1-349 | 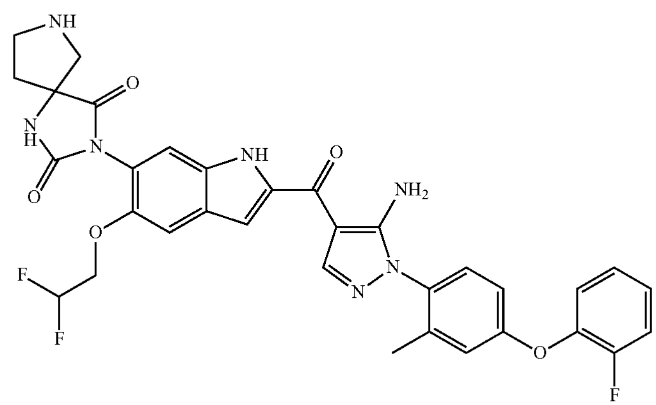 [SMILES: Cc1cc(Oc2ccccc2F)ccc1-n1ncc(C(=O)c2cc3cc(OCC(F)F)c(N4C(=O)NC5(CCNC5)C4=O)cc3[nH]2)c1N] | 3-[2-[5-amino-1-[4-(2-fluorophenoxy)-2-methylphenyl]pyrazole-4-carbonyl]-5-(2,2-difluoroethoxy)-1H-indol-6-yl]-1,3,7-triazaspiro[4.4]nonane-2,4-dione | 660 | 0.94 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-350 | 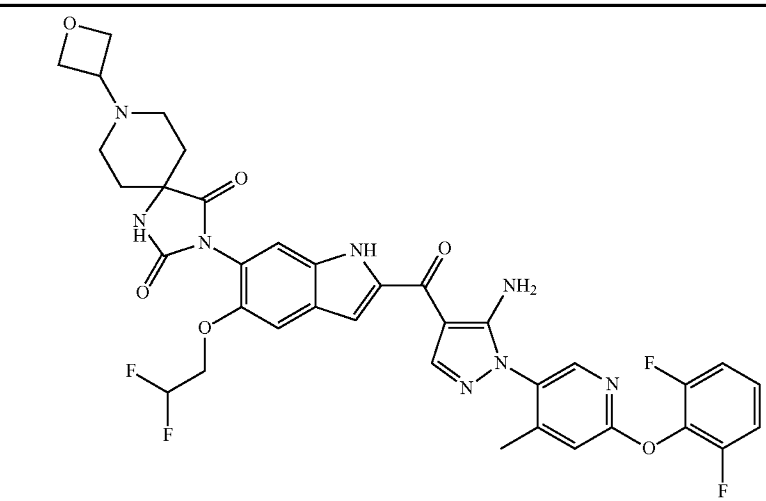 | 3-[2-[5-amino-1-[6-(2,6-difluorophenoxy)-4-methylpyridin-3-yl]pyrazole-4-carbonyl]-5-(2,2-difluoroethoxy)-1H-indol-6-yl]-8-(oxetan-3-yl)-1,3,8-triazaspiro[4.5]decane-2,4-dione | 749 | 0.93 | TFA Rev.7 |
| 5-1-351 | 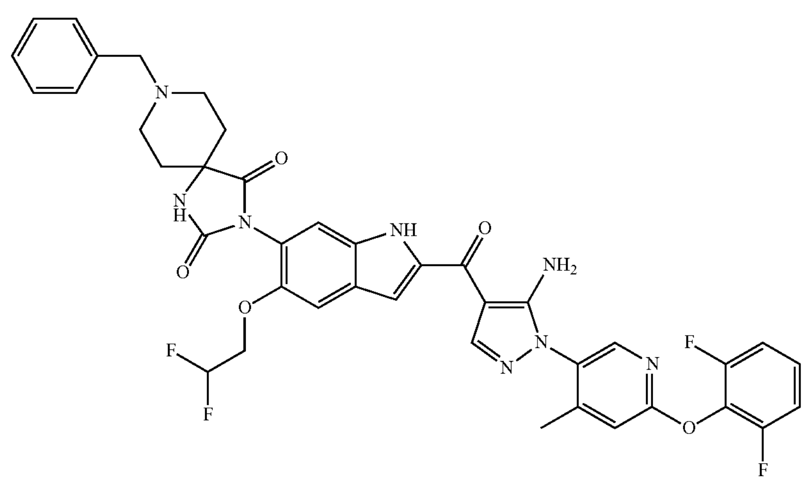 [SMILES: Cc1cc(Oc2c(F)cccc2F)ncc1-n1ncc(C(=O)c2cc3cc(OCC(F)F)c(N4C(=O)NC5(CCN(Cc6ccccc6)CC5)C4=O)cc3[nH]2)c1N] | 3-[2-[5-amino-1-[6-(2,6-difluorophenoxy)-4-methylpyridin-3-yl]pyrazole-4-carbonyl]-5-(2,2-difluoroethoxy)-1H-indol-6-yl]-8-benzyl-1,3,8-triazaspiro[4.5]decane-2,4-dione | 783 | 1.01 | TFA Rev.7 |

| Example No. | Chemical Structure | Compound Name | m/z (M + H) | Reaction Time (Minute) | LCMS Measurement Condition |
|---|---|---|---|---|---|
| 5-1-352 | 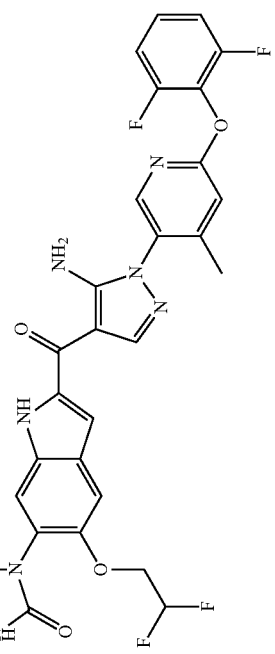 | 3-[2-[5-amino-1-[6-(2,6-difluorophenoxy)-4-methylpyridin-3-yl]pyrazole-4-carbonyl]-5-(2,2-difluoroethoxy)-1H-indol-6-yl]-7-(oxetan-3-yl)-1,3,7-triazaspiro[4.4]nonane-2,4-dione | 735 | 0.93 | TFA Rev.7 |
| 5-1-353 | 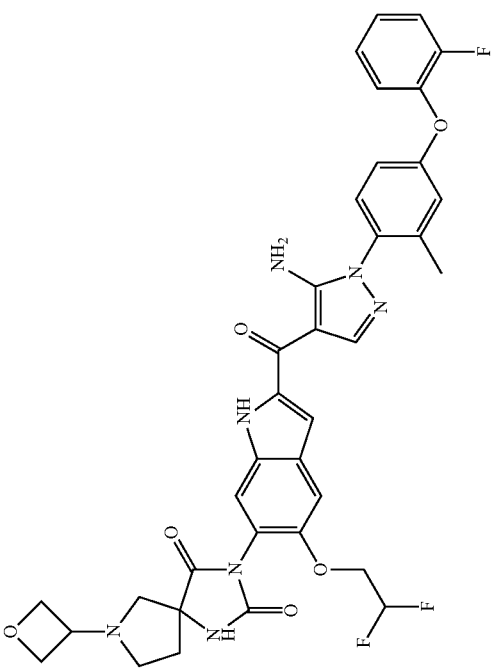 | 3-[2-[5-amino-1-[4-(2-fluorophenoxy)-2-methylphenyl]pyrazole-4-carbonyl]-5-(2,2-difluoroethoxy)-1H-indol-6-yl]-7-(oxetan-3-yl)-1,3,7-triazaspiro[4.4]nonane-2,4-dione | 716 | 0.96 | TFA Rev.7 |

| Example No. | Chemical Structure | Compound Name | m/z (M + H) | Reaction Time (Minute) | LCMS Measurement Condition |
|---|---|---|---|---|---|
| 5-1-354 | 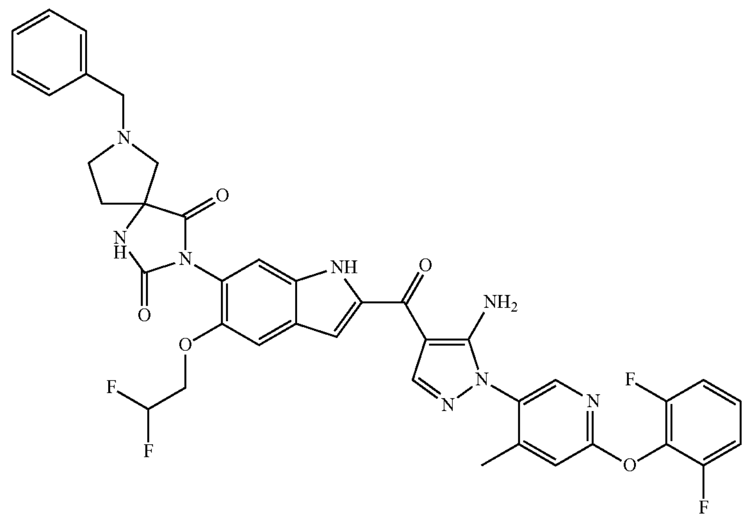 [SMILES: Cc1cc(Oc2c(F)cccc2F)ncc1-n1ncc(C(=O)c2cc3cc(OCC(F)F)c(N4C(=O)NC5(CCN(Cc6ccccc6)C5)C4=O)cc3[nH]2)c1N] | 3-[2-[5-amino-1-[6-(2,6-difluorophenoxy)-4-methylpyridin-3-yl]pyrazole-4-carbonyl]-5-(2,2-difluoroethoxy)-1H-indol-6-yl]-7-benzyl-1,3,7-triazaspiro[4.4]nonane-2,4-dione | 769 | 1.02 | TFA Rev.7 |
| 5-1-355 | 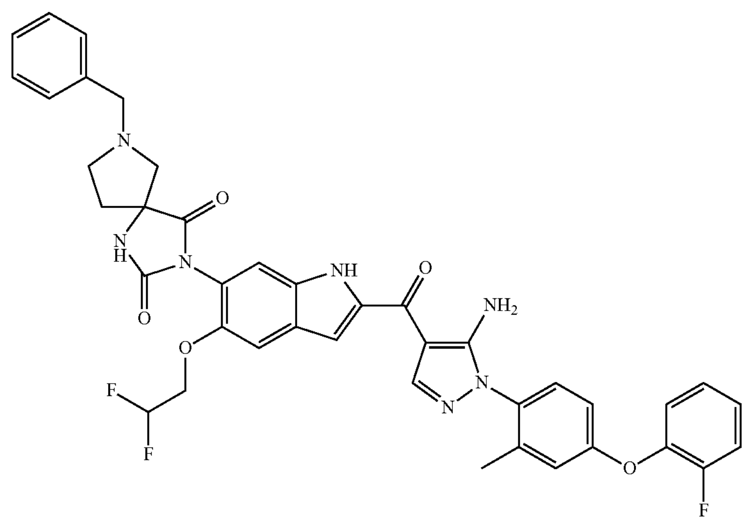 [SMILES: Cc1cc(Oc2ccccc2F)ccc1-n1ncc(C(=O)c2cc3cc(OCC(F)F)c(N4C(=O)NC5(CCN(Cc6ccccc6)C5)C4=O)cc3[nH]2)c1N] | 3-[2-[5-amino-1-[4-(2-fluorophenoxy)-2-methylphenyl]pyrazole-4-carbonyl]-5-(2,2-difluoroethoxy)-1H-indol-6-yl]-7-benzyl-1,3,7-triazaspiro[4.4]nonane-2,4-dione | 750 | 1.04 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-356 | 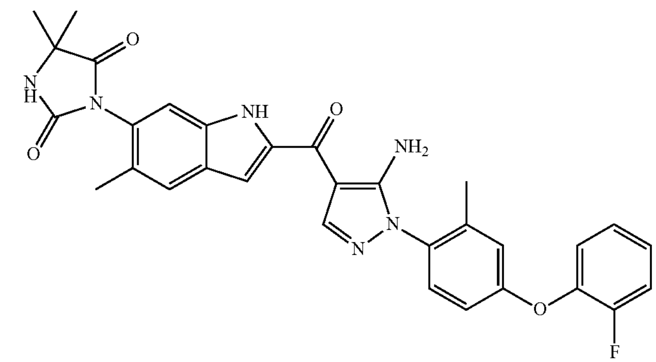 [SMILES: Cc1cc2cc(C(=O)c3cnn(-c4ccc(Oc5ccccc5F)cc4C)c3N)[nH]c2cc1N1C(=O)NC(C)(C)C1=O] | 3-[2-[5-amino-1-[4-(2-fluorophenoxy)-2-methylphenyl]pyrazole-4-carbonyl]-5-methyl-1H-indol-6-yl]-5,5-dimethylimidazolidine-2,4-dione | 567 | 0.99 | AA Rev.11 |
| 5-1-357 | 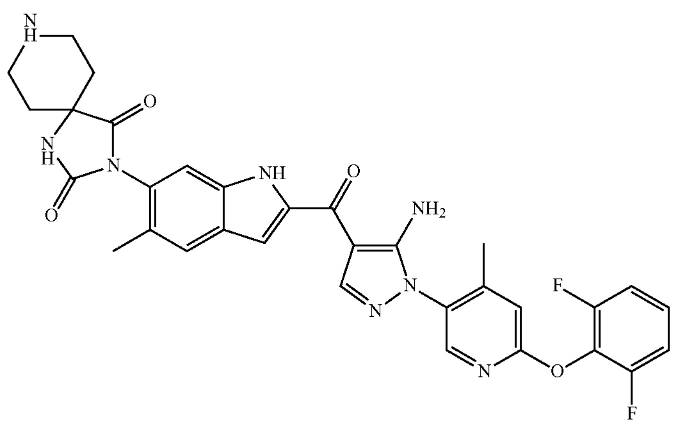 [SMILES: Cc1cc2cc(C(=O)c3cnn(-c4cnc(Oc5c(F)cccc5F)cc4C)c3N)[nH]c2cc1N1C(=O)NC2(CCNCC2)C1=O] | 3-[2-[5-amino-1-[6-(2,6-difluorophenoxy)-4-methylpyridin-3-yl]pyrazole-4-carbonyl]-5-methyl-1H-indol-6-yl]-1,3,8-triazaspiro[4.5]decane-2,4-dione | 627 | 0.91 | TFA Rev.7 |

| Example No. | Chemical Structure | Compound Name | m/z (M + H) | Reaction Time (Minute) | LCMS Measurement Condition |
|---|---|---|---|---|---|
| 5-1-358 | 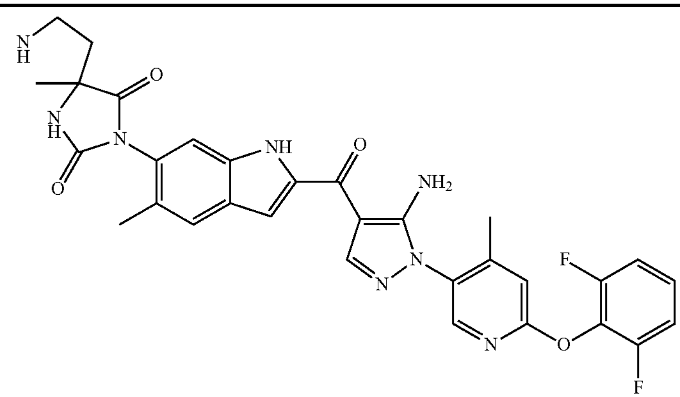 | 3-[2-[5-amino-1-[6-(2,6-difluorophenoxy)-4-methylpyridin-3-yl]pyrazole-4-carbonyl]-5-methyl-1H-indol-6-yl]-1,3,7-triazaspiro[4.4]nonane-2,4-dione | 613 | 0.91 | TFA Rev.7 |
| 5-1-359 | 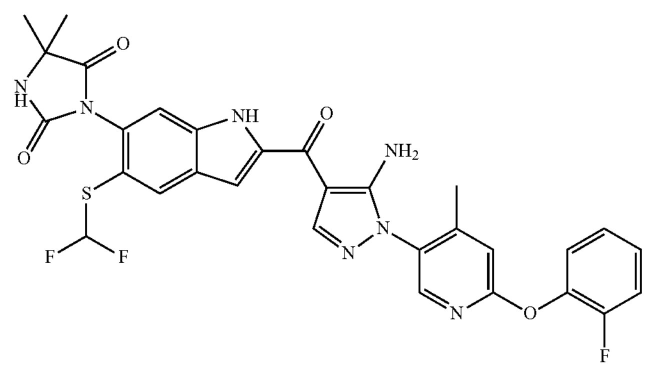 | 3-[2-[5-amino-1-[6-(2-fluorophenoxy)-4-methylpyridin-3-yl]pyrazole-4-carbonyl]-5-(difluoromethylsulfanyl)-1H-indol-6-yl]-5,5-dimethylimidazolidine-2,4-dione | 636 | 1.16 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-360 | 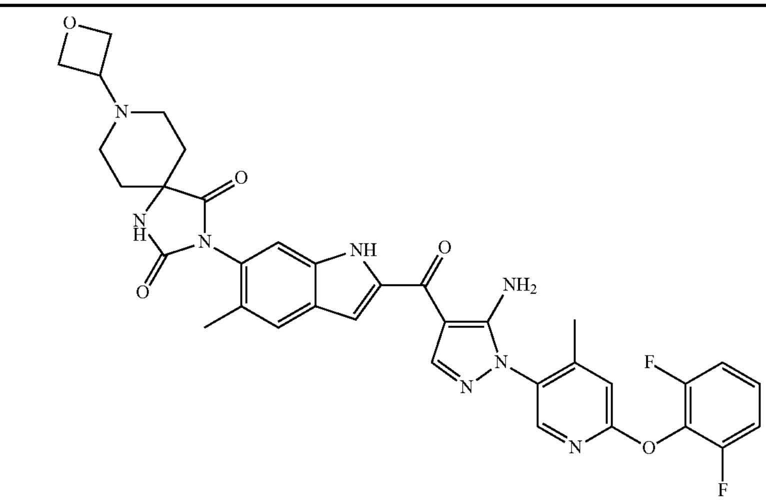 | 3-[2-[5-amino-1-[6-(2,6-difluorophenoxy)-4-methylpyridin-3-yl]pyrazole-4-carbonyl]-5-methyl-1H-indol-6-yl]-8-(oxetan-3-yl)-1,3,8-triazaspiro[4.5]decane-2,4-dione | 683 | 0.92 | TFA Rev.7 |
| 5-1-361 | 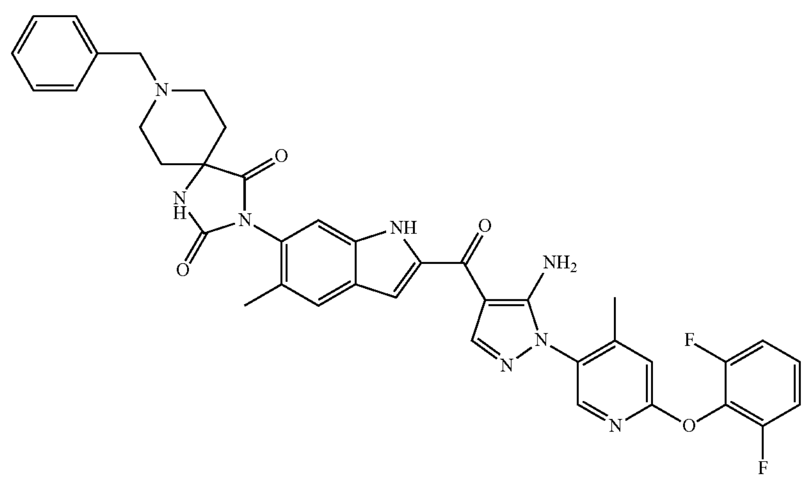 [SMILES: Cc1cc2cc(C(=O)c3cnn(-c4cnc(Oc5c(F)cccc5F)cc4C)c3N)[nH]c2cc1N1C(=O)NC2(CCN(Cc3ccccc3)CC2)C1=O] | 3-[2-[5-amino-1-[6-(2,6-difluorophenoxy)-4-methylpyridin-3-yl]pyrazole-4-carbonyl]-5-methyl-1H-indol-6-yl]-8-benzyl-1,3,8-triazaspiro[4.5]decane-2,4-dione | 717 | 1.00 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-362 | 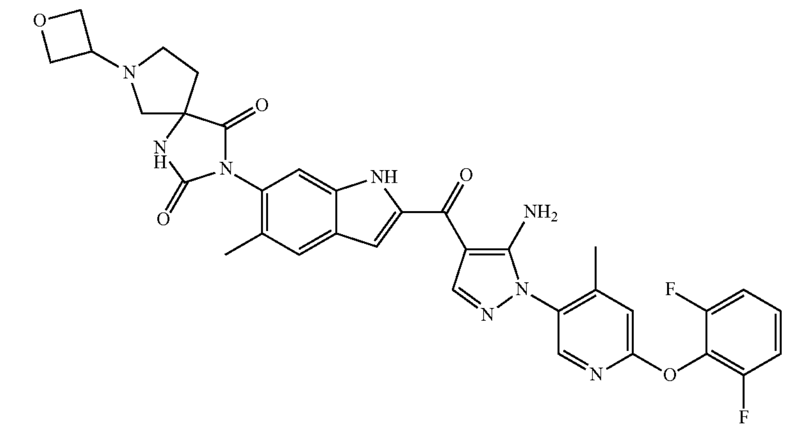 [SMILES: Cc1cc2cc(C(=O)c3cnn(-c4cnc(Oc5c(F)cccc5F)cc4C)c3N)[nH]c2cc1N1C(=O)NC2(CCN(C3COC3)C2)C1=O] | 3-[2-[5-amino-1-[6-(2,6-difluorophenoxy)-4-methylpyridin-3-yl]pyrazole-4-carbonyl]-5-methyl-1H-indol-6-yl]-7-(oxetan-3-yl)-1,3,7-triazaspiro[4.4]nonane-2,4-dione | 669 | 0.92 | TFA Rev.7 |
| 5-1-363 | 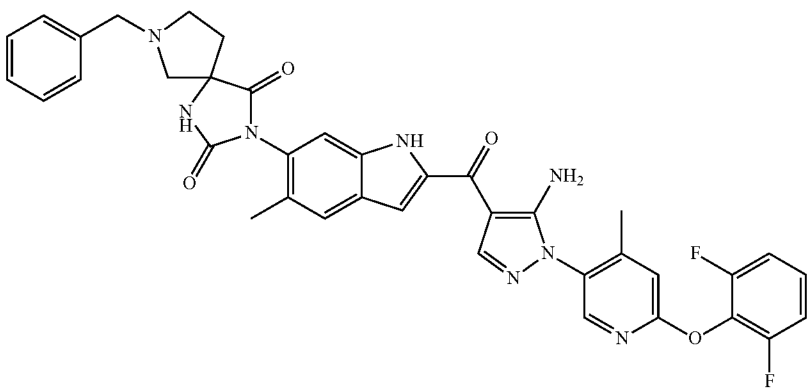 [SMILES: Cc1cc2cc(C(=O)c3cnn(-c4cnc(Oc5c(F)cccc5F)cc4C)c3N)[nH]c2cc1N1C(=O)NC2(CCN(Cc3ccccc3)C2)C1=O] | 3-[2-[5-amino-1-[6-(2,6-difluorophenoxy)-4-methylpyridin-3-yl]pyrazole-4-carbonyl]-5-methyl-1H-indol-6-yl]-7-benzyl-1,3,7-triazaspiro[4.4]nonane-2,4-dione | 703 | 1.07 | AA Rev.11 |

| Example No. | Chemical Structure | Compound Name | m/z (M + H) | Reaction Time (Minute) | LCMS Measurement Condition |
|---|---|---|---|---|---|
| 5-1-364 | 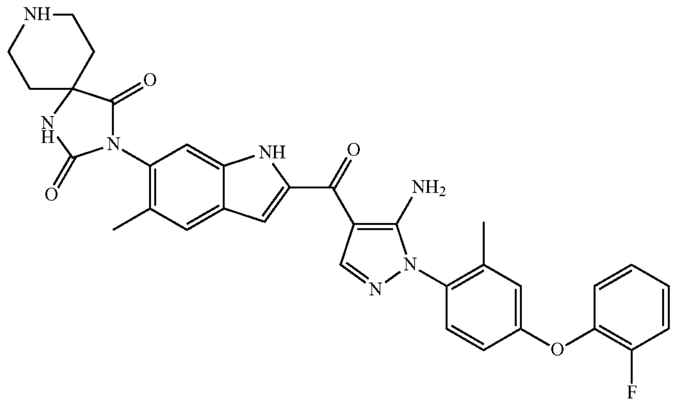 [SMILES: Cc1cc2cc(C(=O)c3cnn(-c4ccc(Oc5ccccc5F)cc4C)c3N)[nH]c2cc1N1C(=O)NC2(CCNCC2)C1=O] | 3-[2-[5-amino-1-[4-(2-fluorophenoxy)-2-methylphenyl]pyrazole-4-carbonyl]-5-methyl-1H-indol-6-yl]-1,3,8-triazaspiro[4.5]decane-2,4-dione | 608 | 0.94 | TFA Rev.7 |
| 5-1-365 | 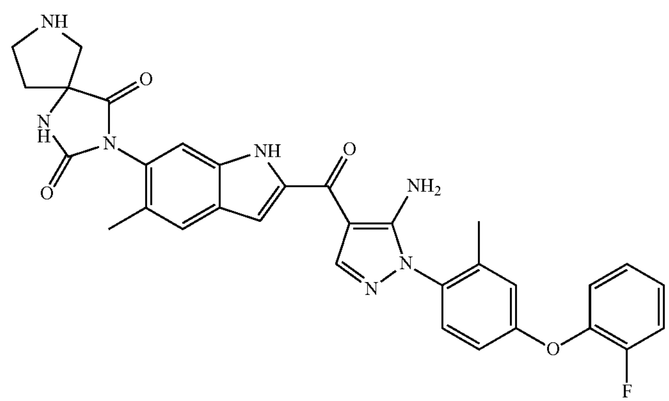 [SMILES: Cc1cc2cc(C(=O)c3cnn(-c4ccc(Oc5ccccc5F)cc4C)c3N)[nH]c2cc1N1C(=O)NC2(CCNC2)C1=O] | 3-[2-[5-amino-1-[4-(2-fluorophenoxy)-2-methylphenyl]pyrazole-4-carbonyl]-5-methyl-1H-indol-6-yl]-1,3,7-triazaspiro[4.4]nonane-2,4-dione | 594 | 0.94 | TFA Rev.7 |

| Example No. | Chemical Structure | Compound Name | m/z (M + H) | Reaction Time (Minute) | LCMS Measurement Condition |
|---|---|---|---|---|---|
| 5-1-366 | 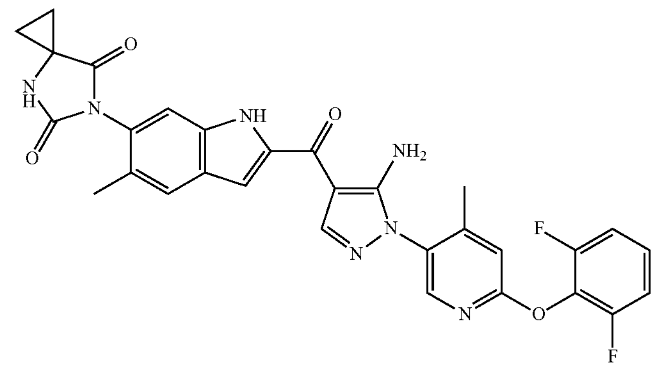 [SMILES: Cc1cc2cc(C(=O)c3cnn(-c4cnc(Oc5c(F)cccc5F)cc4C)c3N)[nH]c2cc1N1C(=O)NC2(CC2)C1=O] | 6-[2-[5-amino-1-[6-(2,6-difluorophenoxy)-4-methylpyridin-3-yl]pyrazole-4-carbonyl]-5-methyl-1H-indol-6-yl]-4,6-diazaspiro[2.4]heptane-5,7-dione | 584 | 1.10 | TFA Rev.7 |
| 5-1-367 | 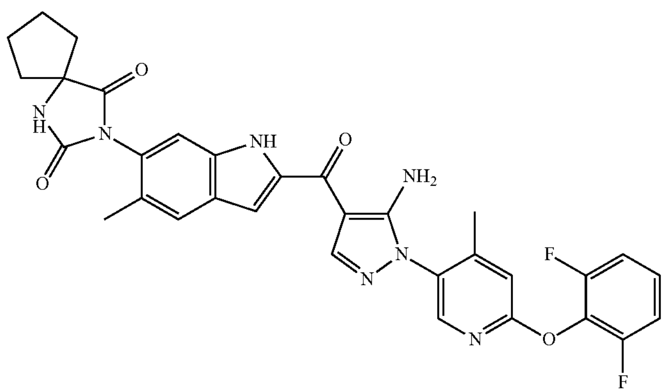 [SMILES: Cc1cc2cc(C(=O)c3cnn(-c4cnc(Oc5c(F)cccc5F)cc4C)c3N)[nH]c2cc1N1C(=O)NC2(CCCC2)C1=O] | 3-[2-[5-amino-1-[6-(2,6-difluorophenoxy)-4-methylpyridin-3-yl]pyrazole-4-carbonyl]-5-methyl-1H-indol-6-yl]-1,3-diazaspiro[4.4]nonane-2,4-dione | 612 | 1.19 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-368 | 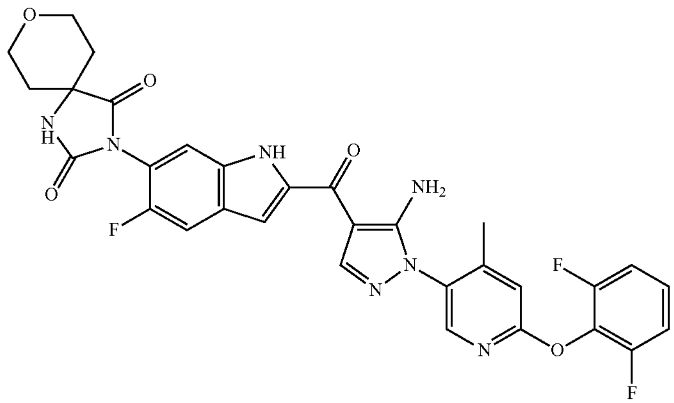 [SMILES: Cc1cc(Oc2c(F)cccc2F)ncc1-n1ncc(C(=O)c2cc3cc(F)c(N4C(=O)NC5(CCOCC5)C4=O)cc3[nH]2)c1N] | 3-[2-[5-amino-1-[6-(2,6-difluorophenoxy)-4-methylpyridin-3-yl]pyrazole-4-carbonyl]-5-fluoro-1H-indol-6-yl]-8-oxa-1,3-diazaspiro[4.5]decane-2,4-dione | 632 | 1.09 | TFA Rev.7 |
| 5-1-369 | 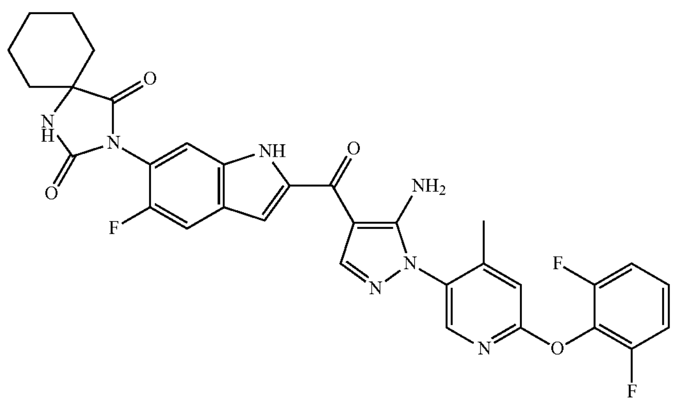 [SMILES: Cc1cc(Oc2c(F)cccc2F)ncc1-n1ncc(C(=O)c2cc3cc(F)c(N4C(=O)NC5(CCCCC5)C4=O)cc3[nH]2)c1N] | 3-[2-[5-amino-1-[6-(2,6-difluorophenoxy)-4-methylpyridin-3-yl]pyrazole-4-carbonyl]-5-fluoro-1H-indol-6-yl]-1,3-diazaspiro[4.5]decane-2,4-dione | 630 | 1.02 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-370 | 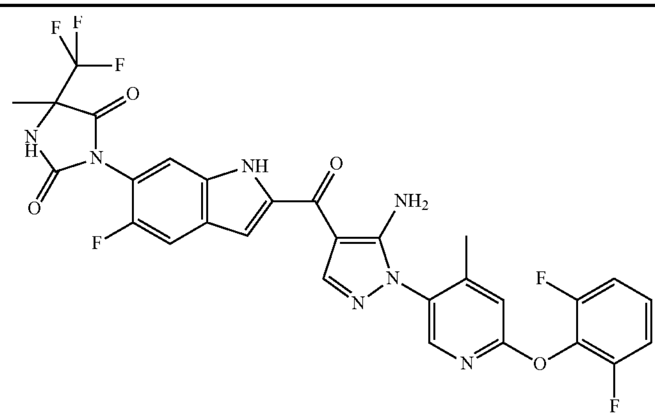 | 3-[2-[5-amino-1-[6-(2,6-difluorophenoxy)-4-methylpyridin-3-yl]pyrazole-4-carbonyl]-5-fluoro-1H-indol-6-yl]-5-methyl-5-(trifluoromethyl)imidazolidine-2,4-dione | 644 | 1.22 | TFA Rev.7 |
| 5-1-371 | 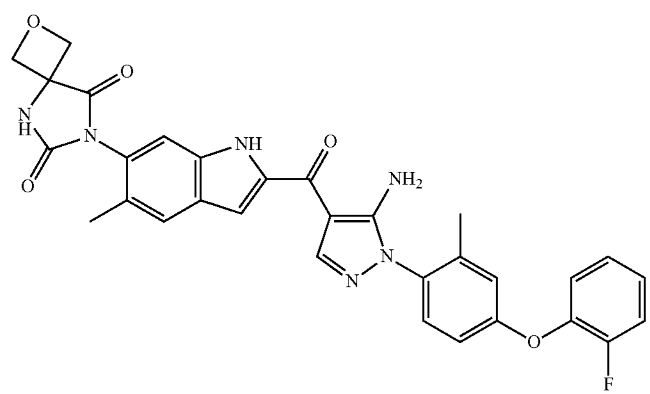 [SMILES: Cc1cc2cc(C(=O)c3cnn(-c4ccc(Oc5ccccc5F)cc4C)c3N)[nH]c2cc1N1C(=O)NC2(COC2)C1=O] | 7-[2-[5-amino-1-[4-(2-fluorophenoxy)-2-methylphenyl]pyrazole-4-carbonyl]-5-methyl-1H-indol-6-yl]-5,7-diazaspiro[3.4]octane-6,8-dione | 579 | 1.19 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-372 | 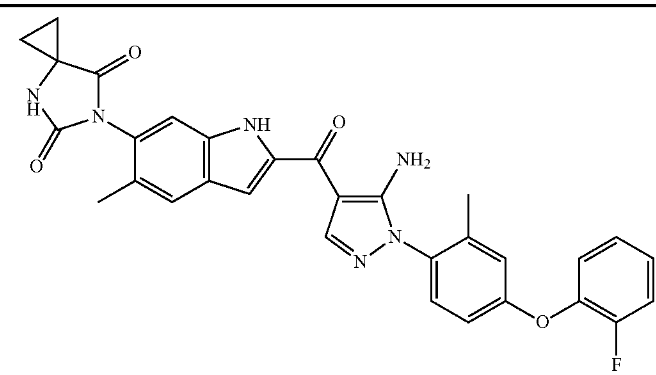 | 6-[2-[5-amino-1-[4-(2-fluorophenoxy)-2-methylphenyl]pyrazole-4-carbonyl]-5-methyl-1H-indol-6-yl]-4,6-diazaspiro[2.4]heptane-5,7-dione | 565 | 1.13 | TFA Rev.7 |
| 5-1-373 | 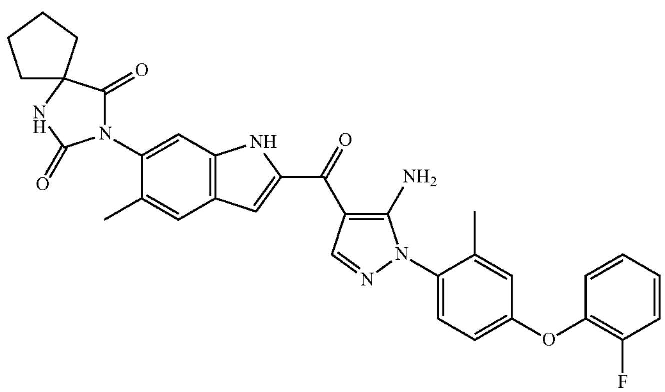 [SMILES: Cc1cc2cc(C(=O)c3cnn(-c4ccc(Oc5ccccc5F)cc4C)c3N)[nH]c2cc1N1C(=O)NC2(CCCC2)C1=O] | 3-[2-[5-amino-1-[4-(2-fluorophenoxy)-2-methylphenyl]pyrazole-4-carbonyl]-5-methyl-1H-indol-6-yl]-1,3-diazaspiro[4.4]nonane-2,4-dione | 593 | 1.22 | TFA Rev.7 |

| Example No. | Chemical Structure | Compound Name | m/z (M + H) | Reaction Time (Minute) | LCMS Measurement Condition |
|---|---|---|---|---|---|
| 5-1-374 | 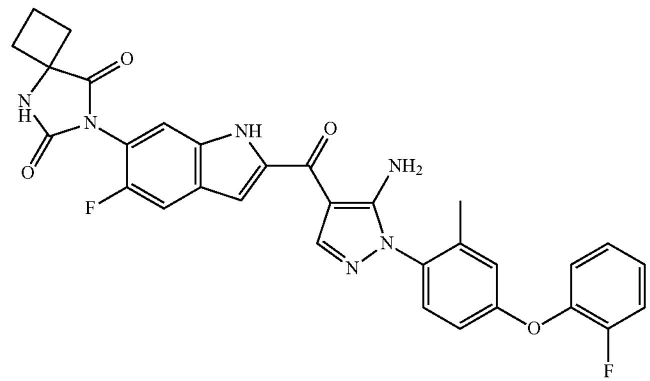 [SMILES: Cc1cc(Oc2ccccc2F)ccc1-n1ncc(C(=O)c2cc3cc(F)c(N4C(=O)NC5(CCC5)C4=O)cc3[nH]2)c1N] | 7-[2-[5-amino-1-[4-(2-fluorophenoxy)-2-methylphenyl]pyrazole-4-carbonyl]-5-fluoro-1H-indol-6-yl]-5,7-diazaspiro[3.4]octane-6,8-dione | 583 | 1.00 | AA Rev.11 |
| 5-1-375 | 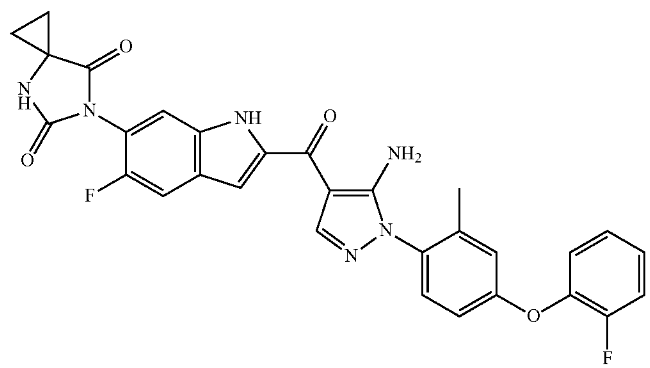 | 6-[2-[5-amino-1-[4-(2-fluorophenoxy)-2-methylphenyl]pyrazole-4-carbonyl]-5-fluoro-1H-indol-6-yl]-4,6-diazaspiro[2.4]heptane-5,7-dione | 569 | 0.98 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-376 | 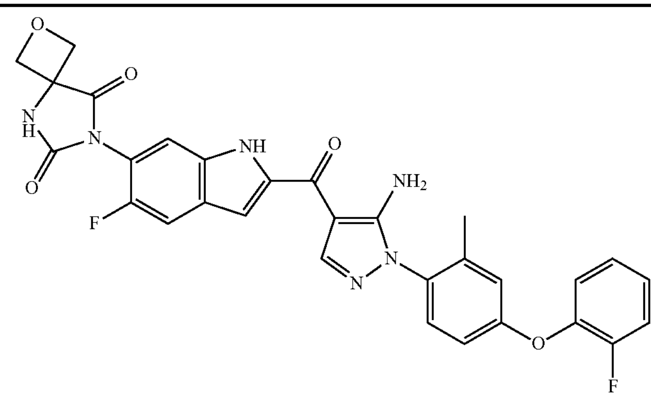 | 7-[2-[5-amino-1-[4-(2-fluorophenoxy)-2-methylphenyl]pyrazole-4-carbonyl]-5-fluoro-1H-indol-6-yl]-2-oxa-5,7-diazaspiro[3.4]octane-6,8-dione | 585 | 0.96 | AA Rev.11 |
| 5-1-377 | 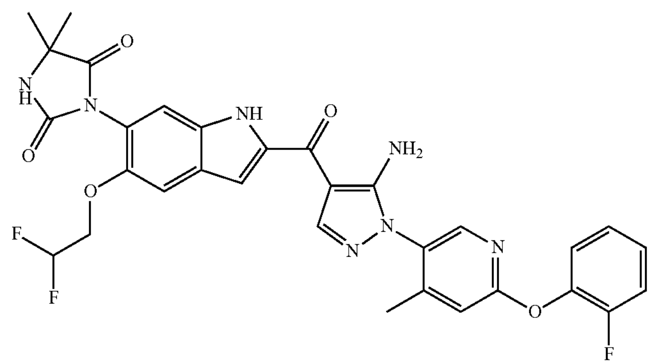 [SMILES: Cc1cc(Oc2ccccc2F)ncc1-n1ncc(C(=O)c2cc3cc(OCC(F)F)c(N4C(=O)NC(C)(C)C4=O)cc3[nH]2)c1N] | 3-[2-[5-amino-1-[6-(2-fluorophenoxy)-4-methylpyridin-3-yl]pyrazole-4-carbonyl]-5-(2,2-difluoroethoxy)-1H-indol-6-yl]-5,5-dimethylimidazolidine-2,4-dione | 634 | 1.10 | TFA Rev.7 |

| Example No. | Chemical Structure | Compound Name | m/z (M + H) | Reaction Time (Minute) | LCMS Measurement Condition |
|---|---|---|---|---|---|
| 5-1-378 | 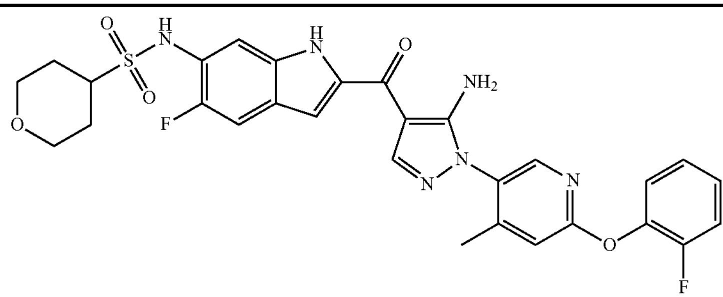 | N-[2-[5-amino-1-[6-(2-fluorophenoxy)-4-methylpyridin-3-yl]pyrazole-4-carbonyl]-5-fluoro-1H-indol-6-yl]oxane-4-sulfonamide | 609 | 1.11 | TFA Rev.7 |
| 5-1-379 | 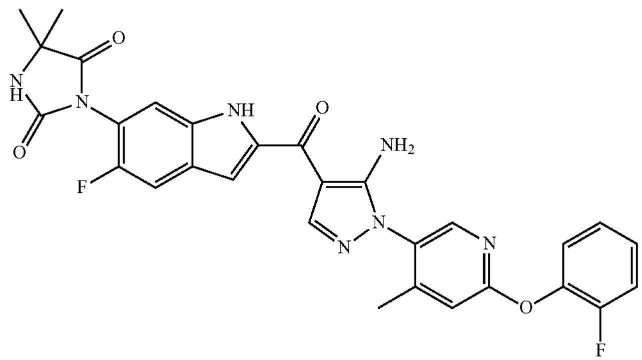 | 3-[2-[5-amino-1-[6-(2-fluorophenoxy)-4-methylpyridin-3-yl]pyrazole-4-carbonyl]-5-fluoro-1H-indol-6-yl]-5,5-dimethylimidazolidine-2,4-dione | 572 | 1.09 | TFA Rev.7 |
| 5-1-380 | 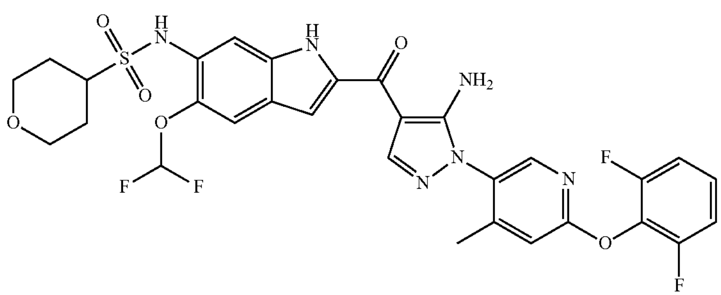 | N-[2-[5-amino-1-[6-(2,6-difluorophenoxy)-4-methylpyridin-3-yl]pyrazole-4-carbonyl]-5-(difluoromethoxy)-1H-indol-6-yl]oxane-4-sulfonamide | 675 | 0.99 | AA Rev.11 |

| Example No. | Chemical Structure | Compound Name | m/z (M + H) | Reaction Time (Minute) | LCMS Measurement Condition |
|---|---|---|---|---|---|
| 5-1-381 | 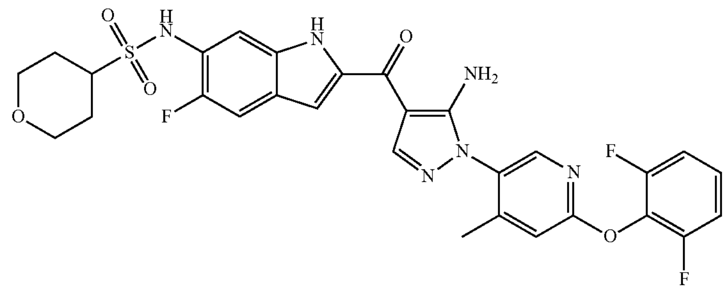 [SMILES: Cc1cc(Oc2ccccc2F)ncc1-n1ncc(C(=O)c2cc3cc(F)c(NS(=O)(=O)C4CCOCC4)cc3[nH]2)c1N] | N-[2-[5-amino-1-[6-(2,6-difluorophenoxy)-4-methylpyridin-3-yl]pyrazole-4-carbonyl]-5-fluoro-1H-indol-6-yl]oxane-4-sulfonamide | 627 | 1.14 | TFA Rev.7 |
| 5-1-382 | 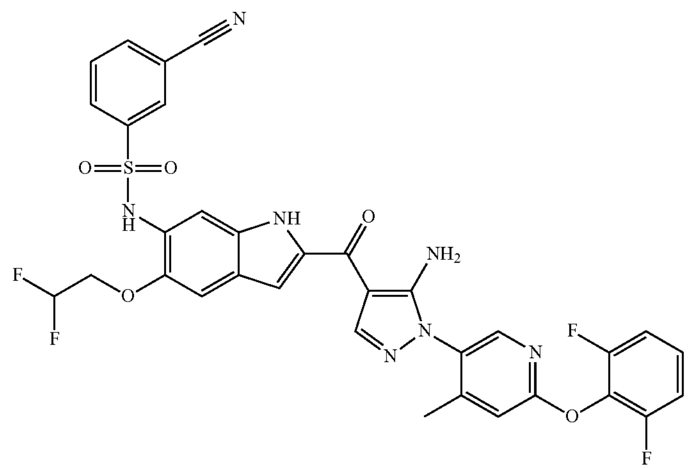 [SMILES: Cc1cc(Oc2c(F)cccc2F)ncc1-n1ncc(C(=O)c2cc3cc(OCC(F)F)c(NS(=O)(=O)c4cccc(C#N)c4)cc3[nH]2)c1N] | N-[2-[5-amino-1-[6-(2,6-difluorophenoxy)-4-methylpyridin-3-yl]pyrazole-4-carbonyl]-5-(2,2-difluoroethoxy)-1H-indol-6-yl]-3-cyanobenzenesulfonamide | 706 | 1.26 | TFA Rev.7 |

| Example No. | Chemical Structure | Compound Name | m/z (M + H) | Reaction Time (Minute) | LCMS Measurement Condition |
|---|---|---|---|---|---|
| 5-1-383 | 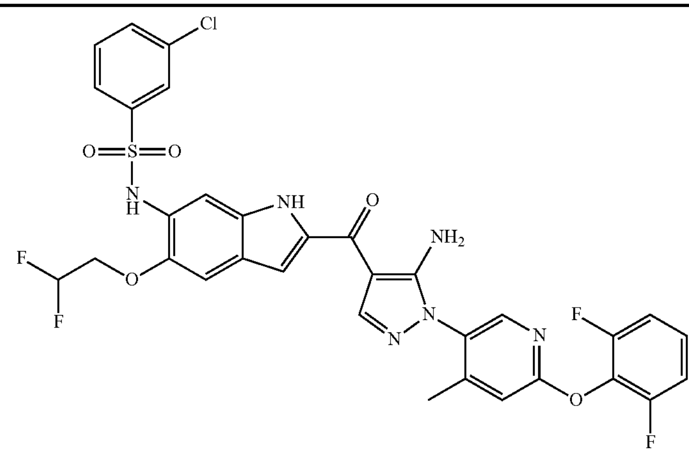 | N-[2-[5-amino-1-[6-(2,6-difluorophenoxy)-4-methylpyridin-3-yl]pyrazole-4-carbonyl]-5-(2,2-difluoroethoxy)-1H-indol-6-yl]-3-chlorobenzenesulfonamide | 715, 717 | 1.34 | TFA Rev.7 |
| 5-1-384 | 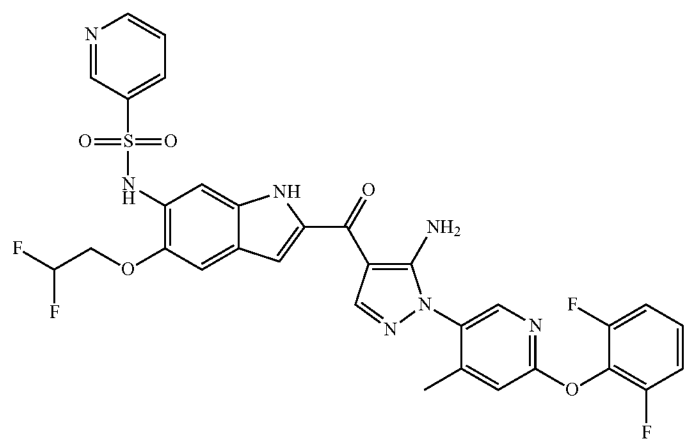 [SMILES: Cc1cc(Oc2c(F)cccc2F)ncc1-n1ncc(C(=O)c2cc3cc(OCC(F)F)c(NS(=O)(=O)c4cccnc4)cc3[nH]2)c1N] | N-[2-[5-amino-1-[6-(2,6-difluorophenoxy)-4-methylpyridin-3-yl]pyrazole-4-carbonyl]-5-(2,2-difluoroethoxy)-1H-indol-6-yl]pyridine-3-sulfonamide | 682 | 0.96 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-385 | 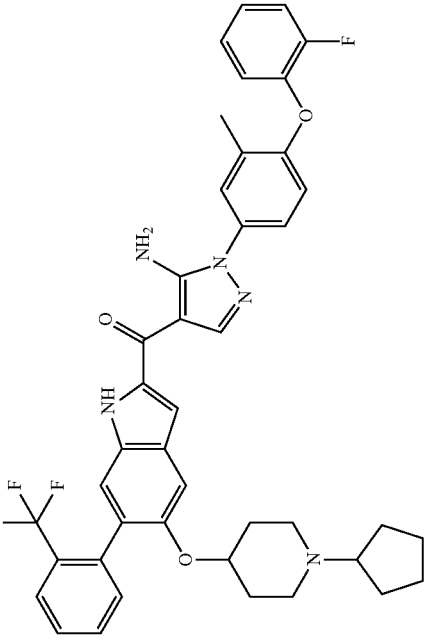 | [5-amino-1-[4-(2-fluorophenoxy)-3-methylphenyl]pyrazol-4-yl]-[5-(1-cyclopentylpiperidin-4-yl)oxy-6-[2-(trifluoromethyl)phenyl]-1H-indol-2-yl]methanone | 738 | 1.13 | AA Rev.11 |
| 5-1-386 | 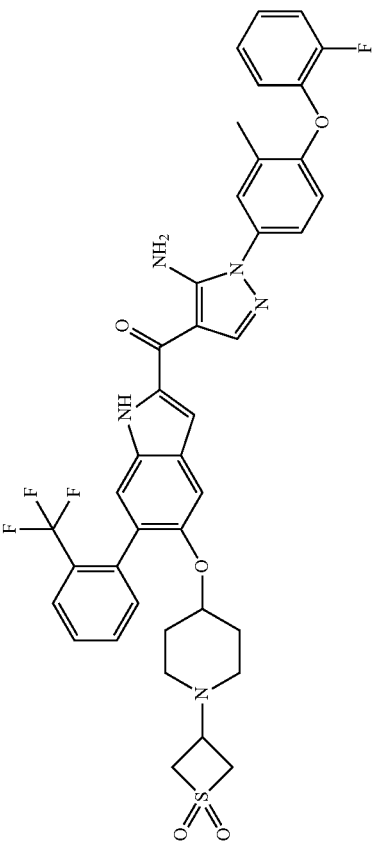 | [5-amino-1-[4-(2-fluorophenoxy)-3-methylphenyl]pyrazol-4-yl]-[5-[1-(1,1-dioxothietan-3-yl)piperidin-4-yl]oxy-6-[2-(trifluoromethyl)phenyl]-1H-indol-2-yl]methanone | 774 | 1.13 | TFA Rev.7 |

| Example No. | Chemical Structure | Compound Name | m/z (M + H) | Reaction Time (Minute) | LCMS Measurement Condition |
|---|---|---|---|---|---|
| 5-1-387 | 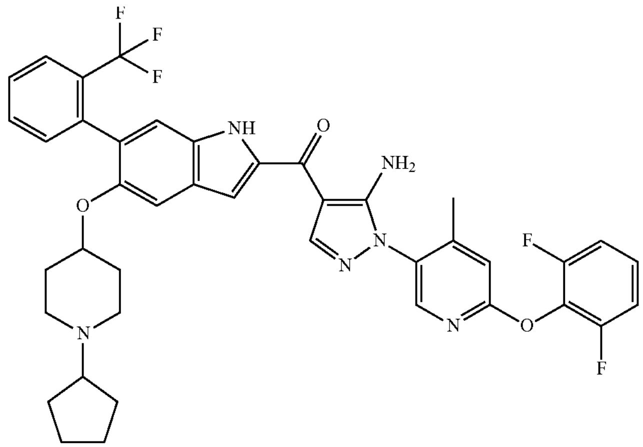 [SMILES: Cc1cc(Oc2c(F)cccc2F)ncc1-n1ncc(C(=O)c2cc3cc(OC4CCN(C5CCCC5)CC4)c(-c4ccccc4C(F)(F)F)cc3[nH]2)c1N] | [5-amino-1-[6-(2,6-difluorophenoxy)-4-methylpyridin-3-yl]pyrazol-4-yl]-[5-(1-cyclopentylpiperidin-4-yl)oxy-6-[2-(trifluoromethyl)phenyl]-1H-indol-2-yl]methanone | 757 | 1.12 | TFA Rev.7 |
| 5-1-388 | 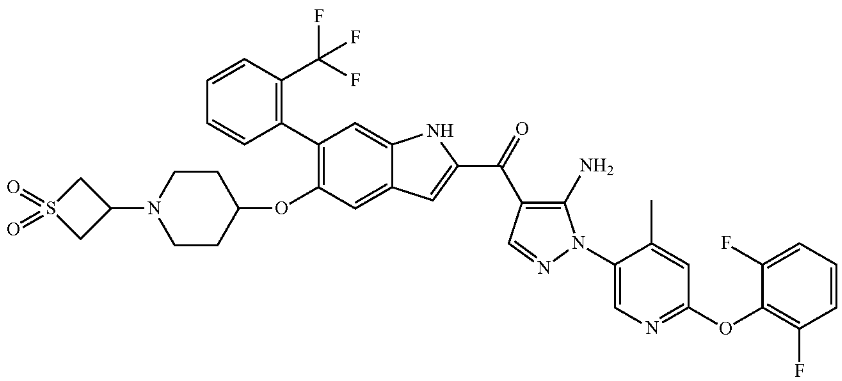 [SMILES: Cc1cc(Oc2c(F)cccc2F)ncc1-n1ncc(C(=O)c2cc3cc(OC4CCN(C5CS(=O)(=O)C5)CC4)c(-c4ccccc4C(F)(F)F)cc3[nH]2)c1N] | [5-amino-1-[6-(2,6-difluorophenoxy)-4-methylpyridin-3-yl]pyrazol-4-yl]-[5-[1-(1,1-dioxothietan-3-yl)piperidin-4-yl]oxy-6-[2-(trifluoromethyl)phenyl]-1H-indol-2-yl]methanone | 793 | 1.07 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-389 | 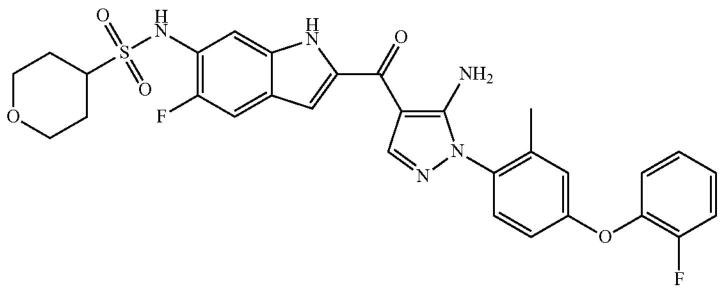 [SMILES: Cc1cc(Oc2ccccc2F)ccc1-n1ncc(C(=O)c2cc3cc(F)c(NS(=O)(=O)C4CCOCC4)cc3[nH]2)c1N] | N-[2-[5-amino-1-[4-(2-fluorophenoxy)-2-methylphenyl]pyrazole-4-carbonyl]-5-fluoro-1H-indol-6-yl]oxane-4-sulfonamide | 608 | 1.18 | TFA Rev.7 |
| 5-1-390 | 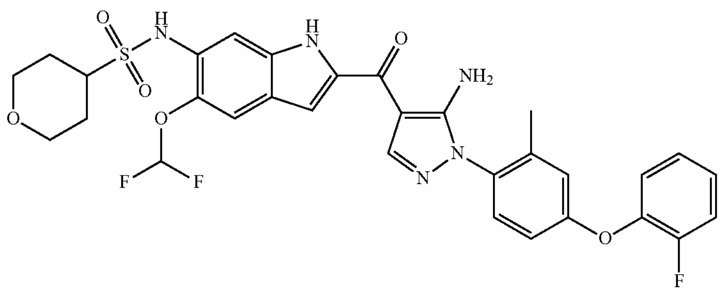 [SMILES: Cc1cc(Oc2ccccc2F)ccc1-n1ncc(C(=O)c2cc3cc(OC(F)F)c(NS(=O)(=O)C4CCOCC4)cc3[nH]2)c1N] | N-[2-[5-amino-1-[4-(2-fluorophenoxy)-2-methylphenyl]pyrazole-4-carbonyl]-5-(difluoromethoxy)-1H-indol-6-yl]oxane-4-sulfonamide | 656 | 1.01 | AA Rev.11 |

| Example No. | Chemical Structure | Compound Name | m/z (M + H) | Reaction Time (Minute) | LCMS Measurement Condition |
|---|---|---|---|---|---|
| 5-1-391 | 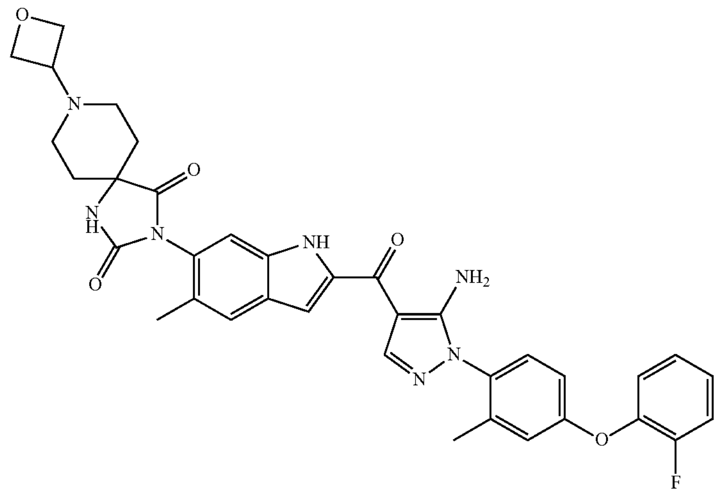 [SMILES: Cc1cc2cc(C(=O)c3cnn(-c4ccc(Oc5ccccc5F)cc4C)c3N)[nH]c2cc1N1C(=O)NC2(CCN(C3COC3)CC2)C1=O] | 3-[2-[5-amino-1-[4-(2-fluorophenoxy)-2-methylphenyl]pyrazole-4-carbonyl]-5-methyl-1H-indol-6-yl]-8-(oxetan-3-yl)-1,3,8-triazaspiro[4.5]decane-2,4-dione | 664 | 0.94 | TFA Rev.7 |
| 5-1-392 | 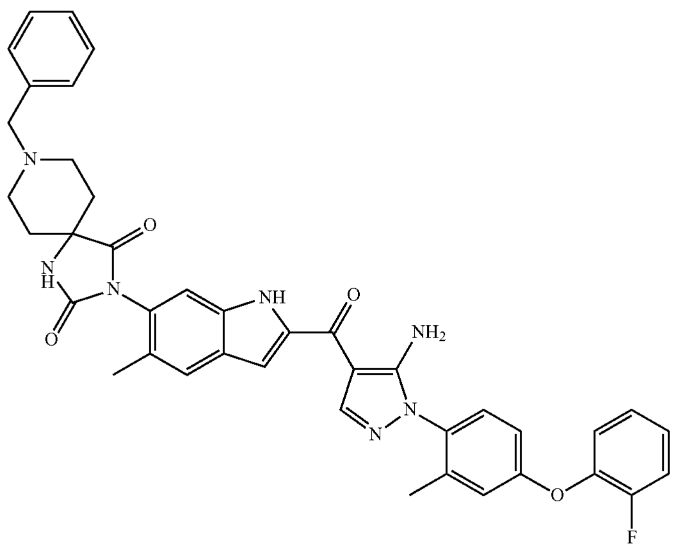 [SMILES: Cc1cc2cc(C(=O)c3cnn(-c4ccc(Oc5ccccc5F)cc4C)c3N)[nH]c2cc1N1C(=O)NC2(CCN(Cc3ccccc3)CC2)C1=O] | 3-[2-[5-amino-1-[4-(2-fluorophenoxy)-2-methylphenyl]pyrazole-4-carbonyl]-5-methyl-1H-indol-6-yl]-8-benzyl-1,3,8-triazaspiro[4.5]decane-2,4-dione | 698 | 1.02 | TFA Rev.7 |

| Example No. | Chemical Structure | Compound Name | m/z (M + H) | Reaction Time (Minute) | LCMS Measurement Condition |
|---|---|---|---|---|---|
| 5-1-393 | 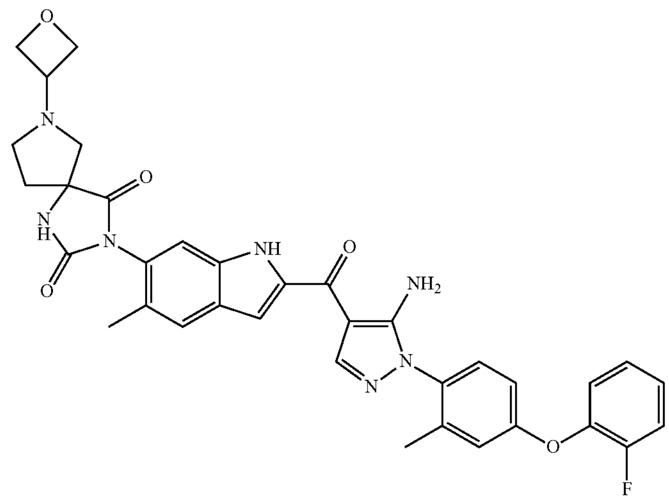 [SMILES: Cc1cc2cc(C(=O)c3cnn(-c4ccc(Oc5ccccc5F)cc4C)c3N)[nH]c2cc1N1C(=O)NC2(CCN(C3COC3)C2)C1=O] | 3-[2-[5-amino-1-[4-(2-fluorophenoxy)-2-methylphenyl]pyrazole-4-carbonyl]-5-methyl-1H-indol-6-yl]-7-(oxetan-3-yl)-1,3,7-triazaspiro[4.4]nonane-2,4-dione | 650 | 0.95 | TFA Rev.7 |
| 5-1-394 | 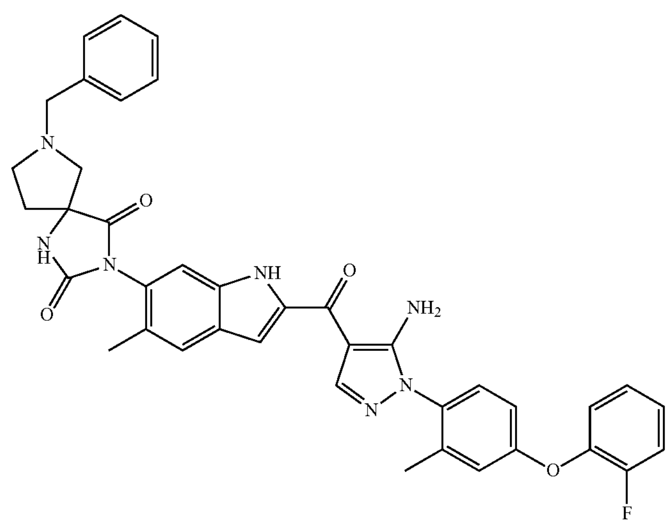 [SMILES: Cc1cc2cc(C(=O)c3cnn(-c4ccc(Oc5ccccc5F)cc4C)c3N)[nH]c2cc1N1C(=O)NC2(CCN(Cc3ccccc3)C2)C1=O] | 3-[2-[5-amino-1-[4-(2-fluorophenoxy)-2-methylphenyl]pyrazole-4-carbonyl]-5-methyl-1H-indol-6-yl]-7-benzyl-1,3,7-triazaspiro[4.4]nonane-2,4-dione | 684 | 1.04 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-395 | 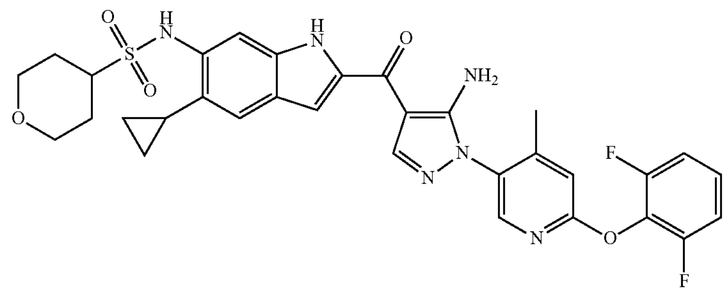 [SMILES: Cc1cc(Oc2c(F)cccc2F)ncc1-n1ncc(C(=O)c2cc3cc(C4CC4)c(NS(=O)(=O)C4CCOCC4)cc3[nH]2)c1N] | N-[2-[5-amino-1-[6-(2,6-difluorophenoxy)-4-methylpyridin-3-yl]pyrazole-4-carbonyl]-5-cyclopropyl-1H-indol-6-yl]oxane-4-sulfonamide | 649 | 1.02 | AA Rev.11 |
| 5-1-396 | 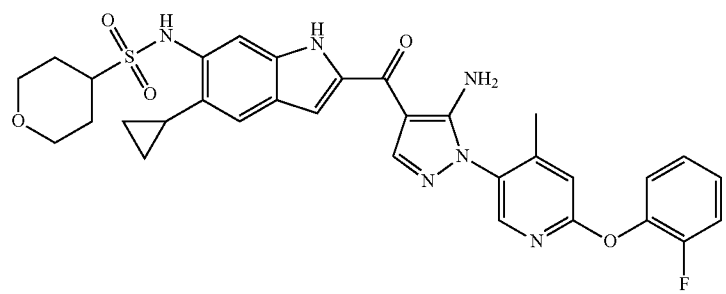 [SMILES: Cc1cc(Oc2ccccc2F)ncc1-n1ncc(C(=O)c2cc3cc(C4CC4)c(NS(=O)(=O)C4CCOCC4)cc3[nH]2)c1N] | N-[2-[5-amino-1-[6-(2-fluorophenoxy)-4-methylpyridin-3-yl]pyrazole-4-carbonyl]-5-cyclopropyl-1H-indol-6-yl]oxane-4-sulfonamide | 631 | 1.22 | TFA Rev.7 |
| 5-1-397 | 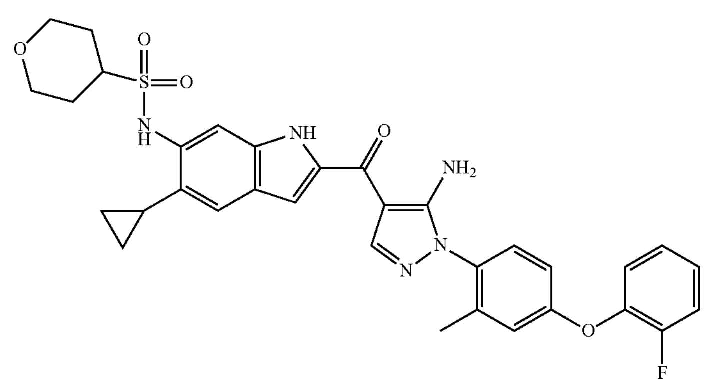 [SMILES: Cc1cc(Oc2ccccc2F)ccc1-n1ncc(C(=O)c2cc3cc(C4CC4)c(NS(=O)(=O)C4CCOCC4)cc3[nH]2)c1N] | N-[2-[5-amino-1-[4-(2-fluorophenoxy)-2-methylphenyl]pyrazole-4-carbonyl]-5-cyclopropyl-1H-indol-6-yl]oxane-4-sulfonamide | 630 | 1.04 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-398 | 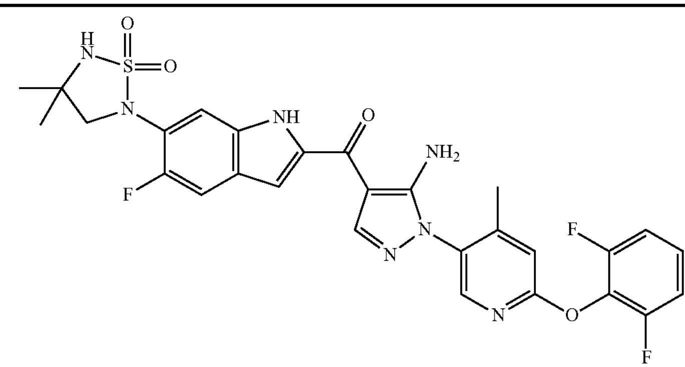 | [5-amino-1-[6-(2,6-difluorophenoxy)-4-methylpyridin-3-yl]pyrazol-4-yl]-[6-(4,4-dimethyl-1,1-dioxo-1,2,5-thiadiazolidin-2-yl)-5-fluoro-1H-indol-2-yl]methanone | 612 | 1.22 | TFA Rev.7 |
| 5-1-399 | 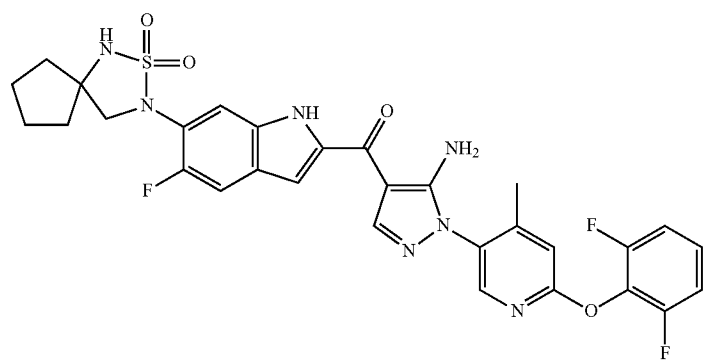 [SMILES: Cc1cc(Oc2c(F)cccc2F)ncc1-n1ncc(C(=O)c2cc3cc(F)c(N4CC5(CCCC5)NS4(=O)=O)cc3[nH]2)c1N] | [5-amino-1-[6-(2,6-difluorophenoxy)-4-methylpyridin-3-yl]pyrazol-4-yl]-[6-(2,2-dioxo-2λ6-thia-1,3-diazaspiro[4.4]nonan-3-yl)-5-fluoro-1H-indol-2-yl]methanone | 638 | 1.29 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-400 | 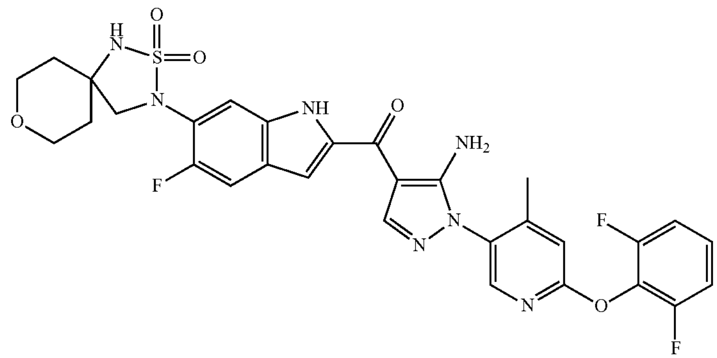 [SMILES: Cc1cc(Oc2c(F)cccc2F)ncc1-n1ncc(C(=O)c2cc3cc(F)c(N4CC5(CCOCC5)NS4(=O)=O)cc3[nH]2)c1N] | [5-amino-1-[6-(2,6-difluorophenoxy)-4-methylpyridin-3-yl]pyrazol-4-yl]-[6-(2,2-dioxo-8-oxa-2λ6-thia-13-diazaspiro[4.5]decan-3-yl)-5-fluoro-1H-indol-2-yl]methanone | 654 | 1.15 | TFA Rev.7 |
| 5-1-401 | 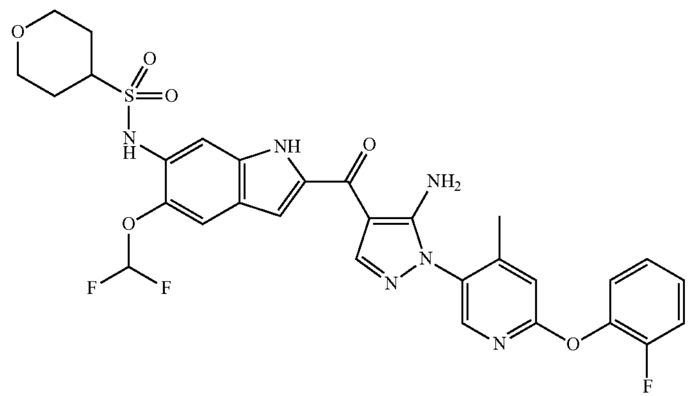 [SMILES: Cc1cc(Oc2ccccc2F)ncc1-n1ncc(C(=O)c2cc3cc(OC(F)F)c(NS(=O)(=O)C4CCOCC4)cc3[nH]2)c1N] | N-[2-[5-amino-1-[6-(2-fluorophenoxy)-4-methylpyridin-3-yl]pyrazole-4-carbonyl]-5-(difluoromethoxy)-1H-indol-6-yl]oxane-4-sulfonamide | 657 | 0.97 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-402 | 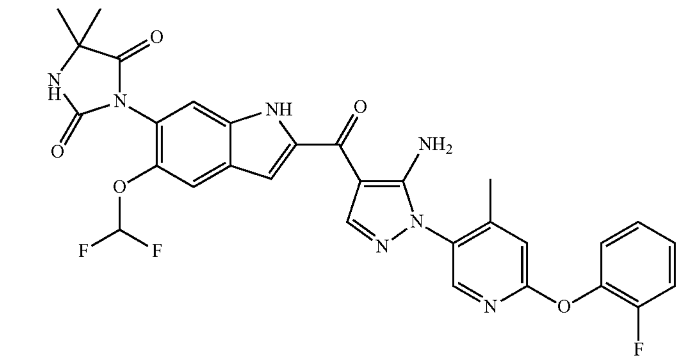 [SMILES: Cc1cc(Oc2ccccc2F)ncc1-n1ncc(C(=O)c2cc3cc(OC(F)F)c(N4C(=O)NC(C)(C)C4=O)cc3[nH]2)c1N] | 3-[2-[5-amino-1-[6-(2-fluorophenoxy)-4-methylpyridin-3-yl]pyrazole-4-carbonyl]-5-(difluoromethoxy)-1H-indol-6-yl]-5,5-dimethylimidazolidine-2,4-dione | 620 | 0.96 | AA Rev.11 |
| 5-1-403 | 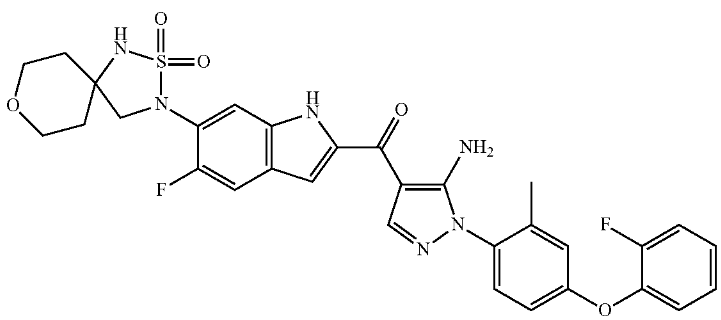 [SMILES: Cc1cc(Oc2ccccc2F)ccc1-n1ncc(C(=O)c2cc3cc(F)c(N4CC5(CCOCC5)NS4(=O)=O)cc3[nH]2)c1N] | [5-amino-1-[4-(2-fluorophenoxy)-2-methylphenyl]pyrazol-4-yl]-[6-(2,2-dioxo-8-oxa-2λ6-thia-1,3-diazaspiro[4.5]decan-3-yl)-5-fluoro-1H-indol-2-yl]methanone | 635 | 1.00 | AA Rev.11 |

| Example No. | Chemical Structure | Compound Name | m/z (M + H) | Reaction Time (Minute) | LCMS Measurement Condition |
|---|---|---|---|---|---|
| 5-1-404 | 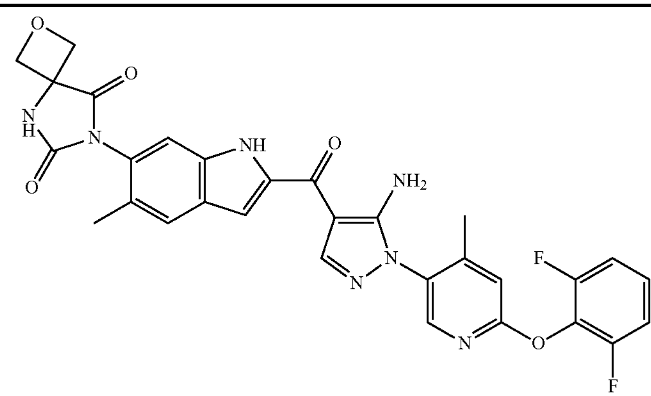 | 7-[2-[5-amino-1-[6-(2,6-difluorophenoxy)-4-methylpyridin-3-yl]pyrazole-4-carbonyl]-5-methyl-1H-indol-6-yl]-2-oxa-5,7-diazaspiro[3.4]octane-6,8-dione | 600 | 0.94 | AA Rev.11 |
| 5-1-405 | 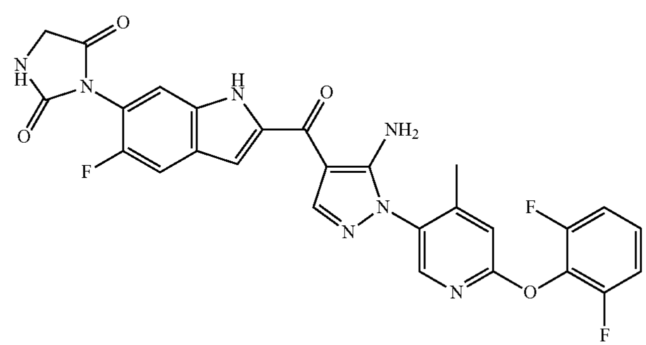 [SMILES: Cc1cc(Oc2c(F)cccc2F)ncc1-n1ncc(C(=O)c2cc3cc(F)c(N4C(=O)CNC4=O)cc3[nH]2)c1N] | 3-[2-[5-amino-1-[6-(2,6-difluorophenoxy)-4-methylpyridin-3-yl]pyrazole-4-carbonyl]-5-fluoro-1H-indol-6-yl]imidazolidine-2,4-dione | 562 | 1.04 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-406 | 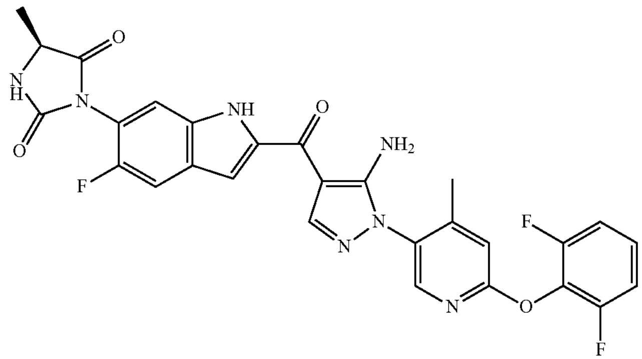 [SMILES: Cc1cc(Oc2c(F)cccc2F)ncc1-n1ncc(C(=O)c2cc3cc(F)c(N4C(=O)N[C@@H](C)C4=O)cc3[nH]2)c1N] | (5S)-3-[2-[5-amino-1-[6-(2,6-difluorophenoxy)-4-methylpyridin-3-yl]pyrazole-4-carbonyl]-5-fluoro-1H-indol-6-yl]-5-methylimidazolidine-2,4-dione | 576 | 0.94 | AA Rev.11 |
| 5-1-407 | 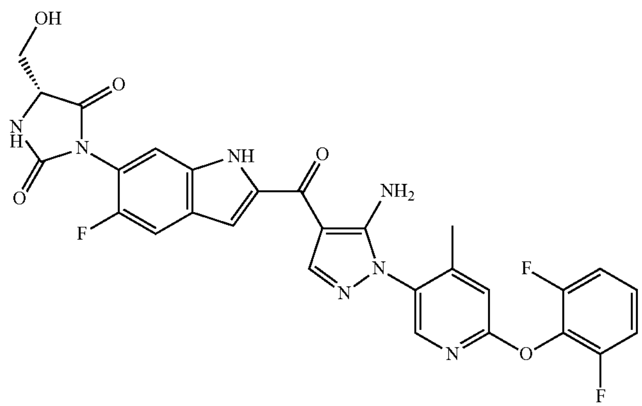 [SMILES: Cc1cc(Oc2c(F)cccc2F)ncc1-n1ncc(C(=O)c2cc3cc(F)c(N4C(=O)N[C@H](CO)C4=O)cc3[nH]2)c1N] | (5S)-3-[2-[5-amino-1-[6-(2,6-difluorophenoxy)-4-methylpyridin-3-yl]pyrazole-4-carbonyl]-5-fluoro-1H-indol-6-yl]-5-(hydroxymethyl)imidazolidine-2,4-dione | 592 | 0.90 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-408 | 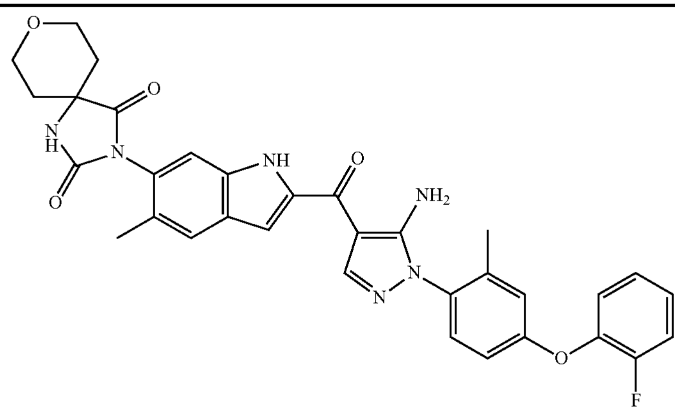 | 3-[2-[5-amino-1-[4-(2-fluorophenoxy)-2-methylphenyl]pyrazole-4-carbonyl]-5-methyl-1H-indol-6-yl]-8-oxa-1,3-diazaspiro[4.5]decane-2,4-dione | 609 | 1.13 | TFA Rev.7 |
| 5-1-409 | 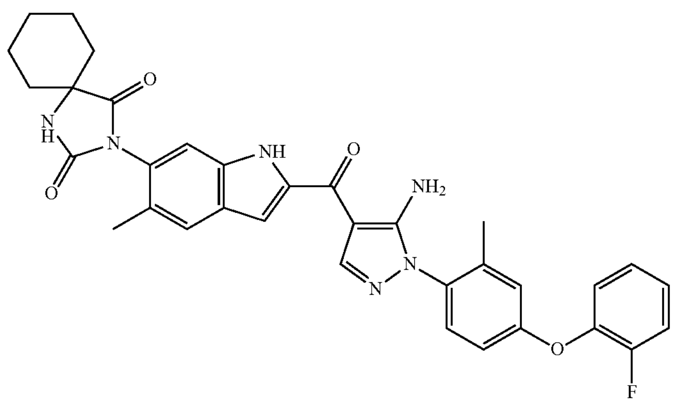 [SMILES: Cc1cc2cc(C(=O)c3cnn(-c4ccc(Oc5ccccc5F)cc4C)c3N)[nH]c2cc1N1C(=O)NC2(CCCCC2)C1=O] | 3-[2-[5-amino-1-[4-(2-fluorophenoxy)-2-methylphenyl]pyrazole-4-carbonyl]-5-methyl-1H-indol-6-yl]-1,3-diazaspiro[4.5]decane-2,4-dione | 607 | 1.27 | TFA Rev.7 |

| Example No. | Chemical Structure | Compound Name | m/z (M + H) | Reaction Time (Minute) | LCMS Measurement Condition |
|---|---|---|---|---|---|
| 5-1-410 | 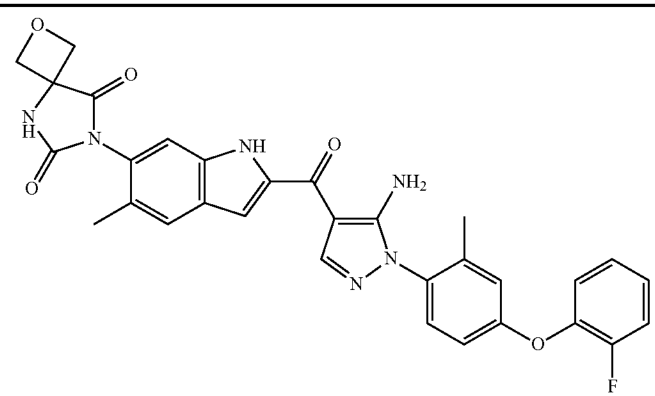 | 7-[2-[5-amino-1-[4-(2-fluorophenoxy)-2-methylphenyl]pyrazole-4-carbonyl]-5-methyl-1H-indol-6-yl]-2-oxa-5,7-diazaspiro[3.4]octane-6,8-dione | 581 | 1.11 | TFA Rev.7 |
| 5-1-411 | 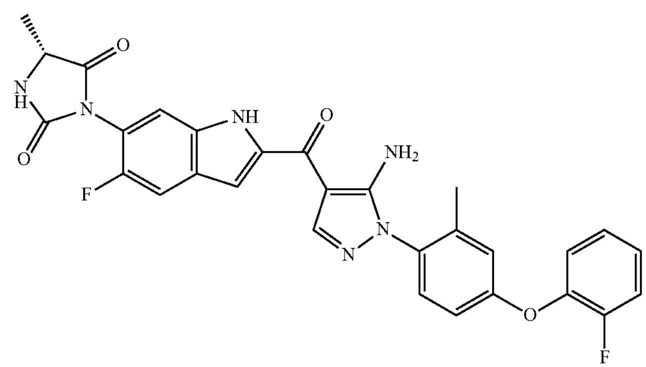 [SMILES: Cc1cc(Oc2ccccc2F)ccc1-n1ncc(C(=O)c2cc3cc(F)c(N4C(=O)N[C@H](C)C4=O)cc3[nH]2)c1N] | (5S)-3-[2-[5-amino-1-[4-(2-fluorophenoxy)-2-methylphenyl]pyrazole-4-carbonyl]-5-fluoro-1H-indol-6-yl]-5-methylimidazolidine-2,4-dione | 557 | 0.97 | AA Rev.11 |

| Example No. | Chemical Structure | Compound Name | m/z (M + H) | Reaction Time (Minute) | LCMS Measurement Condition |
|---|---|---|---|---|---|
| 5-1-412 | 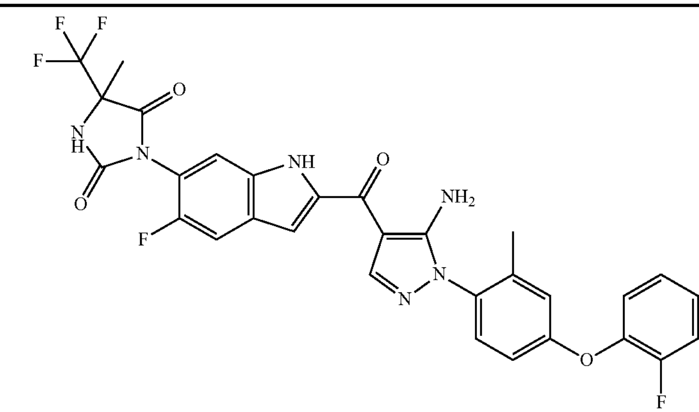 | 3-[2-[5-amino-1-[4-(2-fluorophenoxy)-2-methylphenyl]pyrazole-4-carbonyl]-5-fluoro-1H-indol-6-yl]-5-methyl-5-(trifluoromethyl)imidazolidine-2,4-dione | 625 | 1.25 | TFA Rev.7 |
| 5-1-413 | 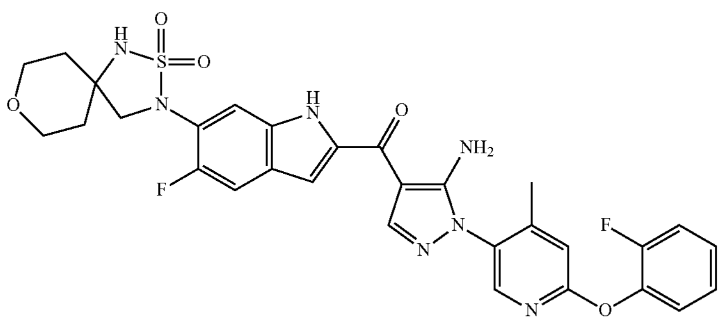 | [5-amino-1-[6-(2-fluorophenoxy)-4-methylpyridin-3-yl]pyrazol-4-yl]-[6-(2,2-dioxo-8-oxa-2λ6-thia-1,3-diazaspiro[4.5]decan-3-yl)-5-fluoro-1H-indol-2-yl]methanone | 636 | 0.96 | AA Rev.11 |

| Example No. | Chemical Structure | Compound Name | m/z (M + H) | Reaction Time (Minute) | LCMS Measurement Condition |
|---|---|---|---|---|---|
| 5-1-414 | 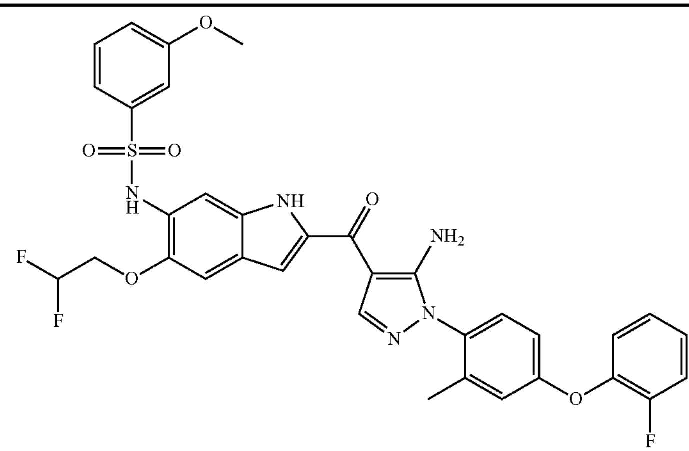 | N-[2-[5-amino-1-[4-(2-fluorophenoxy)-2-methylphenyl]pyrazole-4-carbonyl]-5-(2,2-difluoroethoxy)-1H-indol-6-yl]-3-methoxybenzenesulfonamide | 692 | 1.33 | TFA Rev.7 |
| 5-1-415 | 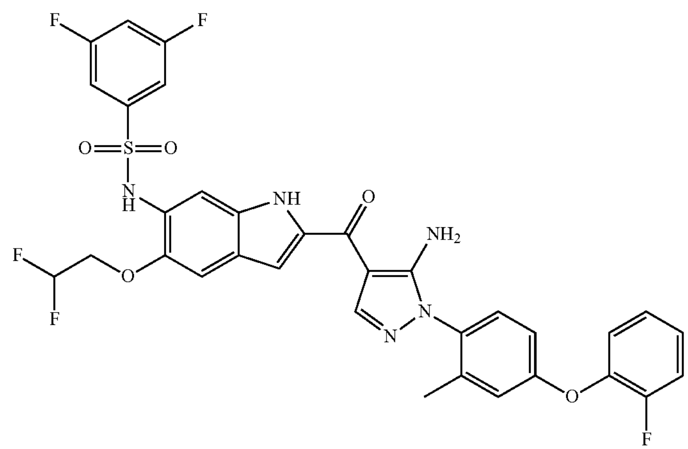 | N-[2-[5-amino-1-[4-(2-fluorophenoxy)-2-methylphenyl]pyrazole-4-carbonyl]-5-(2,2-difluoroethoxy)-1H-indol-6-yl]-3,5-difluorobenzenesulfonamide | 698 | 1.35 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-416 | 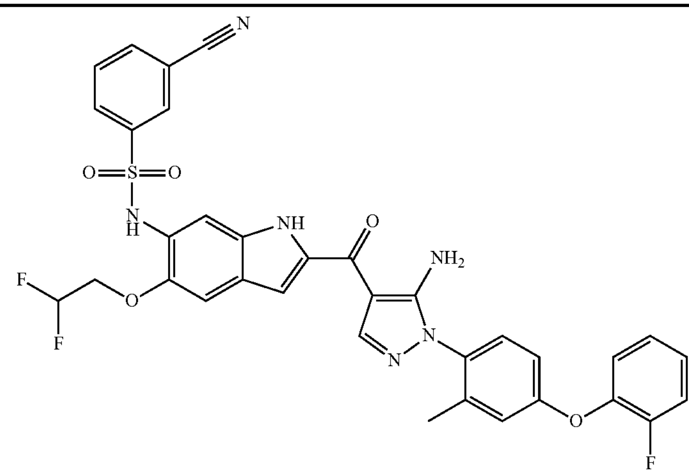 | N-[2-[5-amino-1-[4-(2-fluorophenoxy)-2-methylphenyl]pyrazole-4-carbonyl]-5-(2,2-difluoroethoxy)-1H-indol-6-yl]-3-cyanobenzenesulfonamide | 687 | 1.29 | TFA Rev.7 |
| 5-1-417 | 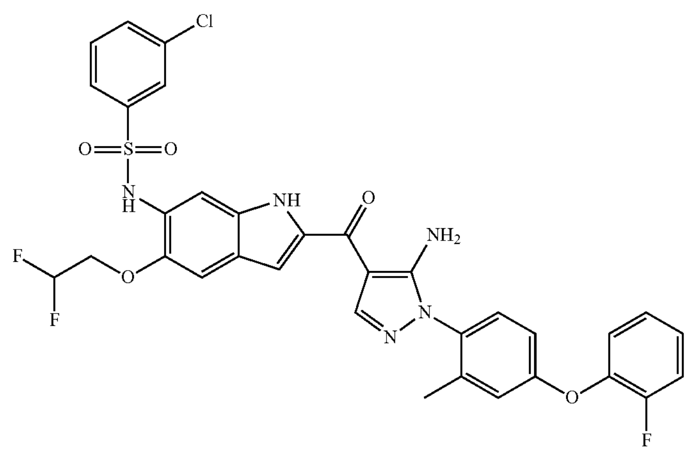 [SMILES: Cc1cc(Oc2ccccc2F)ccc1-n1ncc(C(=O)c2cc3cc(OCC(F)F)c(NS(=O)(=O)c4cccc(Cl)c4)cc3[nH]2)c1N] | N-[2-[5-amino-1-[4-(2-fluorophenoxy)-2-methylphenyl]pyrazole-4-carbonyl]-5-(2,2-difluoroethoxy)-1H-indol-6-yl]-3-chlorobenzenesulfonamide | 696, 698 | 1.37 | TFA Rev.7 |

| Example No. | Chemical Structure | Compound Name | m/z (M + H) | Reaction Time (Minute) | LCMS Measurement Condition |
|---|---|---|---|---|---|
| 5-1-418 | 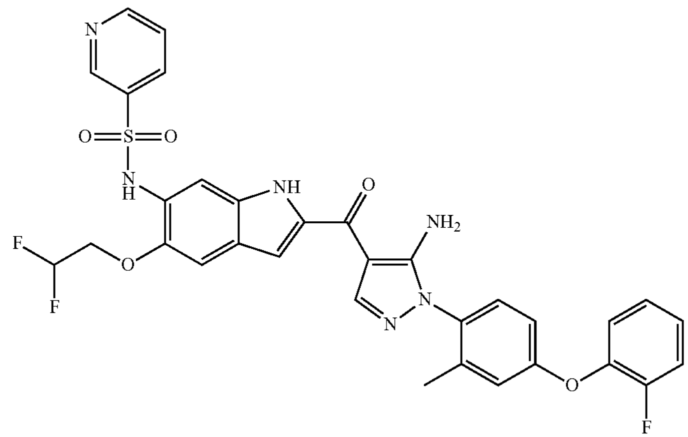 | N-[2-[5-amino-1-[4-(2-fluorophenoxy)-2-methylphenyl]pyrazole-4-carbonyl]-5-(2,2-difluoroethoxy)-1H-indol-6-yl]pyridine-3-sulfonamide | 663 | 1.21 | TFA Rev.7 |
| 5-1-419 | 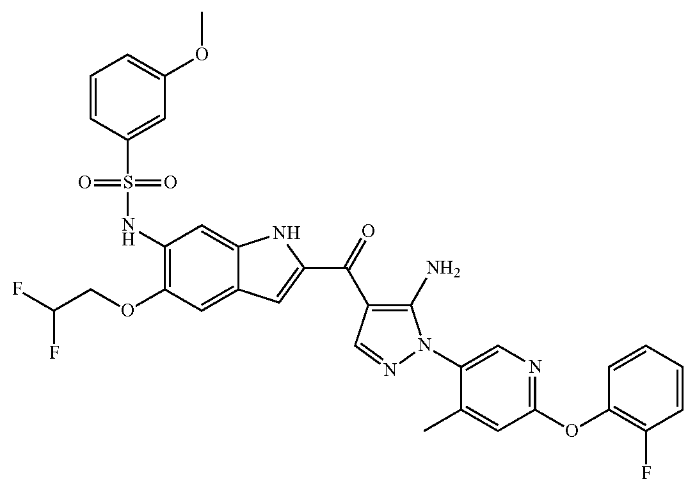 [SMILES: COc1cccc(S(=O)(=O)Nc2cc3[nH]c(C(=O)c4cnn(-c5cnc(Oc6ccccc6F)cc5C)c4N)cc3cc2OCC(F)F)c1] | N-[2-[5-amino-1-[6-(2-fluorophenoxy)-4-methylpyridin-3-yl]pyrazole-4-carbonyl]-5-(2,2-difluoroethoxy)-1H-indol-6-yl]-3-methoxybenzenesulfonamide | 693 | 1.27 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-420 | 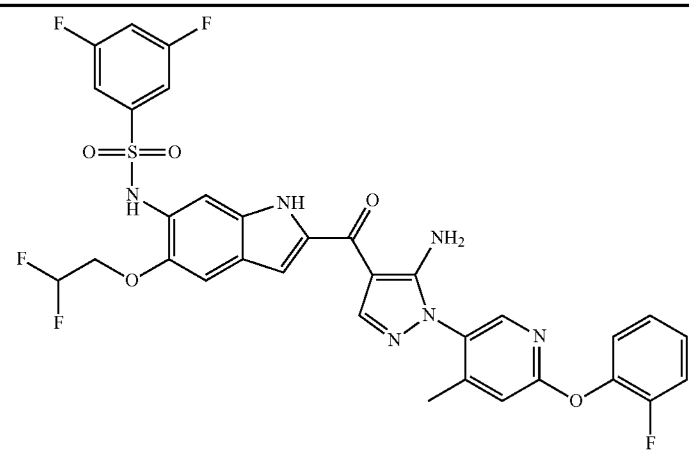 | N-[2-[5-amino-1-[6-(2-fluorophenoxy)-4-methylpyridin-3-yl]pyrazole-4-carbonyl]-5-(2,2-difluoroethoxy)-1H-indol-6-yl]-3,5-difluorobenzenesulfonamide | 699 | 1.30 | TFA Rev.7 |
| 5-1-421 | 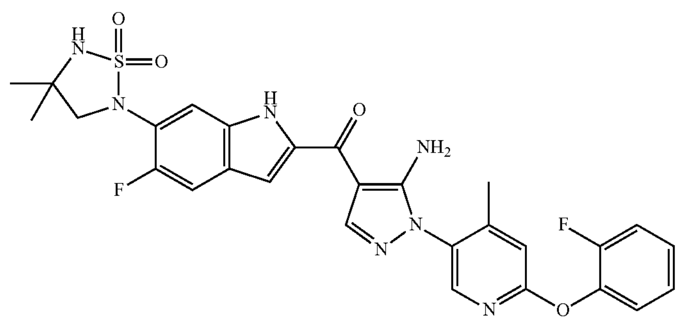 [SMILES: Cc1cc(Oc2ccccc2F)ncc1-n1ncc(C(=O)c2cc3cc(F)c(N4CC(C)(C)NS4(=O)=O)cc3[nH]2)c1N] | [5-amino-1-[6-(2-fluorophenoxy)-4-methylpyridin-3-yl]pyrazol-4-yl]-[6-(4,4-dimethyl-1,1-dioxo-1,2,5-thiadiazolidin-2-yl)-5-fluoro-1H-indol-2-yl]methanone | 594 | 0.99 | AA Rev.11 |

| Example No. | Chemical Structure | Compound Name | m/z (M + H) | Reaction Time (Minute) | LCMS Measurement Condition |
|---|---|---|---|---|---|
| 5-1-422 | 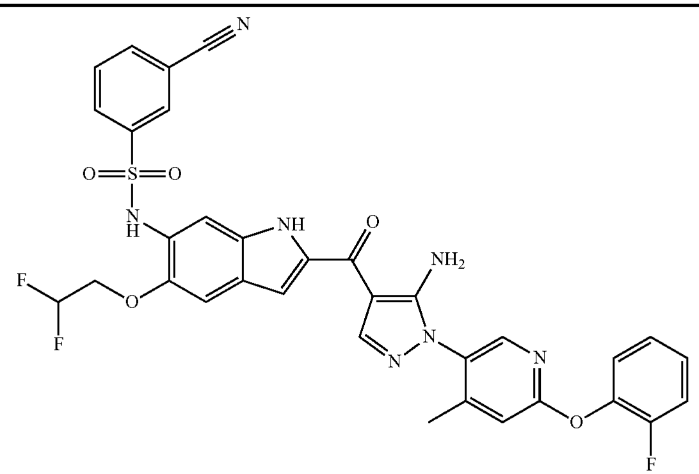 | N-[2-[5-amino-1-[6-(2-fluoropheooxy)-4-methylpyridin-3-yl]pyrazole-4-carbonyl]-5-(2,2-difluoroethoxy)-1H-indol-6-yl]-3-cyanobenzenesulfonamide | 688 | 1.24 | TFA Rev.7 |
| 5-1-423 | 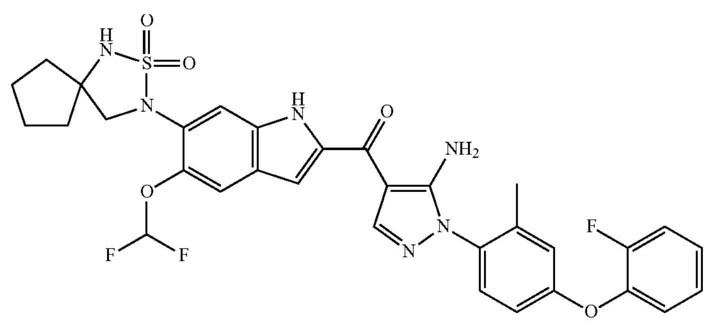 [SMILES: Cc1cc(Oc2ccccc2F)ccc1-n1ncc(C(=O)c2cc3cc(OC(F)F)c(N4CC5(CCCC5)NS4(=O)=O)cc3[nH]2)c1N] | [5-amino-1-[4-(2-fluorophenoxy)-2-methylphenyl]pyrazol-4-yl]-[5-(difluoromethoxy)-6-(2,2-dioxo-2λ6-thia-1,3-diazaspiro[4.4]nonan-3-yl)-1H-indol-2-yl]methanone | 667 | 1.09 | AA Rev.11 |

| Example No. | Chemical Structure | Compound Name | m/z (M + H) | Reaction Time (Minute) | LCMS Measurement Condition |
|---|---|---|---|---|---|
| 5-1-424 | 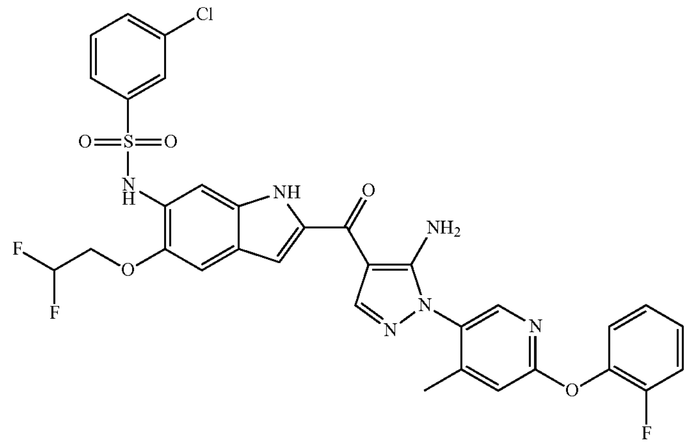 | N-[2-[5-amino-1-[6-(2-fluorophenoxy)-4-methylpyridin-3-yl]pyrazole-4-carbonyl]-5-(2,2-difluoroethoxy)-1H-indol-6-yl]-3-chlorobenzenesulfonamide | 697, 699 | 1.32 | TFA Rev.7 |
| 5-1-425 | 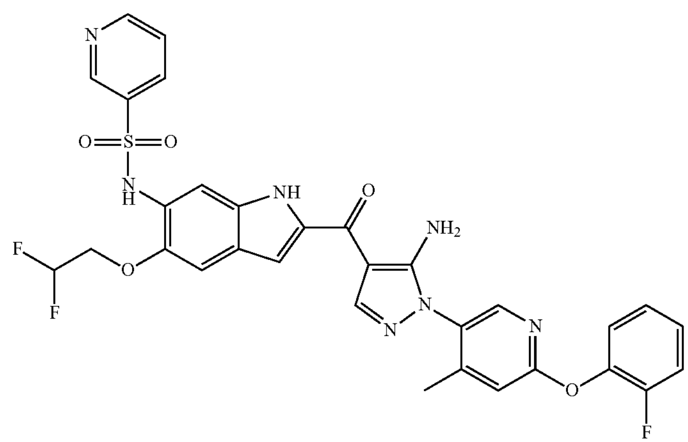 | N-[2-[5-amino-1-[6-(2-fluorophenoxy)-4-methylpyridin-3-yl]pyrazole-4-carbonyl]-5-(2,2-difluoroethoxy)-1H-indol-6-yl]pyridine-3-sulfonamide | 664 | 1.15 | TFA Rev.7 |

| Example No. | Chemical Structure | Compound Name | m/z (M + H) | Reaction Time (Minute) | LCMS Measurement Condition |
|---|---|---|---|---|---|
| 5-1-426 | 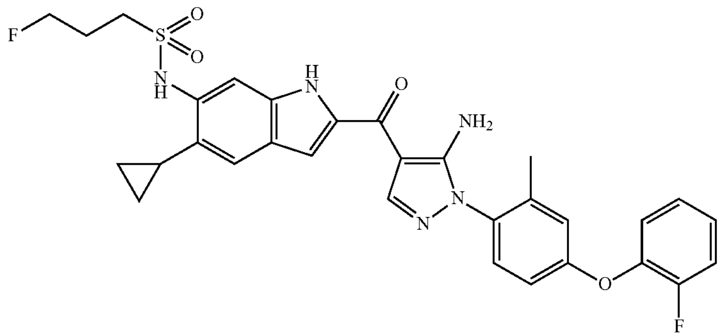 [SMILES: Cc1cc(Oc2ccccc2F)ccc1-n1ncc(C(=O)c2cc3cc(C4CC4)c(NS(=O)(=O)CCCF)cc3[nH]2)c1N] | N-[2-[5-amino-1-[4-(2-fluorophenoxy)-2-methylphenyl]pyrazole-4-carbonyl]-5-cyclopropyl-1H-indol-6-yl]-3-fluoropropane-1-sulfonamide | 606 | 1.04 | AA Rev.11 |
| 5-1-427 | 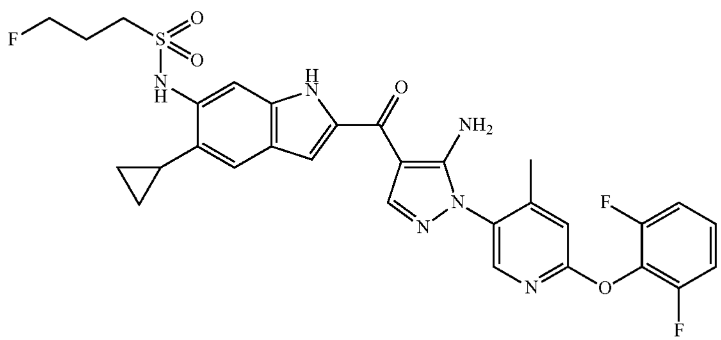 [SMILES: Cc1cc(Oc2c(F)cccc2F)ncc1-n1ncc(C(=O)c2cc3cc(C4CC4)c(NS(=O)(=O)CCCF)cc3[nH]2)c1N] | N-[2-[5-amino-1-[6-(2,6-difluorophenoxy)-4-methylpyridin-3-yl]pyrazole-4-carbonyl]-5-cyclopropyl-1H-indol-6-yl]-3-fluoropropane-1-sulfonamide | 625 | 1.02 | AA Rev.11 |
| 5-1-428 | 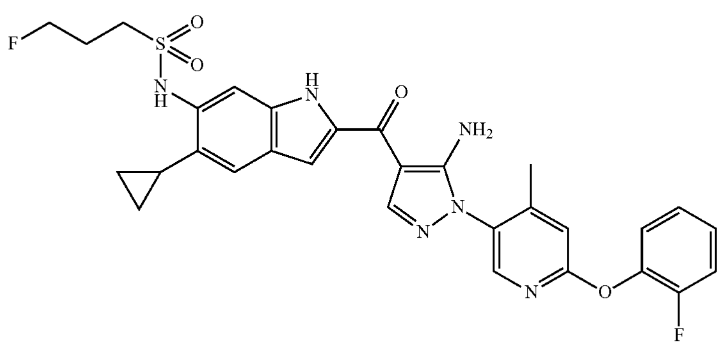 [SMILES: Cc1cc(Oc2ccccc2F)ncc1-n1ncc(C(=O)c2cc3cc(C4CC4)c(NS(=O)(=O)CCCF)cc3[nH]2)c1N] | N-[2-[5-amino-1-[6-(2-fluorophenoxy)-4-methylpyridin-3-yl]pyrazole-4-carbonyl]-5-cyclopropyl-1H-indol-6-yl]-3-fluoropropane-1-sulfonamide | 607 | 1.01 | AA Rev.11 |

| Example No. | Chemical Structure | Compound Name | m/z (M + H) | Reaction Time (Minute) | LCMS Measurement Condition |
|---|---|---|---|---|---|
| 5-1-429 | 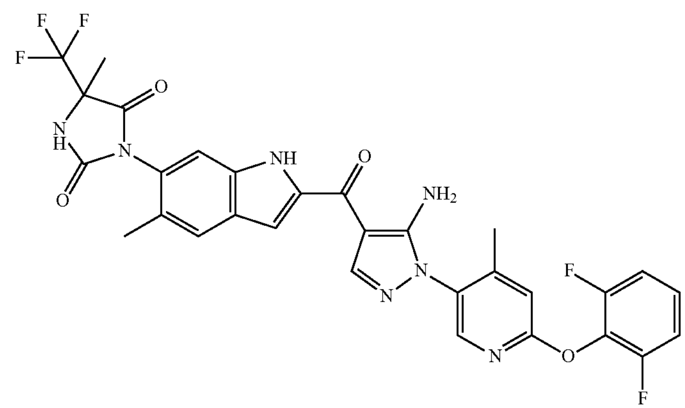 [SMILES: Cc1cc2cc(C(=O)c3cnn(-c4cnc(Oc5c(F)cccc5F)cc4C)c3N)[nH]c2cc1N1C(=O)NC(C)(C(F)(F)F)C1=O] | 3-[2-[5-amino-1-[6-(2,6-difluorophenoxy)-4-methylpyridin-3-yl]pyrazole-4-carbonyl]-5-methyl-1H-indol-6-yl]-5-methyl-5-(trifluoromethyl)imidazolidine-2,4-dione | 640 | 1.03 | AA Rev.11 |
| 5-1-430 | 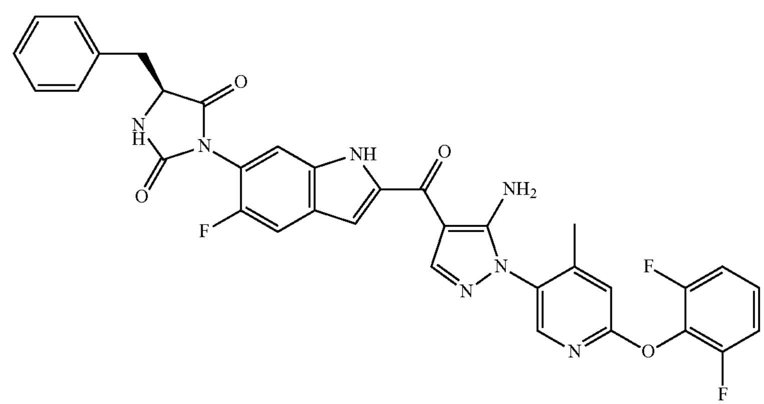 [SMILES: Cc1cc(Oc2c(F)cccc2F)ncc1-n1ncc(C(=O)c2cc3cc(F)c(N4C(=O)N[C@@H](Cc5ccccc5)C4=O)cc3[nH]2)c1N] | (5S)-3-[2-[5-amino-1-[6-(2,6-difluorophenoxy)-4-methylpyridin-3-yl]pyrazole-4-carbonyl]-5-fluoro-1H-indol-6-yl]-5-benzylimidazolidine-2,4-dione | 652 | 1.21 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-431 | 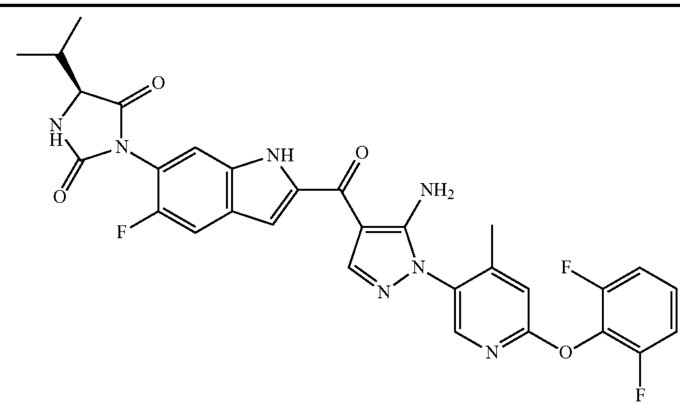 | (5S)-3-[2-[5-amino-1-[6-(2,6-difluorophenoxy)-4-methylpyridin-3-yl]pyrazole-4-carbonyl]-5-fluoro-1H-indol-6-yl]-5-propan-2-ylimidazolidine-2,4-dione | 604 | 1.17 | TFA Rev.7 |
| 5-1-432 | 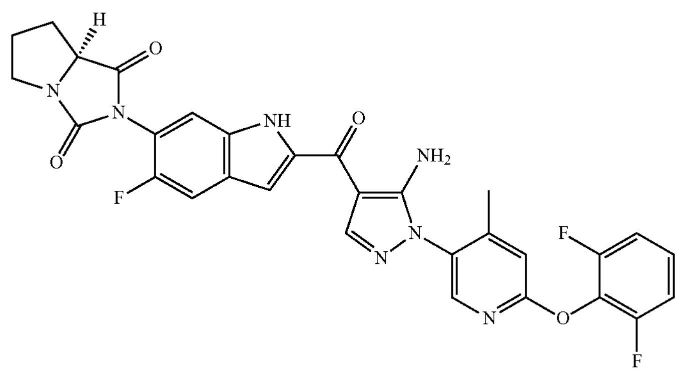 [SMILES: Cc1cc(Oc2c(F)cccc2F)ncc1-n1ncc(C(=O)c2cc3cc(F)c(N4C(=O)[C@@H]5CCCN5C4=O)cc3[nH]2)c1N] | (7aS)-2-[2-[5-amino-1-[6-(2,6-difluorophenoxy)-4-methylpyridin-3-yl]pyrazole-4-carbonyl]-5-fluoro-1H-indol-6-yl]-5,6,7,7a-tetrahydropyrrolo[1,2-c]imidazole-1,3-dione | 602 | 1.17 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-433 | 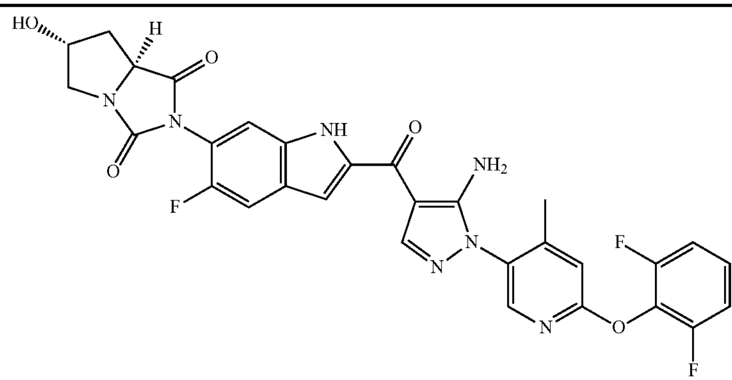 | (6R,7aS)-2-[2-[5-amino-1-[6-(2,6-difluorophenoxy)-4-methylpyridin-3-yl]pyrazole-4-carbonyl]-5-fluoro-1H-indol-6-yl]-6-hydroxy-5,6,7,7a-tetrahydropyrrolo[1,2-c]imidazole-1,3-dione | 618 | 1.06 | TFA Rev.7 |
| 5-1-434 | 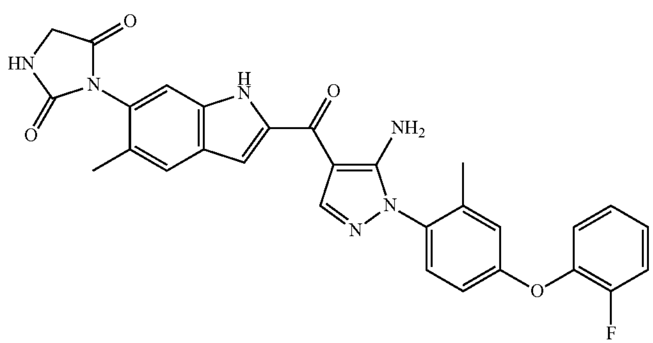 [SMILES: Cc1cc2cc(C(=O)c3cnn(-c4ccc(Oc5ccccc5F)cc4C)c3N)[nH]c2cc1N1C(=O)CNC1=O] | 3-[2-[5-amino-1-[4-(2-fluorophenoxy)-2-methylphenyl]pyrazole-4-carbonyl]-5-methyl-1H-indol-6-yl]imidazolidine-2,4-dione | 539 | 1.08 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-435 | 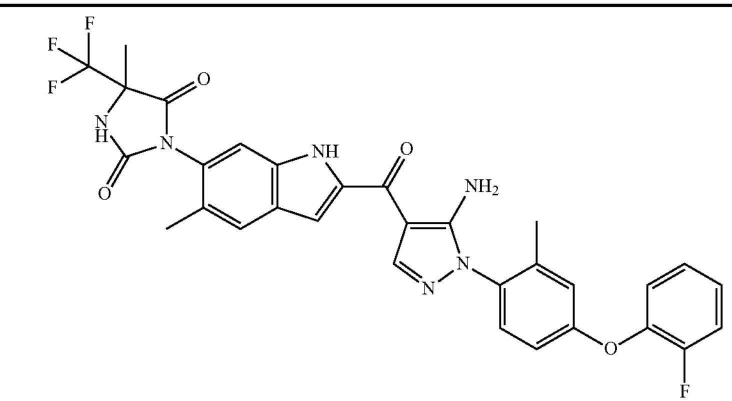 | 3-[2-[5-amino-1-[4-(2-fluorophenoxy)-2-methylphenyl]pyrazole-4-carbonyl]-5-methyl-1H-indol-6-yl]-5-methyl-5-(trifluoromethyl)imidazolidine-2,4-dione | 621 | 1.05 | AA Rev.11 |
| 5-1-436 | 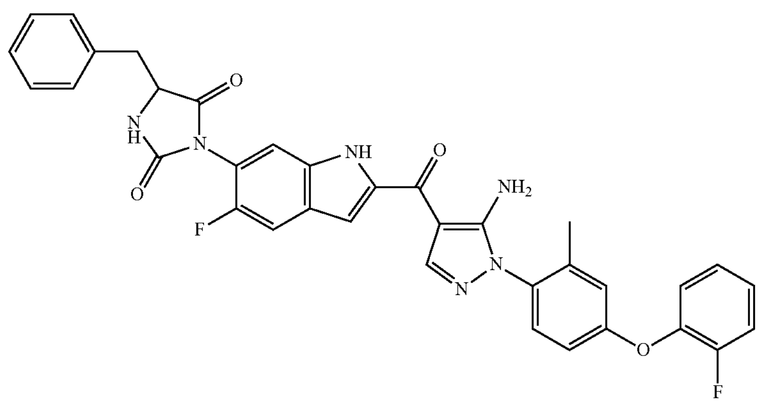 [SMILES: Cc1cc(Oc2ccccc2F)ccc1-n1ncc(C(=O)c2cc3cc(F)c(N4C(=O)NC(Cc5ccccc5)C4=O)cc3[nH]2)c1N] | (5S)-3-[2-[5-amino-1-[4-(2-fluorophenoxy)-2-methylphenyl]pyrazole-4-carbonyl]-5-fluoro-1H-indol-6-yl]-5-benzylimidazolidine-2,4-dione | 633 | 1.03 | AA Rev.11 |

| Example No. | Chemical Structure | Compound Name | m/z (M + H) | Reaction Time (Minute) | LCMS Measurement Condition |
|---|---|---|---|---|---|
| 5-1-437 | 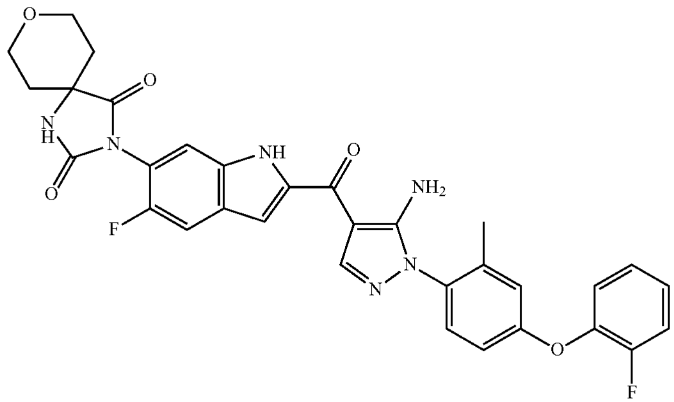 [SMILES: Cc1cc(Oc2ccccc2F)ccc1-n1ncc(C(=O)c2cc3cc(F)c(N4C(=O)NC5(CCOCC5)C4=O)cc3[nH]2)c1N] | 3-[2-[5-amino-1-[4-(2-fluorophenoxy)-2-methylphenyl]pyrazole-4-carbonyl]-5-fluoro-1H-indol-6-yl]-8-oxa-1,3-diazaspiro[4.5]decane-2,4-dione | 613 | 1.13 | TFA Rev.7 |
| 5-1-438 | 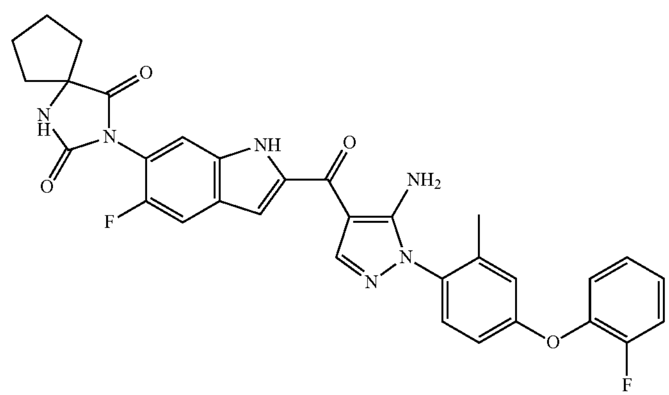 [SMILES: Cc1cc(Oc2ccccc2F)ccc1-n1ncc(C(=O)c2cc3cc(F)c(N4C(=O)NC5(CCCC5)C4=O)cc3[nH]2)c1N] | 3-[2-[5-amino-1-[4-(2-fluorophenoxy)-2-methylphenyl]pyrazole-4-carbonyl]-5-fluoro-1H-indol-6-yl]-1,3-diazaspiro[4.4]nonane-2,4-dione | 597 | 1.21 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-439 | 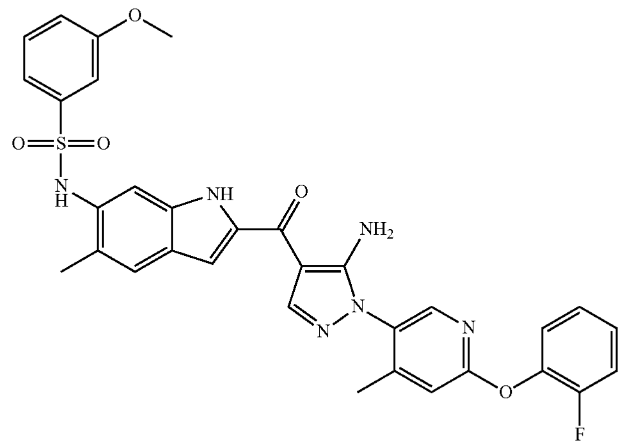 [SMILES: COc1cccc(S(=O)(=O)Nc2cc3[nH]c(C(=O)c4cnn(-c5cnc(Oc6ccccc6F)cc5C)c4N)cc3cc2C)c1] | N-[2-[5-amino-1-[6-(2-fluorophenoxy)-4-methylpyridin-3-yl]pyrazole-4-carbonyl]-5-methyl-1H-indol-6-yl]-3-methoxybenzenesulfonamide | 627 | 1.03 | AA Rev.11 |
| 5-1-440 | 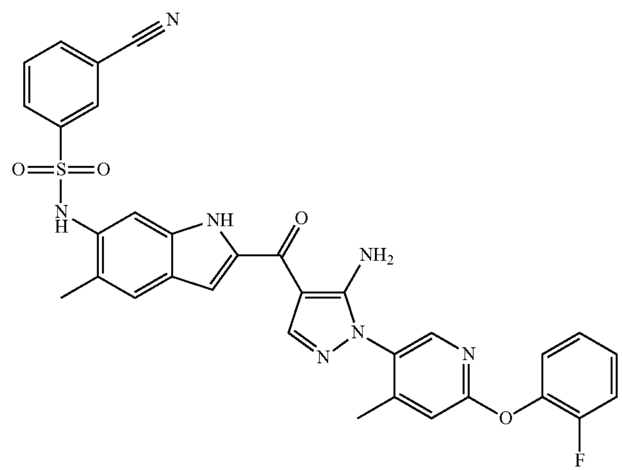 | N-[2-[5-amino-1-[6-(2-fluorophenoxy)-4-methylpyridin-3-yl]pyrazole-4-carbonyl]-5-methyl-1H-indol-6-yl]-3-cyanobenzenesulfonamide | 622 | 1.23 | TFA Rev.7 |

| Example No. | Chemical Structure | Compound Name | m/z (M + H) | Reaction Time (Minute) | LCMS Measurement Condition |
|---|---|---|---|---|---|
| 5-1-441 | 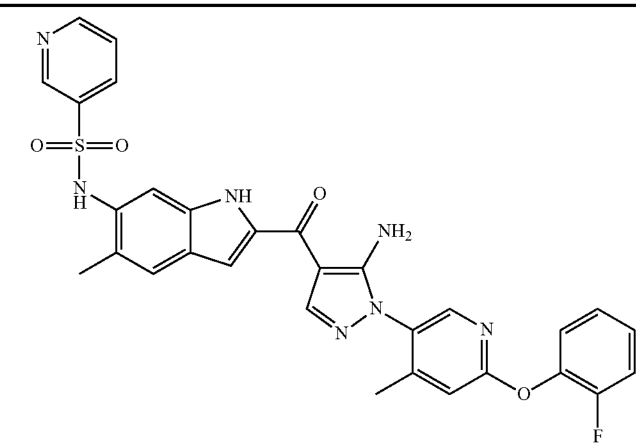 | N-[2-[5-amino-1-[6-(2-fluorophenoxy)-4-methylpyridin-3-yl]pyrazole-4-carbonyl]-5-methyl-1H-indol-6-yl]pyridine-3-sulfonamide | 598 | 0.98 | AA Rev.11 |
| 5-1-442 | 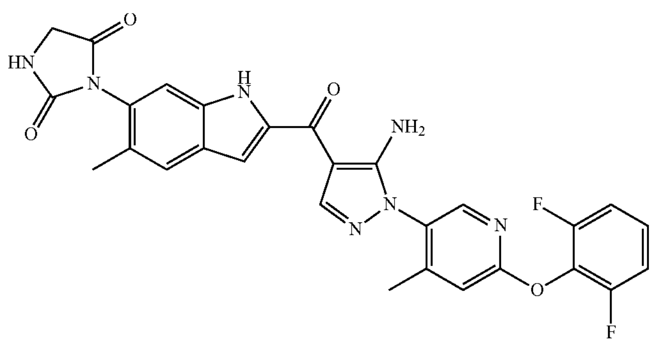 [SMILES: Cc1cc2cc(C(=O)c3cnn(-c4cnc(Oc5c(F)cccc5F)cc4C)c3N)[nH]c2cc1N1C(=O)CNC1=O] | 3-[2-[5-amino-1-[6-(2,6-difluorophenoxy)-4-methylpyridin-3-yl]pyrazolo-4-carbonyl]-5-methyl-1H-indol-6-yl]imidazolidine-2,4-dione | 558 | 0.95 | AA Rev.11 |

-continued
| Example No. | Chemical Structure | Compound Name | m/z (M + H) | Reaction Time (Minute) | LCMS Measurement Condition |
|---|---|---|---|---|---|
| 5-1-443 | 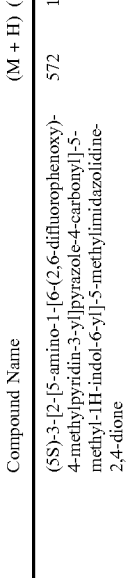 | (5S)-3-[2-[5-amino-1-[6-(2,6-difluorophenoxy)-4-methylpyridin-3-yl]pyrazole-4-carbonyl]-5-methyl-1H-indol-6-yl]-5-methylimidazolidine-2,4-dione | 572 | 1.09 | TFA Rev.7 |
| 5-1-444 | 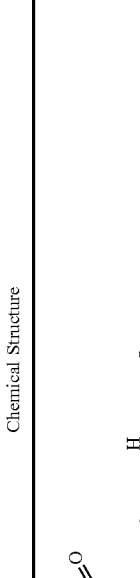 | (5S)-3-[2-[5-amino-1-[4-(2-fluorophenoxy)-2-methylphenyl]pyrazole-4-carbonyl]-5-methyl-1H-indol-6-yl]-5-methylimidazolidine-2,4-dione | 553 | 1.13 | TFA Rev.7 |

| Example No. | Chemical Structure | Compound Name | m/z (M + H) | Reaction Time (Minute) | LCMS Measurement Condition |
|---|---|---|---|---|---|
| 5-1-445 | 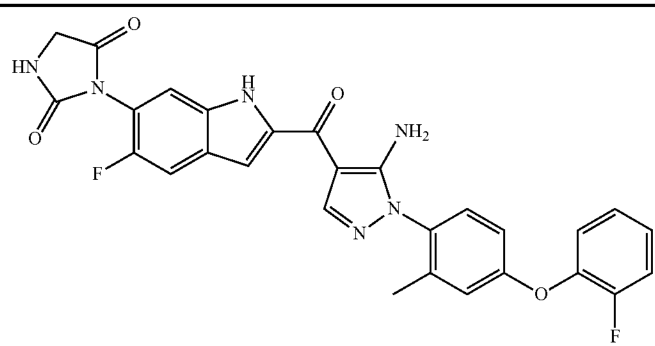 | 3-[2-[5-amino-1-[4-(2-fluorophenoxy)-2-methylphenyl]pyrazole-4-carbonyl]-5-fluoro-1H-indol-6-yl]imidazolidine-2,4-dione | 543 | 0.97 | AA Rev.11 |
| 5-1-446 | 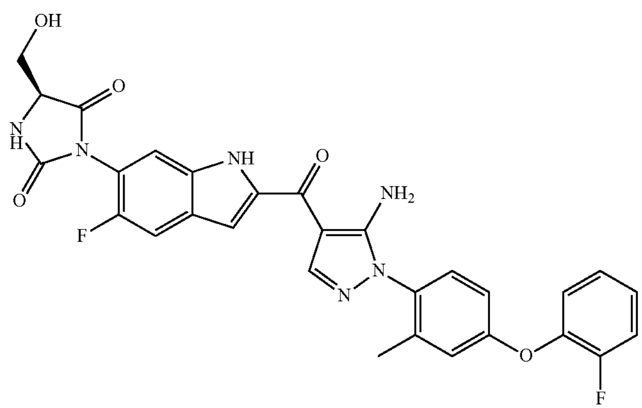 [SMILES: Cc1cc(Oc2ccccc2F)ccc1-n1ncc(C(=O)c2cc3cc(F)c(N4C(=O)N[C@@H](CO)C4=O)cc3[nH]2)c1N] | (5S)-3-[2-[5-amino-1-[4-(2-fluorophenoxy)-2-methylphenyl]pyrazole-4-carbonyl]-5-fluoro-1H-indol-6-yl]-5-(hydroxymethyl)imidazolidine-2,4-dione | 573 | 0.95 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-447 | 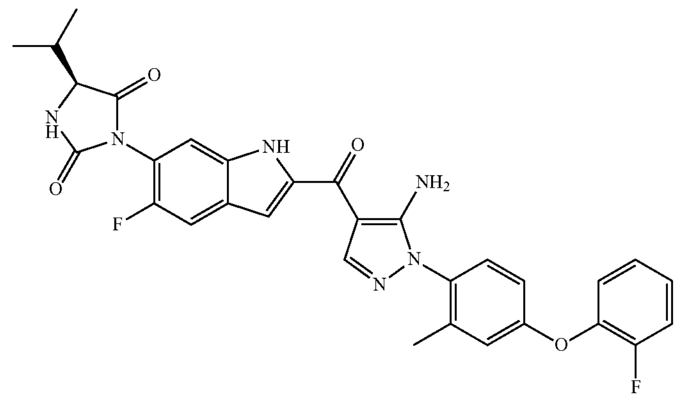 | (5S)-3-[2-[5-amino-1-[4-(2-fluorophenoxy)-2-methylphenyl]pyrazole-4-carbonyl]-5-fluoro-1H-indol-6-yl]-5-propan-2-ylimidazolidine-2,4-dione | 585 | 1.03 | AA Rev.11 |
| 5-1-448 | 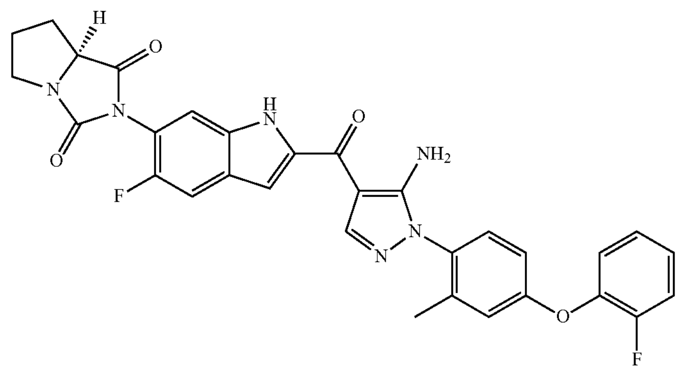 | (7aS)-2-[2-[5-amino-1-[4-(2-fluorophenoxy)-2-methylphenyl]pyrazole-4-carbonyl]-5-fluoro-1H-indol-6-yl]-5,6,7,7a-tetrahydropyrrolo[1,2-c]imidazole-1,3-dione | 583 | 1.01 | AA Rev.11 |

| Example No. | Chemical Structure | Compound Name | m/z (M + H) | Reaction Time (Minute) | LCMS Measurement Condition |
|---|---|---|---|---|---|
| 5-1-449 | 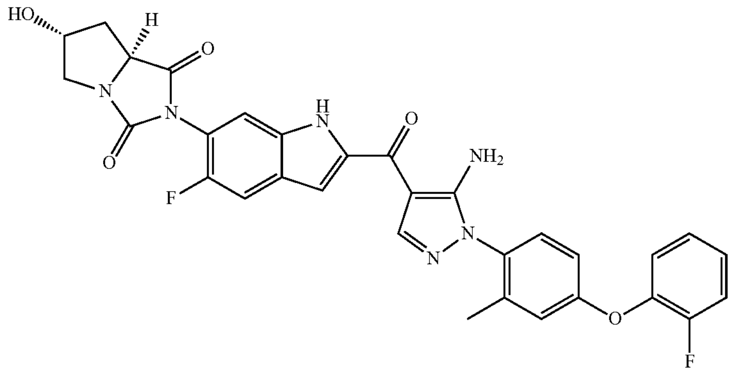 | (6R,7aS)-2-[2-[5-amino-1-[4-(2-fluorophenoxy)-2-methylphenyl]pyrazole-4-carbonyl]-5-fluoro-1H-indol-6-yl]-6-hydroxy-5,6,7,7a-tetrahydropyrrolo[1,2-c]imidazole-1,3-dione | 599 | 0.98 | AA Rev.11 |
| 5-1-450 | 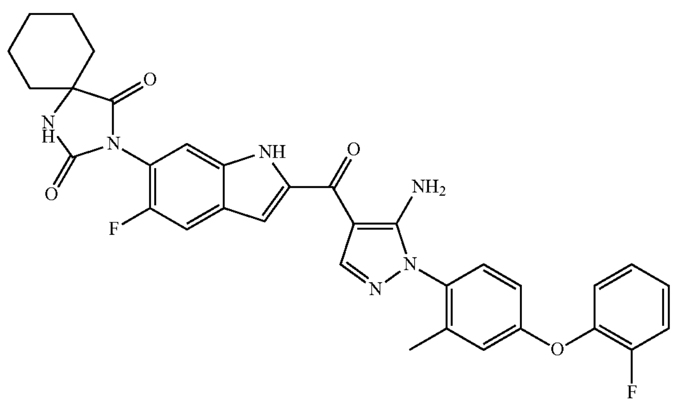 [SMILES: Cc1cc(Oc2ccccc2F)ccc1-n1ncc(C(=O)c2cc3cc(F)c(N4C(=O)NC5(CCCCC5)C4=O)cc3[nH]2)c1N] | 3-[2-[5-amino-1-[4-(2-fluorophenoxy)-2-methylphenyl]pyrazole-4-carbonyl]-5-fluoro-1H-indol-6-yl]-1,3-diazaspiro[4.5]decane-2,4-dione | 611 | 1.26 | TFA Rev.7 |

| Example No. | Chemical Structure | Compound Name | m/z (M + H) | Reaction Time (Minute) | LCMS Measurement Condition |
|---|---|---|---|---|---|
| 5-1-451 | 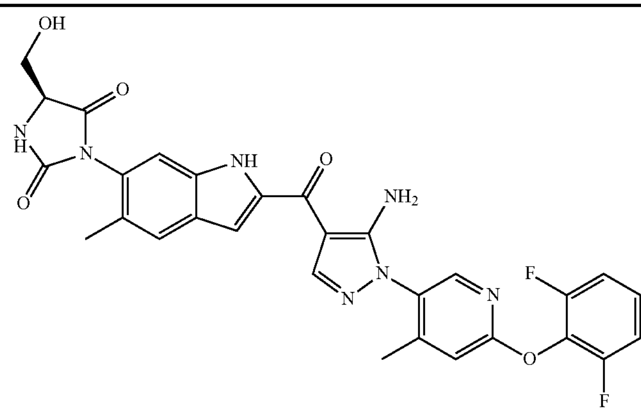 | (5S)-3-[2-[5-amino-1-[6-(2,6-difluorophenoxy)-4-methylpyridin-3-yl]pyrazole-4-carbonyl]-5-methyl-1H-indol-6-yl]-5-(hydroxymethyl)imidazolidine-2,4-dione | 588 | 0.95 | AA Rev.11 |
| 5-1-452 | 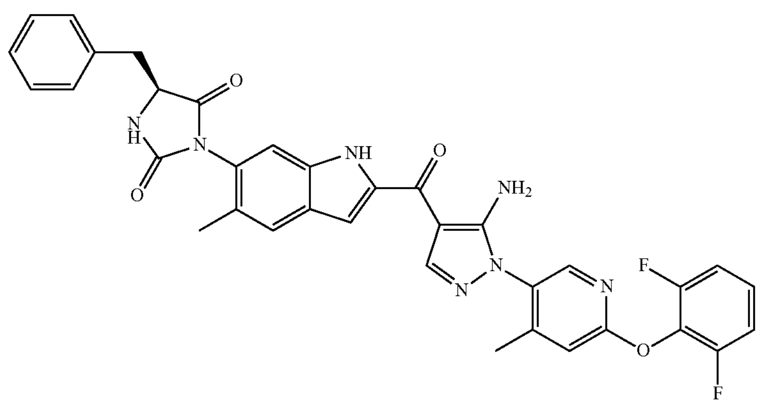 [SMILES: Cc1cc2cc(C(=O)c3cnn(-c4cnc(Oc5c(F)cccc5F)cc4C)c3N)[nH]c2cc1N1C(=O)N[C@@H](Cc2ccccc2)C1=O] | (5S)-3-[2-[5-amino-1-[6-(2,6-difluorophenoxy)-4-methylpyridin-3-yl]pyrazole-4-carbonyl]-5-methyl-1H-indol-6-yl]-5-benzylimidazolidine-2,4-dione | 648 | 1.04 | AA Rev.11 |

| Example No. | Chemical Structure | Compound Name | m/z (M + H) | Reaction Time (Minute) | LCMS Measurement Condition |
|---|---|---|---|---|---|
| 5-1-453 | 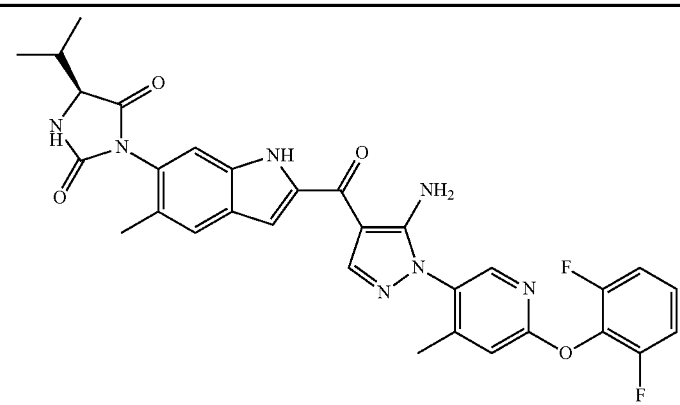 | (5S)-3-[2-[5-amino-1-[6-(2,6-difluorophenoxy)-4-methylpyridin-3-yl]pyrazole-4-carbonyl]-5-methyl-1H-indol-6-yl]-5-propan-2-ylimidazolidine-2,4-dione | 600 | 1.03 | AA Rev.11 |
| 5-1-454 | 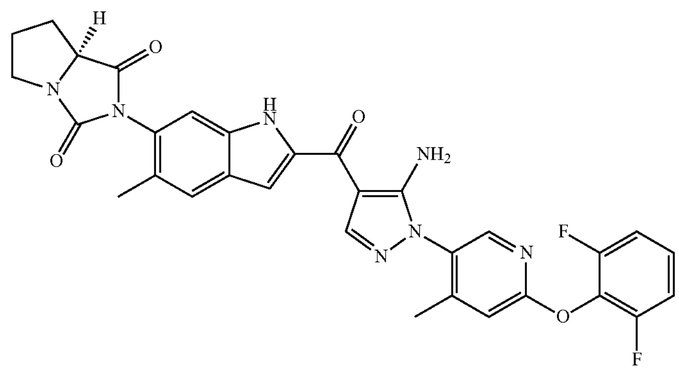 [SMILES: Cc1cc2cc(C(=O)c3cnn(-c4cnc(Oc5c(F)cccc5F)cc4C)c3N)[nH]c2cc1N1C(=O)[C@@H]2CCCN2C1=O] | (7aS)-2-[2-[5-amino-1-[6-(2,6-difluorophenoxy)-4-methylpyridin-3-yl]pyrazole-4-carbonyl]-5-methyl-1H-indol-6-yl]-5,6,7,7a-tetrahydropyrrolo[1,2-c]imidazole-1,3-dione | 598 | 1.17 | TFA Rev.7 |

| Example No. | Chemical Structure | Compound Name | m/z (M + H) | Reaction Time (Minute) | LCMS Measurement Condition |
|---|---|---|---|---|---|
| 5-1-455 | 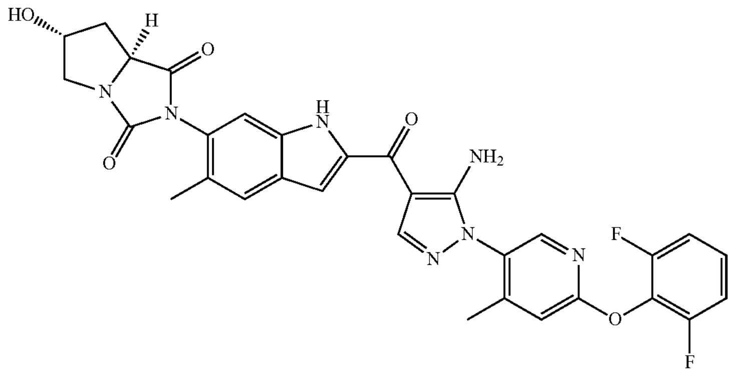 [SMILES: Cc1cc2cc(C(=O)c3cnn(-c4cnc(Oc5c(F)cccc5F)cc4C)c3N)[nH]c2cc1N1C(=O)[C@@H]2C[C@@H](O)CN2C1=O] | (6R,7aS)-2-[2-[5-amino-1-[6-(2,6-difluorophenoxy)-4-methylpyridin-3-yl]pyrazole-4-carbonyl]-5-methyl-1H-indol-6-yl]-6-hydroxy-5,6,7,7a-tetrahydropyrrolo[1,2-c]imidazole-1,3-dione | 614 | 1.06 | TFA Rev.7 |
| 5-1-456 | 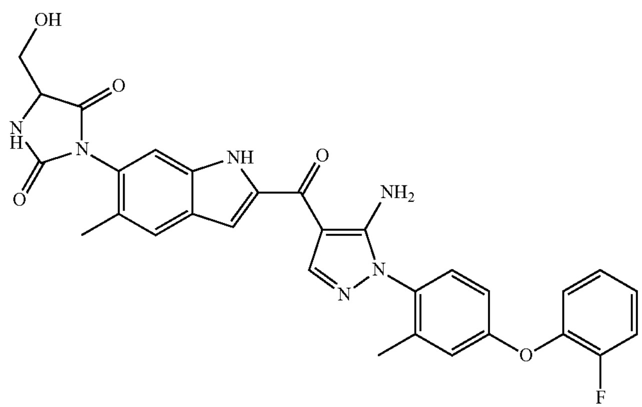 [SMILES: Cc1cc2cc(C(=O)c3cnn(-c4ccc(Oc5ccccc5F)cc4C)c3N)[nH]c2cc1N1C(=O)NC(CO)C1=O] | (5S)-3-[2-[5-amino-1-[4-(2-fluorophenoxy)-2-methylphenyl]pyrazole-4-carbonyl]-5-methyl-1H-indol-6-yl]-5-(hydroxymethyl)imidazolidine-2,4-dione | 569 | 1.02 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-457 | 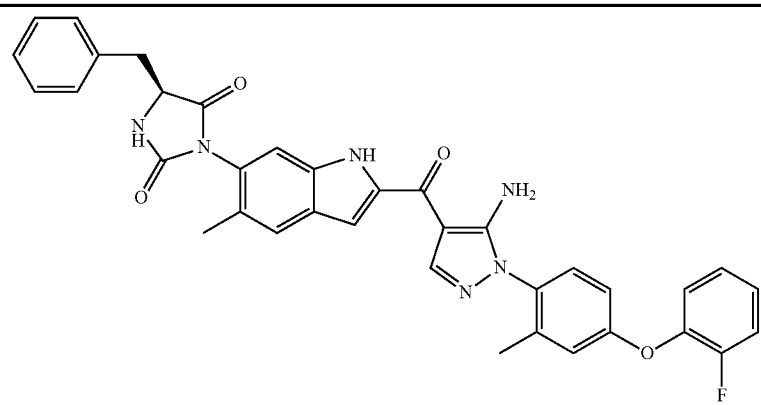 | (5S)-3-[2-[5-amino-1-[4-(2-fluorophenoxy)-2-methylphenyl]pyrazole-4-carbonyl]-5-methyl-1H-indol-6-yl]-5-benzylimidazolidine-2,4-dione | 629 | 1.26 | TFA Rev.7 |
| 5-1-458 | 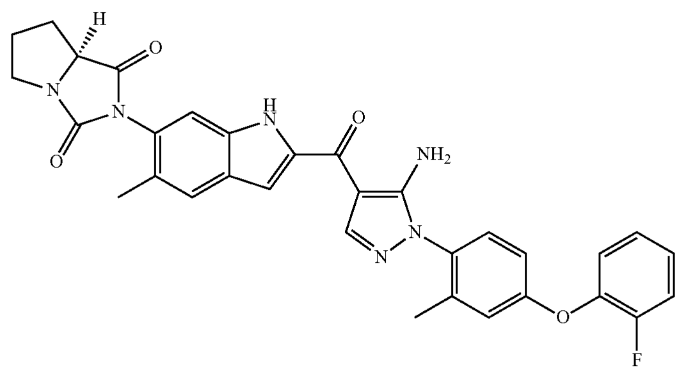 [SMILES: Cc1cc2cc(C(=O)c3cnn(-c4ccc(Oc5ccccc5F)cc4C)c3N)[nH]c2cc1N1C(=O)[C@@H]2CCCN2C1=O] | (7aS)-2-[2-[5-amino-1-[4-(2-fluorophenoxy)-2-methylphenyl]pyrazole-4-carbonyl]-5-methyl-1H-indol-6-yl]-5,6,7,7a-tetrahydropyrrolo[1,2-c]imidazole-1,3-dione | 579 | 1.21 | TFA Rev.7 |

| Example No. | Chemical Structure | Compound Name | m/z (M + H) | Reaction Time (Minute) | LCMS Measurement Condition |
|---|---|---|---|---|---|
| 5-1-459 | 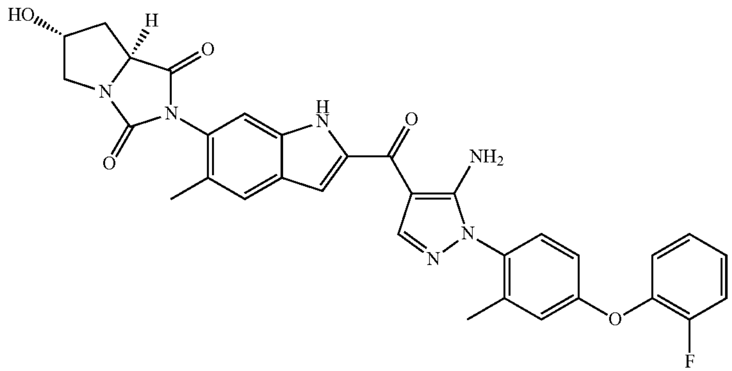 [SMILES: Cc1cc2cc(C(=O)c3cnn(-c4ccc(Oc5ccccc5F)cc4C)c3N)[nH]c2cc1N1C(=O)[C@@H]2C[C@@H](O)CN2C1=O] | (6R,7aS)-2-[2-[5-amino-1-[4-(2-fluorophenoxy)-2-methylphenyl]pyrazole-4-carbonyl]-5-methyl-1H-indol-6-yl]-6-hydroxy-5,6,7,7a-tetrahydropyrrolo[1,2-c]imidazole-1,3-dione | 595 | 1.10 | TFA Rev.7 |
| 5-1-460 | 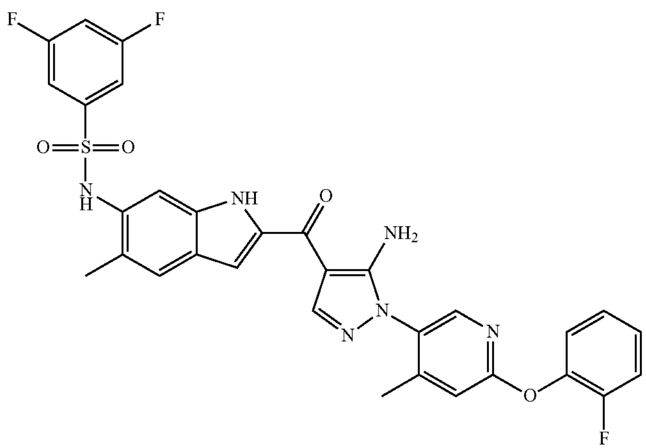 [SMILES: Cc1cc2cc(C(=O)c3cnn(-c4cnc(Oc5ccccc5F)cc4C)c3N)[nH]c2cc1NS(=O)(=O)c1cc(F)cc(F)c1] | N-[2-[5-amino-1-[6-(2-fluorophenoxy)-4-methylpyridin-3-yl]pyrazole-4-carbonyl]-5-methyl-1H-indol-6-yl]-3,5-difluorobenzenesulfonamide | 633 | 1.29 | TFA Rev.7 |

| Example No. | Chemical Structure | Compound Name | m/z (M + H) | Reaction Time (Minute) | LCMS Measurement Condition |
|---|---|---|---|---|---|
| 5-1-461 | 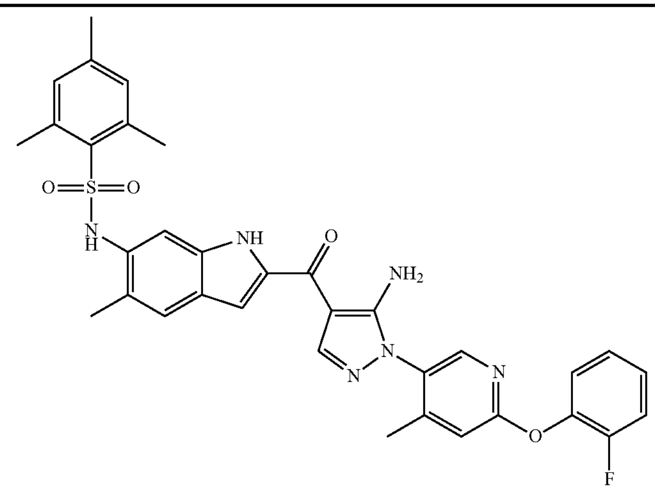 | N-[2-[5-amino-1-[6-(2-fluorophenoxy)-4-methylpyridin-3-yl]pyrazole-4-carbonyl]-5-methyl-1H-indol-6-yl]-2,4,5-trimethylbenzenesulfonamide | 639 | 1.09 | AA Rev.11 |
| 5-1-462 | 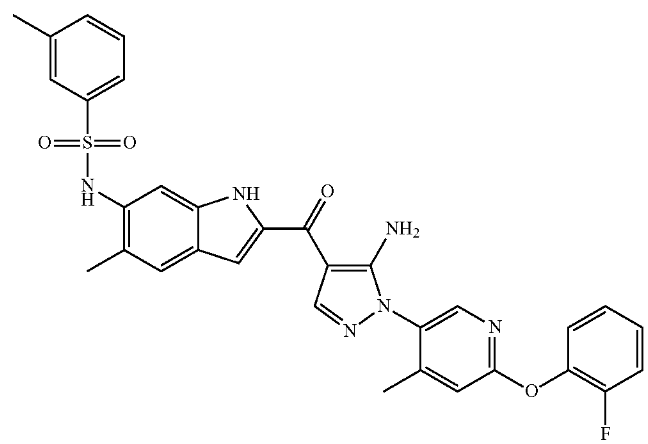 | N-[2-[5-amino-1-[6-(2-fluorophenoxy)-4-methylpyridin-3-yl]pyrazole-4-carbonyl]-5-methyl-1H-indol-6-yl]-3-methylbenzenesulfonamide | 611 | 1.28 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-463 | 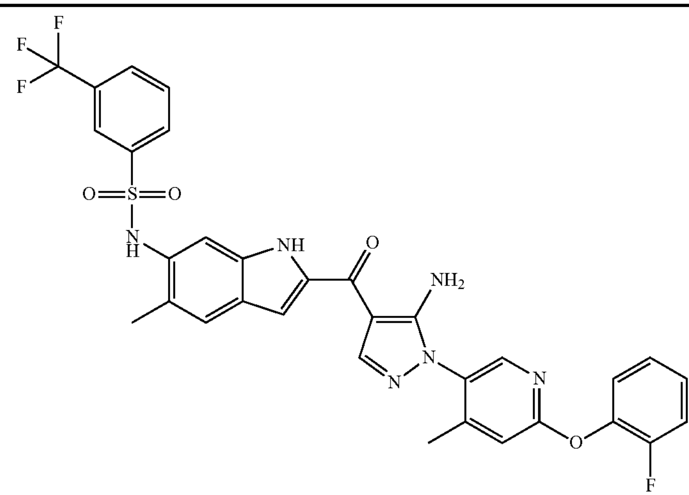 | N-[2-[5-amino-1-[6-(2-fluorophenoxy)-4-methylpyridin-3-yl]pyrazole-4-carbonyl]-5-methyl-1H-indol-6-yl]-3-(trifluoromethyl)benzenesulfonamide | 665 | 1.33 | TFA Rev.7 |
| 5-1-464 | 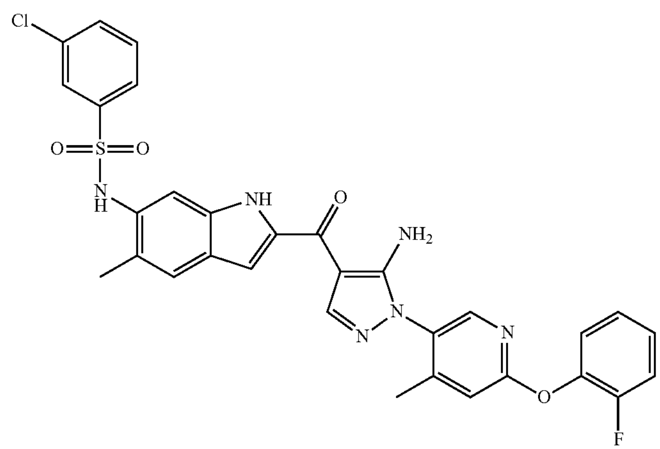 | N-[2-[5-amino-1-[6-(2-fluorophenoxy)-4-methylpyridin-3-yl]pyrazole-4-carbonyl]-5-methyl-1H-indol-6-yl]-3-chlorobenzenesulfonamide | 631, 633 | 1.31 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-465 | 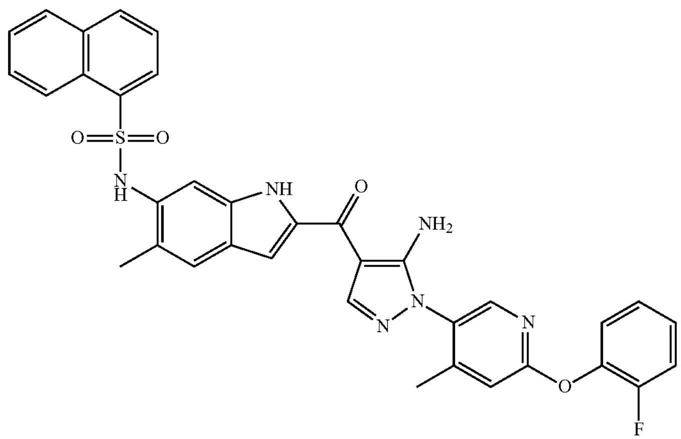 [SMILES: Cc1cc2cc(C(=O)c3cnn(-c4cnc(Oc5ccccc5F)cc4C)c3N)[nH]c2cc1NS(=O)(=O)c1cccc2ccccc12] | N-[2-[5-amino-1-[6-(2-fluorophenoxy)-4-methylpyridin-3-yl]pyrazole-4-carbonyl]-5-methyl-1H-indol-6-yl]naphthalene-1-sulfonamide | 647 | 1.32 | TFA Rev.7 |
| 5-1-466 | 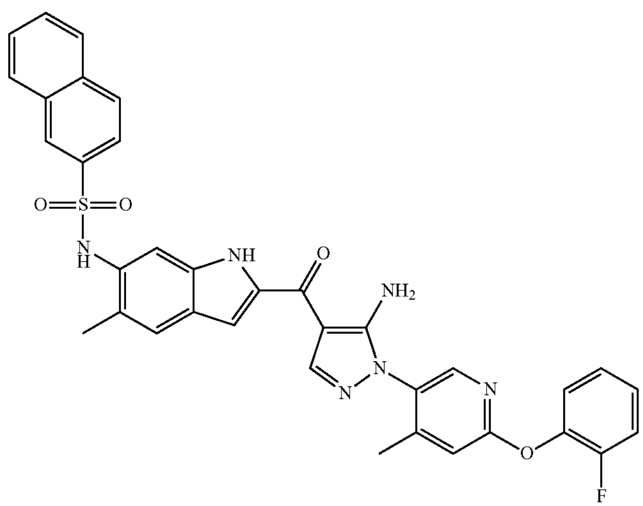 [SMILES: Cc1cc2cc(C(=O)c3cnn(-c4cnc(Oc5ccccc5F)cc4C)c3N)[nH]c2cc1NS(=O)(=O)c1ccc2ccccc2c1] | N-[2-[5-amino-1-[6-(2-fluorophenoxy)-4-methylpyridin-3-yl]pyrazole-4-carbonyl]-5-methyl-1H-indol-6-yl]naphthalene-2-sulfonamide | 647 | 1.32 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-467 | 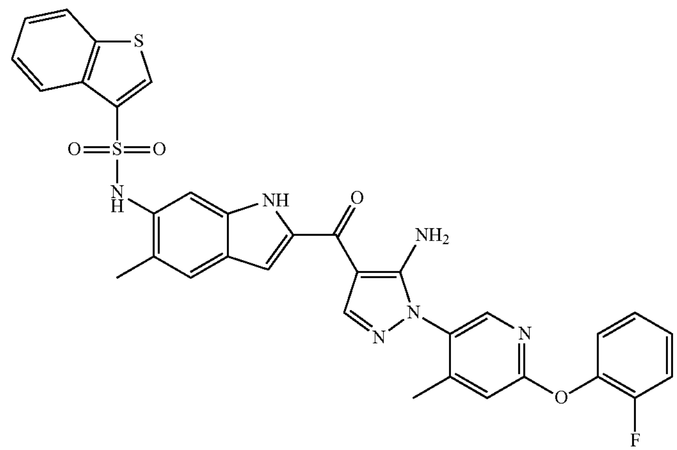 [SMILES: Cc1cc2cc(C(=O)c3cnn(-c4cnc(Oc5ccccc5F)cc4C)c3N)[nH]c2cc1NS(=O)(=O)c1csc2ccccc12] | N-[2-[5-amino-1-[6-(2-fluorophenoxy)-4-methylpyridin-3-yl]pyrazole-4-carbonyl]-5-methyl-1H-indol-6-yl]-1-benzothiophene-3-sulfonamide | 653 | 1.32 | TFA Rev.7 |
| 5-1-468 | 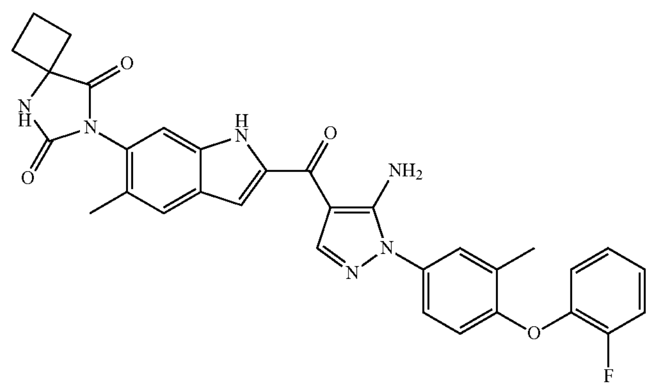 [SMILES: Cc1cc(-n2ncc(C(=O)c3cc4cc(C)c(N5C(=O)NC6(CCC6)C5=O)cc4[nH]3)c2N)ccc1Oc1ccccc1F] | 7-[2-[5-amino-1-[4-(2-fluorophenoxy)-3-methylphenyl]pyrazole-4-carbonyl]-5-methyl-1H-indol-6-yl]-5,7-diazaspiro[3.4]octane-6,8-dione | 579 | 1.24 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-469 | 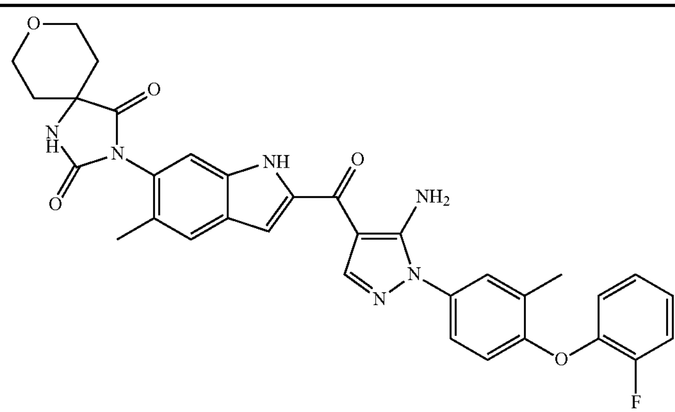 | 3-[2-[5-amino-1-[4-(2-fluorophenoxy)-3-methylphenyl]pyrazole-4-carbonyl]-5-methyl-1H-indol-6-yl]-8-oxa-1,3-diazaspiro[4.5]decane-2,4-dione | 609 | 1.18 | TFA Rev.7 |
| 5-1-470 | 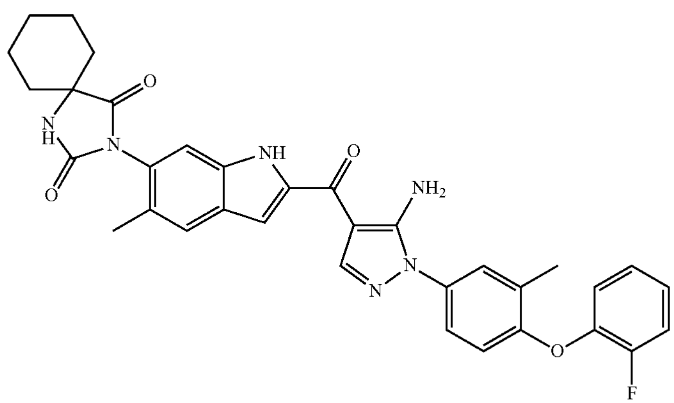 [SMILES: Cc1cc(-n2ncc(C(=O)c3cc4cc(C)c(N5C(=O)NC6(CCCCC6)C5=O)cc4[nH]3)c2N)ccc1Oc1ccccc1F] | 3-[2-[5-amino-1-[4-(2-fluorophenoxy)-3-methylphenyl]pyrazole-4-carbonyl]-5-methyl-1H-indol-6-yl]-1,3-diazaspiro[4.5]decane-2,4-dione | 607 | 1.08 | AA Rev.11 |

| Example No. | Chemical Structure | Compound Name | m/z (M + H) | Reaction Time (Minute) | LCMS Measurement Condition |
|---|---|---|---|---|---|
| 5-1-471 | 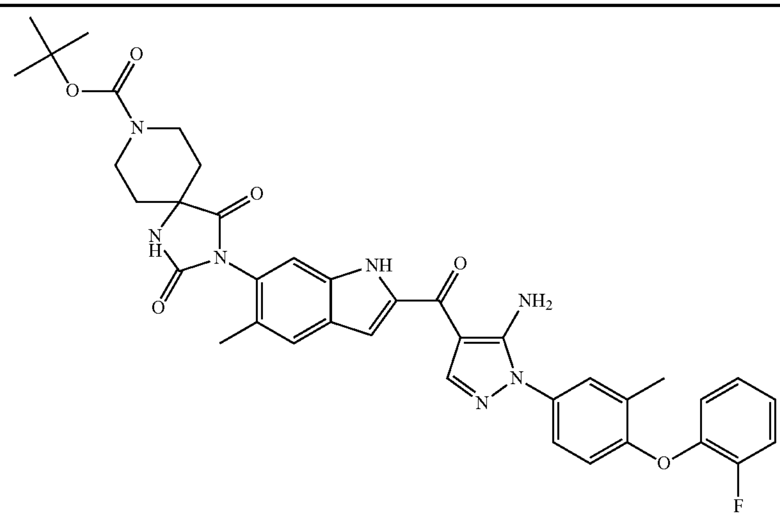 | tert-Butyl 3-[2-[5-amino-1-[4-(2-fluorophenoxy)-3-methylphenyl]pyrazole-4-carbonyl]-5-methyl-1H-indol-6-yl]-2,4-dioxo-1,3,8-triazaspiro[4.5]decane-8-carboxylate | 708 | 1.36 | TFA Rev.7 |
| 5-1-472 | 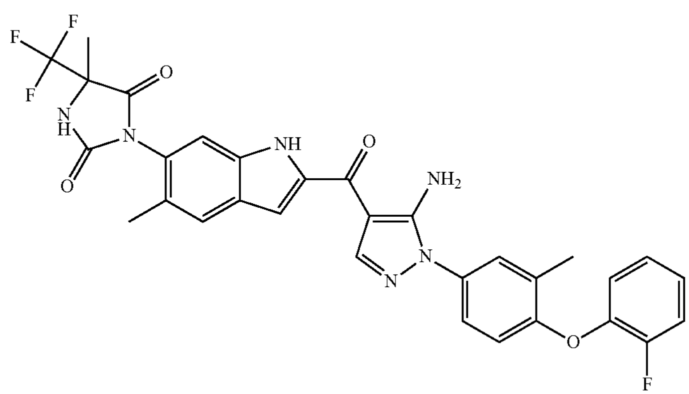 [SMILES: Cc1cc(-n2ncc(C(=O)c3cc4cc(C)c(N5C(=O)NC(C)(C(F)(F)F)C5=O)cc4[nH]3)c2N)ccc1Oc1ccccc1F] | 3-[2-[5-amino-1-[4-(2-fluorophenoxy)-3-methylphenyl]pyrazole-4-carbonyl]-5-methyl-1H-indol-6-yl]-5-methyl-5-(trifluoromethyl)imidazolidine-2,4-dione | 621 | 1.33 | TFA Rev.7 |

| Example No. | Chemical Structure | Compound Name | m/z (M + H) | Reaction Time (Minute) | LCMS Measurement Condition |
|---|---|---|---|---|---|
| 5-1-473 | 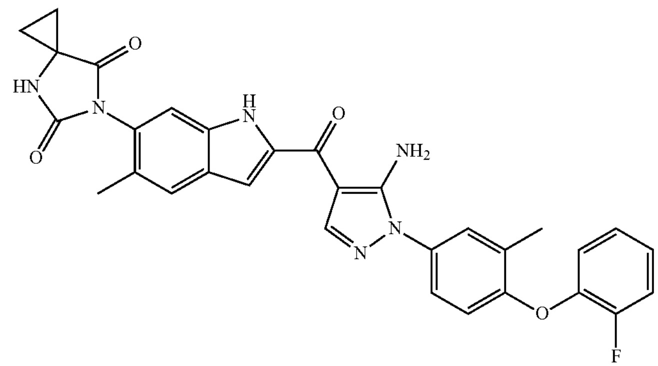 [SMILES: Cc1cc(-n2ncc(C(=O)c3cc4cc(C)c(N5C(=O)NC6(CC6)C5=O)cc4[nH]3)c2N)ccc1Oc1ccccc1F] | 6-[2-[5-amino-1-[4-(2-fluorophenoxy)-3-methylphenyl]pyrazole-4-carbonyl]-5-methyl-1H-indol-6-yl]-4,6-diazaspiro[2.4]heptane-5,7-dione | 565 | 1.03 | AA Rev.11 |
| 5-1-474 | 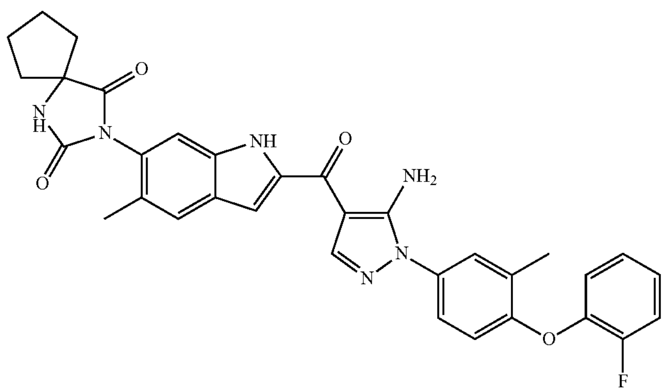 [SMILES: Cc1cc(-n2ncc(C(=O)c3cc4cc(C)c(N5C(=O)NC6(CCCC6)C5=O)cc4[nH]3)c2N)ccc1Oc1ccccc1F] | 3-[2-[5-amino-1-[4-(2-fluorophenoxy)-3-methylphenyl]pyrazole-4-carbonyl]-5-methyl-1H-indol-6-yl]-1,3-diazaspiro[4.4]nonane-2,4-dione | 593 | 1.27 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-475 | 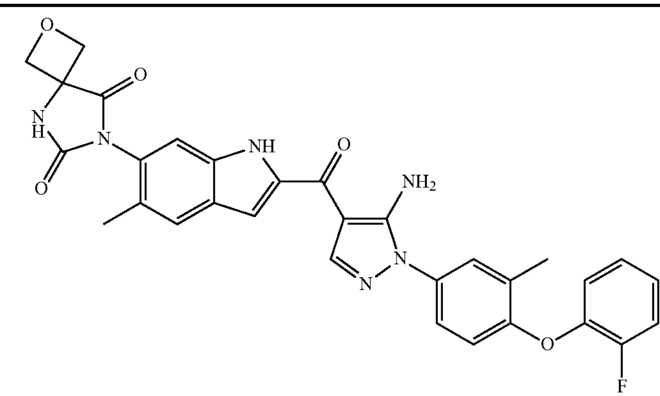 | 7-[2-[5-amino-1-[4-(2-fluorophenoxy)-3-methylphenyl]pyrazole-4-carbonyl]-5-methyl-1H-indol-6-yl]-2-oxa-5,7-diazaspiro[3.4]octane-6,8-dione | 581 | 1.16 | TFA Rev.7 |
| 5-1-476 | 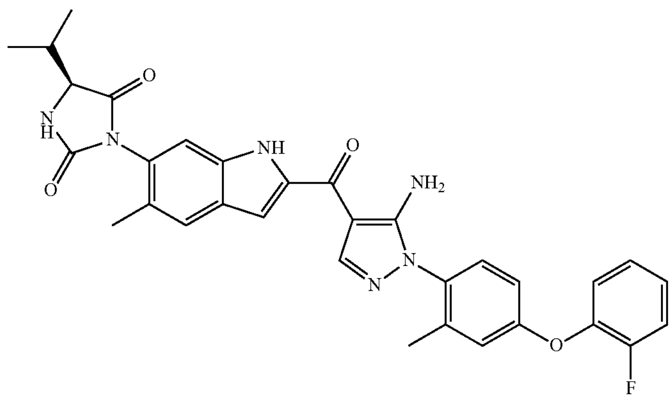 [SMILES: Cc1cc2cc(C(=O)c3cnn(-c4ccc(Oc5ccccc5F)cc4C)c3N)[nH]c2cc1N1C(=O)N[C@@H](C(C)C)C1=O] | (5S)-3-[2-[5-amino-1-[4-(2-fluorophenoxy)-2-methylphenyl]pyrazole-4-carbonyl]-5-methyl-1H-indol-6-yl]-5-propan-2-ylimidazolidine-2,4-dione | 581 | 1.23 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-477 | 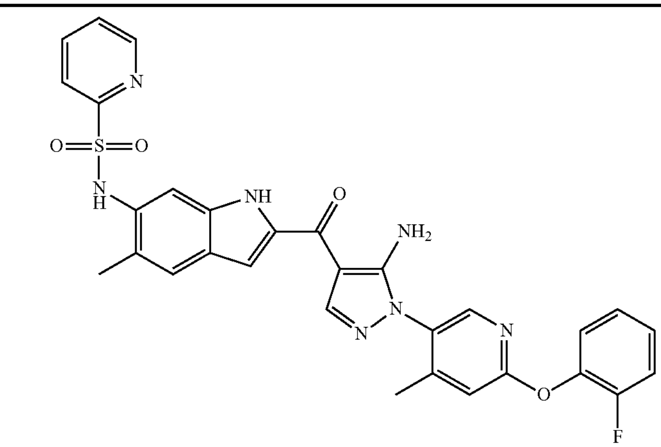 | N-[2-[5-amino-1-[6-(2-fluorophenoxy)-4-methylpyridin-3-yl]pyrazole-4-carbonyl]-5-methyl-1H-indol-6-yl]pyridine-2-sulfonamide | 598 | 1.16 | TFA Rev.7 |
| 5-1-478 | 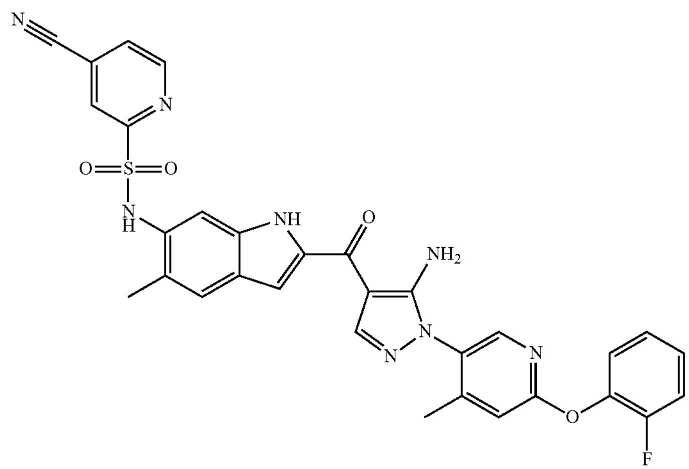 [SMILES: Cc1cc2cc(C(=O)c3cnn(-c4cnc(Oc5ccccc5F)cc4C)c3N)[nH]c2cc1NS(=O)(=O)c1cc(C#N)ccn1] | N-[2-[5-amino-1-[6-(2-fluorophenoxy)-4-methylpyridin-3-yl]pyrazole-4-carbonyl]-5-methyl-1H-indol-6-yl]-4-cyanopyridine-2-sulfonamide | 623 | 1.19 | TFA Rev.7 |

| Example No. | Chemical Structure | Compound Name | m/z (M + H) | Reaction Time (Minute) | LCMS Measurement Condition |
|---|---|---|---|---|---|
| 5-1-479 | 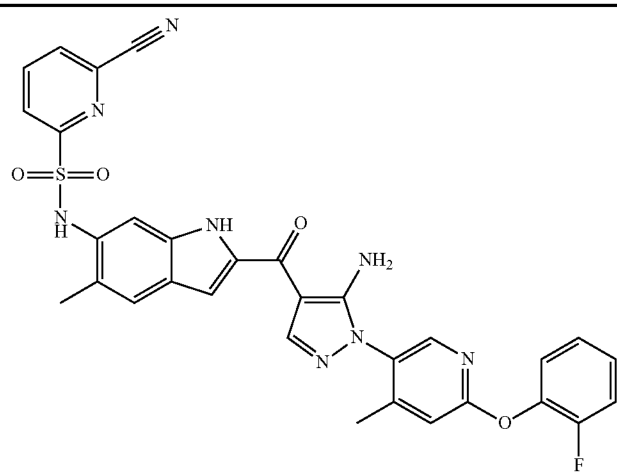 | N-[2-[5-amino-1-[6-(2-fluorophenoxy)-4-methylpyridin-3-yl]pyrazole-4-carbonyl]-5-methyl-1H-indol-6-yl]-6-cyanopyridine-2-sulfonamide | 623 | 0.96 | AA Rev.11 |
| 5-1-480 | 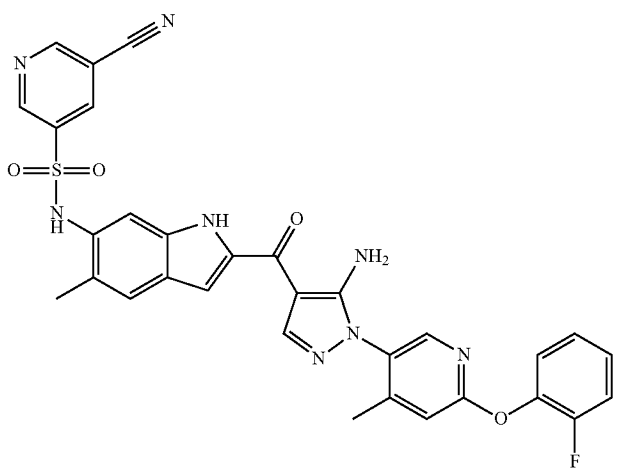 | N-[2-[5-amino-1-[6-(2-fluorophenoxy)-4-methylpyridin-3-yl]pyrazole-4-carbonyl]-5-methyl-1H-indol-6-yl]-5-cyanopyridine-3-sulfonamide | 623 | 1.19 | TFA Rev.7 |

| Example No. | Chemical Structure | Compound Name | m/z (M + H) | Reaction Time (Minute) | LCMS Measurement Condition |
|---|---|---|---|---|---|
| 5-1-481 | 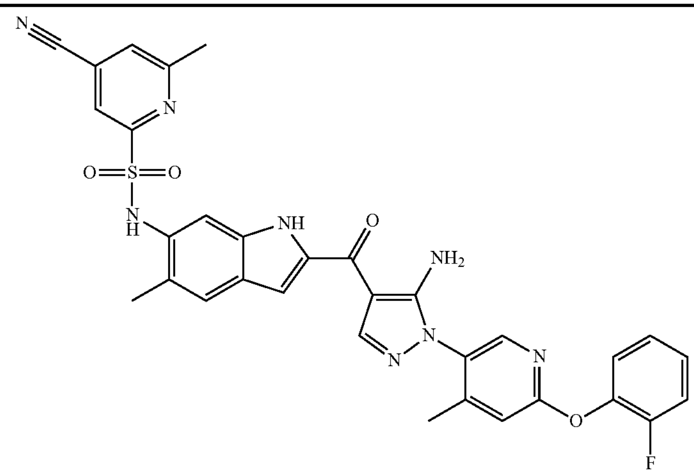 | N-[2-[5-amino-1-[6-(2-fluorophenoxy)-4-methylpyridin-3-yl]pyrazole-4-carbonyl]-5-methyl-1H-indol-6-yl]-4-cyano-6-methylpyridine-2-sulfonamide | 637 | 1.22 | TFA Rev.7 |
| 5-1-482 | 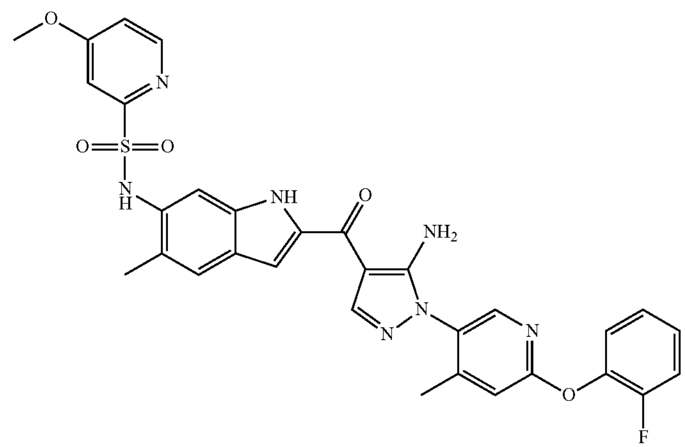 [SMILES: COc1ccnc(S(=O)(=O)Nc2cc3[nH]c(C(=O)c4cnn(-c5cnc(Oc6ccccc6F)cc5C)c4N)cc3cc2C)c1] | N-[2-[5-amino-1-[6-(2-fluorophenoxy)-4-methylpyridin-3-yl]pyrazole-4-carbonyl]-5-methyl-1H-indol-6-yl]-4-methoxypyridine-2-sulfonamide | 628 | 1.17 | TFA Rev.7 |

| Example No. | Chemical Structure | Compound Name | m/z (M + H) | Reaction Time (Minute) | LCMS Measurement Condition |
|---|---|---|---|---|---|
| 5-1-483 | 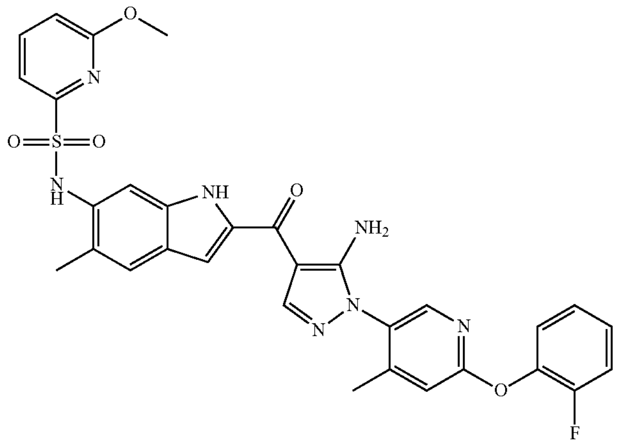 [SMILES: COc1cccc(S(=O)(=O)Nc2cc3[nH]c(C(=O)c4cnn(-c5cnc(Oc6ccccc6F)cc5C)c4N)cc3cc2C)n1] | N-[2-[5-amino-1-[6-(2-fluorophenoxy)-4-methylpyridin-3-yl]pyrazole-4-carbonyl]-5-methyl-1H-indol-6-yl]-6-methoxypyridine-2-sulfonamide | 628 | 1.24 | TFA Rev.7 |
| 5-1-484 | 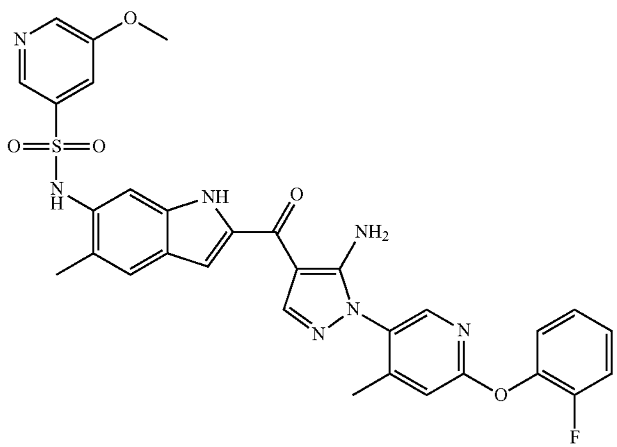 | N-[2-[5-amino-1-[6-(2-fluorophenoxy)-4-methylpyridin-3-yl]pyrazole-4-carbonyl]-5-methyl-1H-indol-6-yl]-5-methoxypyridine-3-sulfonamide | 628 | 0.99 | AA Rev.11 |

| Example No. | Chemical Structure | Compound Name | m/z (M + H) | Reaction Time (Minute) | LCMS Measurement Condition |
|---|---|---|---|---|---|
| 5-1-485 | 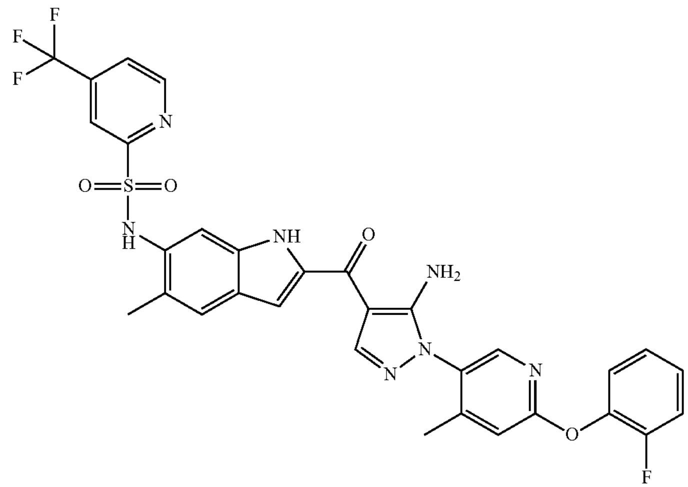 [SMILES: Cc1cc2cc(C(=O)c3cnn(-c4cnc(Oc5ccccc5F)cc4C)c3N)[nH]c2cc1NS(=O)(=O)c1cc(C(F)(F)F)ccn1] | N-[2-[5-amino-1-[6-(2-fluorophenoxy)-4-methylpyridin-3-yl]pyrazole-4-carbonyl]-5-methyl-1H-indol-6-yl]-4-(trifluoromethyl)pyridine-2-sulfonamide | 666 | 1.27 | TFA Rev.7 |
| 5-1-486 | 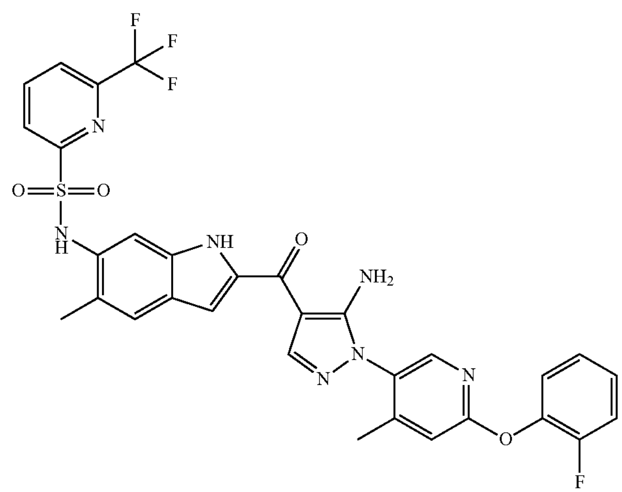 [SMILES: Cc1cc2cc(C(=O)c3cnn(-c4cnc(Oc5ccccc5F)cc4C)c3N)[nH]c2cc1NS(=O)(=O)c1cccc(C(F)(F)F)n1] | N-[2-[5-amino-1-[6-(2-fluorophenoxy)-4-methylpyridin-3-yl]pyrazole-4-carbonyl]-5-methyl-1H-indol-6-yl]-6-(trifluoromethyl)pyridine-2-sulfonamide | 666 | 1.28 | TFA Rev.7 |

| Example No. | Chemical Structure | Compound Name | m/z (M + H) | Reaction Time (Minute) | LCMS Measurement Condition |
|---|---|---|---|---|---|
| 5-1-487 | 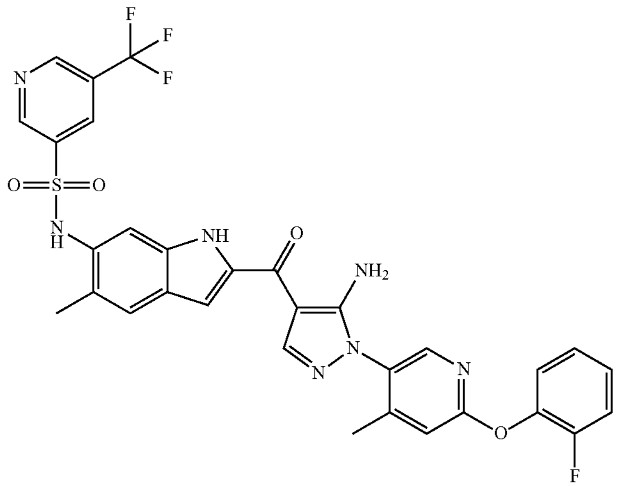 [SMILES: Cc1cc2cc(C(=O)c3cnn(-c4cnc(Oc5ccccc5F)cc4C)c3N)[nH]c2cc1NS(=O)(=O)c1cncc(C(F)(F)F)c1] | N-[2-[5-amino-1-[6-(2-fluorophenoxy)-4-methylpyridin-3-yl]pyrazole-4-carbonyl]-5-methyl-1H-indol-6-yl]-5-(trifluoromethyl)pyridine-3-sulfonamide | 666 | 1.28 | AA Rev.7 |
| 5-1-488 | 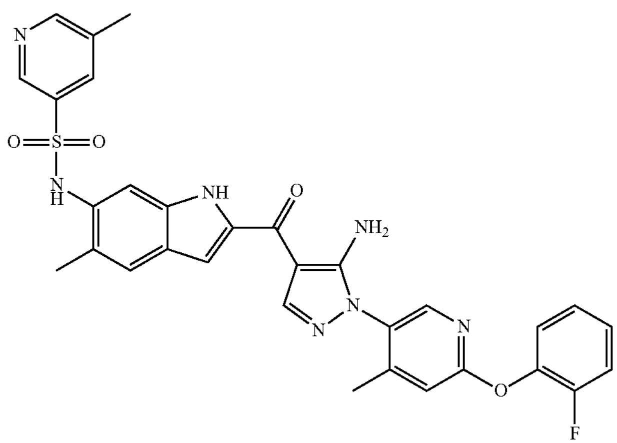 [SMILES: Cc1cncc(S(=O)(=O)Nc2cc3[nH]c(C(=O)c4cnn(-c5cnc(Oc6ccccc6F)cc5C)c4N)cc3cc2C)c1] | N-[2-[5-amino-1-[6-(2-fluorophenoxy)-4-methylpyridin-3-yl]pyrazole-4-carbonyl]-5-methyl-1H-indol-6-yl]-5-methylpyridine-3-sulfonamide | 612 | 0.99 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-489 | 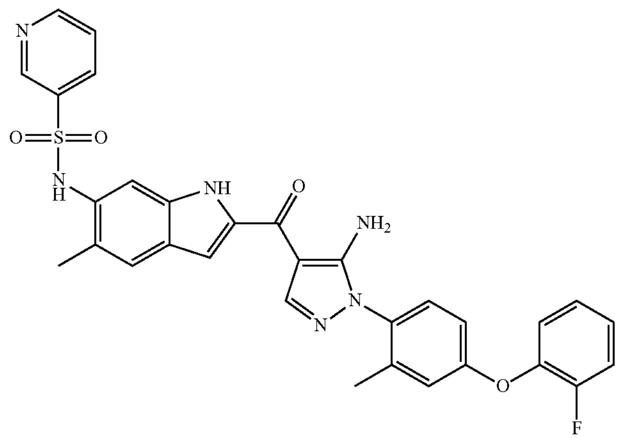 | N-[2-[5-amino-1-[4-(2-fluorophenoxy)-2-methylphenyl]pyrazole-4-carbonyl]-5-fluoro-1H-indol-6-yl]pyridine-3-sulfonamide | 601 | 0.98 | AA Rev.11 |
| 5-1-490 | 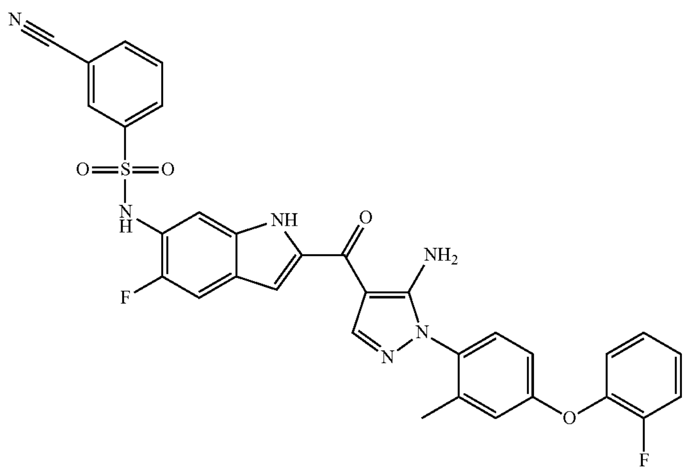 | N-[2-[5-amino-1-[4-(2-fluorophenoxy)-2-methylphenyl]pyrazole-4-carbonyl]-5-fluoro-1H-indol-6-yl]-3-cyanobenzenesulfonamide | 625 | 1.00 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-491 | 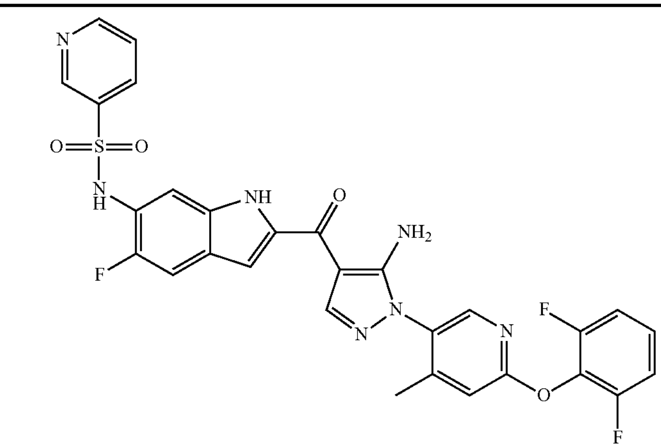 | N-[2-[5-amino-1-[6-(2,6-difluorophenoxy)-4-methylpyridin-3-yl]pyrazole-4-carbonyl]-5-fluoro-1H-indol-6-yl]pyridine-3-sulfonamide | 620 | 0.95 | AA Rev.11 |
| 5-1-492 | 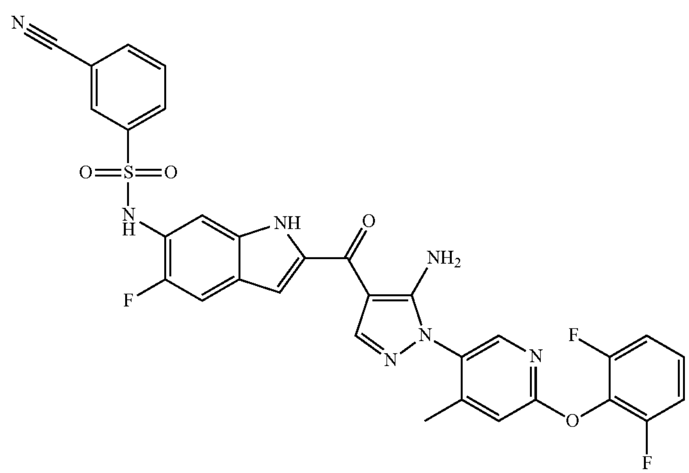 | N-[2-[5-amino-1-[6-(2,6-difluorophenoxy)-4-methylpyridin-3-yl]pyrazole-4-carbonyl]-5-fluoro-1H-indol-6-yl]-3-cyanobenzenesulfonamide | 644 | 0.98 | AA Rev.11 |

| Example No. | Chemical Structure | Compound Name | m/z (M + H) | Reaction Time (Minute) | LCMS Measurement Condition |
|---|---|---|---|---|---|
| 5-1-493 | 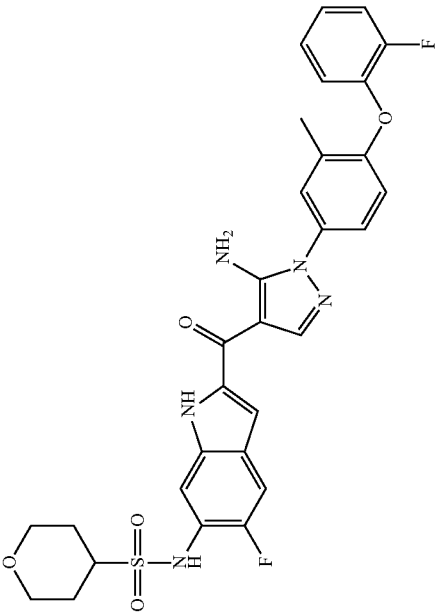 | N-[2-[5-amino-1-[4-(2-fluorophenoxy)-3-methylphenyl]pyrazole-4-carbonyl]-5-fluoro-1H-indol-6-yl]oxane-4-sulfonamide | 608 | 1.23 | TFA Rev.7 |
| 5-1-494 | 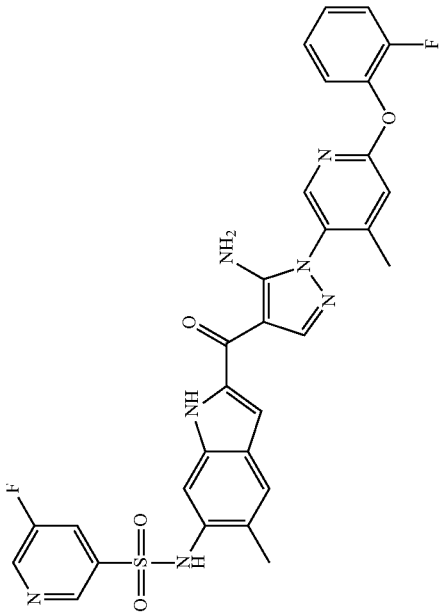 | N-[2-[5-amino-1-[6-(2-fluorophenoxy)-4-methylpyridin-3-yl]pyrazole-4-carbonyl]-5-methyl-1H-indol-6-yl]-5-fluoropyridine-3-sulfonamide | 616 | 1.20 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-495 | 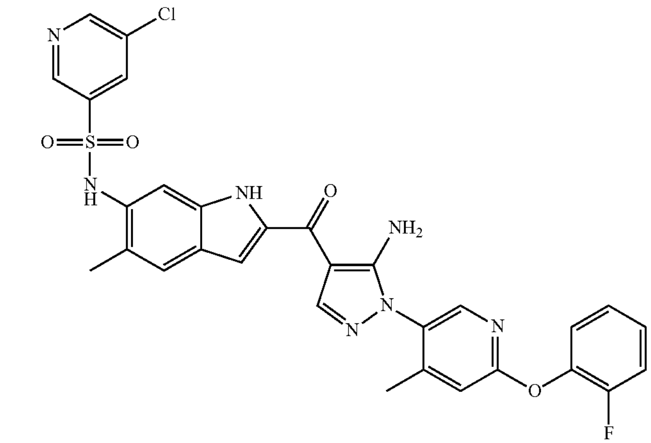 | N-[2-[5-amino-1-[6-(2-fluorophenoxy)-4-methylpyridin-3-yl]pyrazole-4-carbonyl]-5-methyl-1H-indol-6-yl]-5-chloropyridine-3-sulfonamide | 632, 634 | 1.25 | TFA Rev.7 |
| 5-1-496 | 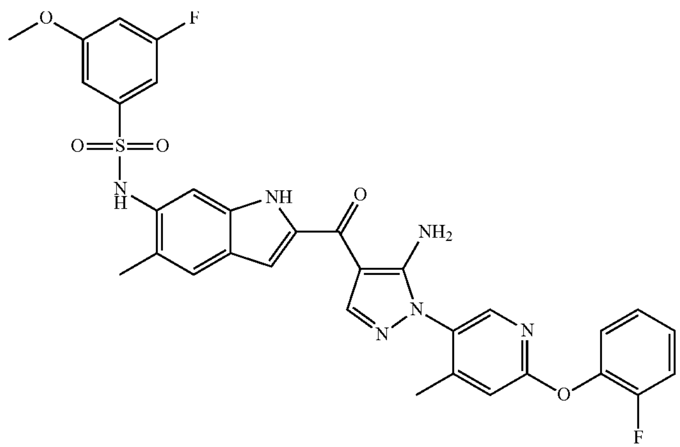 | N-[2-[5-amino-1-[6-(2-fluorophenoxy)-4-methylpyridin-3-yl]pyrazole-4-carbonyl]-5-methyl-1H-indol-6-yl]-3-fluoro-5-methoxybenzenesulfonamide | 645 | 1.29 | TFA Rev.7 |

| Example No. | Chemical Structure | Compound Name | m/z (M + H) | Reaction Time (Minute) | LCMS Measurement Condition |
|---|---|---|---|---|---|
| 5-1-497 | 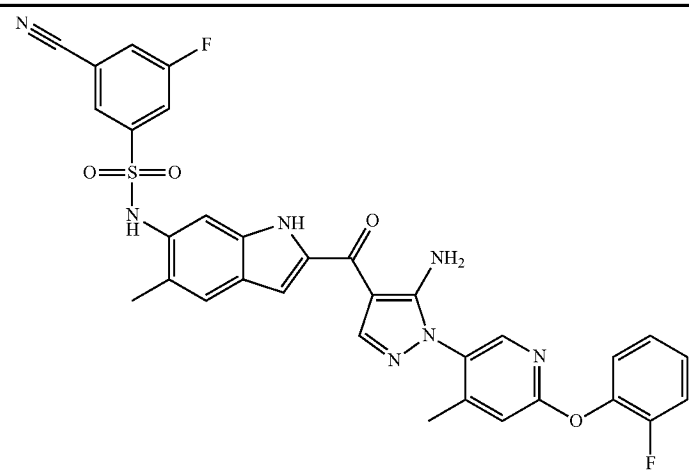 | N-[2-[5-amino-1-[6-(2-fluorophenoxy)-4-methylpyridin-3-yl]pyrazole-4-carbonyl]-5-methyl-1H-indol-6-yl]-3-cyano-5-fluorobenzenesulfonamide | 640 | 1.26 | TFA Rev.7 |
| 5-1-498 | 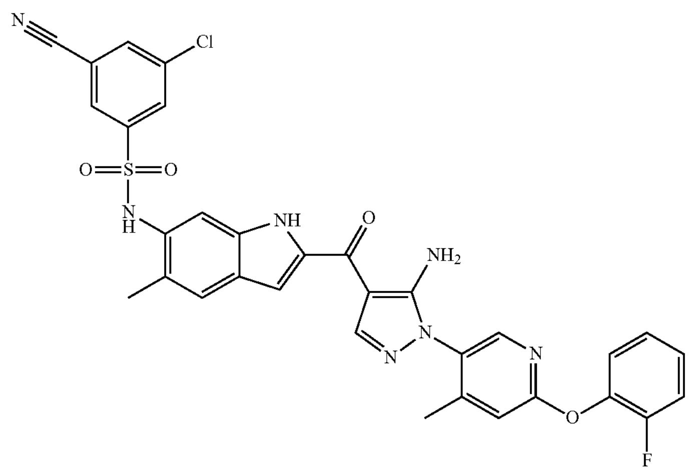 [SMILES: Cc1cc2cc(C(=O)c3cnn(-c4cnc(Oc5ccccc5F)cc4C)c3N)[nH]c2cc1NS(=O)(=O)c1cc(F)cc(C#N)c1] | N-[2-[5-amino-1-[6-(2-fluorophenoxy)-4-methylpyridin-3-yl]pyrazole-4-carbonyl]-5-methyl-1H-indol-6-yl]-3-chloro-5-cyanobenzenesulfonamide | 656, 658 | 1.30 | TFA Rev.7 |

| Example No. | Chemical Structure | Compound Name | m/z (M + H) | Reaction Time (Minute) | LCMS Measurement Condition |
|---|---|---|---|---|---|
| 5-1-499 | 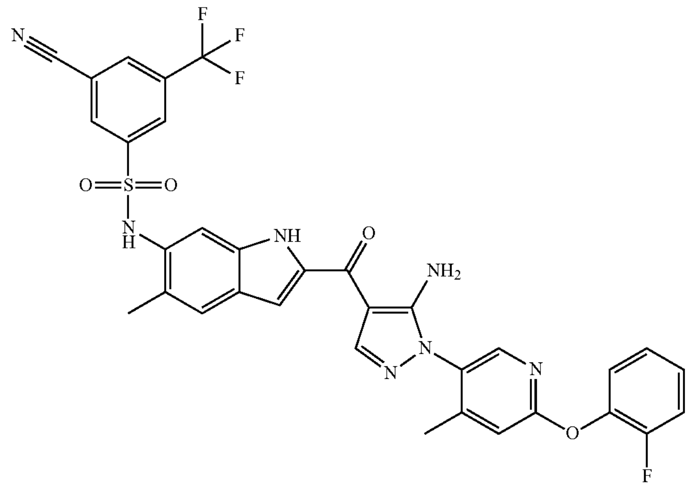 [SMILES: Cc1cc2cc(C(=O)c3cnn(-c4cnc(Oc5ccccc5F)cc4C)c3N)[nH]c2cc1NS(=O)(=O)c1cc(C#N)cc(C(F)(F)F)c1] | N-[2-[5-amino-1-[6-(2-fluorophenoxy)-4-methylpyridin-3-yl]pyrazole-4-carbonyl]-5-methyl-1H-indol-6-yl]-3-cyano-5-(trifluoromethyl)benzenesulfonamide | 690 | 1.32 | TFA Rev.7 |
| 5-1-500 | 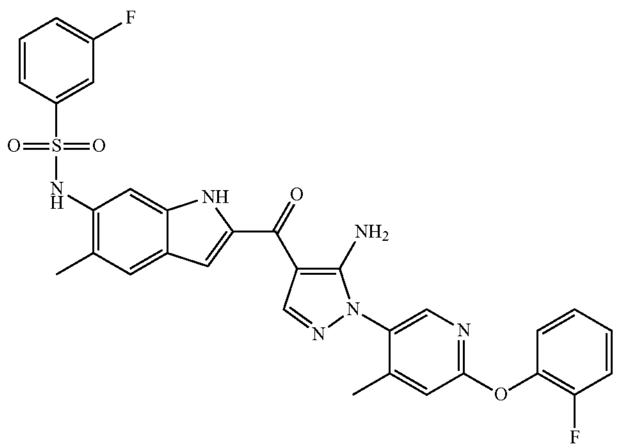 | N-[2-[5-amino-1-[6-(2-fluorophenoxy)-4-methylpyridin-3-yl]pyrazole-4-carbonyl]-5-methyl-1H-indol-6-yl]-3-fluorobenzenesulfonamide | 615 | 1.02 | AA Rev.11 |

| Example No. | Chemical Structure | Compound Name | m/z (M+H) | Reaction Time (Minute) | LCMS Measurement Condition |
|---|---|---|---|---|---|
| 5-1-501 | 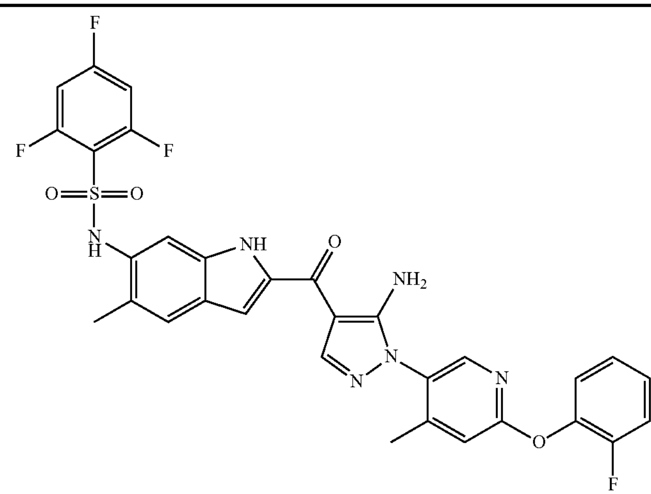 | N-[2-[5-amino-1-[6-(2-fluorophenoxy)-4-methylpyridin-3-yl]pyrazole-4-carbonyl]-5-methyl-1H-indol-6-yl]-2,4,6-trifluorobenzenesulfonamide | 651 | 1.01 | AA Rev.11 |
| 5-1-502 | 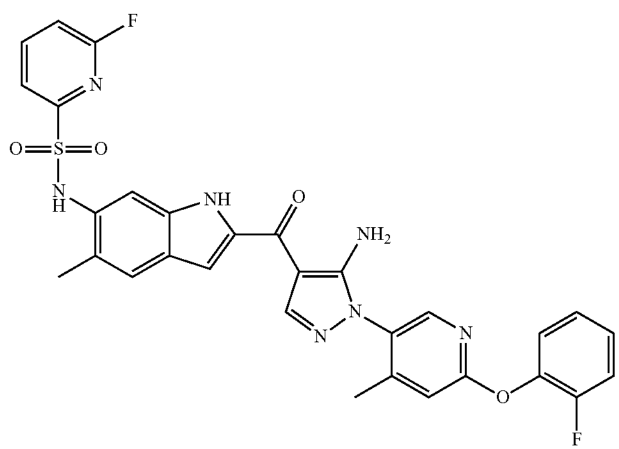 | N-[2-[5-amino-1-[6-(2-fluorophenoxy)-4-methylpyridin-3-yl]pyrazole-4-carbonyl]-5-methyl-1H-indol-6-yl]-6-fluoropyridine-2-sulfonamide | 616 | 0.97 | AA Rev.11 |

| Example No. | Chemical Structure | Compound Name | m/z (M+H) | Reaction Time (Minute) | LCMS Measurement Condition |
|---|---|---|---|---|---|
| 5-1-503 | 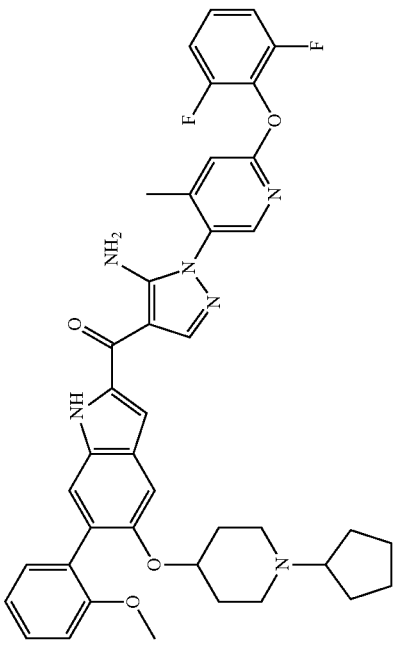 | [5-amino-1-[6-(2,6-difluorophenoxy)-4-methylpyridin-3-yl]pyrazol-4-yl]-[5-(1-cyclopentylpiperidin-4-yl)oxy-6-(2-methoxyphenyl)-1H-indol-2-yl]methanone | 719 | 1.08 | TFA Rev.7 |
| 5-1-504 | 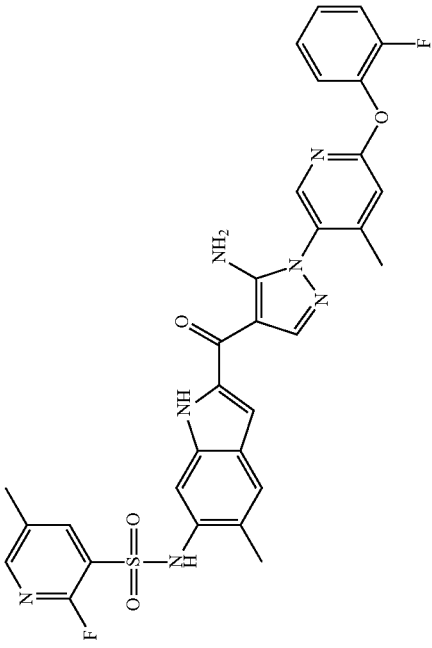 | N-[2-[5-amino-1-[6-(2-fluorophenoxy)-4-methylpyridin-3-yl]pyrazole-4-carbonyl]-5-methyl-1H-indol-6-yl]-2-fluoro-5-methylpyridine-3-sulfonamide | 630 | 0.99 | AA Rev.11 |

| Example No. | Chemical Structure | Compound Name | m/z (M + H) | Reaction Time (Minute) | LCMS Measurement Condition |
|---|---|---|---|---|---|
| 5-1-505 | 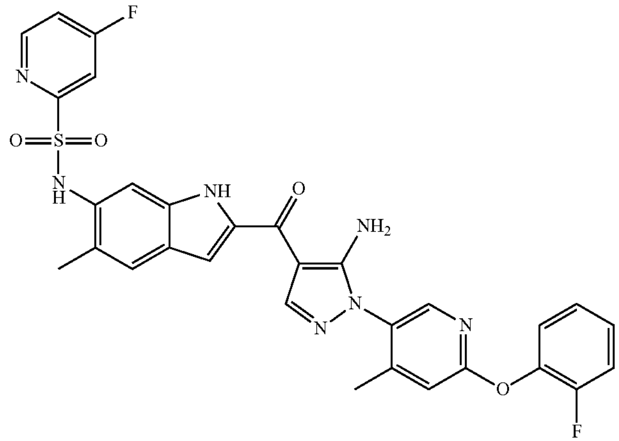 | N-[2-[5-amino-1-[6-(2-fluorophenoxy)-4-methylpyridin-3-yl]pyrazole-4-carbonyl]-5-methyl-1H-indol-6-yl]-4-fluoropyridine-2-sulfonamide | 616 | 1.20 | TFA Rev.7 |
| 5-1-506 | 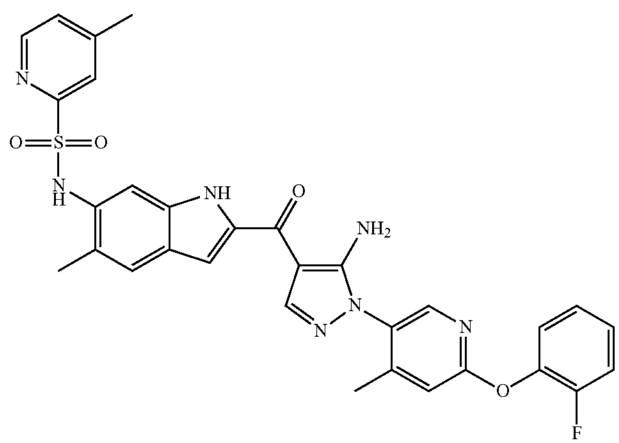 | N-[2-[5-amino-1-[6-(2-fluorophenoxy)-4-methylpyridin-3-yl]pyrazole-4-carbonyl]-5-methyl-1H-indol-6-yl]-4-methylpyridine-2-sulfonamide | 612 | 0.98 | AA Rev.11 |

| Example No. | Chemical Structure | Compound Name | m/z (M + H) | Reaction Time (Minute) | LCMS Measurement Condition |
|---|---|---|---|---|---|
| 5-1-507 | 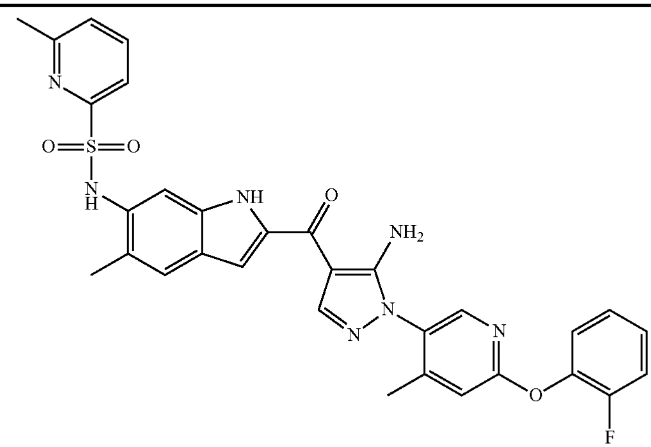 | N-[2-[5-amino-1-[6-(2-fluorophenoxy)-4-methylpyridin-3-yl]pyrazole-4-carbonyl]-5-methyl-1H-indol-6-yl]-6-methylpyridine-2-sulfonamide | 612 | 0.98 | AA Rev.11 |
| 5-1-508 | 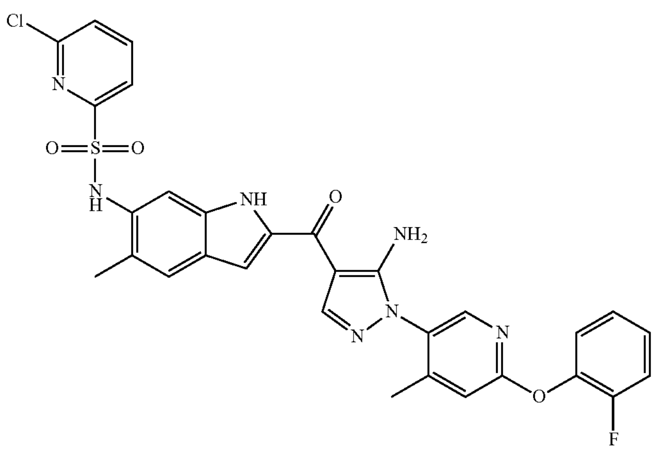 [SMILES: Cc1cc2cc(C(=O)c3cnn(-c4cnc(Oc5ccccc5F)cc4C)c3N)[nH]c2cc1NS(=O)(=O)c1cccc(Cl)n1] | N-[2-[5-amino-1-[6-(2-fluorophenoxy)-4-methylpyridin-3-yl]pyrazole-4-carbonyl]-5-methyl-1H-indol-6-yl]-6-chloropyridine-2-sulfonamide | 632, 634 | 0.99 | AA Rev.11 |

| Example No. | Chemical Structure | Compound Name | m/z (M + H) | Reaction Time (Minute) | LCMS Measurement Condition |
|---|---|---|---|---|---|
| 5-1-509 | 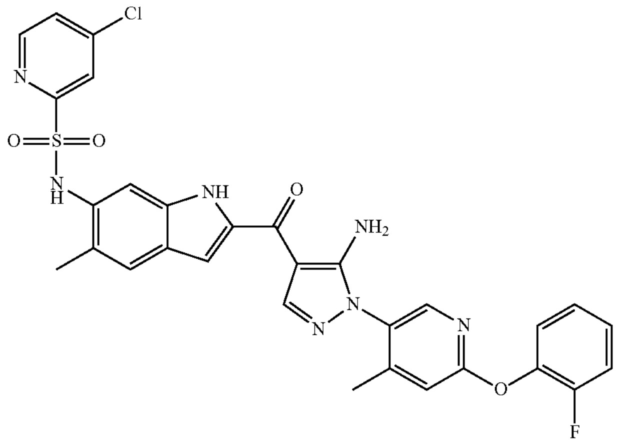 | N-[2-[5-amino-1-[6-(2-fluorophenoxy)-4-methylpyridin-3-yl][pyrazole-4-carbonyl]-5-methyl-1H-indol-6-yl]-4-chloropyridine-2-sulfonamide | 632, 634 | 1.01 | AA Rev.11 |
| 5-1-510 | 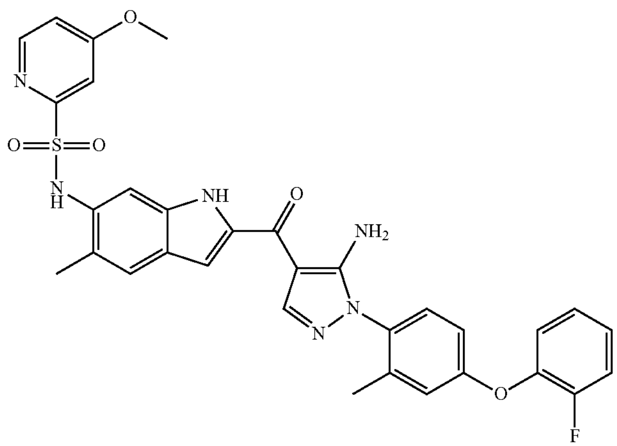 | N-[2-[5-amino-1-[4-(2-fluorophenoxy)-2-methylphenyl][pyrazole-4-carbonyl]-5-methyl-1H-indol-6-yl]-4-methoxypyridine-2-sulfonamide | 627 | 1.24 | TFA Rev.7 |

| Example No. | Chemical Structure | Compound Name | m/z (M + H) | Reaction Time (Minute) | LCMS Measurement Condition |
|---|---|---|---|---|---|
| 5-1-511 | 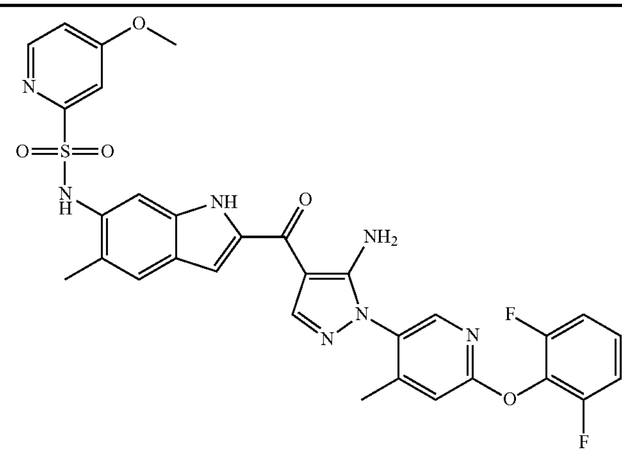 | N-[2-[5-amino-1-[6-(2,6-difluorophenoxy)-4-methylpyridin-3-yl]pyrazole-4-carbonyl]-5-methyl-1H-indol-6-yl]-4-methoxypyridine-2-sulfonamide | 646 | 0.99 | AA Rev.11 |
| 5-1-512 | 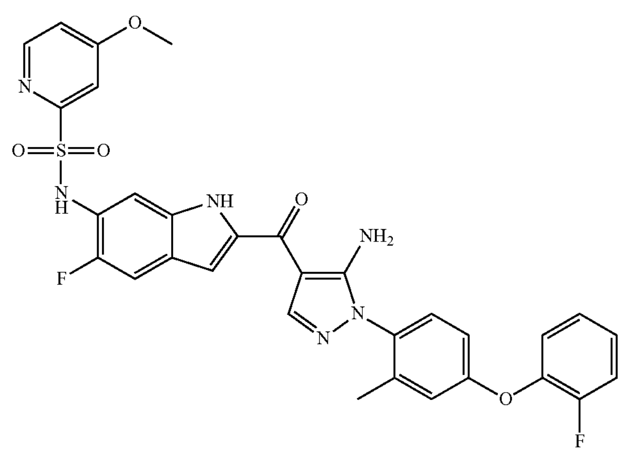 [SMILES: COc1ccnc(S(=O)(=O)Nc2cc3[nH]c(C(=O)c4cnn(-c5ccc(Oc6ccccc6F)cc5C)c4N)cc3cc2F)c1] | N-[2-[5-amino-1-[4-(2-fluorophenoxy)-2-methylphenyl]pyrazole-4-carbonyl]-5-fluoro-1H-indol-6-yl]-4-methoxypyridine-2-sulfonamide | 631 | 1.22 | TFA Rev.7 |

| Example No. | Chemical Structure | Compound Name | m/z (M + H) | Reaction Time (Minute) | LCMS Measurement Condition |
|---|---|---|---|---|---|
| 5-1-513 | 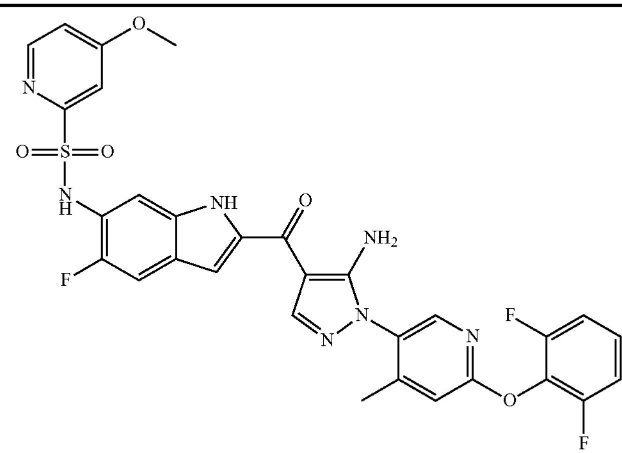 | N-[2-[5-amino-1-[6-(2,6-difluorophenoxy)-4-methylpyridin-3-yl]pyrazole-4-carbonyl]-5-fluoro-1H-indol-6-yl]-4-methoxypyridine-2-sulfonamide | 650 | 0.96 | AA Rev.11 |
| 5-1-514 | 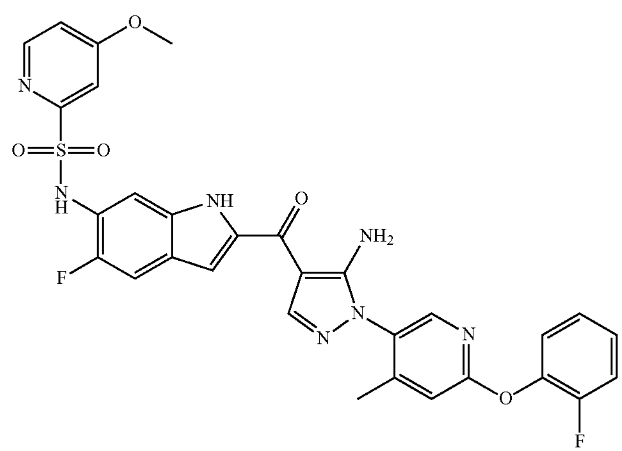 [SMILES: COc1ccnc(S(=O)(=O)Nc2cc3[nH]c(C(=O)c4cnn(-c5cnc(Oc6ccccc6F)cc5C)c4N)cc3cc2F)c1] | N-[2-[5-amino-1-[6-(2-fluorophenoxy)-4-methylpyridin-3-yl]pyrazole-4-carbonyl]-5-fluoro-1H-indol-6-yl]-4-methoxypyridine-2-sulfonamide | 632 | 1.15 | TFA Rev.7 |

| Example No. | Chemical Structure | Compound Name | m/z (M+H) | Reaction Time (Minute) | LCMS Measurement Condition |
|---|---|---|---|---|---|
| 5-1-515 | 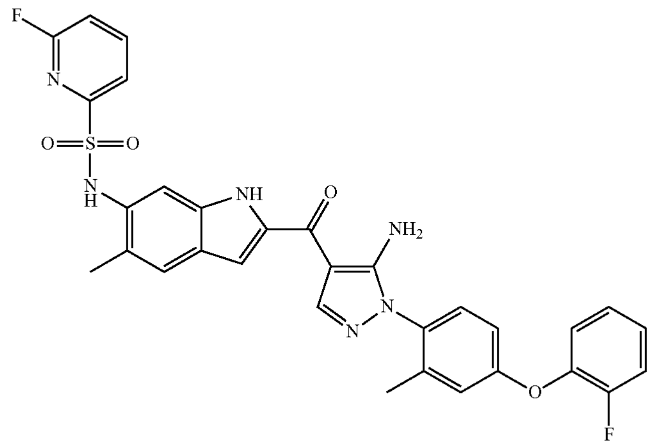 | N-[2-[5-amino-1-[4-(2-fluorophenoxy)-2-methylphenyl]pyrazole-4-carbonyl]-5-methyl-1H-indol-6-yl]-6-fluoropyridine-2-sulfonamide | 615 | 1.01 | AA Rev.11 |
| 5-1-516 | 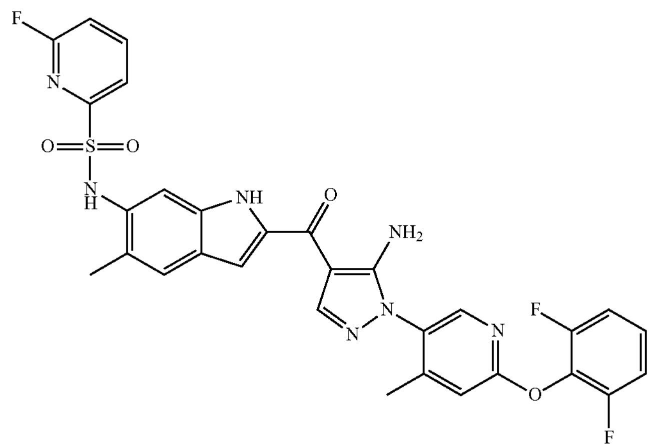 [SMILES: Cc1cc2cc(C(=O)c3cnn(-c4cnc(Oc5c(F)cccc5F)cc4C)c3N)[nH]c2cc1NS(=O)(=O)c1cccc(F)n1] | N-[2-[5-amino-1-[6-(2,6-difluorophenoxy)-4-methylpyridin-3-yl]pyrazole-4-carbonyl]-5-methyl-1H-indol-6-yl]-6-fluoropyridine-2-sulfonamide | 634 | 0.98 | AA Rev.11 |

| Example No. | Chemical Structure | Compound Name | m/z (M + H) | Reaction Time (Minute) | LCMS Measurement Condition |
|---|---|---|---|---|---|
| 5-1-517 | 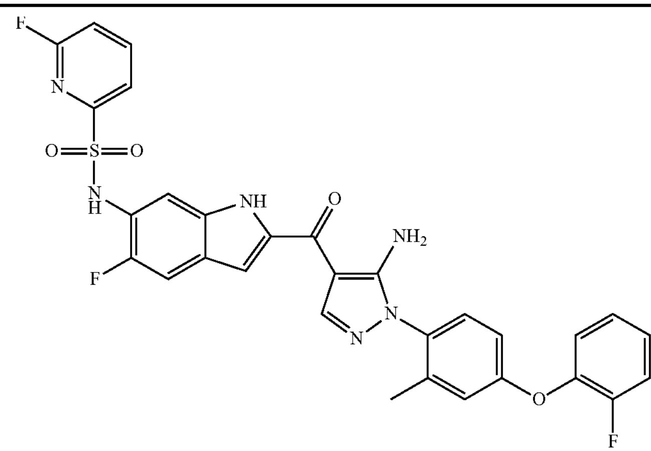 | N-[2-[5-amino-1-[4-(2-fluorophenoxy)-2-methylphenyl]pyrazole-4-carbonyl]-5-fluoro-1H-indol-5-yl]-6-fluoropyridine-2-sulfonamide | 619 | 0.98 | AA Rev.11 |
| 5-1-518 | 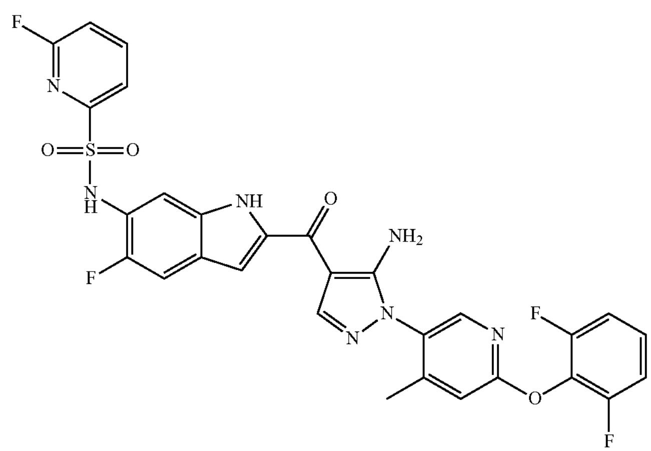 | N-[2-[5-amino-1-[6-(2,6-difluorophenoxy)-4-methylpyridin-3-yl]pyrazole-4-carbonyl]-5-fluoro-1H-indol-6-yl]-6-fluoropyridine-2-sulfonamide | 638 | 0.95 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-519 | 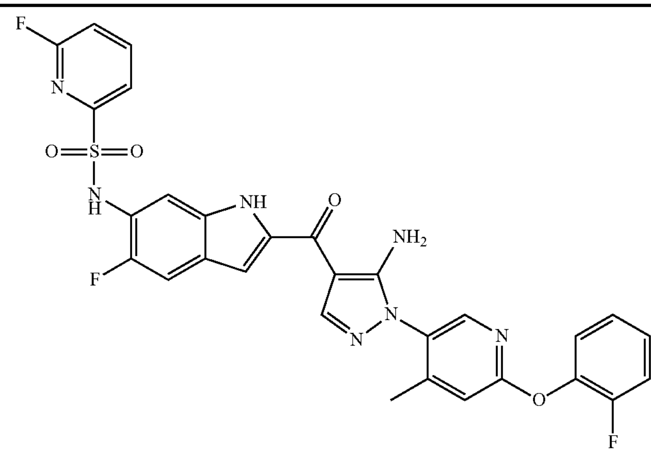 | N-[2-[5-amino-1-[6-(2-fluorophenoxy)-4-methylpyridin-3-yl]pyrazole-4-carbonyl]-5-fluoro-1H-indol-6-yl]-6-fluoropyridine-2-sulfonamide | 620 | 0.94 | AA Rev.11 |
| 5-1-520 | 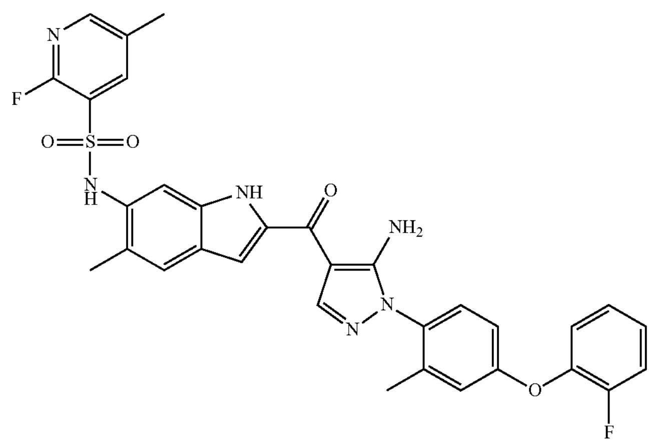 [SMILES: Cc1cnc(F)c(S(=O)(=O)Nc2cc3[nH]c(C(=O)c4cnn(-c5ccc(Oc6ccccc6F)cc5C)c4N)cc3cc2F)c1] | N-[2-[5-amino-1-[4-(2-fluorophenoxy)-2-methylphenyl]pyrazole-4-carbonyl]-1H-indol-5-yl]-2-fluoro-5-methylpyridine-3-sulfonamide | 629 | 1.03 | AA Rev.11 |

| Example No. | Chemical Structure | Compound Name | m/z (M + H) | Reaction Time (Minute) | LCMS Measurement Condition |
|---|---|---|---|---|---|
| 5-1-521 | 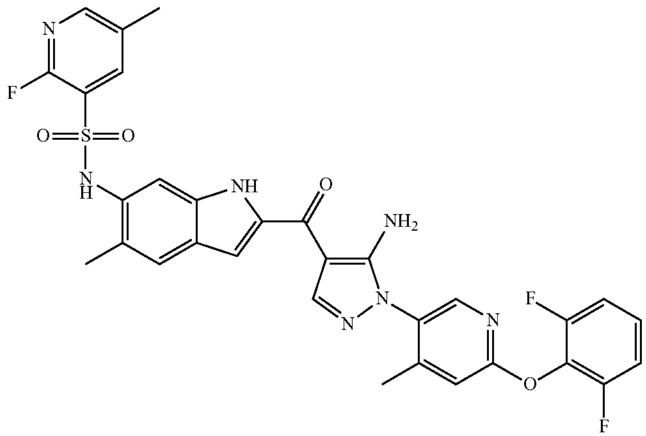 [SMILES: Cc1cnc(F)c(S(=O)(=O)Nc2cc3[nH]c(C(=O)c4cnn(-c5cnc(Oc6c(F)cccc6F)cc5C)c4N)cc3cc2F)c1] | N-[2-[5-amino-1-[6-(2,6-difluorophenoxy)-4-methylpyridin-3-yl]pyrazole-4-carbonyl]-5-methyl-1H-indol-6-yl]-2-fluoro-5-methylpyridine-3-sulfonamide | 648 | 1.00 | AA Rev.11 |
| 5-1-522 | 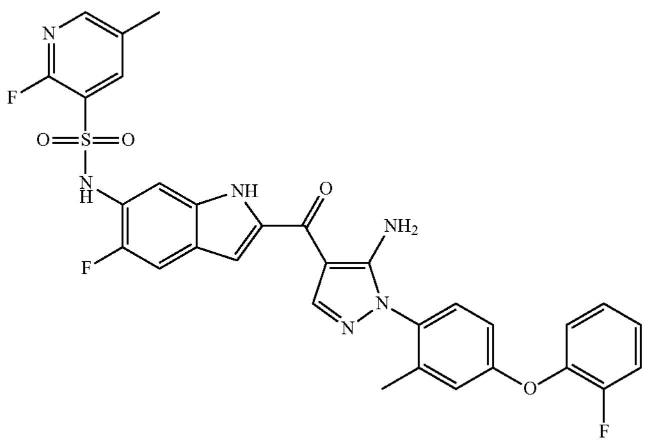 [SMILES: Cc1cnc(F)c(S(=O)(=O)Nc2cc3[nH]c(C(=O)c4cnn(-c5cnc(Oc6ccccc6F)cc5C)c4N)cc3cc2F)c1] | N-[2-[5-amino-1-[4-(2-fluorophenoxy)-2-methylphenyl]pyrazole-4-carbonyl]-5-fluoro-1H-indol-6-yl]-2-fluoro-5-methylpyridine-3-sulfonamide | 633 | 1.00 | AA Rev.11 |

| Example No. | Chemical Structure | Compound Name | m/z (M + H) | Reaction Time (Minute) | LCMS Measurement Condition |
|---|---|---|---|---|---|
| 5-1-523 | 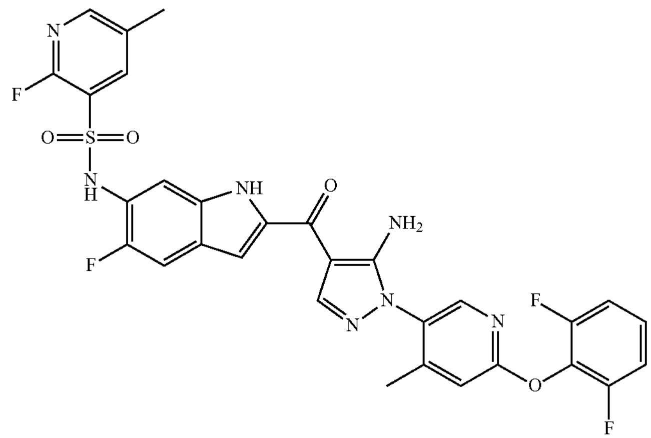 | N-[2-[5-amino-1-[6-(2,6-difluorophenoxy)-4-methylpyridin-3-yl]pyrazole-4-carbonyl]-5-fluoro-1H-indol-6-yl]-2-fluoro-5-methylpyridine-3-sulfonamide | 652 | 0.97 | AA Rev.11 |
| 5-1-524 | 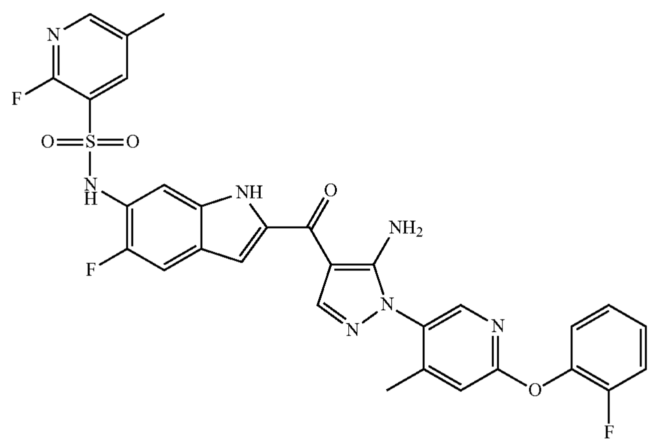 | N-[2-[5-amino-1-[6-(2-fluorophenoxy)-4-methylpyridin-3-yl]pyrazole-4-carbonyl]-5-fluoro-1H-indol-6-yl]-2-fluoro-5-methylpyridine-3-sulfonamide | 634 | 0.96 | AA Rev.11 |

| Example No. | Chemical Structure | Compound Name | m/z (M + H) | Reaction Time (Minute) | LCMS Measurement Condition |
|---|---|---|---|---|---|
| 5-1-525 | 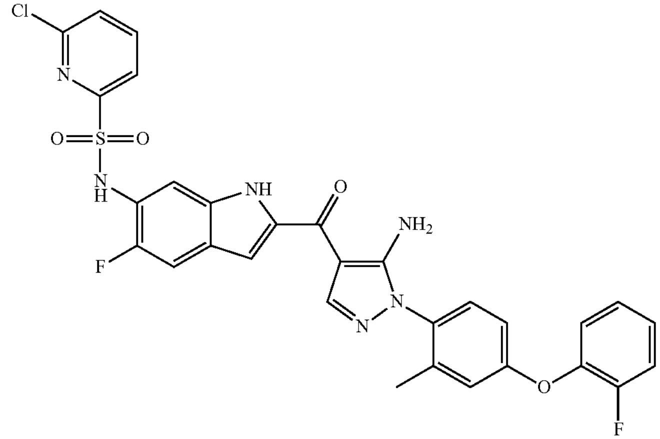 | N-[2-[5-amino-1-[4-(2-fluorophenoxy)-2-methylphenyl]pyrazole-4-carbonyl]-5-methyl-1H-indol-6-yl]-3-chloropyridine-2-sulfonamide | 631, 633 | 1.31 | TFA Rev.7 |
| 5-1-526 | 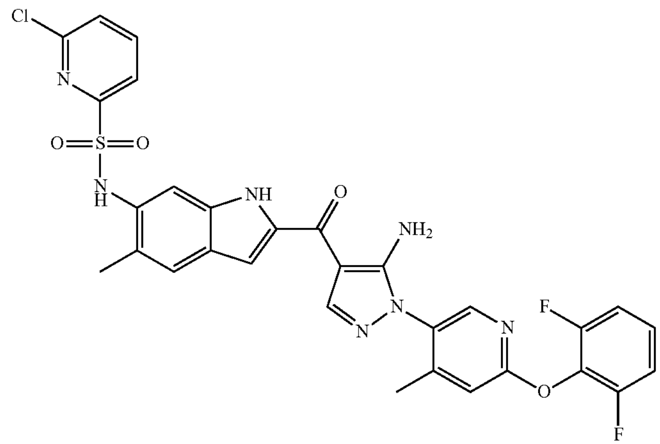 [SMILES: Cc1cc2cc(C(=O)c3cnn(-c4cnc(Oc5c(F)cccc5F)cc4C)c3N)[nH]c2cc1NS(=O)(=O)c1cccc(Cl)n1] | N-[2-[5-amino-1-[6-(2,6-difluorophenoxy)-4-methylpyridin-3-yl]pyrazole-4-carbonyl]-5-methyl-1H-indol-6-yl]-6-chloropyridine-2-sulfonamide | 650, 652 | 1.00 | AA Rev.11 |

| Example No. | Chemical Structure | Compound Name | m/z (M + H) | Reaction Time (Minute) | LCMS Measurement Condition |
|---|---|---|---|---|---|
| 5-1-527 | 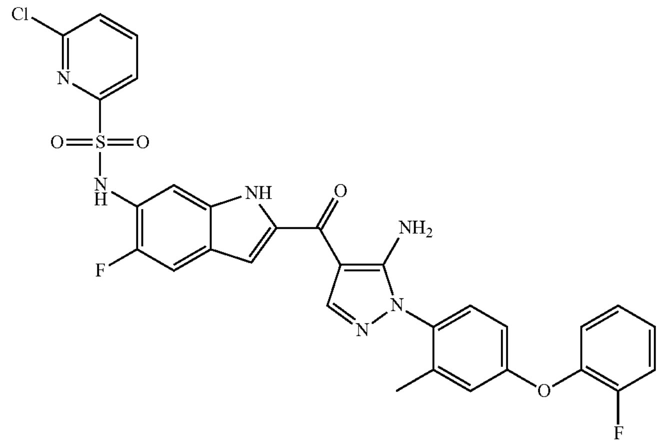 | N-[2-[5-amino-1-[4-(2-fluorophenoxy)-2-methylphenyl]pyrazole-4-carbonyl]-5-fluoro-1H-indol-6-yl]-6-chloropyridine-2-sulfonamide | 635, 637 | 1.00 | AA Rev.11 |
| 5-1-528 | 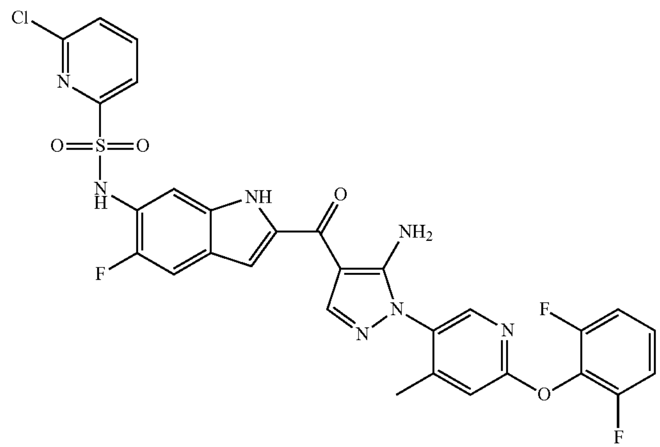 | N-[2-[5-amino-1-[6-(2,6-difluorophenoxy)-4-methylpyridin-3-yl]pyrazole-4-carbonyl]-5-fluoro-1H-indol-6-yl]-6-chloropyridine-2-sulfonamide | 654, 656 | 0.98 | AA Rev.11 |

| Example No. | Chemical Structure | Compound Name | m/z (M + H) | Reaction Time (Minute) | LCMS Measurement Condition |
|---|---|---|---|---|---|
| 5-1-529 | 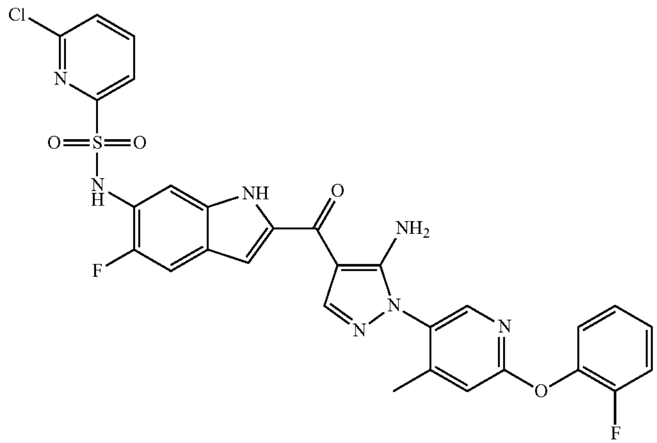 | N-[2-[5-amino-1-[6-(2-fluorophenoxy)-4-methylpyridin-3-yl]pyrazole-4-carbonyl]-5-fluoro-1H-indol-6-yl]-6-chloropyridine-2-sulfonamide | 636, 638 | 0.96 | AA Rev.11 |
| 5-1-530 | 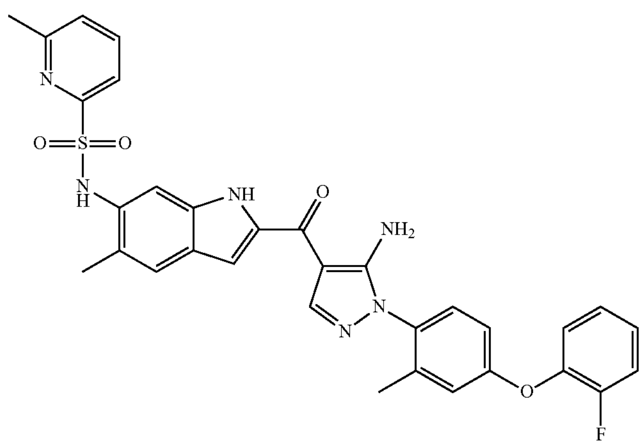 | N-[2-[5-amino-1-[4-(2-fluorophenoxy)-2-methylphenyl]pyrazole-4-carbonyl]-5-methyl-1H-indol-6-yl]-6-methylpyridine-2-sulfonamide | 611 | 1.27 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-531 | 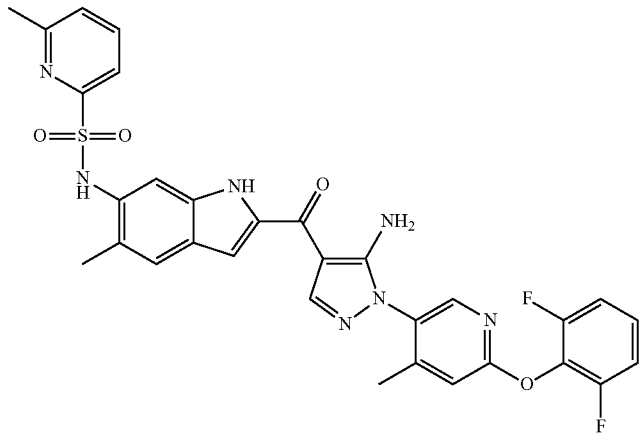 | N-[2-[5-amino-1-[6-(2,6-difluorophenoxy)-4-methylpyridin-3-yl]pyrazole-4-carbonyl]-5-methyl-1H-indol-6-yl]-6-methylpyridine-2-sulfonamide | 630 | 1.23 | TFA Rev.7 |
| 5-1-532 | 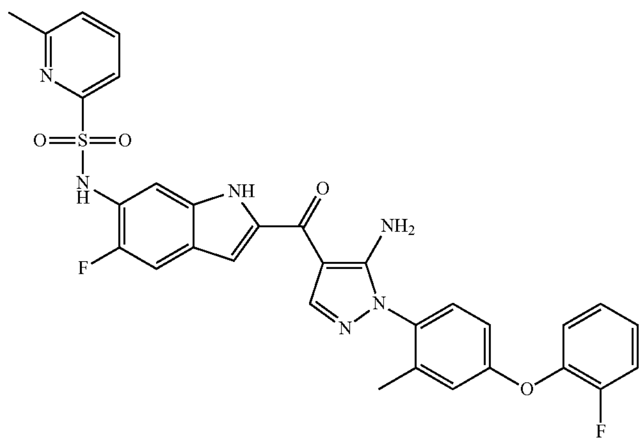 [SMILES: Cc1cccc(S(=O)(=O)Nc2cc3[nH]c(C(=O)c4cnn(-c5ccc(Oc6ccccc6F)cc5C)c4N)cc3cc2C)n1] | N-[2-[5-amino-1-[4-(2-fluorophenoxy)-2-methylphenyl]pyrazole-4-carbonyl]-5-fluoro-1H-indol-6-yl]-6-methylpyridine-2-sulfonamide | 615 | 1.24 | TFA Rev.7 |

| Example No. | Chemical Structure | Compound Name | m/z (M + H) | Reaction Time (Minute) | LCMS Measurement Condition |
|---|---|---|---|---|---|
| 5-1-533 | 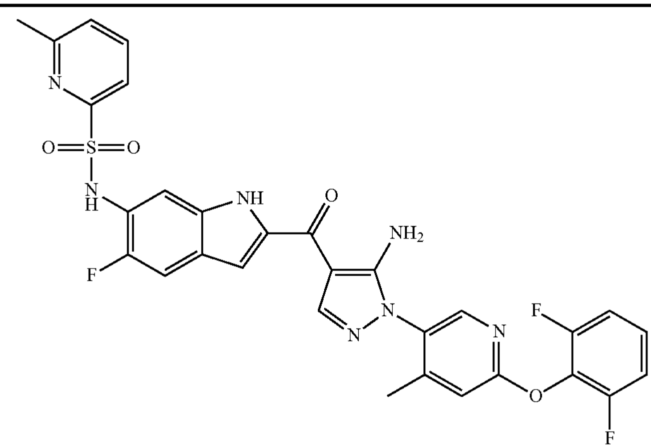 | N-[2-[5-amino-1-[6-(2,6-difluorophenoxy)-4-methylpyridin-3-yl]pyrazole-4-carbonyl]-5-fluoro-1H-indol-6-yl]-6-methylpyridine-2-sulfonamide | 634 | 0.97 | AA Rev.11 |
| 5-1-534 | 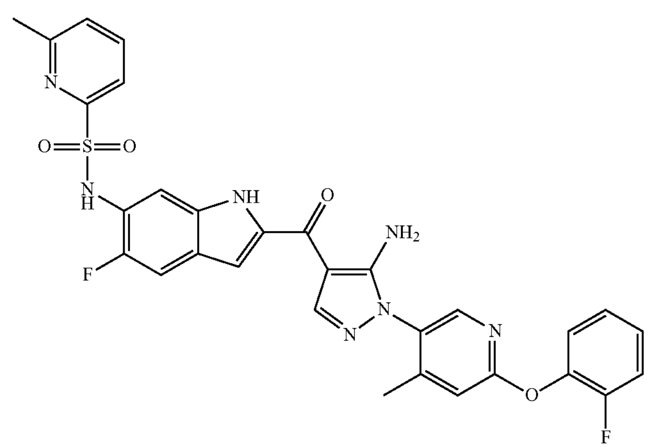 [SMILES: Cc1cccc(S(=O)(=O)Nc2cc3[nH]c(C(=O)c4cnn(-c5cnc(Oc6ccccc6F)cc5C)c4N)cc3cc2F)n1] | N-[2-[5-amino-1-[6-(2-fluorophenoxy)-4-methylpyridin-3-yl]pyrazole-4-carbonyl]-5-fluoro-1H-indol-6-yl]-6-methylpyridine-2-sulfonamide | 616 | 0.96 | AA Rev.11 |

| Example No. | Chemical Structure | Compound Name | m/z (M + H) | Reaction Time (Minute) | LCMS Measurement Condition |
|---|---|---|---|---|---|
| 5-1-535 | 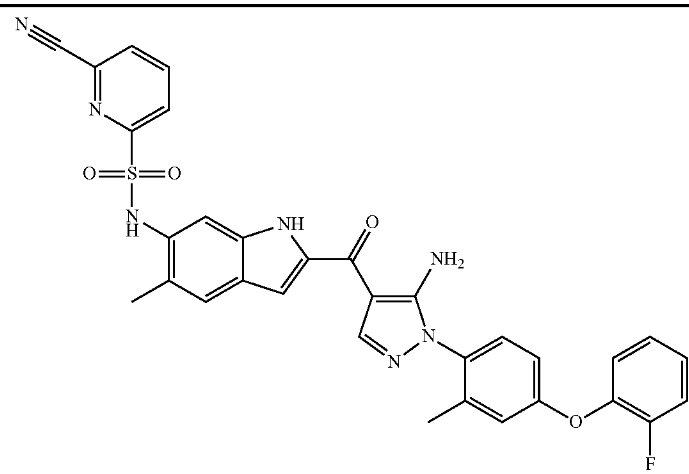 | N-[2-[5-amino-1-[4-(2-fluorophenoxy)-2-methylphenyl]pyrazole-4-carbonyl]-5-methyl-1H-indol-6-yl]-6-cyanopyridine-2-sulfonamide | 622 | 1.26 | TFA Rev.7 |
| 5-1-536 | 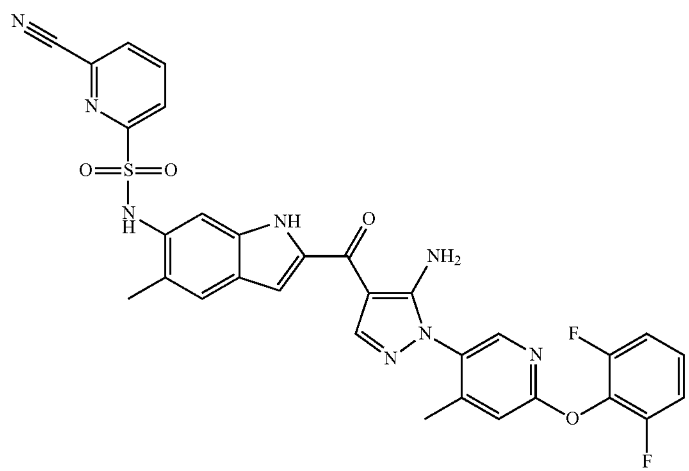 [SMILES: Cc1cc2cc(C(=O)c3cnn(-c4cnc(Oc5c(F)cccc5F)cc4C)c3N)[nH]c2cc1NS(=O)(=O)c1cccc(C#N)n1] | N-[2-[5-amino-1-[6-(2,6-difluorophenoxy)-4-methylpyridin-3-yl]pyrazole-4-carbonyl]-5-methyl-1H-indol-6-yl]-6-cyanopyridine-2-sulfonamide | 641 | 1.23 | TFA Rev.7 |

| Example No. | Chemical Structure | Compound Name | m/z (M + H) | Reaction Time (Minute) | LCMS Measurement Condition |
|---|---|---|---|---|---|
| 5-1-537 | 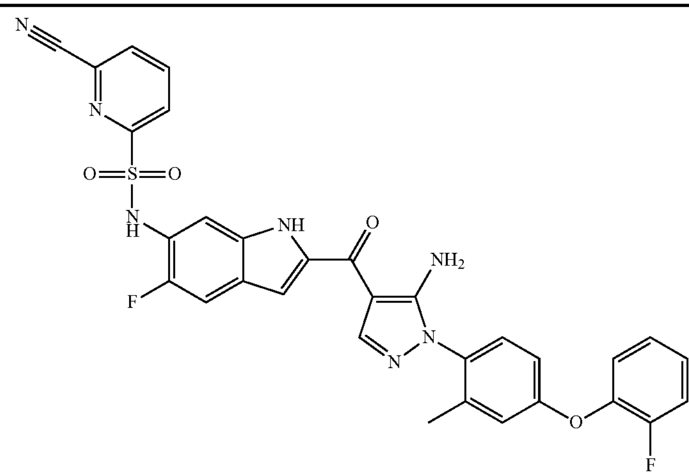 | N-[2-[5-amino-1-[4-(2-fluorophenoxy)-2-methylphenyl]pyrazole-4-carbonyl]-5-fluoro-1H-indol-6-yl]-6-cyanopyridine-2-sulfonamide | 626 | 1.23 | TFA Rev.7 |
| 5-1-538 | 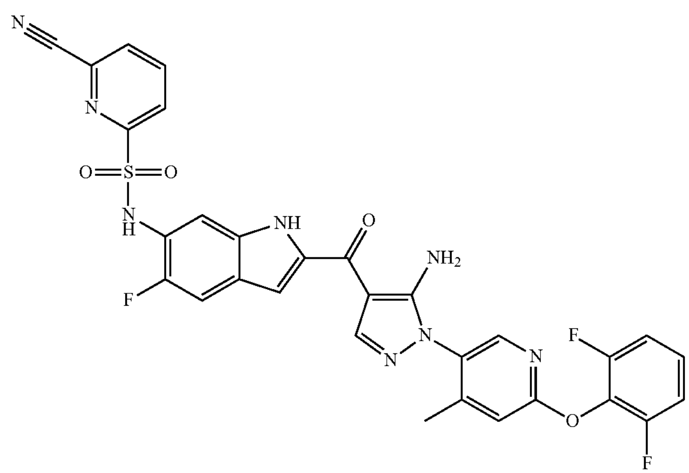 | N-[2-[5-amino-1-[6-(2,6-difluorophenoxy)-4-methylpyridin-3-yl]pyrazole-4-carbonyl]-5-fluoro-1H-indol-6-yl]-6-cyanopyridine-2-sulfonamide | 645 | 1.19 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-539 | 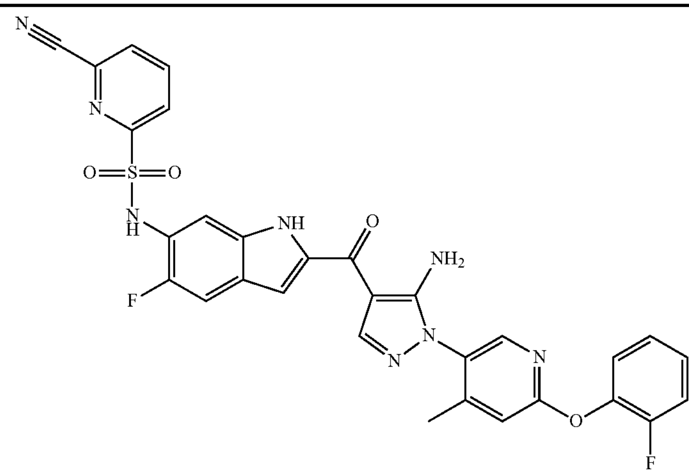 | N-[2-[5-amino-1-[6-(2-fluorophenoxy)-4-methylpyridin-3-yl]pyrazole-4-carbonyl]-5-fluoro-1H-indol-6-yl]-6-cyanopyridine-2-sulfonamide | 627 | 1.17 | TFA Rev.7 |
| 5-1-540 | 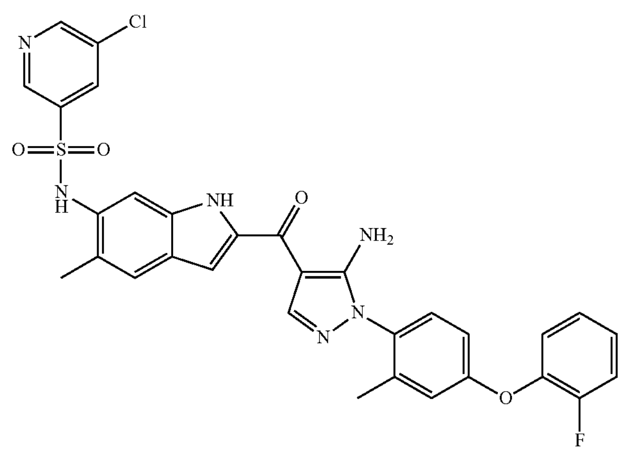 | N-[2-[5-amino-1-[4-(2-fluorophenoxy)-2-methylphenyl]pyrazole-4-carbonyl]-5-methyl-1H-indol-6-yl]-5-chloropyridine-3-sulfonamide | 631, 633 | 1.31 | TFA Rev.7 |

| Example No. | Chemical Structure | Compound Name | m/z (M + H) | Reaction Time (Minute) | LCMS Measurement Condition |
|---|---|---|---|---|---|
| 5-1-541 | 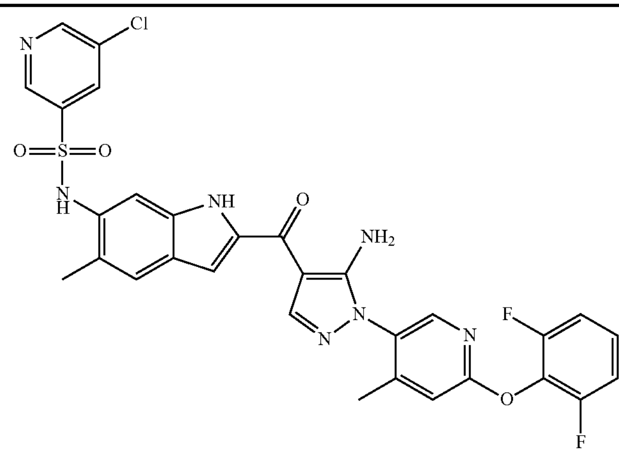 | N-[2-[5-amino-1-[6-(2,6-difluorophenoxy)-4-methylpyridin-3-yl]pyrazole-4-carbonyl]-5-methyl-1H-indol-6-yl]-5-chloropyridine-3-sulfonamide | 650, 652 | 1.28 | TFA Rev.7 |
| 5-1-542 | 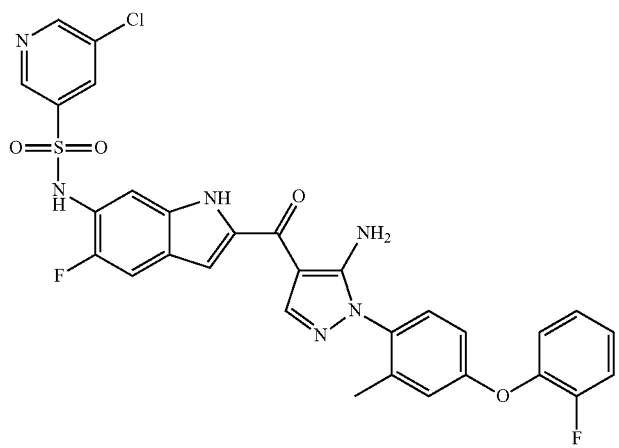 | N-[2-[5-amino-1-[4-(2-fluorophenoxy)-2-methylphenyl]pyrazole-4-carbonyl]-5-fluoro-1H-indol-6-yl]-5-chloropyridine-3-sulfonamide | 635, 637 | 1.02 | AA Rev.11 |

| Example No. | Chemical Structure | Compound Name | m/z (M + H) | Reaction Time (Minute) | LCMS Measurement Condition |
|---|---|---|---|---|---|
| 5-1-543 | 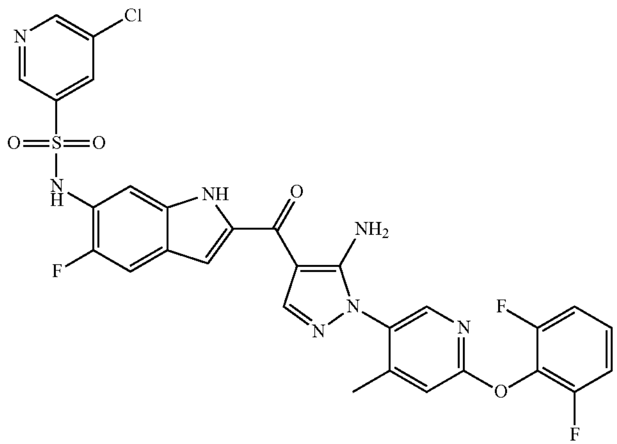 | N-[2-[5-amino-1-[6-(2,6-difluorophenoxy)-4-methylpyridin-3-yl]pyrazole-4-carbonyl]-5-fluoro-1H-indol-6-yl]-5-chloropyridine-3-sulfonamide | 654, 656 | 1.24 | TFA Rev.7 |
| 5-1-544 | 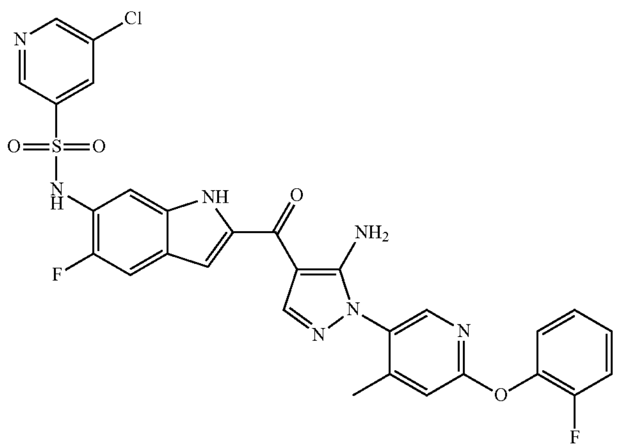 | N-[2-[5-amino-1-[6-(2-fluorophenoxy)-4-methylpyridin-3-yl]pyrazole-4-carbonyl]-5-fluoro-1H-indol-6-yl]-5-chloropyridine-3-sulfonamide | 636, 638 | 1.22 | TFA Rev.7 |

| Example No. | Chemical Structure | Compound Name | m/z (M + H) | Reaction Time (Minute) | LCMS Measurement Condition |
|---|---|---|---|---|---|
| 5-1-545 | 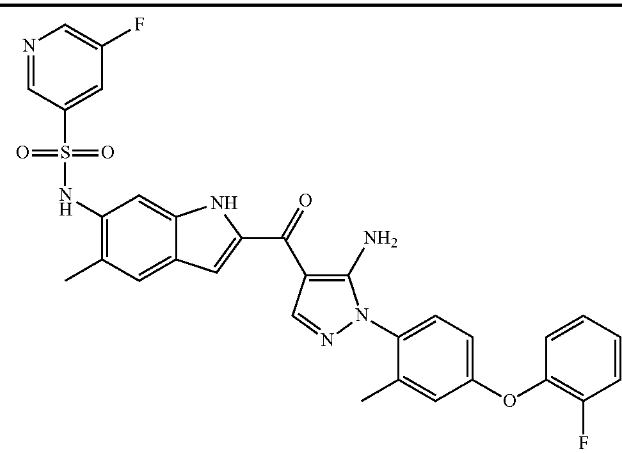 | N-[2-[5-amino-1-[4-(2-fluorophenoxy)-2-methylphenyl]pyrazole-4-carbonyl]-5-methyl-1H-indol-6-yl]-5-fluoropyridine-3-sulfonamide | 615 | 1.27 | TFA Rev.7 |
| 5-1-546 | 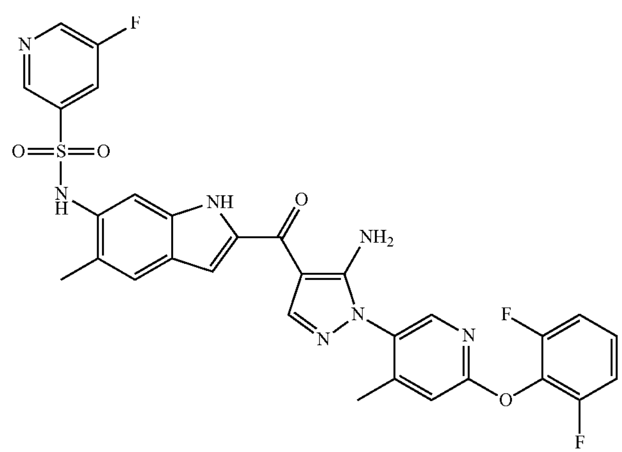 [SMILES: Cc1cc2cc(C(=O)c3cnn(-c4cnc(Oc5c(F)cccc5F)cc4C)c3N)[nH]c2cc1NS(=O)(=O)c1cncc(Cl)c1] | N-[2-[5-amino-1-[6-(2,6-difluorophenoxy)-4-methylpyridin-3-yl]pyrazole-4-carbonyl]-5-methyl-1H-indol-6-yl]-5-fluoropyridine-3-sulfonamide | 634 | 1.23 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-547 | 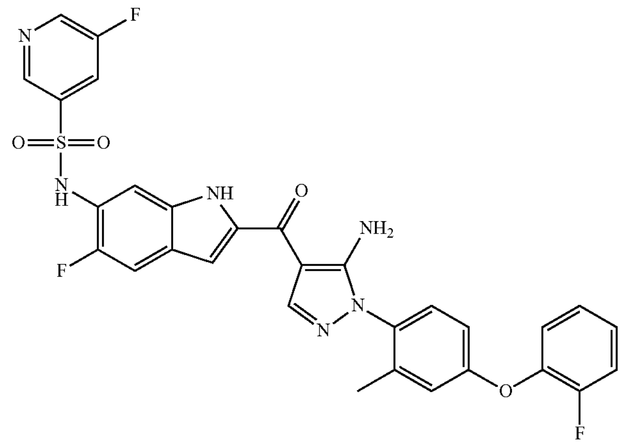 | N-[2-[5-amino-1-[4-(2-fluorophenoxy)-2-methylphenyl]pyrazole-4-carbonyl]-5-fluoro-1H-indol-6-yl]-5-fluoropyridine-3-sulfonamide | 619 | 1.00 | AA Rev.11 |
| 5-1-548 | 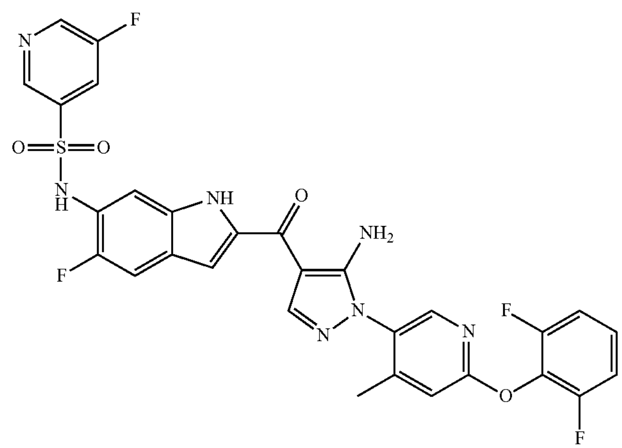 [SMILES: Cc1cc(Oc2c(F)cccc2F)ncc1-n1ncc(C(=O)c2cc3cc(F)c(NS(=O)(=O)c4cncc(Cl)c4)cc3[nH]2)c1N] | N-[2-[5-amino-1-[6-(2,6-difluorophenoxy)-4-methylpyridin-3-yl]pyrazole-4-carbonyl]-5-fluoro-1H-indol-6-yl]-5-fluoropyridine-3-sulfonamide | 638 | 1.20 | TFA Rev.7 |

| Example No. | Chemical Structure | Compound Name | m/z (M + H) | Reaction Time (Minute) | LCMS Measurement Condition |
|---|---|---|---|---|---|
| 5-1-549 | 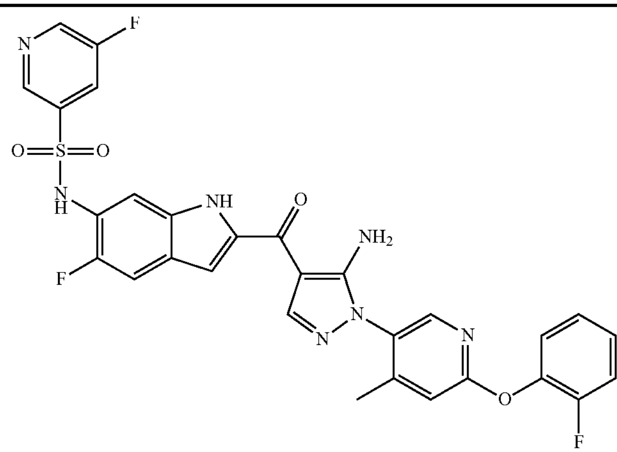 | N-[2-[5-amino-1-[6-(2-fluorophenoxy)-4-methylpyridin-3-yl]pyrazole-4-carbonyl]-5-fluoro-1H-indol-6-yl]-5-fluoropyridine-3-sulfonamide | 620 | 1.18 | TFA Rev.7 |
| 5-1-550 | 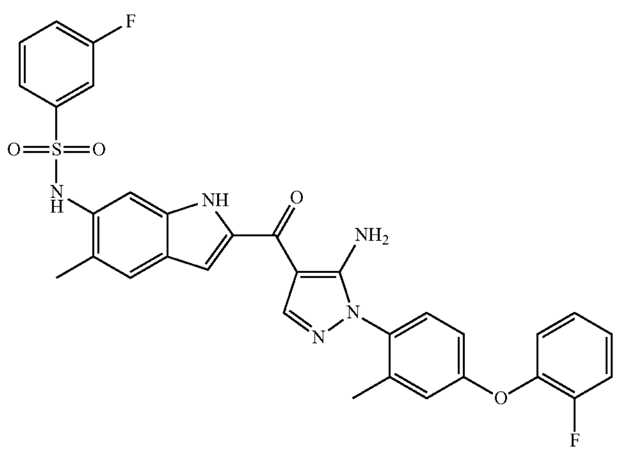 | N-[2-[5-amino-1-[4-(2-fluorophenoxy)-2-methylphenyl]pyrazole-4-carbonyl]-5-methyl-1H-indol-6-yl]-3-fluorobenzenesulfonamide | 614 | 1.33 | TFA Rev.7 |

| Example No. | Chemical Structure | Compound Name | m/z (M + H) | Reaction Time (Minute) | LCMS Measurement Condition |
|---|---|---|---|---|---|
| 5-1-551 | 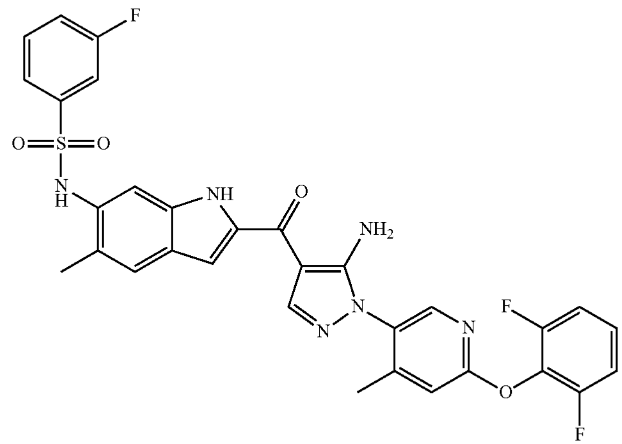 | N-[2-[5-amino-1-[6-(2,6-difluorophenoxy)-4-methylpyridin-3-yl]pyrazole-4-carbonyl]-5-methyl-1H-indol-6-yl]-3-fluorobenzenesulfonamide | 633 | 1.29 | TFA Rev.7 |
| 5-1-552 | 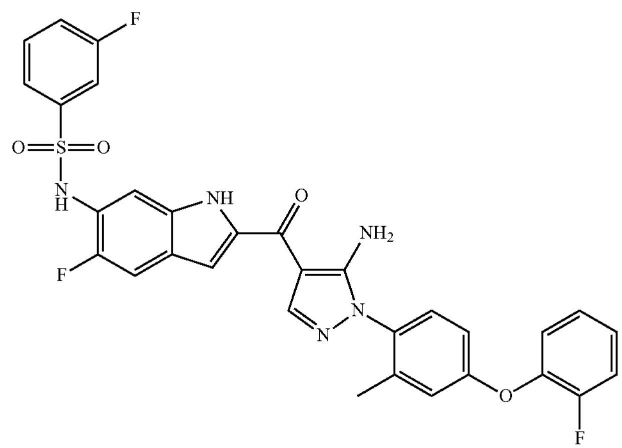 | N-[2-[5-amino-1-[4-(2-fluorophenoxy)-2-methylphenyl]pyrazole-4-carbonyl]-5-fluoro-1H-indol-6-yl]-3-fluorobenzenesulfonamide | 618 | 1.03 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-553 | 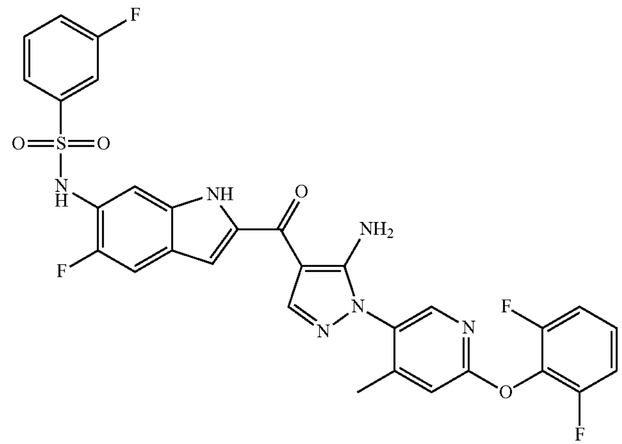 | N-[2-[5-amino-1-[6-(2,6-difluorophenoxy)-4-methylpyridin-3-yl]pyrazole-4-carbonyl]-5-fluoro-1H-indol-6-yl]-3-fluorobenzenesulfonamide | 637 | 1.01 | AA Rev.11 |
| 5-1-554 | 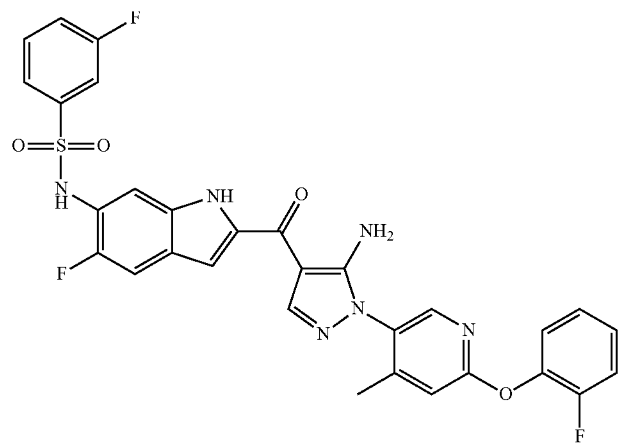 [SMILES: Cc1cc(Oc2ccccc2F)ncc1-n1ncc(C(=O)c2cc3cc(F)c(NS(=O)(=O)c4cccc(F)c4)cc3[nH]2)c1N] | N-[2-[5-amino-1-[6-(2-fluorophenoxy)-4-methylpyridin-3-yl]pyrazole-4-carbonyl]-5-fluoro-1H-indol-6-yl]-3-fluorobenzenesulfonamide | 619 | 1.24 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-555 | 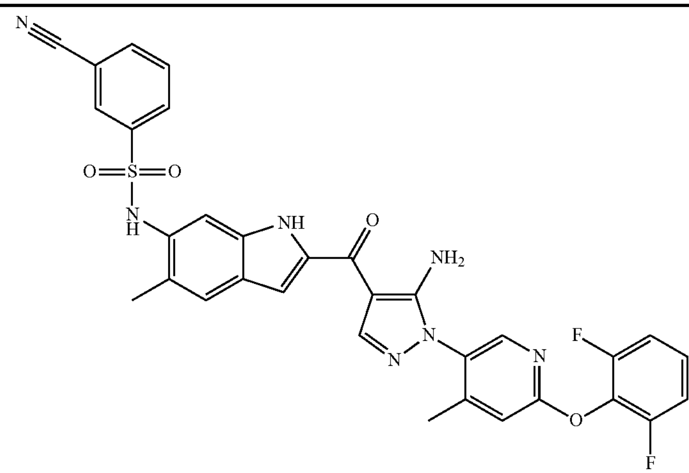 | N-[2-[5-amino-1-[6-(2,6-difluorophenoxy)-4-methylpyridin-3-yl]pyrazole-4-carbonyl]-5-methyl-1H-indol-6-yl]-3-cyanobenzenesulfonamide | 640 | 1.00 | AA Rev.11 |
| 5-1-556 | 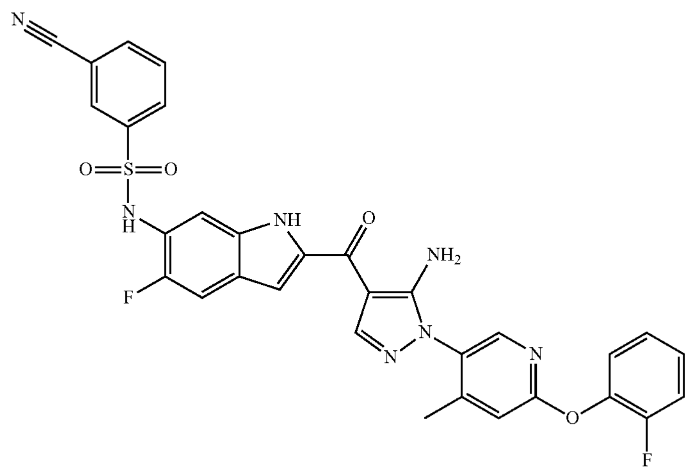 [SMILES: Cc1cc(Oc2ccccc2F)ncc1-n1ncc(C(=O)c2cc3cc(F)c(NS(=O)(=O)c4cccc(C#N)c4)cc3[nH]2)c1N] | N-[2-[5-amino-1-[6-(2-fluorophenoxy)-4-methylpyridin-3-yl]pyrazole-4-carbonyl]-5-fluoro-1H-indol-6-yl]-3-cyanobenzenesulfonamide | 626 | 0.96 | AA Rev.11 |

| Example No. | Chemical Structure | Compound Name | m/z (M + H) | Reaction Time (Minute) | LCMS Measurement Condition |
|---|---|---|---|---|---|
| 5-1-557 | 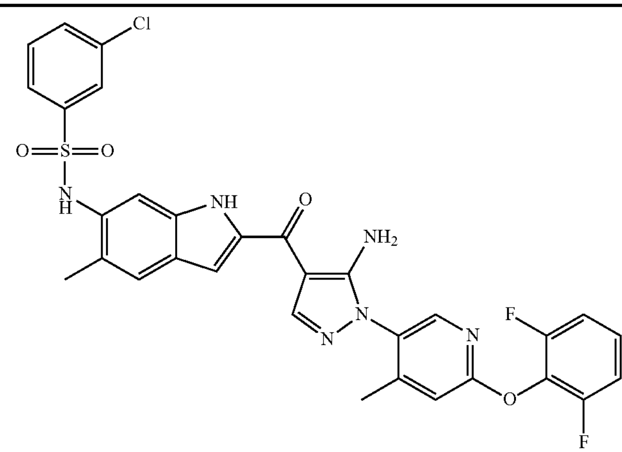 | N-[2-[5-amino-1-[6-(2,6-difluorophenoxy)-4-methylpyridin-3-yl]pyrazole-4-carbonyl]-5-methyl-1H-indol-6-yl]-3-chlorobenzenesulfonamide | 649, 651 | 1.34 | TFA Rev.7 |
| 5-1-558 | 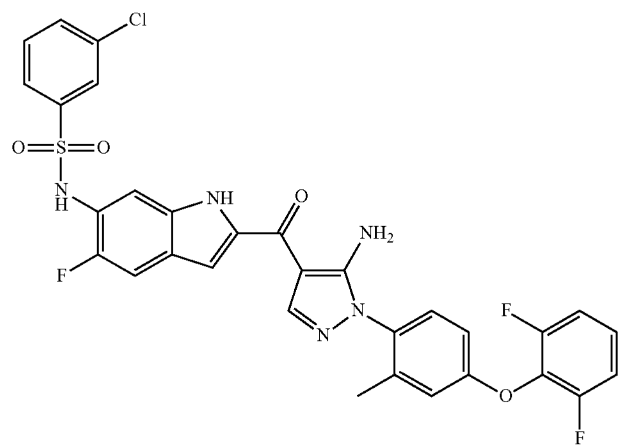 [SMILES: Cc1cc(Oc2c(F)cccc2F)ccc1-n1ncc(C(=O)c2cc3cc(F)c(NS(=O)(=O)c4cccc(Cl)c4)cc3[nH]2)c1N] | N-[2-[5-amino-1-[4-(2-fluorophenoxy)-2-methylphenyl]pyrazole-4-carbonyl]-5-fluoro-1H-indol-6-yl]-3-chlorobenzenesulfonamide | 634, 636 | 1.05 | AA Rev.11 |

| Example No. | Chemical Structure | Compound Name | m/z (M + H) | Reaction Time (Minute) | LCMS Measurement Condition |
|---|---|---|---|---|---|
| 5-1-559 | 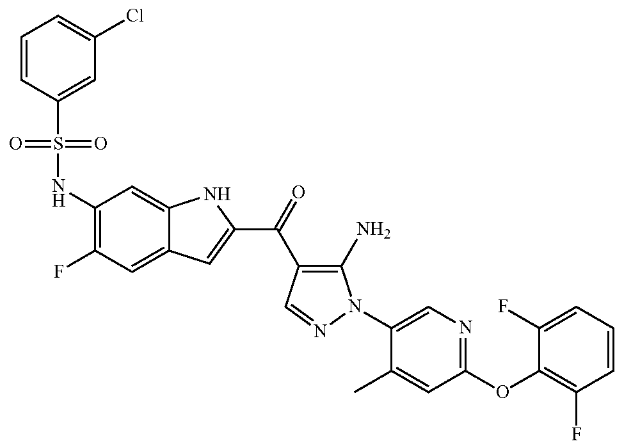 [SMILES: Cc1cc(Oc2c(F)cccc2F)ncc1-n1ncc(C(=O)c2cc3cc(F)c(NS(=O)(=O)c4cccc(Cl)c4)cc3[nH]2)c1N] | N-[2-[5-amino-1-[6-(2,6-difluorophenoxy)-4-methylpyridin-3-yl]pyrazole-4-carbonyl]-5-fluoro-1H-indol-6-yl]-3-chlorobenzenesulfonamide | 653, 655 | 1.03 | AA Rev.11 |
| 5-1-560 | 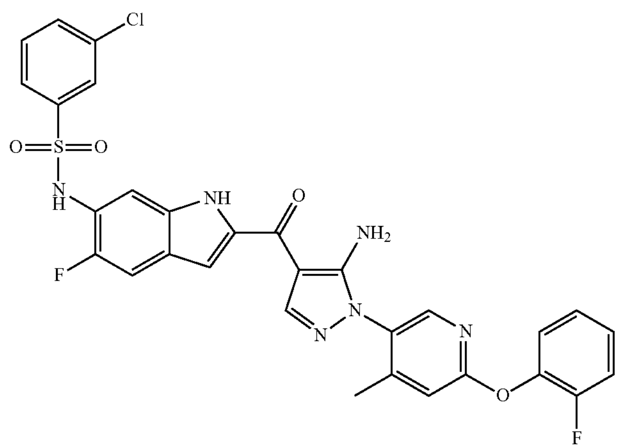 [SMILES: Cc1cc(Oc2ccccc2F)ncc1-n1ncc(C(=O)c2cc3cc(F)c(NS(=O)(=O)c4cccc(Cl)c4)cc3[nH]2)c1N] | N-[2-[5-amino-1-[6-(2-fluorophenoxy)-4-methylpyridin-3-yl]pyrazole-4-carbonyl]-5-fluoro-1H-indol-6-yl]-3-chlorobenzenesulfonamide | 635, 637 | 1.29 | TFA Rev.7 |

| Example No. | Chemical Structure | Compound Name | m/z (M + H) | Reaction Time (Minute) | LCMS Measurement Condition |
|---|---|---|---|---|---|
| 5-1-561 | 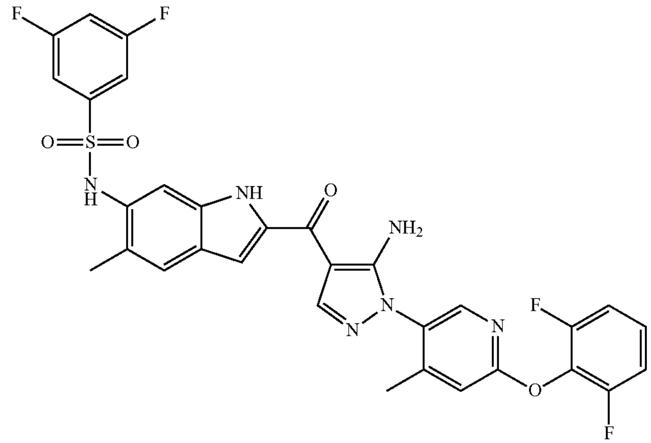 [SMILES: Cc1cc2cc(C(=O)c3cnn(-c4cnc(Oc5c(F)cccc5F)cc4C)c3N)[nH]c2cc1NS(=O)(=O)c1cc(F)cc(F)c1] | N-[2-[5-amino-1-[6-(2,6-difluorophenoxy)-4-methylpyridin-3-yl]pyrazole-4-carbonyl]-5-methyl-1H-indol-6-yl]-3,5-difluorobenzenesulfonamide | 651 | 1.33 | TFA Rev.7 |
| 5-1-562 | 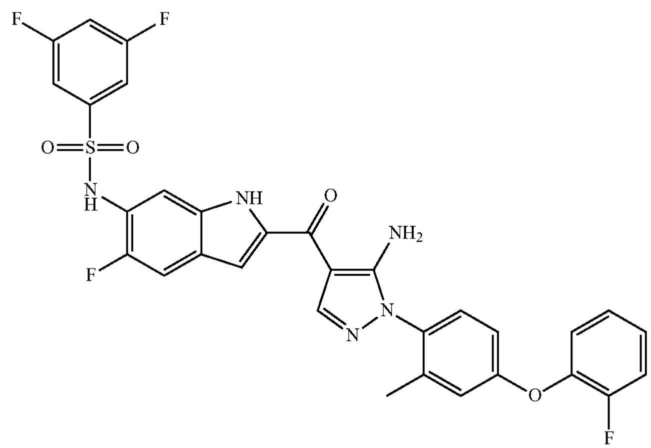 | N-[2-[5-amino-1-[4-(2-fluorophenoxy)-2-methylphenyl]pyrazole-4-carbonyl]-5-fluoro-1H-indol-6-yl]-3,5-difluorobenzenesulfonamide | 636 | 1.05 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-563 | 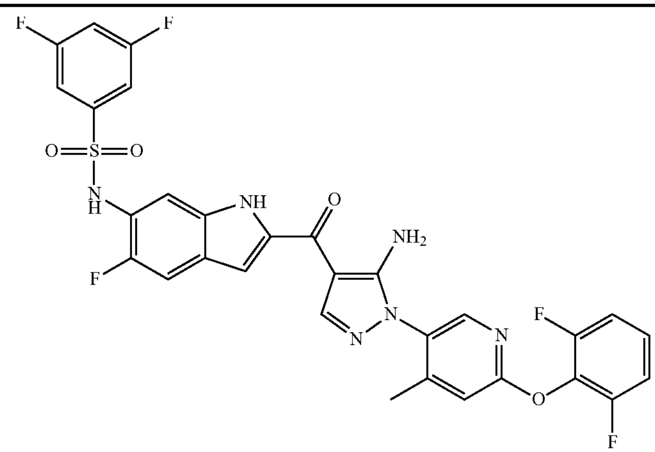 | N-[2-[5-amino-1-[6-(2,6-difluorophenoxy)-4-methylpyridin-3-yl]pyrazole-4-carbonyl]-5-fluoro-1H-indol-6-yl]-3,5-difluorobenzenesulfonamide | 655 | 1.03 | AA Rev.11 |
| 5-1-564 | 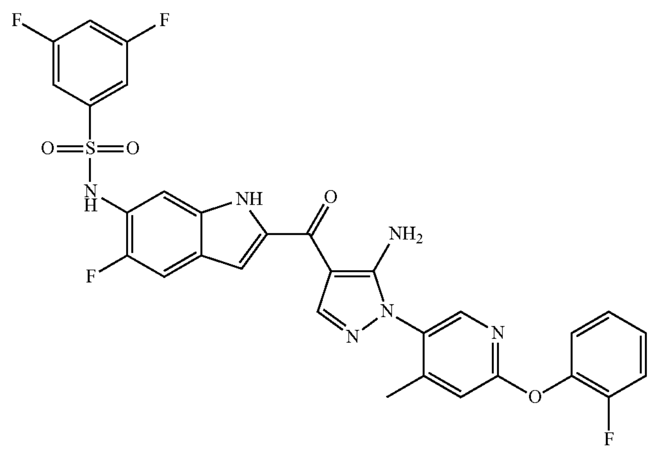 | N-[2-[5-amino-1-[6-(2-fluorophenoxy)-4-methylpyridin-3-yl]pyrazole-4-carbonyl]-5-fluoro-1H-indol-6-yl]-3,5-difluorobenzenesulfonamide | 637 | 1.02 | AA Rev.11 |

| Example No. | Chemical Structure | Compound Name | m/z (M + H) | Reaction Time (Minute) | LCMS Measurement Condition |
|---|---|---|---|---|---|
| 5-1-565 | 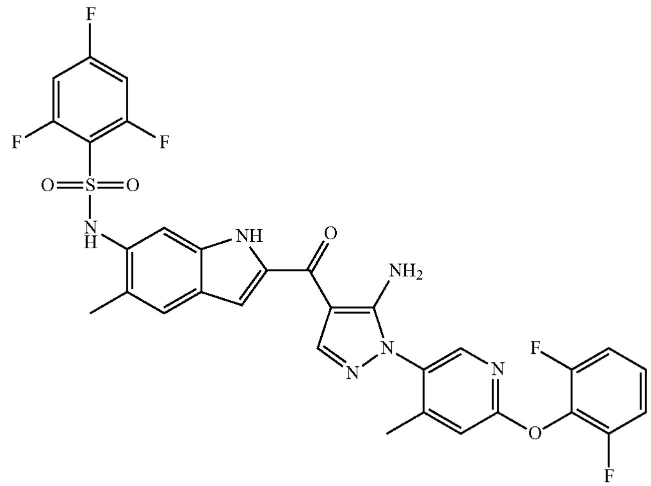 [SMILES: Cc1cc2cc(C(=O)c3cnn(-c4cnc(Oc5c(F)cccc5F)cc4C)c3N)[nH]c2cc1NS(=O)(=O)c1c(F)cc(F)cc1F] | N-[2-[5-amino-1-[6-(2,6-difluorophenoxy)-4-methylpyridin-3-yl]pyrazole-4-carbonyl]-5-methyl-1H-indol-6-yl]-2,4,6-trifluorobenzenesulfonamide | 669 | 1.29 | TFA Rev.7 |
| 5-1-566 | 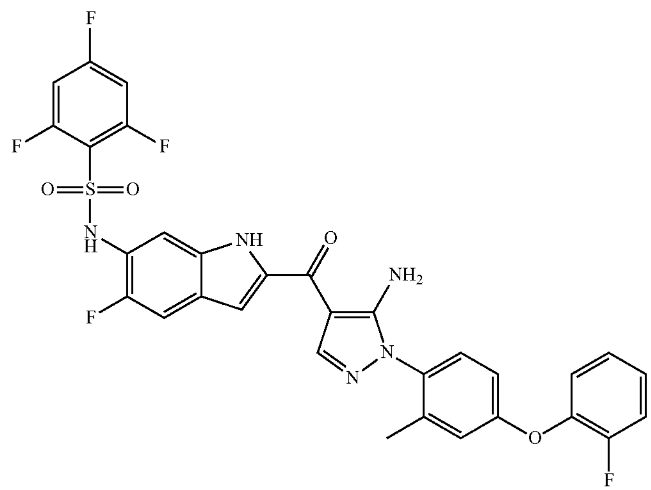 | N-[2-[5-amino-1-[4-(2-fluorophenoxy)-2-methylphenyl]pyrazole-4-carbonyl]-5-fluoro-1H-indol-6-yl]-2,4,6-trifluorobenzenesulfonamide | 654 | 1.02 | AA Rev.11 |

| Example No. | Chemical Structure | Compound Name | m/z (M + H) | Reaction Time (Minute) | LCMS Measurement Condition |
|---|---|---|---|---|---|
| 5-1-567 | 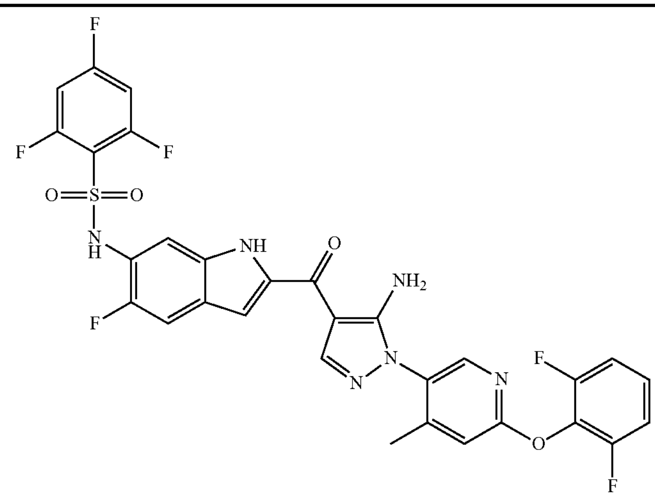 | N-[2-[5-amino-1-[6-(2,6-difluorophenoxy)-4-methylpyridin-3-yl]pyrazole-4-carbonyl]-5-fluoro-1H-indol-6-yl]-2,4,6-trifluorobenzenesulfonamide | 673 | 0.99 | AA Rev.11 |
| 5-1-568 | 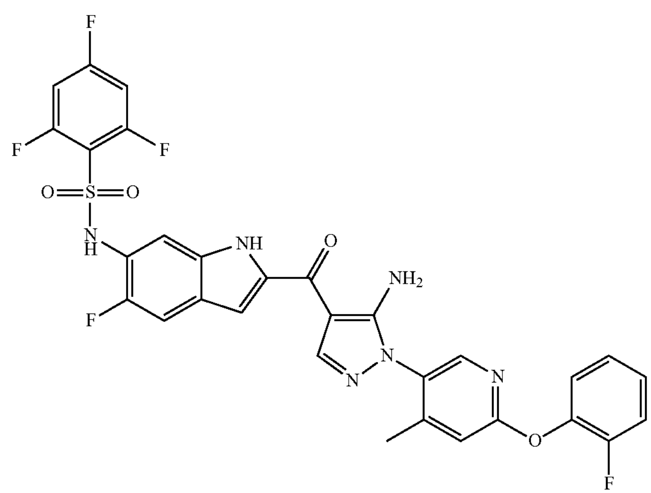 [SMILES: Cc1cc(Oc2ccccc2F)ncc1-n1ncc(C(=O)c2cc3cc(F)c(NS(=O)(=O)c4c(F)cc(F)cc4F)cc3[nH]2)c1N] | N-[2-[5-amino-1-[6-(2-fluorophenoxy)-4-methylpyridin-3-yl]pyrazole-4-carbonyl]-5-fluoro-1H-indol-6-yl]-2,4,6-trifluorobenzenesulfonamide | 655 | 0.98 | AA Rev.11 |

-continued

| Example No. | Chemical Structure | Compound Name | m/z (M + H) | Reaction Time (Minute) | LCMS Measurement Condition |
|---|---|---|---|---|---|
| 5-1-569 | 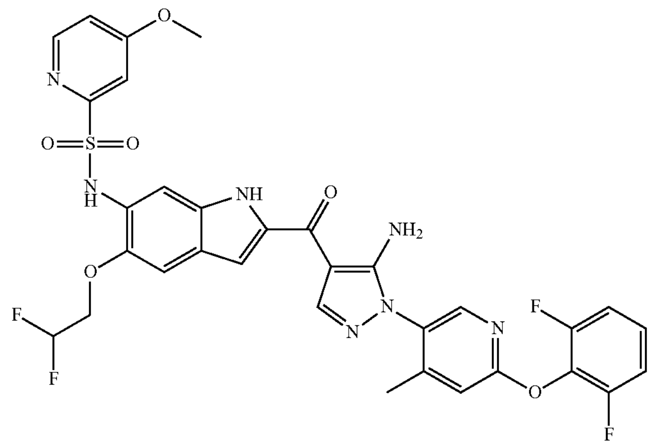 | N-[2-[5-amino-1-[6-(2,6-difluorophenoxy)-4-methylpyridin-3-yl]pyrazole-4-carbonyl]-5-(2,2-difluoroethoxy)-1H-indol-6-yl]-4-methoxypyridine-2-sulfonamide | 712 | 1.23 | TFA Rev.7 |
| 5-1-570 | 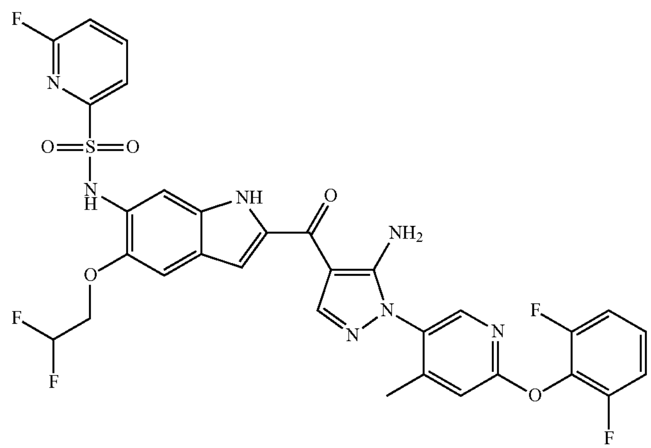 [SMILES: Cc1cc(Oc2c(F)cccc2F)ncc1-n1ncc(C(=O)c2cc3cc(OCC(F)F)c(NS(=O)(=O)c4cccc(F)n4)cc3[nH]2)c1N] | N-[2-[5-amino-1-[6-(2,6-difluorophenoxy)-4-methylpyridin-3-yl]pyrazole-4-carbonyl]-5-(2,2-difluoroethoxy)-1H-indol-6-yl]-6-fluoropyridine-2-sulfonamide | 700 | 1.25 | TFA Rev.7 |

| Example No. | Chemical Structure | Compound Name | m/z (M + H) | Reaction Time (Minute) | LCMS Measurement Condition |
|---|---|---|---|---|---|
| 5-1-571 | 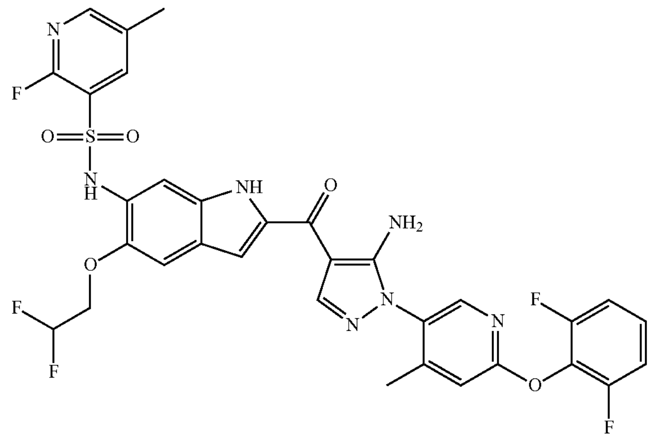 [SMILES: Cc1cnc(F)c(S(=O)(=O)Nc2cc3[nH]c(C(=O)c4cnn(-c5cnc(Oc6c(F)cccc6F)cc5C)c4N)cc3cc2OCC(F)F)c1] | N-[2-[5-amino-1-[6-(2,6-difluorophenoxy)-4-methylpyridin-3-yl]pyrazole-4-carbonyl]-5-(2,2-difluoroethoxy)-1H-indol-6-yl]-2-fluoro-5-methylpyridine-3-sulfonamide | 714 | 1.28 | TFA Rev.7 |
| 5-1-572 | 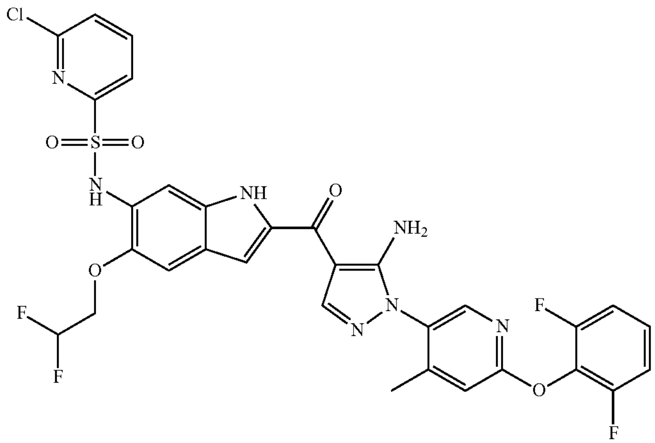 [SMILES: Cc1cc(Oc2c(F)cccc2F)ncc1-n1ncc(C(=O)c2cc3cc(OCC(F)F)c(NS(=O)(=O)c4cccc(Cl)n4)cc3[nH]2)c1N] | N-[2-[5-amino-1-[6-(2,6-difluorophenoxy)-4-methylpyridin-3-yl]pyrazole-4-carbonyl]-5-(2,2-difluoroethoxy)-1H-indol-6-yl]-6-chloropyridine-2-sulfonamide | 716, 718 | 1.28 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-573 | 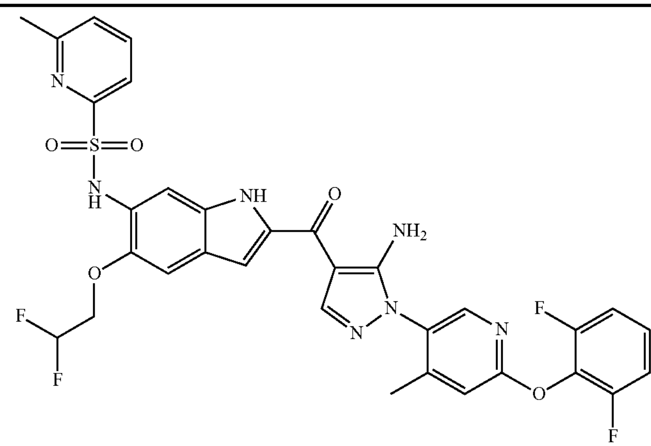 | N-[2-[5-amino-1-[6-(2,6-difluorophenoxy)-4-methylpyridin-3-yl]pyrazole-4-carbonyl]-5-(2,2-difluoroethoxy)-1H-indol-6-yl]-6-methylpyridine-2-sulfonamide | 696 | 1.25 | TFA Rev.7 |
| 5-1-574 | 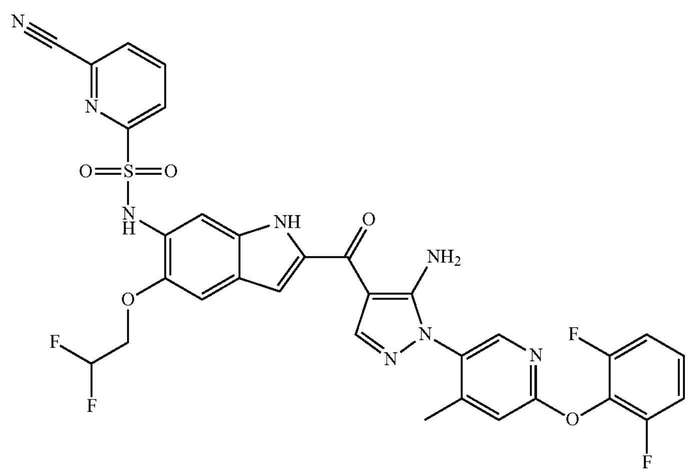 [SMILES: Cc1cc(Oc2c(F)cccc2F)ncc1-n1ncc(C(=O)c2cc3cc(OCC(F)F)c(NS(=O)(=O)c4cccc(C#N)n4)cc3[nH]2)c1N] | N-[2-[5-amino-1-[6-(2,6-difluorophenoxy)-4-methylpyridin-3-yl]pyrazole-4-carbonyl]-5-(2,2-difluoroethoxy)-1H-indol-6-yl]-6-cyanopyridine-2-sulfonamide | 707 | 0.96 | AA Rev.11 |

| Example No. | Chemical Structure | Compound Name | m/z (M + H) | Reaction Time (Minute) | LCMS Measurement Condition |
|---|---|---|---|---|---|
| 5-1-575 | 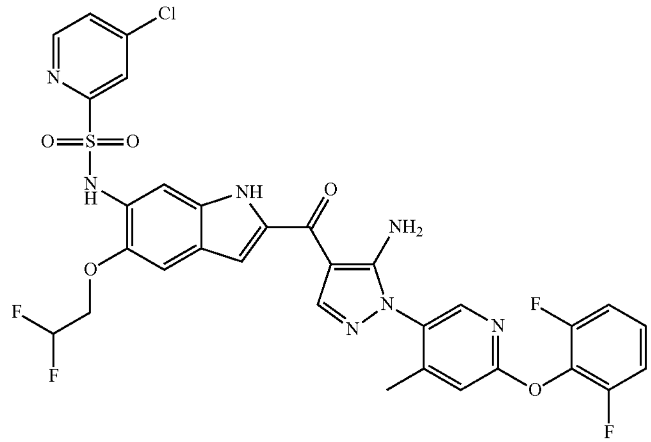 | N-[2-[5-amino-1-[6-(2,6-difluorophenoxy)-4-methylpyridin-3-yl]pyrazole-4-carbonyl]-5-(2,2-difluoroethoxy)-1H-indol-6-yl]-5-chloropyridine-3-sulfonamide | 716, 718 | 1.28 | TFA Rev.7 |
| 5-1-576 | 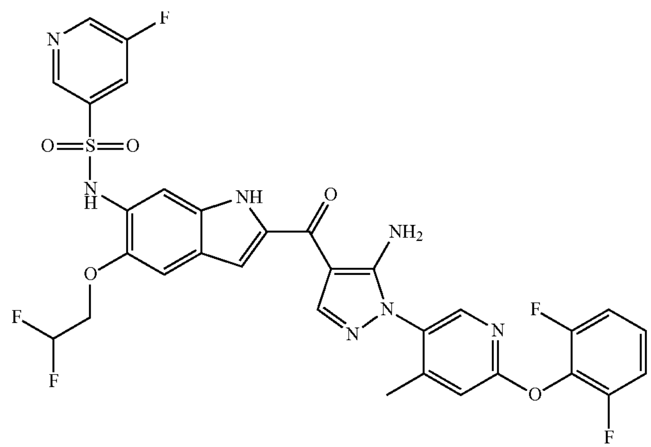 | N-[2-[5-amino-1-[6-(2,6-difluorophenoxy)-4-methylpyridin-3-yl]pyrazole-4-carbonyl]-5-(2,2-difluoroethoxy)-1H-indol-6-yl]-5-fluoropyridine-3-sulfonamide | 700 | 1.24 | TFA Rev.7 |

-continued

| Example No. | Chemical Structure | Compound Name | m/z (M + H) | Reaction Time (Minute) | LCMS Measurement Condition |
|---|---|---|---|---|---|
| 5-1-577 | 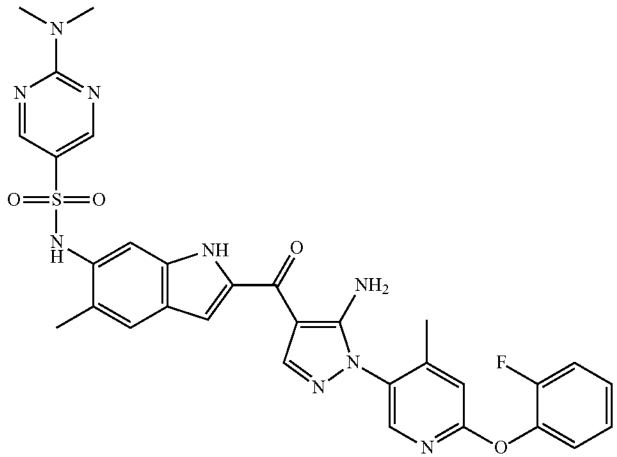 [SMILES: Cc1cc2cc(C(=O)c3cnn(-c4cnc(Oc5ccccc5F)cc4C)c3N)[nH]c2cc1NS(=O)(=O)c1cnc(N(C)C)nc1] | N-[2-[5-amino-1-[6-(2-fluorophenoxy)-4-methylpyridin-3-yl]pyrazole-4-carbonyl]-5-methyl-1H-indol-6-yl]-2-(dimethylamino)pyrimidine-5-sulfonamide | 642 | 1.24 | TFA Rev.7 |

PHARMACOLOGICAL TEST EXAMPLE

1. Yes1 Enzyme Inhibitory Activity

Yes1 inhibitory activity was determined based on activity of inhibiting phosphorylation reaction of a biotinylated peptide (EGPWLEEEEEAYGWMDF) using a human Yes1 enzyme prepared using a baculovirus expression system. The phosphorylated biotinylated peptide was detected by time-resolved fluorometry using an anti-phosphorylated tyrosine antibody conjugated to europium cryptate, and streptavidin conjugated to XL665, an allophycocyanin derivative. The 50% inhibitory concentration (IC50) was calculated from the inhibition rate relative to the control group without containing the test substance.

2. Src Enzyme Inhibitory Activity

Src inhibitory activity was determined based on activity of inhibiting phosphorylation reaction of a biotinylated peptide (EGPWLEEEEEAYGWMDF) using a human Src enzyme (manufactured by Carna Biosciences, Inc., cat 08-173). The phosphorylated biotinylated peptide was detected by time-resolved fluorometry using an anti-phosphorylated tyrosine antibody conjugated to europium cryptate, and streptavidin conjugated to XL665, an allophycocyanin derivative. The 50% inhibitory concentration (IC50) was calculated from the inhibition rate relative to the control group without containing the test substance.

3. Lck Enzyme Inhibitory Activity

Lck inhibitory activity was determined based on activity of inhibiting phosphorylation reaction of a biotinylated peptide (EGPWLEEEEEAYGWMDF) using a human Lck enzyme (manufactured by Carna Biosciences, Inc., cat 08-170). The phosphorylated biotinylated peptide was detected by time-resolved fluorometry using an anti-phosphorylated tyrosine antibody conjugated to europium cryptate, and streptavidin conjugated to XL665, an allophycocyanin derivative. The 50% inhibitory concentration (IC50) was calculated from the inhibition rate relative to the control group without containing the test substance.

The results of these tests are shown below.

| Example No. | YES_IC50 [μM] | SRC_IC50 [μM] | LCK_IC50 [μM] |
|---|---|---|---|
| 4-1-001 | 0.0012 | 0.045 | 0.0082 |
| 4-1-002 | 0.00052 | 0.021 | 0.0076 |
| 4-1-003 | 0.0012 | 0.055 | 0.014 |
| 4-1-004 | 0.00052 | 0.021 | 0.0034 |
| 4-1-005 | 0.0010 | 0.063 | 0.0078 |
| 4-1-006 | 0.0018 | 0.074 | 0.011 |
| 4-1-007 | 0.0011 | 0.061 | 0.0075 |
| 4-1-008 | 0.00069 | 0.052 | 0.0040 |
| 4-1-009 | 0.0011 | 0.059 | 0.0045 |
| 4-1-010 | 0.0011 | 0.046 | 0.025 |
| 4-1-011 | 0.0055 | 0.17 | 0.041 |
| 4-1-012 | 0.034 | 0.090 | 0.039 |
| 4-1-013 | 0.00045 | 0.0026 | 0.0013 |
| 4-1-014 | 0.00036 | 0.0058 | 0.0014 |
| 4-1-015 | 0.0010 | 0.014 | 0.010 |
| 4-1-016 | 0.0021 | 0.014 | 0.0075 |
| 4-1-017 | 0.0031 | 0.10 | 0.0049 |
| 4-2-001 | 0.0010 | 0.0041 | 0.0031 |
| 4-2-002 | 0.00089 | 0.0035 | 0.0037 |
| 4-2-003 | 0.0014 | 0.0064 | 0.0021 |
| 4-2-004 | 0.00093 | 0.0075 | 0.0023 |
| 4-2-005 | 0.0015 | 0.020 | 0.0050 |
| 4-2-006 | 0.0013 | 0.012 | 0.0033 |
| 4-2-007 | 0.00091 | 0.045 | 0.0036 |
| 4-2-008 | 0.0011 | 0.0054 | 0.0025 |
| 4-2-009 | 0.00081 | 0.0051 | 0.0034 |
| 4-2-010 | 0.0012 | 0.0047 | 0.0019 |
| 4-2-011 | 0.0022 | 0.011 | 0.0027 |
| 4-2-012 | 0.0022 | 0.0094 | 0.0049 |
| 4-2-013 | 0.0011 | 0.049 | 0.0097 |
| 4-2-014 | 0.018 | 0.51 | 0.062 |
| 4-2-015 | 0.00067 | 0.019 | 0.010 |
| 4-2-016 | 0.0021 | 0.070 | 0.019 |
| 4-2-017 | 0.00055 | 0.026 | 0.017 |
| 4-2-018 | 0.00052 | 0.022 | 0.015 |
| 4-2-019 | 0.0053 | 0.072 | 0.040 |
| 4-2-020 | 0.0020 | 0.059 | 0.011 |
| 4-2-021 | 0.0015 | 0.043 | 0.0086 |
| 4-2-022 | 0.0054 | 0.14 | 0.026 |
| 4-2-023 | 0.0017 | 0.084 | 0.047 |
| 4-2-024 | 0.0021 | 0.060 | 0.012 |
| 4-2-025 | 0.0024 | 0.052 | 0.035 |
| 4-2-026 | 0.0036 | 0.12 | 0.037 |
| 4-2-027 | 0.010 | 0.095 | 0.030 |
| 4-2-028 | 0.015 | 0.34 | 0.12 |
| 4-2-029 | 0.00064 | 0.028 | 0.0055 |
| 4-2-030 | 0.0017 | 0.11 | 0.026 |
| 4-2-031 | 0.00069 | 0.037 | 0.0043 |
| 4-2-032 | 0.0035 | 0.092 | 0.027 |
| 4-2-033 | 0.00091 | 0.049 | 0.019 |
| 4-2-034 | 0.0046 | 0.14 | 0.044 |
| 4-2-035 | 0.0013 | 0.059 | 0.0067 |
| 4-2-036 | 0.0015 | 0.060 | 0.021 |
| 4-2-037 | 0.0011 | 0.078 | 0.030 |
| 4-2-038 | 0.0019 | 0.13 | 0.040 |
| 4-2-039 | 0.0041 | 0.084 | 0.032 |
| 4-2-040 | 0.0022 | 0.042 | 0.024 |
| 4-2-041 | 0.00079 | 0.084 | 0.038 |
| 4-2-042 | 0.032 | 0.84 | 0.37 |
| 4-2-043 | 0.0014 | 0.087 | 0.028 |
| 4-2-044 | 0.0070 | 0.16 | 0.032 |
| 4-2-045 | 0.0049 | 0.23 | 0.089 |
| 4-2-046 | 0.012 | 0.23 | 0.048 |
| 4-2-047 | 0.0045 | 0.079 | 0.064 |
| 4-2-048 | 0.012 | 0.29 | 0.079 |
| 4-2-049 | 0.00029 | 0.0019 | 0.0017 |
| 4-2-050 | 0.00020 | 0.0070 | 0.0017 |
| 4-2-051 | 0.00059 | 0.0038 | 0.0012 |
| 4-2-052 | 0.00044 | 0.0052 | 0.00097 |
| 4-2-053 | 0.00034 | 0.019 | 0.0051 |
| 4-2-054 | 0.0015 | 0.062 | 0.015 |
| 4-2-055 | 0.0030 | 0.065 | 0.026 |
| 4-2-056 | 0.0039 | 0.097 | 0.024 |
| 4-2-057 | 0.0043 | 0.14 | 0.027 |
| 4-2-058 | 0.0040 | 0.18 | 0.069 |
| 4-2-059 | 0.0077 | 0.39 | 0.11 |
| 4-2-060 | 0.0020 | 0.058 | 0.015 |
| 4-2-061 | 0.00052 | 0.031 | 0.0065 |
| 4-2-062 | 0.0032 | 0.13 | 0.021 |
| 4-2-063 | 0.0020 | 0.078 | 0.0083 |
| 4-2-064 | 0.0024 | 0.063 | 0.014 |
| 4-2-065 | 0.0022 | 0.044 | 0.018 |
| 4-2-066 | 0.0094 | 0.16 | 0.036 |
| 4-2-067 | 0.0063 | 0.097 | 0.059 |
| 4-2-068 | 0.0018 | 0.028 | 0.021 |
| 4-2-069 | 0.0010 | 0.067 | 0.022 |
| 4-2-070 | 0.0076 | 0.14 | 0.047 |
| 4-2-071 | 0.012 | 0.16 | 0.078 |
| 4-2-072 | 0.0018 | 0.088 | 0.020 |
| 4-2-073 | 0.0031 | 0.037 | 0.019 |
| 4-2-074 | 0.0027 | 0.071 | 0.027 |
| 4-2-075 | 0.010 | 0.17 | 0.11 |
| 4-2-076 | 0.018 | 0.13 | 0.062 |
| 4-2-077 | 0.00064 | 0.025 | 0.0043 |
| 4-2-078 | 0.0059 | 0.091 | 0.050 |
| 4-2-079 | 0.0026 | 0.066 | 0.024 |
| 4-2-080 | 0.012 | 0.17 | 0.068 |
| 4-2-081 | 0.014 | 0.21 | 0.083 |
| 4-2-082 | 0.022 | 0.31 | 0.16 |
| 4-2-083 | 0.027 | 0.52 | 0.25 |
| 4-2-084 | 0.0063 | 0.16 | 0.073 |
| 4-2-085 | 0.00081 | 0.051 | 0.0076 |
| 4-2-086 | 0.0016 | 0.099 | 0.0083 |
| 4-2-087 | 0.0027 | 0.22 | 0.055 |
| 4-2-088 | 0.0026 | 0.17 | 0.048 |
| 4-2-089 | 0.0027 | 0.18 | 0.013 |

| Example No. | YES_IC50 [μM] | SRC_IC50 [μM] | LCK_IC50 [μM] |
|---|---|---|---|
| 4-2-090 | 0.0015 | 0.11 | 0.017 |
| 4-2-091 | 0.0097 | 0.35 | 0.14 |
| 4-2-092 | 0.019 | 0.27 | 0.078 |
| 4-2-093 | 0.00089 | 0.019 | 0.0057 |
| 4-2-094 | 0.0020 | 0.033 | 0.0082 |
| 4-2-095 | 0.00085 | 0.014 | 0.0053 |
| 4-2-096 | 0.00038 | 0.0095 | 0.0026 |
| 4-2-097 | 0.00028 | 0.0081 | 0.0018 |
| 4-2-098 | 0.00039 | 0.015 | 0.0025 |
| 4-2-099 | 0.00061 | 0.015 | 0.0028 |
| 4-2-100 | 0.00073 | 0.027 | 0.0021 |
| 4-2-101 | 0.00074 | 0.050 | 0.0029 |
| 4-2-102 | 0.00089 | 0.048 | 0.0039 |
| 4-2-103 | 0.00041 | 0.0070 | 0.00097 |
| 4-2-104 | 0.00056 | 0.022 | 0.0019 |
| 4-2-105 | 0.00036 | 0.10 | 0.024 |
| 4-2-106 | 0.0014 | 0.18 | 0.051 |
| 4-2-107 | 0.0024 | 0.25 | 0.089 |
| 4-2-108 | 0.0010 | 0.094 | 0.031 |
| 4-2-109 | 0.0019 | 0.21 | 0.045 |
| 4-2-110 | 0.0087 | 0.25 | 0.11 |
| 4-2-111 | 0.041 | 0.69 | 0.32 |
| 4-2-112 | 0.00093 | 0.023 | 0.0083 |
| 4-2-113 | 0.00063 | 0.018 | 0.0071 |
| 4-2-114 | 0.0050 | 0.072 | 0.016 |
| 4-2-115 | 0.0041 | 0.063 | 0.016 |
| 4-2-116 | 0.0015 | 0.043 | 0.0093 |
| 4-2-117 | 0.00060 | 0.021 | 0.0048 |
| 4-2-118 | 0.0057 | 0.11 | 0.035 |
| 4-2-119 | 0.0074 | 0.070 | 0.023 |
| 4-2-120 | 0.0010 | 0.028 | 0.0040 |
| 4-2-121 | 0.00054 | 0.0080 | 0.0021 |
| 4-2-122 | 0.0036 | 0.034 | 0.0073 |
| 4-2-123 | 0.0019 | 0.037 | 0.0058 |
| 4-2-124 | 0.0041 | 0.034 | 0.0069 |
| 4-2-125 | 0.0024 | 0.028 | 0.0026 |
| 4-2-126 | 0.0013 | 0.013 | 0.0020 |
| 4-2-127 | 0.0013 | 0.023 | 0.0037 |
| 4-2-128 | 0.0012 | 0.0086 | 0.0027 |
| 4-2-129 | 0.00059 | 0.0032 | 0.0014 |
| 4-2-130 | 0.0014 | 0.034 | 0.0045 |
| 4-3-001 | 0.0043 | 0.092 | 0.024 |
| 4-4-001 | 0.0063 | 0.021 | 0.0082 |
| 4-5-001 | 0.0012 | 0.12 | 0.033 |
| 4-5-002 | 0.00076 | 0.049 | 0.023 |
| 4-5-003 | 0.00067 | 0.029 | 0.011 |
| 4-5-004 | 0.0033 | 0.065 | 0.041 |
| 4-5-005 | 0.00051 | 0.029 | 0.011 |
| 4-5-006 | 0.0068 | 0.14 | 0.062 |
| 4-5-007 | 0.00050 | 0.033 | 0.018 |
| 4-5-008 | 0.00055 | 0.031 | 0.0082 |
| 4-5-009 | 0.00068 | 0.035 | 0.012 |
| 4-5-010 | 0.0018 | 0.034 | 0.022 |
| 4-5-011 | 0.0016 | 0.11 | 0.065 |
| 4-5-012 | 0.0010 | 0.078 | 0.012 |
| 4-6-001 | 0.00092 | 0.070 | 0.013 |
| 4-6-002 | 0.00035 | 0.016 | 0.0046 |
| 4-6-003 | 0.0023 | 0.088 | 0.022 |
| 4-6-004 | 0.0011 | 0.041 | 0.0069 |
| 4-7-001 | 0.0022 | 0.041 | 0.010 |
| 4-7-002 | 0.00043 | 0.0095 | 0.0091 |
| 4-7-003 | 0.0010 | 0.019 | 0.0071 |
| 4-7-004 | 0.0048 | 0.22 | 0.040 |
| 4-7-005 | 0.0028 | 0.16 | 0.045 |
| 4-7-006 | 0.0070 | 0.38 | 0.16 |
| 4-7-007 | 0.0020 | 0.19 | 0.041 |
| 4-7-008 | 0.0059 | 0.49 | 0.14 |
| 4-7-009 | 0.0037 | 0.15 | 0.034 |
| 4-7-010 | 0.0090 | 0.28 | 0.10 |
| 4-7-011 | 0.014 | 0.20 | 0.097 |
| 4-7-012 | 0.014 | 0.33 | 0.16 |
| 4-7-013 | 0.0030 | 0.058 | 0.026 |
| 4-7-014 | 0.0049 | 0.13 | 0.073 |
| 4-7-015 | 0.00092 | 0.11 | 0.017 |
| 4-7-016 | 0.0046 | 0.21 | 0.11 |
| 4-8-001 | 0.0011 | 0.031 | 0.014 |
| 4-9-001 | 0.00046 | 0.013 | 0.0025 |
| 4-9-002 | 0.00072 | 0.0098 | 0.00096 |
| 4-10-001 | 0.0021 | 0.086 | 0.018 |
| 4-10-002 | 0.00077 | 0.027 | 0.011 |
| 4-10-003 | 0.00075 | 0.026 | 0.0049 |
| 4-10-004 | 0.00053 | 0.012 | 0.0083 |
| 4-10-005 | 0.0028 | 0.058 | 0.016 |
| 4-10-006 | 0.0010 | 0.037 | 0.019 |
| 4-10-007 | 0.00048 | 0.013 | 0.0085 |
| 4-10-008 | 0.0020 | 0.054 | 0.0096 |
| 4-10-009 | 0.0027 | 0.033 | 0.019 |
| 4-10-010 | 0.0013 | 0.026 | 0.0071 |
| 4-10-011 | 0.00064 | 0.025 | 0.0038 |
| 4-10-012 | 0.00030 | 0.0098 | 0.0051 |
| 4-10-013 | 0.0012 | 0.029 | 0.011 |
| 4-10-014 | 0.00054 | 0.029 | 0.010 |
| 4-10-015 | 0.0011 | 0.058 | 0.0072 |
| 4-10-016 | 0.00059 | 0.017 | 0.0058 |
| 4-10-017 | 0.00093 | 0.032 | 0.011 |
| 4-11-001 | 0.0015 | 0.033 | 0.0056 |
| 4-12-001 | 0.0029 | 0.14 | 0.045 |
| 4-12-002 | 0.0032 | 0.040 | 0.0080 |
| 4-12-003 | 0.00054 | 0.045 | 0.014 |
| 4-13-001 | 0.0024 | 0.076 | 0.026 |
| 4-13-002 | 0.0024 | 0.027 | 0.020 |
| 4-14-001 | 0.0012 | 0.021 | 0.0058 |
| 4-14-002 | 0.0014 | 0.0088 | 0.0056 |
| 4-15-001 | 0.0011 | 0.018 | 0.0099 |
| 4-16-001 | 0.00062 | 0.016 | 0.0045 |
| 4-17-001 | 0.0045 | 0.026 | 0.012 |
| 4-17-002 | 0.010 | 0.043 | 0.018 |
| 4-17-003 | 0.0074 | 0.023 | 0.020 |
| 4-17-004 | 0.0096 | 0.022 | 0.017 |
| 4-17-005 | 0.0029 | 0.036 | 0.017 |
| 4-17-006 | 0.0034 | 0.025 | 0.013 |
| 4-17-007 | 0.0039 | 0.022 | 0.012 |
| 4-17-008 | 0.0016 | 0.013 | 0.0055 |
| 4-17-009 | 0.0018 | 0.014 | 0.0049 |
| 4-17-010 | 0.0020 | 0.099 | 0.045 |
| 4-17-011 | 0.013 | 0.043 | 0.023 |
| 4-17-012 | 0.016 | 0.045 | 0.030 |
| 4-17-013 | 0.017 | 0.046 | 0.037 |
| 4-17-014 | 0.0045 | 0.027 | 0.013 |
| 4-17-015 | 0.0050 | 0.014 | 0.014 |
| 4-17-016 | 0.0064 | 0.015 | 0.012 |
| 4-17-017 | 0.0021 | 0.017 | 0.0058 |
| 4-17-018 | 0.0024 | 0.019 | 0.011 |
| 4-17-019 | 0.0032 | 0.018 | 0.0091 |
| 4-17-020 | 0.00081 | 0.0083 | 0.0033 |
| 4-17-021 | 0.00076 | 0.0097 | 0.0056 |
| 4-17-022 | 0.0013 | 0.014 | 0.0080 |
| 4-17-023 | 0.0068 | 0.027 | 0.021 |
| 4-17-024 | 0.011 | 0.040 | 0.025 |
| 4-18-001 | 0.0032 | 0.024 | 0.0082 |
| 4-18-002 | 0.0059 | 0.029 | 0.015 |
| 4-18-003 | 0.0048 | 0.023 | 0.011 |
| 4-18-004 | 0.0016 | 0.016 | 0.0092 |
| 4-19-001 | 0.00083 | 0.028 | 0.0039 |
| 4-20-001 | 0.00064 | 0.031 | 0.0035 |
| 4-20-002 | 0.0010 | 0.050 | 0.0083 |
| 4-20-003 | 0.0014 | 0.015 | 0.0021 |
| 4-21-001 | 0.0037 | 0.013 | 0.0062 |
| 4-21-002 | 0.00089 | 0.0054 | 0.0028 |
| 4-21-003 | 0.00053 | 0.0024 | 0.0015 |
| 4-21-004 | 0.0010 | 0.0092 | 0.0030 |
| 4-21-005 | 0.0012 | 0.011 | 0.0043 |
| 4-21-006 | 0.0016 | 0.017 | 0.0055 |
| 4-21-007 | 0.00051 | 0.0087 | 0.0065 |
| 4-21-008 | 0.0041 | 0.025 | 0.0066 |
| 4-21-009 | 0.00083 | 0.0099 | 0.0027 |
| 4-22-001 | 0.0026 | 0.090 | 0.034 |
| 4-22-002 | 0.0030 | 0.24 | 0.068 |
| 4-22-003 | 0.0029 | 0.17 | 0.062 |
| 4-22-004 | 0.0012 | 0.36 | 0.078 |
| 4-22-005 | 0.0018 | 0.044 | 0.020 |
| 4-22-006 | 0.0019 | 0.13 | 0.051 |
| 4-23-001 | 0.0013 | 0.016 | 0.0082 |
| 4-23-002 | 0.0016 | 0.044 | 0.020 |

| Example No. | YES_IC50 [μM] | SRC_IC50 [μM] | LCK_IC50 [μM] |
| --- | --- | --- | --- |
| 4-23-003 | 0.010 | 0.062 | 0.021 |
| 4-23-004 | 0.0055 | 0.048 | 0.018 |
| 4-23-005 | 0.0017 | 0.016 | 0.0082 |
| 4-23-006 | 0.0027 | 0.022 | 0.013 |
| 4-23-007 | 0.0013 | 0.016 | 0.0055 |
| 4-23-008 | 0.0033 | 0.023 | 0.0046 |
| 4-23-009 | 0.0032 | 0.022 | 0.0089 |
| 4-23-010 | 0.0072 | 0.034 | 0.025 |
| 4-23-011 | 0.0076 | 0.063 | 0.019 |
| 4-23-012 | 0.014 | 0.070 | 0.031 |
| 4-23-013 | 0.0016 | 0.040 | 0.0046 |
| 4-23-014 | 0.0035 | 0.022 | 0.0092 |
| 4-23-015 | 0.0054 | 0.049 | 0.023 |
| 4-23-016 | 0.00094 | 0.021 | 0.0054 |
| 4-23-017 | 0.0051 | 0.028 | 0.013 |
| 4-23-018 | 0.0014 | 0.018 | 0.0065 |
| 4-23-019 | 0.0018 | 0.028 | 0.0064 |
| 4-23-020 | 0.0014 | 0.030 | 0.0038 |
| 4-23-021 | 0.0036 | 0.021 | 0.011 |
| 4-23-022 | 0.0013 | 0.024 | 0.0080 |
| 4-23-023 | 0.00045 | 0.017 | 0.0058 |
| 4-23-024 | 0.0072 | 0.053 | 0.013 |
| 4-23-025 | 0.0018 | 0.030 | 0.0056 |
| 4-23-026 | 0.0045 | 0.050 | 0.019 |
| 4-23-027 | 0.0019 | 0.016 | 0.0076 |
| 4-23-028 | 0.020 | 0.070 | 0.041 |
| 4-23-029 | 0.0047 | 0.034 | 0.0061 |
| 4-23-030 | 0.0014 | 0.0064 | 0.0038 |
| 4-23-031 | 0.0015 | 0.014 | 0.0052 |
| 4-23-032 | 0.00058 | 0.017 | 0.0025 |
| 4-23-033 | 0.00050 | 0.0061 | 0.0021 |
| 4-23-034 | 0.0015 | 0.054 | 0.0067 |
| 4-23-035 | 0.00063 | 0.030 | 0.0070 |
| 4-23-036 | 0.0010 | 0.031 | 0.0064 |
| 4-23-037 | 0.00076 | 0.012 | 0.0067 |
| 4-23-038 | 0.0012 | 0.071 | 0.010 |
| 4-23-039 | 0.00081 | 0.060 | 0.016 |
| 4-24-001 | 0.0036 | 0.11 | 0.036 |
| 4-24-002 | 0.0016 | 0.035 | 0.010 |
| 4-24-003 | 0.0027 | 0.055 | 0.025 |
| 4-24-004 | 0.0031 | 0.041 | 0.017 |
| 4-24-005 | 0.0047 | 0.24 | 0.047 |
| 4-24-006 | 0.0045 | 0.20 | 0.051 |
| 4-24-007 | 0.0040 | 0.23 | 0.061 |
| 4-24-008 | 0.0021 | 0.099 | 0.019 |
| 4-24-009 | 0.0036 | 0.12 | 0.039 |
| 4-24-010 | 0.0043 | 0.15 | 0.036 |
| 4-24-011 | 0.0023 | 0.064 | 0.013 |
| 4-24-012 | 0.0040 | 0.10 | 0.028 |
| 4-24-013 | 0.0016 | 0.040 | 0.012 |
| 4-24-014 | 0.0066 | 0.36 | 0.097 |
| 4-24-015 | 0.0013 | 0.077 | 0.016 |
| 4-24-016 | 0.00087 | 0.078 | 0.032 |
| 4-24-017 | 0.0041 | 0.17 | 0.065 |
| 4-24-018 | 0.0026 | 0.091 | 0.027 |
| 4-24-019 | 0.0039 | 0.14 | 0.062 |
| 4-24-020 | 0.0031 | 0.054 | 0.022 |
| 4-24-021 | 0.0017 | 0.022 | 0.0097 |
| 4-24-022 | 0.0032 | 0.030 | 0.022 |
| 4-24-023 | 0.0023 | 0.024 | 0.014 |
| 4-24-024 | 0.0033 | 0.13 | 0.046 |
| 4-24-025 | 0.0016 | 0.059 | 0.013 |
| 4-24-026 | 0.0017 | 0.050 | 0.021 |
| 4-24-027 | 0.0032 | 0.14 | 0.055 |
| 4-24-028 | 0.0012 | 0.037 | 0.014 |
| 4-24-029 | 0.0016 | 0.054 | 0.029 |
| 4-24-030 | 0.0017 | 0.12 | 0.023 |
| 4-24-031 | 0.0012 | 0.021 | 0.0067 |
| 4-24-032 | 0.00064 | 0.057 | 0.014 |
| 4-24-033 | 0.0049 | 0.088 | 0.016 |
| 4-24-034 | 0.00039 | 0.0081 | 0.0047 |
| 4-24-035 | 0.0012 | 0.047 | 0.0050 |
| 4-24-036 | 0.0042 | 0.12 | 0.020 |
| 4-24-037 | 0.00067 | 0.024 | 0.0038 |
| 4-24-038 | 0.00055 | 0.0069 | 0.0029 |
| 4-24-039 | 0.00046 | 0.0083 | 0.0028 |
| 4-25-001 | 0.0016 | 0.029 | 0.0096 |
| 4-25-002 | 0.0031 | 0.037 | 0.015 |
| 4-25-003 | 0.0039 | 0.13 | 0.019 |
| 4-25-004 | 0.0010 | 0.048 | 0.0087 |
| 4-25-005 | 0.0039 | 0.053 | 0.011 |
| 4-25-006 | 0.0011 | 0.018 | 0.0090 |
| 4-25-007 | 0.0011 | 0.023 | 0.0052 |
| 4-25-008 | 0.0015 | 0.022 | 0.0082 |
| 4-25-009 | 0.0035 | 0.032 | 0.018 |
| 4-25-010 | 0.0017 | 0.016 | 0.0074 |
| 4-25-011 | 0.0014 | 0.011 | 0.0041 |
| 4-25-012 | 0.00035 | 0.0030 | 0.0021 |
| 4-25-013 | 0.0010 | 0.016 | 0.0040 |
| 4-25-014 | 0.0011 | 0.026 | 0.0022 |
| 4-25-015 | 0.0049 | 0.044 | 0.0082 |
| 4-25-016 | 0.00048 | 0.013 | 0.0015 |
| 4-25-017 | 0.0013 | 0.0064 | 0.0023 |
| 4-25-018 | 0.00072 | 0.020 | 0.0017 |
| 4-25-019 | 0.0052 | 0.043 | 0.013 |
| 4-25-020 | 0.0012 | 0.013 | 0.0023 |
| 4-25-021 | 0.0021 | 0.016 | 0.0046 |
| 4-25-022 | 0.0059 | 0.059 | 0.010 |
| 4-25-023 | 0.0063 | 0.086 | 0.016 |
| 4-25-024 | 0.00069 | 0.055 | 0.029 |
| 4-25-025 | 0.017 | 0.080 | 0.031 |
| 4-25-026 | 0.00092 | 0.012 | 0.0016 |
| 4-25-027 | 0.00080 | 0.023 | 0.0021 |
| 4-25-028 | 0.00094 | 0.013 | 0.0049 |
| 4-25-029 | 0.0024 | 0.021 | 0.0068 |
| 4-25-030 | 0.0026 | 0.038 | 0.0091 |
| 4-25-031 | 0.0019 | 0.048 | 0.0072 |
| 4-25-032 | 0.00083 | 0.048 | 0.011 |
| 4-26-001 | 0.0015 | 0.026 | 0.0076 |

Pharmacological tests (determinations of Yes1 enzyme inhibitory activity, Src enzyme inhibitory activity, and Lck enzyme inhibitory activity) were also performed for the compounds of Example No. 5 in the similar manner as described above. The results of the tests are shown below.

| Example No. | YES_IC50 [μM] | SRC_IC50 [μM] | LCK_IC50 [μM] |
| --- | --- | --- | --- |
| 5-1-001 | 0.0011 | 0.0076 | 0.0029 |
| 5-1-002 | 0.00087 | 0.0061 | 0.0022 |
| 5-1-003 | 0.0020 | 0.026 | 0.0047 |
| 5-1-004 | 0.00078 | 0.0036 | 0.0028 |
| 5-1-005 | 0.00071 | 0.037 | 0.0042 |
| 5-1-006 | 0.00073 | 0.056 | 0.0060 |
| 5-1-007 | 0.0011 | 0.011 | 0.0022 |
| 5-1-008 | 0.0027 | 0.060 | 0.0046 |
| 5-1-009 | 0.0019 | 0.0093 | 0.0028 |
| 5-1-010 | 0.0025 | 0.038 | 0.0036 |
| 5-1-011 | 0.00086 | 0.014 | 0.0026 |
| 5-1-012 | 0.0025 | 0.31 | 0.023 |
| 5-1-013 | 0.0016 | 0.030 | 0.0025 |
| 5-1-014 | 0.0024 | 0.043 | 0.0030 |
| 5-1-015 | 0.0015 | 0.023 | 0.0022 |
| 5-1-016 | 0.00072 | 0.093 | 0.025 |
| 5-1-017 | 0.0045 | 2.4 | 0.63 |
| 5-1-018 | 0.0022 | 0.11 | 0.033 |
| 5-1-019 | 0.0028 | 0.12 | 0.054 |
| 5-1-020 | 0.0057 | 0.19 | 0.051 |
| 5-1-021 | 0.0098 | 0.31 | 0.072 |
| 5-1-022 | 0.0020 | 0.062 | 0.010 |
| 5-1-023 | 0.016 | 0.24 | 0.064 |
| 5-1-024 | 0.026 | 0.34 | 0.083 |
| 5-1-025 | 0.020 | 0.73 | 0.27 |
| 5-1-026 | 0.064 | 0.66 | 0.39 |
| 5-1-027 | 0.00084 | 0.065 | 0.020 |
| 5-1-028 | 0.013 | 0.35 | 0.20 |
| 5-1-029 | 0.00073 | 0.017 | 0.013 |
| 5-1-030 | 0.0024 | 0.076 | 0.0087 |
| 5-1-031 | 0.0041 | 0.22 | 0.034 |
| 5-1-032 | 0.011 | 0.38 | 0.13 |
| 5-1-033 | 0.0084 | 0.40 | 0.23 |

| Example No. | YES_IC50 [μM] | SRC_IC50 [μM] | LCK_IC50 [μM] |
| --- | --- | --- | --- |
| 5-1-034 | 0.0035 | 0.18 | 0.062 |
| 5-1-035 | 0.00068 | 0.085 | 0.035 |
| 5-1-036 | 0.0015 | 0.14 | 0.065 |
| 5-1-037 | 0.00091 | 0.045 | 0.017 |
| 5-1-038 | 0.016 | 0.27 | 0.066 |
| 5-1-039 | 0.12 | 6.1 | 2.0 |
| 5-1-040 | 0.013 | 0.28 | 0.088 |
| 5-1-041 | 0.093 | 10 | 2.0 |
| 5-1-042 | 0.27 | 10 | 1.9 |
| 5-1-043 | 0.038 | 10 | 2.6 |
| 5-1-044 | 0.052 | 10 | 2.7 |
| 5-1-045 | 0.21 | 10 | 4.4 |
| 5-1-046 | 0.0079 | 0.16 | 0.11 |
| 5-1-047 | 0.00087 | 0.015 | 0.0051 |
| 5-1-048 | 0.0016 | 0.11 | 0.0064 |
| 5-1-049 | 0.0015 | 0.070 | 0.0039 |
| 5-1-050 | 0.00077 | 0.023 | 0.0018 |
| 5-1-051 | 0.060 | 0.32 | 0.082 |
| 5-1-052 | 0.12 | 0.81 | 0.25 |
| 5-1-053 | 0.065 | 0.43 | 0.097 |
| 5-1-054 | 0.15 | 1.0 | 0.35 |
| 5-1-055 | 0.016 | 0.19 | 0.094 |
| 5-1-056 | 0.0017 | 0.076 | 0.024 |
| 5-1-057 | 0.0020 | 0.15 | 0.031 |
| 5-1-058 | 0.0016 | 0.058 | 0.025 |
| 5-1-059 | 0.0034 | 0.13 | 0.033 |
| 5-1-060 | 0.082 | 0.39 | 0.042 |
| 5-1-061 | 0.00096 | 0.012 | 0.0070 |
| 5-1-062 | 0.0024 | 0.048 | 0.013 |
| 5-1-063 | 0.0028 | 0.083 | 0.029 |
| 5-1-064 | 0.024 | 0.34 | 0.26 |
| 5-1-065 | 0.0077 | 0.35 | 0.12 |
| 5-1-066 | 0.0027 | 0.21 | 0.077 |
| 5-1-067 | 0.0023 | 0.062 | 0.0056 |
| 5-1-068 | 0.0056 | 0.015 | 0.0084 |
| 5-1-069 | 0.018 | 0.033 | 0.020 |
| 5-1-070 | 0.00085 | 0.013 | 0.012 |
| 5-1-071 | 0.028 | 0.067 | 0.061 |
| 5-1-072 | 0.0077 | 0.036 | 0.0082 |
| 5-1-073 | 0.0097 | 0.042 | 0.032 |
| 5-1-074 | 0.0016 | 0.025 | 0.0032 |
| 5-1-075 | 0.0028 | 0.073 | 0.018 |
| 5-1-076 | 0.0028 | 0.12 | 0.016 |
| 5-1-077 | 0.0010 | 0.042 | 0.0071 |
| 5-1-078 | 0.00028 | 0.010 | 0.0024 |
| 5-1-079 | 0.0010 | 0.020 | 0.0038 |
| 5-1-080 | 0.0033 | 0.037 | 0.014 |
| 5-1-081 | 0.0024 | 0.11 | 0.0064 |
| 5-1-082 | 0.0019 | 0.026 | 0.011 |
| 5-1-083 | 0.00072 | 0.0072 | 0.0070 |
| 5-1-084 | 0.0041 | 0.034 | 0.0045 |
| 5-1-085 | 0.0023 | 0.021 | 0.0020 |
| 5-1-086 | 0.0014 | 0.0085 | 0.0028 |
| 5-1-087 | 0.00077 | 0.013 | 0.0039 |
| 5-1-088 | 0.0022 | 0.027 | 0.0028 |
| 5-1-089 | 0.0062 | 0.077 | 0.0089 |
| 5-1-090 | 0.0026 | 0.025 | 0.0038 |
| 5-1-091 | 0.0032 | 0.024 | 0.0037 |
| 5-1-092 | 0.00091 | 0.016 | 0.0028 |
| 5-1-093 | 0.0018 | 0.011 | 0.0037 |
| 5-1-094 | 0.0029 | 0.019 | 0.0041 |
| 5-1-095 | 0.00087 | 0.0045 | 0.0015 |
| 5-1-096 | 0.0017 | 0.033 | 0.0027 |
| 5-1-097 | 0.0011 | 0.0087 | 0.0013 |
| 5-1-098 | 0.0019 | 0.015 | 0.0014 |
| 5-1-099 | 0.0021 | 0.011 | 0.0022 |
| 5-1-100 | 0.0016 | 0.0087 | 0.0013 |
| 5-1-101 | 0.0019 | 0.025 | 0.0011 |
| 5-1-102 | 0.00077 | 0.0050 | 0.0013 |
| 5-1-103 | 0.00038 | 0.0052 | 0.0011 |
| 5-1-104 | 0.00063 | 0.0097 | 0.0011 |
| 5-1-105 | 0.00077 | 0.0036 | 0.0016 |
| 5-1-106 | 0.00042 | 0.0020 | 0.0011 |
| 5-1-107 | 0.0015 | 0.096 | 0.0079 |
| 5-1-108 | 0.00057 | 0.021 | 0.0017 |
| 5-1-109 | 0.00070 | 0.037 | 0.0014 |
| 5-1-110 | 0.0077 | 0.068 | 0.010 |
| 5-1-111 | 0.014 | 0.046 | 0.014 |
| 5-1-112 | 0.00081 | 0.026 | 0.0017 |
| 5-1-113 | 0.0039 | 0.041 | 0.0033 |
| 5-1-114 | 0.0017 | 0.041 | 0.0011 |
| 5-1-115 | 0.0023 | 0.052 | 0.0070 |
| 5-1-116 | 0.00051 | 0.0052 | 0.0016 |
| 5-1-117 | 0.00048 | 0.0050 | 0.0013 |
| 5-1-118 | 0.00085 | 0.011 | 0.0027 |
| 5-1-119 | 0.0018 | 0.015 | 0.0048 |
| 5-1-120 | 0.00043 | 0.023 | 0.0061 |
| 5-1-121 | 0.0017 | 0.090 | 0.014 |
| 5-1-122 | 0.00039 | 0.030 | 0.0046 |
| 5-1-123 | 0.0020 | 0.091 | 0.033 |
| 5-1-124 | 0.00099 | 0.070 | 0.010 |
| 5-1-125 | 0.00071 | 0.033 | 0.0092 |
| 5-1-126 | 0.00087 | 0.064 | 0.015 |
| 5-1-127 | 0.00067 | 0.039 | 0.0040 |
| 5-1-128 | 0.00075 | 0.023 | 0.0038 |
| 5-1-129 | 0.00061 | 0.0073 | 0.0046 |
| 5-1-130 | 0.00056 | 0.013 | 0.0038 |
| 5-1-131 | 0.0011 | 0.0074 | 0.0056 |
| 5-1-132 | 0.00071 | 0.0066 | 0.0033 |
| 5-1-133 | 0.00063 | 0.0061 | 0.0025 |
| 5-1-134 | 0.00037 | 0.0046 | 0.0021 |
| 5-1-135 | 0.00084 | 0.012 | 0.0053 |
| 5-1-136 | 0.0015 | 0.027 | 0.023 |
| 5-1-137 | 0.0013 | 0.041 | 0.029 |
| 5-1-138 | 0.0031 | 0.068 | 0.042 |
| 5-1-139 | 0.0018 | 0.023 | 0.025 |
| 5-1-140 | 0.0028 | 0.048 | 0.024 |
| 5-1-141 | 0.0024 | 0.075 | 0.027 |
| 5-1-142 | 0.0056 | 0.099 | 0.052 |
| 5-1-143 | 0.00059 | 0.015 | 0.011 |
| 5-1-144 | 0.0057 | 0.081 | 0.076 |
| 5-1-145 | 0.0016 | 0.016 | 0.0082 |
| 5-1-146 | 0.00027 | 0.0022 | 0.0053 |
| 5-1-147 | 0.00057 | 0.0051 | 0.012 |
| 5-1-148 | 0.00057 | 0.18 | 0.047 |
| 5-1-149 | 0.0050 | 0.057 | 0.043 |
| 5-1-150 | 0.0048 | 10 | 0.32 |
| 5-1-151 | 0.0029 | 0.60 | 0.080 |
| 5-1-152 | 0.0073 | 10 | 7.8 |
| 5-1-153 | 0.00053 | 0.0079 | 0.0030 |
| 5-1-154 | 0.00067 | 0.011 | 0.0043 |
| 5-1-155 | 0.0016 | 0.022 | 0.012 |
| 5-1-156 | 0.0016 | 1.1 | 0.064 |
| 5-1-157 | 0.0019 | 1.1 | 0.48 |
| 5-1-158 | 0.00090 | 0.076 | 0.042 |
| 5-1-159 | 0.0014 | 0.096 | 0.039 |
| 5-1-160 | 0.00071 | 0.23 | 0.033 |
| 5-1-161 | 0.0028 | 0.60 | 0.16 |
| 5-1-162 | 0.0021 | 0.48 | 0.12 |
| 5-1-163 | 0.00064 | 0.059 | 0.0070 |
| 5-1-164 | 0.0018 | 0.70 | 0.069 |
| 5-1-165 | 0.0018 | 0.34 | 0.037 |
| 5-1-166 | 0.0020 | 0.82 | 0.25 |
| 5-1-167 | 0.0036 | 2.0 | 0.37 |
| 5-1-168 | 0.0011 | 0.21 | 0.045 |
| 5-1-169 | 0.00088 | 0.10 | 0.046 |
| 5-1-170 | 0.0013 | 0.49 | 0.089 |
| 5-1-171 | 0.0011 | 0.079 | 0.049 |
| 5-1-172 | 0.00090 | 0.17 | 0.018 |
| 5-1-173 | 0.0026 | 0.34 | 0.10 |
| 5-1-174 | 0.00056 | 0.046 | 0.0045 |
| 5-1-175 | 0.0024 | 0.35 | 0.074 |
| 5-1-176 | 0.0010 | 0.079 | 0.011 |
| 5-1-177 | 0.0024 | 0.34 | 0.082 |
| 5-1-178 | 0.00037 | 0.048 | 0.0034 |
| 5-1-179 | 0.0040 | 0.81 | 0.18 |
| 5-1-180 | 0.00035 | 0.095 | 0.0063 |
| 5-1-181 | 0.0014 | 0.39 | 0.041 |
| 5-1-182 | 0.00017 | 0.024 | 0.0027 |
| 5-1-183 | 0.00044 | 0.0049 | 0.0028 |
| 5-1-184 | 0.00043 | 0.011 | 0.0026 |
| 5-1-185 | 0.00036 | 0.0025 | 0.0017 |
| 5-1-186 | 0.00028 | 0.0019 | 0.0013 |
| 5-1-187 | 0.00062 | 0.0032 | 0.0023 |

| Example No. | YES_IC50 [μM] | SRC_IC50 [μM] | LCK_IC50 [μM] |
|---|---|---|---|
| 5-1-188 | 0.00030 | 0.0046 | 0.0012 |
| 5-1-189 | 0.00038 | 0.0033 | 0.0015 |
| 5-1-190 | 0.00041 | 0.0018 | 0.0013 |
| 5-1-191 | 0.00048 | 0.0022 | 0.0016 |
| 5-1-192 | 0.00029 | 0.0011 | 0.00086 |
| 5-1-193 | 0.00032 | 0.0023 | 0.0013 |
| 5-1-194 | 0.00035 | 0.0015 | 0.0012 |
| 5-1-195 | 0.0013 | 0.19 | 0.045 |
| 5-1-196 | 0.0017 | 0.19 | 0.067 |
| 5-1-197 | 0.00087 | 0.0077 | 0.0083 |
| 5-1-198 | 0.0015 | 0.27 | 0.036 |
| 5-1-199 | 0.0027 | 0.078 | 0.037 |
| 5-1-200 | 0.052 | 0.92 | 0.27 |
| 5-1-201 | 0.00025 | 0.0035 | 0.0032 |
| 5-1-202 | 0.00017 | 0.0031 | 0.0028 |
| 5-1-203 | 0.00036 | 0.0070 | 0.0062 |
| 5-1-204 | 0.00050 | 0.010 | 0.0067 |
| 5-1-205 | 0.00043 | 0.015 | 0.0072 |
| 5-1-206 | 0.0091 | 10 | 10 |
| 5-1-207 | 0.0019 | 0.35 | 0.082 |
| 5-1-208 | 0.0037 | 0.45 | 0.065 |
| 5-1-209 | 0.0044 | 0.42 | 0.098 |
| 5-1-210 | 0.0065 | 0.51 | 0.12 |
| 5-1-211 | 0.026 | 10 | 4.4 |
| 5-1-212 | 0.0045 | 0.22 | 0.060 |
| 5-1-213 | 0.0098 | 0.60 | 0.15 |
| 5-1-214 | 0.00099 | 0.052 | 0.011 |
| 5-1-215 | 0.00081 | 0.082 | 0.0060 |
| 5-1-216 | 0.0017 | 1.0 | 0.047 |
| 5-1-217 | 0.0014 | 0.15 | 0.048 |
| 5-1-218 | 0.00064 | 0.22 | 0.039 |
| 5-1-219 | 0.0013 | 0.46 | 0.083 |
| 5-1-220 | 0.0015 | 0.18 | 0.056 |
| 5-1-221 | 0.00066 | 0.0064 | 0.0075 |
| 5-1-222 | 0.0013 | 0.0047 | 0.0075 |
| 5-1-223 | 0.0015 | 0.0074 | 0.0072 |
| 5-1-224 | 0.00057 | 0.017 | 0.0063 |
| 5-1-225 | 0.00046 | 0.089 | 0.012 |
| 5-1-226 | 0.00034 | 0.0033 | 0.0020 |
| 5-1-227 | 0.0039 | 0.56 | 0.046 |
| 5-1-228 | 0.0013 | 0.013 | 0.0031 |
| 5-1-229 | 0.00077 | 0.0061 | 0.0024 |
| 5-1-230 | 0.00068 | 0.095 | 0.0070 |
| 5-1-231 | 0.0017 | 0.61 | 0.072 |
| 5-1-232 | 0.0014 | 0.23 | 0.030 |
| 5-1-233 | 0.00092 | 0.34 | 0.021 |
| 5-1-234 | 0.0032 | 0.49 | 0.073 |
| 5-1-235 | 0.0029 | 0.43 | 0.085 |
| 5-1-236 | 0.0015 | 0.14 | 0.041 |
| 5-1-237 | 0.0015 | 0.18 | 0.036 |
| 5-1-238 | 0.0081 | 0.86 | 0.34 |
| 5-1-239 | 0.0050 | 0.040 | 0.016 |
| 5-1-240 | 0.0020 | 0.075 | 0.019 |
| 5-1-241 | 0.0018 | 0.0055 | 0.0061 |
| 5-1-242 | 0.0019 | 0.50 | 0.16 |
| 5-1-243 | 0.0011 | 0.0096 | 0.0032 |
| 5-1-244 | 0.0099 | 0.018 | 0.040 |
| 5-1-245 | 0.0071 | 0.023 | 0.057 |
| 5-1-246 | 0.0016 | 0.016 | 0.0071 |
| 5-1-247 | 0.0021 | 0.12 | 0.034 |
| 5-1-248 | 0.00097 | 0.0079 | 0.0047 |
| 5-1-249 | 0.00077 | 0.0074 | 0.0037 |
| 5-1-250 | 0.00076 | 0.0075 | 0.0028 |
| 5-1-251 | 0.0038 | 0.025 | 0.015 |
| 5-1-252 | 0.0012 | 0.014 | 0.0046 |
| 5-1-253 | 0.00033 | 0.023 | 0.046 |
| 5-1-254 | 0.00089 | 0.010 | 0.0031 |
| 5-1-255 | 0.0011 | 0.0089 | 0.0045 |
| 5-1-256 | 0.12 | 10 | 10 |
| 5-1-257 | 0.040 | 0.25 | 0.095 |
| 5-1-258 | 0.018 | 2.9 | 0.72 |
| 5-1-259 | 0.0075 | 0.050 | 0.025 |
| 5-1-260 | 0.0085 | 0.061 | 0.044 |
| 5-1-261 | 0.0079 | 0.39 | 0.20 |
| 5-1-262 | 0.0023 | 0.0064 | 0.012 |
| 5-1-263 | 0.019 | 2.6 | 0.71 |
| 5-1-264 | 0.0052 | 0.026 | 0.021 |
| 5-1-265 | 0.0054 | 0.44 | 0.038 |
| 5-1-266 | 0.0021 | 0.011 | 0.011 |
| 5-1-267 | 0.0020 | 0.021 | 0.017 |
| 5-1-268 | 0.012 | 0.12 | 0.031 |
| 5-1-269 | 0.0020 | 0.11 | 0.023 |
| 5-1-270 | 0.0047 | 0.13 | 0.028 |
| 5-1-271 | 0.00051 | 0.0072 | 0.0032 |
| 5-1-272 | 0.00065 | 0.0078 | 0.0042 |
| 5-1-273 | 0.0018 | 0.033 | 0.015 |
| 5-1-274 | 0.0021 | 0.045 | 0.017 |
| 5-1-275 | 0.00064 | 0.019 | 0.0070 |
| 5-1-276 | 0.0022 | 0.087 | 0.035 |
| 5-1-277 | 0.0015 | 0.039 | 0.012 |
| 5-1-278 | 0.0012 | 0.023 | 0.0087 |
| 5-1-279 | 0.014 | 0.91 | 0.17 |
| 5-1-280 | 0.0018 | 0.080 | 0.031 |
| 5-1-281 | 0.0019 | 0.14 | 0.027 |
| 5-1-282 | 0.0048 | 0.20 | 0.12 |
| 5-1-283 | 0.0020 | 0.27 | 0.032 |
| 5-1-284 | 0.0011 | 0.011 | 0.0069 |
| 5-1-285 | 0.0052 | 2.3 | 0.50 |
| 5-1-286 | 0.0023 | 0.030 | 0.0053 |
| 5-1-287 | 0.0010 | 0.35 | 0.017 |
| 5-1-288 | 0.0019 | 0.052 | 0.017 |
| 5-1-289 | 0.0034 | 10 | 0.40 |
| 5-1-290 | 0.0021 | 0.046 | 0.030 |
| 5-1-291 | 0.010 | 0.42 | 0.13 |
| 5-1-292 | 0.019 | 0.63 | 0.088 |
| 5-1-293 | 0.00073 | 0.44 | 0.018 |
| 5-1-294 | 0.0022 | 0.96 | 0.11 |
| 5-1-295 | 0.0015 | 0.70 | 0.064 |
| 5-1-296 | 0.0059 | 0.15 | 0.046 |
| 5-1-297 | 0.0085 | 0.58 | 0.046 |
| 5-1-298 | 0.0089 | 0.63 | 0.093 |
| 5-1-299 | 0.0097 | 0.61 | 0.12 |
| 5-1-300 | 0.0095 | 0.73 | 0.14 |
| 5-1-301 | 0.0065 | 0.61 | 0.17 |
| 5-1-302 | 0.0019 | 0.050 | 0.022 |
| 5-1-303 | 0.027 | 1.5 | 0.32 |
| 5-1-304 | 0.032 | 1.3 | 0.40 |
| 5-1-305 | 0.0098 | 0.38 | 0.084 |
| 5-1-306 | 0.023 | 0.63 | 0.15 |
| 5-1-307 | 0.026 | 10 | 0.72 |
| 5-1-308 | 0.0077 | 1.3 | 0.20 |
| 5-1-309 | 0.012 | 3.6 | 0.41 |
| 5-1-310 | 0.0034 | 0.038 | 0.022 |
| 5-1-311 | 0.0036 | 0.048 | 0.015 |
| 5-1-312 | 0.0035 | 0.16 | 0.010 |
| 5-1-313 | 0.0028 | 0.073 | 0.019 |
| 5-1-314 | 0.0096 | 0.48 | 0.15 |
| 5-1-315 | 0.0081 | 0.33 | 0.13 |
| 5-1-316 | 0.0062 | 0.17 | 0.029 |
| 5-1-317 | 0.016 | 0.50 | 0.11 |
| 5-1-318 | 0.010 | 0.35 | 0.12 |
| 5-1-319 | 0.0028 | 0.088 | 0.018 |
| 5-1-320 | 0.018 | 0.68 | 0.14 |
| 5-1-321 | 0.0058 | 0.13 | 0.034 |
| 5-1-322 | 0.0041 | 0.070 | 0.022 |
| 5-1-323 | 0.0091 | 0.23 | 0.040 |
| 5-1-324 | 0.010 | 0.23 | 0.019 |
| 5-1-325 | 0.0016 | 0.032 | 0.018 |
| 5-1-326 | 0.00085 | 0.054 | 0.025 |
| 5-1-327 | 0.0073 | 0.92 | 0.27 |
| 5-1-328 | 0.014 | 0.89 | 0.23 |
| 5-1-329 | 0.0090 | 0.72 | 0.15 |
| 5-1-330 | 0.011 | 0.70 | 0.20 |
| 5-1-331 | 0.0070 | 0.33 | 0.18 |
| 5-1-332 | 0.00079 | 0.012 | 0.0025 |
| 5-1-333 | 0.0020 | 0.14 | 0.019 |
| 5-1-334 | 0.0013 | 0.041 | 0.0040 |
| 5-1-335 | 0.0027 | 1.7 | 0.12 |
| 5-1-336 | 0.0042 | 10 | 0.24 |
| 5-1-337 | 0.0023 | 0.12 | 0.018 |
| 5-1-338 | 0.0030 | 0.18 | 0.030 |
| 5-1-339 | 0.0057 | 0.54 | 0.074 |
| 5-1-340 | 0.0021 | 0.13 | 0.020 |
| 5-1-341 | 0.0027 | 0.053 | 0.0074 |

| Example No. | YES_IC50 [μM] | SRC_IC50 [μM] | LCK_IC50 [μM] |
|---|---|---|---|
| 5-1-342 | 0.0017 | 0.048 | 0.0053 |
| 5-1-343 | 0.0030 | 0.10 | 0.0072 |
| 5-1-344 | 0.0047 | 0.15 | 0.013 |
| 5-1-345 | 0.0016 | 0.047 | 0.0032 |
| 5-1-346 | 0.0088 | 0.51 | 0.12 |
| 5-1-347 | 0.00087 | 0.046 | 0.011 |
| 5-1-348 | 0.00080 | 0.013 | 0.0020 |
| 5-1-349 | 0.00051 | 0.0069 | 0.0025 |
| 5-1-350 | 0.00088 | 0.013 | 0.0033 |
| 5-1-351 | 0.00065 | 0.0060 | 0.0024 |
| 5-1-352 | 0.011 | 0.16 | 0.017 |
| 5-1-353 | 0.0055 | 0.073 | 0.014 |
| 5-1-354 | 0.0014 | 0.013 | 0.0029 |
| 5-1-355 | 0.0080 | 0.097 | 0.013 |
| 5-1-356 | 0.00087 | 0.017 | 0.0044 |
| 5-1-357 | 0.0023 | 0.039 | 0.0044 |
| 5-1-358 | 0.0018 | 0.021 | 0.0042 |
| 5-1-359 | 0.0060 | 0.13 | 0.025 |
| 5-1-360 | 0.0022 | 0.019 | 0.0063 |
| 5-1-361 | 0.0092 | 0.17 | 0.026 |
| 5-1-362 | 0.0020 | 0.029 | 0.0065 |
| 5-1-363 | 0.011 | 0.26 | 0.031 |
| 5-1-364 | 0.0013 | 0.018 | 0.0054 |
| 5-1-365 | 0.0015 | 0.018 | 0.0057 |
| 5-1-366 | 0.0037 | 0.039 | 0.0099 |
| 5-1-367 | 0.0056 | 0.077 | 0.016 |
| 5-1-368 | 0.0038 | 0.062 | 0.0087 |
| 5-1-369 | 0.022 | 0.56 | 0.079 |
| 5-1-370 | 0.0083 | 0.15 | 0.027 |
| 5-1-371 | 0.0020 | 0.030 | 0.0098 |
| 5-1-372 | 0.0013 | 0.016 | 0.0061 |
| 5-1-373 | 0.0031 | 0.048 | 0.014 |
| 5-1-374 | 0.0029 | 0.036 | 0.013 |
| 5-1-375 | 0.0020 | 0.024 | 0.0071 |
| 5-1-376 | 0.0014 | 0.014 | 0.0040 |
| 5-1-377 | 0.0020 | 0.017 | 0.0074 |
| 5-1-378 | 0.0028 | 0.063 | 0.037 |
| 5-1-379 | 0.0045 | 0.061 | 0.011 |
| 5-1-380 | 0.0063 | 0.095 | 0.11 |
| 5-1-381 | 0.0033 | 0.056 | 0.043 |
| 5-1-382 | 0.0025 | 0.26 | 0.031 |
| 5-1-383 | 0.0092 | 0.63 | 0.27 |
| 5-1-384 | 0.0024 | 0.090 | 0.044 |
| 5-1-385 | 0.0030 | 2.4 | 0.39 |
| 5-1-386 | 0.0039 | 10 | 1.0 |
| 5-1-387 | 0.0031 | 0.19 | 0.029 |
| 5-1-388 | 0.0042 | 0.22 | 0.047 |
| 5-1-389 | 0.0014 | 0.024 | 0.018 |
| 5-1-390 | 0.0019 | 0.044 | 0.025 |
| 5-1-391 | 0.0013 | 0.011 | 0.0055 |
| 5-1-392 | 0.0029 | 0.089 | 0.014 |
| 5-1-393 | 0.0010 | 0.0098 | 0.0046 |
| 5-1-394 | 0.0029 | 0.093 | 0.021 |
| 5-1-395 | 0.0048 | 0.21 | 0.066 |
| 5-1-396 | 0.0036 | 0.23 | 0.068 |
| 5-1-397 | 0.0018 | 0.090 | 0.031 |
| 5-1-398 | 0.0024 | 0.095 | 0.020 |
| 5-1-399 | 0.0057 | 0.25 | 0.053 |
| 5-1-400 | 0.0021 | 0.076 | 0.014 |
| 5-1-401 | 0.0025 | 0.14 | 0.041 |
| 5-1-402 | 0.0018 | 0.063 | 0.0082 |
| 5-1-403 | 0.00098 | 0.088 | 0.0086 |
| 5-1-404 | 0.0017 | 0.048 | 0.0026 |
| 5-1-405 | 0.0027 | 0.066 | 0.0032 |
| 5-1-406 | 0.0022 | 0.075 | 0.0031 |
| 5-1-407 | 0.0022 | 0.074 | 0.0035 |
| 5-1-408 | 0.0012 | 0.043 | 0.0061 |
| 5-1-409 | 0.0031 | 0.16 | 0.020 |
| 5-1-410 | 0.00056 | 0.022 | 0.0029 |
| 5-1-411 | 0.00073 | 0.037 | 0.0042 |
| 5-1-412 | 0.0030 | 0.10 | 0.017 |
| 5-1-413 | 0.0015 | 0.090 | 0.017 |
| 5-1-414 | 0.0053 | 0.33 | 0.11 |
| 5-1-415 | 0.0059 | 0.28 | 0.11 |
| 5-1-416 | 0.0034 | 0.21 | 0.058 |
| 5-1-417 | 0.0058 | 0.24 | 0.13 |
| 5-1-418 | 0.0014 | 0.078 | 0.021 |
| 5-1-419 | 0.0056 | 0.79 | 0.22 |
| 5-1-420 | 0.0063 | 0.60 | 0.16 |
| 5-1-421 | 0.0011 | 0.084 | 0.017 |
| 5-1-422 | 0.0017 | 0.25 | 0.091 |
| 5-1-423 | 0.0040 | 0.19 | 0.061 |
| 5-1-424 | 0.0056 | 0.48 | 0.20 |
| 5-1-425 | 0.0015 | 0.095 | 0.039 |
| 5-1-426 | 0.0020 | 0.095 | 0.036 |
| 5-1-427 | 0.0038 | 0.17 | 0.043 |
| 5-1-428 | 0.0031 | 0.17 | 0.046 |
| 5-1-429 | 0.0075 | 0.19 | 0.025 |
| 5-1-430 | 0.0084 | 0.28 | 0.037 |
| 5-1-431 | 0.0049 | 0.19 | 0.020 |
| 5-1-432 | 0.0038 | 0.096 | 0.0077 |
| 5-1-433 | 0.0012 | 0.059 | 0.0048 |
| 5-1-434 | 0.00044 | 0.015 | 0.0041 |
| 5-1-435 | 0.0020 | 0.12 | 0.021 |
| 5-1-436 | 0.0017 | 0.23 | 0.035 |
| 5-1-437 | 0.00079 | 0.040 | 0.0078 |
| 5-1-438 | 0.0019 | 0.12 | 0.015 |
| 5-1-439 | 0.0073 | 0.69 | 0.31 |
| 5-1-440 | 0.0037 | 0.44 | 0.13 |
| 5-1-441 | 0.0018 | 0.28 | 0.073 |
| 5-1-442 | 0.0012 | 0.021 | 0.0049 |
| 5-1-443 | 0.0014 | 0.025 | 0.0049 |
| 5-1-444 | 0.00065 | 0.013 | 0.0039 |
| 5-1-445 | 0.00054 | 0.012 | 0.0031 |
| 5-1-446 | 0.00044 | 0.013 | 0.0021 |
| 5-1-447 | 0.0020 | 0.084 | 0.012 |
| 5-1-448 | 0.0012 | 0.023 | 0.0039 |
| 5-1-449 | 0.00066 | 0.013 | 0.0033 |
| 5-1-450 | 0.0030 | 0.15 | 0.022 |
| 5-1-451 | 0.00089 | 0.041 | 0.0046 |
| 5-1-452 | 0.0054 | 0.15 | 0.028 |
| 5-1-453 | 0.0032 | 0.13 | 0.012 |
| 5-1-454 | 0.0017 | 0.040 | 0.0051 |
| 5-1-455 | 0.00086 | 0.023 | 0.0026 |
| 5-1-456 | 0.00040 | 0.0088 | 0.0022 |
| 5-1-457 | 0.0023 | 0.078 | 0.019 |
| 5-1-458 | 0.00073 | 0.016 | 0.0040 |
| 5-1-459 | 0.00044 | 0.0077 | 0.0027 |
| 5-1-460 | 0.0045 | 0.77 | 0.20 |
| 5-1-461 | 0.017 | 3.5 | 0.59 |
| 5-1-462 | 0.0061 | 1.0 | 0.26 |
| 5-1-463 | 0.012 | 1.9 | 0.42 |
| 5-1-464 | 0.0093 | 1.2 | 0.31 |
| 5-1-465 | 0.025 | 4.0 | 0.51 |
| 5-1-466 | 0.028 | 4.4 | 0.52 |
| 5-1-467 | 0.024 | 3.8 | 0.37 |
| 5-1-468 | 0.011 | 7.8 | 0.43 |
| 5-1-469 | 0.0090 | 2.7 | 0.10 |
| 5-1-470 | 0.031 | 10 | 0.87 |
| 5-1-471 | 0.081 | 10 | 0.98 |
| 5-1-472 | 0.040 | 10 | 0.71 |
| 5-1-473 | 0.017 | 3.5 | 0.24 |
| 5-1-474 | 0.027 | 10 | 0.65 |
| 5-1-475 | 0.0082 | 1.4 | 0.071 |
| 5-1-476 | 0.0029 | 0.097 | 0.012 |
| 5-1-477 | 0.0052 | 0.25 | 0.048 |
| 5-1-478 | 0.0048 | 0.28 | 0.077 |
| 5-1-479 | 0.0033 | 0.77 | 0.17 |
| 5-1-480 | 0.0064 | 0.40 | 0.10 |
| 5-1-481 | 0.0054 | 0.45 | 0.11 |
| 5-1-482 | 0.0063 | 0.48 | 0.14 |
| 5-1-483 | 0.0067 | 0.71 | 0.25 |
| 5-1-484 | 0.0069 | 0.57 | 0.14 |
| 5-1-485 | 0.0068 | 0.52 | 0.11 |
| 5-1-486 | 0.0073 | 0.62 | 0.16 |
| 5-1-487 | 0.011 | 0.51 | 0.11 |
| 5-1-488 | 0.0042 | 0.52 | 0.12 |
| 5-1-489 | 0.0019 | 0.19 | 0.049 |
| 5-1-490 | 0.0037 | 0.43 | 0.11 |
| 5-1-491 | 0.0049 | 0.40 | 0.10 |
| 5-1-492 | 0.0080 | 0.76 | 0.15 |
| 5-1-493 | 0.0053 | 10 | 3.0 |
| 5-1-494 | 0.0030 | 0.43 | 0.23 |
| 5-1-495 | 0.0039 | 0.55 | 0.36 |

-continued

| Example No. | YES_IC50 [μM] | SRC_IC50 [μM] | LCK_IC50 [μM] |
|---|---|---|---|
| 5-1-496 | 0.011 | 1.3 | 0.63 |
| 5-1-497 | 0.0047 | 0.66 | 0.17 |
| 5-1-498 | 0.0087 | 1.6 | 0.42 |
| 5-1-499 | 0.016 | 1.8 | 0.55 |
| 5-1-500 | 0.0057 | 0.75 | 0.20 |
| 5-1-501 | 0.0048 | 0.57 | 0.19 |
| 5-1-502 | 0.0023 | 0.35 | 0.11 |
| 5-1-503 | 0.0019 | 0.087 | 0.015 |
| 5-1-504 | 0.0036 | 0.63 | 0.14 |
| 5-1-505 | 0.0025 | 0.47 | 0.068 |
| 5-1-506 | 0.0030 | 0.50 | 0.099 |
| 5-1-507 | 0.0028 | 0.48 | 0.092 |
| 5-1-508 | 0.0040 | 0.92 | 0.14 |
| 5-1-509 | 0.0037 | 0.84 | 0.13 |
| 5-1-510 | 0.00092 | 0.23 | 0.089 |
| 5-1-511 | 0.0027 | 0.52 | 0.24 |
| 5-1-512 | 0.0012 | 0.25 | 0.033 |
| 5-1-513 | 0.0037 | 0.51 | 0.098 |
| 5-1-514 | 0.0033 | 0.76 | 0.14 |
| 5-1-515 | 0.0024 | 0.28 | 0.059 |
| 5-1-516 | 0.0051 | 0.54 | 0.091 |
| 5-1-517 | 0.0021 | 0.30 | 0.034 |
| 5-1-518 | 0.0058 | 0.57 | 0.082 |
| 5-1-519 | 0.0046 | 0.71 | 0.12 |
| 5-1-520 | 0.0027 | 0.27 | 0.067 |
| 5-1-521 | 0.0058 | 0.47 | 0.18 |
| 5-1-522 | 0.0018 | 0.25 | 0.12 |
| 5-1-523 | 0.0063 | 0.45 | 0.20 |
| 5-1-524 | 0.0057 | 0.58 | 0.21 |
| 5-1-525 | 0.0031 | 0.40 | 0.072 |
| 5-1-526 | 0.0080 | 0.62 | 0.25 |
| 5-1-527 | 0.0032 | 0.50 | 0.11 |
| 5-1-528 | 0.0088 | 0.75 | 0.23 |
| 5-1-529 | 0.0086 | 0.84 | 0.26 |
| 5-1-530 | 0.0026 | 0.20 | 0.034 |
| 5-1-531 | 0.0049 | 0.48 | 0.11 |
| 5-1-532 | 0.0016 | 0.29 | 0.038 |
| 5-1-533 | 0.0047 | 0.51 | 0.12 |
| 5-1-534 | 0.0051 | 0.64 | 0.17 |
| 5-1-535 | 0.0041 | 0.39 | 0.078 |
| 5-1-536 | 0.0092 | 0.56 | 0.092 |
| 5-1-537 | 0.0030 | 0.32 | 0.057 |
| 5-1-538 | 0.0096 | 0.68 | 0.14 |
| 5-1-539 | 0.011 | 0.80 | 0.22 |
| 5-1-540 | 0.0035 | 0.35 | 0.096 |
| 5-1-541 | 0.012 | 0.66 | 0.28 |
| 5-1-542 | 0.0036 | 0.43 | 0.18 |
| 5-1-543 | 0.0098 | 0.64 | 0.36 |
| 5-1-544 | 0.0084 | 0.68 | 0.33 |
| 5-1-545 | 0.0031 | 0.15 | 0.022 |
| 5-1-546 | 0.0061 | 0.68 | 0.078 |
| 5-1-547 | 0.0029 | 0.35 | 0.030 |
| 5-1-548 | 0.0076 | 0.64 | 0.078 |
| 5-1-549 | 0.0077 | 0.74 | 0.080 |
| 5-1-550 | 0.0051 | 0.49 | 0.072 |
| 5-1-551 | 0.019 | 0.97 | 0.24 |
| 5-1-552 | 0.0054 | 0.83 | 0.13 |
| 5-1-553 | 0.017 | 1.3 | 0.37 |
| 5-1-554 | 0.013 | 1.5 | 0.26 |
| 5-1-555 | 0.014 | 1.2 | 0.15 |
| 5-1-556 | 0.0088 | 1.0 | 0.15 |
| 5-1-557 | 0.019 | 1.5 | 0.32 |
| 5-1-558 | 0.0049 | 1.5 | 0.23 |
| 5-1-559 | 0.017 | 2.4 | 0.81 |
| 5-1-560 | 0.016 | 2.4 | 0.69 |
| 5-1-561 | 0.017 | 0.94 | 0.27 |
| 5-1-562 | 0.0053 | 0.83 | 0.18 |
| 5-1-563 | 0.017 | 1.2 | 0.59 |
| 5-1-564 | 0.014 | 1.5 | 0.68 |
| 5-1-565 | 0.019 | 1.1 | 0.72 |
| 5-1-566 | 0.0056 | 0.81 | 0.34 |
| 5-1-567 | 0.019 | 1.2 | 0.61 |
| 5-1-568 | 0.017 | 1.3 | 0.75 |
| 5-1-569 | 0.0041 | 0.23 | 0.022 |
| 5-1-570 | 0.0021 | 0.41 | 0.0096 |
| 5-1-571 | 0.0022 | 0.54 | 0.030 |
| 5-1-572 | 0.0035 | 0.69 | 0.021 |

-continued

| Example No. | YES_IC50 [μM] | SRC_IC50 [μM] | LCK_IC50 [μM] |
|---|---|---|---|
| 5-1-573 | 0.0029 | 0.44 | 0.014 |
| 5-1-574 | 0.0028 | 0.54 | 0.013 |
| 5-1-575 | 0.0043 | 0.65 | 0.046 |
| 5-1-576 | 0.0031 | 0.47 | 0.014 |
| 5-1-577 | 0.0066 | 1.1 | 0.38 |

INDUSTRIAL APPLICABILITY

The present invention provides compounds having a Src family kinase inhibitory effect. The present invention also provides medicaments for the prevention and/or treatment of cancer.

The invention claimed is:

1. A compound represented by formula (I) below:

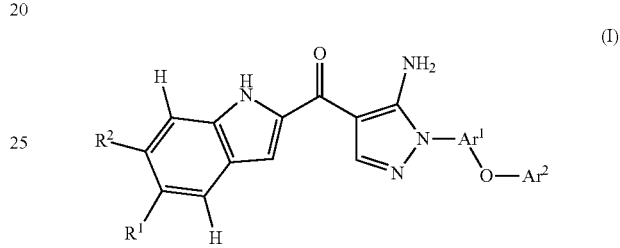

wherein $Ar^1$ is $C_{6-10}$ arylene or 5- to 10-membered heteroarylene optionally substituted with a group selected from Group R;

$Ar^2$ is $C_{6-10}$ aryl or 5- to 10-membered heteroaryl optionally substituted with a group selected from Group R;

$R^1$ and $R^2$ are each independently a halogen atom, $C_{1-6}$ alkyl, $C_{3-6}$ cycloalkyl, $C_{1-6}$ haloalkyl, $C_{2-6}$ alkenyl, $C_{2-6}$ alkynyl, cyano, nitro, $NR^5R^6$, $OR^7$, $SR^8$, $SOR^8$, $SO_2R^8$, $CONR^9R^{10}$, 4- to 6-membered heterocyclyl optionally substituted with a group selected from Group Q, 5- to 10-membered heteroaryl optionally substituted with a group selected from Group Q, or $C_{6-10}$ aryl optionally substituted with a group selected from Group P, where the 4- to 6-membered heterocyclyl optionally substituted with a group selected from Group Q is optionally further linked to 4- to 6-membered heterocyclyl optionally substituted with a group selected from 4- to 6-membered heterocyclyl and $C_{6-10}$ aryl-$C_{1-6}$ alkyl, or to $C_{3-6}$ cycloalkyl through a spiro linkage;

$R^5$ and $R^6$ are each independently a hydrogen atom, $C_{1-6}$ alkyl optionally substituted with 4- to 6-membered heterocyclyl, amino-$C_{1-6}$ alkyl, $C_{1-6}$ alkylcarbonyl optionally substituted with a halogen atom, $-SO_2R^{30}$, $-C(O)OR^{31}$, $-C(O)NR^{32}R^{33}$, 4- to 6-membered heterocyclylcarbonyl, or 4- to 6-membered heterocyclyl optionally substituted with a group selected from Group Q; or alternatively, $R^5$ and $R^6$, together with the nitrogen atom to which they are bonded, form 4- to 6-membered heterocyclyl optionally substituted with a group selected from Group Q;

$R^7$ is a hydrogen atom; $C_{1-6}$ alkyl which optionally has, as a substituent, a group selected from amino, a halogen atom, and hydroxy; 4- to 6-membered heterocyclyl optionally substituted with a group selected from Group Q; or $C_{1-6}$ alkyl having, as a substituent, 4- to 10-membered heterocyclyl optionally substituted with a group selected from Group Q;

$R^8$ is $C_{1-6}$ alkyl, halo-$C_{1-6}$ alkyl, or 4- to 6-membered heterocyclyl optionally substituted with a group selected from Group Q;

$R^9$ and $R^{10}$ are each independently a hydrogen atom or $C_{1-6}$ alkyl; or alternatively, $R^9$ and $R^{10}$, together with the nitrogen atom to which they are bonded, form 4- to 6-membered heterocyclyl optionally substituted with a group selected from Group Q;

$R^{30}$ is optionally substituted $C_{1-6}$ alkyl, $C_{3-6}$ cycloalkyl which optionally has dihydroxy-$C_{1-6}$ alkyl as a substituent, $C_{6-10}$ aryl optionally substituted with a group selected from Group P, 5- to 10-membered heterocyclyl optionally substituted with a group selected from Group Q, 5- to 10-membered heteroaryl optionally substituted with a group selected from Group Q, or —$NR^{34}R^{35}$, where the substituent in the optionally substituted $C_{1-6}$ alkyl is selected from the group consisting of a halogen atom, 4- to 6-membered heterocyclyl optionally substituted with a group selected from Group Q, —C(O)$NR^{36}R^{37}$, and $C_{6-10}$ aryl;

$R^{31}$ represents $C_{1-6}$ alkyl which optionally has fluorene as a substituent;

$R^{32}$ and $R^{33}$ are each independently a hydrogen atom, or $C_{1-6}$ alkyl optionally substituted with a group selected from the group consisting of $C_{1-6}$ alkoxycarbonyl and 5- to 10-membered heteroaryl; or alternatively, $R^{32}$ and $R^{33}$, together with the nitrogen atom to which they are bonded, form 4- to 6-membered heterocyclyl;

$R^{34}$ and $R^{35}$ are each independently a hydrogen atom, $C_{1-6}$ alkyl optionally substituted with a group selected from hydroxy and $C_{1-6}$ alkoxy, 4- to 6-membered heterocyclyl optionally substituted with a group selected from Group Q, $C_{3-6}$ cycloalkyl, or $C_{1-6}$ alkoxy; or alternatively, $R^{34}$ and $R^{35}$, together with the nitrogen atom to which they are bonded, form 4- to 6-membered heterocyclyl optionally substituted with a group selected from Group Q;

$R^{36}$ and $R^{37}$ are each independently a hydrogen atom, $C_{1-6}$ alkyl, or 4- to 6-membered heterocyclyl optionally substituted with a group selected from Group Q; or alternatively, $R^{36}$ and $R^{37}$, together with the nitrogen atom to which they are bonded, form 4- to 6-membered heterocyclyl optionally substituted with a substituent selected from Group Q;

Group P is a halogen atom, cyano, hydroxy, —$NR^{50}R^{51}$, $C_{1-6}$ alkyl, $C_{1-6}$ alkoxy, $C_{1-6}$ alkoxycarbonyl, 5- to 10-membered heteroaryl, and or $C_{1-6}$ haloalkyl;

where $R^{50}$ and $R^{51}$ are each independently a hydrogen atom or $C_{1-6}$ alkyl;

Group Q is cyano, a halogen atom, $C_{1-6}$ alkyl which optionally has a substituent, $C_{1-6}$ alkoxy, $C_{3-6}$ cycloalkyl, 4- to 6-membered heterocyclyl which optionally has oxo as a substituent, $C_{1-6}$ alkylcarbonyl, $C_{1-6}$ alkylsulfonyl, $C_{3-6}$ cycloalkylsulfonyl, $C_{1-6}$ alkyloxycarbonyl, amino-$C_{1-6}$ alkylcarbonyl, oxo, thioxo, hydroxy, or —$NR^{52}R^{53}$;

where the substituent in the $C_{1-6}$ alkyl which optionally has a substituent selected from a halogen atom, hydroxy, 5- to 10-membered heteroaryl, and $C_{6-10}$ aryl, where the $C_{6-10}$ aryl optionally has hydroxy as a substituent;

$R^{52}$ and $R^{53}$ each independently represents a hydrogen atom, $C_{1-6}$ alkyl, $C_{1-6}$ alkylsulfonyl which may have optionally has a halogen atom as a substituent, $C_{6-10}$ arylsulfonyl, $C_{6-10}$ aryl-$C_{1-6}$ alkylsulfonyl, or —C(O)$OR^{54}$, $R^{54}$ represents $C_{1-6}$ alkyl which optionally has a group selected from phenyl, fluorene, and 5- to 10-membered heteroaryl as a substituent; and Group R is a halogen atom, $C_{1-6}$ alkyl, $C_{1-6}$ alkoxy, $C_{1-6}$ haloalkyl, $C_{2-6}$ alkenyl, $C_{2-6}$ alkynyl, $C_{3-6}$ cycloalkyl, nitro, or —$NR^{60}R^{61}$ {where $R^{60}$ and $R^{61}$ are identical or different, and are each a hydrogen atom, optionally substituted $C_{1-6}$ alkyl (in which the substituent is hydroxy, $C_{1-6}$ alkoxycarbonyl, carboxyl, or carboxamide), or amino-$C_{1-6}$ alkyl; or alternatively, $R^{60}$ and $R^{61}$, together with the nitrogen atom to which they are bonded, form a 4- to 6-membered heterocycle}, or a pharmaceutically acceptable salt thereof.

2. The compound or a pharmaceutically acceptable salt thereof according to claim 1, wherein Group R in $Ar^1$ is selected from the group consisting of a halogen atom, $C_{1-6}$ alkyl, and $C_{1-6}$ alkoxy.

3. The compound or a pharmaceutically acceptable salt thereof according to claim 1, wherein Group R in $Ar^2$ is selected from the group consisting of a halogen atom, $C_{1-6}$ alkyl, and $C_{1-6}$ alkoxy.

4. The compound or a pharmaceutically acceptable salt thereof according to claim 1, wherein $Ar^1$ is phenylene or pyridylene optionally substituted with a group selected from Group R.

5. The compound or a pharmaceutically acceptable salt thereof according to claim 1, wherein $Ar^2$ is phenyl or pyridyl optionally substituted with a group selected from Group R.

6. The compound or a pharmaceutically acceptable salt thereof according to claim 1, wherein $R^1$ is a halogen atom, $C_{1-6}$ alkyl, $C_{3-6}$ cycloalkyl, $NR^5R^6$, $OR^7$, $SR^8$, or 4- to 6-membered heterocyclyl optionally substituted with $C_{1-6}$ alkyl;

$R^5$ and $R^6$ are each independently a hydrogen atom, $C_{1-6}$ alkyl optionally substituted with 4- to 6-membered heterocyclyl, or —$SO_2R^{30}$;

$R^7$ is a hydrogen atom, $C_{1-6}$ alkyl which optionally has a halogen atom or hydroxy as a substituent, 4- to 6-membered heterocyclyl optionally substituted with a group selected from Group Q, or $C_{1-6}$ alkyl having 4- to 10-membered heterocyclyl optionally substituted with a group selected from Group Q as a substituent;

Group Q is $C_{1-6}$ alkyl which optionally has hydroxy as a substituent, $C_{3-6}$ cycloalkyl, 4- to 6-membered heterocyclyl which optionally has oxo as a substituent, and or $C_{1-6}$ alkylsulfonyl;

$R^8$ is halo-$C_{1-6}$ alkyl; and $R^{30}$ is $C_{1-6}$ alkyl.

7. The compound or a pharmaceutically acceptable salt thereof according to claim 1, wherein $R^2$ is a halogen atom, $C_{1-6}$ alkyl, $NR^5R^6$, $OR^7$, 4- to 6-membered heterocyclyl optionally substituted with a group selected from Group Q, 5- to 10-membered heteroaryl optionally substituted with a group selected from Group Q, or $C_{6-10}$ aryl optionally substituted with a group selected from Group P, where the 4- to 6-membered heterocyclyl optionally substituted with a group selected from Group Q is optionally further linked to 4- to 6-membered heterocyclyl optionally substituted with a group selected from 4- to 6-membered heterocyclyl and $C_{6-10}$ aryl-$C_{1-6}$ alkyl, or to $C_{3-6}$ cycloalkyl through a spiro linkage;

$R^5$ and $R^6$ are each independently a hydrogen atom, $C_{1-6}$ alkyl optionally substituted with 4- to 6-membered heterocyclyl, $C_{1-6}$ alkylcarbonyl optionally substituted with a halogen atom, —$SO_2R^{30}$, —$C(O)OR^{31}$, —$C(O)NR^{32}R^{33}$, or 4- to 6-membered heterocyclyl optionally substituted with a group selected from Group Q;

$R^7$ is a hydrogen atom, $C_{1-6}$ alkyl, or $C_{1-6}$ alkyl having 4- to 6-membered heterocyclyl as a substituent;

$R^{30}$ is optionally substituted $C_{1-6}$ alkyl, $C_{3-6}$ cycloalkyl which optionally has dihydroxy-$C_{1-6}$ alkyl as a substituent, $C_{6-10}$ aryl optionally substituted with a group selected from Group P, 5- to 10-membered heterocyclyl optionally substituted with a group selected from Group Q, 5- to 10-membered heteroaryl optionally substituted with a group selected from Group Q, or —$NR^{34}R^{35}$, where the substituent in the optionally substituted $C_{1-6}$ alkyl is selected from the group consisting of a halogen atom, 4- to 6-membered heterocyclyl optionally substituted with a group selected from Group Q, —$C(O)NR^{36}R^{37}$, and $C_{6-10}$ aryl;

$R^{31}$ represents $C_{1-6}$ alkyl which optionally has fluorene as a substituent;

$R^{32}$ and $R^{33}$ are each independently a hydrogen atom, or $C_{1-6}$ alkyl optionally substituted with a group selected from the group consisting of $C_{1-6}$ alkoxycarbonyl and 5- to 10-membered heteroaryl; or alternatively, $R^{32}$ and $R^{33}$, together with the nitrogen atom to which they are bonded, form 4- to 6-membered heterocyclyl;

$R^{34}$ and $R^{35}$ are each independently a hydrogen atom, $C_{1-6}$ alkyl optionally substituted with a group selected from hydroxy and $C_{1-6}$ alkoxy, 4- to 6-membered heterocyclyl optionally substituted with a group selected from Group Q, $C_{3-6}$ cycloalkyl, or $C_{1-6}$ alkoxy;

$R^{36}$ and $R^{37}$ are each independently a hydrogen atom or $C_{1-6}$ alkyl; or alternatively, $R^{36}$ and $R^{37}$, together with the nitrogen atom to which they are bonded, form 4- to 6-membered heterocyclyl optionally substituted with a substituent selected from Group Q;

Group P is a halogen atom, cyano, $C_{1-6}$ alkyl, $C_{1-6}$ alkoxy, or $C_{1-6}$ haloalkyl;

Group Q is cyano, a halogen atom, $C_{1-6}$ alkyl which optionally has a substituent, $C_{1-6}$ alkoxy, 4- to 6-membered heterocyclyl, $C_{1-6}$ alkylcarbonyl, $C_{1-6}$ alkylsulfonyl, $C_{3-6}$ cycloalkylsulfonyl, $C_{1-6}$ alkyloxycarbonyl, amino-$C_{1-6}$ alkylcarbonyl, oxo, thioxo, hydroxy, or —$NR^{52}R^{53}$;

where the substituent in the $C_{1-6}$ alkyl which optionally has a substituent is selected from a halogen atom, hydroxy, 5- to 10-membered heteroaryl, and $C_{6-10}$ aryl group, where the $C_{6-10}$ aryl group optionally has hydroxy as a substituent;

$R^{52}$ and $R^{53}$ each independently represents a hydrogen atom, $C_{1-6}$ alkyl, $C_{1-6}$ alkylsulfonyl which optionally has a halogen atom as a substituent, $C_{6-10}$ arylsulfonyl, $C_{6-10}$ aryl-$C_{1-6}$ alkylsulfonyl, or —$C(O)OR^{54}$, and $R^{54}$ represents $C_{1-6}$ alkyl which optionally has a group selected from phenyl, fluorene, and 5- to 10-membered heteroaryl as a substituent.

8. A pharmacological composition comprising the compound or a pharmaceutically acceptable salt thereof according to claim 1, and a carrier.

9. A method of inhibiting a Src family kinase comprising administering an effective amount of a composition comprising the compound or a pharmaceutically acceptable salt thereof according to claim 1 to a patient in need thereof.

10. A method for treating cancer, comprising administering a pharmaceutically effective amount of a composition comprising the compound or a pharmaceutically acceptable salt thereof according to claim 1 to a patient in need of cancer treatment,
wherein the cancer is selected from the group consisting of esophageal cancer, lung cancer, and bile duct cancer.

11. A method of manufacturing a pharmaceutical composition comprising a compound or a pharmaceutically acceptable salt thereof according to claim 1, comprising:
mixing said compound or a pharmaceutically acceptable salt thereof with a carrier.

12. The method of claim 10, wherein the cancer is esophageal cancer.

13. The method of claim 10, wherein the cancer is lung cancer.

14. The method of claim 10, wherein the cancer is bile duct cancer.

15. The compound or a pharmaceutically acceptable salt thereof according to claim 1, wherein the compound or a pharmaceutically acceptable salt thereof is selected from the group consisting of:

(4-1-001) N-[2-[5-amino-1-[6-(2,6-difluorophenoxy)-4-methylpyridin-3-yl]pyrazole-4-carbonyl]-5-methyl-1H-indol-6-yl]methanesulfonamide, (4-1-002) N-[2-[5-amino-1-[4-(2-fluorophenoxy)-2-methylphenyl]pyrazole-4-carbonyl]-5-fluoro-1H-indol-6-yl]methanesulfonamide, (4-1-003) N-[2-[5-amino-1-(2-chloro-4-pyridin-2-yloxyphenyl)pyrazole-4-carbonyl]-5-fluoro-1H-indol-6-yl]methanesulfonamide, (4-1-004) N-[2-[5-amino-1-[4-(2-fluorophenoxy)-2-methylphenyl]pyrazole-4-carbonyl]-5-methoxy-1H-indol-6-yl]methanesulfonamide, (4-1-005) N-[2-[5-amino-1-[4-(2,3-difluorophenoxy)-2-methylphenyl]pyrazole-4-carbonyl]-5-methoxy-1H-indol-6-yl]methanesulfonamide, (4-1-006) N-[2-[5-amino-1-[2-fluoro-4-(2-fluorophenoxy)-6-methylphenyl]pyrazole-4-carbonyl]-5-methoxy-1H-indol-6-yl]methanesulfonamide, (4-1-007) N-[2-[5-amino-1-(2-fluoro-6-methyl-4-phenoxyphenyl)pyrazole-4-carbonyl]-5-methoxy-1H-indol-6-yl]methanesulfonamide, (4-1-008) N-[2-[5-amino-1-[6-(2-fluorophenoxy)-4-methylpyridin-3-yl]pyrazole-4-carbonyl]-5-methoxy-1H-indol-6-yl]methanesulfonamide, (4-1-009) N-[2-[5-amino-1-[6-(2,6-difluorophenoxy)-4-methylpyridin-3-yl]pyrazole-4-carbonyl]-5-methoxy-1H-indol-6-yl]methanesulfonamide, (4-1-010) N-[2-[5-amino-1-[6-(2-chlorophenoxy)-4-methylpyridin-3-yl]pyrazole-4-carbonyl]-5-methoxy-1H-indol-6-yl]methanesulfonamide, (4-1-011) N-[2-[5-amino-1-[6-(3-chlorophenoxy)-4-methylpyridin-3-yl]pyrazole-4-carbonyl]-5-methoxy-1H-indol-6-yl]methanesulfonamide, (4-1-012) tert-butyl 4-[2-[5-amino-1-[6-(2,6-difluorophenoxy)-4-methylpyridin-3-yl]pyrazole-4-carbonyl]-5-(difluoromethoxy)-1H-indol-6-yl]piperidine-1-carboxylate, (4-1-013) N-[2-[5-amino-1-[4-(2-fluorophenoxy)-2-methylphenyl]pyrazole-4-carbonyl]-6-methoxy-1H-indol-5-yl]methanesulfonamide, (4-1-014) N-[2-[5-amino-1-[6-(2-fluorophenoxy)-4-methylpyridin-3-yl]pyrazole-4-carbonyl]-6-methoxy-1H-indol-5-yl]methanesulfonamide, (4-1-015) [5-amino-1-[4-(2-fluorophenoxy)-2-methylphenyl]pyrazol-4-yl]-[5-(2,2-difluoroethoxy)-6-morpholin-4-yl-1H-indol-2-yl]methanone, (4-1-016) [5-amino-1-[6-(2,6-difluorophenoxy)-4-methylpyridin-3-yl]pyrazol-4-yl]-[5-(2,2-difluoroethoxy)-6-morpholin-4-yl-1H-indol-2-yl]methanone, (4-1-017) N-[2-[5-amino-1-[6-(2,6-difluorophenoxy)-4-methylpyridin-3-yl]pyrazole-4-carbonyl]-5-methyl-1H-indol-6-yl]cyclopropanesulfonamide, (4-2-001) [5-amino-1-[4-(2-fluorophenoxy)-2-methylphenyl]pyrazol-4-yl]-[6-fluoro-5-(1-propan-2-ylpiperidin-4-yl)-1H-indol-2-yl]methanone, (4-2-002) [5-amino-1-[4-(2,3-difluorophenoxy)-2-methylphenyl]pyrazol-4-yl]-[6-fluoro-5-(1-propan-2-ylpiperidin-4-yl)-1H-indol-2-yl]methanone, (4-2-003) [5-amino-1-[4-(3-chlorophenoxy)-2-methylphenyl]pyrazol-4-yl]-[6-fluoro-5-(1-propan-2-ylpiperidin-4-yl)-1H-indol-2-yl]methanone, (4-2-004) [5-amino-1-[4-(2,3-difluorophenoxy)phenyl]pyrazol-4-yl]-[6-fluoro-5-(1-propan-2-ylpiperidin-4-yl)-1H-indol-2-yl]methanone, (4-2-005) [5-amino-1-[4-(3-chlorophenoxy)phenyl]pyrazol-4-yl]-[6-fluoro-5-(1-propan-2-ylpiperidin-4-yl)-1H-indol-2-yl]methanone, (4-2-006) [5-amino-1-[4-(3-fluorophenoxy)phenyl]pyrazol-4-yl]-[6-fluoro-5-(1-propan-2-ylpiperidin-4-yl)-1H-indol-2-yl]methanone, (4-2-007) [5-amino-1-[4-(2,3-difluorophenoxy)-2-fluorophenyl]pyrazol-4-yl]-[6-fluoro-5-(1-propan-2-ylpiperidin-4-yl)-1H-indol-2-yl]methanone, (4-2-008) [5-amino-1-[4-(2-chlorophenoxy)-2-fluorophenyl]pyrazol-4-yl]-[6-fluoro-5-(1-propan-2-ylpiperidin-4-yl)-1H-indol-2-yl]methanone, (4-2-009) [5-amino-1-[2-fluoro-4-(2-fluorophenoxy)phenyl]pyrazol-4-yl]-[6-fluoro-5-(1-propan-2-ylpiperidin-4-yl)-1H-indol-2-yl]methanone, (4-2-010) [5-amino-1-[4-(2-fluorophenoxy)-2-methylphenyl]pyrazol-4-yl]-[5-fluoro-6-(1-propan-2-ylpiperidin-4-yl)-1H-indol-2-yl]methanone, (4-2-011) [5-amino-1-[4-(2,3-difluorophenoxy)-2-methylphenyl]pyrazol-4-yl]-[5-fluoro-6-(1-propan-2-ylpiperidin-4-yl)-1H-indol-2-yl]methanone, (4-2-012) [5-amino-1-[4-(2-chlorophenoxy)-2-methylphenyl]pyrazol-4-yl]-[5-fluoro-6-(1-propan-2-ylpiperidin-4-yl)-1H-indol-2-yl]methanone, (4-2-013) [5-amino-1-[4-(3-chlorophenoxy)-2-methylphenyl]pyrazol-4-yl]-[5-fluoro-6-(1-propan-2-ylpiperidin-4-yl)-1H-indol-2-yl]methanone, (4-2-014) [5-amino-1-[4-(2-fluorophenoxy)-3-methylphenyl]pyrazol-4-yl]-[5-fluoro-6-(1-propan-2-ylpiperidin-4-yl)-1H-indol-2-yl]methanone, (4-2-015) N-[2-[5-amino-1-[4-(2-fluorophenoxy)-2-methylphenyl]pyrazole-4-carbonyl]-5-fluoro-1H-indol-6-yl]-3-fluoropropane-1-sulfonamide, (4-2-016) N-[2-[5-amino-1-[4-(2,3-difluorophenoxy)-2-methylphenyl]pyrazole-4-carbonyl]-5-fluoro-1H-indol-6-yl]-3-fluoropropane-1-sulfonamide, (4-2-017) N-[2-[5-amino-1-(2-methyl-4-pyridin-2-yloxyphenyl)pyrazole-4-carbonyl]-5-fluoro-1H-indol-6-yl]-3-fluoropropane-1-sulfonamide, (4-2-018) N-[2-[5-amino-1-(2-chloro-4-pyridin-2-yloxyphenyl)pyrazole-4-carbonyl]-5-fluoro-1H-indol-6-yl]-3-fluoropropane-1-sulfonamide, (4-2-019) N-[2-[5-amino-1-[2-fluoro-4-(2-fluorophenoxy)-6-methylphenyl]pyrazole-4-carbonyl]-5-fluoro-1H-indol-6-yl]-3-fluoropropane-1-sulfonamide, (4-2-020) N-[2-[5-amino-1-[6-(2-fluorophenoxy)-4-methylpyridin-3-yl]pyrazole-4-carbonyl]-5-fluoro-1H-indol-6-yl]-3-fluoropropane-1-sulfonamide, (4-2-021) N-[2-[5-amino-1-[6-(2,6-difluorophenoxy)-4-methylpyridin-3-yl]pyrazole-4-carbonyl]-5-fluoro-1H-indol-6-yl]-3-fluoropropane-1-sulfonamide, (4-2-022) N-[2-[5-amino-1-[6-(2,3-difluorophenoxy)-4-methylpyridin-3-yl]pyrazole-4-carbonyl]-5-fluoro-1H-indol-6-yl]-3-fluoropropane-1-sulfonamide, (4-2-023) N-[2-[5-amino-1-[6-(2-chlorophenoxy)-4-methylpyridin-3-yl]pyrazole-4-carbonyl]-5-fluoro-1H-indol-6-yl]-3-fluoropropane-1-sulfonamide, (4-2-024) N-[2-[5-amino-1-[6-(2-chloro-6-fluorophenoxy)-4-methylpyridin-3-yl]pyrazole-4-carbonyl]-5-fluoro-1H-indol-6-yl]-3-fluoropropane-1-sulfonamide, (4-2-025) N-[2-[5-amino-1-[4-methyl-6-(2-methylphenoxy)pyridin-3-yl]pyrazole-4-carbonyl]-5-fluoro-1H-indol-6-yl]-3-fluoropropane-1-sulfonamide, (4-2-026) N-[2-[5-amino-1-[6-(3-chlorophenoxy)-4-methylpyridin-3-yl]pyrazole-4-carbonyl]-5-fluoro-1H-indol-6-yl]-3-fluoropropane-1-sulfonamide, (4-2-027) N-[2-[5-amino-1-[6-(4-fluorophenoxy)-4-methylpyridin-3-yl]pyrazole-4-carbonyl]-5-fluoro-1H-indol-6-yl]-3-fluoropropane-1-sulfonamide, (4-2-028) N-[2-[5-amino-1-[6-(3,5-difluorophenoxy)-4-methylpyridin-3-yl]pyrazole-4-carbonyl]-5-fluoro-1H-indol-6-yl]-3-fluoropropane-1-sulfonamide, (4-2-029) N-[2-[5-amino-1-[4-(2,3-difluorophenoxy)-2-methylphenyl]pyrazole-4-carbonyl]-5-fluoro-1H-indol-6-yl]methanesulfonamide, (4-2-030) N-[2-[5-amino-1-[6-(2,5-difluorophenoxy)-4-methylpyridin-3-yl]pyrazole-4-carbonyl]-5-fluoro-1H-indol-6-yl]methanesulfonamide, (4-2-031) N-[2-[5-amino-1-[6-(2,6-difluorophenoxy)-4-methylpyridin-3-yl]pyrazole-4-carbonyl]-5-fluoro-1H-indol-6-yl]methanesulfonamide, (4-2-032) N-[2-[5-amino-1-[6-(2,3-difluorophenoxy)-4-methylpyridin-3-yl]pyrazole-4-carbonyl]-5-fluoro-1H-indol-6-yl]methanesulfonamide, (4-2-033) N-[2-[5-amino-1-[6-(2-chlorophenoxy)-4-methylpyridin-3-yl]pyrazole-4-carbonyl]-5-fluoro-1H-indol-6-yl]methanesulfonamide, (4-2-034) N-[2-[5-amino-1-[6-(2-chloro-5-fluorophenoxy)-4-methylpyridin-3-yl]pyrazole-4-carbonyl]-5-fluoro-1H-indol-6-yl]methanesulfonamide, (4-2-035) N-[2-[5-amino-1-[6-(2-chloro-6-fluorophenoxy)-4-methylpyridin-3-yl]pyrazole-4-carbonyl]-5-fluoro-1H-indol-6-yl]methanesulfonamide, (4-2-036) N-[2-[5-amino-1-[4-methyl-6-(2-methylphenoxy)pyridin-3-yl]pyrazole-4-carbonyl]-5-fluoro-1H-indol-6-yl]methanesulfonamide, (4-2-037) N-[2-[5-amino-1-[6-(3-chlorophenoxy)-4-methylpyridin-3-yl]pyrazole-4-carbonyl]-5-fluoro-1H-indol-6-yl]methanesulfonamide, (4-2-038) N-[2-[5-amino-1-[6-(3-fluorophenoxy)-4-methylpyridin-3-yl]pyrazole-4-carbonyl]-5-fluoro-1H-indol-6-yl]methanesulfonamide, (4-2-039) N-[2-[5-amino-1-[6-(4-fluorophenoxy)-4-methylpyridin-3-yl]pyrazole-4-carbonyl]-5-fluoro-1H-indol-6-yl]methanesulfonamide, (4-2-040) N-[2-[5-amino-1-[4-(2-fluorophenoxy)-2-methylphenyl]pyrazole-4-carbonyl]-5-fluoro-1H-indol-6-yl]cyclopropanesulfonamide, (4-2-041) N-[2-[5-amino-1-[4-(2,3-difluorophenoxy)-2-methylphenyl]pyrazole-4-carbonyl]-5-fluoro-1H-indol-6-yl]cyclopropanesulfonamide, (4-2-042) N-[2-[5-amino-1-[4-(2-fluorophenoxy)-2,6-dimethylphenyl]pyrazole-4-carbonyl]-5-fluoro-1H-indol-6-yl]cyclopropanesulfonamide, (4-2-043) N-[2-[5-amino-1-[6-(2-fluorophenoxy)-4-methylpyridin-3-yl]pyrazole-4-carbonyl]-5-fluoro-1H-indol-6-yl]cyclopropanesulfonamide, (4-2-044) N-[2-[5-amino-1-[6-(2,6-difluorophenoxy)-4-methylpyridin-3-yl]pyrazole-4-carbonyl]-5-fluoro-1H-indol-6-yl]cyclopropanesulfonamide, (4-2-045) N-[2-[5-amino-1-[6-(2,3-difluorophenoxy)-4-methylpyridin-3-yl]pyrazole-4-carbonyl]-5-fluoro-1H-indol-6-yl]cyclopropanesulfonamide, (4-2-046) N-[2-[5-amino-1-[6-(2-chloro-6-fluorophenoxy)-4-methylpyridin-3-yl]pyrazole-4-carbonyl]-5-fluoro-1H-indol-6-yl]cyclopropanesulfonamide, (4-2-047) N-[2-[5-amino-1-[4-methyl-6-(2-methylphenoxy)pyridin-3-yl]pyrazole-4-carbonyl]-5-fluoro-1H-indol-6-yl]cyclopropanesulfonamide, (4-2-048) N-[2-[5-amino-1-[6-(3-fluorophenoxy)-4-methylpyridin-3-yl]pyrazole-4-carbonyl]-5-fluoro-1H-indol-6-yl]cyclopropanesulfonamide, (4-2-049) N-[2-[5-amino-1-[4-(2-fluorophenoxy)-2-methylphenyl]pyrazole-4-carbonyl]-6-methyl-1H-indol-5-yl]methanesulfonamide, (4-2-050) N-[2-[5-amino-1-[4-(2,3-difluorophenoxy)-2-methylphenyl]pyrazole-4-carbonyl]-6-methyl-1H-indol-5-yl]methanesulfonamide, (4-2-051) N-[2-[5-amino-1-[2-fluoro-4-(2-fluorophenoxy)-6-methylphenyl]pyrazole-4-carbonyl]-6-methyl-1H-indol-5-yl]methanesulfonamide, (4-2-052) N-[2-[5-amino-1-[6-(2-fluorophenoxy)-4-methylpyridin-3-yl]pyrazole-4-carbonyl]-6-methyl-1H-indol-5-yl]methanesulfonamide, (4-2-053) N-[2-[5-amino-1-[4-(2-fluorophenoxy)-2-methylphenyl]pyrazole-4-carbonyl]-5-methyl-1H-indol-6-yl]methanesulfonamide, (4-2-054) N-[2-[5-amino-1-[4-(2,3-difluorophenoxy)-2-methylphenyl]pyrazole-4-carbonyl]-5-methyl-1H-indol-6-yl]methanesulfonamide, (4-2-055) N-[2-[5-amino-1-[2-fluoro-4-(2-fluorophenoxy)-6-methylphenyl]pyrazole-4-carbonyl]-5-methyl-1H-indol-6-yl]methanesulfonamide, (4-2-056) N-[2-[5-amino-1-[4-(2,3-difluorophenoxy)-2-fluoro-6-methylphenyl]pyrazole-4-carbonyl]-5-methyl-1H-indol-6-yl]methanesulfonamide, (4-2-057) N-[2-[5-amino-1-[4-(2,5-difluorophenoxy)-2-fluoro-6-methylphenyl]pyrazole-4-carbonyl]-5-methyl-1H-indol-6-yl]methanesulfonamide, (4-2-058) N-[2-[5-amino-1-[4-(2-chlorophenoxy)-2-fluoro-6-methylphenyl]pyrazole-4-carbonyl]-5-methyl-1H-indol-6-yl]methanesulfonamide, (4-2-059) N-[2-[5-amino-1-[4-(3-chlorophenoxy)-2-fluoro-6-methylphenyl]pyrazole-4-carbonyl]-5-methyl-1H-indol-6-yl]methanesulfonamide, (4-2-060) N-[2-[5-amino-1-(2-fluoro-6-methyl-4-phenoxyphenyl)pyrazole-4-carbonyl]-5-methyl-1H-indol-6-yl]methanesulfonamide, (4-2-061) N-[2-[5-amino-1-[6-(2-fluorophenoxy)-4-methylpyridin-3-yl]pyrazole-4-carbonyl]-5-methyl-1H-indol-6-yl]methanesulfonamide, (4-2-062) N-[2-[5-amino-1-[6-(2,3-difluorophenoxy)-4-methylpyridin-3-yl]pyrazole-4-carbonyl]-5-methyl-1H-indol-6-yl]methanesulfonamide, (4-2-063) N-[2-[5-amino-1-[6-(2-chlorophenoxy)-4-methylpyridin-3-yl]pyrazole-4-carbonyl]-5-methyl-1H-indol-6-yl]methanesulfonamide, (4-2-064) N-[2-[5-amino-1-[6-(2-chloro-6-fluorophenoxy)-4-methylpyridin-3-yl]pyrazole-4-carbonyl]-5-methyl-1H-indol-6-yl]methanesulfonamide, (4-2-065) N-[2-[5-amino-1-[4-methyl-6-(2-methylphenoxy)pyridin-3-yl]pyrazole-4-carbonyl]-5-methyl-1H-indol-6-yl]methanesulfonamide, (4-2-066) N-[2-[5-amino-1-[6-(3-chlorophenoxy)-4-methylpyridin-3-yl]pyrazole-4-carbonyl]-5-methyl-1H-indol-6-yl]methanesulfonamide, (4-2-067) N-[2-[5-amino-1-[6-(4-fluorophenoxy)-4-methylpyridin-3-yl]pyrazole-4-carbonyl]-5-methyl-1H-indol-6-yl]methanesulfonamide, (4-2-068) N-[2-[5-amino-1-[4-(2-fluorophenoxy)-2-methylphenyl]pyrazole-4-carbonyl]-5-methyl-1H-indol-6-yl]-3-fluoropropane-1-sulfonamide, (4-2-069) N-[2-[5-amino-1-[4-(2,3-difluorophenoxy)-2-methylphenyl]pyrazole-4-carbonyl]-5-methyl-1H-indol-6-yl]-3-fluoropropane-1-sulfonamide, (4-2-070) N-[2-[5-amino-1-[2-fluoro-4-(2-fluorophenoxy)-6-methylphenyl]pyrazole-4-carbonyl]-5-methyl-1H-indol-6-yl]-3-fluoropropane-1-sulfonamide, (4-2-071) N-[2-[5-amino-1-[4-(2,3-difluorophenoxy)-2-fluoro-6-methylphenyl]pyrazole-4-carbonyl]-5-methyl-1H-indol-6-yl]-3-fluoropropane-1-sulfonamide, (4-2-072) N-[2-[5-amino-1-[6-(2-fluorophenoxy)-4-methylpyridin-3-yl]pyrazole-4-carbonyl]-5-methyl-1H-indol-6-yl]-3-fluoropropane-1-sulfonamide, (4-2-073) N-[2-[5-amino-1-[6-(2,6-difluorophenoxy)-4-methylpyridin-3-yl]pyrazole-4-carbonyl]-5-methyl-1H-indol-6-yl]-3-fluoropropane-1-sulfonamide, (4-2-074) N-[2-[5-amino-1-[6-(2-chlorophenoxy)-4-methylpyridin-3-yl]pyrazole-4-carbonyl]-5-methyl-1H-indol-6-yl]-3-fluoropropane-1-sulfonamide, (4-2-075) N-[2-[5-amino-1-[6-(3-chlorophenoxy)-4-methylpyridin-3-yl]pyrazole-4-carbonyl]-5-methyl-1H-indol-6-yl]-3-fluoropropane-1-sulfonamide, (4-2-076) N-[2-[5-amino-1-[6-(4-fluorophenoxy)-4-methylpyridin-3-yl]pyrazole-4-carbonyl]-5-methyl-1H-indol-6-yl]-3-fluoropropane-1-sulfonamide, (4-2-077) N-[2-[5-amino-1-[4-(2-fluorophenoxy)-2-methylphenyl]pyrazole-4-carbonyl]-5-chloro-1H-indol-6-yl]methanesulfonamide, (4-2-078) N-[2-[5-amino-1-[4-(2,3-difluorophenoxy)-2-methylphenyl]pyrazole-4-carbonyl]-5-chloro-1H-indol-6-yl]methanesulfonamide, (4-2-079) N-[2-[5-amino-1-[2-fluoro-4-(2-fluorophenoxy)-6-methylphenyl]pyrazole-4-carbonyl]-5-chloro-1H-indol-6-yl]methanesulfonamide, (4-2-080) N-[2-[5-amino-1-[4-(2,3-difluorophenoxy)-2-fluoro-6-methylphenyl]pyrazole-4-carbonyl]-5-chloro-1H-indol-6-yl]methanesulfonamide, (4-2-081) N-[2-[5-amino-1-[4-(2,5-difluorophenoxy)-2-fluoro-6-methylphenyl]pyrazole-4-carbonyl]-5-chloro-1H-indol-6-yl]methanesulfonamide, (4-2-082) N-[2-[5-amino-1-[4-(2-chlorophenoxy)-2-fluoro-6-methylphenyl]pyrazole-4-carbonyl]-5-chloro-1H-indol-6-yl]methanesulfonamide, (4-2-083) N-[2-[5-amino-1-[4-(3-chlorophenoxy)-2-fluoro-6-methylphenyl]pyrazole-4-carbonyl]-5-chloro-1H-indol-6-yl]methanesulfonamide, (4-2-084) N-[2-[5-amino-1-(2-fluoro-6-methyl-4-phenoxyphenyl)pyrazole-4-carbonyl]-5-chloro-1H-indol-6-yl]methanesulfonamide, (4-2-085) N-[2-[5-amino-1-[6-(2-fluorophenoxy)-4-methylpyridin-3-yl]pyrazole-4-carbonyl]-5-chloro-1H-indol-6-yl]methanesulfonamide, (4-2-086) N-[2-[5-amino-1-[6-(2,6-difluorophenoxy)-4-methylpyridin-3-yl]pyrazole-4-carbonyl]-5-chloro-1H-indol-6-yl]methanesulfonamide, (4-2-087) N-[2-[5-amino-1-[6-(2,3-difluorophenoxy)-4-methylpyridin-3-yl]pyrazole-4-carbonyl]-5-chloro-1H-indol-6-yl]methanesulfonamide, (4-2-088) N-[2-[5-amino-1-[6-(2-chlorophenoxy)-4-methylpyridin-3-yl]pyrazole-4-carbonyl]-5-chloro-1H-indol-6-yl]methanesulfonamide, (4-2-089) N-[2-[5-amino-1-[6-(2-chloro-6-fluorophenoxy)-4-methylpyridin-3-yl]pyrazole-4-carbonyl]-5-chloro-1H-indol-6-yl]methanesulfonamide, (4-2-090) N-[2-[5-amino-1-[4-methyl-6-(2-methylphenoxy)pyridin-3-yl]pyrazole-4-carbonyl]-5-chloro-1H-indol-6-yl]methanesulfonamide, (4-2-091) N-[2-[5-amino-1-[6-(3-chlorophenoxy)-4-methylpyridin-3-yl]pyrazole-4-carbonyl]-5-chloro-1H-indol-6-yl]methanesulfonamide, (4-2-092) N-[2-[5-amino-1-[6-(4-fluorophenoxy)-4-methylpyridin-3-yl]pyrazole-4-carbonyl]-5-chloro-1H-indol-6-yl]methanesulfonamide, (4-2-093) N-[2-[5-amino-1-[2-fluoro-4-(2-fluorophenoxy)-6-methylphenyl]pyrazole-4-carbonyl]-6-chloro-1H-indol-5-yl]methanesulfonamide, (4-2-094) N-[2-[5-amino-1-[4-(2,3-difluorophenoxy)-2-fluoro-6-methylphenyl]pyrazole-4-carbonyl]-6-chloro-1H-indol-5-yl]methanesulfonamide, (4-2-095) N-[2-[5-amino-1-(2-fluoro-6-methyl-4-phenoxyphenyl)pyrazole-4-carbonyl]-6-chloro-1H-indol-5-yl]methanesulfonamide, (4-2-096) N-[2-[5-amino-1-[6-(2-fluorophenoxy)-4-methylpyridin-3-yl]pyrazole-4-carbonyl]-6-chloro-1H-indol-5-yl]methanesulfonamide, (4-2-097) N-[2-[5-amino-1-[4-(2-fluorophenoxy)-2-methylphenyl]pyrazole-4-carbonyl]-6-fluoro-1H-indol-5-yl]methanesulfonamide, (4-2-098) N-[2-[5-amino-1-[4-(2,3-difluorophenoxy)-2-methylphenyl]pyrazole-4-carbonyl]-6-fluoro-1H-indol-5-yl]methanesulfonamide, (4-2-099) N-[2-[5-amino-1-[2-fluoro-4-(2-fluorophenoxy)-6-methylphenyl]pyrazole-4-carbonyl]-6-fluoro-1H-indol-5-yl]methanesulfonamide, (4-2-100) N-[2-[5-amino-1-[4-(2,3-difluorophenoxy)-2-fluoro-6-methylphenyl]pyrazole-4-carbonyl]-6-fluoro-1H-indol-5-yl]methanesulfonamide, (4-2-101) N-[2-[5-amino-1-[4-(2,5-difluorophenoxy)-2-fluoro-6-methylphenyl]pyrazole-4-carbonyl]-6-fluoro-1H-indol-5-yl]methanesulfonamide, (4-2-102) N-[2-[5-amino-1-[4-(2-chlorophenoxy)-2-fluoro-6-methylphenyl]pyrazole-4-carbonyl]-6-fluoro-1H-indol-5-yl]methanesulfonamide, (4-2-103) N-[2-[5-amino-1-(2-fluoro-6-methyl-4-phenoxyphenyl)pyrazole-4-carbonyl]-6-fluoro-1H-indol-5-yl]methanesulfonamide, (4-2-104) N-[2-[5-amino-1-[6-(2-fluorophenoxy)-4-methylpyridin-3-yl]pyrazole-4-carbonyl]-6-fluoro-1H-indol-5-yl]methanesulfonamide, (4-2-105) N-[2-[5-amino-1-[4-(2-fluorophenoxy)-2-methylphenyl]pyrazole-4-carbonyl]-5-methyl-1H-indol-6-yl]morpholine-4-sulfonamide, (4-2-106) N-[2-[5-amino-1-[4-(2,3-difluorophenoxy)-2-methylphenyl]pyrazole-4-carbonyl]-5-methyl-1H-indol-6-yl]morpholine-4-sulfonamide, (4-2-107) N-[2-[5-amino-1-[2-fluoro-4-(2-fluorophenoxy)-6-methylphenyl]pyrazole-4-carbonyl]-5-methyl-1H-indol-6-yl]morpholine-4-sulfonamide, (4-2-108) N-[2-[5-amino-1-[6-(2-fluorophenoxy)-4-methylpyridin-3-yl]pyrazole-4-carbonyl]-5-methyl-1H-indol-6-yl]morpholine-4-sulfonamide, (4-2-109) N-[2-[5-amino-1-[6-(2,6-difluorophenoxy)-4-methylpyridin-3-yl]pyrazole-4-carbonyl]-5-methyl-1H-indol-6-yl]morpholine-4-sulfonamide, (4-2-110) N-[2-[5-amino-1-[6-(2-chlorophenoxy)-4-methylpyridin-3-yl]pyrazole-4-carbonyl]-5-methyl-1H-indol-6-yl]morpholine-4-sulfonamide, (4-2-111) N-[2-[5-amino-1-[6-(3-chlorophenoxy)-4-methylpyridin-3-yl]pyrazole-4-carbonyl]-5-methyl-1H-indol-6-yl]morpholine-4-sulfonamide, (4-2-112) [5-amino-1-[4-(2-fluorophenoxy)-2-methylphenyl]pyrazol-4-yl]-[6-(1,1-dioxo-1,2-thiazolidin-2-yl)-5-methyl-1H-indol-2-yl]methanone, (4-2-113) [5-amino-1-[4-(2,3-difluorophenoxy)-2-methylphenyl]pyrazol-4-yl]-[6-(1,1-dioxo-1,2-thiazolidin-2-yl)-5-methyl-1H-indol-2-yl]methanone, (4-2-114) [5-amino-1-[2-fluoro-4-(2-fluorophenoxy)-6-methylphenyl]pyrazol-4-yl]-[6-(1,1-dioxo-1,2-thiazolidin-2-yl)-5-methyl-1H-indol-2-yl]methanone, (4-2-115) [5-amino-1-[4-(2,3-difluorophenoxy)-2-fluoro-6-methylphenyl]pyrazol-4-yl]-6-(1,1-dioxo-1,2-thiazolidin-2-yl)-5-methyl-1H-indol-2-yl]methanone, (4-2-116) [5-amino-1-[6-(2,6-difluorophenoxy)-4-methylpyridin-3-yl]pyrazol-4-yl]-[6-(1,1-dioxo-1,2-thiazolidin-2-yl)-5-methyl-1H-indol-2-yl]methanone, (4-2-117) [5-amino-1-[6-(2-chlorophenoxy)-4-methylpyridin-3-yl]pyrazol-4-yl]-[6-(1,1-dioxo-1,2-thiazolidin-2-yl)-5-methyl-1H-indol-2-yl]methanone, (4-2-118) [5-amino-1-[6-(3-chlorophenoxy)-4-methylpyridin-3-yl]pyrazol-4-yl]-[6-(1,1-dioxo-1,2-thiazolidin-2-yl)-5-methyl-1H-indol-2-yl]methanone, (4-2-119) [5-amino-1-[6-(4-fluorophenoxy)-4-methylpyridin-3-yl]pyrazol-4-yl]-[6-(1,1-dioxo-1,2-thiazolidin-2-yl)-5-methyl-1H-indol-2-yl]methanone, (4-2-120) [5-amino-1-[2-fluoro-4-(2-fluorophenoxy)-6-methylphenyl]pyrazol-4-yl]-[6-(1,1-dioxo-1,2-thiazolidin-2-yl)-5-methoxy-1H-indol-2-yl]methanone, (4-2-121) [5-amino-1-[6-(2,6-difluorophenoxy)-4-methylpyridin-3-yl]pyrazol-4-yl]-[6-(1,1-dioxo-1,2-thiazolidin-2-yl)-5-methoxy-1H-indol-2-yl]methanone, (4-2-122) [5-amino-1-[4-(2-fluorophenoxy)-2-methylphenyl]pyrazol-4-yl]-(5-methyl-6-morpholin-4-yl-1H-indol-2-yl)methanone, (4-2-123) [5-amino-1-[6-(2-fluorophenoxy)-4-methylpyridin-3-yl]pyrazol-4-yl]-(5-methyl-6-morpholin-4-yl-1H-indol-2-yl)methanone, (4-2-124) [5-amino-1-[6-(2,6-difluorophenoxy)-4-methylpyridin-3-yl]pyrazol-4-yl]-(5-methyl-6-morpholin-4-yl-1H-indol-2-yl)methanone, (4-2-125) [5-amino-1-[6-(2,6-difluorophenoxy)-4-methylpyridin-3-yl]pyrazol-4-yl]-[5-methyl-6-(4-morpholin-4-ylpiperidin-1-yl)-1H-indol-2-yl]methanone, (4-2-126) N-[2-[5-amino-1-[6-(2,6-difluorophenoxy)-4-methylpyridin-3-yl]pyrazole-4-carbonyl]-5-fluoro-1H-indol-6-yl]-N-ethylmethanesulfonamide, (4-2-127) N-[2-[5-amino-1-[6-(2,6-difluorophenoxy)-4-methylpyridin-3-yl]pyrazole-4-carbonyl]-5-fluoro-1H-indol-6-yl]-N-(oxan-4-yl)methanesulfonamide, (4-2-128) N-[2-[5-amino-1-[6-(2,6-difluorophenoxy)-4-methylpyridin-3-yl]pyrazole-4-carbonyl]-5-fluoro-1H-indol-6-yl]-N-(2-morpholin-4-ylethyl)methanesulfonamide, (4-2-129) N-[2-[5-amino-1-[6-(2-fluorophenoxy)-4-methylpyridin-3-yl]pyrazole-4-carbonyl]-6-(2-morpholin-4-ylethoxy)-1H-indol-5-yl]methanesulfonamide, (4-2-130) N-[2-[5-amino-1-[6-(2-fluorophenoxy)-4-methylpyridin-3-yl]pyrazole-4-carbonyl]-6-hydroxy-1H-indol-5-yl]-N-(2-morpholin-4-ylethyl)methanesulfonamide, (4-3-001) [5-amino-1-[4-(2,3-difluorophenoxy)-2-fluoro-6-methylphenyl]pyrazol-4-yl]-(6-amino-5-fluoro-1H-indol-2-yl)methanone, (4-4-001) [5-amino-1-[6-(2,6-difluorophenoxy)-4-methylpyridin-3-yl]pyrazol-4-yl]-[5-(difluoromethoxy)-6-piperidin-4-yl-1H-indol-2-yl]methanone, (4-5-001) N-[2-[5-amino-1-[6-(2-fluorophenoxy)-4-methylpyridin-3-yl]pyrazole-4-carbonyl]-5-fluoro-1H-indol-6-yl]morpholine-4-sulfonamide, (4-5-002) N-[2-[5-amino-1-[4-(2-fluorophenoxy)-2-methylphenyl]pyrazole-4-carbonyl]-5-fluoro-1H-indol-6-yl]morpholine-4-sulfonamide, (4-5-003) [5-amino-1-[4-(2-fluorophenoxy)-2-methylphenyl]pyrazol-4-yl]-[5-fluoro-6-(oxan-4-yl sulfamoylamino)-1H-indol-2-yl]methanone, (4-5-004) [5-amino-1-[4-(2-fluorophenoxy)-2-methylphenyl]pyrazol-4-yl]-[5-fluoro-6-(propan-2-ylsulfamoylamino)-1H-indol-2-yl]methanone, (4-5-005) [5-amino-1-[4-(2-fluorophenoxy)-2-methylphenyl]pyrazol-4-yl]-[5-fluoro-6-(oxetan-3-ylsulfamoylamino)-1H-indol-2-yl]methanone, (4-5-006) [5-amino-1-[4-(2-fluorophenoxy)-2-methylphenyl]pyrazol-4-yl]-[6-(cyclobutylsulfamoylamino)-5-fluoro-1H-indol-2-yl]methanone, (4-5-007) [5-amino-1-[4-(2-fluorophenoxy)-2-methylphenyl]pyrazol-4-yl]-[5-fluoro-6-(2-methoxyethylsulfamoylamino)-1H-indol-2-yl]methanone, (4-5-008) [5-amino-1-[4-(2-fluorophenoxy)-2-methylphenyl]pyrazol-4-yl]-[5-fluoro-6-[(3-methyloxetan-3-yl)sulfamoylamino]-1H-indol-2-yl]methanone, (4-5-009) [5-amino-1-[4-(2-fluorophenoxy)-2-methylphenyl]pyrazol-4-yl]-[5-fluoro-6-(methoxysulfamoylamino)-1H-indol-2-yl]methanone, (4-5-010) [5-amino-1-[4-(2-fluorophenoxy)-2-methylphenyl]pyrazol-4-yl]-[6-(cyclopropylsulfamoylamino)-5-fluoro-1H-indol-2-yl]methanone, (4-5-011) N-[2-[5-amino-1-[4-(2,3-difluorophenoxy)-2-fluoro-6-methylphenyl]pyrazole-4-carbonyl]-5-fluoro-1H-indol-6-yl]morpholine-4-sulfonamide, (4-5-012) [5-amino-1-[6-(2-fluorophenoxy)-4-methylpyridin-3-yl]pyrazol-4-yl]-[5-fluoro-6-(oxan-4-ylsulfamoylamino)-1H-indol-2-yl]methanone, (4-6-001) [5-amino-1-[6-(2-fluorophenoxy)-4-methylpyridin-3-yl]pyrazol-4-yl]-[5-fluoro-6-(2-hydroxyethylsulfamoylamino)-1H-indol-2-yl]methanone, (4-6-002) [5-amino-1-[4-(2-fluorophenoxy)-2-methylphenyl]pyrazol-4-yl]-[5-fluoro-6-(2-hydroxyethylsulfamoylamino)-1H-indol-2-yl]methanone, (4-6-003) [5-amino-1-[4-(2-fluorophenoxy)-2-methylphenyl]pyrazol-4-yl]-[5-fluoro-6-[(1-hydroxy-2-methylpropan-2-yl)sulfamoylamino]-1H-indol-2-yl]methanone, (4-6-004) [5-amino-1-[4-(2-fluorophenoxy)-2-methylphenyl]pyrazol-4-yl]-[5-fluoro-6-[(2-hydroxy-2-methylpropyl)sulfamoylamino]-1H-indol-2-yl]methanone, (4-7-001) N-[2-[5-amino-1-[6-(2-fluorophenoxy)-4-methylpyridin-3-yl]pyrazole-4-carbonyl]-5-fluoro-1H-indol-6-yl]methanesulfonamide, (4-7-002) N-[2-[5-amino-1-[4-(2-fluorophenoxy)-2-methylphenyl]pyrazole-4-carbonyl]-5-fluoro-1H-indol-6-yl]-1-(1,4-dioxan-2-yl)methanesulfonamide, (4-7-003) N-[2-[5-amino-1-[2-fluoro-4-(2-fluorophenoxy)-6-methylphenyl]pyrazole-4-carbonyl]-5-fluoro-1H-indol-6-yl]methanesulfonamide, (4-7-004) N-[2-[5-amino-1-[2-fluoro-4-(2-fluorophenoxy)-6-methylphenyl]pyrazole-4-carbonyl]-5-fluoro-1H-indol-6-yl]cyclopropanesulfonamide, (4-7-005) N-[2-[5-amino-1-[4-(2,3-difluorophenoxy)-2-fluoro-6-methylphenyl]pyrazole-4-carbonyl]-5-fluoro-1H-indol-6-yl]methanesulfonamide, (4-7-006) N-[2-[5-amino-1-[4-(2,3-difluorophenoxy)-2-fluoro-6-methylphenyl]pyrazole-4-carbonyl]-5-fluoro-1H-indol-6-yl]cyclopropanesulfonamide, (4-7-007) N-[2-[5-amino-1-[4-(2,5-difluorophenoxy)-2-fluoro-6-methylphenyl]pyrazole-4-carbonyl]-5-fluoro-1H-indol-6-yl]methanesulfonamide, (4-7-008) N-[2-[5-amino-1-[4-(2,5-difluorophenoxy)-2-fluoro-6-methylphenyl]pyrazole-4-carbonyl]-5-fluoro-1H-indol-6-yl]cyclopropanesulfonamide, (4-7-009) N-[2-[5-amino-1-[4-(2-chlorophenoxy)-2-fluoro-6-methylphenyl]pyrazole-4-carbonyl]-5-fluoro-1H-indol-6-yl]methanesulfonamide, (4-7-010) N-[2-[5-amino-1-[4-(2-chlorophenoxy)-2-fluoro-6-methylphenyl]pyrazole-4-carbonyl]-5-fluoro-1H-indol-6-yl]cyclopropanesulfonamide, (4-7-011) N-[2-[5-amino-1-[4-(3-chlorophenoxy)-2-fluoro-6-methylphenyl]pyrazole-4-carbonyl]-5-fluoro-1H-indol-6-yl]methanesulfonamide, (4-7-012) N-[2-[5-amino-1-[4-(3-chlorophenoxy)-2-fluoro-6-methylphenyl]pyrazole-4-carbonyl]-5-fluoro-1H-indol-6-yl]cyclopropanesulfonamide, (4-7-013) N-[2-[5-amino-1-(2-fluoro-6-methyl-4-phenoxyphenyl)pyrazole-4-carbonyl]-5-fluoro-1H-indol-6-yl]methanesulfonamide, (4-7-014) N-[2-[5-amino-1-(2-fluoro-6-methyl-4-phenoxyphenyl)pyrazole-4-carbonyl]-5-fluoro-1H-indol-6-yl]cyclopropanesulfonamide, (4-7-015) N-[2-[5-amino-1-[6-(2-chlorophenoxy)-4-methylpyridin-3-yl]pyrazole-4-carbonyl]-5-fluoro-1H-indol-6-yl]cyclopropanesulfonamide, (4-7-016) N-[2-[5-amino-1-[6-(3-chlorophenoxy)-4-methylpyridin-3-yl]pyrazole-4-carbonyl]-5-fluoro-1H-indol-6-yl]cyclopropanesulfonamide, (4-8-001) N-[2-[5-amino-1-[4-(2-fluorophenoxy)-2-methylphenyl]pyrazole-4-carbonyl]-5-fluoro-1H-indol-6-yl]-1-(2,3-dihydroxypropyl)cyclopropane-1-sulfonamide, (4-9-001) [5-amino-1-[6-(2-fluorophenoxy)-4-methylpyridin-3-yl]pyrazol-4-yl]-[6-(1,1-dioxo-1,2-thiazolidin-2-yl)-5-fluoro-1H-indol-2-yl]methanone hydrochloride, (4-9-002) [5-amino-1-[6-(2,6-difluorophenoxy)-4-methylpyridin-3-yl]pyrazol-4-yl]-[6-(1,1-dioxo-1,2-thiazolidin-2-yl)-5-fluoro-1H-indol-2-yl]methanone, (4-10-001) 2-[[2-[5-amino-1-[6-(2-fluorophenoxy)-4-methylpyridin-3-yl]pyrazole-4-carbonyl]-5-fluoro-1H-indol-6-yl]sulfamoyl]-N,N-diethylacetamide, (4-10-002) 2-[[2-[5-amino-1-[4-(2-fluorophenoxy)-2-methylphenyl]pyrazole-4-carbonyl]-5-fluoro-1H-indol-6-yl]sulfamoyl]-N-propan-2-ylacetamide, (4-10-003) N-[2-[5-amino-1-[4-(2-fluorophenoxy)-2-methylphenyl]pyrazole-4-carbonyl]-5-fluoro-1H-indol-6-yl]-2-oxo-2-(4-propan-2-ylpiperazin-1-yl)ethanesulfonamide 2,2,2-trifluoroacetate (4-10-004) N-[2-[5-amino-1-[4-(2-fluorophenoxy)-2-methylphenyl]pyrazole-4-carbonyl]-5-fluoro-1H-indol-6-yl]-2-morpholin-4-yl-2-oxoethanesulfonamide, (4-10-005) N-[2-[5-amino-1-[6-(2-fluorophenoxy)-4-methylpyridin-3-yl]pyrazole-4-carbonyl]-5-fluoro-1H-indol-6-yl]-2-oxo-2-pyrrolidin-1-ylethanesulfonamide, (4-10-006) N-[2-[5-amino-1-[6-(2-fluorophenoxy)-4-methylpyridin-3-yl]pyrazole-4-carbonyl]-5-fluoro-1H-indol-6-yl]-2-morpholin-4-yl-2-oxoethanesulfonamide, (4-10-007) N-[2-[5-amino-1-[4-(2-fluorophenoxy)-2-methylphenyl]pyrazole-4-carbonyl]-5-methyl-1H-indol-6-yl]-2-morpholin-4-yl-2-oxoethanesulfonamide, (4-10-008) 2-[[2-[5-amino-1-[4-(2-fluorophenoxy)-2-methylphenyl]pyrazole-4-carbonyl]-5-methyl-1H-indol-6-yl]sulfamoyl]-N-propan-2-ylacetamide, (4-10-009) N-[2-[5-amino-1-[2-fluoro-4-(2-fluorophenoxy)-6-methylphenyl]pyrazole-4-carbonyl]-5-methyl-1H-indol-6-yl]-2-morpholin-4-yl-2-oxoethanesulfonamide, (4-10-010) N-[2-[5-amino-1-[6-(2,6-difluorophenoxy)-4-methylpyridin-3-yl]pyrazole-4-carbonyl]-5-methyl-1H-indol-6-yl]-2-morpholin-4-yl-2-oxoethanesulfonamide, (4-10-011) 2-[[2-[5-amino-1-[4-(2-fluorophenoxy)-2-methylphenyl]pyrazole-4-carbonyl]-5-methoxy-1H-indol-6-yl]sulfamoyl]-N-propan-2-ylacetamide, (4-10-012) N-[2-[5-amino-1-[4-(2-fluorophenoxy)-2-methylphenyl]pyrazole-4-carbonyl]-5-methoxy-1H-indol-6-yl]-2-morpholin-4-yl-2-oxoethanesulfonamide, (4-10-013) N-[2-[5-amino-1-[2-fluoro-4-(2-fluorophenoxy)-6-methylphenyl]pyrazole-4-carbonyl]-5-methoxy-1H-indol-6-yl]-2-morpholin-4-yl-2-oxoethanesulfonamide, (4-10-014) N-[2-[5-amino-1-[6-(2-fluorophenoxy)-4-methylpyridin-3-yl]pyrazole-4-carbonyl]-5-methoxy-1H-indol-6-yl]-2-oxo-2-pyrrolidin-1-ylethanesulfonamide, (4-10-015) 2-[[2-[5-amino-1-[6-(2-fluorophenoxy)-4-methylpyridin-3-yl]pyrazole-4-carbonyl]-5-methoxy-1H-indol-6-yl]sulfamoyl]-N-propan-2-ylacetamide, (4-10-016) N-[2-[5-amino-1-[6-(2-fluorophenoxy)-4-methylpyridin-3-yl]pyrazole-4-carbonyl]-5-methoxy-1H-indol-6-yl]-2-morpholin-4-yl-2-oxoethanesulfonamide, (4-10-017) N-[2-[5-amino-1-[6-(2,6-difluorophenoxy)-4-methylpyridin-3-yl]pyrazole-4-carbonyl]-5-methoxy-1H-indol-6-yl]-2-oxo-2-pyrrolidin-1-ylethanesulfonamide, (4-11-001) N-[2-[5-amino-1-[6-(2-fluorophenoxy)-4-methylpyridin-3-yl]pyrazole-4-carbonyl]-5-methoxy-1H-indol-6-yl]acetamide, (4-12-001) N-[2-[5-amino-1-[6-(2-fluorophenoxy)-4-methylpyridin-3-yl]pyrazole-4-carbonyl]-5-methoxy-1H-indol-6-yl]morpholine-4-sulfonamide, (4-12-002) N-[2-[5-amino-1-[6-(2-fluorophenoxy)-4-methylpyridin-3-yl]pyrazole-4-carbonyl]-5-methoxy-1H-indol-6-yl]morpholine-4-carboxamide, (4-12-003) N-[2-[5-amino-1-[4-(2-fluorophenoxy)-2-methylphenyl]pyrazole-4-carbonyl]-5-methoxy-1H-indol-6-yl]morpholine-4-sulfonamide, (4-13-001) N-[2-[5-amino-1-[6-(2-fluorophenoxy)-4-methylpyridin-3-yl]pyrazole-4-carbonyl]-5-methoxy-1H-indol-6-yl]-3-fluoropropane-1-sulfonamide, (4-13-002) N-[2-[5-amino-1-[4-(2-fluorophenoxy)-2-methylphenyl]pyrazole-4-carbonyl]-5-methoxy-1H-indol-6-yl]-3-fluoropropane-1-sulfonamide, (4-14-001) [5-amino-1-[6-(2-fluorophenoxy)-4-methylpyridin-3-yl]pyrazol-4-yl]-[6-(1,1-dioxo-1,2-thiazolidin-2-yl)-5-methoxy-1H-indol-2-yl]methanone, (4-14-002) [5-amino-1-[4-(2-fluorophenoxy)-2-methylphenyl]pyrazol-4-yl]-[6-(1,1-dioxo-1,2-thiazolidin-2-yl)-5-methoxy-1H-indol-2-yl]methanone, (4-15-001) N-[2-[5-amino-1-[6-(2-fluorophenoxy)-4-methylpyridin-3-yl]pyrazole-4-carbonyl]-5-methyl-1H-indol-6-yl]-2-morpholin-4-yl-2-oxoethanesulfonamide, (4-16-001) [5-amino-1-[6-(2-fluorophenoxy)-4-methylpyridin-3-yl]pyrazol-4-yl]-[6-(1,1-dioxo-1,2-thiazolidin-2-yl)-5-methyl-1H-indol-2-yl]methanone hydrochloride, (4-17-001) 1-[4-[2-[5-amino-1-[6-(2,6-difluorophenoxy)-4-methylpyridin-3-yl]pyrazole-4-carbonyl]-5-(2,2-difluoroethoxy)-1H-indol-6-yl]piperidin-1-yl]ethanone, (4-17-002) 1-[4-[2-[5-amino-1-[4-(2-fluorophenoxy)-2-methylphenyl]pyrazole-4-carbonyl]-5-(difluoromethoxy)-1H-indol-6-yl]piperidin-1-yl]ethanone, (4-17-003) [5-amino-1-[4-(2-fluorophenoxy)-2-methylphenyl]pyrazol-4-yl]-[5-(difluoromethoxy)-6-(1-methyl sulfonylpiperidin-4-yl)-1H-indol-2-yl]methanone, (4-17-004) [5-amino-1-[4-(2-fluorophenoxy)-2-methylphenyl]pyrazol-4-yl]-[6-(1-cyclopropylsulfonylpiperidin-4-yl)-5-(difluoromethoxy)-1H-indol-2-yl]methanone, (4-17-005) 1-[4-[2-[5-amino-1-[2-fluoro-4-(2-fluorophenoxy)-6-methylphenyl]pyrazole-4-carbonyl]-5-(difluoromethoxy)-1H-indol-6-yl]piperidin-1-yl]ethanone, (4-17-006) [5-amino-1-[2-fluoro-4-(2-fluorophenoxy)-6-methylphenyl]pyrazol-4-yl]-[5-(difluoromethoxy)-6-(1-methyl sulfonylpiperidin-4-yl)-1H-indol-2-yl]methanone, (4-17-007) [5-amino-1-[2-fluoro-4-(2-fluorophenoxy)-6-methylphenyl]pyrazol-4-yl]-[6-(1-cyclopropylsulfonylpiperidin-4-yl)-5-(difluoromethoxy)-1H-indol-2-yl]methanone, (4-17-008) 1-[4-[2-[5-amino-1-[6-(2-fluorophenoxy)-4-methylpyridin-3-yl]pyrazole-4-carbonyl]-5-(difluoromethoxy)-1H-indol-6-yl]piperidin-1-yl]ethanone, (4-17-009) [5-amino-1-[6-(2-fluorophenoxy)-4-methylpyridin-3-yl]pyrazol-4-yl]-[5-(difluoromethoxy)-6-(1-methyl sulfonylpiperidin-4-yl)-1H-indol-2-yl]methanone, (4-17-010) [5-amino-1-[6-(2-fluorophenoxy)-4-methylpyridin-3-yl]pyrazol-4-yl]-[6-(1-cyclopropylsulfonylpiperidin-4-yl)-5-(difluoromethoxy)-1H-indol-2-yl]methanone, (4-17-011) 1-[4-[2-[5-amino-1-[6-(2,6-difluorophenoxy)-4-methylpyridin-3-yl]pyrazole-4-carbonyl]-5-(difluoromethoxy)-1H-indol-6-yl]piperidin-1-yl]ethanone, (4-17-012) [5-amino-1-[6-(2,6-difluorophenoxy)-4-methylpyridin-3-yl]pyrazol-4-yl]-[5-(difluoromethoxy)-6-(1-methylsulfonylpiperidin-4-yl)-1H-indol-2-yl]methanone, (4-17-013) [5-amino-1-[6-(2,6-difluorophenoxy)-4-methylpyridin-3-yl]pyrazol-4-yl]-[6-(1-cyclopropylsulfonylpiperidin-4-yl)-5-(difluoromethoxy)-1H-indol-2-yl]methanone, (4-17-014) 1-[4-[2-[5-amino-1-[4-(2-fluorophenoxy)-2-methylphenyl]pyrazole-4-carbonyl]-5-(2,2-difluoroethoxy)-1H-indol-6-yl]piperidin-1-yl]ethanone, (4-17-015) [5-amino-1-[4-(2-fluorophenoxy)-2-methylphenyl]pyrazol-4-yl]-[5-(2,2-difluoroethoxy)-6-(1-methylsulfonylpiperidin-4-yl)-1H-indol-2-yl]methanone, (4-17-016) [5-amino-1-[4-(2-fluorophenoxy)-2-methylphenyl]pyrazol-4-yl]-[6-(1-cyclopropylsulfonylpiperidin-4-yl)-5-(2,2-difluoroethoxy)-1H-indol-2-yl]methanone, (4-17-017) 1-[4-[2-[5-amino-1-[2-fluoro-4-(2-fluorophenoxy)-6-methylphenyl]pyrazole-4-carbonyl]-5-(2,2-difluoroethoxy)-1H-indol-6-yl]piperidin-1-yl]ethanone, (4-17-018) [5-amino-1-[2-fluoro-4-(2-fluorophenoxy)-6-methylphenyl]pyrazol-4-yl]-[5-(2,2-difluoroethoxy)-6-(1-methylsulfonylpiperidin-4-yl)-1H-indol-2-yl]methanone, (4-17-019) [5-amino-1-[2-fluoro-4-(2-fluorophenoxy)-6-methylphenyl]pyrazol-4-yl]-[6-(1-cyclopropylsulfonylpiperidin-4-yl)-5-(2,2-difluoroethoxy)-1H-indol-2-yl]methanone, (4-17-020) 1-[4-[2-[5-amino-1-[6-(2-fluorophenoxy)-4-methylpyridin-3-yl]pyrazole-4-carbonyl]-5-(2,2-difluoroethoxy)-1H-indol-6-yl]piperidin-1-yl]ethanone, (4-17-021) [5-amino-1-[6-(2-fluorophenoxy)-4-methylpyridin-3-yl]pyrazol-4-yl]-[5-(2,2-difluoroethoxy)-6-(1-methylsulfonylpiperidin-4-yl)-1H-indol-2-yl]methanone, (4-17-022) [5-amino-1-[6-(2-fluorophenoxy)-4-methylpyridin-3-yl]pyrazol-4-yl]-[6-(1-cyclopropylsulfonylpiperidin-4-yl)-5-(2,2-difluoroethoxy)-1H-indol-2-yl]methanone, (4-17-023) [5-amino-1-[6-(2,6-difluorophenoxy)-4-methylpyridin-3-yl]pyrazol-4-yl]-[5-(2,2-difluoroethoxy)-6-(1-methylsulfonylpiperidin-4-yl)-1H-indol-2-yl]methanone, (4-17-024) [5-amino-1-[6-(2,6-difluorophenoxy)-4-methylpyridin-3-yl]pyrazol-4-yl]-[6-(1-cyclopropylsulfonylpiperidin-4-yl)-5-(2,2-difluoroethoxy)-1H-indol-2-yl]methanone, (4-18-001) 2-amino-1-[4-[2-[5-amino-1-[6-(2,6-difluorophenoxy)-4-methylpyridin-3-yl]pyrazole-4-carbonyl]-5-(2,2-difluoroethoxy)-1H-indol-6-yl]piperidin-1-yl]ethanone, (4-18-002) 2-amino-1-[4-[2-[5-amino-1-[4-(2-fluorophenoxy)-2-methylphenyl]pyrazole-4-carbonyl]-5-(difluoromethoxy)-1H-indol-6-yl]piperidin-1-yl]ethanone, (4-18-003) 2-amino-1-[4-[2-[5-amino-1-[6-(2,6-difluorophenoxy)-4-methylpyridin-3-yl]pyrazole-4-carbonyl]-5-(difluoromethoxy)-1H-indol-6-yl]piperidin-1-yl]ethanone, (4-18-004) 2-amino-1-[4-[2-[5-amino-1-[4-(2-fluorophenoxy)-2-methylphenyl]pyrazole-4-carbonyl]-5-(2,2-difluoroethoxy)-1H-indol-6-yl]piperidin-1-yl]ethanone, (4-19-001) N-[2-[5-amino-1-[6-(2,6-difluorophenoxy)-4-methylpyridin-3-yl]pyrazole-4-carbonyl]-5-methoxy-1H-indol-6-yl]-3-fluoropropane-1-sulfonamide, (4-20-001) 2-[5-amino-1-[4-(2-fluorophenoxy)-2-methylphenyl]pyrazole-4-carbonyl]-5-fluoro-6-(sulfamoylamino)-1H-indole, (4-20-002) 2-[5-amino-1-[4-(2,3-difluorophenoxy)-2-methylphenyl]pyrazole-4-carbonyl]-5-fluoro-6-(sulfamoylamino)-1H-indole, (4-20-003) 2-[5-amino-1-[4-(2-fluorophenoxy)-3-methylphenyl]pyrazole-4-carbonyl]-5-fluoro-6-(sulfamoylamino)-1H-indole, (4-21-001) 1-[2-[5-amino-1-[6-(2,6-difluorophenoxy)-4-methylpyridin-3-yl]pyrazole-4-carbonyl]-5-(2,2-difluoroethoxy)-1H-indol-6-yl]pyrrolidin-2-one, (4-21-002) 1-[2-[5-amino-1-[4-(2-fluorophenoxy)-2-methylphenyl]pyrazole-4-carbonyl]-5-(2,2-difluoroethoxy)-1H-indol-6-yl]pyrrolidin-2-one, (4-21-003) 3-[2-[5-amino-1-[4-(2-fluorophenoxy)-2-methylphenyl]pyrazole-4-carbonyl]-5-(2,2-difluoroethoxy)-1H-indol-6-yl]-1,3-oxazolidin-2-one, (4-21-004) 1-[2-[5-amino-1-[2-fluoro-4-(2-fluorophenoxy)-6-methylphenyl]pyrazole-4-carbonyl]-5-(2,2-difluoroethoxy)-1H-indol-6-yl]pyrrolidin-2-one, (4-21-005) 3-[2-[5-amino-1-[6-(2,6-difluorophenoxy)-4-methylpyridin-3-yl]pyrazole-4-carbonyl]-5-(2,2-difluoroethoxy)-1H-indol-6-yl]-1,3-oxazolidin-2-one, (4-21-006) 1-[2-[5-amino-1-[4-(2-fluorophenoxy)-2-methylphenyl]pyrazole-4-carbonyl]-5-(difluoromethoxy)-1H-indol-6-yl]pyrrolidin-2-one, (4-21-007) 3-[2-[5-amino-1-[4-(2-fluorophenoxy)-2-methylphenyl]pyrazole-4-carbonyl]-5-(difluoromethoxy)-1H-indol-6-yl]-1,3-oxazolidin-2-one, (4-21-008) 1-[2-[5-amino-1-[6-(2,6-difluorophenoxy)-4-methylpyridin-3-yl]pyrazole-4-carbonyl]-5-(difluoromethoxy)-1H-indol-6-yl]pyrrolidin-2-one, (4-21-009) 3-[2-[5-amino-1-[6-(2,6-difluorophenoxy)-4-methylpyridin-3-yl]pyrazole-4-carbonyl]-5-(difluoromethoxy)-1H-indol-6-yl]-1,3-oxazolidin-2-one, (4-22-001) N-[2-[5-amino-1-[4-(2-fluorophenoxy)-2-methylphenyl]pyrazole-4-carbonyl]-5-(difluoromethoxy)-1H-indol-6-yl]morpholine-4-sulfonamide, (4-22-002) N-[2-[5-amino-1-[6-(2-fluorophenoxy)-4-methylpyridin-3-yl]pyrazole-4-carbonyl]-5-(difluoromethoxy)-1H-indol-6-yl]morpholine-4-sulfonamide, (4-22-003) N-[2-[5-amino-1-[6-(2,6-difluorophenoxy)-4-methylpyridin-3-yl]pyrazole-4-carbonyl]-5-(difluoromethoxy)-1H-indol-6-yl]morpholine-4-sulfonamide, (4-22-004) N-[2-[5-amino-1-[6-(2-fluorophenoxy)-4-methylpyridin-3-yl]pyrazole-4-carbonyl]-5-morpholin-4-yl-1H-indol-6-yl]morpholine-4-sulfonamide, (4-22-005) N-[2-[5-amino-1-[4-(2-fluorophenoxy)-2-methylphenyl]pyrazole-4-carbonyl]-5-(2,2-difluoroethoxy)-1H-indol-6-yl]morpholine-4-sulfonamide, (4-22-006) N-[2-[5-amino-1-[6-(2-fluorophenoxy)-4-methylpyridin-3-yl]pyrazole-4-carbonyl]-5-(2,2-difluoroethoxy)-1H-indol-6-yl]morpholine-4-sulfonamide, (4-23-001) [5-amino-1-[6-(2,6-difluorophenoxy)-4-methylpyridin-3-yl]pyrazol-4-yl]-[5-(2,2-difluoroethoxy)-6-(4-methylsulfonylpiperazin-1-yl)-1H-indol-2-yl]methanone, (4-23-002) [5-amino-1-[4-(2-fluorophenoxy)-2-methylphenyl]pyrazol-4-yl]-[5-(difluoromethoxy)-6-(4-methylsulfonylpiperazin-1-yl)-1H-indol-2-yl]methanone, (4-23-003) [5-amino-1-[2-fluoro-4-(2-fluorophenoxy)-6-methylphenyl]pyrazol-4-yl]-[5-(difluoromethoxy)-6-(4-methylsulfonylpiperazin-1-yl)-1H-indol-2-yl]methanone, (4-23-004) [5-amino-1-[6-(2-fluorophenoxy)-4-methylpyridin-3-yl]pyrazol-4-yl]-[5-(difluoromethoxy)-6-(4-methylsulfonylpiperazin-1-yl)-1H-indol-2-yl]methanone, (4-23-005) [5-amino-1-[4-(2-fluorophenoxy)-2-methylphenyl]pyrazol-4-yl]-[5-(2,2-difluoroethoxy)-6-(4-methylsulfonylpiperazin-1-yl)-1H-indol-2-yl]methanone, (4-23-006) [5-amino-1-[2-fluoro-4-(2-fluorophenoxy)-6-methylphenyl]pyrazol-4-yl]-[5-(2,2-difluoroethoxy)-6-(4-methylsulfonylpiperazin-1-yl)-1H-indol-2-yl]methanone, (4-23-007) [5-amino-1-[6-(2-fluorophenoxy)-4-methylpyridin-3-yl]pyrazol-4-yl]-[5-(2,2-difluoroethoxy)-6-(4-methylsulfonylpiperazin-1-yl)-1H-indol-2-yl]methanone, (4-23-008) [5-amino-1-[6-(2,6-difluorophenoxy)-4-methylpyridin-3-yl]pyrazol-4-yl]-[5-(2,2-difluoroethoxy)-6-(oxetan-3-yl amino)-1H-indol-2-yl]methanone, (4-23-009) [5-amino-1-[4-(2-fluorophenoxy)-2-methylphenyl]pyrazol-4-yl]-[5-(difluoromethoxy)-6-(oxetan-3-ylamino)-1H-indol-2-yl]methanone, (4-23-010) [5-amino-1-[4-(2-fluorophenoxy)-2-methylphenyl]pyrazol-4-yl]-[5-(difluoromethoxy)-6-[(1-methylsulfonylpiperidin-4-yl)amino]-1H-indol-2-yl]methanone, (4-23-011) [5-amino-1-[2-fluoro-4-(2-fluorophenoxy)-6-methylphenyl]pyrazol-4-yl]-[5-(difluoromethoxy)-6-(oxetan-3-ylamino)-1H-indol-2-yl]methanone, (4-23-012) [5-amino-1-[2-fluoro-4-(2-fluorophenoxy)-6-methylphenyl]pyrazol-4-yl]-[5-(difluoromethoxy)-6-[(1-methylsulfonylpiperidin-4-yl)amino]-1H-indol-2-yl]methanone, (4-23-013) [5-amino-1-[6-(2-fluorophenoxy)-4-methylpyridin-3-yl]pyrazol-4-yl]-[5-(difluoromethoxy)-6-(oxetan-3-ylamino)-1H-indol-2-yl]methanone, (4-23-014) [5-amino-1-[6-(2,6-difluorophenoxy)-4-methylpyridin-3-yl]pyrazol-4-yl]-[5-(difluoromethoxy)-6-(oxetan-3-ylamino)-1H-indol-2-yl]methanone, (4-23-015) [5-amino-1-[6-(2,6-difluorophenoxy)-4-methylpyridin-3-yl]pyrazol-4-yl]-[5-(difluoromethoxy)-6-[(1-methylsulfonylpiperidin-4-yl)amino]-1H-indol-2-yl]methanone, (4-23-016) [5-amino-1-[4-(2-fluorophenoxy)-2-methylphenyl]pyrazol-4-yl]-[5-(2,2-difluoroethoxy)-6-(oxetan-3-yl amino)-1H-indol-2-yl]methanone, (4-23-017) [5-amino-1-[4-(2-fluorophenoxy)-2-methylphenyl]pyrazol-4-yl]-[5-(2,2-difluoroethoxy)-6-[(1-methylsulfonylpiperidin-4-yl)amino]-1H-indol-2-yl]methanone, (4-23-018) [5-amino-1-[4-(2-fluorophenoxy)-2-methylphenyl]pyrazol-4-yl]-[5-(2,2-difluoroethoxy)-6-[(1-methylsulfonylazetidin-3-yl)amino]-1H-indol-2-yl]methanone, (4-23-019) [5-amino-1-[2-fluoro-4-(2-fluorophenoxy)-6-methylphenyl]pyrazol-4-yl]-[5-(2,2-difluoroethoxy)-6-(oxetan-3-yl amino)-1H-indol-2-yl]methanone, (4-23-020) [5-amino-1-[6-(2-fluorophenoxy)-4-methylpyridin-3-yl]pyrazol-4-yl]-[5-(2,2-difluoroethoxy)-6-(oxetan-3-yl amino)-1H-indol-2-yl]methanone, (4-23-021) [5-amino-1-[6-(2,6-difluorophenoxy)-4-methylpyridin-3-yl]pyrazol-4-yl]-[5-(2,2-difluoroethoxy)-6-[(1-methylsulfonylpiperidin-4-yl)amino]-1H-indol-2-yl]methanone, (4-23-022) [5-amino-1-[6-(2,6-difluorophenoxy)-4-methylpyridin-3-yl]pyrazol-4-yl]-[5-(2,2-difluoroethoxy)-6-[(1-methylsulfonylazetidin-3-yl)amino]-1H-indol-2-yl]methanone, (4-23-023) [5-amino-1-[4-(2-fluorophenoxy)-2-methylphenyl]pyrazol-4-yl]-[5-(difluoromethoxy)-6-[(1-methylsulfonylazetidin-3-yl)amino]-1H-indol-2-yl]methanone, (4-23-024) [5-amino-1-[2-fluoro-4-(2-fluorophenoxy)-6-methylphenyl]pyrazol-4-yl]-[5-(difluoromethoxy)-6-[(1-methylsulfonylazetidin-3-yl)amino]-1H-indol-2-yl]methanone, (4-23-025) [5-amino-1-[6-(2-fluorophenoxy)-4-methylpyridin-3-yl]pyrazol-4-yl]-[5-(difluoromethoxy)-6-[(1-methylsulfonylazetidin-3-yl)amino]-1H-indol-2-yl]methanone, (4-23-026) [5-amino-1-[6-(2,6-difluorophenoxy)-4-methylpyridin-3-yl]pyrazol-4-yl]-[5-(difluoromethoxy)-6-[(1-methylsulfonylpiperidin-4-yl)amino]-1H-indol-2-yl]methanone, (4-23-027) [5-amino-1-[2-fluoro-4-(2-fluorophenoxy)-6-methylphenyl]pyrazol-4-yl]-[5-(2,2-difluoroethoxy)-6-[(1-methylsulfonylazetidin-3-yl)amino]-1H-indol-2-yl]methanone, (4-23-028) [5-amino-1-[2-fluoro-4-(2-fluorophenoxy)-6-methylphenyl]pyrazol-4-yl]-[5-(2,2-difluoroethoxy)-6-[(1-methylsulfonylpiperidin-4-yl)amino]-1H-indol-2-yl]methanone, (4-23-029) 1-[2-[5-amino-1-[6-(2,6-difluorophenoxy)-4-methylpyridin-3-yl]pyrazole-4-carbonyl]-5-(2,2-difluoroethoxy)-1H-indol-6-yl]-6-methylpyrimidine-2,4-dione, (4-23-030) 1-[2-[5-amino-1-[4-(2-fluorophenoxy)-2-methylphenyl]pyrazole-4-carbonyl]-5-(2,2-difluoroethoxy)-1H-indol-6-yl]-6-methylpyrimidine-2,4-dione, (4-23-031) 1-[2-[5-amino-1-[4-(2-fluorophenoxy)-2-methylphenyl]pyrazole-4-carbonyl]-5-(difluoromethoxy)-1H-indol-6-yl]-6-methylpyrimidine-2,4-dione, (4-23-032) 3-[2-[5-amino-1-[6-(2,6-difluorophenoxy)-4-methylpyridin-3-yl]pyrazole-4-carbonyl]-5-(2,2-difluoroethoxy)-1H-indol-6-yl]-5,5-dimethylimidazolidine-2,4-dione, (4-23-033) 3-[2-[5-amino-1-[4-(2-fluorophenoxy)-2-methylphenyl]pyrazole-4-carbonyl]-5-(2,2-difluoroethoxy)-1H-indol-6-yl]-5,5-dimethylimidazolidine-2,4-dione, (4-23-034) 3-[2-[5-amino-1-[6-(2,6-difluorophenoxy)-4-methylpyridin-3-yl]pyrazole-4-carbonyl]-5-(difluoromethoxy)-1H-indol-6-yl]-5,5-dimethylimidazolidine-2,4-dione, (4-23-035) 3-[2-[5-amino-1-[4-(2-fluorophenoxy)-2-methylphenyl]pyrazole-4-carbonyl]-5-(difluoromethoxy)-1H-indol-6-yl]-5,5-dimethylimidazolidine-2,4-dione, (4-23-036) 3-[2-[5-amino-1-[6-(2,6-difluorophenoxy)-4-methylpyridin-3-yl]pyrazole-4-carbonyl]-5-(2,2-difluoroethoxy)-1H-indol-6-yl]-5,5-dimethyl-2-sulfanylideneimidazolidin-4-one, (4-23-037) 3-[2-[5-amino-1-[4-(2-fluorophenoxy)-2-methylphenyl]pyrazole-4-carbonyl]-5-(2,2-difluoroethoxy)-1H-indol-6-yl]-5,5-dimethyl-2-sulfanylideneimidazolidin-4-one, (4-23-038) 3-[2-[5-amino-1-[6-(2,6-difluorophenoxy)-4-methylpyridin-3-yl]pyrazole-4-carbonyl]-5-(difluoromethoxy)-1H-indol-6-yl]-5,5-dimethyl-2-sulfanylideneimidazolidin-4-one, (4-23-039) 3-[2-[5-amino-1-[4-(2-fluorophenoxy)-2-methylphenyl]pyrazole-4-carbonyl]-5-(difluoromethoxy)-1H-indol-6-yl]-5,5-dimethyl-2-sulfanylideneimidazolidin-4-one, (4-24-001) N-[2-[5-amino-1-[4-(2-fluorophenoxy)-2-methylphenyl]pyrazole-4-carbonyl]-5-(difluoromethoxy)-1H-indol-6-yl]cyclopropanesulfonamide, (4-24-002) N-[2-[5-amino-1-[4-(2-fluorophenoxy)-2-methylphenyl]pyrazole-4-carbonyl]-5-(difluoromethoxy)-1H-indol-6-yl]methanesulfonamide, (4-24-003) N-[2-[5-amino-1-[4-(2-fluorophenoxy)-2-methylphenyl]pyrazole-4-carbonyl]-5-(difluoromethoxy)-1H-indol-6-yl]-3-fluoropropane-1-sulfonamide, (4-24-004) N-[2-[5-amino-1-[4-(2-fluorophenoxy)-2-methylphenyl]pyrazole-4-carbonyl]-5-(difluoromethoxy)-1H-indol-6-yl]-3,3-difluoropropane-1-sulfonamide, (4-24-005) N-[2-[5-amino-1-[2-fluoro-4-(2-fluorophenoxy)-6-methylphenyl]pyrazole-4-carbonyl]-5-(difluoromethoxy)-1H-indol-6-yl]cyclopropanesulfonamide, (4-24-006) N-[2-[5-amino-1-[2-fluoro-4-(2-fluorophenoxy)-6-methylphenyl]pyrazole-4-carbonyl]-5-(difluoromethoxy)-1H-indol-6-yl]-3-fluoropropane-1-sulfonamide, (4-24-007) N-[2-[5-amino-1-[6-(2-fluorophenoxy)-4-methylpyridin-3-yl]pyrazole-4-carbonyl]-5-(difluoromethoxy)-1H-indol-6-yl]cyclopropanesulfonamide, (4-24-008) N-[2-[5-amino-1-[6-(2-fluorophenoxy)-4-methylpyridin-3-yl]pyrazole-4-carbonyl]-5-(difluoromethoxy)-1H-indol-6-yl]methanesulfonamide, (4-24-009) N-[2-[5-amino-1-[6-(2-fluorophenoxy)-4-methylpyridin-3-yl]pyrazole-4-carbonyl]-5-(difluoromethoxy)-1H-indol-6-yl]-3-fluoropropane-1-sulfonamide, (4-24-010) N-[2-[5-amino-1-[6-(2,6-difluorophenoxy)-4-methylpyridin-3-yl]pyrazole-4-carbonyl]-5-(difluoromethoxy)-1H-indol-6-yl]cyclopropanesulfonamide, (4-24-011) N-[2-[5-amino-1-[6-(2,6-difluorophenoxy)-4-methylpyridin-3-yl]pyrazole-4-carbonyl]-5-(difluoromethoxy)-1H-indol-6-yl]methanesulfonamide, (4-24-012) N-[2-[5-amino-1-[6-(2,6-difluorophenoxy)-4-methylpyridin-3-yl]pyrazole-4-carbonyl]-5-(difluoromethoxy)-1H-indol-6-yl]-3-fluoropropane-1-sulfonamide, (4-24-013) N-[2-[5-amino-1-[4-(2-fluorophenoxy)-2-methylphenyl]pyrazole-4-carbonyl]-5-morpholin-4-yl-1H-indol-6-yl]methanesulfonamide, (4-24-014) N-[2-[5-amino-1-[6-(2-fluorophenoxy)-4-methylpyridin-3-yl]pyrazole-4-carbonyl]-5-morpholin-4-yl-1H-indol-6-yl]cyclopropanesulfonamide, (4-24-015) N-[2-[5-amino-1-[6-(2-fluorophenoxy)-4-methylpyridin-3-yl]pyrazole-4-carbonyl]-5-morpholin-4-yl-1H-indol-6-yl]methanesulfonamide, (4-24-016) N-[2-[5-amino-1-[6-(2-fluorophenoxy)-4-methylpyridin-3-yl]pyrazole-4-carbonyl]-5-morpholin-4-yl-1H-indol-6-yl]-3-fluoropropane-1-sulfonamide, (4-24-017) N-[2-[5-amino-1-[6-(2,6-difluorophenoxy)-4-methylpyridin-3-yl]pyrazole-4-carbonyl]-5-morpholin-4-yl-1H-indol-6-yl]cyclopropanesulfonamide, (4-24-018) N-[2-[5-amino-1-[6-(2,6-difluorophenoxy)-4-methylpyridin-3-yl]pyrazole-4-carbonyl]-5-morpholin-4-yl-1H-indol-6-yl]methanesulfonamide, (4-24-019) N-[2-[5-amino-1-[6-(2,6-difluorophenoxy)-4-methylpyridin-3-yl]pyrazole-4-carbonyl]-5-morpholin-4-yl-1H-indol-6-yl]-3-fluoropropane-1-sulfonamide, (4-24-020) N-[2-[5-amino-1-[4-(2-fluorophenoxy)-2-methylphenyl]pyrazole-4-carbonyl]-5-(2,2-difluoroethoxy)-1H-indol-6-yl]cyclopropanesulfonamide, (4-24-021) N-[2-[5-amino-1-[4-(2-fluorophenoxy)-2-methylphenyl]pyrazole-4-carbonyl]-5-(2,2-difluoroethoxy)-1H-indol-6-yl]methanesulfonamide, (4-24-022) N-[2-[5-amino-1-[4-(2-fluorophenoxy)-2-methylphenyl]pyrazole-4-carbonyl]-5-(2,2-difluoroethoxy)-1H-indol-6-yl]-3-fluoropropane-1-sulfonamide, (4-24-023) N-[2-[5-amino-1-[4-(2-fluorophenoxy)-2-methylphenyl]pyrazole-4-carbonyl]-5-(2,2-difluoroethoxy)-1H-indol-6-yl]-3,3-difluoropropane-1-sulfonamide, (4-24-024) N-[2-[5-amino-1-[2-fluoro-4-(2-fluorophenoxy)-6-methylphenyl]pyrazole-4-carbonyl]-5-(2,2-difluoroethoxy)-1H-indol-6-yl]cyclopropanesulfonamide, (4-24-025) N-[2-[5-amino-1-[2-fluoro-4-(2-fluorophenoxy)-6-methylphenyl]pyrazole-4-carbonyl]-5-(2,2-difluoroethoxy)-1H-indol-6-yl]methanesulfonamide, (4-24-026) N-[2-[5-amino-1-[2-fluoro-4-(2-fluorophenoxy)-6-methylphenyl]pyrazole-4-carbonyl]-5-(2,2-difluoroethoxy)-1H-indol-6-yl]-3-fluoropropane-1-sulfonamide, (4-24-027) N-[2-[5-amino-1-[6-(2-fluorophenoxy)-4-methylpyridin-3-yl]pyrazole-4-carbonyl]-5-(2,2-difluoroethoxy)-1H-indol-6-yl]cyclopropanesulfonamide, (4-24-028) N-[2-[5-amino-1-[6-(2-fluorophenoxy)-4-methylpyridin-3-yl]pyrazole-4-carbonyl]-5-(2,2-difluoroethoxy)-1H-indol-6-yl]methanesulfonamide, (4-24-029) N-[2-[5-amino-1-[6-(2-fluorophenoxy)-4-methylpyridin-3-yl]pyrazole-4-carbonyl]-5-(2,2-difluoroethoxy)-1H-indol-6-yl]-3-fluoropropane-1-sulfonamide, (4-24-030) N-[2-[5-amino-1-[6-(2,6-difluorophenoxy)-4-methylpyridin-3-yl]pyrazole-4-carbonyl]-5-(2,2-difluoroethoxy)-1H-indol-6-yl]cyclopropanesulfonamide, (4-24-031) N-[2-[5-amino-1-[6-(2,6-difluorophenoxy)-4-methylpyridin-3-yl]pyrazole-4-carbonyl]-5-(2,2-difluoroethoxy)-1H-indol-6-yl]methanesulfonamide, (4-24-032) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-3-fluoropropane-1-sulfonamide, (4-24-033) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-3,3-difluoropropane-1-sulfonamide, (4-24-034) N-[2-[5-amino-1-[4-(2-fluorophenoxy)-2-methylphenyl]pyrazole-4-carbonyl]-5-(2-morpholin-4-ylethoxy)-1H-indol-6-yl]methanesulfonamide, (4-24-035) N-[2-[5-amino-1-[6-(2,6-difluorophenoxy)-4-methylpyridin-3-yl]pyrazole-4-carbonyl]-5-methoxy-1H-indol-6-yl]cyclopropanesulfonamide, (4-24-036) N-[2-[5-amino-1-[4-(2-fluorophenoxy)-2-methylphenyl]pyrazole-4-carbonyl]-5-(oxan-4-yloxy)-1H-indol-6-yl]methanesulfonamide, (4-24-037) N-[2-[5-amino-1-[4-(2-fluorophenoxy)-2-methylphenyl]pyrazole-4-carbonyl]-5-[2-[(1S,5R)-6-methylsulfonyl-3,6-diazabicyclo[3.1.1]heptan-3-yl]ethoxy]-1H-indol-6-yl]methanesulfonamide, (4-24-038) N-[2-[5-amino-1-[4-(2-fluorophenoxy)-2-methylphenyl]pyrazole-4-carbonyl]-5-[2-[(1S,4S)-2-methylsulfonyl-2,5-diazabicyclo[2.2.1]heptan-5-yl]ethoxy]-1H-indol-6-yl]methanesulfonamide, (4-24-039) N-[2-[5-amino-1-[4-(2-fluorophenoxy)-2-methylphenyl]pyrazole-4-carbonyl]-5-[2-[(1S,5R)-3-oxa-8-azabicyclo[3.2.1]octan-8-yl]ethoxy]-1H-indol-6-yl]methanesulfonamide, (4-25-001) [5-amino-1-[6-(2-fluorophenoxy)-4-methylpyridin-3-yl]pyrazol-4-yl]-[5-(2,2-difluoroethoxy)-6-(1,1-dioxo-1,2-thiazolidin-2-yl)-1H-indol-2-yl]methanone, (4-25-002) [5-amino-1-[4-(2-fluorophenoxy)-2-methylphenyl]pyrazol-4-yl]-[5-(difluoromethoxy)-6-(1,1-dioxo-1,2-thiazolidin-2-yl)-1H-indol-2-yl]methanone, (4-25-003) [5-amino-1-[2-fluoro-4-(2-fluorophenoxy)-6-methylphenyl]pyrazol-4-yl]-[5-(difluoromethoxy)-6-(1,1-dioxo-1,2-thiazolidin-2-yl)-1H-indol-2-yl]methanone, (4-25-004) [5-amino-1-[6-(2-fluorophenoxy)-4-methylpyridin-3-yl]pyrazol-4-yl]-[5-(difluoromethoxy)-6-(1,1-dioxo-1,2-thiazolidin-2-yl)-1H-indol-2-yl]methanone, (4-25-005) [5-amino-1-[6-(2,6-difluorophenoxy)-4-methylpyridin-3-yl]pyrazol-4-yl]-[5-(difluoromethoxy)-6-(1,1-dioxo-1,2-thiazolidin-2-yl)-1H-indol-2-yl]methanone, (4-25-006) [5-amino-1-[4-(2-fluorophenoxy)-2-methylphenyl]pyrazol-4-yl]-[6-(1,1-dioxo-1,2-thiazolidin-2-yl)-5-morpholin-4-yl-1H-indol-2-yl]methanone, (4-25-007) [5-amino-1-[6-(2-fluorophenoxy)-4-methylpyridin-3-yl]pyrazol-4-yl]-[6-(1,1-dioxo-1,2-thiazolidin-2-yl)-5-morpholin-4-yl-1H-indol-2-yl]methanone, (4-25-008) [5-amino-1-[6-(2,6-difluorophenoxy)-4-methylpyridin-3-yl]pyrazol-4-yl]-[6-(1,1-dioxo-1,2-thiazolidin-2-yl)-5-morpholin-4-yl-1H-indol-2-yl]methanone, (4-25-009) [5-amino-1-[4-(2-fluorophenoxy)-2-methylphenyl]pyrazol-4-yl]-[5-(2,2-difluoroethoxy)-6-(1,1-dioxo-1,2-thiazolidin-2-yl)-1H-indol-2-yl]methanone, (4-25-010) [5-amino-1-[2-fluoro-4-(2-fluorophenoxy)-6-methylphenyl]pyrazol-4-yl]-[5-(2,2-difluoroethoxy)-6-(1,1-dioxo-1,2-thiazolidin-2-yl)-1H-indol-2-yl]methanone, (4-25-011) [5-amino-1-[6-(2,6-difluorophenoxy)-4-methylpyridin-3-yl]pyrazol-4-yl]-[5-(2,2-difluoroethoxy)-6-(1,1-dioxo-1,2-thiazolidin-2-yl)-1H-indol-2-yl]methanone, (4-25-012) [5-amino-1-[4-(2-fluorophenoxy)-2-methylphenyl]pyrazol-4-yl]-[6-(1,1-dioxo-1,2-thiazolidin-2-yl)-5-(2-morpholin-4-ylethoxy)-1H-indol-2-yl]methanone, (4-25-013) 1-[2-[5-amino-1-[6-(2-fluorophenoxy)-4-methylpyridin-3-yl]pyrazole-4-carbonyl]-5-(2,2-difluoroethoxy)-1H-indol-6-yl]pyrrolidin-2-one (4-25-014) 1-[2-[5-amino-1-[6-(2-fluorophenoxy)-4-methylpyridin-3-yl]pyrazole-4-carbonyl]-5-(difluoromethoxy)-1H-indol-6-yl]pyrrolidin-2-one (4-25-015) 1-[2-[5-amino-1-[2-fluoro-4-(2-fluorophenoxy)-6-methylphenyl]pyrazole-4-carbonyl]-5-(difluoromethoxy)-1H-indol-6-yl]pyrrolidin-2-one (4-25-016) 3-[2-[5-amino-1-[6-(2-fluorophenoxy)-4-methylpyridin-3-yl]pyrazole-4-carbonyl]-5-(2,2-difluoroethoxy)-1H-indol-6-yl]-1,3-oxazolidin-2-one (4-25-017) 3-[2-[5-amino-1-[2-fluoro-4-(2-fluorophenoxy)-6-methylphenyl]pyrazole-4-carbonyl]-5-(2,2-difluoroethoxy)-1H-indol-6-yl]-1,3-oxazolidin-2-one (4-25-018) 3-[2-[5-amino-1-[6-(2-fluorophenoxy)-4-methylpyridin-3-yl]pyrazole-4-carbonyl]-5-(difluoromethoxy)-1H-indol-6-yl]-1,3-oxazolidin-2-one (4-25-019) 3-[2-[5-amino-1-[2-fluoro-4-(2-fluorophenoxy)-6-methylphenyl]pyrazole-4-carbonyl]-5-(difluoromethoxy)-1H-indol-6-yl]-1,3-oxazolidin-2-one (4-25-020) [5-amino-1-[6-(2-fluorophenoxy)-4-methylpyridin-3-yl]pyrazol-4-yl]-[5-(2,2-difluoroethoxy)-6-morpholin-4-yl-1H-indol-2-yl]methanone, (4-25-021) [5-amino-1-[2-fluoro-4-(2-fluorophenoxy)-6-methylphenyl]pyrazol-4-yl]-[5-(2,2-difluoroethoxy)-6-morpholin-4-yl-1H-indol-2-yl]methanone, (4-25-022) [5-amino-1-[6-(2-fluorophenoxy)-4-methylpyridin-3-yl]pyrazol-4-yl]-[5-(difluoromethoxy)-6-morpholin-4-yl-1H-indol-2-yl]methanone, (4-25-023) [5-amino-1-[6-(2,6-difluorophenoxy)-4-methylpyridin-3-yl]pyrazol-4-yl]-[5-(difluoromethoxy)-6-morpholin-4-yl-1H-indol-2-yl]methanone, (4-25-024) [5-amino-1-[4-(2-fluorophenoxy)-2-methylphenyl]pyrazol-4-yl]-[5-(difluoromethoxy)-6-morpholin-4-yl-1H-indol-2-yl]methanone, (4-25-025) [5-amino-1-[2-fluoro-4-(2-fluorophenoxy)-6-methylphenyl]pyrazol-4-yl]-[5-(difluoromethoxy)-6-morpholin-4-yl-1H-indol-2-yl]methanone, (4-25-026) [5-amino-1-[6-(2-fluorophenoxy)-4-methylpyridin-3-yl]pyrazol-4-yl]-[5-(2,2-difluoroethoxy)-6-(4-morpholin-4-ylpiperidin-1-yl)-1H-indol-2-yl]methanone, (4-25-027) [5-amino-1-[6-(2,6-difluorophenoxy)-4-methylpyridin-3-yl]pyrazol-4-yl]-[5-(2,2-difluoroethoxy)-6-(4-morpholin-4-ylpiperidin-1-yl)-1H-indol-2-yl]methanone, (4-25-028) [5-amino-1-[4-(2-fluorophenoxy)-2-methylphenyl]pyrazol-4-yl]-[5-(2,2-difluoroethoxy)-6-(4-morpholin-4-ylpiperidin-1-yl)-1H-indol-2-yl]methanone, (4-25-029) [5-amino-1-[2-fluoro-4-(2-fluorophenoxy)-6-methylphenyl]pyrazol-4-yl]-[5-(2,2-difluoroethoxy)-6-(4-morpholin-4-ylpiperidin-1-yl)-1H-indol-2-yl]methanone, (4-25-030) [5-amino-1-[6-(2-fluorophenoxy)-4-methylpyridin-3-yl]pyrazol-4-yl]-[5-(difluoromethoxy)-6-(4-morpholin-4-ylpiperidin-1-yl)-1H-indol-2-yl]methanone, (4-25-031) [5-amino-1-[6-(2,6-difluorophenoxy)-4-methylpyridin-3-yl]pyrazol-4-yl]-[5-(difluoromethoxy)-6-(4-morpholin-4-ylpiperidin-1-yl)-1H-indol-2-yl]methanone, (4-25-032) [5-amino-1-[4-(2-fluorophenoxy)-2-methylphenyl]pyrazol-4-yl]-[5-(difluoromethoxy)-6-(4-morpholin-4-ylpiperidin-1-yl)-1H-indol-2-yl]methanone, (4-26-001) N-[2-[5-amino-1-[4-(2-fluorophenoxy)-2-methylphenyl]pyrazole-4-carbonyl]-5-fluoro-1H-indol-6-yl]-2-oxo-2-pyrrolidin-1-ylethanesulfonamide, (5-1-001) [5-amino-1-[4-(2-chlorophenoxy)phenyl]pyrazol-4-yl]-[6-fluoro-5-(1-propan-2-ylpiperidin-4-yl)-1H-indol-2-yl]methanone, (5-1-002) [5-amino-1-[2-fluoro-4-(3-fluorophenoxy)phenyl]pyrazol-4-yl]-[6-fluoro-5-(1-propan-2-ylpiperidin-4-yl)-1H-indol-2-yl]methanone, (5-1-003) [5-amino-1-[4-(3-chlorophenoxy)-2-fluorophenyl]pyrazol-4-yl]-[6-fluoro-5-(1-propan-2-ylpiperidin-4-yl)-1H-indol-2-yl]methanone, (5-1-004) [5-amino-1-[4-(2-fluorophenoxy)phenyl]pyrazol-4-yl]-[6-fluoro-5-(1-propan-2-ylpiperidin-4-yl)-1H-indol-2-yl]methanone, (5-1-005) [5-amino-1-[4-(3-fluorophenoxy)-2-methylphenyl]pyrazol-4-yl]-[6-fluoro-5-(1-propan-2-ylpiperidin-4-yl)-1H-indol-2-yl]methanone, (5-1-006) [5-amino-1-[2-fluoro-4-(3-fluorophenoxy)phenyl]pyrazol-4-yl]-[5-fluoro-6-(1-propan-2-ylpiperidin-4-yl)-1H-indol-2-yl]methanone, (5-1-007) [5-amino-1-[4-(2-fluorophenoxy)phenyl]pyrazol-4-yl]-[5-fluoro-6-(1-propan-2-ylpiperidin-4-yl)-1H-indol-2-yl]methanone, (5-1-008) [5-amino-1-[4-(3-chlorophenoxy)phenyl]pyrazol-4-yl]-[5-fluoro-6-(1-propan-2-ylpiperidin-4-yl)-1H-indol-2-yl]methanone, (5-1-009) [5-amino-1-[4-(3-fluorophenoxy)-2-methylphenyl]pyrazol-4-yl]-[5-fluoro-6-(1-propan-2-ylpiperidin-4-yl)-1H-indol-2-yl]methanone, (5-1-010) [5-amino-1-[4-(3-chlorophenoxy)-2-fluorophenyl]pyrazol-4-yl]-[5-fluoro-6-(1-propan-2-ylpiperidin-4-yl)-1H-indol-2-yl]methanone, (5-1-011) [5-amino-1-[4-(2,3-difluorophenoxy)-2-fluorophenyl]pyrazol-4-yl]-[5-fluoro-6-(1-propan-2-ylpiperidin-4-yl)-1H-indol-2-yl]methanone, (5-1-012) [5-amino-1-[4-(2-fluorophenoxy)-3-methylphenyl]pyrazol-4-yl]-[5-methyl-6-(1-propan-2-ylpiperidin-4-yl)-1H-indol-2-yl]methanone, (5-1-013) [5-amino-1-[4-(2,3-difluorophenoxy)phenyl]pyrazol-4-yl]-[5-fluoro-6-(1-propan-2-ylpiperidin-4-yl)-1H-indol-2-yl]methanone, (5-1-014) [5-amino-1-[4-(3-fluorophenoxy)phenyl]pyrazol-4-yl]-[5-fluoro-6-(1-propan-2-ylpiperidin-4-yl)-1H-indol-2-yl]methanone, (5-1-015) [5-amino-1-[4-(2-chlorophenoxy)phenyl]pyrazol-4-yl]-[5-fluoro-6-(1-propan-2-ylpiperidin-4-yl)-1H-indol-2-yl]methanone, (5-1-016) N-[2-[5-amino-1-[2-chloro-4-(2,3-difluorophenoxy)phenyl]pyrazole-4-carbonyl]-5-fluoro-1H-indol-6-yl]methanesulfonamide, (5-1-017) N-[2-[5-amino-1-[4-(2-fluorophenoxy)-3-methylphenyl]pyrazole-4-carbonyl]-5-fluoro-1H-indol-6-yl]methanesulfonamide, (5-1-018) N-[2-[5-amino-1-[2-chloro-4-(2-fluorophenoxy)phenyl]pyrazole-4-carbonyl]-5-fluoro-1H-indol-6-yl]methanesulfonamide, (5-1-019) N-[2-[5-amino-1-[2,6-difluoro-4-(2-fluorophenoxy)phenyl]pyrazole-4-carbonyl]-5-fluoro-1H-indol-6-yl]cyclopropanesulfonamide, (5-1-020) [5-amino-1-[6-(2-fluorophenoxy)-4-methylpyridin-3-yl]pyrazol-4-yl]-[6-(cyclopropylsulfamoylamino)-5-fluoro-1H-indol-2-yl]methanone, (5-1-021) [5-amino-1-[6-(2-fluorophenoxy)-4-methylpyridin-3-yl]pyrazol-4-yl]-[5-fluoro-6-(propan-2-ylsulfamoylamino)-1H-indol-2-yl]methanone, (5-1-022) N-[2-[5-amino-1-[2,6-difluoro-4-(2-fluorophenoxy)phenyl]pyrazole-4-carbonyl]-5-fluoro-1H-indol-6-yl]methanesulfonamide, (5-1-023) N-[2-[5-amino-1-[2,6-dichloro-4-(2-fluorophenoxy)phenyl]pyrazole-4-carbonyl]-5-fluoro-1H-indol-6-yl]methanesulfonamide, (5-1-024) N-[2-[5-amino-1-[2,6-dichloro-4-(2,3-difluorophenoxy)phenyl]pyrazole-4-carbonyl]-5-fluoro-1H-indol-6-yl]methanesulfonamide, (5-1-025) N-[2-[5-amino-1-[2,6-dichloro-4-(2-fluorophenoxy)phenyl]pyrazole-4-carbonyl]-5-fluoro-1H-indol-6-yl]cyclopropanesulfonamide, (5-1-026) N-[2-[5-amino-1-[2,6-dichloro-4-(2,3-difluorophenoxy)phenyl]pyrazole-4-carbonyl]-5-fluoro-1H-indol-6-yl]cyclopropanesulfonamide, (5-1-027) N-[2-[5-amino-1-[2,6-difluoro-4-(2-fluorophenoxy)phenyl]pyrazole-4-carbonyl]-5-fluoro-1H-indol-6-yl]-3-fluoropropane-1-sulfonamide, (5-1-028) N-[2-[5-amino-1-[2,6-dichloro-4-(2,3-difluorophenoxy)phenyl]pyrazole-4-carbonyl]-5-fluoro-1H-indol-6-yl]-3-fluoropropane-1-sulfonamide, (5-1-029) N-[2-[5-amino-1-[4-(2-fluorophenoxy)-2-methylphenyl]pyrazole-4-carbonyl]-5-fluoro-1H-indol-6-yl]-2,2,2-trifluoroacetamide, (5-1-030) N-[2-[5-amino-1-[4-(2,3-difluorophenoxy)-2,6-difluorophenyl]pyrazole-4-carbonyl]-5-fluoro-1H-indol-6-yl]methanesulfonamide, (5-1-031) N-[2-[5-amino-1-[4-(2,3-difluorophenoxy)-2,6-difluorophenyl]pyrazole-4-carbonyl]-5-fluoro-1H-indol-6-yl]cyclopropanesulfonamide, (5-1-032) N-[2-[5-amino-1-[4-(2-fluorophenoxy)-2,6-dimethylphenyl]pyrazole-4-carbonyl]-5-fluoro-1H-indol-6-yl]methanesulfonamide, (5-1-033) N-[2-[5-amino-1-[2,6-dichloro-4-(2-fluorophenoxy)phenyl]pyrazole-4-carbonyl]-5-fluoro-1H-indol-6-yl]-3-fluoropropane-1-sulfonamide, (5-1-034) N-[2-[5-amino-1-[4-(2,3-difluorophenoxy)-2,6-difluorophenyl]pyrazole-4-carbonyl]-5-fluoro-1H-indol-6-yl]-3-fluoropropane-1-sulfonamide, (5-1-035) N-[2-[5-amino-1-[2-fluoro-4-(3-fluoropyridin-2-yl)oxyphenyl]pyrazole-4-carbonyl]-5-fluoro-1H-indol-6-yl]-3-fluoropropane-1-sulfonamide, (5-1-036) N-[2-[5-amino-1-[4-(3-chloropyridin-2-yl)oxy-2-fluorophenyl]pyrazole-4-carbonyl]-5-fluoro-1H-indol-6-yl]-3-fluoropropane-1-sulfonamide, (5-1-037) N-[2-[5-amino-1-[2-chloro-4-(3-chloropyridin-2-yl)oxyphenyl]pyrazole-4-carbonyl]-5-fluoro-1H-indol-6-yl]-3-fluoropropane-1-sulfonamide, (5-1-038) N-[2-[5-amino-1-[6-(3,5-difluorophenoxy)-4-methylpyridin-3-yl]pyrazole-4-carbonyl]-5-fluoro-1H-indol-6-yl]methanesulfonamide, (5-1-039) N-[2-[5-amino-1-[6-(2-fluorophenoxy)-5-methylpyridin-3-yl]pyrazole-4-carbonyl]-5-fluoro-1H-indol-6-yl]methanesulfonamide, (5-1-040) N-[2-[5-amino-1-[4-(2-fluorophenoxy)-2,6-dimethylphenyl]pyrazole-4-carbonyl]-5-fluoro-1H-indol-6-yl]-3-fluoropropane-1-sulfonamide, (5-1-041) N-[2-[5-amino-1-[6-(2-chlorophenoxy)-5-methylpyridin-3-yl]pyrazole-4-carbonyl]-5-fluoro-1H-indol-6-yl]methanesulfonamide, (5-1-042) N-[2-[5-amino-1-[6-(3-chlorophenoxy)-5-methylpyridin-3-yl]pyrazole-4-carbonyl]-5-fluoro-1H-indol-6-yl]methanesulfonamide, (5-1-043) N-[2-[5-amino-1-[6-(2-chloro-6-fluorophenoxy)-5-methylpyridin-3-yl]pyrazole-4-carbonyl]-5-fluoro-1H-indol-6-yl]methanesulfonamide, (5-1-044) N-[2-[5-amino-1-[6-(2,3-difluorophenoxy)-5-methylpyridin-3-yl]pyrazole-4-carbonyl]-5-fluoro-1H-indol-6-yl]methanesulfonamide, (5-1-045) N-[2-[5-amino-1-[6-(3,5-difluorophenoxy)-5-methylpyridin-3-yl]pyrazole-4-carbonyl]-5-fluoro-1H-indol-6-yl]methanesulfonamide, (5-1-046) N-[2-[5-amino-1-[6-(4-fluorophenoxy)-4-methylpyridin-3-yl]pyrazole-4-carbonyl]-5-fluoro-1H-indol-6-yl]cyclopropanesulfonamide, (5-1-047) N-[2-[5-amino-1-[4-methyl-6-(2-methylphenoxy)pyridin-3-yl]pyrazole-4-carbonyl]-6-fluoro-1H-indol-5-yl]methanesulfonamide, (5-1-048) N-[2-[5-amino-1-[4-(3-chlorophenoxy)-2-fluoro-6-methylphenyl]pyrazole-4-carbonyl]-6-fluoro-1H-indol-5-yl]methanesulfonamide, (5-1-049) N-[2-[5-amino-1-[6-(2,3-difluorophenoxy)-4-methylpyridin-3-yl]pyrazole-4-carbonyl]-6-fluoro-1H-indol-5-yl]methanesulfonamide, (5-1-050) N-[2-[5-amino-1-[6-(2-chlorophenoxy)-4-methylpyridin-3-yl]pyrazole-4-carbonyl]-6-fluoro-1H-indol-5-yl]methanesulfonamide, (5-1-051) N-[2-[5-amino-1-[6-(2-chlorophenoxy)-2,4-dimethylpyridin-3-yl]pyrazole-4-carbonyl]-5-fluoro-1H-indol-6-yl]methanesulfonamide, (5-1-052) N-[2-[5-amino-1-[6-(3-chlorophenoxy)-2,4-dimethylpyridin-3-yl]pyrazole-4-carbonyl]-5-fluoro-1H-indol-6-yl]methanesulfonamide, (5-1-053) N-[2-[5-amino-1-[6-(2,3-difluorophenoxy)-2,4-dimethylpyridin-3-yl]pyrazole-4-carbonyl]-5-fluoro-1H-indol-6-yl]methanesulfonamide, (5-1-054) N-[2-[5-amino-1-[6-(3,5-difluorophenoxy)-2,4-dimethylpyridin-3-yl]pyrazole-4-carbonyl]-5-fluoro-1H-indol-6-yl]methanesulfonamide, (5-1-055) N-[2-[5-amino-1-[6-(2,5-dichlorophenoxy)-4-methylpyridin-3-yl]pyrazole-4-carbonyl]-5-fluoro-1H-indol-6-yl]methanesulfonamide, (5-1-056) 2-[[2-[5-amino-1-[6-(2-fluorophenoxy)-4-methylpyridin-3-yl]pyrazole-4-carbonyl]-5-fluoro-1H-indol-6-yl]sulfamoyl]-N-propan-2-ylacetamide, (5-1-057) [5-amino-1-[6-(2-fluorophenoxy)-4-methylpyridin-3-yl]pyrazol-4-yl]-[5-methyl-6-(oxan-4-ylsulfamoylamino)-1H-indol-2-yl]methanone, (5-1-058) 2-[[2-[5-amino-1-[6-(2-fluorophenoxy)-4-methylpyridin-3-yl]pyrazole-4-carbonyl]-5-methyl-1H-indol-6-yl]sulfamoyl]-N-propan-2-ylacetamide, (5-1-059) N-[2-[5-amino-1-[6-(3-fluorophenoxy)-4-methylpyridin-3-yl]pyrazole-4-carbonyl]-5-fluoro-1H-indol-6-yl]-3-fluoropropane-1-sulfonamide, (5-1-060) N-[2-[5-amino-1-[6-(2-fluorophenoxy)-2,4-dimethylpyridin-3-yl]pyrazole-4-carbonyl]-5-fluoro-1H-indol-6-yl]methanesulfonamide, (5-1-061) N-[2-[5-amino-1-[4-(2-fluorophenoxy)-2-methylphenyl]pyrazole-4-carbonyl]-5-hydroxy-1H-indol-6-yl]methanesulfonamide, (5-1-062) [5-amino-1-[2-chloro-4-(3-chloropyridin-2-yl)oxyphenyl]pyrazol-4-yl]-[6-(1,1-dioxo-1,2-thiazolidin-2-yl)-5-methyl-1H-indol-2-yl]methanone, (5-1-063) N-[2-[5-amino-1-[2-chloro-4-(3-chloropyridin-2-yl)oxyphenyl]pyrazole-4-carbonyl]-5-methyl-1H-indol-6-yl]-3-fluoropropane-1-sulfonamide, (5-1-064) N-[2-[5-amino-1-[6-(4-fluorophenoxy)-4-methylpyridin-3-yl]pyrazole-4-carbonyl]-5-methyl-1H-indol-6-yl]morpholine-4-sulfonamide, (5-1-065) N-[2-[5-amino-1-[2-chloro-4-(3-chloropyridin-2-yl)oxyphenyl]pyrazole-4-carbonyl]-5-methyl-1H-indol-6-yl]morpholine-4-sulfonamide, (5-1-066) N-[2-[5-amino-1-[4-(2,3-difluorophenoxy)-2-fluoro-6-methylphenyl]pyrazole-4-carbonyl]-5-methyl-1H-indol-6-yl]morpholine-4-sulfonamide, (5-1-067) N-[2-[5-amino-1-[6-(2,6-difluorophenoxy)-4-methylpyridin-3-yl]pyrazole-4-carbonyl]-5-fluoro-1H-indol-6-yl]-N-propan-2-ylmethanesulfonamide, (5-1-068) tert-Butyl 4-[2-[5-amino-1-[4-(2-fluorophenoxy)-2-methylphenyl]pyrazole-4-carbonyl]-5-(2,2-difluoroethoxy)-1H-indol-6-yl]piperidine-1-carboxylate, (5-1-069) tert-Butyl 4-[2-[5-amino-1-[6-(2,6-difluorophenoxy)-4-methylpyridin-3-yl]pyrazole-4-carbonyl]-5-(2,2-difluoroethoxy)-1H-indol-6-yl]piperidine-1-carboxylate, (5-1-070) [5-amino-1-[4-(2-fluorophenoxy)-2-methylphenyl]pyrazol-4-yl]-[6-bromo-5-(2,2-difluoroethoxy)-1H-indol-2-yl]methanone, (5-1-071) [5-amino-1-[4-(2-fluorophenoxy)-2-methylphenyl]pyrazol-4-yl]-[6-(1-cyclopropylsulfonylpiperidin-4-yl)-5-ethoxy-1H-indol-2-yl]methanone, (5-1-072) 1-[2-[5-amino-1-[6-(2,6-difluorophenoxy)-4-methylpyridin-3-yl]pyrazole-4-carbonyl]-5-(difluoromethoxy)-1H-indol-6-yl]-6-methylpyrimidine-2,4-dione, (5-1-073) [5-amino-1-[4-(2-fluorophenoxy)-2-methylphenyl]pyrazol-4-yl]-[5-ethoxy-6-(1-methylsulfonylpiperidin-4-yl)-1H-indol-2-yl]methanone, (5-1-074) [6-amino-5-(difluoromethoxy)-1H-indol-2-yl]-[5-amino-1-[6-(2,6-difluorophenoxy)-4-methylpyridin-3-yl]pyrazol-4-yl]methanone, (5-1-075) [5-amino-1-[6-(2,6-difluorophenoxy)-4-methylpyridin-3-yl]pyrazol-4-yl]-[5-(difluoromethoxy)-6-(4-methylsulfonylpiperazin-1-yl)-1H-indol-2-yl]methanone, (5-1-076) N-[2-[5-amino-1-[2-fluoro-4-(2-fluorophenoxy)-6-methylphenyl]pyrazole-4-carbonyl]-5-(difluoromethoxy)-1H-indol-6-yl]methanesulfonamide, (5-1-077) [5-amino-1-[4-(2-fluorophenoxy)-2-methylphenyl]pyrazol-4-yl]-[5-methyl-6-(4-morpholin-4-ylpiperidin-1-yl)-1H-indol-2-yl]methanone, (5-1-078) [5-amino-1-[6-(2-fluorophenoxy)-4-methylpyridin-3-yl]pyrazol-4-yl]-[5-methyl-6-(4-morpholin-4-ylpiperidin-1-yl)-1H-indol-2-yl]methanone, (5-1-079) [5-amino-1-[6-(2,6-difluorophenoxy)-4-methylpyridin-3-yl]pyrazol-4-yl]-[5-(difluoromethoxy)-6-[(1-methylsulfonylazetidin-3-yl)amino]-1H-indol-2-yl]methanone, (5-1-080) [5-amino-1-[6-(2,6-difluorophenoxy)-4-methylpyridin-3-yl]pyrazol-4-yl]-[6-bromo-5-(2,2-difluoroethoxy)-1H-indol-2-yl]methanone, (5-1-081) N-[2-[5-amino-1-[6-(2,5-difluorophenoxy)-4-methylpyridin-3-yl]pyrazole-4-carbonyl]-5-methyl-1H-indol-6-yl]methanesulfonamide, (5-1-082) [5-amino-1-[4-(2-fluorophenoxy)-2-methylphenyl]pyrazol-4-yl]-[6-bromo-5-(difluoromethoxy)-1H-indol-2-yl]methanone, (5-1-083) [6-amino-5-(difluoromethoxy)-1H-indol-2-yl]-[5-amino-1-[4-(2-fluorophenoxy)-2-methylphenyl]pyrazol-4-yl]methanone, (5-1-084) [5-amino-1-[2-fluoro-4-(2-fluorophenoxy)-6-methylphenyl]pyrazol-4-yl]-(5-methyl-6-morpholin-4-yl-1H-indol-2-yl)methanone, (5-1-085) [5-amino-1-[2-fluoro-4-(2-fluorophenoxy)-6-methylphenyl]pyrazol-4-yl]-[5-methyl-6-(4-morpholin-4-ylpiperidin-1-yl)-1H-indol-2-yl]methanone, (5-1-086) [5-amino-1-[4-(2-fluorophenoxy)-2-methylphenyl]pyrazol-4-yl]-[5-methyl-6-(1-methylsulfonylpiperidin-4-yl)-1H-indol-2-yl]methanone, (5-1-087) [5-amino-1-[4-(2-fluorophenoxy)-2-methylphenyl]pyrazol-4-yl]-[5-(2,2-difluoroethoxy)-6-(4-hydroxypiperidin-1-yl)-1H-indol-2-yl]methanone, (5-1-088) N-[2-[5-amino-1-[6-(2,6-difluorophenoxy)-4-methylpyridin-3-yl]pyrazole-4-carbonyl]-5-methyl-1H-indol-6-yl]-2-oxo-2-pyrrolidin-1-ylethanesulfonamide, (5-1-089) 2-[[2-[5-amino-1-[2-fluoro-4-(2-fluorophenoxy)-6-methylphenyl]pyrazole-4-carbonyl]-5-methyl-1H-indol-6-yl]sulfamoyl]-N-propan-2-ylacetamide, (5-1-090) [5-amino-1-[6-(2-fluorophenoxy)-4-methylpyridin-3-yl]pyrazol-4-yl]-[5-methyl-6-(1-methylsulfonylpiperidin-4-yl)-1H-indol-2-yl]methanone, (5-1-091) [5-amino-1-[6-(2,6-difluorophenoxy)-4-methylpyridin-3-yl]pyrazol-4-yl]-[5-methyl-6-(1-methylsulfonylpiperidin-4-yl)-1H-indol-2-yl]methanone, (5-1-092) N-[2-[5-amino-1-[4-(2,6-difluorophenoxy)-2-methylphenyl]pyrazole-4-carbonyl]-5-methyl-1H-indol-6-yl]methanesulfonamide,
(5-1-093) [5-amino-1-[4-(2-fluorophenoxy)-2-methylphenyl]pyrazol-4-yl]-[6-(4-methylsulfonylpiperazin-1-yl)-5-morpholin-4-yl-1H-indol-2-yl]methanone,
(5-1-094) [5-amino-1-[4-(2-fluorophenoxy)-2-methylphenyl]pyrazol-4-yl]-(5,6-dimorpholin-4-yl-1H-indol-2-yl)methanone,
(5-1-095) 3-[2-[5-amino-1-[4-(2-fluorophenoxy)-2-methylphenyl]pyrazole-4-carbonyl]-5-fluoro-1H-indol-6-yl]-1,3-oxazolidin-2-one,
(5-1-096) N-[2-[5-amino-1-[4-(2-chloro-6-fluorophenoxy)-2-methylphenyl]pyrazole-4-carbonyl]-5-methyl-1H-indol-6-yl]methanesulfonamide,
(5-1-097) 3-[2-[5-amino-1-[6-(2,6-difluorophenoxy)-4-methylpyridin-3-yl]pyrazole-4-carbonyl]-5-fluoro-1H-indol-6-yl]-1,3-oxazolidin-2-one,
(5-1-098) 1-[2-[5-amino-1-[6-(2,6-difluorophenoxy)-4-methylpyridin-3-yl]pyrazole-4-carbonyl]-5-fluoro-1H-indol-6-yl]pyrrolidin-2-one,
(5-1-099) [5-amino-1-[6-(2,6-difluorophenoxy)-4-methylpyridin-3-yl]pyrazol-4-yl]-[5-fluoro-6-(4-methylsulfonylpiperazin-1-yl)-1H-indol-2-yl]methanone,
(5-1-100) [5-amino-1-[6-(2,6-difluorophenoxy)-4-methylpyridin-3-yl]pyrazol-4-yl]-(5-fluoro-6-morpholin-4-yl-1H-indol-2-yl)methanone,
(5-1-101) 1-[2-[5-amino-1-[6-(2,6-difluorophenoxy)-4-methylpyridin-3-yl]pyrazole-4-carbonyl]-5-fluoro-1H-indol-6-yl]-6-methylpyrimidine-2,4-dione,
(5-1-102) [5-amino-1-[6-(2,6-difluorophenoxy)-4-methylpyridin-3-yl]pyrazol-4-yl]-[5-fluoro-6-[(1-methylsulfonylazetidin-3-yl)amino]-1H-indol-2-yl]methanone,
(5-1-103) 1-[2-[5-amino-1-[4-(2-fluorophenoxy)-2-methylphenyl]pyrazole-4-carbonyl]-5-fluoro-1H-indol-6-yl]pyrrolidin-2-one,
(5-1-104) 1-[2-[5-amino-1-[4-(2-fluorophenoxy)-2-methylphenyl]pyrazole-4-carbonyl]-5-fluoro-1H-indol-6-yl]-6-methylpyrimidine-2,4-dione,
(5-1-105) 1-[2-[5-amino-1-[4-(2-fluorophenoxy)-2-methylphenyl]pyrazole-4-carbonyl]-5-morpholin-4-yl-1H-indol-6-yl]pyrrolidin-2-one,
(5-1-106) 3-[2-[5-amino-1-[4-(2-fluorophenoxy)-2-methylphenyl]pyrazole-4-carbonyl]-5-morpholin-4-yl-1H-indol-6-yl]-1,3-oxazolidin-2-one,
(5-1-107) N-[2-[5-amino-1-[4-(2,5-difluorophenoxy)-2-methylphenyl]pyrazole-4-carbonyl]-5-methyl-1H-indol-6-yl]methanesulfonamide,
(5-1-108) N-[2-[5-amino-1-(2-methyl-4-phenoxyphenyl)pyrazole-4-carbonyl]-5-methyl-1H-indol-6-yl]methanesulfonamide,
(5-1-109) N-[2-[5-amino-1-(4-methyl-6-phenoxypyridin-3-yl)pyrazole-4-carbonyl]-5-methyl-1H-indol-6-yl]methanesulfonamide,
(5-1-110) N-[2-[5-amino-1-[2-fluoro-4-(2-fluorophenoxy)-6-methylphenyl]pyrazole-4-carbonyl]-5-methyl-1H-indol-6-yl]-2-oxo-2-pyrrolidin-1-ylethanesulfonamide,
(5-1-111) [5-amino-1-[2-fluoro-4-(2-fluorophenoxy)-6-methylphenyl]pyrazol-4-yl]-[5-methyl-6-(1-methylsulfonylpiperidin-4-yl)-1H-indol-2-yl]methanone,
(5-1-112) [5-amino-1-[6-(2,6-difluorophenoxy)-4-methylpyridin-3-yl]pyrazol-4-yl]-[5-fluoro-6-(4-morpholin-4-ylpiperidin-1-yl)-1H-indol-2-yl]methanone,
(5-1-113) [5-amino-1-[6-(2,6-difluorophenoxy)-4-methylpyridin-3-yl]pyrazol-4-yl]-[5-fluoro-6-[(1-methylsulfonylpiperidin-4-yl)amino]-1H-indol-2-yl]methanone,
(5-1-114) 3-[2-[5-amino-1-[6-(2,6-difluorophenoxy)-4-methylpyridin-3-yl]pyrazole-4-carbonyl]-5-fluoro-1H-indol-6-yl]-5,5-dimethylimidazolidine-2,4-dione,
(5-1-115) 3-[2-[5-amino-1-[6-(2,6-difluorophenoxy)-4-methylpyridin-3-yl]pyrazole-4-carbonyl]-5-fluoro-1H-indol-6-yl]-5,5-dimethyl-2-sulfanylideneimidazolidin-4-one,
(5-1-116) 1-[2-[5-amino-1-[4-(2-fluorophenoxy)-2-methylphenyl]pyrazole-4-carbonyl]-5-morpholin-4-yl-1H-indol-6-yl]-6-methylpyrimidine-2,4-dione,
(5-1-117) 3-[2-[5-amino-1-[4-(2-fluorophenoxy)-2-methylphenyl]pyrazole-4-carbonyl]-5-morpholin-4-yl-1H-indol-6-yl]-5,5-dimethylimidazolidine-2,4-dione,
(5-1-118) [5-amino-1-[4-(2-fluorophenoxy)-2-methylphenyl]pyrazol-4-yl]-[5-fluoro-6-[(1-methylsulfonylazetidin-3-yl)amino]-1H-indol-2-yl]methanone,
(5-1-119) [5-amino-1-[4-(2-fluorophenoxy)-2-methylphenyl]pyrazol-4-yl]-(5-fluoro-6-morpholin-4-yl-1H-indol-2-yl)methanone,
(5-1-120) 3-[2-[5-amino-1-[4-(2-fluorophenoxy)-2-methylphenyl]pyrazole-4-carbonyl]-5-morpholin-4-yl-1H-indol-6-yl]-5,5-dimethyl-2-sulfanylideneimidazolidin-4-one,
(5-1-121) N-[2-[5-amino-1-[6-(2-fluorophenoxy)-4-methylpyridin-3-yl]pyrazole-4-carbonyl]-5-methyl-1H-indol-6-yl]-2-oxo-2-pyrrolidin-1-ylethanesulfonamide,
(5-1-122) N-[2-[5-amino-1-[4-(2-fluorophenoxy)-2-methylphenyl]pyrazole-4-carbonyl]-5-methoxy-1H-indol-6-yl]-2-oxo-2-pyrrolidin-1-ylethanesulfonamide,
(5-1-123) [5-amino-1-[6-(2-fluorophenoxy)-4-methylpyridin-3-yl]pyrazol-4-yl]-[6-(1-cyclopropylsulfonylpiperidin-4-yl)-5-methyl-1H-indol-2-yl]methanone,
(5-1-124) [5-amino-1-[4-(2-fluorophenoxy)-2-methylphenyl]pyrazol-4-yl]-[5-morpholin-4-yl-6-(4-morpholin-4-ylpiperidin-1-yl)-1H-indol-2-yl]methanone,
(5-1-125) [5-amino-1-[4-(2-fluorophenoxy)-2-methylphenyl]pyrazol-4-yl]-[5-fluoro-6-(4-methylsulfonylpiperazin-1-yl)-1H-indol-2-yl]methanone,
(5-1-126) 3-[2-[5-amino-1-[4-(2-fluorophenoxy)-2-methylphenyl]pyrazole-4-carbonyl]-5-fluoro-1H-indol-6-yl]-5,5-dimethyl-2-sulfanylideneimidazolidin-4-one,
(5-1-127) 3-[2-[5-amino-1-[4-(2-fluorophenoxy)-2-methylphenyl]pyrazole-4-carbonyl]-5-fluoro-1H-indol-6-yl]-5,5-dimethylimidazolidine-2,4-dione,
(5-1-128) [5-amino-1-[4-(2-fluorophenoxy)-2-methylphenyl]pyrazol-4-yl]-[5-fluoro-6-(4-morpholin-4-ylpiperidin-1-yl)-1H-indol-2-yl]methanone,
(5-1-129) [5-amino-1-[4-(2-fluorophenoxy)-2-methylphenyl]pyrazol-4-yl]-[6-[(1-methylsulfonylpiperidin-4-yl)amino]-5-morpholin-4-yl-1H-indol-2-yl]methanone,
(5-1-130) N-[2-[5-amino-1-[2-fluoro-4-(2-fluorophenoxy)-6-methylphenyl]pyrazole-4-carbonyl]-5-methoxy-1H-indol-6-yl]-2-oxo-2-pyrrolidin-1-ylethanesulfonamide,
(5-1-131) [5-amino-1-[4-(2-fluorophenoxy)-2-methylphenyl]pyrazol-4-yl]-[6-(1-cyclopropylsulfonylpiperidin-4-yl)-5-methyl-1H-indol-2-yl]methanone,
(5-1-132) 1-[4-[2-[5-amino-1-[4-(2-fluorophenoxy)-2-methylphenyl]pyrazole-4-carbonyl]-5-methyl-1H-indol-6-yl]piperidin-1-yl]ethanone, (5-1-133) 1-[4-[2-[5-amino-1-[6-(2-fluorophenoxy)-4-methylpyridin-3-yl]pyrazole-4-carbonyl]-5-methyl-1H-indol-6-yl]piperidin-1-yl]ethanone, (5-1-134) [5-amino-1-[6-(2,6-difluorophenoxy)-4-methylpyridin-3-yl]pyrazol-4-yl]-[6-bromo-5-(1-propan-2-ylpiperidin-4-yl)oxy-1H-indol-2-yl]methanone, (5-1-135) [5-amino-1-[4-(2-fluorophenoxy)-2-methylphenyl]pyrazol-4-yl]-[5-fluoro-6-[(1-methylsulfonylpiperidin-4-yl)amino]-1H-indol-2-yl]methanone, (5-1-136) 2-[[2-[5-amino-1-[6-(2,6-difluorophenoxy)-4-methylpyridin-3-yl]pyrazole-4-carbonyl]-5-methyl-1H-indol-6-yl]sulfamoyl]-N-propan-2-ylacetamide, (5-1-137) 2-[[2-[5-amino-1-[2-fluoro-4-(2-fluorophenoxy)-6-methylphenyl]pyrazole-4-carbonyl]-5-methoxy-1H-indol-6-yl]sulfamoyl]-N-propan-2-ylacetamide, (5-1-138) 1-[4-[2-[5-amino-1-[2-fluoro-4-(2-fluorophenoxy)-6-methylphenyl]pyrazole-4-carbonyl]-5-methyl-1H-indol-6-yl]piperidin-1-yl]ethanone, (5-1-139) 1-[4-[2-[5-amino-1-[6-(2,6-difluorophenoxy)-4-methylpyridin-3-yl]pyrazole-4-carbonyl]-5-methyl-1H-indol-6-yl]piperidin-1-yl]ethanone, (5-1-140) N-[2-[5-amino-1-[4-(2,6-difluorophenoxy)-2-fluoro-6-methylphenyl]pyrazole-4-carbonyl]-5-methyl-1H-indol-6-yl]methanesulfonamide, (5-1-141) N-[2-[5-amino-1-[6-(2,6-difluorophenoxy)-4-methylpyridin-3-yl]pyrazole-4-carbonyl]-5-ethyl-1H-indol-6-yl]methanesulfonamide, (5-1-142) N-[2-[5-amino-1-[4-(2-chloro-6-fluorophenoxy)-2-fluoro-6-methylphenyl]pyrazole-4-carbonyl]-5-methyl-1H-indol-6-yl]methanesulfonamide, (5-1-143) N-[2-[5-amino-1-[6-(2,6-difluorophenoxy)-4-methylpyridin-3-yl]pyrazole-4-carbonyl]-5-methoxy-1H-indol-6-yl]-2-morpholin-4-yl-2-oxoethanesulfonamide, (5-1-144) [5-amino-1-[6-(2,6-difluorophenoxy)-4-methylpyridin-3-yl]pyrazol-4-yl]-[6-(1-cyclopropylsulfonylpiperidin-4-yl)-5-methyl-1H-indol-2-yl]methanone, (5-1-145) [5-amino-1-[6-(2-fluorophenoxy)-4-methylpyridin-3-yl]pyrazol-4-yl]-(6-bromo-5-methoxy-1H-indol-2-yl)methanone, (5-1-146) [5-amino-1-[4-(2-fluorophenoxy)-2-methylphenyl]pyrazol-4-yl]-[6-bromo-5-(1-propan-2-ylpiperidin-4-yl)oxy-1H-indol-2-yl]methanone, (5-1-147) [5-amino-1-[4-(2-fluorophenoxy)-2-methylphenyl]pyrazol-4-yl]-(6-bromo-5-morpholin-4-yl-1H-indol-2-yl)methanone, (5-1-148) [5-amino-1-[4-(2-fluorophenoxy)-3-methylphenyl]pyrazol-4-yl]-[6-bromo-5-(1-propan-2-ylpiperidin-4-yl)oxy-1H-indol-2-yl]methanone, (5-1-149) [5-amino-1-[6-(2,6-difluorophenoxy)-4-methylpyridin-3-yl]pyrazol-4-yl]-[6-bromo-5-(difluoromethoxy)-1H-indol-2-yl]methanone, (5-1-150) [5-amino-1-[4-(2-fluorophenoxy)-3-methylphenyl]pyrazol-4-yl]-[6-bromo-5-(2,2-difluoroethoxy)-1H-indol-2-yl]methanone, (5-1-151) [5-amino-1-[4-(2-fluorophenoxy)-3-methylphenyl]pyrazol-4-yl]-(6-bromo-5-morpholin-4-yl-1H-indol-2-yl)methanone, (5-1-152) [5-amino-1-[4-(2-fluorophenoxy)-3-methylphenyl]pyrazol-4-yl]-[6-bromo-5-(difluoromethoxy)-1H-indol-2-yl]methanone, (5-1-153) [5-amino-1-[6-(2-fluorophenoxy)-4-methylpyridin-3-yl]pyrazol-4-yl]-[6-bromo-5-(1-propan-2-ylpiperidin-4-yl)oxy-1H-indol-2-yl]methanone, (5-1-154) [5-amino-1-[2-fluoro-4-(2-fluorophenoxy)-6-methylphenyl]pyrazol-4-yl]-[6-bromo-5-(1-propan-2-ylpiperidin-4-yl)oxy-1H-indol-2-yl]methanone, (5-1-155) [5-amino-1-[6-(2,6-difluorophenoxy)-4-methylpyridin-3-yl]pyrazol-4-yl]-(6-bromo-5-morpholin-4-yl-1H-indol-2-yl)methanone, (5-1-156) N-[2-[5-amino-1-[4-(2-fluorophenoxy)-3-methylphenyl]pyrazole-4-carbonyl]-5-(1-propan-2-ylpiperidin-4-yl)oxy-1H-indol-6-yl]methanesulfonamide, (5-1-157) N-[2-[5-amino-1-[4-(2-fluorophenoxy)-3-methylphenyl]pyrazole-4-carbonyl]-5-morpholin-4-yl-1H-indol-6-yl]methanesulfonamide, (5-1-158) [5-amino-1-[4-(2-fluorophenoxy)-3-methylphenyl]pyrazol-4-yl]-[6-(4-methylsulfonylpiperazin-1-yl)-5-morpholin-4-yl-1H-indol-2-yl]methanone, (5-1-159) [5-amino-1-[4-(2-fluorophenoxy)-3-methylphenyl]pyrazol-4-yl]-(5,6-dimorpholin-4-yl-1H-indol-2-yl)methanone, (5-1-160) 3-[2-[5-amino-1-[4-(2-fluorophenoxy)-3-methylphenyl]pyrazole-4-carbonyl]-5-morpholin-4-yl-1H-indol-6-yl]-1,3-oxazolidin-2-one, (5-1-161) [6-amino-5-(difluoromethoxy)-1H-indol-2-yl]-[5-amino-1-[4-(2-fluorophenoxy)-3-methylphenyl]pyrazol-4-yl]methanone, (5-1-162) [6-amino-5-(2,2-difluoroethoxy)-1H-indol-2-yl]-[5-amino-1-[4-(2-fluorophenoxy)-3-methylphenyl]pyrazol-4-yl]methanone, (5-1-163) [5-amino-1-[4-(2-fluorophenoxy)-3-methylphenyl]pyrazol-4-yl]-[6-amino-5-(1-propan-2-ylpiperidin-4-yl)oxy-1H-indol-2-yl]methanone, (5-1-164) 3-[2-[5-amino-1-[4-(2-fluorophenoxy)-3-methylphenyl]pyrazole-4-carbonyl]-5-morpholin-4-yl-1H-indol-6-yl]-5,5-dimethylimidazolidine-2,4-dione, (5-1-165) [5-amino-1-[4-(2-fluorophenoxy)-3-methylphenyl]pyrazol-4-yl]-[5-morpholin-4-yl-6-(4-morpholin-4-ylpiperidin-1-yl)-1H-indol-2-yl]methanone, (5-1-166) N-[2-[5-amino-1-[4-(2-fluorophenoxy)-3-methylphenyl]pyrazole-4-carbonyl]-5-(2,2-difluoroethoxy)-1H-indol-6-yl]methanesulfonamide, (5-1-167) N-[2-[5-amino-1-[4-(2-fluorophenoxy)-3-methylphenyl]pyrazole-4-carbonyl]-5-(difluoromethoxy)-1H-indol-6-yl]methanesulfonamide, (5-1-168) 3-[2-[5-amino-1-[4-(2-fluorophenoxy)-3-methylphenyl]pyrazole-4-carbonyl]-5-(2,2-difluoroethoxy)-1H-indol-6-yl]-1,3-oxazolidin-2-one, (5-1-169) [5-amino-1-[4-(2-fluorophenoxy)-3-methylphenyl]pyrazol-4-yl]-[5-(2,2-difluoroethoxy)-6-morpholin-4-yl-1H-indol-2-yl]methanone, (5-1-170) 3-[2-[5-amino-1-[4-(2-fluorophenoxy)-3-methylphenyl]pyrazole-4-carbonyl]-5-(2,2-difluoroethoxy)-1H-indol-6-yl]-5,5-dimethylimidazolidine-2,4-dione, (5-1-171) [5-amino-1-[4-(2-fluorophenoxy)-3-methylphenyl]pyrazol-4-yl]-[5-(2,2-difluoroethoxy)-6-(4-methylsulfonylpiperazin-1-yl)-1H-indol-2-yl]methanone, (5-1-172) [5-amino-1-[4-(2-fluorophenoxy)-3-methylphenyl]pyrazol-4-yl]-[5-(2,2-difluoroethoxy)-6-(4-morpholin-4-ylpiperidin-1-yl)-1H-indol-2-yl]methanone, (5-1-173) [5-amino-1-[4-(2-fluorophenoxy)-3-methylphenyl]pyrazol-4-yl]-[5-(difluoromethoxy)-6-morpholin-4-yl-1H-indol-2-yl]methanone, (5-1-174) [5-amino-1-[4-(2-fluorophenoxy)-3-methylphenyl]pyrazol-4-yl]-[6-morpholin-4-yl-5-(1-propan-2-ylpiperidin-4-yl)oxy-1H-indol-2-yl]methanone, (5-1-175) [5-amino-1-[4-(2-fluorophenoxy)-3-methylphenyl]pyrazol-4-yl]-[5-(difluoromethoxy)-6-(4-methylsulfonylpiperazin-1-yl)-1H-indol-2-yl]methanone, (5-1-176) [5-amino-1-[4-(2-fluorophenoxy)-3-methylphenyl]pyrazol-4-yl]-[6-(4-methylsulfonylpiperazin-1-yl)-5-(1-propan-2-ylpiperidin-4-yl)oxy-1H-indol-2-yl]methanone, (5-1-177) 3-[2-[5-amino-1-[4-(2-fluorophenoxy)-3-methylphenyl]pyrazole-4-carbonyl]-5-(difluoromethoxy)-1H-indol-6-yl]-1,3-oxazolidin-2-one, (5-1-178) 3-[2-[5-amino-1-[4-(2-fluorophenoxy)-3-methylphenyl]pyrazole-4-carbonyl]-5-(1-propan-2-ylpiperidin-4-yl)oxy-1H-indol-6-yl]-1,3-oxazolidin-2-one, (5-1-179) 3-[2-[5-amino-1-[4-(2-fluorophenoxy)-3-methylphenyl]pyrazole-4-carbonyl]-5-(difluoromethoxy)-1H-indol-6-yl]-5,5-dimethylimidazolidine-2,4-dione, (5-1-180) 3-[2-[5-amino-1-[4-(2-fluorophenoxy)-3-methylphenyl]pyrazole-4-carbonyl]-5-(1-propan-2-ylpiperidin-4-yl)oxy-1H-indol-6-yl]-5,5-dimethylimidazolidine-2,4-dione, (5-1-181) [5-amino-1-[4-(2-fluorophenoxy)-3-methylphenyl]pyrazol-4-yl]-[5-(difluoromethoxy)-6-(4-morpholin-4-ylpiperidin-1-yl)-1H-indol-2-yl]methanone, (5-1-182) [5-amino-1-[4-(2-fluorophenoxy)-3-methylphenyl]pyrazol-4-yl]-[6-(4-morpholin-4-ylpiperidin-1-yl)-5-(1-propan-2-ylpiperidin-4-yl)oxy-1H-indol-2-yl]methanone, (5-1-183) [5-amino-1-[6-(2,6-difluorophenoxy)-4-methylpyridin-3-yl]pyrazol-4-yl]-[6-amino-5-(1-propan-2-ylpiperidin-4-yl)oxy-1H-indol-2-yl]methanone, (5-1-184) N-[2-[5-amino-1-[6-(2,6-difluorophenoxy)-4-methylpyridin-3-yl]pyrazole-4-carbonyl]-5-(1-propan-2-ylpiperidin-4-yl)oxy-1H-indol-6-yl]methanesulfonamide, (5-1-185) [5-amino-1-[6-(2,6-difluorophenoxy)-4-methylpyridin-3-yl]pyrazol-4-yl]-[6-morpholin-4-yl-5-(1-propan-2-ylpiperidin-4-yl)oxy-1H-indol-2-yl]methanone, (5-1-186) 3-[2-[5-amino-1-[6-(2,6-difluorophenoxy)-4-methylpyridin-3-yl]pyrazole-4-carbonyl]-5-(1-propan-2-ylpiperidin-4-yl)oxy-1H-indol-6-yl]-1,3-oxazolidin-2-one, (5-1-187) [5-amino-1-[6-(2,6-difluorophenoxy)-4-methylpyridin-3-yl]pyrazol-4-yl]-[6-(4-methylsulfonylpiperazin-1-yl)-5-(1-propan-2-ylpiperidin-4-yl)oxy-1H-indol-2-yl]methanone, (5-1-188) 3-[2-[5-amino-1-[6-(2,6-difluorophenoxy)-4-methylpyridin-3-yl]pyrazole-4-carbonyl]-5-(1-propan-2-ylpiperidin-4-yl)oxy-1H-indol-6-yl]-5,5-dimethylimidazolidine-2,4-dione, (5-1-189) N-[2-[5-amino-1-[4-(2-fluorophenoxy)-2-methylphenyl]pyrazole-4-carbonyl]-5-(1-propan-2-ylpiperidin-4-yl)oxy-1H-indol-6-yl]methanesulfonamide, (5-1-190) [5-amino-1-[4-(2-fluorophenoxy)-2-methylphenyl]pyrazol-4-yl]-[6-morpholin-4-yl-5-(1-propan-2-ylpiperidin-4-yl)oxy-1H-indol-2-yl]methanone, (5-1-191) [5-amino-1-[4-(2-fluorophenoxy)-2-methylphenyl]pyrazol-4-yl]-[6-(4-methylsulfonylpiperazin-1-yl)-5-(1-propan-2-ylpiperidin-4-yl)oxy-1H-indol-2-yl]methanone, (5-1-192) 3-[2-[5-amino-1-[4-(2-fluorophenoxy)-2-methylphenyl]pyrazole-4-carbonyl]-5-(1-propan-2-ylpiperidin-4-yl)oxy-1H-indol-6-yl]-1,3-oxazolidin-2-one, (5-1-193) 3-[2-[5-amino-1-[4-(2-fluorophenoxy)-2-methylphenyl]pyrazole-4-carbonyl]-5-(1-propan-2-ylpiperidin-4-yl)oxy-1H-indol-6-yl]-5,5-dimethylimidazolidine-2,4-dione, (5-1-194) [5-amino-1-[4-(2-fluorophenoxy)-2-methylphenyl]pyrazol-4-yl]-[6-(4-morpholin-4-ylpiperidin-1-yl)-5-(1-propan-2-ylpiperidin-4-yl)oxy-1H-indol-2-yl]methanone, (5-1-195) [5-amino-1-[4-(2-fluorophenoxy)-3-methylphenyl]pyrazol-4-yl]-[6-fluoro-5-(1-propan-2-ylpiperidin-4-yl)oxy-1H-indol-2-yl]methanone, (5-1-196) [5-amino-1-[4-(2-fluorophenoxy)-3-methylphenyl]pyrazol-4-yl]-[6-chloro-5-(1-propan-2-ylpiperidin-4-yl)oxy-1H-indol-2-yl]methanone, (5-1-197) [5-amino-1-[4-(2-fluorophenoxy)-2-methylphenyl]pyrazol-4-yl]-[6-chloro-5-(1-propan-2-ylpiperidin-4-yl)oxy-1H-indol-2-yl]methanone, (5-1-198) N-[2-[5-amino-1-[3-fluoro-4-(2-fluorophenoxy)phenyl]pyrazole-4-carbonyl]-5-methyl-1H-indol-6-yl]methanesulfonamide, (5-1-199) N-[2-[5-amino-1-[5-fluoro-4-(2-fluorophenoxy)-2-methylphenyl]pyrazole-4-carbonyl]-5-methyl-1H-indol-6-yl]methanesulfonamide, (5-1-200) N-[2-[5-amino-1-[4-(2-fluorophenoxy)-2,5-dimethylphenyl]pyrazole-4-carbonyl]-5-methyl-1H-indol-6-yl]methanesulfonamide, (5-1-201) [5-amino-1-[6-(2,6-difluorophenoxy)-4-methylpyridin-3-yl]pyrazol-4-yl]-[6-(4-morpholin-4-ylpiperidin-1-yl)-5-(1-propan-2-ylpiperidin-4-yl)oxy-1H-indol-2-yl]methanone, (5-1-202) [5-amino-1-[6-(2,6-difluorophenoxy)-4-methylpyridin-3-yl]pyrazol-4-yl]-[6-(4-hydroxypiperidin-1-yl)-5-(1-propan-2-ylpiperidin-4-yl)oxy-1H-indol-2-yl]methanone, (5-1-203) [5-amino-1-[4-(2-fluorophenoxy)-2-methylphenyl]pyrazol-4-yl]-[6-fluoro-5-(1-propan-2-ylpiperidin-4-yl)oxy-1H-indol-2-yl]methanone, (5-1-204) [5-amino-1-[6-(2,6-difluorophenoxy)-4-methylpyridin-3-yl]pyrazol-4-yl]-[6-fluoro-5-(1-propan-2-ylpiperidin-4-yl)oxy-1H-indol-2-yl]methanone, (5-1-205) [5-amino-1-[6-(2,6-difluorophenoxy)-4-methylpyridin-3-yl]pyrazol-4-yl]-[6-chloro-5-(1-propan-2-ylpiperidin-4-yl)oxy-1H-indol-2-yl]methanone, (5-1-206) N-[2-[5-amino-1-[2-fluoro-4-(2-fluorophenoxy)-5-methylphenyl]pyrazole-4-carbonyl]-5-methyl-1H-indol-6-yl]methanesulfonamide, (5-1-207) N-[2-[5-amino-1-[2-fluoro-4-(2-fluorophenoxy)-3-methylphenyl]pyrazole-4-carbonyl]-5-methyl-1H-indol-6-yl]methanesulfonamide, (5-1-208) [5-amino-1-[4-(3-fluorophenoxy)-3-methylphenyl]pyrazol-4-yl]-[6-fluoro-5-(1-propan-2-ylpiperidin-4-yl)oxy-1H-indol-2-yl]methanone, (5-1-209) [5-amino-1-[4-(3-fluorophenoxy)-3-methylphenyl]pyrazol-4-yl]-[6-chloro-5-(1-propan-2-ylpiperidin-4-yl)oxy-1H-indol-2-yl]methanone, (5-1-210) [5-amino-1-[4-(3-fluorophenoxy)-3-methylphenyl]pyrazol-4-yl]-[6-bromo-5-(1-propan-2-ylpiperidin-4-yl)oxy-1H-indol-2-yl]methanone, (5-1-211) N-[2-[5-amino-1-[4-(3-fluorophenoxy)-3-methylphenyl]pyrazole-4-carbonyl]-5-methyl-1H-indol-6-yl]methanesulfonamide, (5-1-212) [5-amino-1-[2-fluoro-4-(2-fluorophenoxy)-5-methylphenyl]pyrazol-4-yl]-[6-bromo-5-(1-propan-2-ylpiperidin-4-yl)oxy-1H-indol-2-yl]methanone, (5-1-213) N-[2-[5-amino-1-[4-(2-fluorophenoxy)-2,3-dimethylphenyl]pyrazole-4-carbonyl]-5-methyl-1H-indol-6-yl]methanesulfonamide, (5-1-214) N-[2-[5-amino-1-[2,3-difluoro-4-(2-fluorophenoxy)phenyl]pyrazole-4-carbonyl]-5-methyl-1H-indol-6-yl]methanesulfonamide, (5-1-215) [5-amino-1-[2-fluoro-4-(2-fluorophenoxy)-5-methylphenyl]pyrazol-4-yl]-[6-(4-morpholin-4-ylpiperidin-1-yl)-5-(1-propan-2-ylpiperidin-4-yl)oxy-1H-indol-2-yl]methanone, (5-1-216) [5-amino-1-[4-(2-fluorophenoxy)-3-methylphenyl]pyrazol-4-yl]-[6-bromo-5-(1-cyclopentylpiperidin-4-yl)oxy-1H-indol-2-yl]methanone, (5-1-217) [5-amino-1-[4-(2-fluorophenoxy)-3-methylphenyl]pyrazol-4-yl]-[5-(2,2-difluoroethoxy)-6-(1-methylsulfonylpiperidin-4-yl)-1H-indol-2-yl]methanone, (5-1-218) [5-amino-1-[4-(2-fluorophenoxy)-3-methylphenyl]pyrazol-4-yl]-[6-bromo-5-(1-cyclobutylpiperidin-4-yl)oxy-1H-indol-2-yl]methanone, (5-1-219) [5-amino-1-[4-(2-fluorophenoxy)-3-methylphenyl]pyrazol-4-yl]-[6-bromo-5-(1-cyclopropylpiperidin-4-yl)oxy-1H-indol-2-yl]methanone, (5-1-220) [5-amino-1-[4-(2-fluorophenoxy)-3-methylphenyl]pyrazol-4-yl]-[6-bromo-5-[1-(oxetan-3-yl)piperidin-4-yl]oxy-1H-indol-2-yl]methanone, (5-1-221) [5-amino-1-[6-(2,6-difluorophenoxy)-4-methylpyridin-3-yl]pyrazol-4-yl]-[6-bromo-5-(1-cyclobutylpiperidin-4-yl)oxy-1H-indol-2-yl]methanone, (5-1-222) [5-amino-1-[6-(2,6-difluorophenoxy)-4-methylpyridin-3-yl]pyrazol-4-yl]-[6-bromo-5-[1-(oxetan-3-yl)piperidin-4-yl]oxy-1H-indol-2-yl]methanone, (5-1-223) [5-amino-1-[6-(2,6-difluorophenoxy)-4-methylpyridin-3-yl]pyrazol-4-yl]-[6-bromo-5-(1-cyclopentylpiperidin-4-yl)oxy-1H-indol-2-yl]methanone, (5-1-224) [5-amino-1-[6-(2,6-difluorophenoxy)-4-methylpyridin-3-yl]pyrazol-4-yl]-[6-bromo-5-(1-cyclopropylpiperidin-4-yl)oxy-1H-indol-2-yl]methanone, (5-1-225) [5-amino-1-[4-(2-fluorophenoxy)-3-methylphenyl]pyrazol-4-yl]-[6-bromo-5-[1-(2-hydroxyethyl)piperidin-4-yl]oxy-1H-indol-2-yl]methanone, (5-1-226) [5-amino-1-[6-(2,6-difluorophenoxy)-4-methylpyridin-3-yl]pyrazol-4-yl]-[6-bromo-5-[1-(2-hydroxyethyl)piperidin-4-yl]oxy-1H-indol-2-yl]methanone, (5-1-227) [5-amino-1-[4-(2-fluorophenoxy)-3-methylphenyl]pyrazol-4-yl]-[6-bromo-5-[1-(1,1-dioxothietan-3-yl)piperidin-4-yl]oxy-1H-indol-2-yl]methanone, (5-1-228) [5-amino-1-[6-(2,6-difluorophenoxy)-4-methylpyridin-3-yl]pyrazol-4-yl]-[6-bromo-5-[1-(1,1-dioxothietan-3-yl)piperidin-4-yl]oxy-1H-indol-2-yl]methanone, (5-1-229) [5-amino-1-[6-(2,6-difluorophenoxy)-4-methylpyridin-3-yl]pyrazol-4-yl]-[6-(1-methylsulfonylpiperidin-4-yl)-5-(1-propan-2-ylpiperidin-4-yl)oxy-1H-indol-2-yl]methanone, (5-1-230) [5-amino-1-[4-(2-fluorophenoxy)-3-methylphenyl]pyrazol-4-yl]-[6-(1-methylsulfonylpiperidin-4-yl)-5-(1-propan-2-ylpiperidin-4-yl)oxy-1H-indol-2-yl]methanone, (5-1-231) N-[2-[5-amino-1-[4-(2-fluorophenoxy)-3-methylphenyl]pyrazole-4-carbonyl]-5-(1-cyclobutylpiperidin-4-yl)oxy-1H-indol-6-yl]methanesulfonamide, (5-1-232) [6-amino-5-(1-cyclobutylpiperidin-4-yl)oxy-1H-indol-2-yl]-[5-amino-1-[4-(2-fluorophenoxy)-3-methylphenyl]pyrazol-4-yl]methanone, (5-1-233) 3-[2-[5-amino-1-[4-(2-fluorophenoxy)-3-methylphenyl]pyrazole-4-carbonyl]-5-(1-cyclobutylpiperidin-4-yl)oxy-1H-indol-6-yl]-5,5-dimethylimidazolidine-2,4-dione, (5-1-234) [5-amino-1-[4-(2-fluorophenoxy)-3-methylphenyl]pyrazol-4-yl]-[5-(1-cyclobutylpiperidin-4-yl)oxy-6-fluoro-1H-indol-2-yl]methanone, (5-1-235) [5-amino-1-[4-(2-fluorophenoxy)-3-methylphenyl]pyrazol-4-yl]-[6-chloro-5-(1-cyclobutylpiperidin-4-yl)oxy-1H-indol-2-yl]methanone, (5-1-236) [5-amino-1-[4-(2-fluorophenoxy)-3-methylphenyl]pyrazol-4-yl]-[6-(1-methylpyrazol-4-yl)-5-(1-propan-2-ylpiperidin-4-yl)oxy-1H-indol-2-yl]methanone, (5-1-237) [5-amino-1-[4-(2-fluorophenoxy)-3-methylphenyl]pyrazol-4-yl]-[6-bromo-5-[(2R)-2,3-dihydroxypropoxy]-1H-indol-2-yl]methanone, (5-1-238) [5-amino-1-[4-(2-fluorophenoxy)-3-methylphenyl]pyrazol-4-yl]-[5-(1-propan-2-ylpiperidin-4-yl)oxy-6-thiophen-2-yl-1H-indol-2-yl]methanone, (5-1-239) [5-amino-1-[6-(2,6-difluorophenoxy)-4-methylpyridin-3-yl]pyrazol-4-yl]-[5-(1-propan-2-ylpiperidin-4-yl)oxy-6-thiophen-2-yl-1H-indol-2-yl]methanone, (5-1-240) [5-amino-1-[4-(2-fluorophenoxy)-3-methylphenyl]pyrazol-4-yl]-[5-(1-propan-2-ylpiperidin-4-yl)oxy-6-pyrimidin-5-yl-1H-indol-2-yl]methanone, (5-1-241) [5-amino-1-[6-(2,6-difluorophenoxy)-4-methylpyridin-3-yl]pyrazol-4-yl]-[5-(1-propan-2-ylpiperidin-4-yl)oxy-6-pyrimidin-5-yl-1H-indol-2-yl]methanone, (5-1-242) N-[2-[5-amino-1-[4-(2-fluorophenoxy)-3-methylphenyl]pyrazole-4-carbonyl]-5-[(2R)-2,3-dihydroxypropoxy]-1H-indol-6-yl]methanesulfonamide, (5-1-243) (5 S)-3-[2-[5-amino-1-[4-(2-fluorophenoxy)-2-methylphenyl]pyrazole-4-carbonyl]-5-(2,2-difluoroethoxy)-1H-indol-6-yl]-5-(1H-imidazol-5-ylmethyl)imidazolidine-2,4-dione, (5-1-244) (4R)-3-[2-[5-amino-1-[4-(2-fluorophenoxy)-2-methylphenyl]pyrazole-4-carbonyl]-5-(2,2-difluoroethoxy)-1H-indol-6-yl]-4-benzyl-1,3-oxazolidin-2-one, (5-1-245) (4S)-3-[2-[5-amino-1-[4-(2-fluorophenoxy)-2-methylphenyl]pyrazole-4-carbonyl]-5-(2,2-difluoroethoxy)-1H-indol-6-yl]-4-benzyl-1,3-oxazolidin-2-one, (5-1-246) Methyl (2S)-2-[[2-[5-amino-1-[4-(2-fluorophenoxy)-2-methylphenyl]pyrazole-4-carbonyl]-5-(2,2-difluoroethoxy)-1H-indol-6-yl]carbamoylamino]-3-(1H-imidazol-5-yl)propanoate, (5-1-247) [5-amino-1-[4-(2-fluorophenoxy)-3-methylphenyl]pyrazol-4-yl]-[6-(oxan-4-yl)-5-(1-propan-2-ylpiperidin-4-yl)oxy-1H-indol-2-yl]methanone, (5-1-248) [5-amino-1-[6-(2,6-difluorophenoxy)-4-methylpyridin-3-yl]pyrazol-4-yl]-[6-(oxan-4-yl)-5-(1-propan-2-ylpiperidin-4-yl)oxy-1H-indol-2-yl]methanone, (5-1-249) [5-amino-1-[6-(2,6-difluorophenoxy)-4-methylpyridin-3-yl]pyrazol-4-yl]-[6-(1-methylpyrazol-4-yl)-5-(1-propan-2-ylpiperidin-4-yl)oxy-1H-indol-2-yl]methanone, (5-1-250) (6R,7aS)-2-[2-[5-amino-1-[4-(2-fluorophenoxy)-2-methylphenyl]pyrazole-4-carbonyl]-5-(2,2-difluoroethoxy)-1H-indol-6-yl]-6-hydroxy-5,6,7,7a-tetrahydropyrrolo[1,2-c]imidazole-1,3-dione, (5-1-251) (5S)-3-[2-[5-amino-1-[4-(2-fluorophenoxy)-2-methylphenyl]pyrazole-4-carbonyl]-5-(2,2-difluororoethoxy)-1H-indol-6-yl]-5-[(4-hydroxyphenyl) methyl]imidazolidine-2,4-dione, (5-1-252) (7aS)-2-[2-[5-amino-1-[4-(2-fluorophenoxy)-2-methylphenyl]pyrazole-4-carbonyl]-5-(2,2-difluoroethoxy)-1H-indol-6-yl]-5,6,7,7a-tetrahydropyrrolo[1,2-c]imidazole-1,3-dione, (5-1-253) 9H-fluoren-9-ylmethyl N-[(6 S,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]carbamate, (5-1-254) N-[(6S,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]methanesulfonamide, (5-1-255) N-[(6S,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]-3-fluoropropane-1-sulfonamide, (5-1-256) [5-amino-1-[4-(2-fluorophenoxy)-3-methylphenyl]pyrazol-4-yl]-[5-(2,2-difluoroethoxy)-6-thiophen-2-yl-1H-indol-2-yl]methanone, (5-1-257) [5-amino-1-[6-(2,6-difluorophenoxy)-4-methylpyridin-3-yl]pyrazol-4-yl]-[5-(2,2-difluoroethoxy)-6-thiophen-2-yl-1H-indol-2-yl]methanone, (5-1-258) [5-amino-1-[4-(2-fluorophenoxy)-3-methylphenyl]pyrazol-4-yl]-[5-(2,2-difluoroethoxy)-6-(oxan-4-yl)-1H-indol-2-yl]methanone, (5-1-259) [5-amino-1-[6-(2,6-difluorophenoxy)-4-methylpyridin-3-yl]pyrazol-4-yl]-[5-(2,2-difluoroethoxy)-6-(oxan-4-yl)-1H-indol-2-yl]methanone, (5-1-260) [5-amino-1-[4-(2-fluorophenoxy)-2-methylphenyl]pyrazol-4-yl]-(6-bromo-5-propan-2-yl-1H-indol-2-yl)methanone, (5-1-261) [5-amino-1-[4-(2-fluorophenoxy)-3-methylphenyl]pyrazol-4-yl]-[5-(2,2-difluoroethoxy)-6-pyrimidin-5-yl-1H-indol-2-yl]methanone, (5-1-262) [5-amino-1-[6-(2,6-difluorophenoxy)-4-methylpyridin-3-yl]pyrazol-4-yl]-[5-(2,2-difluoroethoxy)-6-pyrimidin-5-yl-1H-indol-2-yl]methanone, (5-1-263) [5-amino-1-[4-(2-fluorophenoxy)-3-methylphenyl]pyrazol-4-yl]-[5-(2,2-difluoroethoxy)-6-(1-methylpyrazol-4-yl)-1H-indol-2-yl]methanone, (5-1-264) [5-amino-1-[6-(2,6-difluorophenoxy)-4-methylpyridin-3-yl]pyrazol-4-yl]-[5-(2,2-difluoroethoxy)-6-(1-methylpyrazol-4-yl)-1H-indol-2-yl]methanone, (5-1-265) 9H-fluoren-9-ylmethyl N-[(6S,7aS)-2-[2-[5-amino-1-[4-(2-fluorophenoxy)-2-methylphenyl]pyrazole-4-carbonyl]-5-fluoro-1H-indol-6-yl]-1,3-dioxo-5,6,7,7a-tetrahydropyrrolo[1,2-c]imidazol-6-yl]carbamate, (5-1-266) [5-amino-1-[4-(2-fluorophenoxy)-2-methylphenyl]pyrazol-4-yl]-(6-amino-5-propan-2-yl-1H-indol-2-yl)methanone, (5-1-267) N-[2-[5-amino-1-[4-(2-fluorophenoxy)-2-methylphenyl]pyrazole-4-carbonyl]-5-propan-2-yl-1H-indol-6-yl]methanesulfonamide, (5-1-268) 9H-fluoren-9-ylmethyl N-[(6S,7aS)-2-[2-[5-amino-1-[4-(2-fluorophenoxy)-2-methylphenyl]pyrazole-4-carbonyl]-5-methyl-1H-indol-6-yl]-1,3-dioxo-5,6,7,7a-tetrahydropyrrolo[1,2-c]imidazol-6-yl]carbamate, (5-1-269) N-[2-[5-amino-1-[6-(2,6-difluorophenoxy)-4-methylpyridin-3-yl]pyrazole-4-carbonyl]-5-methyl-1H-indol-6-yl]oxane-4-sulfonamide, (5-1-270) 9H-fluoren-9-ylmethyl N-[(6R,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]carbamate, (5-1-271) 3-[2-[5-amino-1-[4-(2-fluorophenoxy)-2-methylphenyl]pyrazole-4-carbonyl]-5-(2,2-difluoroethoxy)-1H-indol-6-yl]-1,3,8-triazaspiro[4.5]decane-2,4-dione, (5-1-272) 3-[2-[5-amino-1-[4-(2-fluorophenoxy)-2-methylphenyl]pyrazole-4-carbonyl]-5-(2,2-difluoroethoxy)-1H-indol-6-yl]-8-(oxetan-3-yl)-1,3,8-triazaspiro[4.5]decane-2,4-dione, (5-1-273) Benzyl N-[(6S,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]carbamate, (5-1-274) 2-methylpropyl N-[(6S,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]carbamate, (5-1-275) N-[(6S,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]-1-phenylmethanesulfonamide, (5-1-276) N-[(6S,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]naphthalene-2-sulfonamide, (5-1-277) 3-[2-[5-amino-1-[4-(2-fluorophenoxy)-2-methylphenyl]pyrazole-4-carbonyl]-5-(2,2-difluoroethoxy)-1H-indol-6-yl]-8-benzyl-1,3,8-triazaspiro[4.5]decane-2,4-dione, (5-1-278) Furan-2-ylmethyl N-[(6S,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]carbamate, (5-1-279) 9H-fluoren-9-ylmethyl N-[2-[5-amino-1-[4-(2-fluorophenoxy)-2-methylphenyl]pyrazole-4-carbonyl]-5-(2,2-difluoroethoxy)-1H-indol-6-yl]carbamate, (5-1-280) N-[2-[5-amino-1-[4-(2-fluorophenoxy)-2-methylphenyl]pyrazole-4-carbonyl]-5-propan-2-yl-1H-indol-6-yl]-3-fluoropropane-1-sulfonamide, (5-1-281) N-[2-[5-amino-1-[6-(2,6-difluorophenoxy)-4-methylpyridin-3-yl]pyrazole-4-carbonyl]-5-methyl-1H-indol-6-yl]oxolane-3-sulfonamide, (5-1-282) N-[2-[5-amino-1-[4-(2-fluorophenoxy)-2-methylphenyl]pyrazole-4-carbonyl]-5-propan-2-yl-1H-indol-6-yl]oxane-4-sulfonamide, (5-1-283) [5-amino-1-[4-(2-fluorophenoxy)-3-methylphenyl]pyrazol-4-yl]-[5-[1-(1,1-dioxothietan-3-yl)piperidin-4-yl]oxy-6-pyrimidin-5-yl-1H-indol-2-yl]methanone, (5-1-284) [5-amino-1-[6-(2,6-difluorophenoxy)-4-methylpyridin-3-yl]pyrazol-4-yl]-[5-[1-(1,1-dioxothietan-3-yl)piperidin-4-yl]oxy-6-pyrimidin-5-yl-1H-indol-2-yl]methanone, (5-1-285) [5-amino-1-[4-(2-fluorophenoxy)-3-methylphenyl]pyrazol-4-yl]-[6-(2-chlorophenyl)-5-(1-cyclopentylpiperidin-4-yl)oxy-1H-indol-2-yl]methanone, (5-1-286) 3-[2-[5-amino-1-[6-(2,6-difluorophenoxy)-4-methylpyridin-3-yl]pyrazole-4-carbonyl]-5-methyl-1H-indol-6-yl]-5,5-dimethylimidazolidine-2,4-dione, (5-1-287) (5 S)-3-[2-[5-amino-1-[4-(2-fluorophenoxy)-3-methylphenyl]pyrazole-4-carbonyl]-5-(1-propan-2-ylpiperidin-4-yl)oxy-1H-indol-6-yl]-5-methylimidazolidine-2,4-dione, (5-1-288) [5-amino-1-[6-(2,6-difluorophenoxy)-4-methylpyridin-3-yl]pyrazol-4-yl]-[6-(2-chlorophenyl)-5-(1-cyclopentylpiperidin-4-yl)oxy-1H-indol-2-yl]methanone, (5-1-289) [5-amino-1-[4-(2-fluorophenoxy)-3-methylphenyl]pyrazol-4-yl]-[6-(2-chlorophenyl)-5-[1-(1,1-dioxothietan-3-yl)piperidin-4-yl]oxy-1H-indol-2-yl]methanone, (5-1-290) [5-amino-1-[6-(2,6-difluorophenoxy)-4-methylpyridin-3-yl]pyrazol-4-yl]-[6-(2-chlorophenyl)-5-[1-(1,1-dioxothietan-3-yl)piperidin-4-yl]oxy-1H-indol-2-yl]methanone, (5-1-291) N-[2-[5-amino-1-[6-(2,6-difluorophenoxy)-4-methylpyridin-3-yl]pyrazole-4-carbonyl]-5-methyl-1H-indol-6-yl]-3-oxa-8-azabicyclo[3.2.1]octane-8-sulfonamide, (5-1-292) (3R)—N-[2-[5-amino-1-[6-(2,6-difluorophenoxy)-4-methylpyridin-3-yl]pyrazole-4-carbonyl]-5-methyl-1H-indol-6-yl]-3-methylmorpholine-4-sulfonamide, (5-1-293) (5 S)-3-[2-[5-amino-1-[4-(2-fluorophenoxy)-3-methylphenyl]pyrazole-4-carbonyl]-5-(1-propan-2-ylpiperidin-4-yl)oxy-1H-indol-6-yl]-5-(hydroxymethyl)imidazolidine-2,4-dione, (5-1-294) (5 S)-3-[2-[5-amino-1-[4-(2-fluorophenoxy)-3-methylphenyl]pyrazole-4-carbonyl]-5-(1-propan-2-ylpiperidin-4-yl)oxy-1H-indol-6-yl]-5-benzylimidazolidine-2,4-dione, (5-1-295) (5 S)-3-[2-[5-amino-1-[4-(2-fluorophenoxy)-3-methylphenyl]pyrazole-4-carbonyl]-5-(1-propan-2-ylpiperidin-4-yl)oxy-1H-indol-6-yl]-5-propan-2-ylimidazolidine-2,4-dione, (5-1-296) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-1-phenylmethanesulfonamide, (5-1-297) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-4-fluorobenzenesulfonamide, (5-1-298) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-4-chlorobenzenesulfonamide, (5-1-299) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-4-methoxybenzenesulfonamide, (5-1-300) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-4-methylbenzenesulfonamide, (5-1-301) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-2-chloro-5-methoxybenzenesulfonamide, (5-1-302) [5-amino-1-[4-(2-fluorophenoxy)-2-methylphenyl]pyrazol-4-yl]-[6-(4,4-dimethyl-, 1-dioxo-1,2,5-thiadiazolidin-2-yl)-5-fluoro-1H-indol-2-yl]methanone, (5-1-303) N-[2-[5-amino-1-[6-(2,6-difluorophenoxy)-4-methylpyridin-3-yl]pyrazole-4-carbonyl]-5-propan-2-yl-1H-indol-6-yl]-3-oxa-8-azabicyclo[3.2.1]octane-8-sulfonamide, (5-1-304) N-[2-[5-amino-1-[6-(2,6-difluorophenoxy)-4-methylpyridin-3-yl]pyrazole-4-carbonyl]-5-propan-2-yl-1H-indol-6-yl]cyclohexanesulfonamide, (5-1-305) N-[2-[5-amino-1-[6-(2,6-difluorophenoxy)-4-methylpyridin-3-yl]pyrazole-4-carbonyl]-5-propan-2-yl-1H-indol-6-yl]-3-fluoropropane-1-sulfonamide, (5-1-306) N-[2-[5-amino-1-[6-(2,6-difluorophenoxy)-4-methylpyridin-3-yl]pyrazole-4-carbonyl]-5-propan-2-yl-1H-indol-6-yl]cyclopentanesulfonamide, (5-1-307) N-[2-[5-amino-1-[4-(2-fluorophenoxy)-3-methylphenyl]pyrazole-4-carbonyl]-5-methyl-1H-indol-6-yl]methanesulfonamide, (5-1-308) [5-amino-1-[4-(2-fluorophenoxy)-3-methylphenyl]pyrazol-4-yl]-[5-(1-cyclopentylpiperidin-4-yl)oxy-6-(2-fluorophenyl)-1H-indol-2-yl]methanone, (5-1-309) [5-amino-1-[4-(2-fluorophenoxy)-3-methylphenyl]pyrazol-4-yl]-[5-[1-(1,1-dioxothietan-3-yl)piperidin-4-yl]oxy-6-(2-fluorophenyl)-1H-indol-2-yl]methanone, (5-1-310) [5-amino-1-[6-(2,6-difluorophenoxy)-4-methylpyridin-3-yl]pyrazol-4-yl]-[5-(1-cyclopentylpiperidin-4-yl)oxy-6-(2-fluorophenyl)-1H-indol-2-yl]methanone, (5-1-311) [5-amino-1-[6-(2,6-difluorophenoxy)-4-methylpyridin-3-yl]pyrazol-4-yl]-[5-[1-(1,1-dioxothietan-3-yl)piperidin-4-yl]oxy-6-(2-fluorophenyl)-1H-indol-2-yl]methanone, (5-1-312) 7-[2-[5-amino-1-[6-(2,6-difluorophenoxy)-4-methylpyridin-3-yl]pyrazole-4-carbonyl]-5-fluoro-1H-indol-6-yl]-5,7-diazaspiro[3.4]octane-6,8-dione, (5-1-313) [5-amino-1-[6-(2,6-difluorophenoxy)-4-methylpyridin-3-yl]pyrazol-4-yl]-[6-(4,4-dimethyl-1,1-dioxo-1,2,5-thiadiazolidin-2-yl)-5-methyl-1H-indol-2-yl]methanone, (5-1-314) N-[2-[5-amino-1-[6-(2,6-difluorophenoxy)-4-methylpyridin-3-yl]pyrazole-4-carbonyl]-5-methyl-1H-indol-6-yl]cyclohexanesulfonamide, (5-1-315) N-[2-[5-amino-1-[6-(2,6-difluorophenoxy)-4-methylpyridin-3-yl]pyrazole-4-carbonyl]-5-(2,2-difluoroethoxy)-1H-indol-6-yl]cyclohexanesulfonamide, (5-1-316) 3-[2-[5-amino-1-[6-(2,6-difluorophenoxy)-4-methylpyridin-3-yl]pyrazole-4-carbonyl]-5-methyl-1H-indol-6-yl]-1,3-diazaspiro[4.5]decane-2,4-dione, (5-1-317) N-[2-[5-amino-1-[6-(2,6-difluorophenoxy)-4-methylpyridin-3-yl]pyrazole-4-carbonyl]-5-methyl-1H-indol-6-yl]cyclopentanesulfonamide, (5-1-318) N-[2-[5-amino-1-[6-(2,6-difluorophenoxy)-4-methylpyridin-3-yl]pyrazole-4-carbonyl]-5-(2,2-difluoroethoxy)-1H-indol-6-yl]cyclopentanesulfonamide, (5-1-319) N-[2-[5-amino-1-[6-(2,6-difluorophenoxy)-4-methylpyridin-3-yl]pyrazole-4-carbonyl]-5-(2,2-difluoroethoxy)-1H-indol-6-yl]oxane-4-sulfonamide, (5-1-320) N-[2-[5-amino-1-[6-(2,6-difluorophenoxy)-4-methylpyridin-3-yl]pyrazole-4-carbonyl]-5-(difluoromethylsulfanyl)-1H-indol-6-yl]-3-fluoropropane-1-sulfonamide, (5-1-321) [5-amino-1-[6-(2,6-difluorophenoxy)-4-methylpyridin-3-yl]pyrazol-4-yl]-[5-(2,2-difluoroethoxy)-6-(4,4-dimethyl-1,1-dioxo-1,2,5-thiadiazolidin-2-yl)-1H-indol-2-yl]methanone, (5-1-322) [5-amino-1-[4-(2-fluorophenoxy)-2-methylphenyl]pyrazol-4-yl]-[5-(2,2-difluoroethoxy)-6-(4,4-dimethyl-1,1-dioxo-1,2,5-thiadiazolidin-2-yl)-1H-indol-2-yl]methanone, (5-1-323) [5-amino-1-[4-(2-fluorophenoxy)-2-methylphenyl]pyrazol-4-yl]-[5-(2,2-difluoroethoxy)-6-(2,2-dioxo-2λ6-thia-1,3-diazaspiro[4.4]nonan-3-yl)-1H-indol-2-yl]methanone, (5-1-324) 3-[2-[5-amino-1-[6-(2,6-difluorophenoxy)-4-methylpyridin-3-yl]pyrazole-4-carbonyl]-5-(difluoromethylsulfanyl)-1H-indol-6-yl]-5,5-dimethylimidazolidine-2,4-dione, (5-1-325) N-[2-[5-amino-1-[4-(2-fluorophenoxy)-2-methylphenyl]pyrazole-4-carbonyl]-5-(2,2-difluoroethoxy)-1H-indol-6-yl]oxane-4-sulfonamide, (5-1-326) N-[2-[5-amino-1-[6-(2-fluorophenoxy)-4-methylpyridin-3-yl]pyrazole-4-carbonyl]-5-(2,2-difluoroethoxy)-1H-indol-6-yl]oxane-4-sulfonamide, (5-1-327) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-3-methoxybenzenesulfonamide, (5-1-328) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-2-chlorobenzenesulfonamide, (5-1-329) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-2-methoxybenzenesulfonamide, (5-1-330) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-3,5-difluorobenzenesulfonamide, (5-1-331) N-[2-[5-amino-1-[4-(2-fluorophenoxy)-2-methylphenyl]pyrazole-4-carbonyl]-5-(2,2-difluoroethoxy)-1H-indol-6-yl]-2-chloro-5-methoxybenzenesulfonamide, (5-1-332) 3-[2-[5-amino-1-[6-(2,6-difluorophenoxy)-4-methylpyridin-3-yl]pyrazole-4-carbonyl]-5-(2,2-difluoroethoxy)-1H-indol-6-yl]-1,3,8-triazaspiro[4.5]decane-2,4-dione, (5-1-333) N-[2-[5-amino-1-[6-(2-fluorophenoxy)-4-methylpyridin-3-yl]pyrazole-4-carbonyl]-5-methyl-1H-indol-6-yl]oxane-4-sulfonamide, (5-1-334) 3-[2-[5-amino-1-[6-(2-fluorophenoxy)-4-methylpyridin-3-yl]pyrazole-4-carbonyl]-5-methyl-1H-indol-6-yl]-5,5-dimethylimidazolidine-2,4-dione, (5-1-335) [5-amino-1-[4-(2-fluorophenoxy)-3-methylphenyl]pyrazol-4-yl]-[5-(1-cyclopentylpiperidin-4-yl)oxy-6-(2-methylphenyl)-1H-indol-2-yl]methanone, (5-1-336) [5-amino-1-[4-(2-fluorophenoxy)-3-methylphenyl]pyrazol-4-yl]-[5-[1-(1,1-dioxothietan-3-yl)piperidin-4-yl]oxy-6-(2-methylphenyl)-1H-indol-2-yl]methanone, (5-1-337) [5-amino-1-[6-(2,6-difluorophenoxy)-4-methylpyridin-3-yl]pyrazol-4-yl]-[5-(1-cyclopentylpiperidin-4-yl)oxy-6-(2-methylphenyl)-1H-indol-2-yl]methanone, (5-1-338) [5-amino-1-[6-(2,6-difluorophenoxy)-4-methylpyridin-3-yl]pyrazol-4-yl]-[5-[1-(1,1-dioxothietan-3-yl)piperidin-4-yl]oxy-6-(2-methylphenyl)-1H-indol-2-yl]methanone, (5-1-339) N-[2-[5-amino-1-[6-(2-fluorophenoxy)-4-methylpyridin-3-yl]pyrazole-4-carbonyl]-5-(difluoromethyl sulfanyl)-1H-indol-6-yl]-3-fluoropropane-1-sulfonamide, (5-1-340) [5-amino-1-[4-(2-fluorophenoxy)-2-methylphenyl]pyrazol-4-yl]-[5-(difluoromethoxy)-6-(4,4-dimethyl-1,1-dioxo-1,2,5-thiadiazolidin-2-yl)-1H-indol-2-yl]methanone, (5-1-341) 7-[2-[5-amino-1-[6-(2,6-difluorophenoxy)-4-methylpyridin-3-yl]pyrazole-4-carbonyl]-5-methyl-1H-indol-6-yl]-5,7-diazaspiro[3.4]octane-6,8-dione, (5-1-342) 3-[2-[5-amino-1-[6-(2,6-difluorophenoxy)-4-methylpyridin-3-yl]pyrazole-4-carbonyl]-5-methyl-1H-indol-6-yl]-8-oxa-1,3-diazaspiro[4.5]decane-2,4-dione, (5-1-343) 6-[2-[5-amino-1-[6-(2,6-difluorophenoxy)-4-methylpyridin-3-yl]pyrazole-4-carbonyl]-5-fluoro-1H-indol-6-yl]-4,6-diazaspiro[2.4]heptane-5,7-dione, (5-1-344) 3-[2-[5-amino-1-[6-(2,6-difluorophenoxy)-4-methylpyridin-3-yl]pyrazole-4-carbonyl]-5-fluoro-1H-indol-6-yl]-1,3-diazaspiro[4.4]nonane-2,4-dione, (5-1-345) 7-[2-[5-amino-1-[6-(2,6-difluorophenoxy)-4-methylpyridin-3-yl]pyrazole-4-carbonyl]-5-fluoro-1H-indol-6-yl]-2-oxa-5,7-diazaspiro[3.4]octane-6,8-dione, (5-1-346) N-[2-[5-amino-1-[6-(2,6-difluorophenoxy)-4-methylpyridin-3-yl]pyrazole-4-carbonyl]-5-(difluoromethylsulfanyl)-1H-indol-6-yl]oxane-4-sulfonamide, (5-1-347) N-[2-[5-amino-1-[4-(2-fluorophenoxy)-2-methylphenyl]pyrazole-4-carbonyl]-5-methyl-1H-indol-6-yl]oxane-4-sulfonamide, (5-1-348) (5 S)-3-[2-[5-amino-1-[6-(2,6-difluorophenoxy)-4-methylpyridin-3-yl]pyrazole-4-carbonyl]-5-(2,2-difluoroethoxy)-1H-indol-6-yl]-1,3,7-triazaspiro[4.4]nonane-2,4-dione, (5-1-349) 3-[2-[5-amino-1-[4-(2-fluorophenoxy)-2-methylphenyl]pyrazole-4-carbonyl]-5-(2,2-difluoroethoxy)-1H-indol-6-yl]-1,3,7-triazaspiro[4.4]nonane-2,4-dione, (5-1-350) 3-[2-[5-amino-1-[6-(2,6-difluorophenoxy)-4-methylpyridin-3-yl]pyrazole-4-carbonyl]-5-(2,2-difluoroethoxy)-1H-indol-6-yl]-8-(oxetan-3-yl)-1,3,8-triazaspiro[4.5]decane-2,4-dione, (5-1-351) 3-[2-[5-amino-1-[6-(2,6-difluorophenoxy)-4-methylpyridin-3-yl]pyrazole-4-carbonyl]-5-(2,2-difluoroethoxy)-1H-indol-6-yl]-8-benzyl-1,3,8-triazaspiro[4.5]decane-2,4-dione, (5-1-352) 3-[2-[5-amino-1-[6-(2,6-difluorophenoxy)-4-methylpyridin-3-yl]pyrazole-4-carbonyl]-5-(2,2-difluoroethoxy)-1H-indol-6-yl]-7-(oxetan-3-yl)-1,3,7-triazaspiro[4.4]nonane-2,4-dione, (5-1-353) 3-[2-[5-amino-1-[4-(2-fluorophenoxy)-2-methylphenyl]pyrazole-4-carbonyl]-5-(2,2-difluoroethoxy)-1H-indol-6-yl]-7-(oxetan-3-yl)-1,3,7-triazaspiro[4.4]nonane-2,4-dione, (5-1-354) 3-[2-[5-amino-1-[6-(2,6-difluorophenoxy)-4-methylpyridin-3-yl]pyrazole-4-carbonyl]-5-(2,2-difluoroethoxy)-1H-indol-6-yl]-7-benzyl-1,3,7-triazaspiro[4.4]nonane-2,4-dione, (5-1-355) 3-[2-[5-amino-1-[4-(2-fluorophenoxy)-2-methylphenyl]pyrazole-4-carbonyl]-5-(2,2-difluoroethoxy)-1H-indol-6-yl]-7-benzyl-1,3,7-triazaspiro[4.4]nonane-2,4-dione, (5-1-356) 3-[2-[5-amino-1-[4-(2-fluorophenoxy)-2-methylphenyl]pyrazole-4-carbonyl]-5-methyl-1H-indol-6-yl]-5,5-dimethylimidazolidine-2,4-dione, (5-1-357) 3-[2-[5-amino-1-[6-(2,6-difluorophenoxy)-4-methylpyridin-3-yl]pyrazole-4-carbonyl]-5-methyl-1H-indol-6-yl]-1,3,8-triazaspiro[4.5]decane-2,4-dione, (5-1-358) 3-[2-[5-amino-1-[6-(2,6-difluorophenoxy)-4-methylpyridin-3-yl]pyrazole-4-carbonyl]-5-methyl-1H-indol-6-yl]-1,3,7-triazaspiro[4.4]nonane-2,4-dione, (5-1-359) 3-[2-[5-amino-1-[6-(2-fluorophenoxy)-4-methylpyridin-3-yl]pyrazole-4-carbonyl]-5-(difluoromethylsulfanyl)-1H-indol-6-yl]-5,5-dimethylimidazolidine-2,4-dione, (5-1-360) 3-[2-[5-amino-1-[6-(2,6-difluorophenoxy)-4-methylpyridin-3-yl]pyrazole-4-carbonyl]-5-methyl-1H-indol-6-yl]-8-(oxetan-3-yl)-1,3,8-triazaspiro[4.5]decane-2,4-dione, (5-1-361) 3-[2-[5-amino-1-[6-(2,6-difluorophenoxy)-4-methylpyridin-3-yl]pyrazole-4-carbonyl]-5-methyl-1H-indol-6-yl]-8-benzyl-1,3,8-triazaspiro[4.5]decane-2,4-dione, (5-1-362) 3-[2-[5-amino-1-[6-(2,6-difluorophenoxy)-4-methylpyridin-3-yl]pyrazole-4-carbonyl]-5-methyl-1H-indol-6-yl]-7-(oxetan-3-yl)-1,3,7-triazaspiro[4.4]nonane-2,4-dione, (5-1-363) 3-[2-[5-amino-1-[6-(2,6-difluorophenoxy)-4-methylpyridin-3-yl]pyrazole-4-carbonyl]-5-methyl-1H-indol-6-yl]-7-benzyl-1,3,7-triazaspiro[4.4]nonane-2,4-dione, (5-1-364) 3-[2-[5-amino-1-[4-(2-fluorophenoxy)-2-methylphenyl]pyrazole-4-carbonyl]-5-methyl-1H-indol-6-yl]-1,3,8-triazaspiro[4.5]decane-2,4-dione, (5-1-365) 3-[2-[5-amino-1-[4-(2-fluorophenoxy)-2-methylphenyl]pyrazole-4-carbonyl]-5-methyl-1H-indol-6-yl]-1,3,7-triazaspiro[4.4]nonane-2,4-dione, (5-1-366) 6-[2-[5-amino-1-[6-(2,6-difluorophenoxy)-4-methylpyridin-3-yl]pyrazole-4-carbonyl]-5-methyl-1H-indol-6-yl]-4,6-diazaspiro[2.4]heptane-5,7-dione, (5-1-367) 3-[2-[5-amino-1-[6-(2,6-difluorophenoxy)-4-methylpyridin-3-yl]pyrazole-4-carbonyl]-5-methyl-1H-indol-6-yl]-1,3-diazaspiro[4.4]nonane-2,4-dione, (5-1-368) 3-[2-[5-amino-1-[6-(2,6-difluorophenoxy)-4-methylpyridin-3-yl]pyrazole-4-carbonyl]-5-fluoro-1H-indol-6-yl]-8-oxa-1,3-diazaspiro[4.5]decane-2,4-dione, (5-1-369) 3-[2-[5-amino-1-[6-(2,6-difluorophenoxy)-4-methylpyridin-3-yl]pyrazole-4-carbonyl]-5-fluoro-1H-indol-6-yl]-1,3-diazaspiro[4.5]decane-2,4-dione, (5-1-370) 3-[2-[5-amino-1-[6-(2,6-difluorophenoxy)-4-methylpyridin-3-yl]pyrazole-4-carbonyl]-5-fluoro-1H-indol-6-yl]-5-methyl-5-(trifluoromethyl)imidazolidine-2,4-dione, (5-1-371) 7-[2-[5-amino-1-[4-(2-fluorophenoxy)-2-methylphenyl]pyrazole-4-carbonyl]-5-methyl-1H-indol-6-yl]-5,7-diazaspiro[3.4]octane-6,8-dione, (5-1-372) 6-[2-[5-amino-1-[4-(2-fluorophenoxy)-2-methylphenyl]pyrazole-4-carbonyl]-5-methyl-1H-indol-6-yl]-4,6-diazaspiro[2.4]heptane-5,7-dione, (5-1-373) 3-[2-[5-amino-1-[4-(2-fluorophenoxy)-2-methylphenyl]pyrazole-4-carbonyl]-5-methyl-1H-indol-6-yl]-1,3-diazaspiro[4.4]nonane-2,4-dione, (5-1-374) 7-[2-[5-amino-1-[4-(2-fluorophenoxy)-2-methylphenyl]pyrazole-4-carbonyl]-5-fluoro-1H-indol-6-yl]-5,7-diazaspiro[3.4]octane-6,8-dione, (5-1-375) 6-[2-[5-amino-1-[4-(2-fluorophenoxy)-2-methylphenyl]pyrazole-4-carbonyl]-5-fluoro-1H-indol-6-yl]-4,6-diazaspiro[2.4]heptane-5,7-dione, (5-1-376) 7-[2-[5-amino-1-[4-(2-fluorophenoxy)-2-methylphenyl]pyrazole-4-carbonyl]-5-fluoro-1H-indol-6-yl]-2-oxa-5,7-diazaspiro[3.4]octane-6,8-dione, (5-1-377) 3-[2-[5-amino-1-[6-(2-fluorophenoxy)-4-methylpyridin-3-yl]pyrazole-4-carbonyl]-5-(2,2-difluoroethoxy)-1H-indol-6-yl]-5,5-dimethylimidazolidine-2,4-dione, (5-1-378) N-[2-[5-amino-1-[6-(2-fluorophenoxy)-4-methylpyridin-3-yl]pyrazole-4-carbonyl]-5-fluoro-1H-indol-6-yl]oxane-4-sulfonamide, (5-1-379) 3-[2-[5-amino-1-[6-(2-fluorophenoxy)-4-methylpyridin-3-yl]pyrazole-4-carbonyl]-5-fluoro-1H-indol-6-yl]-5,5-dimethylimidazolidine-2,4-dione, (5-1-380) N-[2-[5-amino-1-[6-(2,6-difluorophenoxy)-4-methylpyridin-3-yl]pyrazole-4-carbonyl]-5-(difluoromethoxy)-1H-indol-6-yl]oxane-4-sulfonamide, (5-1-381) N-[2-[5-amino-1-[6-(2,6-difluorophenoxy)-4-methylpyridin-3-yl]pyrazole-4-carbonyl]-5-fluoro-1H-indol-6-yl]oxane-4-sulfonamide, (5-1-382) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-3-cyanobenzenesulfonamide, (5-1-383) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-3-chlorobenzenesulfonamide, (5-1-384) N-[2-[5-amino-1-[6-(2,6-difluorophenoxy)-4-methylpyridin-3-yl]pyrazole-4-carbonyl]-5-(2,2-difluoroethoxy)-1H-indol-6-yl]pyridine-3-sulfonamide, (5-1-385) [5-amino-1-[4-(2-fluorophenoxy)-3-methylphenyl]pyrazol-4-yl]-[5-(1-cyclopentylpiperidin-4-yl)oxy-6-[2-(trifluoromethyl)phenyl]-1H-indol-2-yl]methanone, (5-1-386) [5-amino-1-[4-(2-fluorophenoxy)-3-methylphenyl]pyrazol-4-yl]-[5-[1-(1,1-dioxothietan-3-yl)piperidin-4-yl]oxy-6-[2-(trifluoromethyl)phenyl]-1H-indol-2-yl]methanone, (5-1-387) [5-amino-1-[6-(2,6-difluorophenoxy)-4-methylpyridin-3-yl]pyrazol-4-yl]-[5-(1-cyclopentylpiperidin-4-yl)oxy-6-[2-(trifluoromethyl)phenyl]-1H-indol-2-yl]methanone, (5-1-388) [5-amino-1-[6-(2,6-difluorophenoxy)-4-methylpyridin-3-yl]pyrazol-4-yl]-[5-[1-(1,1-dioxothietan-3-yl)piperidin-4-yl]oxy-6-[2-(trifluoromethyl)phenyl]-1H-indol-2-yl]methanone, (5-1-389) N-[2-[5-amino-1-[4-(2-fluorophenoxy)-2-methylphenyl]pyrazole-4-carbonyl]-5-fluoro-1H-indol-6-yl]oxane-4-sulfonamide, (5-1-390) N-[2-[5-amino-1-[4-(2-fluorophenoxy)-2-methylphenyl]pyrazole-4-carbonyl]-5-(difluoromethoxy)-1H-indol-6-yl]oxane-4-sulfonamide, (5-1-391) 3-[2-[5-amino-1-[4-(2-fluorophenoxy)-2-methylphenyl]pyrazole-4-carbonyl]-5-methyl-1H-indol-6-yl]-8-(oxetan-3-yl)-1,3,8-triazaspiro[4.5]decane-2,4-dione, (5-1-392) 3-[2-[5-amino-1-[4-(2-fluorophenoxy)-2-methylphenyl]pyrazole-4-carbonyl]-5-methyl-1H-indol-6-yl]-8-benzyl-1,3,8-triazaspiro[4.5]decane-2,4-dione, (5-1-393) 3-[2-[5-amino-1-[4-(2-fluorophenoxy)-2-methylphenyl]pyrazole-4-carbonyl]-5-methyl-1H-indol-6-yl]-7-(oxetan-3-yl)-1,3,7-triazaspiro[4.4]nonane-2,4-dione, (5-1-394) 3-[2-[5-amino-1-[4-(2-fluorophenoxy)-2-methylphenyl]pyrazole-4-carbonyl]-5-methyl-1H-indol-6-yl]-7-benzyl-1,3,7-triazaspiro[4.4]nonane-2,4-dione, (5-1-395) N-[2-[5-amino-1-[6-(2,6-difluorophenoxy)-4-methylpyridin-3-yl]pyrazole-4-carbonyl]-5-cyclopropyl-1H-indol-6-yl]oxane-4-sulfonamide, (5-1-396) N-[2-[5-amino-1-[6-(2-fluorophenoxy)-4-methylpyridin-3-yl]pyrazole-4-carbonyl]-5-cyclopropyl-1H-indol-6-yl]oxane-4-sulfonamide, (5-1-397) N-[2-[5-amino-1-[4-(2-fluorophenoxy)-2-methylphenyl]pyrazole-4-carbonyl]-5-cyclopropyl-1H-indol-6-yl]oxane-4-sulfonamide, (5-1-398) [5-amino-1-[6-(2,6-difluorophenoxy)-4-methylpyridin-3-yl]pyrazol-4-yl]-[6-(4,4-dimethyl-1,1-dioxo-1,2,5-thiadiazolidin-2-yl)-5-fluoro-1H-indol-2-yl]methanone, (5-1-399) [5-amino-1-[6-(2,6-difluorophenoxy)-4-methylpyridin-3-yl]pyrazol-4-yl]-[6-(2,2-dioxo-2λ6-thia-1,3-diazaspiro[4.4]nonan-3-yl)-5-fluoro-1H-indol-2-yl]methanone, (5-1-400) [5-amino-1-[6-(2,6-difluorophenoxy)-4-methylpyridin-3-yl]pyrazol-4-yl]-[6-(2,2-dioxo-8-oxa-2λ6-thia-1,3-diazaspiro[4.5]decan-3-yl)-5-fluoro-1H-indol-2-yl]methanone, (5-1-401) N-[2-[5-amino-1-[6-(2-fluorophenoxy)-4-methylpyridin-3-yl]pyrazole-4-carbonyl]-5-(difluoromethoxy)-1H-indol-6-yl]oxane-4-sulfonamide, (5-1-402) 3-[2-[5-amino-1-[6-(2-fluorophenoxy)-4-methylpyridin-3-yl]pyrazole-4-carbonyl]-5-(difluoromethoxy)-1H-indol-6-yl]-5,5-dimethylimidazolidine-2,4-dione, (5-1-403) [5-amino-1-[4-(2-fluorophenoxy)-2-methylphenyl]pyrazol-4-yl]-[6-(2,2-dioxo-8-oxa-2λ6-thia-1,3-diazaspiro[4.5]decan-3-yl)-5-fluoro-1H-indol-2-yl]methanone, (5-1-404) 7-[2-[5-amino-1-[6-(2,6-difluorophenoxy)-4-methylpyridin-3-yl]pyrazole-4-carbonyl]-5-methyl-1H-indol-6-yl]-2-oxa-5,7-diazaspiro[3.4]octane-6,8-dione, (5-1-405) 3-[2-[5-amino-1-[6-(2,6-difluorophenoxy)-4-methylpyridin-3-yl]pyrazole-4-carbonyl]-5-fluoro-1H-indol-6-yl]imidazolidine-2,4-dione, (5-1-406) (5 S)-3-[2-[5-amino-1-[6-(2,6-difluorophenoxy)-4-methylpyridin-3-yl]pyrazole-4-carbonyl]-5-fluoro-1H-indol-6-yl]-5-methylimidazolidine-2,4-dione, (5-1-407) (5 S)-3-[2-[5-amino-1-[6-(2,6-difluorophenoxy)-4-methylpyridin-3-yl]pyrazole-4-carbonyl]-5-fluoro-1H-indol-6-yl]-5-(hydroxymethyl)imidazolidine-2,4-dione, (5-1-408) 3-[2-[5-amino-1-[4-(2-fluorophenoxy)-2-methylphenyl]pyrazole-4-carbonyl]-5-methyl-1H-indol-6-yl]-8-oxa-1,3-diazaspiro[4.5]decane-2,4-dione, (5-1-409) 3-[2-[5-amino-1-[4-(2-fluorophenoxy)-2-methylphenyl]pyrazole-4-carbonyl]-5-methyl-1H-indol-6-yl]-1,3-diazaspiro[4.5]decane-2,4-dione, (5-1-410) 7-[2-[5-amino-1-[4-(2-fluorophenoxy)-2-methylphenyl]pyrazole-4-carbonyl]-5-methyl-1H-indol-6-yl]-2-oxa-5,7-diazaspiro[3.4]octane-6,8-dione, (5-1-411) (5 S)-3-[2-[5-amino-1-[4-(2-fluorophenoxy)-2-methylphenyl]pyrazole-4-carbonyl]-5-fluoro-1H-indol-6-yl]-5-methylimidazolidine-2,4-dione, (5-1-412) 3-[2-[5-amino-1-[4-(2-fluorophenoxy)-2-methylphenyl]pyrazole-4-carbonyl]-5-fluoro-1H-indol-6-yl]-5-methyl-5-(trifluoromethyl)imidazolidine-2,4-dione, (5-1-413) [5-amino-1-[6-(2-fluorophenoxy)-4-methylpyridin-3-yl]pyrazol-4-yl]-[6-(2,2-dioxo-8-oxa-2λ6-thia-1,3-diazaspiro[4.5]decan-3-yl)-5-fluoro-1H-indol-2-yl]methanone, (5-1-414) N-[2-[5-amino-1-[4-(2-fluorophenoxy)-2-methylphenyl]pyrazole-4-carbonyl]-5-(2,2-difluoroethoxy)-1H-indol-6-yl]-3-methoxybenzenesulfonamide, (5-1-415) N-[2-[5-amino-1-[4-(2-fluorophenoxy)-2-methylphenyl]pyrazole-4-carbonyl]-5-(2,2-difluoroethoxy)-1H-indol-6-yl]-3,5-difluorobenzenesulfonamide, (5-1-416) N-[2-[5-amino-1-[4-(2-fluorophenoxy)-2-methylphenyl]pyrazole-4-carbonyl]-5-(2,2-difluoroethoxy)-1H-indol-6-yl]-3-cyanobenzenesulfonamide, (5-1-417) N-[2-[5-amino-1-[4-(2-fluorophenoxy)-2-methylphenyl]pyrazole-4-carbonyl]-5-(2,2-difluoroethoxy)-1H-indol-6-yl]-3-chlorobenzenesulfonamide, (5-1-418) N-[2-[5-amino-1-[4-(2-fluorophenoxy)-2-methylphenyl]pyrazole-4-carbonyl]-5-(2,2-difluoroethoxy)-1H-indol-6-yl]pyridine-3-sulfonamide, (5-1-419) N-[2-[5-amino-1-[6-(2-fluorophenoxy)-4-methylpyridin-3-yl]pyrazole-4-carbonyl]-5-(2,2-difluoroethoxy)-1H-indol-6-yl]-3-methoxybenzenesulfonamide, (5-1-420) N-[2-[5-amino-1-[6-(2-fluorophenoxy)-4-methylpyridin-3-yl]pyrazole-4-carbonyl]-5-(2,2-difluoroethoxy)-1H-indol-6-yl]-3,5-difluorobenzenesulfonamide, (5-1-421) [5-amino-1-[6-(2-fluorophenoxy)-4-methylpyridin-3-yl]pyrazol-4-yl]-[6-(4,4-dimethyl-1,1-dioxo-1,2,5-thiadiazolidin-2-yl)-5-fluoro-1H-indol-2-yl]methanone, (5-1-422) N-[2-[5-amino-1-[6-(2-fluorophenoxy)-4-methylpyridin-3-yl]pyrazole-4-carbonyl]-5-(2,2-difluoroethoxy)-1H-indol-6-yl]-3-cyanobenzenesulfonamide, (5-1-423) [5-amino-1-[4-(2-fluorophenoxy)-2-methylphenyl]pyrazol-4-yl]-[5-(difluoromethoxy)-6-(2,2-dioxo-2λ6-thia-1,3-diazaspiro[4.4]nonan-3-yl)-1H-indol-2-yl]methanone, (5-1-424) N-[2-[5-amino-1-[6-(2-fluorophenoxy)-4-methylpyridin-3-yl]pyrazole-4-carbonyl]-5-(2,2-difluoroethoxy)-1H-indol-6-yl]-3-chlorobenzenesulfonamide, (5-1-425) N-[2-[5-amino-1-[6-(2-fluorophenoxy)-4-methylpyridin-3-yl]pyrazole-4-carbonyl]-5-(2,2-difluoroethoxy)-1H-indol-6-yl]pyridine-3-sulfonamide, (5-1-426) N-[2-[5-amino-1-[4-(2-fluorophenoxy)-2-methylphenyl]pyrazole-4-carbonyl]-5-cyclopropyl-1H-indol-6-yl]-3-fluoropropane-1-sulfonamide, (5-1-427) N-[2-[5-amino-1-[6-(2,6-difluorophenoxy)-4-methylpyridin-3-yl]pyrazole-4-carbonyl]-5-cyclopropyl-1H-indol-6-yl]-3-fluoropropane-1-sulfonamide, (5-1-428) N-[2-[5-amino-1-[6-(2-fluorophenoxy)-4-methylpyridin-3-yl]pyrazole-4-carbonyl]-5-cyclopropyl-1H-indol-6-yl]-3-fluoropropane-1-sulfonamide, (5-1-429) 3-[2-[5-amino-1-[6-(2,6-difluorophenoxy)-4-methylpyridin-3-yl]pyrazole-4-carbonyl]-5-methyl-1H-indol-6-yl]-5-methyl-5-(trifluoromethyl)imidazolidine-2,4-dione, (5-1-430) (5 S)-3-[2-[5-amino-1-[6-(2,6-difluorophenoxy)-4-methylpyridin-3-yl]pyrazole-4-carbonyl]-5-fluoro-1H-indol-6-yl]-5-benzylimidazolidine-2,4-dione, (5-1-431) (5S)-3-[2-[5-amino-1-[6-(2,6-difluorophenoxy)-4-methylpyridin-3-yl]pyrazole-4-carbonyl]-5-fluoro-1H-indol-6-yl]-5-propan-2-ylimidazolidine-2,4-dione, (5-1-432) (7aS)-2-[2-[5-amino-1-[6-(2,6-difluorophenoxy)-4-methylpyridin-3-yl]pyrazole-4-carbonyl]-5-fluoro-1H-indol-6-yl]-5,6,7,7a-tetrahydropyrrolo[1,2-c]imidazole-1,3-dione, (5-1-433) (6R,7aS)-2-[2-[5-amino-1-[6-(2,6-difluorophenoxy)-4-methylpyridin-3-yl]pyrazole-4-carbonyl]-5-fluoro-1H-indol-6-yl]-6-hydroxy-5,6,7,7a-tetrahydropyrrolo[1,2-c]imidazole-1,3-dione,
(5-1-434) 3-[2-[5-amino-1-[4-(2-fluorophenoxy)-2-methylphenyl]pyrazole-4-carbonyl]-5-methyl-1H-indol-6-yl]imidazolidine-2,4-dione,
(5-1-435) 3-[2-[5-amino-1-[4-(2-fluorophenoxy)-2-methylphenyl]pyrazole-4-carbonyl]-5-methyl-1H-indol-6-yl]-5-methyl-5-(trifluoromethyl)imidazolidine-2,4-dione,
(5-1-436) (5 S)-3-[2-[5-amino-1-[4-(2-fluorophenoxy)-2-methylphenyl]pyrazole-4-carbonyl]-5-fluoro-1H-indol-6-yl]-5-benzylimidazolidine-2,4-dione,
(5-1-437) 3-[2-[5-amino-1-[4-(2-fluorophenoxy)-2-methylphenyl]pyrazole-4-carbonyl]-5-fluoro-1H-indol-6-yl]-8-oxa-1,3-diazaspiro[4.5]decane-2,4-dione,
(5-1-438) 3-[2-[5-amino-1-[4-(2-fluorophenoxy)-2-methylphenyl]pyrazole-4-carbonyl]-5-fluoro-1H-indol-6-yl]-1,3-diazaspiro[4.4]nonane-2,4-dione,
(5-1-439) N-[2-[5-amino-1-[6-(2-fluorophenoxy)-4-methylpyridin-3-yl]pyrazole-4-carbonyl]-5-methyl-1H-indol-6-yl]-3-methoxybenzenesulfonamide,
(5-1-440) N-[2-[5-amino-1-[6-(2-fluorophenoxy)-4-methylpyridin-3-yl]pyrazole-4-carbonyl]-5-methyl-1H-indol-6-yl]-3-cyanobenzenesulfonamide,
(5-1-441) N-[2-[5-amino-1-[6-(2-fluorophenoxy)-4-methylpyridin-3-yl]pyrazole-4-carbonyl]-5-methyl-1H-indol-6-yl]pyridine-3-sulfonamide,
(5-1-442) 3-[2-[5-amino-1-[6-(2,6-difluorophenoxy)-4-methylpyridin-3-yl]pyrazole-4-carbonyl]-5-methyl-1H-indol-6-yl]imidazolidine-2,4-dione,
(5-1-443) (5 S)-3-[2-[5-amino-1-[6-(2,6-difluorophenoxy)-4-methylpyridin-3-yl]pyrazole-4-carbonyl]-5-methyl-1H-indol-6-yl]-5-methylimidazolidine-2,4-dione,
(5-1-444) (5 S)-3-[2-[5-amino-1-[4-(2-fluorophenoxy)-2-methylphenyl]pyrazole-4-carbonyl]-5-methyl-1H-indol-6-yl]-5-methylimidazolidine-2,4-dione,
(5-1-445) 3-[2-[5-amino-1-[4-(2-fluorophenoxy)-2-methylphenyl]pyrazole-4-carbonyl]-5-fluoro-1H-indol-6-yl]imidazolidine-2,4-dione,
(5-1-446) (5 S)-3-[2-[5-amino-1-[4-(2-fluorophenoxy)-2-methylphenyl]pyrazole-4-carbonyl]-5-fluoro-1H-indol-6-yl]-5-(hydroxymethyl)imidazolidine-2,4-dione,
(5-1-447) (5 S)-3-[2-[5-amino-1-[4-(2-fluorophenoxy)-2-methylphenyl]pyrazole-4-carbonyl]-5-fluoro-1H-indol-6-yl]-5-propan-2-ylimidazolidine-2,4-dione,
(5-1-448) (7aS)-2-[2-[5-amino-1-[4-(2-fluorophenoxy)-2-methylphenyl]pyrazole-4-carbonyl]-5-fluoro-1H-indol-6-yl]-5,6,7,7a-tetrahydropyrrolo[1,2-c]imidazole-1,3-dione,
(5-1-449) (6R,7aS)-2-[2-[5-amino-1-[4-(2-fluorophenoxy)-2-methylphenyl]pyrazole-4-carbonyl]-5-fluoro-1H-indol-6-yl]-6-hydroxy-5,6,7,7a-tetrahydropyrrolo[1,2-c]imidazole-1,3-dione,
(5-1-450) 3-[2-[5-amino-1-[4-(2-fluorophenoxy)-2-methylphenyl]pyrazole-4-carbonyl]-5-fluoro-1H-indol-6-yl]-1,3-diazaspiro[4.5]decane-2,4-dione,
(5-1-451) (5S)-3-[2-[5-amino-1-[6-(2,6-difluorophenoxy)-4-methylpyridin-3-yl]pyrazole-4-carbonyl]-5-methyl-1H-indol-6-yl]-5-(hydroxymethyl)imidazolidine-2,4-dione,
(5-1-452) (5 S)-3-[2-[5-amino-1-[6-(2,6-difluorophenoxy)-4-methylpyridin-3-yl]pyrazole-4-carbonyl]-5-methyl-1H-indol-6-yl]-5-benzylimidazolidine-2,4-dione,
(5-1-453) (5 S)-3-[2-[5-amino-1-[6-(2,6-difluorophenoxy)-4-methylpyridin-3-yl]pyrazole-4-carbonyl]-5-methyl-1H-indol-6-yl]-5-propan-2-ylimidazolidine-2,4-dione,
(5-1-454) (7aS)-2-[2-[5-amino-1-[6-(2,6-difluorophenoxy)-4-methylpyridin-3-yl]pyrazole-4-carbonyl]-5-methyl-1H-indol-6-yl]-5,6,7,7a-tetrahydropyrrolo[1,2-c]imidazole-1,3-dione,
(5-1-455) (6R,7aS)-2-[2-[5-amino-1-[6-(2,6-difluorophenoxy)-4-methylpyridin-3-yl]pyrazole-4-carbonyl]-5-methyl-1H-indol-6-yl]-6-hydroxy-5,6,7,7a-tetrahydropyrrolo[1,2-c]imidazole-1,3-dione,
(5-1-456) (5 S)-3-[2-[5-amino-1-[4-(2-fluorophenoxy)-2-methylphenyl]pyrazole-4-carbonyl]-5-methyl-1H-indol-6-yl]-5-(hydroxymethyl)imidazolidine-2,4-dione,
(5-1-457) (5 S)-3-[2-[5-amino-1-[4-(2-fluorophenoxy)-2-methylphenyl]pyrazole-4-carbonyl]-5-methyl-1H-indol-6-yl]-5-benzylimidazolidine-2,4-dione,
(5-1-458) (7aS)-2-[2-[5-amino-1-[4-(2-fluorophenoxy)-2-methylphenyl]pyrazole-4-carbonyl]-5-methyl-1H-indol-6-yl]-5,6,7,7a-tetrahydropyrrolo[1,2-c]imidazole-1,3-dione,
(5-1-459) (6R,7aS)-2-[2-[5-amino-1-[4-(2-fluorophenoxy)-2-methylphenyl]pyrazole-4-carbonyl]-5-methyl-1H-indol-6-yl]-6-hydroxy-5,6,7,7a-tetrahydropyrrolo[1,2-c]imidazole-1,3-dione,
(5-1-460) N-[2-[5-amino-1-[6-(2-fluorophenoxy)-4-methylpyridin-3-yl]pyrazole-4-carbonyl]-5-methyl-1H-indol-6-yl]-3,5-difluorobenzenesulfonamide,
(5-1-461) N-[2-[5-amino-1-[6-(2-fluorophenoxy)-4-methylpyridin-3-yl]pyrazole-4-carbonyl]-5-methyl-1H-indol-6-yl]-2,4,6-trimethylbenzenesulfonamide,
(5-1-462) N-[2-[5-amino-1-[6-(2-fluorophenoxy)-4-methylpyridin-3-yl]pyrazole-4-carbonyl]-5-methyl-1H-indol-6-yl]-3-methylbenzenesulfonamide,
(5-1-463) N-[2-[5-amino-1-[6-(2-fluorophenoxy)-4-methylpyridin-3-yl]pyrazole-4-carbonyl]-5-methyl-1H-indol-6-yl]-3-(trifluoromethyl)benzenesulfonamide,
(5-1-464) N-[2-[5-amino-1-[6-(2-fluorophenoxy)-4-methylpyridin-3-yl]pyrazole-4-carbonyl]-5-methyl-1H-indol-6-yl]-3-chlorobenzenesulfonamide,
(5-1-465) N-[2-[5-amino-1-[6-(2-fluorophenoxy)-4-methylpyridin-3-yl]pyrazole-4-carbonyl]-5-methyl-1H-indol-6-yl]naphthalene-1-sulfonamide,
(5-1-466) N-[2-[5-amino-1-[6-(2-fluorophenoxy)-4-methylpyridin-3-yl]pyrazole-4-carbonyl]-5-methyl-1H-indol-6-yl]naphthalene-2-sulfonamide,
(5-1-467) N-[2-[5-amino-1-[6-(2-fluorophenoxy)-4-methylpyridin-3-yl]pyrazole-4-carbonyl]-5-methyl-1H-indol-6-yl]-1-benzothiophene-3-sulfonamide,
(5-1-468) 7-[2-[5-amino-1-[4-(2-fluorophenoxy)-3-methylphenyl]pyrazole-4-carbonyl]-5-methyl-1H-indol-6-yl]-5,7-diazaspiro[3.4]octane-6,8-dione,
(5-1-469) 3-[2-[5-amino-1-[4-(2-fluorophenoxy)-3-methylphenyl]pyrazole-4-carbonyl]-5-methyl-1H-indol-6-yl]-8-oxa-1,3-diazaspiro[4.5]decane-2,4-dione,
(5-1-470) 3-[2-[5-amino-1-[4-(2-fluorophenoxy)-3-methylphenyl]pyrazole-4-carbonyl]-5-methyl-1H-indol-6-yl]-1,3-diazaspiro[4.5]decane-2,4-dione,
(5-1-471) tert-Butyl 3-[2-[5-amino-1-[4-(2-fluorophenoxy)-3-methylphenyl]pyrazole-4-carbonyl]-5-methyl-1H-indol-6-yl]-2,4-dioxo-1,3,8-triazaspiro[4.5]decane-8-carboxylate, (5-1-472) 3-[2-[5-amino-1-[4-(2-fluorophenoxy)-3-methylphenyl]pyrazole-4-carbonyl]-5-methyl-1H-indol-6-yl]-5-methyl-5-(trifluoromethyl)imidazolidine-2,4-dione, (5-1-473) 6-[2-[5-amino-1-[4-(2-fluorophenoxy)-3-methylphenyl]pyrazole-4-carbonyl]-5-methyl-1H-indol-6-yl]-4,6-diazaspiro[2.4]heptane-5,7-dione, (5-1-474) 3-[2-[5-amino-1-[4-(2-fluorophenoxy)-3-methylphenyl]pyrazole-4-carbonyl]-5-methyl-1H-indol-6-yl]-1,3-diazaspiro[4.4]nonane-2,4-dione, (5-1-475) 7-[2-[5-amino-1-[4-(2-fluorophenoxy)-3-methylphenyl]pyrazole-4-carbonyl]-5-methyl-1H-indol-6-yl]-2-oxa-5,7-diazaspiro[3.4]octane-6,8-dione, (5-1-476) (5 S)-3-[2-[5-amino-1-[4-(2-fluorophenoxy)-2-methylphenyl]pyrazole-4-carbonyl]-5-methyl-1H-indol-6-yl]-5-propan-2-ylimidazolidine-2,4-dione, (5-1-477) N-[2-[5-amino-1-[6-(2-fluorophenoxy)-4-methylpyridin-3-yl]pyrazole-4-carbonyl]-5-methyl-1H-indol-6-yl]pyridine-2-sulfonamide, (5-1-478) N-[2-[5-amino-1-[6-(2-fluorophenoxy)-4-methylpyridin-3-yl]pyrazole-4-carbonyl]-5-methyl-1H-indol-6-yl]-4-cyanopyridine-2-sulfonamide, (5-1-479) N-[2-[5-amino-1-[6-(2-fluorophenoxy)-4-methylpyridin-3-yl]pyrazole-4-carbonyl]-5-methyl-1H-indol-6-yl]-6-cyanopyridine-2-sulfonamide, (5-1-480) N-[2-[5-amino-1-[6-(2-fluorophenoxy)-4-methylpyridin-3-yl]pyrazole-4-carbonyl]-5-methyl-1H-indol-6-yl]-5-cyanopyridine-3-sulfonamide, (5-1-481) N-[2-[5-amino-1-[6-(2-fluorophenoxy)-4-methylpyridin-3-yl]pyrazole-4-carbonyl]-5-methyl-1H-indol-6-yl]-4-cyano-6-methylpyridine-2-sulfonamide, (5-1-482) N-[2-[5-amino-1-[6-(2-fluorophenoxy)-4-methylpyridin-3-yl]pyrazole-4-carbonyl]-5-methyl-1H-indol-6-yl]-4-methoxypyridine-2-sulfonamide, (5-1-483) N-[2-[5-amino-1-[6-(2-fluorophenoxy)-4-methylpyridin-3-yl]pyrazole-4-carbonyl]-5-methyl-1H-indol-6-yl]-6-methoxypyridine-2-sulfonamide, (5-1-484) N-[2-[5-amino-1-[6-(2-fluorophenoxy)-4-methylpyridin-3-yl]pyrazole-4-carbonyl]-5-methyl-1H-indol-6-yl]-5-methoxypyridine-3-sulfonamide, (5-1-485) N-[2-[5-amino-1-[6-(2-fluorophenoxy)-4-methylpyridin-3-yl]pyrazole-4-carbonyl]-5-methyl-1H-indol-6-yl]-4-(trifluoromethyl)pyridine-2-sulfonamide, (5-1-486) N-[2-[5-amino-1-[6-(2-fluorophenoxy)-4-methylpyridin-3-yl]pyrazole-4-carbonyl]-5-methyl-1H-indol-6-yl]-6-(trifluoromethyl)pyridine-2-sulfonamide, (5-1-487) N-[2-[5-amino-1-[6-(2-fluorophenoxy)-4-methylpyridin-3-yl]pyrazole-4-carbonyl]-5-methyl-1H-indol-6-yl]-5-(trifluoromethyl)pyridine-3-sulfonamide, (5-1-488) N-[2-[5-amino-1-[6-(2-fluorophenoxy)-4-methylpyridin-3-yl]pyrazole-4-carbonyl]-5-methyl-1H-indol-6-yl]-5-methylpyridine-3-sulfonamide, (5-1-489) N-[2-[5-amino-1-[4-(2-fluorophenoxy)-2-methylphenyl]pyrazole-4-carbonyl]-5-fluoro-1H-indol-6-yl]pyridine-3-sulfonamide, (5-1-490) N-[2-[5-amino-1-[4-(2-fluorophenoxy)-2-methylphenyl]pyrazole-4-carbonyl]-5-fluoro-1H-indol-6-yl]-3-cyanobenzenesulfonamide, (5-1-491) N-[2-[5-amino-1-[6-(2,6-difluorophenoxy)-4-methylpyridin-3-yl]pyrazole-4-carbonyl]-5-fluoro-1H-indol-6-yl]pyridine-3-sulfonamide, (5-1-492) N-[2-[5-amino-1-[6-(2,6-difluorophenoxy)-4-methylpyridin-3-yl]pyrazole-4-carbonyl]-5-fluoro-1H-indol-6-yl]-3-cyanobenzenesulfonamide, (5-1-493) N-[2-[5-amino-1-[4-(2-fluorophenoxy)-3-methylphenyl]pyrazole-4-carbonyl]-5-fluoro-1H-indol-6-yl]oxane-4-sulfonamide, (5-1-494) N-[2-[5-amino-1-[6-(2-fluorophenoxy)-4-methylpyridin-3-yl]pyrazole-4-carbonyl]-5-methyl-1H-indol-6-yl]-5-fluoropyridine-3-sulfonamide, (5-1-495) N-[2-[5-amino-1-[6-(2-fluorophenoxy)-4-methylpyridin-3-yl]pyrazole-4-carbonyl]-5-methyl-1H-indol-6-yl]-5-chloropyridine-3-sulfonamide, (5-1-496) N-[2-[5-amino-1-[6-(2-fluorophenoxy)-4-methylpyridin-3-yl]pyrazole-4-carbonyl]-5-methyl-1H-indol-6-yl]-3-fluoro-5-methoxybenzenesulfonamide, (5-1-497) N-[2-[5-amino-1-[6-(2-fluorophenoxy)-4-methylpyridin-3-yl]pyrazole-4-carbonyl]-5-methyl-1H-indol-6-yl]-3-cyano-5-fluorobenzenesulfonamide, (5-1-498) N-[2-[5-amino-1-[6-(2-fluorophenoxy)-4-methylpyridin-3-yl]pyrazole-4-carbonyl]-5-methyl-1H-indol-6-yl]-3-chloro-5-cyanobenzenesulfonamide, (5-1-499) N-[2-[5-amino-1-[6-(2-fluorophenoxy)-4-methylpyridin-3-yl]pyrazole-4-carbonyl]-5-methyl-1H-indol-6-yl]-3-cyano-5-(trifluoromethyl)benzenesulfonamide, (5-1-500) N-[2-[5-amino-1-[6-(2-fluorophenoxy)-4-methylpyridin-3-yl]pyrazole-4-carbonyl]-5-methyl-1H-indol-6-yl]-3-fluorobenzenesulfonamide, (5-1-501) N-[2-[5-amino-1-[6-(2-fluorophenoxy)-4-methylpyridin-3-yl]pyrazole-4-carbonyl]-5-methyl-1H-indol-6-yl]-2,4,6-trifluorobenzenesulfonamide, (5-1-502) N-[2-[5-amino-1-[6-(2-fluorophenoxy)-4-methylpyridin-3-yl]pyrazole-4-carbonyl]-5-methyl-1H-indol-6-yl]-6-fluoropyridine-2-sulfonamide, (5-1-503) [5-amino-1-[6-(2,6-difluorophenoxy)-4-methylpyridin-3-yl]pyrazol-4-yl]-[5-(1-cyclopentylpiperidin-4-yl)oxy-6-(2-methoxyphenyl)-1H-indol-2-yl]methanone, (5-1-504) N-[2-[5-amino-1-[6-(2-fluorophenoxy)-4-methylpyridin-3-yl]pyrazole-4-carbonyl]-5-methyl-1H-indol-6-yl]-2-fluoro-5-methylpyridine-3-sulfonamide, (5-1-505) N-[2-[5-amino-1-[6-(2-fluorophenoxy)-4-methylpyridin-3-yl]pyrazole-4-carbonyl]-5-methyl-1H-indol-6-yl]-4-fluoropyridine-2-sulfonamide, (5-1-506) N-[2-[5-amino-1-[6-(2-fluorophenoxy)-4-methylpyridin-3-yl]pyrazole-4-carbonyl]-5-methyl-1H-indol-6-yl]-4-methylpyridine-2-sulfonamide, (5-1-507) N-[2-[5-amino-1-[6-(2-fluorophenoxy)-4-methylpyridin-3-yl]pyrazole-4-carbonyl]-5-methyl-1H-indol-6-yl]-6-methylpyridine-2-sulfonamide, (5-1-508) N-[2-[5-amino-1-[6-(2-fluorophenoxy)-4-methylpyridin-3-yl]pyrazole-4-carbonyl]-5-methyl-1H-indol-6-yl]-6-chloropyridine-2-sulfonamide, (5-1-509) N-[2-[5-amino-1-[6-(2-fluorophenoxy)-4-methylpyridin-3-yl]pyrazole-4-carbonyl]-5-methyl-1H-indol-6-yl]-4-chloropyridine-2-sulfonamide, (5-1-510) N-[2-[5-amino-1-[4-(2-fluorophenoxy)-2-methylphenyl]pyrazole-4-carbonyl]-5-methyl-1H-indol-6-yl]-4-methoxypyridine-2-sulfonamide, (5-1-511) N-[2-[5-amino-1-[6-(2,6-difluorophenoxy)-4-methylpyridin-3-yl]pyrazole-4-carbonyl]-5-methyl-1H-indol-6-yl]-4-methoxypyridine-2-sulfonamide, (5-1-512) N-[2-[5-amino-1-[4-(2-fluorophenoxy)-2-methylphenyl]pyrazole-4-carbonyl]-5-fluoro-1H-indol-6-yl]-4-methoxypyridine-2-sulfonamide, (5-1-513) N-[2-[5-amino-1-[6-(2,6-difluorophenoxy)-4-methylpyridin-3-yl]pyrazole-4-carbonyl]-5-fluoro-1H-indol-6-yl]-4-methoxypyridine-2-sulfonamide,
(5-1-514) N-[2-[5-amino-1-[6-(2-fluorophenoxy)-4-methylpyridin-3-yl]pyrazole-4-carbonyl]-5-fluoro-1H-indol-6-yl]-4-methoxypyridine-2-sulfonamide,
(5-1-515) N-[2-[5-amino-1-[4-(2-fluorophenoxy)-2-methylphenyl]pyrazole-4-carbonyl]-5-methyl-1H-indol-6-yl]-6-fluoropyridine-2-sulfonamide,
(5-1-516) N-[2-[5-amino-1-[6-(2,6-difluorophenoxy)-4-methylpyridin-3-yl]pyrazole-4-carbonyl]-5-methyl-1H-indol-6-yl]-6-fluoropyridine-2-sulfonamide,
(5-1-517) N-[2-[5-amino-1-[4-(2-fluorophenoxy)-2-methylphenyl]pyrazole-4-carbonyl]-5-fluoro-1H-indol-6-yl]-6-fluoropyridine-2-sulfonamide,
(5-1-518) N-[2-[5-amino-1-[6-(2,6-difluorophenoxy)-4-methylpyridin-3-yl]pyrazole-4-carbonyl]-5-fluoro-1H-indol-6-yl]-6-fluoropyridine-2-sulfonamide,
(5-1-519) N-[2-[5-amino-1-[6-(2-fluorophenoxy)-4-methylpyridin-3-yl]pyrazole-4-carbonyl]-5-fluoro-1H-indol-6-yl]-6-fluoropyridine-2-sulfonamide,
(5-1-520) N-[2-[5-amino-1-[4-(2-fluorophenoxy)-2-methylphenyl]pyrazole-4-carbonyl]-5-methyl-1H-indol-6-yl]-2-fluoro-5-methylpyridine-3-sulfonamide,
(5-1-521) N-[2-[5-amino-1-[6-(2,6-difluorophenoxy)-4-methylpyridin-3-yl]pyrazole-4-carbonyl]-5-methyl-1H-indol-6-yl]-2-fluoro-5-methylpyridine-3-sulfonamide,
(5-1-522) N-[2-[5-amino-1-[4-(2-fluorophenoxy)-2-methylphenyl]pyrazole-4-carbonyl]-5-fluoro-1H-indol-6-yl]-2-fluoro-5-methylpyridine-3-sulfonamide,
(5-1-523) N-[2-[5-amino-1-[6-(2,6-difluorophenoxy)-4-methylpyridin-3-yl]pyrazole-4-carbonyl]-5-fluoro-1H-indol-6-yl]-2-fluoro-5-methylpyridine-3-sulfonamide,
(5-1-524) N-[2-[5-amino-1-[6-(2-fluorophenoxy)-4-methylpyridin-3-yl]pyrazole-4-carbonyl]-5-fluoro-1H-indol-6-yl]-2-fluoro-5-methylpyridine-3-sulfonamide,
(5-1-525) N-[2-[5-amino-1-[4-(2-fluorophenoxy)-2-methylphenyl]pyrazole-4-carbonyl]-5-methyl-1H-indol-6-yl]-6-chloropyridine-2-sulfonamide,
(5-1-526) N-[2-[5-amino-1-[6-(2,6-difluorophenoxy)-4-methylpyridin-3-yl]pyrazole-4-carbonyl]-5-methyl-1H-indol-6-yl]-6-chloropyridine-2-sulfonamide,
(5-1-527) N-[2-[5-amino-1-[4-(2-fluorophenoxy)-2-methylphenyl]pyrazole-4-carbonyl]-5-fluoro-1H-indol-6-yl]-6-chloropyridine-2-sulfonamide,
(5-1-528) N-[2-[5-amino-1-[6-(2,6-difluorophenoxy)-4-methylpyridin-3-yl]pyrazole-4-carbonyl]-5-fluoro-1H-indol-6-yl]-6-chloropyridine-2-sulfonamide,
(5-1-529) N-[2-[5-amino-1-[6-(2-fluorophenoxy)-4-methylpyridin-3-yl]pyrazole-4-carbonyl]-5-fluoro-1H-indol-6-yl]-6-chloropyridine-2-sulfonamide,
(5-1-530) N-[2-[5-amino-1-[4-(2-fluorophenoxy)-2-methylphenyl]pyrazole-4-carbonyl]-5-methyl-1H-indol-6-yl]-6-methylpyridine-2-sulfonamide,
(5-1-531) N-[2-[5-amino-1-[6-(2,6-difluorophenoxy)-4-methylpyridin-3-yl]pyrazole-4-carbonyl]-5-methyl-1H-indol-6-yl]-6-methylpyridine-2-sulfonamide,
(5-1-532) N-[2-[5-amino-1-[4-(2-fluorophenoxy)-2-methylphenyl]pyrazole-4-carbonyl]-5-fluoro-1H-indol-6-yl]-6-methylpyridine-2-sulfonamide,
(5-1-533) N-[2-[5-amino-1-[6-(2,6-difluorophenoxy)-4-methylpyridin-3-yl]pyrazole-4-carbonyl]-5-fluoro-1H-indol-6-yl]-6-methylpyridine-2-sulfonamide,
(5-1-534) N-[2-[5-amino-1-[6-(2-fluorophenoxy)-4-methylpyridin-3-yl]pyrazole-4-carbonyl]-5-fluoro-1H-indol-6-yl]-6-methylpyridine-2-sulfonamide,
(5-1-535) N-[2-[5-amino-1-[4-(2-fluorophenoxy)-2-methylphenyl]pyrazole-4-carbonyl]-5-methyl-1H-indol-6-yl]-6-cyanopyridine-2-sulfonamide,
(5-1-536) N-[2-[5-amino-1-[6-(2,6-difluorophenoxy)-4-methylpyridin-3-yl]pyrazole-4-carbonyl]-5-methyl-1H-indol-6-yl]-6-cyanopyridine-2-sulfonamide,
(5-1-537) N-[2-[5-amino-1-[4-(2-fluorophenoxy)-2-methylphenyl]pyrazole-4-carbonyl]-5-fluoro-1H-indol-6-yl]-6-cyanopyridine-2-sulfonamide,
(5-1-538) N-[2-[5-amino-1-[6-(2,6-difluorophenoxy)-4-methylpyridin-3-yl]pyrazole-4-carbonyl]-5-fluoro-1H-indol-6-yl]-6-cyanopyridine-2-sulfonamide,
(5-1-539) N-[2-[5-amino-1-[6-(2-fluorophenoxy)-4-methylpyridin-3-yl]pyrazole-4-carbonyl]-5-fluoro-1H-indol-6-yl]-6-cyanopyridine-2-sulfonamide,
(5-1-540) N-[2-[5-amino-1-[4-(2-fluorophenoxy)-2-methylphenyl]pyrazole-4-carbonyl]-5-methyl-1H-indol-6-yl]-5-chloropyridine-3-sulfonamide,
(5-1-541) N-[2-[5-amino-1-[6-(2,6-difluorophenoxy)-4-methylpyridin-3-yl]pyrazole-4-carbonyl]-5-methyl-1H-indol-6-yl]-5-chloropyridine-3-sulfonamide,
(5-1-542) N-[2-[5-amino-1-[4-(2-fluorophenoxy)-2-methylphenyl]pyrazole-4-carbonyl]-5-fluoro-1H-indol-6-yl]-5-chloropyridine-3-sulfonamide,
(5-1-543) N-[2-[5-amino-1-[6-(2,6-difluorophenoxy)-4-methylpyridin-3-yl]pyrazole-4-carbonyl]-5-fluoro-1H-indol-6-yl]-5-chloropyridine-3-sulfonamide,
(5-1-544) N-[2-[5-amino-1-[6-(2-fluorophenoxy)-4-methylpyridin-3-yl]pyrazole-4-carbonyl]-5-fluoro-1H-indol-6-yl]-5-chloropyridine-3-sulfonamide,
(5-1-545) N-[2-[5-amino-1-[4-(2-fluorophenoxy)-2-methylphenyl]pyrazole-4-carbonyl]-5-methyl-1H-indol-6-yl]-5-fluoropyridine-3-sulfonamide,
(5-1-546) N-[2-[5-amino-1-[6-(2,6-difluorophenoxy)-4-methylpyridin-3-yl]pyrazole-4-carbonyl]-5-methyl-1H-indol-6-yl]-5-fluoropyridine-3-sulfonamide,
(5-1-547) N-[2-[5-amino-1-[4-(2-fluorophenoxy)-2-methylphenyl]pyrazole-4-carbonyl]-5-fluoro-1H-indol-6-yl]-5-fluoropyridine-3-sulfonamide,
(5-1-548) N-[2-[5-amino-1-[6-(2,6-difluorophenoxy)-4-methylpyridin-3-yl]pyrazole-4-carbonyl]-5-fluoro-1H-indol-6-yl]-5-fluoropyridine-3-sulfonamide,
(5-1-549) N-[2-[5-amino-1-[6-(2-fluorophenoxy)-4-methylpyridin-3-yl]pyrazole-4-carbonyl]-5-fluoro-1H-indol-6-yl]-5-fluoropyridine-3-sulfonamide,
(5-1-550) N-[2-[5-amino-1-[4-(2-fluorophenoxy)-2-methylphenyl]pyrazole-4-carbonyl]-5-methyl-1H-indol-6-yl]-3-fluorobenzenesulfonamide,
(5-1-551) N-[2-[5-amino-1-[6-(2,6-difluorophenoxy)-4-methylpyridin-3-yl]pyrazole-4-carbonyl]-5-methyl-1H-indol-6-yl]-3-fluorobenzenesulfonamide,
(5-1-552) N-[2-[5-amino-1-[4-(2-fluorophenoxy)-2-methylphenyl]pyrazole-4-carbonyl]-5-fluoro-1H-indol-6-yl]-3-fluorobenzenesulfonamide,
(5-1-553) N-[2-[5-amino-1-[6-(2,6-difluorophenoxy)-4-methylpyridin-3-yl]pyrazole-4-carbonyl]-5-fluoro-1H-indol-6-yl]-3-fluorobenzenesulfonamide,
(5-1-554) N-[2-[5-amino-1-[6-(2-fluorophenoxy)-4-methylpyridin-3-yl]pyrazole-4-carbonyl]-5-fluoro-1H-indol-6-yl]-3-fluorobenzenesulfonamide,
(5-1-555) N-[2-[5-amino-1-[6-(2,6-difluorophenoxy)-4-methylpyridin-3-yl]pyrazole-4-carbonyl]-5-methyl-1H-indol-6-yl]-3-cyanobenzenesulfonamide,
(5-1-556) N-[2-[5-amino-1-[6-(2-fluorophenoxy)-4-methylpyridin-3-yl]pyrazole-4-carbonyl]-5-fluoro-1H-indol-6-yl]-3-cyanobenzenesulfonamide, (5-1-557) N-[2-[5-amino-1-[6-(2,6-difluorophenoxy)-4-methylpyridin-3-yl]pyrazole-4-carbonyl]-5-methyl-1H-indol-6-yl]-3-chlorobenzenesulfonamide, (5-1-558) N-[2-[5-amino-1-[4-(2-fluorophenoxy)-2-methylphenyl]pyrazole-4-carbonyl]-5-fluoro-1H-indol-6-yl]-3-chlorobenzenesulfonamide, (5-1-559) N-[2-[5-amino-1-[6-(2,6-difluorophenoxy)-4-methylpyridin-3-yl]pyrazole-4-carbonyl]-5-fluoro-1H-indol-6-yl]-3-chlorobenzenesulfonamide, (5-1-560) N-[2-[5-amino-1-[6-(2-fluorophenoxy)-4-methylpyridin-3-yl]pyrazole-4-carbonyl]-5-fluoro-1H-indol-6-yl]-3-chlorobenzenesulfonamide, (5-1-561) N-[2-[5-amino-1-[6-(2,6-difluorophenoxy)-4-methylpyridin-3-yl]pyrazole-4-carbonyl]-5-methyl-1H-indol-6-yl]-3,5-difluorobenzenesulfonamide, (5-1-562) N-[2-[5-amino-1-[4-(2-fluorophenoxy)-2-methylphenyl]pyrazole-4-carbonyl]-5-fluoro-1H-indol-6-yl]-3,5-difluorobenzenesulfonamide, (5-1-563) N-[2-[5-amino-1-[6-(2,6-difluorophenoxy)-4-methylpyridin-3-yl]pyrazole-4-carbonyl]-5-fluoro-1H-indol-6-yl]-3,5-difluorobenzenesulfonamide, (5-1-564) N-[2-[5-amino-1-[6-(2-fluorophenoxy)-4-methylpyridin-3-yl]pyrazole-4-carbonyl]-5-fluoro-1H-indol-6-yl]-3,5-difluorobenzenesulfonamide, (5-1-565) N-[2-[5-amino-1-[6-(2,6-difluorophenoxy)-4-methylpyridin-3-yl]pyrazole-4-carbonyl]-5-methyl-1H-indol-6-yl]-2,4,6-trifluorobenzenesulfonamide, (5-1-566) N-[2-[5-amino-1-[4-(2-fluorophenoxy)-2-methylphenyl]pyrazole-4-carbonyl]-5-fluoro-1H-indol-6-yl]-2,4,6-trifluorobenzenesulfonamide, (5-1-567) N-[2-[5-amino-1-[6-(2,6-difluorophenoxy)-4-methylpyridin-3-yl]pyrazole-4-carbonyl]-5-fluoro-1H-indol-6-yl]-2,4,6-trifluorobenzenesulfonamide, (5-1-568) N-[2-[5-amino-1-[6-(2-fluorophenoxy)-4-methylpyridin-3-yl]pyrazole-4-carbonyl]-5-fluoro-1H-indol-6-yl]-2,4,6-trifluorobenzenesulfonamide, (5-1-569) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-4-methoxypyridine-2-sulfonamide, (5-1-570) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-6-fluoropyridine-2-sulfonamide, (5-1-571) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-2-fluoro-5-methylpyridine-3-sulfonamide, (5-1-572) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-6-chloropyridine-2-sulfonamide, (5-1-573) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-6-methylpyridine-2-sulfonamide, (5-1-574) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-6-cyanopyridine-2-sulfonamide, (5-1-575) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-5-chloropyridine-3-sulfonamide, (5-1-576) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-5-fluoropyridine-3-sulfonamide, and (5-1-577) N-[2-[5-amino-1-[6-(2-fluorophenoxy)-4-methylpyridin-3-yl]pyrazole-4-carbonyl]-5-methyl-1H-indol-6-yl]-2-(dimethylamino)pyrimidine-5-sulfonamide, or a pharmaceutically acceptable salt thereof.

16. The compound or a pharmaceutically acceptable salt thereof according to claim 1, wherein the compound or a pharmaceutically acceptable salt thereof is selected from the group consisting of:

(4-1-001) N-[2-[5-amino-1-[6-(2,6-difluorophenoxy)-4-methylpyridin-3-yl]pyrazole-4-carbonyl]-5-methyl-1H-indol-6-yl]methanesulfonamide, (4-1-008) N-[2-[5-amino-1-[6-(2-fluorophenoxy)-4-methylpyridin-3-yl]pyrazole-4-carbonyl]-5-methoxy-1H-indol-6-yl]methanesulfonamide, (4-2-015) N-[2-[5-amino-1-[4-(2-fluorophenoxy)-2-methylphenyl]pyrazole-4-carbonyl]-5-fluoro-1H-indol-6-yl]-3-fluoropropane-1-sulfonamide, (4-2-016) N-[2-[5-amino-1-[4-(2,3-difluorophenoxy)-2-methylphenyl]pyrazole-4-carbonyl]-5-fluoro-1H-indol-6-yl]-3-fluoropropane-1-sulfonamide, (4-2-031) N-[2-[5-amino-1-[6-(2,6-difluorophenoxy)-4-methylpyridin-3-yl]pyrazole-4-carbonyl]-5-fluoro-1H-indol-6-yl]methanesulfonamide, (4-2-032) N-[2-[5-amino-1-[6-(2,3-difluorophenoxy)-4-methylpyridin-3-yl]pyrazole-4-carbonyl]-5-fluoro-1H-indol-6-yl]methanesulfonamide, (4-2-053) N-[2-[5-amino-1-[4-(2-fluorophenoxy)-2-methylphenyl]pyrazole-4-carbonyl]-5-methyl-1H-indol-6-yl]methanesulfonamide, (4-2-055) N-[2-[5-amino-1-[2-fluoro-4-(2-fluorophenoxy)-6-methylphenyl]pyrazole-4-carbonyl]-5-methyl-1H-indol-6-yl]methanesulfonamide, (4-2-061) N-[2-[5-amino-1-[6-(2-fluorophenoxy)-4-methylpyridin-3-yl]pyrazole-4-carbonyl]-5-methyl-1H-indol-6-yl]methanesulfonamide, (4-2-063) N-[2-[5-amino-1-[6-(2-chlorophenoxy)-4-methylpyridin-3-yl]pyrazole-4-carbonyl]-5-methyl-1H-indol-6-yl]methanesulfonamide, (4-2-072) N-[2-[5-amino-1-[6-(2-fluorophenoxy)-4-methylpyridin-3-yl]pyrazole-4-carbonyl]-5-methyl-1H-indol-6-yl]-3-fluoropropane-1-sulfonamide, (4-2-073) N-[2-[5-amino-1-[6-(2,6-difluorophenoxy)-4-methylpyridin-3-yl]pyrazole-4-carbonyl]-5-methyl-1H-indol-6-yl]-3-fluoropropane-1-sulfonamide, (4-5-001) N-[2-[5-amino-1-[6-(2-fluorophenoxy)-4-methylpyridin-3-yl]pyrazole-4-carbonyl]-5-fluoro-1H-indol-6-yl]morpholine-4-sulfonamide, (4-7-001) N-[2-[5-amino-1-[6-(2-fluorophenoxy)-4-methylpyridin-3-yl]pyrazole-4-carbonyl]-5-fluoro-1H-indol-6-yl]methanesulfonamide, (4-7-003) N-[2-[5-amino-1-[2-fluoro-4-(2-fluorophenoxy)-6-methylphenyl]pyrazole-4-carbonyl]-5-fluoro-1H-indol-6-yl]methanesulfonamide, (4-14-002) [5-amino-1-[4-(2-fluorophenoxy)-2-methylphenyl]pyrazol-4-yl]-[6-(1,1-dioxo-1,2-thiazolidin-2-yl)-5-methoxy-1H-indol-2-yl]methanone, (4-16-001) [5-amino-1-[6-(2-fluorophenoxy)-4-methylpyridin-3-yl]pyrazol-4-yl]-[6-(1,1-dioxo-1,2-thiazolidin-2-yl)-5-methyl-1H-indol-2-yl]methanone hydrochloride, (4-17-001) 1-[4-[2-[5-amino-1-[6-(2,6-difluorophenoxy)-4-methylpyridin-3-yl]pyrazole-4-carbonyl]-5-(2,2-difluoroethoxy)-1H-indol-6-yl]piperidin-1-yl]ethanone, (4-24-002) N-[2-[5-amino-1-[4-(2-fluorophenoxy)-2-methylphenyl]pyrazole-4-carbonyl]-5-(difluoromethoxy)-1H-indol-6-yl]methanesulfonamide, (4-24-003) N-[2-[5-amino-1-[4-(2-fluorophenoxy)-2-methylphenyl]pyrazole-4-carbonyl]-5-(difluoromethoxy)-1H-indol-6-yl]-3-fluoropropane-1-sulfonamide, (4-24-028) N-[2-[5-amino-1-[6-(2-fluorophenoxy)-4-methylpyridin-3-yl]pyrazole-4-carbonyl]-5-(2,2-difluoroethoxy)-1H-indol-6-yl]methanesulfonamide, (4-24-032) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-3-fluoropropane-1-sulfonamide, (4-25-009) [5-amino-1-[4-(2-fluorophenoxy)-2-methylphenyl]pyrazol-4-yl]-[5-(2,2-difluoroethoxy)-6-(1,1-dioxo-1,2-thiazolidin-2-yl)-1H-indol-2-yl]methanone, (5-1-223) [5-amino-1-[6-(2,6-difluorophenoxy)-4-methylpyridin-3-yl]pyrazol-4-yl]-[6-bromo-5-(1-cyclopentylpiperidin-4-yl)oxy-1H-indol-2-yl]methanone, (5-1-347) N-[2-[5-amino-1-[4-(2-fluorophenoxy)-2-methylphenyl]pyrazole-4-carbonyl]-5-methyl-1H-indol-6-yl]oxane-4-sulfonamide, (5-1-403) [5-amino-1-[4-(2-fluorophenoxy)-2-methylphenyl]pyrazol-4-yl]-[6-(2,2-dioxo-8-oxa-2λ6-thia-1,3-diazaspiro[4.5]decan-3-yl)-5-fluoro-1H-indol-2-yl]methanone, and (5-1-413) [5-amino-1-[6-(2-fluorophenoxy)-4-methylpyridin-3-yl]pyrazol-4-yl]-[6-(2,2-dioxo-8-oxa-2λ6-thia-1,3-diazaspiro[4.5]decan-3-yl)-5-fluoro-1H-indol-2-yl]methanone, or a pharmaceutically acceptable salt thereof.

17. The compound or a pharmaceutically acceptable salt thereof according to claim 1, wherein the compound or a pharmaceutically acceptable salt thereof is N-[2-[5-amino-1-[6-(2,6-difluorophenoxy)-4-methylpyridin-3-yl]pyrazole-4-carbonyl]-5-methyl-1H-indol-6-yl]methanesulfonamide or a pharmaceutically acceptable salt thereof.

18. The method of claim 10, wherein the compound or a pharmaceutically acceptable salt thereof is selected from the group consisting of:

(4-1-001) N-[2-[5-amino-1-[6-(2,6-difluorophenoxy)-4-methylpyridin-3-yl]pyrazole-4-carbonyl]-5-methyl-1H-indol-6-yl]methanesulfonamide, (4-1-002) N-[2-[5-amino-1-[4-(2-fluorophenoxy)-2-methylphenyl]pyrazole-4-carbonyl]-5-fluoro-1H-indol-6-yl]methanesulfonamide, (4-1-003) N-[2-[5-amino-1-(2-chloro-4-pyridin-2-yloxyphenyl)pyrazole-4-carbonyl]-5-fluoro-1H-indol-6-yl]methanesulfonamide, (4-1-004) N-[2-[5-amino-1-[4-(2-fluorophenoxy)-2-methylphenyl]pyrazole-4-carbonyl]-5-methoxy-1H-indol-6-yl]methanesulfonamide, (4-1-005) N-[2-[5-amino-1-[4-(2,3-difluorophenoxy)-2-methylphenyl]pyrazole-4-carbonyl]-5-methoxy-1H-indol-6-yl]methanesulfonamide, (4-1-006) N-[2-[5-amino-1-[2-fluoro-4-(2-fluorophenoxy)-6-methylphenyl]pyrazole-4-carbonyl]-5-methoxy-1H-indol-6-yl]methanesulfonamide, (4-1-007) N-[2-[5-amino-1-(2-fluoro-6-methyl-4-phenoxyphenyl)pyrazole-4-carbonyl]-5-methoxy-1H-indol-6-yl]methanesulfonamide, (4-1-008) N-[2-[5-amino-1-[6-(2-fluorophenoxy)-4-methylpyridin-3-yl]pyrazole-4-carbonyl]-5-methoxy-1H-indol-6-yl]methanesulfonamide, (4-1-009) N-[2-[5-amino-1-[6-(2,6-difluorophenoxy)-4-methylpyridin-3-yl]pyrazole-4-carbonyl]-5-methoxy-1H-indol-6-yl]methanesulfonamide, (4-1-010) N-[2-[5-amino-1-[6-(2-chlorophenoxy)-4-methylpyridin-3-yl]pyrazole-4-carbonyl]-5-methoxy-1H-indol-6-yl]methanesulfonamide, (4-1-011) N-[2-[5-amino-1-[6-(3-chlorophenoxy)-4-methylpyridin-3-yl]pyrazole-4-carbonyl]-5-methoxy-1H-indol-6-yl]methanesulfonamide, (4-1-012) tert-butyl 4-[2-[5-amino-1-[6-(2,6-difluorophenoxy)-4-methylpyridin-3-yl]pyrazole-4-carbonyl]-5-(difluoromethoxy)-1H-indol-6-yl]piperidine-1-carboxylate, (4-1-013) N-[2-[5-amino-1-[4-(2-fluorophenoxy)-2-methylphenyl]pyrazole-4-carbonyl]-6-methoxy-1H-indol-5-yl]methanesulfonamide, (4-1-014) N-[2-[5-amino-1-[6-(2-fluorophenoxy)-4-methylpyridin-3-yl]pyrazole-4-carbonyl]-6-methoxy-1H-indol-5-yl]methanesulfonamide, (4-1-015) [5-amino-1-[4-(2-fluorophenoxy)-2-methylphenyl]pyrazol-4-yl]-[5-(2,2-difluoroethoxy)-6-morpholin-4-yl-1H-indol-2-yl]methanone, (4-1-016) [5-amino-1-[6-(2,6-difluorophenoxy)-4-methylpyridin-3-yl]pyrazol-4-yl]-[5-(2,2-difluoroethoxy)-6-morpholin-4-yl-1H-indol-2-yl]methanone, (4-1-017) N-[2-[5-amino-1-[6-(2,6-difluorophenoxy)-4-methylpyridin-3-yl]pyrazole-4-carbonyl]-5-methyl-1H-indol-6-yl]cyclopropanesulfonamide, (4-2-001) [5-amino-1-[4-(2-fluorophenoxy)-2-methylphenyl]pyrazol-4-yl]-[6-fluoro-5-(1-propan-2-ylpiperidin-4-yl)-1H-indol-2-yl]methanone, (4-2-002) [5-amino-1-[4-(2,3-difluorophenoxy)-2-methylphenyl]pyrazol-4-yl]-[6-fluoro-5-(1-propan-2-ylpiperidin-4-yl)-1H-indol-2-yl]methanone, (4-2-003) [5-amino-1-[4-(3-chlorophenoxy)-2-methylphenyl]pyrazol-4-yl]-[6-fluoro-5-(1-propan-2-ylpiperidin-4-yl)-1H-indol-2-yl]methanone, (4-2-004) [5-amino-1-[4-(2,3-difluorophenoxy)phenyl]pyrazol-4-yl]-[6-fluoro-5-(1-propan-2-ylpiperidin-4-yl)-1H-indol-2-yl]methanone, (4-2-005) [5-amino-1-[4-(3-chlorophenoxy)phenyl]pyrazol-4-yl]-[6-fluoro-5-(1-propan-2-ylpiperidin-4-yl)-1H-indol-2-yl]methanone, (4-2-006) [5-amino-1-[4-(3-fluorophenoxy)phenyl]pyrazol-4-yl]-[6-fluoro-5-(1-propan-2-ylpiperidin-4-yl)-1H-indol-2-yl]methanone, (4-2-007) [5-amino-1-[4-(2,3-difluorophenoxy)-2-fluorophenyl]pyrazol-4-yl]-[6-fluoro-5-(1-propan-2-ylpiperidin-4-yl)-1H-indol-2-yl]methanone, (4-2-008) [5-amino-1-[4-(2-chlorophenoxy)-2-fluorophenyl]pyrazol-4-yl]-[6-fluoro-5-(1-propan-2-ylpiperidin-4-yl)-1H-indol-2-yl]methanone, (4-2-009) [5-amino-1-[2-fluoro-4-(2-fluorophenoxy)phenyl]pyrazol-4-yl]-[6-fluoro-5-(1-propan-2-ylpiperidin-4-yl)-1H-indol-2-yl]methanone, (4-2-010) [5-amino-1-[4-(2-fluorophenoxy)-2-methylphenyl]pyrazol-4-yl]-[5-fluoro-6-(1-propan-2-ylpiperidin-4-yl)-1H-indol-2-yl]methanone, (4-2-011) [5-amino-1-[4-(2,3-difluorophenoxy)-2-methylphenyl]pyrazol-4-yl]-[5-fluoro-6-(1-propan-2-ylpiperidin-4-yl)-1H-indol-2-yl]methanone, (4-2-012) [5-amino-1-[4-(2-chlorophenoxy)-2-methylphenyl]pyrazol-4-yl]-[5-fluoro-6-(1-propan-2-ylpiperidin-4-yl)-1H-indol-2-yl]methanone, (4-2-013) [5-amino-1-[4-(3-chlorophenoxy)-2-methylphenyl]pyrazol-4-yl]-[5-fluoro-6-(1-propan-2-ylpiperidin-4-yl)-1H-indol-2-yl]methanone, (4-2-014) [5-amino-1-[4-(2-fluorophenoxy)-3-methylphenyl]pyrazol-4-yl]-[5-fluoro-6-(1-propan-2-ylpiperidin-4-yl)-1H-indol-2-yl]methanone, (4-2-015) N-[2-[5-amino-1-[4-(2-fluorophenoxy)-2-methylphenyl]pyrazole-4-carbonyl]-5-fluoro-1H-indol-6-yl]-3-fluoropropane-1-sulfonamide, (4-2-016) N-[2-[5-amino-1-[4-(2,3-difluorophenoxy)-2-methylphenyl]pyrazole-4-carbonyl]-5-fluoro-1H-indol-6-yl]-3-fluoropropane-1-sulfonamide, (4-2-017) N-[2-[5-amino-1-(2-methyl-4-pyridin-2-yloxyphenyl)pyrazole-4-carbonyl]-5-fluoro-1H-indol-6-yl]-3-fluoropropane-1-sulfonamide, (4-2-018) N-[2-[5-amino-1-(2-chloro-4-pyridin-2-yloxyphenyl)pyrazole-4-carbonyl]-5-fluoro-1H-indol-6-yl]-3-fluoropropane-1-sulfonamide, (4-2-019) N-[2-[5-amino-1-[2-fluoro-4-(2-fluorophenoxy)-6-methylphenyl]pyrazole-4-carbonyl]-5-fluoro-1H-indol-6-yl]-3-fluoropropane-1-sulfonamide, (4-2-020) N-[2-[5-amino-1-[6-(2-fluorophenoxy)-4-methylpyridin-3-yl]pyrazole-4-carbonyl]-5-fluoro-1H-indol-6-yl]-3-fluoropropane-1-sulfonamide, (4-2-021) N-[2-[5-amino-1-[6-(2,6-difluorophenoxy)-4-methylpyridin-3-yl]pyrazole-4-carbonyl]-5-fluoro-1H-indol-6-yl]-3-fluoropropane-1-sulfonamide, (4-2-022) N-[2-[5-amino-1-[6-(2,3-difluorophenoxy)-4-methylpyridin-3-yl]pyrazole-4-carbonyl]-5-fluoro-1H-indol-6-yl]-3-fluoropropane-1-sulfonamide, (4-2-023) N-[2-[5-amino-1-[6-(2-chlorophenoxy)-4-methylpyridin-3-yl]pyrazole-4-carbonyl]-5-fluoro-1H-indol-6-yl]-3-fluoropropane-1-sulfonamide, (4-2-024) N-[2-[5-amino-1-[6-(2-chloro-6-fluorophenoxy)-4-methylpyridin-3-yl]pyrazole-4-carbonyl]-5-fluoro-1H-indol-6-yl]-3-fluoropropane-1-sulfonamide, (4-2-025) N-[2-[5-amino-1-[4-methyl-6-(2-methylphenoxy)pyridin-3-yl]pyrazole-4-carbonyl]-5-fluoro-1H-indol-6-yl]-3-fluoropropane-1-sulfonamide, (4-2-026) N-[2-[5-amino-1-[6-(3-chlorophenoxy)-4-methylpyridin-3-yl]pyrazole-4-carbonyl]-5-fluoro-1H-indol-6-yl]-3-fluoropropane-1-sulfonamide, (4-2-027) N-[2-[5-amino-1-[6-(4-fluorophenoxy)-4-methylpyridin-3-yl]pyrazole-4-carbonyl]-5-fluoro-1H-indol-6-yl]-3-fluoropropane-1-sulfonamide, (4-2-028) N-[2-[5-amino-1-[6-(3,5-difluorophenoxy)-4-methylpyridin-3-yl]pyrazole-4-carbonyl]-5-fluoro-1H-indol-6-yl]-3-fluoropropane-1-sulfonamide, (4-2-029) N-[2-[5-amino-1-[4-(2,3-difluorophenoxy)-2-methylphenyl]pyrazole-4-carbonyl]-5-fluoro-1H-indol-6-yl]methanesulfonamide, (4-2-030) N-[2-[5-amino-1-[6-(2,5-difluorophenoxy)-4-methylpyridin-3-yl]pyrazole-4-carbonyl]-5-fluoro-1H-indol-6-yl]methanesulfonamide, (4-2-031) N-[2-[5-amino-1-[6-(2,6-difluorophenoxy)-4-methylpyridin-3-yl]pyrazole-4-carbonyl]-5-fluoro-1H-indol-6-yl]methanesulfonamide, (4-2-032) N-[2-[5-amino-1-[6-(2,3-difluorophenoxy)-4-methylpyridin-3-yl]pyrazole-4-carbonyl]-5-fluoro-1H-indol-6-yl]methanesulfonamide, (4-2-033) N-[2-[5-amino-1-[6-(2-chlorophenoxy)-4-methylpyridin-3-yl]pyrazole-4-carbonyl]-5-fluoro-1H-indol-6-yl]methanesulfonamide, (4-2-034) N-[2-[5-amino-1-[6-(2-chloro-5-fluorophenoxy)-4-methylpyridin-3-yl]pyrazole-4-carbonyl]-5-fluoro-1H-indol-6-yl]methanesulfonamide, (4-2-035) N-[2-[5-amino-1-[6-(2-chloro-6-fluorophenoxy)-4-methylpyridin-3-yl]pyrazole-4-carbonyl]-5-fluoro-1H-indol-6-yl]methanesulfonamide, (4-2-036) N-[2-[5-amino-1-[4-methyl-6-(2-methylphenoxy)pyridin-3-yl]pyrazole-4-carbonyl]-5-fluoro-1H-indol-6-yl]methanesulfonamide, (4-2-037) N-[2-[5-amino-1-[6-(3-chlorophenoxy)-4-methylpyridin-3-yl]pyrazole-4-carbonyl]-5-fluoro-1H-indol-6-yl]methanesulfonamide, (4-2-038) N-[2-[5-amino-1-[6-(3-fluorophenoxy)-4-methylpyridin-3-yl]pyrazole-4-carbonyl]-5-fluoro-1H-indol-6-yl]methanesulfonamide, (4-2-039) N-[2-[5-amino-1-[6-(4-fluorophenoxy)-4-methylpyridin-3-yl]pyrazole-4-carbonyl]-5-fluoro-1H-indol-6-yl]methanesulfonamide, (4-2-040) N-[2-[5-amino-1-[4-(2-fluorophenoxy)-2-methylphenyl]pyrazole-4-carbonyl]-5-fluoro-1H-indol-6-yl]cyclopropanesulfonamide, (4-2-041) N-[2-[5-amino-1-[4-(2,3-difluorophenoxy)-2-methylphenyl]pyrazole-4-carbonyl]-5-fluoro-1H-indol-6-yl]cyclopropanesulfonamide, (4-2-042) N-[2-[5-amino-1-[4-(2-fluorophenoxy)-2,6-dimethylphenyl]pyrazole-4-carbonyl]-5-fluoro-1H-indol-6-yl]cyclopropanesulfonamide, (4-2-043) N-[2-[5-amino-1-[6-(2-fluorophenoxy)-4-methylpyridin-3-yl]pyrazole-4-carbonyl]-5-fluoro-1H-indol-6-yl]cyclopropanesulfonamide, (4-2-044) N-[2-[5-amino-1-[6-(2,6-difluorophenoxy)-4-methylpyridin-3-yl]pyrazole-4-carbonyl]-5-fluoro-1H-indol-6-yl]cyclopropanesulfonamide, (4-2-045) N-[2-[5-amino-1-[6-(2,3-difluorophenoxy)-4-methylpyridin-3-yl]pyrazole-4-carbonyl]-5-fluoro-1H-indol-6-yl]cyclopropanesulfonamide, (4-2-046) N-[2-[5-amino-1-[6-(2-chloro-6-fluorophenoxy)-4-methylpyridin-3-yl]pyrazole-4-carbonyl]-5-fluoro-1H-indol-6-yl]cyclopropanesulfonamide, (4-2-047) N-[2-[5-amino-1-[4-methyl-6-(2-methylphenoxy)pyridin-3-yl]pyrazole-4-carbonyl]-5-fluoro-1H-indol-6-yl]cyclopropanesulfonamide, (4-2-048) N-[2-[5-amino-1-[6-(3-fluorophenoxy)-4-methylpyridin-3-yl]pyrazole-4-carbonyl]-5-fluoro-1H-indol-6-yl]cyclopropanesulfonamide, (4-2-049) N-[2-[5-amino-1-[4-(2-fluorophenoxy)-2-methylphenyl]pyrazole-4-carbonyl]-6-methyl-1H-indol-5-yl]methanesulfonamide, (4-2-050) N-[2-[5-amino-1-[4-(2,3-difluorophenoxy)-2-methylphenyl]pyrazole-4-carbonyl]-6-methyl-1H-indol-5-yl]methanesulfonamide, (4-2-051) N-[2-[5-amino-1-[2-fluoro-4-(2-fluorophenoxy)-6-methylphenyl]pyrazole-4-carbonyl]-6-methyl-1H-indol-5-yl]methanesulfonamide, (4-2-052) N-[2-[5-amino-1-[6-(2-fluorophenoxy)-4-methylpyridin-3-yl]pyrazole-4-carbonyl]-6-methyl-1H-indol-5-yl]methanesulfonamide, (4-2-053) N-[2-[5-amino-1-[4-(2-fluorophenoxy)-2-methylphenyl]pyrazole-4-carbonyl]-5-methyl-1H-indol-6-yl]methanesulfonamide, (4-2-054) N-[2-[5-amino-1-[4-(2,3-difluorophenoxy)-2-methylphenyl]pyrazole-4-carbonyl]-5-methyl-1H-indol-6-yl]methanesulfonamide, (4-2-055) N-[2-[5-amino-1-[2-fluoro-4-(2-fluorophenoxy)-6-methylphenyl]pyrazole-4-carbonyl]-5-methyl-1H-indol-6-yl]methanesulfonamide, (4-2-056) N-[2-[5-amino-1-[4-(2,3-difluorophenoxy)-2-fluoro-6-methylphenyl]pyrazole-4-carbonyl]-5-methyl-1H-indol-6-yl]methanesulfonamide, (4-2-057) N-[2-[5-amino-1-[4-(2,5-difluorophenoxy)-2-fluoro-6-methylphenyl]pyrazole-4-carbonyl]-5-methyl-1H-indol-6-yl]methanesulfonamide, (4-2-058) N-[2-[5-amino-1-[4-(2-chlorophenoxy)-2-fluoro-6-methylphenyl]pyrazole-4-carbonyl]-5-methyl-1H-indol-6-yl]methanesulfonamide, (4-2-059) N-[2-[5-amino-1-[4-(3-chlorophenoxy)-2-fluoro-6-methylphenyl]pyrazole-4-carbonyl]-5-methyl-1H-indol-6-yl]methanesulfonamide, (4-2-060) N-[2-[5-amino-1-(2-fluoro-6-methyl-4-phenoxyphenyl)pyrazole-4-carbonyl]-5-methyl-1H-indol-6-yl]methanesulfonamide, (4-2-061) N-[2-[5-amino-1-[6-(2-fluorophenoxy)-4-methylpyridin-3-yl]pyrazole-4-carbonyl]-5-methyl-1H-indol-6-yl]methanesulfonamide, (4-2-062) N-[2-[5-amino-1-[6-(2,3-difluorophenoxy)-4-methylpyridin-3-yl]pyrazole-4-carbonyl]-5-methyl-1H-indol-6-yl]methanesulfonamide, (4-2-063) N-[2-[5-amino-1-[6-(2-chlorophenoxy)-4-methylpyridin-3-yl]pyrazole-4-carbonyl]-5-methyl-1H-indol-6-yl]methanesulfonamide, (4-2-064) N-[2-[5-amino-1-[6-(2-chloro-6-fluorophenoxy)-4-methylpyridin-3-yl]pyrazole-4-carbonyl]-5-methyl-1H-indol-6-yl]methanesulfonamide, (4-2-065) N-[2-[5-amino-1-[4-methyl-6-(2-methylphenoxy)pyridin-3-yl]pyrazole-4-carbonyl]-5-methyl-1H-indol-6-yl]methanesulfonamide, (4-2-066) N-[2-[5-amino-1-[6-(3-chlorophenoxy)-4-methylpyridin-3-yl]pyrazole-4-carbonyl]-5-methyl-1H-indol-6-yl]methanesulfonamide, (4-2-067) N-[2-[5-amino-1-[6-(4-fluorophenoxy)-4-methylpyridin-3-yl]pyrazole-4-carbonyl]-5-methyl-1H-indol-6-yl]methanesulfonamide, (4-2-068) N-[2-[5-amino-1-[4-(2-fluorophenoxy)-2-methylphenyl]pyrazole-4-carbonyl]-5-methyl-1H-indol-6-yl]-3-fluoropropane-1-sulfonamide, (4-2-069) N-[2-[5-amino-1-[4-(2,3-difluorophenoxy)-2-methylphenyl]pyrazole-4-carbonyl]-5-methyl-1H-indol-6-yl]-3-fluoropropane-1-sulfonamide, (4-2-070) N-[2-[5-amino-1-[2-fluoro-4-(2-fluorophenoxy)-6-methylphenyl]pyrazole-4-carbonyl]-5-methyl-1H-indol-6-yl]-3-fluoropropane-1-sulfonamide, (4-2-071) N-[2-[5-amino-1-[4-(2,3-difluorophenoxy)-2-fluoro-6-methylphenyl]pyrazole-4-carbonyl]-5-methyl-1H-indol-6-yl]-3-fluoropropane-1-sulfonamide, (4-2-072) N-[2-[5-amino-1-[6-(2-fluorophenoxy)-4-methylpyridin-3-yl]pyrazole-4-carbonyl]-5-methyl-1H-indol-6-yl]-3-fluoropropane-1-sulfonamide, (4-2-073) N-[2-[5-amino-1-[6-(2,6-difluorophenoxy)-4-methylpyridin-3-yl]pyrazole-4-carbonyl]-5-methyl-1H-indol-6-yl]-3-fluoropropane-1-sulfonamide, (4-2-074) N-[2-[5-amino-1-[6-(2-chlorophenoxy)-4-methylpyridin-3-yl]pyrazole-4-carbonyl]-5-methyl-1H-indol-6-yl]-3-fluoropropane-1-sulfonamide, (4-2-075) N-[2-[5-amino-1-[6-(3-chlorophenoxy)-4-methylpyridin-3-yl]pyrazole-4-carbonyl]-5-methyl-1H-indol-6-yl]-3-fluoropropane-1-sulfonamide, (4-2-076) N-[2-[5-amino-1-[6-(4-fluorophenoxy)-4-methylpyridin-3-yl]pyrazole-4-carbonyl]-5-methyl-1H-indol-6-yl]-3-fluoropropane-1-sulfonamide, (4-2-077) N-[2-[5-amino-1-[4-(2-fluorophenoxy)-2-methylphenyl]pyrazole-4-carbonyl]-5-chloro-1H-indol-6-yl]methanesulfonamide, (4-2-078) N-[2-[5-amino-1-[4-(2,3-difluorophenoxy)-2-methylphenyl]pyrazole-4-carbonyl]-5-chloro-1H-indol-6-yl]methanesulfonamide, (4-2-079) N-[2-[5-amino-1-[2-fluoro-4-(2-fluorophenoxy)-6-methylphenyl]pyrazole-4-carbonyl]-5-chloro-1H-indol-6-yl]methanesulfonamide, (4-2-080) N-[2-[5-amino-1-[4-(2,3-difluorophenoxy)-2-fluoro-6-methylphenyl]pyrazole-4-carbonyl]-5-chloro-1H-indol-6-yl]methanesulfonamide, (4-2-081) N-[2-[5-amino-1-[4-(2,5-difluorophenoxy)-2-fluoro-6-methylphenyl]pyrazole-4-carbonyl]-5-chloro-1H-indol-6-yl]methanesulfonamide, (4-2-082) N-[2-[5-amino-1-[4-(2-chlorophenoxy)-2-fluoro-6-methylphenyl]pyrazole-4-carbonyl]-5-chloro-1H-indol-6-yl]methanesulfonamide, (4-2-083) N-[2-[5-amino-1-[4-(3-chlorophenoxy)-2-fluoro-6-methylphenyl]pyrazole-4-carbonyl]-5-chloro-1H-indol-6-yl]methanesulfonamide, (4-2-084) N-[2-[5-amino-1-(2-fluoro-6-methyl-4-phenoxyphenyl)pyrazole-4-carbonyl]-5-chloro-1H-indol-6-yl]methanesulfonamide, (4-2-085) N-[2-[5-amino-1-[6-(2-fluorophenoxy)-4-methylpyridin-3-yl]pyrazole-4-carbonyl]-5-chloro-1H-indol-6-yl]methanesulfonamide, (4-2-086) N-[2-[5-amino-1-[6-(2,6-difluorophenoxy)-4-methylpyridin-3-yl]pyrazole-4-carbonyl]-5-chloro-1H-indol-6-yl]methanesulfonamide, (4-2-087) N-[2-[5-amino-1-[6-(2,3-difluorophenoxy)-4-methylpyridin-3-yl]pyrazole-4-carbonyl]-5-chloro-1H-indol-6-yl]methanesulfonamide, (4-2-088) N-[2-[5-amino-1-[6-(2-chlorophenoxy)-4-methylpyridin-3-yl]pyrazole-4-carbonyl]-5-chloro-1H-indol-6-yl]methanesulfonamide, (4-2-089) N-[2-[5-amino-1-[6-(2-chloro-6-fluorophenoxy)-4-methylpyridin-3-yl]pyrazole-4-carbonyl]-5-chloro-1H-indol-6-yl]methanesulfonamide, (4-2-090) N-[2-[5-amino-1-[4-methyl-6-(2-methylphenoxy)pyridin-3-yl]pyrazole-4-carbonyl]-5-chloro-1H-indol-6-yl]methanesulfonamide, (4-2-091) N-[2-[5-amino-1-[6-(3-chlorophenoxy)-4-methylpyridin-3-yl]pyrazole-4-carbonyl]-5-chloro-1H-indol-6-yl]methanesulfonamide, (4-2-092) N-[2-[5-amino-1-[6-(4-fluorophenoxy)-4-methylpyridin-3-yl]pyrazole-4-carbonyl]-5-chloro-1H-indol-6-yl]methanesulfonamide, (4-2-093) N-[2-[5-amino-1-[2-fluoro-4-(2-fluorophenoxy)-6-methylphenyl]pyrazole-4-carbonyl]-6-chloro-1H-indol-5-yl]methanesulfonamide, (4-2-094) N-[2-[5-amino-1-[4-(2,3-difluorophenoxy)-2-fluoro-6-methylphenyl]pyrazole-4-carbonyl]-6-chloro-1H-indol-5-yl]methanesulfonamide, (4-2-095) N-[2-[5-amino-1-(2-fluoro-6-methyl-4-phenoxyphenyl)pyrazole-4-carbonyl]-6-chloro-1H-indol-5-yl]methanesulfonamide, (4-2-096) N-[2-[5-amino-1-[6-(2-fluorophenoxy)-4-methylpyridin-3-yl]pyrazole-4-carbonyl]-6-chloro-1H-indol-5-yl]methanesulfonamide, (4-2-097) N-[2-[5-amino-1-[4-(2-fluorophenoxy)-2-methylphenyl]pyrazole-4-carbonyl]-6-fluoro-1H-indol-5-yl]methanesulfonamide, (4-2-098) N-[2-[5-amino-1-[4-(2,3-difluorophenoxy)-2-methylphenyl]pyrazole-4-carbonyl]-6-fluoro-1H-indol-5-yl]methanesulfonamide, (4-2-099) N-[2-[5-amino-1-[2-fluoro-4-(2-fluorophenoxy)-6-methylphenyl]pyrazole-4-carbonyl]-6-fluoro-1H-indol-5-yl]methanesulfonamide, (4-2-100) N-[2-[5-amino-1-[4-(2,3-difluorophenoxy)-2-fluoro-6-methylphenyl]pyrazole-4-carbonyl]-6-fluoro-1H-indol-5-yl]methanesulfonamide,
(4-2-101) N-[2-[5-amino-1-[4-(2,5-difluorophenoxy)-2-fluoro-6-methylphenyl]pyrazole-4-carbonyl]-6-fluoro-1H-indol-5-yl]methanesulfonamide,
(4-2-102) N-[2-[5-amino-1-[4-(2-chlorophenoxy)-2-fluoro-6-methylphenyl]pyrazole-4-carbonyl]-6-fluoro-1H-indol-5-yl]methanesulfonamide,
(4-2-103) N-[2-[5-amino-1-(2-fluoro-6-methyl-4-phenoxyphenyl)pyrazole-4-carbonyl]-6-fluoro-1H-indol-5-yl]methanesulfonamide,
(4-2-104) N-[2-[5-amino-1-[6-(2-fluorophenoxy)-4-methylpyridin-3-yl]pyrazole-4-carbonyl]-6-fluoro-1H-indol-5-yl]methanesulfonamide,
(4-2-105) N-[2-[5-amino-1-[4-(2-fluorophenoxy)-2-methylphenyl]pyrazole-4-carbonyl]-5-methyl-1H-indol-6-yl]morpholine-4-sulfonamide,
(4-2-106) N-[2-[5-amino-1-[4-(2,3-difluorophenoxy)-2-methylphenyl]pyrazole-4-carbonyl]-5-methyl-1H-indol-6-yl]morpholine-4-sulfonamide,
(4-2-107) N-[2-[5-amino-1-[2-fluoro-4-(2-fluorophenoxy)-6-methylphenyl]pyrazole-4-carbonyl]-5-methyl-1H-indol-6-yl]morpholine-4-sulfonamide,
(4-2-108) N-[2-[5-amino-1-[6-(2-fluorophenoxy)-4-methylpyridin-3-yl]pyrazole-4-carbonyl]-5-methyl-1H-indol-6-yl]morpholine-4-sulfonamide,
(4-2-109) N-[2-[5-amino-1-[6-(2,6-difluorophenoxy)-4-methylpyridin-3-yl]pyrazole-4-carbonyl]-5-methyl-1H-indol-6-yl]morpholine-4-sulfonamide,
(4-2-110) N-[2-[5-amino-1-[6-(2-chlorophenoxy)-4-methylpyridin-3-yl]pyrazole-4-carbonyl]-5-methyl-1H-indol-6-yl]morpholine-4-sulfonamide,
(4-2-111) N-[2-[5-amino-1-[6-(3-chlorophenoxy)-4-methylpyridin-3-yl]pyrazole-4-carbonyl]-5-methyl-1H-indol-6-yl]morpholine-4-sulfonamide,
(4-2-112) [5-amino-1-[4-(2-fluorophenoxy)-2-methylphenyl]pyrazol-4-yl]-[6-(1,1-dioxo-1,2-thiazolidin-2-yl)-5-methyl-1H-indol-2-yl]methanone,
(4-2-113) [5-amino-1-[4-(2,3-difluorophenoxy)-2-methylphenyl]pyrazol-4-yl]-[6-(1,1-dioxo-1,2-thiazolidin-2-yl)-5-methyl-1H-indol-2-yl]methanone,
(4-2-114) [5-amino-1-[2-fluoro-4-(2-fluorophenoxy)-6-methylphenyl]pyrazol-4-yl]-[6-(1,1-dioxo-1,2-thiazolidin-2-yl)-5-methyl-1H-indol-2-yl]methanone,
(4-2-115) [5-amino-1-[4-(2,3-difluorophenoxy)-2-fluoro-6-methylphenyl]pyrazol-4-yl]-6-(1,1-dioxo-1,2-thiazolidin-2-yl)-5-methyl-1H-indol-2-yl]methanone,
(4-2-116) [5-amino-1-[6-(2,6-difluorophenoxy)-4-methylpyridin-3-yl]pyrazol-4-yl]-[6-(1,1-dioxo-1,2-thiazolidin-2-yl)-5-methyl-1H-indol-2-yl]methanone,
(4-2-117) [5-amino-1-[6-(2-chlorophenoxy)-4-methylpyridin-3-yl]pyrazol-4-yl]-[6-(1,1-dioxo-1,2-thiazolidin-2-yl)-5-methyl-1H-indol-2-yl]methanone,
(4-2-118) [5-amino-1-[6-(3-chlorophenoxy)-4-methylpyridin-3-yl]pyrazol-4-yl]-[6-(1,1-dioxo-1,2-thiazolidin-2-yl)-5-methyl-1H-indol-2-yl]methanone,
(4-2-119) [5-amino-1-[6-(4-fluorophenoxy)-4-methylpyridin-3-yl]pyrazol-4-yl]-[6-(1,1-dioxo-1,2-thiazolidin-2-yl)-5-methyl-1H-indol-2-yl]methanone,
(4-2-120) [5-amino-1-[2-fluoro-4-(2-fluorophenoxy)-6-methylphenyl]pyrazol-4-yl]-[6-(1,1-dioxo-1,2-thiazolidin-2-yl)-5-methoxy-1H-indol-2-yl]methanone,
(4-2-121) [5-amino-1-[6-(2,6-difluorophenoxy)-4-methylpyridin-3-yl]pyrazol-4-yl]-[6-(1,1-dioxo-1,2-thiazolidin-2-yl)-5-methoxy-1H-indol-2-yl]methanone,
(4-2-122) [5-amino-1-[4-(2-fluorophenoxy)-2-methylphenyl]pyrazol-4-yl]-(5-methyl-6-morpholin-4-yl-1H-indol-2-yl)methanone,
(4-2-123) [5-amino-1-[6-(2-fluorophenoxy)-4-methylpyridin-3-yl]pyrazol-4-yl]-(5-methyl-6-morpholin-4-yl-1H-indol-2-yl)methanone,
(4-2-124) [5-amino-1-[6-(2,6-difluorophenoxy)-4-methylpyridin-3-yl]pyrazol-4-yl]-(5-methyl-6-morpholin-4-yl-1H-indol-2-yl)methanone,
(4-2-125) [5-amino-1-[6-(2,6-difluorophenoxy)-4-methylpyridin-3-yl]pyrazol-4-yl]-[5-methyl-6-(4-morpholin-4-ylpiperidin-1-yl)-1H-indol-2-yl]methanone,
(4-2-126) N-[2-[5-amino-1-[6-(2,6-difluorophenoxy)-4-methylpyridin-3-yl]pyrazole-4-carbonyl]-5-fluoro-1H-indol-6-yl]-N-ethylmethanesulfonamide,
(4-2-127) N-[2-[5-amino-1-[6-(2,6-difluorophenoxy)-4-methylpyridin-3-yl]pyrazole-4-carbonyl]-5-fluoro-1H-indol-6-yl]-N-(oxan-4-yl)methanesulfonamide,
(4-2-128) N-[2-[5-amino-1-[6-(2,6-difluorophenoxy)-4-methylpyridin-3-yl]pyrazole-4-carbonyl]-5-fluoro-1H-indol-6-yl]-N-(2-morpholin-4-ylethyl)methanesulfonamide,
(4-2-129) N-[2-[5-amino-1-[6-(2-fluorophenoxy)-4-methylpyridin-3-yl]pyrazole-4-carbonyl]-6-(2-morpholin-4-ylethoxy)-1H-indol-5-yl]methanesulfonamide,
(4-2-130) N-[2-[5-amino-1-[6-(2-fluorophenoxy)-4-methylpyridin-3-yl]pyrazole-4-carbonyl]-6-hydroxy-1H-indol-5-yl]-N-(2-morpholin-4-ylethyl)methanesulfonamide,
(4-3-001) [5-amino-1-[4-(2,3-difluorophenoxy)-2-fluoro-6-methylphenyl]pyrazol-4-yl]-(6-amino-5-fluoro-1H-indol-2-yl)methanone,
(4-4-001) [5-amino-1-[6-(2,6-difluorophenoxy)-4-methylpyridin-3-yl]pyrazol-4-yl]-[5-(difluoromethoxy)-6-piperidin-4-yl-1H-indol-2-yl]methanone,
(4-5-001) N-[2-[5-amino-1-[6-(2-fluorophenoxy)-4-methylpyridin-3-yl]pyrazole-4-carbonyl]-5-fluoro-1H-indol-6-yl]morpholine-4-sulfonamide,
(4-5-002) N-[2-[5-amino-1-[4-(2-fluorophenoxy)-2-methylphenyl]pyrazole-4-carbonyl]-5-fluoro-1H-indol-6-yl]morpholine-4-sulfonamide,
(4-5-003) [5-amino-1-[4-(2-fluorophenoxy)-2-methylphenyl]pyrazol-4-yl]-[5-fluoro-6-(oxan-4-yl sulfamoylamino)-1H-indol-2-yl]methanone,
(4-5-004) [5-amino-1-[4-(2-fluorophenoxy)-2-methylphenyl]pyrazol-4-yl]-[5-fluoro-6-(propan-2-ylsulfamoylamino)-1H-indol-2-yl]methanone,
(4-5-005) [5-amino-1-[4-(2-fluorophenoxy)-2-methylphenyl]pyrazol-4-yl]-[5-fluoro-6-(oxetan-3-ylsulfamoylamino)-1H-indol-2-yl]methanone,
(4-5-006) [5-amino-1-[4-(2-fluorophenoxy)-2-methylphenyl]pyrazol-4-yl]-[6-(cyclobutylsulfamoylamino)-5-fluoro-1H-indol-2-yl]methanone,
(4-5-007) [5-amino-1-[4-(2-fluorophenoxy)-2-methylphenyl]pyrazol-4-yl]-[5-fluoro-6-(2-methoxyethylsulfamoylamino)-1H-indol-2-yl]methanone,
(4-5-008) [5-amino-1-[4-(2-fluorophenoxy)-2-methylphenyl]pyrazol-4-yl]-[5-fluoro-6-[(3-methyloxetan-3-yl)sulfamoylamino]-1H-indol-2-yl]methanone,
(4-5-009) [5-amino-1-[4-(2-fluorophenoxy)-2-methylphenyl]pyrazol-4-yl]-[5-fluoro-6-(methoxysulfamoylamino)-1H-indol-2-yl]methanone,
(4-5-010) [5-amino-1-[4-(2-fluorophenoxy)-2-methylphenyl]pyrazol-4-yl]-[6-(cyclopropylsulfamoylamino)-5-fluoro-1H-indol-2-yl]methanone, (4-5-011) N-[2-[5-amino-1-[4-(2,3-difluorophenoxy)-2-fluoro-6-methylphenyl]pyrazol-4-carbonyl]-5-fluoro-1H-indol-6-yl]morpholine-4-sulfonamide, (4-5-012) [5-amino-1-[6-(2-fluorophenoxy)-4-methylpyridin-3-yl]pyrazol-4-yl]-[5-fluoro-6-(oxan-4-ylsulfamoylamino)-1H-indol-2-yl]methanone, (4-6-001) [5-amino-1-[6-(2-fluorophenoxy)-4-methylpyridin-3-yl]pyrazol-4-yl]-[5-fluoro-6-(2-hydroxyethylsulfamoylamino)-1H-indol-2-yl]methanone, (4-6-002) [5-amino-1-[4-(2-fluorophenoxy)-2-methylphenyl]pyrazol-4-yl]-[5-fluoro-6-(2-hydroxyethylsulfamoylamino)-1H-indol-2-yl]methanone, (4-6-003) [5-amino-1-[4-(2-fluorophenoxy)-2-methylphenyl]pyrazol-4-yl]-[5-fluoro-6-[(1-hydroxy-2-methylpropan-2-yl)sulfamoylamino]-1H-indol-2-yl]methanone, (4-6-004) [5-amino-1-[4-(2-fluorophenoxy)-2-methylphenyl]pyrazol-4-yl]-[5-fluoro-6-[(2-hydroxy-2-methylpropyl)sulfamoylamino]-1H-indol-2-yl]methanone, (4-7-001) N-[2-[5-amino-1-[6-(2-fluorophenoxy)-4-methylpyridin-3-yl]pyrazole-4-carbonyl]-5-fluoro-1H-indol-6-yl]methanesulfonamide, (4-7-002) N-[2-[5-amino-1-[4-(2-fluorophenoxy)-2-methylphenyl]pyrazole-4-carbonyl]-5-fluoro-1H-indol-6-yl]-1-(1,4-dioxan-2-yl)methanesulfonamide, (4-7-003) N-[2-[5-amino-1-[2-fluoro-4-(2-fluorophenoxy)-6-methylphenyl]pyrazole-4-carbonyl]-5-fluoro-1H-indol-6-yl]methanesulfonamide, (4-7-004) N-[2-[5-amino-1-[2-fluoro-4-(2-fluorophenoxy)-6-methylphenyl]pyrazole-4-carbonyl]-5-fluoro-1H-indol-6-yl]cyclopropanesulfonamide, (4-7-005) N-[2-[5-amino-1-[4-(2,3-difluorophenoxy)-2-fluoro-6-methylphenyl]pyrazole-4-carbonyl]-5-fluoro-1H-indol-6-yl]methanesulfonamide, (4-7-006) N-[2-[5-amino-1-[4-(2,3-difluorophenoxy)-2-fluoro-6-methylphenyl]pyrazole-4-carbonyl]-5-fluoro-1H-indol-6-yl]cyclopropanesulfonamide, (4-7-007) N-[2-[5-amino-1-[4-(2,5-difluorophenoxy)-2-fluoro-6-methylphenyl]pyrazole-4-carbonyl]-5-fluoro-1H-indol-6-yl]methanesulfonamide, (4-7-008) N-[2-[5-amino-1-[4-(2,5-difluorophenoxy)-2-fluoro-6-methylphenyl]pyrazole-4-carbonyl]-5-fluoro-1H-indol-6-yl]cyclopropanesulfonamide, (4-7-009) N-[2-[5-amino-1-[4-(2-chlorophenoxy)-2-fluoro-6-methylphenyl]pyrazole-4-carbonyl]-5-fluoro-1H-indol-6-yl]methanesulfonamide, (4-7-010) N-[2-[5-amino-1-[4-(2-chlorophenoxy)-2-fluoro-6-methylphenyl]pyrazole-4-carbonyl]-5-fluoro-1H-indol-6-yl]cyclopropanesulfonamide, (4-7-011) N-[2-[5-amino-1-[4-(3-chlorophenoxy)-2-fluoro-6-methylphenyl]pyrazole-4-carbonyl]-5-fluoro-1H-indol-6-yl]methanesulfonamide, (4-7-012) N-[2-[5-amino-1-[4-(3-chlorophenoxy)-2-fluoro-6-methylphenyl]pyrazole-4-carbonyl]-5-fluoro-1H-indol-6-yl]cyclopropanesulfonamide, (4-7-013) N-[2-[5-amino-1-(2-fluoro-6-methyl-4-phenoxyphenyl)pyrazole-4-carbonyl]-5-fluoro-1H-indol-6-yl]methanesulfonamide, (4-7-014) N-[2-[5-amino-1-(2-fluoro-6-methyl-4-phenoxyphenyl)pyrazole-4-carbonyl]-5-fluoro-1H-indol-6-yl]cyclopropanesulfonamide, (4-7-015) N-[2-[5-amino-1-[6-(2-chlorophenoxy)-4-methylpyridin-3-yl]pyrazole-4-carbonyl]-5-fluoro-1H-indol-6-yl]cyclopropanesulfonamide, (4-7-016) N-[2-[5-amino-1-[6-(3-chlorophenoxy)-4-methylpyridin-3-yl]pyrazole-4-carbonyl]-5-fluoro-1H-indol-6-yl]cyclopropanesulfonamide, (4-8-001) N-[2-[5-amino-1-[4-(2-fluorophenoxy)-2-methylphenyl]pyrazole-4-carbonyl]-5-fluoro-1H-indol-6-yl]-1-(2,3-dihydroxypropyl)cyclopropane-1-sulfonamide, (4-9-001) [5-amino-1-[6-(2-fluorophenoxy)-4-methylpyridin-3-yl]pyrazol-4-yl]-[6-(1,1-dioxo-1,2-thiazolidin-2-yl)-5-fluoro-1H-indol-2-yl]methanone hydrochloride, (4-9-002) [5-amino-1-[6-(2,6-difluorophenoxy)-4-methylpyridin-3-yl]pyrazol-4-yl]-[6-(1,1-dioxo-1,2-thiazolidin-2-yl)-5-fluoro-1H-indol-2-yl]methanone, (4-10-001) 2-[[2-[5-amino-1-[6-(2-fluorophenoxy)-4-methylpyridin-3-yl]pyrazole-4-carbonyl]-5-fluoro-1H-indol-6-yl]sulfamoyl]-N,N-diethylacetamide, (4-10-002) 2-[[2-[5-amino-1-[4-(2-fluorophenoxy)-2-methylphenyl]pyrazole-4-carbonyl]-5-fluoro-1H-indol-6-yl]sulfamoyl]-N-propan-2-ylacetamide, (4-10-003) N-[2-[5-amino-1-[4-(2-fluorophenoxy)-2-methylphenyl]pyrazole-4-carbonyl]-5-fluoro-1H-indol-6-yl]-2-oxo-2-(4-propan-2-ylpiperazin-1-yl)ethanesulfonamide 2,2,2-trifluoroacetate (4-10-004) N-[2-[5-amino-1-[4-(2-fluorophenoxy)-2-methylphenyl]pyrazole-4-carbonyl]-5-fluoro-1H-indol-6-yl]-2-morpholin-4-yl-2-oxoethanesulfonamide, (4-10-005) N-[2-[5-amino-1-[6-(2-fluorophenoxy)-4-methylpyridin-3-yl]pyrazole-4-carbonyl]-5-fluoro-1H-indol-6-yl]-2-oxo-2-pyrrolidin-1-ylethanesulfonamide, (4-10-006) N-[2-[5-amino-1-[6-(2-fluorophenoxy)-4-methylpyridin-3-yl]pyrazole-4-carbonyl]-5-fluoro-1H-indol-6-yl]-2-morpholin-4-yl-2-oxoethanesulfonamide, (4-10-007) N-[2-[5-amino-1-[4-(2-fluorophenoxy)-2-methylphenyl]pyrazole-4-carbonyl]-5-methyl-1H-indol-6-yl]-2-morpholin-4-yl-2-oxoethanesulfonamide, (4-10-008) 2-[[2-[5-amino-1-[4-(2-fluorophenoxy)-2-methylphenyl]pyrazole-4-carbonyl]-5-methyl-1H-indol-6-yl]sulfamoyl]-N-propan-2-ylacetamide, (4-10-009) N-[2-[5-amino-1-[2-fluoro-4-(2-fluorophenoxy)-6-methylphenyl]pyrazole-4-carbonyl]-5-methyl-1H-indol-6-yl]-2-morpholin-4-yl-2-oxoethanesulfonamide, (4-10-010) N-[2-[5-amino-1-[6-(2,6-difluorophenoxy)-4-methylpyridin-3-yl]pyrazole-4-carbonyl]-5-methyl-1H-indol-6-yl]-2-morpholin-4-yl-2-oxoethanesulfonamide, (4-10-011) 2-[[2-[5-amino-1-[4-(2-fluorophenoxy)-2-methylphenyl]pyrazole-4-carbonyl]-5-methoxy-1H-indol-6-yl]sulfamoyl]-N-propan-2-ylacetamide, (4-10-012) N-[2-[5-amino-1-[4-(2-fluorophenoxy)-2-methylphenyl]pyrazole-4-carbonyl]-5-methoxy-1H-indol-6-yl]-2-morpholin-4-yl-2-oxoethanesulfonamide, (4-10-013) N-[2-[5-amino-1-[2-fluoro-4-(2-fluorophenoxy)-6-methylphenyl]pyrazole-4-carbonyl]-5-methoxy-1H-indol-6-yl]-2-morpholin-4-yl-2-oxoethanesulfonamide, (4-10-014) N-[2-[5-amino-1-[6-(2-fluorophenoxy)-4-methylpyridin-3-yl]pyrazole-4-carbonyl]-5-methoxy-1H-indol-6-yl]-2-oxo-2-pyrrolidin-1-ylethanesulfonamide, (4-10-015) 2-[[2-[5-amino-1-[6-(2-fluorophenoxy)-4-methylpyridin-3-yl]pyrazole-4-carbonyl]-5-methoxy-1H-indol-6-yl]sulfamoyl]-N-propan-2-ylacetamide, (4-10-016) N-[2-[5-amino-1-[6-(2-fluorophenoxy)-4-methylpyridin-3-yl]pyrazole-4-carbonyl]-5-methoxy-1H-indol-6-yl]-2-morpholin-4-yl-2-oxoethanesulfonamide, (4-10-017) N-[2-[5-amino-1-[6-(2,6-difluorophenoxy)-4-methylpyridin-3-yl]pyrazole-4-carbonyl]-5-methoxy-1H-indol-6-yl]-2-oxo-2-pyrrolidin-1-ylethanesulfonamide, (4-11-001) N-[2-[5-amino-1-[6-(2-fluorophenoxy)-4-methylpyridin-3-yl]pyrazole-4-carbonyl]-5-methoxy-1H-indol-6-yl]acetamide, (4-12-001) N-[2-[5-amino-1-[6-(2-fluorophenoxy)-4-methylpyridin-3-yl]pyrazole-4-carbonyl]-5-methoxy-1H-indol-6-yl]morpholine-4-sulfonamide, (4-12-002) N-[2-[5-amino-1-[6-(2-fluorophenoxy)-4-methylpyridin-3-yl]pyrazole-4-carbonyl]-5-methoxy-1H-indol-6-yl]morpholine-4-carboxamide, (4-12-003) N-[2-[5-amino-1-[4-(2-fluorophenoxy)-2-methylphenyl]pyrazole-4-carbonyl]-5-methoxy-1H-indol-6-yl]morpholine-4-sulfonamide, (4-13-001) N-[2-[5-amino-1-[6-(2-fluorophenoxy)-4-methylpyridin-3-yl]pyrazole-4-carbonyl]-5-methoxy-1H-indol-6-yl]-3-fluoropropane-1-sulfonamide, (4-13-002) N-[2-[5-amino-1-[4-(2-fluorophenoxy)-2-methylphenyl]pyrazole-4-carbonyl]-5-methoxy-1H-indol-6-yl]-3-fluoropropane-1-sulfonamide, (4-14-001) [5-amino-1-[6-(2-fluorophenoxy)-4-methylpyridin-3-yl]pyrazol-4-yl]-[6-(1,1-dioxo-1,2-thiazolidin-2-yl)-5-methoxy-1H-indol-2-yl]methanone, (4-14-002) [5-amino-1-[4-(2-fluorophenoxy)-2-methylphenyl]pyrazol-4-yl]-[6-(1,1-dioxo-1,2-thiazolidin-2-yl)-5-methoxy-1H-indol-2-yl]methanone, (4-15-001) N-[2-[5-amino-1-[6-(2-fluorophenoxy)-4-methylpyridin-3-yl]pyrazole-4-carbonyl]-5-methyl-1H-indol-6-yl]-2-morpholin-4-yl-2-oxoethanesulfonamide, (4-16-001) [5-amino-1-[6-(2-fluorophenoxy)-4-methylpyridin-3-yl]pyrazol-4-yl]-[6-(1,1-dioxo-1,2-thiazolidin-2-yl)-5-methyl-1H-indol-2-yl]methanone hydrochloride, (4-17-001) 1-[4-[2-[5-amino-1-[6-(2,6-difluorophenoxy)-4-methylpyridin-3-yl]pyrazole-4-carbonyl]-5-(2,2-difluoroethoxy)-1H-indol-6-yl]piperidin-1-yl]ethanone, (4-17-002) 1-[4-[2-[5-amino-1-[4-(2-fluorophenoxy)-2-methylphenyl]pyrazole-4-carbonyl]-5-(difluoromethoxy)-1H-indol-6-yl]piperidin-1-yl]ethanone, (4-17-003) [5-amino-1-[4-(2-fluorophenoxy)-2-methylphenyl]pyrazol-4-yl]-[5-(difluoromethoxy)-6-(1-methylsulfonylpiperidin-4-yl)-1H-indol-2-yl]methanone, (4-17-004) [5-amino-1-[4-(2-fluorophenoxy)-2-methylphenyl]pyrazol-4-yl]-[6-(1-cyclopropylsulfonylpiperidin-4-yl)-5-(difluoromethoxy)-1H-indol-2-yl]methanone, (4-17-005) 1-[4-[2-[5-amino-1-[2-fluoro-4-(2-fluorophenoxy)-6-methylphenyl]pyrazole-4-carbonyl]-5-(difluoromethoxy)-1H-indol-6-yl]piperidin-1-yl]ethanone, (4-17-006) [5-amino-1-[2-fluoro-4-(2-fluorophenoxy)-6-methylphenyl]pyrazol-4-yl]-[5-(difluoromethoxy)-6-(1-methylsulfonylpiperidin-4-yl)-1H-indol-2-yl]methanone, (4-17-007) [5-amino-1-[2-fluoro-4-(2-fluorophenoxy)-6-methylphenyl]pyrazol-4-yl]-[6-(1-cyclopropylsulfonylpiperidin-4-yl)-5-(difluoromethoxy)-1H-indol-2-yl]methanone, (4-17-008) 1-[4-[2-[5-amino-1-[6-(2-fluorophenoxy)-4-methylpyridin-3-yl]pyrazole-4-carbonyl]-5-(difluoromethoxy)-1H-indol-6-yl]piperidin-1-yl]ethanone, (4-17-009) [5-amino-1-[6-(2-fluorophenoxy)-4-methylpyridin-3-yl]pyrazol-4-yl]-[5-(difluoromethoxy)-6-(1-methylsulfonylpiperidin-4-yl)-1H-indol-2-yl]methanone, (4-17-010) [5-amino-1-[6-(2-fluorophenoxy)-4-methylpyridin-3-yl]pyrazol-4-yl]-[6-(1-cyclopropylsulfonylpiperidin-4-yl)-5-(difluoromethoxy)-1H-indol-2-yl]methanone, (4-17-011) 1-[4-[2-[5-amino-1-[6-(2,6-difluorophenoxy)-4-methylpyridin-3-yl]pyrazole-4-carbonyl]-5-(difluoromethoxy)-1H-indol-6-yl]piperidin-1-yl]ethanone, (4-17-012) [5-amino-1-[6-(2,6-difluorophenoxy)-4-methylpyridin-3-yl]pyrazol-4-yl]-[5-(difluoromethoxy)-6-(1-methylsulfonylpiperidin-4-yl)-1H-indol-2-yl]methanone, (4-17-013) [5-amino-1-[6-(2,6-difluorophenoxy)-4-methylpyridin-3-yl]pyrazol-4-yl]-[6-(1-cyclopropylsulfonylpiperidin-4-yl)-5-(difluoromethoxy)-1H-indol-2-yl]methanone, (4-17-014) 1-[4-[2-[5-amino-1-[4-(2-fluorophenoxy)-2-methylphenyl]pyrazole-4-carbonyl]-5-(2,2-difluoroethoxy)-1H-indol-6-yl]piperidin-1-yl]ethanone, (4-17-015) [5-amino-1-[4-(2-fluorophenoxy)-2-methylphenyl]pyrazol-4-yl]-[5-(2,2-difluoroethoxy)-6-(1-methylsulfonylpiperidin-4-yl)-1H-indol-2-yl]methanone, (4-17-016) [5-amino-1-[4-(2-fluorophenoxy)-2-methylphenyl]pyrazol-4-yl]-[6-(1-cyclopropylsulfonylpiperidin-4-yl)-5-(2,2-difluoroethoxy)-1H-indol-2-yl]methanone, (4-17-017) 1-[4-[2-[5-amino-1-[2-fluoro-4-(2-fluorophenoxy)-6-methylphenyl]pyrazole-4-carbonyl]-5-(2,2-difluoroethoxy)-1H-indol-6-yl]piperidin-1-yl]ethanone, (4-17-018) [5-amino-1-[2-fluoro-4-(2-fluorophenoxy)-6-methylphenyl]pyrazol-4-yl]-[5-(2,2-difluoroethoxy)-6-(1-methylsulfonylpiperidin-4-yl)-1H-indol-2-yl]methanone, (4-17-019) [5-amino-1-[2-fluoro-4-(2-fluorophenoxy)-6-methylphenyl]pyrazol-4-yl]-[6-(1-cyclopropylsulfonylpiperidin-4-yl)-5-(2,2-difluoroethoxy)-1H-indol-2-yl]methanone, (4-17-020) 1-[4-[2-[5-amino-1-[6-(2-fluorophenoxy)-4-methylpyridin-3-yl]pyrazole-4-carbonyl]-5-(2,2-difluoroethoxy)-1H-indol-6-yl]piperidin-1-yl]ethanone, (4-17-021) [5-amino-1-[6-(2-fluorophenoxy)-4-methylpyridin-3-yl]pyrazol-4-yl]-[5-(2,2-difluoroethoxy)-6-(1-methylsulfonylpiperidin-4-yl)-1H-indol-2-yl]methanone, (4-17-022) [5-amino-1-[6-(2-fluorophenoxy)-4-methylpyridin-3-yl]pyrazol-4-yl]-[6-(1-cyclopropylsulfonylpiperidin-4-yl)-5-(2,2-difluoroethoxy)-1H-indol-2-yl]methanone, (4-17-023) [5-amino-1-[6-(2,6-difluorophenoxy)-4-methylpyridin-3-yl]pyrazol-4-yl]-[5-(2,2-difluoroethoxy)-6-(1-methylsulfonylpiperidin-4-yl)-1H-indol-2-yl]methanone, (4-17-024) [5-amino-1-[6-(2,6-difluorophenoxy)-4-methylpyridin-3-yl]pyrazol-4-yl]-[6-(1-cyclopropylsulfonylpiperidin-4-yl)-5-(2,2-difluoroethoxy)-1H-indol-2-yl]methanone, (4-18-001) 2-amino-1-[4-[2-[5-amino-1-[6-(2,6-difluorophenoxy)-4-methylpyridin-3-yl]pyrazole-4-carbonyl]-5-(2,2-difluoroethoxy)-1H-indol-6-yl]piperidin-1-yl]ethanone, (4-18-002) 2-amino-1-[4-[2-[5-amino-1-[4-(2-fluorophenoxy)-2-methylphenyl]pyrazole-4-carbonyl]-5-(difluoromethoxy)-1H-indol-6-yl]piperidin-1-yl]ethanone, (4-18-003) 2-amino-1-[4-[2-[5-amino-1-[6-(2,6-difluorophenoxy)-4-methylpyridin-3-yl]pyrazole-4-carbonyl]-5-(difluoromethoxy)-1H-indol-6-yl]piperidin-1-yl]ethanone, (4-18-004) 2-amino-1-[4-[2-[5-amino-1-[4-(2-fluorophenoxy)-2-methylphenyl]pyrazole-4-carbonyl]-5-(2,2-difluoroethoxy)-1H-indol-6-yl]piperidin-1-yl]ethanone, (4-19-001) N-[2-[5-amino-1-[6-(2,6-difluorophenoxy)-4-methylpyridin-3-yl]pyrazole-4-carbonyl]-5-methoxy-1H-indol-6-yl]-3-fluoropropane-1-sulfonamide, (4-20-001) 2-[5-amino-1-[4-(2-fluorophenoxy)-2-methylphenyl]pyrazole-4-carbonyl]-5-fluoro-6-(sulfamoylamino)-1H-indole, (4-20-002) 2-[5-amino-1-[4-(2,3-difluorophenoxy)-2-methylphenyl]pyrazole-4-carbonyl]-5-fluoro-6-(sulfamoylamino)-1H-indole, (4-20-003) 2-[5-amino-1-[4-(2-fluorophenoxy)-3-methylphenyl]pyrazole-4-carbonyl]-5-fluoro-6-(sulfamoylamino)-1H-indole, (4-21-001) 1-[2-[5-amino-1-[6-(2,6-difluorophenoxy)-4-methylpyridin-3-yl]pyrazole-4-carbonyl]-5-(2,2-difluoroethoxy)-1H-indol-6-yl]pyrrolidin-2-one, (4-21-002) 1-[2-[5-amino-1-[4-(2-fluorophenoxy)-2-methylphenyl]pyrazole-4-carbonyl]-5-(2,2-difluoroethoxy)-1H-indol-6-yl]pyrrolidin-2-one, (4-21-003) 3-[2-[5-amino-1-[4-(2-fluorophenoxy)-2-methylphenyl]pyrazole-4-carbonyl]-5-(2,2-difluoroethoxy)-1H-indol-6-yl]-1,3-oxazolidin-2-one, (4-21-004) 1-[2-[5-amino-1-[2-fluoro-4-(2-fluorophenoxy)-6-methylphenyl]pyrazole-4-carbonyl]-5-(2,2-difluoroethoxy)-1H-indol-6-yl]pyrrolidin-2-one, (4-21-005) 3-[2-[5-amino-1-[6-(2,6-difluorophenoxy)-4-methylpyridin-3-yl]pyrazole-4-carbonyl]-5-(2,2-difluoroethoxy)-1H-indol-6-yl]-1,3-oxazolidin-2-one, (4-21-006) 1-[2-[5-amino-1-[4-(2-fluorophenoxy)-2-methylphenyl]pyrazole-4-carbonyl]-5-(difluoromethoxy)-1H-indol-6-yl]pyrrolidin-2-one, (4-21-007) 3-[2-[5-amino-1-[4-(2-fluorophenoxy)-2-methylphenyl]pyrazole-4-carbonyl]-5-(difluoromethoxy)-1H-indol-6-yl]-1,3-oxazolidin-2-one, (4-21-008) 1-[2-[5-amino-1-[6-(2,6-difluorophenoxy)-4-methylpyridin-3-yl]pyrazole-4-carbonyl]-5-(difluoromethoxy)-1H-indol-6-yl]pyrrolidin-2-one, (4-21-009) 3-[2-[5-amino-1-[6-(2,6-difluorophenoxy)-4-methylpyridin-3-yl]pyrazole-4-carbonyl]-5-(difluoromethoxy)-1H-indol-6-yl]-1,3-oxazolidin-2-one, (4-22-001) N-[2-[5-amino-1-[4-(2-fluorophenoxy)-2-methylphenyl]pyrazole-4-carbonyl]-5-(difluoromethoxy)-1H-indol-6-yl]morpholine-4-sulfonamide, (4-22-002) N-[2-[5-amino-1-[6-(2-fluorophenoxy)-4-methylpyridin-3-yl]pyrazole-4-carbonyl]-5-(difluoromethoxy)-1H-indol-6-yl]morpholine-4-sulfonamide, (4-22-003) N-[2-[5-amino-1-[6-(2,6-difluorophenoxy)-4-methylpyridin-3-yl]pyrazole-4-carbonyl]-5-(difluoromethoxy)-1H-indol-6-yl]morpholine-4-sulfonamide, (4-22-004) N-[2-[5-amino-1-[6-(2-fluorophenoxy)-4-methylpyridin-3-yl]pyrazole-4-carbonyl]-5-morpholin-4-yl-1H-indol-6-yl]morpholine-4-sulfonamide, (4-22-005) N-[2-[5-amino-1-[4-(2-fluorophenoxy)-2-methylphenyl]pyrazole-4-carbonyl]-5-(2,2-difluoroethoxy)-1H-indol-6-yl]morpholine-4-sulfonamide, (4-22-006) N-[2-[5-amino-1-[6-(2-fluorophenoxy)-4-methylpyridin-3-yl]pyrazole-4-carbonyl]-5-(2,2-difluoroethoxy)-1H-indol-6-yl]morpholine-4-sulfonamide, (4-23-001) [5-amino-1-[6-(2,6-difluorophenoxy)-4-methylpyridin-3-yl]pyrazol-4-yl]-[5-(2,2-difluoroethoxy)-6-(4-methylsulfonylpiperazin-1-yl)-1H-indol-2-yl]methanone, (4-23-002) [5-amino-1-[4-(2-fluorophenoxy)-2-methylphenyl]pyrazol-4-yl]-[5-(difluoromethoxy)-6-(4-methylsulfonylpiperazin-1-yl)-1H-indol-2-yl]methanone, (4-23-003) [5-amino-1-[2-fluoro-4-(2-fluorophenoxy)-6-methylphenyl]pyrazol-4-yl]-[5-(difluoromethoxy)-6-(4-methylsulfonylpiperazin-1-yl)-1H-indol-2-yl]methanone, (4-23-004) [5-amino-1-[6-(2-fluorophenoxy)-4-methylpyridin-3-yl]pyrazol-4-yl]-[5-(difluoromethoxy)-6-(4-methylsulfonylpiperazin-1-yl)-1H-indol-2-yl]methanone, (4-23-005) [5-amino-1-[4-(2-fluorophenoxy)-2-methylphenyl]pyrazol-4-yl]-[5-(2,2-difluoroethoxy)-6-(4-methylsulfonylpiperazin-1-yl)-1H-indol-2-yl]methanone, (4-23-006) [5-amino-1-[2-fluoro-4-(2-fluorophenoxy)-6-methylphenyl]pyrazol-4-yl]-[5-(2,2-difluoroethoxy)-6-(4-methylsulfonylpiperazin-1-yl)-1H-indol-2-yl]methanone, (4-23-007) [5-amino-1-[6-(2-fluorophenoxy)-4-methylpyridin-3-yl]pyrazol-4-yl]-[5-(2,2-difluoroethoxy)-6-(4-methylsulfonylpiperazin-1-yl)-1H-indol-2-yl]methanone, (4-23-008) [5-amino-1-[6-(2,6-difluorophenoxy)-4-methylpyridin-3-yl]pyrazol-4-yl]-[5-(2,2-difluoroethoxy)-6-(oxetan-3-yl amino)-1H-indol-2-yl]methanone, (4-23-009) [5-amino-1-[4-(2-fluorophenoxy)-2-methylphenyl]pyrazol-4-yl]-[5-(difluoromethoxy)-6-(oxetan-3-ylamino)-1H-indol-2-yl]methanone, (4-23-010) [5-amino-1-[4-(2-fluorophenoxy)-2-methylphenyl]pyrazol-4-yl]-[5-(difluoromethoxy)-6-[(1-methylsulfonylpiperidin-4-yl)amino]-1H-indol-2-yl]methanone, (4-23-011) [5-amino-1-[2-fluoro-4-(2-fluorophenoxy)-6-methylphenyl]pyrazol-4-yl]-[5-(difluoromethoxy)-6-(oxetan-3-ylamino)-1H-indol-2-yl]methanone, (4-23-012) [5-amino-1-[2-fluoro-4-(2-fluorophenoxy)-6-methylphenyl]pyrazol-4-yl]-[5-(difluoromethoxy)-6-[(1-methylsulfonylpiperidin-4-yl)amino]-1H-indol-2-yl]methanone, (4-23-013) [5-amino-1-[6-(2-fluorophenoxy)-4-methylpyridin-3-yl]pyrazol-4-yl]-[5-(difluoromethoxy)-6-(oxetan-3-ylamino)-1H-indol-2-yl]methanone, (4-23-014) [5-amino-1-[6-(2,6-difluorophenoxy)-4-methylpyridin-3-yl]pyrazol-4-yl]-[5-(difluoromethoxy)-6-(oxetan-3-ylamino)-1H-indol-2-yl]methanone, (4-23-015) [5-amino-1-[6-(2,6-difluorophenoxy)-4-methylpyridin-3-yl]pyrazol-4-yl]-[5-(difluoromethoxy)-6-[(1-methylsulfonylpiperidin-4-yl)amino]-1H-indol-2-yl]methanone, (4-23-016) [5-amino-1-[4-(2-fluorophenoxy)-2-methylphenyl]pyrazol-4-yl]-[5-(2,2-difluoroethoxy)-6-(oxetan-3-yl amino)-1H-indol-2-yl]methanone, (4-23-017) [5-amino-1-[4-(2-fluorophenoxy)-2-methylphenyl]pyrazol-4-yl]-[5-(2,2-difluoroethoxy)-6-[(1-methylsulfonylpiperidin-4-yl)amino]-1H-indol-2-yl]methanone, (4-23-018) [5-amino-1-[4-(2-fluorophenoxy)-2-methylphenyl]pyrazol-4-yl]-[5-(2,2-difluoroethoxy)-6-[(1-methylsulfonylazetidin-3-yl)amino]-1H-indol-2-yl]methanone, (4-23-019) [5-amino-1-[2-fluoro-4-(2-fluorophenoxy)-6-methylphenyl]pyrazol-4-yl]-[5-(2,2-difluoroethoxy)-6-(oxetan-3-yl amino)-1H-indol-2-yl]methanone, (4-23-020) [5-amino-1-[6-(2,6-difluorophenoxy)-4-methylpyridin-3-yl]pyrazol-4-yl]-[5-(2,2-difluoroethoxy)-6-(oxetan-3-yl amino)-1H-indol-2-yl]methanone, (4-23-021) [5-amino-1-[6-(2,6-difluorophenoxy)-4-methylpyridin-3-yl]pyrazol-4-yl]-[5-(2,2-difluoroethoxy)-6-[(1-methylsulfonylpiperidin-4-yl)amino]-1H-indol-2-yl]methanone, (4-23-022) [5-amino-1-[6-(2,6-difluorophenoxy)-4-methylpyridin-3-yl]pyrazol-4-yl]-[5-(2,2-difluoroethoxy)-6-[(1-methylsulfonylazetidin-3-yl)amino]-1H-indol-2-yl]methanone, (4-23-023) [5-amino-1-[4-(2-fluorophenoxy)-2-methylphenyl]pyrazol-4-yl]-[5-(difluoromethoxy)-6-[(1-methylsulfonylazetidin-3-yl)amino]-1H-indol-2-yl]methanone, (4-23-024) [5-amino-1-[2-fluoro-4-(2-fluorophenoxy)-6-methylphenyl]pyrazol-4-yl]-[5-(difluoromethoxy)-6-[(1-methylsulfonylazetidin-3-yl)amino]-1H-indol-2-yl]methanone, (4-23-025) [5-amino-1-[6-(2-fluorophenoxy)-4-methylpyridin-3-yl]pyrazol-4-yl]-[5-(difluoromethoxy)-6-[(1-methylsulfonylazetidin-3-yl)amino]-1H-indol-2-yl]methanone, (4-23-026) [5-amino-1-[6-(2-fluorophenoxy)-4-methylpyridin-3-yl]pyrazol-4-yl]-[5-(difluoromethoxy)-6-[(1-methylsulfonylpiperidin-4-yl)amino]-1H-indol-2-yl]methanone, (4-23-027) [5-amino-1-[2-fluoro-4-(2-fluorophenoxy)-6-methylphenyl]pyrazol-4-yl]-[5-(2,2-difluoroethoxy)-6-[(1-methylsulfonylazetidin-3-yl)amino]-1H-indol-2-yl]methanone, (4-23-028) [5-amino-1-[2-fluoro-4-(2-fluorophenoxy)-6-methylphenyl]pyrazol-4-yl]-[5-(2,2-difluoroethoxy)-6-[(1-methylsulfonylpiperidin-4-yl)amino]-1H-indol-2-yl]methanone, (4-23-029) 1-[2-[5-amino-1-[6-(2,6-difluorophenoxy)-4-methylpyridin-3-yl]pyrazole-4-carbonyl]-5-(2,2-difluoroethoxy)-1H-indol-6-yl]-6-methylpyrimidine-2,4-dione, (4-23-030) 1-[2-[5-amino-1-[4-(2-fluorophenoxy)-2-methylphenyl]pyrazole-4-carbonyl]-5-(2,2-difluoroethoxy)-1H-indol-6-yl]-6-methylpyrimidine-2,4-dione, (4-23-031) 1-[2-[5-amino-1-[4-(2-fluorophenoxy)-2-methylphenyl]pyrazole-4-carbonyl]-5-(difluoromethoxy)-1H-indol-6-yl]-6-methylpyrimidine-2,4-dione, (4-23-032) 3-[2-[5-amino-1-[6-(2,6-difluorophenoxy)-4-methylpyridin-3-yl]pyrazole-4-carbonyl]-5-(2,2-difluoroethoxy)-1H-indol-6-yl]-5,5-dimethylimidazolidine-2,4-dione, (4-23-033) 3-[2-[5-amino-1-[4-(2-fluorophenoxy)-2-methylphenyl]pyrazole-4-carbonyl]-5-(2,2-difluoroethoxy)-1H-indol-6-yl]-5,5-dimethylimidazolidine-2,4-dione, (4-23-034) 3-[2-[5-amino-1-[6-(2,6-difluorophenoxy)-4-methylpyridin-3-yl]pyrazole-4-carbonyl]-5-(difluoromethoxy)-1H-indol-6-yl]-5,5-dimethylimidazolidine-2,4-dione, (4-23-035) 3-[2-[5-amino-1-[4-(2-fluorophenoxy)-2-methylphenyl]pyrazole-4-carbonyl]-5-(difluoromethoxy)-1H-indol-6-yl]-5,5-dimethylimidazolidine-2,4-dione, (4-23-036) 3-[2-[5-amino-1-[6-(2,6-difluorophenoxy)-4-methylpyridin-3-yl]pyrazole-4-carbonyl]-5-(2,2-difluoroethoxy)-1H-indol-6-yl]-5,5-dimethyl-2-sulfanylideneimidazolidin-4-one, (4-23-037) 3-[2-[5-amino-1-[4-(2-fluorophenoxy)-2-methylphenyl]pyrazole-4-carbonyl]-5-(2,2-difluoroethoxy)-1H-indol-6-yl]-5,5-dimethyl-2-sulfanylideneimidazolidin-4-one, (4-23-038) 3-[2-[5-amino-1-[6-(2,6-difluorophenoxy)-4-methylpyridin-3-yl]pyrazole-4-carbonyl]-5-(difluoromethoxy)-1H-indol-6-yl]-5,5-dimethyl-2-sulfanylideneimidazolidin-4-one, (4-23-039) 3-[2-[5-amino-1-[4-(2-fluorophenoxy)-2-methylphenyl]pyrazole-4-carbonyl]-5-(difluoromethoxy)-1H-indol-6-yl]-5,5-dimethyl-2-sulfanylideneimidazolidin-4-one, (4-24-001) N-[2-[5-amino-1-[4-(2-fluorophenoxy)-2-methylphenyl]pyrazole-4-carbonyl]-5-(difluoromethoxy)-1H-indol-6-yl]cyclopropanesulfonamide, (4-24-002) N-[2-[5-amino-1-[4-(2-fluorophenoxy)-2-methylphenyl]pyrazole-4-carbonyl]-5-(difluoromethoxy)-1H-indol-6-yl]methanesulfonamide, (4-24-003) N-[2-[5-amino-1-[4-(2-fluorophenoxy)-2-methylphenyl]pyrazole-4-carbonyl]-5-(difluoromethoxy)-1H-indol-6-yl]-3-fluoropropane-1-sulfonamide, (4-24-004) N-[2-[5-amino-1-[4-(2-fluorophenoxy)-2-methylphenyl]pyrazole-4-carbonyl]-5-(difluoromethoxy)-1H-indol-6-yl]-3,3-difluoropropane-1-sulfonamide, (4-24-005) N-[2-[5-amino-1-[2-fluoro-4-(2-fluorophenoxy)-6-methylphenyl]pyrazole-4-carbonyl]-5-(difluoromethoxy)-1H-indol-6-yl]cyclopropanesulfonamide, (4-24-006) N-[2-[5-amino-1-[2-fluoro-4-(2-fluorophenoxy)-6-methylphenyl]pyrazole-4-carbonyl]-5-(difluoromethoxy)-1H-indol-6-yl]-3-fluoropropane-1-sulfonamide, (4-24-007) N-[2-[5-amino-1-[6-(2-fluorophenoxy)-4-methylpyridin-3-yl]pyrazole-4-carbonyl]-5-(difluoromethoxy)-1H-indol-6-yl]cyclopropanesulfonamide, (4-24-008) N-[2-[5-amino-1-[6-(2-fluorophenoxy)-4-methylpyridin-3-yl]pyrazole-4-carbonyl]-5-(difluoromethoxy)-1H-indol-6-yl]methanesulfonamide, (4-24-009) N-[2-[5-amino-1-[6-(2-fluorophenoxy)-4-methylpyridin-3-yl]pyrazole-4-carbonyl]-5-(difluoromethoxy)-1H-indol-6-yl]-3-fluoropropane-1-sulfonamide, (4-24-010) N-[2-[5-amino-1-[6-(2,6-difluorophenoxy)-4-methylpyridin-3-yl]pyrazole-4-carbonyl]-5-(difluoromethoxy)-1H-indol-6-yl]cyclopropanesulfonamide, (4-24-011) N-[2-[5-amino-1-[6-(2,6-difluorophenoxy)-4-methylpyridin-3-yl]pyrazole-4-carbonyl]-5-(difluoromethoxy)-1H-indol-6-yl]methanesulfonamide, (4-24-012) N-[2-[5-amino-1-[6-(2,6-difluorophenoxy)-4-methylpyridin-3-yl]pyrazole-4-carbonyl]-5-(difluoromethoxy)-1H-indol-6-yl]-3-fluoropropane-1-sulfonamide, (4-24-013) N-[2-[5-amino-1-[4-(2-fluorophenoxy)-2-methylphenyl]pyrazole-4-carbonyl]-5-morpholin-4-yl-1H-indol-6-yl]methanesulfonamide, (4-24-014) N-[2-[5-amino-1-[6-(2-fluorophenoxy)-4-methylpyridin-3-yl]pyrazole-4-carbonyl]-5-morpholin-4-yl-1H-indol-6-yl]cyclopropanesulfonamide, (4-24-015) N-[2-[5-amino-1-[6-(2-fluorophenoxy)-4-methylpyridin-3-yl]pyrazole-4-carbonyl]-5-morpholin-4-yl-1H-indol-6-yl]methanesulfonamide, (4-24-016) N-[2-[5-amino-1-[6-(2-fluorophenoxy)-4-methylpyridin-3-yl]pyrazole-4-carbonyl]-5-morpholin-4-yl-1H-indol-6-yl]-3-fluoropropane-1-sulfonamide, (4-24-017) N-[2-[5-amino-1-[6-(2,6-difluorophenoxy)-4-methylpyridin-3-yl]pyrazole-4-carbonyl]-5-morpholin-4-yl-1H-indol-6-yl]cyclopropanesulfonamide, (4-24-018) N-[2-[5-amino-1-[6-(2,6-difluorophenoxy)-4-methylpyridin-3-yl]pyrazole-4-carbonyl]-5-morpholin-4-yl-1H-indol-6-yl]methanesulfonamide, (4-24-019) N-[2-[5-amino-1-[6-(2,6-difluorophenoxy)-4-methylpyridin-3-yl]pyrazole-4-carbonyl]-5-morpholin-4-yl-1H-indol-6-yl]-3-fluoropropane-1-sulfonamide, (4-24-020) N-[2-[5-amino-1-[4-(2-fluorophenoxy)-2-methylphenyl]pyrazole-4-carbonyl]-5-(2,2-difluoroethoxy)-1H-indol-6-yl]cyclopropanesulfonamide, (4-24-021) N-[2-[5-amino-1-[4-(2-fluorophenoxy)-2-methylphenyl]pyrazole-4-carbonyl]-5-(2,2-difluoroethoxy)-1H-indol-6-yl]methanesulfonamide, (4-24-022) N-[2-[5-amino-1-[4-(2-fluorophenoxy)-2-methylphenyl]pyrazole-4-carbonyl]-5-(2,2-difluoroethoxy)-1H-indol-6-yl]-3-fluoropropane-1-sulfonamide, (4-24-023) N-[2-[5-amino-1-[4-(2-fluorophenoxy)-2-methylphenyl]pyrazole-4-carbonyl]-5-(2,2-difluoroethoxy)-1H-indol-6-yl]-3,3-difluoropropane-1-sulfonamide, (4-24-024) N-[2-[5-amino-1-[2-fluoro-4-(2-fluorophenoxy)-6-methylphenyl]pyrazole-4-carbonyl]-5-(2,2-difluoroethoxy)-1H-indol-6-yl]cyclopropanesulfonamide, (4-24-025) N-[2-[5-amino-1-[2-fluoro-4-(2-fluorophenoxy)-6-methylphenyl]pyrazole-4-carbonyl]-5-(2,2-difluoroethoxy)-1H-indol-6-yl]methanesulfonamide, (4-24-026) N-[2-[5-amino-1-[2-fluoro-4-(2-fluorophenoxy)-6-methylphenyl]pyrazole-4-carbonyl]-5-(2,2-difluoroethoxy)-1H-indol-6-yl]-3-fluoropropane-1-sulfonamide, (4-24-027) N-[2-[5-amino-1-[6-(2-fluorophenoxy)-4-methylpyridin-3-yl]pyrazole-4-carbonyl]-5-(2,2-difluoroethoxy)-1H-indol-6-yl]cyclopropanesulfonamide, (4-24-028) N-[2-[5-amino-1-[6-(2-fluorophenoxy)-4-methylpyridin-3-yl]pyrazole-4-carbonyl]-5-(2,2-difluoroethoxy)-1H-indol-6-yl]methanesulfonamide, (4-24-029) N-[2-[5-amino-1-[6-(2-fluorophenoxy)-4-methylpyridin-3-yl]pyrazole-4-carbonyl]-5-(2,2-difluoroethoxy)-1H-indol-6-yl]-3-fluoropropane-1-sulfonamide, (4-24-030) N-[2-[5-amino-1-[6-(2,6-difluorophenoxy)-4-methylpyridin-3-yl]pyrazole-4-carbonyl]-5-(2,2-difluoroethoxy)-1H-indol-6-yl]cyclopropanesulfonamide, (4-24-031) N-[2-[5-amino-1-[6-(2,6-difluorophenoxy)-4-methylpyridin-3-yl]pyrazole-4-carbonyl]-5-(2,2-difluoroethoxy)-1H-indol-6-yl]methanesulfonamide, (4-24-032) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-3-fluoropropane-1-sulfonamide, (4-24-033) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-3,3-difluoropropane-1-sulfonamide, (4-24-034) N-[2-[5-amino-1-[4-(2-fluorophenoxy)-2-methylphenyl]pyrazole-4-carbonyl]-5-(2-morpholin-4-ylethoxy)-1H-indol-6-yl]methanesulfonamide, (4-24-035) N-[2-[5-amino-1-[6-(2,6-difluorophenoxy)-4-methylpyridin-3-yl]pyrazole-4-carbonyl]-5-methoxy-1H-indol-6-yl]cyclopropanesulfonamide, (4-24-036) N-[2-[5-amino-1-[4-(2-fluorophenoxy)-2-methylphenyl]pyrazole-4-carbonyl]-5-(oxan-4-yloxy)-1H-indol-6-yl]methanesulfonamide, (4-24-037) N-[2-[5-amino-1-[4-(2-fluorophenoxy)-2-methylphenyl]pyrazole-4-carbonyl]-5-[2-[(1S,5R)-6-methylsulfonyl-3,6-diazabicyclo[3.1.1]heptan-3-yl]ethoxy]-1H-indol-6-yl]methanesulfonamide, (4-24-038) N-[2-[5-amino-1-[4-(2-fluorophenoxy)-2-methylphenyl]pyrazole-4-carbonyl]-5-[2-[(1S,4S)-2-methylsulfonyl-2,5-diazabicyclo[2.2.1]heptan-5-yl]ethoxy]-1H-indol-6-yl]methanesulfonamide, (4-24-039) N-[2-[5-amino-1-[4-(2-fluorophenoxy)-2-methylphenyl]pyrazole-4-carbonyl]-5-[2-[(1S,5R)-3-oxa-8-azabicyclo[3.2.1]octan-8-yl]ethoxy]-1H-indol-6-yl]methanesulfonamide, (4-25-001) [5-amino-1-[6-(2-fluorophenoxy)-4-methylpyridin-3-yl]pyrazol-4-yl]-[5-(2,2-difluoroethoxy)-6-(1,1-dioxo-1,2-thiazolidin-2-yl)-1H-indol-2-yl]methanone, (4-25-002) [5-amino-1-[4-(2-fluorophenoxy)-2-methylphenyl]pyrazol-4-yl]-[5-(difluoromethoxy)-6-(1,1-dioxo-1,2-thiazolidin-2-yl)-1H-indol-2-yl]methanone, (4-25-003) [5-amino-1-[2-fluoro-4-(2-fluorophenoxy)-6-methylphenyl]pyrazol-4-yl]-[5-(difluoromethoxy)-6-(1,1-dioxo-1,2-thiazolidin-2-yl)-1H-indol-2-yl]methanone, (4-25-004) [5-amino-1-[6-(2-fluorophenoxy)-4-methylpyridin-3-yl]pyrazol-4-yl]-[5-(difluoromethoxy)-6-(1,1-dioxo-1,2-thiazolidin-2-yl)-1H-indol-2-yl]methanone, (4-25-005) [5-amino-1-[6-(2,6-difluorophenoxy)-4-methylpyridin-3-yl]pyrazol-4-yl]-[5-(difluoromethoxy)-6-(1,1-dioxo-1,2-thiazolidin-2-yl)-1H-indol-2-yl]methanone, (4-25-006) [5-amino-1-[4-(2-fluorophenoxy)-2-methylphenyl]pyrazol-4-yl]-[6-(1,1-dioxo-1,2-thiazolidin-2-yl)-5-morpholin-4-yl-1H-indol-2-yl]methanone, (4-25-007) [5-amino-1-[6-(2-fluorophenoxy)-4-methylpyridin-3-yl]pyrazol-4-yl]-[6-(1,1-dioxo-1,2-thiazolidin-2-yl)-5-morpholin-4-yl-1H-indol-2-yl]methanone, (4-25-008) [5-amino-1-[6-(2,6-difluorophenoxy)-4-methylpyridin-3-yl]pyrazol-4-yl]-[6-(1,1-dioxo-1,2-thiazolidin-2-yl)-5-morpholin-4-yl-1H-indol-2-yl]methanone, (4-25-009) [5-amino-1-[4-(2-fluorophenoxy)-2-methylphenyl]pyrazol-4-yl]-[5-(2,2-difluoroethoxy)-6-(1,1-dioxo-1,2-thiazolidin-2-yl)-1H-indol-2-yl]methanone, (4-25-010) [5-amino-1-[2-fluoro-4-(2-fluorophenoxy)-6-methylphenyl]pyrazol-4-yl]-[5-(2,2-difluoroethoxy)-6-(1,1-dioxo-1,2-thiazolidin-2-yl)-1H-indol-2-yl]methanone, (4-25-011) [5-amino-1-[6-(2,6-difluorophenoxy)-4-methylpyridin-3-yl]pyrazol-4-yl]-[5-(2,2-difluoroethoxy)-6-(1,1-dioxo-1,2-thiazolidin-2-yl)-1H-indol-2-yl]methanone, (4-25-012) [5-amino-1-[4-(2-fluorophenoxy)-2-methylphenyl]pyrazol-4-yl]-[6-(1,1-dioxo-1,2-thiazolidin-2-yl)-5-(2-morpholin-4-ylethoxy)-1H-indol-2-yl]methanone, (4-25-013) 1-[2-[5-amino-1-[6-(2-fluorophenoxy)-4-methylpyridin-3-yl]pyrazole-4-carbonyl]-5-(2,2-difluoroethoxy)-1H-indol-6-yl]pyrrolidin-2-one, (4-25-014) 1-[2-[5-amino-1-[6-(2-fluorophenoxy)-4-methylpyridin-3-yl]pyrazole-4-carbonyl]-5-(difluoromethoxy)-1H-indol-6-yl]pyrrolidin-2-one (4-25-015) 1-[2-[5-amino-1-[2-fluoro-4-(2-fluorophenoxy)-6-methylphenyl]pyrazole-4-carbonyl]-5-(difluoromethoxy)-1H-indol-6-yl]pyrrolidin-2-one (4-25-016) 3-[2-[5-amino-1-[6-(2-fluorophenoxy)-4-methylpyridin-3-yl]pyrazole-4-carbonyl]-5-(2,2-difluoroethoxy)-1H-indol-6-yl]-1,3-oxazolidin-2-one (4-25-017) 3-[2-[5-amino-1-[2-fluoro-4-(2-fluorophenoxy)-6-methylphenyl]pyrazole-4-carbonyl]-5-(2,2-difluoroethoxy)-1H-indol-6-yl]-1,3-oxazolidin-2-one (4-25-018) 3-[2-[5-amino-1-[6-(2-fluorophenoxy)-4-methylpyridin-3-yl]pyrazole-4-carbonyl]-5-(difluoromethoxy)-1H-indol-6-yl]-1,3-oxazolidin-2-one (4-25-019) 3-[2-[5-amino-1-[2-fluoro-4-(2-fluorophenoxy)-6-methylphenyl]pyrazole-4-carbonyl]-5-(difluoromethoxy)-1H-indol-6-yl]-1,3-oxazolidin-2-one (4-25-020) [5-amino-1-[6-(2-fluorophenoxy)-4-methylpyridin-3-yl]pyrazol-4-yl]-[5-(2,2-difluoroethoxy)-6-morpholin-4-yl-1H-indol-2-yl]methanone, (4-25-021) [5-amino-1-[2-fluoro-4-(2-fluorophenoxy)-6-methylphenyl]pyrazol-4-yl]-[5-(2,2-difluoroethoxy)-6-morpholin-4-yl-1H-indol-2-yl]methanone, (4-25-022) [5-amino-1-[6-(2-fluorophenoxy)-4-methylpyridin-3-yl]pyrazol-4-yl]-[5-(difluoromethoxy)-6-morpholin-4-yl-1H-indol-2-yl]methanone, (4-25-023) [5-amino-1-[6-(2,6-difluorophenoxy)-4-methylpyridin-3-yl]pyrazol-4-yl]-[5-(difluoromethoxy)-6-morpholin-4-yl-1H-indol-2-yl]methanone, (4-25-024) [5-amino-1-[4-(2-fluorophenoxy)-2-methylphenyl]pyrazol-4-yl]-[5-(difluoromethoxy)-6-morpholin-4-yl-1H-indol-2-yl]methanone, (4-25-025) [5-amino-1-[2-fluoro-4-(2-fluorophenoxy)-6-methylphenyl]pyrazol-4-yl]-[5-(difluoromethoxy)-6-morpholin-4-yl-1H-indol-2-yl]methanone, (4-25-026) [5-amino-1-[6-(2-fluorophenoxy)-4-methylpyridin-3-yl]pyrazol-4-yl]-[5-(2,2-difluoroethoxy)-6-(4-morpholin-4-ylpiperidin-1-yl)-1H-indol-2-yl]methanone, (4-25-027) [5-amino-1-[6-(2,6-difluorophenoxy)-4-methylpyridin-3-yl]pyrazol-4-yl]-[5-(2,2-difluoroethoxy)-6-(4-morpholin-4-ylpiperidin-1-yl)-1H-indol-2-yl]methanone, (4-25-028) [5-amino-1-[4-(2-fluorophenoxy)-2-methylphenyl]pyrazol-4-yl]-[5-(2,2-difluoroethoxy)-6-(4-morpholin-4-ylpiperidin-1-yl)-1H-indol-2-yl]methanone, (4-25-029) [5-amino-1-[2-fluoro-4-(2-fluorophenoxy)-6-methylphenyl]pyrazol-4-yl]-[5-(2,2-difluoroethoxy)-6-(4-morpholin-4-ylpiperidin-1-yl)-1H-indol-2-yl]methanone, (4-25-030) [5-amino-1-[6-(2-fluorophenoxy)-4-methylpyridin-3-yl]pyrazol-4-yl]-[5-(difluoromethoxy)-6-(4-morpholin-4-ylpiperidin-1-yl)-1H-indol-2-yl]methanone, (4-25-031) [5-amino-1-[6-(2,6-difluorophenoxy)-4-methylpyridin-3-yl]pyrazol-4-yl]-[5-(difluoromethoxy)-6-(4-morpholin-4-ylpiperidin-1-yl)-1H-indol-2-yl]methanone, (4-25-032) [5-amino-1-[4-(2-fluorophenoxy)-2-methylphenyl]pyrazol-4-yl]-[5-(difluoromethoxy)-6-(4-morpholin-4-ylpiperidin-1-yl)-1H-indol-2-yl]methanone, (4-26-001) N-[2-[5-amino-1-[4-(2-fluorophenoxy)-2-methylphenyl]pyrazole-4-carbonyl]-5-fluoro-1H-indol-6-yl]-2-oxo-2-pyrrolidin-1-ylethanesulfonamide, (5-1-001) [5-amino-1-[4-(2-chlorophenoxy)phenyl]pyrazol-4-yl]-[6-fluoro-5-(1-propan-2-ylpiperidin-4-yl)-1H-indol-2-yl]methanone, (5-1-002) [5-amino-1-[2-fluoro-4-(3-fluorophenoxy)phenyl]pyrazol-4-yl]-[6-fluoro-5-(1-propan-2-ylpiperidin-4-yl)-1H-indol-2-yl]methanone, (5-1-003) [5-amino-1-[4-(3-chlorophenoxy)-2-fluorophenyl]pyrazol-4-yl]-[6-fluoro-5-(1-propan-2-ylpiperidin-4-yl)-1H-indol-2-yl]methanone, (5-1-004) [5-amino-1-[4-(2-fluorophenoxy)phenyl]pyrazol-4-yl]-[6-fluoro-5-(1-propan-2-ylpiperidin-4-yl)-1H-indol-2-yl]methanone, (5-1-005) [5-amino-1-[4-(3-fluorophenoxy)-2-methylphenyl]pyrazol-4-yl]-[6-fluoro-5-(1-propan-2-ylpiperidin-4-yl)-1H-indol-2-yl]methanone, (5-1-006) [5-amino-1-[2-fluoro-4-(3-fluorophenoxy)phenyl]pyrazol-4-yl]-[5-fluoro-6-(1-propan-2-ylpiperidin-4-yl)-1H-indol-2-yl]methanone, (5-1-007) [5-amino-1-[4-(2-fluorophenoxy)phenyl]pyrazol-4-yl]-[5-fluoro-6-(1-propan-2-ylpiperidin-4-yl)-1H-indol-2-yl]methanone, (5-1-008) [5-amino-1-[4-(3-chlorophenoxy)phenyl]pyrazol-4-yl]-[5-fluoro-6-(1-propan-2-ylpiperidin-4-yl)-1H-indol-2-yl]methanone, (5-1-009) [5-amino-1-[4-(3-fluorophenoxy)-2-methylphenyl]pyrazol-4-yl]-[5-fluoro-6-(1-propan-2-ylpiperidin-4-yl)-1H-indol-2-yl]methanone, (5-1-010) [5-amino-1-[4-(3-chlorophenoxy)-2-fluorophenyl]pyrazol-4-yl]-[5-fluoro-6-(1-propan-2-ylpiperidin-4-yl)-1H-indol-2-yl]methanone, (5-1-011) [5-amino-1-[4-(2,3-difluorophenoxy)-2-fluorophenyl]pyrazol-4-yl]-[5-fluoro-6-(1-propan-2-ylpiperidin-4-yl)-1H-indol-2-yl]methanone, (5-1-012) [5-amino-1-[4-(2-fluorophenoxy)-3-methylphenyl]pyrazol-4-yl]-[5-methyl-6-(1-propan-2-ylpiperidin-4-yl)-1H-indol-2-yl]methanone, (5-1-013) [5-amino-1-[4-(2,3-difluorophenoxy)phenyl]pyrazol-4-yl]-[5-fluoro-6-(1-propan-2-ylpiperidin-4-yl)-1H-indol-2-yl]methanone, (5-1-014) [5-amino-1-[4-(3-fluorophenoxy)phenyl]pyrazol-4-yl]-[5-fluoro-6-(1-propan-2-ylpiperidin-4-yl)-1H-indol-2-yl]methanone, (5-1-015) [5-amino-1-[4-(2-chlorophenoxy)phenyl]pyrazol-4-yl]-[5-fluoro-6-(1-propan-2-ylpiperidin-4-yl)-1H-indol-2-yl]methanone, (5-1-016) N-[2-[5-amino-1-[2-chloro-4-(2,3-difluorophenoxy)phenyl]pyrazole-4-carbonyl]-5-fluoro-1H-indol-6-yl]methanesulfonamide, (5-1-017) N-[2-[5-amino-1-[4-(2-fluorophenoxy)-3-methylphenyl]pyrazole-4-carbonyl]-5-fluoro-1H-indol-6-yl]methanesulfonamide, (5-1-018) N-[2-[5-amino-1-[2-chloro-4-(2-fluorophenoxy)phenyl]pyrazole-4-carbonyl]-5-fluoro-1H-indol-6-yl]methanesulfonamide, (5-1-019) N-[2-[5-amino-1-[2,6-difluoro-4-(2-fluorophenoxy)phenyl]pyrazole-4-carbonyl]-5-fluoro-1H-indol-6-yl]cyclopropanesulfonamide, (5-1-020) [5-amino-1-[6-(2-fluorophenoxy)-4-methylpyridin-3-yl]pyrazol-4-yl]-[6-(cyclopropylsulfamoylamino)-5-fluoro-1H-indol-2-yl]methanone, (5-1-021) [5-amino-1-[6-(2-fluorophenoxy)-4-methylpyridin-3-yl]pyrazol-4-yl]-[5-fluoro-6-(propan-2-ylsulfamoylamino)-1H-indol-2-yl]methanone, (5-1-022) N-[2-[5-amino-1-[2,6-difluoro-4-(2-fluorophenoxy)phenyl]pyrazole-4-carbonyl]-5-fluoro-1H-indol-6-yl]methanesulfonamide, (5-1-023) N-[2-[5-amino-1-[2,6-dichloro-4-(2-fluorophenoxy)phenyl]pyrazole-4-carbonyl]-5-fluoro-1H-indol-6-yl]methanesulfonamide, (5-1-024) N-[2-[5-amino-1-[2,6-dichloro-4-(2,3-difluorophenoxy)phenyl]pyrazole-4-carbonyl]-5-fluoro-1H-indol-6-yl]methanesulfonamide, (5-1-025) N-[2-[5-amino-1-[2,6-dichloro-4-(2-fluorophenoxy)phenyl]pyrazole-4-carbonyl]-5-fluoro-1H-indol-6-yl]cyclopropanesulfonamide, (5-1-026) N-[2-[5-amino-1-[2,6-dichloro-4-(2,3-difluorophenoxy)phenyl]pyrazole-4-carbonyl]-5-fluoro-1H-indol-6-yl]cyclopropanesulfonamide, (5-1-027) N-[2-[5-amino-1-[2,6-difluoro-4-(2-fluorophenoxy)phenyl]pyrazole-4-carbonyl]-5-fluoro-1H-indol-6-yl]-3-fluoropropane-1-sulfonamide, (5-1-028) N-[2-[5-amino-1-[2,6-dichloro-4-(2,3-difluorophenoxy)phenyl]pyrazole-4-carbonyl]-5-fluoro-1H-indol-6-yl]-3-fluoropropane-1-sulfonamide, (5-1-029) N-[2-[5-amino-1-[4-(2-fluorophenoxy)-2-methylphenyl]pyrazole-4-carbonyl]-5-fluoro-1H-indol-6-yl]-2,2,2-trifluoroacetamide, (5-1-030) N-[2-[5-amino-1-[4-(2,3-difluorophenoxy)-2,6-difluorophenyl]pyrazole-4-carbonyl]-5-fluoro-1H-indol-6-yl]methanesulfonamide, (5-1-031) N-[2-[5-amino-1-[4-(2,3-difluorophenoxy)-2,6-difluorophenyl]pyrazole-4-carbonyl]-5-fluoro-1H-indol-6-yl]cyclopropanesulfonamide, (5-1-032) N-[2-[5-amino-1-[4-(2-fluorophenoxy)-2,6-dimethylphenyl]pyrazole-4-carbonyl]-5-fluoro-1H-indol-6-yl]methanesulfonamide, (5-1-033) N-[2-[5-amino-1-[2,6-dichloro-4-(2-fluorophenoxy)phenyl]pyrazole-4-carbonyl]-5-fluoro-1H-indol-6-yl]-3-fluoropropane-1-sulfonamide, (5-1-034) N-[2-[5-amino-1-[4-(2,3-difluorophenoxy)-2,6-difluorophenyl]pyrazole-4-carbonyl]-5-fluoro-1H-indol-6-yl]-3-fluoropropane-1-sulfonamide, (5-1-035) N-[2-[5-amino-1-[2-fluoro-4-(3-fluoropyridin-2-yl)oxyphenyl]pyrazole-4-carbonyl]-5-fluoro-1H-indol-6-yl]-3-fluoropropane-1-sulfonamide, (5-1-036) N-[2-[5-amino-1-[4-(3-chloropyridin-2-yl)oxy-2-fluorophenyl]pyrazole-4-carbonyl]-5-fluoro-1H-indol-6-yl]-3-fluoropropane-1-sulfonamide, (5-1-037) N-[2-[5-amino-1-[2-chloro-4-(3-chloropyridin-2-yl)oxyphenyl]pyrazole-4-carbonyl]-5-fluoro-1H-indol-6-yl]-3-fluoropropane-1-sulfonamide, (5-1-038) N-[2-[5-amino-1-[6-(3,5-difluorophenoxy)-4-methylpyridin-3-yl]pyrazole-4-carbonyl]-5-fluoro-1H-indol-6-yl]methanesulfonamide, (5-1-039) N-[2-[5-amino-1-[6-(2-fluorophenoxy)-5-methylpyridin-3-yl]pyrazole-4-carbonyl]-5-fluoro-1H-indol-6-yl]methanesulfonamide, (5-1-040) N-[2-[5-amino-1-[4-(2-fluorophenoxy)-2,6-dimethylphenyl]pyrazole-4-carbonyl]-5-fluoro-1H-indol-6-yl]-3-fluoropropane-1-sulfonamide, (5-1-041) N-[2-[5-amino-1-[6-(2-chlorophenoxy)-5-methylpyridin-3-yl]pyrazole-4-carbonyl]-5-fluoro-1H-indol-6-yl]methanesulfonamide, (5-1-042) N-[2-[5-amino-1-[6-(3-chlorophenoxy)-5-methylpyridin-3-yl]pyrazole-4-carbonyl]-5-fluoro-1H-indol-6-yl]methanesulfonamide, (5-1-043) N-[2-[5-amino-1-[6-(2-chloro-6-fluorophenoxy)-5-methylpyridin-3-yl]pyrazole-4-carbonyl]-5-fluoro-1H-indol-6-yl]methanesulfonamide, (5-1-044) N-[2-[5-amino-1-[6-(2,3-difluorophenoxy)-5-methylpyridin-3-yl]pyrazole-4-carbonyl]-5-fluoro-1H-indol-6-yl]methanesulfonamide, (5-1-045) N-[2-[5-amino-1-[6-(3,5-difluorophenoxy)-5-methylpyridin-3-yl]pyrazole-4-carbonyl]-5-fluoro-1H-indol-6-yl]methanesulfonamide, (5-1-046) N-[2-[5-amino-1-[6-(4-fluorophenoxy)-4-methylpyridin-3-yl]pyrazole-4-carbonyl]-5-fluoro-1H-indol-6-yl]cyclopropanesulfonamide, (5-1-047) N-[2-[5-amino-1-[4-methyl-6-(2-methylphenoxy)pyridin-3-yl]pyrazole-4-carbonyl]-6-fluoro-1H-indol-5-yl]methanesulfonamide, (5-1-048) N-[2-[5-amino-1-[4-(3-chlorophenoxy)-2-fluoro-6-methylphenyl]pyrazole-4-carbonyl]-6-fluoro-1H-indol-5-yl]methanesulfonamide, (5-1-049) N-[2-[5-amino-1-[6-(2,3-difluorophenoxy)-4-methylpyridin-3-yl]pyrazole-4-carbonyl]-6-fluoro-1H-indol-5-yl]methanesulfonamide, (5-1-050) N-[2-[5-amino-1-[6-(2-chlorophenoxy)-4-methylpyridin-3-yl]pyrazole-4-carbonyl]-6-fluoro-1H-indol-5-yl]methanesulfonamide, (5-1-051) N-[2-[5-amino-1-[6-(2-chlorophenoxy)-2,4-dimethylpyridin-3-yl]pyrazole-4-carbonyl]-5-fluoro-1H-indol-6-yl]methanesulfonamide, (5-1-052) N-[2-[5-amino-1-[6-(3-chlorophenoxy)-2,4-dimethylpyridin-3-yl]pyrazole-4-carbonyl]-5-fluoro-1H-indol-6-yl]methanesulfonamide, (5-1-053) N-[2-[5-amino-1-[6-(2,3-difluorophenoxy)-2,4-dimethylpyridin-3-yl]pyrazole-4-carbonyl]-5-fluoro-1H-indol-6-yl]methanesulfonamide, (5-1-054) N-[2-[5-amino-1-[6-(3,5-difluorophenoxy)-2,4-dimethylpyridin-3-yl]pyrazole-4-carbonyl]-5-fluoro-1H-indol-6-yl]methanesulfonamide, (5-1-055) N-[2-[5-amino-1-[6-(2,5-dichlorophenoxy)-4-methylpyridin-3-yl]pyrazole-4-carbonyl]-5-fluoro-1H-indol-6-yl]methanesulfonamide, (5-1-056) 2-[[2-[5-amino-1-[6-(2-fluorophenoxy)-4-methylpyridin-3-yl]pyrazole-4-carbonyl]-5-fluoro-1H-indol-6-yl]sulfamoyl]-N-propan-2-ylacetamide, (5-1-057) [5-amino-1-[6-(2-fluorophenoxy)-4-methylpyridin-3-yl]pyrazol-4-yl]-[5-methyl-6-(oxan-4-ylsulfamoylamino)-1H-indol-2-yl]methanone, (5-1-058) 2-[[2-[5-amino-1-[6-(2-fluorophenoxy)-4-methylpyridin-3-yl]pyrazole-4-carbonyl]-5-methyl-1H-indol-6-yl]sulfamoyl]-N-propan-2-ylacetamide, (5-1-059) N-[2-[5-amino-1-[6-(3-fluorophenoxy)-4-methylpyridin-3-yl]pyrazole-4-carbonyl]-5-fluoro-1H-indol-6-yl]-3-fluoropropane-1-sulfonamide, (5-1-060) N-[2-[5-amino-1-[6-(2-fluorophenoxy)-2,4-dimethylpyridin-3-yl]pyrazole-4-carbonyl]-5-fluoro-1H-indol-6-yl]methanesulfonamide, (5-1-061) N-[2-[5-amino-1-[4-(2-fluorophenoxy)-2-methylphenyl]pyrazole-4-carbonyl]-5-hydroxy-1H-indol-6-yl]methanesulfonamide, (5-1-062) [5-amino-1-[2-chloro-4-(3-chloropyridin-2-yl)oxyphenyl]pyrazol-4-yl]-[6-(1,1-dioxo-1,2-thiazolidin-2-yl)-5-methyl-1H-indol-2-yl]methanone, (5-1-063) N-[2-[5-amino-1-[2-chloro-4-(3-chloropyridin-2-yl)oxyphenyl]pyrazole-4-carbonyl]-5-methyl-1H-indol-6-yl]-3-fluoropropane-1-sulfonamide, (5-1-064) N-[2-[5-amino-1-[6-(4-fluorophenoxy)-4-methylpyridin-3-yl]pyrazole-4-carbonyl]-5-methyl-1H-indol-6-yl]morpholine-4-sulfonamide, (5-1-065) N-[2-[5-amino-1-[2-chloro-4-(3-chloropyridin-2-yl)oxyphenyl]pyrazole-4-carbonyl]-5-methyl-1H-indol-6-yl]morpholine-4-sulfonamide, (5-1-066) N-[2-[5-amino-1-[4-(2,3-difluorophenoxy)-2-fluoro-6-methylphenyl]pyrazole-4-carbonyl]-5-methyl-1H-indol-6-yl]morpholine-4-sulfonamide, (5-1-067) N-[2-[5-amino-1-[6-(2,6-difluorophenoxy)-4-methylpyridin-3-yl]pyrazole-4-carbonyl]-5-fluoro-1H-indol-6-yl]-N-propan-2-ylmethanesulfonamide, (5-1-068) tert-Butyl 4-[2-[5-amino-1-[4-(2-fluorophenoxy)-2-methylphenyl]pyrazole-4-carbonyl]-5-(2,2-difluoroethoxy)-1H-indol-6-yl]piperidine-1-carboxylate, (5-1-069) tert-Butyl 4-[2-[5-amino-1-[6-(2,6-difluorophenoxy)-4-methylpyridin-3-yl]pyrazole-4-carbonyl]-5-(2,2-difluoroethoxy)-1H-indol-6-yl]piperidine-1-carboxylate, (5-1-070) [5-amino-1-[4-(2-fluorophenoxy)-2-methylphenyl]pyrazol-4-yl]-[6-bromo-5-(2,2-difluoroethoxy)-1H-indol-2-yl]methanone, (5-1-071) [5-amino-1-[4-(2-fluorophenoxy)-2-methylphenyl]pyrazol-4-yl]-[6-(1-cyclopropylsulfonylpiperidin-4-yl)-5-ethoxy-1H-indol-2-yl]methanone, (5-1-072) 1-[2-[5-amino-1-[6-(2,6-difluorophenoxy)-4-methylpyridin-3-yl]pyrazole-4-carbonyl]-5-(difluoromethoxy)-1H-indol-6-yl]-6-methylpyrimidine-2,4-dione, (5-1-073) [5-amino-1-[4-(2-fluorophenoxy)-2-methylphenyl]pyrazol-4-yl]-[5-ethoxy-6-(1-methylsulfonylpiperidin-4-yl)-1H-indol-2-yl]methanone, (5-1-074) [6-amino-5-(difluoromethoxy)-1H-indol-2-yl]-[5-amino-1-[6-(2,6-difluorophenoxy)-4-methylpyridin-3-yl]pyrazol-4-yl]methanone, (5-1-075) [5-amino-1-[6-(2,6-difluorophenoxy)-4-methylpyridin-3-yl]pyrazol-4-yl]-[5-(difluoromethoxy)-6-(4-methylsulfonylpiperazin-1-yl)-1H-indol-2-yl]methanone, (5-1-076) N-[2-[5-amino-1-[2-fluoro-4-(2-fluorophenoxy)-6-methylphenyl]pyrazole-4-carbonyl]-5-(difluoromethoxy)-1H-indol-6-yl]methanesulfonamide, (5-1-077) [5-amino-1-[4-(2-fluorophenoxy)-2-methylphenyl]pyrazol-4-yl]-[5-methyl-6-(4-morpholin-4-ylpiperidin-1-yl)-1H-indol-2-yl]methanone, (5-1-078) [5-amino-1-[6-(2-fluorophenoxy)-4-methylpyridin-3-yl]pyrazol-4-yl]-[5-methyl-6-(4-morpholin-4-ylpiperidin-1-yl)-1H-indol-2-yl]methanone, (5-1-079) [5-amino-1-[6-(2,6-difluorophenoxy)-4-methylpyridin-3-yl]pyrazol-4-yl]-[5-(difluoromethoxy)-6-[(1-methylsulfonylazetidin-3-yl)amino]-1H-indol-2-yl]methanone, (5-1-080) [5-amino-1-[6-(2,6-difluorophenoxy)-4-methylpyridin-3-yl]pyrazol-4-yl]-[6-bromo-5-(2,2-difluoroethoxy)-1H-indol-2-yl]methanone, (5-1-081) N-[2-[5-amino-1-[6-(2,5-difluorophenoxy)-4-methylpyridin-3-yl]pyrazole-4-carbonyl]-5-methyl-1H-indol-6-yl]methanesulfonamide, (5-1-082) [5-amino-1-[4-(2-fluorophenoxy)-2-methylphenyl]pyrazol-4-yl]-[6-bromo-5-(difluoromethoxy)-1H-indol-2-yl]methanone, (5-1-083) [6-amino-5-(difluoromethoxy)-1H-indol-2-yl]-[5-amino-1-[4-(2-fluorophenoxy)-2-methylphenyl]pyrazol-4-yl]methanone, (5-1-084) [5-amino-1-[2-fluoro-4-(2-fluorophenoxy)-6-methylphenyl]pyrazol-4-yl]-(5-methyl-6-morpholin-4-yl-1H-indol-2-yl)methanone, (5-1-085) [5-amino-1-[2-fluoro-4-(2-fluorophenoxy)-6-methylphenyl]pyrazol-4-yl]-[5-methyl-6-(4-morpholin-4-ylpiperidin-1-yl)-1H-indol-2-yl]methanone, (5-1-086) [5-amino-1-[4-(2-fluorophenoxy)-2-methylphenyl]pyrazol-4-yl]-[5-methyl-6-(1-methylsulfonylpiperidin-4-yl)-1H-indol-2-yl]methanone, (5-1-087) [5-amino-1-[4-(2-fluorophenoxy)-2-methylphenyl]pyrazol-4-yl]-[5-(2,2-difluoroethoxy)-6-(4-hydroxypiperidin-1-yl)-1H-indol-2-yl]methanone, (5-1-088) N-[2-[5-amino-1-[6-(2,6-difluorophenoxy)-4-methylpyridin-3-yl]pyrazole-4-carbonyl]-5-methyl-1H-indol-6-yl]-2-oxo-2-pyrrolidin-1-ylethanesulfonamide, (5-1-089) 2-[[2-[5-amino-1-[2-fluoro-4-(2-fluorophenoxy)-6-methylphenyl]pyrazole-4-carbonyl]-5-methyl-1H-indol-6-yl]sulfamoyl]-N-propan-2-ylacetamide, (5-1-090) [5-amino-1-[6-(2-fluorophenoxy)-4-methylpyridin-3-yl]pyrazol-4-yl]-[5-methyl-6-(1-methylsulfonylpiperidin-4-yl)-1H-indol-2-yl]methanone, (5-1-091) [5-amino-1-[6-(2,6-difluorophenoxy)-4-methylpyridin-3-yl]pyrazol-4-yl]-[5-methyl-6-(1-methylsulfonylpiperidin-4-yl)-1H-indol-2-yl]methanone, (5-1-092) N-[2-[5-amino-1-[4-(2,6-difluorophenoxy)-2-methylphenyl]pyrazole-4-carbonyl]-5-methyl-1H-indol-6-yl]methanesulfonamide, (5-1-093) [5-amino-1-[4-(2-fluorophenoxy)-2-methylphenyl]pyrazol-4-yl]-[6-(4-methylsulfonylpiperazin-1-yl)-5-morpholin-4-yl-1H-indol-2-yl]methanone, (5-1-094) [5-amino-1-[4-(2-fluorophenoxy)-2-methylphenyl]pyrazol-4-yl]-(5,6-dimorpholin-4-yl-1H-indol-2-yl)methanone, (5-1-095) 3-[2-[5-amino-1-[4-(2-fluorophenoxy)-2-methylphenyl]pyrazole-4-carbonyl]-5-fluoro-1H-indol-6-yl]-1,3-oxazolidin-2-one, (5-1-096) N-[2-[5-amino-1-[4-(2-chloro-6-fluorophenoxy)-2-methylphenyl]pyrazole-4-carbonyl]-5-methyl-1H-indol-6-yl]methanesulfonamide, (5-1-097) 3-[2-[5-amino-1-[6-(2,6-difluorophenoxy)-4-methylpyridin-3-yl]pyrazole-4-carbonyl]-5-fluoro-1H-indol-6-yl]-1,3-oxazolidin-2-one, (5-1-098) 1-[2-[5-amino-1-[6-(2,6-difluorophenoxy)-4-methylpyridin-3-yl]pyrazole-4-carbonyl]-5-fluoro-1H-indol-6-yl]pyrrolidin-2-one, (5-1-099) [5-amino-1-[6-(2,6-difluorophenoxy)-4-methylpyridin-3-yl]pyrazol-4-yl]-[5-fluoro-6-(4-methylsulfonylpiperazin-1-yl)-1H-indol-2-yl]methanone, (5-1-100) [5-amino-1-[6-(2,6-difluorophenoxy)-4-methylpyridin-3-yl]pyrazol-4-yl]-(5-fluoro-6-morpholin-4-yl-1H-indol-2-yl)methanone, (5-1-101) 1-[2-[5-amino-1-[6-(2,6-difluorophenoxy)-4-methylpyridin-3-yl]pyrazole-4-carbonyl]-5-fluoro-1H-indol-6-yl]-6-methylpyrimidine-2,4-dione, (5-1-102) [5-amino-1-[6-(2,6-difluorophenoxy)-4-methylpyridin-3-yl]pyrazol-4-yl]-[5-fluoro-6-[(1-methylsulfonylazetidin-3-yl)amino]-1H-indol-2-yl]methanone, (5-1-103) 1-[2-[5-amino-1-[4-(2-fluorophenoxy)-2-methylphenyl]pyrazole-4-carbonyl]-5-fluoro-1H-indol-6-yl]pyrrolidin-2-one, (5-1-104) 1-[2-[5-amino-1-[4-(2-fluorophenoxy)-2-methylphenyl]pyrazole-4-carbonyl]-5-fluoro-1H-indol-6-yl]-6-methylpyrimidine-2,4-dione, (5-1-105) 1-[2-[5-amino-1-[4-(2-fluorophenoxy)-2-methylphenyl]pyrazole-4-carbonyl]-5-morpholin-4-yl-1H-indol-6-yl]pyrrolidin-2-one, (5-1-106) 3-[2-[5-amino-1-[4-(2-fluorophenoxy)-2-methylphenyl]pyrazole-4-carbonyl]-5-morpholin-4-yl-1H-indol-6-yl]-1,3-oxazolidin-2-one, (5-1-107) N-[2-[5-amino-1-[4-(2,5-difluorophenoxy)-2-methylphenyl]pyrazole-4-carbonyl]-5-methyl-1H-indol-6-yl]methanesulfonamide, (5-1-108) N-[2-[5-amino-1-(2-methyl-4-phenoxyphenyl)pyrazole-4-carbonyl]-5-methyl-1H-indol-6-yl]methanesulfonamide, (5-1-109) N-[2-[5-amino-1-(4-methyl-6-phenoxypyridin-3-yl)pyrazole-4-carbonyl]-5-methyl-1H-indol-6-yl]methanesulfonamide, (5-1-110) N-[2-[5-amino-1-[2-fluoro-4-(2-fluorophenoxy)-6-methylphenyl]pyrazole-4-carbonyl]-5-methyl-1H-indol-6-yl]-2-oxo-2-pyrrolidin-1-ylethanesulfonamide, (5-1-111) [5-amino-1-[2-fluoro-4-(2-fluorophenoxy)-6-methylphenyl]pyrazol-4-yl]-[5-methyl-6-(1-methylsulfonylpiperidin-4-yl)-1H-indol-2-yl]methanone, (5-1-112) [5-amino-1-[6-(2,6-difluorophenoxy)-4-methylpyridin-3-yl]pyrazol-4-yl]-[5-fluoro-6-(4-morpholin-4-ylpiperidin-1-yl)-1H-indol-2-yl]methanone, (5-1-113) [5-amino-1-[6-(2,6-difluorophenoxy)-4-methylpyridin-3-yl]pyrazol-4-yl]-[5-fluoro-6-[(1-methylsulfonylpiperidin-4-yl)amino]-1H-indol-2-yl]methanone, (5-1-114) 3-[2-[5-amino-1-[6-(2,6-difluorophenoxy)-4-methylpyridin-3-yl]pyrazole-4-carbonyl]-5-fluoro-1H-indol-6-yl]-5,5-dimethylimidazolidine-2,4-dione, (5-1-115) 3-[2-[5-amino-1-[6-(2,6-difluorophenoxy)-4-methylpyridin-3-yl]pyrazole-4-carbonyl]-5-fluoro-1H-indol-6-yl]-5,5-dimethyl-2-sulfanylideneimidazolidin-4-one, (5-1-116) 1-[2-[5-amino-1-[4-(2-fluorophenoxy)-2-methylphenyl]pyrazole-4-carbonyl]-5-morpholin-4-yl-1H-indol-6-yl]-6-methylpyrimidine-2,4-dione, (5-1-117) 3-[2-[5-amino-1-[4-(2-fluorophenoxy)-2-methylphenyl]pyrazole-4-carbonyl]-5-morpholin-4-yl-1H-indol-6-yl]-5,5-dimethylimidazolidine-2,4-dione, (5-1-118) [5-amino-1-[4-(2-fluorophenoxy)-2-methylphenyl]pyrazol-4-yl]-[5-fluoro-6-[(1-methylsulfonylazetidin-3-yl)amino]-1H-indol-2-yl]methanone, (5-1-119) [5-amino-1-[4-(2-fluorophenoxy)-2-methylphenyl]pyrazol-4-yl]-(5-fluoro-6-morpholin-4-yl-1H-indol-2-yl)methanone, (5-1-120) 3-[2-[5-amino-1-[4-(2-fluorophenoxy)-2-methylphenyl]pyrazole-4-carbonyl]-5-morpholin-4-yl-1H-indol-6-yl]-5,5-dimethyl-2-sulfanylideneimidazolidin-4-one, (5-1-121) N-[2-[5-amino-1-[6-(2-fluorophenoxy)-4-methylpyridin-3-yl]pyrazole-4-carbonyl]-5-methyl-1H-indol-6-yl]-2-oxo-2-pyrrolidin-1-ylethanesulfonamide, (5-1-122) N-[2-[5-amino-1-[4-(2-fluorophenoxy)-2-methylphenyl]pyrazole-4-carbonyl]-5-methoxy-1H-indol-6-yl]-2-oxo-2-pyrrolidin-1-ylethanesulfonamide, (5-1-123) [5-amino-1-[6-(2-fluorophenoxy)-4-methylpyridin-3-yl]pyrazol-4-yl]-[6-(1-cyclopropylsulfonylpiperidin-4-yl)-5-methyl-1H-indol-2-yl]methanone, (5-1-124) [5-amino-1-[4-(2-fluorophenoxy)-2-methylphenyl]pyrazol-4-yl]-[5-morpholin-4-yl-6-(4-morpholin-4-ylpiperidin-1-yl)-1H-indol-2-yl]methanone, (5-1-125) [5-amino-1-[4-(2-fluorophenoxy)-2-methylphenyl]pyrazol-4-yl]-[5-fluoro-6-(4-methylsulfonylpiperazin-1-yl)-1H-indol-2-yl]methanone, (5-1-126) 3-[2-[5-amino-1-[4-(2-fluorophenoxy)-2-methylphenyl]pyrazole-4-carbonyl]-5-fluoro-1H-indol-6-yl]-5,5-dimethyl-2-sulfanylideneimidazolidin-4-one, (5-1-127) 3-[2-[5-amino-1-[4-(2-fluorophenoxy)-2-methylphenyl]pyrazole-4-carbonyl]-5-fluoro-1H-indol-6-yl]-5,5-dimethylimidazolidine-2,4-dione, (5-1-128) [5-amino-1-[4-(2-fluorophenoxy)-2-methylphenyl]pyrazol-4-yl]-[5-fluoro-6-(4-morpholin-4-ylpiperidin-1-yl)-1H-indol-2-yl]methanone, (5-1-129) [5-amino-1-[4-(2-fluorophenoxy)-2-methylphenyl]pyrazol-4-yl]-[6-[(1-methylsulfonylpiperidin-4-yl)amino]-5-morpholin-4-yl-1H-indol-2-yl]methanone, (5-1-130) N-[2-[5-amino-1-[2-fluoro-4-(2-fluorophenoxy)-6-methylphenyl]pyrazole-4-carbonyl]-5-methoxy-1H-indol-6-yl]-2-oxo-2-pyrrolidin-1-ylethanesulfonamide, (5-1-131) [5-amino-1-[4-(2-fluorophenoxy)-2-methylphenyl]pyrazol-4-yl]-[6-(1-cyclopropylsulfonylpiperidin-4-yl)-5-methyl-1H-indol-2-yl]methanone, (5-1-132) 1-[4-[2-[5-amino-1-[4-(2-fluorophenoxy)-2-methylphenyl]pyrazole-4-carbonyl]-5-methyl-1H-indol-6-yl]piperidin-1-yl]ethanone, (5-1-133) 1-[4-[2-[5-amino-1-[6-(2-fluorophenoxy)-4-methylpyridin-3-yl]pyrazole-4-carbonyl]-5-methyl-1H-indol-6-yl]piperidin-1-yl]ethanone, (5-1-134) [5-amino-1-[6-(2,6-difluorophenoxy)-4-methylpyridin-3-yl]pyrazol-4-yl]-[6-bromo-5-(1-propan-2-ylpiperidin-4-yl)oxy-1H-indol-2-yl]methanone, (5-1-135) [5-amino-1-[4-(2-fluorophenoxy)-2-methylphenyl]pyrazol-4-yl]-[5-fluoro-6-[(1-methylsulfonylpiperidin-4-yl)amino]-1H-indol-2-yl]methanone, (5-1-136) 2-[[2-[5-amino-1-[6-(2,6-difluorophenoxy)-4-methylpyridin-3-yl]pyrazole-4-carbonyl]-5-methyl-1H-indol-6-yl]sulfamoyl]-N-propan-2-ylacetamide, (5-1-137) 2-[[2-[5-amino-1-[2-fluoro-4-(2-fluorophenoxy)-6-methylphenyl]pyrazole-4-carbonyl]-5-methoxy-1H-indol-6-yl]sulfamoyl]-N-propan-2-ylacetamide, (5-1-138) 1-[4-[2-[5-amino-1-[2-fluoro-4-(2-fluorophenoxy)-6-methylphenyl]pyrazole-4-carbonyl]-5-methyl-1H-indol-6-yl]piperidin-1-yl]ethanone, (5-1-139) 1-[4-[2-[5-amino-1-[6-(2,6-difluorophenoxy)-4-methylpyridin-3-yl]pyrazole-4-carbonyl]-5-methyl-1H-indol-6-yl]piperidin-1-yl]ethanone, (5-1-140) N-[2-[5-amino-1-[4-(2,6-difluorophenoxy)-2-fluoro-6-methylphenyl]pyrazole-4-carbonyl]-5-methyl-1H-indol-6-yl]methanesulfonamide, (5-1-141) N-[2-[5-amino-1-[6-(2,6-difluorophenoxy)-4-methylpyridin-3-yl]pyrazole-4-carbonyl]-5-ethyl-1H-indol-6-yl]methanesulfonamide, (5-1-142) N-[2-[5-amino-1-[4-(2-chloro-6-fluorophenoxy)-2-fluoro-6-methylphenyl]pyrazole-4-carbonyl]-5-methyl-1H-indol-6-yl]methanesulfonamide, (5-1-143) N-[2-[5-amino-1-[6-(2,6-difluorophenoxy)-4-methylpyridin-3-yl]pyrazole-4-carbonyl]-5-methoxy-1H-indol-6-yl]-2-morpholin-4-yl-2-oxoethanesulfonamide, (5-1-144) [5-amino-1-[6-(2,6-difluorophenoxy)-4-methylpyridin-3-yl]pyrazol-4-yl]-[6-(1-cyclopropylsulfonylpiperidin-4-yl)-5-methyl-1H-indol-2-yl]methanone, (5-1-145) [5-amino-1-[6-(2-fluorophenoxy)-4-methylpyridin-3-yl]pyrazol-4-yl]-(6-bromo-5-methoxy-1H-indol-2-yl)methanone, (5-1-146) [5-amino-1-[4-(2-fluorophenoxy)-2-methylphenyl]pyrazol-4-yl]-[6-bromo-5-(1-propan-2-ylpiperidin-4-yl)oxy-1H-indol-2-yl]methanone, (5-1-147) [5-amino-1-[4-(2-fluorophenoxy)-2-methylphenyl]pyrazol-4-yl]-(6-bromo-5-morpholin-4-yl-1H-indol-2-yl)methanone, (5-1-148) [5-amino-1-[4-(2-fluorophenoxy)-3-methylphenyl]pyrazol-4-yl]-[6-bromo-5-(1-propan-2-ylpiperidin-4-yl)oxy-1H-indol-2-yl]methanone, (5-1-149) [5-amino-1-[6-(2,6-difluorophenoxy)-4-methylpyridin-3-yl]pyrazol-4-yl]-[6-bromo-5-(difluoromethoxy)-1H-indol-2-yl]methanone, (5-1-150) [5-amino-1-[4-(2-fluorophenoxy)-3-methylphenyl]pyrazol-4-yl]-[6-bromo-5-(2,2-difluoroethoxy)-1H-indol-2-yl]methanone,
(5-1-151) [5-amino-1-[4-(2-fluorophenoxy)-3-methylphenyl]pyrazol-4-yl]-(6-bromo-5-morpholin-4-yl-1H-indol-2-yl)methanone,
(5-1-152) [5-amino-1-[4-(2-fluorophenoxy)-3-methylphenyl]pyrazol-4-yl]-[6-bromo-5-(difluoromethoxy)-1H-indol-2-yl]methanone,
(5-1-153) [5-amino-1-[6-(2-fluorophenoxy)-4-methylpyridin-3-yl]pyrazol-4-yl]-[6-bromo-5-(1-propan-2-ylpiperidin-4-yl)oxy-1H-indol-2-yl]methanone,
(5-1-154) [5-amino-1-[2-fluoro-4-(2-fluorophenoxy)-6-methylphenyl]pyrazol-4-yl]-[6-bromo-5-(1-propan-2-ylpiperidin-4-yl)oxy-1H-indol-2-yl]methanone,
(5-1-155) [5-amino-1-[6-(2,6-difluorophenoxy)-4-methylpyridin-3-yl]pyrazol-4-yl]-(6-bromo-5-morpholin-4-yl-1H-indol-2-yl)methanone,
(5-1-156) N-[2-[5-amino-1-[4-(2-fluorophenoxy)-3-methylphenyl]pyrazole-4-carbonyl]-5-(1-propan-2-ylpiperidin-4-yl)oxy-1H-indol-6-yl]methanesulfonamide,
(5-1-157) N-[2-[5-amino-1-[4-(2-fluorophenoxy)-3-methylphenyl]pyrazole-4-carbonyl]-5-morpholin-4-yl-1H-indol-6-yl]methanesulfonamide,
(5-1-158) [5-amino-1-[4-(2-fluorophenoxy)-3-methylphenyl]pyrazol-4-yl]-[6-(4-methylsulfonylpiperazin-1-yl)-5-morpholin-4-yl-1H-indol-2-yl]methanone,
(5-1-159) [5-amino-1-[4-(2-fluorophenoxy)-3-methylphenyl]pyrazol-4-yl]-(5,6-dimorpholin-4-yl-1H-indol-2-yl)methanone,
(5-1-160) 3-[2-[5-amino-1-[4-(2-fluorophenoxy)-3-methylphenyl]pyrazole-4-carbonyl]-5-morpholin-4-yl-1H-indol-6-yl]-1,3-oxazolidin-2-one,
(5-1-161) [6-amino-5-(difluoromethoxy)-1H-indol-2-yl]-[5-amino-1-[4-(2-fluorophenoxy)-3-methylphenyl]pyrazol-4-yl]methanone,
(5-1-162) [6-amino-5-(2,2-difluoroethoxy)-1H-indol-2-yl]-[5-amino-1-[4-(2-fluorophenoxy)-3-methylphenyl]pyrazol-4-yl]methanone,
(5-1-163) [5-amino-1-[4-(2-fluorophenoxy)-3-methylphenyl]pyrazol-4-yl]-[6-amino-5-(1-propan-2-ylpiperidin-4-yl)oxy-1H-indol-2-yl]methanone,
(5-1-164) 3-[2-[5-amino-1-[4-(2-fluorophenoxy)-3-methylphenyl]pyrazole-4-carbonyl]-5-morpholin-4-yl-1H-indol-6-yl]-5,5-dimethylimidazolidine-2,4-dione,
(5-1-165) [5-amino-1-[4-(2-fluorophenoxy)-3-methylphenyl]pyrazol-4-yl]-[5-morpholin-4-yl-6-(4-morpholin-4-ylpiperidin-1-yl)-1H-indol-2-yl]methanone,
(5-1-166) N-[2-[5-amino-1-[4-(2-fluorophenoxy)-3-methylphenyl]pyrazole-4-carbonyl]-5-(2,2-difluoroethoxy)-1H-indol-6-yl]methanesulfonamide,
(5-1-167) N-[2-[5-amino-1-[4-(2-fluorophenoxy)-3-methylphenyl]pyrazole-4-carbonyl]-5-(difluoromethoxy)-1H-indol-6-yl]methanesulfonamide,
(5-1-168) 3-[2-[5-amino-1-[4-(2-fluorophenoxy)-3-methylphenyl]pyrazole-4-carbonyl]-5-(2,2-difluoroethoxy)-1H-indol-6-yl]-1,3-oxazolidin-2-one,
(5-1-169) [5-amino-1-[4-(2-fluorophenoxy)-3-methylphenyl]pyrazol-4-yl]-[5-(2,2-difluoroethoxy)-6-morpholin-4-yl-1H-indol-2-yl]methanone,
(5-1-170) 3-[2-[5-amino-1-[4-(2-fluorophenoxy)-3-methylphenyl]pyrazole-4-carbonyl]-5-(2,2-difluoroethoxy)-1H-indol-6-yl]-5,5-dimethylimidazolidine-2,4-dione,
(5-1-171) [5-amino-1-[4-(2-fluorophenoxy)-3-methylphenyl]pyrazol-4-yl]-[5-(2,2-difluoroethoxy)-6-(4-methylsulfonylpiperazin-1-yl)-1H-indol-2-yl]methanone,
(5-1-172) [5-amino-1-[4-(2-fluorophenoxy)-3-methylphenyl]pyrazol-4-yl]-[5-(2,2-difluoroethoxy)-6-(4-morpholin-4-ylpiperidin-1-yl)-1H-indol-2-yl]methanone,
(5-1-173) [5-amino-1-[4-(2-fluorophenoxy)-3-methylphenyl]pyrazol-4-yl]-[5-(difluoromethoxy)-6-morpholin-4-yl-1H-indol-2-yl]methanone,
(5-1-174) [5-amino-1-[4-(2-fluorophenoxy)-3-methylphenyl]pyrazol-4-yl]-[6-morpholin-4-yl-5-(1-propan-2-ylpiperidin-4-yl)oxy-1H-indol-2-yl]methanone,
(5-1-175) [5-amino-1-[4-(2-fluorophenoxy)-3-methylphenyl]pyrazol-4-yl]-[5-(difluoromethoxy)-6-(4-methylsulfonylpiperazin-1-yl)-1H-indol-2-yl]methanone,
(5-1-176) [5-amino-1-[4-(2-fluorophenoxy)-3-methylphenyl]pyrazol-4-yl]-[6-(4-methylsulfonylpiperazin-1-yl)-5-(1-propan-2-ylpiperidin-4-yl)oxy-1H-indol-2-yl]methanone,
(5-1-177) 3-[2-[5-amino-1-[4-(2-fluorophenoxy)-3-methylphenyl]pyrazole-4-carbonyl]-5-(difluoromethoxy)-1H-indol-6-yl]-1,3-oxazolidin-2-one,
(5-1-178) 3-[2-[5-amino-1-[4-(2-fluorophenoxy)-3-methylphenyl]pyrazole-4-carbonyl]-5-(1-propan-2-ylpiperidin-4-yl)oxy-1H-indol-6-yl]-1,3-oxazolidin-2-one,
(5-1-179) 3-[2-[5-amino-1-[4-(2-fluorophenoxy)-3-methylphenyl]pyrazole-4-carbonyl]-5-(difluoromethoxy)-1H-indol-6-yl]-5,5-dimethylimidazolidine-2,4-dione,
(5-1-180) 3-[2-[5-amino-1-[4-(2-fluorophenoxy)-3-methylphenyl]pyrazole-4-carbonyl]-5-(1-propan-2-ylpiperidin-4-yl)oxy-1H-indol-6-yl]-5,5-dimethylimidazolidine-2,4-dione,
(5-1-181) [5-amino-1-[4-(2-fluorophenoxy)-3-methylphenyl]pyrazol-4-yl]-[5-(difluoromethoxy)-6-(4-morpholin-4-ylpiperidin-1-yl)-1H-indol-2-yl]methanone,
(5-1-182) [5-amino-1-[4-(2-fluorophenoxy)-3-methylphenyl]pyrazol-4-yl]-[6-(4-morpholin-4-ylpiperidin-1-yl)-5-(1-propan-2-ylpiperidin-4-yl)oxy-1H-indol-2-yl]methanone,
(5-1-183) [5-amino-1-[6-(2,6-difluorophenoxy)-4-methylpyridin-3-yl]pyrazol-4-yl]-[6-amino-5-(1-propan-2-ylpiperidin-4-yl)oxy-1H-indol-2-yl]methanone,
(5-1-184) N-[2-[5-amino-1-[6-(2,6-difluorophenoxy)-4-methylpyridin-3-yl]pyrazole-4-carbonyl]-5-(1-propan-2-ylpiperidin-4-yl)oxy-1H-indol-6-yl]methanesulfonamide,
(5-1-185) [5-amino-1-[6-(2,6-difluorophenoxy)-4-methylpyridin-3-yl]pyrazol-4-yl]-[6-morpholin-4-yl-5-(1-propan-2-ylpiperidin-4-yl)oxy-1H-indol-2-yl]methanone,
(5-1-186) 3-[2-[5-amino-1-[6-(2,6-difluorophenoxy)-4-methylpyridin-3-yl]pyrazole-4-carbonyl]-5-(1-propan-2-ylpiperidin-4-yl)oxy-1H-indol-6-yl]-1,3-oxazolidin-2-one,
(5-1-187) [5-amino-1-[6-(2,6-difluorophenoxy)-4-methylpyridin-3-yl]pyrazol-4-yl]-[6-(4-methylsulfonylpiperazin-1-yl)-5-(1-propan-2-ylpiperidin-4-yl)oxy-1H-indol-2-yl]methanone,
(5-1-188) 3-[2-[5-amino-1-[6-(2,6-difluorophenoxy)-4-methylpyridin-3-yl]pyrazole-4-carbonyl]-5-(1-propan-2-ylpiperidin-4-yl)oxy-1H-indol-6-yl]-5,5-dimethylimidazolidine-2,4-dione, (5-1-189) N-[2-[5-amino-1-[4-(2-fluorophenoxy)-2-methylphenyl]pyrazole-4-carbonyl]-5-(1-propan-2-ylpiperidin-4-yl)oxy-1H-indol-6-yl]methanesulfonamide, (5-1-190) [5-amino-1-[4-(2-fluorophenoxy)-2-methylphenyl]pyrazol-4-yl]-[6-morpholin-4-yl-5-(1-propan-2-ylpiperidin-4-yl)oxy-1H-indol-2-yl]methanone, (5-1-191) [5-amino-1-[4-(2-fluorophenoxy)-2-methylphenyl]pyrazol-4-yl]-[6-(4-methylsulfonylpiperazin-1-yl)-5-(1-propan-2-ylpiperidin-4-yl)oxy-1H-indol-2-yl]methanone, (5-1-192) 3-[2-[5-amino-1-[4-(2-fluorophenoxy)-2-methylphenyl]pyrazole-4-carbonyl]-5-(1-propan-2-ylpiperidin-4-yl)oxy-1H-indol-6-yl]-1,3-oxazolidin-2-one, (5-1-193) 3-[2-[5-amino-1-[4-(2-fluorophenoxy)-2-methylphenyl]pyrazole-4-carbonyl]-5-(1-propan-2-ylpiperidin-4-yl)oxy-1H-indol-6-yl]-5,5-dimethylimidazolidine-2,4-dione, (5-1-194) [5-amino-1-[4-(2-fluorophenoxy)-2-methylphenyl]pyrazol-4-yl]-[6-(4-morpholin-4-ylpiperidin-1-yl)-5-(1-propan-2-ylpiperidin-4-yl)oxy-1H-indol-2-yl]methanone, (5-1-195) [5-amino-1-[4-(2-fluorophenoxy)-3-methylphenyl]pyrazol-4-yl]-[6-fluoro-5-(1-propan-2-ylpiperidin-4-yl)oxy-1H-indol-2-yl]methanone, (5-1-196) [5-amino-1-[4-(2-fluorophenoxy)-3-methylphenyl]pyrazol-4-yl]-[6-chloro-5-(1-propan-2-ylpiperidin-4-yl)oxy-1H-indol-2-yl]methanone, (5-1-197) [5-amino-1-[4-(2-fluorophenoxy)-2-methylphenyl]pyrazol-4-yl]-[6-chloro-5-(1-propan-2-ylpiperidin-4-yl)oxy-1H-indol-2-yl]methanone, (5-1-198) N-[2-[5-amino-1-[3-fluoro-4-(2-fluorophenoxy)phenyl]pyrazole-4-carbonyl]-5-methyl-1H-indol-6-yl]methanesulfonamide, (5-1-199) N-[2-[5-amino-1-[5-fluoro-4-(2-fluorophenoxy)-2-methylphenyl]pyrazole-4-carbonyl]-5-methyl-1H-indol-6-yl]methanesulfonamide, (5-1-200) N-[2-[5-amino-1-[4-(2-fluorophenoxy)-2,5-dimethylphenyl]pyrazole-4-carbonyl]-5-methyl-1H-indol-6-yl]methanesulfonamide, (5-1-201) [5-amino-1-[6-(2,6-difluorophenoxy)-4-methylpyridin-3-yl]pyrazol-4-yl]-[6-(4-morpholin-4-ylpiperidin-1-yl)-5-(1-propan-2-ylpiperidin-4-yl)oxy-1H-indol-2-yl]methanone, (5-1-202) [5-amino-1-[6-(2,6-difluorophenoxy)-4-methylpyridin-3-yl]pyrazol-4-yl]-[6-(4-hydroxypiperidin-1-yl)-5-(1-propan-2-ylpiperidin-4-yl)oxy-1H-indol-2-yl]methanone, (5-1-203) [5-amino-1-[4-(2-fluorophenoxy)-2-methylphenyl]pyrazol-4-yl]-[6-fluoro-5-(1-propan-2-ylpiperidin-4-yl)oxy-1H-indol-2-yl]methanone, (5-1-204) [5-amino-1-[6-(2,6-difluorophenoxy)-4-methylpyridin-3-yl]pyrazol-4-yl]-[6-fluoro-5-(1-propan-2-ylpiperidin-4-yl)oxy-1H-indol-2-yl]methanone, (5-1-205) [5-amino-1-[6-(2,6-difluorophenoxy)-4-methylpyridin-3-yl]pyrazol-4-yl]-[6-chloro-5-(1-propan-2-ylpiperidin-4-yl)oxy-1H-indol-2-yl]methanone, (5-1-206) N-[2-[5-amino-1-[2-fluoro-4-(2-fluorophenoxy)-5-methylphenyl]pyrazole-4-carbonyl]-5-methyl-1H-indol-6-yl]methanesulfonamide, (5-1-207) N-[2-[5-amino-1-[2-fluoro-4-(2-fluorophenoxy)-3-methylphenyl]pyrazole-4-carbonyl]-5-methyl-1H-indol-6-yl]methanesulfonamide, (5-1-208) [5-amino-1-[4-(3-fluorophenoxy)-3-methylphenyl]pyrazol-4-yl]-[6-fluoro-5-(1-propan-2-ylpiperidin-4-yl)oxy-1H-indol-2-yl]methanone, (5-1-209) [5-amino-1-[4-(3-fluorophenoxy)-3-methylphenyl]pyrazol-4-yl]-[6-chloro-5-(1-propan-2-ylpiperidin-4-yl)oxy-1H-indol-2-yl]methanone, (5-1-210) [5-amino-1-[4-(3-fluorophenoxy)-3-methylphenyl]pyrazol-4-yl]-[6-bromo-5-(1-propan-2-ylpiperidin-4-yl)oxy-1H-indol-2-yl]methanone, (5-1-211) N-[2-[5-amino-1-[4-(3-fluorophenoxy)-3-methylphenyl]pyrazole-4-carbonyl]-5-methyl-1H-indol-6-yl]methanesulfonamide, (5-1-212) [5-amino-1-[2-fluoro-4-(2-fluorophenoxy)-5-methylphenyl]pyrazol-4-yl]-[6-bromo-5-(1-propan-2-ylpiperidin-4-yl)oxy-1H-indol-2-yl]methanone, (5-1-213) N-[2-[5-amino-1-[4-(2-fluorophenoxy)-2,3-dimethylphenyl]pyrazole-4-carbonyl]-5-methyl-1H-indol-6-yl]methanesulfonamide, (5-1-214) N-[2-[5-amino-1-[2,3-difluoro-4-(2-fluorophenoxy)phenyl]pyrazole-4-carbonyl]-5-methyl-1H-indol-6-yl]methanesulfonamide, (5-1-215) [5-amino-1-[2-fluoro-4-(2-fluorophenoxy)-5-methylphenyl]pyrazol-4-yl]-[6-(4-morpholin-4-ylpiperidin-1-yl)-5-(1-propan-2-ylpiperidin-4-yl)oxy-1H-indol-2-yl]methanone, (5-1-216) [5-amino-1-[4-(2-fluorophenoxy)-3-methylphenyl]pyrazol-4-yl]-[6-bromo-5-(1-cyclopentylpiperidin-4-yl)oxy-1H-indol-2-yl]methanone, (5-1-217) [5-amino-1-[4-(2-fluorophenoxy)-3-methylphenyl]pyrazol-4-yl]-[5-(2,2-difluoroethoxy)-6-(1-methylsulfonylpiperidin-4-yl)-1H-indol-2-yl]methanone, (5-1-218) [5-amino-1-[4-(2-fluorophenoxy)-3-methylphenyl]pyrazol-4-yl]-[6-bromo-5-(1-cyclobutylpiperidin-4-yl)oxy-1H-indol-2-yl]methanone, (5-1-219) [5-amino-1-[4-(2-fluorophenoxy)-3-methylphenyl]pyrazol-4-yl]-[6-bromo-5-(1-cyclopropylpiperidin-4-yl)oxy-1H-indol-2-yl]methanone, (5-1-220) [5-amino-1-[4-(2-fluorophenoxy)-3-methylphenyl]pyrazol-4-yl]-[6-bromo-5-[1-(oxetan-3-yl)piperidin-4-yl]oxy-1H-indol-2-yl]methanone, (5-1-221) [5-amino-1-[6-(2,6-difluorophenoxy)-4-methylpyridin-3-yl]pyrazol-4-yl]-[6-bromo-5-(1-cyclobutylpiperidin-4-yl)oxy-1H-indol-2-yl]methanone, (5-1-222) [5-amino-1-[6-(2,6-difluorophenoxy)-4-methylpyridin-3-yl]pyrazol-4-yl]-[6-bromo-5-[1-(oxetan-3-yl)piperidin-4-yl]oxy-1H-indol-2-yl]methanone, (5-1-223) [5-amino-1-[6-(2,6-difluorophenoxy)-4-methylpyridin-3-yl]pyrazol-4-yl]-[6-bromo-5-(1-cyclopentylpiperidin-4-yl)oxy-1H-indol-2-yl]methanone, (5-1-224) [5-amino-1-[6-(2,6-difluorophenoxy)-4-methylpyridin-3-yl]pyrazol-4-yl]-[6-bromo-5-(1-cyclopropylpiperidin-4-yl)oxy-1H-indol-2-yl]methanone, (5-1-225) [5-amino-1-[4-(2-fluorophenoxy)-3-methylphenyl]pyrazol-4-yl]-[6-bromo-5-[1-(2-hydroxyethyl)piperidin-4-yl]oxy-1H-indol-2-yl]methanone, (5-1-226) [5-amino-1-[6-(2,6-difluorophenoxy)-4-methylpyridin-3-yl]pyrazol-4-yl]-[6-bromo-5-[1-(2-hydroxyethyl)piperidin-4-yl]oxy-1H-indol-2-yl]methanone, (5-1-227) [5-amino-1-[4-(2-fluorophenoxy)-3-methylphenyl]pyrazol-4-yl]-[6-bromo-5-[1-(1,1-dioxothietan-3-yl)piperidin-4-yl]oxy-1H-indol-2-yl]methanone, (5-1-228) [5-amino-1-[6-(2,6-difluorophenoxy)-4-methylpyridin-3-yl]pyrazol-4-yl]-[6-bromo-5-[1-(1,1-dioxothietan-3-yl)piperidin-4-yl]oxy-1H-indol-2-yl]methanone, (5-1-229) [5-amino-1-[6-(2,6-difluorophenoxy)-4-methylpyridin-3-yl]pyrazol-4-yl]-[6-(1-methylsulfonylpiperidin-4-yl)-5-(1-propan-2-ylpiperidin-4-yl)oxy-1H-indol-2-yl]methanone, (5-1-230) [5-amino-1-[4-(2-fluorophenoxy)-3-methylphenyl]pyrazol-4-yl]-[6-(1-methylsulfonylpiperidin-4-yl)-5-(1-propan-2-ylpiperidin-4-yl)oxy-1H-indol-2-yl]methanone, (5-1-231) N-[2-[5-amino-1-[4-(2-fluorophenoxy)-3-methylphenyl]pyrazole-4-carbonyl]-5-(1-cyclobutylpiperidin-4-yl)oxy-1H-indol-6-yl]methanesulfonamide, (5-1-232) [6-amino-5-(1-cyclobutylpiperidin-4-yl)oxy-1H-indol-2-yl]-[5-amino-1-[4-(2-fluorophenoxy)-3-methylphenyl]pyrazol-4-yl]methanone, (5-1-233) 3-[2-[5-amino-1-[4-(2-fluorophenoxy)-3-methylphenyl]pyrazole-4-carbonyl]-5-(1-cyclobutylpiperidin-4-yl)oxy-1H-indol-6-yl]-5,5-dimethylimidazolidine-2,4-dione, (5-1-234) [5-amino-1-[4-(2-fluorophenoxy)-3-methylphenyl]pyrazol-4-yl]-[5-(1-cyclobutylpiperidin-4-yl)oxy-6-fluoro-1H-indol-2-yl]methanone, (5-1-235) [5-amino-1-[4-(2-fluorophenoxy)-3-methylphenyl]pyrazol-4-yl]-[6-chloro-5-(1-cyclobutylpiperidin-4-yl)oxy-1H-indol-2-yl]methanone, (5-1-236) [5-amino-1-[4-(2-fluorophenoxy)-3-methylphenyl]pyrazol-4-yl]-[6-(1-methylpyrazol-4-yl)-5-(1-propan-2-ylpiperidin-4-yl)oxy-1H-indol-2-yl]methanone, (5-1-237) [5-amino-1-[4-(2-fluorophenoxy)-3-methylphenyl]pyrazol-4-yl]-[6-bromo-5-[(2R)-2,3-dihydroxypropoxy]-1H-indol-2-yl]methanone, (5-1-238) [5-amino-1-[4-(2-fluorophenoxy)-3-methylphenyl]pyrazol-4-yl]-[5-(1-propan-2-ylpiperidin-4-yl)oxy-6-thiophen-2-yl-1H-indol-2-yl]methanone, (5-1-239) [5-amino-1-[6-(2,6-difluorophenoxy)-4-methylpyridin-3-yl]pyrazol-4-yl]-[5-(1-propan-2-ylpiperidin-4-yl)oxy-6-thiophen-2-yl-1H-indol-2-yl]methanone, (5-1-240) [5-amino-1-[4-(2-fluorophenoxy)-3-methylphenyl]pyrazol-4-yl]-[5-(1-propan-2-ylpiperidin-4-yl)oxy-6-pyrimidin-5-yl-1H-indol-2-yl]methanone, (5-1-241) [5-amino-1-[6-(2,6-difluorophenoxy)-4-methylpyridin-3-yl]pyrazol-4-yl]-[5-(1-propan-2-ylpiperidin-4-yl)oxy-6-pyrimidin-5-yl-1H-indol-2-yl]methanone, (5-1-242) N-[2-[5-amino-1-[4-(2-fluorophenoxy)-3-methylphenyl]pyrazole-4-carbonyl]-5-[(2R)-2,3-dihydroxypropoxy]-1H-indol-6-yl]methanesulfonamide, (5-1-243) (5 S)-3-[2-[5-amino-1-[4-(2-fluorophenoxy)-2-methylphenyl]pyrazole-4-carbonyl]-5-(2,2-difluoroethoxy)-1H-indol-6-yl]-5-(1H-imidazol-5-ylmethyl)imidazolidine-2,4-dione, (5-1-244) (4R)-3-[2-[5-amino-1-[4-(2-fluorophenoxy)-2-methylphenyl]pyrazole-4-carbonyl]-5-(2,2-difluoroethoxy)-1H-indol-6-yl]-4-benzyl-1,3-oxazolidin-2-one, (5-1-245) (4S)-3-[2-[5-amino-1-[4-(2-fluorophenoxy)-2-methylphenyl]pyrazole-4-carbonyl]-5-(2,2-difluoroethoxy)-1H-indol-6-yl]-4-benzyl-1,3-oxazolidin-2-one, (5-1-246) Methyl (2S)-2-[[2-[5-amino-1-[4-(2-fluorophenoxy)-2-methylphenyl]pyrazole-4-carbonyl]-5-(2,2-difluoroethoxy)-1H-indol-6-yl]carbamoylamino]-3-(1H-imidazol-5-yl)propanoate, (5-1-247) [5-amino-1-[4-(2-fluorophenoxy)-3-methylphenyl]pyrazol-4-yl]-[6-(oxan-4-yl)-5-(1-propan-2-ylpiperidin-4-yl)oxy-1H-indol-2-yl]methanone, (5-1-248) [5-amino-1-[6-(2,6-difluorophenoxy)-4-methylpyridin-3-yl]pyrazol-4-yl]-[6-(oxan-4-yl)-5-(1-propan-2-ylpiperidin-4-yl)oxy-1H-indol-2-yl]methanone, (5-1-249) [5-amino-1-[6-(2,6-difluorophenoxy)-4-methylpyridin-3-yl]pyrazol-4-yl]-[6-(1-methylpyrazol-4-yl)-5-(1-propan-2-ylpiperidin-4-yl)oxy-1H-indol-2-yl]methanone, (5-1-250) (6R,7aS)-2-[2-[5-amino-1-[4-(2-fluorophenoxy)-2-methylphenyl]pyrazole-4-carbonyl]-5-(2,2-difluoroethoxy)-1H-indol-6-yl]-6-hydroxy-5,6,7,7a-tetrahydropyrrolo[1,2-c]imidazole-1,3-dione, (5-1-251) (5S)-3-[2-[5-amino-1-[4-(2-fluorophenoxy)-2-methylphenyl]pyrazole-4-carbonyl]-5-(2,2-difluoroethoxy)-1H-indol-6-yl]-5-[(4-hydroxyphenyl)methyl]imidazolidine-2,4-dione, (5-1-252) (7aS)-2-[2-[5-amino-1-[4-(2-fluorophenoxy)-2-methylphenyl]pyrazole-4-carbonyl]-5-(2,2-difluoroethoxy)-1H-indol-6-yl]-5,6,7,7a-tetrahydropyrrolo[1,2-c]imidazole-1,3-dione, (5-1-253) 9H-fluoren-9-ylmethyl N-[(6S,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]carbamate, (5-1-254) N-[(6S,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]methanesulfonamide, (5-1-255) N-[(6S,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]-3-fluoropropane-1-sulfonamide, (5-1-256) [5-amino-1-[4-(2-fluorophenoxy)-3-methylphenyl]pyrazol-4-yl]-[5-(2,2-difluoroethoxy)-6-thiophen-2-yl-1H-indol-2-yl]methanone, (5-1-257) [5-amino-1-[6-(2,6-difluorophenoxy)-4-methylpyridin-3-yl]pyrazol-4-yl]-[5-(2,2-difluoroethoxy)-6-thiophen-2-yl-1H-indol-2-yl]methanone, (5-1-258) [5-amino-1-[4-(2-fluorophenoxy)-3-methylphenyl]pyrazol-4-yl]-[5-(2,2-difluoroethoxy)-6-(oxan-4-yl)-1H-indol-2-yl]methanone, (5-1-259) [5-amino-1-[6-(2,6-difluorophenoxy)-4-methylpyridin-3-yl]pyrazol-4-yl]-[5-(2,2-difluoroethoxy)-6-(oxan-4-yl)-1H-indol-2-yl]methanone, (5-1-260) [5-amino-1-[4-(2-fluorophenoxy)-2-methylphenyl]pyrazol-4-yl]-(6-bromo-5-propan-2-yl-1H-indol-2-yl)methanone, (5-1-261) [5-amino-1-[4-(2-fluorophenoxy)-3-methylphenyl]pyrazol-4-yl]-[5-(2,2-difluoroethoxy)-6-pyrimidin-5-yl-1H-indol-2-yl]methanone, (5-1-262) [5-amino-1-[6-(2,6-difluorophenoxy)-4-methylpyridin-3-yl]pyrazol-4-yl]-[5-(2,2-difluoroethoxy)-6-pyrimidin-5-yl-1H-indol-2-yl]methanone, (5-1-263) [5-amino-1-[4-(2-fluorophenoxy)-3-methylphenyl]pyrazol-4-yl]-[5-(2,2-difluoroethoxy)-6-(1-methylpyrazol-4-yl)-1H-indol-2-yl]methanone, (5-1-264) [5-amino-1-[6-(2,6-difluorophenoxy)-4-methylpyridin-3-yl]pyrazol-4-yl]-[5-(2,2-difluoroethoxy)-6-(1-methylpyrazol-4-yl)-1H-indol-2-yl]methanone, (5-1-265) 9H-fluoren-9-ylmethyl N-[(6S,7aS)-2-[2-[5-amino-1-[4-(2-fluorophenoxy)-2-methylphenyl]pyrazole-4-carbonyl]-5-fluoro-1H-indol-6-yl]-1,3-dioxo-5,6,7,7a-tetrahydropyrrolo[1,2-c]imidazol-6-yl]carbamate, (5-1-266) [5-amino-1-[4-(2-fluorophenoxy)-2-methylphenyl]pyrazol-4-yl]-(6-amino-5-propan-2-yl-1H-indol-2-yl)methanone, (5-1-267) N-[2-[5-amino-1-[4-(2-fluorophenoxy)-2-methylphenyl]pyrazole-4-carbonyl]-5-propan-2-yl-1H-indol-6-yl]methanesulfonamide, (5-1-268) 9H-fluoren-9-ylmethyl N-[(6S,7aS)-2-[2-[5-amino-1-[4-(2-fluorophenoxy)-2-methylphenyl]pyrazole-4-carbonyl]-5-methyl-1H-indol-6-yl]-1,3-dioxo-5,6,7,7a-tetrahydropyrrolo[1,2-c]imidazol-6-yl]carbamate, (5-1-269) N-[2-[5-amino-1-[6-(2,6-difluorophenoxy)-4-methylpyridin-3-yl]pyrazole-4-carbonyl]-5-methyl-1H-indol-6-yl]oxane-4-sulfonamide, (5-1-270) 9H-fluoren-9-ylmethyl N-[(6R,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]carbamate, (5-1-271) 3-[2-[5-amino-1-[4-(2-fluorophenoxy)-2-methylphenyl]pyrazole-4-carbonyl]-5-(2,2-difluoroethoxy)-1H-indol-6-yl]-1,3,8-triazaspiro[4.5]decane-2,4-dione, (5-1-272) 3-[2-[5-amino-1-[4-(2-fluorophenoxy)-2-methylphenyl]pyrazole-4-carbonyl]-5-(2,2-difluoroethoxy)-1H-indol-6-yl]-8-(oxetan-3-yl)-1,3,8-triazaspiro[4.5]decane-2,4-dione, (5-1-273) Benzyl N-[(6S,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]carbamate, (5-1-274) 2-methylpropyl N-[(6S,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]carbamate, (5-1-275) N-[(6S,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]-1-phenylmethanesulfonamide, (5-1-276) N-[(6S,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]naphthalene-2-sulfonamide, (5-1-277) 3-[2-[5-amino-1-[4-(2-fluorophenoxy)-2-methylphenyl]pyrazole-4-carbonyl]-5-(2,2-difluoroethoxy)-1H-indol-6-yl]-8-benzyl-1,3,8-triazaspiro[4.5]decane-2,4-dione, (5-1-278) Furan-2-ylmethyl N-[(6S,7aS)-2-[2-[5-amino-1-[4-(2-fluorophenoxy)-2-methylphenyl]pyrazole-4-carbonyl]-5-(2,2-difluoroethoxy)-1H-indol-6-yl]-1,3-dioxo-5,6,7,7a-tetrahydropyrrolo[1,2-c]imidazol-6-yl]carbamate, (5-1-279) 9H-fluoren-9-ylmethyl N-[2-[5-amino-1-[4-(2-fluorophenoxy)-2-methylphenyl]pyrazole-4-carbonyl]-5-(2,2-difluoroethoxy)-1H-indol-6-yl]carbamate, (5-1-280) N-[2-[5-amino-1-[4-(2-fluorophenoxy)-2-methylphenyl]pyrazole-4-carbonyl]-5-propan-2-yl-1H-indol-6-yl]-3-fluoropropane-1-sulfonamide, (5-1-281) N-[2-[5-amino-1-[6-(2,6-difluorophenoxy)-4-methylpyridin-3-yl]pyrazole-4-carbonyl]-5-methyl-1H-indol-6-yl]oxolane-3-sulfonamide, (5-1-282) N-[2-[5-amino-1-[4-(2-fluorophenoxy)-2-methylphenyl]pyrazole-4-carbonyl]-5-propan-2-yl-1H-indol-6-yl]oxane-4-sulfonamide, (5-1-283) [5-amino-1-[4-(2-fluorophenoxy)-3-methylphenyl]pyrazol-4-yl]-[5-[1-(1,1-dioxothietan-3-yl)piperidin-4-yl]oxy-6-pyrimidin-5-yl-1H-indol-2-yl]methanone, (5-1-284) [5-amino-1-[6-(2,6-difluorophenoxy)-4-methylpyridin-3-yl]pyrazol-4-yl]-[5-[1-(1,1-dioxothietan-3-yl)piperidin-4-yl]oxy-6-pyrimidin-5-yl-1H-indol-2-yl]methanone, (5-1-285) [5-amino-1-[4-(2-fluorophenoxy)-3-methylphenyl]pyrazol-4-yl]-[6-(2-chlorophenyl)-5-(1-cyclopentylpiperidin-4-yl)oxy-1H-indol-2-yl]methanone, (5-1-286) 3-[2-[5-amino-1-[6-(2,6-difluorophenoxy)-4-methylpyridin-3-yl]pyrazole-4-carbonyl]-5-methyl-1H-indol-6-yl]-5,5-dimethylimidazolidine-2,4-dione, (5-1-287) (5 S)-3-[2-[5-amino-1-[4-(2-fluorophenoxy)-3-methylphenyl]pyrazole-4-carbonyl]-5-(1-propan-2-ylpiperidin-4-yl)oxy-1H-indol-6-yl]-5-methylimidazolidine-2,4-dione, (5-1-288) [5-amino-1-[6-(2,6-difluorophenoxy)-4-methylpyridin-3-yl]pyrazol-4-yl]-[6-(2-chlorophenyl)-5-(1-cyclopentylpiperidin-4-yl)oxy-1H-indol-2-yl]methanone, (5-1-289) [5-amino-1-[4-(2-fluorophenoxy)-3-methylphenyl]pyrazol-4-yl]-[6-(2-chlorophenyl)-5-[1-(1,1-dioxothietan-3-yl)piperidin-4-yl]oxy-1H-indol-2-yl]methanone, (5-1-290) [5-amino-1-[6-(2,6-difluorophenoxy)-4-methylpyridin-3-yl]pyrazol-4-yl]-[6-(2-chlorophenyl)-5-[1-(1,1-dioxothietan-3-yl)piperidin-4-yl]oxy-1H-indol-2-yl]methanone, (5-1-291) N-[2-[5-amino-1-[6-(2,6-difluorophenoxy)-4-methylpyridin-3-yl]pyrazole-4-carbonyl]-5-methyl-1H-indol-6-yl]-3-oxa-8-azabicyclo[3.2.1]octane-8-sulfonamide, (5-1-292) (3R)—N-[2-[5-amino-1-[6-(2,6-difluorophenoxy)-4-methylpyridin-3-yl]pyrazole-4-carbonyl]-5-methyl-1H-indol-6-yl]-3-methylmorpholine-4-sulfonamide, (5-1-293) (5 S)-3-[2-[5-amino-1-[4-(2-fluorophenoxy)-3-methylphenyl]pyrazole-4-carbonyl]-5-(1-propan-2-ylpiperidin-4-yl)oxy-1H-indol-6-yl]-5-(hydroxymethyl)imidazolidine-2,4-dione, (5-1-294) (5 S)-3-[2-[5-amino-1-[4-(2-fluorophenoxy)-3-methylphenyl]pyrazole-4-carbonyl]-5-(1-propan-2-ylpiperidin-4-yl)oxy-1H-indol-6-yl]-5-benzylimidazolidine-2,4-dione, (5-1-295) (5 S)-3-[2-[5-amino-1-[4-(2-fluorophenoxy)-3-methylphenyl]pyrazole-4-carbonyl]-5-(1-propan-2-ylpiperidin-4-yl)oxy-1H-indol-6-yl]-5-propan-2-ylimidazolidine-2,4-dione, (5-1-296) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-1-phenylmethanesulfonamide, (5-1-297) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-4-fluorobenzenesulfonamide, (5-1-298) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-4-chlorobenzenesulfonamide, (5-1-299) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-4-methoxybenzenesulfonamide, (5-1-300) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-4-methylbenzenesulfonamide, (5-1-301) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-2-chloro-5-methoxybenzenesulfonamide, (5-1-302) [5-amino-1-[4-(2-fluorophenoxy)-2-methylphenyl]pyrazol-4-yl]-[6-(4,4-dimethyl-1,1-dioxo-1,2,5-thiadiazolidin-2-yl)-5-fluoro-1H-indol-2-yl]methanone, (5-1-303) N-[2-[5-amino-1-[6-(2,6-difluorophenoxy)-4-methylpyridin-3-yl]pyrazole-4-carbonyl]-5-propan-2-yl-1H-indol-6-yl]-3-oxa-8-azabicyclo[3.2.1]octane-8-sulfonamide, (5-1-304) N-[2-[5-amino-1-[6-(2,6-difluorophenoxy)-4-methylpyridin-3-yl]pyrazole-4-carbonyl]-5-propan-2-yl-1H-indol-6-yl]cyclohexanesulfonamide, (5-1-305) N-[2-[5-amino-1-[6-(2,6-difluorophenoxy)-4-methylpyridin-3-yl]pyrazole-4-carbonyl]-5-propan-2-yl-1H-indol-6-yl]-3-fluoropropane-1-sulfonamide, (5-1-306) N-[2-[5-amino-1-[6-(2,6-difluorophenoxy)-4-methylpyridin-3-yl]pyrazole-4-carbonyl]-5-propan-2-yl-1H-indol-6-yl]cyclopentanesulfonamide, (5-1-307) N-[2-[5-amino-1-[4-(2-fluorophenoxy)-3-methylphenyl]pyrazole-4-carbonyl]-5-methyl-1H-indol-6-yl]methanesulfonamide, (5-1-308) [5-amino-1-[4-(2-fluorophenoxy)-3-methylphenyl]pyrazol-4-yl]-[5-(1-cyclopentylpiperidin-4-yl)oxy-6-(2-fluorophenyl)-1H-indol-2-yl]methanone, (5-1-309) [5-amino-1-[4-(2-fluorophenoxy)-3-methylphenyl]pyrazol-4-yl]-[5-[1-(1,1-dioxothietan-3-yl)piperidin-4-yl]oxy-6-(2-fluorophenyl)-1H-indol-2-yl]methanone, (5-1-310) [5-amino-1-[6-(2,6-difluorophenoxy)-4-methylpyridin-3-yl]pyrazol-4-yl]-[5-(1-cyclopentylpiperidin-4-yl)oxy-6-(2-fluorophenyl)-1H-indol-2-yl]methanone, (5-1-311) [5-amino-1-[6-(2,6-difluorophenoxy)-4-methylpyridin-3-yl]pyrazol-4-yl]-[5-[1-(1,1-dioxothietan-3-yl)piperidin-4-yl]oxy-6-(2-fluorophenyl)-1H-indol-2-yl]methanone, (5-1-312) 7-[2-[5-amino-1-[6-(2,6-difluorophenoxy)-4-methylpyridin-3-yl]pyrazole-4-carbonyl]-5-fluoro-1H-indol-6-yl]-5,7-diazaspiro[3.4]octane-6,8-dione, (5-1-313) [5-amino-1-[6-(2,6-difluorophenoxy)-4-methylpyridin-3-yl]pyrazol-4-yl]-[6-(4,4-dimethyl-1,1-dioxo-1,2,5-thiadiazolidin-2-yl)-5-methyl-1H-indol-2-yl]methanone, (5-1-314) N-[2-[5-amino-1-[6-(2,6-difluorophenoxy)-4-methylpyridin-3-yl]pyrazole-4-carbonyl]-5-methyl-1H-indol-6-yl]cyclohexanesulfonamide, (5-1-315) N-[2-[5-amino-1-[6-(2,6-difluorophenoxy)-4-methylpyridin-3-yl]pyrazole-4-carbonyl]-5-(2,2-difluoroethoxy)-1H-indol-6-yl]cyclohexanesulfonamide, (5-1-316) 3-[2-[5-amino-1-[6-(2,6-difluorophenoxy)-4-methylpyridin-3-yl]pyrazole-4-carbonyl]-5-methyl-1H-indol-6-yl]-1,3-diazaspiro[4.5]decane-2,4-dione, (5-1-317) N-[2-[5-amino-1-[6-(2,6-difluorophenoxy)-4-methylpyridin-3-yl]pyrazole-4-carbonyl]-5-methyl-1H-indol-6-yl]cyclopentanesulfonamide, (5-1-318) N-[2-[5-amino-1-[6-(2,6-difluorophenoxy)-4-methylpyridin-3-yl]pyrazole-4-carbonyl]-5-(2,2-difluoroethoxy)-1H-indol-6-yl]cyclopentanesulfonamide, (5-1-319) N-[2-[5-amino-1-[6-(2,6-difluorophenoxy)-4-methylpyridin-3-yl]pyrazole-4-carbonyl]-5-(2,2-difluoroethoxy)-1H-indol-6-yl]oxane-4-sulfonamide, (5-1-320) N-[2-[5-amino-1-[6-(2,6-difluorophenoxy)-4-methylpyridin-3-yl]pyrazole-4-carbonyl]-5-(difluoromethylsulfanyl)-1H-indol-6-yl]-3-fluoropropane-1-sulfonamide, (5-1-321) [5-amino-1-[6-(2,6-difluorophenoxy)-4-methylpyridin-3-yl]pyrazol-4-yl]-[5-(2,2-difluoroethoxy)-6-(4,4-dimethyl-1,1-dioxo-1,2,5-thiadiazolidin-2-yl)-1H-indol-2-yl]methanone, (5-1-322) [5-amino-1-[4-(2-fluorophenoxy)-2-methylphenyl]pyrazol-4-yl]-[5-(2,2-difluoroethoxy)-6-(4,4-dimethyl-1,1-dioxo-1,2,5-thiadiazolidin-2-yl)-1H-indol-2-yl]methanone, (5-1-323) [5-amino-1-[4-(2-fluorophenoxy)-2-methylphenyl]pyrazol-4-yl]-[5-(2,2-difluoroethoxy)-6-(2,2-dioxo-2λ6-thia-1,3-diazaspiro[4.4]nonan-3-yl)-1H-indol-2-yl]methanone, (5-1-324) 3-[2-[5-amino-1-[6-(2,6-difluorophenoxy)-4-methylpyridin-3-yl]pyrazole-4-carbonyl]-5-(difluoromethylsulfanyl)-1H-indol-6-yl]-5,5-dimethylimidazolidine-2,4-dione, (5-1-325) N-[2-[5-amino-1-[4-(2-fluorophenoxy)-2-methylphenyl]pyrazole-4-carbonyl]-5-(2,2-difluoroethoxy)-1H-indol-6-yl]oxane-4-sulfonamide, (5-1-326) N-[2-[5-amino-1-[6-(2-fluorophenoxy)-4-methylpyridin-3-yl]pyrazole-4-carbonyl]-5-(2,2-difluoroethoxy)-1H-indol-6-yl]oxane-4-sulfonamide, (5-1-327) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-3-methoxybenzenesulfonamide, (5-1-328) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-2-chlorobenzenesulfonamide, (5-1-329) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-2-methoxybenzenesulfonamide, (5-1-330) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-3,5-difluorobenzenesulfonamide, (5-1-331) N-[2-[5-amino-1-[4-(2-fluorophenoxy)-2-methylphenyl]pyrazole-4-carbonyl]-5-(2,2-difluoroethoxy)-1H-indol-6-yl]-2-chloro-5-methoxybenzenesulfonamide, (5-1-332) 3-[2-[5-amino-1-[6-(2,6-difluorophenoxy)-4-methylpyridin-3-yl]pyrazole-4-carbonyl]-5-(2,2-difluoroethoxy)-1H-indol-6-yl]-1,3,8-triazaspiro[4.5]decane-2,4-dione, (5-1-333) N-[2-[5-amino-1-[6-(2-fluorophenoxy)-4-methylpyridin-3-yl]pyrazole-4-carbonyl]-5-methyl-1H-indol-6-yl]oxane-4-sulfonamide, (5-1-334) 3-[2-[5-amino-1-[6-(2-fluorophenoxy)-4-methylpyridin-3-yl]pyrazole-4-carbonyl]-5-methyl-1H-indol-6-yl]-5,5-dimethylimidazolidine-2,4-dione, (5-1-335) [5-amino-1-[4-(2-fluorophenoxy)-3-methylphenyl]pyrazol-4-yl]-[5-(1-cyclopentylpiperidin-4-yl)oxy-6-(2-methylphenyl)-1H-indol-2-yl]methanone, (5-1-336) [5-amino-1-[4-(2-fluorophenoxy)-3-methylphenyl]pyrazol-4-yl]-[5-[1-(1,1-dioxothietan-3-yl)piperidin-4-yl]oxy-6-(2-methylphenyl)-1H-indol-2-yl]methanone, (5-1-337) [5-amino-1-[6-(2,6-difluorophenoxy)-4-methylpyridin-3-yl]pyrazol-4-yl]-[5-(1-cyclopentylpiperidin-4-yl)oxy-6-(2-methylphenyl)-1H-indol-2-yl]methanone, (5-1-338) [5-amino-1-[6-(2,6-difluorophenoxy)-4-methylpyridin-3-yl]pyrazol-4-yl]-[5-[1-(1,1-dioxothietan-3-yl)piperidin-4-yl]oxy-6-(2-methylphenyl)-1H-indol-2-yl]methanone, (5-1-339) N-[2-[5-amino-1-[6-(2-fluorophenoxy)-4-methylpyridin-3-yl]pyrazole-4-carbonyl]-5-(difluoromethyl sulfanyl)-1H-indol-6-yl]-3-fluoropropane-1-sulfonamide, (5-1-340) [5-amino-1-[4-(2-fluorophenoxy)-2-methylphenyl]pyrazol-4-yl]-[5-(difluoromethoxy)-6-(4,4-dimethyl-1,1-dioxo-1,2,5-thiadiazolidin-2-yl)-1H-indol-2-yl]methanone, (5-1-341) 7-[2-[5-amino-1-[6-(2,6-difluorophenoxy)-4-methylpyridin-3-yl]pyrazole-4-carbonyl]-5-methyl-1H-indol-6-yl]-5,7-diazaspiro[3.4]octane-6,8-dione, (5-1-342) 3-[2-[5-amino-1-[6-(2,6-difluorophenoxy)-4-methylpyridin-3-yl]pyrazole-4-carbonyl]-5-methyl-1H-indol-6-yl]-8-oxa-1,3-diazaspiro[4.5]decane-2,4-dione, (5-1-343) 6-[2-[5-amino-1-[6-(2,6-difluorophenoxy)-4-methylpyridin-3-yl]pyrazole-4-carbonyl]-5-fluoro-1H-indol-6-yl]-4,6-diazaspiro[2.4]heptane-5,7-dione, (5-1-344) 3-[2-[5-amino-1-[6-(2,6-difluorophenoxy)-4-methylpyridin-3-yl]pyrazole-4-carbonyl]-5-fluoro-1H-indol-6-yl]-1,3-diazaspiro[4.4]nonane-2,4-dione, (5-1-345) 7-[2-[5-amino-1-[6-(2,6-difluorophenoxy)-4-methylpyridin-3-yl]pyrazole-4-carbonyl]-5-fluoro-1H-indol-6-yl]-2-oxa-5,7-diazaspiro[3.4]octane-6,8-dione, (5-1-346) N-[2-[5-amino-1-[6-(2,6-difluorophenoxy)-4-methylpyridin-3-yl]pyrazole-4-carbonyl]-5-(difluoromethylsulfanyl)-1H-indol-6-yl]oxane-4-sulfonamide, (5-1-347) N-[2-[5-amino-1-[4-(2-fluorophenoxy)-2-methylphenyl]pyrazole-4-carbonyl]-5-methyl-1H-indol-6-yl]oxane-4-sulfonamide, (5-1-348) (5 S)-3-[2-[5-amino-1-[6-(2,6-difluorophenoxy)-4-methylpyridin-3-yl]pyrazole-4-carbonyl]-5-(2,2-difluoroethoxy)-1H-indol-6-yl]-1,3,7-triazaspiro[4.4]nonane-2,4-dione, (5-1-349) 3-[2-[5-amino-1-[4-(2-fluorophenoxy)-2-methylphenyl]pyrazole-4-carbonyl]-5-(2,2-difluoroethoxy)-1H-indol-6-yl]-1,3,7-triazaspiro[4.4]nonane-2,4-dione, (5-1-350) 3-[2-[5-amino-1-[6-(2,6-difluorophenoxy)-4-methylpyridin-3-yl]pyrazole-4-carbonyl]-5-(2,2-difluoroethoxy)-1H-indol-6-yl]-8-(oxetan-3-yl)-1,3,8-triazaspiro[4.5]decane-2,4-dione, (5-1-351) 3-[2-[5-amino-1-[6-(2,6-difluorophenoxy)-4-methylpyridin-3-yl]pyrazole-4-carbonyl]-5-(2,2-difluoroethoxy)-1H-indol-6-yl]-8-benzyl-1,3,8-triazaspiro[4.5]decane-2,4-dione, (5-1-352) 3-[2-[5-amino-1-[6-(2,6-difluorophenoxy)-4-methylpyridin-3-yl]pyrazole-4-carbonyl]-5-(2,2-difluoroethoxy)-1H-indol-6-yl]-7-(oxetan-3-yl)-1,3,7-triazaspiro[4.4]nonane-2,4-dione, (5-1-353) 3-[2-[5-amino-1-[4-(2-fluorophenoxy)-2-methylphenyl]pyrazole-4-carbonyl]-5-(2,2-difluoroethoxy)-1H-indol-6-yl]-7-(oxetan-3-yl)-1,3,7-triazaspiro[4.4]nonane-2,4-dione, (5-1-354) 3-[2-[5-amino-1-[6-(2,6-difluorophenoxy)-4-methylpyridin-3-yl]pyrazole-4-carbonyl]-5-(2,2-difluoroethoxy)-1H-indol-6-yl]-7-benzyl-1,3,7-triazaspiro[4.4]nonane-2,4-dione, (5-1-355) 3-[2-[5-amino-1-[4-(2-fluorophenoxy)-2-methylphenyl]pyrazole-4-carbonyl]-5-(2,2-difluoroethoxy)-1H-indol-6-yl]-7-benzyl-1,3,7-triazaspiro[4.4]nonane-2,4-dione, (5-1-356) 3-[2-[5-amino-1-[4-(2-fluorophenoxy)-2-methylphenyl]pyrazole-4-carbonyl]-5-methyl-1H-indol-6-yl]-5,5-dimethylimidazolidine-2,4-dione, (5-1-357) 3-[2-[5-amino-1-[6-(2,6-difluorophenoxy)-4-methylpyridin-3-yl]pyrazole-4-carbonyl]-5-methyl-1H-indol-6-yl]-1,3,8-triazaspiro[4.5]decane-2,4-dione, (5-1-358) 3-[2-[5-amino-1-[6-(2,6-difluorophenoxy)-4-methylpyridin-3-yl]pyrazole-4-carbonyl]-5-methyl-1H-indol-6-yl]-1,3,7-triazaspiro[4.4]nonane-2,4-dione, (5-1-359) 3-[2-[5-amino-1-[6-(2-fluorophenoxy)-4-methylpyridin-3-yl]pyrazole-4-carbonyl]-5-(difluoromethylsulfanyl)-1H-indol-6-yl]-5,5-dimethylimidazolidine-2,4-dione, (5-1-360) 3-[2-[5-amino-1-[6-(2,6-difluorophenoxy)-4-methylpyridin-3-yl]pyrazole-4-carbonyl]-5-methyl-1H-indol-6-yl]-8-(oxetan-3-yl)-1,3,8-triazaspiro[4.5]decane-2,4-dione, (5-1-361) 3-[2-[5-amino-1-[6-(2,6-difluorophenoxy)-4-methylpyridin-3-yl]pyrazole-4-carbonyl]-5-methyl-1H-indol-6-yl]-8-benzyl-1,3,8-triazaspiro[4.5]decane-2,4-dione, (5-1-362) 3-[2-[5-amino-1-[6-(2,6-difluorophenoxy)-4-methylpyridin-3-yl]pyrazole-4-carbonyl]-5-methyl-1H-indol-6-yl]-7-(oxetan-3-yl)-1,3,7-triazaspiro[4.4]nonane-2,4-dione, (5-1-363) 3-[2-[5-amino-1-[6-(2,6-difluorophenoxy)-4-methylpyridin-3-yl]pyrazole-4-carbonyl]-5-methyl-1H-indol-6-yl]-7-benzyl-1,3,7-triazaspiro[4.4]nonane-2,4-dione, (5-1-364) 3-[2-[5-amino-1-[4-(2-fluorophenoxy)-2-methylphenyl]pyrazole-4-carbonyl]-5-methyl-1H-indol-6-yl]-1,3,8-triazaspiro[4.5]decane-2,4-dione, (5-1-365) 3-[2-[5-amino-1-[4-(2-fluorophenoxy)-2-methylphenyl]pyrazole-4-carbonyl]-5-methyl-1H-indol-6-yl]-1,3,7-triazaspiro[4.4]nonane-2,4-dione, (5-1-366) 6-[2-[5-amino-1-[6-(2,6-difluorophenoxy)-4-methylpyridin-3-yl]pyrazole-4-carbonyl]-5-methyl-1H-indol-6-yl]-4,6-diazaspiro[2.4]heptane-5,7-dione, (5-1-367) 3-[2-[5-amino-1-[6-(2,6-difluorophenoxy)-4-methylpyridin-3-yl]pyrazole-4-carbonyl]-5-methyl-1H-indol-6-yl]-1,3-diazaspiro[4.4]nonane-2,4-dione, (5-1-368) 3-[2-[5-amino-1-[6-(2,6-difluorophenoxy)-4-methylpyridin-3-yl]pyrazole-4-carbonyl]-5-fluoro-1H-indol-6-yl]-8-oxa-1,3-diazaspiro[4.5]decane-2,4-dione, (5-1-369) 3-[2-[5-amino-1-[6-(2,6-difluorophenoxy)-4-methylpyridin-3-yl]pyrazole-4-carbonyl]-5-fluoro-1H-indol-6-yl]-1,3-diazaspiro[4.5]decane-2,4-dione, (5-1-370) 3-[2-[5-amino-1-[6-(2,6-difluorophenoxy)-4-methylpyridin-3-yl]pyrazole-4-carbonyl]-5-fluoro-1H-indol-6-yl]-5-methyl-5-(trifluoromethyl)imidazolidine-2,4-dione, (5-1-371) 7-[2-[5-amino-1-[4-(2-fluorophenoxy)-2-methylphenyl]pyrazole-4-carbonyl]-5-methyl-1H-indol-6-yl]-5,7-diazaspiro[3.4]octane-6,8-dione, (5-1-372) 6-[2-[5-amino-1-[4-(2-fluorophenoxy)-2-methylphenyl]pyrazole-4-carbonyl]-5-methyl-1H-indol-6-yl]-4,6-diazaspiro[2.4]heptane-5,7-dione, (5-1-373) 3-[2-[5-amino-1-[4-(2-fluorophenoxy)-2-methylphenyl]pyrazole-4-carbonyl]-5-methyl-1H-indol-6-yl]-1,3-diazaspiro[4.4]nonane-2,4-dione, (5-1-374) 7-[2-[5-amino-1-[4-(2-fluorophenoxy)-2-methylphenyl]pyrazole-4-carbonyl]-5-fluoro-1H-indol-6-yl]-5,7-diazaspiro[3.4]octane-6,8-dione, (5-1-375) 6-[2-[5-amino-1-[4-(2-fluorophenoxy)-2-methylphenyl]pyrazole-4-carbonyl]-5-fluoro-1H-indol-6-yl]-4,6-diazaspiro[2.4]heptane-5,7-dione, (5-1-376) 7-[2-[5-amino-1-[4-(2-fluorophenoxy)-2-methylphenyl]pyrazole-4-carbonyl]-5-fluoro-1H-indol-6-yl]-2-oxa-5,7-diazaspiro[3.4]octane-6,8-dione, (5-1-377) 3-[2-[5-amino-1-[6-(2-fluorophenoxy)-4-methylpyridin-3-yl]pyrazole-4-carbonyl]-5-(2,2-difluoroethoxy)-1H-indol-6-yl]-5,5-dimethylimidazolidine-2,4-dione, (5-1-378) N-[2-[5-amino-1-[6-(2-fluorophenoxy)-4-methylpyridin-3-yl]pyrazole-4-carbonyl]-5-fluoro-1H-indol-6-yl]oxane-4-sulfonamide, (5-1-379) 3-[2-[5-amino-1-[6-(2-fluorophenoxy)-4-methylpyridin-3-yl]pyrazole-4-carbonyl]-5-fluoro-1H-indol-6-yl]-5,5-dimethylimidazolidine-2,4-dione, (5-1-380) N-[2-[5-amino-1-[6-(2,6-difluorophenoxy)-4-methylpyridin-3-yl]pyrazole-4-carbonyl]-5-(difluoromethoxy)-1H-indol-6-yl]oxane-4-sulfonamide, (5-1-381) N-[2-[5-amino-1-[6-(2,6-difluorophenoxy)-4-methylpyridin-3-yl]pyrazole-4-carbonyl]-5-fluoro-1H-indol-6-yl]oxane-4-sulfonamide, (5-1-382) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-3-cyanobenzenesulfonamide, (5-1-383) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-3-chlorobenzenesulfonamide, (5-1-384) N-[2-[5-amino-1-[6-(2,6-difluorophenoxy)-4-methylpyridin-3-yl]pyrazole-4-carbonyl]-5-(2,2-difluoroethoxy)-1H-indol-6-yl]pyridine-3-sulfonamide, (5-1-385) [5-amino-1-[4-(2-fluorophenoxy)-3-methylphenyl]pyrazol-4-yl]-[5-(1-cyclopentylpiperidin-4-yl)oxy-6-[2-(trifluoromethyl)phenyl]-1H-indol-2-yl]methanone, (5-1-386) [5-amino-1-[4-(2-fluorophenoxy)-3-methylphenyl]pyrazol-4-yl]-[5-[1-(1,1-dioxothietan-3-yl)piperidin-4-yl]oxy-6-[2-(trifluoromethyl)phenyl]-1H-indol-2-yl]methanone, (5-1-387) [5-amino-1-[6-(2,6-difluorophenoxy)-4-methylpyridin-3-yl]pyrazol-4-yl]-[5-(1-cyclopentylpiperidin-4-yl)oxy-6-[2-(trifluoromethyl)phenyl]-1H-indol-2-yl]methanone, (5-1-388) [5-amino-1-[6-(2,6-difluorophenoxy)-4-methylpyridin-3-yl]pyrazol-4-yl]-[5-[1-(1,1-dioxothietan-3-yl)piperidin-4-yl]oxy-6-[2-(trifluoromethyl)phenyl]-1H-indol-2-yl]methanone, (5-1-389) N-[2-[5-amino-1-[4-(2-fluorophenoxy)-2-methylphenyl]pyrazole-4-carbonyl]-5-fluoro-1H-indol-6-yl]oxane-4-sulfonamide, (5-1-390) N-[2-[5-amino-1-[4-(2-fluorophenoxy)-2-methylphenyl]pyrazole-4-carbonyl]-5-(difluoromethoxy)-1H-indol-6-yl]oxane-4-sulfonamide, (5-1-391) 3-[2-[5-amino-1-[4-(2-fluorophenoxy)-2-methylphenyl]pyrazole-4-carbonyl]-5-methyl-1H-indol-6-yl]-8-(oxetan-3-yl)-1,3,8-triazaspiro[4.5]decane-2,4-dione, (5-1-392) 3-[2-[5-amino-1-[4-(2-fluorophenoxy)-2-methylphenyl]pyrazole-4-carbonyl]-5-methyl-1H-indol-6-yl]-8-benzyl-1,3,8-triazaspiro[4.5]decane-2,4-dione, (5-1-393) 3-[2-[5-amino-1-[4-(2-fluorophenoxy)-2-methylphenyl]pyrazole-4-carbonyl]-5-methyl-1H-indol-6-yl]-7-(oxetan-3-yl)-1,3,7-triazaspiro[4.4]nonane-2,4-dione, (5-1-394) 3-[2-[5-amino-1-[4-(2-fluorophenoxy)-2-methylphenyl]pyrazole-4-carbonyl]-5-methyl-1H-indol-6-yl]-7-benzyl-1,3,7-triazaspiro[4.4]nonane-2,4-dione, (5-1-395) N-[2-[5-amino-1-[6-(2,6-difluorophenoxy)-4-methylpyridin-3-yl]pyrazole-4-carbonyl]-5-cyclopropyl-1H-indol-6-yl]oxane-4-sulfonamide, (5-1-396) N-[2-[5-amino-1-[6-(2-fluorophenoxy)-4-methylpyridin-3-yl]pyrazole-4-carbonyl]-5-cyclopropyl-1H-indol-6-yl]oxane-4-sulfonamide, (5-1-397) N-[2-[5-amino-1-[4-(2-fluorophenoxy)-2-methylphenyl]pyrazole-4-carbonyl]-5-cyclopropyl-1H-indol-6-yl]oxane-4-sulfonamide, (5-1-398) [5-amino-1-[6-(2,6-difluorophenoxy)-4-methylpyridin-3-yl]pyrazol-4-yl]-[6-(4,4-dimethyl-1,1-dioxo-1,2,5-thiadiazolidin-2-yl)-5-fluoro-1H-indol-2-yl]methanone, (5-1-399) [5-amino-1-[6-(2,6-difluorophenoxy)-4-methylpyridin-3-yl]pyrazol-4-yl]-[6-(2,2-dioxo-2λ6-thia-1,3-diazaspiro[4.4]nonan-3-yl)-5-fluoro-1H-indol-2-yl]methanone, (5-1-400) [5-amino-1-[6-(2,6-difluorophenoxy)-4-methylpyridin-3-yl]pyrazol-4-yl]-[6-(2,2-dioxo-8-oxa-2λ6-thia-1,3-diazaspiro[4.5]decan-3-yl)-5-fluoro-1H-indol-2-yl]methanone, (5-1-401) N-[2-[5-amino-1-[6-(2-fluorophenoxy)-4-methylpyridin-3-yl]pyrazole-4-carbonyl]-5-(difluoromethoxy)-1H-indol-6-yl]oxane-4-sulfonamide, (5-1-402) 3-[2-[5-amino-1-[6-(2-fluorophenoxy)-4-methylpyridin-3-yl]pyrazole-4-carbonyl]-5-(difluoromethoxy)-1H-indol-6-yl]-5,5-dimethylimidazolidine-2,4-dione, (5-1-403) [5-amino-1-[4-(2-fluorophenoxy)-2-methylphenyl]pyrazol-4-yl]-[6-(2,2-dioxo-8-oxa-2λ6-thia-1,3-diazaspiro[4.5]decan-3-yl)-5-fluoro-1H-indol-2-yl]methanone, (5-1-404) 7-[2-[5-amino-1-[6-(2,6-difluorophenoxy)-4-methylpyridin-3-yl]pyrazole-4-carbonyl]-5-methyl-1H-indol-6-yl]-2-oxa-5,7-diazaspiro[3.4]octane-6,8-dione, (5-1-405) 3-[2-[5-amino-1-[6-(2,6-difluorophenoxy)-4-methylpyridin-3-yl]pyrazole-4-carbonyl]-5-fluoro-1H-indol-6-yl]imidazolidine-2,4-dione, (5-1-406) (5 S)-3-[2-[5-amino-1-[6-(2,6-difluorophenoxy)-4-methylpyridin-3-yl]pyrazole-4-carbonyl]-5-fluoro-1H-indol-6-yl]-5-methylimidazolidine-2,4-dione, (5-1-407) (5 S)-3-[2-[5-amino-1-[6-(2,6-difluorophenoxy)-4-methylpyridin-3-yl]pyrazole-4-carbonyl]-5-fluoro-1H-indol-6-yl]-5-(hydroxymethyl)imidazolidine-2,4-dione, (5-1-408) 3-[2-[5-amino-1-[4-(2-fluorophenoxy)-2-methylphenyl]pyrazole-4-carbonyl]-5-methyl-1H-indol-6-yl]-8-oxa-1,3-diazaspiro[4.5]decane-2,4-dione, (5-1-409) 3-[2-[5-amino-1-[4-(2-fluorophenoxy)-2-methylphenyl]pyrazole-4-carbonyl]-5-methyl-1H-indol-6-yl]-1,3-diazaspiro[4.5]decane-2,4-dione, (5-1-410) 7-[2-[5-amino-1-[4-(2-fluorophenoxy)-2-methylphenyl]pyrazole-4-carbonyl]-5-methyl-1H-indol-6-yl]-2-oxa-5,7-diazaspiro[3.4]octane-6,8-dione, (5-1-411) (5 S)-3-[2-[5-amino-1-[4-(2-fluorophenoxy)-2-methylphenyl]pyrazole-4-carbonyl]-5-fluoro-1H-indol-6-yl]-5-methylimidazolidine-2,4-dione, (5-1-412) 3-[2-[5-amino-1-[4-(2-fluorophenoxy)-2-methylphenyl]pyrazole-4-carbonyl]-5-fluoro-1H-indol-6-yl]-5-methyl-5-(trifluoromethyl)imidazolidine-2,4-dione, (5-1-413) [5-amino-1-[6-(2-fluorophenoxy)-4-methylpyridin-3-yl]pyrazol-4-yl]-[6-(2,2-dioxo-8-oxa-2λ6-thia-1,3-diazaspiro[4.5]decan-3-yl)-5-fluoro-1H-indol-2-yl]methanone, (5-1-414) N-[2-[5-amino-1-[4-(2-fluorophenoxy)-2-methylphenyl]pyrazole-4-carbonyl]-5-(2,2-difluoroethoxy)-1H-indol-6-yl]-3-methoxybenzenesulfonamide, (5-1-415) N-[2-[5-amino-1-[4-(2-fluorophenoxy)-2-methylphenyl]pyrazole-4-carbonyl]-5-(2,2-difluoroethoxy)-1H-indol-6-yl]-3,5-difluorobenzenesulfonamide, (5-1-416) N-[2-[5-amino-1-[4-(2-fluorophenoxy)-2-methylphenyl]pyrazole-4-carbonyl]-5-(2,2-difluoroethoxy)-1H-indol-6-yl]-3-cyanobenzenesulfonamide, (5-1-417) N-[2-[5-amino-1-[4-(2-fluorophenoxy)-2-methylphenyl]pyrazole-4-carbonyl]-5-(2,2-difluoroethoxy)-1H-indol-6-yl]-3-chlorobenzenesulfonamide, (5-1-418) N-[2-[5-amino-1-[4-(2-fluorophenoxy)-2-methylphenyl]pyrazole-4-carbonyl]-5-(2,2-difluoroethoxy)-1H-indol-6-yl]pyridine-3-sulfonamide, (5-1-419) N-[2-[5-amino-1-[6-(2-fluorophenoxy)-4-methylpyridin-3-yl]pyrazole-4-carbonyl]-5-(2,2-difluoroethoxy)-1H-indol-6-yl]-3-methoxybenzenesulfonamide, (5-1-420) N-[2-[5-amino-1-[6-(2-fluorophenoxy)-4-methylpyridin-3-yl]pyrazole-4-carbonyl]-5-(2,2-difluoroethoxy)-1H-indol-6-yl]-3,5-difluorobenzenesulfonamide, (5-1-421) [5-amino-1-[6-(2-fluorophenoxy)-4-methylpyridin-3-yl]pyrazol-4-yl]-[6-(4,4-dimethyl-1,1-dioxo-1,2,5-thiadiazolidin-2-yl)-5-fluoro-1H-indol-2-yl]methanone, (5-1-422) N-[2-[5-amino-1-[6-(2-fluorophenoxy)-4-methylpyridin-3-yl]pyrazole-4-carbonyl]-5-(2,2-difluoroethoxy)-1H-indol-6-yl]-3-cyanobenzenesulfonamide, (5-1-423) [5-amino-1-[4-(2-fluorophenoxy)-2-methylphenyl]pyrazol-4-yl]-[5-(difluoromethoxy)-6-(2,2-dioxo-2λ6-thia-1,3-diazaspiro[4.4]nonan-3-yl)-1H-indol-2-yl]methanone, (5-1-424) N-[2-[5-amino-1-[6-(2-fluorophenoxy)-4-methylpyridin-3-yl]pyrazole-4-carbonyl]-5-(2,2-difluoroethoxy)-1H-indol-6-yl]-3-chlorobenzenesulfonamide, (5-1-425) N-[2-[5-amino-1-[6-(2-fluorophenoxy)-4-methylpyridin-3-yl]pyrazole-4-carbonyl]-5-(2,2-difluoroethoxy)-1H-indol-6-yl]pyridine-3-sulfonamide, (5-1-426) N-[2-[5-amino-1-[4-(2-fluorophenoxy)-2-methylphenyl]pyrazole-4-carbonyl]-5-cyclopropyl-1H-indol-6-yl]-3-fluoropropane-1-sulfonamide, (5-1-427) N-[2-[5-amino-1-[6-(2,6-difluorophenoxy)-4-methylpyridin-3-yl]pyrazole-4-carbonyl]-5-cyclopropyl-1H-indol-6-yl]-3-fluoropropane-1-sulfonamide, (5-1-428) N-[2-[5-amino-1-[6-(2-fluorophenoxy)-4-methylpyridin-3-yl]pyrazole-4-carbonyl]-5-cyclopropyl-1H-indol-6-yl]-3-fluoropropane-1-sulfonamide, (5-1-429) 3-[2-[5-amino-1-[6-(2,6-difluorophenoxy)-4-methylpyridin-3-yl]pyrazole-4-carbonyl]-5-methyl-1H-indol-6-yl]-5-methyl-5-(trifluoromethyl)imidazolidine-2,4-dione, (5-1-430) (5 S)-3-[2-[5-amino-1-[6-(2,6-difluorophenoxy)-4-methylpyridin-3-yl]pyrazole-4-carbonyl]-5-fluoro-1H-indol-6-yl]-5-benzylimidazolidine-2,4-dione, (5-1-431) (5S)-3-[2-[5-amino-1-[6-(2,6-difluorophenoxy)-4-methylpyridin-3-yl]pyrazole-4-carbonyl]-5-fluoro-1H-indol-6-yl]-5-propan-2-ylimidazolidine-2,4-dione, (5-1-432) (7aS)-2-[2-[5-amino-1-[6-(2,6-difluorophenoxy)-4-methylpyridin-3-yl]pyrazole-4-carbonyl]-5-fluoro-1H-indol-6-yl]-5,6,7,7a-tetrahydropyrrolo[1,2-c]imidazole-1,3-dione, (5-1-433) (6R,7aS)-2-[2-[5-amino-1-[6-(2,6-difluorophenoxy)-4-methylpyridin-3-yl]pyrazole-4-carbonyl]-5-fluoro-1H-indol-6-yl]-6-hydroxy-5,6,7,7a-tetrahydropyrrolo[1,2-c]imidazole-1,3-dione, (5-1-434) 3-[2-[5-amino-1-[4-(2-fluorophenoxy)-2-methylphenyl]pyrazole-4-carbonyl]-5-methyl-1H-indol-6-yl]imidazolidine-2,4-dione, (5-1-435) 3-[2-[5-amino-1-[4-(2-fluorophenoxy)-2-methylphenyl]pyrazole-4-carbonyl]-5-methyl-1H-indol-6-yl]-5-methyl-5-(trifluoromethyl)imidazolidine-2,4-dione, (5-1-436) (5 S)-3-[2-[5-amino-1-[4-(2-fluorophenoxy)-2-methylphenyl]pyrazole-4-carbonyl]-5-fluoro-1H-indol-6-yl]-5-benzylimidazolidine-2,4-dione, (5-1-437) 3-[2-[5-amino-1-[4-(2-fluorophenoxy)-2-methylphenyl]pyrazole-4-carbonyl]-5-fluoro-1H-indol-6-yl]-8-oxa-1,3-diazaspiro[4.5]decane-2,4-dione, (5-1-438) 3-[2-[5-amino-1-[4-(2-fluorophenoxy)-2-methylphenyl]pyrazole-4-carbonyl]-5-fluoro-1H-indol-6-yl]-1,3-diazaspiro[4.4]nonane-2,4-dione, (5-1-439) N-[2-[5-amino-1-[6-(2-fluorophenoxy)-4-methylpyridin-3-yl]pyrazole-4-carbonyl]-5-methyl-1H-indol-6-yl]-3-methoxybenzenesulfonamide, (5-1-440) N-[2-[5-amino-1-[6-(2-fluorophenoxy)-4-methylpyridin-3-yl]pyrazole-4-carbonyl]-5-methyl-1H-indol-6-yl]-3-cyanobenzenesulfonamide, (5-1-441) N-[2-[5-amino-1-[6-(2-fluorophenoxy)-4-methylpyridin-3-yl]pyrazole-4-carbonyl]-5-methyl-1H-indol-6-yl]pyridine-3-sulfonamide, (5-1-442) 3-[2-[5-amino-1-[6-(2,6-difluorophenoxy)-4-methylpyridin-3-yl]pyrazole-4-carbonyl]-5-methyl-1H-indol-6-yl]imidazolidine-2,4-dione, (5-1-443) (5 S)-3-[2-[5-amino-1-[6-(2,6-difluorophenoxy)-4-methylpyridin-3-yl]pyrazole-4-carbonyl]-5-methyl-1H-indol-6-yl]-5-methylimidazolidine-2,4-dione, (5-1-444) (5 S)-3-[2-[5-amino-1-[4-(2-fluorophenoxy)-2-methylphenyl]pyrazole-4-carbonyl]-5-methyl-1H-indol-6-yl]-5-methylimidazolidine-2,4-dione, (5-1-445) 3-[2-[5-amino-1-[4-(2-fluorophenoxy)-2-methylphenyl]pyrazole-4-carbonyl]-5-fluoro-1H-indol-6-yl]imidazolidine-2,4-dione, (5-1-446) (5 S)-3-[2-[5-amino-1-[4-(2-fluorophenoxy)-2-methylphenyl]pyrazole-4-carbonyl]-5-fluoro-1H-indol-6-yl]-5-(hydroxymethyl)imidazolidine-2,4-dione, (5-1-447) (5 S)-3-[2-[5-amino-1-[4-(2-fluorophenoxy)-2-methylphenyl]pyrazole-4-carbonyl]-5-fluoro-1H-indol-6-yl]-5-propan-2-ylimidazolidine-2,4-dione, (5-1-448) (7aS)-2-[2-[5-amino-1-[4-(2-fluorophenoxy)-2-methylphenyl]pyrazole-4-carbonyl]-5-fluoro-1H-indol-6-yl]-5,6,7,7a-tetrahydropyrrolo[1,2-c]imidazole-1,3-dione, (5-1-449) (6R,7aS)-2-[2-[5-amino-1-[4-(2-fluorophenoxy)-2-methylphenyl]pyrazole-4-carbonyl]-5-fluoro- 1H-indol-6-yl]-6-hydroxy-5,6,7,7a-tetrahydropyrrolo[1,2-c]imidazole-1,3-dione, (5-1-450) 3-[2-[5-amino-1-[4-(2-fluorophenoxy)-2-methylphenyl]pyrazole-4-carbonyl]-5-fluoro-1H-indol-6-yl]-1,3-diazaspiro[4.5]decane-2,4-dione, (5-1-451) (5 S)-3-[2-[5-amino-1-[6-(2,6-difluorophenoxy)-4-methylpyridin-3-yl]pyrazole-4-carbonyl]-5-methyl-1H-indol-6-yl]-5-(hydroxymethyl)imidazolidine-2,4-dione, (5-1-452) (5 S)-3-[2-[5-amino-1-[6-(2,6-difluorophenoxy)-4-methylpyridin-3-yl]pyrazole-4-carbonyl]-5-methyl-1H-indol-6-yl]-5-benzylimidazolidine-2,4-dione, (5-1-453) (5 S)-3-[2-[5-amino-1-[6-(2,6-difluorophenoxy)-4-methylpyridin-3-yl]pyrazole-4-carbonyl]-5-methyl-1H-indol-6-yl]-5-propan-2-ylimidazolidine-2,4-dione, (5-1-454) (7aS)-2-[2-[5-amino-1-[6-(2,6-difluorophenoxy)-4-methylpyridin-3-yl]pyrazole-4-carbonyl]-5-methyl-1H-indol-6-yl]-5,6,7,7a-tetrahydropyrrolo[1,2-c]imidazole-1,3-dione, (5-1-455) (6R,7aS)-2-[2-[5-amino-1-[6-(2,6-difluorophenoxy)-4-methylpyridin-3-yl]pyrazole-4-carbonyl]-5-methyl-1H-indol-6-yl]-6-hydroxy-5,6,7,7a-tetrahydropyrrolo[1,2-c]imidazole-1,3-dione, (5-1-456) (5 S)-3-[2-[5-amino-1-[4-(2-fluorophenoxy)-2-methylphenyl]pyrazole-4-carbonyl]-5-methyl-1H-indol-6-yl]-5-(hydroxymethyl)imidazolidine-2,4-dione, (5-1-457) (5 S)-3-[2-[5-amino-1-[4-(2-fluorophenoxy)-2-methylphenyl]pyrazole-4-carbonyl]-5-methyl-1H-indol-6-yl]-5-benzylimidazolidine-2,4-dione, (5-1-458) (7aS)-2-[2-[5-amino-1-[4-(2-fluorophenoxy)-2-methylphenyl]pyrazole-4-carbonyl]-5-methyl-1H-indol-6-yl]-5,6,7,7a-tetrahydropyrrolo[1,2-c]imidazole-1,3-dione, (5-1-459) (6R,7aS)-2-[2-[5-amino-1-[4-(2-fluorophenoxy)-2-methylphenyl]pyrazole-4-carbonyl]-5-methyl-1H-indol-6-yl]-6-hydroxy-5,6,7,7a-tetrahydropyrrolo[1,2-c]imidazole-1,3-dione, (5-1-460) N-[2-[5-amino-1-[6-(2-fluorophenoxy)-4-methylpyridin-3-yl]pyrazole-4-carbonyl]-5-methyl-1H-indol-6-yl]-3,5-difluorobenzenesulfonamide, (5-1-461) N-[2-[5-amino-1-[6-(2-fluorophenoxy)-4-methylpyridin-3-yl]pyrazole-4-carbonyl]-5-methyl-1H-indol-6-yl]-2,4,6-trimethylbenzenesulfonamide, (5-1-462) N-[2-[5-amino-1-[6-(2-fluorophenoxy)-4-methylpyridin-3-yl]pyrazole-4-carbonyl]-5-methyl-1H-indol-6-yl]-3-methylbenzenesulfonamide, (5-1-463) N-[2-[5-amino-1-[6-(2-fluorophenoxy)-4-methylpyridin-3-yl]pyrazole-4-carbonyl]-5-methyl-1H-indol-6-yl]-3-(trifluoromethyl)benzenesulfonamide, (5-1-464) N-[2-[5-amino-1-[6-(2-fluorophenoxy)-4-methylpyridin-3-yl]pyrazole-4-carbonyl]-5-methyl-1H-indol-6-yl]-3-chlorobenzenesulfonamide, (5-1-465) N-[2-[5-amino-1-[6-(2-fluorophenoxy)-4-methylpyridin-3-yl]pyrazole-4-carbonyl]-5-methyl-1H-indol-6-yl]naphthalene-1-sulfonamide, (5-1-466) N-[2-[5-amino-1-[6-(2-fluorophenoxy)-4-methylpyridin-3-yl]pyrazole-4-carbonyl]-5-methyl-1H-indol-6-yl]naphthalene-2-sulfonamide, (5-1-467) N-[2-[5-amino-1-[6-(2-fluorophenoxy)-4-methylpyridin-3-yl]pyrazole-4-carbonyl]-5-methyl-1H-indol-6-yl]-1-benzothiophene-3-sulfonamide, (5-1-468) 7-[2-[5-amino-1-[4-(2-fluorophenoxy)-3-methylphenyl]pyrazole-4-carbonyl]-5-methyl-1H-indol-6-yl]-5,7-diazaspiro[3.4]octane-6,8-dione, (5-1-469) 3-[2-[5-amino-1-[4-(2-fluorophenoxy)-3-methylphenyl]pyrazole-4-carbonyl]-5-methyl-1H-indol-6-yl]-8-oxa-1,3-diazaspiro[4.5]decane-2,4-dione, (5-1-470) 3-[2-[5-amino-1-[4-(2-fluorophenoxy)-3-methylphenyl]pyrazole-4-carbonyl]-5-methyl-1H-indol-6-yl]-1,3-diazaspiro[4.5]decane-2,4-dione, (5-1-471) tert-Butyl 3-[2-[5-amino-1-[4-(2-fluorophenoxy)-3-methylphenyl]pyrazole-4-carbonyl]-5-methyl-1H-indol-6-yl]-2,4-dioxo-1,3,8-triazaspiro[4.5]decane-8-carboxylate, (5-1-472) 3-[2-[5-amino-1-[4-(2-fluorophenoxy)-3-methylphenyl]pyrazole-4-carbonyl]-5-methyl-1H-indol-6-yl]-5-methyl-5-(trifluoromethyl)imidazolidine-2,4-dione, (5-1-473) 6-[2-[5-amino-1-[4-(2-fluorophenoxy)-3-methylphenyl]pyrazole-4-carbonyl]-5-methyl-1H-indol-6-yl]-4,6-diazaspiro[2.4]heptane-5,7-dione, (5-1-474) 3-[2-[5-amino-1-[4-(2-fluorophenoxy)-3-methylphenyl]pyrazole-4-carbonyl]-5-methyl-1H-indol-6-yl]-1,3-diazaspiro[4.4]nonane-2,4-dione, (5-1-475) 7-[2-[5-amino-1-[4-(2-fluorophenoxy)-3-methylphenyl]pyrazole-4-carbonyl]-5-methyl-1H-indol-6-yl]-2-oxa-5,7-diazaspiro[3.4]octane-6,8-dione, (5-1-476) (5 S)-3-[2-[5-amino-1-[4-(2-fluorophenoxy)-2-methylphenyl]pyrazole-4-carbonyl]-5-methyl-1H-indol-6-yl]-5-propan-2-ylimidazolidine-2,4-dione, (5-1-477) N-[2-[5-amino-1-[6-(2-fluorophenoxy)-4-methylpyridin-3-yl]pyrazole-4-carbonyl]-5-methyl-1H-indol-6-yl]pyridine-2-sulfonamide, (5-1-478) N-[2-[5-amino-1-[6-(2-fluorophenoxy)-4-methylpyridin-3-yl]pyrazole-4-carbonyl]-5-methyl-1H-indol-6-yl]-4-cyanopyridine-2-sulfonamide, (5-1-479) N-[2-[5-amino-1-[6-(2-fluorophenoxy)-4-methylpyridin-3-yl]pyrazole-4-carbonyl]-5-methyl-1H-indol-6-yl]-6-cyanopyridine-2-sulfonamide, (5-1-480) N-[2-[5-amino-1-[6-(2-fluorophenoxy)-4-methylpyridin-3-yl]pyrazole-4-carbonyl]-5-methyl-1H-indol-6-yl]-5-cyanopyridine-3-sulfonamide, (5-1-481) N-[2-[5-amino-1-[6-(2-fluorophenoxy)-4-methylpyridin-3-yl]pyrazole-4-carbonyl]-5-methyl-1H-indol-6-yl]-4-cyano-6-methylpyridine-2-sulfonamide, (5-1-482) N-[2-[5-amino-1-[6-(2-fluorophenoxy)-4-methylpyridin-3-yl]pyrazole-4-carbonyl]-5-methyl-1H-indol-6-yl]-4-methoxypyridine-2-sulfonamide, (5-1-483) N-[2-[5-amino-1-[6-(2-fluorophenoxy)-4-methylpyridin-3-yl]pyrazole-4-carbonyl]-5-methyl-1H-indol-6-yl]-6-methoxypyridine-2-sulfonamide, (5-1-484) N-[2-[5-amino-1-[6-(2-fluorophenoxy)-4-methylpyridin-3-yl]pyrazole-4-carbonyl]-5-methyl-1H-indol-6-yl]-5-methoxypyridine-3-sulfonamide, (5-1-485) N-[2-[5-amino-1-[6-(2-fluorophenoxy)-4-methylpyridin-3-yl]pyrazole-4-carbonyl]-5-methyl-1H-indol-6-yl]-4-(trifluoromethyl)pyridine-2-sulfonamide, (5-1-486) N-[2-[5-amino-1-[6-(2-fluorophenoxy)-4-methylpyridin-3-yl]pyrazole-4-carbonyl]-5-methyl-1H-indol-6-yl]-6-(trifluoromethyl)pyridine-2-sulfonamide, (5-1-487) N-[2-[5-amino-1-[6-(2-fluorophenoxy)-4-methylpyridin-3-yl]pyrazole-4-carbonyl]-5-methyl-1H-indol-6-yl]-5-(trifluoromethyl)pyridine-3-sulfonamide, (5-1-488) N-[2-[5-amino-1-[6-(2-fluorophenoxy)-4-methylpyridin-3-yl]pyrazole-4-carbonyl]-5-methyl-1H-indol-6-yl]-5-methylpyridine-3-sulfonamide, (5-1-489) N-[2-[5-amino-1-[4-(2-fluorophenoxy)-2-methylphenyl]pyrazole-4-carbonyl]-5-fluoro-1H-indol-6-yl]pyridine-3-sulfonamide,
(5-1-490) N-[2-[5-amino-1-[4-(2-fluorophenoxy)-2-methylphenyl]pyrazole-4-carbonyl]-5-fluoro-1H-indol-6-yl]-3-cyanobenzenesulfonamide,
(5-1-491) N-[2-[5-amino-1-[6-(2,6-difluorophenoxy)-4-methylpyridin-3-yl]pyrazole-4-carbonyl]-5-fluoro-1H-indol-6-yl]pyridine-3-sulfonamide,
(5-1-492) N-[2-[5-amino-1-[6-(2,6-difluorophenoxy)-4-methylpyridin-3-yl]pyrazole-4-carbonyl]-5-fluoro-1H-indol-6-yl]-3-cyanobenzenesulfonamide,
(5-1-493) N-[2-[5-amino-1-[4-(2-fluorophenoxy)-3-methylphenyl]pyrazole-4-carbonyl]-5-fluoro-1H-indol-6-yl]oxane-4-sulfonamide,
(5-1-494) N-[2-[5-amino-1-[6-(2-fluorophenoxy)-4-methylpyridin-3-yl]pyrazole-4-carbonyl]-5-methyl-1H-indol-6-yl]-5-fluoropyridine-3-sulfonamide,
(5-1-495) N-[2-[5-amino-1-[6-(2-fluorophenoxy)-4-methylpyridin-3-yl]pyrazole-4-carbonyl]-5-methyl-1H-indol-6-yl]-5-chloropyridine-3-sulfonamide,
(5-1-496) N-[2-[5-amino-1-[6-(2-fluorophenoxy)-4-methylpyridin-3-yl]pyrazole-4-carbonyl]-5-methyl-1H-indol-6-yl]-3-fluoro-5-methoxybenzenesulfonamide,
(5-1-497) N-[2-[5-amino-1-[6-(2-fluorophenoxy)-4-methylpyridin-3-yl]pyrazole-4-carbonyl]-5-methyl-1H-indol-6-yl]-3-cyano-5-fluorobenzenesulfonamide,
(5-1-498) N-[2-[5-amino-1-[6-(2-fluorophenoxy)-4-methylpyridin-3-yl]pyrazole-4-carbonyl]-5-methyl-1H-indol-6-yl]-3-chloro-5-cyanobenzenesulfonamide,
(5-1-499) N-[2-[5-amino-1-[6-(2-fluorophenoxy)-4-methylpyridin-3-yl]pyrazole-4-carbonyl]-5-methyl-1H-indol-6-yl]-3-cyano-5-(trifluoromethyl)benzenesulfonamide,
(5-1-500) N-[2-[5-amino-1-[6-(2-fluorophenoxy)-4-methylpyridin-3-yl]pyrazole-4-carbonyl]-5-methyl-1H-indol-6-yl]-3-fluorobenzenesulfonamide,
(5-1-501) N-[2-[5-amino-1-[6-(2-fluorophenoxy)-4-methylpyridin-3-yl]pyrazole-4-carbonyl]-5-methyl-1H-indol-6-yl]-2,4,6-trifluorobenzenesulfonamide,
(5-1-502) N-[2-[5-amino-1-[6-(2-fluorophenoxy)-4-methylpyridin-3-yl]pyrazole-4-carbonyl]-5-methyl-1H-indol-6-yl]-6-fluoropyridine-2-sulfonamide,
(5-1-503) [5-amino-1-[6-(2,6-difluorophenoxy)-4-methylpyridin-3-yl]pyrazol-4-yl]-[5-(1-cyclopentylpiperidin-4-yl)oxy-6-(2-methoxyphenyl)-1H-indol-2-yl]methanone,
(5-1-504) N-[2-[5-amino-1-[6-(2-fluorophenoxy)-4-methylpyridin-3-yl]pyrazole-4-carbonyl]-5-methyl-1H-indol-6-yl]-2-fluoro-5-methylpyridine-3-sulfonamide,
(5-1-505) N-[2-[5-amino-1-[6-(2-fluorophenoxy)-4-methylpyridin-3-yl]pyrazole-4-carbonyl]-5-methyl-1H-indol-6-yl]-4-fluoropyridine-2-sulfonamide,
(5-1-506) N-[2-[5-amino-1-[6-(2-fluorophenoxy)-4-methylpyridin-3-yl]pyrazole-4-carbonyl]-5-methyl-1H-indol-6-yl]-4-methylpyridine-2-sulfonamide,
(5-1-507) N-[2-[5-amino-1-[6-(2-fluorophenoxy)-4-methylpyridin-3-yl]pyrazole-4-carbonyl]-5-methyl-1H-indol-6-yl]-6-methylpyridine-2-sulfonamide,
(5-1-508) N-[2-[5-amino-1-[6-(2-fluorophenoxy)-4-methylpyridin-3-yl]pyrazole-4-carbonyl]-5-methyl-1H-indol-6-yl]-6-chloropyridine-2-sulfonamide,
(5-1-509) N-[2-[5-amino-1-[6-(2-fluorophenoxy)-4-methylpyridin-3-yl]pyrazole-4-carbonyl]-5-methyl-1H-indol-6-yl]-4-chloropyridine-2-sulfonamide,
(5-1-510) N-[2-[5-amino-1-[4-(2-fluorophenoxy)-2-methylphenyl]pyrazole-4-carbonyl]-5-methyl-1H-indol-6-yl]-4-methoxypyridine-2-sulfonamide,
(5-1-511) N-[2-[5-amino-1-[6-(2,6-difluorophenoxy)-4-methylpyridin-3-yl]pyrazole-4-carbonyl]-5-methyl-1H-indol-6-yl]-4-methoxypyridine-2-sulfonamide,
(5-1-512) N-[2-[5-amino-1-[4-(2-fluorophenoxy)-2-methylphenyl]pyrazole-4-carbonyl]-5-fluoro-1H-indol-6-yl]-4-methoxypyridine-2-sulfonamide,
(5-1-513) N-[2-[5-amino-1-[6-(2,6-difluorophenoxy)-4-methylpyridin-3-yl]pyrazole-4-carbonyl]-5-fluoro-1H-indol-6-yl]-4-methoxypyridine-2-sulfonamide,
(5-1-514) N-[2-[5-amino-1-[6-(2-fluorophenoxy)-4-methylpyridin-3-yl]pyrazole-4-carbonyl]-5-fluoro-1H-indol-6-yl]-4-methoxypyridine-2-sulfonamide,
(5-1-515) N-[2-[5-amino-1-[4-(2-fluorophenoxy)-2-methylphenyl]pyrazole-4-carbonyl]-5-methyl-1H-indol-6-yl]-6-fluoropyridine-2-sulfonamide,
(5-1-516) N-[2-[5-amino-1-[6-(2,6-difluorophenoxy)-4-methylpyridin-3-yl]pyrazole-4-carbonyl]-5-methyl-1H-indol-6-yl]-6-fluoropyridine-2-sulfonamide,
(5-1-517) N-[2-[5-amino-1-[4-(2-fluorophenoxy)-2-methylphenyl]pyrazole-4-carbonyl]-5-fluoro-1H-indol-6-yl]-6-fluoropyridine-2-sulfonamide,
(5-1-518) N-[2-[5-amino-1-[6-(2,6-difluorophenoxy)-4-methylpyridin-3-yl]pyrazole-4-carbonyl]-5-fluoro-1H-indol-6-yl]-6-fluoropyridine-2-sulfonamide,
(5-1-519) N-[2-[5-amino-1-[6-(2-fluorophenoxy)-4-methylpyridin-3-yl]pyrazole-4-carbonyl]-5-fluoro-1H-indol-6-yl]-6-fluoropyridine-2-sulfonamide,
(5-1-520) N-[2-[5-amino-1-[4-(2-fluorophenoxy)-2-methylphenyl]pyrazole-4-carbonyl]-5-methyl-1H-indol-6-yl]-2-fluoro-5-methylpyridine-3-sulfonamide,
(5-1-521) N-[2-[5-amino-1-[6-(2,6-difluorophenoxy)-4-methylpyridin-3-yl]pyrazole-4-carbonyl]-5-methyl-1H-indol-6-yl]-2-fluoro-5-methylpyridine-3-sulfonamide,
(5-1-522) N-[2-[5-amino-1-[4-(2-fluorophenoxy)-2-methylphenyl]pyrazole-4-carbonyl]-5-fluoro-1H-indol-6-yl]-2-fluoro-5-methylpyridine-3-sulfonamide,
(5-1-523) N-[2-[5-amino-1-[6-(2,6-difluorophenoxy)-4-methylpyridin-3-yl]pyrazole-4-carbonyl]-5-fluoro-1H-indol-6-yl]-2-fluoro-5-methylpyridine-3-sulfonamide,
(5-1-524) N-[2-[5-amino-1-[6-(2-fluorophenoxy)-4-methylpyridin-3-yl]pyrazole-4-carbonyl]-5-fluoro-1H-indol-6-yl]-2-fluoro-5-methylpyridine-3-sulfonamide,
(5-1-525) N-[2-[5-amino-1-[4-(2-fluorophenoxy)-2-methylphenyl]pyrazole-4-carbonyl]-5-methyl-1H-indol-6-yl]-6-chloropyridine-2-sulfonamide,
(5-1-526) N-[2-[5-amino-1-[6-(2,6-difluorophenoxy)-4-methylpyridin-3-yl]pyrazole-4-carbonyl]-5-methyl-1H-indol-6-yl]-6-chloropyridine-2-sulfonamide,
(5-1-527) N-[2-[5-amino-1-[4-(2-fluorophenoxy)-2-methylphenyl]pyrazole-4-carbonyl]-5-fluoro-1H-indol-6-yl]-6-chloropyridine-2-sulfonamide,
(5-1-528) N-[2-[5-amino-1-[6-(2,6-difluorophenoxy)-4-methylpyridin-3-yl]pyrazole-4-carbonyl]-5-fluoro-1H-indol-6-yl]-6-chloropyridine-2-sulfonamide,
(5-1-529) N-[2-[5-amino-1-[6-(2-fluorophenoxy)-4-methylpyridin-3-yl]pyrazole-4-carbonyl]-5-fluoro-1H-indol-6-yl]-6-chloropyridine-2-sulfonamide,
(5-1-530) N-[2-[5-amino-1-[4-(2-fluorophenoxy)-2-methylphenyl]pyrazole-4-carbonyl]-5-methyl-1H-indol-6-yl]-6-methylpyridine-2-sulfonamide,
(5-1-531) N-[2-[5-amino-1-[6-(2,6-difluorophenoxy)-4-methylpyridin-3-yl]pyrazole-4-carbonyl]-5-methyl-1H-indol-6-yl]-6-methylpyridine-2-sulfonamide, (5-1-532) N-[2-[5-amino-1-[4-(2-fluorophenoxy)-2-methylphenyl]pyrazole-4-carbonyl]-5-fluoro-1H-indol-6-yl]-6-methylpyridine-2-sulfonamide,
(5-1-533) N-[2-[5-amino-1-[6-(2,6-difluorophenoxy)-4-methylpyridin-3-yl]pyrazole-4-carbonyl]-5-fluoro-1H-indol-6-yl]-6-methylpyridine-2-sulfonamide,
(5-1-534) N-[2-[5-amino-1-[6-(2-fluorophenoxy)-4-methylpyridin-3-yl]pyrazole-4-carbonyl]-5-fluoro-1H-indol-6-yl]-6-methylpyridine-2-sulfonamide,
(5-1-535) N-[2-[5-amino-1-[4-(2-fluorophenoxy)-2-methylphenyl]pyrazole-4-carbonyl]-5-methyl-1H-indol-6-yl]-6-cyanopyridine-2-sulfonamide,
(5-1-536) N-[2-[5-amino-1-[6-(2,6-difluorophenoxy)-4-methylpyridin-3-yl]pyrazole-4-carbonyl]-5-methyl-1H-indol-6-yl]-6-cyanopyridine-2-sulfonamide,
(5-1-537) N-[2-[5-amino-1-[4-(2-fluorophenoxy)-2-methylphenyl]pyrazole-4-carbonyl]-5-fluoro-1H-indol-6-yl]-6-cyanopyridine-2-sulfonamide,
(5-1-538) N-[2-[5-amino-1-[6-(2,6-difluorophenoxy)-4-methylpyridin-3-yl]pyrazole-4-carbonyl]-5-fluoro-1H-indol-6-yl]-6-cyanopyridine-2-sulfonamide,
(5-1-539) N-[2-[5-amino-1-[6-(2-fluorophenoxy)-4-methylpyridin-3-yl]pyrazole-4-carbonyl]-5-fluoro-1H-indol-6-yl]-6-cyanopyridine-2-sulfonamide,
(5-1-540) N-[2-[5-amino-1-[4-(2-fluorophenoxy)-2-methylphenyl]pyrazole-4-carbonyl]-5-methyl-1H-indol-6-yl]-5-chloropyridine-3-sulfonamide,
(5-1-541) N-[2-[5-amino-1-[6-(2,6-difluorophenoxy)-4-methylpyridin-3-yl]pyrazole-4-carbonyl]-5-methyl-1H-indol-6-yl]-5-chloropyridine-3-sulfonamide,
(5-1-542) N-[2-[5-amino-1-[4-(2-fluorophenoxy)-2-methylphenyl]pyrazole-4-carbonyl]-5-fluoro-1H-indol-6-yl]-5-chloropyridine-3-sulfonamide,
(5-1-543) N-[2-[5-amino-1-[6-(2,6-difluorophenoxy)-4-methylpyridin-3-yl]pyrazole-4-carbonyl]-5-fluoro-1H-indol-6-yl]-5-chloropyridine-3-sulfonamide,
(5-1-544) N-[2-[5-amino-1-[6-(2-fluorophenoxy)-4-methylpyridin-3-yl]pyrazole-4-carbonyl]-5-fluoro-1H-indol-6-yl]-5-chloropyridine-3-sulfonamide,
(5-1-545) N-[2-[5-amino-1-[4-(2-fluorophenoxy)-2-methylphenyl]pyrazole-4-carbonyl]-5-methyl-1H-indol-6-yl]-5-fluoropyridine-3-sulfonamide,
(5-1-546) N-[2-[5-amino-1-[6-(2,6-difluorophenoxy)-4-methylpyridin-3-yl]pyrazole-4-carbonyl]-5-methyl-1H-indol-6-yl]-5-fluoropyridine-3-sulfonamide,
(5-1-547) N-[2-[5-amino-1-[4-(2-fluorophenoxy)-2-methylphenyl]pyrazole-4-carbonyl]-5-fluoro-1H-indol-6-yl]-5-fluoropyridine-3-sulfonamide,
(5-1-548) N-[2-[5-amino-1-[6-(2,6-difluorophenoxy)-4-methylpyridin-3-yl]pyrazole-4-carbonyl]-5-fluoro-1H-indol-6-yl]-5-fluoropyridine-3-sulfonamide,
(5-1-549) N-[2-[5-amino-1-[6-(2-fluorophenoxy)-4-methylpyridin-3-yl]pyrazole-4-carbonyl]-5-fluoro-1H-indol-6-yl]-5-fluoropyridine-3-sulfonamide,
(5-1-550) N-[2-[5-amino-1-[4-(2-fluorophenoxy)-2-methylphenyl]pyrazole-4-carbonyl]-5-methyl-1H-indol-6-yl]-3-fluorobenzenesulfonamide,
(5-1-551) N-[2-[5-amino-1-[6-(2,6-difluorophenoxy)-4-methylpyridin-3-yl]pyrazole-4-carbonyl]-5-methyl-1H-indol-6-yl]-3-fluorobenzenesulfonamide,
(5-1-552) N-[2-[5-amino-1-[4-(2-fluorophenoxy)-2-methylphenyl]pyrazole-4-carbonyl]-5-fluoro-1H-indol-6-yl]-3-fluorobenzenesulfonamide,
(5-1-553) N-[2-[5-amino-1-[6-(2,6-difluorophenoxy)-4-methylpyridin-3-yl]pyrazole-4-carbonyl]-5-fluoro-1H-indol-6-yl]-3-fluorobenzenesulfonamide,
(5-1-554) N-[2-[5-amino-1-[6-(2-fluorophenoxy)-4-methylpyridin-3-yl]pyrazole-4-carbonyl]-5-fluoro-1H-indol-6-yl]-3-fluorobenzenesulfonamide,
(5-1-555) N-[2-[5-amino-1-[6-(2,6-difluorophenoxy)-4-methylpyridin-3-yl]pyrazole-4-carbonyl]-5-methyl-1H-indol-6-yl]-3-cyanobenzenesulfonamide,
(5-1-556) N-[2-[5-amino-1-[6-(2-fluorophenoxy)-4-methylpyridin-3-yl]pyrazole-4-carbonyl]-5-fluoro-1H-indol-6-yl]-3-cyanobenzenesulfonamide,
(5-1-557) N-[2-[5-amino-1-[6-(2,6-difluorophenoxy)-4-methylpyridin-3-yl]pyrazole-4-carbonyl]-5-methyl-1H-indol-6-yl]-3-chlorobenzenesulfonamide,
(5-1-558) N-[2-[5-amino-1-[4-(2-fluorophenoxy)-2-methylphenyl]pyrazole-4-carbonyl]-5-fluoro-1H-indol-6-yl]-3-chlorobenzenesulfonamide,
(5-1-559) N-[2-[5-amino-1-[6-(2,6-difluorophenoxy)-4-methylpyridin-3-yl]pyrazole-4-carbonyl]-5-fluoro-1H-indol-6-yl]-3-chlorobenzenesulfonamide,
(5-1-560) N-[2-[5-amino-1-[6-(2-fluorophenoxy)-4-methylpyridin-3-yl]pyrazole-4-carbonyl]-5-fluoro-1H-indol-6-yl]-3-chlorobenzenesulfonamide,
(5-1-561) N-[2-[5-amino-1-[6-(2,6-difluorophenoxy)-4-methylpyridin-3-yl]pyrazole-4-carbonyl]-5-methyl-1H-indol-6-yl]-3,5-difluorobenzenesulfonamide,
(5-1-562) N-[2-[5-amino-1-[4-(2-fluorophenoxy)-2-methylphenyl]pyrazole-4-carbonyl]-5-fluoro-1H-indol-6-yl]-3,5-difluorobenzenesulfonamide,
(5-1-563) N-[2-[5-amino-1-[6-(2,6-difluorophenoxy)-4-methylpyridin-3-yl]pyrazole-4-carbonyl]-5-fluoro-1H-indol-6-yl]-3,5-difluorobenzenesulfonamide,
(5-1-564) N-[2-[5-amino-1-[6-(2-fluorophenoxy)-4-methylpyridin-3-yl]pyrazole-4-carbonyl]-5-fluoro-1H-indol-6-yl]-3,5-difluorobenzenesulfonamide,
(5-1-565) N-[2-[5-amino-1-[6-(2,6-difluorophenoxy)-4-methylpyridin-3-yl]pyrazole-4-carbonyl]-5-methyl-1H-indol-6-yl]-2,4,6-trifluorobenzenesulfonamide,
(5-1-566) N-[2-[5-amino-1-[4-(2-fluorophenoxy)-2-methylphenyl]pyrazole-4-carbonyl]-5-fluoro-1H-indol-6-yl]-2,4,6-trifluorobenzenesulfonamide,
(5-1-567) N-[2-[5-amino-1-[6-(2,6-difluorophenoxy)-4-methylpyridin-3-yl]pyrazole-4-carbonyl]-5-fluoro-1H-indol-6-yl]-2,4,6-trifluorobenzenesulfonamide,
(5-1-568) N-[2-[5-amino-1-[6-(2-fluorophenoxy)-4-methylpyridin-3-yl]pyrazole-4-carbonyl]-5-fluoro-1H-indol-6-yl]-2,4,6-trifluorobenzenesulfonamide,
(5-1-569) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-4-methoxypyridine-2-sulfonamide,
(5-1-570) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-6-fluoropyridine-2-sulfonamide,
(5-1-571) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-2-fluoro-5-methylpyridine-3-sulfonamide,
(5-1-572) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-6-chloropyridine-2-sulfonamide,
(5-1-573) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-6-methylpyridine-2-sulfonamide, (5-1-574) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-6-cyanopyridine-2-sulfonamide, (5-1-575) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-5-chloropyridine-3-sulfonamide, (5-1-576) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-5-fluoropyridine-3-sulfonamide, and (5-1-577) N-[2-[5-amino-1-[6-(2-fluorophenoxy)-4-methylpyridin-3-yl]pyrazole-4-carbonyl]-5-methyl-1H-indol-6-yl]-2-(dimethylamino)pyrimidine-5-sulfonamide, or a pharmaceutically acceptable salt thereof.

19. The method of claim 10, wherein the compound or a pharmaceutically acceptable salt thereof is selected from the group consisting of:

(4-1-001) N-[2-[5-amino-1-[6-(2,6-difluorophenoxy)-4-methylpyridin-3-yl]pyrazole-4-carbonyl]-5-methyl-1H-indol-6-yl]methanesulfonamide, (4-1-008) N-[2-[5-amino-1-[6-(2-fluorophenoxy)-4-methylpyridin-3-yl]pyrazole-4-carbonyl]-5-methoxy-1H-indol-6-yl]methanesulfonamide, (4-2-015) N-[2-[5-amino-1-[4-(2-fluorophenoxy)-2-methylphenyl]pyrazole-4-carbonyl]-5-fluoro-1H-indol-6-yl]-3-fluoropropane-1-sulfonamide, (4-2-016) N-[2-[5-amino-1-[4-(2,3-difluorophenoxy)-2-methylphenyl]pyrazole-4-carbonyl]-5-fluoro-1H-indol-6-yl]-3-fluoropropane-1-sulfonamide, (4-2-031) N-[2-[5-amino-1-[6-(2,6-difluorophenoxy)-4-methylpyridin-3-yl]pyrazole-4-carbonyl]-5-fluoro-1H-indol-6-yl]methanesulfonamide, (4-2-032) N-[2-[5-amino-1-[6-(2,3-difluorophenoxy)-4-methylpyridin-3-yl]pyrazole-4-carbonyl]-5-fluoro-1H-indol-6-yl]methanesulfonamide, (4-2-053) N-[2-[5-amino-1-[4-(2-fluorophenoxy)-2-methylphenyl]pyrazole-4-carbonyl]-5-methyl-1H-indol-6-yl]methanesulfonamide, (4-2-055) N-[2-[5-amino-1-[2-fluoro-4-(2-fluorophenoxy)-6-methylphenyl]pyrazole-4-carbonyl]-5-methyl-1H-indol-6-yl]methanesulfonamide, (4-2-061) N-[2-[5-amino-1-[6-(2-fluorophenoxy)-4-methylpyridin-3-yl]pyrazole-4-carbonyl]-5-methyl-1H-indol-6-yl]methanesulfonamide, (4-2-063) N-[2-[5-amino-1-[6-(2-chlorophenoxy)-4-methylpyridin-3-yl]pyrazole-4-carbonyl]-5-methyl-1H-indol-6-yl]methanesulfonamide, (4-2-072) N-[2-[5-amino-1-[6-(2-fluorophenoxy)-4-methylpyridin-3-yl]pyrazole-4-carbonyl]-5-methyl-1H-indol-6-yl]-3-fluoropropane-1-sulfonamide, (4-2-073) N-[2-[5-amino-1-[6-(2,6-difluorophenoxy)-4-methylpyridin-3-yl]pyrazole-4-carbonyl]-5-methyl-1H-indol-6-yl]-3-fluoropropane-1-sulfonamide, (4-5-001) N-[2-[5-amino-1-[6-(2-fluorophenoxy)-4-methylpyridin-3-yl]pyrazole-4-carbonyl]-5-fluoro-1H-indol-6-yl]morpholine-4-sulfonamide, (4-7-001) N-[2-[5-amino-1-[6-(2-fluorophenoxy)-4-methylpyridin-3-yl]pyrazole-4-carbonyl]-5-fluoro-1H-indol-6-yl]methanesulfonamide, (4-7-003) N-[2-[5-amino-1-[2-fluoro-4-(2-fluorophenoxy)-6-methylphenyl]pyrazole-4-carbonyl]-5-fluoro-1H-indol-6-yl]methanesulfonamide, (4-14-002) [5-amino-1-[4-(2-fluorophenoxy)-2-methylphenyl]pyrazol-4-yl]-[6-(1,1-dioxo-1,2-thiazolidin-2-yl)-5-methoxy-1H-indol-2-yl]methanone, (4-16-001) [5-amino-1-[6-(2-fluorophenoxy)-4-methylpyridin-3-yl]pyrazol-4-yl]-[6-(1,1-dioxo-1,2-thiazolidin-2-yl)-5-methyl-1H-indol-2-yl]methanone hydrochloride, (4-17-001) 1-[4-[2-[5-amino-1-[6-(2,6-difluorophenoxy)-4-methylpyridin-3-yl]pyrazole-4-carbonyl]-5-(2,2-difluoroethoxy)-1H-indol-6-yl]piperidin-1-yl]ethanone, (4-24-002) N-[2-[5-amino-1-[4-(2-fluorophenoxy)-2-methylphenyl]pyrazole-4-carbonyl]-5-(difluoromethoxy)-1H-indol-6-yl]methanesulfonamide, (4-24-003) N-[2-[5-amino-1-[4-(2-fluorophenoxy)-2-methylphenyl]pyrazole-4-carbonyl]-5-(difluoromethoxy)-1H-indol-6-yl]-3-fluoropropane-1-sulfonamide, (4-24-028) N-[2-[5-amino-1-[6-(2-fluorophenoxy)-4-methylpyridin-3-yl]pyrazole-4-carbonyl]-5-(2,2-difluoroethoxy)-1H-indol-6-yl]methanesulfonamide, (4-24-032) N-[2-[5-amino-1-[6-(2,6-difluorophenoxy)-4-methylpyridin-3-yl]pyrazole-4-carbonyl]-5-(2,2-difluoroethoxy)-1H-indol-6-yl]-3-fluoropropane-1-sulfonamide, (4-25-009) [5-amino-1-[4-(2-fluorophenoxy)-2-methylphenyl]pyrazol-4-yl]-[5-(2,2-difluoroethoxy)-6-(1,1-dioxo-1,2-thiazolidin-2-yl)-1H-indol-2-yl]methanone, (5-1-223) [5-amino-1-[6-(2,6-difluorophenoxy)-4-methylpyridin-3-yl]pyrazol-4-yl]-[6-bromo-5-(1-cyclopentylpiperidin-4-yl)oxy-1H-indol-2-yl]methanone, (5-1-347) N-[2-[5-amino-1-[4-(2-fluorophenoxy)-2-methylphenyl]pyrazole-4-carbonyl]-5-methyl-1H-indol-6-yl]oxane-4-sulfonamide, (5-1-403) [5-amino-1-[4-(2-fluorophenoxy)-2-methylphenyl]pyrazol-4-yl]-[6-(2,2-dioxo-8-oxa-2λ6-thia-1,3-diazaspiro[4.5]decan-3-yl)-5-fluoro-1H-indol-2-yl]methanone, and (5-1-413) [5-amino-1-[6-(2-fluorophenoxy)-4-methylpyridin-3-yl]pyrazol-4-yl]-[6-(2,2-dioxo-8-oxa-2λ6-thia-1,3-diazaspiro[4.5]decan-3-yl)-5-fluoro-1H-indol-2-yl]methanone, or a pharmaceutically acceptable salt thereof.

20. The method of claim 10, wherein the compound or a pharmaceutically acceptable salt thereof is N-[2-[5-amino-1-[6-(2,6-difluorophenoxy)-4-methylpyridin-3-yl]pyrazole-4-carbonyl]-5-methyl-1H-indol-6-yl]methanesulfonamide or a pharmaceutically acceptable salt thereof.

\* \* \* \* \*

UNITED STATES PATENT AND TRADEMARK OFFICE
CERTIFICATE OF CORRECTION

PATENT NO. : 10,479,780 B2
APPLICATION NO. : 15/736821
DATED : November 19, 2019
INVENTOR(S) : Hirosato Ebiike et al.

Page 1 of 6

It is certified that error appears in the above-identified patent and that said Letters Patent is hereby corrected as shown below:

In the Specification

Column 99, Lines 30-35:

In Example 1-4-13, delete " 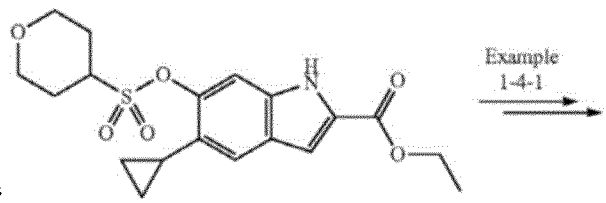 "; and replace it with -- 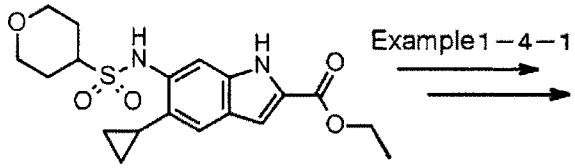 -- therefor.

Column 99, Lines 35-45:

In Example 1-4-13, delete " 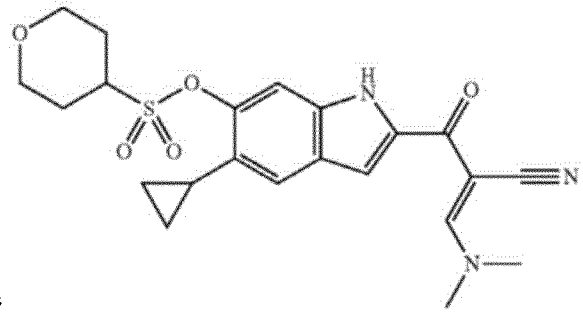 "; and

Signed and Sealed this
Third Day of March, 2020

Andrei Iancu
*Director of the United States Patent and Trademark Office*

Column 107, Example 1-4-13, Compound I-H078:
delete " 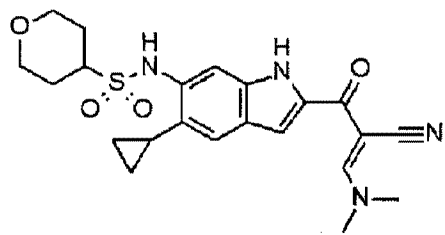 "; and
replace it with -- 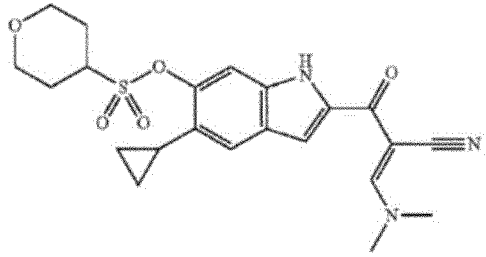 -- therefor.
Column 107, Example 1-4-14, Compound I-H079:
delete " 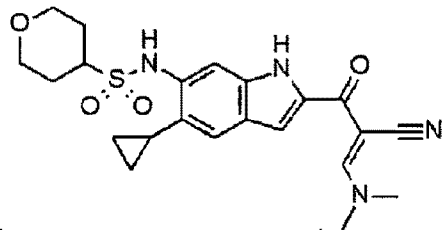 "; and
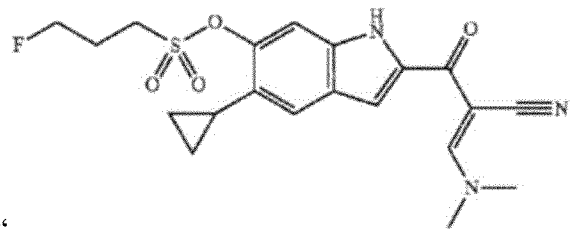
replace it with -- 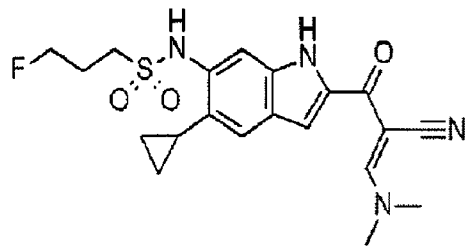 -- therefor.

Columns 585-586, Example 4-10-007:

delete " 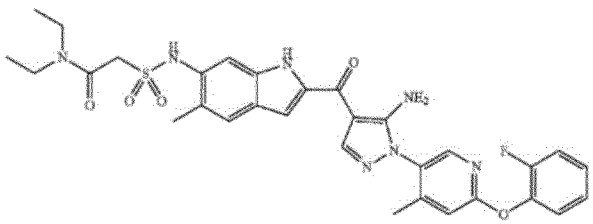 "; and replace it with -- 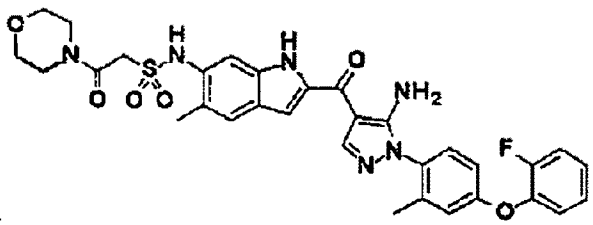 -- therefor.

In the Claims

Column 1593, Line 55: In Claim 1, after "heteroaryl," delete "and".

Column 1594, Line 5: In Claim 1, after "which" delete "may have".

Column 1594, Line 56: In Claim 6, after "substituent," delete "and".

Column 1595, Line 57: In Claim 7, after "substituent" delete "is".

Column 1602, Line 33: In Claim 15, delete "-6-" and insert -- -[6- -- therefor.

Column 1603, Lines 29-30: In Claim 15, delete "(oxan-4-yl sulfamoylamino)" and insert -- (oxan-4-ylsulfamoylamino) -- therefor.

Column 1605, Line 7: In Claim 15, after "trifluoroacetate" insert -- , --.

Column 1606, Line 33: In Claim 15, delete "methyl sulfonylpiperidin-" and insert -- methylsulfonylpiperidin- -- therefor.

Column 1606, Line 44: In Claim 15, delete "(1-methyl sulfonylpiperidin-" and insert -- (1-methylsulfonylpiperidin- -- therefor.

Column 1606, Line 55: In Claim 15, delete "methyl sulfonylpiperidin-" and insert -- methylsulfonylpiperidin- -- therefor.

Column 1609, Line 16 (approx.): In Claim 15, delete "-yl amino)" and insert -- -ylamino) -- therefor.

Column 1609, Line 44: In Claim 15, delete "-yl amino)" and insert -- -ylamino) -- therefor.

Column 1609, Line 55 (approx.): In Claim 15, delete "-yl amino)" and insert -- -ylamino) -- therefor.

Column 1609, Line 59 (approx.): In Claim 15, delete "-yl amino)" and insert -- -ylamino) -- therefor.

Column 1613, Line 52: In Claim 15, after "one" insert -- , --.

Column 1613, Line 55: In Claim 15, after "one" insert -- , --.

Column 1613, Line 58: In Claim 15, after "one" insert -- , --.

Column 1613, Line 61: In Claim 15, after "one" insert -- , --.

Column 1613, Line 64: In Claim 15, after "one" insert -- , --.

Column 1613, Line 67: In Claim 15, after "one" insert -- , --.

Column 1614, Line 3: In Claim 15, after "one" insert -- , --.

Column 1626, Line 36: In Claim 15, delete "(5 S)-" and insert -- (5S)- -- therefor.

Column 1627, Line 7: In Claim 15, delete "(6 S," and insert -- (6S, -- therefor.

Column 1629, Line 1: In Claim 15, delete "(5 S)-" and insert -- (5S)- -- therefor.

Column 1629, Line 26: In Claim 15, delete "(5 S)-" and insert -- (5S)- -- therefor.

Column 1629, Line 31 (approx.): In Claim 15, delete "(5 S)-" and insert -- (5S)- -- therefor.

Column 1629, Line 35 (approx.): In Claim 15, delete "(5 S)-" and insert -- (5S)- -- therefor.

Column 1629, Line 65: In Claim 15, delete "-dimethyl-, 1-dioxo" and insert -- -dimethyl-1,1-dioxo -- therefor.

Column 1631, Lines 65-66: In Claim 15, delete "(difluoromethyl sulfanyl)" and insert -- (difluoromethylsulfanyl) -- therefor.

Column 1632, Line 28: In Claim 15, delete "(5 S)-" and insert -- (5S)- -- therefor.

Column 1635, Line 36: In Claim 15, delete "(5 S)-" and insert -- (5S)- -- therefor.

Column 1635, Line 40: In Claim 15, delete "(5 S)-" and insert -- (5S)- -- therefor.

Column 1635, Line 53: In Claim 15, delete "(5 S)-" and insert -- (5S)- -- therefor.

Column 1636, Line 56: In Claim 15, delete "(5 S)-" and insert -- (5S)- -- therefor.

Column 1637, Line 12: In Claim 15, delete "(5 S)-" and insert -- (5S)- -- therefor.

Column 1637, Line 33: In Claim 15, delete "(5 S)-" and insert -- (5S)- -- therefor.

Column 1637, Line 37: In Claim 15, delete "(5 S)-" and insert -- (5S)- -- therefor.

Column 1637, Line 43: In Claim 15, delete "(5 S)-" and insert -- (5S)- -- therefor.

Column 1637, Line 46: In Claim 15, delete "(5 S)-" and insert -- (5S)- -- therefor.

Column 1637, Line 64: In Claim 15, delete "(5 S)-" and insert -- (5S)- -- therefor.

Column 1638, Line 1: In Claim 15, delete "(5 S)-" and insert -- (5S)- -- therefor.

Column 1638, Line 14 (approx.): In Claim 15, delete "(5 S)-" and insert -- (5S)- -- therefor.

Column 1638, Line 17 (approx.): In Claim 15, delete "(5 S)-" and insert -- (5S)- -- therefor.

Column 1639, Line 14 (approx.): In Claim 15, delete "(5 S)-" and insert -- (5S)- -- therefor.

Column 1651, Line 48: In Claim 18, delete "-6-" and insert -- [6- -- therefor.

Column 1652, Lines 45-46: In Claim 18, delete "yl sulfamoylamino)" and insert
-- ylsulfamoylamino) -- therefor.

Column 1654, Line 22: In Claim 18, after "trifluoroacetate" insert -- , --.

Column 1658, Line 26: In Claim 18, delete "-yl amino)-" and insert -- -ylamino)- -- therefor.

Column 1658, Line 53: In Claim 18, delete "-yl amino)-" and insert -- -ylamino)- -- therefor.

Column 1658, Line 64: In Claim 18, delete "-yl amino)-" and insert -- -ylamino)- -- therefor.

Column 1658, Line 67: In Claim 18, delete "-yl amino)-" and insert -- -ylamino)- -- therefor.

Column 1662, Line 64: In Claim 18, after "one" insert -- , --.

Column 1662, Line 67: In Claim 18, after "one" insert -- , --.

Column 1663, Line 3: In Claim 18, after "one" insert -- , --.

Column 1663, Line 6: In Claim 18, after "one" insert -- , --.

Column 1663, Line 9: In Claim 18, after "one" insert -- , --.

Column 1663, Line 13: In Claim 18, after "one" insert -- , --.

Column 1663, Line 16 (approx.): In Claim 18, after "one" insert -- , --.

CERTIFICATE OF CORRECTION (continued)
U.S. Pat. No. 10,479,780 B2

Column 1675, Line 49: In Claim 18, delete "(5 S)-" and insert -- (5S)- -- therefor.

Column 1678, Line 16: In Claim 18, delete "(5 S)-" and insert -- (5S)- -- therefor.

Column 1678, Line 40: In Claim 18, delete "(5 S)-" and insert -- (5S)- -- therefor.

Column 1678, Line 44: In Claim 18, delete "(5 S)-" and insert -- (5S)- -- therefor.

Column 1678, Line 48: In Claim 18, delete "(5 S)-" and insert -- (5S)- -- therefor.

Column 1681, Lines 11-12 (approx.): In Claim 18, delete "(difluoromethyl sulfanyl)" and insert -- (difluoromethylsulfanyl) -- therefor.

Column 1681, Line 41: In Claim 18, delete "(5 S)-" and insert -- (5S)- -- therefor.

Column 1684, Line 48: In Claim 18, delete "(5 S)-" and insert -- (5S)- -- therefor.

Column 1684, Line 52: In Claim 18, delete "(5 S)-" and insert -- (5S)- -- therefor.

Column 1684, Line 65: In Claim 18, delete "(5 S)-" and insert -- (5S)- -- therefor.

Column 1686, Line 1: In Claim 18, delete "(5 S)-" and insert -- (5S)- -- therefor.

Column 1686, Line 25: In Claim 18, delete "(5 S)-" and insert -- (5S)- -- therefor.

Column 1686, Line 46: In Claim 18, delete "(5 S)-" and insert -- (5S)- -- therefor.

Column 1686, Line 50: In Claim 18, delete "(5 S)-" and insert -- (5S)- -- therefor.

Column 1686, Line 56: In Claim 18, delete "(5 S)-" and insert -- (5S)- -- therefor.

Column 1686, Line 59: In Claim 18, delete "(5 S)-" and insert -- (5S)- -- therefor.

Column 1687, Line 6: In Claim 18, delete "(5 S)-" and insert -- (5S)- -- therefor.

Column 1687, Line 10: In Claim 18, delete "(5 S)-" and insert -- (5S)- -- therefor.

Column 1687, Line 14: In Claim 18, delete "(5 S)-" and insert -- (5S)- -- therefor.

Column 1687, Line 26: In Claim 18, delete "(5 S)-" and insert -- (5S)- -- therefor.

Column 1687, Line 29: In Claim 18, delete "(5 S)-" and insert -- (5S)- -- therefor.

Column 1688, Line 25: In Claim 18, delete "(5 S)-" and insert -- (5S)- -- therefor.